US010881730B2

(12) United States Patent
Huang et al.

(10) Patent No.: US 10,881,730 B2
(45) Date of Patent: Jan. 5, 2021

(54) IMMUNOMODULATORY THERAPEUTIC MRNA COMPOSITIONS ENCODING ACTIVATING ONCOGENE MUTATION PEPTIDES

(71) Applicant: ModernaTX, Inc., Cambridge, MA (US)

(72) Inventors: Eric Yi-Chun Huang, Boston, MA (US); Sze-Wah Tse, Cambridge, MA (US); Jared Iacovelli, Waltham, MA (US); Kristine McKinney, Cambridge, MA (US); Nicholas Valiante, Cambridge, MA (US)

(73) Assignee: ModernaTX, Inc., Cambridge, MA (US)

( * ) Notice: Subject to any disclaimer, the term of this patent is extended or adjusted under 35 U.S.C. 154(b) by 0 days.

(21) Appl. No.: 16/279,372

(22) Filed: Feb. 19, 2019

(65) Prior Publication Data

US 2019/0175727 A1 Jun. 13, 2019

Related U.S. Application Data

(63) Continuation of application No. 16/233,614, filed on Dec. 27, 2018, now abandoned, which is a continuation of application No. PCT/US2018/016510, filed on Feb. 1, 2018.

(60) Provisional application No. 62/541,571, filed on Aug. 4, 2017, provisional application No. 62/490,523, filed on Apr. 26, 2017, provisional application No. 62/467,063, filed on Mar. 3, 2017, provisional application No. 62/453,465, filed on Feb. 1, 2017.

(51) Int. Cl.

| | |
|---|---|
| ***A61K 39/39*** | (2006.01) |
| ***A61K 9/50*** | (2006.01) |
| ***C07K 14/725*** | (2006.01) |
| ***A61K 39/00*** | (2006.01) |
| ***A61K 9/00*** | (2006.01) |
| ***A61K 9/51*** | (2006.01) |
| ***A61P 35/00*** | (2006.01) |
| *A61K 35/00* | (2006.01) |

(52) U.S. Cl.

CPC ............ *A61K 39/39* (2013.01); *A61K 9/0019* (2013.01); *A61K 9/5015* (2013.01); *A61K 9/5123* (2013.01); *A61K 39/0011* (2013.01); *A61K 39/001164* (2018.08); *A61P 35/00* (2018.01); *C07K 14/7051* (2013.01); *A61K 2039/53* (2013.01); *A61K 2039/55561* (2013.01); *A61K 2039/572* (2013.01); *A61K 2039/575* (2013.01)

(58) Field of Classification Search

CPC .................... A61K 39/0011; A61K 39/001164

See application file for complete search history.

(56) References Cited

U.S. PATENT DOCUMENTS

| | | | |
|---|---|---|---|
| 5,703,055 | A | 12/1997 | Felgner et al. |
| 5,961,978 | A | 10/1999 | Gaudernack et al. |
| 6,080,725 | A | 6/2000 | Marciani |
| 6,503,503 | B1 | 1/2003 | Bigner et al. |
| 7,250,404 | B2 | 7/2007 | Felgner et al. |
| 7,465,454 | B2 | 12/2008 | Franzusoff et al. |
| 7,563,447 | B2 | 7/2009 | Franzusoff et al. |
| 8,067,559 | B2 | 11/2011 | Franzusoff et al. |
| 8,153,595 | B2 | 4/2012 | Chen |
| 8,343,502 | B2 | 1/2013 | Franzusoff et al. |
| 8,470,313 | B2 | 6/2013 | Guo et al. |
| 9,572,874 | B2 | 2/2017 | Fotin-Mleczek et al. |
| 9,750,824 | B2 | 9/2017 | Kariko et al. |
| 9,775,892 | B2 | 10/2017 | Eriksen |
| 10,010,592 | B2 | 7/2018 | Thess et al. |
| 2004/0110939 | A1 | 6/2004 | Dumas Milne Edwards et al. |
| 2004/0223949 | A1 | 11/2004 | Astsaturov et al. |
| 2005/0032730 | A1 | 2/2005 | Von Der Mulbe et al. |
| 2007/0185017 | A1 | 8/2007 | Aggarwal et al. |
| 2011/0165223 | A1 | 7/2011 | Sgouros et al. |
| 2014/0004134 | A1 | 1/2014 | Birkholz et al. |
| 2014/0044755 | A1 | 2/2014 | Naoi et al. |
| 2014/0178438 | A1 | 6/2014 | Sahin et al. |
| 2014/0329889 | A1 | 11/2014 | Vance et al. |
| 2015/0125477 | A1 | 5/2015 | Kuttruff-Coqui et al. |
| 2016/0058853 | A1 | 3/2016 | Sahin et al. |
| 2016/0068560 | A1 | 3/2016 | Patel et al. |
| 2016/0166676 | A1 | 6/2016 | Bahrami |

(Continued)

FOREIGN PATENT DOCUMENTS

| | | | |
|---|---|---|---|
| EP | 1392341 | B1 | 3/2005 |
| GB | 2328689 | A | 3/1999 |
| WO | 92/14756 | A1 | 9/1992 |
| WO | 00/66153 | A1 | 11/2000 |
| WO | 2003048202 | A2 | 6/2003 |
| WO | 2004026337 | A1 | 4/2004 |
| WO | 2009034172 | A1 | 3/2009 |
| WO | 2009/046738 | A1 | 4/2009 |
| WO | 2009/149539 | A1 | 12/2009 |
| WO | 2010017248 | A2 | 2/2010 |

(Continued)

OTHER PUBLICATIONS

International Preliminary Report on Patentability, PCT/US2017/058585, dated Aug. 8, 2019, 9 pages.

(Continued)

*Primary Examiner* — Antonio Galisteo Gonzalez

(74) *Attorney, Agent, or Firm* — Nelson Mullins Riley & Scarborough LLP; Amy E. Mandragouras, Esq.; Ariana D. Harris

(57) ABSTRACT

The disclosure features immunomodulatory therapeutic compositions of an mRNA encoding an activating oncogene mutation peptide and an mRNA encoding a polypeptide that enhances immune responses to the activating oncogene mutation peptide, for example an mRNA encoding an immune potentiator. The disclosure also features methods of using the same, for example, to stimulate anti-cancer immune responses.

44 Claims, 38 Drawing Sheets

Specification includes a Sequence Listing.

(56) References Cited

U.S. PATENT DOCUMENTS

| | | | |
|---|---|---|---|
| 2016/0175357 A1 | 6/2016 | Weinschenk et al. | |
| 2016/0210400 A1 | 7/2016 | Patel et al. | |
| 2016/0331820 A1* | 11/2016 | Eriksen | C07K 14/82 |
| 2016/0331822 A1 | 11/2016 | Hacohen et al. | |
| 2016/0333355 A1 | 11/2016 | Deng et al. | |
| 2017/0028044 A1 | 2/2017 | Soon-Shiong et al. | |
| 2017/0065694 A1* | 3/2017 | Eriksen | A61K 35/17 |
| 2017/0100479 A1 | 4/2017 | Wu et al. | |
| 2018/0055922 A1 | 3/2018 | Hacohen et al. | |
| 2018/0163226 A1 | 6/2018 | Florkiewicz | |
| 2018/0311343 A1 | 11/2018 | Huang et al. | |

FOREIGN PATENT DOCUMENTS

| | | | |
|---|---|---|---|
| WO | 2010/037408 | A1 | 4/2010 |
| WO | 2013/036201 | A1 | 3/2013 |
| WO | 2013/151666 | A2 | 10/2013 |
| WO | 2013151665 | A2 | 10/2013 |
| WO | 2013166000 | A1 | 11/2013 |
| WO | 2013185052 | A1 | 12/2013 |
| WO | 2014/037124 | A1 | 3/2014 |
| WO | 2014/039961 | A1 | 3/2014 |
| WO | 2014127296 | A1 | 8/2014 |
| WO | 2014/145038 | A1 | 9/2014 |
| WO | 2014/179760 | A1 | 11/2014 |
| WO | 2014189805 | A1 | 11/2014 |
| WO | 2014189806 | A1 | 11/2014 |
| WO | 2015061294 | A2 | 4/2015 |
| WO | 2015077354 | A1 | 5/2015 |
| WO | 2015086590 | A2 | 6/2015 |
| WO | 2015108595 | A1 | 7/2015 |
| WO | 2015/123532 | A1 | 8/2015 |
| WO | 2015164674 | A1 | 10/2015 |
| WO | 2015169804 | A1 | 11/2015 |
| WO | 2016/046357 | A1 | 3/2016 |
| WO | 2016081947 | A2 | 5/2016 |
| WO | 2016/154544 | A1 | 9/2016 |
| WO | 2016/170176 | A1 | 10/2016 |
| WO | 2016176330 | A1 | 11/2016 |
| WO | 2016187508 | A2 | 11/2016 |
| WO | 2016/202937 | A1 | 12/2016 |
| WO | 2016201450 | A2 | 12/2016 |
| WO | 2016203025 | A1 | 12/2016 |
| WO | 2017/020026 | A1 | 2/2017 |
| WO | 2017023779 | A1 | 2/2017 |
| WO | 2017/068482 | A1 | 4/2017 |
| WO | 2017112830 | A1 | 6/2017 |
| WO | 2017118702 | A1 | 7/2017 |
| WO | 2017152042 | A2 | 9/2017 |
| WO | 2017177204 | A1 | 10/2017 |
| WO | 2017190242 | A1 | 11/2017 |
| WO | 2017191274 | A2 | 11/2017 |
| WO | 2017205810 | A1 | 11/2017 |
| WO | 2017223085 | A2 | 12/2017 |
| WO | 2018015433 | A2 | 1/2018 |
| WO | 2018039303 | A1 | 3/2018 |
| WO | 2018/081459 | A1 | 5/2018 |
| WO | 2018083220 | A2 | 5/2018 |
| WO | 2018102584 | A1 | 6/2018 |
| WO | 2018102585 | A1 | 6/2018 |
| WO | 2018111902 | A1 | 6/2018 |
| WO | 2018/144775 | A1 | 8/2018 |

OTHER PUBLICATIONS

Abrams, S. I., et al., "Generation of Stable CD4+ and CD8+ T Cell Lines from Patients Immunized with ras Oncogene-Derived Peptides Reflecting Codon 12 Mutations," Cellular Immunology, vol. 182(2): 137-151 (1997).

Barber, G., "STING: infection, inflammation and cancer," The Journal of Immunology, vol. 15(12):760-770 (2015).

Bryant, K. et al., "KRAS: feeding pancreatic cancer proliferation," Trends in Biochemical Sciences, vol. 39:2: 91-100 (2014).

Corrales L. et al., "The host STING pathway at the interface of cancer and immunity," Journal of Clinical Investigation, vol. 126 (7):2404-2411 (2016).

Cox, A., et al., "Drugging the undruggable Ras: mission possible?," Nat Rev Drug Discov., vol. 13(11): 828-851 (2014).

Deng, L. et al., "STING-Dependent Cytosolic DNA Sensing Promotes Radiation-Induced Type I Interferon-Dependent Antitumor Immunity in Immunogenic Tumors," Immunity, vol. 41:843-852 (2014).

Diaz, L. et al., "The molecular evolution of acquired resistance to targeted EGFR blockade in colorectal cancers," Nature, vol. 486(7404): 537-540 (2012).

Fu, J. et al., "STING agonist formulated cancer vaccines can cure established tumors resistant to PD-1 blockade," Sci Transl Med., vol. 7(283): (283ra52) 24 pages (2015).

Fumoto, S. et al., "Targeted Gene Delivery: Importance of Administration Routes," Intech, Chapter 1:3-31 (2013).

Gjersten, M. et al. "Intradermal ras peptide vaccination with granulocyte-macrophage colony-stimulating factor as adjuvant: Clinical and immunological responses in patients with pancreatic adenocarcinoma," Int. J. Cancer, vol. 92:441-450 (2001).

Gjertsen, MK, et al., "HLA-A3 restricted mutant ras specific cytotoxic T-lymphocytes induced by vaccination with T-helper epitopes," J Mol Med., vol. 81:43-50 (2003).

Gutjahr, A. et al., "Triggering Intracellular Receptors for Vaccine Adjuvantation," Trends in Immunology, vol. 37(9): 573-587 (2016).

Hanson, M. et al., "Nanoparticulate STING agonists are potent lymph node-targeted vaccine adjuvants," The Journal of Clinical Investigation, vol. 125(6): 2532-2546 (2015).

Hunger, R.E., et al. "Successful induction of immune responses against mutant ras in melanoma patients using intradermal injection of peptides and GM-CSF as adjuvant," Exp. Dermatol., vol. 10: 161-167 (2001).

International Search Report and Written Opinion, PCT/US2017/058585, dated Mar. 26, 2018, 29 pages.

International Search Report and Written Opinion, PCT/US2018/016510, dated May 14, 2018, 12 pages.

Ishikawa, H. et al., "STING is an endoplasmic reticulum adaptor that facilitates innate immune signaling," vol. 455: 674-678 (2008).

Ishikawa, H. et al., "STING regulates intracellular DNA-mediated, type I interferon-dependent innate immunity.," Nature, vol. 461:788-792 (2009).

Kauer, B. et al., "Immunotherapy: Training the body to fight cancer," The Conversation, pp. 1-4 (2017).

Kobiyama, K. et al., "Innate Immune Signaling by, Genetic Adjuvants for, DNA Vaccination," Vaccines, vol. 1: 278-292 (2013).

Kubuschok, B, et al., "Naturally occurring T-cell response against mutated p21 ras oncoprotein in pancreatic cancer," Clin Cancer Res., vol. 12:1365-1372 (2006).

Linard, B, et al., "A ras-mutated peptide targeted by CTL infiltrating a human melanoma lesion," J Immunol., vol. 168:4802-4808 (2002).

Marabelle, A. et al, "Intratumoral immunotherapy: using the tumor as the remedy," Annals of Oncology, vol. 28 (Supplement 12): xii33-xii43 (2017).

Mellema, W. et al., "Comparison of clinical outcome after first-line platinum-based chemotherapy in different types of KRAS mutated advanced NSCLC," Lung Cancer, vol. 90 (2):249-254 (2015).

Misale, S. et al., "Emergence of KRAS mutations and acquired resistance to anti-EGFR therapy in colorectal cancer," Nature, vol. 486(7404): 532-536 (2012).

Neumann, J. et al, "Frequency and type of KRAS mutations in routine diagnostic analysis of metastatic colorectal cancer," Pathology Research and Practice, vol. 205:858-862 (2009).

Prior, I. et al., "A comprehensive study of Ras mutations in cancer," Cancer Res., vol. 72(10): 2457-2467(2012).

Pylayeva-Gupta, Y, et al., "RAS oncogenes: weaving a tumorigenic web," Nat Rev. Cancer, vol. 11(11): 761-774 (2011).

Tang, E.D., et al., "Single Amino Acid Change in STING Leads to Constitutive Active Signaling," PLoS One, 10(3): e0120090:1-10 (2015).

Tran E. et al., "T-Cell Transfer Therapy Targeting Mutant KRAS in Cancer," New England Journal of Medicine, vol. 375(23): 2255-2262 (2016).

(56) References Cited

OTHER PUBLICATIONS

Tran, E., et al., "Immunogenicity of somatic mutations in human gastrointestinal cancers," Science, vol. 350(6266): 1387-1390 (2015).
Van Der Jeught, K. et al, "Intratumoral delivery of mRNA: Overcoming obstacles for effective immunotherapy," Oncolmmunology, vol. 4(5):1-3 (2015).
Van Lint, S et al., "Preclinical Evaluation of TriMix and Antigen mRNA-Based Antitumor Therapy," Cancer Research, vol. 72(7): 1661-1671 (2012).
Wang, Q. et al., "Identification of T-cell receptors targeting KRAS-mutated human tumors," Cancer Immunology Research, vol. 4(3): 204-214 (2016).
Weden, S. et al., "Long-term follow-up of patients with resected pancreatic cancer following vaccination against mutant K-ras," Int. J. Cancer, vol. 128(5):1120-1128 (2011).
Woo, S-R et al., "STING-Dependent Cytosolic DNA Sensing Mediates Innate Immune Recognition of Immunogenic Tumors," Immunity, vol. 41: 830-842 (2014).
Xu, D. et al., "miR-22 represses cancer progression by inducing cellular senescence," J. Cell Biol., vol. 193 (2):409-424 (2011).
Yegorov, O. et al., "The co-transfection of monocyte derived dendritic cells by different combinations of HIV antigen RNA and molecular adjuvant RNA enhanced the response of HIV-specific CD8+ T cells," Jan. 1, 2008 (Jan. 1, 2008), XP055457108, Retrieved from the Internet: HYPERLINK "URL: http://library.iasociety.org/PrintAbstract.aspx?abstractId=9619&confID=2008" URL:http://library.iasociety.org/PrintAbstract.aspx?abstractId=9619&confID=2008 [retrieved on Mar. 7, 2018].

* cited by examiner

IL-6 (25)

IMMUNOMODULATORY THERAPEUTIC MRNA COMPOSITIONS ENCODING ACTIVATING ONCOGENE MUTATION PEPTIDES

RELATED APPLICATIONS

This application is a continuation of U.S. Continuation patent application Ser. No. 16/233,614, filed on Dec. 27, 2018, which is a continuation of International Application No. PCT/US2018/016510, filed Feb. 1, 2018, which claims the benefit of U.S. Provisional Patent Application Ser. No. 62/541,571 filed on Aug. 4, 2017; U.S. Provisional Patent Application Ser. No. 62/490,523 filed on Apr. 26, 2017; U.S. Provisional Patent Application Ser. No. 62/467,063 filed on Mar. 3, 2017; and U.S. Provisional Patent Application Ser. No. 62/453,465 filed on Feb. 1, 2017. The entire contents of the above-referenced applications are incorporated herein by this reference.

STATEMENT REGARDING SEQUENCE LISTING

The instant application contains a Sequence Listing which has been submitted in ASCII format via EFS-Web and is hereby incorporated by reference in its entirety. Said ASCII copy, created Feb. 19, 2019, is named MDN_015PCCN3_Sequence_Listing.txt and is 491000 bytes in size.

BACKGROUND OF THE DISCLOSURE

The ability to modulate an immune response is beneficial in a variety of clinical situations, including the treatment of cancer and pathogenic infections, as well as in potentiating vaccine responses to provide protective immunity. A number of therapeutic tools exist for modulating the function of biological pathways and/or molecules that are involved in diseases such as cancer and pathogenic infections. These tools include, for example, small molecule inhibitors, cytokines and therapeutic antibodies. Some of these tools function through modulating immune responses in a subject, such as cytokines that modulate the activity of cells within the immune system or immune checkpoint inhibitor antibodies, such as anti-CTLA-4 or anti-PD-L1 that modulate the regulation of immune responses.

Additionally, vaccines have long been used to stimulate an immune response against antigens of pathogens to thereby provide protective immunity against later exposure to the pathogens. More recently, vaccines have been developed using antigens found on tumor cells to thereby enhance anti-tumor imunoresponsiveness. In addition to the antigen(s) used in the vaccine, other agents may be included in a vaccine preparation, or used in combination with the vaccine preparation, to further boost the immune response to the vaccine. Such agents that enhance vaccine responsiveness are referred to in the art as adjuvants. Examples of commonly used vaccine adjuvants include aluminum gels and salts, monophosphoryl lipid A, MF59 oil-in-water emulsion, Freund's complete adjuvant, Freund's incomplete adjuvant, detergents and plant saponins. These adjuvants typically are used with protein or peptide based vaccines. Alternative types of vaccines, such as RNA based vaccines, are now being developed.

There exists a need in the art for additional effective agents that enhance immune responses to an antigen of interest.

SUMMARY OF THE DISCLOSURE

Provided herein are immunomodulatory therapeutic compositions, including lipid-based compositions such as lipid nanoparticles, which include an RNA (e.g., messenger RNA (mRNA)) that can safely direct the body's cellular machinery to produce a cancer protein or fragment thereof of interest, e.g., an activating oncogene mutation peptide. In some embodiments, the RNA is a modified RNA. The immunomodulatory therapeutic compositions, including mRNA compositions and/or lipid nanoparticles comprising the same are useful to induce a balanced immune response against cancers, comprising both cellular and humoral immunity, without risking the possibility of insertional mutagenesis, for example.

The immunomodulatory therapeutic compositions, including mRNA compositions and/or lipid nanoparticles of the disclosure may be utilized in various settings depending on the prevalence of the cancer or the degree or level of unmet medical need. The immunomodulatory therapeutic compositions, including mRNA compositions and lipid nanoparticles of the disclosure may be utilized to treat and/or prevent a cancer of various stages or degrees of metastasis. The immunomodulatory therapeutic compositions and lipid nanoparticles of the disclosure have superior properties in that they produce much larger antibody titers and produce responses earlier than alternative anti-cancer therapies including cancer vaccines. While not wishing to be bound by theory, it is believed that the provided compositions, such as mRNA polynucleotides, are better designed to produce the appropriate protein conformation upon translation as the RNA co-opt natural cellular machinery. Unlike traditional therapies and vaccines which are manufactured ex vivo and may trigger unwanted cellular responses, RNA of the provided compositions are presented to the cellular system in a more native fashion.

In some aspects, the disclosure provides an immunomodulatory therapeutic composition, comprising: one or more mRNA each comprising an open reading frame encoding an activating oncogene mutation peptide, and optionally one or more mRNA each comprising an open reading frame encoding a polypeptide that enhances an immune response to the activating oncogene mutation peptide in a subject, wherein the immune response comprises a cellular or humoral immune response characterized by: (i) stimulating Type I interferon pathway signaling, (ii) stimulating NFkB pathway signaling, (iii) stimulating an inflammatory response, (iv) stimulating cytokine production, (v) stimulating dendritic cell development, activity or mobilization, and (vi) a combination of any of (i)-(v); and a pharmaceutically acceptable carrier.

In some aspects, the disclosure provides an immunomodulatory therapeutic composition, including mRNA compositions and/or lipid nanoparticles comprising the same, that enhances an immune response by, for example, stimulating Type I interferon pathway signaling, stimulating NFkB pathway signaling, stimulating an inflammatory response, stimulating cytokine production or stimulating dendritic cell development, activity or mobilization. Enhancement of an immune response to an antigen of interest by an immune potentiator mRNA results in, for example, stimulation of cytokine production, stimulation of cellular immunity (T cell responses), such as antigen-specific $CD8^+$ or $CD4^+$ T cell responses and/or stimulation of humoral immunity (B cell responses), such as antigen-specific antibody responses.

In some aspects, the disclosure provides an immunomodulatory therapeutic composition wherein the activating oncogene mutation is a KRAS mutation. In some aspects, the KRAS mutation is a G12 mutation. In some aspects, the G12 KRAS mutation is selected from G12D, G12V, G12S, G12C, G12A, and G12R KRAS mutations. In other aspects, the G12 KRAS mutation is selected from G12D, G12V, and G12C KRAS mutations. In some aspects, the KRAS mutation is a G13 mutation. In some aspects, the G13 KRAS mutation is a G13D KRAS mutation. In other aspects, the disclosure provides an immunomodulatory therapeutic composition wherein the activating oncogene mutation is a H-RAS or N-RAS mutation.

In some embodiments the skilled artisan will select a KRAS mutation, a HLA subtype and a tumor type based on the guidance provided herein and prepare a KRAS vaccine for therapy. In some embodiments the KRAS mutation is selected from: G12C, G12V, G12D, G13D. In some embodiments the HLA subtype is selected from: A*02:01, C*07:01, C*04:01, C*07:02, HLA-A11 and/or HLA-008. In some embodiments the tumor type is selected from colorectal, pancreatic, lung (e.g., non-small cell lung cancer (NSCLC), and endometrioid.

In some embodiments, the HRAS mutation is a mutation at codon 12, codon 13, or codon 61. In some embodiments, the HRAS mutation is a 12V, 61L, or 61R mutation.

In some embodiments, the NRAS mutation is a mutation at codon 12, codon 13, or codon 61. In some embodiments, the NRAS mutation is a 12D, 13D, 61K, or 61R mutation.

In some aspects, the disclosure provides an immunomodulatory therapeutic composition of any one of the foregoing or related embodiments, wherein the mRNA has an open reading frame encoding a concatemer of two or more activating oncogene mutation peptides. In some aspects, the concatemer comprises 3, 4, 5, 6, 7, 8, 9, or 10 activating oncogene mutation peptides. In some aspects, the concatemer comprises 4 activating oncogene mutation peptides.

In other aspects, the disclosure provides an immunomodulatory therapeutic composition, comprising: an mRNA comprising an open reading frame encoding a concatemer of two or more activating oncogene mutation peptides, wherein the concatemer comprises KRAS activating oncogene mutation peptides G12D, G12V, G12C, and G13D; and one or more mRNA each comprising an open reading frame encoding a polypeptide that enhances an immune response to the KRAS activating oncogene mutation peptides in a subject. In some aspects, the concatemer comprises from N- to C-terminus G12D, G12V, G13D, and G12C. In some aspects, the concatemer comprises from N- to C-terminus G12C, G13D, G12V, and G12D.

Some embodiments of the present disclosure provide immunomodulatory therapeutic compositions that include an mRNA comprising an open reading frame encoding a concatemer of two or more activating oncogene mutation peptides. In some embodiments, at least two of the peptide epitopes are separated from one another by a single Glycine. In some embodiments, the concatemer comprises 3-10 activating oncogene mutation peptides. In some such embodiments, all of the peptide epitopes are separated from one another by a single Glycine. In other embodiments, at least two of the peptide epitopes are linked directly to one another without a linker.

In some aspects, the disclosure provides an immunomodulatory therapeutic composition, comprising: 1, 2, 3, or 4 mRNAs encoding 1, 2, 3, or 4 activating oncogene mutation peptides; and one or more mRNA each comprising an open reading frame encoding a polypeptide that enhances an immune response to the activating oncogene mutation peptide in a subject. In some aspects, the composition comprises 4 mRNAs encoding 4 activating oncogene mutation peptides. In some aspects, the 4 mRNAs encode KRAS activating oncogene mutation peptides G12D, G12V, G12C, and G13D.

In some aspects, the disclosure provides an immunomodulatory therapeutic composition of any one of the foregoing or related embodiments, wherein the activating oncogene mutation peptide comprises 10-30, 15-25, or 20-25 amino acids in length. In some aspects, the activating oncogene mutation peptide comprises 20, 21, 22, 23, 24, or 25 amino acids in length. In some aspects, the activating oncogene mutation peptide comprises 25 amino acids in length.

In some aspects, the disclosure provides an immunomodulatory therapeutic composition of any one of the foregoing or related embodiments, wherein the mRNA encoding a polypeptide that enhances an immune response to the activating oncogene mutation peptide in a subject encodes a constitutively active human STING polypeptide. In some aspects, the constitutively active human STING polypeptide comprises one or more mutations selected from the group consisting of V147L, N154S, V155M, R284M, R284K, R284T, E315Q, R375A, and combinations thereof.

In some aspects, the constitutively active human STING polypeptide comprises mutation V155M (e.g., having the amino acid sequence shown in SEQ ID NO: 1 or encoded by a nucleotide sequence shown in SEQ ID NO: 139 or 170). In some aspects the constitutively active human STING polypeptide comprises mutations V147L/N154S/V155M. In some aspects, the constitutively active human STING polypeptide comprises mutations R284M/V147L/N154S/V155M.

In other aspects, the constitutively active human STING polypeptide comprises an amino acid sequence set forth in any one of SEQ ID NOs: 1-10 and 164. In another aspect, the constitutively active human STING polypeptide is encoded by a nucleotide sequence set forth in any one of SEQ ID NOs: 139-148, 165, 168, 170, 201-209 and 225. In some aspects, the constitutively active human STING polypeptide comprises a 3' UTR comprising at least one miR-122 microRNA binding site, such as for example set forth in SEQ ID NO: 149.

In some aspects, the disclosure provides an immunomodulatory therapeutic composition of any one of the foregoing or related embodiments, wherein the mRNA encoding a polypeptide that enhances an immune response to the activating oncogene mutation peptide in a subject encodes a constitutitively active human IRF3 polypeptide. In one aspect, the constitutively active human IRF3 polypeptide comprises an S396D mutation. In one aspect, the constitutively active human IRF3 polypeptide comprises an amino acid sequence set forth in SEQ ID NO: 12 or is encoded by a nucleotide sequence set forth in SEQ ID NO: 151 or 212. In one aspect, the constitutively active IRF3 polypeptide is a mouse IRF3 polypeptide, for example comprising an amino acid sequence set forth in SEQ ID NO: 11 or encoded by the nucleotide sequence shown in SEQ ID NO: 150 or 211.

In some aspects, the disclosure provides an immunomodulatory therapeutic composition of any one of the foregoing or related embodiments, wherein the mRNA encoding a polypeptide that enhances an immune response to the activating oncogene mutation peptide in a subject encodes a constitutitively active human IRF7 polypeptide. In one aspect, the constitutively active human IRF7 polypeptide comprises one or more mutations selected from the group consisting of S475D, S476D, S477D, S479D, L480D, S483D, S487D, and combinations thereof; deletion of amino acids 247-467; and combinations of the foregoing mutations and/or deletions. In one embodiment, the constitutively active human IRF7 polypeptide comprises an amino acid sequence set forth in any one of SEQ ID NOs: 14-18. In one embodiment, the constitutively active human IRF7 polypeptide is encoded by a nucleotide sequence set forth in any one of SEQ ID NOs: 153-157 and 214-218.

In yet other aspects, the disclosure provides an immune potentiator mRNA encoding a polypeptide selected from the group consisting of MyD88, TRAM, IRF1, IRF8, IRF9, TBK1, IKKi, STAT1, STAT2, STAT4, STAT6, c-FLIP, IKKβ, RIPK1, TAK-TAB1 fusion, DIABLO, Btk, self-activating caspase-1 and Flt3.

In some aspects, the disclosure provides an immunomodulatory therapeutic composition of any one of the foregoing embodiments, wherein the composition further comprises a cancer therapeutic agent. In some aspects, the composition further comprises an inhibitory checkpoint polypeptide. In some aspects, the inhibitory checkpoint polypeptide is an antibody or fragment thereof that specifically binds to a molecule selected from the group consisting of PD-1, PD-L1, TIM-3, VISTA, A2AR, B7-H3, B7-H4, BTLA, CTLA-4, IDO, KIR and LAG3.

In other embodiments, the composition further comprises a recall antigen. For example, in some embodiments, the recall antigen is an infectious disease antigen.

In some embodiments, the composition does not comprise a stabilization agent.

In some aspects, the disclosure provides an immunomodulatory therapeutic composition of any one of the foregoing embodiments, wherein the mRNA is formulated in a lipid nanoparticle. In some aspects, the lipid nanoparticle comprises a molar ratio of about 20-60% ionizable amino lipid:5-25% phospholipid:25-55% sterol; and 0.5-15% PEG-modified lipid. In some aspects, the inonizable amino lipid is selected from the group consisting of for example, 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319). In some aspects, the ionizable amino lipid comprises a compound of any of Formulae (I), (IA), (II), (IIa), (IIb), (IIc), (IId), and (IIe). In some aspects, the ionizable amino lipid comprises a compound of Formula (I). In some aspects, the compound of Formula (I) is Compound 25.

In some aspects, the disclosure provides an immunomodulatory therapeutic composition of any one of the foregoing embodiments, wherein each mRNA includes at least one chemical modification. In some aspects, the chemical modification is selected from the group consisting of pseudouridine, N1-methylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methyluridine, 5-methoxyuridine, and 2'-O-methyl uridine. In some aspects, the chemical modification is pseudouridine or a pseudouridine analog. In some aspects, the chemical modification is N1-methylpseudouridine. In some aspects, each mRNA comprises fully modified N1-methylpseudouridine.

In some aspects, the disclosure provides an immunomodulatory therapeutic composition, including mRNA compositions and lipid-based compositions such as lipid nanoparticles, comprising: one or more mRNA each comprising an open reading frame encoding a KRAS activating oncogene mutation peptide, and optionally one or more mRNA each comprising an open reading frame encoding a constitutively active human STING polypeptide; and a pharmaceutically acceptable carrier. In some aspects, the constitutively active human STING polypeptide comprises mutation V155M. In some aspects, the constitutively active human STING polypeptide comprises an amino acid sequence shown in SEQ ID NO: 1. In some aspects, the constitutively active human STING polypeptide comprises a 3' UTR comprising at least one miR-122 microRNA binding site.

In some aspects, the disclosure provides an immunomodulatory therapeutic composition of any one of the foregoing embodiments, wherein the KRAS activating oncogene mutation peptide is selected from G12D, G12V, G12S, G12C, G12A, G12R, and G13D. In some aspects, the KRAS activating oncogene mutation peptide is selected from G12D, G12V, G12C, and G13D.

In some aspects, the disclosure provides an immunomodulatory therapeutic composition of any one of the foregoing embodiments, wherein the mRNA comprises an open reading frame encoding a concatemer of two or more KRAS activating oncogene mutation peptides. In some aspects, the concatemer comprises 3, 4, 5, 6, 7, 8, 9 or 10 KRAS activating oncogene mutation peptides. In some aspects, the concatemer comprises 4 KRAS activating oncogene mutation peptides. In some aspects, the concatemer comprises G12D, G12V, G12C, and G13D. In some aspects, the concatemer comprises from N- to C-terminus G12D, G12V, G13D, and G12C. In some aspects, the concatemer comprises from N- to C-terminus G12C, G13D, G12V, and G12D.

In some aspects, the disclosure provides an immunomodulatory therapeutic composition of any one of the foregoing embodiments, wherein the composition comprises 1, 2, 3, or 4 mRNAs encoding 1, 2, 3, or 4 KRAS activating oncogene mutation peptides. In some aspects, the composition comprises 4 mRNAs encoding 4 KRAS activating oncogene mutation peptides. In some aspects, the 4 KRAS activating oncogene mutation peptides comprise G12D, G12V, G12C, and G13D.

In some aspects, the disclosure provides an immunomodulatory therapeutic composition of any one of the foregoing or related embodiments, wherein the KRAS activating oncogene mutation peptide comprises 10-30, 15-25, or 20-25 amino acids in length. In some aspects, the KRAS activating oncogene mutation peptide comprises 20, 21, 22, 23, 24, or 25 amino acids in length. In some aspects, the activating oncogene mutation peptide comprises 25 amino acids in length.

In some aspects, the disclosure provides an immunomodulatory therapeutic composition of any one of the foregoing or related embodiments, wherein the mRNA has an open reading frame encoding a concatemer of two or more KRAS activating oncogene mutation peptides and the concatemer comprises an amino acid sequence selected from the group set forth in SEQ ID NOS: 42-47, 73 and 137. In some aspects, wherein the mRNA encoding the concatemer comprises a nucleotide sequence selected from the group set forth in SEQ ID NOS: 129-131, 133, 138, 167, 169, 193-195 and 197-198.

In some aspects, the disclosure provides an immunomodulatory therapeutic composition of any one of the foregoing or related embodiments, wherein the composition comprises 1, 2, 3, or 4 mRNAs encoding 1, 2, 3, or 4 KRAS activating oncogene mutation peptides, and wherein the KRAS activating oncogene mutation peptides comprise an amino acid sequence selected from the group set forth in SEQ ID NOs: 36-41, 72 and 125. In some aspects, the KRAS activating oncogene mutation peptides comprise the amino acid sequence set forth in SEQ ID NOs: 39-41 and 72. In some aspects, the mRNA encoding the KRAS activating oncogene mutation peptide comprises a nucleotide sequence selected from the group set forth in SEQ ID NOs: 126-128, 132, 190-192 and 196.

In other aspects, the disclosure provides an immunomodulatory therapeutic composition, including mRNA compositions and/or lipid nanoparticles comprising the same, comprising an mRNA construct encoding at least one mutant human KRAS antigen and a constitutively active human STING polypeptide, for example wherein the mRNA (e.g., a modified mRNA) encodes an amino acid sequence as set forth in any one of SEQ ID NOs: 48-71.

In some aspects, the disclosure provides an immunomodulatory therapeutic composition of any one of the foregoing or related embodiments, wherein each mRNA is formulated in the same or different lipid nanoparticle. In some aspects, each mRNA encoding a KRAS activating oncogene mutation peptide is formulated in the same or different lipid nanoparticle. In some aspects, each mRNA encoding constitutively active human STING is formulated in the same or different lipid nanoparticle. In some aspects, each mRNA encoding a KRAS activating oncogene mutation peptide is formulated in the same lipid nanoparticle and each mRNA encoding constitutively active human STING is formulated in a different lipid nanoparticle. In some aspects, each mRNA encoding a KRAS activating oncogene mutation peptide is formulated in the same lipid nanoparticle and each mRNA encoding constitutively active human STING is formulated in the same lipid nanoparticle as each mRNA encoding a KRAS activating oncogene mutation peptide. In some aspects, each mRNA encoding a KRAS activating oncogene mutation peptide is formulated in a different lipid nanoparticle and each mRNA encoding constitutively active human STING is formulated in the same lipid nanoparticle as each mRNA encoding each KRAS activating oncogene mutation peptide.

In some aspects, the disclosure provides an immunomodulatory therapeutic composition of any one of the foregoing embodiments, wherein the immunomodulatory therapeutic composition is formulated in a lipid nanoparticle, wherein the lipid nanoparticle comprises a molar ratio of about 20-60% ionizable amino lipid:5-25% phospholipid: 25-55% sterol; and 0.5-15% PEG-modified lipid. In some aspects, the ionizable amino lipid is selected from the group consisting of for example, 2,2-dilinoleyl-4-dimethylaminoethyl-[1,3]-dioxolane (DLin-KC2-DMA), dilinoleylmethyl-4-dimethylaminobutyrate (DLin-MC3-DMA), and di((Z)-non-2-en-1-yl) 9-((4-(dimethylamino)butanoyl)oxy) heptadecanedioate (L319). In some aspects, the ionizable amino lipid comprises a compound of any of Formulae (I), (IA), (II), (IIa), (IIb), (IIc), (IId), and (IIe). In some aspects, the ionizable amino lipid comprises a compound of Formula (I). In some aspects, the compound of Formula (I) is Compound 25.

In certain embodiments, the lipid nanoparticle comprises Compound 25 (as the ionizable amino lipid), DSPC (as the phospholipid), cholesterol (as the sterol) and PEG-DMG (as the PEG-modified lipid). In certain embodiments, the lipid nanoparticle comprises a molar ratio of about 20-60% Compound 25:5-25% DSPC:25-55% cholesterol; and 0.5-15% PEG-DMG. In one embodiment, the lipid nanoparticle comprises a molar ratio of about 50% Compound 25:about 10% DSPC:about 38.5% cholesterol:about 1.5% PEG-DMG (i.e., Compound 25:DSPC:cholesterol:PEG-DMG at about a 50:10:38.5:1.5 ratio). In one embodiment, the lipid nanoparticle comprises a molar ratio of 50% Compound 25:10% DSPC:38.5% cholesterol:1.5% PEG-DMG (i.e., Compound 25:DSPC:cholesterol:PEG-DMG at a 50:10:38.5:1.5 ratio).

In some aspects, the disclosure provides an immunomodulatory therapeutic composition of any one of the foregoing or related embodiments, wherein each mRNA includes at least one chemical modification. In some aspects, the chemical modification is selected from the group consisting of pseudouridine, N1-methylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methyluridine, 5-methoxyuridine, and 2'-O-methyl uridine. In some aspects, the chemical modification is pseudouridine or a pseudouridine analog. In some aspects, the chemical modification is N1-methylpseudouridine. In some aspects, each mRNA comprises fully modified N1-methylpseudouridine.

In some aspects, the disclosure provides a lipid nanoparticle comprising: an mRNA comprising an open reading frame encoding a concatemer of 4 KRAS activating oncogene mutation peptides, wherein the 4 KRAS activating oncogene mutation peptides comprise G12D, G12V, G12C, and G13D; an mRNA comprising an open reading frame encoding a constitutively active human STING polypeptide. In some aspects, the concatemer comprises from N- to C-terminus G12D, G12V, G13D, and G12C. In some aspects, the concatemer comprises from N- to C-terminus G12C, G13D, G12V, and G12D.

In some aspects, the disclosure provides lipid nanoparticle of any one of the foregoing embodiments, wherein each KRAS activating oncogene mutation peptide comprises 20, 21, 22, 23, 24, or 25 amino acids in length. In some aspects, each KRAS activating oncogene mutation peptide comprises 25 amino acids in length.

In some aspects, the disclosure provides a lipid nanoparticle comprising: an mRNA comprising an open reading frame encoding a concatemer of 4 KRAS activating oncogene mutation peptides, wherein the 4 KRAS activating oncogene mutation peptides comprise G12D, G12V, G12C, and G13D, and wherein the concatemer comprises the amino acid sequence set forth in SEQ ID NO:137; an mRNA comprising an open reading frame encoding a constitutively active human STING polypeptide. In some aspects, the mRNA encoding the concatemer of 4 KRAS activating oncogene mutation peptides comprises the nucleotide sequence set forth in SEQ ID NO: 138, SEQ ID NO: 167 or SEQ ID NO: 169. In some aspects, the constitutively active human STING polypeptide comprises mutation V155M. In some aspects, the constitutively active human STING polypeptide comprises the amino acid sequence shown in SEQ ID NO: 1. In some aspects, the mRNA encoding the constitutively active human STING polypeptide comprises a 3' UTR comprising at least one miR-122 microRNA binding site. In some aspects, the mRNA encoding the constitutively active human STING polypeptide comprises the nucleotide sequence shown in SEQ ID NO:

139, SEQ ID NO: 168, or SEQ ID NO: 170.

In other aspects, the disclosure provides a lipid nanoparticle comprising:

a first mRNAs comprising an open reading frame encoding a KRAS activating oncogene mutation peptide comprising G12D;

a second mRNA comprising an open reading frame encoding a KRAS activating oncogene mutation peptide comprising G12V;

a third mRNA comprising an open reading frame encoding a KRAS activating oncogene mutation peptide comprising G12C;

a fourth mRNA comprising an open reading frame encoding a KRAS activating oncogene mutation peptide comprising G13D; and a fifth mRNA comprising an open reading frame encoding a constitutively active human STING polypeptide. In certain embodiments, the mRNAs are present at a KRAS:STING mass ratio selected from the group consisting of 1:1, 2:1, 3:1, 4:1, 5:1, 6:1, 7:1, 8:1, 9:1 and 10:1. In one embodiment, the mRNAs are present at a KRAS:STING mass ratio of 5:1.

In some aspects of the foregoing lipid nanoparticle, each KRAS activating oncogene mutation peptide comprises 20, 21, 22, 23, 24, or 25 amino acids in length. In some aspects, each KRAS activating oncogene mutation peptide comprises 25 amino acids in length.

In some aspects of the foregoing lipid nanoparticle, the KRAS activating oncogene mutation peptides comprise the amino acid sequences set forth in SEQ ID NOs: 39-41 and 72. In some aspects, the mRNAs encoding the KRAS activating oncogene mutation peptides comprise the nucleotide sequences set forth in SEQ ID NOs: 126-128, 132, 190-192 and 196.

In some aspects of the foregoing lipid nanoparticle, the constitutively active human STING polypeptide comprises mutation V155M. In some aspects, the constitutively active human STING polypeptide comprises the amino acid sequence shown in SEQ ID NO: 1. In some aspects, the mRNA encoding the constitutively active human STING polypeptide comprises a 3' UTR comprising at least one miR-122 microRNA binding site. In some aspects, the mRNA encoding the constitutively active human STING polypeptide comprises the nucleotide sequence shown in SEQ ID NO: 139, SEQ ID NO: 168, or SEQ ID NO: 170.

In some aspects, the disclosure provides a lipid nanoparticle of any one of the foregoing embodiments, wherein the lipid nanoparticle comprises a molar ratio of about 20-60% ionizable amino lipid:5-25% phopholipid:25-55% sterol; and 0.5-15% PEG-modified lipid. In some aspects, the inonizable amino lipid is selected from the group consisting of for example, 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy) heptadecanedioate (L319). In some aspects, the ionizable amino lipid comprises a compound of any of Formulae (I), (IA), (II), (IIa), (IIb), (IIc), (IId), and (IIe). In some aspects, the ionizable amino lipid comprises a compound of Formula (I). In some aspects, the compound of Formula (I) is Compound 25.

In some aspects, the disclosure provides a lipid nanoparticle of any one of the foregoing embodiments, wherein each mRNA includes at least one chemical modification. In some aspects, the chemical modification is selected from the group consisting of pseudouridine, N1-methylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methyluridine, 5-methoxyuridine, and 2'-O-methyl uridine. In some aspects, the chemical modification is pseudouridine or a pseudouridine analog. In some aspects, the chemical modification is N1-methylpseudouridine. In some aspects, each mRNA comprises fully modified N1-methylpseudouridine.

In some aspects, the disclosure provides a drug product comprising any of the foregoing or related lipid nanoparticles for use in cancer therapy, optionally with instructions for use in cancer therapy.

In other aspects, the disclosure provides a first lipid nanoparticle comprising: an mRNA comprising an open reading frame encoding a KRAS activating oncogene mutation peptide comprising G12D; and an mRNA comprising an open reading frame encoding a constitutively active human STING polypeptide.

In some aspects, the disclosure provides a second lipid nanoparticle comprising: an mRNA comprising an open reading frame encoding a KRAS activating oncogene mutation peptide comprising G12V; and an mRNA comprising an open reading frame encoding a constitutively active human STING polypeptide.

In some aspects, the disclosure provides a third lipid nanoparticle comprising an mRNA comprising an open reading frame encoding a KRAS activating oncogene mutation peptide comprising G12C; and an mRNA comprising an open reading frame encoding a constitutively active human STING polypeptide.

In some aspects, the disclosure provides a fourth lipid nanoparticle comprising: an mRNA comprising an open reading frame encoding a KRAS activating oncogene mutation peptide comprising G13D; and an mRNA comprising an open reading frame encoding a constitutively active human STING polypeptide.

In some aspects of the foregoing first, second, third and fourth lipid nanoparticles, each KRAS activating oncogene mutation peptide comprises 20, 21, 22, 23, 24, or 25 amino acids in length. In some aspects, each KRAS activating oncogene mutation peptide comprises 25 amino acids in length.

In some aspects of the foregoing first, second, third and fourth lipid nanoparticles, the KRAS activating oncogene mutation peptide comprises the amino acid sequences set forth in SEQ ID NO: 39. In some aspects, the mRNA encoding the KRAS activating oncogene mutation peptide comprises the nucleotide sequence set forth in SEQ ID NOs: 126 or 190.

In some aspects of the foregoing first, second, third and fourth lipid nanoparticles, the KRAS activating oncogene mutation peptide comprises the amino acid sequences set forth in SEQ ID NO: 40. In some aspect, the mRNA encoding the KRAS activating oncogene mutation peptide comprises the nucleotide sequence set forth in SEQ ID NOs: 127 or 191.

In some aspects of the foregoing first, second, third and fourth lipid nanoparticles, the KRAS activating oncogene mutation peptide comprises the amino acid sequences set forth in SEQ ID NO: 72. In some aspects, the mRNA encoding the KRAS activating oncogene mutation peptide comprises the nucleotide sequence set forth in SEQ ID NOs: 132 or 196.

In some aspects of the foregoing first, second, third and fourth lipid nanoparticles, wherein the KRAS activating oncogene mutation peptide comprises the amino acid sequences set forth in SEQ ID NO: 41. In some aspects, the mRNA encoding the KRAS activating oncogene mutation peptide comprises the nucleotide sequence set forth in SEQ ID NOs: 128 or 192.

In some aspects of the foregoing first, second, third and fourth lipid nanoparticles, the constitutively active human STING polypeptide comprises mutation V155M. In some aspects, the constitutively active human STING polypeptide comprises the amino acid sequence shown in SEQ ID NO: 1. In some aspects, the constitutively active human STING polypeptide comprises a 3' UTR comprising at least one miR-122 microRNA binding site. In some aspects, the mRNA encoding the constitutively active human STING polypeptide comprises the nucleotide sequence shown in SEQ ID NO: 139, SEQ ID NO: 168, or SEQ ID NO: 170.

In some aspects, the disclosure provides a drug product comprising any of the foregoing or related lipid nanoparticles for use in cancer therapy, optionally with instructions for use in cancer therapy. In some aspects, the disclosure provides a drug product comprising any of the foregoing first, second, third and fourth lipid nanoparticles, for use in cancer therapy, optionally with instructions for use in cancer therapy.

In some aspects, the disclosure provides a drug product comprising a first, second, third and fourth lipid nanoparticles, for use in cancer therapy, optionally with instructions for use in cancer therapy, wherein:

(i) the first lipid nanoparticle comprises: an mRNA comprising an open reading frame encoding a KRAS activating oncogene mutation peptide comprising G12D; and an mRNA comprising an open reading frame encoding a constitutively active human STING polypeptide;

(ii) the second lipid nanoparticle comprises: an mRNA comprising an open reading frame encoding a KRAS activating oncogene mutation peptide comprising G12V; and an mRNA comprising an open reading frame encoding a constitutively active human STING polypeptide;

(iii) the third lipid nanoparticle comprises: an mRNA comprising an open reading frame encoding a KRAS activating oncogene mutation peptide comprising G12C; and an mRNA comprising an open reading frame encoding a constitutively active human STING polypeptide; and (iv) the fourth lipid nanoparticle comprises: an mRNA comprising an open reading frame encoding a KRAS activating oncogene mutation peptide comprising G13D; and an mRNA comprising an open reading frame encoding a constitutively active human STING polypeptide.

In any of the foregoing or related aspects, the disclosure provides a method for treating a subject, comprising: administering to a subject having cancer any of the foregoing or related immunomodulatory therapeutic compositions or any of the foregoing or related lipid nanoparticle. In some aspects, the immunomodulatory therapeutic composition or lipid nanoparticle is administered in combination with a cancer therapeutic agent. In some aspects, the immunomodulatory therapeutic composition or lipid nanoparticle is administered in combination with an inhibitory checkpoint polypeptide. In some aspects, the inhibitory checkpoint polypeptide is an antibody or fragment thereof that specifically binds to a molecule selected from the group consisting of PD-1, PD-L1, TIM-3, VISTA, A2AR, B7-H3, B7-H4, BTLA, CTLA-4, IDO, KIR and LAGS.

Methods provided herein may be used for treating a subject having cancer. In some embodiments, the cancer is selected from cancer of the pancreas, peritoneum, large intestine, small intestine, biliary tract, lung, endometrium, ovary, genital tract, gastrointestinal tract, cervix, stomach, urinary tract, colon, rectum, and hematopoietic and lymphoid tissues. In some embodiments, the cancer is colorectal cancer. In some embodiments, the cancer is pancreatic cancer. In some embodiments, the cancer is lung cancer, such as non-small cell lung cancer (NSCLC). In some embodiments, the cancer is selected from the group consisting of colorectal cancer, pancreatic cancer and lung cancer (e.g., NSCLC).

An mRNA (e.g., mmRNA) construct of the disclosure (e.g., an immune potentiator mRNA, antigen-encoding mRNA, or combination thereof) can comprise, for example, a 5' UTR, a codon optimized open reading frame encoding the polypeptide, a 3' UTR and a 3' tailing region of linked nucleosides. In one embodiment, the mRNA further comprises one or more microRNA (miRNA) binding sites.

In one embodiment, a modified mRNA construct of the disclosure is fully modified. For example, in one embodiment, the mmRNA comprises pseudouridine (ψ), pseudouridine (ψ) and 5-methyl-cytidine ($m^5C$), 1-methyl-pseudouridine ($m^1\psi$), 1-methyl-pseudouridine ($m^1\psi$) and 5-methyl-cytidine ($m^5C$), 2-thiouridine ($s^2U$), 2-thiouridine and 5-methyl-cytidine ($m^5C$), 5-methoxy-uridine ($mo^5U$), 5-methoxy-uridine ($mo^5U$) and 5-methyl-cytidine ($m^5C$), 2'-O-methyl uridine, 2'-O-methyl uridine and 5-methyl-cytidine ($m^5C$), N6-methyl-adenosine ($m^6A$) or N6-methyl-adenosine ($m^6A$) and 5-methyl-cytidine ($m^5C$). In another embodiment, the mmRNA comprises pseudouridine (ψ), N1-methylpseudouridine ($m^1\psi$), 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, or 2'-O-methyl uridine, or combinations thereof. In yet another embodiment, the mmRNA comprises 1-methyl-pseudouridine ($m^1\psi$), 5-methoxy-uridine ($mo^5U$), 5-methyl-cytidine ($m^5C$), pseudouridine (ψ), α-thio-guanosine, or α-thio-adenosine, or combinations thereof. In some aspects, the mmRNA comprises pseudouridine or a pseudouridine analog. In some aspects, the mmRNA comprises N1-methylpseudouridine. In some aspects, each mmRNA comprises fully modified N1-methylpseudouridine.

In some embodiments the dosage of the RNA polynucleotide in the immunomodulatory therapeutic composition is 1-5 μg, 5-10 μg, 10-15 μg, 15-20 μg, 10-25 μg, 20-25 μg, 20-50 μg, 30-50 μg, 40-50 μg, 40-60 μg, 60-80 μg, 60-100 μg, 50-100 μg, 80-120 μg, 40-120 μg, 40-150 μg, 50-150 μg, 50-200 μg, 80-200 μg, 100-200 μg, 100-300 μg, 120-250 μg, 150-250 μg, 180-280 μg, 200-300 μg, 30-300 μg, 50-300 μg, 80-300 μg, 100-300 μg, 40-300 μg, 50-350 μg, 100-350 μg, 200-350 μg, 300-350 μg, 320-400 μg, 40-380 μg, 40-100 μg, 100-400 μg, 200-400 μg, or 300-400 μg per dose. In some embodiments, the immunomodulatory therapeutic composition is administered to the subject by intradermal or intramuscular injection. In some embodiments, the immunomodulatory therapeutic composition is administered to the subject on day zero. In some embodiments, a second dose of the immunomodulatory therapeutic composition is administered to the subject on day twenty one.

In some embodiments, a dosage of 25 micrograms of the RNA polynucleotide is included in the immunomodulatory therapeutic composition administered to the subject. In some embodiments, a dosage of 10 micrograms of the RNA polynucleotide is included in the immunomodulatory therapeutic composition administered to the subject. In some embodiments, a dosage of 30 micrograms of the RNA polynucleotide is included in the immunomodulatory therapeutic composition administered to the subject. In some embodiments, a dosage of 100 micrograms of the RNA polynucleotide is included in the immunomodulatory therapeutic composition administered to the subject. In some embodiments, a dosage of 50 micrograms of the RNA polynucleotide is included in the immunomodulatory therapeutic composition administered to the subject. In some embodiments, a dosage of 75 micrograms of the RNA polynucleotide is included in the immunomodulatory therapeutic composition administered to the subject. In some embodiments, a dosage of 150 micrograms of the RNA polynucleotide is included in the immunomodulatory therapeutic composition administered to the subject. In some embodiments, a dosage of 400 micrograms of the RNA polynucleotide is included in the immunomodulatory therapeutic composition administered to the subject. In some embodiments, a dosage of 300 micrograms of the RNA polynucleotide is included in the immunomodulatory therapeutic composition administered to the subject. In some embodiments, a dosage of 200 micrograms of the RNA polynucleotide is included in the immunomodulatory therapeutic composition administered to the subject. In some embodiments, the RNA polynucleotide accumulates at a 100 fold higher level in the local lymph node in comparison with the distal lymph node. In other embodiments the immunomodulatory therapeutic composition is chemically modified and in other embodiments the immunomodulatory therapeutic composition is not chemically modified.

In some embodiments, the effective amount is a total dose of 1-100 μg. In some embodiments, the effective amount is a total dose of 100 μg. In some embodiments, the effective amount is a dose of 25 μg administered to the subject a total of one or two times. In some embodiments, the effective amount is a dose of 100 μg administered to the subject a total of two times. In some embodiments, the effective amount is a dose of 1 μg-10 μg, 1 μg-20 μg, 1 μg-30 μg, 5 μg-10 μg, 5 μg-20 μg, 5 μg-30 μg, 5 μg-40 μg, 5 μg-50 μg, 10 μg-15 μg, 10 μg-20 μg, 10 μg-25 μg, 10 μg-30 μg, 10 μg-40 μg, 10 μg-50 μg, 10 μg-60 μg, 15 μg-20 μg, 15 μg-25 μg, 15 μg-30 μg, 15 μg-40 μg, 15 μg-50 μg, 20 μg-25 μg, 20 μg-30 μg, 20 μg-40 μg 20 μg-50 μg, 20 μg-60 μg, 20 μg-70 μg, 20 μg-75 μg, 30 μg-35 μg, 30 μg-40 μg, 30 μg-45 μg 30 μg-50 μg, 30 μg-60 μg, 30 μg-70 μg, 30 μg-75 μg which may be administered to the subject a total of one or two times or more.

In some aspects, the disclosure provides a composition (e.g., a vaccine) comprising an mRNA encoding a KRAS activating oncogene mutation peptide and an mRNA encoding a constitutively active human STING polypeptide wherein the mRNA encoding the KRAS activating oncogene mutation peptide and the mRNA encoding the constitutively active human STING polypeptide are present at a KRAS:STING mass ratio of 1:1, 2:1, 3:1, 4:1, 5:1, 6:1, 7:1, 8:1, 9:1, 10:1 or 20:1, or alternatively at a STING:KRAS mass ratio of 1:1, 1:2, 1:3, 1:4, 1:5, 1:6, 1:7, 1:8, 1:9, 1:10 or 1:20. In some aspects, the mRNAs are present at a mass ratio of 5:1 of mRNA encoding the KRAS activating oncogene mutation peptide to the mRNA encoding the constitutively active human STING polypeptide (KRAS:STING mass ratio of 5:1 or alternatively a STING:KRAS mass ratio of 1:5). In some aspects, the mRNAs are present at a mass ratio of 10:1 of mRNA encoding the KRAS activating oncogene mutation peptide to the mRNA encoding the constitutively active human STING polypeptide (KRAS:STING mass ratio of 10:1 or alternatively a STING:KRAS ratio of 1:10).

Other aspects of the disclosure relate to a lipid nanoparticle comprising:

an mRNA comprising an open reading frame encoding a concatemer of 4 KRAS activating oncogene mutation peptides, wherein the 4 KRAS activating oncogene mutation peptides comprise G12D, G12V, G12C, and G13D;

an mRNA comprising an open reading frame encoding a constitutively active human STING polypeptide;

wherein the mRNAs are present at a KRAS:STING mass ratio selected from the group consisting of of 1:1, 2:1, 3:1, 4:1, 5:1, 6:1, 7:1, 8:1, 9:1 or 10:1.

In some aspects, the disclosure relates to a lipid nanoparticle comprising:

a first mRNAs comprising an open reading frame encoding a KRAS activating oncogene mutation peptide comprising G12D;

a second mRNA comprising an open reading frame encoding a KRAS activating oncogene mutation peptide comprising G12V;

a third mRNA comprising an open reading frame encoding a KRAS activating oncogene mutation peptide comprising G12C;

a fourth mRNA comprising an open reading frame encoding a KRAS activating oncogene mutation peptide comprising G13D;

a fifth mRNA comprising an open reading frame encoding a constitutively active human STING polypeptide;

wherein the first, second, third, fourth and fifth mRNAs are present at an KRAS:STING mass ratio selected from the group consisting of of 1:1, 2:1, 3:1, 4:1, 5:1, 6:1, 7:1, 8:1, 9:1 or 10:1.

In some of the foregoing and related aspects, the concatemer comprises from N- to C-terminus G12D, G12V, G13D, and G12C. In some aspects, the concatemer comprises from N- to C-terminus G12C, G13D, G12V, and G12D. In some aspects, each KRAS activating oncogene mutation peptide comprises 20, 21, 22, 23, 24, or 25 amino acids in length. In some aspects, each KRAS activating oncogene mutation peptide comprises 25 amino acids in length. In some aspects, the concatemer comprises an amino acid sequence set forth in SEQ ID NO: 137. In some aspects, the mRNA encoding the concatemer of 4 KRAS activating oncogene mutation peptides comprises the nucleotide sequence set forth in SEQ ID NO: 138, SEQ ID NO: 167 or SEQ ID NO: 169. In some aspects, the constitutively active human STING polypeptide comprises mutation V155M. In some aspects, the constitutively active human STING polypeptide comprises the amino acid sequence shown in SEQ ID NO: 1. In some aspects, the mRNA encoding the constitutively active human STING polypeptide comprises a 3' UTR comprising at least one miR-122 microRNA binding site. In some aspects, the mRNA encoding the constitutively active human STING polypeptide comprises the nucleotide sequence shown in SEQ ID NO: 139, SEQ ID NO: 168, or SEQ ID NO: 170.

In some of the foregoing and related aspects, the lipid nanoparticle comprises mRNAs present at an KRAS:STING mass ratio of 1:1. In some aspects, the mRNAs are present at a KRAS:STING mass ratio of 2:1. In some aspects, the mRNAs are present at a KRAS:STING mass ratio of 3:1. In some aspects, the the mRNAs are present at a KRAS:STING mass ratio of 4:1. In some aspects, the mRNAs are present at a KRAS:STING mass ratio of 5:1. In some aspects, the mRNAs are present at a KRAS:STING mass ratio of 6:1. In some aspects, the mRNAs are present at a KRAS:STING mass ratio of 7:1. In some aspects, the mRNAs are present at a KRAS:STING mass ratio of 8:1. In some aspects, the mRNAs are present at a KRAS:STING mass ratio of 9:1. In some aspects, the mRNAS are present at a KRAS:STING mass ratio of 10:1.

In another aspect, the disclosure pertains to a lipid nanoparticle comprising a modified mRNA of the disclosure. In one embodiment, the lipid nanoparticle is a liposome. In another embodiment, the lipid nanoparticle comprises a cationic and/or ionizable amino lipid. In one embodiment, the cationic and/or ionizable amino lipid is 2,2-dilinoleyl-4-methylaminoethyl-[1,3]-dioxolane (DLin-KC2-DMA) or dilinoleyl-methyl-4-dimethylaminobutyrate (DLin-MC3-DMA). In some aspects, the ionizable amino lipid comprises a compound of any of Formulae (I), (IA), (II), (IIa), (IIb), (IIc), (IId), and (IIe). In some aspects, the ionizable amino lipid comprises a compound of Formula (I). In one embodiment, the ionizable amino lipid is Compound 25. In one embodiment, the lipid nanoparticle further comprises a targeting moiety conjugated to the outer surface of the lipid nanoparticle.

In another aspect, the disclosure pertains to a pharmaceutical composition comprising a modified mRNA of the disclosure or a lipid nanoparticle of the disclosure, and a pharmaceutically acceptable carrier, diluent or excipient.

In another aspect, the disclosure pertains to a method for enhancing an immune response to an antigen(s) of interest, the method comprising administering to a subject in need thereof a mRNA composition of disclosure encoding an antigen(s) of interest and a polypeptide that enhances an immune response to the antigen(s) of interest, or lipid nanoparticle thereof, or pharmaceutical composition thereof, such that an immune response to the antigen of interest is enhanced in the subject. In one aspect, enhancing an immune response in a subject comprises stimulating cytokine production (e.g., IFN-γ or TNF-α). In another aspect, enhancing an immune response in a subject comprises stimulating antigen-specific $CD8^+$ T cell activity, e.g., priming, proliferation and/or survival (e.g., increasing the effector/memory T cell population). In one aspect, enhancing an immune response in a subject comprises stimulating antigen-specific $CD4^+$ T cell activity (e.g., increasing helper T cell activity). In other aspects, enhancing an immune response in a subject comprises stimulating B cell responses (e.g., increasing antibody production).

In one aspect, the disclosure provides methods for enhancing an immune response to an activating oncogene mutation peptide, wherein the subject is administered two different immune potentiator mRNA (e.g., mmRNA) constructs (wherein one or both constructs also encode, or are administered with an mRNA (e.g., mmRNA) construct that encodes, the activating oncogene mutation peptide), either at the same time or sequentially. In one aspect, the subject is administered an immune potentiator mmRNA composition that stimulates dendritic cell development or activity prior to administering to the subject an immune potentiator mRNA composition that stimulates Type I interferon pathway signaling.

In other aspects, the disclosure provides methods of stimulating an immune response to a tumor in a subject in need thereof, wherein the method comprises administering to the subject an effective amount of a composition comprising at least one mRNA construct encoding a tumor antigen(s) and an mRNA construct encoding a polypeptide that enhances an immune response to the tumor antigen(s), or a lipid nanoparticle thereof, or a pharmaceutical composition thereof, such that an immune response to the tumor is stimulated in the subject. In one aspect, the tumor is a liver cancer, a colorectal cancer, a pancreatic cancer, a non-small cell lung cancer (NSCLC), a melanoma cancer, a cervical cancer or a head or neck cancer.

In another aspect, the disclosure provides a composition comprising:

(i) a first mRNA comprising an open reading frame encoding a concatemer of 4 KRAS activating oncogene mutation peptides, wherein the concatemer comprises from N- to C-terminus G12D, G12V, G13D, and G12C, and (ii) a second mRNA comprising an open reading frame encoding a constitutively active human STING polypeptide, wherein the constitutively active human STING polypeptide comprises mutation V155M, wherein the first mRNA and second mRNA are present at a KRAS:STING mass ratio selected from the group consisting of 1:1, 2:1, 3:1, 4:1, 5:1, 6:1, 7:1, 8:1, 9:1 or 10:1;

and a pharmaceutically acceptable carrier.

In some aspects of the foregoing composition, the concatemer of 4 KRAS activating oncogene mutation peptides comprises the amino acid sequence set forth in SEQ ID NO: 137. In some aspects, the first mRNA encoding the concatemer of 4 KRAS activating oncogene mutation peptides comprises the nucleotide sequence set forth in SEQ ID NO: 169. In some aspects, the constitutively active human STING polypeptide comprises the amino acid sequence shown in SEQ ID NO: 1. In some aspects, the mRNA encoding the constitutively active human STING polypeptide comprises the nucleotide sequence shown in SEQ ID NO: 170. In some aspects, the first mRNA comprises a 5' UTR comprising the nucleotide sequence set forth in SEQ ID NO: 176. In some aspects, the second mRNA comprises a 5' UTR comprising the nucleotide sequence set forth in SEQ ID NO: 176. In some aspects, the second mRNA encoding the constitutively active human STING polypeptide comprises a 3' UTR having a miR-122 microRNA binding site. In some aspects, the miR-122 microRNA binding site comprises the nucleotide sequence shown in SEQ ID NO: 175. In some aspects, the first mRNA and second mRNA each comprise a poly A tail. In some aspects, the poly A tail comprises about 100 nucleotides. In some aspects, the first and second mRNAs each comprise a 5' Cap 1 structure. In some aspects, the first and second mRNAs each comprise at least one chemical modification. In some aspects, the chemical modification is N1-methylpseudouridine. In some aspects, the first mRNA is fully modified with N1-methylpseudouridine. In some aspects, the second mRNA is fully modified with N1-methylpseudouridine. In some aspects, the pharmaceutically acceptable carrier comprises a buffer solution.

In another aspect, the disclosure provides a composition comprising:

(i) a first mRNA comprising the nucleotide sequence set forth in SEQ ID NO: 167, and (ii) a second mRNA comprising the nucleotide sequence set forth in SEQ ID NO: 168, wherein the first and second mRNA are each fully modified with N1-methylpseudouridine, and wherein the first mRNA and second mRNA are present at a KRAS:STING mass ratio selected from the group consisting of 1:1, 2:1, 3:1, 4:1, 5:1, 6:1, 7:1, 8:1, 9:1 or 10:1;

and a pharmaceutically acceptable carrier.

In one aspect of the foregoing composition, the pharmaceutically acceptable carrier comprises a buffer solution.

In any of the foregoing or related aspects, the disclosure provides a composition wherein the first and second mRNAs are present at a KRAS:STING mass ratio of 1:1.

In any of the foregoing or related aspects, the disclosure provides a composition wherein the first and second mRNAs are present at a KRAS:STING mass ratio of 2:1.

In any of the foregoing or related aspects, the disclosure provides a composition wherein the first and second mRNAs are present at a KRAS:STING mass ratio of 3:1.

In any of the foregoing or related aspects, the disclosure provides a composition wherein the first and second mRNAs are present at a KRAS:STING mass ratio of 4:1.

In any of the foregoing or related aspects, the disclosure provides a composition wherein the first and second mRNAs are present at a KRAS:STING mass ratio of 5:1.

In any of the foregoing or related aspects, the disclosure provides a composition wherein the first and second mRNAs are present KRAS:STING mass ratio of 6:1.

In any of the foregoing or related aspects, the disclosure provides a composition wherein the first and second mRNAs are present at a KRAS:STING mass ratio of 7:1.

In any of the foregoing or related aspects, the disclosure provides a composition wherein the first and second mRNAs are present at a KRAS:STING mass ratio of 8:1.

In any of the foregoing or related aspects, the disclosure provides a composition wherein the first and second mRNAs are present at a KRAS:STING mass ratio of 9:1.

In any of the foregoing or related aspects, the disclosure provides a composition wherein the first and second mRNAs are present at a KRAS:STING mass ratio of 10:1.

In any of the foregoing or related aspects, the disclosure provides a composition which is formulated in a lipid nanoparticle. In some aspects, the lipid nanoparticle comprises a molar ratio of about 20-60% ionizable amino lipid:5-25% phospholipid:25-55% sterol; and 0.5-15% PEG-modified lipid. In some aspects, the lipid nanoparticle comprises a molar ratio of about 50% Compound 25:about 10% DSPC:about 38.5% cholesterol; and about 1.5% PEG-DMG.

In any of the foregoing or related aspects, the disclosure provides a composition which is formulated for intramuscular delivery.

In some aspects, the disclosure provides a lipid nanoparticle comprising:

(i) a first mRNA comprising an open reading frame encoding a concatemer of 4 KRAS activating oncogene mutation peptides, wherein the concatemer comprises from N- to C-terminus G12D, G12V, G13D, and G12C; and (ii) a second mRNA comprising an open reading frame encoding a constitutively active human STING polypeptide, wherein the constitutively active human STING polypeptide comprises mutation V155M, wherein the first mRNA and second mRNA are present at a KRAS:STING mass ratio of 5:1.

In some aspects of the foregoing lipid nanoparticle, the concatemer of 4 KRAS activating oncogene mutation peptides comprises the amino acid sequence set forth in SEQ ID NO: 137. In some aspects, the first mRNA encoding the concatemer of 4 KRAS activating oncogene mutation peptides comprises the nucleotide sequence set forth in SEQ ID NO: 169. In some aspects, the constitutively active human STING polypeptide comprises the amino acid sequence shown in SEQ ID NO: 1. In some aspects, the mRNA encoding the constitutively active human STING polypeptide comprises the nucleotide sequence shown in SEQ ID NO: 170. In some aspects, the first mRNA comprises a 5' UTR comprising the nucleotide sequence shown in SEQ ID NO: 176. In some aspects, the second mRNA comprises a 5' UTR comprising the nucleotide sequence shown in SEQ ID NO: 176. In some aspects, the second mRNA encoding the constitutively active human STING polypeptide comprises a 3' UTR having a miR-122 microRNA binding site. In some aspects, the miR-122 microRNA binding site comprises the nucleotide sequence shown in SEQ ID NO: 175. In some aspects, the first and second mRNAs each comprise a poly A tail. In some aspects, the poly A tail comprises about 100 nucleotides. In some aspects, the first and second mRNAs each comprise a 5' Cap 1 structure. In some aspects, the first and second mRNAs each comprise at least one chemical modification. In some aspects, the chemical modification is N1-methylpseudouridine. In some aspects, the first mRNA is fully modified with N1-methylpseudouridine. In some aspects, the second mRNA is fully modified with N1-methylpseudouridine.

In some aspects, the disclosure provides a lipid nanoparticle comprising:

(i) a first mRNA comprising the nucleotide sequence set forth in SEQ ID NO: 167; and (ii) a second mRNA comprising the nucleotide sequence set forth in SEQ ID NO: 168, wherein the first and second mRNA are each fully modified with N1-methylpseudouridine, and wherein the first mRNA and second mRNA are present at a KRAS:STING mass ratio of 5:1.

In some aspects of the foregoing lipid nanoparticle, the lipid nanoparticle comprises a molar ratio of about 20-60% ionizable amino lipid:5-25% phospholipid:25-55% sterol; and 0.5-15% PEG-modified lipid. In some aspects, the ionizable amino lipid comprises a compound of any of Formulae (I), (IA), (II), (IIa), (IIb), (IIc), (IId), and (IIe). In some aspects, the ionizable amino lipid comprises a compound of Formula (I). In some aspects, the compound of Formula (I) is Compound 25. In some aspects, the lipid nanoparticle comprises a molar ratio of about 50% Compound 25:about 10% DSPC:about 38.5% cholesterol; and about 1.5% PEG-DMG.

In any of the foregoing or related aspects, the disclosure provides pharmaceutical composition comprising the lipid nanoparticle, and a pharmaceutically acceptable carrier. In some aspects, the pharmaceutical composition is formulated for intramuscular delivery.

In any of the foregoing or related aspects, the disclosure provides a lipid nanoparticle, and an optional pharmaceutically acceptable carrier, or a pharmaceutical composition for use in treating or delaying progression of cancer in an individual, wherein the treatment comprises administration of the composition in combination with a second composition, wherein the second composition comprises a checkpoint inhibitor polypeptide and an optional pharmaceutically acceptable carrier.

In any of the foregoing or related aspects, the disclosure provides use of a lipid nanoparticle, and an optional pharmaceutically acceptable carrier, in the manufacture of a medicament for treating or delaying progression of cancer in an individual, wherein the medicament comprises the lipid nanoparticle and an optional pharmaceutically acceptable carrier and wherein the treatment comprises administration of the medicament in combination with a composition comprising a checkpoint inhibitor polypeptide and an optional pharmaceutically acceptable carrier.

In any of the foregoing or related aspects, the disclosure provides a kit comprising a container comprising a lipid nanoparticle, and an optional pharmaceutically acceptable carrier, or a pharmaceutical composition, and a package insert comprising instructions for administration of the lipid nanoparticle or pharmaceutical composition for treating or delaying progression of cancer in an individual. In some aspects, the package insert further comprises instructions for administration of the lipid nanoparticle or pharmaceutical composition in combination with a composition comprising a checkpoint inhibitor polypeptide and an optional pharmaceutically acceptable carrier for treating or delaying progression of cancer in an individual.

In any of the foregoing or related aspects, the disclosure provides a kit comprising a medicament comprising a lipid nanoparticle, and an optional pharmaceutically acceptable carrier, or a pharmaceutical composition, and a package insert comprising instructions for administration of the medicament alone or in combination with a composition comprising a checkpoint inhibitor polypeptide and an optional pharmaceutically acceptable carrier for treating or delaying progression of cancer in an individual. In some aspects, the kit further comprises a package insert comprising instructions for administration of the first medicament prior to, current with, or subsequent to administration of the second medicament for treating or delaying progression of cancer in an individual.

In any of the foregoing or related aspects, the disclosure provides a lipid nanoparticle, a composition, or the use thereof, or a kit comprising a lipid nanoparticle or a composition as described herein, wherein the checkpoint inhibitor polypeptide inhibits PD1, PD-L1, CTLA4, or a combination thereof. In some aspects, the checkpoint inhibitor polypeptide is an antibody. In some aspects, the checkpoint inhibitor polypeptide is an antibody selected from an anti-CTLA4 antibody or antigen-binding fragment thereof that specifically binds CTLA4, an anti-PD1 antibody or antigen-binding fragment thereof that specifically binds PD1, an anti-PD-L1 antibody or antigen-binding fragment thereof that specifically binds PD-L1, and a combination thereof. In some aspects, the checkpoint inhibitor polypeptide is an anti-PD-L1 antibody selected from atezolizumab, avelumab, or durvalumab. In some aspects, the checkpoint inhibitor polypeptide is an anti-CTLA-4 antibody selected from tremelimumab or ipilimumab. In some aspects, the checkpoint inhibitor polypeptide is an anti-PD1 antibody selected from nivolumab or pembrolizumab. In some aspects, the checkpoint inhibitor polypeptide is an anti-PD1 antibody, wherein the anti-PD1 antibody is pembrolizumab.

In related aspects, the disclosure provides a method of reducing or decreasing a size of a tumor or inhibiting a tumor growth in a subject in need thereof comprising administering to the subject any of the foregoing or related lipid nanoparticles of the disclosure, or any of the foregoing or related compositions of the disclosure.

In related aspects, the disclosure provides a method inducing an anti-tumor response in a subject with cancer comprising administering to the subject any of the foregoing or related lipid nanoparticles of the disclosure, or any of the foregoing or related compositions of the disclosure. In some aspects, the anti-tumor response comprises a T-cell response. In some aspects, the T-cell response comprises CD8+ T cells.

In some aspects of the foregoing methods, the composition is administered by intramuscular injection.

In some aspects of the foregoing methods, the method further comprises administering a second composition comprising a checkpoint inhibitor polypeptide, and an optional pharmaceutically acceptable carrier. In some aspects, the checkpoint inhibitor polypeptide inhibits PD1, PD-L1, CTLA4, or a combination thereof. In some aspects, the checkpoint inhibitor polypeptide is an antibody. In some aspects, the checkpoint inhibitor polypeptide is an antibody selected from an anti-CTLA4 antibody or antigen-binding fragment thereof that specifically binds CTLA4, an anti-PD1 antibody or antigen-binding fragment thereof that specifically binds PD1, an anti-PD-L1 antibody or antigen-binding fragment thereof that specifically binds PD-L1, and a combination thereof. In some aspects, the checkpoint inhibitor polypeptide is an anti-PD-L1 antibody selected from atezolizumab, avelumab, or durvalumab. In some aspects, the checkpoint inhibitor polypeptide is an anti-CTLA-4 antibody selected from tremelimumab or ipilimumab. In some aspects, the checkpoint inhibitor polypeptide is an anti-PD1 antibody selected from nivolumab or pembrolizumab. In some asepcts, the checkpoint inhibitor polypeptide is an anti-PD1 antibody, wherein the anti-PD1 antibody is pembrolizumab.

In some aspects of any of the foregoing or related methods, the composition comprising the checkpoint inhibitor polypeptide is administered by intravenous injection. In some aspects, the composition comprising the checkpoint inhibitor polypeptide is administered once every 2 to 3 weeks. In some aspects, the composition comprising the checkpoint inhibitor polypeptide is administered once every 2 weeks or once every 3 weeks. In some aspects, the composition comprising the checkpoint inhibitor polypeptide is administered prior to, concurrent with, or subsequent to administration of the lipid nanoparticle or pharmaceutical composition thereof.

In some aspects of any of the foregoing or related methods, the subject has a histologically confirmed KRAS mutation selected from G12D, G12V, G13D or G12C.

In some aspects of any of the foregoing or related methods, the subject has metastatic colorectal cancer.

In some aspects of any of the foregoing or related methods, the subject has non-small cell lung cancer (NSCLC).

In some aspects of any of the foregoing or related methods, the subject has pancreatic cancer In other aspects, the disclosure provides a method of reducing or decreasing a size of a tumor, inhibiting a tumor growth or inducing an anti-tumor response in a subject in need thereof, comprising administering to the subject an immunomodulatory therapeutic composition comprising: one or more first mRNA each comprising an open reading frame encoding a KRAS activating oncogene mutation peptide, and optionally one or more second mRNA each comprising an open reading frame encoding a constitutively active human STING polypeptide, and optionally wherein the first mRNA and second mRNA are at a mass ratio selected from the group consisting of 1:1, 2:1, 3:1, 4:1, 5:1, 6:1, 7:1, 8:1, 9:1 or 10:1; and a pharmaceutically acceptable carrier, thereby reducing or decreasing a size of a tumor, inhibiting a tumor growth or inducing an anti-tumor response in the subject. In some aspects, the composition comprises 1, 2, 3, or 4 mRNAs encoding 1, 2, 3, or 4 KRAS activating oncogene mutation peptides. In some aspects, the composition comprises 4 mRNAs encoding 4 KRAS activating oncogene mutation peptides. In some aspects, the 4 KRAS activating oncogene mutation peptides comprise G12D, G12V, G12C, and G13D.

In other aspects, the method comprises administering an immunomodulatory therapeutic composition comprising a first, second, third, fourth, and fifth mRNA, wherein the first mRNA comprises an open reading frame encoding a KRAS activating oncogene mutation peptide comprising G12D;

the second mRNA comprises an open reading frame encoding a KRAS activating oncogene mutation peptide comprises G12V;

the third mRNA comprises an open reading frame encoding a KRAS activating oncogene mutation peptide comprising G12C;

the fourth mRNA comprises an open reading frame encoding a KRAS activating oncogene mutation peptide comprising G13D; and the fifth mRNA comprises an open reading frame encoding a constitutively active human STING polypeptide, wherein the first, second, third, fourth and fifth mRNAs are present at a KRAS:STING mass ratio selected from the group consisting of 1:1, 2:1, 3:1, 4:1, 5:1, 6:1, 7:1, 8:1, 9:1 or 10:1.

In some aspects, KRAS activating oncogene mutation peptides comprise the amino acid sequences set forth in SEQ ID NOs: 39-41 and 72. In some aspects, the mRNA encoding the KRAS activating oncogene mutation peptide comprises the nucleotide sequences set forth in SEQ ID NOs: 126-128 and 132.

In other aspects, the method comprises administering an immunomodulatory therapeutic composition comprising an mRNA comprising an open reading frame encoding a concatemer of two or more KRAS activating oncogene mutation peptides. In some aspects, the concatemer comprises G12D, G12V, G12C, and G13D. In some aspects, the concatemer comprises from N- to C-terminus G12D, G12V, G13D, and G12C. In some aspects, the concatemer comprises from N- to C-terminus G12C, G13D, G12V, and G12D. In some aspects, the concatemer comprises an amino acid sequence selected from the group set forth in SEQ ID NOs: 42-47, 73 and 137. In some aspects, the mRNA encoding the concatemer comprises the nucleotide sequence selected from the group set forth in SEQ ID NOs: 129-131, 133 and 138.

In some aspects, the disclosure provides a method of reducing or decreasing a size of a tumor, inhibiting a tumor growth or inducing an anti-tumor response in a subject in need thereof, comprising administering to the subject a lipid nanoparticle comprising:

(i) one or more first mRNAs selected from the group consisting of:
   (a) an mRNA comprising an open reading frame encoding a KRAS activating oncogene mutation peptide comprising G12D;
   (b) an mRNA comprising an open reading frame encoding a KRAS activating oncogene mutation peptide comprising G12V;
   (c) an mRNA comprising an open reading frame encoding a KRAS activating oncogene mutation peptide comprising G12C;
   (d) an mRNA comprising an open reading frame encoding a KRAS activating oncogene mutation peptide comprising G13D;
   (e) an mRNA comprising an open reading frame encoding a concatemer of 2, 3, or 4 KRAS activating oncogene mutation peptides, wherein the KRAS activating oncogene mutation peptides comprise G12D, G12V, G12C, and G13D; and
   (f) any combination of mRNAs set forth in (a)-(d); and
(ii) one or more second mRNAs each comprising an open reading frame encoding a constitutively active human STING polypeptide, optionally wherein the first mRNA and second mRNA are present at a KRAS:STING mass ratio selected from the group consisting of 1:1, 2:1, 3:1, 4:1, 5:1, 6:1, 7:1, 8:1, 9:1 or 10:1, thereby reducing or decreasing a size of a tumor, inhibiting a tumor growth or inducing an anti-tumor response in the subject.

In some aspects, the lipid nanoparticle comprises (i) a combination of mRNAs set forth in (a)-(d); and (ii) a second mRNA comprising an open reading frame encoding a constitutively active human STING polypeptide, wherein the constitutively active human STING polypeptide comprises mutation V155M, wherein the first mRNA and second mRNA are present at a KRAS:STING mass ratio selected from the group consisting of 1:1, 2:1, 3:1, 4:1, 5:1, 6:1, 7:1, 8:1, 9:1 or 10:1.

In some aspects, the lipid nanoparticle comprises (i) a first mRNA comprises an open reading frame encoding a concatemer of 4 KRAS activating oncogene mutation peptides, wherein the concatemer comprises from N- to C-terminus G12D, G12V, G13D, and G12C; and (ii) a second mRNA comprising an open reading frame encoding a constitutively active human STING polypeptide, wherein the constitutively active human STING polypeptide comprises mutation V155M, wherein the first mRNA and second mRNA are present at a KRAS:STING mass ratio selected from the group consisting of 1:1, 2:1, 3:1, 4:1, 5:1, 6:1, 7:1, 8:1, 9:1 or 10:1.

In some aspects, the disclosure provides a method of reducing or decreasing a size of a tumor, inhibiting a tumor growth or inducing an anti-tumor response in a subject in need thereof, comprising administering to the subject a lipid nanoparticle comprising:

(i) a first mRNA comprising the nucleotide sequence set forth in SEQ ID NO: 167; and (ii) a second mRNA comprising the nucleotide sequence set forth in SEQ ID NO: 168, wherein the first and second mRNA are each fully modified with N1-methylpseudouridine, and wherein the first mRNA and second mRNA are present at a mass ratio of 5:1. In some aspects, the lipid nanoparticle comprises a molar ratio of about 50% Compound 25:about 10% DSPC:about 38.5% cholesterol; and about 1.5% PEG-DMG.

In some aspects, the lipid nanoparticle or composition is administered by intramuscular injection.

In some aspects, the anti-tumor response comprises a T-cell response, such as a CD8+ T cell response.

In some aspects, the disclosure provides a method of reducing or decreasing a size of a tumor, inhibiting a tumor growth or inducing an anti-tumor response in a subject in need thereof, comprising administering to the subject an immunomodulatory therapeutic composition or lipid nanoparticle of the disclosure in combination with (prior to, concurrent with or consecutively) a second composition comprising a checkpoint inhibitor polypeptide or polynucleotide encoding the same, and an optional pharmaceutically acceptable carrier. In some aspects, the checkpoint inhibitor polypeptide inhibits PD1, PD-L1, CTLA4, or a combination thereof. In some aspects, the checkpoint inhibitor polypeptide is an antibody. In some aspects, the checkpoint inhibitor polypeptide is an antibody selected from an anti-CTLA4 antibody or antigen-binding fragment thereof that specifically binds CTLA4, an anti-PD1 antibody or antigen-binding fragment thereof that specifically binds PD1, an anti-PD-L1 antibody or antigen-binding fragment thereof that specifically binds PD-L1, and a combination thereof. In some aspects, the checkpoint inhibitor polypeptide is an anti-PD-L1 antibody selected from atezolizumab, avelumab, or durvalumab. In some aspects, the checkpoint inhibitor polypeptide is an anti-CTLA-4 antibody selected from tremelimumab or ipilimumab. In some aspects, the checkpoint inhibitor polypeptide is an anti-PD1 antibody selected from nivolumab or pembrolizumab.

In some aspects, the composition comprising the checkpoint inhibitor polypeptide is administered by intravenous injection. In some aspects, the composition comprising the checkpoint inhibitor polypeptide is administered once every 2 to 3 weeks. In some aspects, the composition comprising the checkpoint inhibitor polypeptide is administered once every 2 weeks or once every 3 weeks. In some aspects, the composition comprising the checkpoint inhibitor polypeptide is administered prior to, concurrent with, or subsequent to administration of the lipid nanoparticle or composition.

In some aspects, the disclosure provides methods for treating subjects having a histologically confirmed KRAS mutation selected from G12D, G12V, G13D or G12C. In some aspects, the subject has a histologically confirmed HLA subtype selected from HLA-A11 and/or HLA-C*08.

In some aspects, wherein the tumor is metastatic colorectal cancer. In some aspects, the tumor is non-small cell lung cancer (NSCLC). In some aspects, the tumor is pancreatic cancer.

In some aspects, the subject is administered a chemotherapeutic agent prior to, concurrent with, or subsequent to administration of the lipid nanoparticle or composition.

BRIEF DESCRIPTION OF THE DRAWINGS

FIG. 11A shows E7-specific responses for IFN-γ ICS. FIG. 11B shows E7-specific responses for TNF-α ICS.

FIG. 12A shows E6-specific responses for IFN-γ ICS. FIG. 12B shows E6-specific responses for TNF-α ICS.

FIG. 16A (d21) and 16B (d53) show increased % of CD8 with effector memory 'CD62Llo phenotype. FIGS. 16C and 16D show increased % of E7-tetramer$^+$ CD8 are CD62Llo.

FIGS. 18D-18I show control treatments.

FIG. 21A shows responses to the Adpk1 peptide within the ADR composition. FIG. 21B shows the response to the Reps1 peptide within the ADR composition. FIG. 21C shows the response to the Dpagt1 peptide within the ADR composition.

FIG. 23A shows intracellular staining (ICS) of CD8+ splenocytes for IFN-γ from mice immunized at the indicated Ag:STING ratios on day 21 post immunization. FIG. 23B shows H2-Kb/E7 peptide-tetramer staining of day 21 CD8+ splenocytes from mice immunized at the indicated Ag:STING ratios.

DETAILED DESCRIPTION

Figure 1:
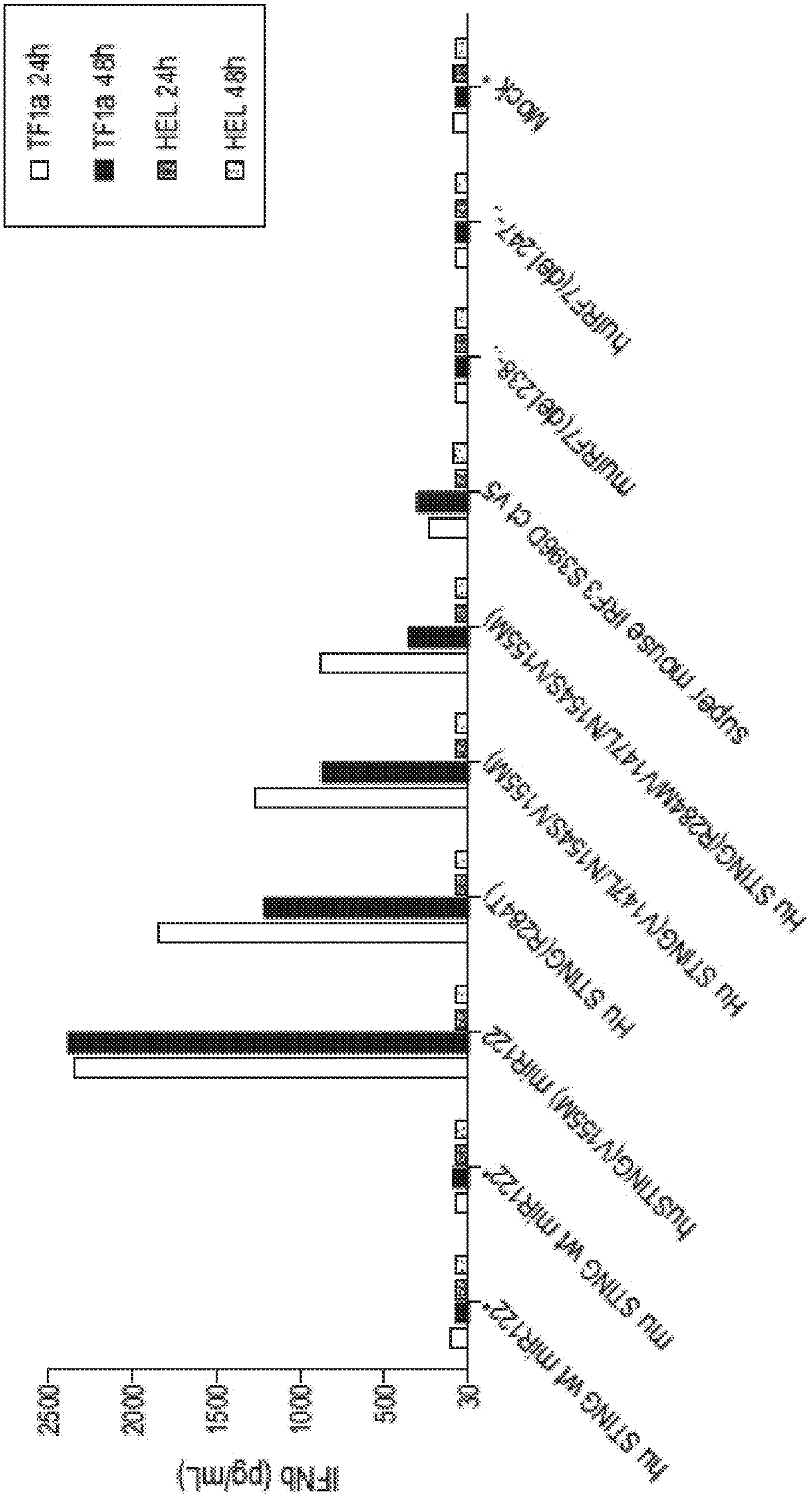
FIG. 1 is a bar graph showing stimulation of IFN-β production in TF1a cells transfected with constitutively active STING mmRNA constructs.

Provided herein are immunomodulatory therapeutic compositions, including mRNA compositions and/or lipid nanoparticles comprising the same, comprising one or more RNAs (e.g., messenger RNAs (mRNAs)) that can safely direct the body's cellular machinery to produce a cancer protein or fragment thereof of interest, e.g., an activating oncogene mutation peptide. In some embodiments, the RNA is a modified RNA. The immunomodulatory therapeutic compositions and lipid nanoparticles of the present disclosure may be used to induce a balanced immune response against cancers, comprising both cellular and humoral immunity, without risking the possibility of insertional mutagenesis, for example.

Accordingly, in some aspects, the disclosure provides an immunomodulatory therapeutic composition, including a lipid-based composition such as a lipid nanoparticles, comprising: one or more mRNA each having an open reading frame encoding an activating oncogene mutation peptide, and optionally one or more mRNA each having an open reading frame encoding a polypeptide that enhances an immune response to the activating oncogene mutation peptide in a subject, wherein the immune response comprises a cellular or humoral immune.

In one aspect, the disclosure provides an immunomodulatory therapeutic composition comprising four different activating oncogene mutation peptides (e.g., KRAS G12D, G12C, G12V and G13D), which is capable of treating patients having any one of colorectal cancer, pancreactic carcinoma, and non-small cell lung carcinoma. The ability to target to four different mutations and three different cancers is a significant advantage of the compositions and methods provided herein.

An mRNA encoding a polypeptide that enhances an immune response to the activating oncogene mutation peptide in a subject is also referred to herein as "an immune potentiator mRNA" or "mRNA encoding an immune potentiator" or simply "immune potentiator." An enhanced immune response can be a cellular response, a humoral response or both. As used herein, a "cellular" immune response is intended to encompass immune responses that involve or are mediated by T cells, whereas a "humoral" immune response is intended to encompass immune responses that involve or are mediated by B cells. An mRNA encoding an immune potentiator may enhance an immune response by, for example, (i) stimulating Type I interferon pathway signaling;
(ii) stimulating NFkB pathway signaling;
(iii) stimulating an inflammatory response;
(iv) stimulating cytokine production; or
(v) stimulating dendritic cell development, activity or mobilization; and
(vi) a combination of any of (i)-(v).

As used herein, "stimulating Type I interferon pathway signaling" is intended to encompass activating one or more components of the Type I interferon signaling pathway (e.g., modifying phosphorylation, dimerization or the like of such components to thereby activate the pathway), stimulating transcription from an interferon-sensitive response element (ISRE) and/or stimulating production or secretion of Type I interferon (e.g., IFN-$\alpha$, IFN-$\beta$, IFN-$\varepsilon$, IFN-$\kappa$ and/or IFN-$\omega$). As used herein, "stimulating NFkB pathway signaling" is intended to encompass activating one or more components of the NFkB signaling pathway (e.g., modifying phosphorylation, dimerization or the like of such components to thereby activate the pathway), stimulating transcription from an NFkB site and/or stimulating production of a gene product whose expression is regulated by NFkB. As used herein, "stimulating an inflammatory response" is intended to encompass stimulating the production of inflammatory cytokines (including but not limited to Type I interferons, IL-6 and/or TNF$\alpha$). As used herein, "stimulating dendritic cell development, activity or mobilization" is intended to encompass directly or indirectly stimulating dendritic cell maturation, proliferation and/or functional activity.

The present disclosure provides compositions, including mRNA compositions and/or lipid nanoparticles comprising the same, which include one or more mRNA constructs encoding a polypeptide that enhances immune responses to an activating oncogene mutation peptide (also referred to herein as "an antigen of interest"), referred to herein as immune potentiator mRNA or immune potentiator mRNAs, including chemically modified mRNAs (mmRNAs). The immune potentiator mRNAs of the disclosure enhance immune responses by, for example, activating Type I interferon pathway signaling such that antigen-specific responses to an antigen of interest (i.e., activating oncogene mutation peptide(s)) are stimulated.

The immune potentiator mRNAs of the disclosure enhance immune responses to an exogenous antigen that is administered to the subject with the immune potentiator mRNA (e.g., an mRNA construct encoding activating oncogene mutation peptide(s) that is coformulated and coadministered with the immune potentiator mRNA or an mRNA construct encoding activating oncogene mutation peptide(s) that is formulated and administered separately from the immune potentiator mRNA). Administration of an immune potentiator mRNA enhances an immune response in a subject by stimulating, for example, cytokine production, T cells responses (e.g., antigen-specific $CD8^+$ or $CD4^+$ T cell responses) or B cell responses (e.g., antigen-specific antibody production) in the subject.

In other aspects, the disclosure provides compositions, including mRNA compositions and lipid nanoparticles, comprising one or more mRNA constructs (e.g., one or more mmRNA constructs), wherein the one or more mRNA constructs encode an activating oncogene mutation peptide(s) and, in the same or a separate mRNA construct, encode a polypeptide that enhances an immune response to the antigen of interest. In some aspects, the disclosure provides nanoparticles, e.g., lipid nanoparticles, which include an immune potentiator mRNA that enhances an immune response, alone or in combination with mRNAs that encode activating oncogene mutation peptide(s). The disclosure also provides pharmaceutical compositions comprising any of the mRNAs as described herein or nanoparticles, e.g., lipid nanoparticles comprising any of the mRNAs as described herein.

In other aspects, the disclosure provides methods for enhancing an immune response to an activating oncogene mutation peptide(s) by administering to a subject one or more mRNAs encoding activating oncogene mutation peptide(s) and a mRNA encoding a polypeptide that enhances an immune response to the peptide(s) of interest, or lipid nanoparticle thereof, or pharmaceutical composition therof, such that an immune response to the activating oncogene mutation peptide(s) is enhanced in the subject. The methods of enhancing an immune response can be used, for example, to stimulate an immunogenic response to a tumor in a subject.

Cancer Antigens of Interest

The immune potentiators mRNAs of the disclosure are useful in combination with any type of antigen for which enhancement of an immune response is desired, including with mRNA sequences encoding at least one antigen of interest (on either the same or a separate mRNA construct) to enhance immune responses against the antigen of interest, such as a tumor antigen. Thus, the immune potentiator mRNAs of the disclosure enhance, for example, mRNA vaccine responses, thereby acting as genetic adjuvants.

Activating Oncogene Mutation Peptides

In one embodiment, the antigen(s) of interest is a tumor antigen. In one embodiment, the tumor antigen comprises a tumor neoepitope, e.g., mutant peptide from a tumor antigen. In one embodiment, the tumor antigen is a Ras antigen. A comprehensive survey of Ras mutations in cancer has been described in the art (Prior, I. A. et al. (2012) *Cancer Res.* 72:2457-2467). Accordingly, a Ras amino acid sequence comprising at least one mutation associated with cancer can be used as an antigen of interest. In one embodiment, the tumor antigen is a mutant KRAS antigen. Mutant KRAS antigens have been implicated in acquired resistance to certain therapeutic agents (see e.g., Misale, S. et al. (2012) *Nature* 486:532-536; Diaz, L. A. et al. (2012) *Nature* 486:537-540).

Although attempts have been made to produce functional immunomodulatory therapeutic compositions, including mRNA compositions, the therapeutic efficacy of these RNA compositions has not yet been fully established. Quite surprisingly, the inventors have discovered a class of formulations for delivering mRNA immunomodulatory therapeutic compositions that results in significantly enhanced, and in many respects synergistic, immune responses including enhanced T cell responses. KRAS is the most frequently mutated oncogene in human cancer (~15%). Such KRAS mutations are mostly conserved in a few "hotspots" and activate the oncogene.

The immunomodulatory therapeutic compositions of the invention include activating oncogene mutation peptides, such as KRAS mutation peptides. Prior research has shown limited ability to raise T cells specific to the oncogenic mutation. Much of this research was done in the context of the most common HLA allele (A2, which occurs in ~50% of Caucasians). More recent work has explored the generation of specific T cells against point mutations in the context of less common HLA alleles (A11, C8). These findings have significant implications for the treatment of cancer. Oncogenic mutations are common in many cancers. The ability to target these mutations and generate T cells that are sufficient to kill tumors has broad applicability to cancer therapy. It is quite surprising that delivery of antigens using mRNA would have such a significant advantage over the delivery of peptide vaccines. Thus the invention involves, in some aspects, the surprising finding that activating oncogenic mutation antigens delivered in vivo in the form of an mRNA significantly enhances the generation of T cell effector and memory responses.

HLA class I molecules are highly polymorphic transmembrane glycoproteins composed of two polypeptide chains (heavy chain and light chain). Human leucocyte antigen, the major histocompatibility complex in humans, is specific to each individual and has hereditary features. The class I heavy chains are encoded by three genes: HLA-A, HLA-B and HLA-C. HLA class I molecules are important for establishing an immune response by presenting endogenous antigens to T lymphocytes, which initiates a chain of immune reactions that lead to tumor cell elimination by cytotoxic T cells. Altered levels of production of HLA class I antigens is a widespread phenomenon in malignancies and is accompanied by significant inhibition of anti-tumor T cell function. It represents one of the main mechanisms used by cancer cells to evade immuno-surveillance. Down regulated levels of HLA class I antigens were detected in 90% of NSCLC tumors (n=65). A reduction or loss of HLA was detected in 76% of pancreatic tumor samples (n=19). The expression of HLA class I antigens in colon cancer was dramatically reduced or undetectable in 96% of tumor samples (n=25).

Mounting evidence suggests that two general strategies are utilized by tumor cells to escape immune surveillance: immunoselection (poorly immunogenic tumor cell variants) and immunosubversion (subversion of the immune system). A correlation between changes in HLA class I antigens and the presence of KRAS codon 12 mutations was demonstrated, which suggests a possible inductive effect of KRAS codon 12 mutations on HLA class I antigen regulation in cancer progression. Many frequent cancer mutations are predicted to bind HLA Class I alleles with high-affinity (IC50<=50 nM)7 and may be suitable for prophylactic cancer vaccination.

The generation of cancer antigens that elicit a desired immune response (e.g. T-cell responses) against targeted polypeptide sequences in immunomodulatory therapeutic development remains a challenging task. The invention involves technology to overcome hurdles associated with such development. Through the use of the technology of the invention, it is possible to elicit a desired immune response by selecting appropriate activating oncogene mutation peptides and formulating the mRNA encoding peptides for effective delivery in vivo.

The immunomodulatory therapeutic compositions provide unique therapeutic alternatives to peptide based or DNA vaccines. When the mRNA containing immunomodulatory therapeutic composition is delivered to a cell, the mRNA will be translated into a polypeptide by the intracellular machinery which can then process the polypeptide into sensitive fragments capable of being presented on MDC and stimulating an immune response against the tumor.

The immunomodulatory therapeutic compositions described herein include at least one ribonucleic acid (RNA) polynucleotide having an open reading frame encoding at least one cancer antigenic polypeptide or an immunogenic fragment thereof (e.g., an immunogenic fragment capable of inducing an immune response to cancer). The antigenic peptide includes an activating oncogenic mutation. In some preferred embodiments the composition is multiple epitopes of a mixture of activating oncogenic mutations. Many activating oncogenic mutations are known in the art.

When oncogenes are activated they can inhibit programmed cell death and/or cause abnormal cellular proliferation. Such oncogene activation can lead to cancer. The KRAS gene (Ki-ras2 Kirsten rat sarcoma viral oncogene homolog) is an oncogene that encodes a small GTPase transductor protein. KRAS relays external signals to the cell nucleus and contributes to regulation of cell division. Activating mutations in the KRAS gene impair the ability of the KRAS protein to switch between active and inactive states. KRAS activation leads to cell transformation and increased resistance to chemotherapy and biological therapies targeting epidermal growth factor receptors. (Jancik, Sylwia et al. Clinical Relevance of KRAS in Human Cancers, Journal of Biomedicine and Biotechnology, Volume 2010 Article ID 150960 (2010)). Human KRAS amino acid sequence is provided below (UniProtKB P01116). KRAS mutations are common in many cancers, and G12 is the site of most common KRAS mutations.

```
>sp|P01116|1-186
                                              (SEQ ID NO: 166)
MTEYKLVVVGAGGVGKSALTIQLIQNHFVDEYDPTIEDSYRKQVVIDGET

CLLDILDTAGQEEYSAMRDQYMRTGEGFLCVFAINNTKSFEDIHHYREQI

KRVKDSEDVPMVLVGNKCDLPSRTVDTKQAQDLARSYGIPFIETSAKTRQ

RVEDAFYTLVREIRQYRLKKISKEEKTPGCVKIKKC
```

Mutant N-RAS proteins are highly prevalent in certain types of cancers and are useful as cancer vaccines. For instance, 29% of Cutaneous Melanoma involves a RAS mutation, of which 94% are of N-RAS origin. This represents about 2,500 new US cases/year of the most aggressive form of melanoma accounting for the majority of melanoma deaths. (Channing Der, Are A11 RAS Proteins Created Equal in Cancer?, Sep. 22, 2014, cancer.gov). There are 30,280 news cases of multiple myeloma annually, of which 26% are NRAS*. This represents ~6,100 new NRAS* cases per year. Thus, the N-Ras vaccines described herein are useful in some embodiments in the treatment of melanoma and multiple myeloma as well as other malignancies that harbor NRAS mutations.

Accordingly, in some aspects, the present invention provides mRNA encoding peptide sequences resulting from certain activating mutations in one or more oncogenes, not limited to missense SNVs and often resulting in alternative splicing, for use as targets for therapeutic vaccination. In some embodiments, the activating oncogene mutation is a KRAS mutation. In some embodiments, the KRAS mutation is a G12 mutation. In some embodiments, the G12 KRAS mutation is selected from a G12D, G12V, G12S, G12C, G12A, and a G12R KRAS mutation, e.g., the G12 KRAS mutation is selected from a G12D, G12V, and a G12S KRAS mutation. In some embodiments, the G12 KRAS mutation is selected from a G12D, G12V, and a G12C KRAS mutation. In other embodiments, the KRAS mutation is a G13 mutation, e.g., the G13 KRAS mutation is a G13D KRAS mutation. In some embodiments, the activating oncogene mutation is a H-RAS or N-RAS mutation.

In one embodiment, one or more mRNAs encode a mutant KRAS peptide(s) comprising an amino acid sequence having one or more mutations selected from G12D, G12V, G13D and G12C, and combinations thereof. Non-limiting examples of mutant KRAS antigens include those comprising one or more of the amino acid sequences shown in SEQ ID NOs: 36-41 and 72, 125.

CD8+ T cells specific for the G12D or G12V mutations can be restricted by HLA-A*02:01, A*03:01; -A*11:01, -B*35:01, -Cw*08:02, and potentially others. Accordingly, in some embodiments, a KRAS mutation is selected for inclusion in an immunomodulatory therapeutic composition for a subject having T cells that are restricted by HLA-A*02:01, A*03:01; -A*11:01, -B*35:01, or -Cw*08:02. In some embodiments, the subject has T cells that are HLA-A*02:01 restricted.

In one embodiment, the mutant KRAS antigen is one or more mutant KRAS 15-mer peptides comprising a mutation selected from G12D, G12V, G13D and G12C, non-limiting examples of which are shown in SEQ ID NO: 36-38 and 125.

In another embodiment, the mutant KRAS antigen is one or more mutant KRAS 25-mer peptides comprising a mutation selected from G12D, G12V, G13D and G12C, non-limiting examples of which are shown in SEQ ID NO: 39-41 and 72.

In another embodiment, the mutant KRAS antigen is one or more mutant KRAS 3x15mer peptides (3 copies of the 15-mer peptide) comprising a mutation selected from G12D, G12V, G13D and G12C, non-limiting examples of which are shown in SEQ ID NO: 42-44 and 183.

In another embodiment, the mutant KRAS antigen is one or more mutant KRAS 3x25mer peptides (three copies of the 25-mer peptide) comprising a mutation selected from G12D, G12V, G13D and G12C, non-limiting examples of which are shown in SEQ ID NO: 45-47 and 73.

In another embodiment, the mutant KRAS antigen is a 100-mer concatemer peptide of the 25-mer peptides containing the G12D, G12V, G13D and G12C mutations (i.e., a 100-mer concatemer of SEQ ID NOs: 39, 40, 41 and 72). Accordingly, in one embodiment, the mutant KRAS antigen comprises an mRNA construct encoding SEQ ID NOs: 39, 40, 41 and 72. Non-limiting examples of nucleotide sequences encoding a concatemer of peptides containing G12D, G12V, G13D and G12C mutations include SEQ ID NO: 138, SEQ ID NO: 167 and SEQ ID NO: 169. Further description of mutant KRAS antigens, amino acid sequences thereof, and mRNA sequences encoding therefor, are disclosed in U.S. Application Ser. No. 62/453,465, the entire contents of which is expressly incorporated herein by reference.

Some embodiments of the present disclosure provide immunomodulatory therapeutic compositions that include an mRNA having an open reading frame encoding a concatemer of two or more activating oncogene mutation peptides. In some embodiments, at least two of the peptide epitopes are separated from one another by a single Glycine. In some embodiments, the concatemer comprises 3-10 activating oncogene mutation peptides. In some such embodiments, all of the peptide epitopes are separated from one another by a single Glycine. In other embodiments, at least two of the peptide epitopes are linked directly to one another without a linker.

In one embodiment, a tumor antigen is encoded by an mRNA construct that also comprises an immune potentiator (i.e., also encodes a polypeptide that enhances an immune response against the tumor antigen). Non-limiting examples of such constructs include the KRAS-STING constructs encoding one of the amino acid sequences shown in SEQ ID NOs: 48-71. Non-limiting examples of nucleotide sequences encoding the KRAS-STING constructs are shown in SEQ ID NOs: 160-163 and 221-224.

The disclosure provides an immunomodulatory therapeutic composition, comprising: an mRNA having an open reading frame encoding a concatemer of two or more activating oncogene mutation peptides, wherein the concatemer comprises KRAS activating oncogene mutation peptides G12D, G12V, G12C, and G13D; and one or more mRNA each having an open reading frame encoding a polypeptide that enhances an immune response to the KRAS activating oncogene mutation peptides in a subject, such as a STING immune potentiator mRNA. Such an immunomodulatory composition targets somatic point mutations of KRAS, which constitute not only exquisitely specific tumor neoantigens but also significant oncogenic driver mutations in various malignancies. Unlike many neoantigens, which are largely passenger mutations, maintenance of KRAS mutant expression is important to cancer cells' survival as it helps drive aberrant cell proliferation and is likely to be a truncal event (an early event and therefore present in many tumor cells).

In order to model KRAS mutant antigens in preclinical studies described herein examining the immune potentiating capacity of STING, two model antigens were selected: (1) HPV E6 and E7 and (2) the ADR concatemer of three point mutations from three genes found in the murine cell line MC38. These antigens are appropriate models of the KRAS mutant antigens for a number of reasons. For example, HPV E6 and E7 are viral oncogenic proteins whose expression is vital for the transformed phenotype, like mutant KRAS. Accordingly, HPV E6 and E7 are suitable model antigens because, similar to mutant KRAS, they are oncogenic drivers. The three ADR mutant epitopes, in contrast, are stereotypical neoantigens in that they are most likely passenger mutations. However, ADR more effectively models other properties of KRAS antigens encoded by our vaccine in that: (1) each antigen contains a single missense mutation relative to its wild-type counterpart which is likely to be more challenging to recognize as "non-self" by the immune system than a viral antigen and (2) they are concatemerized.

The immunomodulatory therapeutic compositions of the disclosure may include one or more cancer antigens. In some embodiments the immunomodulatory therapeutic composition is composed of 2 or more, 3 or more, 4 or more, 5 or more 6 or more 7 or more, 8 or more, 9 or more antigens, e.g., activating oncogene mutation peptides. In other embodiments the immunomodulatory therapeutic composition is composed of 1000 or less, 900 or less, 500 or less, 100 or less, 75 or less, 50 or less, 40 or less, 30 or less, 20 or less or 100 or less cancer antigens, e.g., activating oncogene mutation peptides. In yet other embodiments the immunomodulatory therapeutic composition has 3-10, 3-100, 5-100, 10-100, 15-100, 20-100, 25-100, 30-100, 35-100, 40-100, 45-100, 50-100, 55-100, 60-100, 65-100, 70-100, 75-100, 80-100, 90-100, 5-50, 10-50, 15-50, 20-50, 25-50, 30-50, 35-50, 40-50, 45-50, 100-150, 100-200, 100-300, 100-400, 100-500, 50-500, 50-800, 50-1,000, or 100-1,000 cancer antigens, e.g., activating oncogene mutation peptides.

An epitope, also known as an antigenic determinant, as used herein is a portion of an antigen that is recognized by the immune system in the appropriate context, specifically by antibodies, B cells, or T cells. Epitopes include B cell epitopes and T cell epitopes. B-cell epitopes are peptide sequences which are required for recognition by specific antibody producing B-cells. B cell epitopes refer to a specific region of the antigen that is recognized by an antibody. The portion of an antibody that binds to the epitope is called a paratope. An epitope may be a conformational epitope or a linear epitope, based on the structure and interaction with the paratope. A linear, or continuous, epitope is defined by the primary amino acid sequence of a particular region of a protein. The sequences that interact with the antibody are situated next to each other sequentially on the protein, and the epitope can usually be mimicked by a single peptide. Conformational epitopes are epitopes that are defined by the conformational structure of the native protein. These epitopes may be continuous or discontinuous, i.e. components of the epitope can be situated on disparate parts of the protein, which are brought close to each other in the folded native protein structure.

T-cell epitopes are peptide sequences which, in association with proteins on APC, are required for recognition by specific T-cells. T cell epitopes are processed intracellularly and presented on the surface of APCs, where they are bound to MHC molecules including MHC class II and MHC class I. The peptide epitope may be any length that is reasonable for an epitope. In some embodiments the peptide epitope is 9-30 amino acids. In other embodiments the length is 9-22, 9-29, 9-28, 9-27, 9-26, 9-25, 9-24, 9-23, 9-21, 9-20, 9-19, 9-18, 10-22, 10-21, 10-20, 11-22, 22-21, 11-20, 12-22, 12-21, 12-20, 13-22, 13-21, 13-20, 14-19, 15-18, or 16-17 amino acids.

In some embodiments the immunomodulatory therapeutic composition may include a recall antigen, also sometimes referred to as a memory antigen. A recall antigen is an antigen that has previously been encountered by an individual and for which there are pre-existent memory lymphocytes. In some embodiments the recall antigen may be an infectious disease antigen that the individual has likely encountered such as an influenza antigen. The recall antigen helps promote a more robust immune response.

The therapeutic mRNA can be delivered alone or in combination with other cancer therapeutics such as checkpoint inhibitors to provide a significantly enhanced immune response against tumors. The checkpoint inhibitors can enhance the effects of the mRNA encoding activing oncogenic peptides by eliminating some of the obstacles to promoting an immune response, thus allowing the activated T cells to efficiently promote an immune response against the tumor.

The mRNA may be delivered to the subject in the form of carrier such as a lipid nanoparticle (LNP). A number of LNPs are known in the art. For instance some LNPs such as those which have been used previously to deliver siRNA various in animal models as well as in humans have been observed to cause an undesirable inflammatory response associated with a transient IgM response, typically leading to a reduction in antigen production and a compromised immune response. In contrast to the findings observed with siRNA, lipid nanoparticle-mRNA immunomodulatory therapeutic compositions are provided herein that generate T cell responses sufficient for therapeutic methods rather than promoting transient IgM responses. The LNPs described herein are not liposomes. A liposome as used herein is a lipid based structure having a simple lipid bilayer shell with a nucleic acid payload in the core.

An mRNA construct encoding an antigen(s) of interest typically comprises, in addition to the antigen-encoding sequences, other structural properties as described herein for mRNA constructs (e.g., modified nucleobases, 5' cap, 5' UTR, 3' UTR, miR binding site(s), polyA tail, as described herein). Suitable mRNA construct components are as described herein.

Personalized Cancer Antigens—Neoepitopes

The cancer antigens can be personalized cancer antigens. Personalized immunomodulatory therapeutic compositions, for instance, may include RNA encoding for one or more known cancer antigens specific for the tumor or cancer antigens specific for each subject, referred to as neoepitopes or subject specific epitopes or antigens. A "subject specific cancer antigen" is an antigen that has been identified as being expressed in a tumor of a particular patient. The subject specific cancer antigen may or may not be typically present in tumor samples generally. Tumor associated antigens that are not expressed or rarely expressed in non-cancerous cells, or whose expression in non-cancerous cells is sufficiently reduced in comparison to that in cancerous cells and that induce an immune response induced upon vaccination, are referred to as neoepitopes. Neoepitopes, like tumor associated antigens, are completely foreign to the body and thus would not produce an immune response against healthy tissue or be masked by the protective components of the immune system. In some embodiments personalized immunomodulatory therapeutic compositions based on neoepitopes are desirable because such vaccine formulations will maximize specificity against a patient's specific tumor. Mutation-derived neoepitopes can arise from point mutations, non-synonymous mutations leading to different amino acids in the protein; read-through mutations in which a stop codon is modified or deleted, leading to translation of a longer protein with a novel tumor-specific sequence at the C-terminus; splice site mutations that lead to the inclusion of an intron in the mature mRNA and thus a unique tumor-specific protein sequence; chromosomal rearrangements that give rise to a chimeric protein with tumor-specific sequences at the junction of 2 proteins (i.e., gene fusion); frameshift mutations or deletions that lead to a new open reading frame with a novel tumor-specific protein sequence; and translocations. Thus, in some embodiments the immunomodulatory therapeutic compositions include at least 1 cancer antigens including mutations selected from the group consisting of frame-shift mutations and recombinations or any of the other mutations described herein.

Methods for generating personalized immunomodulatory therapeutic compositions generally involve identification of mutations, e.g., using deep nucleic acid or protein sequencing techniques, identification of neoepitopes, e.g., using application of validated peptide-MHC binding prediction algorithms or other analytical techniques to generate a set of candidate T cell epitopes that may bind to patient HLA alleles and are based on mutations present in tumors, optional demonstration of antigen-specific T cells against selected neoepitopes or demonstration that a candidate neoepitope is bound to HLA proteins on the tumor surface and development of the vaccine. The immunomodulatory therapeutic compositions of the invention may include multiple copies of a single neoepitope, multiple different neoepitopes based on a single type of mutation, i.e. point mutation, multiple different neoepitopes based on a variety of mutation types, neoepitopes and other antigens, such as tumor associated antigens or recall antigens.

Examples of techniques for identifying mutations include but are not limited to dynamic allele-specific hybridization (DASH), microplate array diagonal gel electrophoresis (MADGE), pyrosequencing, oligonucleotide-specific ligation, the TaqMan system as well as various DNA "chip"

technologies i.e. Affymetrix SNP chips, and methods based on the generation of small signal molecules by invasive cleavage followed by mass spectrometry or immobilized padlock probes and rolling-circle amplification.

The deep nucleic acid or protein sequencing techniques are known in the art. Any type of sequence analysis method can be used. Nucleic acid sequencing may be performed on whole tumor genomes, tumor exomes (protein-encoding DNA), tumor transcriptomes, or exosomes. Real-time single molecule sequencing-by-synthesis technologies rely on the detection of fluorescent nucleotides as they are incorporated into a nascent strand of DNA that is complementary to the template being sequenced. Other rapid high throughput sequencing methods also exist. Protein sequencing may be performed on tumor proteomes. Additionally, protein mass spectrometry may be used to identify or validate the presence of mutated peptides bound to MHC proteins on tumor cells. Peptides can be acid-eluted from tumor cells or from HLA molecules that are immunoprecipitated from tumor cells, and then identified using mass spectrometry. The results of the sequencing may be compared with known control sets or with sequencing analysis performed on normal tissue of the patient.

Accordingly, the present invention relates to methods for identifying and/or detecting neoepitopes of an antigen, such as T-cell epitopes. Specifically, the invention provides methods of identifying and/or detecting tumor specific neoepitopes that are useful in inducing a tumor specific immune response in a subject. Optionally, these neoepitopes bind to class I HLA proteins with a greater affinity than the wild-type peptide and/or are capable of activating anti-tumor CD8 T-cells. Identical mutations in any particular gene are rarely found across tumors.

Proteins of MHC class I are present on the surface of almost all cells of the body, including most tumor cells. The proteins of MHC class I are loaded with antigens that usually originate from endogenous proteins or from pathogens present inside cells, and are then presented to cytotoxic T-lymphocytes (CTLs). T-Cell receptors are capable of recognizing and binding peptides complexed with the molecules of MHC class I. Each cytotoxic T-lymphocyte expresses a unique T-cell receptor which is capable of binding specific MHC/peptide complexes.

Using computer algorithms, it is possible to predict potential neoepitopes such as T-cell epitopes, i.e. peptide sequences, which are bound by the MHC molecules of class I or class II in the form of a peptide-presenting complex and then, in this form, recognized by the T-cell receptors of T-lymphocytes. Examples of programs useful for identifying peptides which will bind to MHC include for instance: Lonza Epibase, SYFPEITHI (Rammensee et al., Immunogenetics, 50 (1999), 213-219) and HLA_BIND (Parker et al., J. Immunol., 152 (1994), 163-175).

Once putative neoepitopes are selected, they can be further tested using in vitro and/or in vivo assays. Conventional in vitro lab assays, such as Elispot assays may be used with an isolate from each patient, to refine the list of neoepitopes selected based on the algorithm's predictions. Neoepitope vaccines, methods of use thereof and methods of preparing are all described in PCT/US2016/044918 which is incorporated herein by reference in its entirety.

Endogeous Tumor Antigens

In another embodiment, the tumor antigen is an endogenous tumor antigen, such as a tumor antigen that is released upon destruction of tumor cells in situ. It has been established in the art that natural mechanisms exist that results in cell death in vivo leading to release of intracellular components such that an immune response may be stimulated against the intracellular components. Such mechanisms are referred to herein as immunogenic cell death and include necroptosis and pyroptosis. Accordingly, in one embodiment, an immune potentiator mRNA construct of the disclosure is administered to a tumor-bearing subject under conditions in which endogenous immunogenic cell death is occurring such that one or more endogenous tumor antigens are released, to thereby enhance an immune response against the tumor antigens. In one embodiment, the immune potentiator mRNA construct is administered to a tumor-bearing subject together with a second mRNA construct encoding an "executioner mRNA construct", which stimulates immunogenic cell death of tumor cells in the subject. Examples of executioner mRNA constructs include those encoding MLKL, RIPK3, RIPK1, DIABLO, FADD, GSDMD, caspase-4, caspase-5, caspase-11, Pyrin, NLRP3 and ASC/PYCARD. Executioner mRNA constructs, and their use in combination with an immune potentiator mRNA construct, are described in further detail in U.S. Application Ser. No. 62/412,933, the entire contents of which is expressly incorporated herein by reference.

Characteristics of Cancer Antigens

The activating oncogene mutation peptides selected for inclusion in the immunomodulatory therapeutic composition typically will be high affinity binding peptides. In some aspect the activating oncogene mutation peptide binds an HLA protein with greater affinity than a wild-type peptide. The activating oncogene mutation peptides has an IC50 of at least less than 5000 nM, at least less than 500 nM, at least less than 250 nM, at least less than 200 nM, at least less than 150 nM, at least less than 100 nM, at least less than 50 nM or less in some embodiments. Typically, peptides with predicted IC50<50 nM, are generally considered medium to high affinity binding peptides and will be selected for testing their affinity empirically using biochemical assays of HLA-binding.

In some embodiments, subject specific activating oncogene mutation peptides may be identified in a sample of a patient. For instance, the sample may be a tissue sample or a tumor sample. For instance, a sample of one or more tumor cells may be examined for the presence of subject specific activating oncogene mutations. The tumor sample may be examined using whole genome, exome or transcriptome analysis in order to identify the subject specific activating oncogene mutations.

Alternatively the subject specific activating oncogene mutation peptides may be identified in an exosome of the subject. When the activating oncogene mutation peptides are identified in an exosome of the subject, such peptides are said to be representative of exosome peptides of the subject.

Exosomes are small microvesicles shed by cells, typically having a diameter of approximately 30-100 nm. Exosomes are classically formed from the inward invagination and pinching off of the late endosomal membrane, resulting in the formation of a multivesicular body (MVB) laden with small lipid bilayer vesicles, each of which contains a sample of the parent cell's cytoplasm. Fusion of the MVB with the cell membrane results in the release of these exosomes from the cell, and their delivery into the blood, urine, cerebrospinal fluid, or other bodily fluids. Exosomes can be recovered from any of these biological fluids for further analysis.

Nucleic acids within exosomes have a role as biomarkers for tumor antigens. An advantage of analyzing exosomes in order to identify subject specific cancer antigens, is that the method circumvents the need for biopsies. This can be particularly advantageous when the patient needs to have several rounds of therapy including identification of cancer antigens, and vaccination.

A number of methods of isolating exosomes from a biological sample have been described in the art. For example, the following methods can be used: differential centrifugation, low speed centrifugation, anion exchange and/or gel permeation chromatography, sucrose density gradients or organelle electrophoresis, magnetic activated cell sorting (MACS), nanomembrane ultrafiltration concentration, Percoll gradient isolation and using microfluidic devices. Exemplary methods are described in US Patent Publication No. 2014/0212871 for instance.

Immune Potentiator mRNAs

One aspect of the disclosure pertains to mRNAs that encode a polypeptide that stimulates or enhances an immune response against one or more antigens of interest (activating oncogene mutation peptide(s)). Such mRNAs that enhance immune responses to an antigen(s) of interest are referred to herein as immune potentiator mRNA constructs or immune potentiator mRNAs, including chemically modified mRNAs (mmRNAs). In some aspects, the disclosure provides an mRNA encoding a polypeptide that stimulates or enhances an immune response in a subject in need thereof (e.g., potentiates an immune response in the subject) by, for example, inducing adaptive immunity (e.g., by stimulating Type I interferon production), stimulating an inflammatory response, stimulating NFkB signaling and/or stimulating dendritic cell (DC) development, activity or mobilization in the subject. In some aspects, administration of an immune potentiator mRNA to a subject in need thereof enhances cellular immunity (e.g., T cell-mediated immunity), humoral immunity (e.g., B cell-mediated immunity) or both cellular and humoral immunity in the subject. In some aspects, administration of an immune potentiator mRNA stimulates cytokine production (e.g., inflammatory cytokine production), stimulates antigen-specific $CD8^+$ effector cell responses, stimulates antigen-specific $CD4^+$ helper cell responses, increases the effector memory $CD62L^{lo}$ T cell population, stimulates B cell activity or stimulates antigen-specific antibody production, including combinations of the foregoing responses.

In some aspects, administration of an immune potentiator mRNA stimulates cytokine production (e.g., inflammatory cytokine production) and stimulates antigen-specific $CD8^+$ effector cell responses. In some aspects, administration of an immune potentiator mRNA stimulates cytokine production (e.g., inflammatory cytokine production), and stimulates antigen-specific $CD4^+$ helper cell responses. In some aspects, administration of an immune potentiator mRNA stimulates cytokine production (e.g., inflammatory cytokine production), and increases the effector memory $CD62L^{lo}$ T cell population. In some aspects, administration of an immune potentiator mRNA stimulates cytokine production (e.g., inflammatory cytokine production), and stimulates B cell activity or stimulates antigen-specific antibody production.

Immune Potentiators mRNAs that Stimulate Type I Interferon

In some aspects, the disclosure provides an immune potentiator mRNA encoding a polypeptide that stimulates or enhances an immune response against an antigen of interest by simulating or enhancing Type I interferon pathway signaling, thereby stimulating or enhancing Type I interferon (IFN) production. It has been established that successful induction of anti-tumor or anti-microbial adaptive immunity requires Type I IFN signaling (see e.g., Fuertes, M. B. et al. (2013) Trends Immunol. 34:67-73). The production of Type I IFNs (including IFN-α, IFN-β, IFN-ε, IFN-κ and IFN-ω) plays a role in clearance of microbial infections, such as viral infections. It has also been appreciated that host cell DNA (for example derived from damaged or dying cells) is capable of inducing Type I interferon production and that the Type I IFN signaling pathway plays a role in the development of adaptive anti-tumor immunity. However, many pathogens and cancer cells have evolved mechanisms to reduce or inhibit Type I interferon responses. Thus, activation (including stimulation and/or enhancement) of the Type I IFN signaling pathway in a subject in need thereof, by providing an immune potentiator mRNA of the disclosure to the subject, stimulates or enhances an immune response in the subject in a wide variety of clinical situations, including treatment of cancer and pathogenic infections, as well as in potentiating vaccine responses to provide protective immunity.

Type I interferons (IFNs) are pro-inflammatory cytokines that are rapidly produced in multiple different cell types, typically upon viral infection, and known to have a wide variety of effects. The canonical consequences of type I IFN production in vivo is the activation of antimicrobial cellular programs and the development of innate and adaptive immune responses. Type I IFN induces a cell-intrinsic antimicrobial state in infected and neighboring cells that limits the spread of infectious agents, particularly viral pathogens. Type I IFN also modulates innate immune cell activation (e.g., maturation of dendritic cells) to promote antigen presentation and nature killer cell functions. Type I IFN also promotes the development of high-affinity antigen-specific T and B cell responses and immunological memory (Ivashkiv and Donlin (2014) *Nat Rev Immunol* 14(1):36-49).

Type I IFN activates dendritic cells (DCs) and promotes their T cell stimulatory capacity through autocrine signaling (Montoya et al., (2002) *Blood* 99:3263-3271). Type I IFN exposure facilitates maturation of DCs via increasing the expression of chemokine receptors and adhesion molecules (e.g., to promote DC migration into draining lymph nodes), co-stimulatory molecules, and MHC class I and class II antigen presentation. DCs that mature following type I IFN exposure can effectively prime protective T cell responses (Wijesundara et al., (2014) Front Immunol 29(412) and references therein).

Type I IFN can either promote or inhibit T cell activation, proliferation, differentiation and survival depending largely on the timing of type I IFN signaling relative to T cell receptor signaling (Crouse et al., (2015) *Nat Rev Immunol* 15:231-242). Early studies revealed that MHC-I expression is upregulated in response to type I IFN in multiple cell types (Lindahl et al., (1976), *J Infect Dis* 133(Suppl):A66-A68; Lindahl et al., (1976) *Proc Natl Acad Sci USA* 17:1284-1287) which is a requirement for optimal T cell stimulation, differentiation, expansion and cytolytic activity. Type I IFN can exert potent co-stimulatory effects on CD8 T cells, enhancing CD8 T cell proliferation and differentiation (Curtsinger et al., (2005) *J Immunol* 174:4465-4469; Kolumam et al., (2005) *J Exp Med* 202:637-650).

Similar to effects on T cells, type I IFN signaling has both positive and negative effects on B cell responses depending on the timing and context of exposure (Braun et al., (2002) Int Immunol 14(4):411-419; Lin et al, (1998) 187(1):79-87). The survival and maturation of immature B cells can be inhibited by type I IFN signaling. In contrast to immature B cells, type I IFN exposure has been shown to promote B cell activation, antibody production and isotype switch following viral infection or following experimental immunization (Le Bon et al., (2006) *J Immunol* 176:4:2074-2078; Swanson et al., (2010) J Exp Med 207:1485-1500).

A number of components involved in Type I IFN pathway signaling have been established, including STING, Interferon Regulatory Factors, such as IRF1, IRF3, IRF5, IRF7, IRF8, and IRF9, TBK1, IKKi, MyD88 and TRAM. Additional components involved in Type I IFN pathway signaling include TRAF3, TRAF6, IRAK-1, IRAK-4, TRIF, IPS-1, TLR-3, TLR-4, TLR-7, TLR-8, TLR-9, RIG-1, DAI and IFI16.

Accordingly, in one embodiment, an immune potentiator mRNA encodes any of the foregoing components involved in Type I IFN pathway signaling.

Immune Potentiator mRNA Encoding STING

The present disclosure encompasses mRNA (including mmRNA) encoding STING, including constitutively active forms of STING, as immune potentiators. STING (STimulator of INterferon Genes; also known as transmembrane protein 173 (TMEM173), mediator of IRF3 activation (MITA), methionine-proline-tyrosine-serine (MPYS), and ER IFN stimulator (ERIS)) is a 379 amino acid, endoplasmic reticulum (ER) resident transmembrane protein that functions as a signaling molecule controlling the transcription of immune response genes, including type I IFNs and pro-inflammatory cytokines (Ishikawa & Barber, (2008) *Nature* 455:647-678; Ishikawa et al., (2009) *Nature* 461:788-792; Barber (2010) *Nat Rev Immunol* 15(12):760-770).

STING functions as a signaling adaptor linking the cytosolic detection of DNA to the TBK1/IRF3/Type I IFN signaling axis. The signaling adaptor functions of STING are activated through the direct sensing of cyclic dinucleotides (CDNs). Examples of CDNs include cyclic di-GMP (guanosine 5'-monophosphate), cyclic di-AMP (adenosine 5'-monophosphate) and cyclic GMP-AMP (cGAMP). Initially characterized as ubiquitous bacterial secondary messengers, CDNs are now known to constitute a class of pathogen-associated molecular pattern molecules (PAMPs) that activate the TBK1/IRF3/type I IFN signaling axis via direct interaction with STING. STING is capable of sensing aberrant DNA species and/or CDNs in the cytosol of the cell, including CDNs derived from bacteria, and/or from the host protein cyclic GMP-AMP synthase (cGAS). The cGAS protein is a DNA sensor that produces cGAMP in response to detection of DNA in the cytosol (Burdette et al., (2011) *Nature* 478:515-518; Sun et al., (2013) *Science* 339:786-791; Diner et al., (2013) *Cell Rep* 3:1355-1361; Ablasser et al., (2013) *Nature* 498:380-384).

Upon binding to a CDN, STING dimerizes and undergoes a conformational change that promotes formation of a complex with TANK-binding kinase 1 (TBK1) (Ouyang et al., (2012) *Immunity* 36(6):1073-1086). This complex translocates to the perinuclear Golgi, resulting in delivery of TBK1 to endolysosomal compartments where it phosphorylates IRF3 and NF-κB transcription factors (Zhong et al., (2008) *Immunity* 29:538-550). A recent study has shown that STING functions as a scaffold by binding to both TBK1 and IRF3 to specifically promote the phosphorylation of IRF3 by TBK1 (Tanaka & Chen, (2012) *Sci Signal* 5(214):ra20). Activation of the IRF3-, IRF7- and NF-κB-dependent signaling pathways induces the production of cytokines and other immune response-related proteins, such as type I IFNs, which promote anti-pathogen and/or anti-tumor activity.

A number of studies have investigated the use of CDN agonists of STING as potential vaccine adjuvants or immunomodulatory agents to elicit humoral and cellular immune responses (Dubensky et al., (2013) *Ther Adv Vaccines* 1(4): 131-143 and references therein). Initial studies demonstrated that administration of the CDN c-di-GMP attenuated *Staphylococcus aureus* infection in vivo, reducing the number of recovered bacterial cells in a mouse infection model yet c-di-GMP had no observable inhibitory or bactericidal effect on bacterial cells in vitro suggesting the reduction in bacterial cells was due to an effect on the host immune system (Karaolis et al., (2005) *Antimicrob Agents Chemother* 49:1029-1038; Karaolis et al., (2007) *Infect Immun* 75:4942-4950). Recent studies have shown that synthetic CDN derivative molecules formulated with granulocyte-macrophage colony-stimulating factor (GM-CSF)-producing cancer vaccines (termed STINGVAX) elicit enhanced in vivo antitumor effects in therapeutic animal models of cancer as compared to immunization with GM-CSF vaccine alone (Fu et al., (2015) *Sci Transl Med* 7(283): 283ra52), suggesting that CDN are potent vaccine adjuvants.

Mutant STING proteins resulting from polymorphisms mapped to the human TMEM173 gene have been described exhibiting a gain-of function or constitutively active phenotype. When expressed in vitro, mutant STING alleles were shown to potently stimulate induction of type I IFN (Liu et al., (2014) *N Engl J Med* 371:507-518; Jeremiah et al., (2014) *J Clin Invest* 124:5516-5520; Dobbs et al., (2015) *Cell Host Microbe* 18(2):157-168; Tang & Wang, (2015) *PLoS ONE* 10(3):e0120090; Melki et al., (2017) *J Allergy Clin Immunol* In Press; Konig et al., (2017) *Ann Rheum Dis* 76(2):468-472; Burdette et al. (2011) *Nature* 478:515-518).

Provided herein are mRNAs (e.g., mmRNAs) encoding constitutively active forms of STING, including mutant human STING isoforms for use as immune potentiators as described herein. mmRNAs encoding constitutively active forms of STING, including mutant human STING isoforms are set forth in the Sequence Listing herein. The amino acid residue numbering for mutant human STING polypeptides used herein corresponds to that used for the 379 amino acid residue wild type human STING (isoform 1) available in the art as Genbank Accession Number NP 938023.

Accordingly, in one aspect, the disclosure provides a mRNA (e.g., mmRNA) encoding a mutant human STING protein having a mutation at amino acid residue 155, in particular an amino acid substitution, such as a V155M mutation. In one embodiment, the mRNA (e.g., mmRNAs) encodes an amino acid sequence as set forth in SEQ ID NO:1. In one embodiment, the STING V155M mutant is encoded by a nucleotide sequence shown in SEQ ID NO: 139, SEQ ID NO: 168 or SEQ ID NO: 170. In one embodiment, the mRNA (e.g., mmRNAs) comprises a 3' UTR sequence as shown in SEQ ID NO: 149, which includes an miR122 binding site.

In other aspects, the disclosure provides a mRNA (e.g., mmRNA) encoding a mutant human STING protein having a mutation at amino acid residue 284, such as an amino acid substitution. Non-limiting examples of residue 284 substitutions include R284T, R284M and R284K. In certain embodiments, the mutant human STING protein has as a R284T mutation, for example has the amino acid sequence set forth in SEQ ID NO: 2 or is encoded by an the nucleotide sequence shown in SEQ ID NO: 140 or 201. In certain embodiments, the mutant human STING protein has a R284M mutation, for example has the amino acid sequence as set forth in SEQ ID NO: 3 or is encoded by the nucleotide sequence shown in SEQ ID NO: 141 or 202. In certain embodiments, the mutant human STING protein has a R284K mutation, for example has the amino acid sequence as set forth in SEQ ID NO: 4 or 164, or is encoded by the nucleotide sequence shown in SEQ ID NO: 142, 165, 203 or 225.

In other aspects, the disclosure provides a mRNA (e.g., mmRNA) encoding a mutant human STING protein having a mutation at amino acid residue 154, such as an amino acid substitution, such as a N154S mutation. In certain embodiments, the mutant human STING protein has a N154S mutation, for example has the amino acid sequence as set forth in SEQ ID NO: 5 or is encoded by the nucleotide sequence shown in SEQ ID NO: 143 or 204.

In yet other aspects, the disclosure provides a mRNA (e.g., mmRNA) encoding a mutant human STING protein having a mutation at amino acid residue 147, such as an amino acid substitution, such as a V147L mutation. In certain embodiments, the mutant human STING protein having a V147L mutation has the amino acid sequence as set forth in SEQ ID NO: 6 or is encoded by the nucleotide sequence shown in SEQ ID NO: 144 or 205.

In other aspects, the disclosure provides a mRNA (e.g., mmRNA) encoding a mutant human STING protein having a mutation at amino acid residue 315, such as an amino acid substitution, such as a E315Q mutation. In certain embodiments, the mutant human STING protein having a E315Q mutation has the amino acid sequence as set forth in SEQ ID NO: 7 or is encoded by the nucleotide sequence shown in SEQ ID NO: 145 or 206.

In other aspects, the disclosure provides a mRNA (e.g., mmRNA) encoding a mutant human STING protein having a mutation at amino acid residue 375, such as an amino acid substitution, such as a R375A mutation. In certain embodiments, the mutant human STING protein having a R375A mutation has the amino acid sequence as set forth in SEQ ID NO: 8 or is encoded by the nucleotide sequence shown in SEQ ID NO: 146 or 207.

In other aspects, the disclosure provides a mRNA (e.g., mmRNA) encoding a mutant human STING protein having a one or more or a combination of two, three, four or more of the foregoing mutations. Accordingly, in one aspect the disclosure provides a mRNA (e.g., mmRNA) encoding a mutant human STING protein having one or more mutations selected from the group consisting of: V147L, N154S, V155M, R284T, R284M, R284K, E315Q and R375A, and combinations thereof. In other aspects, the disclosure provides a mRNA (e.g., mmRNA) encoding a mutant human STING protein having a combination of mutations selected from the group consisting of: V155M and R284T; V155M and R284M; V155M and R284K; V155M and V147L; V155M and N154S; V155M and E315Q; and V155M and R375A.

In other aspects, the disclosure provides a mRNA (e.g., mmRNA) encoding a mutant human STING protein having a V155M and one, two, three or more of the following mutations: R284T; R284M; R284K; V147L; N154S; E315Q; and R375A. In other aspects, the disclosure provides a mRNA (e.g., mmRNA) encoding a mutant human STING protein having V155M, V147L and N154S mutations. In other aspects, the disclosure provides a mRNA (e.g., mmRNA) encoding a mutant human STING protein having V155M, V147L, N154S mutations, and, optionally, a mutation at amino acid 284. In yet other aspects, the disclosure provides a mRNA (e.g., mmRNA) encoding a mutant human STING protein having V155M, V147L, N154S mutations, and a mutation at amino acid 284 selected from R284T, R284M and R284K. In other aspects, the disclosure provides a mRNA (e.g., mmRNA) encoding a mutant human STING protein having V155M, V147L, N154S, and R284T mutations. In other aspects, the disclosure provides a mRNA (e.g., mmRNA) encoding a mutant human STING protein having V155M, V147L, N154S, and R284M mutations. In other aspects, the disclosure provides a mRNA (e.g., mmRNA) encoding a mutant human STING protein having V155M, V147L, N154S, and R284K mutations.

In other embodiments, the disclosure provides a mRNA (e.g., mmRNA) encoding a mutant human STING protein having a combination of mutations at amino acid residue 147, 154, 155 and, optionally, 284, in particular amino acid substitutions, such as a V147L, N154S, V155M and, optionally, R284M. In certain embodiments, the mutant human STING protein has V147N, N154S and V155M mutations, such as the amino acid sequence as set forth in SEQ ID NO: 9 or encoded by the nucleotide sequence shown in SEQ ID NO: 147. In certain embodiments, the mutant human STING protein has R284M, V147N, N154S and V155M mutations, such as the amino acid sequence as set forth in SEQ ID NO: 10 or encoded by the nucleotide sequence shown in SEQ ID NO: 148 or 209.

In another embodiment, the disclosure provides a mRNA (e.g., mmRNA) encoding a mutant human STING protein that is a constitutively active truncated form of the full-length 379 amino acid wild type protein, such as a constitutively active human STING polypeptide consisting of amino acids 137-379.

Immune Potentiator mRNA Encoding Immune Regulatory Factor (IRF)

The present disclosure provides mRNA (including mmRNA) encoding Interferon Regulatory Factors, such as IRF1, IRF3, IRF5, IRF7, IRF8, and IRF9 as immune potentiators. The IRF transcription factor family is involved in the regulation of gene expression leading to the production of type I interferons (IFNs) during innate immune responses. Nine human IRFs have been identified to date (IRF-1-IRF-9), with each family member sharing extensive sequence homology within their N-terminal binding domains (DBDs) (Mamane et al., (1999) *Gene* 237:1-14; Taniguchi et al., (2001) *Annu Rev Immunol* 19:623-655). Within the IRF family, IRF1, IRF3, IRF5, and IRF7 have been specifically implicated as positive regulators of type I IFN gene transcription (Honda et al., (2006) *Immunity* 25(3):349-360). IRF1 was the first family member discovered to activate type I IFN gene promoters (Miyamoto et al., (1988) *Cell* 54:903-913). Although studies show that IRF1 participates in type I IFN gene expression, normal induction of type I IFN was observed in virus-infected IRF1−/− murine fibroblasts, suggesting dispensability (Matsuyama et al., (1993) *Cell* 75:83-97). IRF5 was also shown to be dispensable for type I IFN induction by viruses or TLR agonists (Takaoka et al., (2005) *Nature* 434:243-249).

Accordingly, in some aspects, the disclosure provides mRNA encoding constitutively active forms of human IRF1, IRF3, IRF5, IRF7, IRF8, and IRF9 as immune potentiators. In some aspects, the disclosure provides mRNA encoding constitutively active forms of human IRF3 and/or IRF7.

During innate immune responses, IRF-3 plays a critical role in the early induction of type I IFNs. The IRF3 transcription factor is constitutively expressed and shuttles between the nucleus and cytoplasm of cells in latent form, with a predominantly cytosolic localization prior to phosphorylation (Hiscott (2007) *J Biol Chem* 282(21):15325-15329; Kumar et al., (2000) *Mol Cell Biol* 20(11):4159-4168). Upon phosphorylation of serine residues at the C-terminus by TBK-1 (TANK binding kinase 1; also known as T2K and NAK) and/or IKKε (inducible IκB kinase; also known as IKKi), IRF3 translocates from the cytoplasm into the nucleus (Fitzgerald et al., (2003) *Nat Immuno* 4(5):491-496; Sharma et al., (2003) *Science* 300:1148-1151; Hemmi et al., (2004) *J Exp Med* 199:1641-1650). The transcriptional activity of IRF3 is mediated by these phosphorylation and translocation events. A model for IRF3 activation proposes that C-terminal phosphorylation induces a conformational change in IRF3 that promotes homo- and/or heterodimerization (e.g. with IRF7; see Honda et al., (2006) *Immunity* 25(3):346-360), nuclear localization, and association with the transcriptional co-activators CBP and/or p300 (Lin et al., (1999) *Mol Cell Biol* 19(4):2465-2474). While inactive IRF3 constitutively shuttles into and out of the nucleus, phosphorylated IRF3 proteins remain associated with CBP and/or p300, are retained in the nucleus, and induce transcription of IFN and other genes (Kumar et al., (2000) *Mol Cell Biol* 20(11):4159-4168).

In contrast to IRF3, IRF7 exhibits a low expression level in most cells, but is strongly induced by type I IFN-mediated signaling, supporting the notion that IRF3 is primarily responsible for the early induction of IFN genes and that IRF7 is involved in the late induction phase (Sato et al., (2000) *Immunity* 13(4):539-548). Ligand-binding to the type I IFN receptor results in the activation of a heterotrimeric transcriptional activator, termed IFN-stimulated gene factor 3 (ISGF3), which consists of IRF9, STAT1, and STAT2, and is responsible for the induction of the IRF7 gene (Marie et al., (1998) *EMBO J* 17(22):6660-6669) Like IRF3, IRF7 can partition between cytoplasm and nucleus after serine phosphorylation of its C-terminal region, allowing its dimerization and nuclear translocation. IRF7 forms a homodimer or a heterodimer with IRF3, and each of these different dimers differentially acts on the type I IFN gene family members. IRF3 is more potent in activating the IFN-β gene than the IFN-α genes, whereas IRF7 efficiently activates both IFN-α and IFN-β genes (Marie et al., (1998) *EMBO J* 17(22):6660-6669).

Provided herein are mRNAs (e.g., mmRNAs) encoding constitutively active forms of IRF3 and IRF7 including mutant human IRF3 and mutant human IRF7 isoforms for use as immune potentiators as described herein. mRNAs (e.g., mmRNAs) encoding constitutively active forms of IRF3 and IRF7, including mutant human IRF3 and IRF7 isoforms are set forth in the Sequence Listing herein. The amino acid residue numbering for mutant human IRF3 polypeptides used herein corresponds to that used for the 427 amino acid residue wild type human IRF3 (isoform 1) available in the art as Genbank Accession Number NP_001562. The amino acid residue numbering for mutant human IRF7 polypeptides used herein corresponds to that used for the 503 amino acid residue wild type human IRF7 (isoform a) available in the art as Genbank Accession Number NP_001563.

Accordingly, in some aspects, the disclosure provides a mRNA (e.g., mmRNA) encoding a mutant human IRF3 protein that is constitutively active, e.g., having a mutation at amino acid residue 396, such as an amino acid substitution, such as a S396D mutation, for example as set forth in the amino acid sequence of SEQ ID NO: 12 or encoded by the nucleotide sequence shown in SEQ ID NO: 151 or 212. In other aspects, the mRNA (e.g., mmRNA) construct encodes a constitutively active mouse IRF3 polypeptide comprising an S396D mutation, for example as set forth in the amino acid sequence of SEQ ID NO: 11 or encoded by the nucleotide sequence shown in SEQ ID NO: 150 or 211.

In other aspects, the disclosure provides a mRNA (e.g., mmRNA) encoding a mutant human IRF7 protein that is constitutively active. In one aspect, the disclosure provides a mRNA (e.g., mmRNA) encoding a constitutively active IR7 protein comprising one or more point mutations (amino acid substitutions compared to wild-type). In other aspects, the disclosure provides a mRNA (e.g., mmRNA) encoding a constitutively active IR7 protein comprising a truncated form of the protein (amino acid deletions compared to wild-type). In yet other aspects, the disclosure provides a mRNA (e.g., mmRNA) encoding a constitutively active IR7 protein comprising a truncated form of the protein that also includes one or more point mutations (a combination of amino acid deletions and amino acid substitutions compared to wild-type).

The wild-type amino acid sequence of human IRF7 (isoform a) is set forth in SEQ ID NO: 13, encoded by the nucleotide sequence shown in SEQ ID NO: 152 or 213. A series of constitutively active forms of human IRF7 were prepared comprising point mutations, deletions, or both, as compared to the wild-type sequence. In one aspect, the disclosure provides an immune potentiator mRNA construct encoding a constitutively active IRF7 polypeptide comprising one or more of the following mutations: S475D, S476D, S477D, S479D, L480D, S483D and S487D, and combinations thereof. In other aspects, the disclosure provides a mRNA (e.g., mmRNA) encoding a constitutively active IRF7 polypeptide comprising mutations S477D and S479D, as set forth in the amino acid sequence of SEQ ID NO: 14, encoded by the nucleotide sequence shown in SEQ ID NO: 153 or 214. In another aspect, the disclosure provides a mRNA (e.g., mmRNA) encoding a constitutively active IRF7 polypeptide comprising mutations S475D, S477D and L480D, as set forth in the amino acid sequence of SEQ ID NO: 15, encoded by the nucleotide sequence shown in SEQ ID NO: 154 or 215. In other aspects, the disclosure provides a mRNA (e.g., mmRNAs) encoding a constitutively active IRF7 polypeptide comprising mutations S475D, S476D, S477D, S479D, S483D and S487D, as set forth in the amino acid sequence of SEQ ID NO: 16, encoded by the nucleotide sequence shown in SEQ ID NO: 155 or 216. In another aspect, the disclosure provides a mRNA (e.g., mmRNA) encoding a constitutively active IRF7 polypeptide comprising a deletion of amino acid residues 247-467 (i.e., comprising amino acid residues 1-246 and 468-503), as set forth in the amino acid sequence of SEQ ID NO: 17, encoded by the nucleotide sequence shown in SEQ ID NO: 156 or 217. In yet other aspects, the disclosure provides a mRNA (e.g., mmRNA) encoding a constitutively active IRF7 polypeptide comprising a deletion of amino acid residues 247-467 (i.e., comprising amino acid residues 1-246 and 468-503) and further comprising mutations S475D, S476D, S477D, S479D, S483D and S487D, as set forth in the amino acid sequence of SEQ ID NO: 18, encoded by the nucleotide sequence shown in SEQ ID NO: 157 or 218.

In other aspects, the disclosure provides a mRNA (e.g., mmRNA) encoding a truncated IRF7 inactive "null" polypeptide construct comprising a deletion of residues 152-246 (i.e., comprising amino acid residues 1-151 and 247-503), as set forth in the amio acid sequence of SEQ ID NO: 19, encoded by the nucleotide sequence shown in SEQ ID NO: 158 or 219 (used, for example, for control purposes). In other aspects, the disclosure provides a mRNA (e.g., mmRNA) encoding a truncated IRF7 inactive "null" polypeptide construct comprising a deletion of residues 1-151 (i.e., comprising amino acid residues 152-503), as set forth in the amino acid sequence of SEQ ID NO: 20, encoded by the nucleotide sequence shown in SEQ ID NO: 159 or 220 (used, for example, for control purposes).

Additional Immune Potentiator mRNAs that Activate Type I IFN

In addition to the STING and IRF mRNA constructs described above, the disclosure provides mRNA constructs encoding additional components of the Type I IFN signaling pathway that can be use as immune potentiators to enhance immune responses through activation of the Type I IFN signaling pathway. For example, in one embodiment, the immune potentiator mRNA construct encodes a MyD88 protein. MyD88 is known in the art to signal upstream of IRF7. In one aspect, the disclosure provides a mRNA (e.g., mmRNA) encoding a constitutively active MyD88 protein, such as mutant MyD88 protein having one or more point mutations. In one aspect, the disclosure provides a mRNA (e.g., mmRNA) encoding a mutant human or mouse MyD88 protein having a L265P substitutions, as set forth in SEQ ID NOs: 75 and 76, respectively.

In another aspect, an immune potentiator mRNA construct encodes a TRAM (TICAM2) protein. TRAM is known in the art to signal upstream of IRF3. In one aspect, the disclosure encompasses a mRNA (e.g., mmRNA) encoding a constitutively active TRAM protein, such as mutant TRAM protein having one or more point mutations. In another aspect, the disclosure encompasses a wild-type TRAM protein that is overexpressed. In one aspect, the disclosure provides a mRNA (e.g., mmRNA) encoding a mouse TRAM protein as shown in SEQ ID NO: 77.

In yet other aspects, the disclosure provides an immune potentiator mRNA construct encoding a TANK-binding kinase 1 (TBK1) or an inducible IκB kinase (IKKi, also known as IKKc), including constitutively active forms of TBK1 or IKKi, as immune potentiators. TBK1 and IKKi have been demonstrated to be components of the virus-activated kinase that phosphorylates IRF3 and IRF7, thus acting upstream from IRF3 and IRF7 in the Type I IFN signaling pathway (Sharma, S. et al. (2003) *Science* 300: 1148-1151). TBK1 and IKKi are involved in the phosphorylation and activation of transcription factors (e.g. IRF3/7 & NF-κB) that induce expression of type I IFN genes as well as IFN-inducible genes (Fitzgerald, K. A. et al., (2003) *Nat Immunol* 4(5):491-496).

Accordingly, in one aspect, the disclosure provides an immune potentiator mRNA construct that encodes a TBK1 protein, including a constitutively active form of TBK1, including mutant human TBK1 isoforms. In yet other aspects, an immune potentiator mRNA construct encodes a IKKi protein, including a constitutively active form of IKKi, including mutant human IKKi isoforms.

Immune Potentiators mRNAs that Stimulate Inflammatory Responses

In other aspects, the disclosure provides immune potentiator mRNA constructs that enhance an immune response by stimulating an inflammatory response. Non-limiting examples of agents that stimulate an inflammatory response include STAT1, STAT2, STAT4 and STAT6. Accordingly, the disclosure provides an immune potentiator mRNA construct encoding one or a combination of these inflammation-inducing proteins, including a constitutively active form.

Provided herein are mRNAs (e.g., mmRNAs) encoding constitutively active forms of STAT6, including mutant human STAT6 isoforms for use as immune potentiators as described herein. mRNAs (e.g., mmRNAs) encoding constitutively active forms of STAT6, including mutant human STAT6 isoforms are set forth in the Sequence Listing herein. The amino acid residue numbering for mutant human STAT6 polypeptides used herein corresponds to that used for the 847 amino acid residue wild type human STAT6 (isoform 1) available in the art as Genbank Accession Number NP_001171550.1.

In one embodiment, the disclosure provides a mRNA construct encoding a constitutively active human STAT6 construct comprising one or more amino acid mutations selected from the group consisting of 5407D, V547A, T548A, Y641F, and combinations thereof. In another embodiment, the mRNA construct encodes a constitutively active human STAT6 construct comprising V547A and T548A mutations, such as the sequence shown in SEQ ID NO: 78. In another embodiment, the mRNA construct encodes a constitutively active human STAT6 construct comprising a 5407D mutation, such as the sequence shown in SEQ ID NO: 79. In another embodiment, the mRNA construct encodes a constitutively active human STAT6 construct comprising 5407D, V547A and T548A mutations, such as the sequence shown in SEQ ID NO: 80. In another embodiment, the mRNA construct encodes a constitutively active human STAT6 construct comprising V547A, T548A and Y641F mutations, such as the sequence shown in SEQ ID NO: 81.

Immune Potentiator mRNAs that Stimulate NFkB Signaling

In other aspects, the disclosure provides immune potentiator mRNA constructs that enhance an immune response by stimulating an NFkB signaling, which is known to be involved in stimulation of immune responses. Non-limiting examples of proteins that stimulate NFkB signaling include c-FLIP, IKKβ, RIPK1, Btk and TAK-TAB1. Accordingly, an immune potentiator mRNA construct of the present disclosure can encode any of these NFkB pathway-inducing proteins, for example in a constitutively active form.

In one embodiment, the disclosure provides an immune potentiator mRNA construct that activates NFκB signaling encodes a c-FLIP (cellular caspase 8 (FLICE)-like inhibitory protein) protein (also known in the art as CASP8 and FADD-like apoptosis regulator), including a constitutively active c-FLIP. Provided herein are mRNAs (e.g., mmRNAs) encoding constitutively active forms of c-FLIP, including mutant human c-FLIP isoforms for use as immune potentiators as described herein. mRNAs (e.g., mmRNAs) encoding constitutively active forms of c-FLIP, including mutant human c-FLIP isoforms are set forth in the Sequence Listing herein. The amino acid residue numbering for mutant human c-FLIP polypeptides used herein corresponds to that used for the 480 amino acid residue wild type human c-FLIP (isoform 1) available in the art as Genbank Accession Number NP_003870.

In one embodiment, the mRNA encodes a c-FLIP long (L) isoform comprising two DED domains, a p20 domain and a p12 domain, such as having the sequence shown in SEQ ID NO: 82. In another embodiment, the mRNA encodes a c-FLIP short (S) isoform, encoding amino acids 1-227, comprising two DED domains, such as having the sequence shown in SEQ ID NO: 83. In another embodiment, the mRNA encodes a c-FLIP p22 cleavage product, encoding amino acids 1-198, such as having the sequence shown in SEQ ID NO: 84. In another embodiment, the mRNA encodes a c-FLIP p43 cleavage product, encoding amino acids 1-376, such as having the sequence shown in SEQ ID NO: 85. In another embodiment, the mRNA encodes a c-FLIP p12 cleavage product, encoding amino acids 377-480, such as having the sequence shown in SEQ ID NO: 86.

In another embodiment, an immune potentiator mRNA construct that activates NFκB signaling encodes a constitutively active IKKα mRNA construct or a constitutively active IKKβ mRNA construct. In one embodiment, the constitutively active human IKKβ polypeptide comprises S177E and S181E mutations, such as the sequence shown in SEQ ID NO: 87. In another embodiment, the constitutively active human IKKβ polypeptide comprises S177A and S181A mutations, such as the sequence shown in SEQ ID NO: 88. In another embodiment, the mRNA construct encodes a constitutively active mouse IKKβ polypeptide. In one embodiment, the constitutively active mouse IKKβ polypeptide comprises S177E and S181E mutations, such as the sequence shown in SEQ ID NO: 148. In another embodiment, the constitutively active mouse IKKβ polypeptide comprises S177A and S181A mutations, such as the sequence shown in SEQ ID NO: 89. In another embodiment, the mRNA construct encodes a constitutively active human or mouse IKKα polypeptide comprising a PEST mutation, such as having a sequence as shown in SEQ ID NOs: 91-92 (human) or 95-96 (mouse). In another embodiment, the mRNA construct encodes a constitutively active human or mouse IKKβ polypeptide comprising a PEST mutation, such as having the sequence shown in SEQ ID NOs: 93-94 (human) or 97-98 (mouse).

In another embodiment, the disclosure provides an immune potentiator mRNA construct that activates NFκB signaling encoding a receptor-interacting protein kinase 1 (RIPK1) protein. Structure of DNA constucts encoding RIPK1 constructs that induce immunogenic cell death are described in the art, for example, Yatim, N. et al. (2015) *Science* 350:328-334 or Orozco, S. et al. (2014) *Cell Death Differ.* 21:1511-1521, and can be used in the design of suitable RNA constructs that are shown herein to also active NFkB signaling (see Examples). In one embodiment, the mRNA construct encodes RIPK1 amino acids 1-555 of a human or mouse RIPK1 polypeptide as well as an IZ domain, such as having the sequence shown in SEQ ID N: 99 (human) or 102 (mouse). In one embodiment, the mRNA construct encodes RIPK1 amino acids 1-555 of a human or mouse RIPK1 polypeptide as well as EE and DM domains, such as having the sequence shown in SEQ ID NO: 100 (human) or 103 (mouse). In one embodiment, the mRNA construct encodes RIPK1 amino acids 1-555 of a human or mouse RIPK1 polypeptide as well as RR and DM domains, such as having the sequence shown in SEQ ID NO: 101 (human) or 104 (mouse).

In yet another embodiment, an immune potentiator mRNA construct that activates NFκB signaling encodes a Btk polypeptide, such as a mutant Btk polypeptide such as a Btk(E41K) polypeptide (e.g., encoding an ORF amino acid sequence shown in SEQ ID NO: 114)

In yet another embodiment, an immune potentiator mRNA construct that activates NFκB signaling encodes a TAK-TAB1 protein, such as a constitutively active TAK-TAB1. In one embodiment, an immune potentiator mRNA construct encodes a human TAK-TAB1 protein, such as having the sequence shown in SEQ ID NO: 105.

Additional Immune Potentiator mRNAs

The present disclosure provides additional immune potentiator mRNA constructs. For example, in one embodiment, an immune potentiator mRNA construct encodes direct IAP binding protein with low pI (DIABLO) (also known as SMAC/DIABLO). As described in the examples herein, DIABLO constructs induce release of cytokines. In one embodiment, the disclosure provides a mRNA construct encoding a wild-type human DIABLO Isoform 1 sequence, such as having the sequence shown in SEQ ID NO: 106 (corresponding to the 239 amino acid human DIABLO isoform 1 precursor disclosed in the art as Genbank Accession No. NP_063940.1). In another embodiment, the mRNA construct encodes a human DIABLO Isoform 1 sequence comprising an S126L mutation, such as having the sequence shown in SEQ ID NO: 107. In another embodiment, the mRNA construct encodes amino acids 56-239 of human DIABLO Isoform 1, such as having the sequence shown in SEQ ID N: 108. In another embodiment, the mRNA construct encodes amino acids 56-239 of human DIABLO Isoform 1 and comprises an S126L mutation, such as having the sequence shown in SEQ ID NO: 109. In another embodiment, the mRNA construct encodes a wild-type human DIABLO Isoform 3 sequence, such as having the sequence shown in SEQ ID NO: 110 (corresponding to the 195 amino acid human DIABLO isoform 3 disclosed in the art as Genbank Accession No. NP_001265271.1). In another embodiment, the mRNA construct encodes a human DIABLO Isoform 3 sequence comprising an S82L mutation, such as having the sequence shown in SEQ ID NO: 110. In another embodiment, the mRNA construct encodes amino acids 56-195 of human DIABLO Isoform 3, such as having the sequence shown in SEQ ID NO: 111. In another embodiment, the mRNA construct encodes amino acids 56-195 of human DIABLO Isoform 3 and comprises an S82L mutation, such as having the sequence shown in SEQ ID NO: 112.

In additional embodiments, the immune potentiator mRNA construct encodes a SOC3 polypeptide (e.g., encoding an ORF amino acid sequence shown in SEQ ID NO: 115) or encodes a self-activating caspase-1 polypeptide (e.g, encoding any of the ORF amino acid sequences shown in SEQ ID NOs: 116-119), which can promote cleavage of pro-IL1β and pro-IL18 to their respective mature forms.

In yet other embodiments, an immune potentiator mRNA construct encodes a protein that modulates dendritic cell (DC) activity, such as stimulating DC production, activity or mobilization. A non-limiting example of a protein that stimulates DC mobilization is FLT3. Accordingly, in one embodiment, the immune potentiator mRNA construct encodes a FLT3 protein.

An immune potentiator mRNA construct typically comprises, in addition to the polypeptide-encoding sequences, other structural properties as described herein for mRNA constructs (e.g., modified nucleobases, 5' cap, 5' UTR, 3' UTR, miR binding site(s), polyA tail, as described herein). Suitable mRNA construct components are as described herein.

Compositions of Cancer Antigens of Interest and Immune Potentiators

In another aspect, the disclosure provides a composition comprising at least one messenger RNA (e.g., modified mRNA (mmRNA)) encoding: (i) at least one antigen of interest (an activating oncogene mutation peptide(s)); and (ii) a polypeptide that enhances an immune response against the at least one antigen of interest (an activating oncogene mutation peptide(s)) when the at least on mRNA is administered to a subject, wherein said mRNA comprises one or more modified nucleobases. Thus, the disclosure provides compositions comprising an immune potentiator mRNA and an mRNA encoding an antigen of interest (an activating oncogene mutation peptide(s)), wherein a single mRNA construct can encode both the antigen(s) or interest and the polypeptide that enhances an immune response to the antigen(s) or, alternatively, the composition can comprise two or more separate mRNA constructs, a first mRNA and a second mRNA (or third or fourth mRNA), wherein the first mRNA encodes the at least one antigen of interest and the second mRNA encodes the polypeptide that enhances an immune response to the antigen(s) (i.e., the second mRNA comprises the immune potentiator).

In those embodiments comprising a first mRNA encoding an antigen(s) of interest and a second mRNA encoding the polypeptide that enhances an immune response to the antigen(s) of interest, the first mRNA and the second mRNAs can be coformulated together (e.g., prior to coadministration), such as coformulated in the same lipid nanoparticle.

In those embodiments comprising a single mRNA encoding both the antigen(s) of interest and the polypeptide that enhances an immune response to the antigen(s) of interest, the sequences encoding the polypeptide can be positioned on the mRNA construct either upstream or downstream of the sequences encoding the antigen of interest. For example, non-limiting examples of mRNA constructs encoding both an antigen and an immunostimulatory polypeptide include those encoding at least one mutant KRAS antigen and a constitutively active STING polypeptide, e.g., encoding an amino acid sequence shown in any one of SEQ ID NOs: 48-71. In one embodiment, the constitutively active STING polypeptide is located at the N-terminal end of the construct (i.e., upstream of the antigen-encoding sequences), as shown in SEQ ID NOs: 48-57. In another embodiment, the constitutively active STING polypeptide is located at the C-terminal end of the construct (i.e., downstream of the antigen-encoding sequences), as shown in SEQ ID NOs: 58-71.

Various mRNAs encoding antigens of interest (e.g., mRNA vaccines) that can be used in combination with an immune potentiator mRNA of the disclosure are described in further detail below.

mRNA Construct Components

An mRNA may be a naturally or non-naturally occurring mRNA. An mRNA may include one or more modified nucleobases, nucleosides, or nucleotides, as described below, in which case it may be referred to as a "modified mRNA" or "mmRNA." As described herein "nucleoside" is defined as a compound containing a sugar molecule (e.g., a pentose or ribose) or derivative thereof in combination with an organic base (e.g., a purine or pyrimidine) or a derivative thereof (also referred to herein as "nucleobase"). As described herein, "nucleotide" is defined as a nucleoside including a phosphate group.

An mRNA may include a 5' untranslated region (5'-UTR), a 3' untranslated region (3'-UTR), and/or a coding region (e.g., an open reading frame). An exemplary 5' UTR for use in the constructs is shown in SEQ ID NO: 21. An exemplary 3' UTR for use in the constructs is shown in SEQ ID NO: 22. An exemplary 3' UTR comprising miR-122 and miR-142.3p binding sites for use in the constructs is shown in SEQ ID NO: 23. An mRNA may include any suitable number of base pairs, including tens (e.g., 10, 20, 30, 40, 50, 60, 70, 80, 90 or 100), hundreds (e.g., 200, 300, 400, 500, 600, 700, 800, or 900) or thousands (e.g., 1000, 2000, 3000, 4000, 5000, 6000, 7000, 8000, 9000, 10,000) of base pairs. Any number (e.g., all, some, or none) of nucleobases, nucleosides, or nucleotides may be an analog of a canonical species, substituted, modified, or otherwise non-naturally occurring. In certain embodiments, all of a particular nucleobase type may be modified.

In some embodiments, an mRNA as described herein may include a 5' cap structure, a chain terminating nucleotide, optionally a Kozak sequence (also known as a Kozak consensus sequence), a stem loop, a polyA sequence, and/or a polyadenylation signal.

A 5' cap structure or cap species is a compound including two nucleoside moieties joined by a linker and may be selected from a naturally occurring cap, a non-naturally occurring cap or cap analog, or an anti-reverse cap analog (ARCA). A cap species may include one or more modified nucleosides and/or linker moieties. For example, a natural mRNA cap may include a guanine nucleotide and a guanine (G) nucleotide methylated at the 7 position joined by a triphosphate linkage at their 5' positions, e.g., $m^7G(5')ppp(5')G$, commonly written as $m^7GpppG$. A cap species may also be an anti-reverse cap analog. A non-limiting list of possible cap species includes $m^7GpppG$, $m^7Gpppm^7G$, $m^73'dGpppG$, $m_2^{7,O3'}GpppG$, $m_2^{7,O3'}GppppG$, $m_2^{7,O2'}GppppG$, $m^7Gpppm^7G$, $m^{73'}dGpppG$, $m_2^{7,O3'}GpppG$, $m_2^{7,O3'}GppppG$, and $m_2^{7,O2'}GppppG$.

An mRNA may instead or additionally include a chain terminating nucleoside. For example, a chain terminating nucleoside may include those nucleosides deoxygenated at the 2' and/or 3' positions of their sugar group. Such species may include 3'-deoxyadenosine (cordycepin), 3'-deoxyuridine, 3'-deoxycytosine, 3'-deoxyguanosine, 3'-deoxythymine, and 2',3'-dideoxynucleosides, such as 2',3'-dideoxyadenosine, 2',3'-dideoxyuridine, 2',3'-dideoxycytosine, 2',3'-dideoxyguanosine, and 2',3'-dideoxythymine. In some embodiments, incorporation of a chain terminating nucleotide into an mRNA, for example at the 3'-terminus, may result in stabilization of the mRNA, as described, for example, in International Patent Publication No. WO 2013/103659.

An mRNA may instead or additionally include a stem loop, such as a histone stem loop. A stem loop may include 2, 3, 4, 5, 6, 7, 8, or more nucleotide base pairs. For example, a stem loop may include 4, 5, 6, 7, or 8 nucleotide base pairs. A stem loop may be located in any region of an mRNA. For example, a stem loop may be located in, before, or after an untranslated region (a 5' untranslated region or a 3' untranslated region), a coding region, or a polyA sequence or tail. In some embodiments, a stem loop may affect one or more function(s) of an mRNA, such as initiation of translation, translation efficiency, and/or transcriptional termination.

An mRNA may instead or additionally include a polyA sequence and/or polyadenylation signal. A polyA sequence may be comprised entirely or mostly of adenine nucleotides or analogs or derivatives thereof. A polyA sequence may be a tail located adjacent to a 3' untranslated region of an mRNA. In some embodiments, a polyA sequence may affect the nuclear export, translation, and/or stability of an mRNA.

An mRNA may instead or additionally include a microRNA binding site.

In some embodiments, an mRNA is a bicistronic mRNA comprising a first coding region and a second coding region with an intervening sequence comprising an internal ribosome entry site (IRES) sequence that allows for internal translation initiation between the first and second coding regions, or with an intervening sequence encoding a self-cleaving peptide, such as a 2A peptide. IRES sequences and 2A peptides are typically used to enhance expression of multiple proteins from the same vector. A variety of IRES sequences are known and available in the art and may be used, including, e.g., the encephalomyocarditis virus IRES.

In one embodiment, the polynucleotides of the present disclosure may include a sequence encoding a self-cleaving peptide. The self-cleaving peptide may be, but is not limited to, a 2A peptide. A variety of 2A peptides are known and available in the art and may be used, including e.g., the foot and mouth disease virus (FMDV) 2A peptide, the equine rhinitis A virus 2A peptide, the Thosea asigna virus 2A peptide, and the porcine teschovirus-1 2A peptide. 2A peptides are used by several viruses to generate two proteins from one transcript by ribosome-skipping, such that a normal peptide bond is impaired at the 2A peptide sequence, resulting in two discontinuous proteins being produced from one translation event. As a non-limiting example, the 2A peptide may have the protein sequence: GSGATNFSLLKQAGDVEENPGP (SEQ ID NO: 24), fragments or variants thereof. In one embodiment, the 2A peptide cleaves between the last glycine and last proline. As another non-limiting example, the polynucleotides of the present disclosure may include a polynucleotide sequence encoding the 2A peptide having the protein sequence GSGATNFSLLKQAGDVEENPGP (SEQ ID NO:24) fragments or variants thereof. One example of a polynucleotide sequence encoding the 2A peptide is: GGAAGCGGAGCTACTAACTTCAGCCTGCTGAAGCAGGCTGGAGACGTGGAGGAG AACCCTGGACCT (SEQ ID NO: 25). In one illustrative embodiment, a 2A peptide is encoded by the following sequence: 5'-TCCGGACTCAGATCCGGGGATCTCAAAATTGTCGCTCCTGTCAAACAAACTCTTA ACTTTGATTTACTCAAACTGGCTGGGGATGTAGAAAGCAATCCAGGTCCACTC-3'(SEQ ID NO: 26). The polynucleotide sequence of the 2A peptide may be modified or codon optimized by the methods described herein and/or are known in the art.

In one embodiment, this sequence may be used to separate the coding regions of two or more polypeptides of interest. As a non-limiting example, the sequence encoding the F2A peptide may be between a first coding region A and a second coding region B (A-F2Apep-B). The presence of the F2A peptide results in the cleavage of the one long protein between the glycine and the proline at the end of the F2A peptide sequence (NPGP is cleaved to result in NPG and P) thus creating separate protein A (with 21 amino acids of the F2A peptide attached, ending with NPG) and separate protein B (with 1 amino acid, P, of the F2A peptide attached) Likewise, for other 2A peptides (P2A, T2A and E2A), the presence of the peptide in a long protein results in cleavage between the glycine and proline at the end of the 2A peptide sequence (NPGP is cleaved to result in NPG and P). Protein A and protein B may be the same or different peptides or polypeptides of interest. In particular embodiments, protein A is a polypeptide that induces immunogenic cell death and protein B is another polypeptide that stimulates an inflammatory and/or immune response and/or regulates immune responsiveness (as described further below).

Modified mRNAs

In some embodiments, an mRNA of the disclosure comprises one or more modified nucleobases, nucleosides, or nucleotides (termed "modified mRNAs" or "mmRNAs"). In some embodiments, modified mRNAs may have useful properties, including enhanced stability, intracellular retention, enhanced translation, and/or the lack of a substantial induction of the innate immune response of a cell into which the mRNA is introduced, as compared to a reference unmodified mRNA. Therefore, use of modified mRNAs may enhance the efficiency of protein production, intracellular retention of nucleic acids, as well as possess reduced immunogenicity.

In some embodiments, an mRNA includes one or more (e.g., 1, 2, 3 or 4) different modified nucleobases, nucleosides, or nucleotides. In some embodiments, an mRNA includes one or more (e.g., 1, 2, 3, 4, 5, 6, 7, 8, 9, 10, 20, 30, 40, 50, 60, 70, 80, 90, 100, or more) different modified nucleobases, nucleosides, or nucleotides. In some embodiments, the modified mRNA may have reduced degradation in a cell into which the mRNA is introduced, relative to a corresponding unmodified mRNA.

In some embodiments, the modified nucleobase is a modified uracil. Exemplary nucleobases and nucleosides having a modified uracil include pseudouridine ($\psi$), pyridin-4-one ribonucleoside, 5-aza-uridine, 6-aza-uridine, 2-thio-5-aza-uridine, 2-thio-uridine ($s^2U$), 4-thio-uridine ($s^4U$), 4-thio-pseudouridine, 2-thio-pseudouridine, 5-hydroxy-uridine ($ho^5U$), 5-aminoallyl-uridine, 5-halo-uridine (e.g., 5-iodo-uridineor 5-bromo-uridine), 3-methyl-uridine ($m^3U$), 5-methoxy-uridine ($mo^5U$), uridine 5-oxyacetic acid ($cmo^5U$), uridine 5-oxyacetic acid methyl ester ($mcmo^5U$), 5-carboxymethyl-uridine ($cm^5U$), 1-carboxymethyl-pseudouridine, 5-carboxyhydroxymethyl-uridine ($chm^5U$), 5-carboxyhydroxymethyl-uridine methyl ester ($mchm^5U$), 5-methoxycarbonylmethyl-uridine ($mcm^5U$), 5-methoxycarbonylmethyl-2-thio-uridine ($mcm^5s^2U$), 5-aminomethyl-2-thio-uridine ($nm^5s^2U$), 5-methylaminomethyl-uridine ($mnm^5U$), 5-methylaminomethyl-2-thio-uridine ($mnm^5s^2U$), 5-methylaminomethyl-2-seleno-uridine ($mnm^5se^2U$), 5-carbamoylmethyl-uridine ($ncm^5U$), 5-carboxymethylaminomethyl-uridine ($cmnm^5U$), 5-carboxymethylaminomethyl-2-thio-uridine ($cmnm^5s^2U$), 5-propynyl-uridine, 1-propynyl-pseudouridine, 5-taurinomethyl-uridine ($ncm^5U$), 1-taurinomethyl-pseudouridine, 5-taurinomethyl-2-thio-uridine($ncm^5s^2U$), 1-taurinomethyl-4-thio-pseudouridine, 5-methyl-uridine ($m^5U$, i.e., having the nucleobase deoxythymine), 1-methyl-pseudouridine ($m^1\psi$), 5-methyl-2-thio-uridine ($m^5s^2U$), 1-methyl-4-thio-pseudouridine ($m^1$ pseudouridine$^4\psi$), 4-thio-1-methyl-pseudouridine, 3-methyl-pseudouridine ($m^3\psi$), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine ($m^5D$), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl)uridine ($acp^3U$), 1-methyl-3-(3-amino-3-carboxypropyl)pseudouridine ($acp^3\psi$), 5-(isopentenylaminomethyl)uridine ($inm^5U$), 5-(isopentenylaminomethyl)-2-thio-uridine ($inm^5s^2U$), $\alpha$-thio-uridine, 2'-O-methyl-uridine (Um), 5,2'-O-dimethyl-uridine ($m^5Um$), 2'-O-methyl-pseudouridine ($\psi m$), 2-thio-2'-O-methyl-uridine ($s^2Um$), 5-methoxycarbonylmethyl-2'-O-methyl-uridine ($mcm^5Um$), 5-carbamoylmethyl-2'-O-methyl-uridine ($ncm^5Um$), 5-carboxymethylaminomethyl-2'-O-methyl-uridine ($cmnm^5Um$), 3,2'-O-dimethyl-uridine ($m^3Um$), and 5-(isopentenylaminomethyl)-2'-O-methyl-uridine ($inm^5Um$), 1-thio-uridine, deoxythymidine, 2'-F-ara-uridine, 2'-F-uridine, 2'-OH-ara-uridine, 5-(2-carbomethoxyvinyl) uridine, and 5-[3-(1-E-propenylamino)] uridine.

In some embodiments, the modified nucleobase is a modified cytosine. Exemplary nucleobases and nucleosides having a modified cytosine include 5-aza-cytidine, 6-aza-cytidine, pseudoisocytidine, 3-methyl-cytidine ($m^3C$), N4-acetyl-cytidine ($ac^4C$), 5-formyl-cytidine ($f^5C$), N4-methyl-cytidine ($m^4C$), 5-methyl-cytidine ($m^5C$), 5-halo-cytidine (e.g., 5-iodo-cytidine), 5-hydroxymethyl-cytidine ($hm^5C$), 1-methyl-pseudoisocytidine, pyrrolo-cytidine, pyrrolo-pseudoisocytidine, 2-thio-cytidine ($s^2C$), 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, lysidine ($k_2C$), $\alpha$-thio-cytidine, 2'-O-methyl-cytidine (Cm), 5,2'-O- dimethyl-cytidine ($m^5Cm$), N4-acetyl-2'-O-methyl-cytidine ($ac^4Cm$), N4,2'-O-dimethyl-cytidine ($m^4Cm$), 5-formyl-2'-O-methyl-cytidine ($f^5Cm$), N4,N4,2'-O-trimethyl-cytidine ($m^4_2Cm$), 1-thio-cytidine, 2'-F-ara-cytidine, 2'-F-cytidine, and 2'-OH-ara-cytidine.

In some embodiments, the modified nucleobase is a modified adenine. Exemplary nucleobases and nucleosides having a modified adenine include α-thio-adenosine, 2-amino-purine, 2, 6-diaminopurine, 2-amino-6-halo-purine (e.g., 2-amino-6-chloro-purine), 6-halo-purine (e.g., 6-chloro-purine), 2-amino-6-methyl-purine, 8-azido-adenosine, 7-deaza-adenine, 7-deaza-8-aza-adenine, 7-deaza-2-amino-purine, 7-deaza-8-aza-2-amino-purine, 7-deaza-2, 6-diaminopurine, 7-deaza-8-aza-2,6-diaminopurine, 1-methyl-adenosine ($m^1A$), 2-methyl-adenine ($m^2A$), N6-methyl-adenosine ($m^6A$), 2-methylthio-N6-methyl-adenosine ($ms^2$ $m^6A$), N6-isopentenyl-adenosine ($i^6A$), 2-methylthio-N6-isopentenyl-adenosine ($ms^2i^6A$), N6-(cis-hydroxyisopentenyl)adenosine ($io^6A$), 2-methylthio-N6-(cis-hydroxyisopentenyl)adenosine ($ms^2io^6A$), N6-glycinylcarbamoyl-adenosine ($g^6A$), N6-threonylcarbamoyl-adenosine ($t^6A$), N6-methyl-N6-threonylcarbamoyl-adenosine ($m^6t^6A$),2-methylthio-N6-threonylcarbamoyl-adenosine ($ms^2g^6A$), N6,N6-dimethyl-adenosine ($m^6_2A$), N6-hydroxynorvalylcarbamoyl-adenosine ($hn^6A$), 2-methylthio-N6-hydroxynorvalylcarbamoyl-adenosine ($ms^2hn^6A$), N6-acetyl-adenosine ($ac^6A$), 7-methyl-adenine, 2-methylthio-adenine, 2-methoxy-adenine, α-thio-adenosine, 2'-O-methyl-adenosine (Am), N6,2'-O-dimethyl-adenosine ($m^6Am$), N6,N6,2'-O-trimethyl-adenosine ($m^6_2Am$), 1,2'-O-dimethyl-adenosine ($m^1Am$), 2'-O-ribosyladenosine (phosphate) (Ar(p)), 2-amino-N6-methyl-purine, 1-thio-adenosine, 8-azido-adenosine, 2'-F-ara-adenosine, 2'-F-adenosine, 2'-OH-ara-adenosine, and N6-(19-amino-pentaoxanonadecyl)-adenosine.

In some embodiments, the modified nucleobase is a modified guanine. Exemplary nucleobases and nucleosides having a modified guanine include α-thio-guanosine, inosine (I), 1-methyl-inosine ($m^1I$), wyosine (imG), methylwyosine (mimG), 4-demethyl-wyosine (imG-14), isowyosine (imG2), wybutosine (yW), peroxywybutosine (o2yW), hydroxywybutosine (OhyW), undermodified hydroxywybutosine (OhyW*), 7-deaza-guanosine, queuosine (Q), epoxyqueuosine (oQ), galactosyl-queuosine (galQ), mannosyl-queuosine (manQ), 7-cyano-7-deaza-guanosine (preQo), 7-aminomethyl-7-deaza-guanosine (preQi), archaeosine ($G^+$), 7-deaza-8-aza-guanosine, 6-thio-guanosine, 6-thio-7-deaza-guanosine, 6-thio-7-deaza-8-aza-guanosine, 7-methyl-guanosine ($m^7G$), 6-thio-7-methyl-guanosine, 7-methyl-inosine, 6-methoxy-guanosine, 1-methyl-guanosine ($m^1G$), N2-methyl-guanosine ($m^2G$), N2,N2-dimethyl-guanosine ($m^2_2G$), N2,7-dimethyl-guanosine ($m^{2,7}G$), N2, N2,7-dimethyl-guanosine ($m^{2,2,7}G$), 8-oxo-guanosine, 7-methyl-8-oxo-guanosine, 1-methyl-6-thio-guanosine, N2-methyl-6-thio-guanosine, N2,N2-dimethyl-6-thio-guanosine, α-thio-guanosine, 2'-O-methyl-guanosine (Gm), N2-methyl-2'-O-methyl-guanosine ($m^2Gm$), N2,N2-dimethyl-2'-O-methyl-guanosine ($m^2_2Gm$), 1-methyl-2'-O-methyl-guanosine ($m^1Gm$), N2,7-dimethyl-2'-O-methyl-guanosine ($m^{2,7}Gm$), 2'-O-methyl-inosine (Im), 1,2'-O-dimethyl-inosine ($m^1Im$), 2'-O-ribosylguanosine (phosphate) (Gr(p)), 1-thio-guanosine, 06-methyl-guanosine, 2'-F-ara-guanosine, and 2'-F-guanosine.

In some embodiments, an mRNA of the disclosure includes a combination of one or more of the aforementioned modified nucleobases (e.g., a combination of 2, 3 or 4 of the aforementioned modified nucleobases.)

In some embodiments, the modified nucleobase is pseudouridine (ψ), N1-methylpseudouridine ($m^1ψ$), 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, or 2'-O-methyl uridine. In some embodiments, an mRNA of the disclosure includes a combination of one or more of the aforementioned modified nucleobases (e.g., a combination of 2, 3 or 4 of the aforementioned modified nucleobases.) In one embodiment, the modified nucleobase is N1-methylpseudouridine ($m^1ψ$) and the mRNA of the disclosure is fully modified with N1-methylpseudouridine ($m^1ψ$). In some embodiments, N1-methylpseudouridine ($m^1ψ$) represents from 75-100% of the uracils in the mRNA. In some embodiments, N1-methylpseudouridine ($m^1ψ$) represents 100% of the uracils in the mRNA.

In some embodiments, the modified nucleobase is a modified cytosine. Exemplary nucleobases and nucleosides having a modified cytosine include N4-acetyl-cytidine ($ac^4C$), 5-methyl-cytidine ($m^5C$), 5-halo-cytidine (e.g., 5-iodo-cytidine), 5-hydroxymethyl-cytidine ($hm^5C$), 1-methyl-pseudoisocytidine, 2-thio-cytidine ($s^2C$), 2-thio-5-methyl-cytidine. In some embodiments, an mRNA of the disclosure includes a combination of one or more of the aforementioned modified nucleobases (e.g., a combination of 2, 3 or 4 of the aforementioned modified nucleobases.)

In some embodiments, the modified nucleobase is a modified adenine. Exemplary nucleobases and nucleosides having a modified adenine include 7-deaza-adenine, 1-methyl-adenosine ($m^1A$), 2-methyl-adenine ($m^2A$), N6-methyl-adenosine ($m^6A$). In some embodiments, an mRNA of the disclosure includes a combination of one or more of the aforementioned modified nucleobases (e.g., a combination of 2, 3 or 4 of the aforementioned modified nucleobases.)

In some embodiments, the modified nucleobase is a modified guanine. Exemplary nucleobases and nucleosides having a modified guanine include inosine (I), 1-methyl-inosine ($m^1I$), wyosine (imG), methylwyosine (mimG), 7-deaza-guanosine, 7-cyano-7-deaza-guanosine (preQo), 7-aminomethyl-7-deaza-guano sine (preQi), 7-methyl-guanosine ($m^7G$), 1-methyl-guanosine ($m^1G$), 8-oxo-guanosine, 7-methyl-8-oxo-guanosine. In some embodiments, an mRNA of the disclosure includes a combination of one or more of the aforementioned modified nucleobases (e.g., a combination of 2, 3 or 4 of the aforementioned modified nucleobases.)

In some embodiments, the modified nucleobase is 1-methyl-pseudouridine ($m^1ψ$), 5-methoxy-uridine ($mo^5U$), 5-methyl-cytidine ($m^5C$), pseudouridine (ψ), α-thio-guanosine, or α-thio-adenosine. In some embodiments, an mRNA of the disclosure includes a combination of one or more of the aforementioned modified nucleobases (e.g., a combination of 2, 3 or 4 of the aforementioned modified nucleobases.)

In some embodiments, the mRNA comprises pseudouridine (ψ). In some embodiments, the mRNA comprises pseudouridine (ψ) and 5-methyl-cytidine ($m^5C$). In some embodiments, the mRNA comprises 1-methyl-pseudouridine ($m^1ψ$). In some embodiments, the mRNA comprises 1-methyl-pseudouridine ($m^1ψ$) and 5-methyl-cytidine ($m^5C$). In some embodiments, the mRNA comprises 2-thiouridine ($s^2U$). In some embodiments, the mRNA comprises 2-thiouridine and 5-methyl-cytidine ($m^5C$). In some embodiments, the mRNA comprises 5-methoxy-uridine ($mo^5U$). In some embodiments, the mRNA comprises 5-methoxy-uridine ($mo^5U$) and 5-methyl-cytidine ($m^5C$). In some embodiments, the mRNA comprises 2'-O-methyl uridine. In some embodiments, the mRNA comprises 2'-O-methyl uridine and 5-methyl-cytidine ($m^5C$). In some embodiments, the mRNA comprises comprises N6-methyl-adenosine ($m^6A$). In some embodiments, the mRNA comprises N6-methyl-adenosine ($m^6A$) and 5-methyl-cytidine ($m^5C$).

In certain embodiments, an mRNA of the disclosure is uniformly modified (i.e., fully modified, modified throughout the entire sequence) for a particular modification. For example, an mRNA can be uniformly modified with N1-methylpseudouridine ($m^1\psi$) or 5-methyl-cytidine ($m^5C$), meaning that all uridines or all cytosine nucleosides in the mRNA sequence are replaced with N1-methylpseudouridine ($m^1\psi$) or 5-methyl-cytidine ($m^5C$). Similarly, mRNAs of the disclosure can be uniformly modified for any type of nucleoside residue present in the sequence by replacement with a modified residue such as those set forth above.

In some embodiments, an mRNA of the disclosure may be modified in a coding region (e.g., an open reading frame encoding a polypeptide). In other embodiments, an mRNA may be modified in regions besides a coding region. For example, in some embodiments, a 5'-UTR and/or a 3'-UTR are provided, wherein either or both may independently contain one or more different nucleoside modifications. In such embodiments, nucleoside modifications may also be present in the coding region.

Examples of nucleoside modifications and combinations thereof that may be present in mmRNAs of the present disclosure include, but are not limited to, those described in PCT Patent Application Publications: WO2012045075, WO2014081507, WO2014093924, WO2014164253, and WO2014159813.

The mmRNAs of the disclosure can include a combination of modifications to the sugar, the nucleobase, and/or the internucleoside linkage. These combinations can include any one or more modifications described herein.

Examples of modified nucleosides and modified nucleoside combinations are provided below in Table 1 and Table 2. These combinations of modified nucleotides can be used to form the mmRNAs of the disclosure. In certain embodiments, the modified nucleosides may be partially or completely substituted for the natural nucleotides of the mRNAs of the disclosure. As a non-limiting example, the natural nucleotide uridine may be substituted with a modified nucleoside described herein. In another non-limiting example, the natural nucleoside uridine may be partially substituted (e.g., about 0.1%, 1%, 5%, 10%, 15%, 20%, 25%, 30%, 35%, 40%, 45%, 50%, 55%, 60%, 65%, 70%, 75%, 80%, 85%, 90%, 95% or 99.9% of the natural uridines) with at least one of the modified nucleoside disclosed herein.

TABLE 1

Combinations of Nucleoside Modifications

| Modified Nucleotide | Modified Nucleotide Combination |
|---|---|
| α-thio-cytidine | α-thio-cytidine/5-iodo-uridine |
| | α-thio-cytidine/N1-methyl-pseudouridine |
| | α-thio-cytidine/α-thio-uridine |
| | α-thio-cytidine/5-methyl-uridine |
| | α-thio-cytidine/pseudo-uridine |
| | about 50% of the cytosines are α-thio-cytidine |

TABLE 1-continued

Combinations of Nucleoside Modifications

| Modified Nucleotide | Modified Nucleotide Combination |
|---|---|
| pseudoisocytidine | pseudoisocytidine/5-iodo-uridine |
| | pseudoisocytidine/N1-methyl-pseudouridine |
| | pseudoisocytidine/α-thio-uridine |
| | pseudoisocytidine/5-methyl-uridine |
| | pseudoisocytidine/pseudouridine |
| | about 25% of cytosines are pseudoisocytidine |
| | pseudoisocytidine/about 50% of uridines are N1-methyl-pseudouridine and about 50% of uridines are pseudouridine |
| | pseudoisocytidine/about 25% of uridines are N1-methyl-pseudouridine and about 25% of uridines are pseudouridine |
| pyrrolo-cytidine | pyrrolo-cytidine/5-iodo-uridine |
| | pyrrolo-cytidine/N1-methyl-pseudouridine |
| | pyrrolo-cytidine/α-thio-uridine |
| | pyrrolo-cytidine/5-methyl-uridine |
| | pyrrolo-cytidine/pseudouridine |
| | about 50% of the cytosines are pyrrolo-cytidine |
| 5-methyl-cytidine | 5-methyl-cytidine/5-iodo-uridine |
| | 5-methyl-cytidine/N1-methyl-pseudouridine |
| | 5-methyl-cytidine/α-thio-uridine |
| | 5-methyl-cytidine/5-methyl-uridine |
| | 5-methyl-cytidine/pseudouridine |
| | about 25% of cytosines are 5-methyl-cytidine |
| | about 50% of cytosines are 5-methyl-cytidine |
| | 5-methyl-cytidine/5-methoxy-uridine |
| | 5-methyl-cytidine/5-bromo-uridine |
| | 5-methyl-cytidine/2-thio-uridine |
| | 5-methyl-cytidine/about 50% of uridines are 2-thio-uridine |
| | about 50% of uridines are 5-methyl-cytidine/about 50% of uridines are 2-thio-uridine |
| N4-acetyl-cytidine | N4-acetyl-cytidine/5-iodo-uridine |
| | N4-acetyl-cytidine/N1-methyl-pseudouridine |
| | N4-acetyl-cytidine/α-thio-uridine |
| | N4-acetyl-cytidine/5-methyl-uridine |
| | N4-acetyl-cytidine/pseudouridine |
| | about 50% of cytosines are N4-acetyl-cytidine |
| | about 25% of cytosines are N4-acetyl-cytidine |
| | N4-acetyl-cytidine/5-methoxy-uridine |
| | N4-acetyl-cytidine/5-bromo-uridine |
| | N4-acetyl-cytidine/2-thio-uridine |
| | about 50% of cytosines are N4-acetyl-cytidine/about 50% of uridines are 2-thio-uridine |

TABLE 2

| Modified Nucleosides and Combinations Thereof |
|---|
| 1-(2,2,2-Trifluoroethyl)pseudo-UTP |
| 1-Ethyl-pseudo-UTP |
| 1-Methyl-pseudo-U-alpha-thio-TP |
| 1-methyl-pseudouridine TP, ATP, GTP, CTP |
| 1-methyl-pseudo-UTP/5-methyl-CTP/ATP/GTP |
| 1-methyl-pseudo-UTP/CTP/ATP/GTP |
| 1-Propyl-pseudo-UTP |
| 25% 5-Aminoallyl-CTP + 75% CTP/25% 5-Methoxy-UTP + 75% UTP |
| 25% 5-Aminoallyl-CTP + 75% CTP/75% 5-Methoxy-UTP + 25% UTP |
| 25% 5-Bromo-CTP + 75% CTP/25% 5-Methoxy-UTP + 75% UTP |
| 25% 5-Bromo-CTP + 75% CTP/75% 5-Methoxy-UTP + 25% UTP |
| 25% 5-Bromo-CTP + 75% CTP/1-Methyl-pseudo-UTP |
| 25% 5-Carboxy-CTP + 75% CTP/25% 5-Methoxy-UTP + 75% UTP |
| 25% 5-Carboxy-CTP + 75% CTP/75% 5-Methoxy-UTP + 25% UTP |
| 25% 5-Ethyl-CTP + 75% CTP/25% 5-Methoxy-UTP + 75% UTP |
| 25% 5-Ethyl-CTP + 75% CTP/75% 5-Methoxy-UTP + 25% UTP |
| 25% 5-Ethynyl-CTP + 75% CTP/25% 5-Methoxy-UTP + 75% UTP |
| 25% 5-Ethynyl-CTP + 75% CTP/75% 5-Methoxy-UTP + 25% UTP |
| 25% 5-Fluoro-CTP + 75% CTP/25% 5-Methoxy-UTP + 75% UTP |
| 25% 5-Fluoro-CTP + 75% CTP/75% 5-Methoxy-UTP + 25% UTP |
| 25% 5-Formyl-CTP + 75% CTP/25% 5-Methoxy-UTP + 75% UTP |

TABLE 2-continued

| Modified Nucleosides and Combinations Thereof |
|---|
| 25% 5-Formyl-CTP + 75% CTP/75% 5-Methoxy-UTP + 25% UTP |
| 25% 5-Hydroxymethyl-CTP + 75% CTP/25% 5-Methoxy-UTP + 75% UTP |
| 25% 5-Hydroxymethyl-CTP + 75% CTP/75% 5-Methoxy-UTP + 25% UTP |
| 25% 5-Iodo-CTP + 75% CTP/25% 5-Methoxy-UTP + 75% UTP |
| 25% 5-Iodo-CTP + 75% CTP/75% 5-Methoxy-UTP + 25% UTP |
| 25% 5-Methoxy-CTP + 75% CTP/25% 5-Methoxy-UTP + 75% UTP |
| 25% 5-Methoxy-CTP + 75% CTP/75% 5-Methoxy-UTP + 25% UTP |
| 25% 5-Methyl-CTP + 75% CTP/25% 5-Methoxy-UTP + 75% 1-Methyl-pseudo-UTP |
| 25% 5-Methyl-CTP + 75% CTP/25% 5-Methoxy-UTP + 75% UTP |
| 25% 5-Methyl-CTP + 75% CTP/50% 5-Methoxy-UTP + 50% 1-Methyl-pseudo-UTP |
| 25% 5-Methyl-CTP + 75% CTP/50% 5-Methoxy-UTP + 50% UTP |
| 25% 5-Methyl-CTP + 75% CTP/5-Methoxy-UTP |
| 25% 5-Methyl-CTP + 75% CTP/75% 5-Methoxy-UTP + 25% 1-Methyl-pseudo-UTP |
| 25% 5-Methyl-CTP + 75% CTP/75% 5-Methoxy-UTP + 25% UTP |
| 25% 5-Phenyl-CTP + 75% CTP/25% 5-Methoxy-UTP + 75% UTP |
| 25% 5-Phenyl-CTP + 75% CTP/75% 5-Methoxy-UTP + 25% UTP |
| 25% 5-Trifluoromethyl-CTP + 75% CTP/25% 5-Methoxy-UTP + 75% UTP |
| 25% 5-Trifluoromethyl-CTP + 75% CTP/75% 5-Methoxy-UTP + 25% UTP |
| 25% 5-Trifluoromethyl-CTP + 75% CTP/1-Methyl-pseudo-UTP |
| 25% N4-Ac-CTP + 75% CTP/25% 5-Methoxy-UTP + 75% UTP |
| 25% N4-Ac-CTP + 75% CTP/75% 5-Methoxy-UTP + 25% UTP |
| 25% N4-Bz-CTP + 75% CTP/25% 5-Methoxy-UTP + 75% UTP |
| 25% N4-Bz-CTP + 75% CTP/75% 5-Methoxy-UTP + 25% UTP |
| 25% N4-Methyl-CTP + 75% CTP/25% 5-Methoxy-UTP + 75% UTP |
| 25% N4-Methyl-CTP + 75% CTP/75% 5-Methoxy-UTP + 25% UTP |
| 25% Pseudo-iso-CTP + 75% CTP/25% 5-Methoxy-UTP + 75% UTP |
| 25% Pseudo-iso-CTP + 75% CTP/75% 5-Methoxy-UTP + 25% UTP |
| 25% 5-Bromo-CTP/75% CTP/Pseudo-UTP |
| 25% 5-methoxy-UTP/25% 5-methyl-CTP/ATP/GTP |
| 25% 5-methoxy-UTP/5-methyl-CTP/ATP/GTP |
| 25% 5-methoxy-UTP/75% 5-methyl-CTP/ATP/GTP |
| 25% 5-methoxy-UTP/CTP/ATP/GTP |
| 25% 5-metoxy-UTP/50% 5-methyl-CTP/ATP/GTP |
| 2-Amino-ATP |
| 2-Thio-CTP |
| 2-thio-pseudouridine TP, ATP, GTP, CTP |
| 2-Thio-pseudo-UTP |
| 2-Thio-UTP |
| 3-Methyl-CTP |
| 3-Methyl-pseudo-UTP |
| 4-Thio-UTP |
| 50% 5-Bromo-CTP + 50% CTP/1-Methyl-pseudo-UTP |
| 50% 5-Hydroxymethyl-CTP + 50% CTP/1-Methyl-pseudo-UTP |
| 50% 5-methoxy-UTP/5-methyl-CTP/ATP/GTP |
| 50% 5-Methyl-CTP + 50% CTP/25% 5-Methoxy-UTP + 75% 1-Methyl-pseudo-UTP |
| 50% 5-Methyl-CTP + 50% CTP/25% 5-Methoxy-UTP + 75% UTP |
| 50% 5-Methyl-CTP + 50% CTP/50% 5-Methoxy-UTP + 50% 1-Methyl-pseudo-UTP |
| 50% 5-Methyl-CTP + 50% CTP/50% 5-Methoxy-UTP + 50% UTP |
| 50% 5-Methyl-CTP + 50% CTP/5-Methoxy-UTP |
| 50% 5-Methyl-CTP + 50% CTP/75% 5-Methoxy-UTP + 25% 1-Methyl-pseudo-UTP |
| 50% 5-Methyl-CTP + 50% CTP/75% 5-Methoxy-UTP + 25% UTP |
| 50% 5-Trifluoromethyl-CTP + 50% CTP/1-Methyl-pseudo-UTP |
| 50% 5-Bromo-CTP/50% CTP/Pseudo-UTP |
| 50% 5-methoxy-UTP/25% 5-methyl-CTP/ATP/GTP |
| 50% 5-methoxy-UTP/50% 5-methyl-CTP/ATP/GTP |
| 50% 5-methoxy-UTP/75% 5-methyl-CTP/ATP/GTP |
| 50% 5-methoxy-UTP/CTP/ATP/GTP |
| 5-Aminoallyl-CTP |
| 5-Aminoallyl-CTP/5-Methoxy-UTP |
| 5-Aminoallyl-UTP |
| 5-Bromo-CTP |
| 5-Bromo-CTP/5-Methoxy-UTP |
| 5-Bromo-CTP/1-Methyl-pseudo-UTP |
| 5-Bromo-CTP/Pseudo-UTP |
| 5-bromocytidine TP, ATP, GTP, UTP |
| 5-Bromo-UTP |
| 5-Carboxy-CTP/5-Methoxy-UTP |

TABLE 2-continued

| Modified Nucleosides and Combinations Thereof |
|---|
| 5-Ethyl-CTP/5-Methoxy-UTP |
| 5-Ethynyl-CTP/5-Methoxy-UTP |
| 5-Fluoro-CTP/5-Methoxy-UTP |
| 5-Formyl-CTP/5-Methoxy-UTP |
| 5-Hydroxy- methyl-CTP/5-Methoxy-UTP |
| 5-Hydroxymethyl-CTP |
| 5-Hydroxymethyl-CTP/1-Methyl-pseudo-UTP |
| 5-Hydroxymethyl-CTP/5-Methoxy-UTP |
| 5-hydroxymethyl-cytidine TP, ATP, GTP, UTP |
| 5-Iodo-CTP/5-Methoxy-UTP |
| 5-Me-CTP/5-Methoxy-UTP |
| 5-Methoxy carbonyl methyl-UTP |
| 5-Methoxy-CTP/5-Methoxy-UTP |
| 5-methoxy-uridine TP, ATP, GTP, UTP |
| 5-methoxy-UTP |
| 5-Methoxy-UTP |
| 5-Methoxy-UTP/N6-Isopentenyl-ATP |
| 5-methoxy-UTP/25% 5-methyl-CTP/ATP/GTP |
| 5-methoxy-UTP/5-methyl-CTP/ATP/GTP |
| 5-methoxy-UTP/75% 5-methyl-CTP/ATP/GTP |
| 5-methoxy-UTP/CTP/ATP/GTP |
| 5-Methyl-2-thio-UTP |
| 5-Methylaminomethyl-UTP |
| 5-Methyl-CTP/5-Methoxy-UTP |
| 5-Methyl-CTP/5-Methoxy-UTP(cap 0) |
| 5-Methyl-CTP/5-Methoxy-UTP(No cap) |
| 5-Methyl-CTP/25% 5-Methoxy-UTP + 75% 1-Methyl-pseudo-UTP |
| 5-Methyl-CTP/25% 5-Methoxy-UTP + 75% UTP |
| 5-Methyl-CTP/50% 5-Methoxy-UTP + 50% 1-Methyl-pseudo-UTP |
| 5-Methyl-CTP/50% 5-Methoxy-UTP + 50% UTP |
| 5-Methyl-CTP/5-Methoxy-UTP/N6-Me-ATP |
| 5-Methyl-CTP/75% 5-Methoxy-UTP + 25% 1-Methyl-pseudo-UTP |
| 5-Methyl-CTP/75% 5-Methoxy-UTP + 25% UTP |
| 5-Phenyl-CTP/5-Methoxy-UTP |
| 5-Trifluoro- methyl-CTP/5-Methoxy-UTP |
| 5-Trifluoromethyl-CTP |
| 5-Trifluoromethyl-CTP/5-Methoxy-UTP |
| 5-Trifluoromethyl-CTP/1-Methyl-pseudo-UTP |
| 5-Trifluoromethyl-CTP/Pseudo-UTP |
| 5-Trifluoromethyl-UTP |
| 5-trifluromethylcytidine TP, ATP, GTP, UTP |
| 75% 5-Aminoallyl-CTP + 25% CTP/25% 5-Methoxy-UTP + 75% UTP |
| 75% 5-Aminoallyl-CTP + 25% CTP/75% 5-Methoxy-UTP + 25% UTP |
| 75% 5-Bromo-CTP + 25% CTP/25% 5-Methoxy-UTP + 75% UTP |
| 75% 5-Bromo-CTP + 25% CTP/75% 5-Methoxy-UTP + 25% UTP |
| 75% 5-Carboxy-CTP + 25% CTP/25% 5-Methoxy-UTP + 75% UTP |
| 75% 5-Carboxy-CTP + 25% CTP/75% 5-Methoxy-UTP + 25% UTP |
| 75% 5-Ethyl-CTP + 25% CTP/25% 5-Methoxy-UTP + 75% UTP |
| 75% 5-Ethyl-CTP + 25% CTP/75% 5-Methoxy-UTP + 25% UTP |
| 75% 5-Ethynyl-CTP + 25% CTP/25% 5-Methoxy-UTP + 75% UTP |
| 75% 5-Ethynyl-CTP + 25% CTP/75% 5-Methoxy-UTP + 25% UTP |
| 75% 5-Fluoro-CTP + 25% CTP/25% 5-Methoxy-UTP + 75% UTP |
| 75% 5-Fluoro-CTP + 25% CTP/75% 5-Methoxy-UTP + 25% UTP |
| 75% 5-Formyl-CTP + 25% CTP/25% 5-Methoxy-UTP + 75% UTP |
| 75% 5-Formyl-CTP + 25% CTP/75% 5-Methoxy-UTP + 25% UTP |
| 75% 5-Hydroxymethyl-CTP + 25% CTP/25% 5-Methoxy-UTP + 75% UTP |
| 75% 5-Hydroxymethyl-CTP + 25% CTP/75% 5-Methoxy-UTP + 25% UTP |
| 75% 5-Iodo-CTP + 25% CTP/25% 5-Methoxy-UTP + 75% UTP |
| 75% 5-Iodo-CTP + 25% CTP/75% 5-Methoxy-UTP + 25% UTP |
| 75% 5-Methoxy-CTP + 25% CTP/25% 5-Methoxy-UTP + 75% UTP |
| 75% 5-Methoxy-CTP + 25% CTP/75% 5-Methoxy-UTP + 25% UTP |
| 75% 5-methoxy-UTP/5-methyl-CTP/ATP/GTP |
| 75% 5-Methyl-CTP + 25% CTP/25% 5-Methoxy-UTP + 75% 1-Methyl-pseudo-UTP |
| 75% 5-Methyl-CTP + 25% CTP/25% 5-Methoxy-UTP + 75% UTP |
| 75% 5-Methyl-CTP + 25% CTP/50% 5-Methoxy-UTP + 50% 1-Methyl-pseudo-UTP |
| 75% 5-Methyl-CTP + 25% CTP/50% 5-Methoxy-UTP + 50% UTP |
| 75% 5-Methyl-CTP + 25% CTP/5-Methoxy-UTP |
| 75% 5-Methyl-CTP + 25% CTP/75% 5-Methoxy-UTP + 25% 1-Methyl-pseudo-UTP |
| 75% 5-Methyl-CTP + 25% CTP/75% 5-Methoxy-UTP + 25% UTP |
| 75% 5-Phenyl-CTP + 25% CTP/25% 5-Methoxy-UTP + 75% UTP |
| 75% 5-Phenyl-CTP + 25% CTP/75% 5-Methoxy-UTP + 25% UTP |

TABLE 2-continued

| Modified Nucleosides and Combinations Thereof |
|---|
| 75% 5-Trifluoromethyl-CTP + 25% CTP/25% 5-Methoxy-UTP + 75% UTP |
| 75% 5-Trifluoromethyl-CTP + 25% CTP/75% 5-Methoxy-UTP + 25% UTP |
| 75% 5-Trifluoromethyl-CTP + 25% CTP/1-Methyl-pseudo-UTP |
| 75% N4-Ac-CTP + 25% CTP/25% 5-Methoxy-UTP + 75% UTP |
| 75% N4-Ac-CTP + 25% CTP/75% 5-Methoxy-UTP + 25% UTP |
| 75% N4-Bz-CTP + 25% CTP/25% 5-Methoxy-UTP + 75% UTP |
| 75% N4-Bz-CTP + 25% CTP/75% 5-Methoxy-UTP + 25% UTP |
| 75% N4-Methyl-CTP + 25% CTP/25% 5-Methoxy-UTP + 75% UTP |
| 75% N4-Methyl-CTP + 25% CTP/75% 5-Methoxy-UTP + 25% UTP |
| 75% Pseudo-iso-CTP + 25% CTP/25% 5-Methoxy-UTP + 75% UTP |
| 75% Pseudo-iso-CTP + 25% CTP/75% 5-Methoxy-UTP + 25% UTP |
| 75% 5-Bromo-CTP/25% CTP/1-Methyl-pseudo-UTP |
| 75% 5-Bromo-CTP/25% CTP/Pseudo-UTP |
| 75% 5-methoxy-UTP/25% 5-methyl-CTP/ATP/GTP |
| 75% 5-methoxy-UTP/50% 5-methyl-CTP/ATP/GTP |
| 75% 5-methoxy-UTP/75% 5-methyl-CTP/ATP/GTP |
| 75% 5-methoxy-UTP/CTP/ATP/GTP |
| 8-Aza-ATP |
| Alpha-thio-CTP |
| CTP/25% 5-Methoxy-UTP + 75% 1-Methyl-pseudo-UTP |
| CTP/25% 5-Methoxy-UTP + 75% UTP |
| CTP/50% 5-Methoxy-UTP + 50% 1-Methyl-pseudo-UTP |
| CTP/50% 5-Methoxy-UTP + 50% UTP |
| CTP/5-Methoxy-UTP |
| CTP/5-Methoxy-UTP (cap 0) |
| CTP/5-Methoxy-UTP(No cap) |
| CTP/75% 5-Methoxy-UTP + 25% 1-Methyl-pseudo-UTP |
| CTP/75% 5-Methoxy-UTP + 25% UTP |
| CTP/UTP(No cap) |
| N1-Me-GTP |
| N4-Ac-CTP |
| N4Ac-CTP/1-Methyl-pseudo-UTP |
| N4Ac-CTP/5-Methoxy-UTP |
| N4-acetyl-cytidine TP, ATP, GTP, UTP |
| N4-Bz-CTP/5-Methoxy-UTP |
| N4-methyl CTP |
| N4-Methyl-CTP/5-Methoxy-UTP |
| Pseudo-iso-CTP/5-Methoxy-UTP |
| PseudoU-alpha-thio-TP |
| pseudouridine TP, ATP, GTP, CTP |
| pseudo-UTP/5-methyl-CTP/ATP/GTP |
| UTP-5-oxyacetic acid Me ester |
| Xanthosine |

According to the disclosure, polynucleotides of the disclosure may be synthesized to comprise the combinations or single modifications of Table 1 or Table 2.

Where a single modification is listed, the listed nucleoside or nucleotide represents 100 percent of that A, U, G or C nucleotide or nucleoside having been modified. Where percentages are listed, these represent the percentage of that particular A, U, G or C nucleobase triphosphate of the total amount of A, U, G, or C triphosphate present. For example, the combination: 25% 5-Aminoallyl-CTP+75% CTP/25% 5-Methoxy-UTP+75% UTP refers to a polynucleotide where 25% of the cytosine triphosphates are 5-Aminoallyl-CTP while 75% of the cytosines are CTP; whereas 25% of the uracils are 5-methoxy UTP while 75% of the uracils are UTP. Where no modified UTP is listed then the naturally occurring ATP, UTP, GTP and/or CTP is used at 100% of the sites of those nucleotides found in the polynucleotide. In this example all of the GTP and ATP nucleotides are left unmodified.

The mRNAs of the present disclosure, or regions thereof, may be codon optimized. Codon optimization methods are known in the art and may be useful for a variety of purposes: matching codon frequencies in host organisms to ensure proper folding, bias GC content to increase mRNA stability or reduce secondary structures, minimize tandem repeat codons or base runs that may impair gene construction or expression, customize transcriptional and translational control regions, insert or remove proteins trafficking sequences, remove/add post translation modification sites in encoded proteins (e.g., glycosylation sites), add, remove or shuffle protein domains, insert or delete restriction sites, modify ribosome binding sites and mRNA degradation sites, adjust translation rates to allow the various domains of the protein to fold properly, or to reduce or eliminate problem secondary structures within the polynucleotide. Codon optimization tools, algorithms and services are known in the art; non-limiting examples include services from GeneArt (Life Technologies), DNA2.0 (Menlo Park, Calif.) and/or proprietary methods. In one embodiment, the mRNA sequence is optimized using optimization algorithms, e.g., to optimize expression in mammalian cells or enhance mRNA stability.

In certain embodiments, the present disclosure includes polynucleotides having at least 80%, at least 85%, at least 90%, at least 95%, at least 98%, or at least 99% sequence identity to any of the polynucleotide sequences described herein.

mRNAs of the present disclosure may be produced by means available in the art, including but not limited to in vitro transcription (IVT) and synthetic methods. Enzymatic (IVT), solid-phase, liquid-phase, combined synthetic methods, small region synthesis, and ligation methods may be utilized. In one embodiment, mRNAs are made using IVT enzymatic synthesis methods. Methods of making polynucleotides by IVT are known in the art and are described in International Application PCT/US2013/30062, the contents of which are incorporated herein by reference in their entirety. Accordingly, the present disclosure also includes polynucleotides, e.g., DNA, constructs and vectors that may be used to in vitro transcribe an mRNA described herein.

Non-natural modified nucleobases may be introduced into polynucleotides, e.g., mRNA, during synthesis or post-synthesis. In certain embodiments, modifications may be on internucleoside linkages, purine or pyrimidine bases, or sugar. In particular embodiments, the modification may be introduced at the terminal of a polynucleotide chain or anywhere else in the polynucleotide chain; with chemical synthesis or with a polymerase enzyme. Examples of modified nucleic acids and their synthesis are disclosed in PCT application No. PCT/US2012/058519. Synthesis of modified polynucleotides is also described in Verma and Eckstein, Annual Review of Biochemistry, vol. 76, 99-134 (1998).

Either enzymatic or chemical ligation methods may be used to conjugate polynucleotides or their regions with different functional moieties, such as targeting or delivery agents, fluorescent labels, liquids, nanoparticles, etc. Conjugates of polynucleotides and modified polynucleotides are reviewed in Goodchild, Bioconjugate Chemistry, vol. 1(3), 165-187 (1990).

MicroRNA (miRNA) Binding Sites

Polynucleotides of the disclosure can include regulatory elements, for example, microRNA (miRNA) binding sites, transcription factor binding sites, structured mRNA sequences and/or motifs, artificial binding sites engineered to act as pseudo-receptors for endogenous nucleic acid binding molecules, and combinations thereof. In some embodiments, polynucleotides including such regulatory elements are referred to as including "sensor sequences." Non-limiting examples of sensor sequences are described in U.S. Publication 2014/0200261, the contents of which are incorporated herein by reference in their entirety.

In some embodiments, a polynucleotide (e.g., a ribonucleic acid (RNA), e.g., a messenger RNA (mRNA)) of the disclosure comprises an open reading frame (ORF) encoding a polypeptide of interest and further comprises one or more miRNA binding site(s). Inclusion or incorporation of miRNA binding site(s) provides for regulation of polynucleotides of the disclosure, and in turn, of the polypeptides encoded therefrom, based on tissue-specific and/or cell-type specific expression of naturally-occurring miRNAs.

A miRNA, e.g., a natural-occurring miRNA, is a 19-25 nucleotide long noncoding RNA that binds to a polynucleotide and down-regulates gene expression either by reducing stability or by inhibiting translation of the polynucleotide. A miRNA sequence comprises a "seed" region, i.e., a sequence in the region of positions 2-8 of the mature miRNA. A miRNA seed can comprise positions 2-8 or 2-7 of the mature miRNA. In some embodiments, a miRNA seed can comprise 7 nucleotides (e.g., nucleotides 2-8 of the mature miRNA), wherein the seed-complementary site in the corresponding miRNA binding site is flanked by an adenosine (A) opposed to miRNA position 1. In some embodiments, a miRNA seed can comprise 6 nucleotides (e.g., nucleotides 2-7 of the mature miRNA), wherein the seed-complementary site in the corresponding miRNA binding site is flanked by an adenosine (A) opposed to miRNA position 1. See, for example, Grimson A, Farh K K, Johnston W K, Garrett-Engele P, Lim L P, Bartel D P; Mol Cell. 2007 Jul. 6; 27(1):91-105. miRNA profiling of the target cells or tissues can be conducted to determine the presence or absence of miRNA in the cells or tissues. In some embodiments, a polynucleotide (e.g., a ribonucleic acid (RNA), e.g., a messenger RNA (mRNA)) of the disclosure comprises one or more microRNA binding sites, microRNA target sequences, microRNA complementary sequences, or microRNA seed complementary sequences. Such sequences can correspond to, e.g., have complementarity to, any known microRNA such as those taught in US Publication US2005/0261218 and US Publication US2005/0059005, the contents of each of which are incorporated herein by reference in their entirety.

As used herein, the term "microRNA (miRNA or miR) binding site" refers to a sequence within a polynucleotide, e.g., within a DNA or within an RNA transcript, including in the 5'UTR and/or 3'UTR, that has sufficient complementarity to all or a region of a miRNA to interact with, associate with or bind to the miRNA. In some embodiments, a polynucleotide of the disclosure comprising an ORF encoding a polypeptide of interest and further comprises one or more miRNA binding site(s). In exemplary embodiments, a 5'UTR and/or 3'UTR of the polynucleotide (e.g., a ribonucleic acid (RNA), e.g., a messenger RNA (mRNA)) comprises the one or more miRNA binding site(s).

A miRNA binding site having sufficient complementarity to a miRNA refers to a degree of complementarity sufficient to facilitate miRNA-mediated regulation of a polynucleotide, e.g., miRNA-mediated translational repression or degradation of the polynucleotide. In exemplary aspects of the disclosure, a miRNA binding site having sufficient complementarity to the miRNA refers to a degree of complementarity sufficient to facilitate miRNA-mediated degradation of the polynucleotide, e.g., miRNA-guided RNA-induced silencing complex (RISC)-mediated cleavage of mRNA. The miRNA binding site can have complementarity to, for example, a 19-25 nucleotide miRNA sequence, to a 19-23 nucleotide miRNA sequence, or to a 22 nucleotide miRNA sequence. A miRNA binding site can be complementary to only a portion of a miRNA, e.g., to a portion less than 1, 2, 3, or 4 nucleotides of the full length of a naturally-occurring miRNA sequence. Full or complete complementarity (e.g., full complementarity or complete complementarity over all or a significant portion of the length of a naturally-occurring miRNA) is preferred when the desired regulation is mRNA degradation.

In some embodiments, a miRNA binding site includes a sequence that has complementarity (e.g., partial or complete complementarity) with a miRNA seed sequence. In some embodiments, the miRNA binding site includes a sequence that has complete complementarity with a miRNA seed sequence. In some embodiments, a miRNA binding site includes a sequence that has complementarity (e.g., partial or complete complementarity) with an miRNA sequence. In some embodiments, the miRNA binding site includes a sequence that has complete complementarity with a miRNA sequence. In some embodiments, a miRNA binding site has complete complementarity with a miRNA sequence but for 1, 2, or 3 nucleotide substitutions, terminal additions, and/or truncations.

In some embodiments, the miRNA binding site is the same length as the corresponding miRNA. In other embodiments, the miRNA binding site is one, two, three, four, five, six, seven, eight, nine, ten, eleven or twelve nucleotide(s) shorter than the corresponding miRNA at the 5' terminus, the 3' terminus, or both. In still other embodiments, the microRNA binding site is two nucleotides shorter than the corresponding microRNA at the 5' terminus, the 3' terminus, or both. The miRNA binding sites that are shorter than the corresponding miRNAs are still capable of degrading the mRNA incorporating one or more of the miRNA binding sites or preventing the mRNA from translation.

In some embodiments, the miRNA binding site binds the corresponding mature miRNA that is part of an active RISC containing Dicer. In another embodiment, binding of the miRNA binding site to the corresponding miRNA in RISC degrades the mRNA containing the miRNA binding site or prevents the mRNA from being translated. In some embodiments, the miRNA binding site has sufficient complementarity to miRNA so that a RISC complex comprising the miRNA cleaves the polynucleotide comprising the miRNA binding site. In other embodiments, the miRNA binding site has imperfect complementarity so that a RISC complex comprising the miRNA induces instability in the polynucleotide comprising the miRNA binding site. In another embodiment, the miRNA binding site has imperfect complementarity so that a RISC complex comprising the miRNA represses transcription of the polynucleotide comprising the miRNA binding site.

In some embodiments, the miRNA binding site has one, two, three, four, five, six, seven, eight, nine, ten, eleven or twelve mismatch(es) from the corresponding miRNA.

In some embodiments, the miRNA binding site has at least about ten, at least about eleven, at least about twelve, at least about thirteen, at least about fourteen, at least about fifteen, at least about sixteen, at least about seventeen, at least about eighteen, at least about nineteen, at least about twenty, or at least about twenty-one contiguous nucleotides complementary to at least about ten, at least about eleven, at least about twelve, at least about thirteen, at least about fourteen, at least about fifteen, at least about sixteen, at least about seventeen, at least about eighteen, at least about nineteen, at least about twenty, or at least about twenty-one, respectively, contiguous nucleotides of the corresponding miRNA.

By engineering one or more miRNA binding sites into a polynucleotide of the disclosure, the polynucleotide can be targeted for degradation or reduced translation, provided the miRNA in question is available. This can reduce off-target effects upon delivery of the polynucleotide. For example, if a polynucleotide of the disclosure is not intended to be delivered to a tissue or cell but ends up is said tissue or cell, then a miRNA abundant in the tissue or cell can inhibit the expression of the gene of interest if one or multiple binding sites of the miRNA are engineered into the 5'UTR and/or 3'UTR of the polynucleotide.

Conversely, miRNA binding sites can be removed from polynucleotide sequences in which they naturally occur in order to increase protein expression in specific tissues. For example, a binding site for a specific miRNA can be removed from a polynucleotide to improve protein expression in tissues or cells containing the miRNA.

In one embodiment, a polynucleotide of the disclosure can include at least one miRNA-binding site in the 5'UTR and/or 3'UTR in order to regulate cytotoxic or cytoprotective mRNA therapeutics to specific cells such as, but not limited to, normal and/or cancerous cells. In another embodiment, a polynucleotide of the disclosure can include two, three, four, five, six, seven, eight, nine, ten, or more miRNA-binding sites in the 5'-UTR and/or 3'-UTR in order to regulate cytotoxic or cytoprotective mRNA therapeutics to specific cells such as, but not limited to, normal and/or cancerous cells.

Regulation of expression in multiple tissues can be accomplished through introduction or removal of one or more miRNA binding sites, e.g., one or more distinct miRNA binding sites. The decision whether to remove or insert a miRNA binding site can be made based on miRNA expression patterns and/or their profilings in tissues and/or cells in development and/or disease. Identification of miRNAs, miRNA binding sites, and their expression patterns and role in biology have been reported (e.g., Bonauer et al., Curr Drug Targets 2010 11:943-949; Anand and Cheresh Curr Opin Hematol 2011 18:171-176; Contreras and Rao Leukemia 2012 26:404-413 (2011 Dec. 20. doi: 10.1038/1eu.2011.356); Bartel Cell 2009 136:215-233; Landgraf et al, Cell, 2007 129:1401-1414; Gentner and Naldini, Tissue Antigens. 2012 80:393-403 and all references therein; each of which is incorporated herein by reference in its entirety).

miRNAs and miRNA binding sites can correspond to any known sequence, including non-limiting examples described in U.S. Publication Nos. 2014/0200261, 2005/0261218, and 2005/0059005, each of which are incorporated herein by reference in their entirety.

Examples of tissues where miRNA are known to regulate mRNA, and thereby protein expression, include, but are not limited to, liver (miR-122), muscle (miR-133, miR-206, miR-208), endothelial cells (miR-17-92, miR-126), myeloid cells (miR-142-3p, miR-142-5p, miR-16, miR-21, miR-223, miR-24, miR-27), adipose tissue (let-7, miR-30c), heart (miR-id, miR-149), kidney (miR-192, miR-194, miR-204), and lung epithelial cells (let-7, miR-133, miR-126).

Specifically, miRNAs are known to be differentially expressed in immune cells (also called hematopoietic cells), such as antigen presenting cells (APCs) (e.g., dendritic cells and macrophages), macrophages, monocytes, B lymphocytes, T lymphocytes, granulocytes, natural killer cells, etc. Immune cell specific miRNAs are involved in immunogenicity, autoimmunity, the immune response to infection, inflammation, as well as unwanted immune response after gene therapy and tissue/organ transplantation. Immune cell specific miRNAs also regulate many aspects of development, proliferation, differentiation and apoptosis of hematopoietic cells (immune cells). For example, miR-142 and miR-146 are exclusively expressed in immune cells, particularly abundant in myeloid dendritic cells. It has been demonstrated that the immune response to a polynucleotide can be shut-off by adding miR-142 binding sites to the 3'-UTR of the polynucleotide, enabling more stable gene transfer in tissues and cells. miR-142 efficiently degrades exogenous polynucleotides in antigen presenting cells and suppresses cytotoxic elimination of transduced cells (e.g., Annoni A et al., blood, 2009, 114, 5152-5161; Brown B D, et al., Nat med. 2006, 12(5), 585-591; Brown B D, et al., blood, 2007, 110(13): 4144-4152, each of which is incorporated herein by reference in its entirety).

An antigen-mediated immune response can refer to an immune response triggered by foreign antigens, which, when entering an organism, are processed by the antigen presenting cells and displayed on the surface of the antigen presenting cells. T cells can recognize the presented antigen and induce a cytotoxic elimination of cells that express the antigen.

Introducing a miR-142 binding site into the 5'UTR and/or 3'UTR of a polynucleotide of the disclosure can selectively repress gene expression in antigen presenting cells through miR-142 mediated degradation, limiting antigen presentation in antigen presenting cells (e.g., dendritic cells) and thereby preventing antigen-mediated immune response after the delivery of the polynucleotide. The polynucleotide is then stably expressed in target tissues or cells without triggering cytotoxic elimination.

In one embodiment, binding sites for miRNAs that are known to be expressed in immune cells, in particular, antigen presenting cells, can be engineered into a polynucleotide of the disclosure to suppress the expression of the polynucleotide in antigen presenting cells through miRNA mediated RNA degradation, subduing the antigen-mediated immune response. Expression of the polynucleotide is maintained in non-immune cells where the immune cell specific miRNAs are not expressed. For example, in some embodiments, to prevent an immunogenic reaction against a liver specific protein, any miR-122 binding site can be removed and a miR-142 (and/or mirR-146) binding site can be engineered into the 5'UTR and/or 3'UTR of a polynucleotide of the disclosure.

To further drive the selective degradation and suppression in APCs and macrophage, a polynucleotide of the disclosure can include a further negative regulatory element in the 5'UTR and/or 3'UTR, either alone or in combination with miR-142 and/or miR-146 binding sites. As a non-limiting example, the further negative regulatory element is a Constitutive Decay Element (CDE).

Immune cell specific miRNAs include, but are not limited to, hsa-let-7a-2-3p, hsa-let-7a-3p, hsa-7a-5p, hsa-let-7c, hsa-let-7e-3p, hsa-let-7e-5p, hsa-let-7g-3p, hsa-let-7g-5p, hsa-let-7i-3p, hsa-let-7i-5p, miR-10a-3p, miR-10a-5p, miR-1184, hsa-let-7f-1-3p, hsa-let-7f-2-5p, hsa-let-7f-5p, miR-125b-1-3p, miR-125b-2-3p, miR-125b-5p, miR-1279, miR-130a-3p, miR-130a-5p, miR-132-3p, miR-132-5p, miR-142-3p, miR-142-5p, miR-143-3p, miR-143-5p, miR-146a-3p, miR-146a-5p, miR-146b-3p, miR-146b-5p, miR-147a, miR-147b, miR-148a-5p, miR-148a-3p, miR-150-3p, miR-150-5p, miR-151b, miR-155-3p, miR-155-5p, miR-15a-3p, miR-15a-5p, miR-15b-5p, miR-15b-3p, miR-16-1-3p, miR-16-2-3p, miR-16-5p, miR-17-5p, miR-181a-3p, miR-181a-5p, miR-181a-2-3p, miR-182-3p, miR-182-5p, miR-19'7-3p, miR-197-5p, miR-21-5p, miR-21-3p, miR-214-3p, miR-214-5p, miR-223-3p, miR-223-5p, miR-221-3p, miR-221-5p, miR-23b-3p, miR-23b-5p, miR-24-1-5p, miR-24-2-5p, miR-24-3p, miR-26a-1-3p, miR-26a-2-3p, miR-26a-5p, miR-26b-3p, miR-26b-5p, miR-27a-3p, miR-27a-5p, miR-27b-3p, miR-27b-5p, miR-28-3p, miR-28-5p, miR-2909, miR-29a-3p, miR-29a-5p, miR-29b-1-5p, miR-29b-2-5p, miR-29c-3p, miR-29c-5p-miR-30e-3p, miR-30e-5p, miR-331-5p, miR-339-3p, miR-339-5p, miR-345-3p, miR-345-5p, miR-346, miR-34a-3p, miR-34a-5p-miR-363-3p, miR-363-5p, miR-372, miR-377-3p, miR-377-5p, miR-493-3p, miR-493-5p, miR-542, miR-548b-5p, miR548c-5p, miR-548i, miR-548j, miR-548n, miR-574-3p, miR-598, miR-718, miR-935, miR-99a-3p, miR-99a-5p, miR-99b-3p, and miR-99b-5p. Furthermore, novel miRNAs can be identified in immune cell through micro-array hybridization and microtome analysis (e.g., Jima D D et al, Blood, 2010, 116:e118-e127; Vaz C et al., BMC Genomics, 2010, 11, 288, the content of each of which is incorporated herein by reference in its entirety.)

miRNAs that are known to be expressed in the liver include, but are not limited to, miR-107, miR-122-3p, miR-122-5p, miR-1228-3p, miR-1228-5p, miR-1249, miR-129-5p, miR-1303, miR-151a-3p, miR-151a-5p, miR-152, miR-194-3p, miR-194-5p, miR-199a-3p, miR-199a-5p, miR-199b-3p, miR-199b-5p, miR-296-5p, miR-557, miR-581, miR-939-3p, and miR-939-5p. miRNA binding sites from any liver specific miRNA can be introduced to or removed from a polynucleotide of the disclosure to regulate expression of the polynucleotide in the liver. Liver specific miRNA binding sites can be engineered alone or further in combination with immune cell (e.g., APC) miRNA binding sites in a polynucleotide of the disclosure.

miRNAs that are known to be expressed in the lung include, but are not limited to, let-7a-2-3p, let-7a-3p, let-7a-5p, miR-126-3p, miR-126-5p, miR-127-3p, miR-127-5p, miR-130a-3p, miR-130a-5p, miR-130b-3p, miR-130b-5p, miR-133a, miR-133b, miR-134, miR-18a-3p, miR-18a-5p, miR-18b-3p, miR-18b-5p, miR-24-1-5p, miR-24-2-5p, miR-24-3p, miR-296-3p, miR-296-5p, miR-32-3p, miR-337-3p, miR-337-5p, miR-381-3p, and miR-381-5p. miRNA binding sites from any lung specific miRNA can be introduced to or removed from a polynucleotide of the disclosure to regulate expression of the polynucleotide in the lung. Lung specific miRNA binding sites can be engineered alone or further in combination with immune cell (e.g., APC) miRNA binding sites in a polynucleotide of the disclosure.

miRNAs that are known to be expressed in the heart include, but are not limited to, miR-1, miR-133a, miR-133b, miR-149-3p, miR-149-5p, miR-186-3p, miR-186-5p, miR-208a, miR-208b, miR-210, miR-296-3p, miR-320, miR-451a, miR-451b, miR-499a-3p, miR-499a-5p, miR-499b-3p, miR-499b-5p, miR-744-3p, miR-744-5p, miR-92b-3p, and miR-92b-5p. miRNA binding sites from any heart specific microRNA can be introduced to or removed from a polynucleotide of the disclosure to regulate expression of the polynucleotide in the heart. Heart specific miRNA binding sites can be engineered alone or further in combination with immune cell (e.g., APC) miRNA binding sites in a polynucleotide of the disclosure.

miRNAs that are known to be expressed in the nervous system include, but are not limited to, miR-124-5p, miR-125a-3p, miR-125a-5p, miR-125b-1-3p, miR-125b-2-3p, miR-125b-5p, miR-1271-3p, miR-1271-5p, miR-128, miR-132-5p, miR-135a-3p, miR-135a-5p, miR-135b-3p, miR-135b-5p, miR-137, miR-139-5p, miR-139-3p, miR-149-3p, miR-149-5p, miR-153, miR-181c-3p, miR-181c-5p, miR-183-3p, miR-183-5p, miR-190a, miR-190b, miR-212-3p, miR-212-5p, miR-219-1-3p, miR-219-2-3p, miR-23a-3p, miR-23a-5p, miR-30a-5p, miR-30b-3p, miR-30b-5p, miR-30c-1-3p, miR-30c-2-3p, miR-30c-5p, miR-30d-3p, miR-30d-5p, miR-329, miR-342-3p, miR-3665, miR-3666, miR-380-3p, miR-380-5p, miR-383, miR-410, miR-425-3p, miR-425-5p, miR-454-3p, miR-454-5p, miR-483, miR-510, miR-516a-3p, miR-548b-5p, miR-548c-5p, miR-571, miR-7-1-3p, miR-7-2-3p, miR-7-5p, miR-802, miR-922, miR-9-3p, and miR-9-5p. miRNAs enriched in the nervous system further include those specifically expressed in neurons, including, but not limited to, miR-132-3p, miR-132-3p, miR-148b-3p, miR-148b-5p, miR-151a-3p, miR-151a-5p, miR-212-3p, miR-212-5p, miR-320b, miR-320e, miR-323a-3p, miR-323a-5p, miR-324-5p, miR-325, miR-326, miR-328, miR-922 and those specifically expressed in glial cells, including, but not limited to, miR-1250, miR-219-1-3p, miR-219-2-3p, miR-219-5p, miR-23a-3p, miR-23a-5p, miR-3065-3p, miR-3065-5p, miR-30e-3p, miR-30e-5p, miR-32-5p, miR-338-5p, and miR-657. miRNA binding sites from any CNS specific miRNA can be introduced to or removed from a polynucleotide of the disclosure to regulate expression of the polynucleotide in the nervous system. Nervous system specific miRNA binding sites can be engineered alone or further in combination with immune cell (e.g., APC) miRNA binding sites in a polynucleotide of the disclosure.

miRNAs that are known to be expressed in the pancreas include, but are not limited to, miR-105-3p, miR-105-5p, miR-184, miR-195-3p, miR-195-5p, miR-196a-3p, miR-196a-5p, miR-214-3p, miR-214-5p, miR-216a-3p, miR-216a-5p, miR-30a-3p, miR-33a-3p, miR-33a-5p, miR-375, miR-7-1-3p, miR-7-2-3p, miR-493-3p, miR-493-5p, and miR-944. miRNA binding sites from any pancreas specific miRNA can be introduced to or removed from a polynucleotide of the disclosure to regulate expression of the polynucleotide in the pancreas. Pancreas specific miRNA binding sites can be engineered alone or further in combination with immune cell (e.g. APC) miRNA binding sites in a polynucleotide of the disclosure.

miRNAs that are known to be expressed in the kidney include, but are not limited to, miR-122-3p, miR-145-5p, miR-17-5p, miR-192-3p, miR-192-5p, miR-194-3p, miR-194-5p, miR-20a-3p, miR-20a-5p, miR-204-3p, miR-204-5p, miR-210, miR-216a-3p, miR-216a-5p, miR-296-3p, miR-30a-3p, miR-30a-5p, miR-30b-3p, miR-30b-5p, miR-30c-1-3p, miR-30c-2-3p, miR30c-5p, miR-324-3p, miR-335-3p, miR-335-5p, miR-363-3p, miR-363-5p, and miR-562. miRNA binding sites from any kidney specific miRNA can be introduced to or removed from a polynucleotide of the disclosure to regulate expression of the polynucleotide in the kidney. Kidney specific miRNA binding sites can be engineered alone or further in combination with immune cell (e.g., APC) miRNA binding sites in a polynucleotide of the disclosure.

miRNAs that are known to be expressed in the muscle include, but are not limited to, let-7g-3p, let-7g-5p, miR-1, miR-1286, miR-133a, miR-133b, miR-140-3p, miR-143-3p, miR-143-5p, miR-145-3p, miR-145-5p, miR-188-3p, miR-188-5p, miR-206, miR-208a, miR-208b, miR-25-3p, and miR-25-5p. miRNA binding sites from any muscle specific miRNA can be introduced to or removed from a polynucleotide of the disclosure to regulate expression of the polynucleotide in the muscle. Muscle specific miRNA binding sites can be engineered alone or further in combination with immune cell (e.g., APC) miRNA binding sites in a polynucleotide of the disclosure.

miRNAs are also differentially expressed in different types of cells, such as, but not limited to, endothelial cells, epithelial cells, and adipocytes.

miRNAs that are known to be expressed in endothelial cells include, but are not limited to, let-7b-3p, let-7b-5p, miR-100-3p, miR-100-5p, miR-101-3p, miR-101-5p, miR- 126-3p, miR-126-5p, miR-1236-3p, miR-1236-5p, miR-130a-3p, miR-130a-5p, miR-17-5p, miR-17-3p, miR-18a-3p, miR-18a-5p, miR-19a-3p, miR-19a-5p, miR-19b-1-5p, miR-19b-2-5p, miR-19b-3p, miR-20a-3p, miR-20a-5p, miR-217, miR-210, miR-21-3p, miR-21-5p, miR-221-3p, miR-221-5p, miR-222-3p, miR-222-5p, miR-23a-3p, miR-23a-5p, miR-296-5p, miR-361-3p, miR-361-5p, miR-421, miR-424-3p, miR-424-5p, miR-513a-5p, miR-92a-1-5p, miR-92a-2-5p, miR-92a-3p, miR-92b-3p, and miR-92b-5p. Many novel miRNAs are discovered in endothelial cells from deep-sequencing analysis (e.g., Voellenkle C et al., *RNA,* 2012, 18, 472-484, incorporated herein by reference in its entirety). miRNA binding sites from any endothelial cell specific miRNA can be introduced to or removed from a polynucleotide of the disclosure to regulate expression of the polynucleotide in the endothelial cells.

miRNAs that are known to be expressed in epithelial cells include, but are not limited to, let-7b-3p, let-7b-5p, miR-1246, miR-200a-3p, miR-200a-5p, miR-200b-3p, miR-200b-5p, miR-200c-3p, miR-200c-5p, miR-338-3p, miR-429, miR-451a, miR-451b, miR-494, miR-802 and miR-34a, miR-34b-5p, miR-34c-5p, miR-449a, miR-449b-3p, miR-449b-5p specific in respiratory ciliated epithelial cells, let-7 family, miR-133a, miR-133b, miR-126 specific in lung epithelial cells, miR-382-3p, miR-382-5p specific in renal epithelial cells, and miR-762 specific in corneal epithelial cells. miRNA binding sites from any epithelial cell specific miRNA can be introduced to or removed from a polynucleotide of the disclosure to regulate expression of the polynucleotide in the epithelial cells.

In addition, a large group of miRNAs are enriched in embryonic stem cells, controlling stem cell self-renewal as well as the development and/or differentiation of various cell lineages, such as neural cells, cardiac, hematopoietic cells, skin cells, osteogenic cells and muscle cells (e.g., Kuppusamy K T et al., Curr. Mol Med, 2013, 13(5), 757-764; Vidigal J A and Ventura A, Semin Cancer Biol. 2012, 22(5-6), 428-436; Goff L A et al., PLoS One, 2009, 4:e7192; Morin R D et al., Genome Res, 2008, 18, 610-621; Yoo J K et al., Stem Cells Dev. 2012, 21(11), 2049-2057, each of which is incorporated herein by reference in its entirety). miRNAs abundant in embryonic stem cells include, but are not limited to, let-7a-2-3p, let-a-3p, let-7a-5p, let7d-3p, let-7d-5p, miR-103a-2-3p, miR-103a-5p, miR-106b-3p, miR-106b-5p, miR-1246, miR-1275, miR-138-1-3p, miR-138-2-3p, miR-138-5p, miR-154-3p, miR-154-5p, miR-200c-3p, miR-200c-5p, miR-290, miR-301a-3p, miR-301a-5p, miR-302a-3p, miR-302a-5p, miR-302b-3p, miR-302b-5p, miR-302c-3p, miR-302c-5p, miR-302d-3p, miR-302d-5p, miR-302e, miR-367-3p, miR-367-5p, miR-369-3p, miR-369-5p, miR-370, miR-371, miR-373, miR-380-5p, miR-423-3p, miR-423-5p, miR-486-5p, miR-520c-3p, miR-548e, miR-548f, miR-548g-3p, miR-548g-5p, miR-548i, miR-548k, miR-5481, miR-548m, miR-548n, miR-548o-3p, miR-548o-5p, miR-548p, miR-664a-3p, miR-664a-5p, miR-664b-3p, miR-664b-5p, miR-766-3p, miR-766-5p, miR-885-3p, miR-885-5p, miR-93-3p, miR-93-5p, miR-941, miR-96-3p, miR-96-5p, miR-99b-3p and miR-99b-5p. Many predicted novel miRNAs are discovered by deep sequencing in human embryonic stem cells (e.g., Morin R D et al., Genome Res, 2008, 18, 610-621; Goff L A et al., PLoS One, 2009, 4:e7192; Bar M et al., Stem cells, 2008, 26, 2496-2505, the content of each of which is incorporated herein by reference in its entirety).

In one embodiment, the binding sites of embryonic stem cell specific miRNAs can be included in or removed from the 3'UTR of a polynucleotide of the disclosure to modulate the development and/or differentiation of embryonic stem cells, to inhibit the senescence of stem cells in a degenerative condition (e.g. degenerative diseases), or to stimulate the senescence and apoptosis of stem cells in a disease condition (e.g. cancer stem cells).

Many miRNA expression studies are conducted to profile the differential expression of miRNAs in various cancer cells/tissues and other diseases. Some miRNAs are abnormally over-expressed in certain cancer cells and others are under-expressed. For example, miRNAs are differentially expressed in cancer cells (WO2008/154098, US2013/0059015, US2013/0042333, WO2011/157294); cancer stem cells (US2012/0053224); pancreatic cancers and diseases (US2009/0131348, US2011/0171646, US2010/0286232, U.S. Pat. No. 8,389,210); asthma and inflammation (U.S. Pat. No. 8,415,096); prostate cancer (US2013/0053264); hepatocellular carcinoma (WO2012/151212, US2012/0329672, WO2008/054828, U.S. Pat. No. 8,252,538); lung cancer cells (WO2011/076143, WO2013/033640, WO2009/070653, US2010/0323357); cutaneous T cell lymphoma (WO2013/011378); colorectal cancer cells (WO2011/0281756, WO2011/076142); cancer positive lymph nodes (WO2009/100430, US2009/0263803); nasopharyngeal carcinoma (EP2112235); chronic obstructive pulmonary disease (US2012/0264626, US2013/0053263); thyroid cancer (WO2013/066678); ovarian cancer cells (US2012/0309645, WO2011/095623); breast cancer cells (WO2008/154098, WO2007/081740, US2012/0214699), leukemia and lymphoma (WO2008/073915, US2009/0092974, US2012/0316081, US2012/0283310, WO2010/018563), the content of each of which is incorporated herein by reference in its entirety.

As a non-limiting example, miRNA binding sites for miRNAs that are over-expressed in certain cancer and/or tumor cells can be removed from the 3'UTR of a polynucleotide of the disclosure, restoring the expression suppressed by the over-expressed miRNAs in cancer cells, thus ameliorating the corresponsive biological function, for instance, transcription stimulation and/or repression, cell cycle arrest, apoptosis and cell death. Normal cells and tissues, wherein miRNAs expression is not up-regulated, will remain unaffected.

miRNA can also regulate complex biological processes such as angiogenesis (e.g., miR-132) (Anand and Cheresh Curr Opin Hematol 2011 18:171-176). In the polynucleotides of the disclosure, miRNA binding sites that are involved in such processes can be removed or introduced, in order to tailor the expression of the polynucleotides to biologically relevant cell types or relevant biological processes. In this context, the polynucleotides of the disclosure are defined as auxotrophic polynucleotides.

In some embodiments, the therapeutic window and/or differential expression (e.g., tissue-specific expression) of a polypeptide of the disclosure may be altered by incorporation of a miRNA binding site into an mRNA encoding the polypeptide. In one example, an mRNA may include one or more miRNA binding sites that are bound by miRNAs that have higher expression in one tissue type as compared to another. In another example, an mRNA may include one or more miRNA binding sites that are bound by miRNAs that have lower expression in a cancer cell as compared to a non-cancerous cell of the same tissue of origin. When present in a cancer cell that expresses low levels of such an miRNA, the polypeptide encoded by the mRNA typically will show increased expression.

Liver cancer cells (e.g., hepatocellular carcinoma cells) typically express low levels of miR-122 as compared to normal liver cells. Therefore, an mRNA encoding a polypeptide that includes at least one miR-122 binding site (e.g., in the 3'-UTR of the mRNA) will typically express comparatively low levels of the polypeptide in normal liver cells and comparatively high levels of the polypeptide in liver cancer cells.

In some embodiments, the mRNA includes at least one miR-122 binding site, at least two miR-122 binding sites, at least three miR-122 binding sites, at least four miR-122 binding sites, or at least five miR-122 binding sites. In one aspect, the miRNA binding site binds miR-122 or is complementary to miR-122. In another aspect, the miRNA binding site binds to miR-122-3p or miR-122-5p. In a particular aspect, the miRNA binding site comprises a nucleotide sequence at least 80%, at least 85%, at least 90%, at least 95%, or 100% identical to SEQ ID NO: 175, wherein the miRNA binding site binds to miR-122. In another particular aspect, the miRNA binding site comprises a nucleotide sequence at least 80%, at least 85%, at least 90%, at least 95%, or 100% identical to SEQ ID NO: 173, wherein the miRNA binding site binds to miR-122. These sequences are shown below in Table 3.

In some embodiments, a polynucleotide of the disclosure comprises a miRNA binding site, wherein the miRNA binding site comprises one or more nucleotide sequences selected from Table 3, including one or more copies of any one or more of the miRNA binding site sequences. In some embodiments, a polynucleotide of the disclosure further comprises at least one, two, three, four, five, six, seven, eight, nine, ten, or more of the same or different miRNA binding sites selected from Table 3, including any combination thereof. In some embodiments, the miRNA binding site binds to miR-142 or is complementary to miR-142. In some embodiments, the miR-142 comprises SEQ ID NO: 27. In some embodiments, the miRNA binding site binds to miR-142-3p or miR-142-5p. In some embodiments, the miR-142-3p binding site comprises SEQ ID NO: 29. In some embodiments, the miR-142-5p binding site comprises SEQ ID NO: 31. In some embodiments, the miRNA binding site comprises a nucleotide sequence at least 80%, at least 85%, at least 90%, at least 95%, or 100% identical to SEQ ID NO: 29 or SEQ ID NO: 31

TABLE 3

Representative microRNAs and microRNA binding sites

| SEQ ID NO. | Description | Sequence |
|---|---|---|
| 27 | miR-142 | GACAGUGCAGUCACCCAUAAAGUAGAAAGCACUACUAACAGCACUGGAGGGUGUAGUGUUUCCUACUUUAUGGAUGAGUGUACUGUG |
| 28 | miR-142-3p | UGUAGUGUUUCCUACUUUAUGGA |
| 29 | miR-142-3p binding site | UCCAUAAAGUAGGAAACACUACA |
| 30 | miR-142-5p | CAUAAAGUAGAAAGCACUACU |
| 31 | miR-142-5p binding site | AGUAGUGCUUUCUACUUUAUG |
| 171 | miR-122 | CCUUAGCAGAGCUGUGGAGUGUGACAAUGGUGUUUGUGUCUAAACUAUCAAACGCCAUUAUCACACUAAAUAGCUACUGCUAGGC |

TABLE 3-continued

Representative microRNAs and microRNA binding sites

| SEQ ID NO. | Description | Sequence |
|---|---|---|
| 172 | miR-122-3p | AACGCCAUUAUCACACUAAAUA |
| 173 | miR-122-3p binding site | UAUUUAGUGUGAUAAUGGCGUU |
| 174 | miR-122-5p | UGGAGUGUGACAAUGGUGUUUG |
| 175 | miR-122-5p binding site | CAAACACCAUUGUCACACUCCA |

In some embodiments, a miRNA binding site is inserted in the polynucleotide of the disclosure in any position of the polynucleotide (e.g., the 5'UTR and/or 3'UTR). In some embodiments, the 5'UTR comprises a miRNA binding site. In some embodiments, the 3'UTR comprises a miRNA binding site. In some embodiments, the 5'UTR and the 3'UTR comprise a miRNA binding site. The insertion site in the polynucleotide can be anywhere in the polynucleotide as long as the insertion of the miRNA binding site in the polynucleotide does not interfere with the translation of a functional polypeptide in the absence of the corresponding miRNA; and in the presence of the miRNA, the insertion of the miRNA binding site in the polynucleotide and the binding of the miRNA binding site to the corresponding miRNA are capable of degrading the polynucleotide or preventing the translation of the polynucleotide.

In some embodiments, a miRNA binding site is inserted in at least about 30 nucleotides downstream from the stop codon of an ORF in a polynucleotide of the disclosure comprising the ORF. In some embodiments, a miRNA binding site is inserted in at least about 10 nucleotides, at least about 15 nucleotides, at least about 20 nucleotides, at least about 25 nucleotides, at least about 30 nucleotides, at least about 35 nucleotides, at least about 40 nucleotides, at least about 45 nucleotides, at least about 50 nucleotides, at least about 55 nucleotides, at least about 60 nucleotides, at least about 65 nucleotides, at least about 70 nucleotides, at least about 75 nucleotides, at least about 80 nucleotides, at least about 85 nucleotides, at least about 90 nucleotides, at least about 95 nucleotides, or at least about 100 nucleotides downstream from the stop codon of an ORF in a polynucleotide of the disclosure. In some embodiments, a miRNA binding site is inserted in about 10 nucleotides to about 100 nucleotides, about 20 nucleotides to about 90 nucleotides, about 30 nucleotides to about 80 nucleotides, about 40 nucleotides to about 70 nucleotides, about 50 nucleotides to about 60 nucleotides, about 45 nucleotides to about 65 nucleotides downstream from the stop codon of an ORF in a polynucleotide of the disclosure.

miRNA gene regulation can be influenced by the sequence surrounding the miRNA such as, but not limited to, the species of the surrounding sequence, the type of sequence (e.g., heterologous, homologous, exogenous, endogenous, or artificial), regulatory elements in the surrounding sequence and/or structural elements in the surrounding sequence. The miRNA can be influenced by the 5'UTR and/or 3'UTR. As a non-limiting example, a non-human 3'UTR can increase the regulatory effect of the miRNA sequence on the expression of a polypeptide of interest compared to a human 3'UTR of the same sequence type.

In one embodiment, other regulatory elements and/or structural elements of the 5'UTR can influence miRNA mediated gene regulation. One example of a regulatory element and/or structural element is a structured IRES (Internal Ribosome Entry Site) in the 5'UTR, which is necessary for the binding of translational elongation factors to initiate protein translation. EIF4A2 binding to this secondarily structured element in the 5'-UTR is necessary for miRNA mediated gene expression (Meijer H A et al., Science, 2013, 340, 82-85, incorporated herein by reference in its entirety). The polynucleotides of the disclosure can further include this structured 5'UTR in order to enhance microRNA mediated gene regulation.

At least one miRNA binding site can be engineered into the 3'UTR of a polynucleotide of the disclosure. In this context, at least two, at least three, at least four, at least five, at least six, at least seven, at least eight, at least nine, at least ten, or more miRNA binding sites can be engineered into a 3'UTR of a polynucleotide of the disclosure. For example, 1 to 10, 1 to 9, 1 to 8, 1 to 7, 1 to 6, 1 to 5, 1 to 4, 1 to 3, 2, or 1 miRNA binding sites can be engineered into the 3'UTR of a polynucleotide of the disclosure. In one embodiment, miRNA binding sites incorporated into a polynucleotide of the disclosure can be the same or can be different miRNA sites. A combination of different miRNA binding sites incorporated into a polynucleotide of the disclosure can include combinations in which more than one copy of any of the different miRNA sites are incorporated. In another embodiment, miRNA binding sites incorporated into a polynucleotide of the disclosure can target the same or different tissues in the body. As a non-limiting example, through the introduction of tissue-, cell-type-, or disease-specific miRNA binding sites in the 3'-UTR of a polynucleotide of the disclosure, the degree of expression in specific cell types (e.g., hepatocytes, myeloid cells, endothelial cells, cancer cells, etc.) can be reduced.

In one embodiment, a miRNA binding site can be engineered near the 5' terminus of the 3'UTR, about halfway between the 5' terminus and 3' terminus of the 3'UTR and/or near the 3' terminus of the 3'UTR in a polynucleotide of the disclosure. As a non-limiting example, a miRNA binding site can be engineered near the 5' terminus of the 3'UTR and about halfway between the 5' terminus and 3' terminus of the 3'UTR. As another non-limiting example, a miRNA binding site can be engineered near the 3' terminus of the 3'UTR and about halfway between the 5' terminus and 3' terminus of the 3'UTR. As yet another non-limiting example, a miRNA binding site can be engineered near the 5' terminus of the 3'UTR and near the 3' terminus of the 3'UTR.

In another embodiment, a 3'UTR can comprise 1, 2, 3, 4, 5, 6, 7, 8, 9, or 10 miRNA binding sites. The miRNA binding sites can be complementary to a miRNA, miRNA seed sequence, and/or miRNA sequences flanking the seed sequence.

In one embodiment, a polynucleotide of the disclosure can be engineered to include more than one miRNA site expressed in different tissues or different cell types of a subject. As a non-limiting example, a polynucleotide of the disclosure can be engineered to include miR-192 and miR-122 to regulate expression of the polynucleotide in the liver and kidneys of a subject. In another embodiment, a polynucleotide of the disclosure can be engineered to include more than one miRNA site for the same tissue.

In some embodiments, the therapeutic window and or differential expression associated with the polypeptide encoded by a polynucleotide of the disclosure can be altered with a miRNA binding site. For example, a polynucleotide encoding a polypeptide that provides a death signal can be designed to be more highly expressed in cancer cells by virtue of the miRNA signature of those cells. Where a cancer cell expresses a lower level of a particular miRNA, the polynucleotide encoding the binding site for that miRNA (or miRNAs) would be more highly expressed. Hence, the polypeptide that provides a death signal triggers or induces cell death in the cancer cell. Neighboring noncancer cells, harboring a higher expression of the same miRNA would be less affected by the encoded death signal as the polynucleotide would be expressed at a lower level due to the effects of the miRNA binding to the binding site or "sensor" encoded in the 3'UTR. Conversely, cell survival or cytoprotective signals can be delivered to tissues containing cancer and non-cancerous cells where a miRNA has a higher expression in the cancer cells—the result being a lower survival signal to the cancer cell and a larger survival signal to the normal cell. Multiple polynucleotides can be designed and administered having different signals based on the use of miRNA binding sites as described herein.

In some embodiments, the expression of a polynucleotide of the disclosure can be controlled by incorporating at least one sensor sequence in the polynucleotide and formulating the polynucleotide for administration. As a non-limiting example, a polynucleotide of the disclosure can be targeted to a tissue or cell by incorporating a miRNA binding site and formulating the polynucleotide in a lipid nanoparticle comprising a cationic lipid, including any of the lipids described herein.

A polynucleotide of the disclosure can be engineered for more targeted expression in specific tissues, cell types, or biological conditions based on the expression patterns of miRNAs in the different tissues, cell types, or biological conditions. Through introduction of tissue-specific miRNA binding sites, a polynucleotide of the disclosure can be designed for optimal protein expression in a tissue or cell, or in the context of a biological condition.

In some embodiments, a polynucleotide of the disclosure can be designed to incorporate miRNA binding sites that either have 100% identity to known miRNA seed sequences or have less than 100% identity to miRNA seed sequences. In some embodiments, a polynucleotide of the disclosure can be designed to incorporate miRNA binding sites that have at least: 60%, 65%, 70%, 75%, 80%, 85%, 90%, 95%, 96%, 97%, 98%, or 99% identity to known miRNA seed sequences. The miRNA seed sequence can be partially mutated to decrease miRNA binding affinity and as such result in reduced downmodulation of the polynucleotide. In essence, the degree of match or mis-match between the miRNA binding site and the miRNA seed can act as a rheostat to more finely tune the ability of the miRNA to modulate protein expression. In addition, mutation in the non-seed region of a miRNA binding site can also impact the ability of a miRNA to modulate protein expression.

In one embodiment, a miRNA sequence can be incorporated into the loop of a stem loop.

In another embodiment, a miRNA seed sequence can be incorporated in the loop of a stem loop and a miRNA binding site can be incorporated into the 5' or 3' stem of the stem loop.

In one embodiment, a translation enhancer element (TEE) can be incorporated on the 5'end of the stem of a stem loop and a miRNA seed can be incorporated into the stem of the stem loop. In another embodiment, a TEE can be incorporated on the 5' end of the stem of a stem loop, a miRNA seed can be incorporated into the stem of the stem loop and a miRNA binding site can be incorporated into the 3' end of the stem or the sequence after the stem loop. The miRNA seed and the miRNA binding site can be for the same and/or different miRNA sequences.

In one embodiment, the incorporation of a miRNA sequence and/or a TEE sequence changes the shape of the stem loop region which can increase and/or decrease translation. (see e.g, Kedde et al., "A *Pumilio*-induced RNA structure switch in p27-3'UTR controls miR-221 and miR-22 accessibility." Nature Cell Biology. 2010, incorporated herein by reference in its entirety).

In one embodiment, the 5'-UTR of a polynucleotide of the disclosure can comprise at least one miRNA sequence. The miRNA sequence can be, but is not limited to, a 19 or 22 nucleotide sequence and/or a miRNA sequence without the seed.

In one embodiment the miRNA sequence in the 5'UTR can be used to stabilize a polynucleotide of the disclosure described herein.

In another embodiment, a miRNA sequence in the 5'UTR of a polynucleotide of the disclosure can be used to decrease the accessibility of the site of translation initiation such as, but not limited to a start codon. See, e.g., Matsuda et al., PLoS One. 2010 11(5):e15057; incorporated herein by reference in its entirety, which used antisense locked nucleic acid (LNA) oligonucleotides and exon-junction complexes (EJCs) around a start codon (−4 to +37 where the A of the AUG codons is +1) in order to decrease the accessibility to the first start codon (AUG). Matsuda showed that altering the sequence around the start codon with an LNA or EJC affected the efficiency, length and structural stability of a polynucleotide. A polynucleotide of the disclosure can comprise a miRNA sequence, instead of the LNA or EJC sequence described by Matsuda et al, near the site of translation initiation in order to decrease the accessibility to the site of translation initiation. The site of translation initiation can be prior to, after or within the miRNA sequence. As a non-limiting example, the site of translation initiation can be located within a miRNA sequence such as a seed sequence or binding site. As another non-limiting example, the site of translation initiation can be located within a miR-122 sequence such as the seed sequence or the mir-122 binding site.

In some embodiments, a polynucleotide of the disclosure can include at least one miRNA in order to dampen the antigen presentation by antigen presenting cells. The miRNA can be the complete miRNA sequence, the miRNA seed sequence, the miRNA sequence without the seed, or a combination thereof. As a non-limiting example, a miRNA incorporated into a polynucleotide of the disclosure can be specific to the hematopoietic system. As another non-limiting example, a miRNA incorporated into a polynucleotide of the disclosure to dampen antigen presentation is miR-142-3p.

In some embodiments, a polynucleotide of the disclosure can include at least one miRNA in order to dampen expression of the encoded polypeptide in a tissue or cell of interest. As a non-limiting example, a polynucleotide of the disclosure can include at least one miR-122 binding site in order to dampen expression of an encoded polypeptide of interest in the liver. As another non-limiting example a polynucleotide of the disclosure can include at least one miR-142-3p binding site, miR-142-3p seed sequence, miR-142-3p binding site without the seed, miR-142-5p binding site, miR-142-5p seed sequence, miR-142-5p binding site without the seed, miR-146 binding site, miR-146 seed sequence and/or miR-146 binding site without the seed sequence.

In some embodiments, a polynucleotide of the disclosure can comprise at least one miRNA binding site in the 3'UTR in order to selectively degrade mRNA therapeutics in the immune cells to subdue unwanted immunogenic reactions caused by therapeutic delivery. As a non-limiting example, the miRNA binding site can make a polynucleotide of the disclosure more unstable in antigen presenting cells. Non-limiting examples of these miRNAs include mir-142-5p, mir-142-3p, mir-146a-5p, and mir-146-3p.

In one embodiment, a polynucleotide of the disclosure comprises at least one miRNA sequence in a region of the polynucleotide that can interact with a RNA binding protein.

In some embodiments, the polynucleotide of the disclosure (e.g., a RNA, e.g., a mRNA) comprising (i) a sequence-optimized nucleotide sequence (e.g., an ORF) and (ii) a miRNA binding site (e.g., a miRNA binding site that binds to miR-142).

In some embodiments, the polynucleotide of the disclosure comprises a uracil-modified sequence encoding a polypeptide disclosed herein and a miRNA binding site disclosed herein, e.g., a miRNA binding site that binds to miR-142 or miR-122. In some embodiments, the uracil-modified sequence encoding a polypeptide comprises at least one chemically modified nucleobase, e.g., 5-methoxyuracil. In some embodiments, at least 95% of a type of nucleobase (e.g., uracil) in a uracil-modified sequence encoding a polypeptide of the disclosure are modified nucleobases. In some embodiments, at least 95% of uricil in a uracil-modified sequence encoding a polypeptide is 5-methoxyuridine. In some embodiments, the polynucleotide comprising a nucleotide sequence encoding a polypeptide disclosed herein and a miRNA binding site is formulated with a delivery agent, e.g., a compound having the Formula (I), e.g., any of Compounds 1-147.

Modified Polynucleotides Comprising Functional RNA Elements

The present disclosure provides synthetic polynucleotides comprising a modification (e.g., an RNA element), wherein the modification provides a desired translational regulatory activity. In some embodiments, the disclosure provides a polynucleotide comprising a 5' untranslated region (UTR), an initiation codon, a full open reading frame encoding a polypeptide, a 3' UTR, and at least one modification, wherein the at least one modification provides a desired translational regulatory activity, for example, a modification that promotes and/or enhances the translational fidelity of mRNA translation. In some embodiments, the desired translational regulatory activity is a cis-acting regulatory activity. In some embodiments, the desired translational regulatory activity is an increase in the residence time of the 43S pre-initiation complex (PIC) or ribosome at, or proximal to, the initiation codon. In some embodiments, the desired translational regulatory activity is an increase in the initiation of polypeptide synthesis at or from the initiation codon. In some embodiments, the desired translational regulatory activity is an increase in the amount of polypeptide translated from the full open reading frame. In some embodiments, the desired translational regulatory activity is an increase in the fidelity of initiation codon decoding by the PIC or ribosome. In some embodiments, the desired translational regulatory activity is inhibition or reduction of leaky scanning by the PIC or ribosome. In some embodiments, the desired translational regulatory activity is a decrease in the rate of decoding the initiation codon by the PIC or ribosome. In some embodiments, the desired translational regulatory activity is inhibition or reduction in the initiation of polypeptide synthesis at any codon within the mRNA other than the initiation codon. In some embodiments, the desired translational regulatory activity is inhibition or reduction of the amount of polypeptide translated from any open reading frame within the mRNA other than the full open reading frame. In some embodiments, the desired translational regulatory activity is inhibition or reduction in the production of aberrant translation products. In some embodiments, the desired translational regulatory activity is a combination of one or more of the foregoing translational regulatory activities.

Accordingly, the present disclosure provides a polynucleotide, e.g., an mRNA, comprising an RNA element that comprises a sequence and/or an RNA secondary structure(s) that provides a desired translational regulatory activity as described herein. In some aspects, the mRNA comprises an RNA element that comprises a sequence and/or an RNA secondary structure(s) that promotes and/or enhances the translational fidelity of mRNA translation. In some aspects, the mRNA comprises an RNA element that comprises a sequence and/or an RNA secondary structure(s) that provides a desired translational regulatory activity, such as inhibiting and/or reducing leaky scanning. In some aspects, the disclosure provides an mRNA that comprises an RNA element that comprises a sequence and/or an RNA secondary structure(s) that inhibits and/or reduces leaky scanning thereby promoting the translational fidelity of the mRNA.

In some embodiments, the RNA element comprises natural and/or modified nucleotides. In some embodiments, the RNA element comprises of a sequence of linked nucleotides, or derivatives or analogs thereof, that provides a desired translational regulatory activity as described herein. In some embodiments, the RNA element comprises a sequence of linked nucleotides, or derivatives or analogs thereof, that forms or folds into a stable RNA secondary structure, wherein the RNA secondary structure provides a desired translational regulatory activity as described herein. RNA elements can be identified and/or characterized based on the primary sequence of the element (e.g., GC-rich element), by RNA secondary structure formed by the element (e.g. stem-loop), by the location of the element within the RNA molecule (e.g., located within the 5' UTR of an mRNA), by the biological function and/or activity of the element (e.g., “translational enhancer element”), and any combination thereof.

In some aspects, the disclosure provides an mRNA having one or more structural modifications that inhibits leaky scanning and/or promotes the translational fidelity of mRNA translation, wherein at least one of the structural modifications is a GC-rich RNA element. In some aspects, the disclosure provides a modified mRNA comprising at least one modification, wherein at least one modification is a GC-rich RNA element comprising a sequence of linked nucleotides, or derivatives or analogs thereof, preceding a Kozak consensus sequence in a 5' UTR of the mRNA. In one embodiment, the GC-rich RNA element is located about 30, about 25, about 20, about 15, about 10, about 5, about 4, about 3, about 2, or about 1 nucleotide(s) upstream of a Kozak consensus sequence in the 5' UTR of the mRNA. In another embodiment, the GC-rich RNA element is located 15-30, 15-20, 15-25, 10-15, or 5-10 nucleotides upstream of a Kozak consensus sequence. In another embodiment, the GC-rich RNA element is located immediately adjacent to a Kozak consensus sequence in the 5' UTR of the mRNA.

In any of the foregoing or related aspects, the disclosure provides a GC-rich RNA element which comprises a sequence of 3-30, 5-25, 10-20, 15-20, about 20, about 15, about 12, about 10, about 7, about 6 or about 3 nucleotides, derivatives or analogs thereof, linked in any order, wherein the sequence composition is 70-80% cytosine, 60-70% cytosine, 50%-60% cytosine, 40-50% cytosine, 30-40% cytosine bases. In any of the foregoing or related aspects, the disclosure provides a GC-rich RNA element which comprises a sequence of 3-30, 5-25, 10-20, 15-20, about 20, about 15, about 12, about 10, about 7, about 6 or about 3 nucleotides, derivatives or analogs thereof, linked in any order, wherein the sequence composition is about 80% cytosine, about 70% cytosine, about 60% cytosine, about 50% cytosine, about 40% cytosine, or about 30% cytosine.

In any of the foregoing or related aspects, the disclosure provides a GC-rich RNA element which comprises a sequence of 20, 19, 18, 17, 16, 15, 14, 13, 12, 11, 10, 9, 8, 7, 6, 5, 4, or 3 nucleotides, or derivatives or analogs thereof, linked in any order, wherein the sequence composition is 70-80% cytosine, 60-70% cytosine, 50%-60% cytosine, 40-50% cytosine, or 30-40% cytosine. In any of the foregoing or related aspects, the disclosure provides a GC-rich RNA element which comprises a sequence of 20, 19, 18, 17, 16, 15, 14, 13, 12, 11, 10, 9, 8, 7, 6, 5, 4, or 3 nucleotides, or derivatives or analogs thereof, linked in any order, wherein the sequence composition is about 80% cytosine, about 70% cytosine, about 60% cytosine, about 50% cytosine, about 40% cytosine, or about 30% cytosine.

In some embodiments, the disclosure provides a modified mRNA comprising at least one modification, wherein at least one modification is a GC-rich RNA element comprising a sequence of linked nucleotides, or derivatives or analogs thereof, preceding a Kozak consensus sequence in a 5' UTR of the mRNA, wherein the GC-rich RNA element is located about 30, about 25, about 20, about 15, about 10, about 5, about 4, about 3, about 2, or about 1 nucleotide(s) upstream of a Kozak consensus sequence in the 5' UTR of the mRNA, and wherein the GC-rich RNA element comprises a sequence of 3, 4, 5, 6, 7, 8, 9, 10, 11, 12, 13, 14, 15, 16, 17, 18, 19, or 20 nucleotides, or derivatives or analogs thereof, linked in any order, wherein the sequence composition is >50% cytosine. In some embodiments, the sequence composition is >55% cytosine, >60% cytosine, >65% cytosine, >70% cytosine, >75% cytosine, >80% cytosine, >85% cytosine, or >90% cytosine.

In other aspects, the disclosure provides a modified mRNA comprising at least one modification, wherein at least one modification is a GC-rich RNA element comprising a sequence of linked nucleotides, or derivatives or analogs thereof, preceding a Kozak consensus sequence in a 5' UTR of the mRNA, wherein the GC-rich RNA element is located about 30, about 25, about 20, about 15, about 10, about 5, about 4, about 3, about 2, or about 1 nucleotide(s) upstream of a Kozak consensus sequence in the 5' UTR of the mRNA, and wherein the GC-rich RNA element comprises a sequence of about 3-30, 5-25, 10-20, 15-20 or about 20, about 15, about 12, about 10, about 6 or about 3 nucleotides, or derivatives or analogues thereof, wherein the sequence comprises a repeating GC-motif, wherein the repeating GC-motif is [CCG]n, wherein n=1 to 10, n=2 to 8, n=3 to 6, or n=4 to 5. In some embodiments, the sequence comprises a repeating GC-motif [CCG]n, wherein n=1, 2, 3, 4 or 5. In some embodiments, the sequence comprises a repeating GC-motif [CCG]n, wherein n=1, 2, or 3. In some embodiments, the sequence comprises a repeating GC-motif

[CCG]n, wherein n=1. In some embodiments, the sequence comprises a repeating GC-motif [CCG]n, wherein n=2. In some embodiments, the sequence comprises a repeating GC-motif [CCG]n, wherein n=3. In some embodiments, the sequence comprises a repeating GC-motif [CCG]n, wherein n=4 (SEQ ID NO: 177). In some embodiments, the sequence comprises a repeating GC-motif [CCG]n, wherein n=5 (SEQ ID NO: 178).

In another aspect, the disclosure provides a modified mRNA comprising at least one modification, wherein at least one modification is a GC-rich RNA element comprising a sequence of linked nucleotides, or derivatives or analogs thereof, preceding a Kozak consensus sequence in a 5' UTR of the mRNA, wherein the GC-rich RNA element comprises any one of the sequences set forth in Table 4. In one embodiment, the GC-rich RNA element is located about 30, about 25, about 20, about 15, about 10, about 5, about 4, about 3, about 2, or about 1 nucleotide(s) upstream of a Kozak consensus sequence in the 5' UTR of the mRNA. In another embodiment, the GC-rich RNA element is located about 15-30, 15-20, 15-25, 10-15, or 5-10 nucleotides upstream of a Kozak consensus sequence. In another embodiment, the GC-rich RNA element is located immediately adjacent to a Kozak consensus sequence in the 5' UTR of the mRNA.

In other aspects, the disclosure provides a modified mRNA comprising at least one modification, wherein at least one modification is a GC-rich RNA element comprising the sequence V1 [CCCCGGCGCC] (SEQ ID NO: 179) as set forth in Table 4, or derivatives or analogs thereof, preceding a Kozak consensus sequence in the 5' UTR of the mRNA. In some embodiments, the GC-rich element comprises the sequence V1 as set forth in Table 4 located immediately adjacent to and upstream of the Kozak consensus sequence in the 5' UTR of the mRNA. In some embodiments, the GC-rich element comprises the sequence V1 as set forth in Table 4 located 1, 2, 3, 4, 5, 6, 7, 8, 9 or 10 bases upstream of the Kozak consensus sequence in the 5' UTR of the mRNA. In other embodiments, the GC-rich element comprises the sequence V1 as set forth in Table 4 located 1-3, 3-5, 5-7, 7-9, 9-12, or 12-15 bases upstream of the Kozak consensus sequence in the 5' UTR of the mRNA.

In other aspects, the disclosure provides a modified mRNA comprising at least one modification, wherein at least one modification is a GC-rich RNA element comprising the sequence V2 [CCCCGGC] as set forth in Table 4, or derivatives or analogs thereof, preceding a Kozak consensus sequence in the 5' UTR of the mRNA. In some embodiments, the GC-rich element comprises the sequence V2 as set forth in Table 4 located immediately adjacent to and upstream of the Kozak consensus sequence in the 5' UTR of the mRNA. In some embodiments, the GC-rich element comprises the sequence V2 as set forth in Table 4 located 1, 2, 3, 4, 5, 6, 7, 8, 9 or 10 bases upstream of the Kozak consensus sequence in the 5' UTR of the mRNA. In other embodiments, the GC-rich element comprises the sequence V2 as set forth in Table 4 located 1-3, 3-5, 5-7, 7-9, 9-12, or 12-15 bases upstream of the Kozak consensus sequence in the 5' UTR of the mRNA.

In other aspects, the disclosure provides a modified mRNA comprising at least one modification, wherein at least one modification is a GC-rich RNA element comprising the sequence EK [GCCGCC] as set forth in Table 4, or derivatives or analogs thereof, preceding a Kozak consensus sequence in the 5' UTR of the mRNA. In some embodiments, the GC-rich element comprises the sequence EK as set forth in Table 4 located immediately adjacent to and upstream of the Kozak consensus sequence in the 5' UTR of the mRNA. In some embodiments, the GC-rich element comprises the sequence EK as set forth in Table 4 located 1, 2, 3, 4, 5, 6, 7, 8, 9 or 10 bases upstream of the Kozak consensus sequence in the 5' UTR of the mRNA. In other embodiments, the GC-rich element comprises the sequence EK as set forth in Table 4 located 1-3, 3-5, 5-7, 7-9, 9-12, or 12-15 bases upstream of the Kozak consensus sequence in the 5' UTR of the mRNA.

In yet other aspects, the disclosure provides a modified mRNA comprising at least one modification, wherein at least one modification is a GC-rich RNA element comprising the sequence V1 [CCCCGGCGCC] (SEQ ID NO: 179) as set forth in Table 4, or derivatives or analogs thereof, preceding a Kozak consensus sequence in the 5' UTR of the mRNA, wherein the 5' UTR comprises the following sequence shown in Table 4:

(SEQ ID NO: 180)
GGGAAATAAGAGAGAAAAGAAGAGTAAGAAGAAATATAAGA.

In some embodiments, the GC-rich element comprises the sequence V1 as set forth in Table 4 located immediately adjacent to and upstream of the Kozak consensus sequence in the 5' UTR sequence shown in Table 4. In some embodiments, the GC-rich element comprises the sequence V1 as set forth in Table 4 located 1, 2, 3, 4, 5, 6, 7, 8, 9 or 10 bases upstream of the Kozak consensus sequence in the 5' UTR of the mRNA, wherein the 5' UTR comprises the following sequence shown in Table 4:

(SEQ ID NO: 180)
GGGAAATAAGAGAGAAAAGAAGAGTAAGAAGAAATATAAGA.

In other embodiments, the GC-rich element comprises the sequence V1 as set forth in Table 4 located 1-3, 3-5, 5-7, 7-9, 9-12, or 12-15 bases upstream of the Kozak consensus sequence in the 5' UTR of the mRNA, wherein the 5' UTR comprises the following sequence shown in Table 4:

(SEQ ID NO: 180)
GGGAAATAAGAGAGAAAAGAAGAGTAAGAAGAAATATAAGA.

In some embodiments, the 5' UTR comprises the following sequence set forth in Table 4:

(SEQ ID NO: 181)
GGGAAATAAGAGAGAAAAGAAGAGTAAGAAGAAATATAAGACCCCGGCGC

CGCCACC

In some embodiments, the 5' UTR comprises the following sequence set forth in Table 4:

(SEQ ID NO: 182)
GGGAAATAAGAGAGAAAAGAAGAGTAAGAAGAAATATAAGACCCCGGCGC

CACC

TABLE 4

| SEQ ID NO: | 5' UTRs | 5'UTR Sequence |
|---|---|---|
| 176 | Standard | GGGAAATAAGAGAGAAAAGAAGAGTAAGAA GAATATAAGAGCCACC |
| 180 | UTR | GGGAAATAAGAGAGAAAAGAAGAGTAAGAA GAAATATAAGA |
| 181 | V1-UTR | GGGAAATAAGAGAGAAAAGAAGAGTAAGAA GAAATATAAGACCCCGGCGCCGCCACC |
| 182 | V2-UTR | GGGAAATAAGAGAGAAAAGAAGAGTAAGAA GAAATATAAGACCCCGGCGCCACC |
| **SEQ ID NO:** | **GC-Rich RNA Elements** | **Sequence** |
| | K0 (Traditional Kozak consensus) | [GCCA/GCC] |
| | EK | [GCCGCC] |
| 179 | V1 | [CCCCGGCGCC] |
| | V2 | [CCCCGGC] |
| | $(CCG)_n$, where n = 1-10 | $[CCG]_n$ |
| | $(GCC)_n$, where N = 1-10 | $[GCC]_n$ |
| 177 | $(CCG)_n$, where n = 4 | [CCGCCGCCGCCG] |
| 178 | $(CCG)_n$, where n = 5 | [CCGCCGCCGCCGCCG] |

In another aspect, the disclosure provides a modified mRNA comprising at least one modification, wherein at least one modification is a GC-rich RNA element comprising a stable RNA secondary structure comprising a sequence of nucleotides, or derivatives or analogs thereof, linked in an order which forms a hairpin or a stem-loop. In one embodiment, the stable RNA secondary structure is upstream of the Kozak consensus sequence. In another embodiment, the stable RNA secondary structure is located about 30, about 25, about 20, about 15, about 10, or about 5 nucleotides upstream of the Kozak consensus sequence. In another embodiment, the stable RNA secondary structure is located about 20, about 15, about 10 or about 5 nucleotides upstream of the Kozak consensus sequence. In another embodiment, the stable RNA secondary structure is located about 5, about 4, about 3, about 2, about 1 nucleotides upstream of the Kozak consensus sequence. In another embodiment, the stable RNA secondary structure is located about 15-30, about 15-20, about 15-25, about 10-15, or about 5-10 nucleotides upstream of the Kozak consensus sequence. In another embodiment, the stable RNA secondary structure is located 12-15 nucleotides upstream of the Kozak consensus sequence. In another embodiment, the stable RNA secondary structure has a deltaG of about −30 kcal/mol, about −20 to −30 kcal/mol, about −20 kcal/mol, about −10 to −20 kcal/mol, about −10 kcal/mol, about −5 to −10 kcal/mol.

In another embodiment, the modification is operably linked to an open reading frame encoding a polypeptide and wherein the modification and the open reading frame are heterologous.

In another embodiment, the sequence of the GC-rich RNA element is comprised exclusively of guanine (G) and cytosine (C) nucleobases.

RNA elements that provide a desired translational regulatory activity as described herein can be identified and characterized using known techniques, such as ribosome profiling. Ribosome profiling is a technique that allows the determination of the positions of PICs and/or ribosomes bound to mRNAs (see e.g., Ingolia et al., (2009) Science 324(5924):218-23, incorporated herein by reference). The technique is based on protecting a region or segment of mRNA, by the PIC and/or ribosome, from nuclease digestion. Protection results in the generation of a 30-bp fragment of RNA termed a ‘footprint’. The sequence and frequency of RNA footprints can be analyzed by methods known in the art (e.g., RNA-seq). The footprint is roughly centered on the A-site of the ribosome. If the PIC or ribosome dwells at a particular position or location along an mRNA, footprints generated at these position would be relatively common. Studies have shown that more footprints are generated at positions where the PIC and/or ribosome exhibits decreased processivity and fewer footprints where the PIC and/or ribosome exhibits increased processivity (Gardin et al., (2014) eLife 3:e03735). In some embodiments, residence time or the time of occupancy of a the PIC or ribosome at a discrete position or location along an polynucleotide comprising any one or more of the RNA elements described herein is determined by ribosome profiling.

Preparation of High Purity RNA

In order to enhance the purity of synthetically produced RNA, modified in vitro transcription (IVT) processes which produce RNA preparations having vastly different properties from RNA produced using a traditional IVT process may be used. The RNA preparations produced according to these methods have properties that enable the production of qualitatively and quantitatively superior compositions. Even when coupled with extensive purification processes, RNA produced using traditional IVT methods is qualitatively and quantitatively distinct from the RNA preparations produced by the modified IVT processes. For instance, the purified RNA preparations are less immunogenic in comparison to RNA preparations made using traditional IVT. Additionally, increased protein expression levels with higher purity are produced from the purified RNA preparations.

Traditional IVT reactions are performed by incubating a DNA template with an RNA polymerase and equimolar quantities of nucleotide triphosphates, including GTP, ATP, CTP, and UTP in a transcription buffer. An RNA transcript having a 5' terminal guanosine triphosphate is produced from this reaction. These reactions also result in the production of a number of impurities such as double stranded and single stranded RNAs which are immunostimulatory and may have an additive impact. The purity methods described herein prevent formation of reverse complements and thus prevent the innate immune recognition of both species. In some embodiments the modified IVT methods result in the production of RNA having significantly reduced T cell activity than an RNA preparation made using prior art methods with equimolar NTPs. The prior art attempts to remove these undesirable components using a series of subsequent purification steps. Such purification methods are undesirable because they involve additional time and resources and also result in the incorporation of residual organic solvents in the final product, which is undesirable for a pharmaceutical product. It is labor and capital intensive to scale up processes like reverse phase chromatography (RP): utilizing for instance explosion proof facilities, HPLC columns and purification systems rated for high pressure, high temperature, flammable solvents etc. The scale and throughput for large scale manufacture are limited by these factors. Subsequent purification is also required to remove alkylammonium ion pair utilized in RP process. In contrast the methods described herein even enhance currently utilized methods (eg RP). Lower impurity load leads to higher purification recovery of full length RNA devoid of cytokine inducing contaminants eg. higher quality of materials at the outset.

The modified IVT methods involve the manipulation of one or more of the reaction parameters in the IVT reaction to produce a RNA preparation of highly functional RNA without one or more of the undesirable contaminants produced using the prior art processes. One parameter in the IVT reaction that may be manipulated is the relative amount of a nucleotide or nucleotide analog in comparison to one or more other nucleotides or nucleotide analogs in the reaction mixture (e.g., disparate nucleotide amounts or concentration). For instance, the IVT reaction may include an excess of a nucleotides, e.g., nucleotide monophosphate, nucleotide diphosphate or nucleotide triphosphate and/or an excess of nucleotide analogs and/or nucleoside analogs. The methods produce a high yield product which is significantly more pure than products produced by traditional IVT methods.

Nucleotide analogs are compounds that have the general structure of a nucleotide or are structurally similar to a nucleotide or portion thereof. In particular, nucleotide analogs are nucleotides which contain, for example, an analogue of the nucleic acid portion, sugar portion and/or phosphate groups of the nucleotide. Nucleotides include, for instance, nucleotide monophosphates, nucleotide diphosphates, and nucleotide triphosphates. A nucleotide analog, as used herein is structurally similar to a nucleotide or portion thereof but does not have the typical nucleotide structure (nucleobase-ribose-phosphate). Nucleoside analogs are compounds that have the general structure of a nucleoside or are structurally similar to a nucleoside or portion thereof. In particular, nucleoside analogs are nucleosides which contain, for example, an analogue of the nucleic acid and/or sugar portion of the nucleoside.

The nucleotide analogs useful in the methods are structurally similar to nucleotides or portions thereof but, for example, are not polymerizable by T7. Nucleotide/nucleoside analogs as used herein (including C, T, A, U, G, dC, dT, dA, dU, or dG analogs) include for instance, antiviral nucleotide analogs, phosphate analogs (soluble or immobilized, hydrolyzable or non-hydrolyzable), dinucleotide, trinucleotide, tetranucleotide, e.g., a cap analog, or a precursor/substrate for enzymatic capping (vaccinia, or ligase), a nucleotide labelled with a functional group to facilitate ligation/conjugation of cap or 5' moiety (IRES), a nucleotide labelled with a 5' $PO_4$ to facilitate ligation of cap or 5' moiety, or a nucleotide labelled with a functional group/protecting group that can be chemically or enzymatically cleavable. Antiviral nucleotide/nucleoside analogs include but are not limited to Ganciclovir, Entecavir, Telbivudine, Vidarabine and Cidofovir.

The IVT reaction typically includes the following: an RNA polymerase, e.g., a T7 RNA polymerase at a final concentration of, e.g., 1000-12000 U/mL, e.g., 7000 U/mL; the DNA template at a final concentration of, e.g., 10-70 nM, e.g., 40 nM; nucleotides (NTPs) at a final concentration of e.g., 0.5-10 mM, e.g., 7.5 mM each; magnesium at a final concentration of, e.g., 12-60 mM, e.g., magnesium acetate at 40 mM; a buffer such as, e.g., HEPES or Tris at a pH of, e.g., 7-8.5, e.g. 40 mM Tris HCl, pH 8. In some embodiments 5 mM dithiothreitol (DTT) and/or 1 mM spermidine may be included. In some embodiments, an RNase inhibitor is included in the IVT reaction to ensure no RNase induced degradation during the transcription reaction. For example, murine RNase inhibitor can be utilized at a final concentration of 1000 U/mL. In some embodiments a pyrophosphatase is included in the IVT reaction to cleave the inorganic pyrophosphate generated following each nucleotide incorporation into two units of inorganic phosphate. This ensures that magnesium remains in solution and does not precipitate as magnesium pyrophosphate. For example, an *E. coli* inorganic pyrophosphatase can be utilized at a final concentration of 1 U/mL.

Similar to traditional methods, the modified method may also be produced by forming a reaction mixture comprising a DNA template, and one or more NTPs such as ATP, CTP, UTP, GTP (or corresponding analog of aforementioned components) and a buffer. The reaction is then incubated under conditions such that the RNA is transcribed. However, the modified methods utilize the presence of an excess amount of one or more nucleotides and/or nucleotide analogs that can have significant impact on the end product. These methods involve a modification in the amount (e.g., molar amount or quantity) of nucleotides and/or nucleotide analogs in the reaction mixture. In some aspects, one or more nucleotides and/or one or more nucleotide analogs may be added in excess to the reaction mixture. An excess of nucleotides and/or nucleotide analogs is any amount greater than the amount of one or more of the other nucleotides such as NTPs in the reaction mixture. For instance, an excess of a nucleotide and/or nucleotide analog may be a greater amount than the amount of each or at least one of the other individual NTPs in the reaction mixture or may refer to an amount greater than equimolar amounts of the other NTPs.

In the embodiment when the nucleotide and/or nucleotide analog that is included in the reaction mixture is an NTP, the NTP may be present in a higher concentration than all three of the other NTPs included in the reaction mixture. The other three NTPs may be in an equimolar concentration to one another. Alternatively one or more of the three other NTPs may be in a different concentration than one or more of the other NTPs.

Thus, in some embodiments the IVT reaction may include an equimolar amount of nucleotide triphosphate relative to at least one of the other nucleotide triphosphates.

In some embodiments the RNA is produced by a process or is preparable by a process comprising (a) forming a reaction mixture comprising a DNA template and NTPs including adenosine triphosphate (ATP), cytidine triphosphate (CTP), uridine triphosphate (UTP), guanosine triphosphate (GTP) and optionally guanosine diphosphate (GDP), and (eg. buffer containing T7 co-factor eg. magnesium).

(b) incubating the reaction mixture under conditions such that the RNA is transcribed, wherein the concentration of at least one of GTP, CTP, ATP, and UTP is at least 2× greater than the concentration of any one or more of ATP, CTP or UTP or the reaction further comprises a nucleotide analog and wherein the concentration of the nucleotide analog is at least 2× greater than the concentration of any one or more of ATP, CTP or UTP.

In some embodiments the ratio of concentration of GTP to the concentration of any one ATP, CTP or UTP is at least 2:1, at least 3:1, at least 4:1, at least 5:1 or at least 6:1. The ratio of concentration of GTP to concentration of ATP, CTP and UTP is, in some embodiments 2:1, 4:1 and 4:1, respectively. In other embodiments the ratio of concentration of GTP to concentration of ATP, CTP and UTP is 3:1, 6:1 and 6:1, respectively. The reaction mixture may comprise GTP and GDP and wherein the ratio of concentration of GTP plus GDP to the concentration of any one of ATP, CTP or UTP is at least 2:1, at least 3:1, at least 4:1, at least 5:1 or at least 6:1 In some embodiments the ratio of concentration of GTP plus GDP to concentration of ATP, CTP and UTP is 3:1, 6:1 and 6:1, respectively.

In some embodiments the method involves incubating the reaction mixture under conditions such that the RNA is transcribed, wherein the effective concentration of phosphate in the reaction is at least 150 mM phosphate, at least 160 mM, at least 170 mM, at least 180 mM, at least 190 mM, at least 200 mM, at least 210 mM or at least 220 mM. The effective concentration of phosphate in the reaction may be 180 mM. The effective concentration of phosphate in the reaction in some embodiments is 195 mM. In other embodiments the effective concentration of phosphate in the reaction is 225 mM.

In other embodiments the RNA is produced by a process or is preparable by a process comprising wherein a buffer magnesium-containing buffer is used when forming the reaction mixture comprising a DNA template and ATP, CTP, UTP, GTP. In some embodiments the magnesium-containing buffer comprises Mg2+ and wherein the molar ratio of concentration of ATP plus CTP plus UTP pus GTP to concentration of Mg2+ is at least 1.0, at least 1.25, at least 1.5, at least 1.75, at least 1.85, at least 3 or higher. The molar ratio of concentration of ATP plus CTP plus UTP pus GTP to concentration of Mg2+ may be 1.5. The molar ratio of concentration of ATP plus CTP plus UTP pus GTP to concentration of Mg2+ in some embodiments is 1.88. The molar ratio of concentration of ATP plus CTP plus UTP pus GTP to concentration of Mg2+ in some embodiments is 3.

In some embodiments the composition is produced by a process which does not comprise an dsRNase (e.g., RNaseIII) treatment step. In other embodiments the composition is produced by a process which does not comprise a reverse phase (RP) chromatography purification step. In yet other embodiments the composition is produced by a process which does not comprise a high-performance liquid chromatography (HPLC) purification step.

In some embodiments the ratio of concentration of GTP to the concentration of any one ATP, CTP or UTP is at least 2:1, at least 3:1, at least 4:1, at least 5:1 or at least 6:1 to produce the RNA.

The purity of the products may be assessed using known analytical methods and assays. For instance, the amount of reverse complement transcription product or cytokine-inducing RNA contaminant may be determined by high-performance liquid chromatography (such as reverse-phase chromatography, size-exclusion chromatography), Bioanalyzer chip-based electrophoresis system, ELISA, flow cytometry, acrylamide gel, a reconstitution or surrogate type assay. The assays may be performed with or without nuclease treatment (P1, RNase III, RNase H etc.) of the RNA preparation. Electrophoretic/chromatographic/mass spec analysis of nuclease digestion products may also be performed.

In some embodiments the purified RNA preparations comprise contaminant transcripts that have a length less than a full length transcript, such as for instance at least 100, 200, 300, 400, 500, 600, 700, 800, or 900 nucleotides less than the full length. Contaminant transcripts can include reverse or forward transcription products (transcripts) that have a length less than a full length transcript, such as for instance at least 100, 200, 300, 400, 500, 600, 700, 800, or 900 nucleotides less than the full length. Exemplary forward transcripts include, for instance, abortive transcripts. In certain embodiments the composition comprises a tri-phosphate poly-U reverse complement of less than 30 nucleotides. In some embodiments the composition comprises a tri-phosphate poly-U reverse complement of any length hybridized to a full length transcript. In other embodiments the composition comprises a single stranded tri-phosphate forward transcript. In other embodiments the composition comprises a single stranded RNA having a terminal tri-phosphate-G. In other embodiments the composition comprises single or double stranded RNA of less than 12 nucleotides or base pairs (including forward or reverse complement transcripts). In any of these embodiments the composition may include less than 50%, 45%, 40%, 35%, 30%, 25%, 20%, 15%, 10%, 9%, 8%, 7%, 6%, 5%, 4%, 3%, 2%, 1%, or 0.5% of any one of or combination of these less than full length transcripts.

Delivery Vehicles

General

The mRNAs of the disclosure may be formulated in nanoparticles or other delivery vehicles, e.g., to protect them from degradation when delivered to a subject. Illustrative nanoparticles are described in Panyam, J. & Labhasetwar, V. Adv. Drug Deliv. Rev. 55, 329-347 (2003) and Peer, D. et al. Nature Nanotech. 2, 751-760 (2007). In certain embodiments, an mRNA of the disclosure is encapsulated within a nanoparticle. In particular embodiments, a nanoparticle is a particle having at least one dimension (e.g., a diameter) less than or equal to 1000 nM, less than or equal to 500 nM or less than or equal to 100 nM. In particular embodiments, a nanoparticle includes a lipid. Lipid nanoparticles include, but are not limited to, liposomes and micelles. Any of a number of lipids may be present, including cationic and/or ionizable lipids, anionic lipids, neutral lipids, amphipathic lipids, PEGylated lipids, and/or structural lipids. Such lipids can be used alone or in combination. In particular embodiments, a lipid nanoparticle comprises one or more mRNAs described herein.

In some embodiments, the lipid nanoparticle formulations of the mRNAs described herein may include one or more (e.g., 1, 2, 3, 4, 5, 6, 7, or 8) cationic and/or ionizable lipids. Such cationic and/or ionizable lipids include, but are not limited to, 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraaza-octatriacontane (KL-25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino)butanoate (DLin-MC3-DMA), 2,2-dilinoleyl-4-(2-dimethylaminoethyl)-[1,3]-dioxolane (DLin-KC2-DMA), 2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA), (2R)-2-({8-[(3β)-cholest-5-en-3-yloxy]octyl}oxy)-N,N-dimethyl-3-[(9Z,12Z)-octadeca-9,12-dien-1-yloxy]propan-(Octyl-CLinDMA (2R)), (2S)-2-({8-[(3β)-cholest-5-en-3-yloxy]octyl}oxy)-N,N-dimethyl-3-[(9Z,12Z)-octadeca-9,12-dien- 1-yloxy]propan-1-amine (Octyl-CLinDMA (2S)). N,N-dioleyl-N,N-dimethylammonium chloride ("DODAC"); N-(2,3-dioleyloxy)propyl-N,N—N-triethylammonium chloride ("DOTMA"); N,N-distearyl-N,N-dimethylammonium bromide ("DDAB"); N-(2,3-dioleoyloxy)propyl)-N,N,N-trimethylammonium chloride ("DOTAP"); 1,2-Dioleyloxy-3-trimethylaminopropane chloride salt ("DOTAP.C1"); 3-β-(N—(N',N'-dimethylaminoethane)-carbamoyl)cholesterol ("DC-Chol"), N-(1-(2,3-dioleyloxy)propyl)-N-2-(sperminecarboxamido)ethyl)-N,N-dimethyl-ammonium trifluoracetate ("DOSPA"), dioctadecylamidoglycyl carboxyspermine ("DOGS"), 1,2-dioleoyl-3-dimethylammonium propane ("DODAP"), N,N-dimethyl-2,3-dioleyloxy)propylamine ("DODMA"), and N-(1,2-dimyristyloxyprop-3-yl)-N,N-dimethyl-N-hydroxyethyl ammonium bromide ("DMRIE"). Additionally, a number of commercial preparations of cationic and/or ionizable lipids can be used, such as, e.g., LIPOFECTIN® (including DOTMA and DOPE, available from GIBCO/BRL), and LIPOFECTAMINE® (including DOSPA and DOPE, available from GIBCO/BRL). KL10, KL22, and KL25 are described, for example, in U.S. Pat. No. 8,691,750, which is incorporated herein by reference in its entirety. In particular embodiments, the lipid is DLin-MC3-DMA or DLin-KC2-DMA.

Anionic lipids suitable for use in lipid nanoparticles of the disclosure include, but are not limited to, phosphatidylglycerol, cardiolipin, diacylphosphatidylserine, diacylphosphatidic acid, N-dodecanoyl phosphatidylethanoloamine, N-succinyl phosphatidylethanolamine, N-glutaryl phosphatidylethanolamine, lysylphosphatidylglycerol, and other anionic modifying groups joined to neutral lipids.

Neutral lipids suitable for use in lipid nanoparticles of the disclosure include, but are not limited to, diacylphosphatidylcholine, diacylphosphatidylethanolamine, ceramide, sphingomyelin, dihydrosphingomyelin, cephalin, and cerebrosides. Lipids having a variety of acyl chain groups of varying chain length and degree of saturation are available or may be isolated or synthesized by well-known techniques. Additionally, lipids having mixtures of saturated and unsaturated fatty acid chains can be used. In some embodiments, the neutral lipids used in the disclosure are DOPE, DSPC, DPPC, POPC, or any related phosphatidylcholine. In some embodiments, the neutral lipid may be composed of sphingomyelin, dihydrosphingomyeline, or phospholipids with other head groups, such as serine and inositol.

In some embodiments, amphipathic lipids are included in nanoparticles of the disclosure. Exemplary amphipathic lipids suitable for use in nanoparticles of the disclosure include, but are not limited to, sphingolipids, phospholipids, and aminolipids. In some embodiments, a phospholipid is selected from the group consisting of 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine,1,2-dioleoyl-sn-glycero-3-phosphoetha nolamine (DOPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), and sphingomyelin. Other phosphorus-lacking compounds, such as sphingolipids, glycosphingolipid families, diacylglycerols, and β-acyloxyacids, may also be used. Additionally, such amphipathic lipids can be readily mixed with other lipids, such as triglycerides and sterols.

In some embodiments, the lipid component of a nanoparticle of the disclosure may include one or more PEGylated lipids. A PEGylated lipid (also known as a PEG lipid or a PEG-modified lipid) is a lipid modified with polyethylene glycol. The lipid component may include one or more PEGylated lipids. A PEGylated lipid may be selected from the non-limiting group consisting of PEG-modified phosphatidylethanolamines, PEG-modified phosphatidic acids, PEG-modified ceramides, PEG-modified dialkylamines, PEG-modified diacylglycerols, and PEG-modified dialkylglycerols. For example, a PEGylated lipid may be PEG-c-DOMG, PEG-DMG, PEG-DLPE, PEG-DMPE, PEG-DPPC, or a PEG-DSPE lipid.

A lipid nanoparticle of the disclosure may include one or more structural lipids. Exemplary, non-limiting structural lipids that may be present in the lipid nanoparticles of the disclosure include cholesterol, fecosterol, sitosterol, campesterol, stigmasterol, brassicasterol, ergosterol, tomatidine, tomatine, ursolic acid, or alpha-tocopherol.

In some embodiments, one or more mRNA of the disclosure may be formulated in a lipid nanoparticle having a diameter from about 1 nm to about 900 nm, e.g., about 1 nm to about 100 nm, about 1 nm to about 200 nm, about 1 nm to about 300 nm, about 1 nm to about 400 nm, about 1 nm to about 500 nm, about 1 nm to about 600 nm, about 1 nm to about 700 nm, about 1 nm to 800 nm, about 1 nm to about 900 nm. In some embodiments, the nanoparticle may have a diameter from about 10 nm to about 300 nm, about 20 nm to about 200 nm, about 30 nm to about 100 nm, or about 40 nm to about 80 nm. In some embodiments, the nanoparticle may have a diameter from about 30 nm to about 300 nm, about 40 nm to about 200 nm, about 50 nm to about 150 nm, about 70 to about 110 nm, or about 80 nm to about 120 nm. In one embodiment, an mRNA may be formulated in a lipid nanoparticle having a diameter from about 10 to about 100 nm including ranges in between such as, but not limited to, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm, and/or about 90 to about 100 nm. In one embodiment, an mRNA may be formulated in a lipid nanoparticle having a diameter from about 30 nm to about 300 nm, about 40 nm to about 200 nm, about 50 nm to about 150 nm, about 70 to about 110 nm, or about 80 nm to about 120 nm including ranges in between.

In some embodiments, a lipid nanoparticle may have a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, or greater than 950 nm.

In some embodiments, the particle size of the lipid nanoparticle may be increased and/or decreased. The change in particle size may be able to help counter a biological reaction such as, but not limited to, inflammation, or may increase the biological effect of the mRNA delivered to a patient or subject.

In certain embodiments, it is desirable to target a nanoparticle, e.g., a lipid nanoparticle, of the disclosure using a targeting moiety that is specific to a cell type and/or tissue type. In some embodiments, a nanoparticle may be targeted to a particular cell, tissue, and/or organ using a targeting moiety. In particular embodiments, a nanoparticle comprises one or more mRNA described herein and a targeting moiety. Exemplary non-limiting targeting moieties include ligands, cell surface receptors, glycoproteins, vitamins (e.g., riboflavin) and antibodies (e.g., full-length antibodies, antibody fragments (e.g., Fv fragments, single chain Fv (scFv) fragments, Fab' fragments, or F(ab')2 fragments), single domain antibodies, camelid antibodies and fragments thereof, human antibodies and fragments thereof, monoclonal antibodies, and multispecific antibodies (e.g., bispecific antibodies)). In some embodiments, the targeting moiety may be a polypeptide. The targeting moiety may include the entire polypeptide (e.g., peptide or protein) or fragments thereof. A targeting moiety is typically positioned on the outer surface of the nanoparticle in such a manner that the targeting moiety is available for interaction with the target, for example, a cell surface receptor. A variety of different targeting moieties and methods are known and available in the art, including those described, e.g., in Sapra et al., *Prog. Lipid Res.* 42(5):439-62, 2003 and Abra et al., *J. Liposome Res.* 12:1-3, 2002.

In some embodiments, a lipid nanoparticle (e.g., a liposome) may include a surface coating of hydrophilic polymer chains, such as polyethylene glycol (PEG) chains (see, e.g., Allen et al., *Biochimica et Biophysica Acta* 1237: 99-108, 1995; DeFrees et al., *Journal of the American Chemistry Society* 118: 6101-6104, 1996; Blume et al., *Biochimica et Biophysica Acta* 1149: 180-184, 1993; Klibanov et al., *Journal of Liposome Research* 2: 321-334, 1992; U.S. Pat. No. 5,013,556; Zalipsky, Bioconjugate Chemistry 4: 296-299, 1993*; Zalipsky, FEBS Letters* 353: 71-74, 1994; Zalipsky, in *Stealth Liposomes* Chapter 9 (Lasic and Martin, Eds) CRC Press, Boca Raton Fla., 1995). In one approach, a targeting moiety for targeting the lipid nanoparticle is linked to the polar head group of lipids forming the nanoparticle. In another approach, the targeting moiety is attached to the distal ends of the PEG chains forming the hydrophilic polymer coating (see, e.g., Klibanov et al., *Journal of Liposome Research* 2: 321-334, 1992; Kirpotin et al., *FEBS Letters* 388: 115-118, 1996).

Standard methods for coupling the targeting moiety or moieties may be used. For example, phosphatidylethanolamine, which can be activated for attachment of targeting moieties, or derivatized lipophilic compounds, such as lipid-derivatized bleomycin, can be used. Antibody-targeted liposomes can be constructed using, for instance, liposomes that incorporate protein A (see, e.g., Renneisen et al., *J. Bio. Chem.,* 265:16337-16342, 1990 and Leonetti et al., *Proc. Natl. Acad. Sci.* (USA), 87:2448-2451, 1990). Other examples of antibody conjugation are disclosed in U.S. Pat. No. 6,027,726. Examples of targeting moieties can also include other polypeptides that are specific to cellular components, including antigens associated with neoplasms or tumors. Polypeptides used as targeting moieties can be attached to the liposomes via covalent bonds (see, for example Heath, Covalent Attachment of Proteins to Liposomes, 149 Methods in Enzymology 111-119 (Academic Press, Inc. 1987)). Other targeting methods include the biotin-avidin system.

In some embodiments, a lipid nanoparticle of the disclosure includes a targeting moiety that targets the lipid nanoparticle to a cell including, but not limited to, hepatocytes, colon cells, epithelial cells, hematopoietic cells, epithelial cells, endothelial cells, lung cells, bone cells, stem cells, mesenchymal cells, neural cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes, and tumor cells (including primary tumor cells and metastatic tumor cells). In particular embodiments, the targeting moiety targets the lipid nanoparticle to a hepatocyte. In other embodiments, the targeting moiety targets the lipid nanoparticle to a colon cell. In some embodiments, the targeting moiety targets the lipid nanoparticle to a liver cancer cell (e.g., a hepatocellular carcinoma cell) or a colorectal cancer cell (e.g., a primary tumor or a metastasis).

Lipid Nanoparticles

In one set of embodiments, lipid nanoparticles (LNPs) are provided. In one embodiment, a lipid nanoparticle comprises lipids including an ionizable lipid, a structural lipid, a phospholipid, and one or more mRNAs. Each of the LNPs described herein may be used as a formulation for the mRNA described herein. In one embodiment, a lipid nanoparticle comprises an ionizable lipid, a structural lipid, a phospholipid, a PEG-modified lipid and one or more mRNAs. In some embodiments, the LNP comprises an ionizable lipid, a PEG-modified lipid, a sterol and a phospholipid. In some embodiments, the LNP has a molar ratio of about 20-60% ionizable lipid:about 5-25% phospholipid: about 25-55% sterol; and about 0.5-15% PEG-modified lipid. In some embodiments, the LNP comprises a molar ratio of about 50% ionizable lipid, about 1.5% PEG-modified lipid, about 38.5% cholesterol and about 10% phospholipid. In some embodiments, the LNP comprises a molar ratio of about 55% ionizable lipid, about 2.5% PEG lipid, about 32.5% cholesterol and about 10% phospholipid. In some embodiments, the ionizable lipid is an ionizable amino or cationic lipid and the neutral lipid is a phospholipid, and the sterol is a cholesterol. In some embodiments, the LNP has a molar ratio of 50:38.5:10:1.5 of ionizable lipid: cholesterol:DSPC (1,2-dioctadecanoyl-sn-glycero-3-phosphocholine):PEG-DMG.

a. Ionizable Lipid

The present disclosure provides pharmaceutical compositions with advantageous properties. For example, the lipids described herein (e.g. those having any of Formula (I), (IA), (II), (IIa), (IIb), (IIc), (IId), (IIe), (III), (IV), (V), or (VI) may be advantageously used in lipid nanoparticle compositions for the delivery of therapeutic and/or prophylactic agents to mammalian cells or organs. For example, the lipids described herein have little or no immunogenicity. For example, the lipid compounds disclosed hereinhave a lower immunogenicity as compared to a reference lipid (e.g., MC3, KC2, or DLinDMA). For example, a formulation comprising a lipid disclosed herein and a therapeutic or prophylactic agent has an increased therapeutic index as compared to a corresponding formulation which comprises a reference lipid (e.g., MC3, KC2, or DLinDMA) and the same therapeutic or prophylactic agent. In particular, the present application provides pharmaceutical compositions comprising:

(a) a polynucleotide comprising a nucleotide sequence encoding a polypeptide of interest; and (b) a delivery agent.

In some embodiments, the delivery agent comprises a lipid compound having the Formula (I)

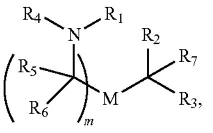

(I)

wherein $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, C1-14 alkyl, C2-14 alkenyl, —R*YR", —YR", and —R*OR", or $R_2$ and $R_3$, together with the atom to which they are attached, form a heterocycle or carbocycle;

$R_4$ is selected from the group consisting of a C3-6 carbocycle, —$(CH_2)_n$Q, —$(CH_2)_n$CHQR, —CHQR, —CQ$(R)_2$, and unsubstituted $C_{1-6}$ alkyl, where Q is selected from a carbocycle, heterocycle, —OR, —O$(CH_2)_n$N$(R)_2$, —C(O)OR, —OC(O)R, —$CX_3$, —$CX_2$H, —$CXH_2$, —CN, —N$(R)_2$, —C(O)N$(R)_2$, —N(R)C(O)R, —N(R)S$(O)_2$R, —N(R)C(O)N$(R)_2$, —N(R)C(S)N$(R)_2$, —N(R)$R_8$, —O$(CH_2)_n$OR, —N(R)C(=N$R_9$)N$(R)_2$, —N(R)C(=CH$R_9$)N$(R)_2$, —OC(O)N$(R)_2$, —N(R)C(O)OR, —N(OR)C(O)R, —N(OR)S$(O)_2$R, —N(OR)C(O)OR, —N(OR)C(O)N$(R)_2$, —N(OR)C(S)N$(R)_2$, —N(OR)C(=N$R_9$)N$(R)_2$, —N(OR)C(=CH$R_9$)N$(R)_2$, —C(=N$R_9$)N$(R)_2$, —C(=N$R_9$)R, —C(O)N(R)OR, and —C(R)N$(R)_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S$(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —S$(O)_2$R, —S$(O)_2$N$(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In some embodiments, a subset of compounds of Formula (I) includes those in which $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —CQ$(R)_2$, and unsubstituted $C_{1-6}$ alkyl, where Q is selected from a carbocycle, heterocycle, —OR, —O$(CH_2)_n$N$(R)_2$, —C(O)OR, —OC(O)R, —$CX_3$, —$CX_2$H, —$CXH_2$, —CN, —N$(R)_2$, —C(O)N$(R)_2$, —N(R)C(O)R, —N(R)S$(O)_2$R, —N(R)C(O)N$(R)_2$, —N(R)C(S)N$(R)_2$, and —C(R)N$(R)_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S$(O)_2$—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof, wherein alkyl and alkenyl groups may be linear or branched.

In some embodiments, a subset of compounds of Formula (I) includes those in which when $R_4$ is —$(CH_2)_n$Q, —$(CH_2)_n$CHQR, —CHQR, or —CQ$(R)_2$, then (i) Q is not —N$(R)_2$ when n is 1, 2, 3, 4 or 5, or (ii) Q is not 5, 6, or 7-membered heterocycloalkyl when n is 1 or 2.

In another embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —CQ$(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O$(CH_2)_n$N$(R)_2$, —C(O)OR, —OC(O)R, —$CX_3$, —$CX_2$H, —$CXH_2$, —CN, —C(O)N$(R)_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —O C(O)N(R)$_2$, —N(R)C(O)OR, —N(OR)C(O)R, —N(OR)S(O)$_2$R, —N(OR)C(O)OR, —N(OR)C(O)N( R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C (=NR$_9$)R, —C(O)N(R)OR, and a 5- to 14-membered heterocycloalkyl having one or more heteroatoms selected from N, O, and S which is substituted with one or more substituents selected from oxo (=O), OH, amino, and $C_{1-3}$ alkyl, and each n is independently selected from 1, 2, 3, 4, and 5;

each R$_5$ is independently selected from the group consisting of $C_{1-3}$ alkyl, $C_{2-3}$ alkenyl, and H;

each R$_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

R$_7$ is selected from the group consisting of $C_{1-3}$ alkyl, $C_{2-3}$ alkenyl, and H;

R$_8$ is selected from the group consisting of $C_{3-6}$ carbocycle and heterocycle;

R$_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In another embodiments, another subset of compounds of Formula (I) includes those in which R$_1$ is selected from the group consisting of $C_{5-30}$ alkyl, $C_{5-20}$ alkenyl, —R*YR", —YR", and —R"M'R';

R$_2$ and R$_3$ are independently selected from the group consisting of H, $C_{1-14}$ alkyl, $C_{2-14}$ alkenyl, —R*YR", —YR", and —R*OR", or R$_2$ and R$_3$, together with the atom to which they are attached, form a heterocycle or carbocycle;

R$_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, and a 5- to 14-membered heterocycloalkyl having one or more heteroatoms selected from N, O, and S which is substituted with one or more substituents selected from oxo (=O), OH, amino, and $C_{1-3}$ alkyl, and each n is independently selected from 1, 2, 3, 4, and 5;

each R$_5$ is independently selected from the group consisting of $C_{1-3}$ alkyl, $C_{2-3}$ alkenyl, and H;

each R$_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;

R$_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In yet another embodiments, another subset of compounds of Formula (I) includes those in which R$_1$ is selected from the group consisting of $C_{5-20}$ alkyl, $C_{5-20}$ alkenyl, —R*YR", —YR", and —R"M'R';

R$_2$ and R$_3$ are independently selected from the group consisting of H, $C_{1-14}$ alkyl, $C_{2-14}$ alkenyl, —R*YR", —YR", and —R*OR", or R$_2$ and R$_3$, together with the atom to which they are attached, form a heterocycle or carbocycle;

R$_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a $C_{3-6}$ carbocycle, a 5- to 14-membered heterocycle having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)R, —C(O)N(R)OR, and —C(=NR$_9$)N(R)$_2$, and each n is independently selected from 1, 2, 3, 4, and 5; and when Q is a 5- to 14-membered heterocycle and (i) R$_4$ is —(CH$_2$)$_n$Q in which n is 1 or 2, or (ii) R$_4$ is —(CH$_2$)$_n$CHQR in which n is 1, or (iii) R$_4$ is —CHQR, and —CQ(R)$_2$, then Q is either a 5- to 14-membered heteroaryl or 8- to 14-membered heterocycloalkyl;

each R$_5$ is independently selected from the group consisting of $C_{1-3}$ alkyl, $C_{2-3}$ alkenyl, and H;

each R$_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

R$_7$ is selected from the group consisting of $C_{1-3}$ alkyl, $C_{2-3}$ alkenyl, and H;

R$_8$ is selected from the group consisting of $C_{3-6}$ carbocycle and heterocycle;

R$_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In yet another embodiments, another subset of compounds of Formula (I) includes those in which $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, $—(CH_2)_nQ$, $—(CH_2)_nCHQR$, —CHQR, $—CQ(R)_2$, and unsubstituted $C_{1-6}$ alkyl, where Q is selected from a $C_{3-6}$ carbocycle, a 5- to 14-membered heterocycle having one or more heteroatoms selected from N, O, and S, —OR, $—O(CH_2)_nN(R)_2$, —C(O)OR, —OC(O)R, $—CX_3$, $—CX_2H$, $—CXH_2$, —CN, $—C(O)N(R)_2$, —N(R)C(O)R, $—N(R)S(O)_2R$, $—N(R)C(O)N(R)_2$, $—N(R)C(S)N(R)_2$, $—CRN(R)_2C(O)OR$, and each n is independently selected from 1, 2, 3, 4, and 5; and when Q is a 5- to 14-membered heterocycle and (i) $R_4$ is $—(CH_2)_nQ$ in which n is 1 or 2, or (ii) $R_4$ is $—(CH_2)_nCHQR$ in which n is 1, or (iii) $R_4$ is —CHQR, and $—CQ(R)_2$, then Q is either a 5- to 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In still another embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, $—(CH_2)_nQ$, $—(CH_2)_nCHQR$, —CHQR, $—CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, $—O(CH_2)_nN(R)_2$, —C(O)OR, —OC(O)R, $—CX_3$, $—CX_2H$, $—CXH_2$, —CN, $—C(O)N(R)_2$, —N(R)C(O)R, $—N(R)S(O)_2R$, $—N(R)C(O)N(R)_2$, $—N(R)C(S)N(R)_2$, $—CRN(R)_2C(O)OR$, $—N(R)R_8$, $—O(CH_2)_nOR$, $—N(R)C({=}NR_9)N(R)_2$, $—N(R)C({=}CHR_9)N(R)_2$, $—OC(O)N(R)_2$, —N(R)C(O)OR, —N(OR)C(O)R, $—N(OR)S(O)_2R$, —N(OR)C(O)OR, $—N(OR)C(O)N(R)_2$, $—N(OR)C(S)N(R)_2$, $—N(OR)C({=}NR_9)N(R)_2$, $—N(OR)C({=}CHR_9)N(R)_2$, $—C({=}NR_9)R$, —C(O)N(R)OR, and $—C({=}NR_9)N(R)_2$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, $—S(O)_2R$, $—S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In still another embodiments, another subset of compounds of Formula (I) includes those in which $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, $—(CH_2)_nQ$, $—(CH_2)_nCHQR$, —CHQR, $—CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, $—O(CH_2)_nN(R)_2$, —C(O)OR, —OC(O)R, $—CX_3$, $—CX_2H$, $—CXH_2$, —CN, $—C(O)N(R)_2$, —N(R)C(O)R, $—N(R)S(O)_2R$, $—N(R)C(O)N(R)_2$, $—N(R)C(S)N(R)_2$, $—CRN(R)_2C(O)OR$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In yet another embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is —$(CH_2)_n$Q or —$(CH_2)_n$CHQR, where Q is —$N(R)_2$, and n is selected from 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In yet another embodiments, another subset of compounds of Formula (I) includes those in which $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is —$(CH_2)_n$Q or —$(CH_2)_n$CHQR, where Q is —$N(R)_2$, and n is selected from 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In still other embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of —$(CH_2)_n$Q, —$(CH_2)_n$CHQR, —CHQR, and —$CQ(R)_2$, where Q is —$N(R)_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In still other embodiments, another subset of compounds of Formula (I) includes those in which $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of —$(CH_2)_n$Q, —$(CH_2)_n$CHQR, —CHQR, and —$CQ(R)_2$, where Q is —$N(R)_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In certain embodiments, a subset of compounds of Formula (I) includes those of Formula (IA):

(IA)

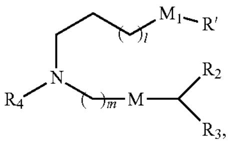

or a salt or stereoisomer thereof, wherein l is selected from 1, 2, 3, 4, and 5; m is selected from 5, 6, 7, 8, and 9; $M_1$ is a bond or M'; $R_4$ is unsubstituted $C_{1-3}$ alkyl, or $—(CH_2)_nQ$, in which Q is OH, $—NHC(S)N(R)_2$, $—NHC(O)N(R)_2$, —N(R)C(O)R, $—N(R)S(O)_2R$, $—N(R)R_8$, $—NHC({=}NR_9)N(R)_2$, $—NHC({=}CHR_9)N(R)_2$, $—OC(O)N(R)_2$, —N(R)C(O)OR, heteroaryl, or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (IA), or a salt or stereoisomer thereof, wherein l is selected from 1, 2, 3, 4, and 5; m is selected from 5, 6, 7, 8, and 9;

$M_1$ is a bond or M';

$R_4$ is unsubstituted $C_{1-3}$ alkyl, or $—(CH_2)_nQ$, in which Q is OH, $—NHC(S)N(R)_2$, or $—NHC(O)N(R)_2$;

M and M' are independently selected from —C(O)O—, —OC(O)—, —C(O)N(R')—, —P(O)(OR')O—, an aryl group, and a heteroaryl group; and $R_2$ and $R_3$ are independently selected from the group consisting of H, $C_{1-14}$ alkyl, and $C_{2-14}$ alkenyl.

In certain embodiments, a subset of compounds of Formula (I) includes those of Formula (II):

(II)

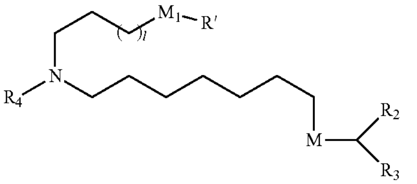

or a salt or stereoisomer thereof, wherein l is selected from 1, 2, 3, 4, and 5; $M_1$ is a bond or M'; $R_4$ is unsubstituted $C_{1-3}$ alkyl, or $—(CH_2)_nQ$, in which n is 2, 3, or 4, and Q is OH, $—NHC(S)N(R)_2$, $—NHC(O)N(R)_2$, —N(R)C(O)R, $—N(R)S(O)_2R$, $—N(R)R_8$, $—NHC({=}NR_9)N(R)_2$, $—NHC({=}CHR_9)N(R)_2$, $—OC(O)N(R)_2$, —N(R)C(O)OR, heteroaryl, or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (II), or a salt or stereoisomer thereof, wherein l is selected from 1, 2, 3, 4, and 5;

$M_1$ is a bond or M';

$R_4$ is unsubstituted $C_{1-3}$ alkyl, or $—(CH_2)_nQ$, in which n is 2, 3, or 4, and Q is OH, $—NHC(S)N(R)_2$, or $—NHC(O)N(R)_2$;

M and M' are independently selected from —C(O)O—, —OC(O)—, —C(O)N(R')—, —P(O)(OR')O—, an aryl group, and a heteroaryl group; and $R_2$ and $R_3$ are independently selected from the group consisting of H, $C_{1-14}$ alkyl, and $C_{2-14}$ alkenyl.

In some embodiments, the compound of formula (I) is of the formula (IIa), (IIa)

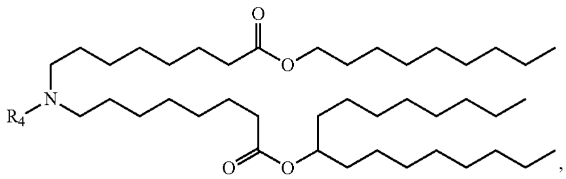

or a salt thereof, wherein $R_4$ is as described above.

In some embodiments, the compound of formula (I) is of the formula (IIb), (IIb)

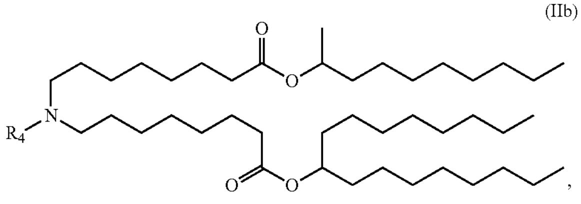

or a salt thereof, wherein $R_4$ is as described above.

In some embodiments, the compound of formula (I) is of the formula (IIc), (IIc)

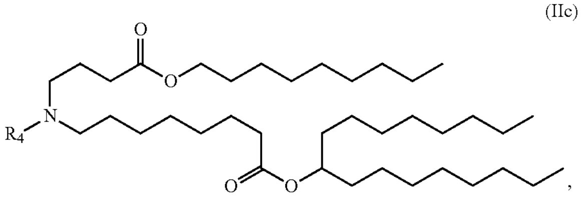

or a salt thereof, wherein $R_4$ is as described above.

In some embodiments, the compound of formula (I) is of the formula (IIe):

(IIe)

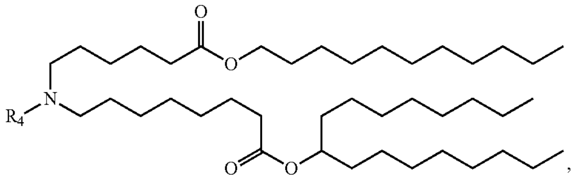

or a salt thereof, wherein $R_4$ is as described above.

In some embodiments, the compound of formula (IIa), (IIb), (IIc), or (IIe) comprises an $R_4$ which is selected from —$(CH_2)_nQ$ and —$(CH_2)_nCHQR$, wherein Q, R and n are as defined above.

In some embodiments, Q is selected from the group consisting of —OR, —OH, —$O(CH_2)_nN(R)_2$, —OC(O)R, —$CX_3$, —CN, —N(R)C(O)R, —N(H)C(O)R, —N(R)S$(O)_2$R, —N(H)S$(O)_2$R, —N(R)C(O)N$(R)_2$, —N(H)C(O)N$(R)_2$, —N(H)C(O)N(H)(R), —N(R)C(S)N$(R)_2$, —N(H)C(S)N$(R)_2$, —N(H)C(S)N(H)(R), and a heterocycle, wherein R is as defined above. In some aspects, n is 1 or 2. In some embodiments, Q is OH, —NHC(S)N$(R)_2$, or —NHC(O)N$(R)_2$.

In some embodiments, the compound of formula (I) is of the formula (IId), (IId)

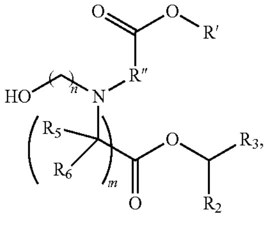

or a salt thereof, wherein $R_2$ and $R_3$ are independently selected from the group consisting of $C_{5-14}$ alkyl and $C_{5-14}$ alkenyl, n is selected from 2, 3, and 4, and R', R", $R_5$, $R_6$ and m are as defined above.

In some aspects of the compound of formula (IId), $R_2$ is $C_8$ alkyl. In some aspects of the compound of formula (IId), $R_3$ is $C_5$-$C_9$ alkyl. In some aspects of the compound of formula (IId), m is 5, 7, or 9. In some aspects of the compound of formula (IId), each $R_5$ is H. In some aspects of the compound of formula (IId), each $R_6$ is H.

In another aspect, the present application provides a lipid composition (e.g., a lipid nanoparticle (LNP)) comprising: (1) a compound having the formula (I); (2) optionally a helper lipid (e.g. a phospholipid); (3) optionally a structural lipid (e.g. a sterol); and (4) optionally a lipid conjugate (e.g. a PEG-lipid). In exemplary embodiments, the lipid composition (e.g., LNP) further comprises a polynucleotide encoding a polypeptide of interest, e.g., a polynucleotide encapsulated therein.

As used herein, the term "alkyl" or "alkyl group" means a linear or branched, saturated hydrocarbon including one or more carbon atoms (e.g., one, two, three, four, five, six, seven, eight, nine, ten, eleven, twelve, thirteen, fourteen, fifteen, sixteen, seventeen, eighteen, nineteen, twenty, or more carbon atoms).

The notation "$C_{1-14}$ alkyl" means a linear or branched, saturated hydrocarbon including 1-14 carbon atoms. An alkyl group can be optionally substituted.

As used herein, the term "alkenyl" or "alkenyl group" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one double bond.

The notation "$C_{2-14}$ alkenyl" means a linear or branched hydrocarbon including 2-14 carbon atoms and at least one double bond. An alkenyl group can include one, two, three, four, or more double bonds. For example, $C_{18}$ alkenyl can include one or more double bonds. A $C_{18}$ alkenyl group including two double bonds can be a linoleyl group. An alkenyl group can be optionally substituted.

As used herein, the term "carbocycle" or "carbocyclic group" means a mono- or multi-cyclic system including one or more rings of carbon atoms. Rings can be three, four, five, six, seven, eight, nine, ten, eleven, twelve, thirteen, fourteen, or fifteen membered rings.

The notation "$C_{3-6}$ carbocycle" means a carbocycle including a single ring having 3-6 carbon atoms. Carbocycles can include one or more double bonds and can be aromatic (e.g., aryl groups). Examples of carbocycles include cyclopropyl, cyclopentyl, cyclohexyl, phenyl, naphthyl, and 1,2-dihydronaphthyl groups. Carbocycles can be optionally substituted.

As used herein, the term "heterocycle" or "heterocyclic group" means a mono- or multi-cyclic system including one or more rings, where at least one ring includes at least one heteroatom. Heteroatoms can be, for example, nitrogen, oxygen, or sulfur atoms. Rings can be three, four, five, six, seven, eight, nine, ten, eleven, or twelve membered rings. Heterocycles can include one or more double bonds and can be aromatic (e.g., heteroaryl groups). Examples of heterocycles include imidazolyl, imidazolidinyl, oxazolyl, oxazolidinyl, thiazolyl, thiazolidinyl, pyrazolidinyl, pyrazolyl, isoxazolidinyl, isoxazolyl, isothiazolidinyl, isothiazolyl, morpholinyl, pyrrolyl, pyrrolidinyl, furyl, tetrahydrofuryl, thiophenyl, pyridinyl, piperidinyl, quinolyl, and isoquinolyl groups. Heterocycles can be optionally substituted.

As used herein, a "biodegradable group" is a group that can facilitate faster metabolism of a lipid in a subject. A biodegradable group can be, but is not limited to, —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, an aryl group, and a heteroaryl group.

As used herein, an "aryl group" is a carbocyclic group including one or more aromatic rings. Examples of aryl groups include phenyl and naphthyl groups.

As used herein, a "heteroaryl group" is a heterocyclic group including one or more aromatic rings. Examples of heteroaryl groups include pyrrolyl, furyl, thiophenyl, imidazolyl, oxazolyl, and thiazolyl. Both aryl and heteroaryl groups can be optionally substituted. For example, M and M' can be selected from the non-limiting group consisting of optionally substituted phenyl, oxazole, and thiazole. In the formulas herein, M and M' can be independently selected from the list of biodegradable groups above.

Alkyl, alkenyl, and cyclyl (e.g., carbocyclyl and heterocyclyl) groups can be optionally substituted unless otherwise specified. Optional substituents can be selected from the group consisting of, but are not limited to, a halogen atom (e.g., a chloride, bromide, fluoride, or iodide group), a carboxylic acid (e.g., —C(O)OH), an alcohol (e.g., a hydroxyl, —OH), an ester (e.g., —C(O)OR or —OC(O)R), an aldehyde (e.g., —C(O)H), a carbonyl (e.g., —C(O)R, alternatively represented by C═O), an acyl halide (e.g., —C(O)X, in which X is a halide selected from bromide, fluoride, chloride, and iodide), a carbonate (e.g., —OC(O)OR), an alkoxy (e.g., —OR), an acetal (e.g., $—C(OR)_2R''''$, in which each OR are alkoxy groups that can be the same or different and R'''' is an alkyl or alkenyl group), a phosphate (e.g., $P(O)_4^{3-}$), a thiol (e.g., —SH), a sulfoxide (e.g., —S(O)R), a sulfinic acid (e.g., —S(O)OH), a sulfonic acid (e.g., $—S(O)_2OH$), a thial (e.g., —C(S)H), a sulfate (e.g., $S(O)_4^{2-}$), a sulfonyl (e.g., $—S(O)_2^-$), an amide (e.g., $—C(O)NR_2$, or —N(R)C(O)R), an azido (e.g., $—N_3$), a nitro (e.g., $—NO_2$), a cyano (e.g., —CN), an isocyano (e.g., —NC), an acyloxy (e.g., —OC(O)R), an amino (e.g., $—NR_2$, —NRH, or $—NH_2$), a carbamoyl (e.g., $—OC(O)NR_2$, —OC(O)NRH, or $—OC(O)NH_2$), a sulfonamide (e.g., $—S(O)_2NR_2$, $—S(O)_2NRH$, $—S(O)_2NH_2$, $—N(R)S(O)_2R$, $—N(H)S(O)_2R$, $—N(R)S(O)_2H$, or $—N(H)S(O)_2H$), an alkyl group, an alkenyl group, and a cyclyl (e.g., carbocyclyl or heterocyclyl) group.

In any of the preceding, R is an alkyl or alkenyl group, as defined herein. In some embodiments, the substituent groups themselves can be further substituted with, for example, one, two, three, four, five, or six substituents as defined herein. For example, a $C_{1-6}$ alkyl group can be further substituted with one, two, three, four, five, or six substituents as described herein.

The compounds of any one of formulae (I), (IA), (II), (IIa), (IIb), (IIc), (IId), and (IIe) include one or more of the following features when applicable.

In some embodiments, $R_4$ is selected from the group consisting of a $C_{3-6}$ carbocycle, $—(CH_2)_nQ$, $—(CH_2)_nCHQR$, —CHQR, and $—CQ(R)_2$, where Q is selected from a $C_{3-6}$ carbocycle, 5- to 14-membered aromatic or non-aromatic heterocycle having one or more heteroatoms selected from N, O, S, and P, —OR, $—O(CH_2)_nN(R)_2$, —C(O)OR, —OC(O)R, $—CX_3$, $—CX_2H$, $—CXH_2$, —CN, $—N(R)_2$, $—C(O)N(R)_2$, —N(R)C(O)R, $—N(R)S(O)_2R$, $—N(R)C(O)N(R)_2$, $—N(R)C(S)N(R)_2$, and $—C(R)N(R)_2C(O)OR$, and each n is independently selected from 1, 2, 3, 4, and 5.

In another embodiment, $R_4$ is selected from the group consisting of a $C_{3-6}$ carbocycle, $—(CH_2)_nQ$, $—(CH_2)_nCHQR$, —CHQR, and $—CQ(R)_2$, where Q is selected from a $C_{3-6}$ carbocycle, a 5- to 14-membered heteroaryl having one or more heteroatoms selected from N, O, and S, —OR, $—O(CH_2)_nN(R)_2$, —C(O)OR, —OC(O)R, $—CX_3$, $—CX_2H$, $—CXH_2$, —CN, $—C(O)N(R)_2$, —N(R)C(O)R, $—N(R)S(O)_2R$, $—N(R)C(O)N(R)_2$, $—N(R)C(S)N(R)_2$, $—C(R)N(R)_2C(O)OR$, and a 5- to 14-membered heterocycloalkyl having one or more heteroatoms selected from N, O, and S which is substituted with one or more substituents selected from oxo (═O), OH, amino, and $C_{1-3}$ alkyl, and each n is independently selected from 1, 2, 3, 4, and 5.

In another embodiment, $R_4$ is selected from the group consisting of a $C_{3-6}$ carbocycle, $—(CH_2)_nQ$, $—(CH_2)_nCHQR$, —CHQR, and $—CQ(R)_2$, where Q is selected from a $C_{3-6}$ carbocycle, a 5- to 14-membered heterocycle having one or more heteroatoms selected from N, O, and S, —OR, $—O(CH_2)_nN(R)_2$, —C(O)OR, —OC(O)R, $—CX_3$, $—CX_2H$, $—CXH_2$, —CN, $—C(O)N(R)_2$, —N(R)C(O)R, $—N(R)S(O)_2R$, $—N(R)C(O)N(R)_2$, $—N(R)C(S)N(R)_2$, $—C(R)N(R)_2C(O)OR$, and each n is independently selected from 1, 2, 3, 4, and 5; and when Q is a 5- to 14-membered heterocycle and (i) $R_4$ is $—(CH_2)_nQ$ in which n is 1 or 2, or (ii) $R_4$ is $—(CH_2)_nCHQR$ in which n is 1, or (iii) $R_4$ is —CHQR, and $—CQ(R)_2$, then Q is either a 5- to 14-membered heteroaryl or 8-to 14-membered heterocycloalkyl.

In another embodiment, $R_4$ is selected from the group consisting of a $C_{3-6}$ carbocycle, $—(CH_2)_nQ$, $—(CH_2)_nCHQR$, —CHQR, and $—CQ(R)_2$, where Q is selected from a $C_{3-6}$ carbocycle, a 5- to 14-membered heteroaryl having one or more heteroatoms selected from N, O, and S, —OR, $—O(CH_2)_nN(R)_2$, —C(O)OR, —OC(O)R, $—CX_3$, $—CX_2H$, $—CXH_2$, —CN, $—C(O)N(R)_2$, —N(R)C(O)R, $—N(R)S(O)_2R$, $—N(R)C(O)N(R)_2$, $—N(R)C(S)N(R)_2$, $—C(R)N(R)_2C(O)OR$, and each n is independently selected from 1, 2, 3, 4, and 5.

In another embodiment, $R_4$ is unsubstituted $C_{14}$ alkyl, e.g., unsubstituted methyl.

In certain embodiments, the disclosure provides a compound having the Formula (I), wherein $R_4$ is $—(CH_2)_nQ$ or $—(CH_2)_nCHQR$, where Q is $—N(R)_2$, and n is selected from 3, 4, and 5.

In certain embodiments, the disclosure provides a compound having the Formula (I), wherein $R_4$ is selected from the group consisting of $—(CH_2)_nQ$, $—(CH_2)_nCHQR$, —CHQR, and $—CQ(R)_2$, where Q is $—N(R)_2$, and n is selected from 1, 2, 3, 4, and 5.

In certain embodiments, the disclosure provides a compound having the Formula (I), wherein $R_2$ and $R_3$ are independently selected from the group consisting of $C_{2-14}$ alkyl, $C_{2-14}$ alkenyl, —R*YR", —YR", and —R*OR", or $R_2$ and $R_3$, together with the atom to which they are attached, form a heterocycle or carbocycle, and $R_4$ is $—(CH_2)_nQ$ or $—(CH_2)_nCHQR$, where Q is $—N(R)_2$, and n is selected from 3, 4, and 5.

In certain embodiments, $R_2$ and $R_3$ are independently selected from the group consisting of $C_{2-14}$ alkyl, $C_{2-14}$ alkenyl, —R*YR", —YR", and —R*OR", or $R_2$ and $R_3$, together with the atom to which they are attached, form a heterocycle or carbocycle.

In some embodiments, $R_1$ is selected from the group consisting of $C_{5-20}$ alkyl and $C_{5-20}$ alkenyl.

In other embodiments, $R_1$ is selected from the group consisting of —R*YR", —YR", and —R"M'R'.

In certain embodiments, $R_1$ is selected from —R*YR" and —YR". In some embodiments, Y is a cyclopropyl group. In some embodiments, R* is $C_8$ alkyl or $C_8$ alkenyl. In certain embodiments, R" is $C_{3-12}$ alkyl. For example, R" can be $C_3$ alkyl. For example, R" can be $C_{4-8}$ alkyl (e.g., $C_4$, $C_5$, $C_6$, $C_7$, or $C_8$ alkyl).

In some embodiments, $R_1$ is $C_{5-20}$ alkyl. In some embodiments, $R_1$ is $C_6$ alkyl. In some embodiments, $R_1$ is $C_8$ alkyl. In other embodiments, $R_1$ is $C_9$ alkyl. In certain embodiments, $R_1$ is $C_{14}$ alkyl. In other embodiments, $R_1$ is $C_{18}$ alkyl.

In some embodiments, $R_1$ is $C_{5-20}$ alkenyl. In certain embodiments, $R_1$ is $C_{18}$ alkenyl. In some embodiments, $R_1$ is linoleyl.

In certain embodiments, $R_1$ is branched (e.g., decan-2-yl, undecan-3-yl, dodecan-4-yl, tridecan-5-yl, tetradecan-6-yl, 2-methylundecan-3-yl, 2-methyldecan-2-yl, 3-methylundecan-3-yl, 4-methyldodecan-4-yl, or heptadeca-9-yl). In certain embodiments, $R_1$ is

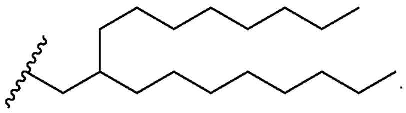 [SMILES: *CC(CCCCCCCC)CCCCCCCC]

In certain embodiments, $R_1$ is unsubstituted $C_{5-20}$ alkyl or $C_{5-20}$ alkenyl. In certain embodiments, R' is substituted $C_{5-20}$ alkyl or $C_{5-20}$ alkenyl (e.g., substituted with a $C_{3-6}$ carbocycle such as 1-cyclopropylnonyl).

In other embodiments, $R_1$ is —R"M'R'.

In some embodiments, R' is selected from —R*YR" and —YR". In some embodiments, Y is $C_{3-8}$ cycloalkyl. In some embodiments, Y is $C_{6-10}$ aryl. In some embodiments, Y is a cyclopropyl group. In some embodiments, Y is a cyclohexyl group. In certain embodiments, R* is $C_1$ alkyl.

In some embodiments, R" is selected from the group consisting of $C_{3-12}$ alkyl and $C_{3-12}$ alkenyl. In some embodiments, R" adjacent to Y is $C_1$ alkyl. In some embodiments, R" adjacent to Y is $C_{4-9}$ alkyl (e.g., $C_4$, $C_5$, $C_6$, $C_7$ or $C_8$ or $C_9$ alkyl).

In some embodiments, R' is selected from $C_4$ alkyl and $C_4$ alkenyl. In certain embodiments, R' is selected from $C_5$ alkyl and $C_5$ alkenyl. In some embodiments, R' is selected from $C_6$ alkyl and $C_6$ alkenyl. In some embodiments, R' is selected from $C_7$ alkyl and $C_7$ alkenyl. In some embodiments, R' is selected from $C_9$ alkyl and $C_9$ alkenyl.

In other embodiments, R' is selected from $C_{11}$ alkyl and $C_{11}$ alkenyl. In other embodiments, R' is selected from Cu alkyl, Cu alkenyl, $C_{13}$ alkyl, $C_{13}$ alkenyl, $C_{14}$ alkyl, $C_{14}$ alkenyl, $C_{15}$ alkyl, $C_{15}$ alkenyl, $C_{16}$ alkyl, $C_{16}$ alkenyl, $C_{17}$ alkyl, $C_{17}$ alkenyl, $C_{18}$ alkyl, and $C_{18}$ alkenyl. In certain embodiments, R' is branched (e.g., decan-2-yl, undecan-3-yl, dodecan-4-yl, tridecan-5-yl, tetradecan-6-yl, 2-methylundecan-3-yl, 2-methyldecan-2-yl, 3-methylundecan-3-yl, 4-methyldodecan-4-yl or heptadeca-9-yl). In certain embodiments, R' is

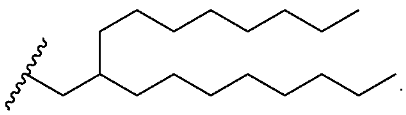 [SMILES: *CC(CCCCCCCC)CCCCCCCC]

In certain embodiments, R' is unsubstituted $C_{1-18}$ alkyl. In certain embodiments, R' is substituted $C_{1-18}$ alkyl (e.g., $C_{1-15}$ alkyl substituted with a $C_{3-6}$ carbocycle such as 1-cyclopropylnonyl).

In some embodiments, R" is selected from the group consisting of $C_{3-14}$ alkyl and $C_{3-14}$ alkenyl. In some embodiments, R" is $C_3$ alkyl, $C_4$ alkyl, $C_5$ alkyl, $C_6$ alkyl, $C_7$ alkyl, or $C_8$ alkyl. In some embodiments, R" is $C_9$ alkyl, $C_{10}$ alkyl, $C_{11}$ alkyl, Cu alkyl, $C_{13}$ alkyl, or $C_{14}$ alkyl.

In some embodiments, M' is —C(O)O—. In some embodiments, M' is —OC(O)—.

In other embodiments, M' is an aryl group or heteroaryl group. For example, M' can be selected from the group consisting of phenyl, oxazole, and thiazole.

In some embodiments, M is —C(O)O— In some embodiments, M is —OC(O)—. In some embodiments, M is —C(O)N(R')—. In some embodiments, M is —P(O)(OR')O—.

In other embodiments, M is an aryl group or heteroaryl group. For example, M can be selected from the group consisting of phenyl, oxazole, and thiazole.

In some embodiments, M is the same as M'. In other embodiments, M is different from M'.

In some embodiments, each $R_5$ is H. In certain such embodiments, each $R_6$ is also H.

In some embodiments, $R_7$ is H. In other embodiments, $R_7$ is $C_{1-3}$ alkyl (e.g., methyl, ethyl, propyl, or i-propyl).

In some embodiments, $R_2$ and $R_3$ are independently $C_{5-14}$ alkyl or $C_{5-14}$ alkenyl.

In some embodiments, $R_2$ and $R_3$ are the same. In some embodiments, $R_2$ and $R_3$ are $C_8$ alkyl. In certain embodiments, $R_2$ and $R_3$ are $C_2$ alkyl. In other embodiments, $R_2$ and $R_3$ are $C_3$ alkyl. In some embodiments, $R_2$ and $R_3$ are $C_4$ alkyl. In certain embodiments, $R_2$ and $R_3$ are $C_5$ alkyl. In other embodiments, $R_2$ and $R_3$ are $C_6$ alkyl. In some embodiments, $R_2$ and $R_3$ are $C_7$ alkyl.

In other embodiments, $R_2$ and $R_3$ are different. In certain embodiments, $R_2$ is $C_8$ alkyl.

In some embodiments, $R_3$ is $C_{1-7}$ (e.g., $C_1$, $C_2$, $C_3$, $C_4$, $C_5$, $C_6$, or $C_7$ alkyl) or $C_9$ alkyl.

In some embodiments, $R_7$ and $R_3$ are H.

In certain embodiments, $R_2$ is H.

In some embodiments, m is 5, 7, or 9.

In some embodiments, $R_4$ is selected from $—(CH_2)_nQ$ and $—(CH_2)_nCHQR$.

In some embodiments, Q is selected from the group consisting of —OR, —OH, $—O(CH_2)_nN(R)_2$, —OC(O)R, $—CX_3$, —CN, —N(R)C(O)R, —N(H)C(O)R, $—N(R)S(O)_2R$, $—N(H)S(O)_2R$, $—N(R)C(O)N(R)_2$, $—N(H)C(O)N(R)_2$, —N(H)C(O)N(H)(R), $—N(R)C(S)N(R)_2$, $—N(H)C(S)N(R)_2$, —N(H)C(S)N(H)(R), $—C(R)N(R)_2C(O)OR$, a carbocycle, and a heterocycle.

In certain embodiments, Q is —OH.

In certain embodiments, Q is a substituted or unsubstituted 5- to 10-membered heteroaryl, e.g., Q is an imidazole, a pyrimidine, a purine, 2-amino-1,9-dihydro-6H-purin-6-one-9-yl (or guanin-9-yl), adenin-9-yl, cytosin-1-yl, or uracil-1-yl. In certain embodiments, Q is a substituted 5- to 14-membered heterocycloalkyl, e.g., substituted with one or more substituents selected from oxo (=O), OH, amino, and $C_{1-3}$ alkyl. For example, Q is 4-methylpiperazinyl, 4-(4-methoxybenzyl)piperazinyl, or isoindolin-2-yl-1,3-dione.

In certain embodiments, Q is an unsubstituted or substituted $C_{6-10}$ aryl (such as phenyl) or $C_{3-6}$ cycloalkyl.

In some embodiments, n is 1. In other embodiments, n is 2. In further embodiments, n is 3. In certain other embodiments, n is 4. For example, $R_4$ can be $—(CH_2)_2OH$. For example, $R_4$ can be $—(CH_2)_3OH$. For example, $R_4$ can be $—(CH_2)_4OH$. For example, $R_4$ can be benzyl. For example, $R_4$ can be 4-methoxybenzyl.

In some embodiments, $R_4$ is a $C_{3-6}$ carbocycle. In some embodiments, $R_4$ is a $C_{3-6}$ cycloalkyl. For example, $R_4$ can be cyclohexyl optionally substituted with e.g., OH, halo, $C_{1-6}$ alkyl, etc. For example, $R_4$ can be 2-hydroxycyclohexyl.

In some embodiments, R is H.

In some embodiments, R is unsubstituted $C_{1-3}$ alkyl or unsubstituted $C_{2-3}$ alkenyl. For example, $R_4$ can be —$CH_2CH(OH)CH_3$ or —$CH_2CH(OH)CH_2CH_3$.

In some embodiments, R is substituted $C_{1-3}$ alkyl, e.g., $CH_2OH$. For example, $R_4$ can be —$CH_2CH(OH)CH_2OH$.

In some embodiments, $R_2$ and $R_3$, together with the atom to which they are attached, form a heterocycle or carbocycle. In some embodiments, $R_2$ and $R_3$, together with the atom to which they are attached, form a 5- to 14-membered aromatic or non-aromatic heterocycle having one or more heteroatoms selected from N, O, S, and P. In some embodiments, $R_2$ and $R_3$, together with the atom to which they are attached, form an optionally substituted $C_{3-20}$ carbocycle (e.g., $C_{3-18}$ carbocycle, $C_{3-15}$ carbocycle, $C_{3-12}$ carbocycle, or $C_{3-10}$ carbocycle), either aromatic or non-aromatic. In some embodiments, $R_2$ and $R_3$, together with the atom to which they are attached, form a $C_{3-6}$ carbocycle. In other embodiments, $R_2$ and $R_3$, together with the atom to which they are attached, form a $C_6$ carbocycle, such as a cyclohexyl or phenyl group. In certain embodiments, the heterocycle or $C_{3-6}$ carbocycle is substituted with one or more alkyl groups (e.g., at the same ring atom or at adjacent or non-adjacent ring atoms). For example, $R_2$ and $R_3$, together with the atom to which they are attached, can form a cyclohexyl or phenyl group bearing one or more $C_5$ alkyl substitutions. In certain embodiments, the heterocycle or $C_{3-6}$ carbocycle formed by $R_2$ and $R_3$, is substituted with a carbocycle groups. For example, $R_2$ and $R_3$, together with the atom to which they are attached, can form a cyclohexyl or phenyl group that is substituted with cyclohexyl. In some embodiments, $R_2$ and $R_3$, together with the atom to which they are attached, form a $C_{7-15}$ carbocycle, such as a cycloheptyl, cyclopentadecanyl, or naphthyl group.

In some embodiments, $R_4$ is selected from —$(CH_2)_nQ$ and —$(CH_2)_nCHQR$. In some embodiments, Q is selected from the group consisting of —OR, —OH, —$O(CH_2)_nN(R)_2$, —OC(O)R, —$CX_3$, —CN, —N(R)C(O)R, —N(H)C(O)R, —$N(R)S(O)_2R$, —$N(H)S(O)_2R$, —$N(R)C(O)N(R)_2$, —$N(H)C(O)N(R)_2$, —N(H)C(O)N(H)(R), —$N(R)C(S)N(R)_2$, —$N(H)C(S)N(R)_2$, —N(H)C(S)N(H)(R), and a heterocycle. In other embodiments, Q is selected from the group consisting of an imidazole, a pyrimidine, and a purine.

In some embodiments, $R_2$ and $R_3$, together with the atom to which they are attached, form a heterocycle or carbocycle. In some embodiments, $R_2$ and $R_3$, together with the atom to which they are attached, form a $C_{3-6}$ carbocycle, such as a phenyl group. In certain embodiments, the heterocycle or $C_{3-6}$ carbocycle is substituted with one or more alkyl groups (e.g., at the same ring atom or at adjacent or non-adjacent ring atoms). For example, $R_2$ and $R_3$, together with the atom to which they are attached, can form a phenyl group bearing one or more $C_5$ alkyl substitutions.

In some embodiments, the pharmaceutical compositions of the present disclosure, the compound of formula (I) is selected from the group consisting of:

(Compound 1)

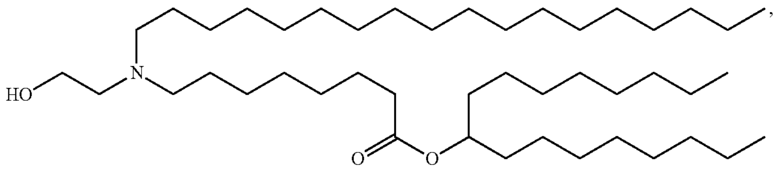
, (Compound 2)

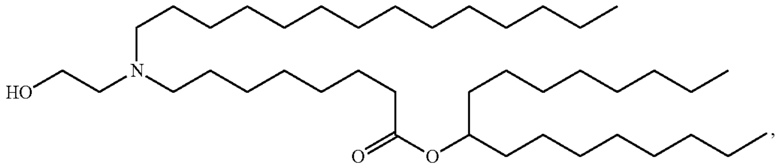
, (Compound 3)

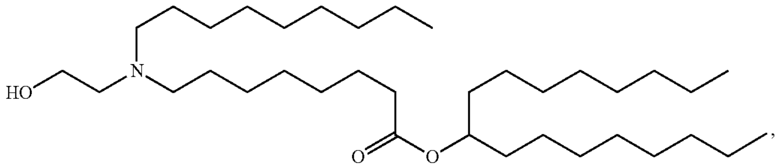
, (Compound 4)

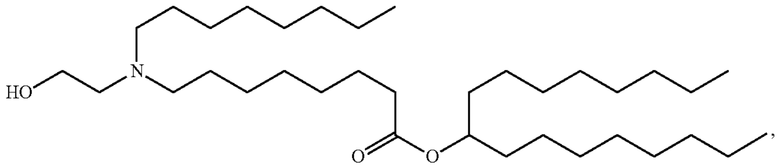
, (Compound 5)

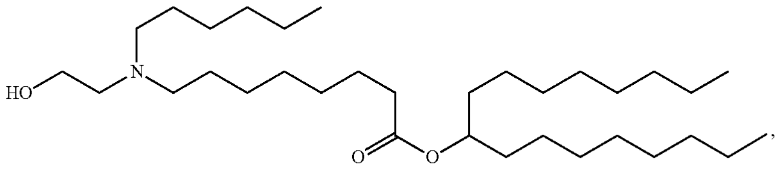
,

-continued
(Compound 6)
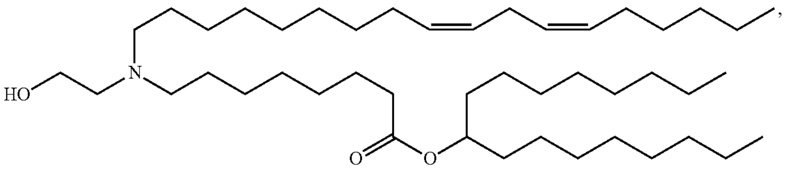
(Compound 7)
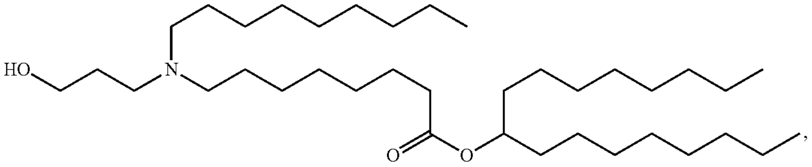
(Compound 8)
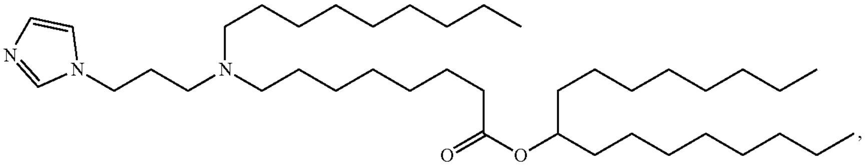
(Compound 9)
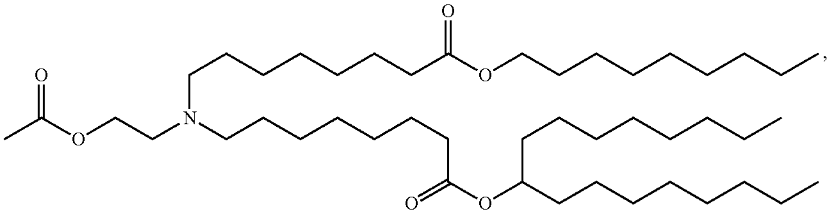
(Compound 10)
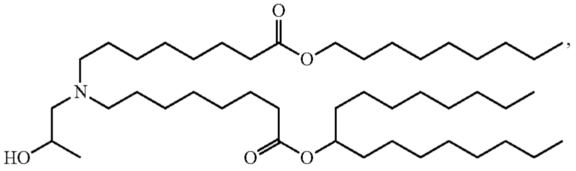
(Compound 11)
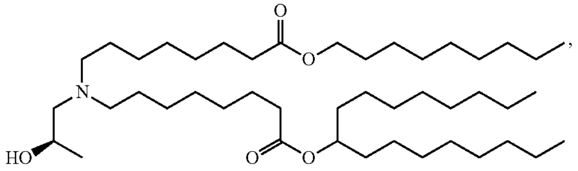
(Compound 12)
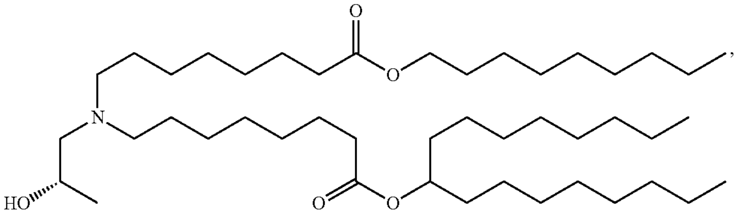
(Compound 13)
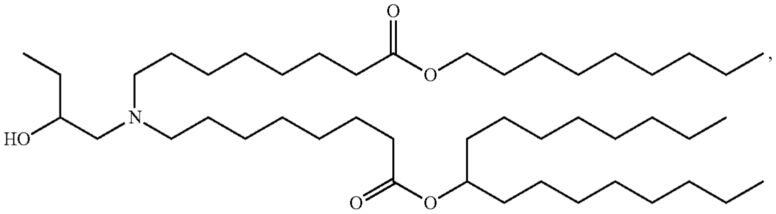
(Compound 14)
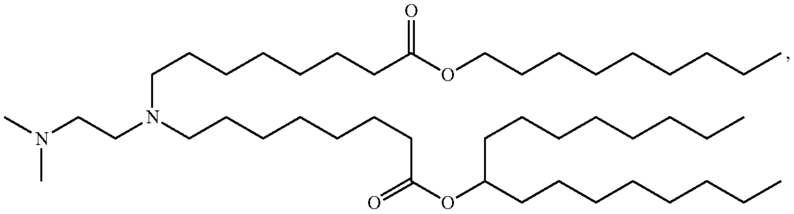

-continued
(Compound 15)
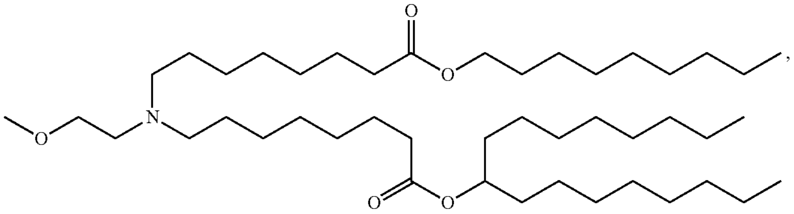
(Compound 16)
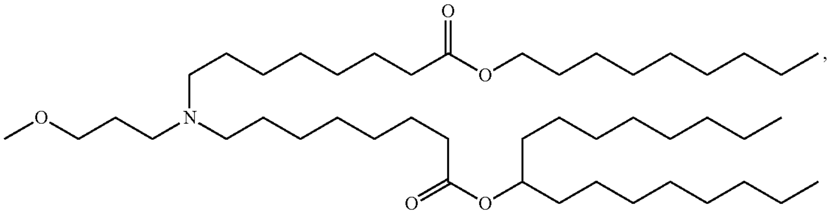
(Compound 17)
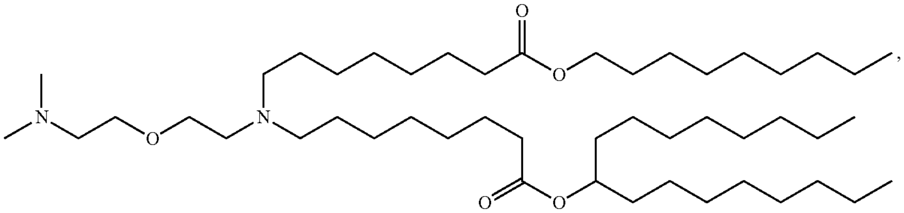
(Compound 18)
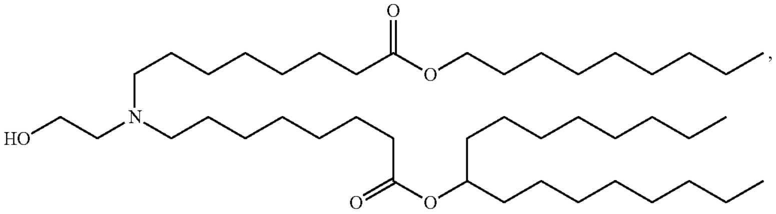
(Compound 19)
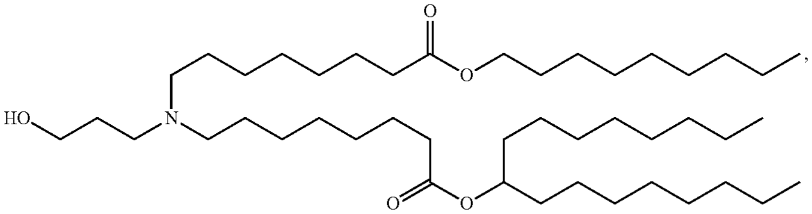
(Compound 20)
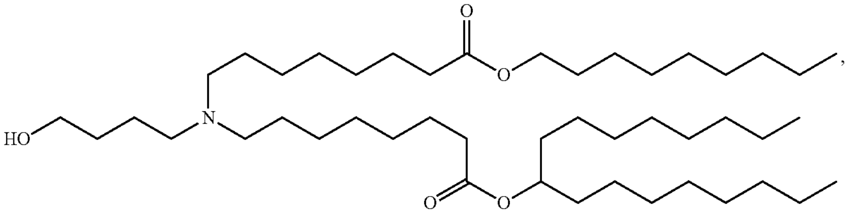
(Compound 21)
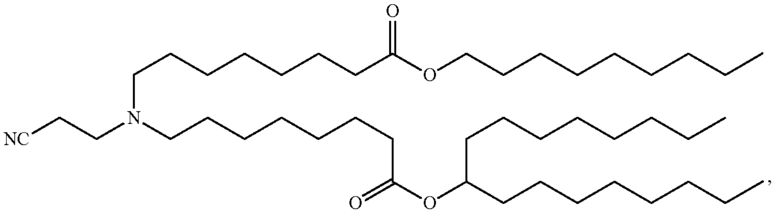

-continued
(Compound 22)
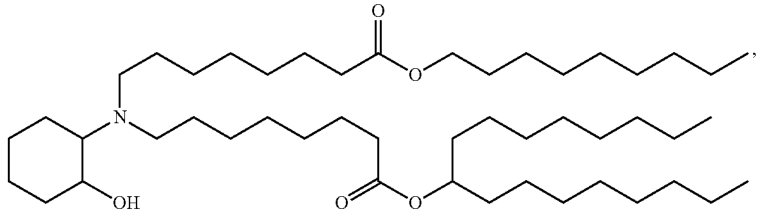
(Compound 23)
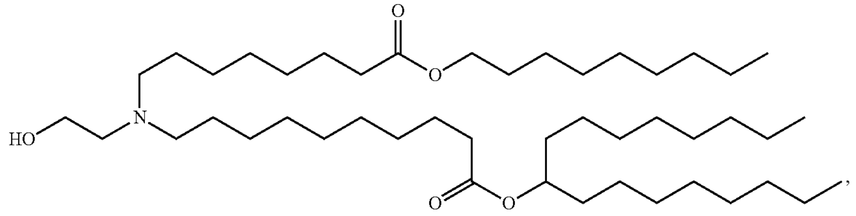
(Compound 24)
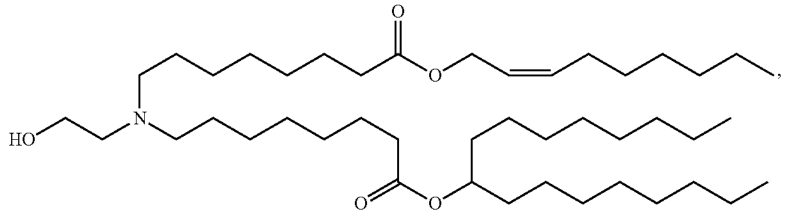
(Compound 25)
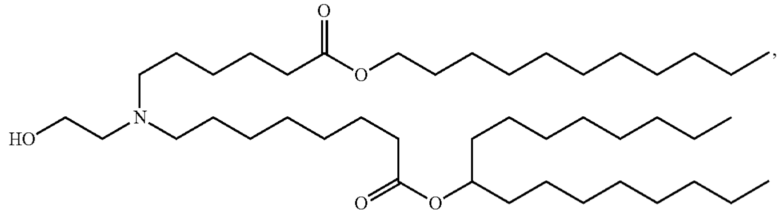
(Compound 26)
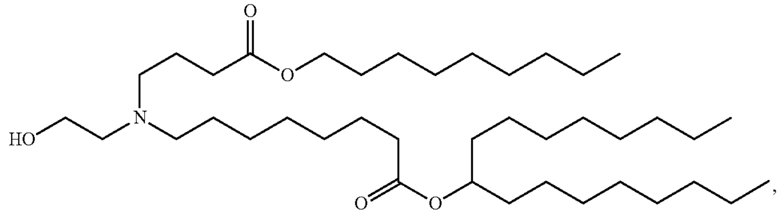
(Compound 27)
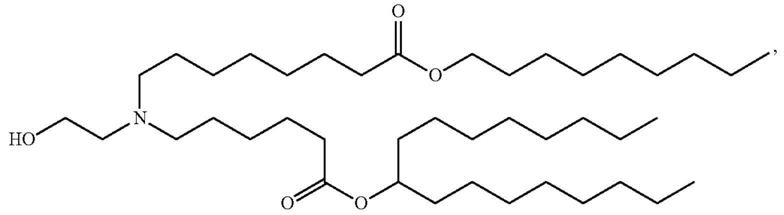
(Compound 28)
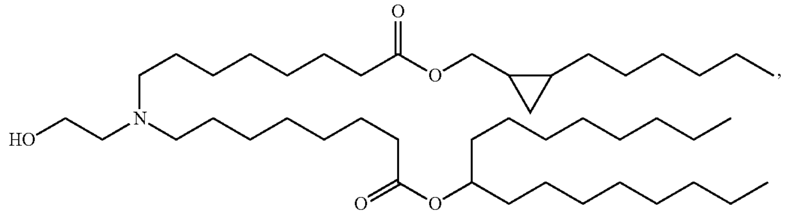

-continued
(Compound 29)
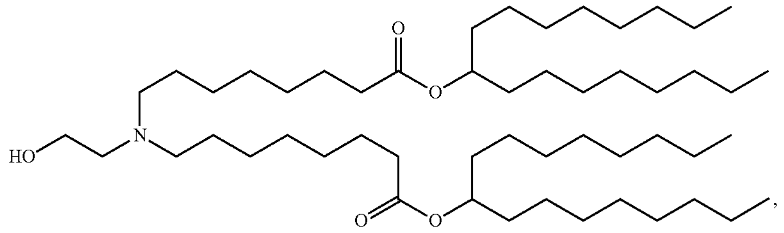
(Compound 30)
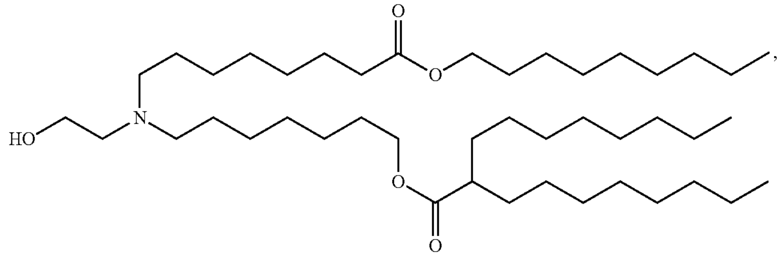
(Compound 31)
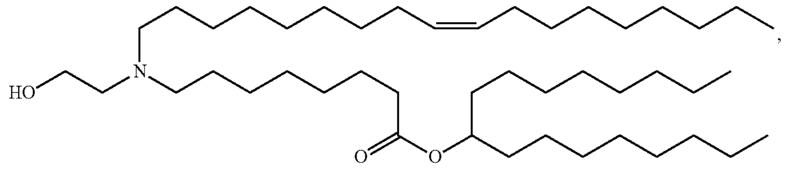
(Compound 32)
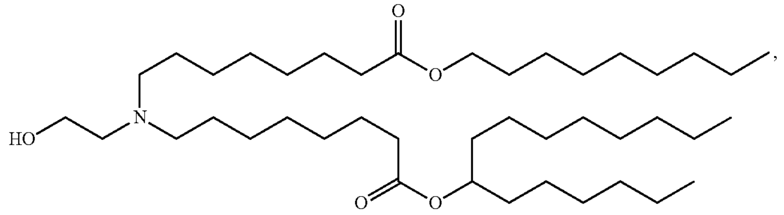
(Compound 33)
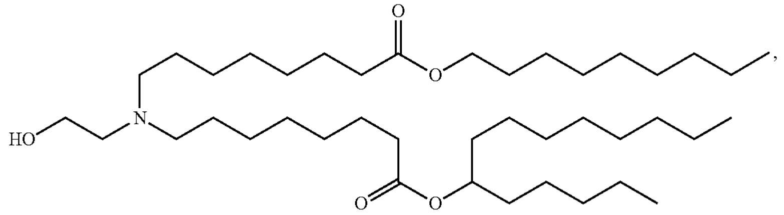
(Compound 34)
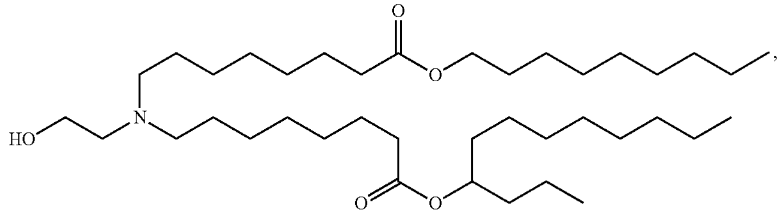
(Compound 35)
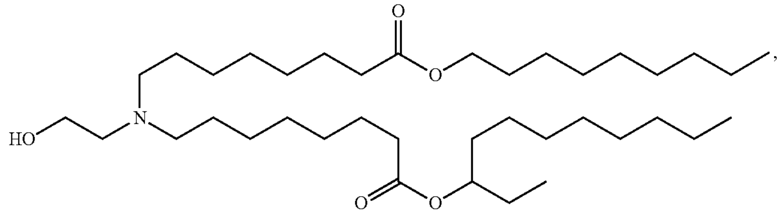

-continued
(Compound 36)
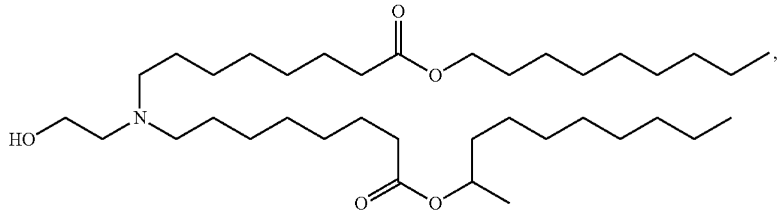
(Compound 37)
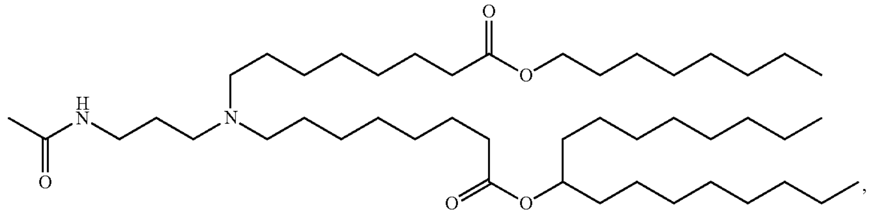
(Compound 38)
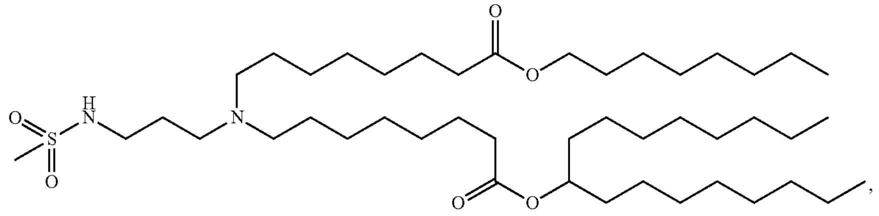
(Compound 39)
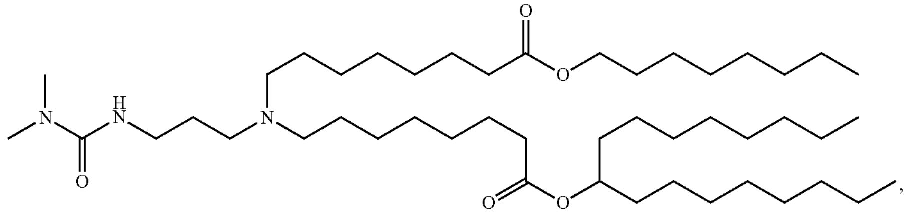
(Compound 40)
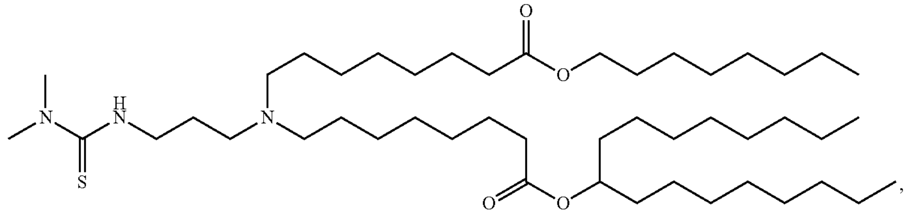
(Compound 41)
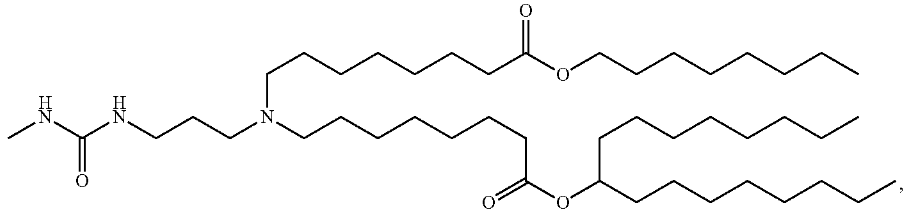
(Compound 42)
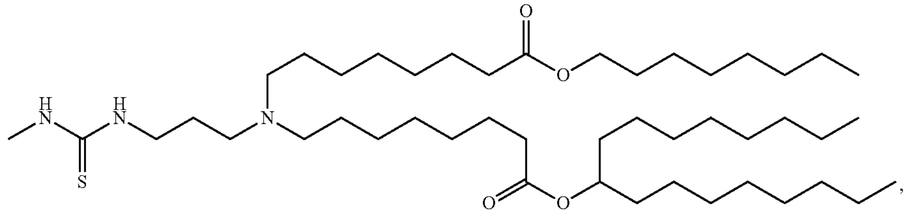

-continued
(Compound 43)
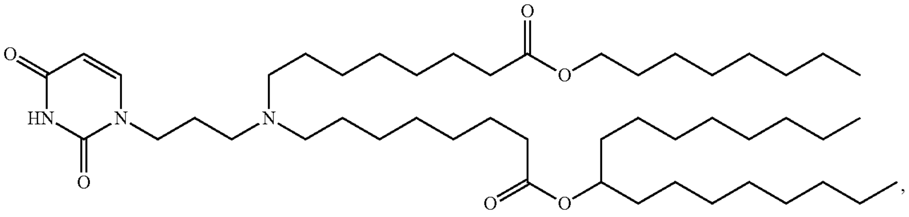
(Compound 44)
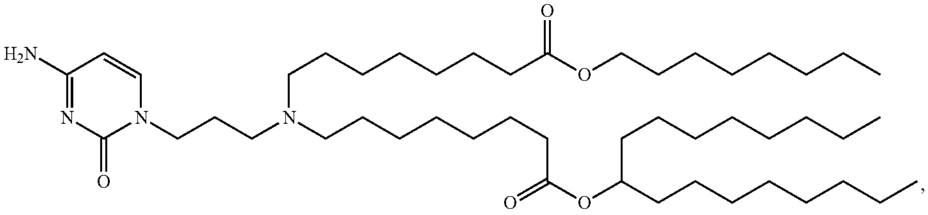
(Compound 45)
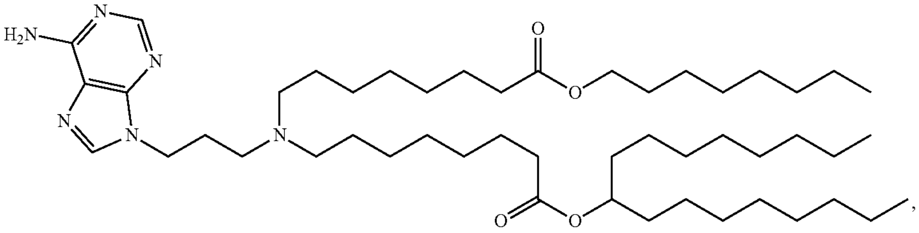
(Compound 46)
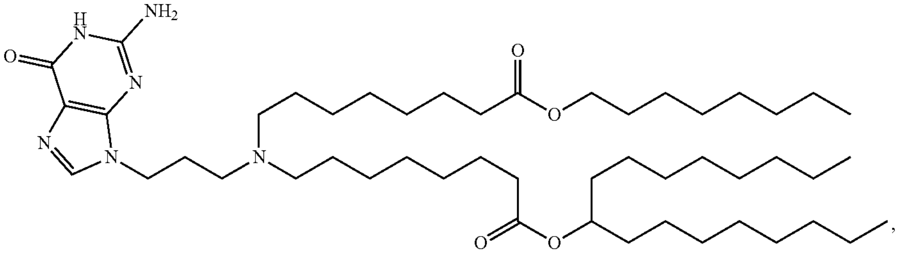
(Compound 47)
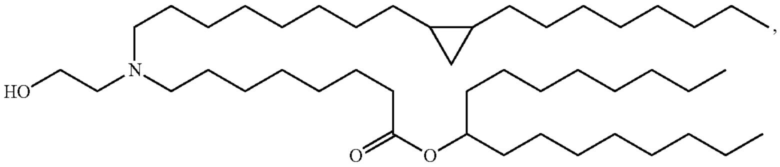
(Compound 48)
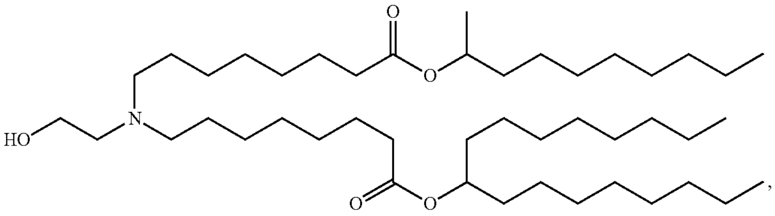
(Compound 49)
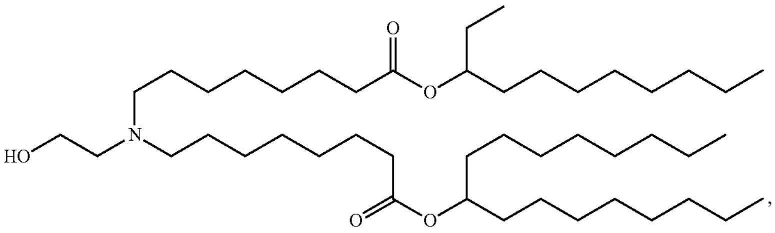

-continued
(Compound 50)
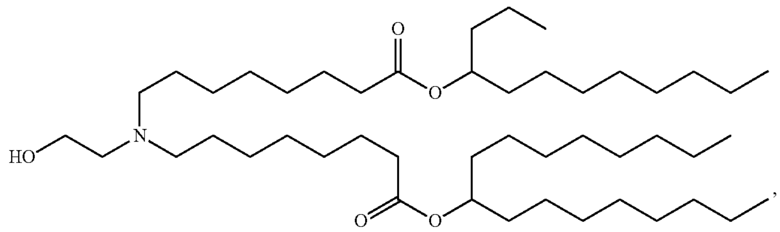
,
(Compound 51)
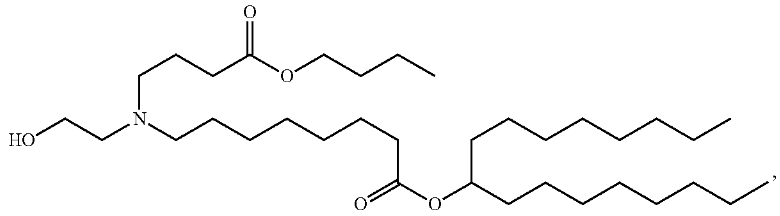
,
(Compound 52)
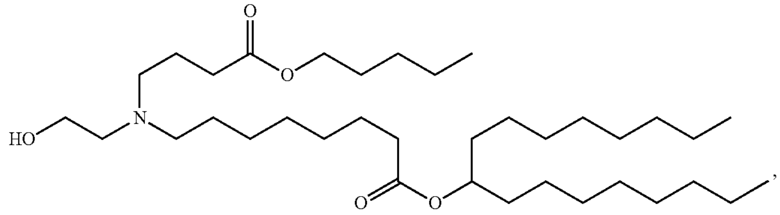
,
(Compound 53)
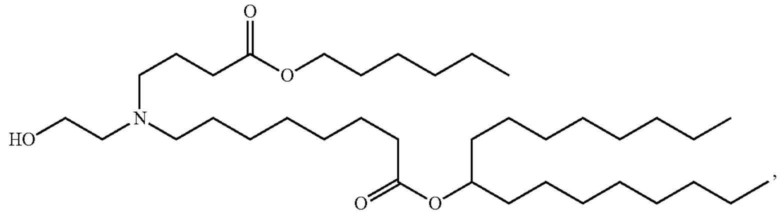
,
(Compound 54)
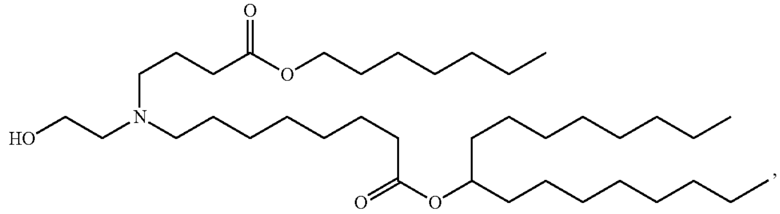
,
(Compound 55)
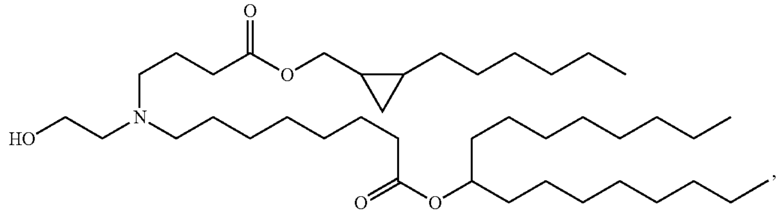
,
(Compound 56)
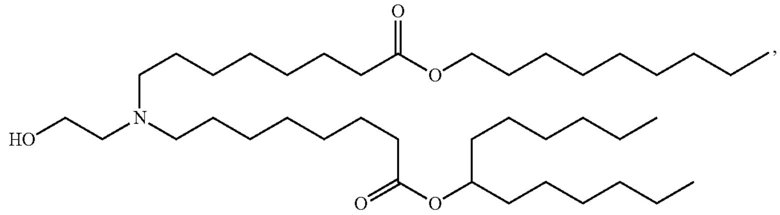
, -continued
(Compound 57)
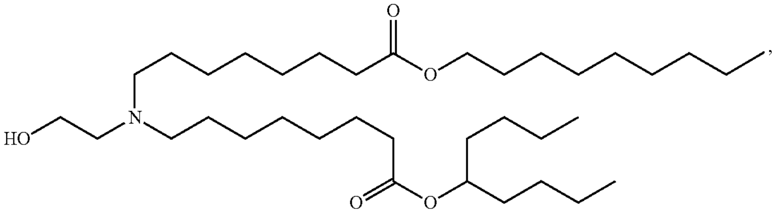
(Compound 58)
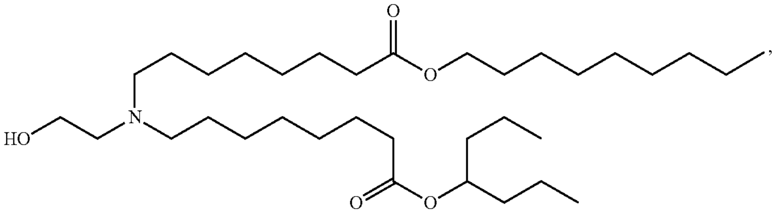
(Compound 59)
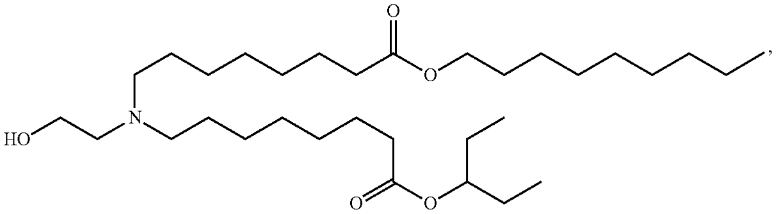
(Compound 60)
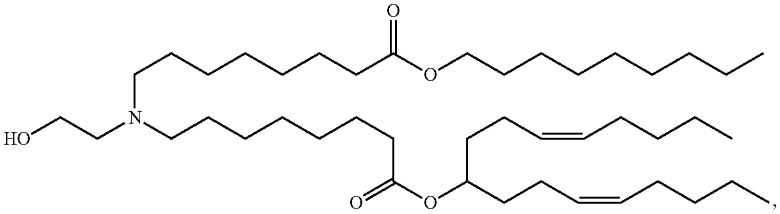
(Compound 61)
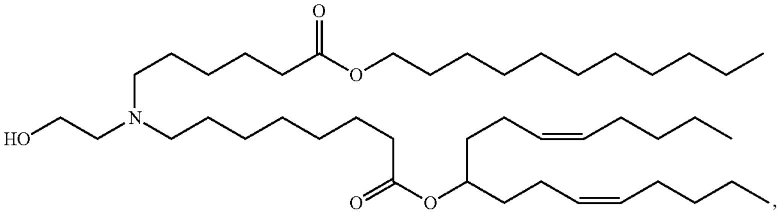
(Compound 62)
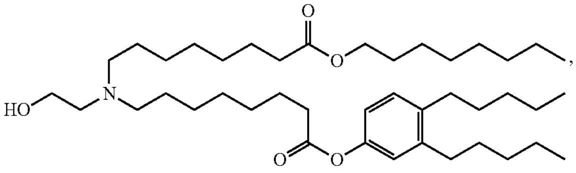
(Compound 63)
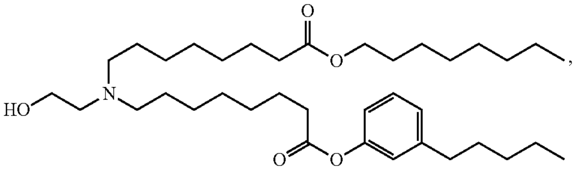
(Compound 64)
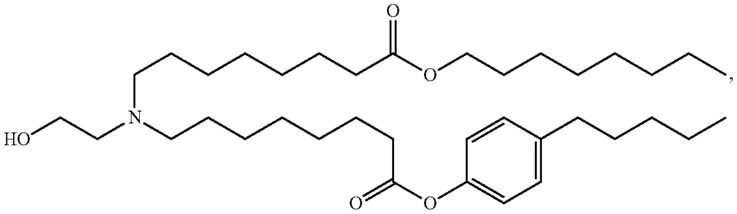

-continued
(Compound 65)
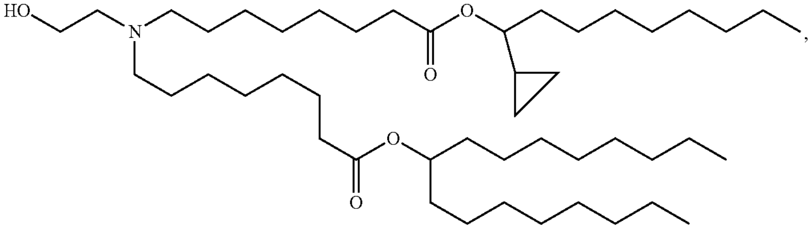,
(Compound 66)
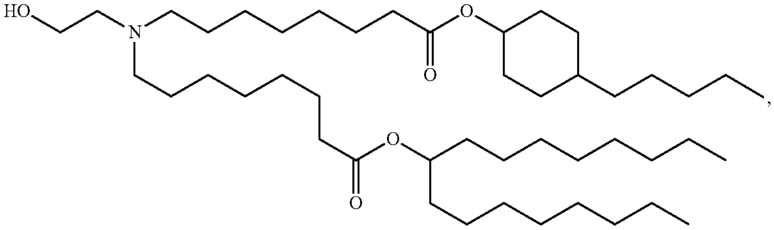,
(Compound 67)
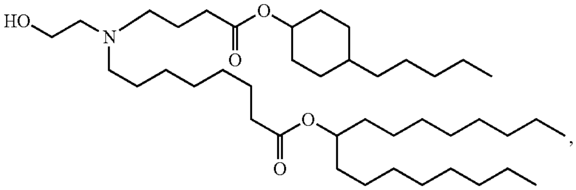,
(Compound 68)
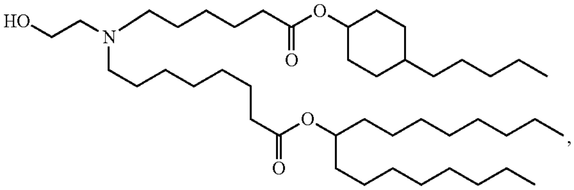,
(Compound 69)
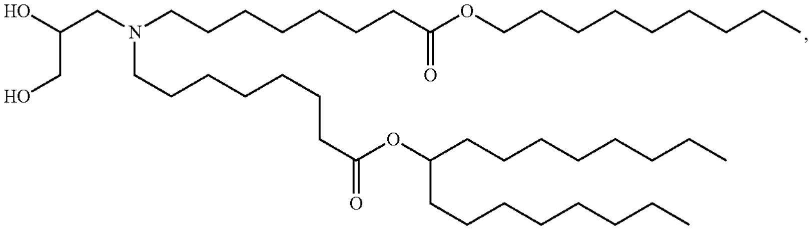,
(Compound 70)
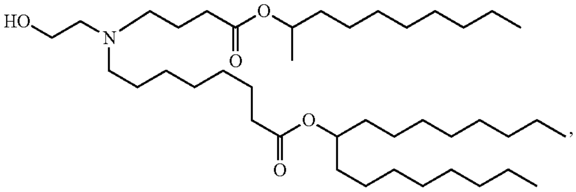,
(Compound 71)
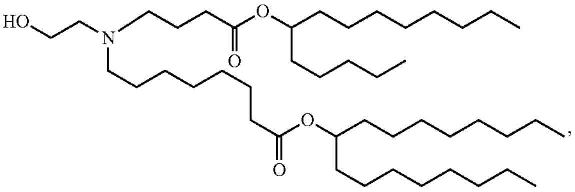,
(Compound 72)
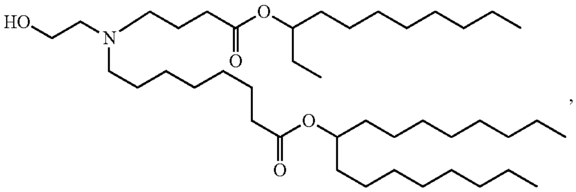,
(Compound 73)
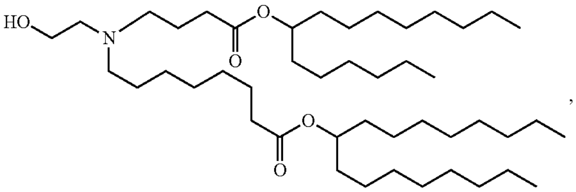,
(Compound 74)
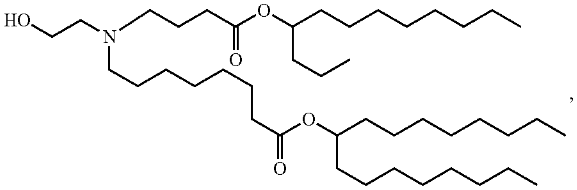,
(Compound 75)
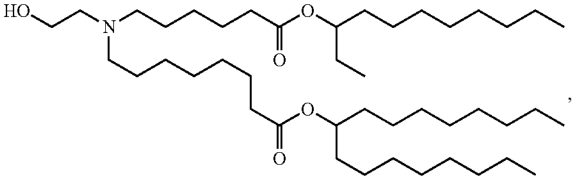, -continued
(Compound 76)
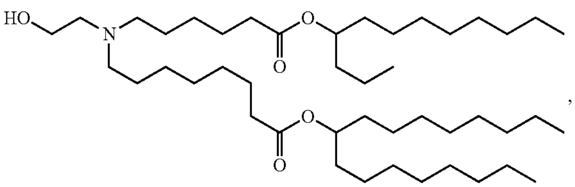
,
(Compound 77)
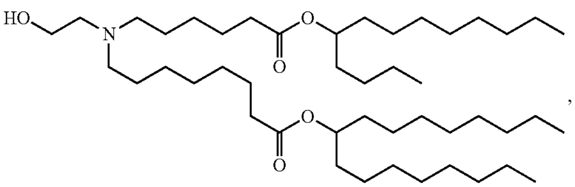
,
(Compound 78)
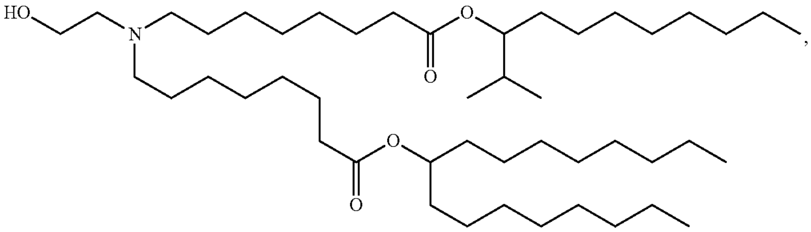
,
(Compound 79)
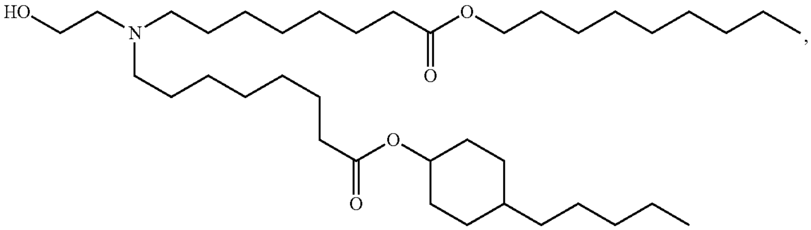
,
(Compound 80)
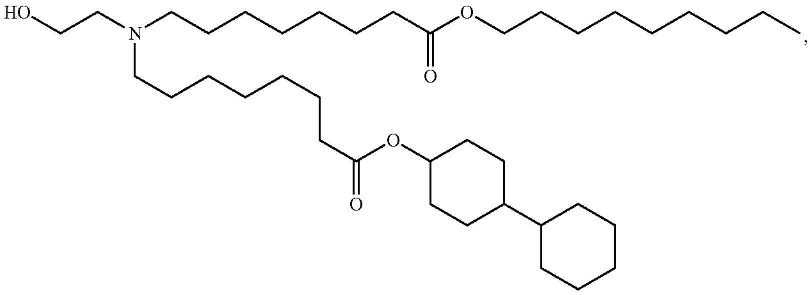
,
(Compound 81)
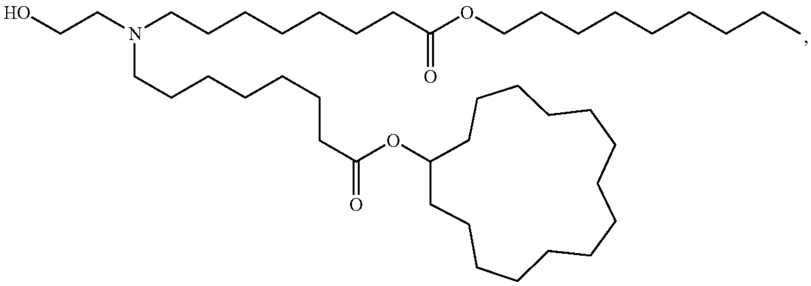
,
(Compound 82)
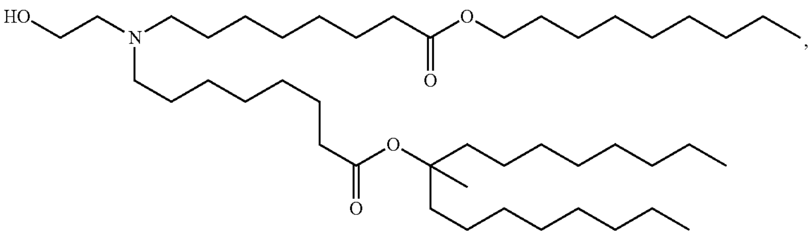
, -continued
(Compound 83)
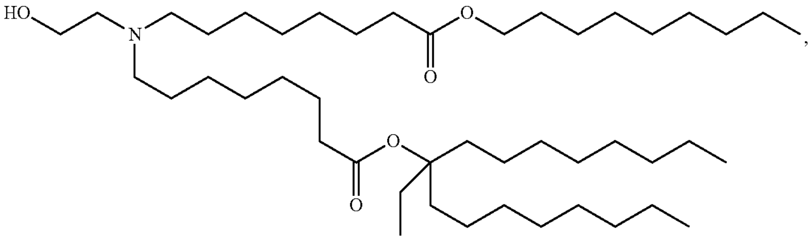
,
(Compound 84)
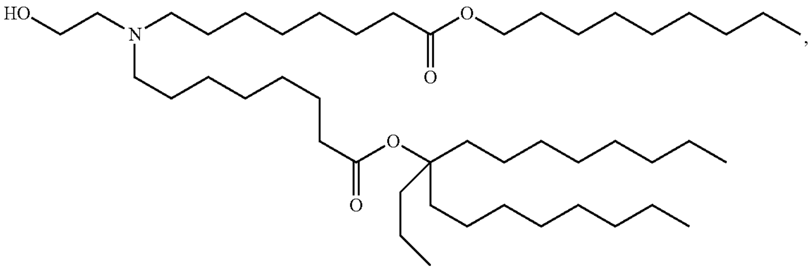
,
(Compound 85)
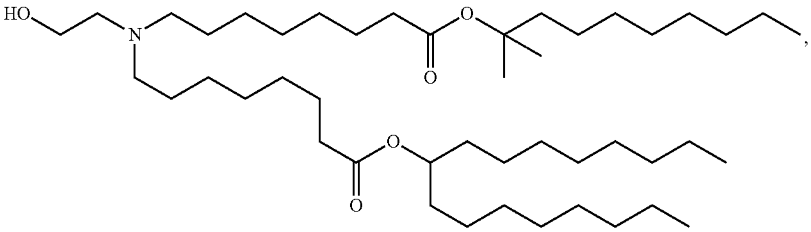
,
(Compound 86)
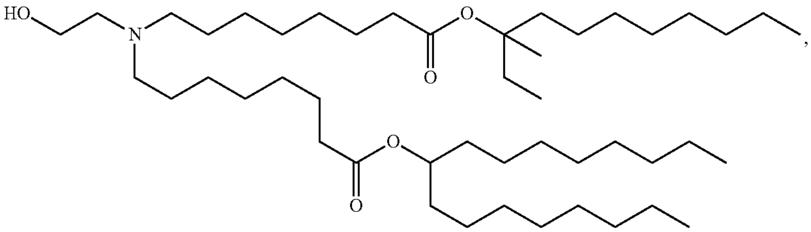
,
(Compound 87)
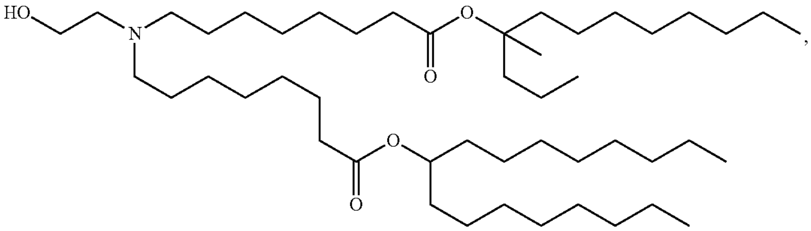
,
(Compound 88)
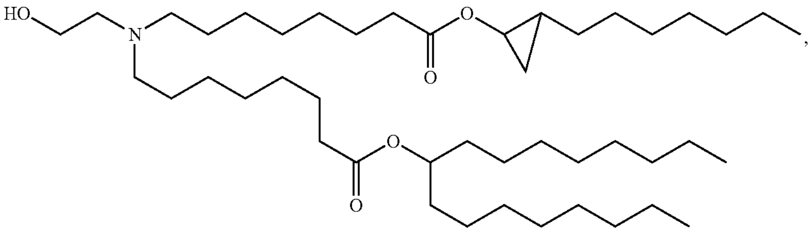
, -continued
(Compound 89)
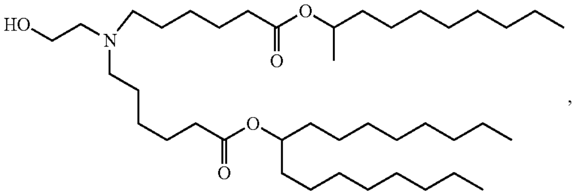
,
(Compound 90)
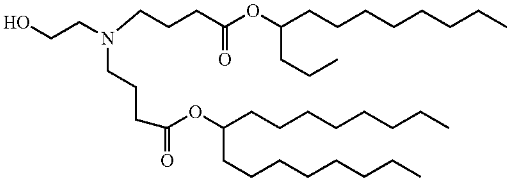
,
(Compound 91)
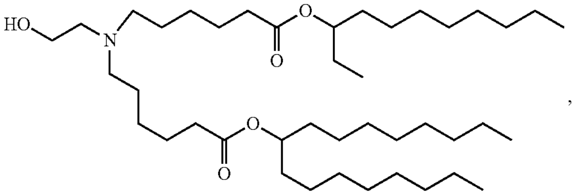
,
(Compound 92)
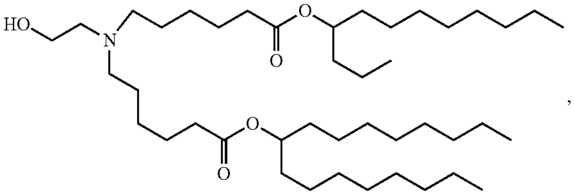
,
(Compound 93)
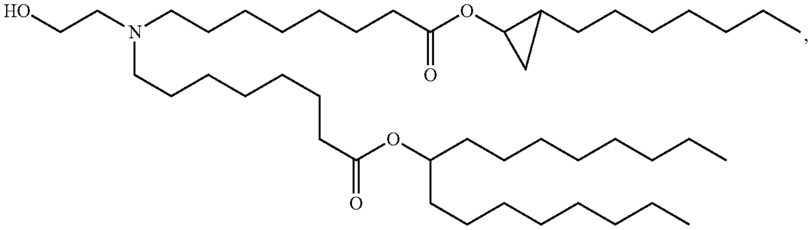
,
(Compound 94)
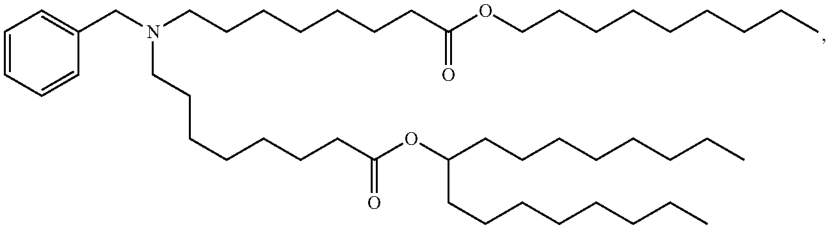
,
(Compound 95)
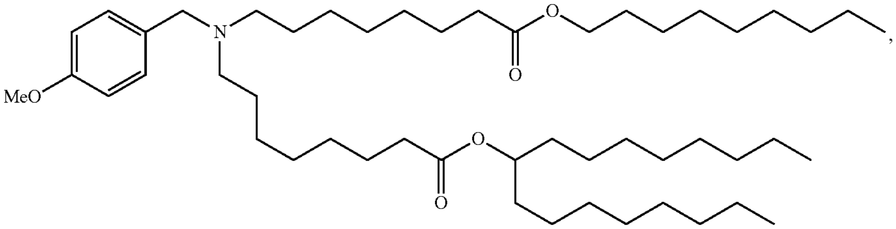
,
(Compound 96)
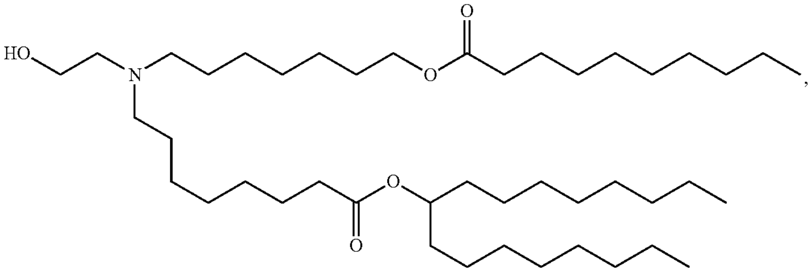
, -continued
(Compound 97)
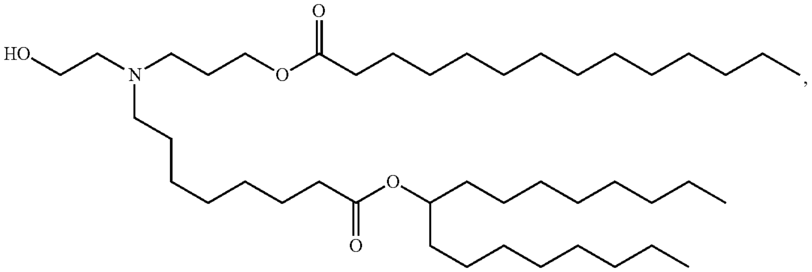
(Compound 98)
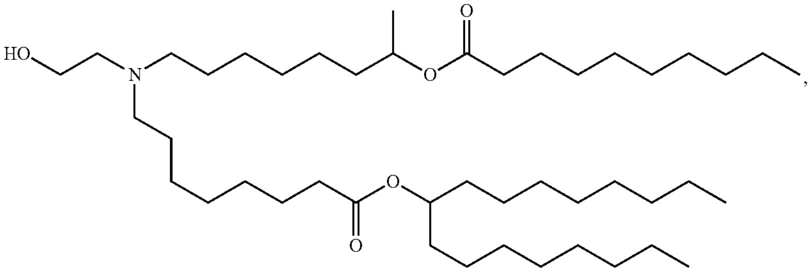
(Compound 99)
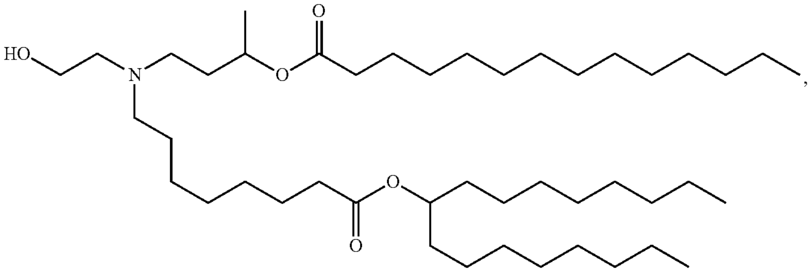
(Compound 100)
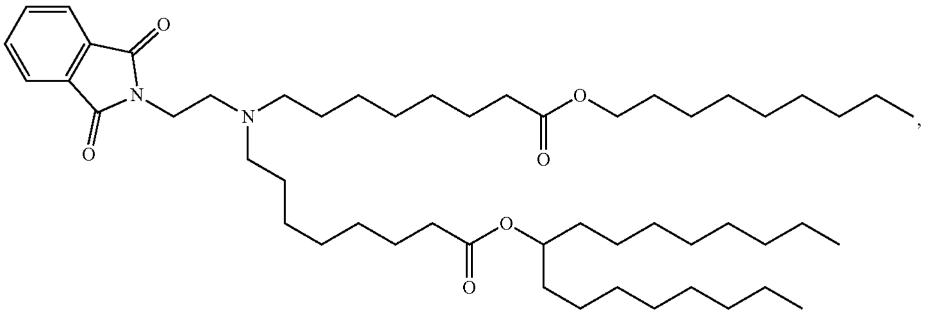
(Compound 101)
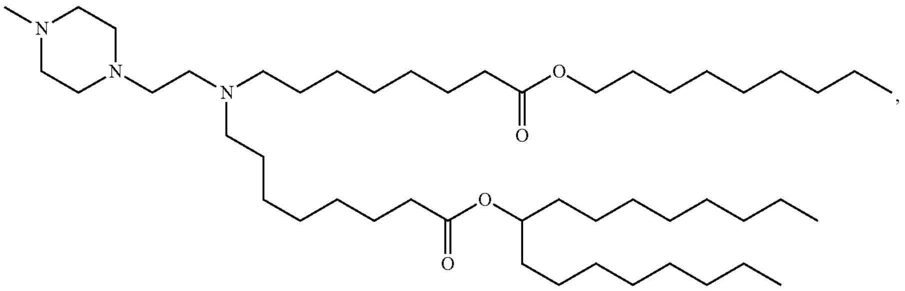

-continued
(Compound 102)
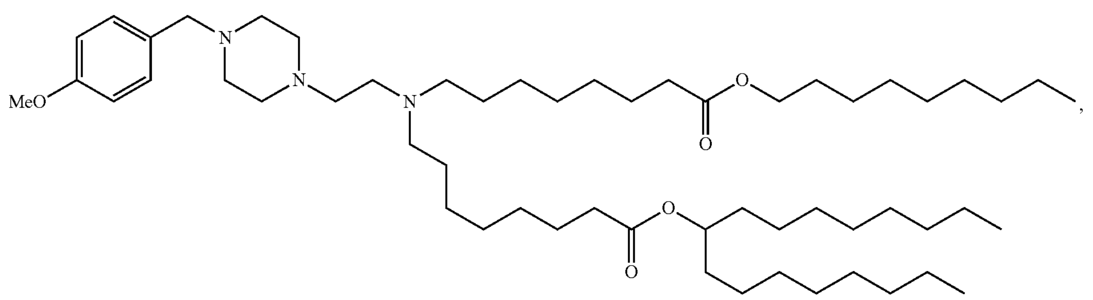
(Compound 103)
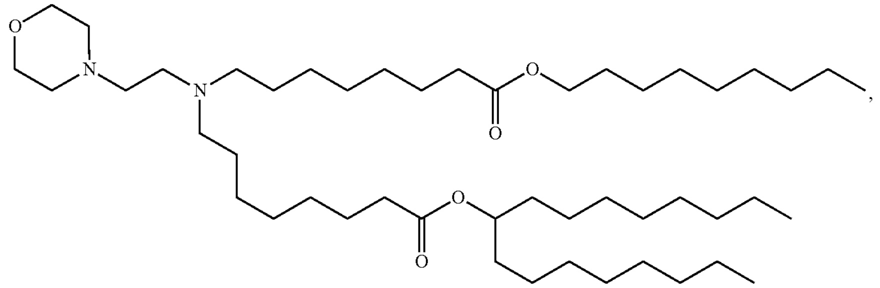
(Compound 104)
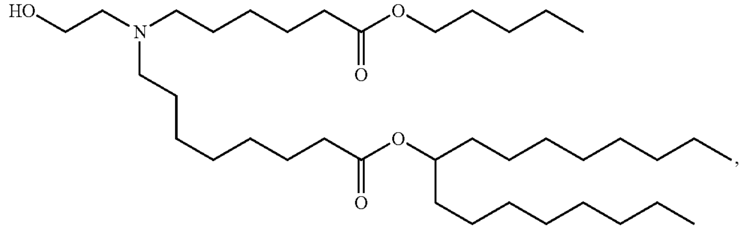
(Compound 105)
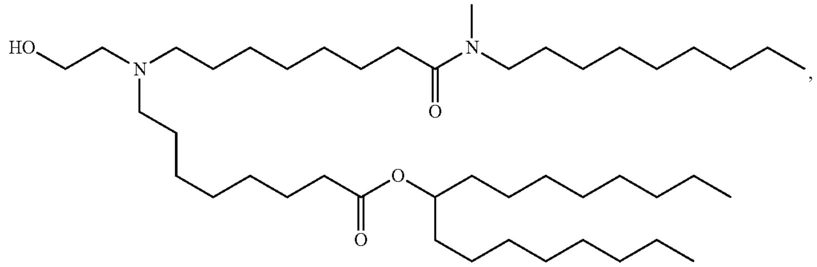
(Compound 106)
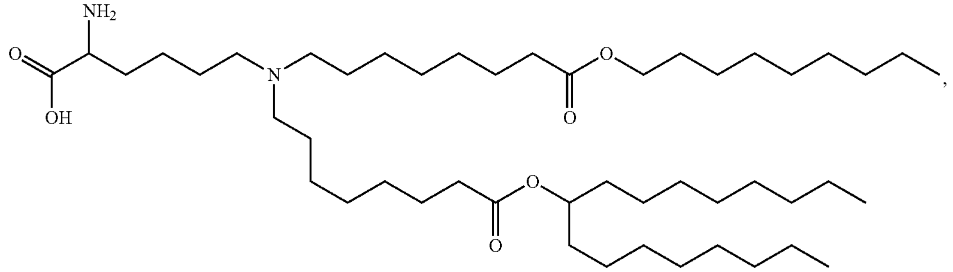
(Compound 107)
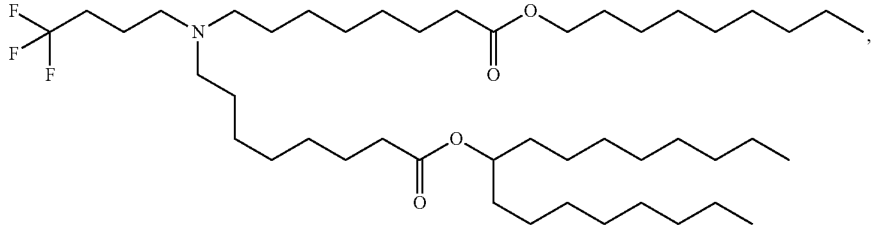

-continued
(Compound 108)
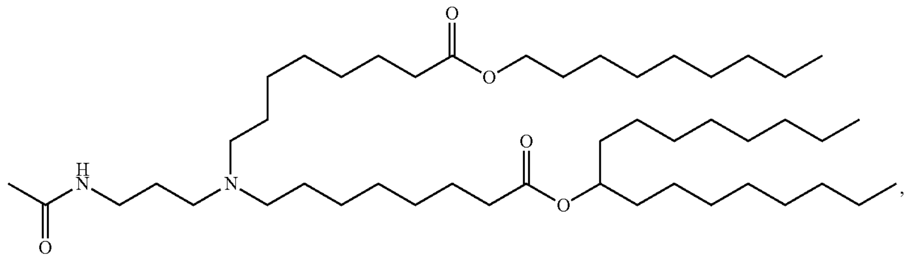
,
(Compound 109)
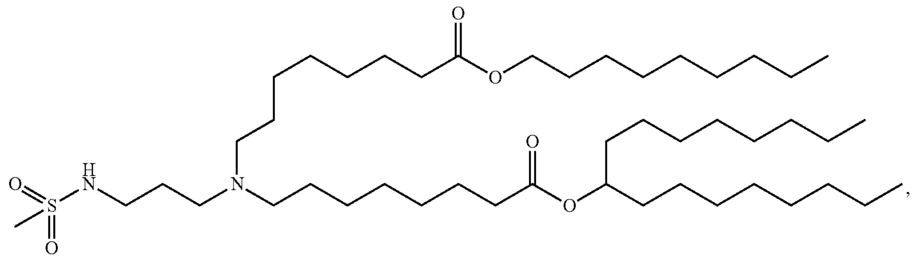
,
(Compound 110)
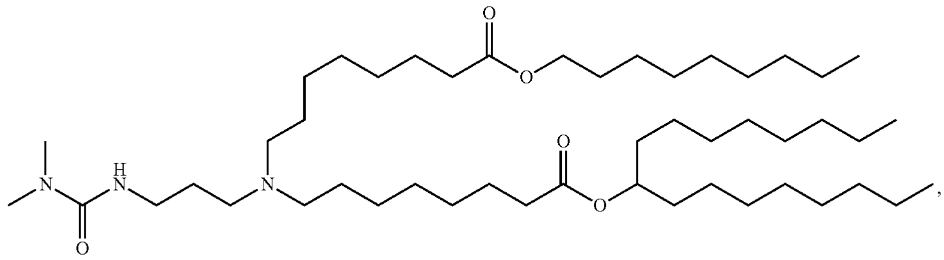
,
(Compound 111)
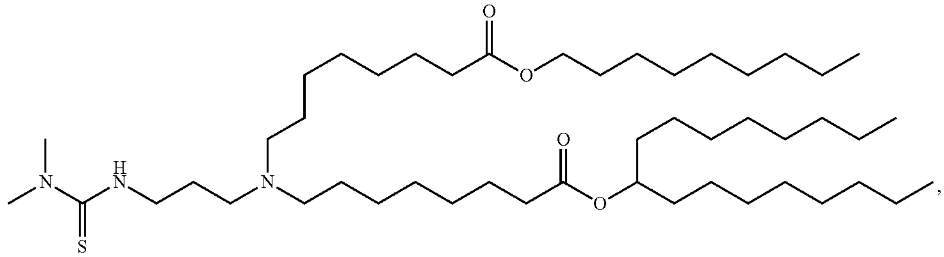
,
(Compound 112)
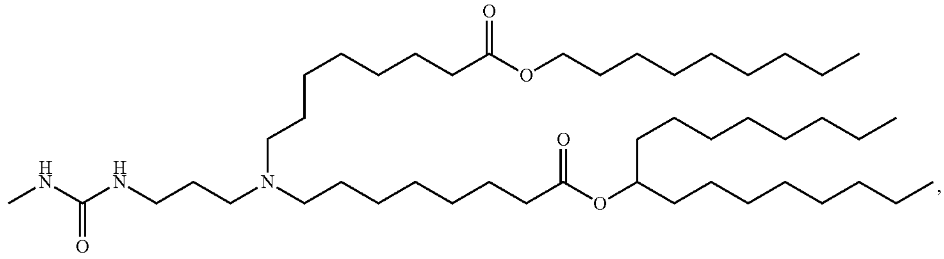
,
(Compound 113)
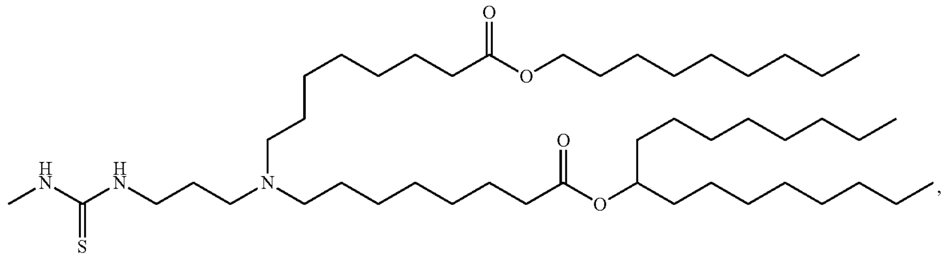
, -continued
(Compound 114)
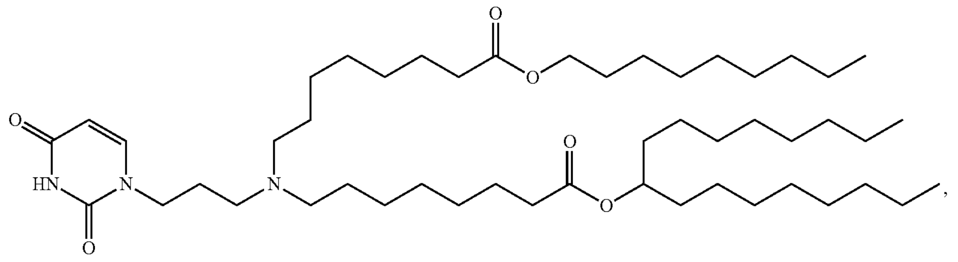
(Compound 115)
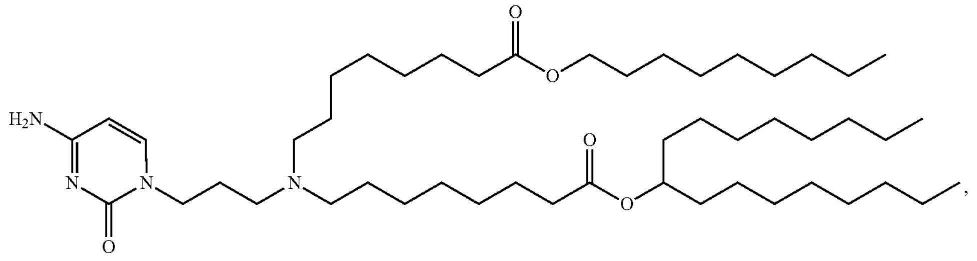
(Compound 116)
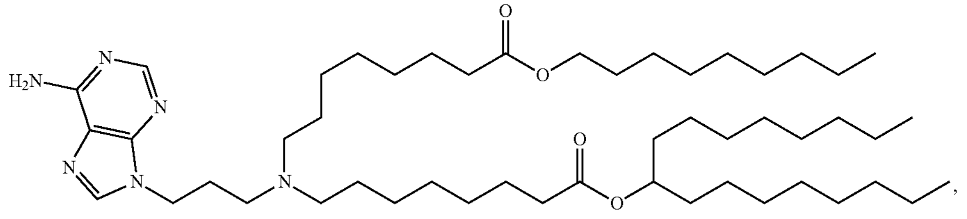
(Compound 117)
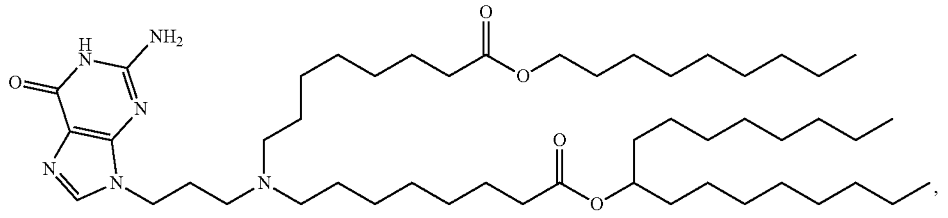
(Compound 118)
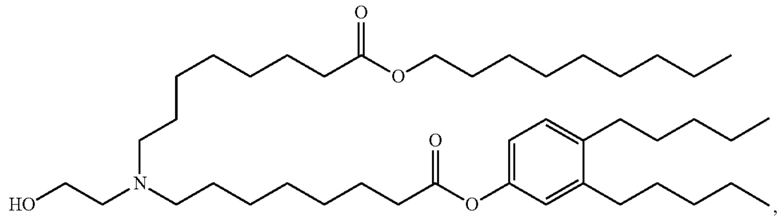
(Compound 119)
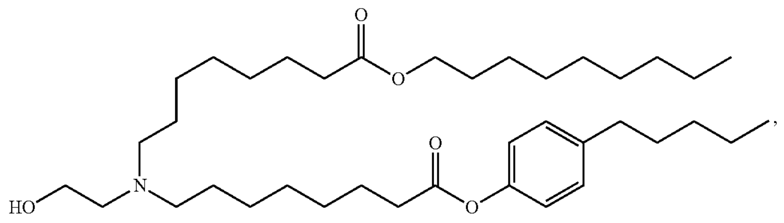

-continued
(Compound 120)
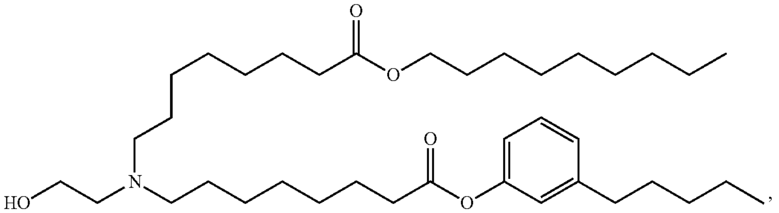
(Compound 121)
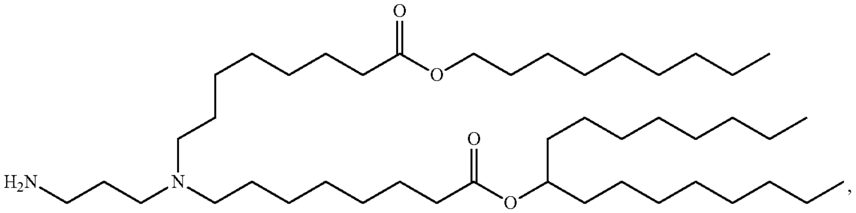
(Compound 122)
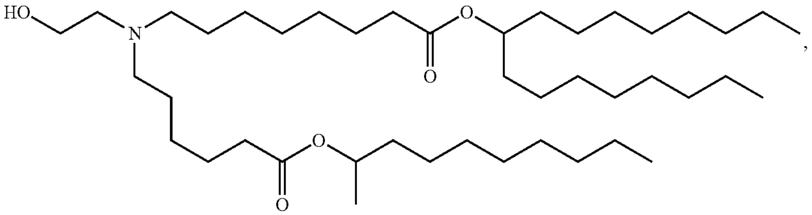
(Compound 123)
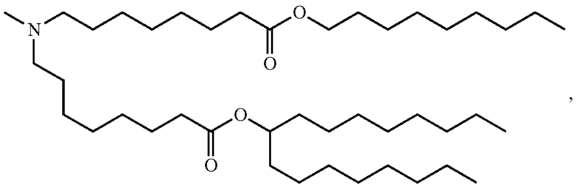
(Compound 124)
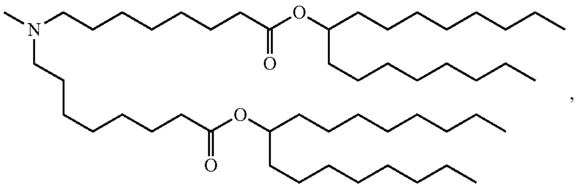
(Compound 125)
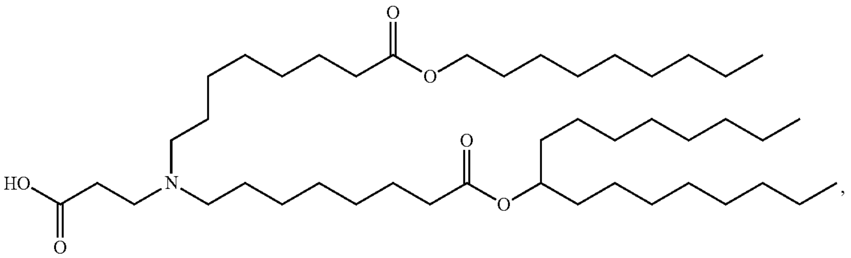
(Compound 126)
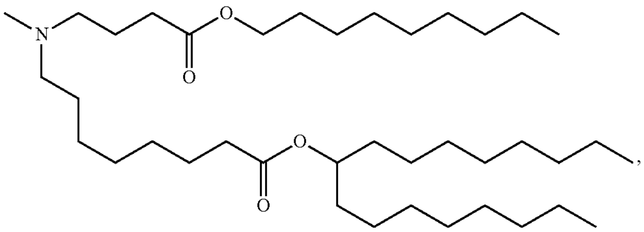
(Compound 127)
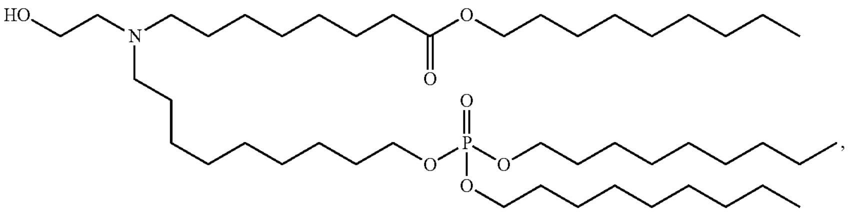

-continued
(Compound 128)
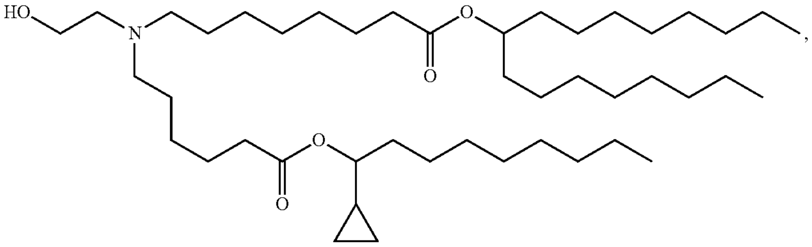
(Compound 129)
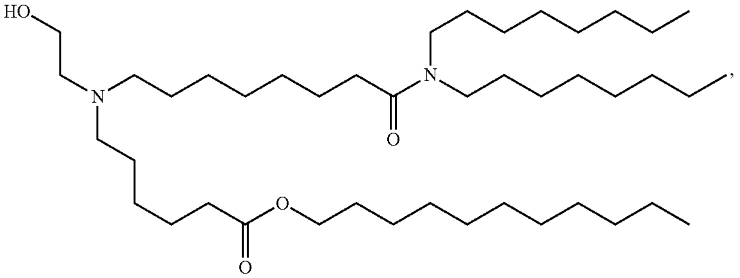
(Compound 130)
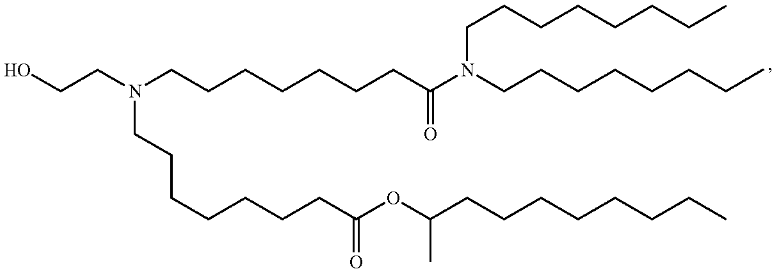
(Compound 131)
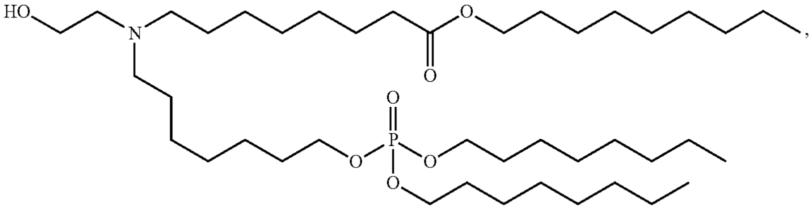
(Compound 132)
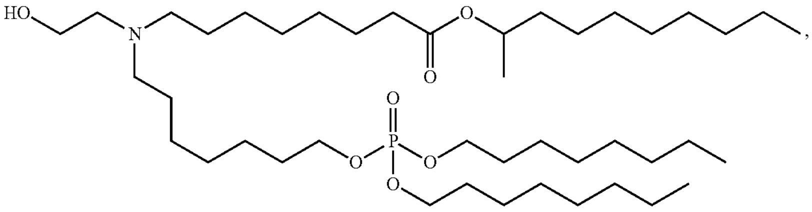
(Compound 133)
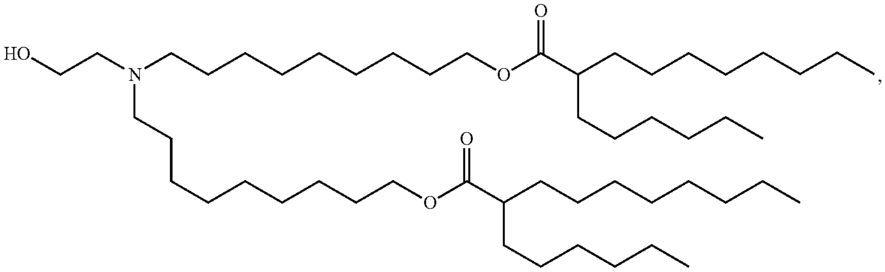

-continued
(Compound 134)
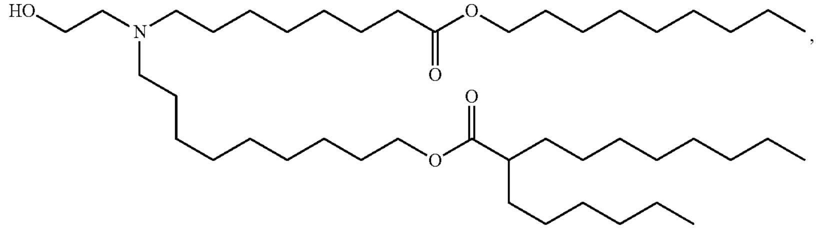
(Compound 135)
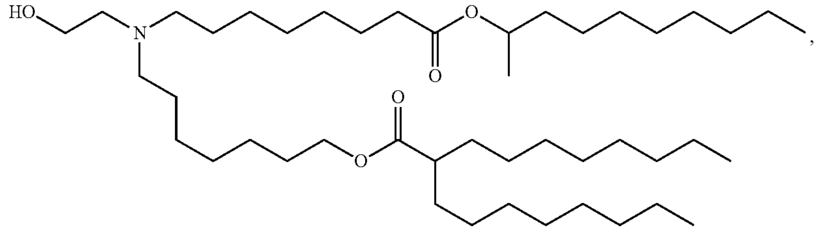
(Compound 136)
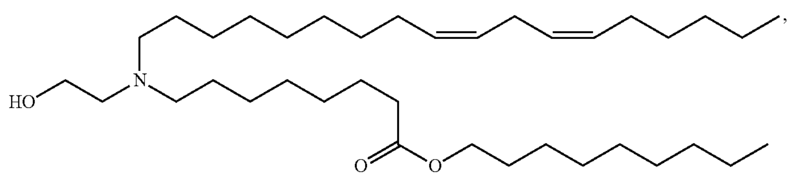
(Compound 137)
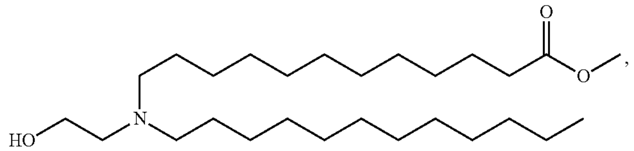
(Compound 138)
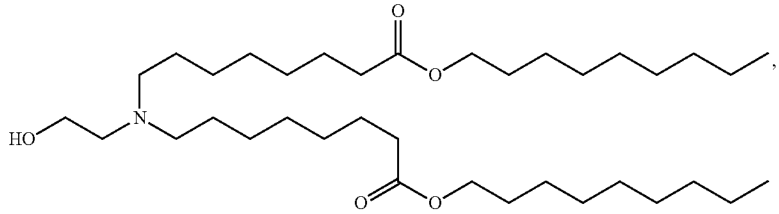
(Compound 139)
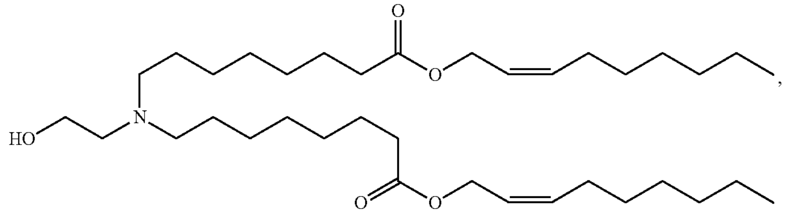
(Compound 140)
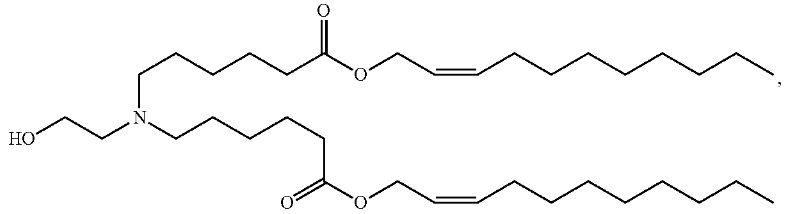

-continued
(Compound 141)
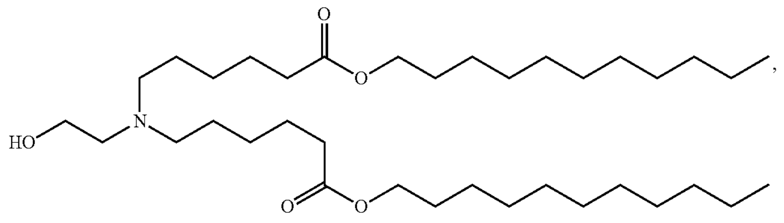
(Compound 142)
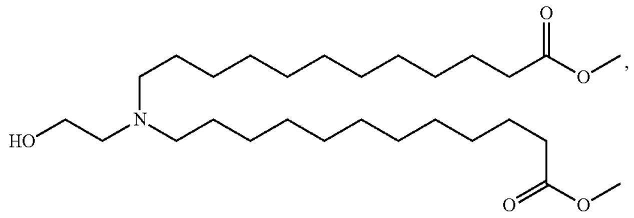
(Compound 143)
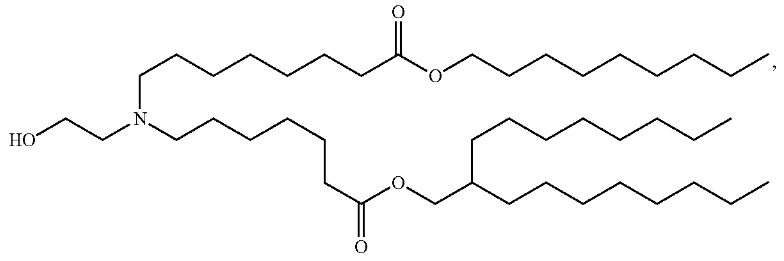
(Compound 144)
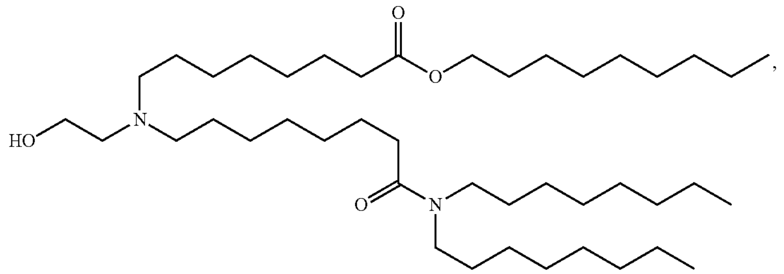
(Compound 145)
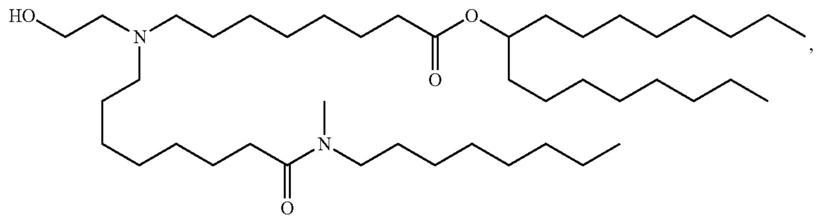
(Compound 146)
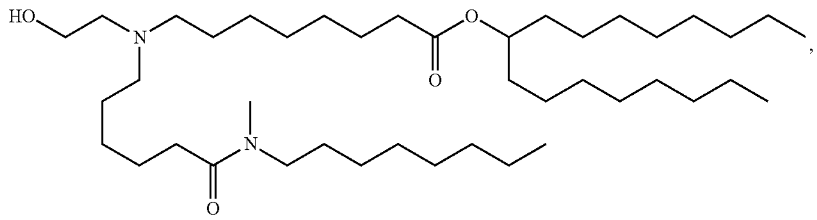

-continued
(Compound 147)
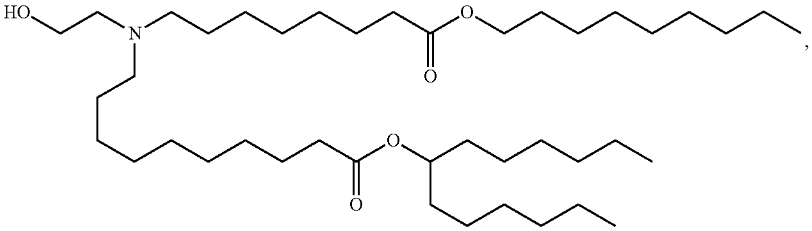
,
(Compound 148)
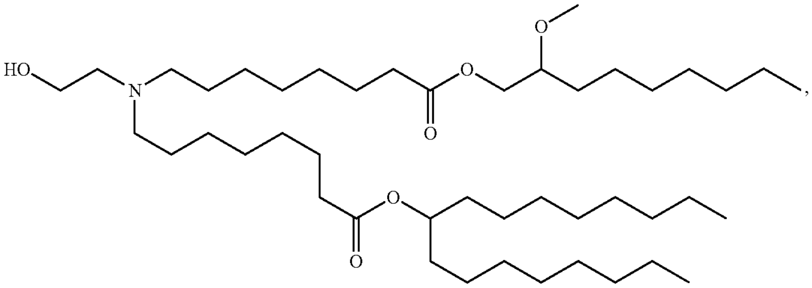
,
(Compound 149)
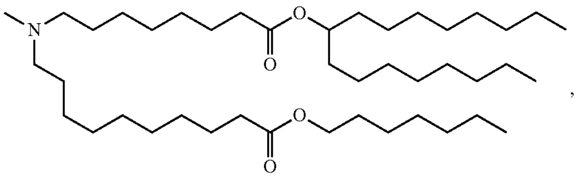
,
(Compound 150)
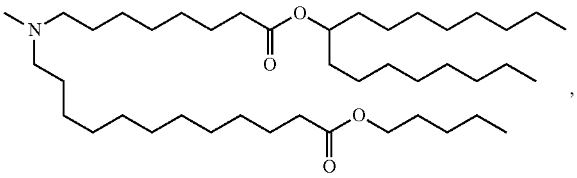
,
(Compound 151)
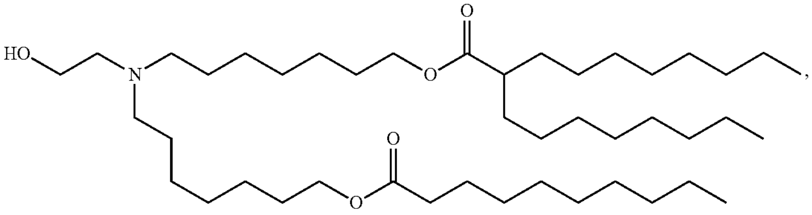
,
(Compound 152)
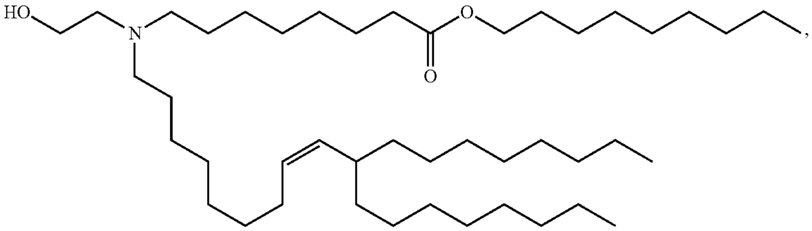
,
(Compound 153)
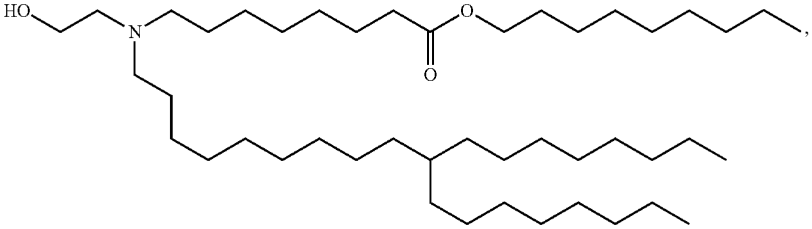
, -continued
(Compound 154)
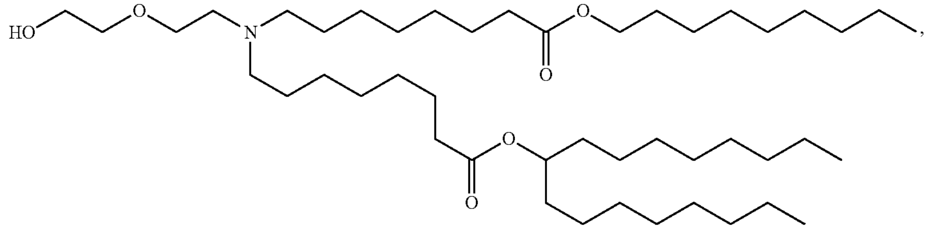
(Compound 155)
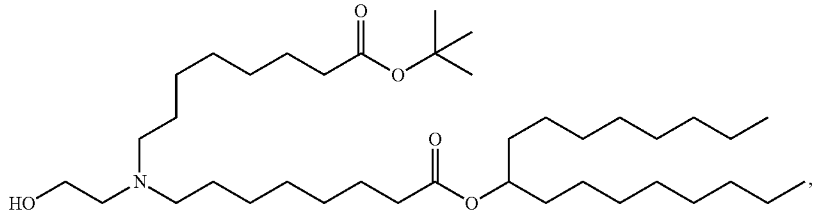
(Compound 156)
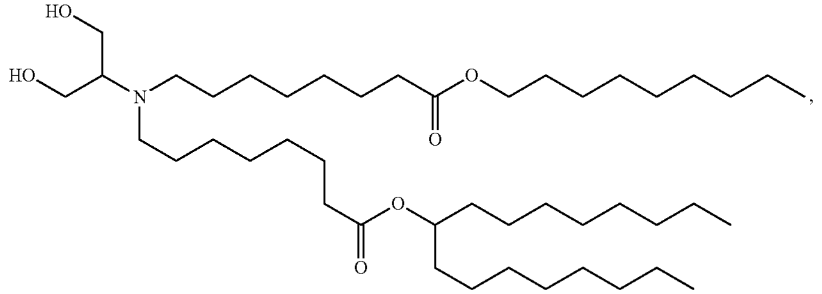
(Compound 157)
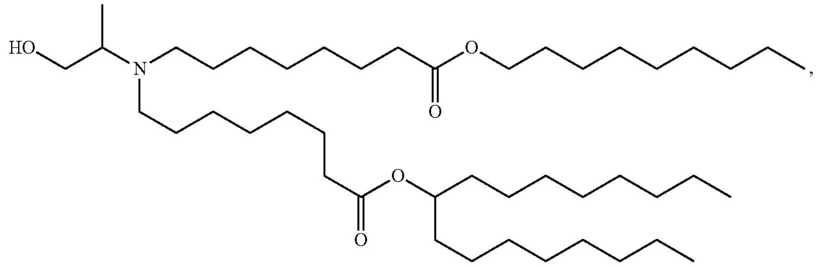
(Compound 158)
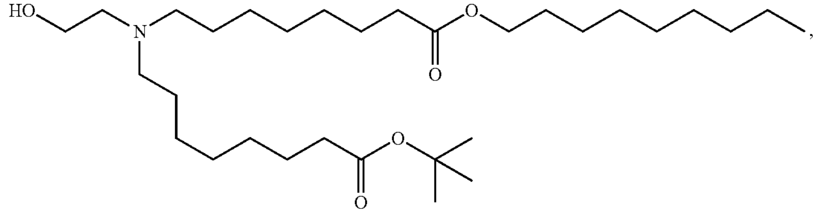
(Compound 159)
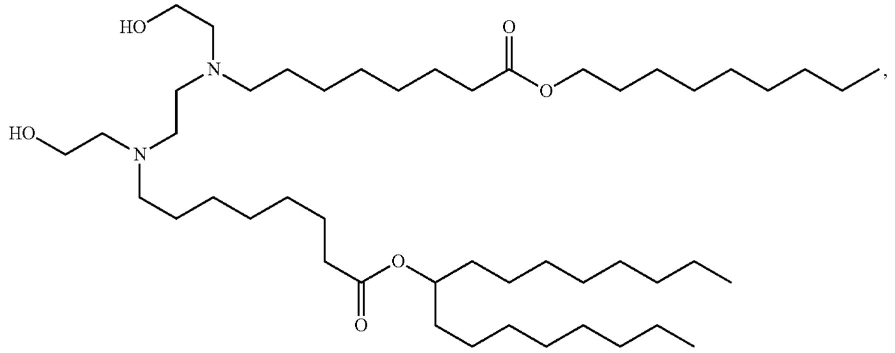

-continued
(Compound 160)
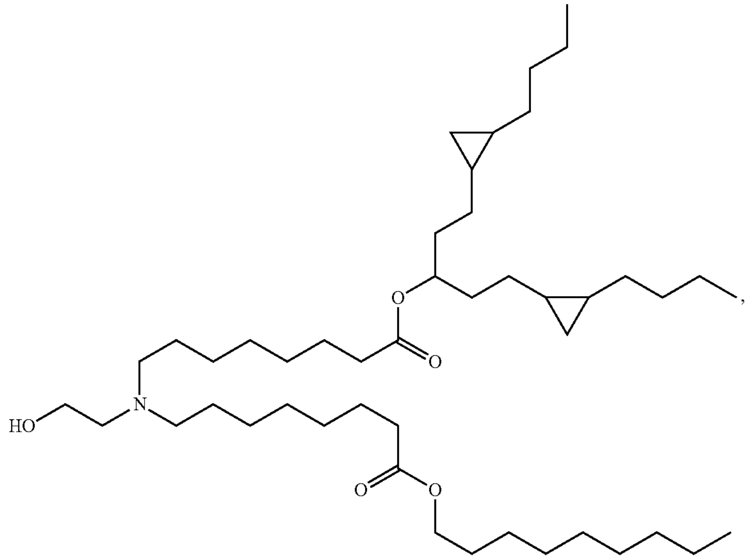
,
(Compound 161)
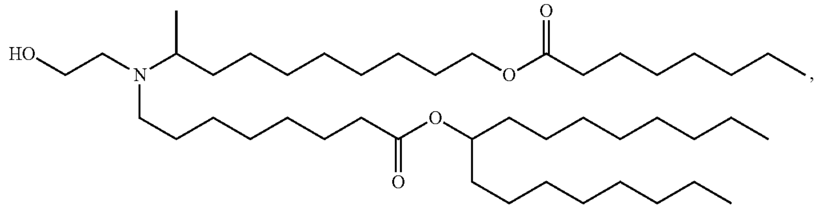
,
(Compound 162)
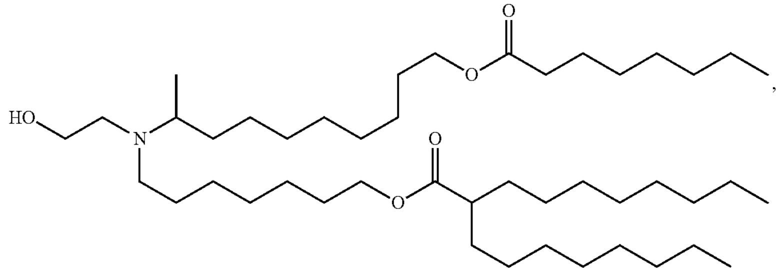
,
(Compound 163)
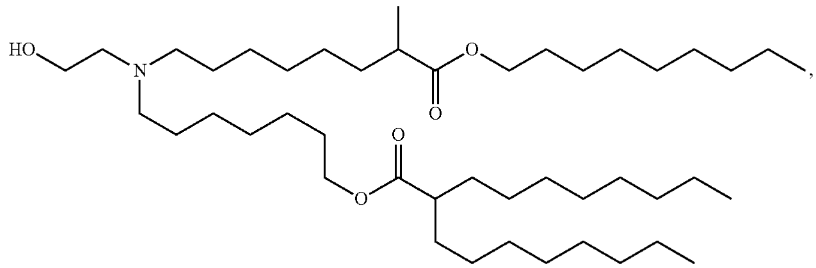
,
(Compound 164)
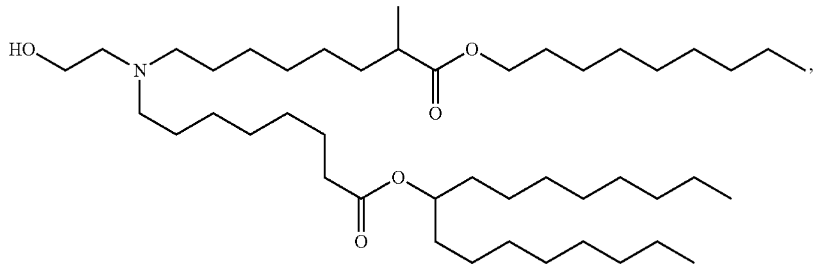
, -continued
(Compound 165)
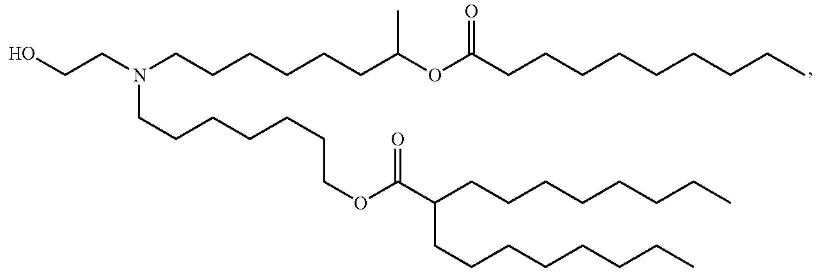
(Compound 166)
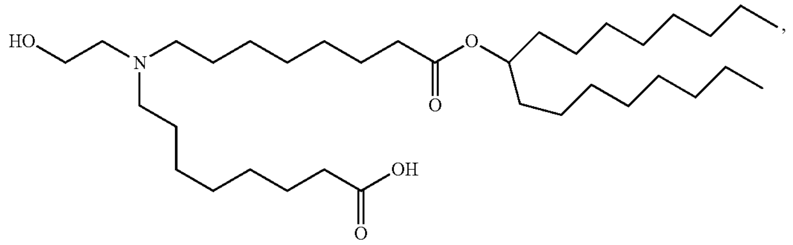
(Compound 167)
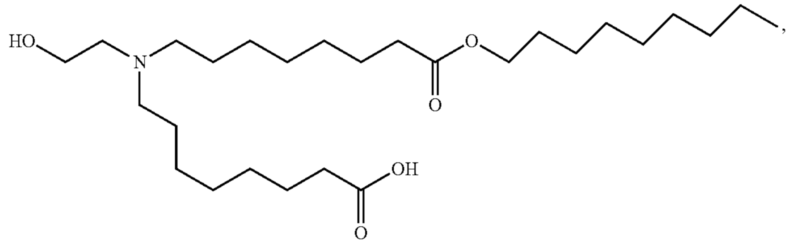
(Compound 168)
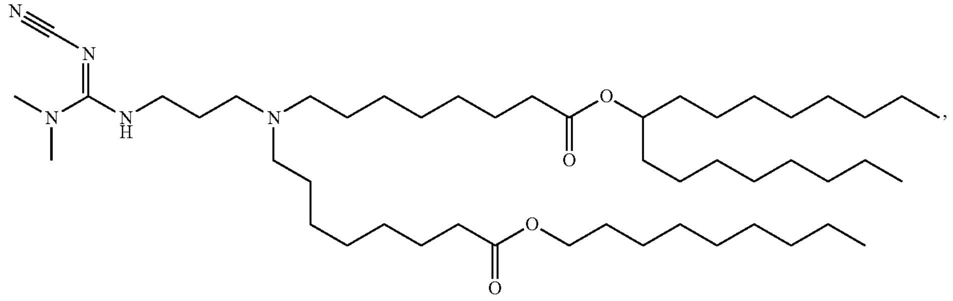
(Compound 169)
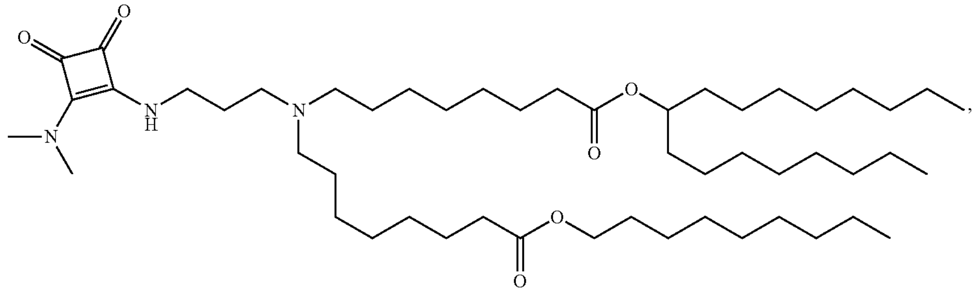

-continued
(Compound 170)
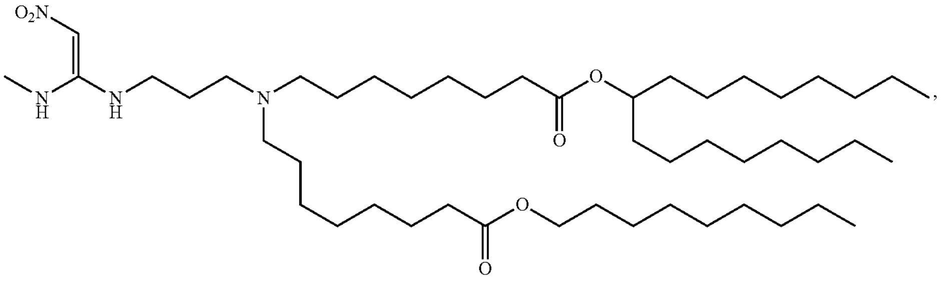
(Compound 171)
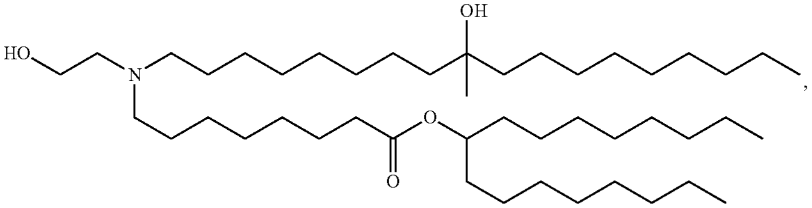
(Compound 172)
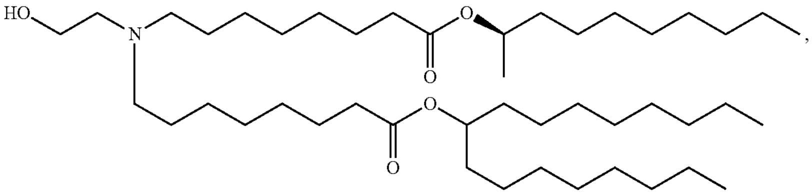
(Compound 173)
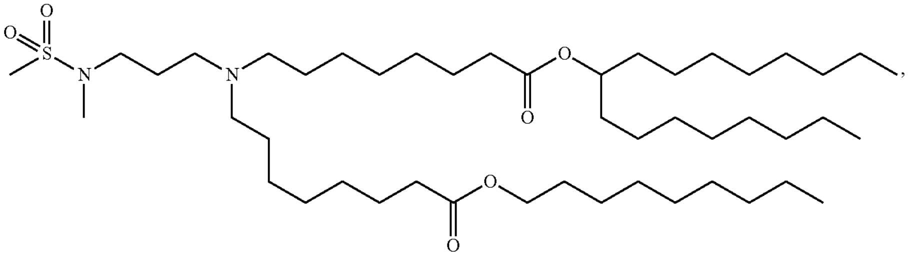
(Compound 174)
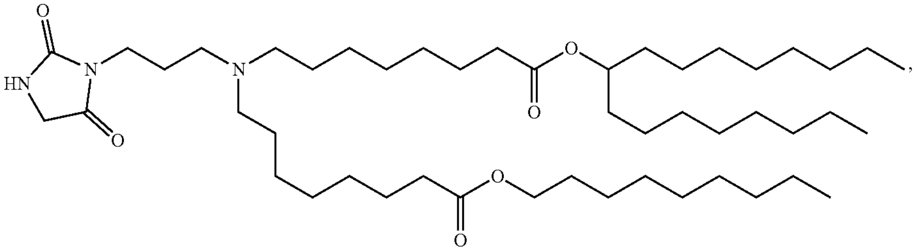
(Compound 175)
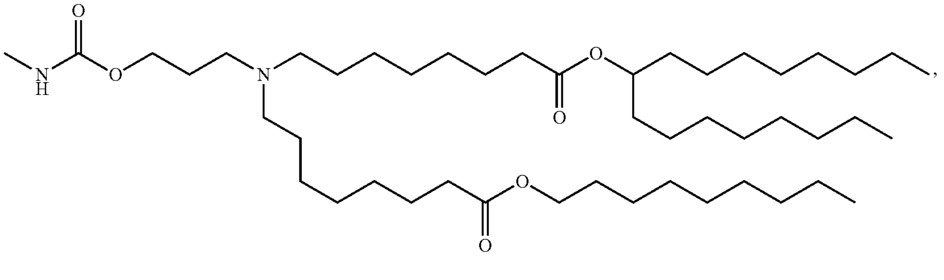

-continued
(Compound 176)
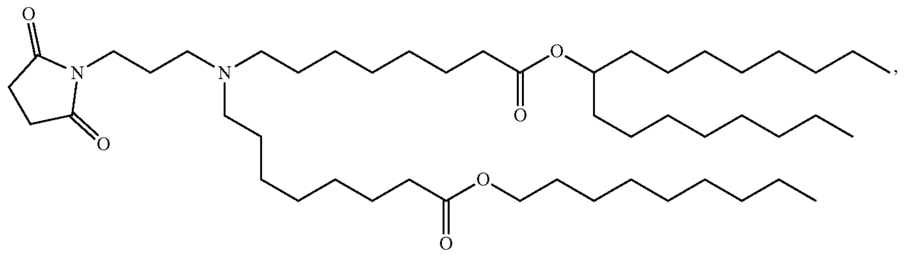
(Compound 177)
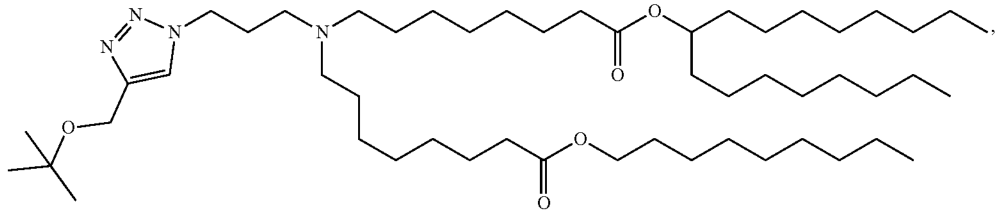
(Compound 178)
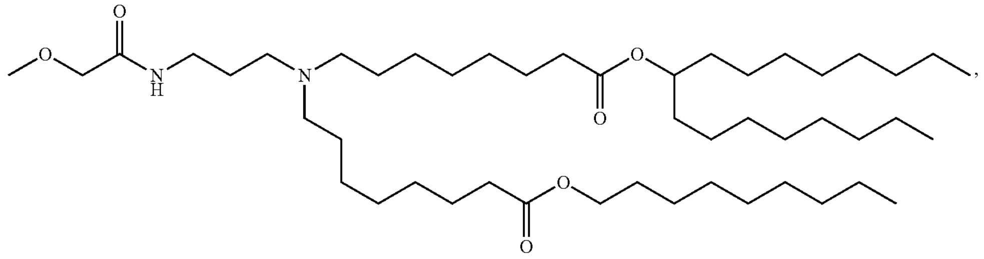
(Compound 179)
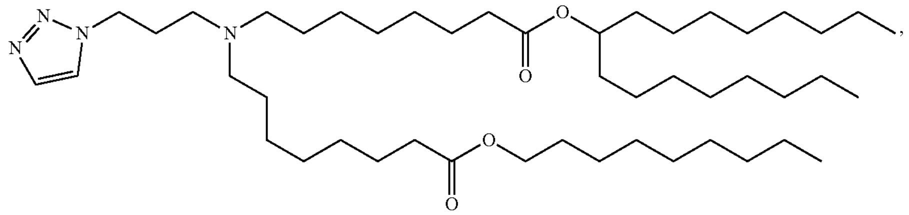
(Compound 180)
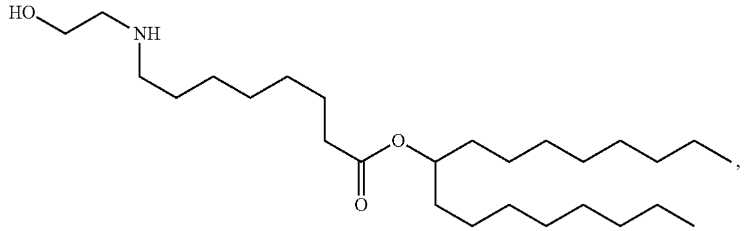
(Compound 181)
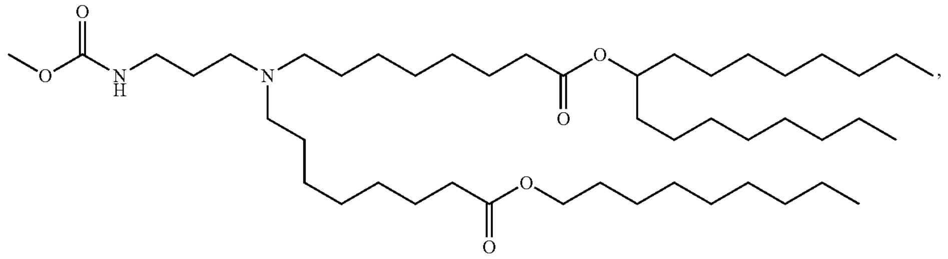

-continued
(Compound 182)
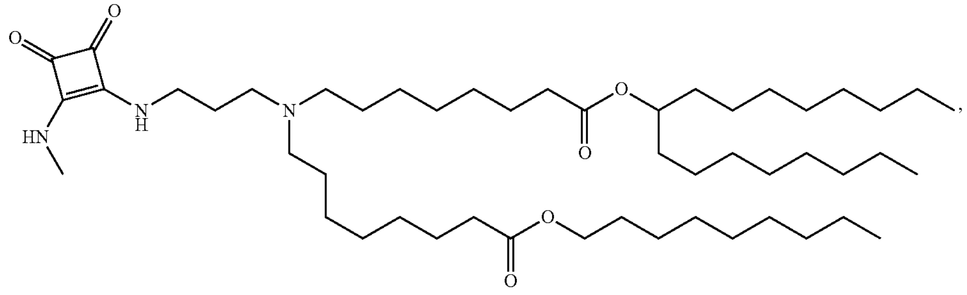
(Compound 183)
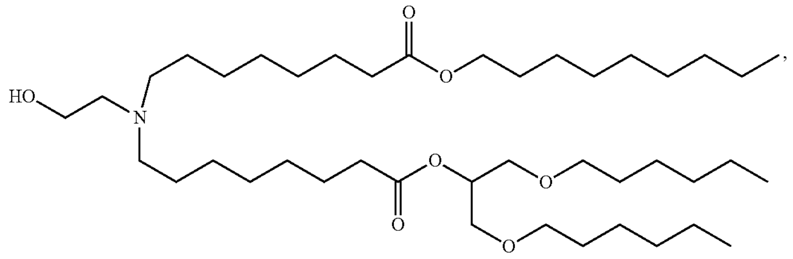
(Compound 184)
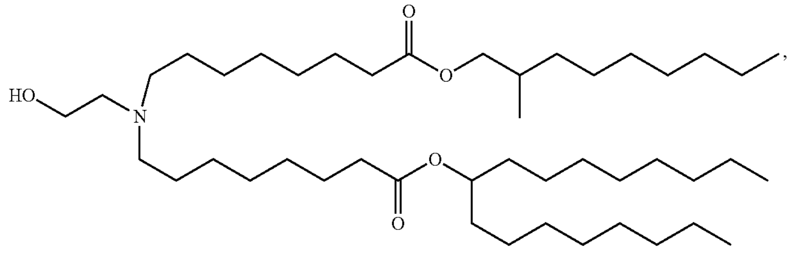
(Compound 185)
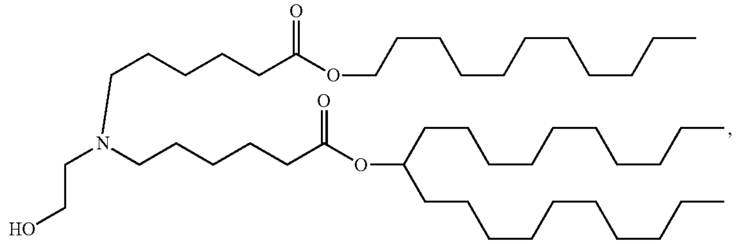
(Compound 186)
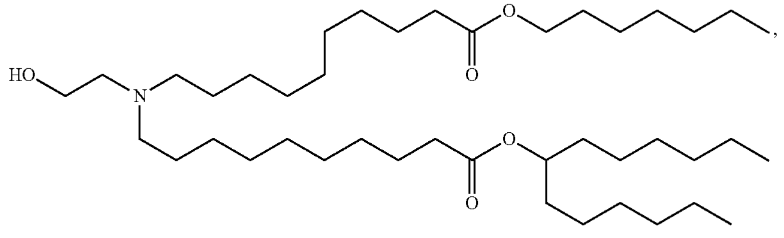
(Compound 187)
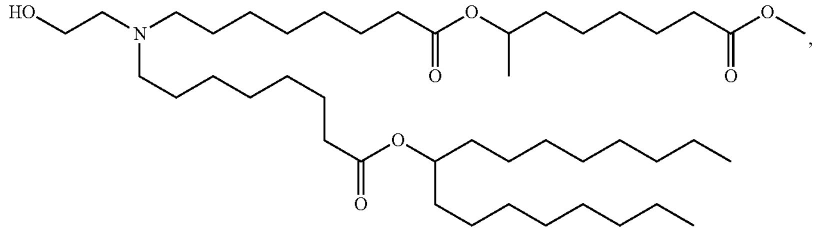

-continued
(Compound 188)
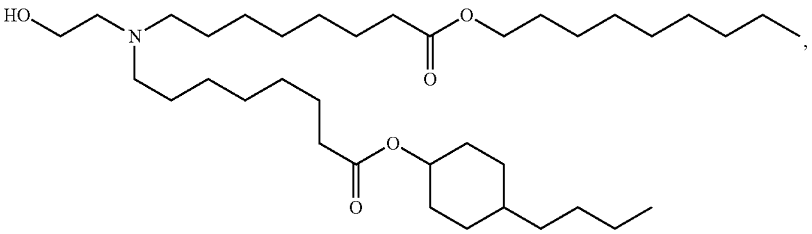
(Compound 189)
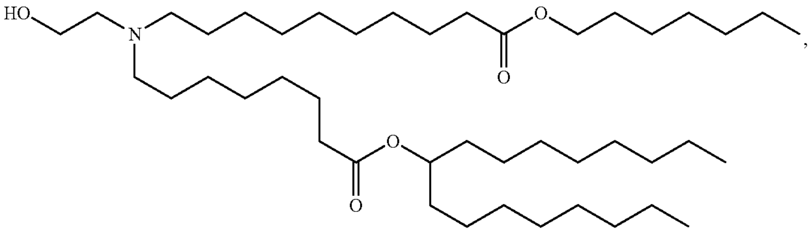
(Compound 190)
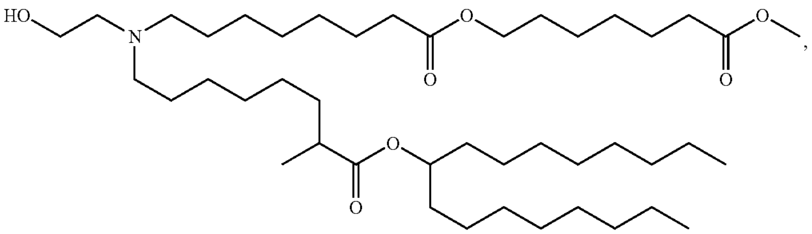
(Compound 191)
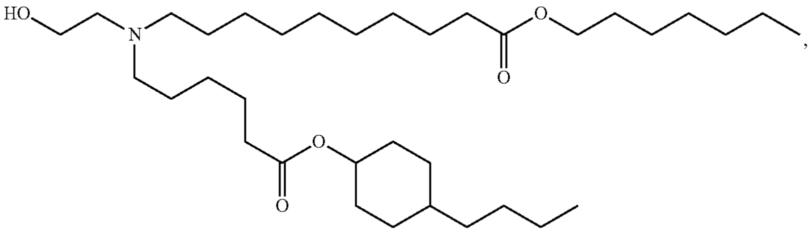
(Compound 192)
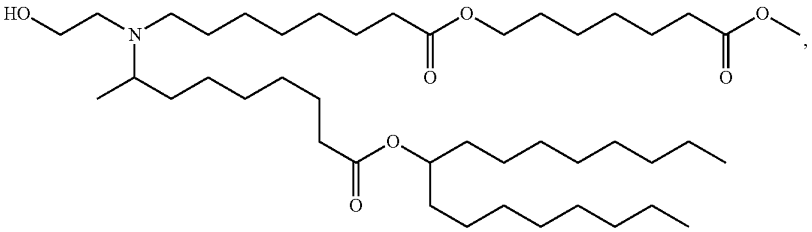
(Compound 193)
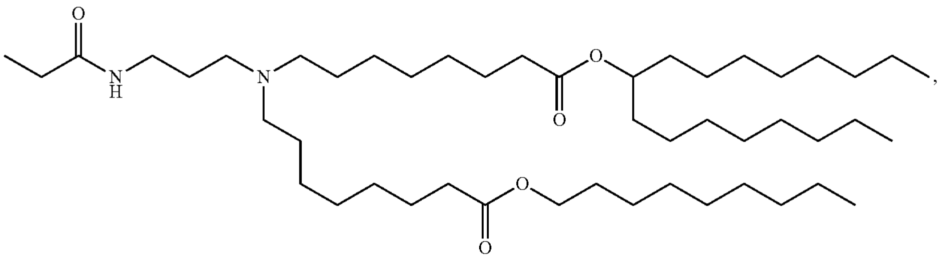

-continued
(Compound 194)
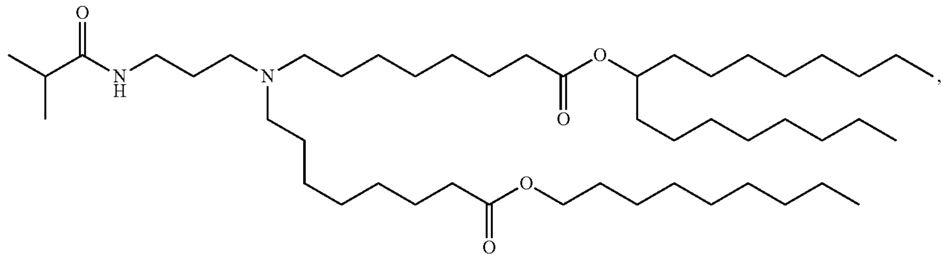
(Compound 195)
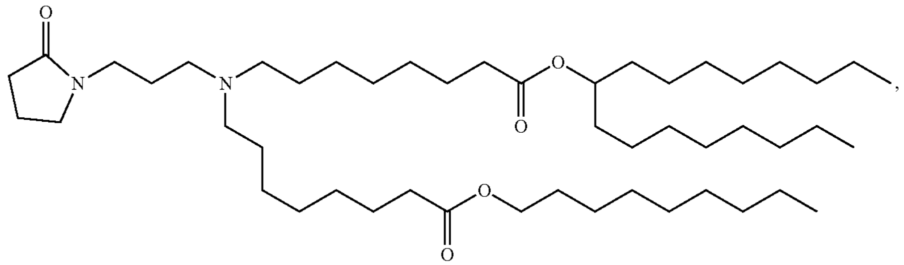
(Compound 196)
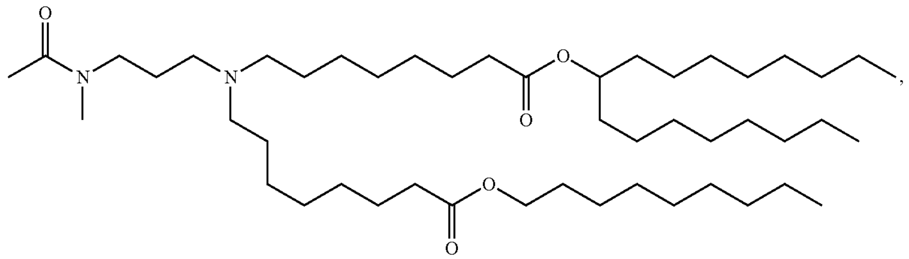
(Compound 197)
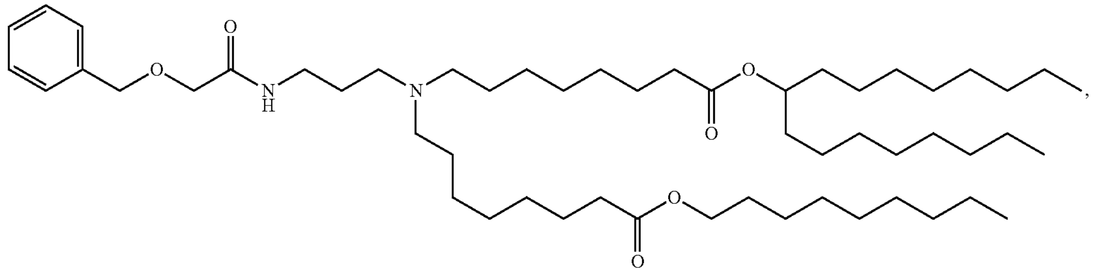
(Compound 198)
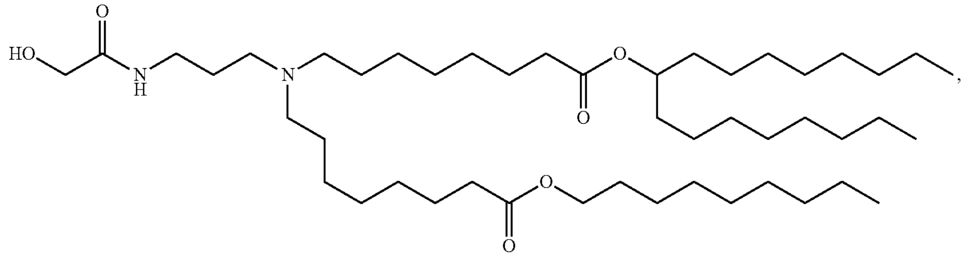
(Compound 199)
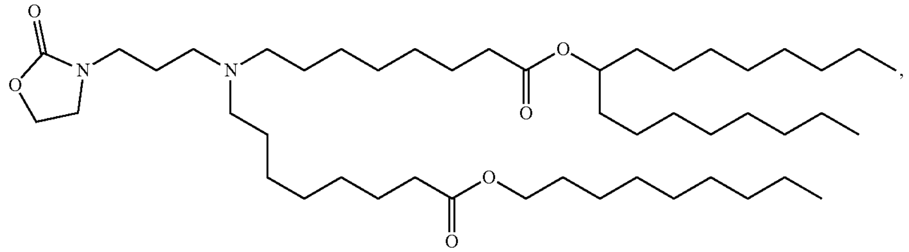

-continued
(Compound 200)
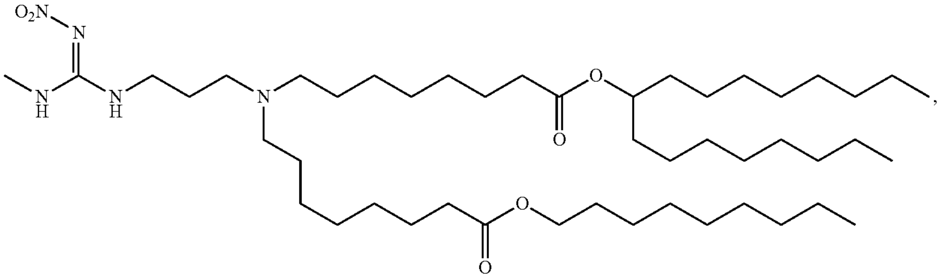
(Compound 201)
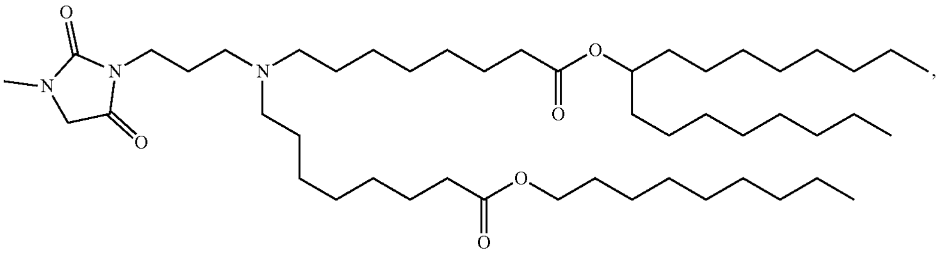
(Compound 202)
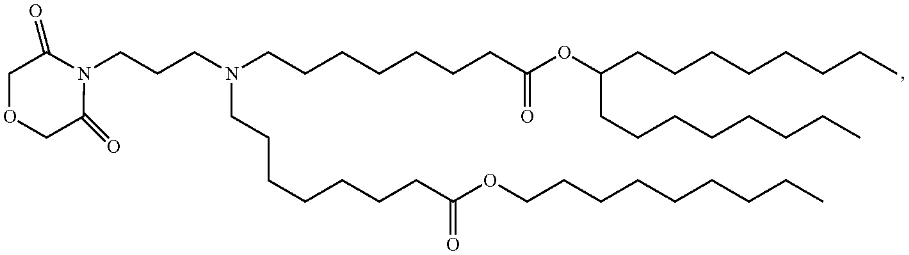
(Compound 203)
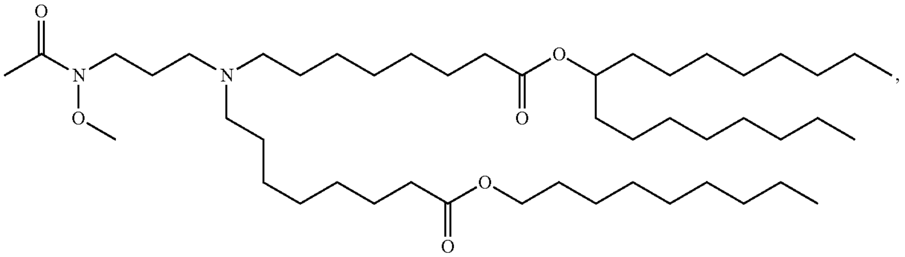
(Compound 204)
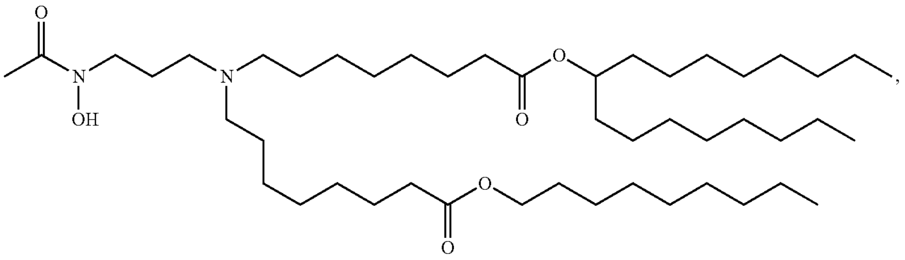
(Compound 205)
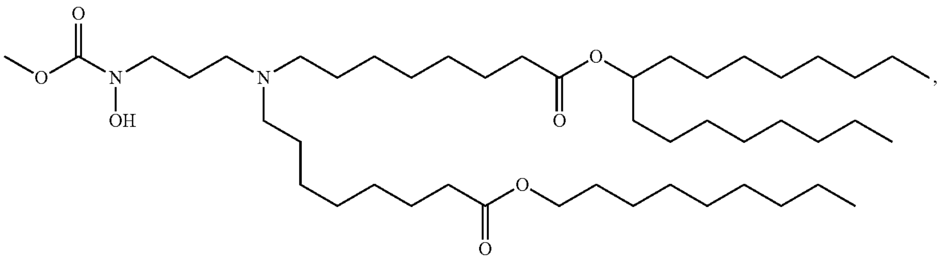

-continued
(Compound 206)
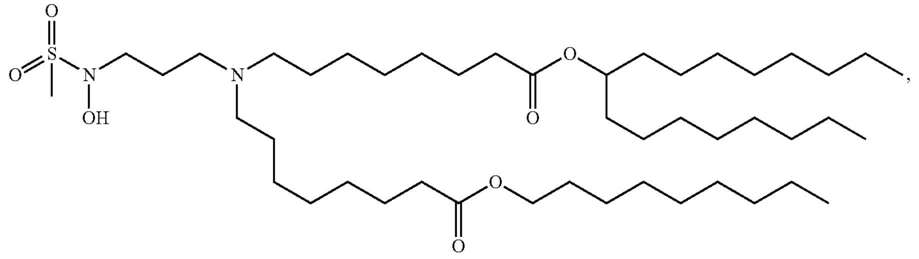
(Compound 207)
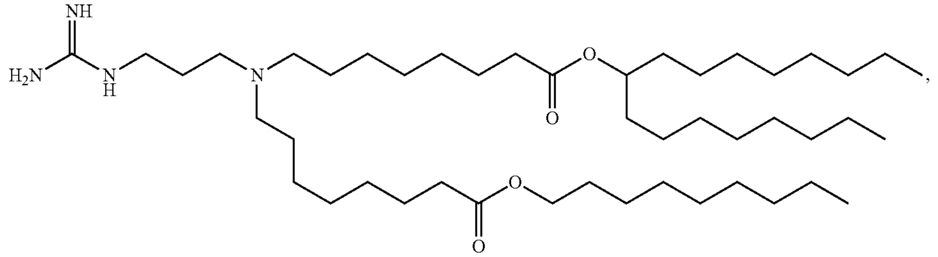
(Compound 208)
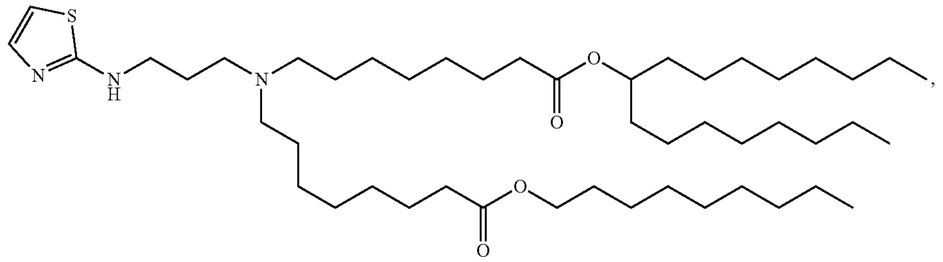
(Compound 209)
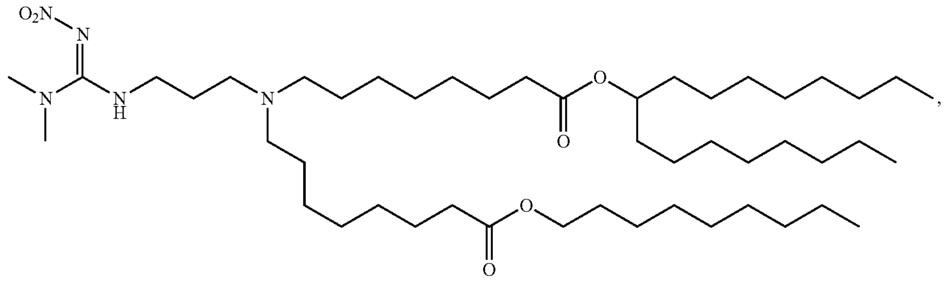
(Compound 210)
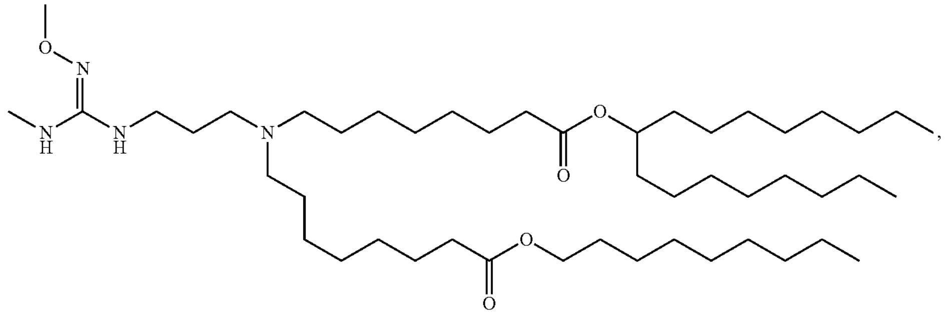

-continued
(Compound 211)
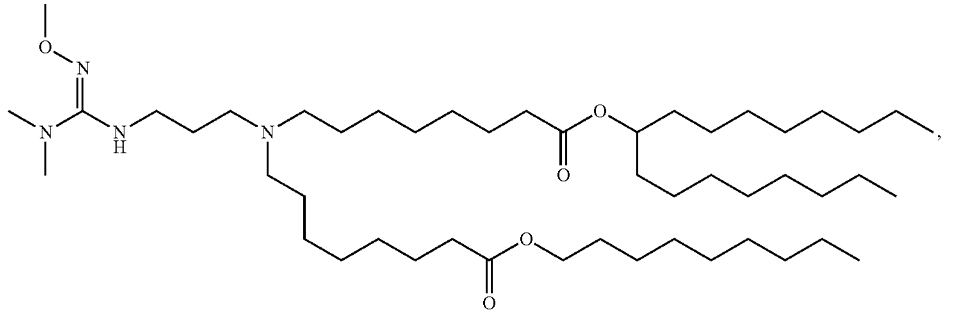
(Compound 212)
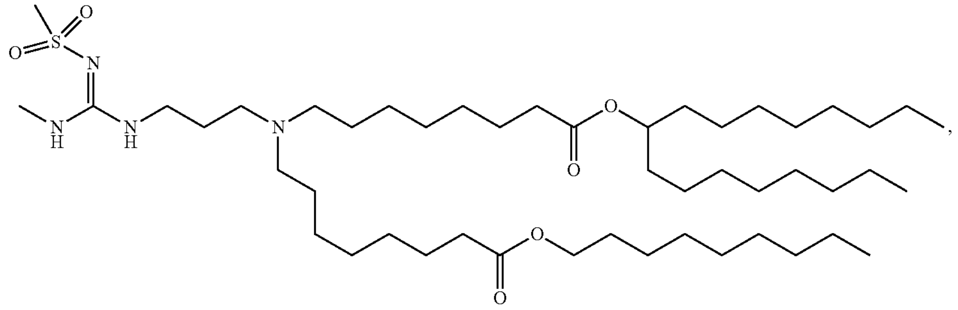
(Compound 213)
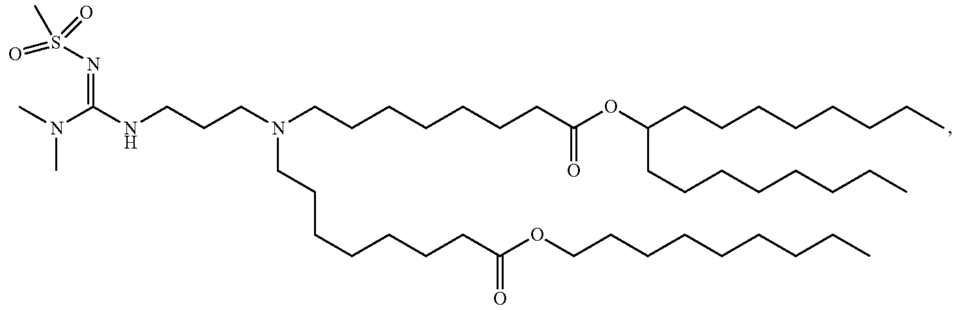
(Compound 214)
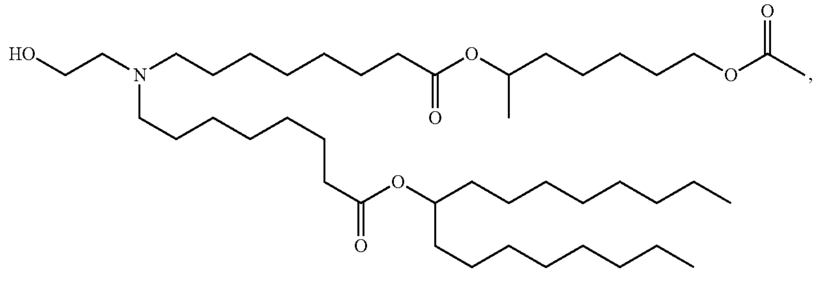
(Compound 215)
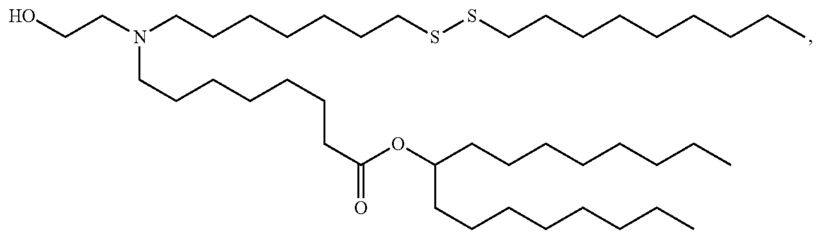

-continued
(Compound 216)
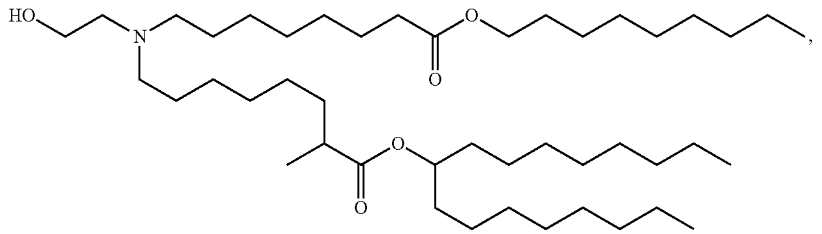
(Compound 217)
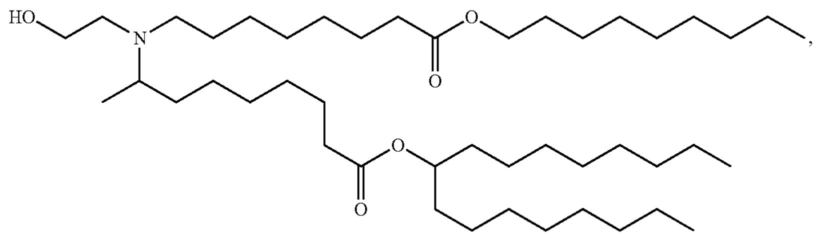
(Compound 218)
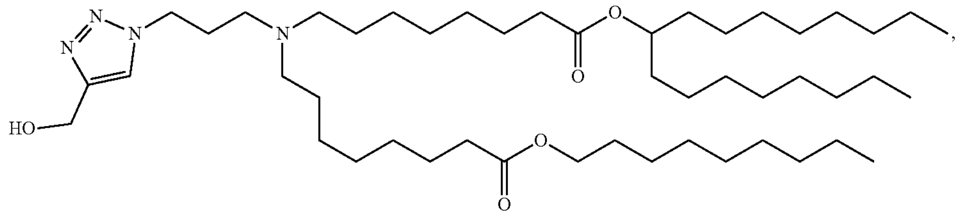
(Compound 219)
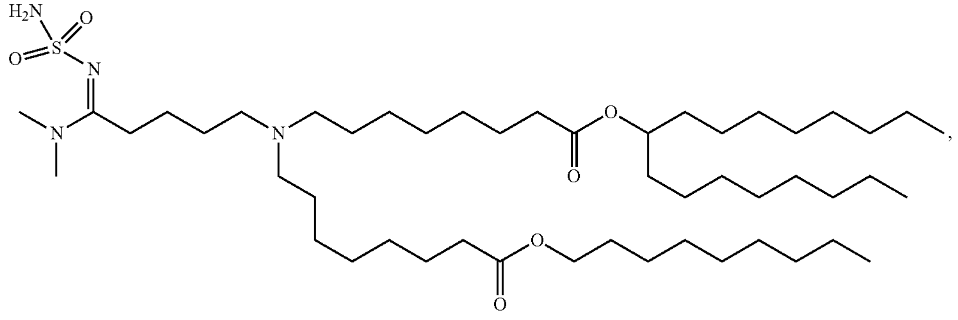
(Compound 220)
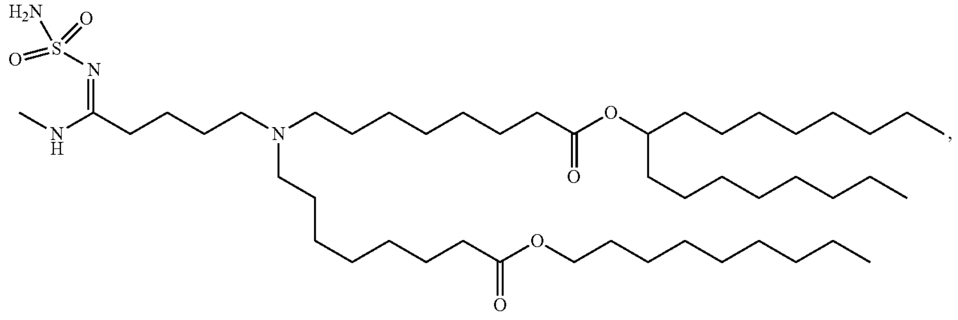

-continued
(Compound 221)
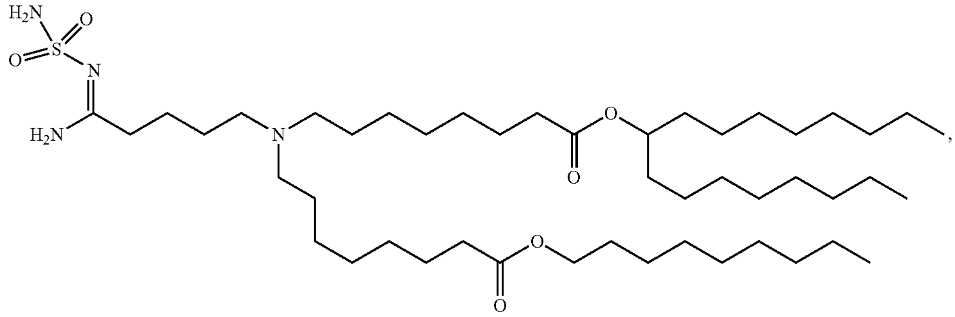
,
(Compound 222)
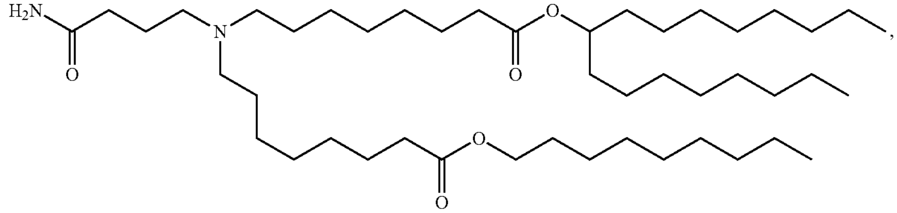
,
(Compound 223)
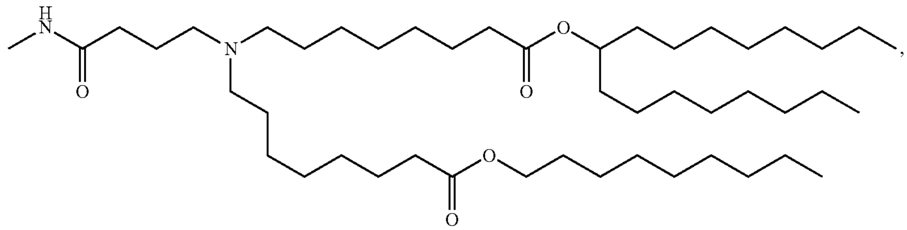
,
(Compound 224)
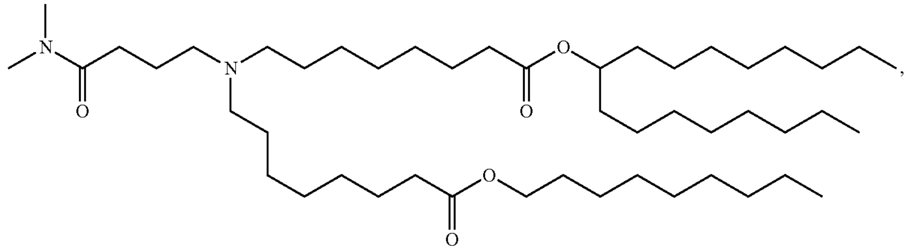
,
(Compound 225)
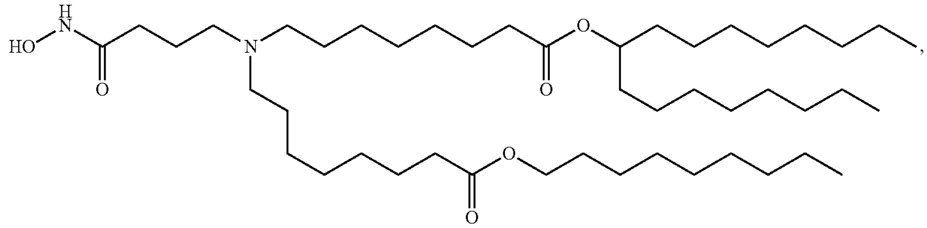
,
(Compound 226)
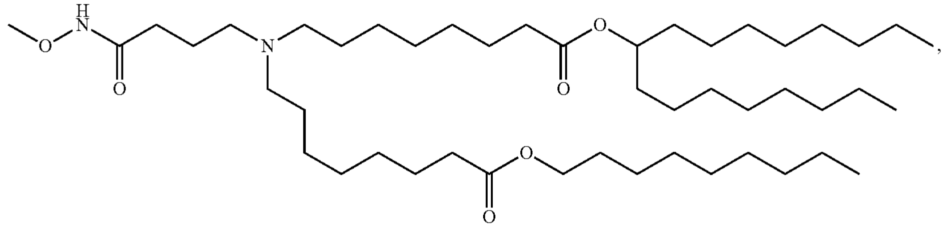
, -continued (Compound 227)

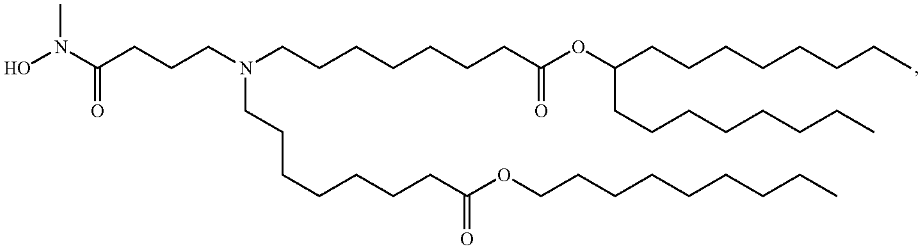

(Compound 228)

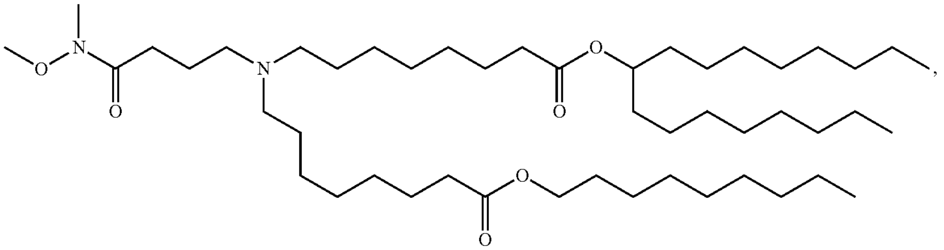

(Compound 229)

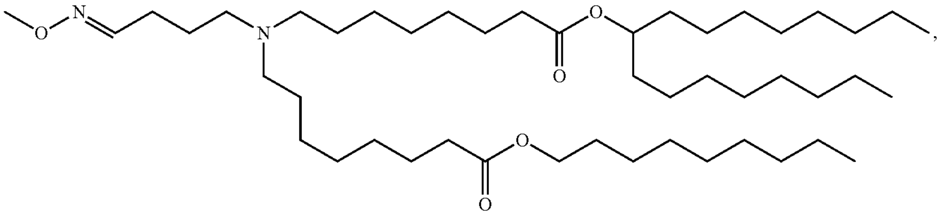

(Compound 230)

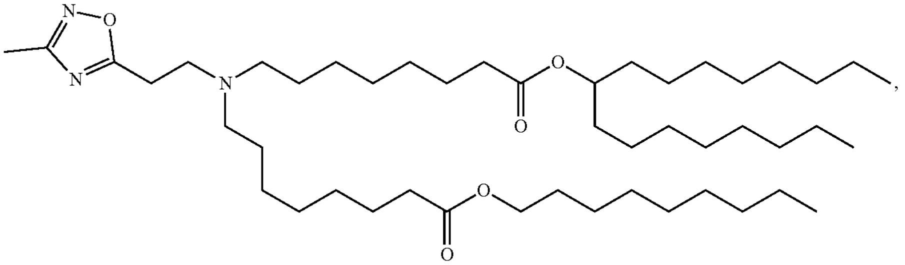

(Compound 231)

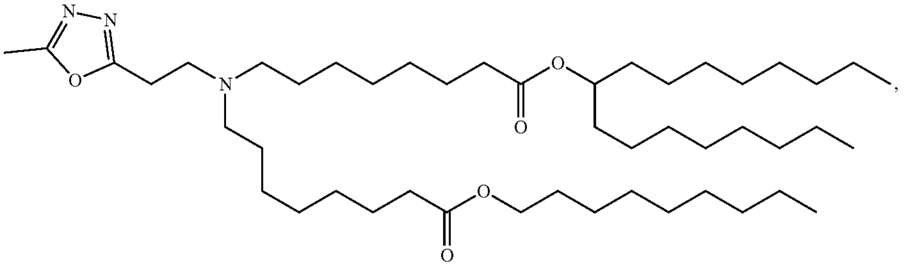

(Compound 232)

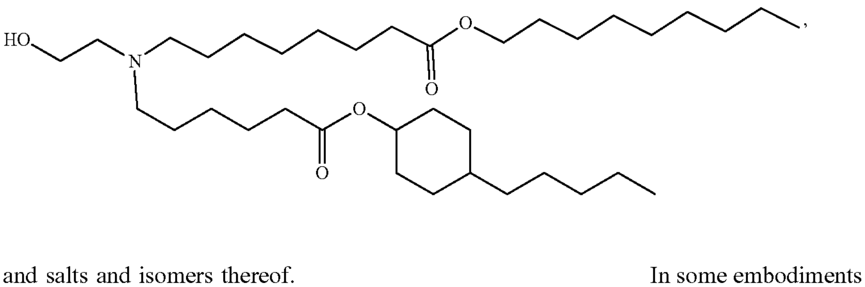

and salts and isomers thereof.

In other embodiments, the compound of Formula (I) is selected from the group consisting of Compound 1-Compound 147, or salt or stereoisomers thereof.

In some embodiments ionizable lipids including a central piperazine moiety are provided. The lipids described herein may be advantageously used in lipid nanoparticle compositions for the delivery of therapeutic and/or prophylactic agents to mammalian cells or organs. For example, the lipids described herein have little or no immunogenicity. For example, the lipid compounds disclosed hereinhave a lower immunogenicity as compared to a reference lipid (e.g., MC3, KC2, or DLinDMA). For example, a formulation comprising a lipid disclosed herein and a therapeutic or prophylactic agent has an increased therapeutic index as compared to a corresponding formulation which comprises a reference lipid (e.g., MC3, KC2, or DLinDMA) and the same therapeutic or prophylactic agent.

In some embodiments, the delivery agent comprises a lipid compound having the formula (III)

(III)

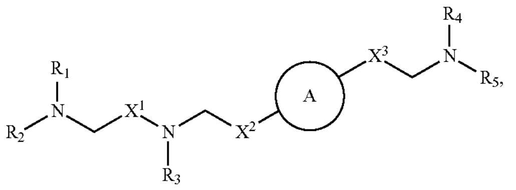

or salts or stereoisomers thereof, wherein ring A is

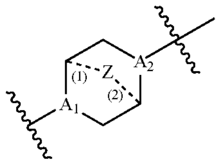

or

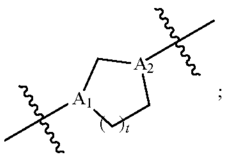

;

t is 1 or 2;

$A_1$ and $A_2$ are each independently selected from CH or N;

Z is $CH_2$ or absent wherein when Z is $CH_2$, the dashed lines (1) and (2) each represent a single bond; and when Z is absent, the dashed lines (1) and (2) are both absent;

$R_1$, $R_2$, $R_3$, $R_4$, and $R_5$ are independently selected from the group consisting of $C_{5-20}$alkyl, $C_{5-20}$ alkenyl, —R"MR', —R*YR", —YR", and —R*OR";

each M is independently selected from the group consisting of —C(O)O—, —OC(O)—, —OC(O)O—, —C(O)N(R')—, —N(R')C(O)—, —C(O)—, —C(S)—, —C(S)S—, —SC(S)—, —CH(OH)—, —P(O)(OR')O—, —$S(O)_2$—, an aryl group, and a heteroaryl group;

$X^1$, $X^2$, and $X^3$ are independently selected from the group consisting of a bond, —$CH_2$—, —$(CH_2)_2$—, —CHR—, —CHY—, —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, —$CH_2$—OC(O)—, —CH(OH)—, —C(S)—, and —CH(SH—;

each Y is independently a $C_{3-6}$ carbocycle;

each R* is independently selected from the group consisting of $C_{1-12}$ alkyl and $C_{2-12}$ alkenyl;

each R is independently selected from the group consisting of $C_{1-3}$ alkyl and a $C_{3-6}$ carbocycle;

each R' is independently selected from the group consisting of $C_{1-12}$ alkyl, $C_{2-12}$ alkenyl, and H; and each R" is independently selected from the group consisting of $C_{3-12}$ alkyl and $C_{3-12}$ alkenyl, wherein when ring A is

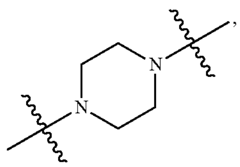 [SMILES: *N1CCN(*)CC1]

then i) at least one of $X^1$, $X^2$, and $X^3$ is not —$CH_2$—; and/or ii) at least one of $R_1$, $R_2$, $R_3$, $R_4$, and $R_5$ is —R"MR'.

In some embodiments, the compound is of any of formulae (IIIa1)-(IIIa6):

(IIIa1)

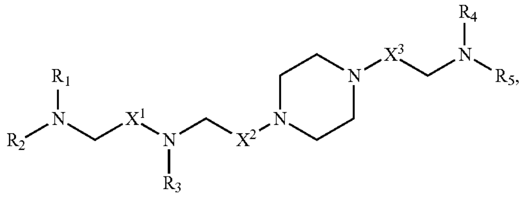

(IIIa2)

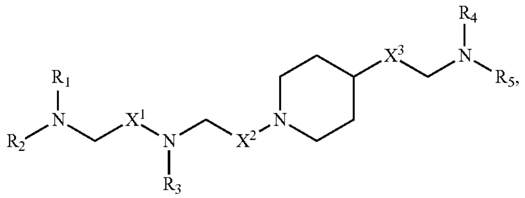

(IIIa3)

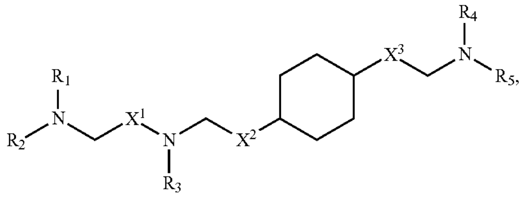

(IIIa4)

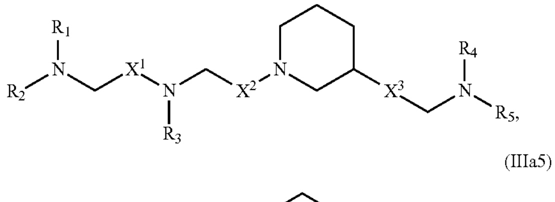

(IIIa5)

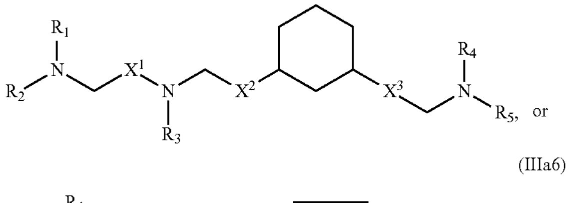

or (IIIa6)

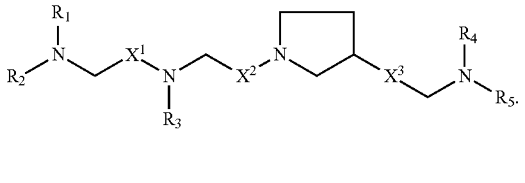

The compounds of Formula (III) or any of (IIIa1)-(IIIa6) include one or more of the following features when applicable.

In some embodiments, ring A is

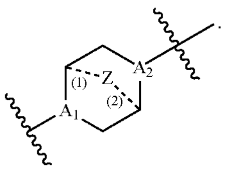

In some embodiments, ring A is

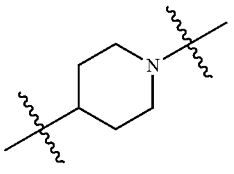

or

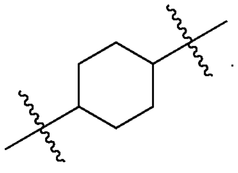

In some embodiments, ring A is

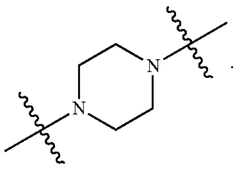 [SMILES: *N1CCN(*)CC1]

In some embodiments, ring A is

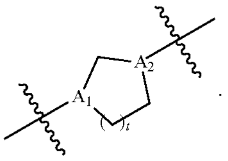

In some embodiments, ring A is

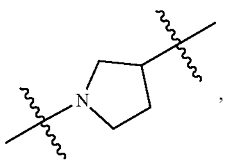

,

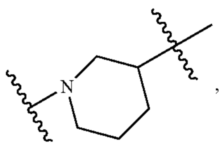

, or

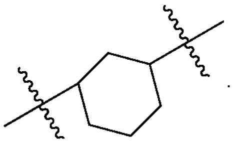

In some embodiments, ring A is

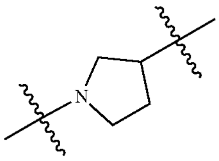

or

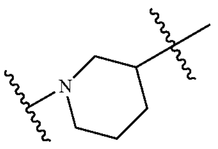

wherein ring, in which the N atom is connected with $X^2$.

In some embodiments, Z is $CH_2$.

In some embodiments, Z is absent.

In some embodiments, at least one of $A_1$ and $A_2$ is N.

In some embodiments, each of $A_1$ and $A_2$ is N.

In some embodiments, each of $A_1$ and $A_2$ is CH.

In some embodiments, $A_1$ is N and $A_2$ is CH.

In some embodiments, $A_1$ is CH and $A_2$ is N.

In some embodiments, at least one of $X^1$, $X^2$, and $X^3$ is not $—CH_2—$. For example, in certain embodiments, $X^1$ is not $—CH_2—$. In some embodiments, at least one of $X^1$, $X^2$, and $X^3$ is —C(O)—.

In some embodiments, $X^2$ is —C(O)—, —C(O)O—, —OC(O)—, $—C(O)—CH_2—$, $—CH_2—C(O)—$, $—C(O)O—CH_2—$, $—OC(O)—CH_2—$, $—CH_2—C(O)O—$, or $—CH_2—OC(O)—$.

In some embodiments, $X^3$ is —C(O)—, —C(O)O—, —OC(O)—, $—C(O)—CH_2—$, $—CH_2—C(O)—$, $—C(O)O—CH_2—$, $—OC(O)—CH_2—$, $—CH_2—C(O)O—$, or $—CH_2—OC(O)—$. In other embodiments, $X^3$ is $—CH_2—$.

In some embodiments, $X^3$ is a bond or $—(CH_2)_2—$.

In some embodiments, $R_1$ and $R_2$ are the same. In certain embodiments, $R_1$, $R_2$, and $R_3$ are the same. In some embodiments, $R_4$ and $R_5$ are the same. In certain embodiments, $R_1$, $R_2$, $R_3$, $R_4$, and $R_5$ are the same.

In some embodiments, at least one of $R_1$, $R_2$, $R_3$, $R_4$, and $R_5$ is —R"MR'. In some embodiments, at most one of $R_1$, $R_2$, $R_3$, $R_4$, and $R_5$ is —R"MR'. For example, at least one of $R_1$, $R_2$, and $R_3$ may be —R"MR', and/or at least one of $R_4$ and $R_5$ is —R"MR'. In certain embodiments, at least one M is —C(O)O—. In some embodiments, each M is —C(O)O—. In some embodiments, at least one M is —OC(O)—. In some embodiments, each M is —OC(O)—. In some embodiments, at least one M is —OC(O)O—. In some embodiments, each M is —OC(O)O—. In some embodiments, at least one R" is $C_3$ alkyl. In certain embodiments, each R" is $C_3$ alkyl. In some embodiments, at least one R" is $C_5$ alkyl. In certain embodiments, each R" is $C_5$ alkyl. In some embodiments, at least one R" is $C_6$ alkyl. In certain embodiments, each R" is $C_6$ alkyl. In some embodiments, at least one R" is $C_7$ alkyl. In certain embodiments, each R" is $C_7$ alkyl. In some embodiments, at least one R' is $C_5$ alkyl. In certain embodiments, each R' is $C_5$ alkyl. In other embodiments, at least one R' is $C_1$ alkyl. In certain embodiments, each R' is $C_1$ alkyl. In some embodiments, at least one R' is $C_2$ alkyl. In certain embodiments, each R' is $C_2$ alkyl.

In some embodiments, at least one of $R_1$, $R_2$, $R_3$, $R_4$, and $R_5$ is $C_{12}$ alkyl. In certain embodiments, each of $R_1$, $R_2$, $R_3$, $R_4$, and $R_5$ are $C_{12}$ alkyl.

In certain embodiments, the compound is selected from the group consisting of:
(Compound 233)
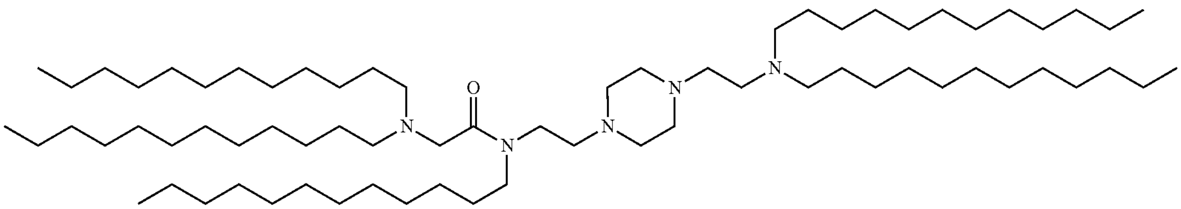
,
(Compound 234)
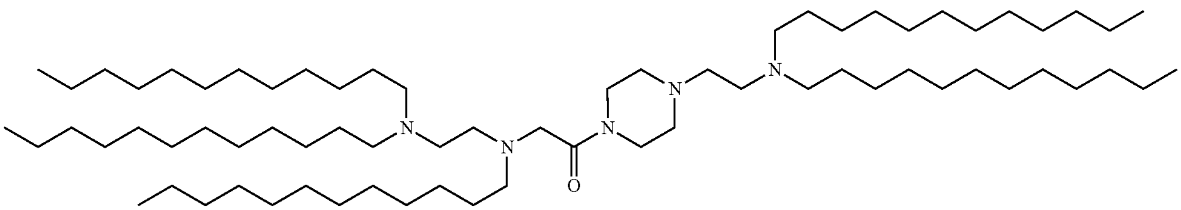
,
(Compound 235)
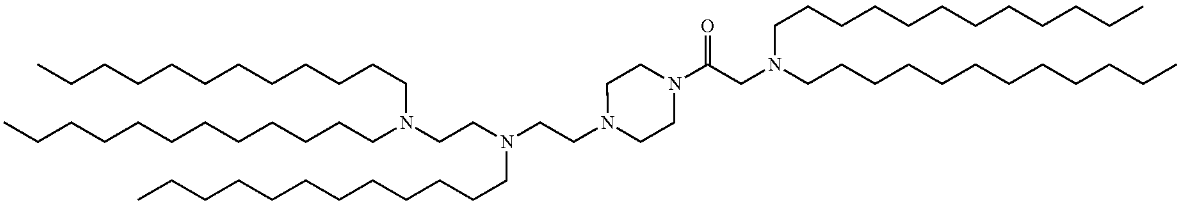
,
(Compound 236)
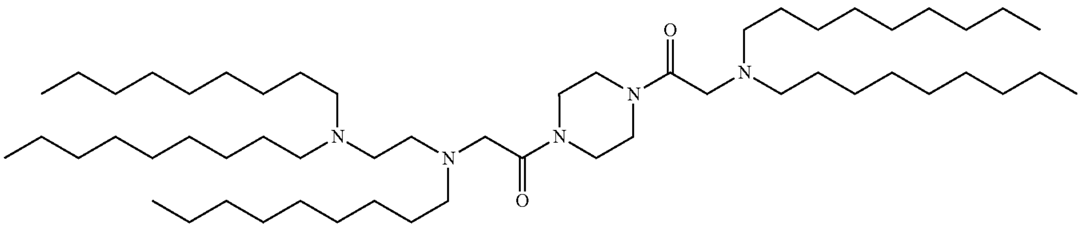
,
(Compound 237)
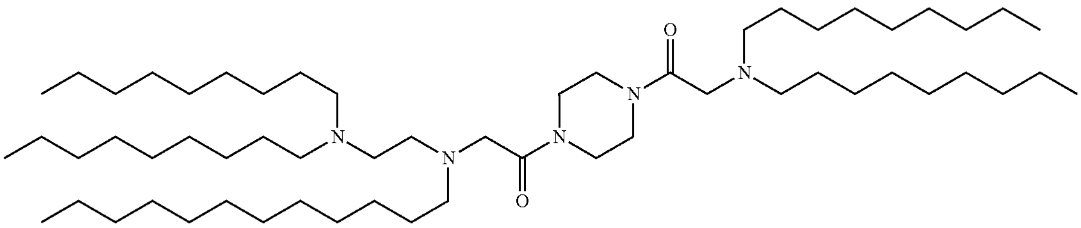
,
(Compound 238)
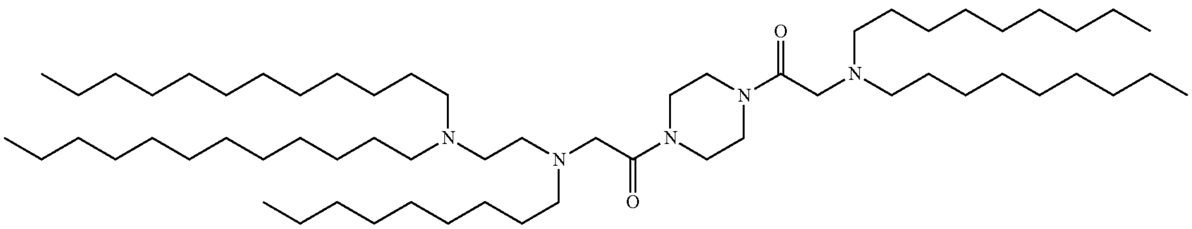
, -continued
(Compound 239)
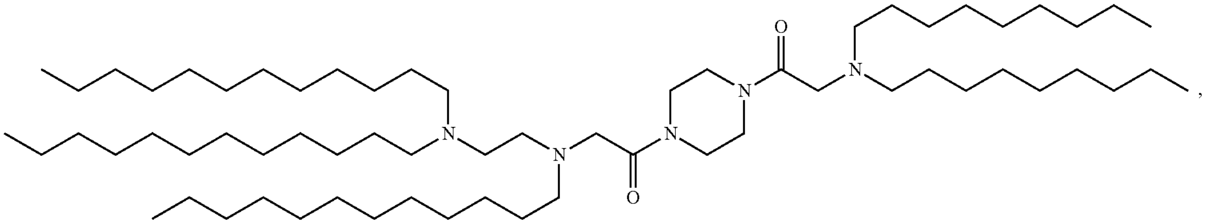
(Compound 240)
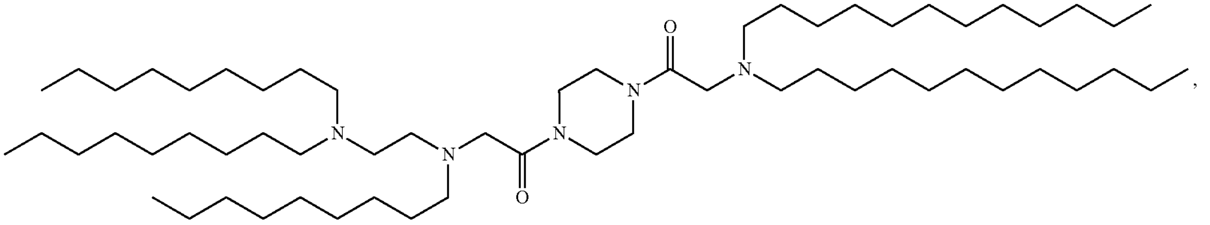
(Compound 241)
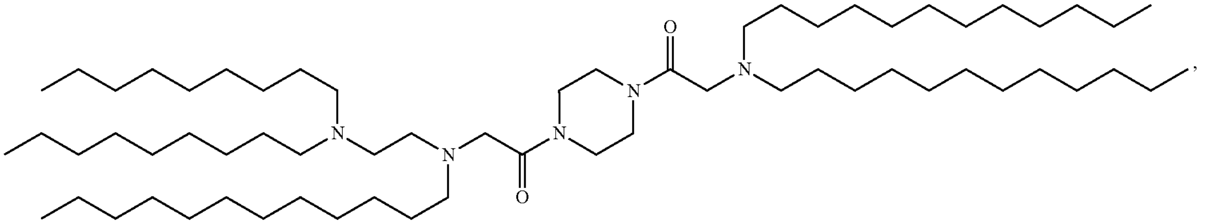
(Compound 242)
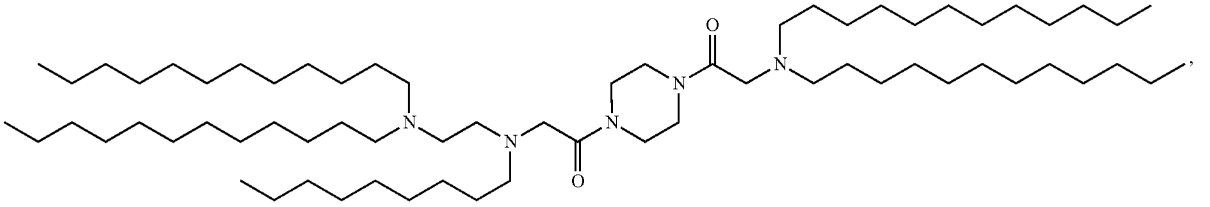
(Compound 243)
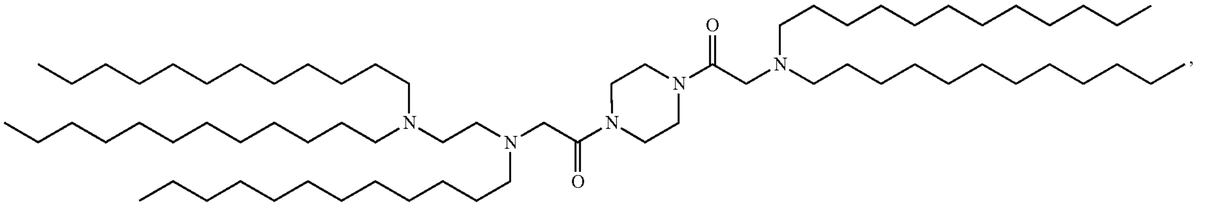
(Compound 244)
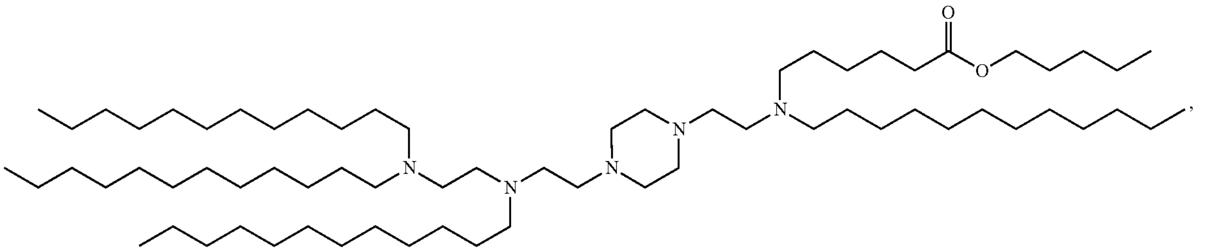

-continued
(Compound 245)
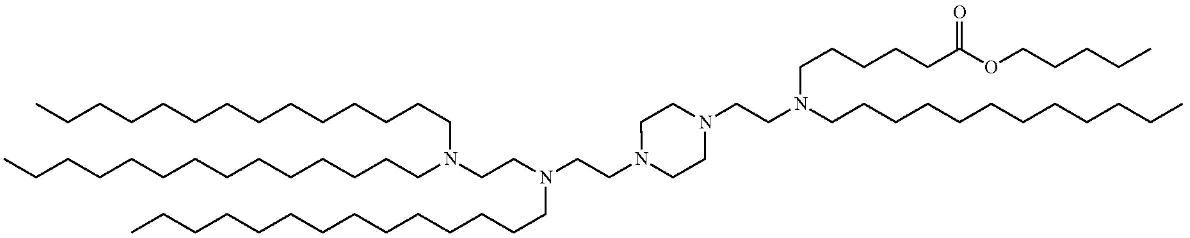,
(Compound 246)
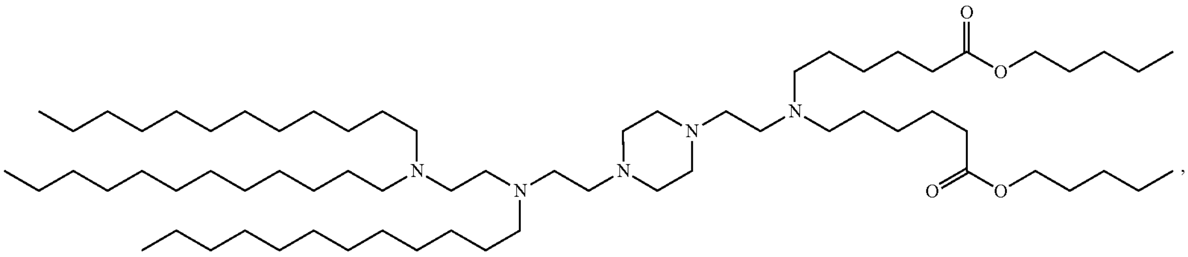,
(Compound 247)
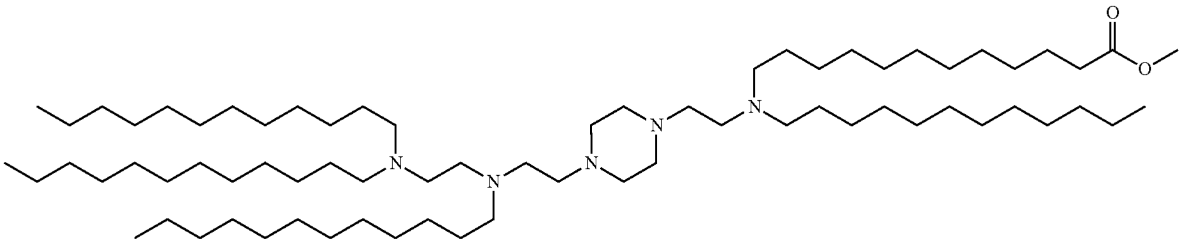,
(Compound 248)
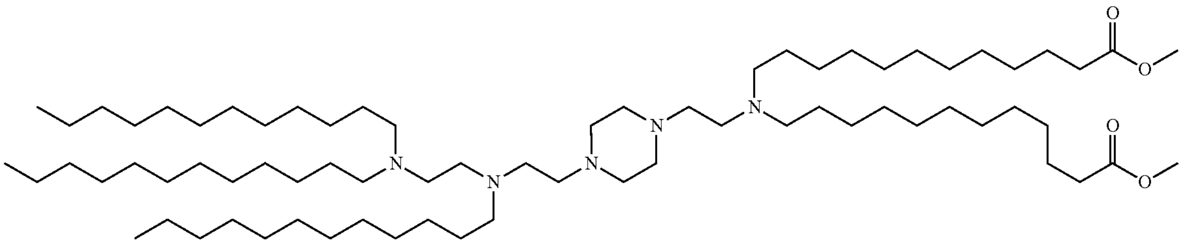,
(Compound 274)
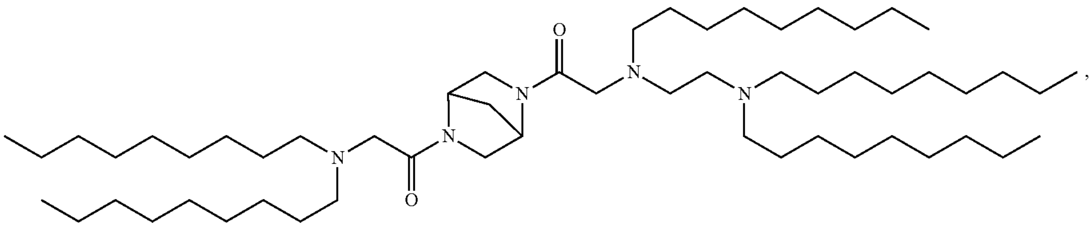,
(Compound 275)
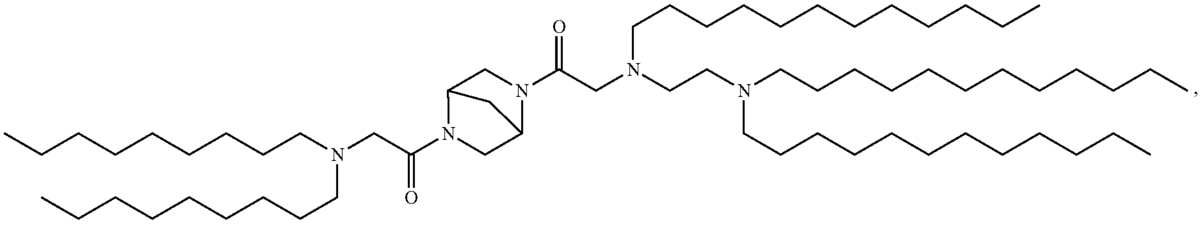, -continued
(Compound 276)
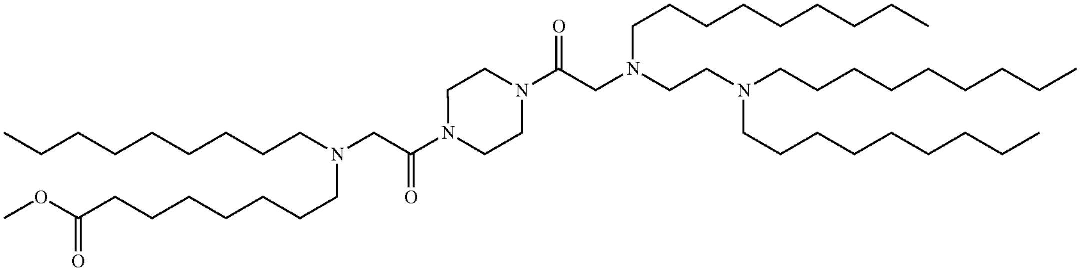
,
(Compound 277)
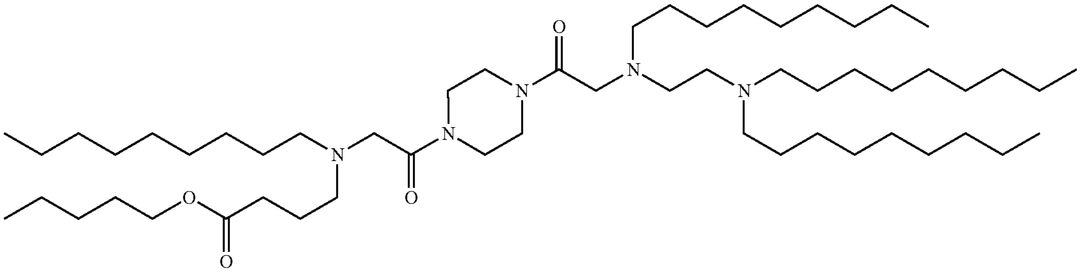
,
(Compound 278)
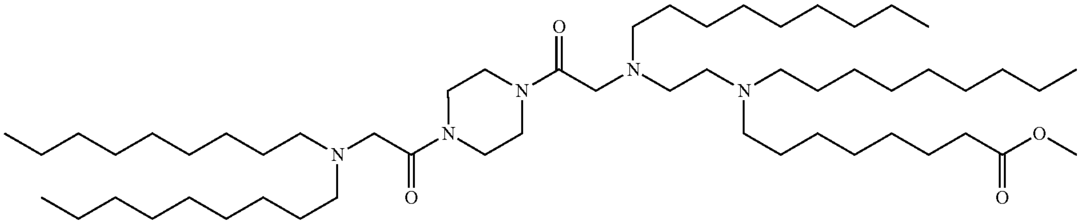
,
(Compound 279)
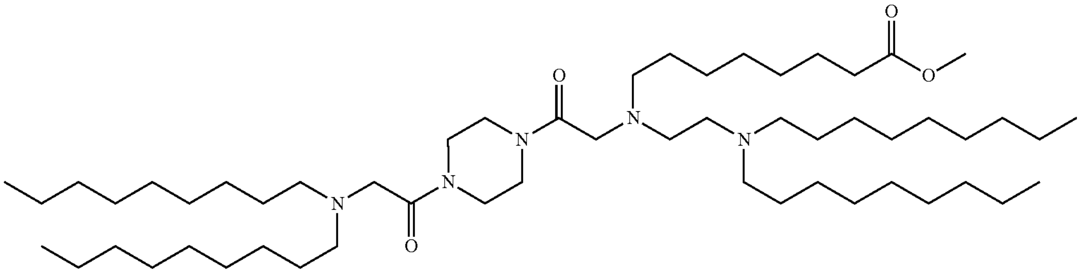
,
(Compound 280)
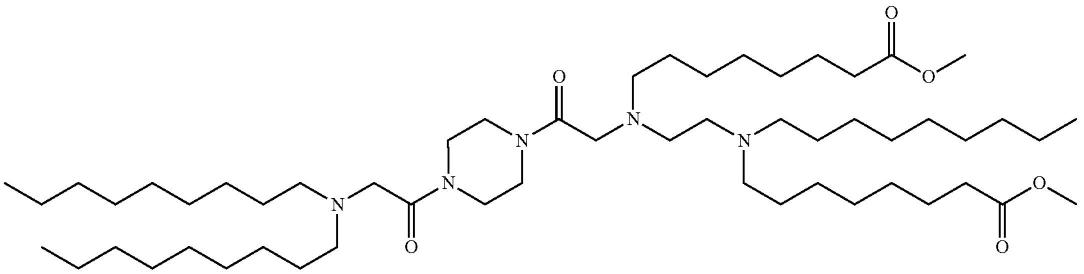
, -continued
(Compound 281)
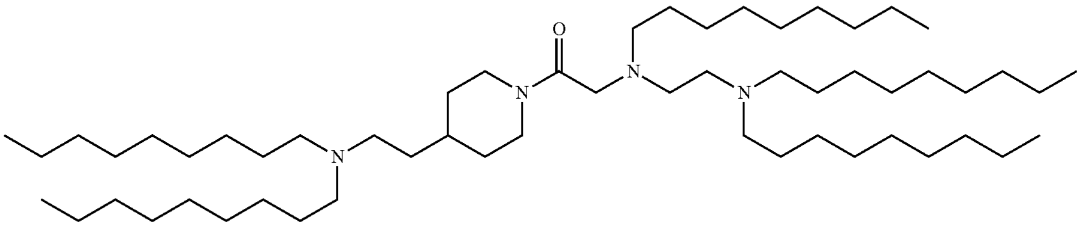
,
(Compound 282)
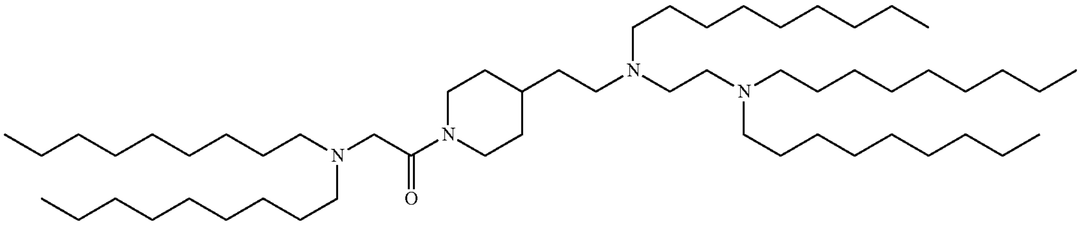
,
(Compound 283)
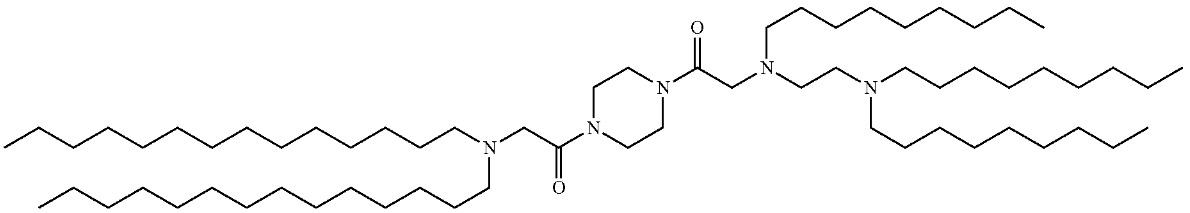
,
(Compound 284)
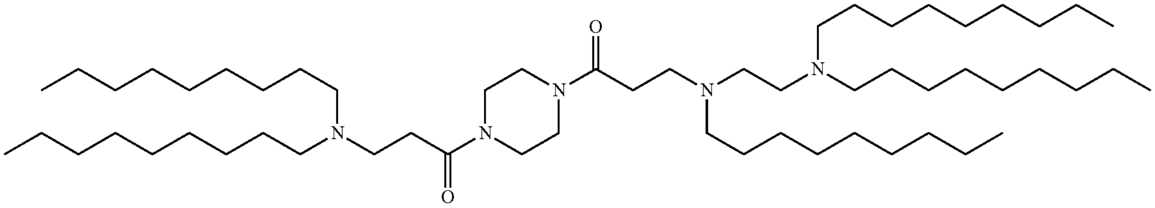
,
(Compound 285)
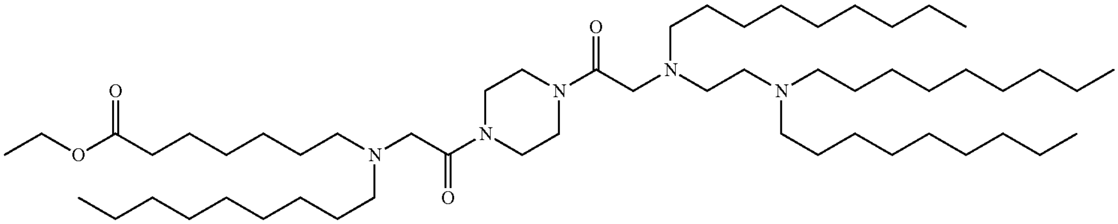
,
(Compound 286)
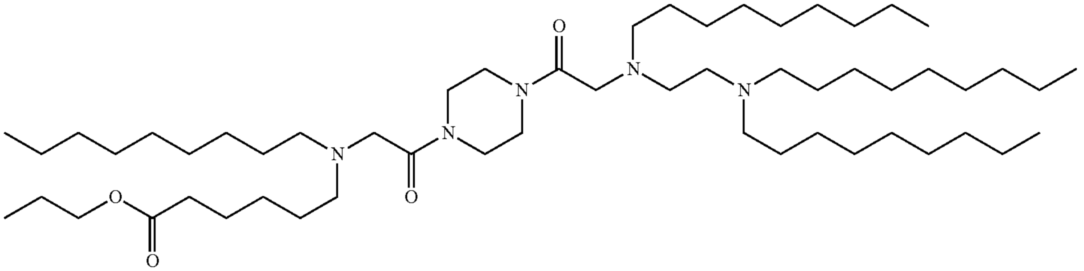
, -continued
(Compound 287)
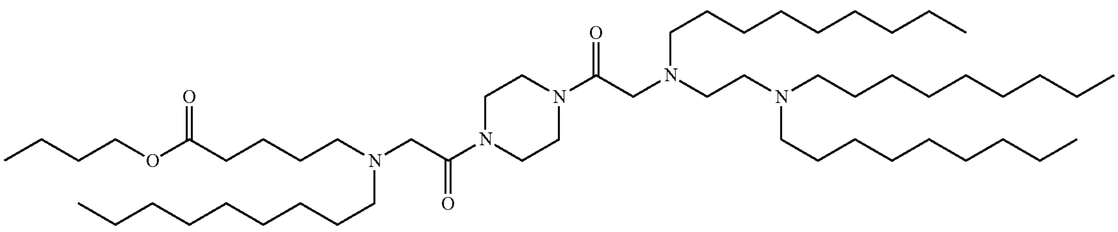
,
(Compound 288)
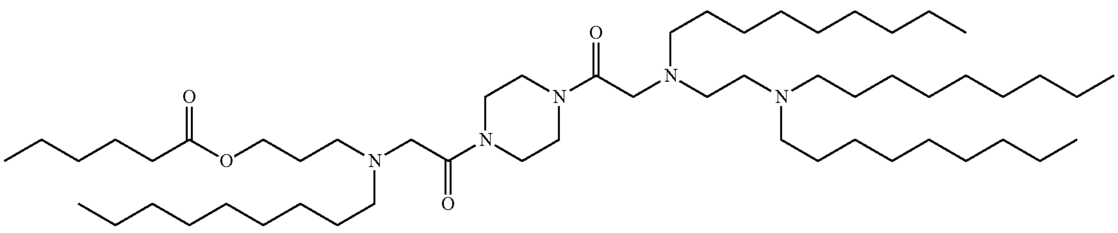
,
(Compound 289)
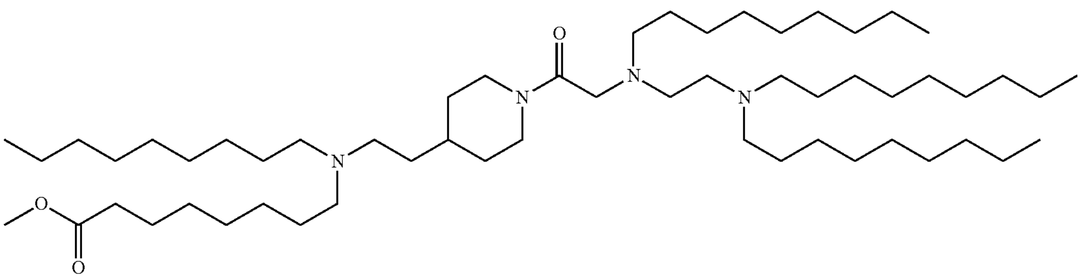
,
(Compound 290)
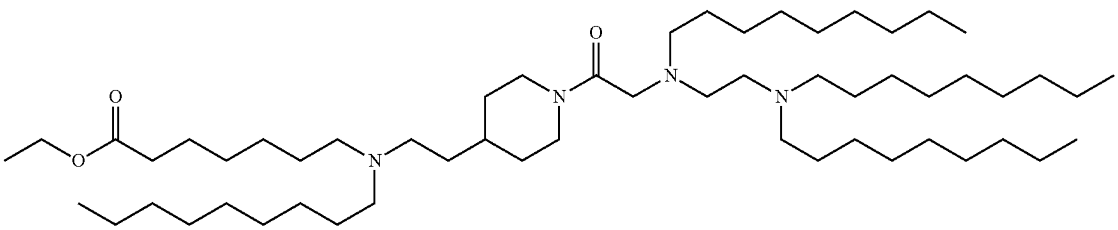
,
(Compound 291)
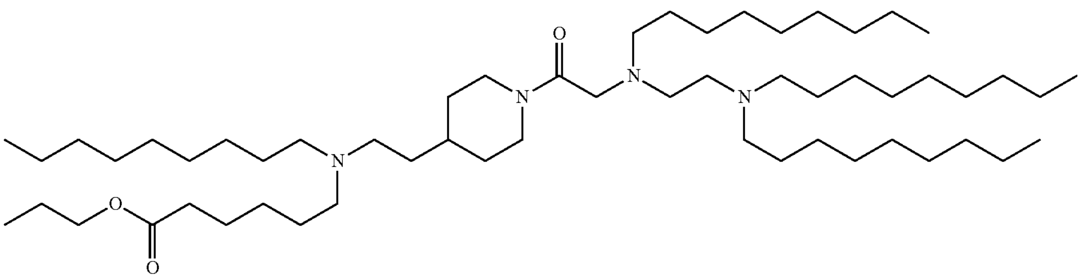
,
(Compound 292)
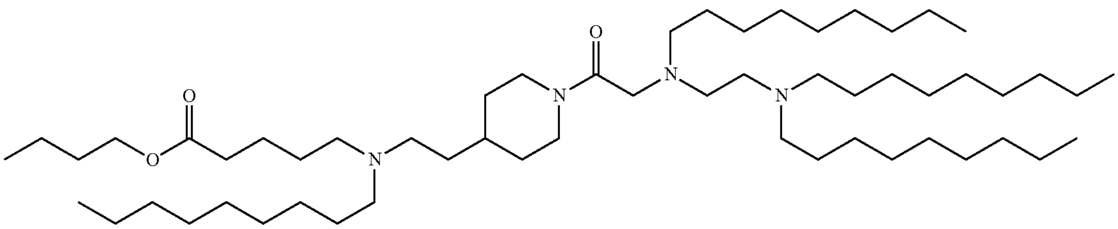
, -continued
(Compound 293)
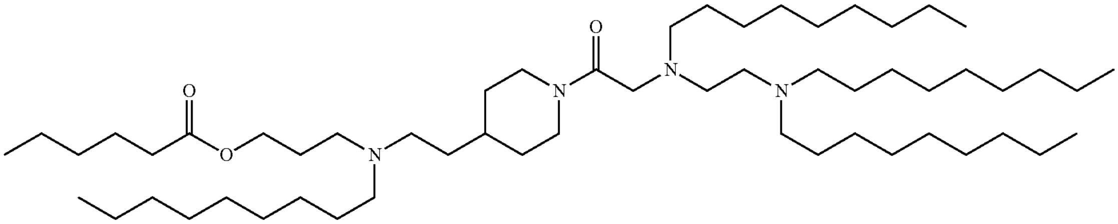
,
(Compound 294)
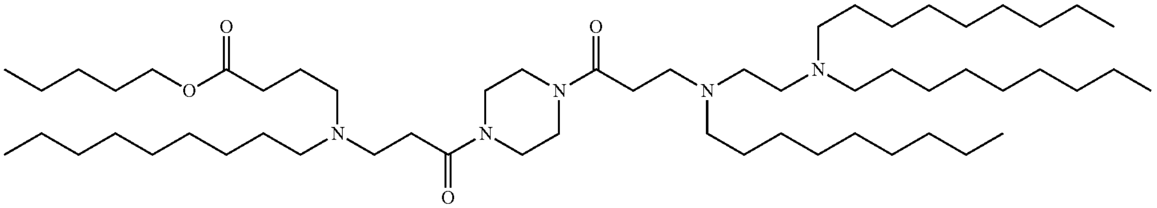
,
(Compound 295)
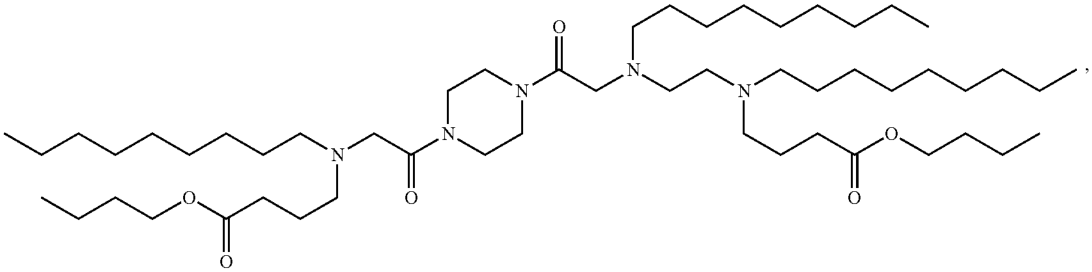
,
(Compound 296)
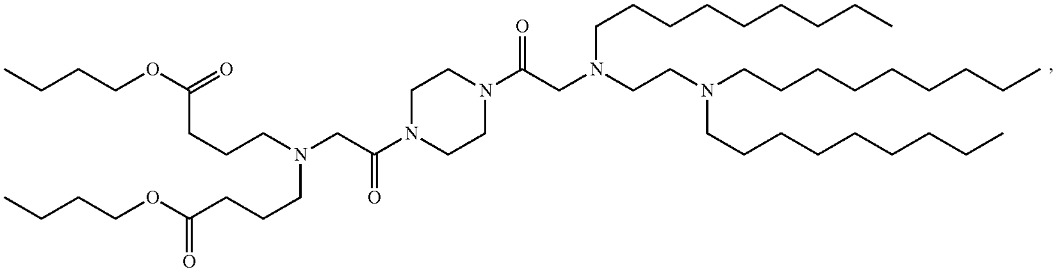
,
(Compound 297)
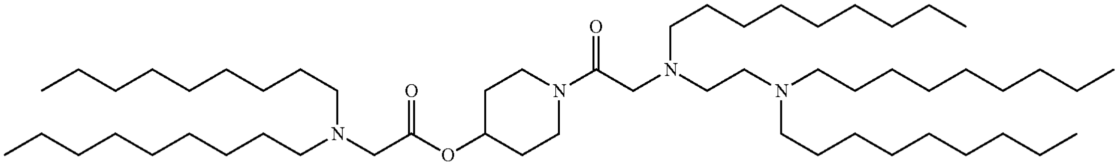
,
(Compound 298)
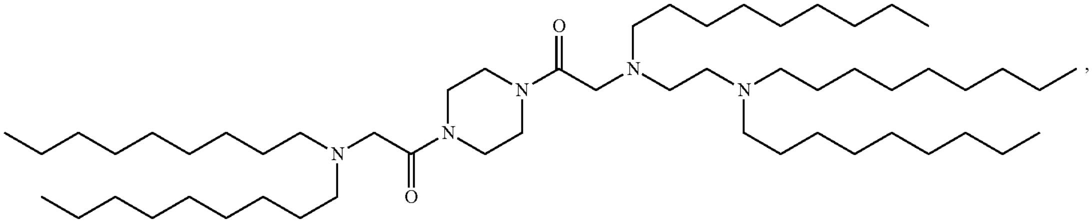
, -continued
(Compound 300)
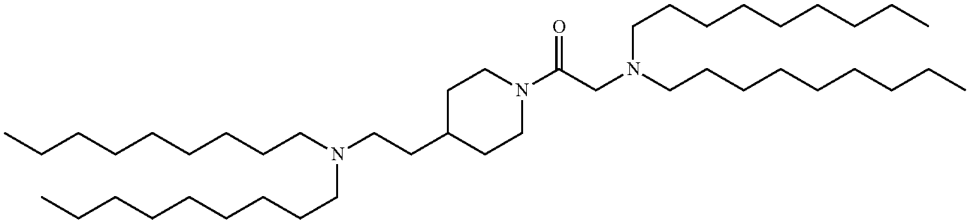
,
(Compound 301)
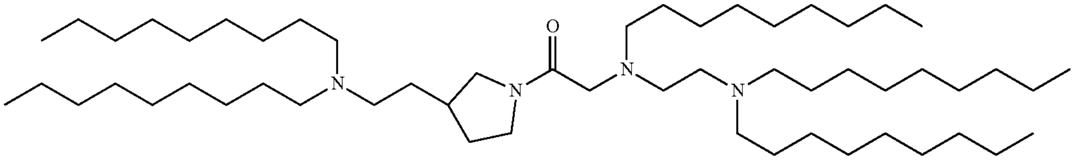
,
(Compound 302)
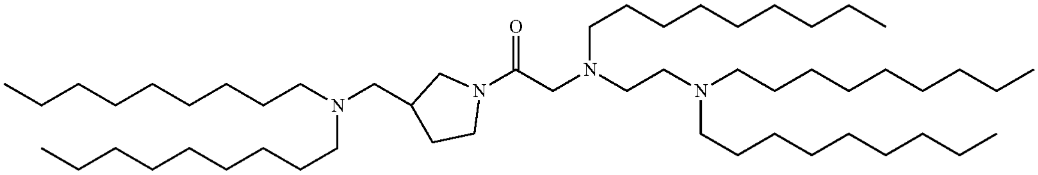
,
(Compound 303)
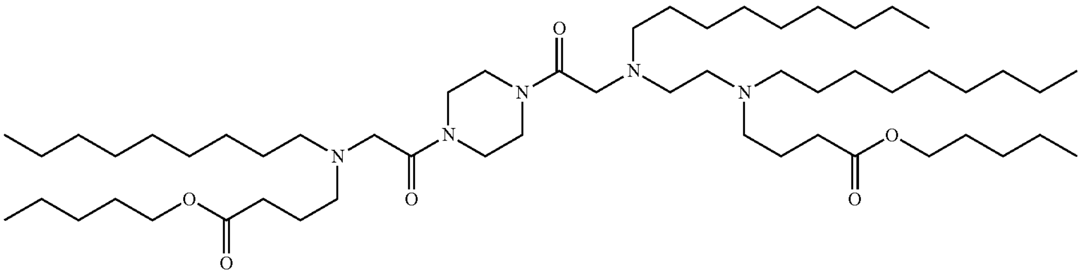
,
(Compound 304)
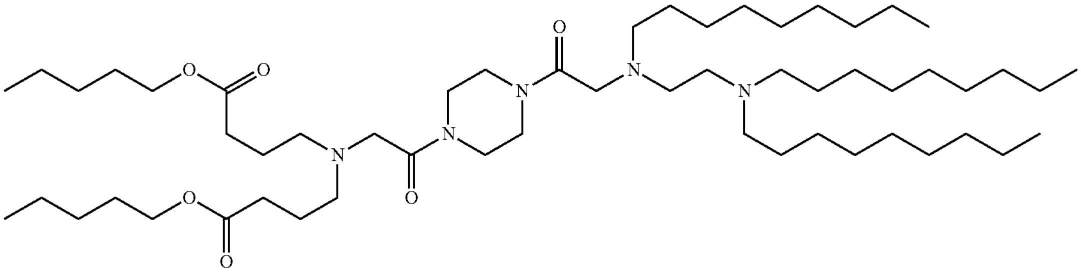
,
(Compound 305)
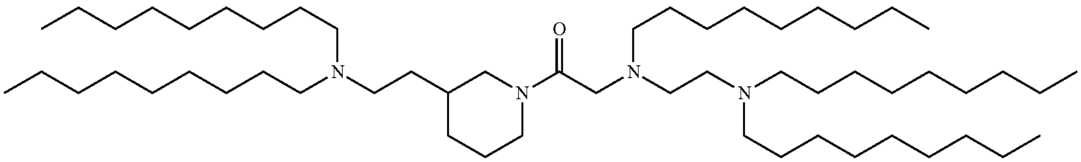
,
(Compound 306)
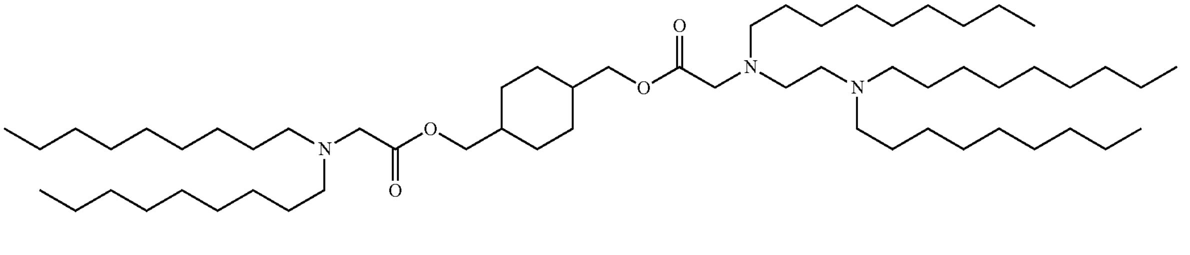
, -continued
(Compound 307)
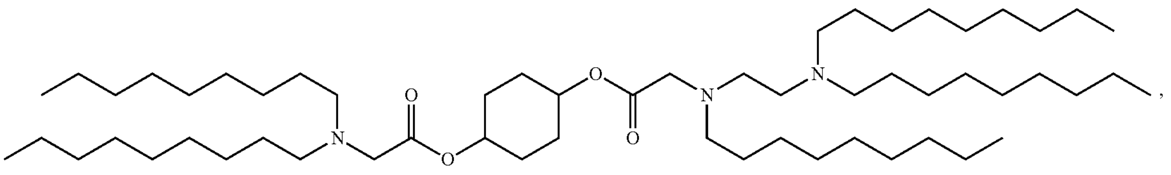
(Compound 308)
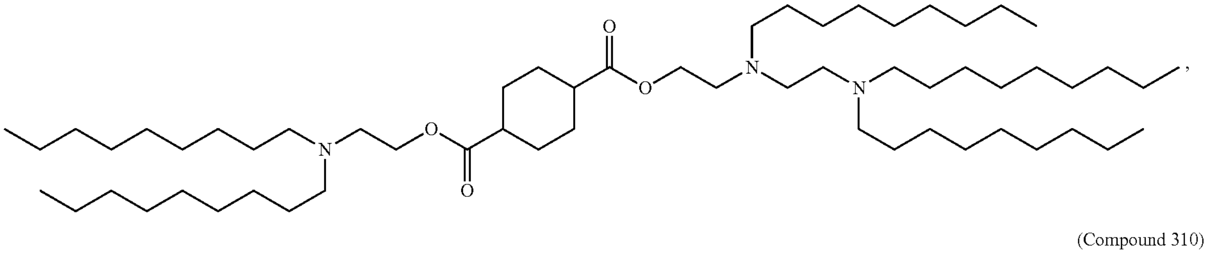
(Compound 310)
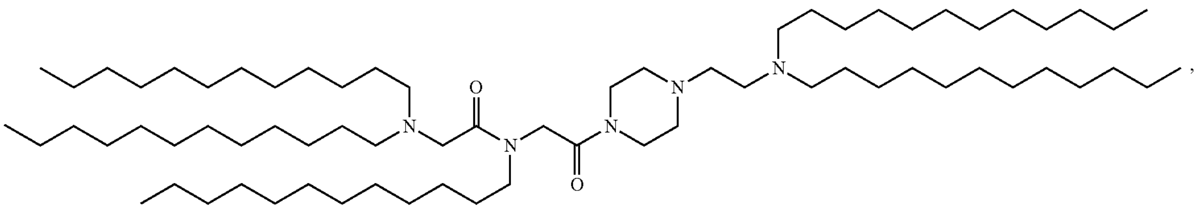
(Compound 311)
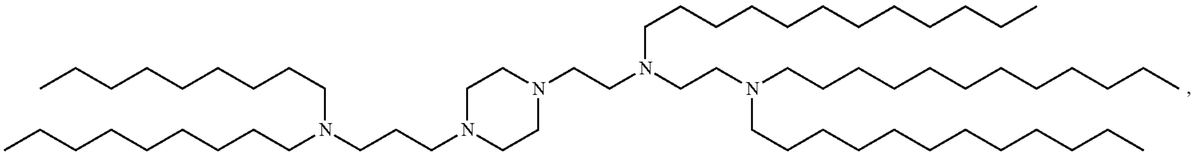
(Compound 312)
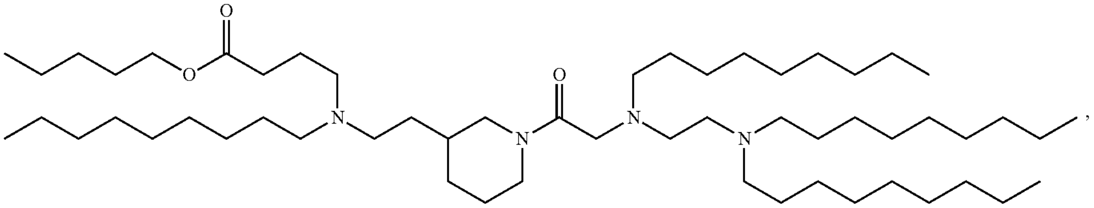
(Compound 313)
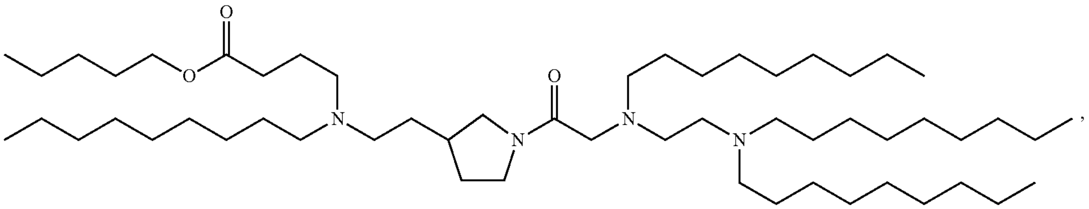
(Compound 314)
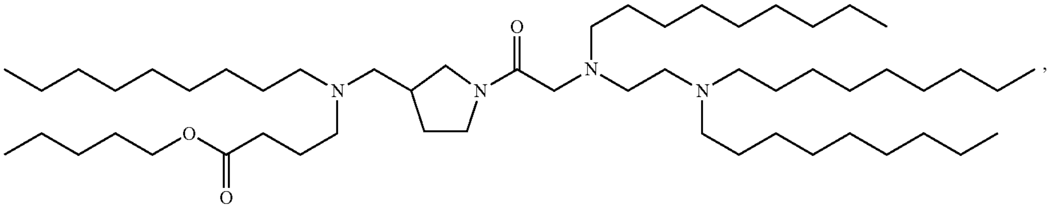

-continued
(Compound 315)
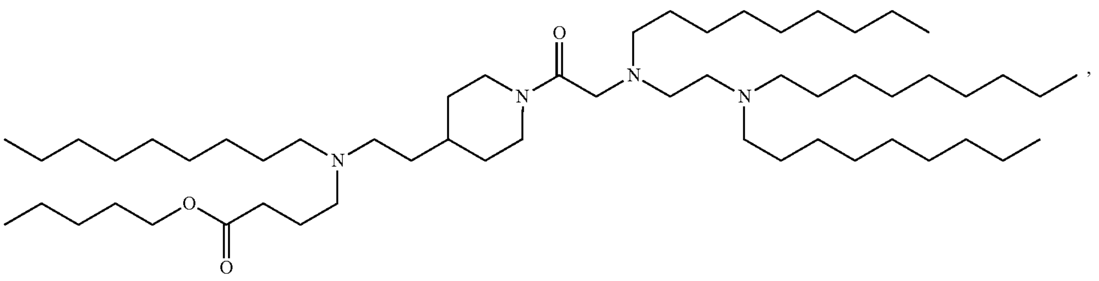
(Compound 316)
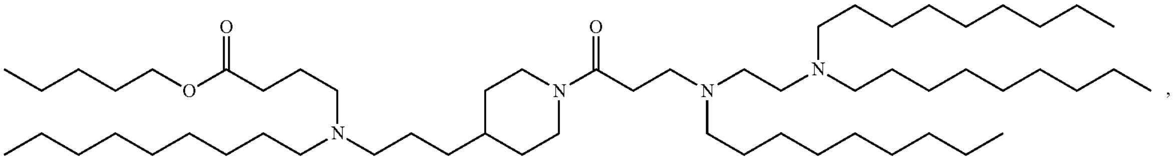
(Compound 317)
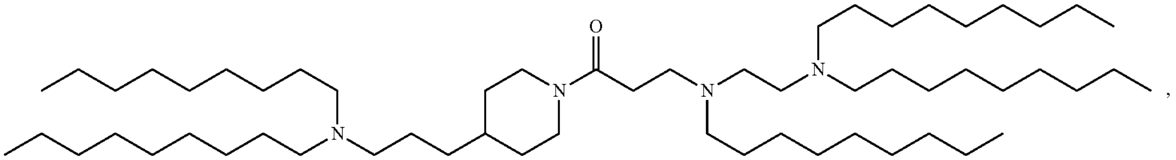
(Compound 318)
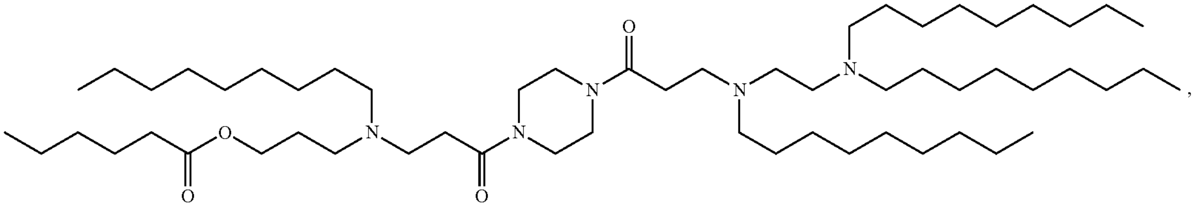
(Compound 319)
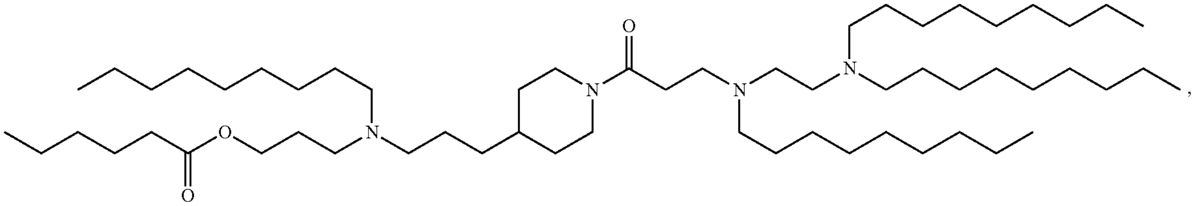
(Compound 320)
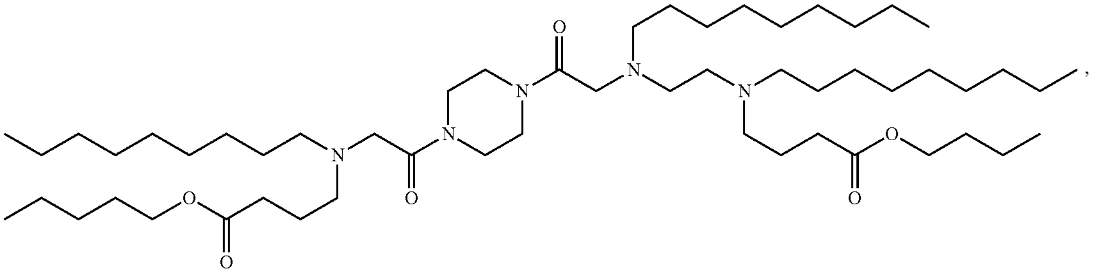

-continued
(Compound 321)
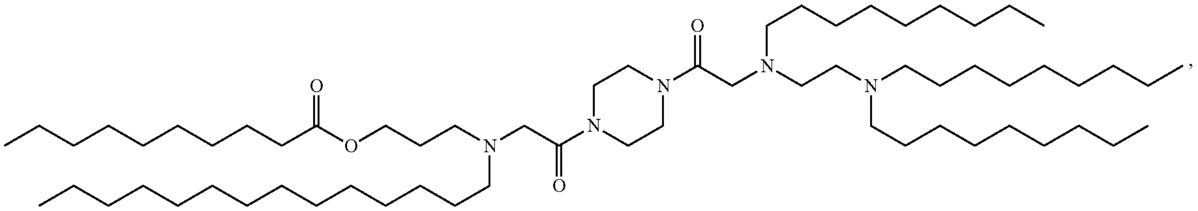
(Compound 322)
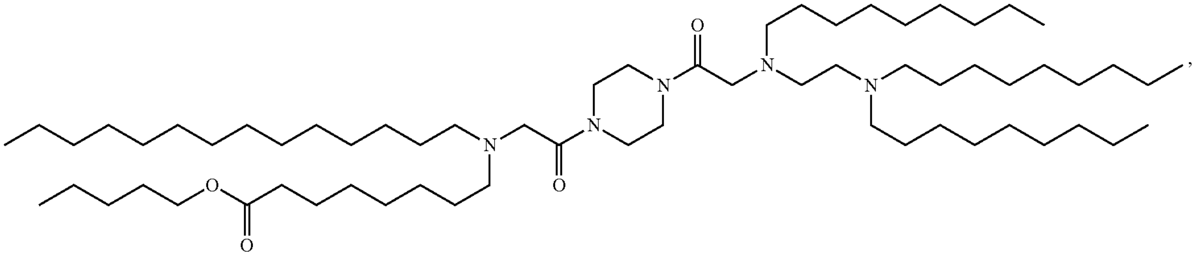
(Compound 323)
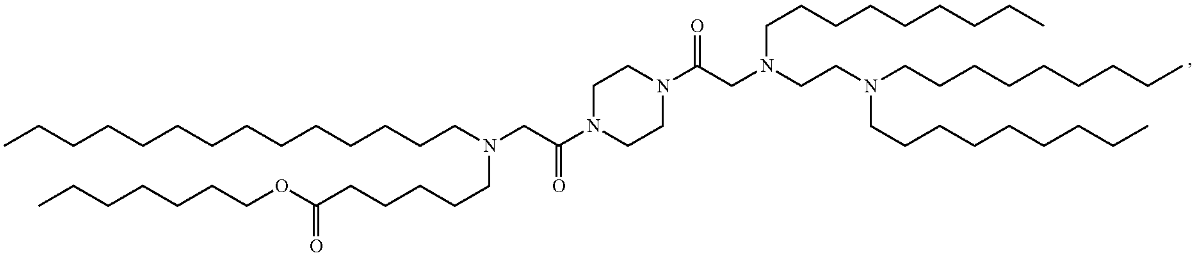
(Compound 324)
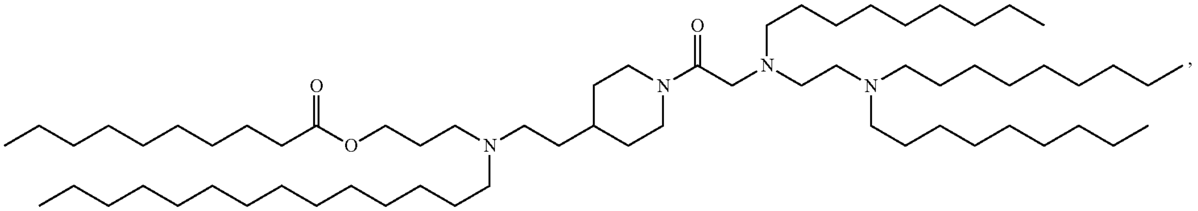
(Compound 325)
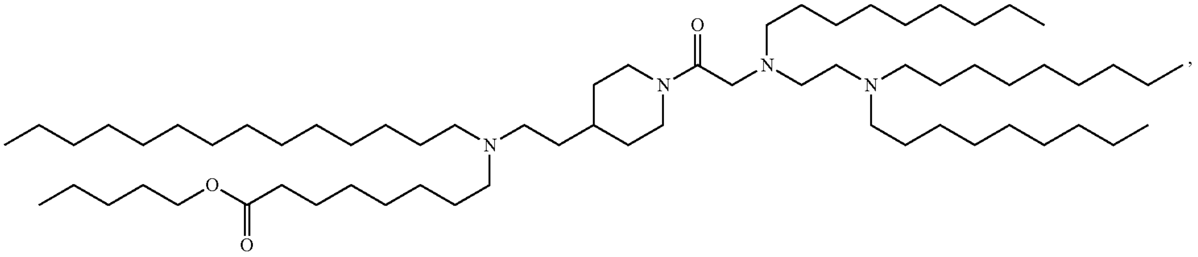
(Compound 326)
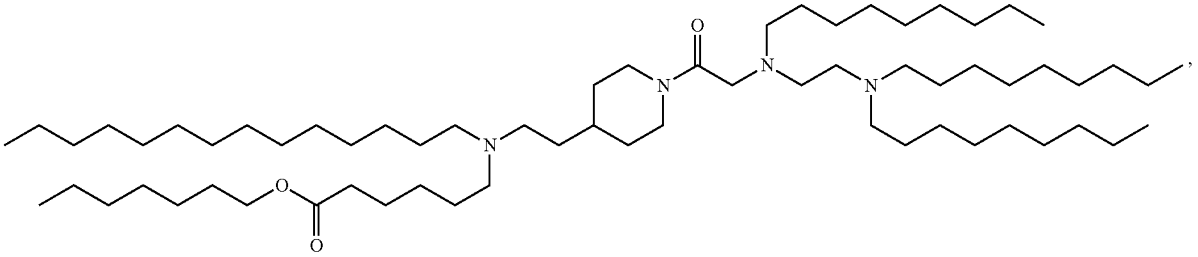

-continued
(Compound 327)
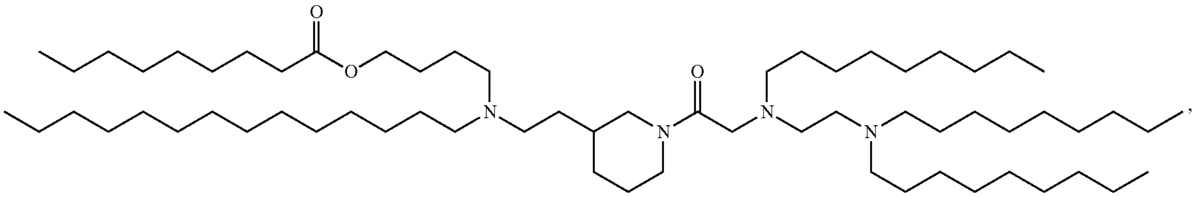
(Compound 328)
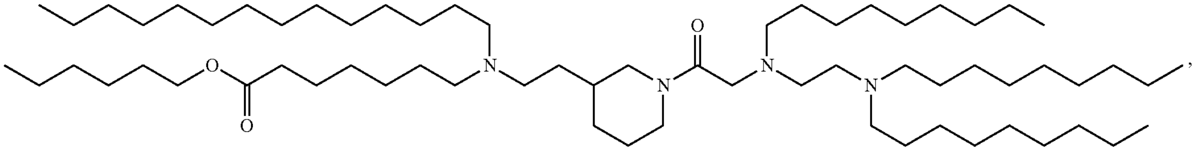
(Compound 329)
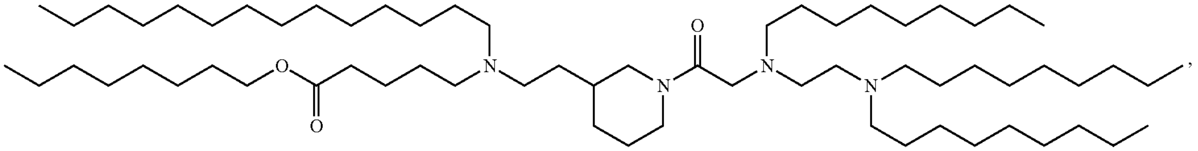
(Compound 330)
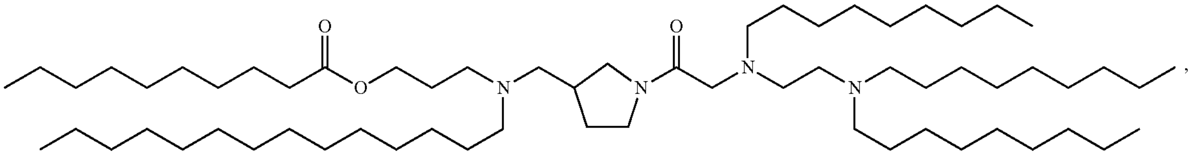
(Compound 331)
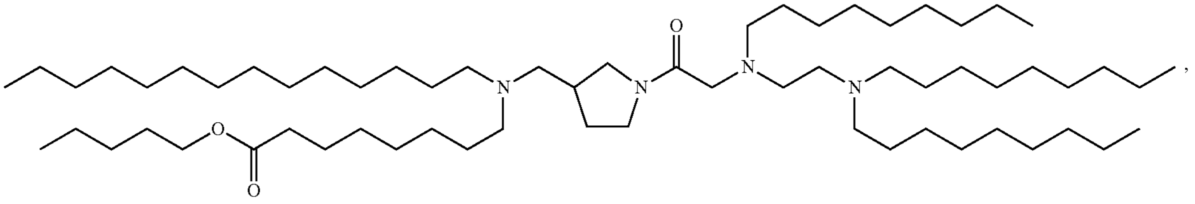
(Compound 332)
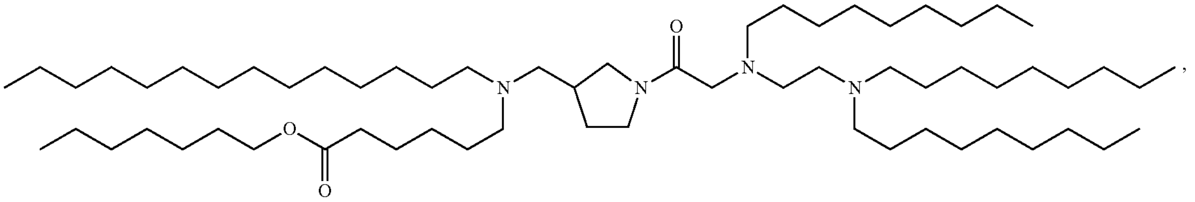
(Compound 333)
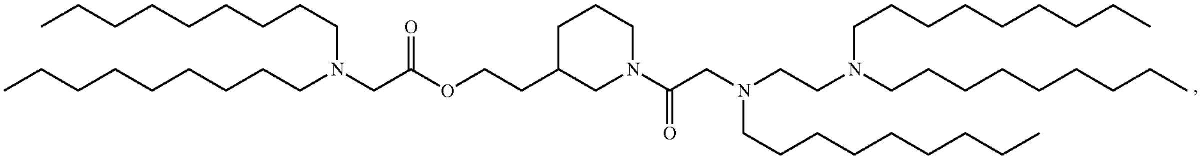
(Compound 334)
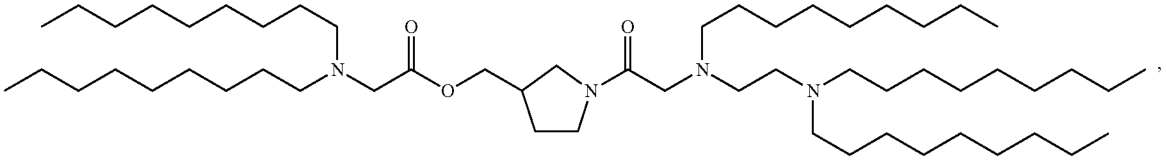

-continued
(Compound 335)
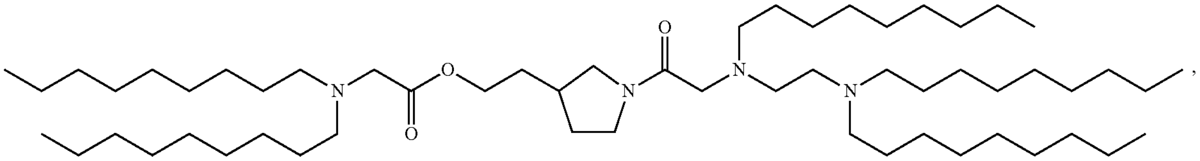
(Compound 336)
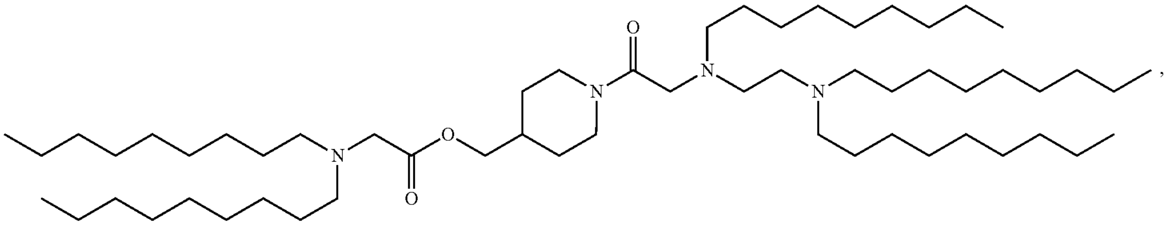
(Compound 337)
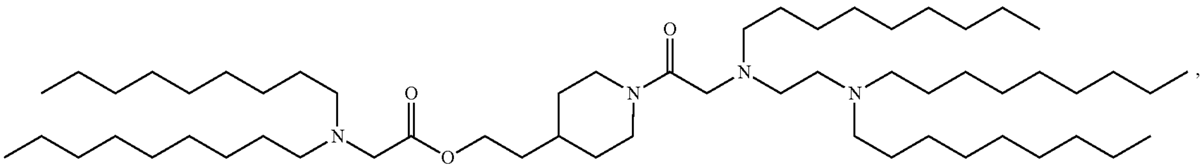
(Compound 338)
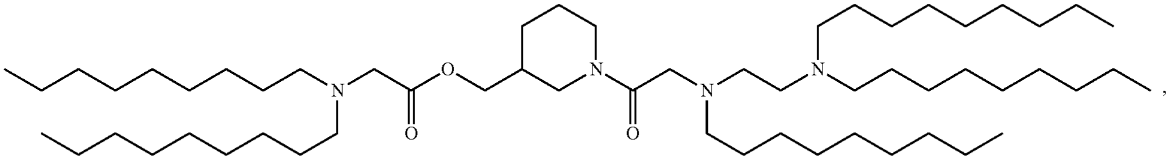
(Compound 339)
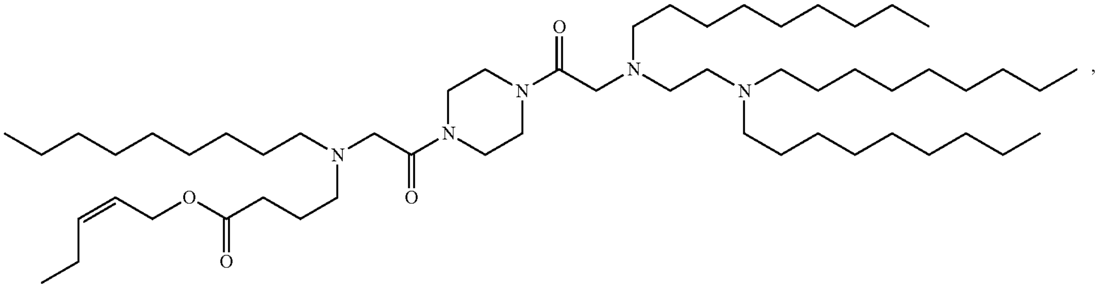

-continued (Compound 340)

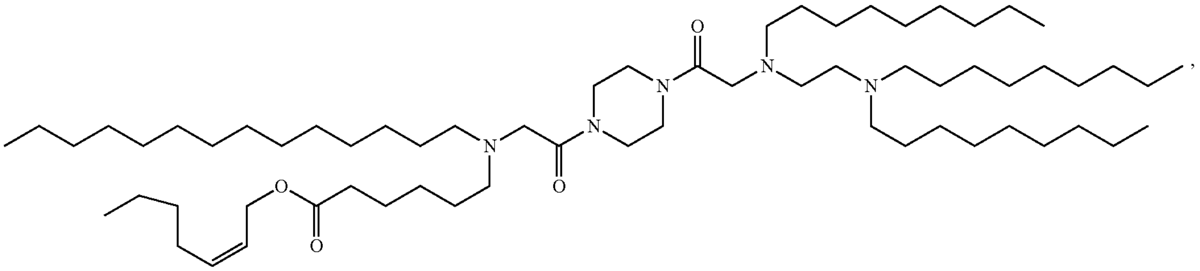

and (Compound 341)

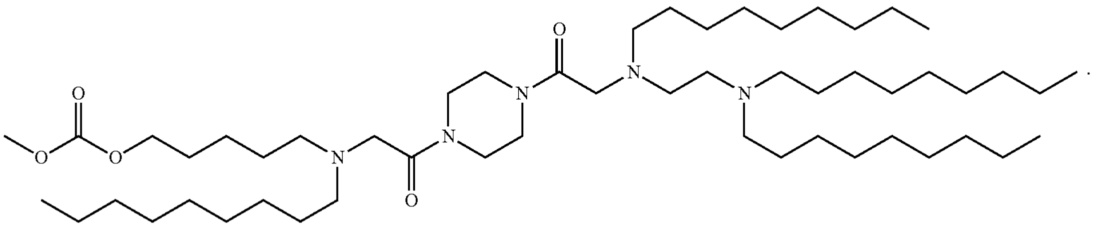

In some embodiments, the delivery agent comprises Compound 236.

In some embodiments, the delivery agent comprises a compound having the formula (IV)

(IV)

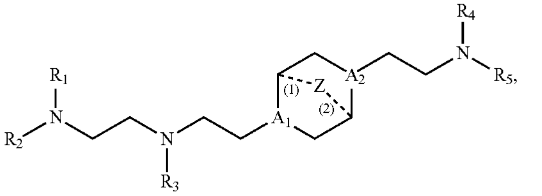

or salts or stereoisomer thereof, wherein $A_1$ and $A_2$ are each independently selected from CH or N and at least one of $A_1$ and $A_2$ is N;

Z is $CH_2$ or absent wherein when Z is $CH_2$, the dashed lines (1) and (2) each represent a single bond; and when Z is absent, the dashed lines (1) and (2) are both absent;

$R_1$, $R_2$, $R_3$, $R_4$, and $R_5$ are independently selected from the group consisting of $C_{6-20}$ alkyl and $C_{6-20}$ alkenyl;

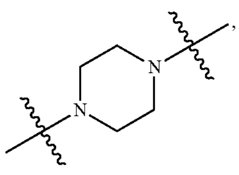 [SMILES: *N1CCN(*)CC1]

wherein when ring A is then i) $R_1$, $R_2$, $R_3$, $R_4$, and $R_5$ are the same, wherein $R_1$ is not $C_{12}$ alkyl, $C_{18}$ alkyl, or $C_{18}$ alkenyl;

ii) only one of $R_1$, $R_2$, $R_3$, $R_4$, and $R_5$ is selected from $C_{6-20}$ alkenyl;

iii) at least one of $R_1$, $R_2$, $R_3$, $R_4$, and $R_5$ have a different number of carbon atoms than at least one other of $R_1$, $R_2$, $R_3$, $R_4$, and $R_5$;

iv) $R_1$, $R_2$, and $R_3$ are selected from $C_{6-20}$ alkenyl, and $R_4$ and $R_5$ are selected from $C_{6-20}$ alkyl; or v) $R_1$, $R_2$, and $R_3$ are selected from $C_{6-20}$ alkyl, and $R_4$ and $R_5$ are selected from $C_{6-20}$ alkenyl.

In some embodiments, the compound is of formula (IVa):

(IVa)

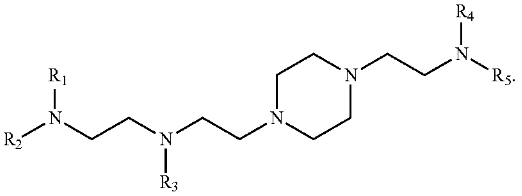

The compounds of Formula (IV) or (IVa) include one or more of the following features when applicable.

In some embodiments, Z is $CH_2$.

In some embodiments, Z is absent.

In some embodiments, at least one of $A_1$ and $A_2$ is N.

In some embodiments, each of $A_1$ and $A_2$ is N.

In some embodiments, each of $A_1$ and $A_2$ is CH.

In some embodiments, $A_1$ is N and $A_2$ is CH.

In some embodiments, $A_1$ is CH and $A_2$ is N.

In some embodiments, $R_1$, $R_2$, $R_3$, $R_4$, and $R_5$ are the same, and are not $C_{12}$ alkyl, $C_{18}$ alkyl, or $C_{18}$ alkenyl. In some embodiments, $R_1$, $R_2$, $R_3$, $R_4$, and $R_5$ are the same and are $C_9$ alkyl or $C_{14}$ alkyl.

In some embodiments, only one of $R_1$, $R_2$, $R_3$, $R_4$, and $R_5$ is selected from $C_{6-20}$ alkenyl. In certain such embodiments, $R_1$, $R_2$, $R_3$, $R_4$, and $R_5$ have the same number of carbon atoms. In some embodiments, $R_4$ is selected from $C_{5-20}$ alkenyl. For example, $R_4$ may be $C_{12}$ alkenyl or $C_{18}$ alkenyl.

In some embodiments, at least one of $R_1$, $R_2$, $R_3$, $R_4$, and $R_5$ have a different number of carbon atoms than at least one other of $R_1$, $R_2$, $R_3$, $R_4$, and $R_5$.

In certain embodiments, $R_1$, $R_2$, and $R_3$ are selected from $C_{6-20}$ alkenyl, and $R_4$ and $R_5$ are selected from $C_{6-20}$ alkyl. In other embodiments, $R_1$, $R_2$, and $R_3$ are selected from $C_{6-20}$ alkyl, and $R_4$ and $R_5$ are selected from $C_{6-20}$ alkenyl. In some embodiments, $R_1$, $R_2$, and $R_3$ have the same number of carbon atoms, and/or $R_4$ and $R_5$ have the same number of carbon atoms. For example, $R_1$, $R_2$, and $R_3$, or $R_4$ and $R_5$, may have 6, 8, 9, 12, 14, or 18 carbon atoms. In some embodiments, $R_1$, $R_2$, and $R_3$, or $R_4$ and $R_5$, are $C_{18}$ alkenyl (e.g., linoleyl). In some embodiments, $R_1$, $R_2$, and $R_3$, or $R_4$ and $R_5$, are alkyl groups including 6, 8, 9, 12, or 14 carbon atoms.

In some embodiments, $R_1$ has a different number of carbon atoms than $R_2$, $R_3$, $R_4$, and $R_5$. In other embodiments, $R_3$ has a different number of carbon atoms than $R_1$, $R_2$, $R_4$, and $R_5$. In further embodiments, $R_4$ has a different number of carbon atoms than $R_1$, $R_2$, $R_3$, and $R_5$.

In some embodiments, the compound is selected from the group consisting of:

(Compound 249)

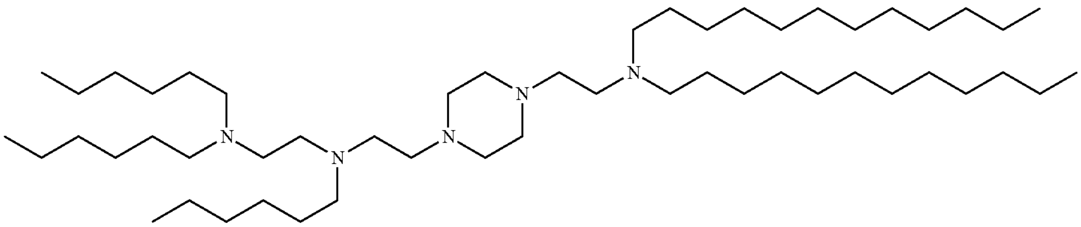

, (Compound 250)

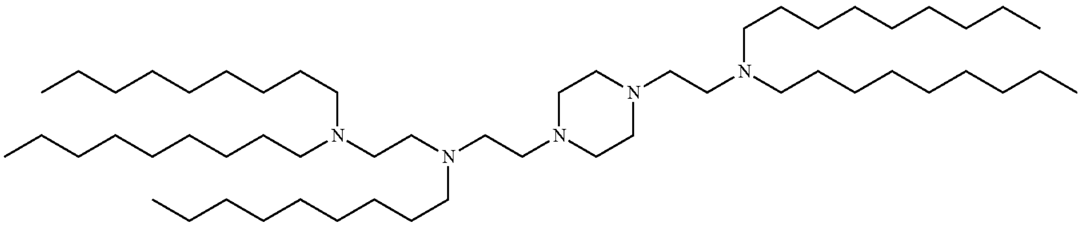

, (Compound 251)

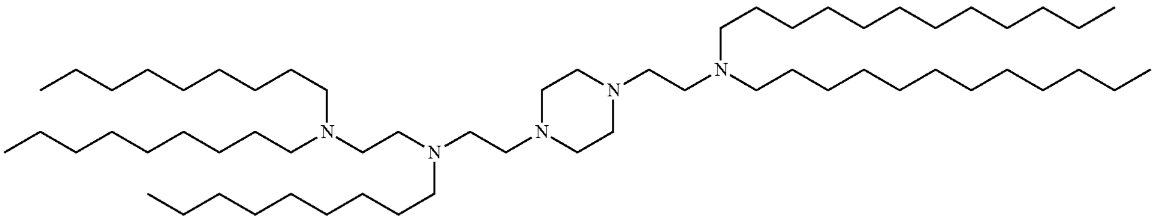

, (Compound 252)

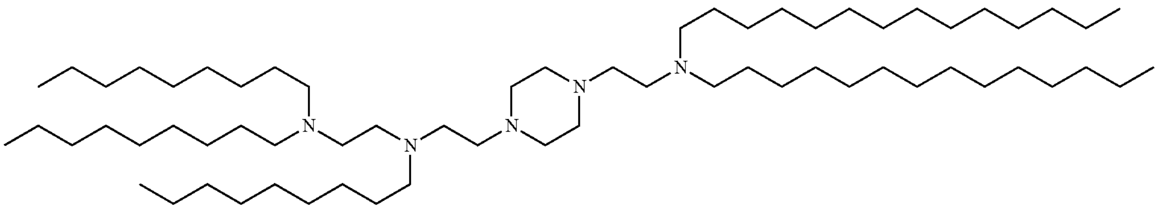

, (Compound 253)

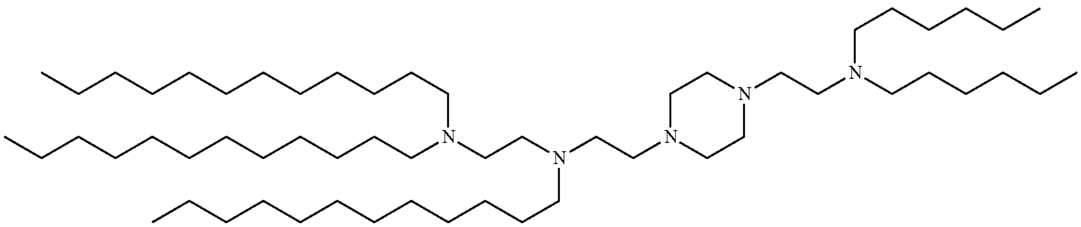

,

-continued
(Compound 254)
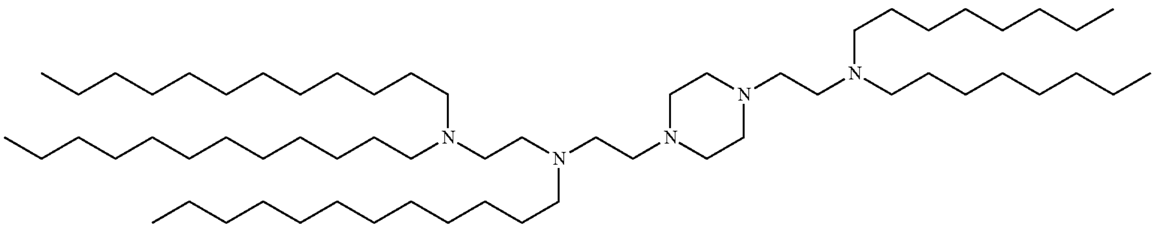
,
(Compound 255)
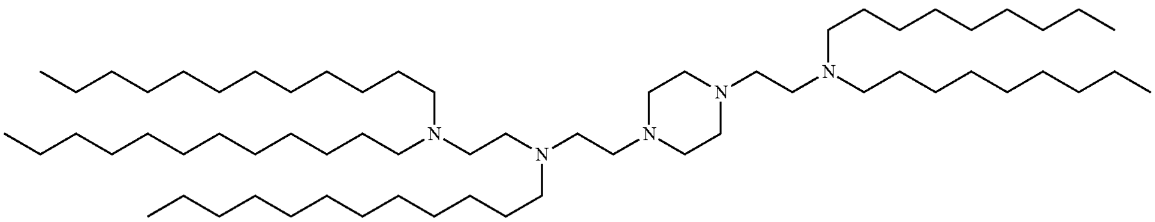
,
(Compound 256)
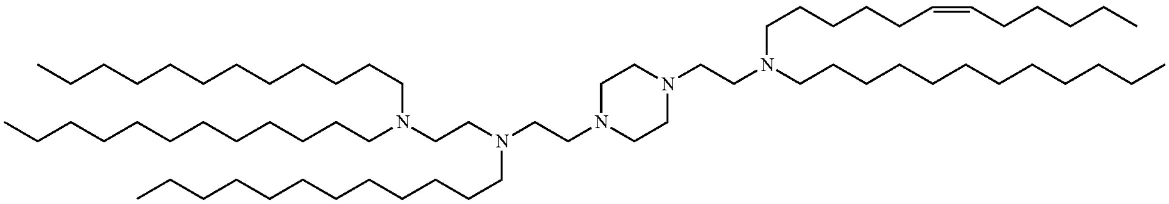
,
(Compound 257)
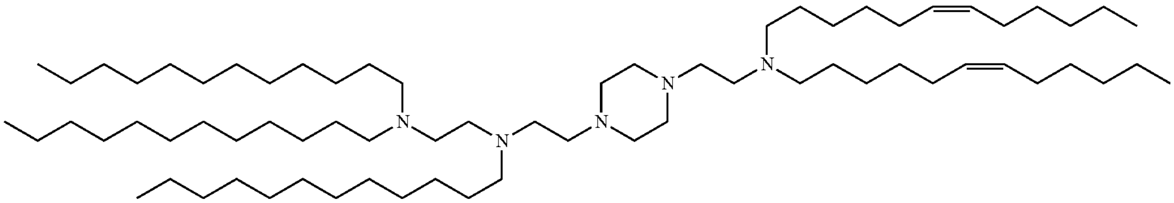
,
(Compound 258)
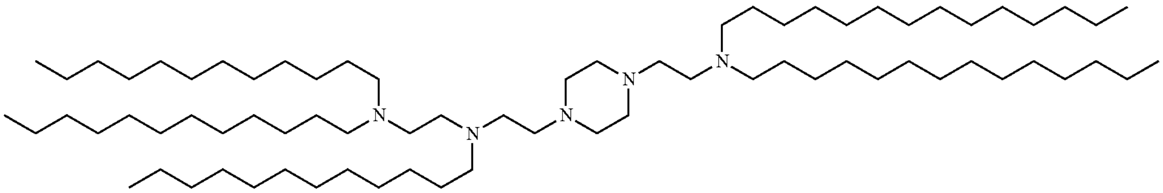
,
(Compound 259)
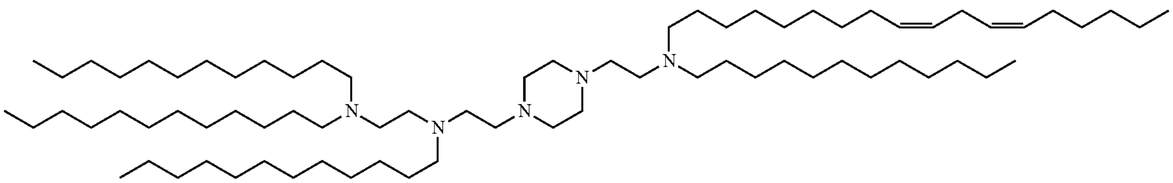
,
(Compound 260)
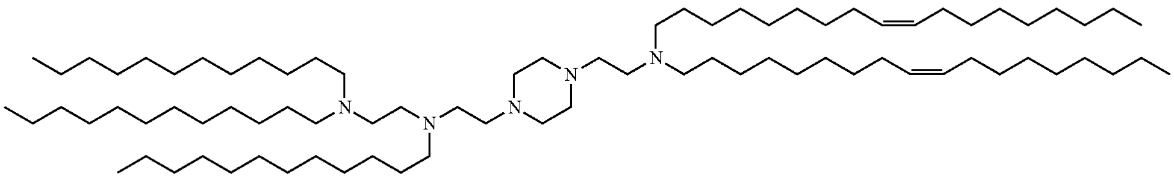
, -continued (Compound 261)

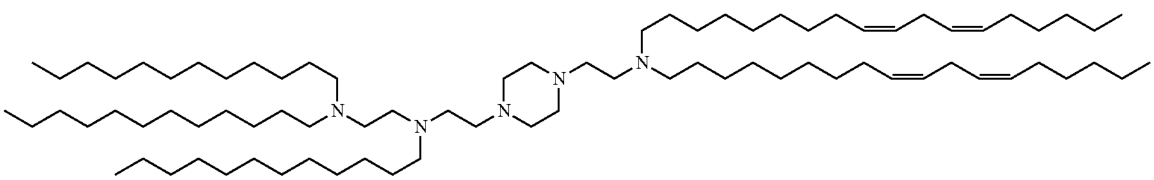

, (Compound 262)

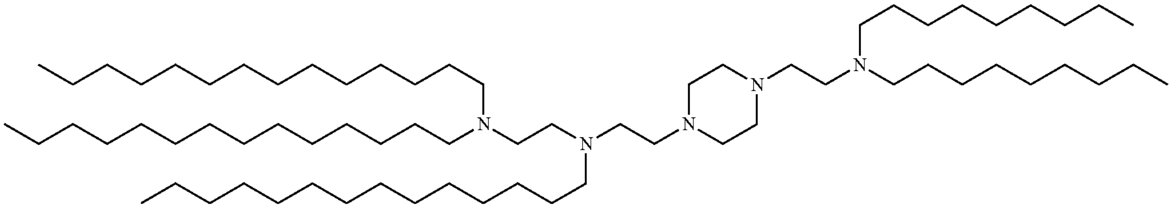

, (Compound 263)

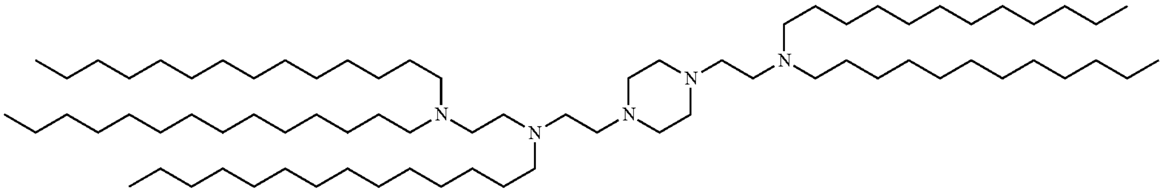

, (Compound 264)

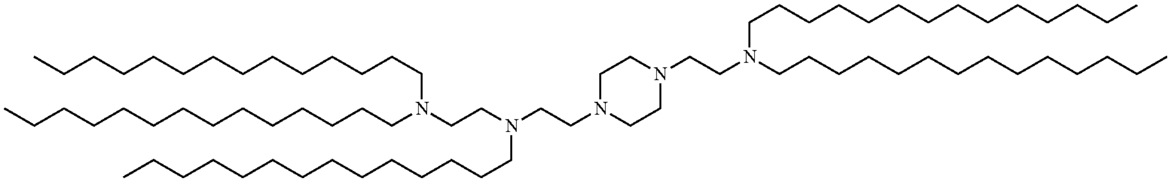

, (Compound 265)

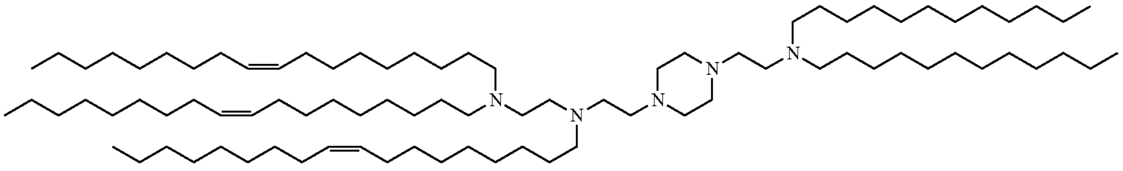

, and (Compound 266)

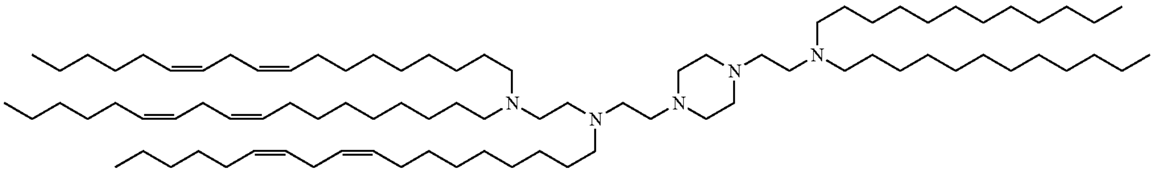

.

In other embodiments, the delivery agent comprises a compound having the formula (V)

(V)

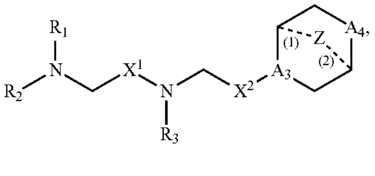

or salts or stereoisomers thereof, in which $A_3$ is CH or N;

$A_4$ is $CH_2$ or NH; and at least one of $A_3$ and $A_4$ is N or NH;

Z is $CH_2$ or absent wherein when Z is $CH_2$, the dashed lines (1) and (2) each represent a single bond; and when Z is absent, the dashed lines (1) and (2) are both absent;

$R_1$, $R_2$, and $R_3$ are independently selected from the group consisting of $C_{5-20}$ alkyl, $C_{5-20}$ alkenyl, —R"MR', —R*YR", —YR", and —R*OR";

each M is independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, an aryl group, and a heteroaryl group;

$X^1$ and $X^2$ are independently selected from the group consisting of $—CH_2—$, $—(CH_2)_2—$, —CHR—, —CHY—, —C(O)—, —C(O)O—, —OC(O)—, $—C(O)—CH_2—$, —$CH_2$—C(O)—, —C(O)O—$CH_2$—, —OC(O)—$CH_2$—, —$CH_2$—C(O)O—, —$CH_2$—OC(O)—, —CH(OH)—, —C(S)—, and —CH(SH)—;

each Y is independently a $C_{3-6}$ carbocycle;

each R* is independently selected from the group consisting of $C_{1-12}$ alkyl and $C_{2-12}$ alkenyl;

each R is independently selected from the group consisting of $C_{1-3}$ alkyl and a $C_{3-6}$ carbocycle;

each R' is independently selected from the group consisting of $C_{1-12}$ alkyl, $C_{2-12}$ alkenyl, and H; and each R" is independently selected from the group consisting of $C_{3-12}$ alkyl and $C_{3-12}$ alkenyl.

In some embodiments, the compound is of formula (Va):

(Va)

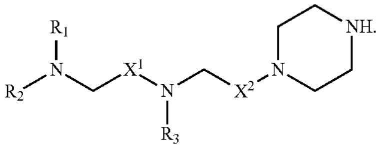

The compounds of Formula (V) or (Va) include one or more of the following features when applicable.

In some embodiments, Z is $CH_2$.

In some embodiments, Z is absent.

In some embodiments, at least one of $A_3$ and $A_4$ is N or NH.

In some embodiments, $A_3$ is N and $A_4$ is NH.

In some embodiments, $A_3$ is N and $A_4$ is $CH_2$.

In some embodiments, $A_3$ is CH and $A_4$ is NH.

In some embodiments, at least one of $X^1$ and $X^2$ is not —$CH_2$—. For example, in certain embodiments, $X^1$ is not —$CH_2$—. In some embodiments, at least one of $X^1$ and $X^2$ is —C(O)—.

In some embodiments, $X^2$ is —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, or —$CH_2$—OC(O)—.

In some embodiments, $R_1$, $R_2$, and $R_3$ are independently selected from the group consisting of $C_{5-20}$ alkyl and $C_{5-20}$ alkenyl. In some embodiments, $R_1$, $R_2$, and $R_3$ are the same. In certain embodiments, $R_1$, $R_2$, and $R_3$ are $C_6$, $C_9$, $C_{12}$, or $C_{14}$ alkyl. In other embodiments, $R_1$, $R_2$, and $R_3$ are $C_{18}$ alkenyl. For example, $R_1$, $R_2$, and $R_3$ may be linoleyl.

In some embodiments, the compound is selected from the group consisting of:

(Compound 267)

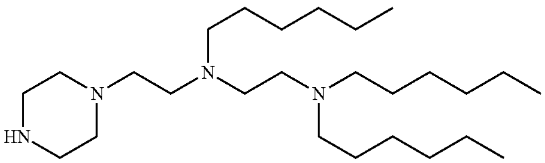

, (Compound 268)

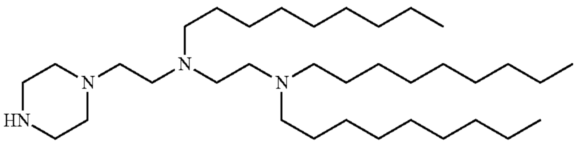

, (Compound 269)

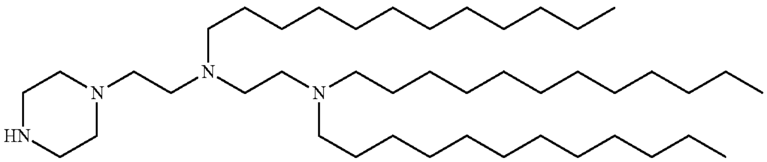

, (Compound 270)

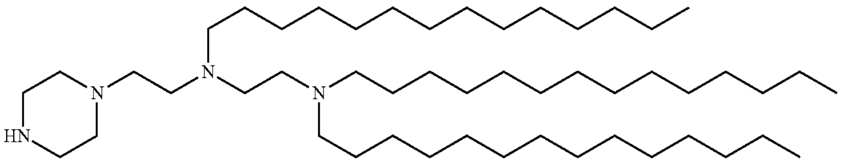

, (Compound 271)

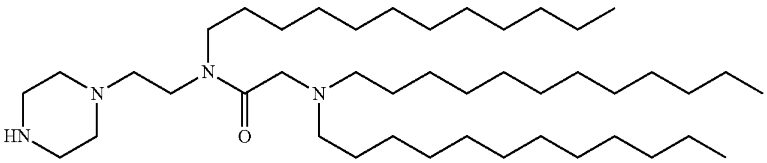

, (Compound 272)

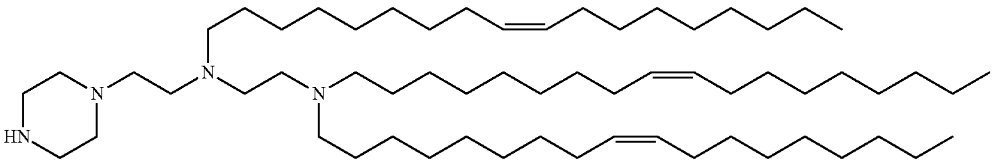

,

-continued (Compound 273)

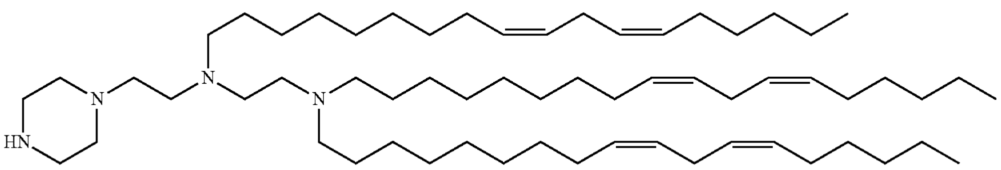

, and (Compound 309)

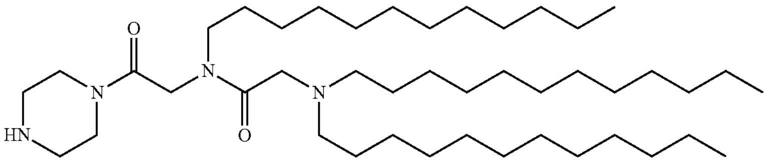

.

In other embodiments, the delivery agent comprises a compound having the formula (VI):

(VI)

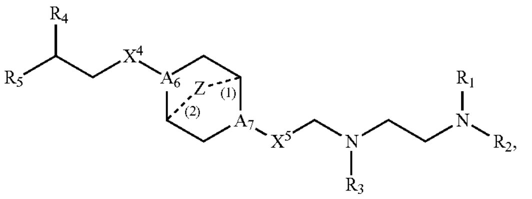

or salts or stereoisomers thereof, in which $A_6$ and $A_7$ are each independently selected from CH or N, wherein at least one of $A_6$ and $A_7$ is N;

Z is $CH_2$ or absent wherein when Z is $CH_2$, the dashed lines (1) and (2) each represent a single bond; and when Z is absent, the dashed lines (1) and (2) are both absent;

$X^4$ and $X^5$ are independently selected from the group consisting of —$CH_2$—, —$CH_2)_2$—, —CHR—, —CHY—, —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, —$CH_2$—OC(O)—, —CH(OH)—, —C(S)—, and —CH(SH)—;

$R_1$, $R_2$, $R_3$, $R_4$, and $R_5$ each are independently selected from the group consisting of $C_{5-20}$ alkyl, $C_{5-20}$ alkenyl, —R"MR', —R*YR", —YR", and —R*OR";

each M is independently selected from the group consisting of —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$— an aryl group, and a heteroaryl group;

each Y is independently a $C_{3-6}$ carbocycle;

each R* is independently selected from the group consisting of $C_{1-12}$ alkyl and $C_{2-12}$ alkenyl;

each R is independently selected from the group consisting of $C_{1-3}$ alkyl and a $C_{3-6}$ carbocycle;

each R' is independently selected from the group consisting of $C_{1-12}$ alkyl, $C_{2-12}$ alkenyl, and H; and each R" is independently selected from the group consisting of $C_{3-12}$ alkyl and $C_{3-12}$ alkenyl.

In some embodiments, $R_1$, $R_2$, $R_3$, $R_4$, and $R_5$ each are independently selected from the group consisting of $C_{6-20}$ alkyl and $C_{6-20}$ alkenyl.

In some embodiments, $R_1$ and $R_2$ are the same. In certain embodiments, $R_1$, $R_2$, and $R_3$ are the same. In some embodiments, $R_4$ and $R_5$ are the same. In certain embodiments, $R_1$, $R_2$, $R_3$, $R_4$, and $R_5$ are the same.

In some embodiments, at least one of $R_1$, $R_2$, $R_3$, $R_4$, and $R_5$ is $C_{9-12}$ alkyl. In certain embodiments, each of $R_1$, $R_2$, $R_3$, $R_4$, and $R_5$ independently is $C_9$, $C_{12}$ or $C_{14}$ alkyl. In certain embodiments, each of $R_1$, $R_2$, $R_3$, $R_4$, and $R_5$ is $C_9$ alkyl.

In some embodiments, $A_6$ is N and $A_7$ is N. In some embodiments, $A_6$ is CH and $A_7$ is N.

In some embodiments, $X^4$ is —$CH_2$— and $X^5$ is —C(O)—. In some embodiments, $X^4$ and $X^5$ are —C(O)—.

In some embodiments, when $A_6$ is N and $A_7$ is N, at least one of $X^4$ and $X^5$ is not —$CH_2$—, e.g., at least one of $X^4$ and $X^5$ is —C(O)—. In some embodiments, when $A_6$ is N and $A_7$ is N, at least one of $R_1$, $R_2$, $R_3$, $R_4$, and $R_5$ is —R"MR'.

In some embodiments, at least one of $R_1$, $R_2$, $R_3$, $R_4$, and $R_5$ is not —R"MR'.

In some embodiments, the compound is (Compound 299)

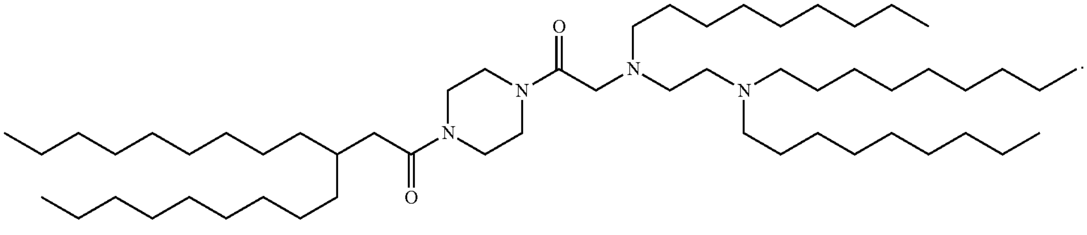

.

In other embodiments, the delivery agent comprises a compound having the formula:

(Compound 342)

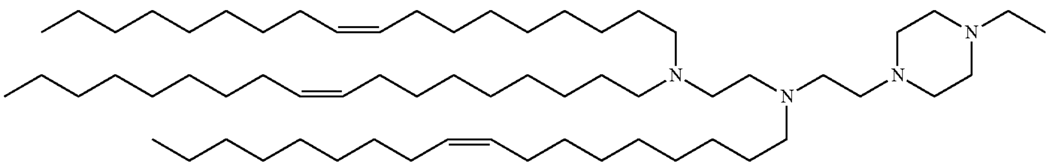

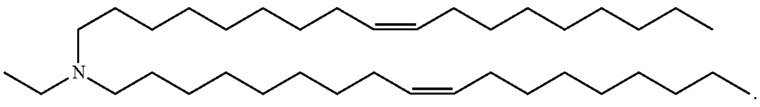

Amine moieties of the lipid compounds disclosed herein can be protonated under certain conditions. For example, the central amine moiety of a lipid according to formula (I) is typically protonated (i.e., positively charged) at a pH below the pKa of the amino moiety and is substantially not charged at a pH above the pKa. Such lipids can be referred to ionizable amino lipids.

In one specific embodiment, the ionizable amino lipid is Compound 18. In another embodiment, the ionizable amino lipid is Compound 236.

In some embodiments, the amount the ionizable amino lipid, e.g., compound of formula (I) ranges from about 1 mol % to 99 mol % in the lipid composition.

In one embodiment, the amount of the ionizable amino lipid, e.g., compound of formula (I) is at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 mol % in the lipid composition.

In one embodiment, the amount of the ionizable amino lipid, e.g., the compound of formula (I) ranges from about 30 mol % to about 70 mol %, from about 35 mol % to about 65 mol %, from about 40 mol % to about 60 mol %, and from about 45 mol % to about 55 mol % in the lipid composition.

In one specific embodiment, the amount of the ionizable amino lipid, e.g., compound of formula (I) is about 50 mol % in the lipid composition.

In addition to the ionizable amino lipid disclosed herein, e.g., compound of formula (I), the lipid composition of the pharmaceutical compositions disclosed herein can comprise additional components such as phospholipids, structural lipids, PEG-lipids, and any combination thereof.

b. Phospholipids

The lipid composition of the pharmaceutical composition disclosed herein can comprise one or more phospholipids, for example, one or more saturated or (poly)unsaturated phospholipids or a combination thereof. In general, phospholipids comprise a phospholipid moiety and one or more fatty acid moieties.

A phospholipid moiety can be selected, for example, from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin.

A fatty acid moiety can be selected, for example, from the non-limiting group consisting of lauric acid, myristic acid, myristoleic acid, palmitic acid, palmitoleic acid, stearic acid, oleic acid, linoleic acid, alpha-linolenic acid, erucic acid, phytanoic acid, arachidic acid, arachidonic acid, eicosapentaenoic acid, behenic acid, docosapentaenoic acid, and docosahexaenoic acid.

Particular phospholipids can facilitate fusion to a membrane. For example, a cationic phospholipid can interact with one or more negatively charged phospholipids of a membrane (e.g., a cellular or intracellular membrane). Fusion of a phospholipid to a membrane can allow one or more elements (e.g., a therapeutic agent) of a lipid-containing composition (e.g., LNPs) to pass through the membrane permitting, e.g., delivery of the one or more elements to a target tissue.

Non-natural phospholipid species including natural species with modifications and substitutions including branching, oxidation, cyclization, and alkynes are also contemplated. For example, a phospholipid can be functionalized with or cross-linked to one or more alkynes (e.g., an alkenyl group in which one or more double bonds is replaced with a triple bond). Under appropriate reaction conditions, an alkyne group can undergo a copper-catalyzed cycloaddition upon exposure to an azide. Such reactions can be useful in functionalizing a lipid bilayer of a nanoparticle composition to facilitate membrane permeation or cellular recognition or in conjugating a nanoparticle composition to a useful component such as a targeting or imaging moiety (e.g., a dye).

Phospholipids include, but are not limited to, glycerophospholipids such as phosphatidylcholines, phosphatidylethanolamines, phosphatidylserines, phosphatidylinositols, phosphatidy glycerols, and phosphatidic acids. Phospholipids also include phosphosphingolipid, such as sphingomyelin.

Examples of phospholipids include, but are not limited to, the following:

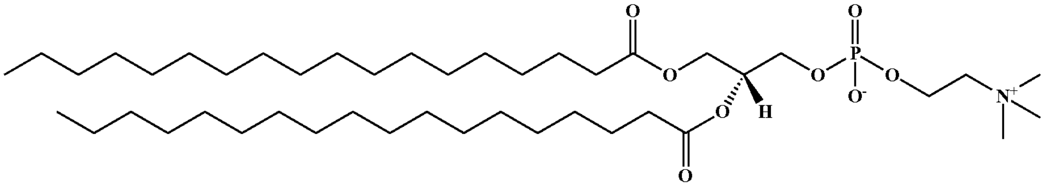

,

-continued
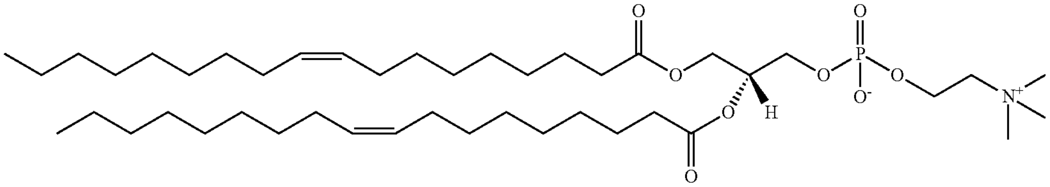
,
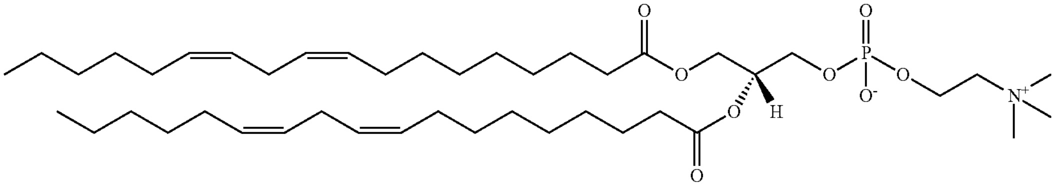
,
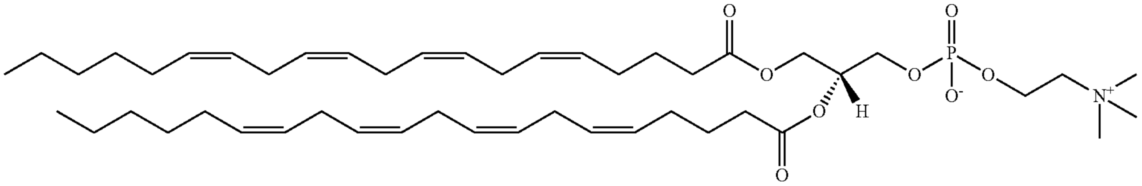
,
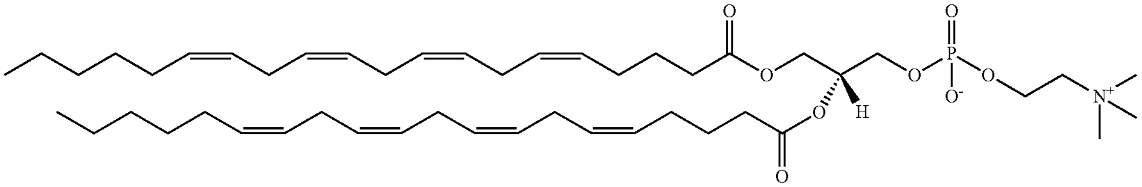
,
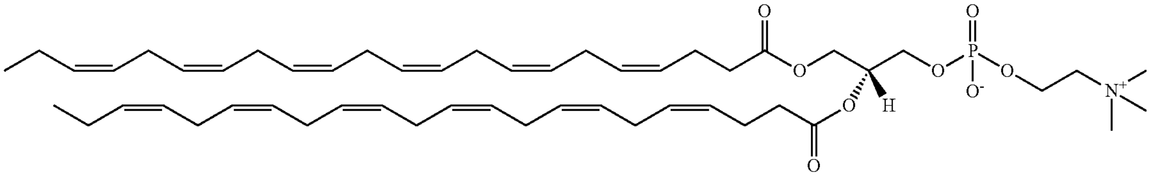
,
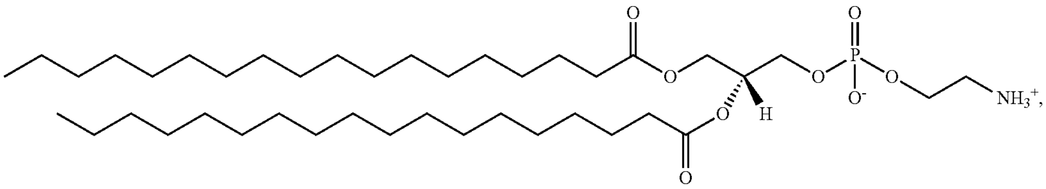
,
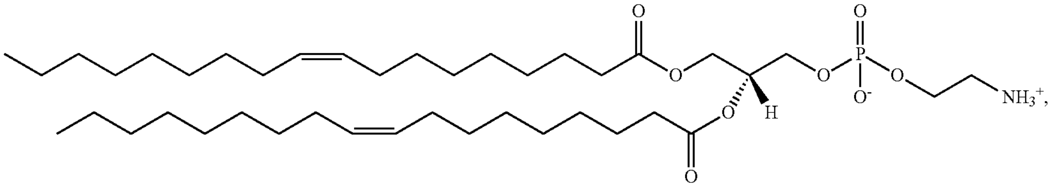
,
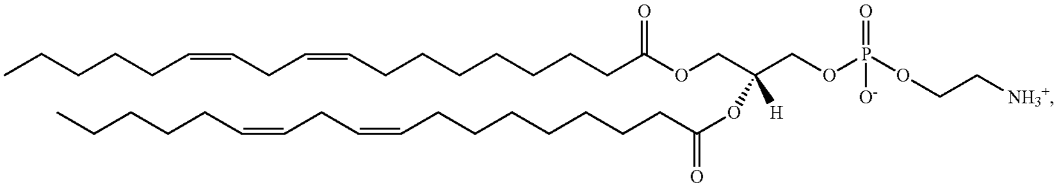
,
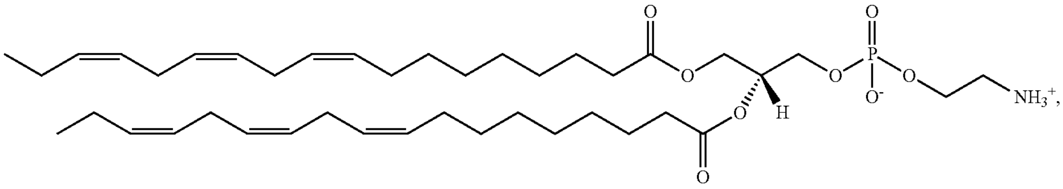
, -continued

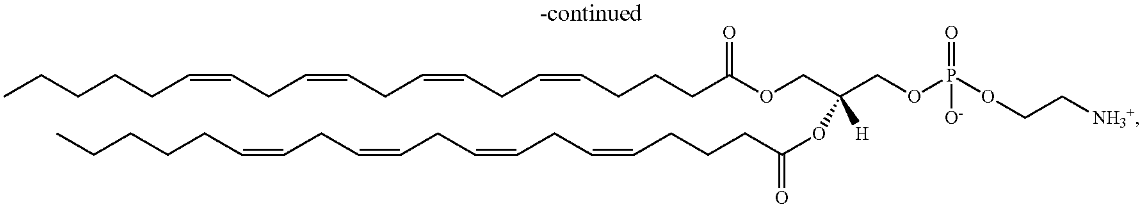

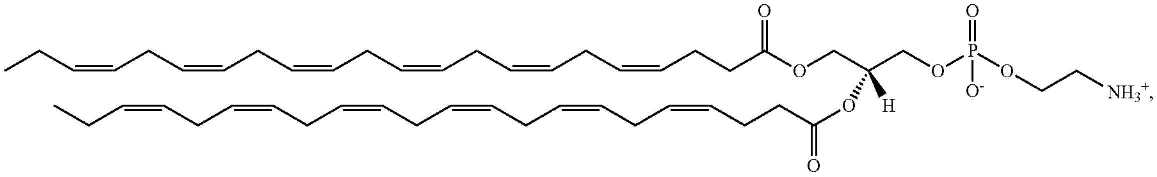

,

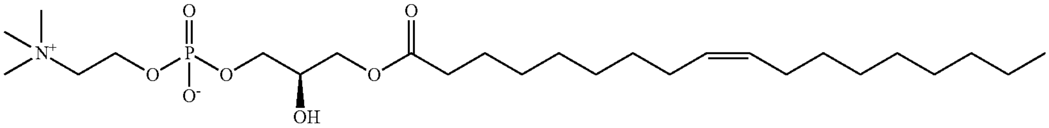

,

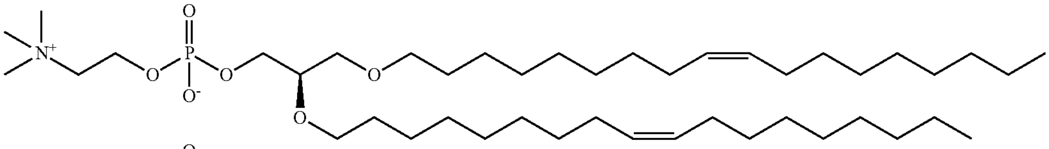

,

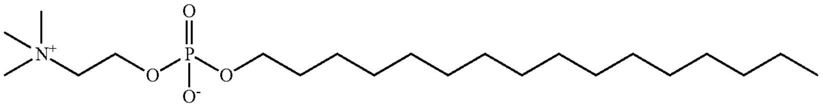

,

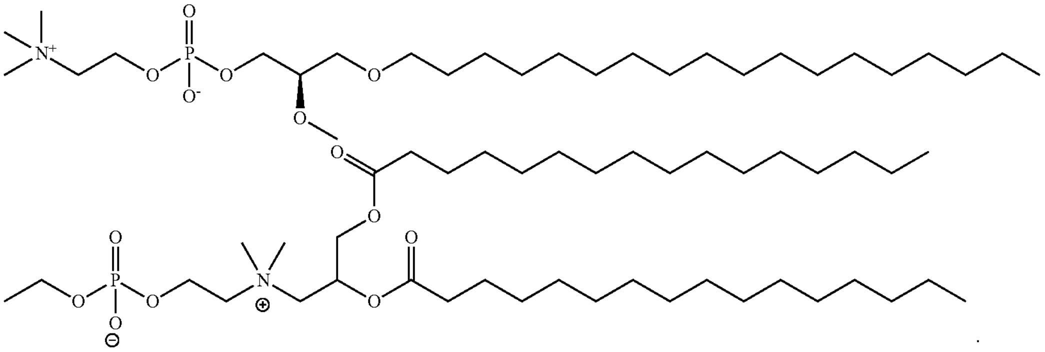

, and

.

In certain embodiments, a phospholipid useful or potentially useful in the present invention is an analog or variant of DSPC (1,2-dioctadecanoyl-sn-glycero-3-phosphocholine). In certain embodiments, a phospholipid useful or potentially useful in the present invention is a compound of Formula (IX):

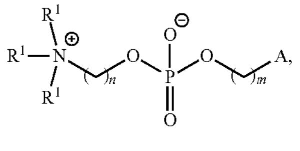

(IX)

(or a salt thereof, wherein:

each $R^1$ is independently optionally substituted alkyl; or optionally two $R^1$ are joined together with the intervening atoms to form optionally substituted monocyclic carbocyclyl or optionally substituted monocyclic heterocyclyl; or optionally three $R^1$ are joined together with the intervening atoms to form optionally substituted bicyclic carbocyclyl or optionally substitute bicyclic heterocyclyl;

n is 1, 2, 3, 4, 5, 6, 7, 8, 9, or 10;

m is 0, 1, 2, 3, 4, 5, 6, 7, 8, 9, or 10;

A is of the formula:

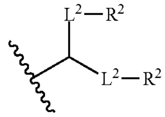

or

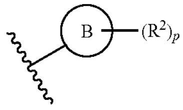

;

each instance of $L^2$ is independently a bond or optionally substituted $C_{1-6}$ alkylene, wherein one methylene unit of the optionally substituted $C_{1-6}$ alkylene is optionally replaced with —O—, —N($R^N$)—, —S—, —C(O)—, —C(O)N($R^N$)—, —$NR^N$C(O)—, —C(O)O—, —OC(O)—, —OC(O)O—, —OC(O)N($R^N$)—, —$NR^N$C(O)O—, or —$NR^N$C(O)N($R^N$)—;

each instance of $R^2$ is independently optionally substituted $C_{1-30}$ alkyl, optionally substituted $C_{1-30}$ alkenyl, or optionally substituted $C_{1-30}$ alkynyl; optionally wherein one or more methylene units of $R^2$ are independently replaced with optionally substituted carbocyclylene, optionally substituted heterocyclylene, optionally substituted arylene, optionally substituted heteroarylene, —N($R^N$)—, —O—, —S—, —C(O)—, —C(O)N($R^N$)—, —$NR^N$C(O)—, —$NR^N$C(O)N($R^N$)—, —C(O)O—, —OC(O)—, —OC(O)O—, —OC(O)N($R^N$)—, —$NR^N$C(O)O—, —C(O)S—, —SC(O)—, —C(=$NR^N$)—, —C(=$NR^N$)N($R^N$)—, —$NR^N$C(=$NR^N$)—, —$NR^N$C(=$NR^N$)N($R^N$)—, —C(S)—, —C(S)N($R^N$)—, —$NR^N$C(S)—, —$NR^N$C(S)N($R^N$)—, —S(O)—, —OS(O)—, —S(O)O—, —OS(O)O—, —OS$(O)_2$—, —$S(O)_2O$—, —$OS(O)_2O$—, —N($R^N$)S(O)—, —S(O)N($R^N$)—, —N($R^N$)S(O)N($R^N$)—, —OS(O)N($R^N$)—, —N($R^N$)S(O)O—, —$S(O)_2$—, —N($R^N$)$S(O)_2$—, —$S(O)_2$N($R^N$)—, —N($R^N$)$S(O)_2$N($R^N$)—, —$OS(O)_2$N($R^N$)—, or —N($R^N$)$S(O)_2O$—;

each instance of $R^N$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2;

provided that the compound is not of the formula:

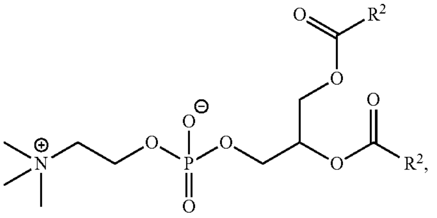

wherein each instance of $R^2$ is independently unsubstituted alkyl, unsubstituted alkenyl, or unsubstituted alkynyl.

i) Phospholipid Head Modifications

In certain embodiments, a phospholipid useful or potentially useful in the present invention comprises a modified phospholipid head (e.g., a modified choline group). In certain embodiments, a phospholipid with a modified head is DSPC, or analog thereof, with a modified quaternary amine.

For example, in embodiments of Formula (IX), at least one of $R^1$ is not methyl. In certain embodiments, at least one of $R^1$ is not hydrogen or methyl. In certain embodiments, the compound of Formula (IX) is of one of the following formulae:

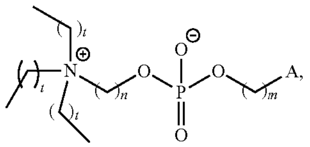

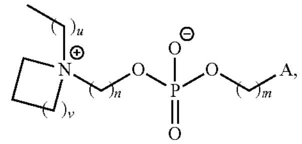

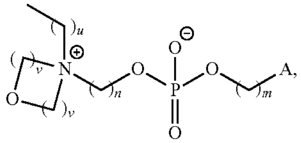

-continued

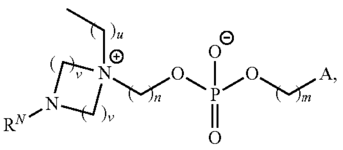

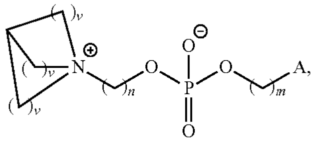

or a salt thereof, wherein:

each t is independently 1, 2, 3, 4, 5, 6, 7, 8, 9, or 10;

each u is independently 0, 1, 2, 3, 4, 5, 6, 7, 8, 9, or 10; and each v is independently 1, 2, or 3.

In certain embodiments, the compound of Formula (IX) is of one of the following formulae:

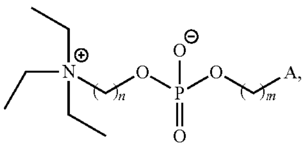

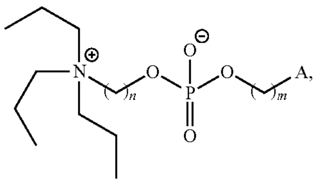

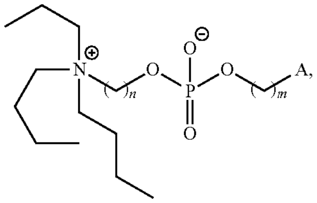

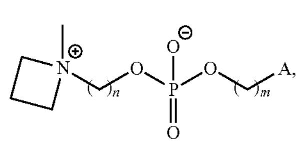

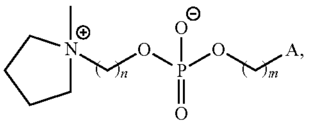

-continued
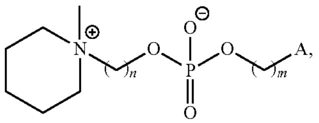
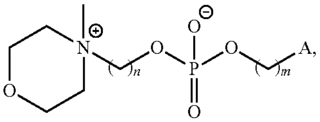
-continued
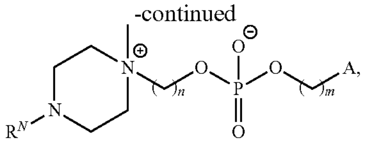
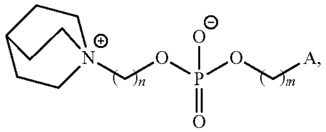
or a salt thereof.
In certain embodiments, a compound of Formula (IX) is one of the following:
(Compound 400)
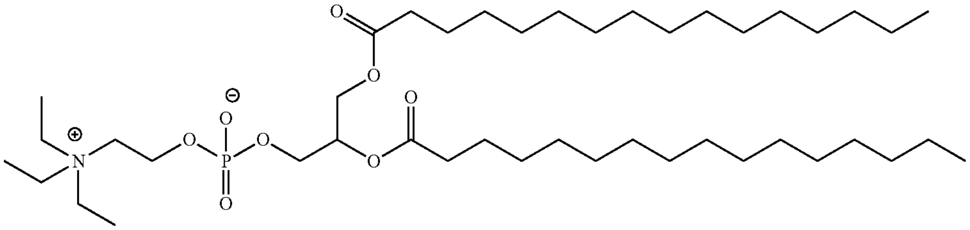
(Compound 401)
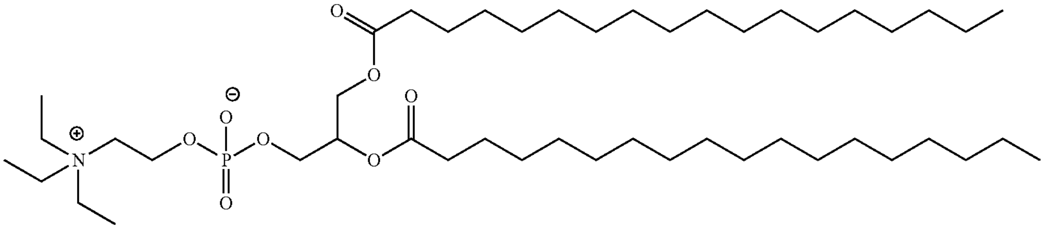
(Compound 402)
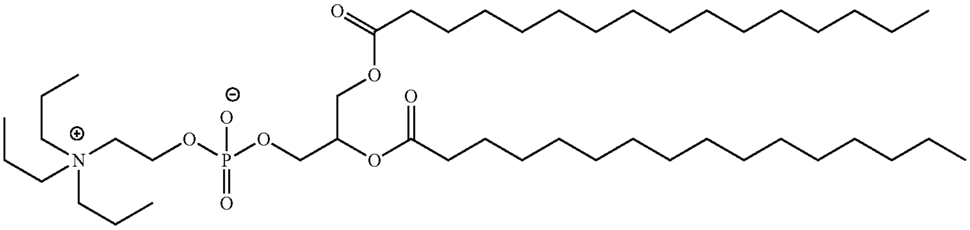
(Compound 403)
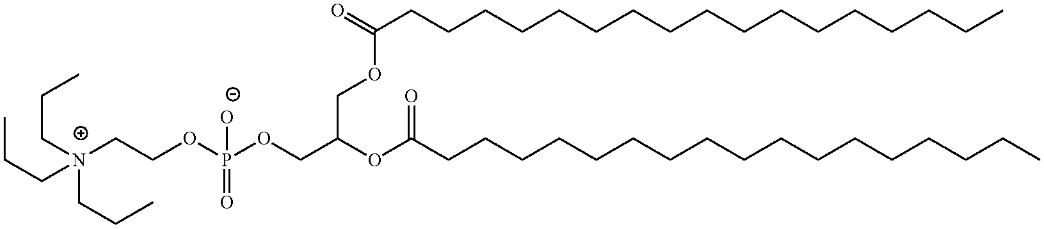
(Compound 404)
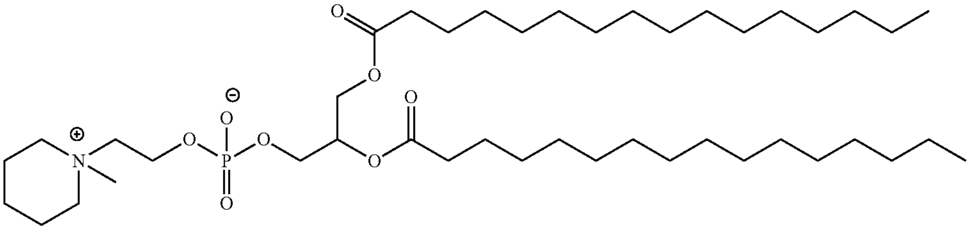

-continued (Compound 405)

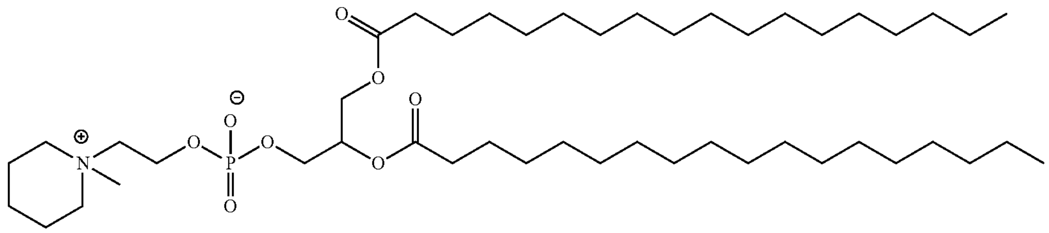

(Compound 406)

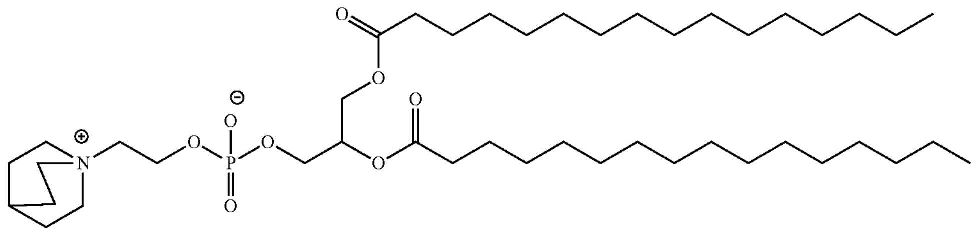

(Compound 407)

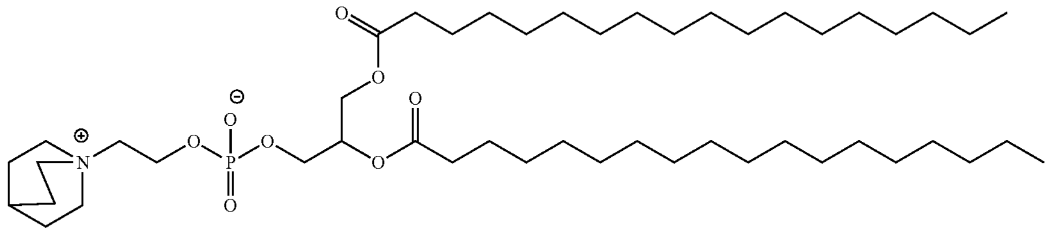

(Compound 408)

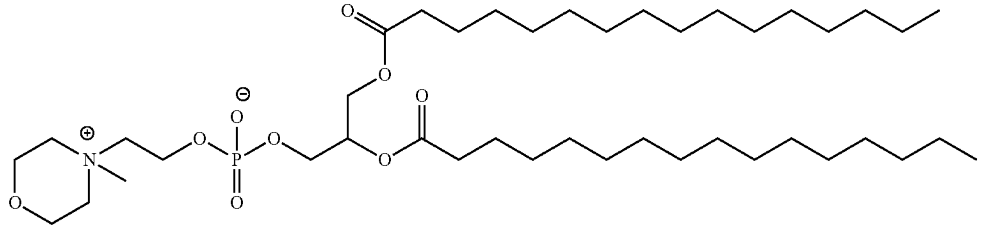

(Compound 409)

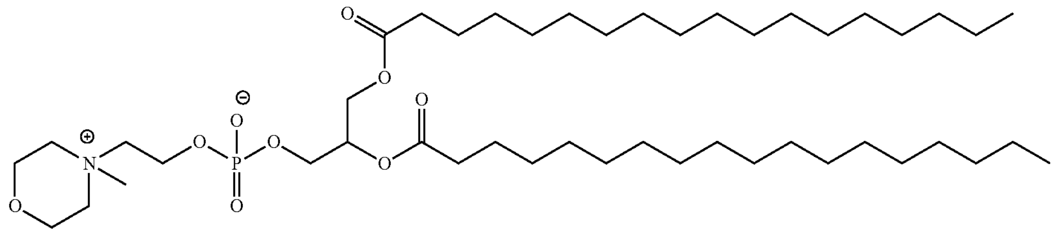

, or a salt thereof.

In certain embodiments, a compound of Formula (IX) is of Formula (IX-a):

(IX-a)

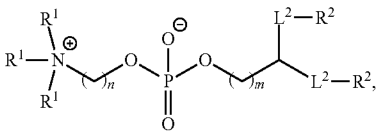

or a salt thereof.

In certain embodiments, phospholipids useful or potentially useful in the present invention comprise a modified core. In certain embodiments, a phospholipid with a modified core described herein is DSPC, or analog thereof, with a modified core structure. For example, in certain embodiments of Formula (IX-a), group A is not of the following formula:

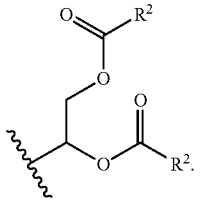

In certain embodiments, the compound of Formula (IX-a) is of one of the following formulae:

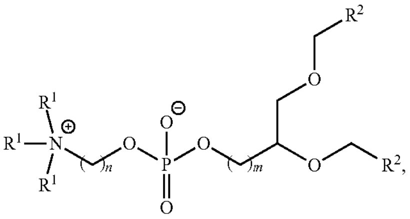
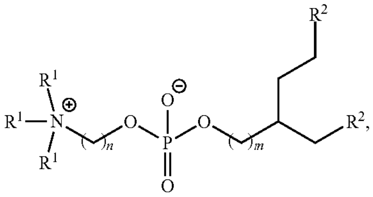
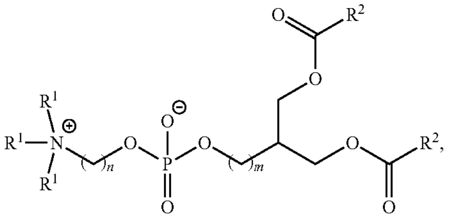
-continued
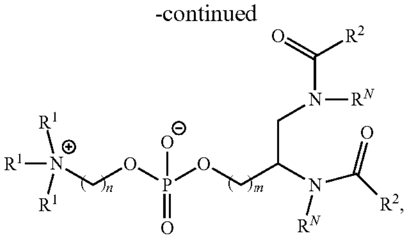
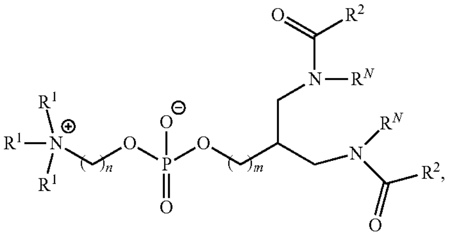
or a salt thereof.
In certain embodiments, a compound of Formula (IX) is one of the following:
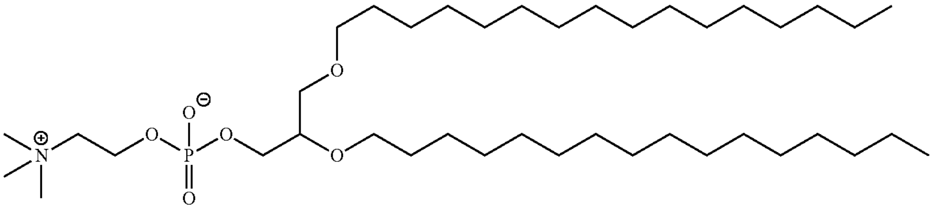
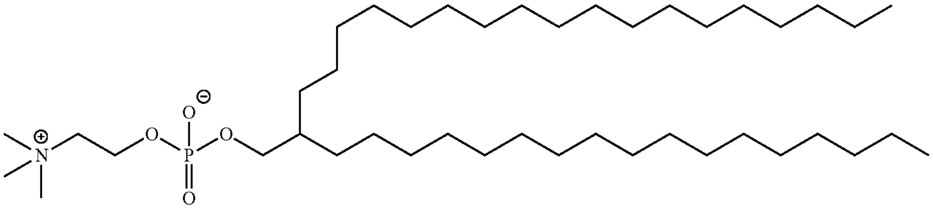
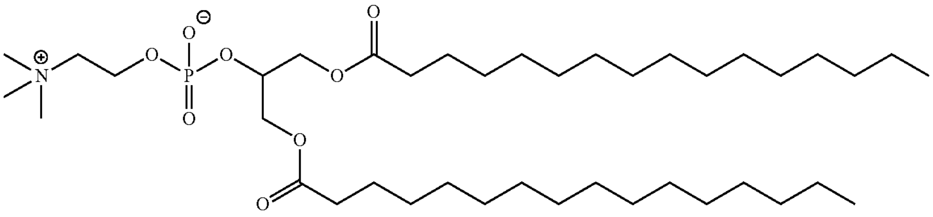
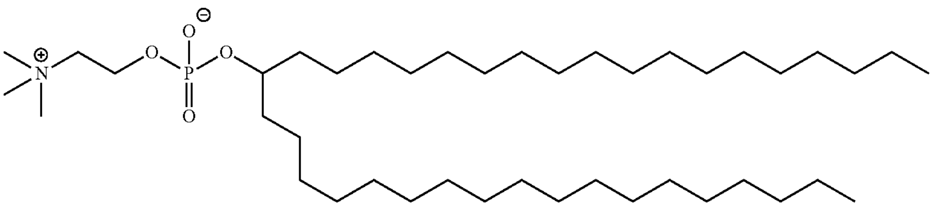

-continued

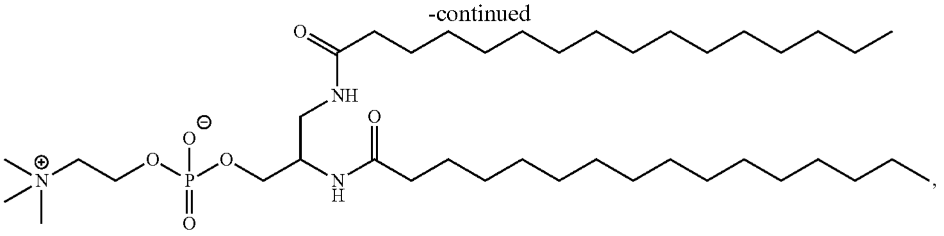

or salts thereof.

In certain embodiments, a phospholipid useful or potentially useful in the present invention comprises a cyclic moiety in place of the glyceride moiety. In certain embodiments, a phospholipid useful in the present invention is DSPC (1,2-dioctadecanoyl-sn-glycero-3-phosphocholine), or analog thereof, with a cyclic moiety in place of the glyceride moiety. In certain embodiments, the compound of Formula (IX) is of Formula (IX-b):

(IX-b)

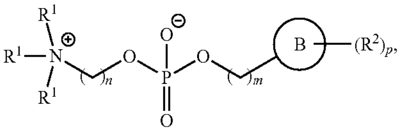

or a salt thereof.

In certain embodiments, the compound of Formula (IX-b) is of Formula (IX-b-1):

(IX-b-1)

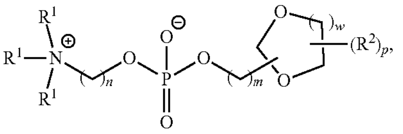

or a salt thereof, wherein:

w is 0, 1, 2, or 3.

In certain embodiments, the compound of Formula (IX-b) is of Formula (IX-b-2):

(IX-b-2)

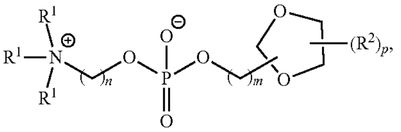

or a salt thereof.

In certain embodiments, the compound of Formula (IX-b) is of Formula (IX-b-3):

(IX-b-3)

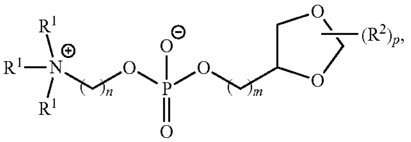

or a salt thereof.

In certain embodiments, the compound of Formula (IX-b) is of Formula (IX-b-4):

(IX-b-4)

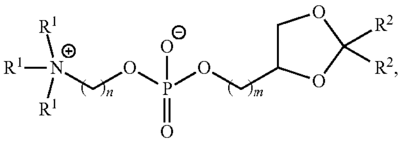

or a salt thereof.

In certain embodiments, the compound of Formula (IX-b) is one of the following:

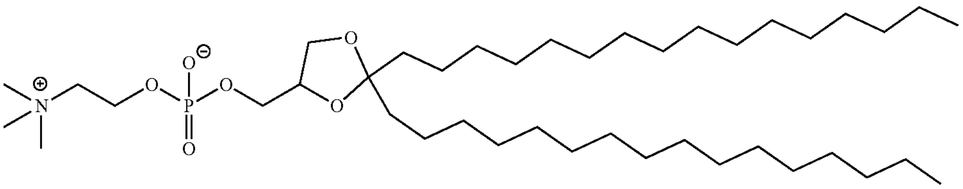

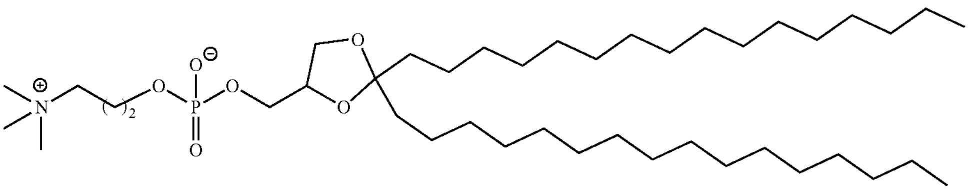

-continued

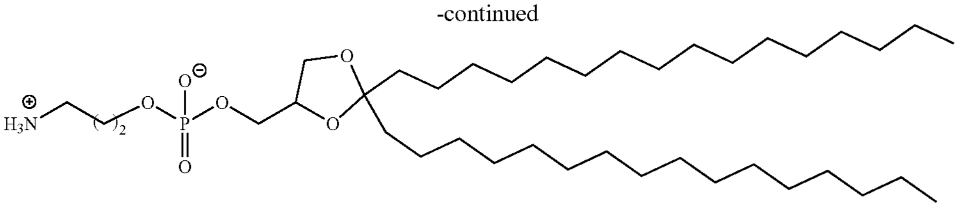

, or salts thereof.

(ii) Phospholipid Tail Modifications

In certain embodiments, a phospholipid useful or potentially useful in the present invention comprises a modified tail. In certain embodiments, a phospholipid useful or potentially useful in the present invention is DSPC (1,2-dioctadecanoyl-sn-glycero-3-phosphocholine), or analog thereof, with a modified tail. As described herein, a "modified tail" may be a tail with shorter or longer aliphatic chains, aliphatic chains with branching introduced, aliphatic chains with substituents introduced, aliphatic chains wherein one or more methylenes are replaced by cyclic or heteroatom groups, or any combination thereof. For example, in certain embodiments, the compound of (IX) is of Formula (IX-a), or a salt thereof, wherein at least one instance of $R^2$ is each instance of $R^2$ is optionally substituted $C_{1-30}$ alkyl, wherein one or more methylene units of $R^2$ are independently replaced with optionally substituted carbocyclylene, optionally substituted heterocyclylene, optionally substituted arylene, optionally substituted heteroarylene, —N($R^N$)—, —O—, —S—, —C(O)—, —C(O)N($R^N$)—, —NR$^N$C(O)—, —NR$^N$C(O)N($R^N$)—, —C(O)O—, —OC(O)—, —OC(O)O—, —OC(O)N($R^N$)—, —NR$^N$C(O)O—, —C(O)S—, —SC(O)—, —C(=NR$^N$)—, —C(=NR$^N$)N($R^N$)—, NR$^N$C(=NR$^N$)—, NR$^N$C(—NR$_N$)N($R^N$)—, —C(S)—, —C(S)N($R^N$)—, —NR$^N$C(S)—, —NR$^N$C(S)N($R^N$)—, —S(O)—, —OS(O)—, —S(O)O—, —OS(O)O—, —OS(O)$_2$—, —S(O)$_2$O—, —OS(O)$_2$O—, —N($R^N$)S(O)—, —S(O)N($R^N$)—, —N($R^N$)S(O)N($R^N$)—, —OS(O)N($R^N$)—, —N($R^N$)S(O)O—, —S(O)$_2$—, —N($R^N$)S(O)$_2$—, —S(O)$_2$N($R^N$)—, —N($R^N$)S(O)$_2$N($R^N$)—, —OS(O)$_2$N($R^N$)—, or —N($R^N$)S(O)$_2$O—.

In certain embodiments, the compound of Formula (IX) is of Formula (IX-c):

(IX-c)

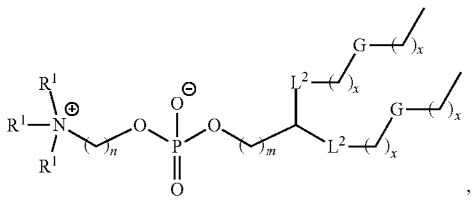

, or a salt thereof, wherein:

each x is independently an integer between 0-30, inclusive; and each instance is G is independently selected from the group consisting of optionally substituted carbocyclylene, optionally substituted heterocyclylene, optionally substituted arylene, optionally substituted heteroarylene, —N($R^N$)—, —O—, —S—, —C(O)—, —C(O)N($R^N$)—, —NR$^N$C(O)—, —SR$^N$C(O)N($R^N$)—, —C(O)O—, —OC(O)—, —OC(O)O—, —OC(O)N($R^N$)—, —NR$^N$C(O)O—, —C(O)S—, —SC(O)—, —C(=NR$^N$)—, —C(=NR$^N$)N($R^N$)—, —NR$^N$C(=NR$^N$)—, —NR$^N$C(=NR$^N$)N($R^N$)—, —C(S)—, —C(S)N($R^N$)—, —NR$^N$C(S)—, —NR$^N$C(S)N($R^N$)—, —S(O)—, —OS(O)—, —S(O)O—, —OS(O)O—, —OS(O)$_2$—, —S(O)$_2$O—, —OS(O)$_2$O—, —N($R^N$)S(O)—, —S(O)N($R^N$)—, —N($R^N$)S(O)N($R^N$)—, —OS(O)N($R^N$)—, —N($R^N$)S(O)O—, —S(O)$_2$—, —N($R^N$)S(O)$_2$—, —S(O)$_2$N($R^N$)—, —N($R^N$)S(O)$_2$N($R^N$)—, —OS(O)$_2$N($R^N$)—, or —N($R^N$)S(O)$_2$O—. Each possibility represents a separate embodiment of the present invention.

In certain embodiments, the compound of Formula (IX-c) is of Formula (IX-c-1):

(IX-c-1)

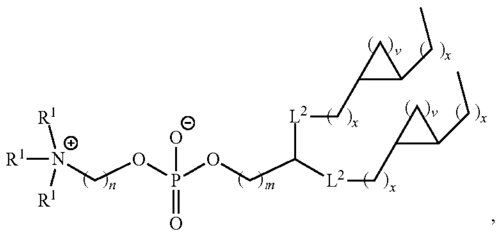

, or salt thereof, wherein:

each instance of v is independently 1, 2, or 3.

In certain embodiments, the compound of Formula (IX-c) is of Formula (IX-c-2):

(IX-c-2)

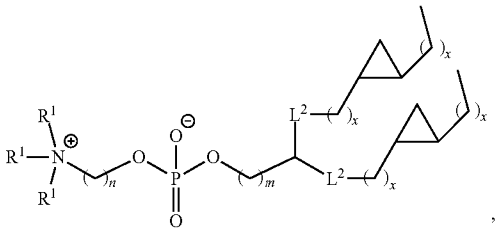

, or a salt thereof.

In certain embodiments, the compound of Formula (IX-c) is of the following formula:

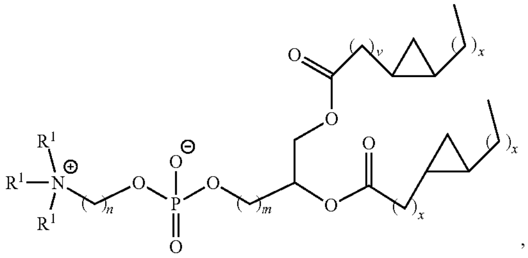

, or a salt thereof.

In certain embodiments, the compound of Formula (IX-c) is the following:

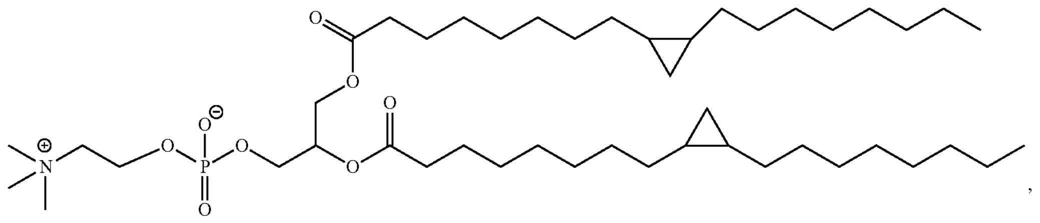 [SMILES: CCCCCCCCC1CC1CCCCCCCC(=O)OCC(COP(=O)([O-])OCC[N+](C)(C)C)OC(=O)CCCCCCCC1CC1CCCCCCCC]

or a salt thereof.

In certain embodiments, the compound of Formula (IX-c) is of Formula (IX-c-3):

(IX-c-3)

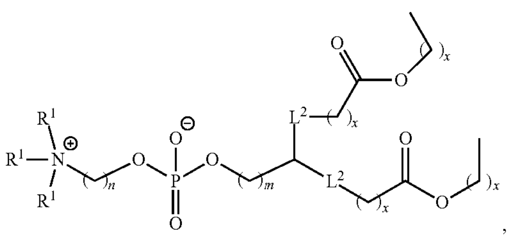

or a salt thereof.

In certain embodiments, the compound of Formula (IX-c) is of the following formulae:

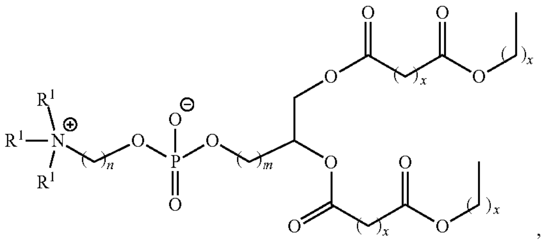

or a salt thereof.

In certain embodiments, the compound of Formula (IX-c) is the following:

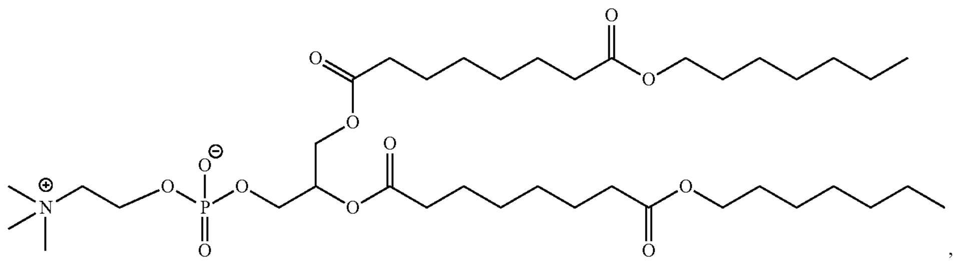 [SMILES: CCCCCCCOC(=O)CCCCCCC(=O)OCC(COP(=O)([O-])OCC[N+](C)(C)C)OC(=O)CCCCCCC(=O)OCCCCCCC]

or a salt thereof.

In certain embodiments, a phospholipid useful or potentially useful in the present invention comprises a modified phosphocholine moiety, wherein the alkyl chain linking the quaternary amine to the phosphoryl group is not ethylene (e.g., n is not 2). Therefore, in certain embodiments, a phospholipid useful or potentially useful in the present invention is a compound of Formula (IX), wherein n is 1, 3, 4, 5, 6, 7, 8, 9, or 10. For example, in certain embodiments, a compound of Formula (IX) is of one of the following formulae:

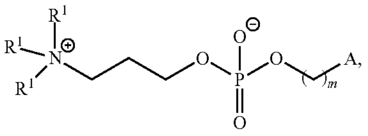

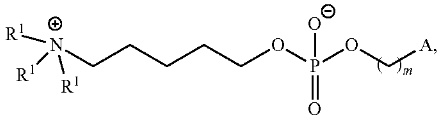

or a salt thereof.

In certain embodiments, a compound of Formula (IX) is one of the following:
(Compound 411)
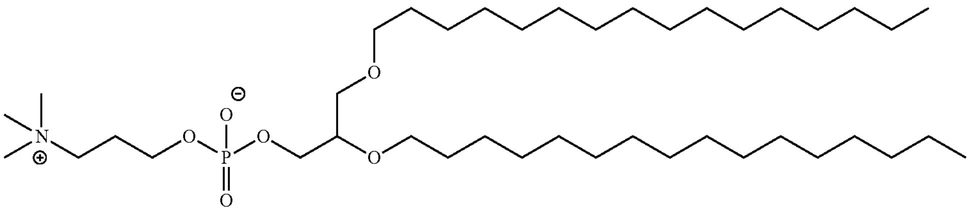
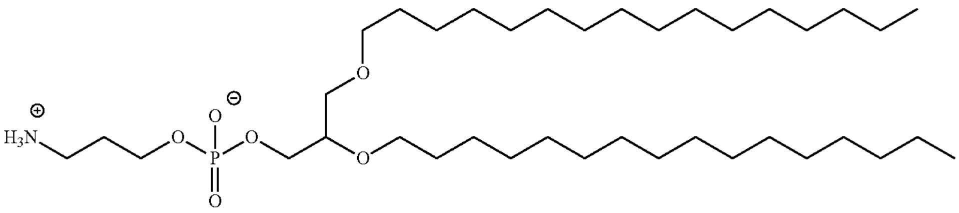
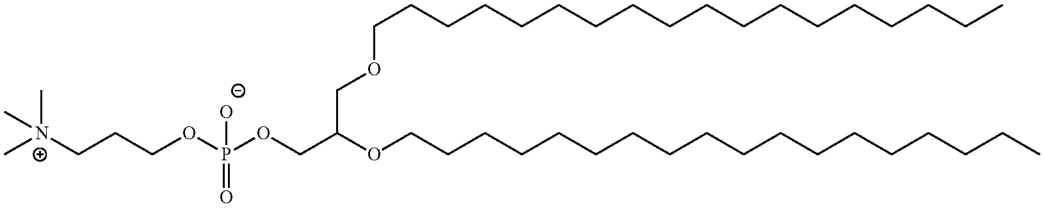
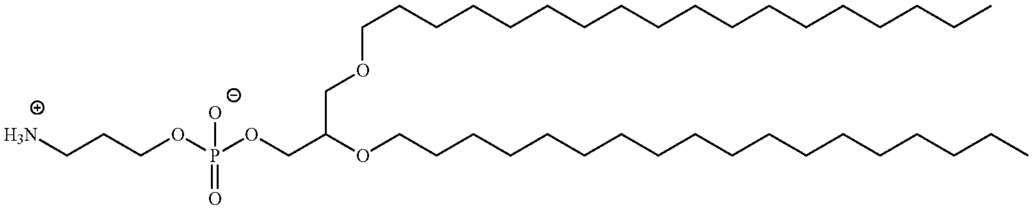
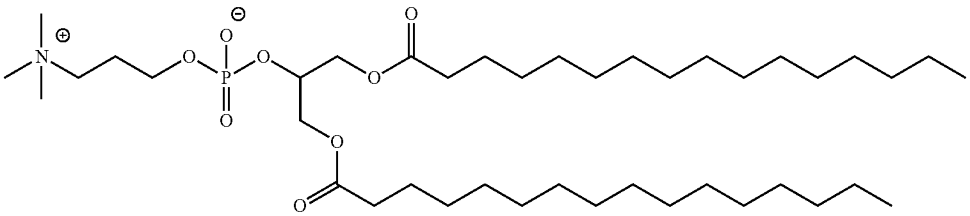
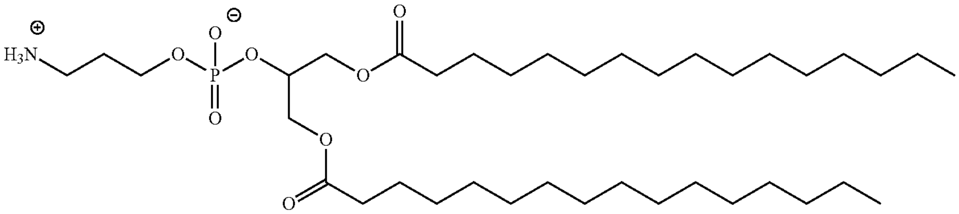
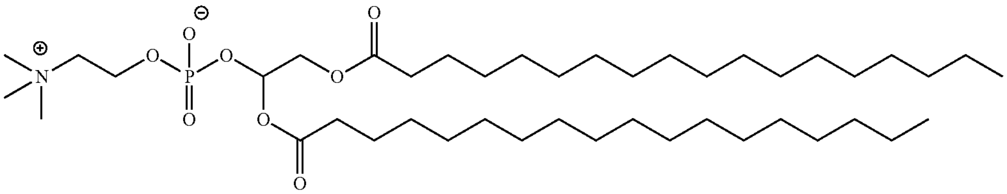

-continued
(Compound 412)
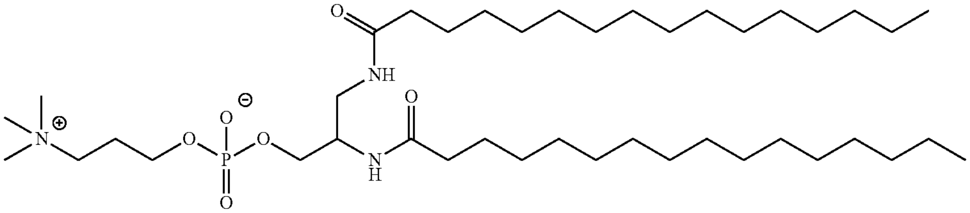
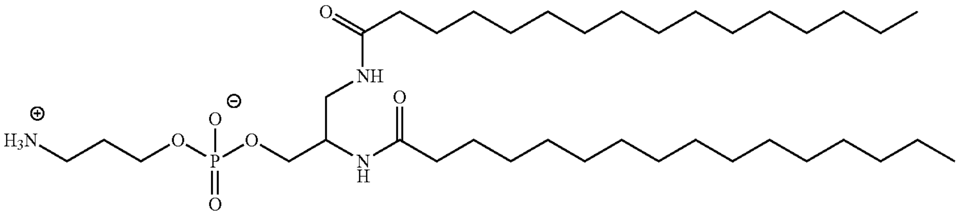
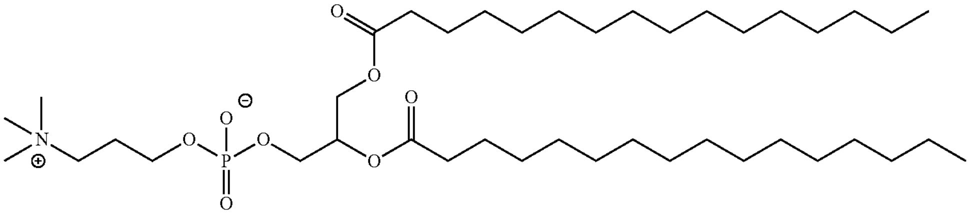
(Compound 413)
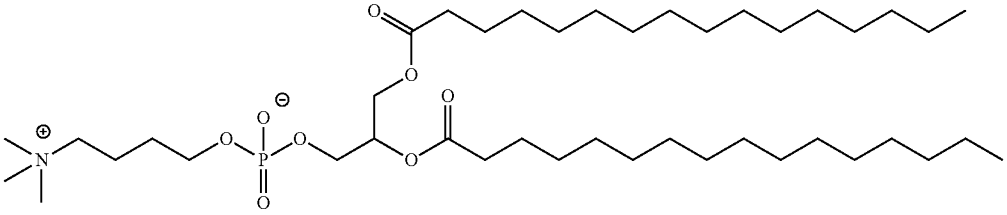
(Compound 414)
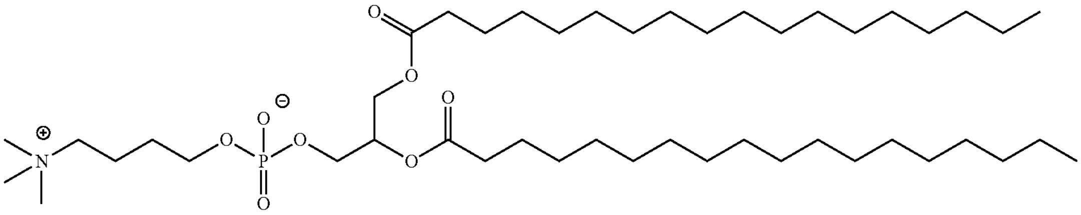
,
or salts thereof.
c. Alternative Lipids
In certain embodiments, an alternative lipid is used in place of a phospholipid of the invention. Non-limiting examples of such alternative lipids include the following:
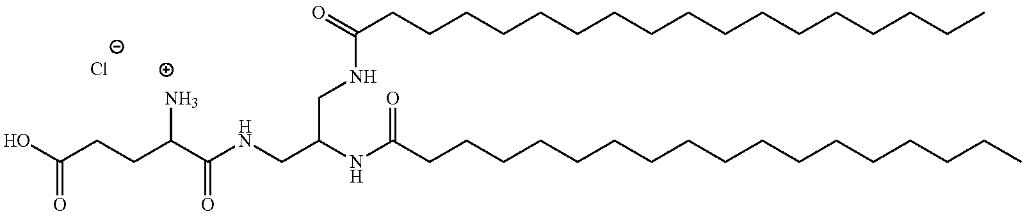
, -continued

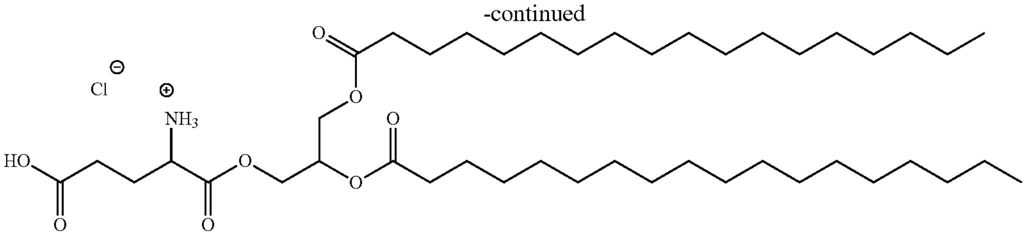

,

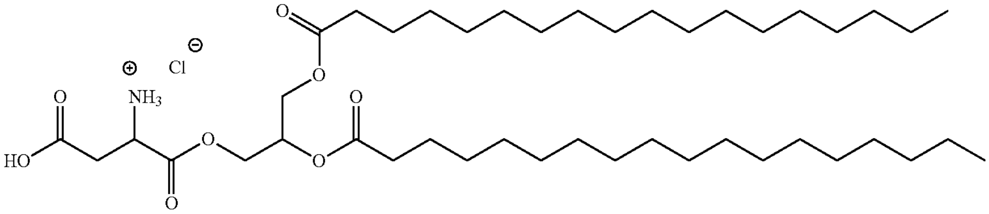

,

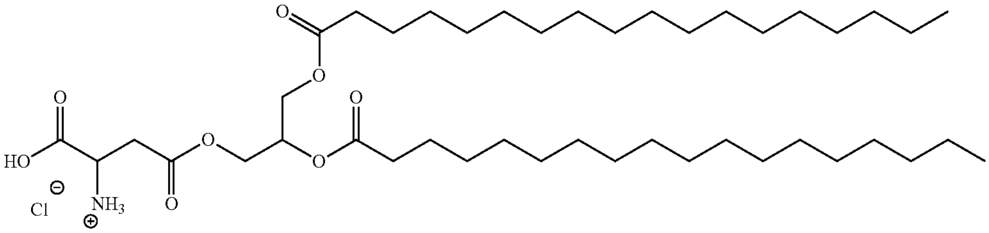

,

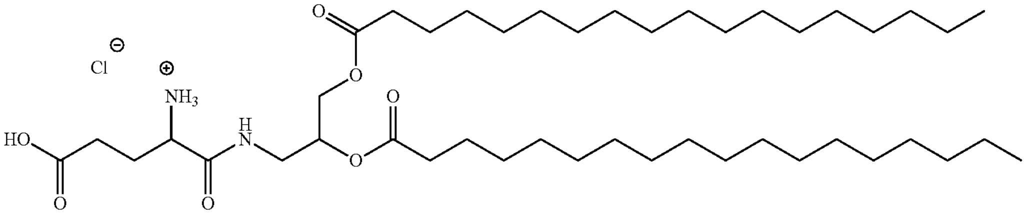

,

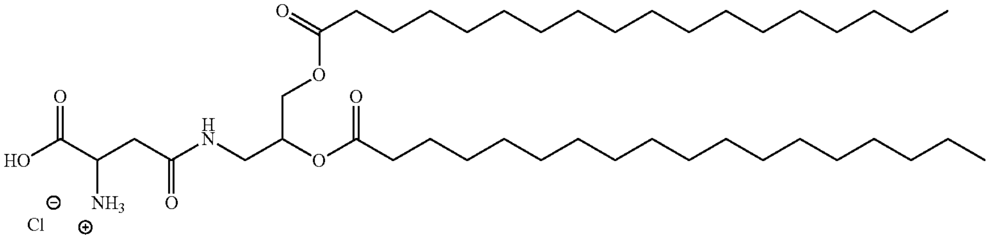

, and

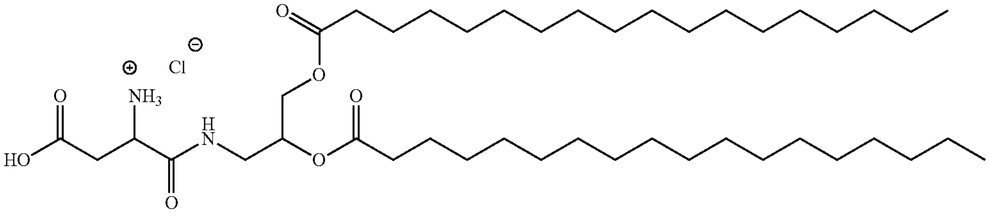

.

d. Structural Lipids

The lipid composition of a pharmaceutical composition disclosed herein can comprise one or more structural lipids. As used herein, the term "structural lipid" refers to sterols and also to lipids containing sterol moieties.

Incorporation of structural lipids in the lipid nanoparticle may help mitigate aggregation of other lipids in the particle. Structural lipids can be selected from the group including but not limited to, cholesterol, fecosterol, sitosterol, ergosterol, campesterol, stigmasterol, bras sicasterol, tomatidine, tomatine, ursolic acid, alpha-tocopherol, hopanoids, phytosterols, steroids, and mixtures thereof. In some embodiments, the structural lipid is a sterol. As defined herein, "sterols" are a subgroup of steroids consisting of steroid alcohols. In certain embodiments, the structural lipid is a steroid. In certain embodiments, the structural lipid is cholesterol. In certain embodiments, the structural lipid is an analog of cholesterol. In certain embodiments, the structural lipid is alpha-tocopherol. Examples of structural lipids include, but are not limited to, the following:

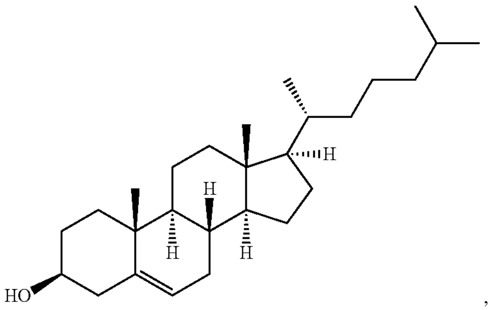

,

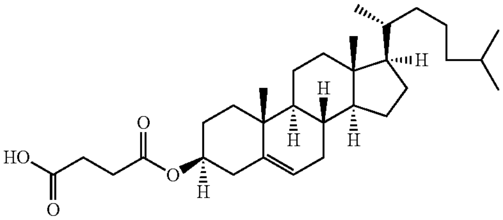

, and

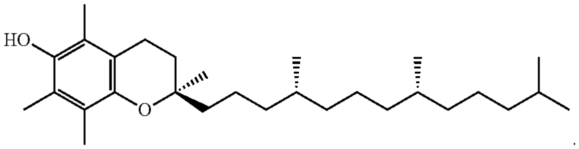

.

In one embodiment, the amount of the structural lipid (e.g., an sterol such as cholesterol) in the lipid composition of a pharmaceutical composition disclosed herein ranges from about 20 mol % to about 60 mol %, from about 25 mol % to about 55 mol %, from about 30 mol % to about 50 mol %, or from about 35 mol % to about 45 mol %.

In one embodiment, the amount of the structural lipid (e.g., an sterol such as cholesterol) in the lipid composition disclosed herein ranges from about 25 mol % to about 30 mol %, from about 30 mol % to about 35 mol %, or from about 35 mol % to about 40 mol %.

In one embodiment, the amount of the structural lipid (e.g., a sterol such as cholesterol) in the lipid composition disclosed herein is about 24 mol %, about 29 mol %, about 34 mol %, or about 39 mol %.

In some embodiments, the amount of the structural lipid (e.g., an sterol such as cholesterol) in the lipid composition disclosed herein is at least about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 mol %.

e. Polyethylene Glycol (PEG)-Lipids

The lipid composition of a pharmaceutical composition disclosed herein can comprise one or more a polyethylene glycol (PEG) lipid.

As used herein, the term "PEG-lipid" refers to polyethylene glycol (PEG)-modified lipids. Non-limiting examples of PEG-lipids include PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Such lipids are also referred to as PEGylated lipids. For example, a PEG lipid can be PEG-c-DOMG, PEG-DMG, PEG-DLPE, PEG-DMPE, PEG-DPPC, or a PEG-DSPE lipid.

In some embodiments, the PEG-lipid includes, but not limited to 1,2-dimyristoyl-sn-glycerol methoxypolyethylene glycol (PEG-DMG), 1,2-distearoyl-sn-glycero-3-phosphoethanolamine-N-[amino(polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA).

In one embodiment, the PEG-lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof.

In some embodiments, the lipid moiety of the PEG-lipids includes those having lengths of from about $C_{14}$ to about $C_{22}$, preferably from about $C_{14}$ to about $C_{16}$. In some embodiments, a PEG moiety, for example an mPEG-$NH_2$, has a size of about 1000, 2000, 5000, 10,000, 15,000 or 20,000 daltons. In one embodiment, the PEG-lipid is PEG2k-DMG.

In one embodiment, the lipid nanoparticles described herein can comprise a PEG lipid which is a non-diffusible PEG. Non-limiting examples of non-diffusible PEGs include PEG-DSG and PEG-DSPE.

PEG-lipids are known in the art, such as those described in U.S. Pat. No. 8,158,601 and International Publ. No. WO 2015/130584 A2, which are incorporated herein by reference in their entirety.

In general, some of the other lipid components (e.g., PEG lipids) of various formulae, described herein may be synthesized as described International Patent Application No. PCT/US2016/000129, filed Dec. 10, 2016, entitled "Compositions and Methods for Delivery of Therapeutic Agents," which is incorporated herein by reference in its entirety.

The lipid component of a lipid nanoparticle composition may include one or more molecules comprising polyethylene glycol, such as PEG or PEG-modified lipids. Such species may be alternately referred to as PEGylated lipids. A PEG lipid is a lipid modified with polyethylene glycol. A PEG lipid may be selected from the non-limiting group including PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. For example, a PEG lipid may be PEG-c-DOMG, PEG-DMG, PEG-DLPE, PEG-DMPE, PEG-DPPC, or a PEG-DSPE lipid.

In some embodiments the PEG-modified lipids are a modified form of PEG DMG. PEG-DMG has the following structure:

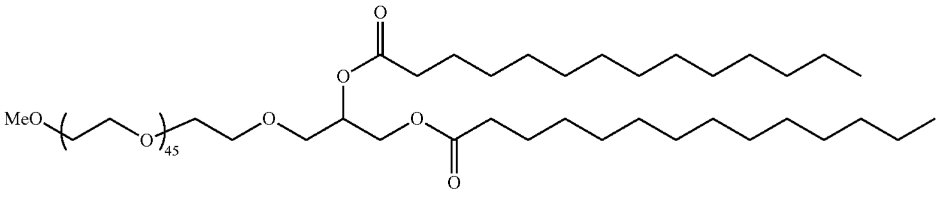

In one embodiment, PEG lipids useful in the present invention can be PEGylated lipids described in International Publication No. WO2012099755, the contents of which is incorporated herein by reference in its entirety. Any of these exemplary PEG lipids described herein may be modified to comprise a hydroxyl group on the PEG chain. In certain embodiments, the PEG lipid is a PEG-OH lipid. As generally defined herein, a "PEG-OH lipid" (also referred to herein as "hydroxy-PEGylated lipid") is a PEGylated lipid having one or more hydroxyl (—OH) groups on the lipid. In certain embodiments, the PEG-OH lipid includes one or more hydroxyl groups on the PEG chain. In certain embodiments, a PEG-OH or hydroxy-PEGylated lipid comprises an —OH group at the terminus of the PEG chain. Each possibility represents a separate embodiment of the present invention.

In certain embodiments, a PEG lipid useful in the present invention is a compound of Formula (VII). Provided herein are compounds of Formula (VII):

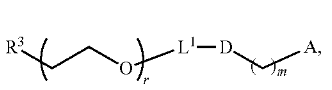

(VII)

or salts thereof, wherein:

$R^3$ is —$OR^O$;

$R^O$ is hydrogen, optionally substituted alkyl, or an oxygen protecting group;

r is an integer between 1 and 100, inclusive;

$L^1$ is optionally substituted $C_{1-10}$ alkylene, wherein at least one methylene of the optionally substituted $C_{1-10}$alkylene is independently replaced with optionally substituted carbocyclylene, optionally substituted heterocyclylene, optionally substituted arylene, optionally substituted heteroarylene, 0, $N(R^N)$, S, C(O), $C(O)N(R^N)$, $NR^NC(O)$, C(O)O, —OC(O), OC(O)O, $OC(O)N(R^N)$, $NR^NC(O)O$, or $NR^NC(O)N(R^N)$;

D is a moiety obtained by click chemistry or a moiety cleavable under physiological conditions;

m is 0, 1, 2, 3, 4, 5, 6, 7, 8, 9, or 10;

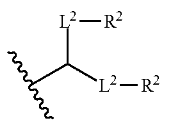

or

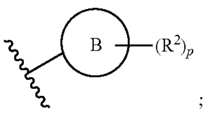

;

A is of the formula:

each instance of $L^2$ is independently a bond or optionally substituted $C_{1-6}$ alkylene, wherein one methylene unit of the optionally substituted $C_{1-6}$ alkylene is optionally replaced with O, $N(R^N)$, S, C(O), $C(O)N(R^N)$, $NR^NC(O)$, C(O)O, OC(O), OC(O)O, $OC(O)N(R^N)$, —$NR^NC(O)O$, or $NR^NC(O)N(R^N)$;

each instance of $R^2$ is independently optionally substituted $C_{1-30}$ alkyl, optionally substituted $C_{1-30}$ alkenyl, or optionally substituted $C_{1-30}$ alkynyl; optionally wherein one or more methylene units of $R^2$ are independently replaced with optionally substituted carbocyclylene, optionally substituted heterocyclylene, optionally substituted arylene, optionally substituted heteroarylene, $N(R^N)$, O, S, C(O), $C(O)N(R^N)$, $NR^NC(O)$, —$NR^NC(O)N(R^N)$, C(O)O, OC(O), OC(O)O, $OC(O)N(R^N)$, $NR^NC(O)O$, C(O)S, SC(O), —$C(=NR^N)$, $C(=NR^N)N(R^N)$, $NR^NC(=NR^N)$, $NR^NC(=NR^N)N(R^N)$, C(S), $C(S)N(R^N)$, $NR^NC(S)$, $NR^NC(S)N(R^N)$, S(O), OS(O), S(O)O, OS(O)O, $OS(O)_2$, $S(O)_{20}$, $OS(O)_{20}$, $N(R^N)S(O)$, —$S(O)N(R^N)$, $N(R^N)S(O)N(R^N)$, $OS(O)N(R^N)$, $N(R^N)S(O)O$, $S(O)_2$, $N(R^N)S(O)_2$, $S(O)_2N(R^N)$, $N(R^N)S(O)_2N(R^N)$, $OS(O)_2N(R^N)$, or $N(R^N)S(O)_{20}$;

each instance of $R^N$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2.

In certain embodiments, the compound of Fomula (VII) is a PEG-OH lipid (i.e., $R^3$ is —$OR^O$, and $R^O$ is hydrogen). In certain embodiments, the compound of Formula (VII) is of Formula (VII-OH):

(VII-OH)

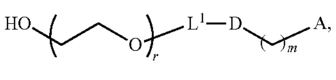

or a salt thereof.

In certain embodiments, D is a moiety obtained by click chemistry (e.g., triazole). In certain embodiments, the compound of Formila (VII) is of Formula (VII-a-1) or (VII-a-2):

(VII-a-1)

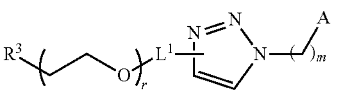

or (VII-a-2)

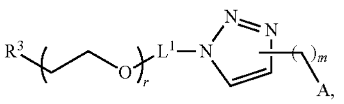

or a salt thereof.

In certain embodiments, the compound of Formula (VII) is of one of the following formulae:

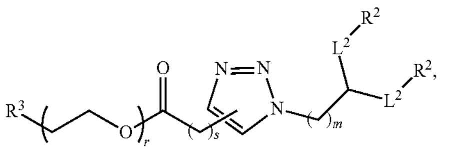

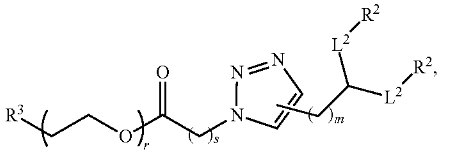

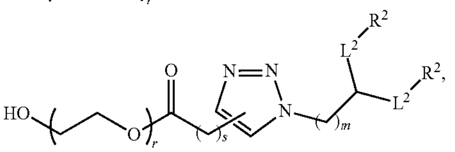

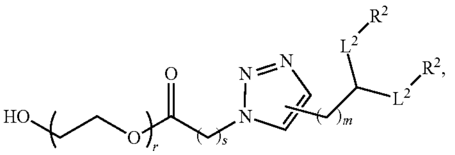

or a salt thereof, wherein s is 0, 1, 2, 3, 4, 5, 6, 7, 8, 9, or 10.

In certain embodiments, the compound of Formula (VII) is of one of the following formulae:
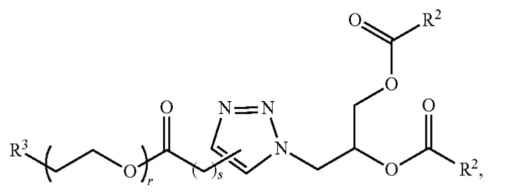
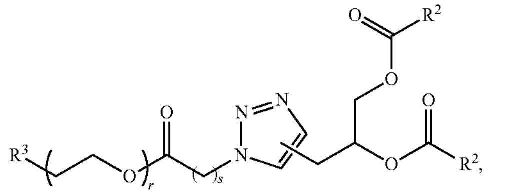
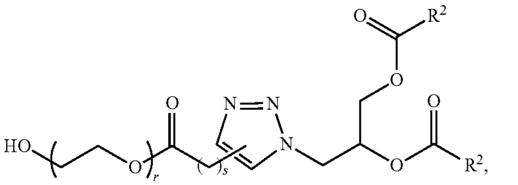
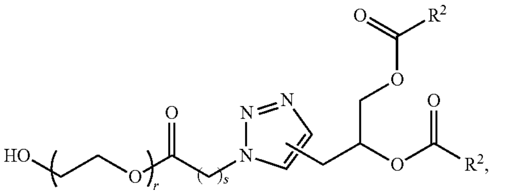
or a salt thereof.
In certain embodiments, a compound of Formula (VII) is of one of the following formulae:
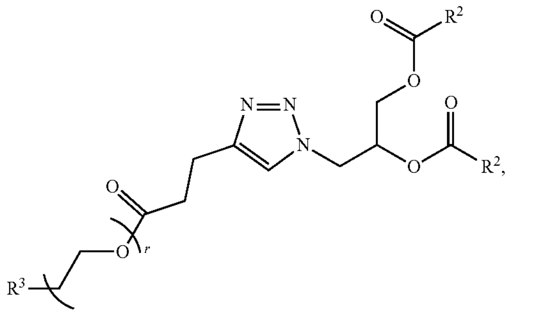
-continued
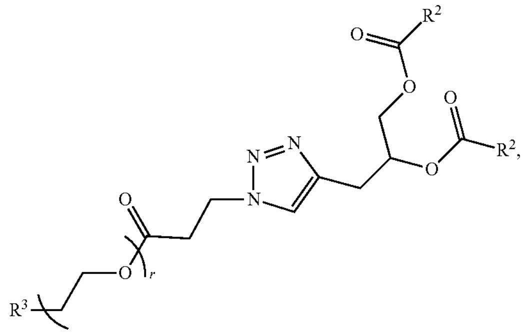
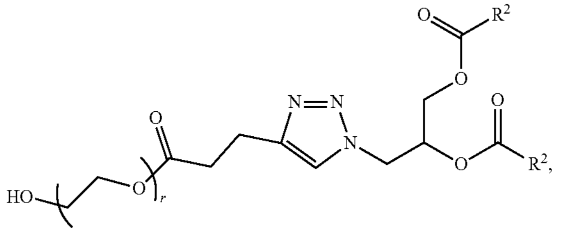
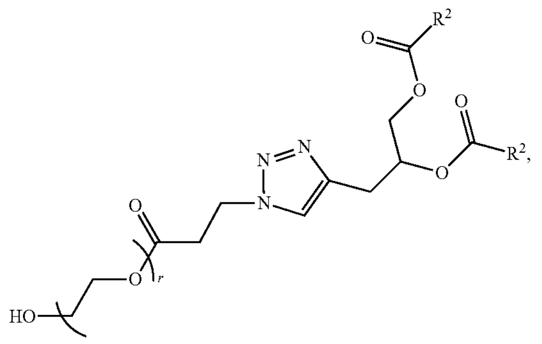
or a salt thereof.
In certain embodiments, a compound of Formula (VII) is of one of the following formulae:
(Compound 415)
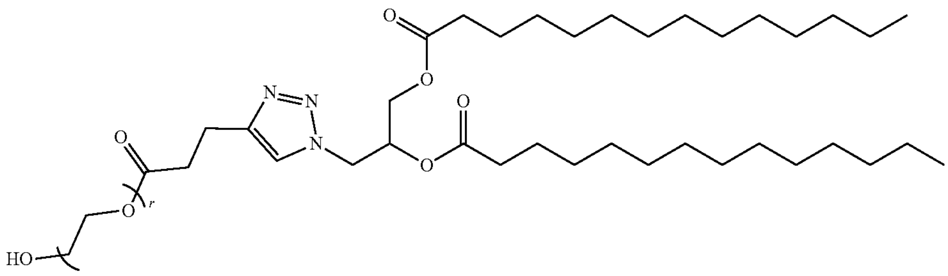
, -continued (Compound 416)

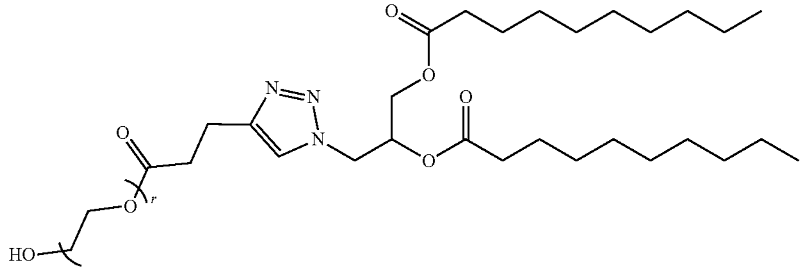

, (Compound 417)

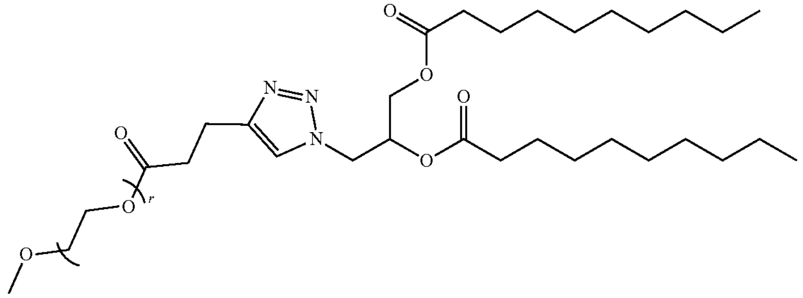

, (Compound 418)

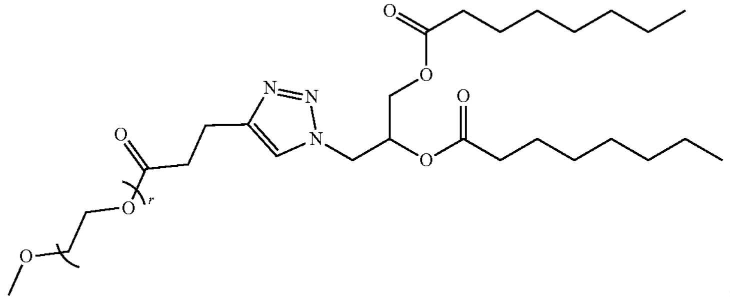

, or a salt thereof.

In certain embodiments, D is a moiety cleavable under physiological conditions (e.g., ester, amide, carbonate, carbamate, urea). In certain embodiments, a compound of Formula (VII) is of Formula (VII-b-1) or (VII-b-2):

(VII-b-1)

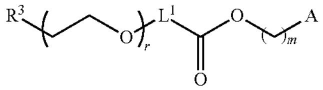

(VII-b-2)

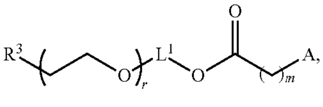

or a salt thereof.

In certain embodiments, a compound of Formula (VII) is of Formula (VII-b-1-OH) or (VII-b-2-OH):

(VII-b-1-OH)

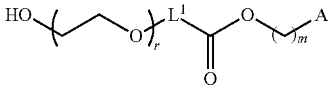

-continued (VII-b-2-OH)

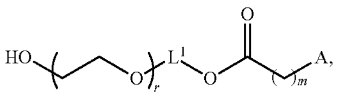

or a salt thereof.

In certain embodiments, the compound of Formula (VII) is of one of the following formulae:

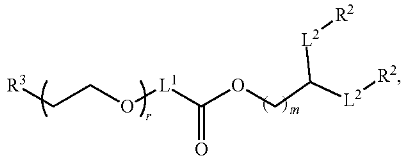

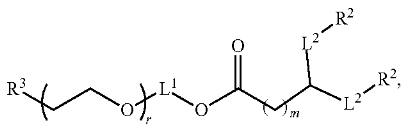

-continued
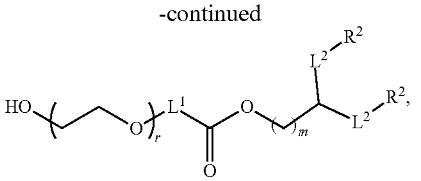
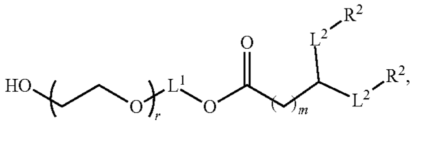
or a salt thereof.
In certain embodiments, a compound of Formula (VII) is of one of the following formulae:
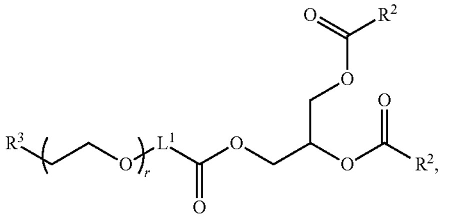
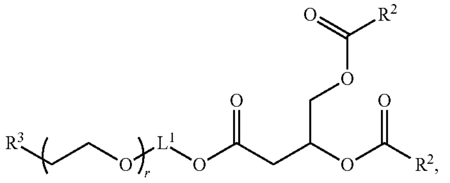
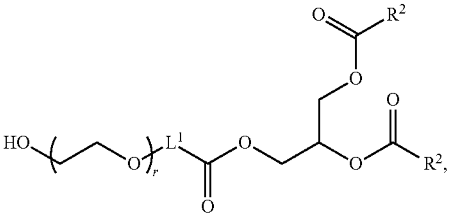
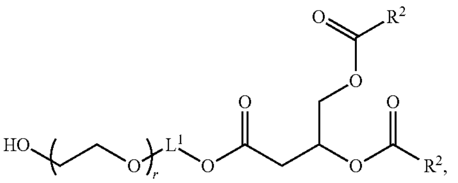
or a salt thereof.
In certain embodiments, a compound of Formula (VII) is of one of the following formulae:
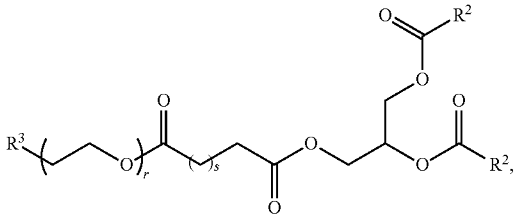
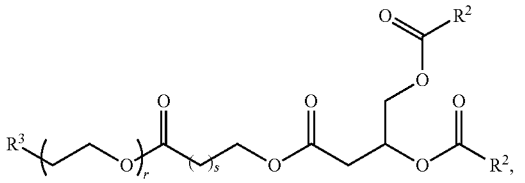
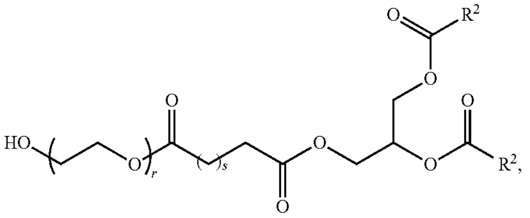
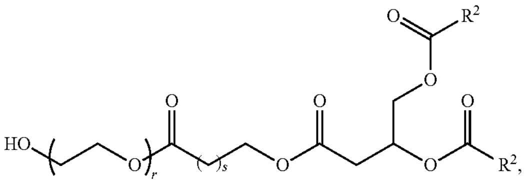
or a salt thereof.
In certain embodiments, a compound of Formula (VII) is of one of the following formulae:
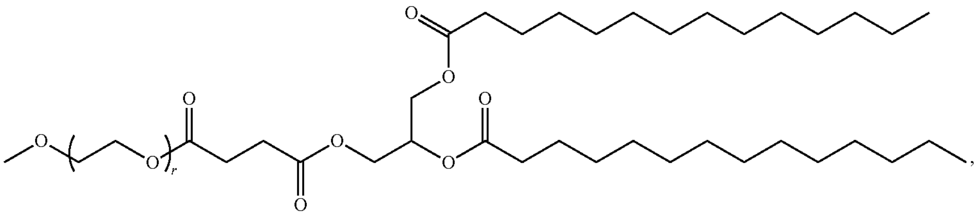

-continued

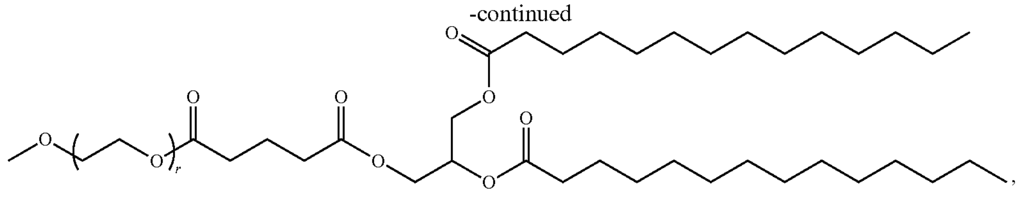

or salts thereof.

In certain embodiments, a PEG lipid useful in the present invention is a PEGylated fatty acid. In certain embodiments, a PEG lipid useful in the present invention is a compound of Formula (VIII). Provided herein are compounds of Formula (VIII):

(VIII)

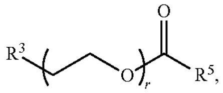

or a salts thereof, wherein:

$R^3$ is-00;

$R^O$ is hydrogen, optionally substituted alkyl or an oxygen protecting group;

r is an integer between 1 and 100, inclusive;

$R^5$ is optionally substituted $C_{10-40}$ alkyl, optionally substituted $C_{10-40}$ alkenyl, or optionally substituted $C_{10-40}$ alkynyl; and optionally one or more methylene groups of $R^5$ are replaced with optionally substituted carbocyclylene, optionally substituted heterocyclylene, optionally substituted arylene, optionally substituted heteroarylene, $N(R^N)$, O, S, C(O), —$C(O)N(R^N)$, $NR^NC(O)$, $NR^NC(O)N(R^N)$, C(O)O, OC(O), OC(O)O, $OC(O)N(R^N)$, —$NR^NC(O)O$, C(O)S, SC(O), $C(=NR^N)$, $C(=NR^N)N(R^N)$, $NR^NC(=NR^N)$, $NR^NC(=NR^N)N(R^N)$, —C(S), $C(S)N(R^N)$, $NR^NC(S)$, $NR^NC(S)N(R^N)$, S(O), OS(O), S(O)O, OS(O)O, $OS(O)_2$, —$S(O)_{20}$, $OS(O)_{20}$, $N(R^N)S(O)$, $S(O)N(R^N)$, $N(R^N)S(O)N(R^N)$, $OS(O)N(R^N)$, $N(R^N)S(O)O$, —$S(O)_2$, $N(R^N)S(O)_2$, $S(O)_2N(R^N)$, $N(R^N)S(O)_2N(R^N)$, $OS(O)_2N(R^N)$, or $N(R^N)S(O)_{20}$; and each instance of $R^N$ is independently hydrogen, optionally substituted alkyl, or a nitrogen protecting group.

In certain embodiments, the compound of Formula (VIII) is of Formula (VIII-OH):

(VIII-OH)

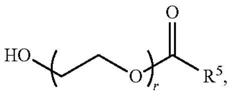

or a salt thereof. In some embodiments, r is 45.

In certain embodiments, a compound of Formula (VIII) is of one of the following formulae:

(Compound 419)

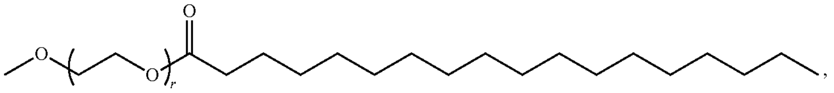

(Compound 420)

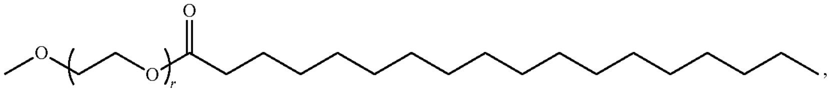

(Compound 421)

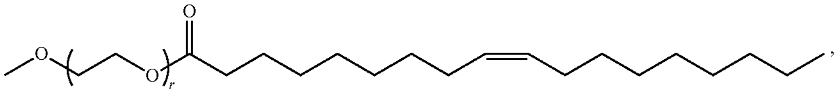

(Compound 422)

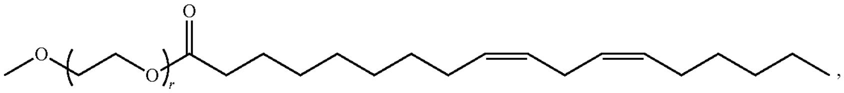

(Compound 423)

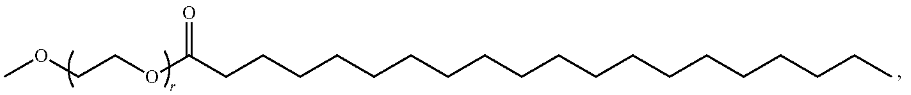

(Compound 424)

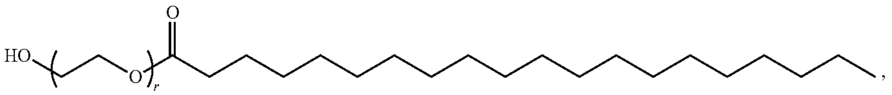

(Compound 425)

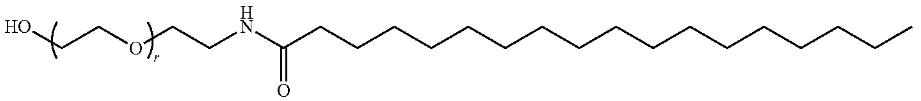

-continued (Compound 426)

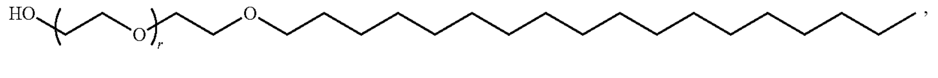

or a salt thereof. In some embodiments, r is 45.

In yet other embodiments the compound of Formula (VIII) is:

(Compound 427)

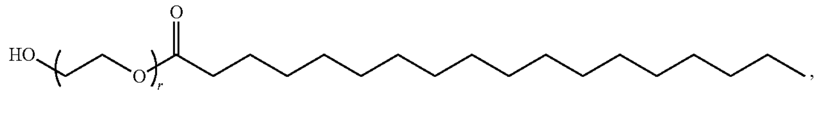

or a salt thereof.

In one embodiment, the compound of Formula (VIII) is (Compound 428)

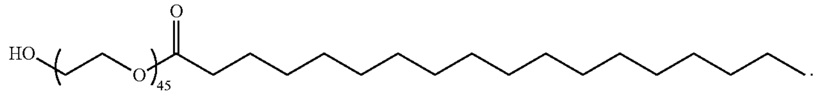

In one embodiment, the amount of PEG-lipid in the lipid composition of a pharmaceutical composition disclosed herein ranges from about 0.1 mol % to about 5 mol %, from about 0.5 mol % to about 5 mol %, from about 1 mol % to about 5 mol %, from about 1.5 mol % to about 5 mol %, from about 2 mol % to about 5 mol % mol %, from about 0.1 mol % to about 4 mol %, from about 0.5 mol % to about 4 mol %, from about 1 mol % to about 4 mol %, from about 1.5 mol % to about 4 mol %, from about 2 mol % to about 4 mol %, from about 0.1 mol % to about 3 mol %, from about 0.5 mol % to about 3 mol %, from about 1 mol % to about 3 mol %, from about 1.5 mol % to about 3 mol %, from about 2 mol % to about 3 mol %, from about 0.1 mol % to about 2 mol %, from about 0.5 mol % to about 2 mol %, from about 1 mol % to about 2 mol %, from about 1.5 mol % to about 2 mol %, from about 0.1 mol % to about 1.5 mol %, from about 0.5 mol % to about 1.5 mol %, or from about 1 mol % to about 1.5 mol %.

In one embodiment, the amount of PEG-lipid in the lipid composition disclosed herein is about 2 mol %. In one embodiment, the amount of PEG-lipid in the lipid composition disclosed herein is about 1.5 mol %.

In one embodiment, the amount of PEG-lipid in the lipid composition disclosed herein is at least about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or 5 mol %.

In some aspects, the lipid composition of the pharmaceutical compositions disclosed herein does not comprise a PEG-lipid.

f. Other Ionizable Amino Lipids

The lipid composition of the pharmaceutical composition disclosed herein can comprise one or more ionizable amino lipids in addition to or instead of a lipid according to Formula (I), (II), (III), (IV), (V), or (VI).

Ionizable lipids can be selected from the non-limiting group consisting of 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino) butanoate (DLin-MC3-DMA), 2,2-dilinoleyl-4-(2-dimethylaminoethyl)-[1,3]-dioxolane (DLin-KC2-DMA), 1,2-dioleyloxy-N,N-dimethylaminopropane (DODMA), (13Z, 165Z)—N,N-dimethyl-3-nonydocosa-13-16-dien-1-amine (L608), 2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA), (2R)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2R)), and (2S)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2S)). In addition to these, an ionizable amino lipid can also be a lipid including a cyclic amine group.

Ionizable lipids can also be the compounds disclosed in International Publication No. WO 2017/075531 A1, incorporated herein by reference in its entirety. For example, the ionizable amino lipids include, but not limited to:

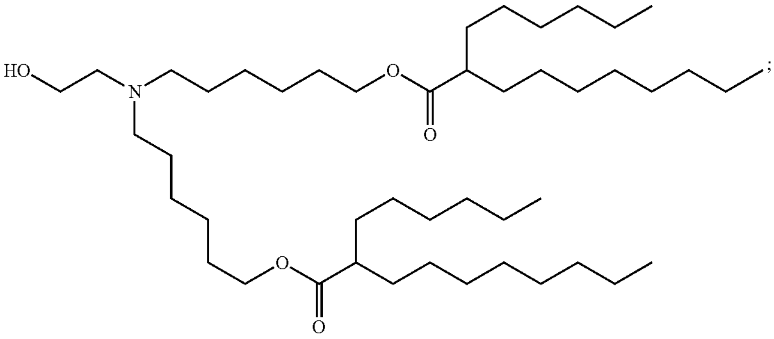
;
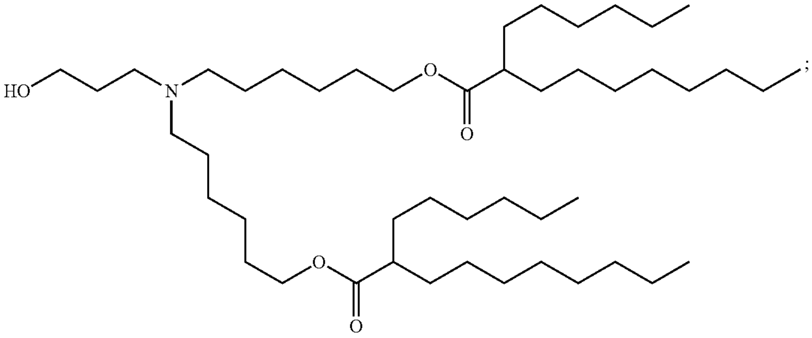
;
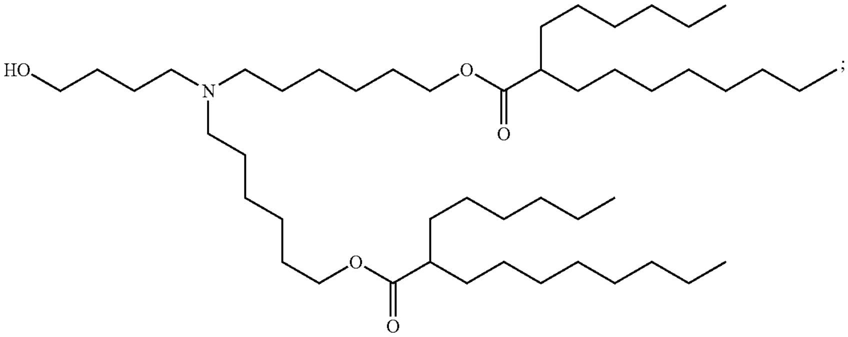
;
and any combination thereof.
Ionizable lipids can also be the compounds disclosed in International Publication No. WO 2015/199952 A1, incorporated herein by reference in its entirety. For example, the ionizable amino lipids include, but not limited to:
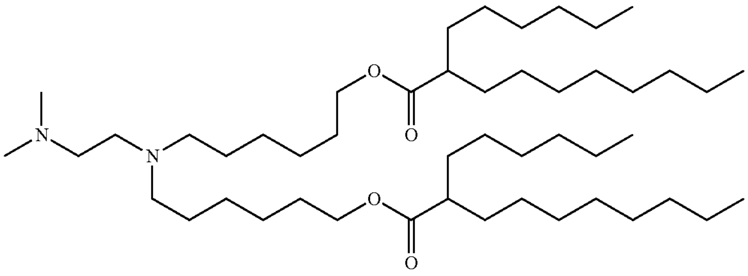
;

-continued
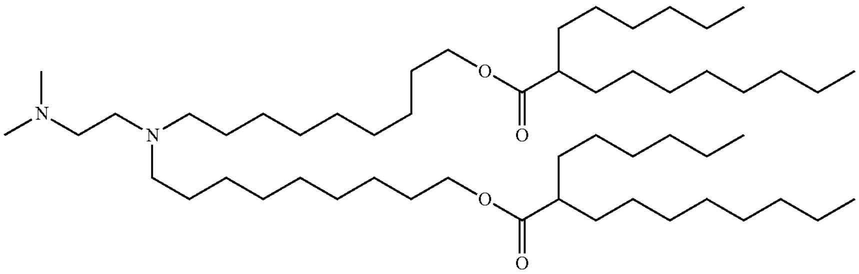
;
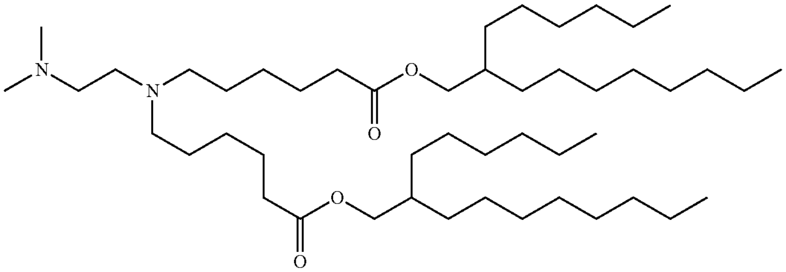
;
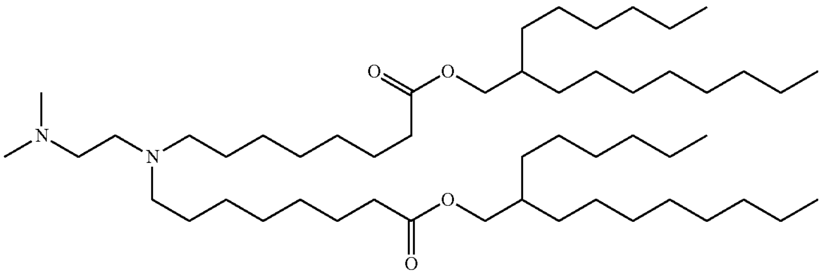
;
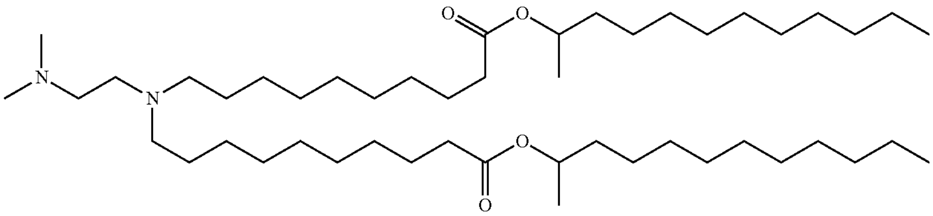
;
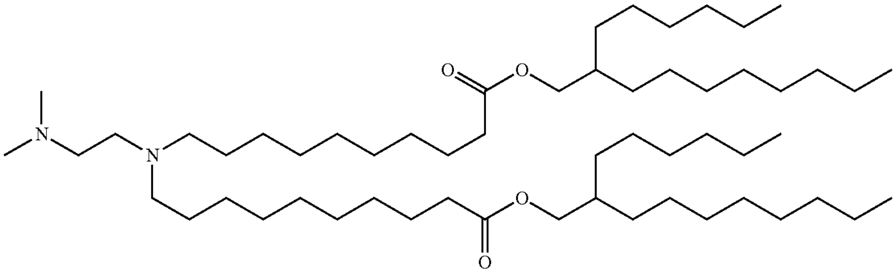
;
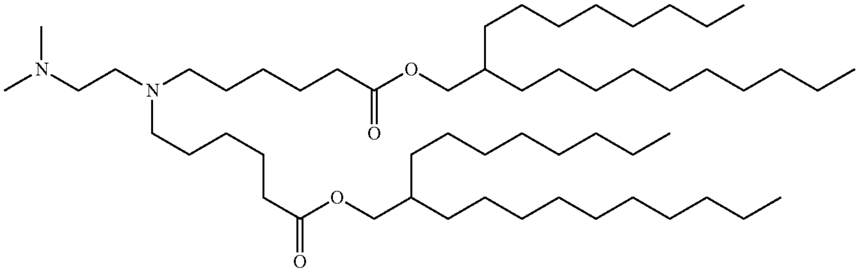
;

-continued

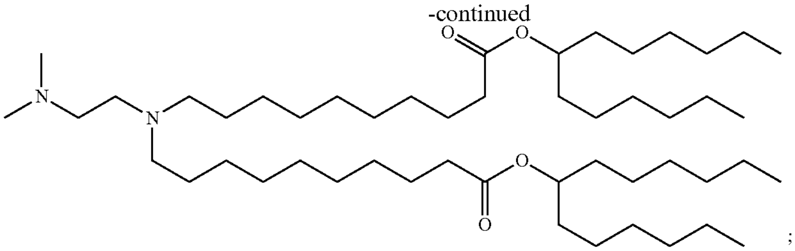

;

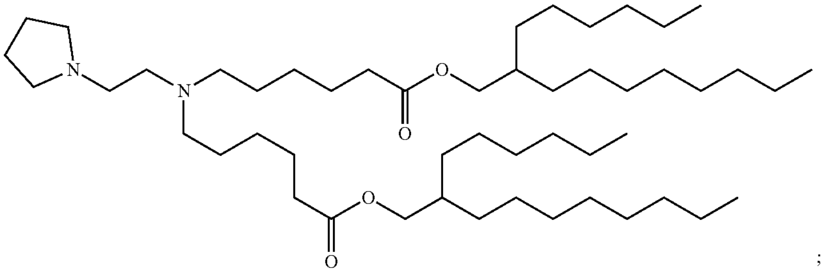

;

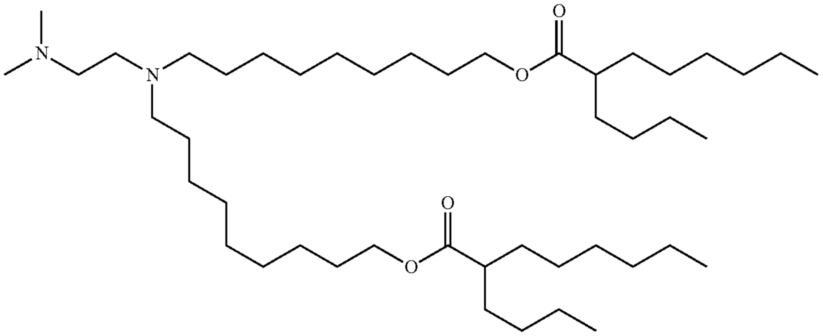

;

and any combination thereof.

g. Nanoparticle Compositions

The lipid composition of a pharmaceutical composition disclosed herein can include one or more components in addition to those described above. For example, the lipid composition can include one or more permeability enhancer molecules, carbohydrates, polymers, surface altering agents (e.g., surfactants), or other components. For example, a permeability enhancer molecule can be a molecule described by U.S. Patent Application Publication No. 2005/0222064. Carbohydrates can include simple sugars (e.g., glucose) and polysaccharides (e.g., glycogen and derivatives and analogs thereof).

A polymer can be included in and/or used to encapsulate or partially encapsulate a pharmaceutical composition disclosed herein (e.g., a pharmaceutical composition in lipid nanoparticle form). A polymer can be biodegradable and/or biocompatible. A polymer can be selected from, but is not limited to, polyamines, polyethers, polyamides, polyesters, polycarbamates, polyureas, polycarbonates, polystyrenes, polyimides, polysulfones, polyurethanes, polyacetylenes, polyethylenes, polyethyleneimines, polyisocyanates, polyacrylates, polymethacrylates, polyacrylonitriles, and polyarylates.

The ratio between the lipid composition and the polynucleotide range can be from about 10:1 to about 60:1 (wt/wt).

In some embodiments, the ratio between the lipid composition and the polynucleotide can be about 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1 or 60:1 (wt/wt). In some embodiments, the wt/wt ratio of the lipid composition to the polynucleotide encoding a therapeutic agent is about 20:1 or about 15:1.

In one embodiment, the lipid nanoparticles described herein can comprise polynucleotides (e.g., mRNA) in a lipid:polynucleotide weight ratio of 5:1, 10:1, 15:1, 20:1, 25:1, 30:1, 35:1, 40:1, 45:1, 50:1, 55:1, 60:1 or 70:1, or a range or any of these ratios such as, but not limited to, 5:1 to about 10:1, from about 5:1 to about 15:1, from about 5:1 to about 20:1, from about 5:1 to about 25:1, from about 5:1 to about 30:1, from about 5:1 to about 35:1, from about 5:1 to about 40:1, from about 5:1 to about 45:1, from about 5:1 to about 50:1, from about 5:1 to about 55:1, from about 5:1 to about 60:1, from about 5:1 to about 70:1, from about 10:1 to about 15:1, from about 10:1 to about 20:1, from about 10:1 to about 25:1, from about 10:1 to about 30:1, from about 10:1 to about 35:1, from about 10:1 to about 40:1, from about 10:1 to about 45:1, from about 10:1 to about 50:1, from about 10:1 to about 55:1, from about 10:1 to about 60:1, from about 10:1 to about 70:1, from about 15:1 to about 20:1, from about 15:1 to about 25:1, from about 15:1 to about 30:1, from about 15:1 to about 35:1, from about 15:1 to about 40:1, from about 15:1 to about 45:1, from about 15:1 to about 50:1, from about 15:1 to about 55:1, from about 15:1 to about 60:1 or from about 15:1 to about 70:1.

In one embodiment, the lipid nanoparticles described herein can comprise the polynucleotide in a concentration from approximately 0.1 mg/ml to 2 mg/ml such as, but not limited to, 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1.0 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2.0 mg/ml or greater than 2.0 mg/ml.

In some embodiments, the pharmaceutical compositions disclosed herein are formulated as lipid nanoparticles (LNP). Accordingly, the present disclosure also provides nanoparticle compositions comprising (i) a lipid composition comprising a delivery agent such as a compound of Formula (I) or (III) as described herein, and (ii) a polynucleotide encoding a polypeptide of interest. In such nanoparticle composition, the lipid composition disclosed herein can encapsulate the polynucleotide encoding a polypeptide of interest.

Nanoparticle compositions are typically sized on the order of micrometers or smaller and can include a lipid bilayer. Nanoparticle compositions encompass lipid nanoparticles (LNPs), liposomes (e.g., lipid vesicles), and lipoplexes. For example, a nanoparticle composition can be a liposome having a lipid bilayer with a diameter of 500 nm or less.

Nanoparticle compositions include, for example, lipid nanoparticles (LNPs), liposomes, and lipoplexes. In some embodiments, nanoparticle compositions are vesicles including one or more lipid bilayers. In certain embodiments, a nanoparticle composition includes two or more concentric bilayers separated by aqueous compartments. Lipid bilayers can be functionalized and/or crosslinked to one another. Lipid bilayers can include one or more ligands, proteins, or channels.

In some embodiments, the nanoparticle compositions of the present disclosure comprise at least one compound according to Formula (I), (III), (IV), (V), or (VI). For example, the nanoparticle composition can include one or more of Compounds 1-147, or one or more of Compounds 1-342. Nanoparticle compositions can also include a variety of other components. For example, the nanoparticle composition may include one or more other lipids in addition to a lipid according to Formula (I), (II), (III), (IV), (V), or (VI), such as (i) at least one phospholipid, (ii) at least one structural lipid, (iii) at least one PEG-lipid, or (iv) any combination thereof. Inclusion of structural lipid can be optional, for example when lipids according to formula III are used in the lipid nanoparticle compositins of the invention.

In some embodiments, the nanoparticle composition comprises a compound of Formula (I), (e.g., Compounds 18, 25, 26 or 48). In some embodiments, the nanoparticle composition comprises a compound of Formula (I) (e.g., Compounds 18, 25, 26 or 48) and a phospholipid (e.g., DSPC).

In some embodiments, the nanoparticle composition comprises a compound of Formula (III) (e.g., Compound 236). In some embodiments, the nanoparticle composition comprises a compound of Formula (III) (e.g., Compound 236) and a phospholipid (e.g., DOPE or DSPC).

In some embodiments, the nanoparticle composition comprises a lipid composition consisting or consisting essentially of compound of Formula (I) (e.g., Compounds 18, 25, 26 or 48). In some embodiments, the nanoparticle composition comprises a lipid composition consisting or consisting essentially of a compound of Formula (I) (e.g., Compounds 18, 25, 26 or 48) and a phospholipid (e.g., DSPC).

In some embodiments, the nanoparticle composition comprises a lipid composition consisting or consisting essentially of compound of Formula (III) (e.g., Compound 236). In some embodiments, the nanoparticle composition comprises a lipid composition consisting or consisting essentially of a compound of Formula (III) (e.g., Compound 236) and a phospholipid (e.g., DOPE or DSPC).

In one embodiment, a lipid nanoparticle comprises an ionizable lipid, a structural lipid, a phospholipid, a PEG-modified lipid, and mRNA. In some embodiments, the LNP comprises an ionizable lipid, a PEG-modified lipid, a sterol and a phospholipid. In some embodiments, the LNP has a molar ratio of about 20-60% ionizable lipid:about 5-25% phospholipid:about 25-55% sterol; and about 0.5-15% PEG-modified lipid. In some embodiments, the LNP comprises a molar ratio of about 50% ionizable lipid, about 1.5% PEG-modified lipid, about 38.5% cholesterol and about 10% phospholipid. In some embodiments, the LNP comprises a molar ratio of about 55% ionizable lipid, about 2.5% PEG lipid, about 32.5% cholesterol and about 10% phospholipid. In some embodiments, the ionizable lipid is an ionizable amino lipid, the neutral lipid is a phospholipid, and the sterol is a cholesterol. In some embodiments, the LNP has a molar ratio of 50:38.5:10:1.5 of ionizable lipid:cholesterol:DSPC:PEG lipid. In some embodiments, the ionizable lipid is Compound 18 or Compound 236, and the PEG lipid is Compound 428 or PEG-DMG.

In some embodiments, the LNP has a molar ratio of 50:38.5:10:1.5 of Compound 18:Cholesterol:Phospholipid:Compound 428. In some embodiments, the LNP has a molar ratio of 50:38.5:10:1.5 of Compound 18:Cholesterol:DSPC:Compound 428. In some embodiments, the LNP has a molar ratio of 50:38.5:10:1.5 of Compound 18:Cholesterol:Phospholipid:PEG-DMG. In some embodiments, the LNP has a molar ratio of 50:38.5:10:1.5 of Compound 18:Cholesterol:DSPC:PEG-DMG.

In some embodiments, the LNP has a molar ratio of 50:38.5:10:1.5 of Compound 236:Cholesterol:Phospholipid:Compound 428. In some embodiments, the LNP has a molar ratio of 50:38.5:10:1.5 of Compound 236:Cholesterol:DSPC:Compound 428.

In some embodiments, the LNP has a molar ratio of 40:38.5:20:1.5 of Compound 18:Cholesterol:Phospholipid:Compound 428. In some embodiments, the LNP has a molar ratio of 40:38.5:20:1.5 of Compound 18:Cholesterol:DSPC:Compound 428. In some embodiments, the LNP has a molar ratio of 40:38.5:20:1.5 of Compound 18:Cholesterol:Phospholipid:PEG-DMG. In some embodiments, the LNP has a molar ratio of 40:38.5:20:1.5 of Compound 18:Cholesterol:DSPC:PEG-DMG.

In some embodiments, a nanoparticle composition can have the formulation of Compound 18:Phospholipid:Chol:Compound 428 with a mole ratio of 50:10:38.5:1.5. In some embodiments, a nanoparticle composition can have the formulation of Compound 18:DSPC:Chol:Compound 428 with a mole ratio of 50:10:38.5:1.5. In some embodiments, a nanoparticle composition can have the formulation of Compound 18:Phospholipid:Chol:PEG-DMG with a mole ratio of 50:10:38.5:1.5. In some embodiments, a nanoparticle composition can have the formulation of Compound 18:DSPC:Chol:PEG-DMG with a mole ratio of 50:10:38.5:1.5.

In some embodiments, the LNP has a polydispersity value of less than 0.4. In some embodiments, the LNP has a net neutral charge at a neutral pH. In some embodiments, the LNP has a mean diameter of 50-150 nm. In some embodiments, the LNP has a mean diameter of 80-100 nm.

As generally defined herein, the term "lipid" refers to a small molecule that has hydrophobic or amphiphilic properties. Lipids may be naturally occurring or synthetic. Examples of classes of lipids include, but are not limited to, fats, waxes, sterol-containing metabolites, vitamins, fatty acids, glycerolipids, glycerophospholipids, sphingolipids, saccharolipids, and polyketides, and prenol lipids. In some instances, the amphiphilic properties of some lipids leads them to form liposomes, vesicles, or membranes in aqueous media.

In some embodiments, a lipid nanoparticle (LNP) may comprise an ionizable lipid. As used herein, the term "ionizable lipid" has its ordinary meaning in the art and may refer to a lipid comprising one or more charged moieties. In some embodiments, an ionizable lipid may be positively charged or negatively charged. An ionizable lipid may be positively charged, in which case it can be referred to as "cationic lipid". In certain embodiments, an ionizable lipid molecule may comprise an amine group, and can be referred to as an ionizable amino lipids. As used herein, a "charged moiety" is a chemical moiety that carries a formal electronic charge, e.g., monovalent (+1, or −1), divalent (+2, or −2), trivalent (+3, or −3), etc. The charged moiety may be anionic (i.e., negatively charged) or cationic (i.e., positively charged). Examples of positively-charged moieties include amine groups (e.g., primary, secondary, and/or tertiary amines), ammonium groups, pyridinium group, guanidine groups, and imidizolium groups. In a particular embodiment, the charged moieties comprise amine groups. Examples of negatively-charged groups or precursors thereof, include carboxylate groups, sulfonate groups, sulfate groups, phosphonate groups, phosphate groups, hydroxyl groups, and the like. The charge of the charged moiety may vary, in some cases, with the environmental conditions, for example, changes in pH may alter the charge of the moiety, and/or cause the moiety to become charged or uncharged. In general, the charge density of the molecule may be selected as desired.

It should be understood that the terms "charged" or "charged moiety" does not refer to a "partial negative charge" or "partial positive charge" on a molecule. The terms "partial negative charge" and "partial positive charge" are given its ordinary meaning in the art. A "partial negative charge" may result when a functional group comprises a bond that becomes polarized such that electron density is pulled toward one atom of the bond, creating a partial negative charge on the atom. Those of ordinary skill in the art will, in general, recognize bonds that can become polarized in this way.

In some embodiments, the ionizable lipid is an ionizable amino lipid, sometimes referred to in the art as an "ionizable cationic lipid". In one embodiment, the ionizable amino lipid may have a positively charged hydrophilic head and a hydrophobic tail that are connected via a linker structure.

In addition to these, an ionizable lipid may also be a lipid including a cyclic amine group.

In one embodiment, the ionizable lipid may be selected from, but not limited to, a ionizable lipid described in International Publication Nos. WO2013086354 and WO2013116126; the contents of each of which are incorporated herein by reference in their entirety.

In yet another embodiment, the ionizable lipid may be selected from, but not limited to, formula CLI-CLXXXXII of U.S. Pat. No. 7,404,969; each of which is incorporated herein by reference in their entirety.

In one embodiment, the lipid may be a cleavable lipid such as those described in International Publication No. WO2012170889, incorporated herein by reference in its entirety. In one embodiment, the lipid may be synthesized by methods known in the art and/or as described in International Publication Nos. WO2013086354; the contents of each of which are incorporated herein by reference in their entirety.

Nanoparticle compositions can be characterized by a variety of methods. For example, microscopy (e.g., transmission electron microscopy or scanning electron microscopy) can be used to examine the morphology and size distribution of a nanoparticle composition. Dynamic light scattering or potentiometry (e.g., potentiometric titrations) can be used to measure zeta potentials. Dynamic light scattering can also be utilized to determine particle sizes. Instruments such as the Zetasizer Nano ZS (Malvern Instruments Ltd, Malvern, Worcestershire, UK) can also be used to measure multiple characteristics of a nanoparticle composition, such as particle size, polydispersity index, and zeta potential.

In some embodiments, the nanoparticle composition comprises a lipid composition consisting or consisting essentially of compound of Formula (I) (e.g., Compounds 18, 25, 26 or 48). In some embodiments, the nanoparticle composition comprises a lipid composition consisting or consisting essentially of a compound of Formula (I) (e.g., Compounds 18, 25, 26 or 48) and a phospholipid (e.g., DSPC or MSPC).

Nanoparticle compositions can be characterized by a variety of methods. For example, microscopy (e.g., transmission electron microscopy or scanning electron microscopy) can be used to examine the morphology and size distribution of a nanoparticle composition. Dynamic light scattering or potentiometry (e.g., potentiometric titrations) can be used to measure zeta potentials. Dynamic light scattering can also be utilized to determine particle sizes. Instruments such as the Zetasizer Nano ZS (Malvern Instruments Ltd, Malvern, Worcestershire, UK) can also be used to measure multiple characteristics of a nanoparticle composition, such as particle size, polydispersity index, and zeta potential.

The size of the nanoparticles can help counter biological reactions such as, but not limited to, inflammation, or can increase the biological effect of the polynucleotide.

As used herein, "size" or "mean size" in the context of nanoparticle compositions refers to the mean diameter of a nanoparticle composition.

In one embodiment, the polynucleotide encoding a polypeptide of interest are formulated in lipid nanoparticles having a diameter from about 10 to about 100 nm such as, but not limited to, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm, about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In one embodiment, the nanoparticles have a diameter from about 10 to 500 nm. In one embodiment, the nanoparticle has a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In some embodiments, the largest dimension of a nanoparticle composition is 1 μm or shorter (e.g., 1 μm, 900 nm, 800 nm, 700 nm, 600 nm, 500 nm, 400 nm, 300 nm, 200 nm, 175 nm, 150 nm, 125 nm, 100 nm, 75 nm, 50 nm, or shorter).

A nanoparticle composition can be relatively homogenous. A polydispersity index can be used to indicate the homogeneity of a nanoparticle composition, e.g., the particle size distribution of the nanoparticle composition. A small (e.g., less than 0.3) polydispersity index generally indicates a narrow particle size distribution. A nanoparticle composition can have a polydispersity index from about 0 to about 0.25, such as 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25. In some embodiments, the polydispersity index of a nanoparticle composition disclosed herein can be from about 0.10 to about 0.20.

The zeta potential of a nanoparticle composition can be used to indicate the electrokinetic potential of the composition. For example, the zeta potential can describe the surface charge of a nanoparticle composition. Nanoparticle compositions with relatively low charges, positive or negative, are generally desirable, as more highly charged species can interact undesirably with cells, tissues, and other elements in the body. In some embodiments, the zeta potential of a nanoparticle composition disclosed herein can be from about −10 mV to about +20 mV, from about −10 mV to about +15 mV, from about 10 mV to about +10 mV, from about −10 mV to about +5 mV, from about −10 mV to about 0 mV, from about −10 mV to about −5 mV, from about −5 mV to about +20 mV, from about −5 mV to about +15 mV, from about −5 mV to about +10 mV, from about −5 mV to about +5 mV, from about −5 mV to about 0 mV, from about 0 mV to about +20 mV, from about 0 mV to about +15 mV, from about 0 mV to about +10 mV, from about 0 mV to about +5 mV, from about +5 mV to about +20 mV, from about +5 mV to about +15 mV, or from about +5 mV to about +10 mV.

In some embodiments, the zeta potential of the lipid nanoparticles can be from about 0 mV to about 100 mV, from about 0 mV to about 90 mV, from about 0 mV to about 80 mV, from about 0 mV to about 70 mV, from about 0 mV to about 60 mV, from about 0 mV to about 50 mV, from about 0 mV to about 40 mV, from about 0 mV to about 30 mV, from about 0 mV to about 20 mV, from about 0 mV to about 10 mV, from about 10 mV to about 100 mV, from about 10 mV to about 90 mV, from about 10 mV to about 80 mV, from about 10 mV to about 70 mV, from about 10 mV to about 60 mV, from about 10 mV to about 50 mV, from about 10 mV to about 40 mV, from about 10 mV to about 30 mV, from about 10 mV to about 20 mV, from about 20 mV to about 100 mV, from about 20 mV to about 90 mV, from about 20 mV to about 80 mV, from about 20 mV to about 70 mV, from about 20 mV to about 60 mV, from about 20 mV to about 50 mV, from about 20 mV to about 40 mV, from about 20 mV to about 30 mV, from about 30 mV to about 100 mV, from about 30 mV to about 90 mV, from about 30 mV to about 80 mV, from about 30 mV to about 70 mV, from about 30 mV to about 60 mV, from about 30 mV to about 50 mV, from about 30 mV to about 40 mV, from about 40 mV to about 100 mV, from about 40 mV to about 90 mV, from about 40 mV to about 80 mV, from about 40 mV to about 70 mV, from about 40 mV to about 60 mV, and from about 40 mV to about 50 mV. In some embodiments, the zeta potential of the lipid nanoparticles can be from about 10 mV to about 50 mV, from about 15 mV to about 45 mV, from about 20 mV to about 40 mV, and from about 25 mV to about 35 mV. In some embodiments, the zeta potential of the lipid nanoparticles can be about 10 mV, about 20 mV, about 30 mV, about 40 mV, about 50 mV, about 60 mV, about 70 mV, about 80 mV, about 90 mV, and about 100 mV.

The term "encapsulation efficiency" of a polynucleotide describes the amount of the polynucleotide that is encapsulated by or otherwise associated with a nanoparticle composition after preparation, relative to the initial amount provided. As used herein, "encapsulation" can refer to complete, substantial, or partial enclosure, confinement, surrounding, or encasement.

Encapsulation efficiency is desirably high (e.g., close to 100%). The encapsulation efficiency can be measured, for example, by comparing the amount of the polynucleotide in a solution containing the nanoparticle composition before and after breaking up the nanoparticle composition with one or more organic solvents or detergents.

Fluorescence can be used to measure the amount of free polynucleotide in a solution. For the nanoparticle compositions described herein, the encapsulation efficiency of a polynucleotide can be at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency can be at least 80%. In certain embodiments, the encapsulation efficiency can be at least 90%.

The amount of a polynucleotide present in a pharmaceutical composition disclosed herein can depend on multiple factors such as the size of the polynucleotide, desired target and/or application, or other properties of the nanoparticle composition as well as on the properties of the polynucleotide.

For example, the amount of an mRNA useful in a nanoparticle composition can depend on the size (expressed as length, or molecular mass), sequence, and other characteristics of the mRNA. The relative amounts of a polynucleotide in a nanoparticle composition can also vary. The relative amounts of the lipid composition and the polynucleotide present in a lipid nanoparticle composition of the present disclosure can be optimized according to considerations of efficacy and tolerability. For compositions including an mRNA as a polynucleotide, the N:P ratio can serve as a useful metric.

As the N:P ratio of a nanoparticle composition controls both expression and tolerability, nanoparticle compositions with low N:P ratios and strong expression are desirable. N:P ratios vary according to the ratio of lipids to RNA in a nanoparticle composition.

In general, a lower N:P ratio is preferred. The one or more RNA, lipids, and amounts thereof can be selected to provide an N:P ratio from about 2:1 to about 30:1, such as 2:1, 3:1, 4:1, 5:1, 6:1, 7:1, 8:1, 9:1, 10:1, 12:1, 14:1, 16:1, 18:1, 20:1, 22:1, 24:1, 26:1, 28:1, or 30:1. In certain embodiments, the N:P ratio can be from about 2:1 to about 8:1. In other embodiments, the N:P ratio is from about 5:1 to about 8:1. In certain embodiments, the N:P ratio is between 5:1 and 6:1. In one specific aspect, the N:P ratio is about is about 5.67:1.

In addition to providing nanoparticle compositions, the present disclosure also provides methods of producing lipid nanoparticles comprising encapsulating a polynucleotide. Such method comprises using any of the pharmaceutical compositions disclosed herein and producing lipid nanoparticles in accordance with methods of production of lipid nanoparticles known in the art. See, e.g., Wang et al. (2015) "Delivery of oligonucleotides with lipid nanoparticles" Adv. Drug Deliv. Rev. 87:68-80; Silva et al. (2015) "Delivery Systems for Biopharmaceuticals. Part I: Nanoparticles and Microparticles" Curr. Pharm. Technol. 16: 940-954; Naseri et al. (2015) "Solid Lipid Nanoparticles and Nanostructured Lipid Carriers: Structure, Preparation and Application" Adv. Pharm. Bull. 5:305-13; Silva et al. (2015) "Lipid nanoparticles for the delivery of biopharmaceuticals" Curr. Pharm. Biotechnol. 16:291-302, and references cited therein.

Applications Related to Nanoparticles

It has been discovered that the immunomodulatory therapeutic compositions described herein are superior to current compositions in several ways. First, the lipid nanoparticle (LNP) delivery is superior to other formulations including liposome or protamine based approaches described in the literature and no additional adjuvants are to be necessary. The use of LNPs enables the effective delivery of chemically modified or unmodified mRNA compositions. Both modified and unmodified LNP formulated mRNA compositions are superior to conventional compositions by a significant degree. In some embodiments the immunomodulatory therapeutic compositions of the invention are superior to conventional compositions by a factor of at least 10 fold, 20 fold, 40 fold, 50 fold, 100 fold, 500 fold or 1,000 fold.

Although attempts have been made to produce functional RNA vaccines, including mRNA vaccines and self-replicating RNA vaccines, the therapeutic efficacy of these RNA vaccines have not yet been fully established. Quite surprisingly, the inventors have discovered, according to aspects of the invention, a class of formulations for delivering immunomodulatory therapeutic compositions in vivo that results in significantly enhanced, and in many respects synergistic, immune responses including enhanced antigen generation and functional antibody production with neutralization capability. These results can be achieved even when significantly lower doses of the mRNA are administered in comparison with mRNA doses used in other classes of lipid based formulations. The formulations of the invention have demonstrated significant unexpected in vivo immune responses sufficient to establish the efficacy of functional mRNA compositions as immunomodulatory therapeutic agents. Additionally, self-replicating RNA vaccines rely on viral replication pathways to deliver enough RNA to a cell to produce an immunogenic response. The formulations of the invention do not require viral replication to produce enough protein to result in a strong immune response. Thus, the mRNA of the invention are not self-replicating RNA and do not include components necessary for viral replication.

The invention involves, in some aspects, the surprising finding that lipid nanoparticle (LNP) formulations significantly enhance the effectiveness of mRNA compositions, including chemically modified and unmodified mRNA immunomodulatory therapeutic compositions. The efficacy of mRNA containing immunomodulatory therapeutic compositions formulated in LNP was examined in vivo using several distinct tumor antigens. In addition to providing an enhanced immune response, the formulations of the invention generate a more rapid immune response with fewer doses of antigen than other compositions tested. The mRNA-LNP formulations of the invention also produce quantitatively and qualitatively better immune responses than compositions formulated in a different carriers. Additionally, the mRNA-LNP formulations of the invention are superior to other compositions even when the dose of mRNA is lower than other compositions.

The LNP used in the studies described herein has been used previously to deliver siRNA in various animal models as well as in humans. In view of the observations made in association with the siRNA delivery of LNP formulations, the fact that LNP is useful in cancer immunomodulatory therapeutic compositions is quite surprising. It has been observed that therapeutic delivery of siRNA formulated in LNP causes an undesirable inflammatory response associated with a transient IgM response, typically leading to a reduction in antigen production and a compromised immune response. In contrast to the findings observed with siRNA, the LNP-mRNA formulations of the invention are demonstrated herein to generate enhanced IgG levels, sufficient for prophylactic and therapeutic methods rather than transient IgM responses.

Pharmaceutical Compositions

The present disclosure includes pharmaceutical compositions comprising an mRNA or a nanoparticle (e.g., a lipid nanoparticle) described herein, in combination with one or more pharmaceutically acceptable excipient, carrier or diluent. In particular embodiments, the mRNA is present in a nanoparticle, e.g., a lipid nanoparticle. In particular embodiments, the mRNA or nanoparticle is present in a pharmaceutical composition. In various embodiments, the one or more mRNA present in the pharmaceutical composition is encapsulated in a nanoparticle, e.g., a lipid nanoparticle. In particular embodiments, the molar ratio of the first mRNA to the second mRNA is about 1:50, about 1:25, about 1:10, about 1:5, about 1:4, about 1:3, about 1:2, about 1:1, about 2:1, about 3:1, about 4:1, or about 5:1, about 10:1, about 25:1 or about 50:1. In particular embodiments, the molar ratio of the first mRNA to the second mRNA is greater than 1:1.

In some embodiments, a composition described herein comprises an mRNA encoding an antigen of interest (Ag) and an mRNA encoding a polypeptide that enhances an immune response to the antigen of interest (e.g., immune potentiator, e.g., STING polypeptide) (IP) wherein the mRNA encoding the antigen of interest (Ag) and the mRNA encoding the polypeptide that enhances an immune response to the antigen of interest (e.g., immune potentiator, e.g., STING polypeptide)(IP) are formulated at an Ag:IP mass ratio of 1:1, 2:1, 3:1, 4:1, 5:1, 6:1, 7:1, 8:1, 9:1, 10:1 or 20:1 (or alternatively, an IP:Ag mass ratio of 1:1, 1:2, 1:3, 1:4, 1:5, 1:6, 1:7, 1:8, 1:9, 1:10 or 1:20). In some embodiments, the composition is formulated at an Ag:IP mass ratio of 1:1. 1.25:1, 1.50:1, 1.75:1, 2.0:1, 2.25:1, 2.50:1, 2.75:1, 3.0:1, 3.25:1, 3.50:1, 3.75:1, 4.0:1, 4.25:1, 4.50:1, 4.75:1 or 5:1 of mRNA encoding the antigen of interest to the mRNA encoding the polypeptide that enhances an immune to the antigen of interest (e.g., immune potentiator, e.g., STING polypeptide). In some embodiments, the composition is formulated at a mass ratio of 5:1 of mRNA encoding the antigen of interest to the mRNA encoding the polypeptide that enhances an immune to the antigen of interest (e.g., immune potentiator, e.g., STING polypeptide) (Ag:IP mass ratio of 5:1, or alternatively an IP:Ag mass ratio of 1:5). In some embodiments, the composition is formulated at a mass ratio of 10:1 of mRNA encoding the antigen of interest to the mRNA encoding the polypeptide that enhances an immune to the antigen of interest (e.g., immune potentiator, e.g., STING polypeptide) (Ag:IP mass ratio of 10:1, or alternatively an IP:Ag mass ratio of 1:10).

In some embodiments, a composition described herein comprises an mRNA encoding a KRAS activating oncogene mutation peptide and an mRNA encoding a constitutively active human STING polypeptide wherein the mRNA encoding the KRAS activating oncogene mutation peptide and the mRNA encoding the constitutively active human STING polypeptide are present at a KRAS:STING mass ratio of 1:1, 2:1, 3:1, 4:1, 5:1, 6:1, 7:1, 8:1, 9:1, 10:1 or 20:1, or alternatively a STING:KRAS mass ratio of 1:1, 1:2, 1:3, 1:4, 1:5, 1:6, 1:7, 1:8, 1:9, 1:10 or 1:20. In some embodiments, the mRNAs are present at a KRAS:STING mass ratio of 1:1. 1.25:1, 1.50:1, 1.75:1, 2.0:1, 2.25:1, 2.50:1, 2.75:1, 3.0:1, 3.25:1, 3.50:1, 3.75:1, 4.0:1, 4.25:1, 4.50:1, 4.75:1 or 5:1 of mRNA encoding the antigen of interest to the mRNA encoding the polypeptide that enhances an immune to the antigen of interest (e.g., immune potentiator, e.g., STING polypeptide). In some embodiments, the mRNAs are present at a mass ratio of 5:1 of mRNA encoding the KRAS activating oncogene mutation peptide to the mRNA encoding the constitutively active human STING polypeptide (KRAS:STING mass ratio of 5:1, or alternatively STING: KRAS mass ratio of 1:5). In some embodiments, the mRNAs are present at a mass ratio of 10:1 of mRNA encoding the KRAS activating oncogene mutation peptide to the mRNA encoding the constitutively active human STING polypeptide (KRAS:STING mass ratio of 10:1, or alternatively STING:KRAS mass ratio of 1:10).

Pharmaceutical compositions may optionally include one or more additional active substances, for example, therapeutically and/or prophylactically active substances. Pharmaceutical compositions of the present disclosure may be sterile and/or pyrogen-free. General considerations in the formulation and/or manufacture of pharmaceutical agents may be found, for example, in *Remington: The Science and Practice of Pharmacy* 21$^{st}$ ed., Lippincott Williams & Wilkins, 2005 (incorporated herein by reference in its entirety). In particular embodiments, a pharmaceutical composition comprises an mRNA and a lipid nanoparticle, or complexes thereof.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the disclosure will vary, depending upon the identity, size, and/or condition of the subject treated and further depending upon the route by which the composition is to be administered. By way of example, the composition may include between 0.1% and 100%, e.g., between 0.5% and 70%, between 1% and 30%, between 5% and 80%, or at least 80% (w/w) active ingredient.

The mRNAs of the disclosure can be formulated using one or more excipients to: (1) increase stability; (2) increase cell transfection; (3) permit the sustained or delayed release (e.g., from a depot formulation of the mRNA); (4) alter the biodistribution (e.g., target the mRNA to specific tissues or cell types); (5) increase the translation of a polypeptide encoded by the mRNA in vivo; and/or (6) alter the release profile of a polypeptide encoded by the mRNA in vivo. In addition to traditional excipients such as any and all solvents, dispersion media, diluents, or other liquid vehicles, dispersion or suspension aids, surface active agents, isotonic agents, thickening or emulsifying agents, preservatives, excipients of the present disclosure can include, without limitation, lipidoids, liposomes, lipid nanoparticles (e.g., liposomes and micelles), polymers, lipoplexes, core-shell nanoparticles, peptides, proteins, carbohydrates, cells transfected with mRNAs (e.g., for transplantation into a subject), hyaluronidase, nanoparticle mimics and combinations thereof. Accordingly, the formulations of the disclosure can include one or more excipients, each in an amount that together increases the stability of the mRNA, increases cell transfection by the mRNA, increases the expression of a polypeptide encoded by the mRNA, and/or alters the release profile of a mRNA-encoded polypeptide. Further, the mRNAs of the present disclosure may be formulated using self-assembled nucleic acid nanoparticles.

Various excipients for formulating pharmaceutical compositions and techniques for preparing the composition are known in the art (see Remington: *The Science and Practice of Pharmacy,* 21st Edition, A. R. Gennaro, Lippincott, Williams & Wilkins, Baltimore, Md., 2006; incorporated herein by reference in its entirety). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition. Excipients may include, for example: antiadherents, antioxidants, binders, coatings, compression aids, disintegrants, dyes (colors), emollients, emulsifiers, fillers (diluents), film formers or coatings, glidants (flow enhancers), lubricants, preservatives, printing inks, sorbents, suspensing or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

In some embodiments, the formulations described herein may include at least one pharmaceutically acceptable salt. Examples of pharmaceutically acceptable salts that may be included in a formulation of the disclosure include, but are not limited to, acid addition salts, alkali or alkaline earth metal salts, mineral or organic acid salts of basic residues such as amines; alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

In some embodiments, the formulations described herein may contain at least one type of polynucleotide. As a non-limiting example, the formulations may contain 1, 2, 3, 4, 5 or more than 5 mRNAs described herein. In some embodiments, the formulations described herein may contain at least one mRNA encoding a polypeptide and at least one nucleic acid sequence such as, but not limited to, an siRNA, an shRNA, a snoRNA, and an miRNA.

Liquid dosage forms for e.g., parenteral administration include, but are not limited to, pharmaceutically acceptable emulsions, microemulsions, nanoemulsions, solutions, suspensions, syrups, and/or elixirs. In addition to active ingredients, liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and/or suspending agents. In certain embodiments for parenteral administration, compositions are mixed with solubilizing agents such as CREMAPHOR®, alcohols, oils, modified oils, glycols, polysorbates, cyclodextrins, polymers, and/or combinations thereof.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables. Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In some embodiments, pharmaceutical compositions including at least one mRNA described herein are administered to mammals (e.g., humans). Although the descriptions of pharmaceutical compositions provided herein are principally directed to pharmaceutical compositions which are suitable for administration to humans, it will be understood by the skilled artisan that such compositions are generally suitable for administration to any other animal, e.g., to a non-human mammal. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as poultry, chickens, ducks, geese, and/or turkeys. In particular embodiments, a subject is provided with two or more mRNAs described herein. In particular embodiments, the first and second mRNAs are provided to the subject at the same time or at different times, e.g., sequentially. In particular embodiments, the first and second mRNAs are provided to the subject in the same pharmaceutical composition or formulation, e.g., to facilitate uptake of both mRNAs by the same cells.

The present disclosure also includes kits comprising a container comprising a mRNA encoding a polypeptide that enhances an immune response. In another embodiment, the kit comprises a container comprising a mRNA encoding a polypeptide that enhances an immune response, as well as one or more additional mRNAs encoding one or more antigens or interest. In other embodiments, the kit comprises a first container comprising the mRNA encoding a polypeptide that enhances an immune response and a second container comprising one or more mRNAs encoding one or more antigens of interest. In particular embodiments, the mRNAs for enhancing an immune response and the mRNA(s) encoding an antigen(s) are present in the same or different nanoparticles and/or pharmaceutical compositions. In particular embodiments, the mRNAs are lyophilized, dried, or freeze-dried.

Methods of Enhancing Immune Responses

The disclosure provides a method for enhancing an immune response to an antigen of interest in a subject, e.g., a human subject. In one embodiment, the method comprises administering to the subject a composition of the disclosure (or lipid nanoparticle thereof, or pharmaceutical composition thereof) comprising at least one mRNA construct encoding: (i) at least one antigen of interest and (ii) a polypeptide that enhances an immune response against the antigen(s) of interest, such that an immune response to the antigen(s) of interest is enhanced. In one embodiment, enhancing an immune response comprises stimulating cytokine production. In another embodiment, enhancing an immune response comprises enhancing cellular immunity (T cell responses), such as stimulating antigen-specific $CD8^+$ T cell activity, stimulating antigen-specific $CD4^+$ T cell activity or increasing the percentage of "effector memory" $CD62L^{lo}$ T cells. In another embodiment, enhancing an immune response comprises enhancing humoral immunity (B cell responses), such as stimulating antigen-specific antibody production.

In one embodiment of the method, the immune potentiator mRNA encodes a polypeptide that stimulates Type I interferon pathway signaling (e.g., the immune potentiator encodes a polypeptide such as STING, IRF3, IRF7 or any of the additional immune potentiators described herein). In various other embodiment of the method, the immune potentiator encodes a polypeptide that stimulates NFkB pathway signaling, stimulates an inflammatory response or stimulates dendritic cell development, activity or mobilization. In one embodiment, the method comprises administering to the subject an mRNA composition that stimulates dendritic cell development, activity or mobilization prior to administering to the subject an mRNA composition that stimulates Type I interferon pathway signaling. For example, the mRNA composition that stimulates dendritic cell development or activity can be administered 1-30 days, e.g., 3 days, 5 days, 7 days, 10 days, 14 days, 21 days, 28 days, prior to administering the mRNA composition that stimulates Type I interferon pathway signaling.

Enhancement of an immune response in a subject against an antigen(s) of interest by an immune potenitator of the disclosure can be evaluated by a variety of methods established in the art for assessing immune responses, including but not limited to the methods described in the Examples. For example, in various embodiments, enhancement is evaluated by levels of intracellular staining (ICS) of $CD8^+$ cells for IFN-γ or TNF-α, percentage of splenic or peripheral $CD8b^+$ cells, or percentage of splenic or peripheral "effector memory" $CD62L^{lo}$ cells.

Compositions of the disclosure are administered to the subject at an effective amount. In general, an effective amount of the composition will allow for efficient production of the encoded polypeptide in the cell. Metrics for efficiency may include polypeptide translation (indicated by polypeptide expression), level of mRNA degradation, and immune response indicators.

Therapeutic Methods

The methods of the disclosure for enhancing an immune response to an antigen(s) of interest in a subject can be used in a variety of clinical or therapeutic applications. For example, the methods can be used to stimulate anti-tumor immunity in a subject with a tumor. Accordingly, in one aspect, the disclosure pertains to a method of stimulating an immunogenic response to a tumor in a subject in need thereof, the method comprising administering to the subject a composition of the disclosure (or lipid nanoparticle thereof, or pharmaceutical composition thereof) comprising at least one mRNA construct encoding: (i) at least one tumor antigen of interest and (ii) a polypeptide that enhances an immune response against the tumor antigen(s) of interest, such that an immune response to the tumor antigen(s) of interest is enhanced. Suitable tumor antigens of interest include those described herein (e.g. tumor neoantigens, including mutant KRAS antigens). In one embodiment of the method, the subject is administered a mutant KRAS antigen-STING mRNA construct encoding a sequence shown in any of SEQ ID NOs: 107-130.

The disclosure also provides methods of treating or preventing a cancer in a subject in need thereof that involve providing or administering at least one mRNA composition described herein (i.e., an immune potentiator mRNA and an antigen-encoding mRNA, in the same or separate mRNA constructs) to the subject. In related embodiments, the subject is provided with or administered a nanoparticle (e.g., a lipid nanoparticle) comprising the mRNA(s). In further related embodiments, the subject is provided with or administered a pharmaceutical composition of the disclosure to the subject. In particular embodiments, the pharmaceutical composition comprises an mRNA(s) encoding an antigen and an immunostimulatory polypeptide as described herein, or it comprises a nanoparticle comprising the mRNA(s). In particular embodiments, the mRNA(s) is present in a nanoparticle, e.g., a lipid nanoparticle. In particular embodiments, the mRNA(s) or nanoparticle is present in a pharmaceutical composition.

In certain embodiments, the subject in need thereof has been diagnosed with a cancer, or is considered to be at risk of developing a cancer. In some embodiments, the cancer is liver cancer, colorectal cancer, a melanoma cancer, a pancreatic cancer, a NSCLC, a cervical cancer or a head or neck cancer. In particular embodiments, the liver cancer is hepatocellular carcinoma. In some embodiments, the colorectal cancer is a primary tumor or a metastasis. In some embodiments, the cancer is a hematopoetic cancer. In some embodiments, the cancer is an acute myeloid leukemia, a chronic myeloid leukemia, a chronic myelomonocytic leukemia, a myelodystrophic syndrome (including refractory anemias and refractory cytopenias) or a myeloproliferative neoplasm or disease (including polycythemia vera, essential thrombocytosis and primary myelofibrosis). In other embodiments, the cancer is a blood-based cancer or a hematopoetic cancer. Selectivity for a particular cancer type can be achieved through the combination of use of an appropriate LNP formulation (e.g., targeting specific cell types) in combination with appropriate regulatory site(s) (e.g., microRNAs) engineered into the mRNA constructs.

In some embodiments, the mRNA(s), nanoparticle, or pharmaceutical composition is administered to the patient parenterally. In particular embodiments, the subject is a mammal, e.g., a human. In various embodiments, the subject is provided with an effective amount of the mRNA(s).

The methods of treating cancer can further include treatment of the subject with additional agents that enhance an anti-tumor response in the subject and/or that are cytotoxic to the tumor (e.g., chemotherapeutic agents). Suitable therapeutic agents for use in combination therapy include small molecule chemotherapeutic agents, including protein tyrosine kinase inhibitors, as well as biological anti-cancer agents, such as anti-cancer antibodies, including but not limited to those discussed further below. Combination therapy can include administering to the subject an immune checkpoint inhibitor to enhance anti-tumor immunity, such as PD-1 inhibitors, PD-L1 inhibitors and CTLA-4 inhibitors. Other modulators of immune checkpoints may target OX-40, OX-40L or ICOS. In one embodiment, an agent that modulates an immune checkpoint is an antibody. In another embodiment, an agent that modulates an immune checkpoint is a protein or small molecule modulator. In another embodiment, the agent (such as an mRNA) encodes an antibody modulator of an immune checkpoint. Non-limiting examples of immune checkpoint inhibitors that can be used in combination therapy include pembrolizumab, alemtuzumab, nivolumab, pidilizumab, ofatumumab, rituximab, MEDI0680 and PDR001, AMP-224, PF-06801591, BGB-A317, REGN2810, SHR-1210, TSR-042, affimer, avelumab (MSB0010718C), atezolizumab (MPDL3280A), durvalumab (MEDI4736), BMS936559, ipilimumab, tremelimumab, AGEN1884, MEDI6469 and MOXR0916.

A pharmaceutical composition including one or more mRNAs of the disclosure may be administered to a subject by any suitable route. In some embodiments, compositions of the disclosure are administered by one or more of a variety of routes, including parenteral (e.g., subcutaneous, intracutaneous, intravenous, intraperitoneal, intramuscular, intraarticular, intraarterial, intrasynovial, intrasternal, intrathecal, intralesional, or intracranial injection, as well as any suitable infusion technique), oral, trans- or intra-dermal, interdermal, rectal, intravaginal, topical (e.g. by powders, ointments, creams, gels, lotions, and/or drops), mucosal, nasal, buccal, enteral, vitreal, intratumoral, sublingual, intranasal; by intratracheal instillation, bronchial instillation, and/or inhalation; as an oral spray and/or powder, nasal spray, and/or aerosol, and/or through a portal vein catheter. In some embodiments, a composition may be administered intravenously, intramuscularly, intradermally, intra-arterially, intratumorally, subcutaneously, or by inhalation. In some embodiments, a composition is administered intramuscularly. However, the present disclosure encompasses the delivery of compositions of the disclosure by any appropriate route taking into consideration likely advances in the sciences of drug delivery. In general, the most appropriate route of administration will depend upon a variety of factors including the nature of the pharmaceutical composition including one or more mRNAs (e.g., its stability in various bodily environments such as the bloodstream and gastrointestinal tract), and the condition of the patient (e.g., whether the patient is able to tolerate particular routes of administration).

In certain embodiments, compositions of the disclosure may be administered at dosage levels sufficient to deliver from about 0.0001 mg/kg to about 10 mg/kg, from about 0.001 mg/kg to about 10 mg/kg, from about 0.005 mg/kg to about 10 mg/kg, from about 0.01 mg/kg to about 10 mg/kg, from about 0.1 mg/kg to about 10 mg/kg, from about 1 mg/kg to about 10 mg/kg, from about 2 mg/kg to about 10 mg/kg, from about 5 mg/kg to about 10 mg/kg, from about 0.0001 mg/kg to about 5 mg/kg, from about 0.001 mg/kg to about 5 mg/kg, from about 0.005 mg/kg to about 5 mg/kg, from about 0.01 mg/kg to about 5 mg/kg, from about 0.1 mg/kg to about 10 mg/kg, from about 1 mg/kg to about 5 mg/kg, from about 2 mg/kg to about 5 mg/kg, from about 0.0001 mg/kg to about 1 mg/kg, from about 0.001 mg/kg to about 1 mg/kg, from about 0.005 mg/kg to about 1 mg/kg, from about 0.01 mg/kg to about 1 mg/kg, or from about 0.1 mg/kg to about 1 mg/kg in a given dose, where a dose of 1 mg/kg provides 1 mg of mRNA or nanoparticle per 1 kg of subject body weight. In particular embodiments, a dose of about 0.005 mg/kg to about 5 mg/kg of mRNA or nanoparticle of the disclosure may be administrated.

A dose may be administered one or more times per day, in the same or a different amount, to obtain a desired level of mRNA expression and/or effect (e.g., a therapeutic effect) . The desired dosage may be delivered, for example, three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations). In some embodiments, a single dose may be administered, for example, prior to or after a surgical procedure or in the instance of an acute disease, disorder, or condition. The specific therapeutically effective, prophylactically effective, or otherwise appropriate dose level for any particular patient will depend upon a variety of factors including the severity and identify of a disorder being treated, if any; the one or more mRNAs employed; the specific composition employed; the age, body weight, general health, sex, and diet of the patient; the time of administration, route of administration, and rate of excretion of the specific pharmaceutical composition employed; the duration of the treatment; drugs used in combination or coincidental with the specific pharmaceutical composition employed; and like factors well known in the medical arts.

The immunomodulatory therapeutic compositions RNA (e.g., mRNA) and lipid nanoparticles of the disclosure may be administered by any route which results in a therapeutically effective outcome. These include, but are not limited, to intradermal, intramuscular, intranasal, and/or subcutaneous administration. The present disclosure provides methods comprising administering RNA compositions and lipid nanoparticles of the disclosure to a subject in need thereof. The exact amount required will vary from subject to subject, depending on the species, age, and general condition of the subject, the severity of the disease, the particular composition, its mode of administration, its mode of activity, and the like. RNA compositions and lipid nanoparticles of the disclosure are typically formulated in dosage unit form for ease of administration and uniformity of dosage. It will be understood, however, that the total daily usage of RNA (e.g., mRNA) compositions may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The effective amount of an RNA composition or lipid nanoparticle of the disclosure, as provided herein, may be as low as 10 μg, administered for example as a single dose or as two 5 μg doses. In some embodiments, the effective amount is a total dose of 10 μg-300 μg. For example, the effective amount may be a total dose of 10 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 110 μg, 120 μg, 130 μg, 140 μg, 150 μg, 160 μg, 170 μg, 180 μg, 190 μg or 200 μg, 210 μg, 220 μg, 230 μg, 240 μg, 250 μg, 260 μg, 270 μg, 280 μg, 290 μg or 300 μg. In some embodiments, the effective amount is a total dose of 10 μg-300 μg. In some embodiments, the effective amount is a total dose of 30 μg-100 μg or 50 μg-200 μg.

In some embodiments, RNA (e.g., mRNA) compositions and lipid nanoparticles may be administered at dosage levels sufficient to deliver 0.0001 mg/kg to 100 mg/kg, 0.001 mg/kg to 0.05 mg/kg, 0.005 mg/kg to 0.05 mg/kg, 0.001 mg/kg to 0.005 mg/kg, 0.05 mg/kg to 0.5 mg/kg, 0.01 mg/kg to 50 mg/kg, 0.1 mg/kg to 40 mg/kg, 0.5 mg/kg to 30 mg/kg, 0.01 mg/kg to 10 mg/kg, 0.1 mg/kg to 10 mg/kg, or 1 mg/kg to 25 mg/kg, of subject body weight per day, one or more times a day, per week, per month, etc. to obtain the desired therapeutic, diagnostic, prophylactic, or imaging effect (see e.g., the range of unit doses described in International Publication No. WO2013078199, herein incorporated by reference in its entirety). The desired dosage may be delivered three times a day, two times a day, once a day, every other day, every third day, every week, every two weeks, every three weeks, every four weeks, every 2 months, every three months, every 6 months, etc. In certain embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used. In exemplary embodiments, RNA (e.g., mRNA) compositions may be administered at dosage levels sufficient to deliver 0.0005 mg/kg to 0.01 mg/kg, e.g., about 0.0005 mg/kg to about 0.0075 mg/kg, e.g., about 0.0005 mg/kg, about 0.001 mg/kg, about 0.002 mg/kg, about 0.003 mg/kg, about 0.004 mg/kg or about 0.005 mg/kg.

In some embodiments, RNA (e.g., mRNA) compositions may be administered once or twice (or more) at dosage levels sufficient to deliver 0.025 mg/kg to 0.250 mg/kg, 0.025 mg/kg to 0.500 mg/kg, 0.025 mg/kg to 0.750 mg/kg, or 0.025 mg/kg to 1.0 mg/kg.

In some embodiments, RNA (e.g., mRNA) compositions may be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.0100 mg, 0.025 mg, 0.050 mg, 0.075 mg, 0.100 mg, 0.125 mg, 0.150 mg, 0.175 mg, 0.200 mg, 0.225 mg, 0.250 mg, 0.275 mg, 0.300 mg, 0.325 mg, 0.350 mg, 0.375 mg, 0.400 mg, 0.425 mg, 0.450 mg, 0.475 mg, 0.500 mg, 0.525 mg, 0.550 mg, 0.575 mg, 0.600 mg, 0.625 mg, 0.650 mg, 0.675 mg, 0.700 mg, 0.725 mg, 0.750 mg, 0.775 mg, 0.800 mg, 0.825 mg, 0.850 mg, 0.875 mg, 0.900 mg, 0.925 mg, 0.950 mg, 0.975 mg, or 1.0 mg. Higher and lower dosages and frequency of administration are encompassed by the present disclosure. For example, a RNA (e.g., mRNA) composition may be administered three or four times.

In some embodiments, RNA (e.g., mRNA) compositions or lipid nanoparticles comprising the same may be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.010 mg, 0.025 mg, 0.100 mg or 0.400 mg.

In some embodiments, the RNA (e.g., mRNA) composition or lipid nanoparticles comprising the same for use in a method of vaccinating a subject is administered the subject a single dosage of between 10 μg/kg and 400 μg/kg of the nucleic acid vaccine in an effective amount to vaccinate the subject. In some embodiments, the RNA composition or lipid nanoparticles comprising the same for use in a method of vaccinating a subject is administered the subject a single dosage of between 10 μg and 400 μg of the nucleic acid vaccine in an effective amount to vaccinate the subject. In some embodiments, a RNA (e.g., mRNA) composition or lipid nanoparticles comprising the same for use in a method of vaccinating a subject is administered to the subject as a single dosage of 25-1000 μg (e.g., a single dosage of mRNA encoding an antigen). In some embodiments, a RNA composition is administered to the subject as a single dosage of 25, 50, 100, 150, 200, 250, 300, 350, 400, 450, 500, 550, 600, 650, 700, 750, 800, 850, 900, 950 or 1000 μg. For example, a RNA composition may be administered to a subject as a single dose of 25-100, 25-500, 50-100, 50-500, 50-1000, 100-500, 100-1000, 250-500, 250-1000, or 500-1000 μg. In some embodiments, a RNA (e.g., mRNA) composition or lipid nanoparticles comprising the same for use in a method of vaccinating a subject is administered to the subject as two dosages, the combination of which equals 25-1000 μg of the RNA (e.g., mRNA) composition.

An RNA (e.g., mRNA) composition or lipid nanoparticles comprising the same described herein can be formulated into a dosage form described herein, such as an intranasal, intratracheal, or injectable (e.g., intravenous, intraocular, intravitreal, intramuscular, intradermal, intracardiac, intraperitoneal, and subcutaneous).

In some embodiments, a pharmaceutical composition of the disclosure may be administered in combination with another agent, for example, another therapeutic agent, a prophylactic agent, and/or a diagnostic agent. By "in combination with," it is not intended to imply that the agents must be administered at the same time and/or formulated for delivery together, although these methods of delivery are within the scope of the present disclosure. For example, one or more compositions including one or more different mRNAs may be administered in combination. Compositions can be administered concurrently with, prior to, or subsequent to, one or more other desired therapeutics or medical procedures. In general, each agent will be administered at a dose and/or on a time schedule determined for that agent. In some embodiments, the present disclosure encompasses the delivery of compositions of the disclosure, or imaging, diagnostic, or prophylactic compositions thereof in combination with agents that improve their bioavailability, reduce and/or modify their metabolism, inhibit their excretion, and/or modify their distribution within the body.

Exemplary therapeutic agents that may be administered in combination with the compositions of the disclosure include, but are not limited to, cytotoxic, chemotherapeutic, and other therapeutic agents. Cytotoxic agents may include, for example, taxol, cytochalasin B, gramicidin D, ethidium bromide, emetine, mitomycin, etoposide, teniposide, vincristine, vinblastine, colchicine, doxorubicin, daunorubicin, dihydroxyanthracinedione, mitoxantrone, mithramycin, actinomycin D, 1-dehydrotestosterone, glucocorticoids, procaine, tetracaine, lidocaine, propranolol, puromycin, maytansinoids, rachelmycin, and analogs thereof. Radioactive ions may also be used as therapeutic agents and may include, for example, radioactive iodine, strontium, phosphorous, palladium, cesium, iridium, cobalt, yttrium, samarium, and praseodymium. Other therapeutic agents may include, for example, antimetabolites (e.g., methotrexate, 6-mercaptopurine, 6-thioguanine, cytarabine, and 5-fluorouracil, and decarbazine), alkylating agents (e.g., mechlorethamine, thiotepa, chlorambucil, rachelmycin, melphalan, carmustine, lomustine, cyclophosphamide, busulfan, dibromomannitol, streptozotocin, mitomycin C, and cis-dichlorodiamine platinum (II) (DDP), and cisplatin), anthracyclines (e.g., daunorubicin and doxorubicin), antibiotics (e.g., dactinomycin, bleomycin, mithramycin, and anthramycin), and anti-mitotic agents (e.g., vincristine, vinblastine, taxol, and maytansinoids).

The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, a composition useful for treating cancer may be administered concurrently with a chemotherapeutic agent), or they may achieve different effects (e.g., control of any adverse effects).

Immune checkpoint inhibitors such as pembrolizumab or nivolumab, which target the interaction between programmed death receptor 1/programmed death ligand 1 (PD-1/PD-L1) and PD-L2, have been recently approved for the treatment of various malignancies and are currently being investigated in clinical trials for various cancers including melanoma, head and neck squamous cell carcinoma (HNSCC).

Accordingly, one aspect of the disclosure relates to combination therapy in which a subject is previously treated with a PD-1 antagonist prior to administration of a lipid nanoparticle or composition of the present disclosure. In another aspect, the subject has been treated with a monoclonal antibody that binds to PD-1 prior to administration of a lipid nanoparticle or composition of the present disclosure. In another aspect, the subject has been administered a lipid nanoparticle or composition of the disclosure prior to treatment with an anti-PD-1 monoclonal antibody therapy. In some aspects, the anti-PD-1 monoclonal antibody therapy comprises nivolumab, pembrolizumab, pidilizumab, or any combination thereof. In some aspects, the anti-PD-1 monoclonal antibody comprises pembrolizumab.

In another aspect, the subject has been treated with a monoclonal antibody that binds to PD-L1 prior to administration of a lipid nanoparticle or composition of the present disclosure. In another aspect, the subject is administered a lipid nanoparticle or composition prior to treatment with an anti-PD-L1 monoclonal antibody therapy. In some aspects, the anti-PD-L1 monoclonal antibody therapy comprises durvalumab, avelumab, MEDI473, BMS-936559, aezolizumab, or any combination thereof.

In some aspects, the subject has been treated with a CTLA-4 antagonist prior to treatment with the compositions of present disclosure. In another aspect, the subject has been previously treated with a monoclonal antibody that binds to CTLA-4 prior to administration of a lipid nanoparticle or composition of the present disclosure. In some aspects, the subject has been administered a lipid nanoparticle or composition prior to treatment with an anti-CTLA-4 monoclonal antibody. In some aspects, the anti-CTLA-4 antibody therapy comprises ipilimumab or tremelimumab.

In any of the foregoing or related aspects, the disclosure provides a lipid nanoparticle, and an optional pharmaceutically acceptable carrier, or a pharmaceutical composition for use in treating or delaying progression of cancer in an individual, wherein the treatment comprises administration of the composition in combination with a second composition, wherein the second composition comprises a checkpoint inhibitor polypeptide and an optional pharmaceutically acceptable carrier.

In any of the foregoing or related aspects, the disclosure provides use of a lipid nanoparticle, and an optional pharmaceutically acceptable carrier, in the manufacture of a medicament for treating or delaying progression of cancer in an individual, wherein the medicament comprises the lipid nanoparticle and an optional pharmaceutically acceptable carrier and wherein the treatment comprises administration of the medicament in combination with a composition comprising a checkpoint inhibitor polypeptide and an optional pharmaceutically acceptable carrier.

In any of the foregoing or related aspects, the disclosure provides a kit comprising a container comprising a lipid nanoparticle, and an optional pharmaceutically acceptable carrier, or a pharmaceutical composition, and a package insert comprising instructions for administration of the lipid nanoparticle or pharmaceutical composition for treating or delaying progression of cancer in an individual. In some aspects, the package insert further comprises instructions for administration of the lipid nanoparticle or pharmaceutical composition in combination with a composition comprising a checkpoint inhibitor polypeptide and an optional pharmaceutically acceptable carrier for treating or delaying progression of cancer in an individual.

In any of the foregoing or related aspects, the disclosure provides a kit comprising a medicament comprising a lipid nanoparticle, and an optional pharmaceutically acceptable carrier, or a pharmaceutical composition, and a package insert comprising instructions for administration of the medicament alone or in combination with a composition comprising a checkpoint inhibitor polypeptide and an optional pharmaceutically acceptable carrier for treating or delaying progression of cancer in an individual. In some aspects, the kit further comprises a package insert comprising instructions for administration of the first medicament prior to, current with, or subsequent to administration of the second medicament for treating or delaying progression of cancer in an individual.

In any of the foregoing or related aspects, the disclosure provides a lipid nanoparticle, a composition, or the use thereof, or a kit comprising a lipid nanoparticle or a composition as described herein, wherein the checkpoint inhibitor polypeptide inhibits PD1, PD-L1, CTLA4, or a combination thereof. In some aspects, the checkpoint inhibitor polypeptide is an antibody. In some aspects, the checkpoint inhibitor polypeptide is an antibody selected from an anti-CTLA4 antibody or antigen-binding fragment thereof that specifically binds CTLA4, an anti-PD1 antibody or antigen-binding fragment thereof that specifically binds PD1, an anti-PD-L1 antibody or antigen-binding fragment thereof that specifically binds PD-L1, and a combination thereof. In some aspects, the checkpoint inhibitor polypeptide is an anti-PD-L1 antibody selected from atezolizumab, avelumab, or durvalumab. In some aspects, the checkpoint inhibitor polypeptide is an anti-CTLA-4 antibody selected from tremelimumab or ipilimumab. In some aspects, the checkpoint inhibitor polypeptide is an anti-PD1 antibody selected from nivolumab or pembrolizumab. In some asepcts, the checkpoint inhibitor polypeptide is an anti-PD1 antibody, wherein the anti-PD1 antibody is pembrolizumab.

In related aspects, the disclosure provides a method of reducing or decreasing a size of a tumor or inhibiting a tumor growth in a subject in need thereof comprising administering to the subject any of the foregoing or related lipid nanoparticles of the disclosure, or any of the foregoing or related compositions of the disclosure.

In related aspects, the disclosure provides a method inducing an anti-tumor response in a subject with cancer comprising administering to the subject any of the foregoing or related lipid nanoparticles of the disclosure, or any of the foregoing or related compositions of the disclosure. In some aspects, the anti-tumor response comprises a T-cell response. In some aspects, the T-cell response comprises CD8+ T cells.

In some aspects of the foregoing methods, the method further comprises administering a second composition comprising a checkpoint inhibitor polypeptide, and an optional pharmaceutically acceptable carrier. In some aspects, the checkpoint inhibitor polypeptide inhibits PD1, PD-L1, CTLA4, or a combination thereof. In some aspects, the checkpoint inhibitor polypeptide is an antibody. In some aspects, the checkpoint inhibitor polypeptide is an antibody selected from an anti-CTLA4 antibody or antigen-binding fragment thereof that specifically binds CTLA4, an anti-PD1 antibody or antigen-binding fragment thereof that specifically binds PD1, an anti-PD-L1 antibody or antigen-binding fragment thereof that specifically binds PD-L1, and a combination thereof. In some aspects, the checkpoint inhibitor polypeptide is an anti-PD-L1 antibody selected from atezolizumab, avelumab, or durvalumab. In some aspects, the checkpoint inhibitor polypeptide is an anti-CTLA-4 antibody selected from tremelimumab or ipilimumab. In some aspects, the checkpoint inhibitor polypeptide is an anti-PD1 antibody selected from nivolumab or pembrolizumab. In some asepcts, the checkpoint inhibitor polypeptide is an anti-PD1 antibody, wherein the anti-PD1 antibody is pembrolizumab.

In some aspects of any of the foregoing or related methods, the composition comprising the checkpoint inhibitor polypeptide is administered by intravenous injection. In some aspects, the composition comprising the checkpoint inhibitor polypeptide is administered once every 2 to 3 weeks. In some aspects, the composition comprising the checkpoint inhibitor polypeptide is administered once every 2 weeks or once every 3 weeks. In some aspects, the composition comprising the checkpoint inhibitor polypeptide is administered prior to, concurrent with, or subsequent to administration of the lipid nanoparticle or pharmaceutical composition thereof.

In some aspects of any of the foregoing or related methods, the subject has a histologically confirmed KRAS mutation selected from G12D, G12V, G13D or G12C.

In some aspects of any of the foregoing or related methods, the subject has metastatic colorectal cancer.

In some aspects of any of the foregoing or related methods, the subject has non-small cell lung cancer (NSCLC).

In some aspects of any of the foregoing or related methods, the subject has pancreatic cancer.

In any of the foregoing or related aspects, the disclosure provides pharmaceutical composition comprising the lipid nanoparticle, and a pharmaceutically acceptable carrier. In some aspects, the pharmaceutical composition is formulated for intramuscular delivery.

Other Embodiments of the Disclosure

E1. An immunomodulatory therapeutic composition, comprising:

one or more mRNA each having an open reading frame encoding an activating oncogene mutation peptide;

one or more mRNA each having an open reading frame encoding a polypeptide that enhances an immune response to the activating oncogene mutation peptide in a subject, wherein the immune response comprises a cellular or humoral immune response characterized by:

(i) stimulating Type I interferon pathway signaling, (ii) stimulating NFkB pathway signaling, (iii) stimulating an inflammatory response, (iv) stimulating cytokine production, (v) stimulating dendritic cell development, activity or mobilization, and (vi) a combination of any of (i)-(v); and a pharmaceutically acceptable carrier.

E2. The immunomodulatory therapeutic composition of embodiment 1, wherein the activating oncogene mutation is a KRAS mutation.

E3. The immunomodulatory therapeutic composition of embodiment 2, wherein the KRAS mutation is a G12 mutation.

E4. The immunomodulatory therapeutic composition of embodiment 3, wherein the G12 KRAS mutation is selected from G12D, G12V, G12S, G12C, G12A, and G12R KRAS mutations.

E5. The immunomodulatory therapeutic composition of embodiment 3, wherein the G12 KRAS mutation is selected from G12D, G12V, and G12C KRAS mutations.

E6. The immunomodulatory therapeutic composition of any one of embodiments 2-5, wherein the KRAS mutation is a G13 mutation.

E7. The immunomodulatory therapeutic composition of embodiment 6, wherein the G13 KRAS mutation is a G13D KRAS mutation.

E8. The immunomodulatory therapeutic composition of embodiment 1, wherein the activating oncogene mutation is a H-RAS or N-RAS mutation.

E9. The immunomodulatory therapeutic composition of any one of embodiments 1-8, wherein the mRNA has an open reading frame encoding a concatemer of two or more activating oncogene mutation peptides.

E10. The immunomodulatory therapeutic composition of embodiment 9, wherein the concatemer comprises 3, 4, 5, 6, 7, 8, 9, or 10 activating oncogene mutation peptides.

E11. The immunomodulatory therapeutic composition of embodiment 9, wherein the concatemer comprises 4 activating oncogene mutation peptides.

E12. The immunomodulatory therapeutic composition of embodiment 11, wherein the concatemer comprises KRAS activating oncogene mutation peptides G12D, G12V, G12C, and G13D.

E13. The immunomodulatory therapeutic composition of embodiment 12, wherein the concatemer comprises from N- to C-terminus G12D, G12V, G13D, and G12C.

E14. The immunomodulatory therapeutic composition of embodiment 12, wherein the concatemer comprises from N- to C-terminus G12C, G13D, G12V, and G12D.

E15. The immunomodulatory therapeutic composition of any one of embodiments 1-8, wherein the composition comprises 1, 2, 3, or 4 mRNAs encoding 1, 2, 3, or 4 activating oncogene mutation peptides.

E16. The immunomodulatory therapeutic composition of embodiment 15, wherein the composition comprises 4 mRNAs encoding 4 activating oncogene mutation peptides.

E17. The immunomodulatory therapeutic composition of embodiment 16, wherein the 4 mRNAs encode KRAS activating oncogene mutation peptides G12D, G12V, G12C, and G13D.

E18. The immunomodulatory therapeutic composition of any one of embodiments 1-17, wherein the activating oncogene mutation peptide comprises 10-30, 15-25, or 20-25 amino acids in length.

E19. The immunomodulatory therapeutic composition of embodiment 18, wherein the activating oncogene mutation peptide comprises 20, 21, 22, 23, 24, or 25 amino acids in length.

E20. The immunomodulatory therapeutic composition of embodiment 19, wherein the activating oncogene mutation peptide comprises 25 amino acids in length.

E21. The immunomodulatory therapeutic composition of any one of embodiments 1-20, wherein the mRNA encoding a polypeptide that enhances an immune response to the activating oncogene mutation peptide in a subject encodes a constitutively active human STING polypeptide.

E22. The immunomodulatory therapeutic composition of embodiment 21, wherein the constitutively active human STING polypeptide comprises one or more mutations selected from the group consisting of V147L, N154S, V155M, R284M, R284K, R284T, E315Q, R375A, and combinations thereof.

E23. The immunomodulatory therapeutic composition of embodiment 22, wherein the constitutively active human STING polypeptide comprises mutation V155M.

E24. The immunomodulatory therapeutic composition of embodiment 22, wherein the constitutively active human STING polypeptide comprises mutations V147L/N154S/V155M.

E25. The immunomodulatory therapeutic composition of embodiment 22, wherein the constitutively active human STING polypeptide comprises mutations R284M/V147L/N154S/V155M.

E26. The immunomodulatory therapeutic composition of embodiment 22, wherein the constitutively active human STING polypeptide comprises an amino acid sequence shown in any one of SEQ ID NOs: 1-10 and 164.

E27. The immunomodulatory therapeutic composition of any one of embodiments 21-26, wherein the mRNA encoding the constitutively active human STING polypeptide comprises a 3' UTR comprising at least one miR-122 microRNA binding site.

E28. The immunomodulatory therapeutic composition of any one of embodiments 1-20, wherein the mRNA encoding a polypeptide that enhances an immune response to the activating oncogene mutation peptide in a subject encodes a constitutively active human IRF3 polypeptide.

E29. The immunomodulatory therapeutic composition of embodiment 28, wherein the constitutively active human IRF3 polypeptide comprises an S396D mutation.

E30. The immunomodulatory therapeutic composition of embodiment 28, wherein the constitutively active human IRF3 polypeptide comprises an amino acid sequence shown in SEQ ID NOs: 12.

E31. The immunomodulatory therapeutic composition of any one of embodiments 1-20, wherein the mRNA encoding a polypeptide that enhances an immune response to the activating oncogene mutation peptide in a subject encodes a constitutively active human IRF7 polypeptide.

E32. The immunomodulatory therapeutic composition of embodiment 31, wherein the constitutively active human IRF7 polypeptide comprises one or more mutations selected from the group consisting of S475D, S476D, S477D, S479D, L480D, S483D, S487D, deletion of amino acids 247-467, deletion of amino acid residues 152-246, deletion of amino acid residues 1-151, and combinations thereof.

E33. The immunomodulatory therapeutic composition of embodiment 31, wherein the constitutively active human IRF7 polypeptide comprises an amino acid sequence shown in any one of SEQ ID NOs: 14-18.

E34. The immunomodulatory therapeutic composition of any one of embodiments 1-33, wherein the composition further comprises a cancer therapeutic agent.

E35. The immunomodulatory therapeutic composition of any one of embodiments 1-33, wherein the composition further comprises an inhibitory checkpoint polypeptide.

E36. The immunomodulatory therapeutic composition of embodiment 35, wherein the inhibitory checkpoint polypeptide is an antibody or fragment thereof that specifically binds to a molecule selected from the group consisting of PD-1, PD-L1, TIM-3, VISTA, $A_2AR$, B7-H3, B7-H4, BTLA, CTLA-4, IDO, KIR and LAGS.

E37. The immunomodulatory therapeutic composition of any one of embodiments 1-33, wherein the mRNA is formulated in a lipid nanoparticle.

E38. The immunomodulatory therapeutic composition of embodiment 37, wherein the lipid nanoparticle comprises a molar ratio of about 20-60% ionizable amino lipid:5-25% phospholipid:25-55% sterol; and 0.5-15% PEG-modified lipid.

E39. The immunomodulatory therapeutic composition of embodiment 38, wherein the ionizable amino lipid is selected from the group consisting of for example, 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319).

E40. The immunomodulatory therapeutic composition of any one of embodiments 1-39, wherein each mRNA includes at least one chemical modification.

E41. The immunomodulatory therapeutic composition of embodiment 40, wherein the chemical modification is selected from the group consisting of pseudouridine, N1-methylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methyluridine, 5-methoxyuridine, and 2'-O-methyl uridine.

E42. An immunomodulatory therapeutic composition, comprising:

one or more mRNA each having an open reading frame encoding a KRAS activating oncogene mutation peptide;

one or more mRNA each having an open reading frame encoding a constitutively active human STING polypeptide; and a pharmaceutically acceptable carrier.

E43. The immunomodulatory therapeutic composition of embodiment 42, wherein the constitutively active human STING polypeptide comprises mutation V155M.

E44. The immunomodulatory therapeutic composition of embodiment 43, wherein the constitutively active human STING polypeptide comprises an amino acid sequence shown in SEQ ID NO: 1.

E45. The immunomodulatory therapeutic composition of any one of embodiments 42-44, wherein the mRNA encoding the constitutively active human STING polypeptide comprises a 3' UTR comprising at least one miR-122 microRNA binding site.

E46. The immunomodulatory therapeutic composition of any one of embodiments 42-45, wherein the KRAS activating oncogene mutation peptide is selected from G12D, G12V, G12S, G12C, G12A, G12R, and G13D.

E47. The immunomodulatory therapeutic composition of embodiment 46, wherein the KRAS activating oncogene mutation peptide is selected from G12D, G12V, G12C, and G13D.

E48. The immunomodulatory therapeutic composition of any one of embodiments 42-47, wherein the mRNA has an open reading frame encoding a concatemer of two or more KRAS activating oncogene mutation peptides.

E49. The immunomodulatory therapeutic composition of embodiment 48, wherein the concatemer comprises 3, 4, 5, 6, 7, 8, 9 or 10 KRAS activating oncogene mutation peptides.

E50. The immunomodulatory therapeutic composition of embodiment 49, wherein the concatemer comprises 4 KRAS activating oncogene mutation peptides.

E51. The immunomodulatory therapeutic composition of embodiment 50, wherein the concatemer comprises G12D, G12V, G12C, and G13D.

E52. The immunomodulatory therapeutic composition of embodiment 51, wherein the concatemer comprises from N- to C-terminus G12D, G12V, G13D, and G12C.

E53. The immunomodulatory therapeutic composition of embodiment 51, wherein the concatemer comprises from N- to C-terminus G12C, G13D, G12V, and G12D.

E54. The immunomodulatory therapeutic composition of any one of embodiments 42-47, wherein the composition comprises 1, 2, 3, or 4 mRNAs encoding 1, 2, 3, or 4 KRAS activating oncogene mutation peptides.

E55. The immunomodulatory therapeutic composition of embodiment 54, wherein the composition comprises 4 mRNAs encoding 4 KRAS activating oncogene mutation peptides.

E56. The immunomodulatory therapeutic composition of embodiment 54, wherein the 4 KRAS activating oncogene mutation peptides comprise G12D, G12V, G12C, and G13D.

E57. The immunomodulatory therapeutic composition of any one of embodiments 42-56, wherein the KRAS activating oncogene mutation peptide comprises 10-30, 15-25, or 20-25 amino acids in length.

E58. The immunomodulatory therapeutic composition of embodiment 57, wherein the KRAS activating oncogene mutation peptide comprises 20, 21, 22, 23, 24, or 25 amino acids in length.

E59. The immunomodulatory therapeutic composition of embodiment 58, wherein the activating oncogene mutation peptide comprises 25 amino acids in length.

E60. The immunomodulatory therapeutic composition of embodiment 51, wherein the concatemer comprises an amino acid sequence selected from the group set forth in SEQ ID NOs: 42-47, 73 and 137.

E61. The immunomodulatory therapeutic composition of embodiment 51, wherein the mRNA encoding the concatemer comprises the nucleotide sequence selected from the group set forth in SEQ ID NOs: 129-131, 133 and 138.

E62. The immunomodulatory therapeutic composition of embodiment 54, wherein the KRAS activating oncogene mutation peptides comprise an amino acid sequence selected from the group set forth in SEQ ID NOs: 36-41, 72 and 125.

E63. The immunomodulatory therapeutic composition of embodiment 54, wherein the KRAS activating oncogene mutation peptides comprise the amino acid sequence set forth in SEQ ID NOs: 39-41.

E64. The immunomodulatory therapeutic composition of embodiment 55, wherein the KRAS activating oncogene mutation peptides comprise the amino acid sequences set forth in SEQ ID NOs: 39-41 and 72.

E65. The immunomodulatory therapeutic composition of embodiment 63, wherein the mRNA encoding the KRAS activating oncogene mutation peptide comprises a nucleotide sequence selected from the group set forth in SEQ ID NOs: 126-128.

E66. The immunomodulatory therapeutic composition of embodiment 64, wherein the mRNA encoding the KRAS activating oncogene mutation peptide comprises the nucleotide sequences set forth in SEQ ID NOs: 126-128 and 132.

E67. The immunomodulatory therapeutic composition of any one of embodiments 42-66, wherein each mRNA is formulated in the same or different lipid nanoparticle.

E68. The immunomodulatory therapeutic composition of embodiment 67, wherein each mRNA encoding a KRAS activating oncogene mutation peptide is formulated in the same or different lipid nanoparticle.

E69. The immunomodulatory therapeutic composition of embodiment 68, wherein each mRNA encoding constitutively active human STING is formulated in the same or different lipid nanoparticle.

E70. The immunomodulatory therapeutic composition of any one of embodiments 68-69, wherein each mRNA encoding a KRAS activating oncogene mutation peptide is formulated in the same lipid nanoparticle and each mRNA encoding constitutively active human STING is formulated in a different lipid nanoparticle.

E71. The immunomodulatory therapeutic composition of any one of embodiments 68-69, wherein each mRNA encoding a KRAS activating oncogene mutation peptide is formulated in the same lipid nanoparticle and each mRNA encoding constitutively active human STING is formulated in the same lipid nanoparticle as each mRNA encoding a KRAS activating oncogene mutation peptide.

E72. The immunomodulatory therapeutic composition of any one of embodiments 68-69, wherein each mRNA encoding a KRAS activating oncogene mutation peptide is formulated in a different lipid nanoparticle and each mRNA encoding constitutively active human STING is formulated in the same lipid nanoparticle as each mRNA encoding each KRAS activating oncogene mutation peptide.

E73. The immunomodulatory therapeutic composition of any one of embodiments 68-72, wherein the lipid nanoparticle comprises a molar ratio of about 20-60% ionizable amino lipid:5-25% phospholipid:25-55% sterol; and 0.5-15% PEG-modified lipid.

E74. The immunomodulatory therapeutic composition of embodiment 73, wherein the ionizable amino lipid is selected from the group consisting of for example, 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319).

E75. The immunomodulatory therapeutic composition of any one of embodiments 42-74, wherein each mRNA includes at least one chemical modification.

E76. The immunomodulatory therapeutic composition of embodiment 75, wherein the chemical modification is selected from the group consisting of pseudouridine, N1-methylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methyluridine, 5-methoxyuridine, and 2'-O-methyl uridine.

E77. A lipid nanoparticle comprising:

an mRNA having an open reading frame encoding a concatemer of 4 KRAS activating oncogene mutation peptides, wherein the 4 KRAS activating oncogene mutation peptides comprise G12D, G12V, G12C, and G13D; and an mRNA having an open reading frame encoding a constitutively active human STING polypeptide.

E78. The lipid nanoparticle of embodiment 77, wherein the concatemer comprises from N- to C-terminus G12D, G12V, G13D, and G12C.

E79. The lipid nanoparticle of embodiment 77, wherein the concatemer comprises from N- to C-terminus G12C, G13D, G12V, and G12D.

E80. The lipid nanoparticle of any one of embodiments 77 to 79, wherein each KRAS activating oncogene mutation peptide comprises 20, 21, 22, 23, 24, or 25 amino acids in length.

E81. The lipid nanoparticle of embodiment 80, wherein each KRAS activating oncogene mutation peptide comprises 25 amino acids in length.

E82. The lipid nanoparticle of embodiment 77, wherein the concatemer comprises an amino acid sequence set forth in SEQ ID NO: 137.

E83. The lipid nanoparticle of embodiment 77, wherein the mRNA encoding the concatemer of 4 KRAS activating oncogene mutation peptides comprises the nucleotide sequence set forth in SEQ ID NO: 138.

E84. The lipid nanoparticle of any one of embodiments 77-83, wherein the constitutively active human STING polypeptide comprises mutation V155M.

E85. The lipid nanoparticle of embodiment 84, wherein the constitutively active human STING polypeptide comprises the amino acid sequence shown in SEQ ID NO: 1.

E86. The lipid nanoparticle of embodiment 84, wherein the mRNA encoding the constitutively active human STING polypeptide comprises a 3' UTR comprising at least one miR-122 microRNA binding site.

E87. The lipid nanoparticle of embodiment 84, wherein the mRNA encoding the constitutively active human STING polypeptide comprises the nucleotide sequence shown in SEQ ID NO: 139.

E88. A lipid nanoparticle comprising:

an mRNA having an open reading frame encoding a KRAS activating oncogene mutation peptide comprising G12D;

an mRNA having an open reading frame encoding a KRAS activating oncogene mutation peptide comprising G12V;

an mRNA having an open reading frame encoding a KRAS activating oncogene mutation peptide comprising G12C;

an mRNA having an open reading frame encoding a KRAS activating oncogene mutation peptide comprising G13D; and an mRNA having an open reading frame encoding a constitutively active human STING polypeptide.

E89. The lipid nanoparticle of embodiment 88, wherein each KRAS activating oncogene mutation peptide comprises 20, 21, 22, 23, 24, or 25 amino acids in length.

E90. The lipid nanoparticle of embodiment 89, wherein each KRAS activating oncogene mutation peptide comprises 25 amino acids in length.

E91. The lipid nanoparticle of embodiment 88, wherein the KRAS activating oncogene mutation peptides comprise the amino acid sequences set forth in SEQ ID NOs: 39-41 and 72.

E92. The lipid nanoparticle of embodiment 88, wherein the mRNAs encoding the KRAS activating oncogene mutation peptides comprise the nucleotide sequences set forth in SEQ ID NOs: 126-128 and 132.

E93. The lipid nanoparticle of any one of embodiments 88-92, wherein the constitutively active human STING polypeptide comprises mutation V155M.

E94. The lipid nanoparticle of embodiment 93, wherein the constitutively active human STING polypeptide comprises the amino acid sequence shown in SEQ ID NO: 1.

E95. The lipid nanoparticle of embodiment 94, wherein the mRNA encoding the constitutively active human STING polypeptide comprises a 3' UTR comprising at least one miR-122 microRNA binding site.

E96. The lipid nanoparticle of embodiment 94, wherein the mRNA encoding the constitutively active human STING polypeptide comprises the nucleotide sequence shown in SEQ ID NO:

139.

E97. A lipid nanoparticle comprising:

an mRNA having an open reading frame encoding a KRAS activating oncogene mutation peptide comprising G12D; and an mRNA having an open reading frame encoding a constitutively active human STING polypeptide.

E98. A lipid nanoparticle comprising:

an mRNA having an open reading frame encoding a KRAS activating oncogene mutation peptide comprising G12V; and an mRNA having an open reading frame encoding a constitutively active human STING polypeptide.

E99. A lipid nanoparticle comprising:

an mRNA having an open reading frame encoding a KRAS activating oncogene mutation peptide comprising G12C; and an mRNA having an open reading frame encoding a constitutively active human STING polypeptide.

E100. A lipid nanoparticle comprising:

an mRNA having an open reading frame encoding a KRAS activating oncogene mutation peptide comprising G13D; and an mRNA having an open reading frame encoding a constitutively active human STING polypeptide.

E101. The lipid nanoparticle of any one of embodiments 97-100, wherein each KRAS activating oncogene mutation peptide comprises 20, 21, 22, 23, 24, or 25 amino acids in length.

E102. The lipid nanoparticle of embodiment 101, wherein each KRAS activating oncogene mutation peptide comprises 25 amino acids in length.

E103. The lipid nanoparticle of embodiment 97, wherein the KRAS activating oncogene mutation peptide comprises the amino acid sequence set forth in SEQ ID NO: 39.

E104. The lipid nanoparticle of embodiment 97, wherein the mRNA encoding the KRAS activating oncogene mutation peptide comprises the nucleotide sequence set forth in SEQ ID NOs: 126.

E105. The lipid nanoparticle of embodiment 98, wherein the KRAS activating oncogene mutation peptide comprises the amino acid sequence set forth in SEQ ID NO:40.

E106. The lipid nanoparticle of embodiment 98, wherein the mRNA encoding the KRAS activating oncogene mutation peptide comprises the nucleotide sequence set forth in SEQ ID NOs: 127.

E107. The lipid nanoparticle of embodiment 99, wherein the KRAS activating oncogene mutation peptide comprises the amino acid sequence set forth in SEQ ID NO: 72.

E108. The lipid nanoparticle of embodiment 99, wherein the mRNA encoding the KRAS activating oncogene mutation peptide comprises the nucleotide sequence set forth in SEQ ID NO: 132.

E109. The lipid nanoparticle of embodiment 100, wherein the KRAS activating oncogene mutation peptide comprises the amino acid sequence set forth in SEQ ID NO: 41.

E110. The lipid nanoparticle of embodiment 100, wherein the mRNA encoding the KRAS activating oncogene mutation peptide comprises the nucleotide sequence set forth in SEQ ID NO: 128.

E111. The lipid nanoparticle of any one of embodiments 97-110, wherein the constitutively active human STING polypeptide comprises mutation V155M.

E112. The lipid nanoparticle of embodiment 111, wherein the constitutively active human STING polypeptide comprises the amino acid sequence shown in SEQ ID NO: 1.

E113. The lipid nanoparticle of embodiment 111, wherein the mRNA encoding the constitutively active human STING polypeptide comprises a 3' UTR comprising at least one miR-122 microRNA binding site.

E114. The lipid nanoparticle of embodiment 111, wherein the mRNA encoding the constitutively active human STING polypeptide comprises the nucleotide sequence shown in SEQ ID NO: 139.

E115. A method for treating a subject, comprising:

administering to a subject having cancer the immunomodulatory therapeutic composition of any one of embodiments 1-76 or the lipid nanoparticle of any one of embodiments 77-114.

E116. The method of embodiment 115, wherein immunomodulatory therapeutic composition or lipid nanoparticle is administered in combination with a cancer therapeutic agent.

E117. The method of embodiment 115 or 116, wherein immunomodulatory therapeutic composition or lipid nanoparticle is administered in combination with an inhibitory checkpoint polypeptide.

E118. The method of embodiment 117, wherein the inhibitory checkpoint polypeptide is an antibody or fragment thereof that specifically binds to a molecule selected from the group consisting of PD-1, PD-L1, TIM-3, VISTA, A2AR, B7-H3, B7-H4, BTLA, CTLA-4, IDO, KIR and LAGS.

E119. The method of any one of embodiments 115-118, wherein the cancer is selected from cancer of the pancreas, peritoneum, large intestine, small intestine, biliary tract, lung, endometrium, ovary, genital tract, gastrointestinal tract, cervix, stomach, urinary tract, colon, rectum, and hematopoietic and lymphoid tissues.

E120. The method of embodiment 113, wherein the cancer is colorectal cancer.

E121. A lipid nanoparticle comprising:

a first mRNA having an open reading frame encoding a concatemer of 4 KRAS activating oncogene mutation peptides, wherein the 4 KRAS activating oncogene mutation peptides comprise G12D, G12V, G12C, and G13D; and a second mRNA having an open reading frame encoding a constitutively active human STING polypeptide, wherein the first mRNA and second mRNA are present at a KRAS:STING mass ratio selected from the group consisting of 1:1, 2:1, 3:1, 4:1, 5:1, 6:1, 7:1, 8:1, 9:1 or 10:1.

E122. The lipid nanoparticle of embodiment 121, wherein the concatemer comprises from N- to C-terminus G12D, G12V, G13D, and G12C.

E123. The lipid nanoparticle of embodiment 121, wherein the concatemer comprises from N- to C-terminus G12C, G13D, G12V, and G12D.

E124. The lipid nanoparticle of any one of embodiments 121 to 123, wherein each KRAS activating oncogene mutation peptide comprises 20, 21, 22, 23, 24, or 25 amino acids in length.

E125. The lipid nanoparticle of embodiment 124, wherein each KRAS activating oncogene mutation peptide comprises 25 amino acids in length.

E126. The lipid nanoparticle of embodiment 121, wherein the concatemer comprises an amino acid sequence set forth in SEQ ID NO: 137.

E127. The lipid nanoparticle of embodiment 121, wherein the mRNA encoding the concatemer of 4 KRAS activating oncogene mutation peptides comprises the nucleotide sequence set forth in SEQ ID NO: 138.

E128. The lipid nanoparticle of any one of embodiments 121-127, wherein the constitutively active human STING polypeptide comprises mutation V155M.

E129. The lipid nanoparticle of embodiment 128, wherein the constitutively active human STING polypeptide comprises the amino acid sequence shown in SEQ ID NO: 1.

E130. The lipid nanoparticle of embodiment 128, wherein the mRNA encoding the constitutively active human STING polypeptide comprises a 3' UTR comprising at least one miR-122 microRNA binding site.

E131. The lipid nanoparticle of embodiment 128, wherein the mRNA encoding the constitutively active human STING polypeptide comprises the nucleotide sequence shown in SEQ ID NO: 139.

E132. A lipid nanoparticle comprising:

a first mRNA having an open reading frame encoding a KRAS activating oncogene mutation peptide comprising G12D;

a second mRNA having an open reading frame encoding a KRAS activating oncogene mutation peptide comprising G12V;

a third mRNA having an open reading frame encoding a KRAS activating oncogene mutation peptide comprising G12C;

a fourth mRNA having an open reading frame encoding a KRAS activating oncogene mutation peptide comprising G13D; and a fifth mRNA having an open reading frame encoding a constitutively active human STING polypeptide, wherein the first, second, third, fourth and fifth mRNAs are present at a KRAS:STING mass ratio selected from the group consisting of 1:1, 2:1, 3:1, 4:1, 5:1, 6:1, 7:1, 8:1, 9:1 or 10:1.

E133. The lipid nanoparticle of embodiment 132, wherein each KRAS activating oncogene mutation peptide comprises 20, 21, 22, 23, 24, or 25 amino acids in length.

E134. The lipid nanoparticle of embodiment 133, wherein each KRAS activating oncogene mutation peptide comprises 25 amino acids in length.

E135. The lipid nanoparticle of embodiment 132, wherein the KRAS activating oncogene mutation peptides comprise the amino acid sequences set forth in SEQ ID NOs: 39-41 and 72.

E136. The lipid nanoparticle of embodiment 132, wherein the mRNAs encoding the KRAS activating oncogene mutation peptides comprise the nucleotide sequences set forth in SEQ ID NOs: 126-128 and 132.

E137. The lipid nanoparticle of any one of embodiments 132-136, wherein the constitutively active human STING polypeptide comprises mutation V155M.

E138. The lipid nanoparticle of embodiment 137, wherein the constitutively active human STING polypeptide comprises the amino acid sequence shown in SEQ ID NO: 1.

E139. The lipid nanoparticle of embodiment 138, wherein the mRNA encoding the constitutively active human STING polypeptide comprises a 3' UTR comprising at least one miR-122 microRNA binding site.

E140. The lipid nanoparticle of embodiment 137, wherein the mRNA encoding the constitutively active human STING polypeptide comprises the nucleotide sequence shown in SEQ ID NO: 139.

E141. The lipid nanoparticle of any one of embodiments 121-131, wherein the first and second mRNAs are present at a KRAS:STING mass ratio of 1:1.

E142. The lipid nanoparticle of any one of embodiments 121-131, wherein the first and second mRNAs are present at a KRAS:STING mass ratio of 2:1.

E143. The lipid nanoparticle of any one of embodiments 121-131, wherein the first and second mRNAs are present at a KRAS:STING mass ratio of 3:1.

E144. The lipid nanoparticle of any one of embodiments 121-131, wherein the first and second mRNAs are present at a KRAS:STING mass ratio of 4:1.

E145. The lipid nanoparticle of any one of embodiments 121-131, wherein the first and second mRNAs are present at a KRAS:STING mass ratio of 5:1.

E146. The lipid nanoparticle of any one of embodiments 121-131, wherein the first and second mRNAs are present KRAS:STING mass ratio of 6:1.

E147. The lipid nanoparticle of any one of embodiments 121-131, wherein the first and second mRNAs are present at a KRAS:STING mass ratio of 7:1.

E148. The lipid nanoparticle of any one of embodiments 121-131, wherein the first and second mRNAs are present at a KRAS:STING mass ratio of 8:1.

E149. The lipid nanoparticle of any one of embodiments 121-140, wherein the first and second mRNAs are present at a KRAS:STING mass ratio of 9:1.

E150. The lipid nanoparticle of any one of embodiments 121-140, wherein the first and second mRNAs are present at a KRAS:STING mass ratio of 10:1.

E151. A composition comprising:

(i) a first mRNA having an open reading frame encoding a concatemer of 4 KRAS activating oncogene mutation peptides, wherein the concatemer comprises from N- to C-terminus G12D, G12V, G13D, and G12C, and (ii) a second mRNA having an open reading frame encoding a constitutively active human STING polypeptide, wherein the constitutively active human STING polypeptide comprises mutation V155M, wherein the first mRNA and second mRNA are present at a KRAS:STING mass ratio selected from the group consisting of 1:1, 2:1, 3:1, 4:1, 5:1, 6:1, 7:1, 8:1, 9:1 or 10:1;

and a pharmaceutically acceptable carrier.

E152. The composition of embodiment 151, wherein the concatemer of 4 KRAS activating oncogene mutation peptides comprises the amino acid sequence set forth in SEQ ID NO: 137.

E153. The composition of embodiment 151 or 152, wherein the first mRNA encoding the concatemer of 4 KRAS activating oncogene mutation peptides comprises the nucleotide sequence set forth in SEQ ID NO: 169.

E154. The composition of any one of embodiments 151-153, wherein the constitutively active human STING polypeptide comprises the amino acid sequence shown in SEQ ID NO: 1.

E155. The composition of any one of embodiments 151-154, wherein the mRNA encoding the constitutively active human STING polypeptide comprises the nucleotide sequence shown in SEQ ID NO: 170.

E156. The composition of any one of embodiments 151-155, wherein the first mRNA comprises a 5' UTR comprising the nucleotide sequence set forth in SEQ ID NO: 176.

E157. The composition of any one of embodiments 151-155, wherein the second mRNA comprises a 5' UTR comprising the nucleotide sequence set forth in SEQ ID NO: 176.

E158. The composition of any one of embodiments 151-157, wherein the second mRNA encoding the constitutively active human STING polypeptide comprises a 3' UTR having a miR-122 microRNA binding site.

E159. The composition of embodiment 158, wherein the miR-122 microRNA binding site comprises the nucleotide sequence shown in SEQ ID NO: 175.

E160. The composition of any one of embodiments 151-159, wherein the first mRNA and second mRNA each comprise a poly A tail.

E161. The composition of embodiment 160, wherein the poly A tail comprises about 100 nucleotides.

E162. The composition of any one of embodiments 151-161, wherein the first and second mRNAs each comprise a 5' Cap 1 structure.

E163. The composition of any one of embodiments 151-162, wherein the first and second mRNAs each comprise at least one chemical modification.

E164. The composition of embodiment 163, wherein the chemical modification is N1-methylpseudouridine.

E165. The composition of embodiment 164, wherein the first mRNA is fully modified with N1-methylpseudouridine.

E166. The composition of embodiment 164, wherein the second mRNA is fully modified with N1-methylpseudouridine.

E167. The composition of any one of embodiments 151-166, wherein the pharmaceutically acceptable carrier comprises a buffer solution.

E168. A composition comprising:

(i) a first mRNA comprising the nucleotide sequence set forth in SEQ ID NO: 167, and (ii) a second mRNA comprising the nucleotide sequence set forth in SEQ ID NO: 168, wherein the first and second mRNA are each fully modified with N1-methylpseudouridine, and wherein the first mRNA and second mRNA are present at a KRAS:STING mass ratio selected from the group consisting of 1:1, 2:1, 3:1, 4:1, 5:1, 6:1, 7:1, 8:1, 9:1 or 10:1;

and a pharmaceutically acceptable carrier.

E169. The composition of embodiment 168, wherein the pharmaceutically acceptable carrier comprises a buffer solution.

E170. The composition of any one of embodiments 151-169, wherein the first and second mRNAs are present at a KRAS:STING mass ratio of 1:1.

E171. The composition of any one of embodiments 151-169, wherein the first and second mRNAs are present at a KRAS:STING mass ratio of 2:1.

E172. The composition of any one of embodiments 151-169, wherein the first and second mRNAs are present at a KRAS:STING mass ratio of 3:1.

E173. The composition of any one of embodiments 151-169, wherein the first and second mRNAs are present at a KRAS:STING mass ratio of 4:1.

E174. The composition of any one of embodiments 151-169, wherein the first and second mRNAs are present at a KRAS:STING mass ratio of 5:1.

E175. The composition of any one of embodiments 151-169, wherein the first and second mRNAs are present KRAS:STING mass ratio of 6:1.

E176. The composition of any one of embodiments 151-169, wherein the first and second mRNAs are present at a KRAS:STING mass ratio of 7:1.

E177. The composition of any one of embodiments 151-169, wherein the first and second mRNAs are present at a KRAS:STING mass ratio of 8:1.

E178. The composition of any one of embodiments 151-169, wherein the first and second mRNAs are present at a KRAS:STING mass ratio of 9:1.

E179. The composition of any one of embodiments 151-169, wherein the first and second mRNAs are present at a KRAS:STING mass ratio of 10:1.

E180. The composition of any one of embodiments 151-179, which is formulated in a lipid nanoparticle.

E181. The composition of embodiment 180, wherein the lipid nanoparticle comprises a molar ratio of about 20-60% ionizable amino lipid:5-25% phospholipid:25-55% sterol; and 0.5-15% PEG-modified lipid.

E182. The composition of embodiment 181, wherein the lipid nanoparticle comprises a molar ratio of about 50% Compound 25:about 10% DSPC:about 38.5% cholesterol; and about 1.5% PEG-DMG.

E183. The composition of any one of embodiments 151-182, which is formulated for intramuscular delivery.

E184. A lipid nanoparticle comprising:

(i) a first mRNA having an open reading frame encoding a concatemer of 4 KRAS activating oncogene mutation peptides, wherein the concatemer comprises from N- to C-terminus G12D, G12V, G13D, and G12C; and (ii) a second mRNA having an open reading frame encoding a constitutively active human STING polypeptide, wherein the constitutively active human STING polypeptide comprises mutation V155M, wherein the first mRNA and second mRNA are present at a KRAS:STING mass ratio of 5:1.

E185. The lipid nanoparticle of embodiment 184, wherein the concatemer of 4 KRAS activating oncogene mutation peptides comprises the amino acid sequence set forth in SEQ ID NO: 137.

E186. The lipid nanoparticle of embodiment 184 or 185, wherein the first mRNA encoding the concatemer of 4 KRAS activating oncogene mutation peptides comprises the nucleotide sequence set forth in SEQ ID NO: 169.

E187. The lipid nanoparticle of any one of embodiments 184-186, wherein the constitutively active human STING polypeptide comprises the amino acid sequence shown in SEQ ID NO: 1.

E188. The lipid nanoparticle of any one of embodiments 184-187, wherein the mRNA encoding the constitutively active human STING polypeptide comprises the nucleotide sequence shown in SEQ ID NO: 170.

E189. The lipid nanoparticle of any one of embodiments 184-188, wherein the first mRNA comprises a 5' UTR comprising the nucleotide sequence shown in SEQ ID NO: 176.

E190. The lipid nanoparticle of any one of embodiments 184-188, wherein the second mRNA comprises a 5' UTR comprising the nucleotide sequence shown in SEQ ID NO: 176.

E191. The lipid nanoparticle of any one of embodiments 184-190, wherein the second mRNA encoding the constitutively active human STING polypeptide comprises a 3' UTR having a miR-122 microRNA binding site.

E192. The lipid nanoparticle of embodiment 191, wherein the miR-122 microRNA binding site comprises the nucleotide sequence shown in SEQ ID NO: 175.

E193. The lipid nanoparticle of any one of embodiments 184-192, wherein the first and second mRNAs each comprise a poly A tail.

E194. The lipid nanoparticle of embodiment 193, wherein the poly A tail comprises about 100 nucleotides.

E195. The lipid nanoparticle of any one of embodiments 184-194, wherein the first and second mRNAs each comprise a 5' Cap 1 structure.

E196. The lipid nanoparticle of any one of embodiments 184-195, wherein the first and second mRNAs each comprise at least one chemical modification.

E197. The lipid nanoparticle of embodiment 196, wherein the chemical modification is N1-methylpseudouridine.

E198. The lipid nanoparticle of embodiment 197, wherein the first mRNA is fully modified with N1-methylpseudouridine.

E199. The lipid nanoparticle of embodiment 197, wherein the second mRNA is fully modified with N1-methylpseudouridine.

E200. A lipid nanoparticle comprising:

(i) a first mRNA comprising the nucleotide sequence set forth in SEQ ID NO: 167; and (ii) a second mRNA comprising the nucleotide sequence set forth in SEQ ID NO: 168, wherein the first and second mRNA are each fully modified with N1-methylpseudouridine, and wherein the first mRNA and second mRNA are present at a KRAS:STING mass ratio of 5:1.

E201. The lipid nanoparticle of any one of embodiments 184-200, wherein the lipid nanoparticle comprises a molar ratio of about 20-60% ionizable amino lipid:5-25% phospholipid:25-55% sterol; and 0.5-15% PEG-modified lipid.

E202. The lipid nanoparticle of embodiment 201, wherein the lipid nanoparticle comprises a molar ratio of about 50% Compound 25:about 10% DSPC:about 38.5% cholesterol; and about 1.5% PEG-DMG.

E203. A pharmaceutical composition comprising the lipid nanoparticle of any one of embodiments 184-202, and a pharmaceutically acceptable carrier.

E204. The pharmaceutical composition of embodiment 203 which is formulated for intramuscular delivery.

E205. The lipid nanoparticle of any one of embodiments 184-202, and an optional pharmaceutically acceptable carrier, or the pharmaceutical composition of any one of embodiments 203-204 for use in treating or delaying progression of cancer in an individual, wherein the treatment comprises administration of the composition in combination with a second composition, wherein the second composition comprises a checkpoint inhibitor polypeptide and an optional pharmaceutically acceptable carrier.

E206. Use of a lipid nanoparticle of any one of embodiments 184-202, and an optional pharmaceutically acceptable carrier, in the manufacture of a medicament for treating or delaying progression of cancer in an individual, wherein the medicament comprises the lipid nanoparticle and an optional pharmaceutically acceptable carrier and wherein the treatment comprises administration of the medicament in combination with a composition comprising a checkpoint inhibitor polypeptide and an optional pharmaceutically acceptable carrier.

E207. A kit comprising a container comprising the lipid nanoparticle of any one of embodiments 184-202, and an optional pharmaceutically acceptable carrier, or the pharmaceutical composition of any one of embodiments 203-204, and a package insert comprising instructions for administration of the lipid nanoparticle or pharmaceutical composition for treating or delaying progression of cancer in an individual.

E208. The kit of embodiment 207, wherein the package insert further comprises instructions for administration of the lipid nanoparticle or pharmaceutical composition in combination with a composition comprising a checkpoint inhibitor polypeptide and an optional pharmaceutically acceptable carrier for treating or delaying progression of cancer in an individual.

E209. A kit comprising a medicament comprising a lipid nanoparticle of any one of embodiments 184-202, and an optional pharmaceutically acceptable carrier, or the pharmaceutical composition of any one of embodiments 203-204, and a package insert comprising instructions for administration of the medicament alone or in combination with a composition comprising a checkpoint inhibitor polypeptide and an optional pharmaceutically acceptable carrier for treating or delaying progression of cancer in an individual.

E210. The kit of embodiment 209, wherein the kit further comprises a package insert comprising instructions for administration of the first medicament prior to, current with, or subsequent to administration of the second medicament for treating or delaying progression of cancer in an individual.

E211. The lipid nanoparticle of any one of embodiments 184-202, the composition of any one of embodiments 203-204, the use of embodiments 205-206 or the kit of any one of embodiments 207-210, wherein the checkpoint inhibitor polypeptide inhibits PD1, PD-L1, CTLA4, or a combination thereof.

E212. The lipid nanoparticle of any one of embodiments 184-202, the composition of embodiments 203-204, the use of embodiment 205-206 or the kit of any one of embodiments 207-210, wherein the checkpoint inhibitor polypeptide is an antibody.

E213. The lipid nanoparticle of any one of embodiments 184-202, the composition of embodiments 203-204, the use of embodiment 205-206 or the kit of any one of embodiments 207-210, wherein the checkpoint inhibitor polypeptide is an antibody selected from an anti-CTLA4 antibody or antigen-binding fragment thereof that specifically binds CTLA4, an anti-PD1 antibody or antigen-binding fragment thereof that specifically binds PD1, an anti-PD-L1 antibody or antigen-binding fragment thereof that specifically binds PD-L1, and a combination thereof.

E214. The lipid nanoparticle of any one of embodiments 184-202, the composition of embodiments 203-204, the use of embodiment 205-206 or the kit of any one of embodiments 207-210, wherein the checkpoint inhibitor polypeptide is an anti-PD-L1 antibody selected from atezolizumab, avelumab, or durvalumab.

E215. The lipid nanoparticle of any one of embodiments 184-202, the composition of embodiments 203-204, the use of embodiment 205-206 or the kit of any one of embodiments 197-200, wherein the checkpoint inhibitor polypeptide is an anti-CTLA-4 antibody selected from tremelimumab or ipilimumab.

E216. The lipid nanoparticle of any one of embodiments 184-202, the composition of embodiments 203-204, the use of embodiment 205-206 or the kit of any one of embodiments 197-200, wherein the checkpoint inhibitor polypeptide is an anti-PD1 antibody selected from nivolumab or pembrolizumab.

E217. A method of reducing or decreasing a size of a tumor or inhibiting a tumor growth in a subject in need thereof comprising administering to the subject the lipid nanoparticle of any one of embodiments 184-202 or the composition of any one of embodiments 203-204.

E218. A method of inducing an anti-tumor response in a subject with cancer, comprising administering to the subject the lipid nanoparticle of any one of embodiments 184-202 or the composition of any one of embodiments 203-204.

E219. The method of embodiment 218, wherein the anti-tumor response comprises a T-cell response.

E220. The method of embodiment 219, wherein the T-cell response comprises $CD8^+$ T cells.

E221. The method of any one of embodiments 217-220, wherein the composition is administered by intramuscular injection.

E222. The method of any one of embodiments 217-220, further comprising administering a second composition comprising a checkpoint inhibitor polypeptide, and an optional pharmaceutically acceptable carrier.

E223. The method of embodiment 222, wherein the checkpoint inhibitor polypeptide inhibits PD1, PD-L1, CTLA4, or a combination thereof.

E224. The method of embodiment 223, wherein the checkpoint inhibitor polypeptide is an antibody.

E225. The method of embodiment 224, wherein the checkpoint inhibitor polypeptide is an antibody selected from an anti-CTLA4 antibody or antigen-binding fragment thereof that specifically binds CTLA4, an anti-PD1 antibody or antigen-binding fragment thereof that specifically binds PD1, an anti-PD-L1 antibody or antigen-binding fragment thereof that specifically binds PD-L1, and a combination thereof.

E226. The method of embodiment 225, wherein the checkpoint inhibitor polypeptide is an anti-PD-L1 antibody selected from atezolizumab, avelumab, or durvalumab.

E227. The method of embodiment 225, wherein the checkpoint inhibitor polypeptide is an anti-CTLA-4 antibody selected from tremelimumab or ipilimumab.

E228. The method of embodiment 225, wherein the checkpoint inhibitor polypeptide is an anti-PD1 antibody selected from nivolumab or pembrolizumab.

E229. The method of any one of embodiments 222-228, wherein the composition comprising the checkpoint inhibitor polypeptide is administered by intravenous injection.

E230. The method of embodiment 229, wherein the composition comprising the checkpoint inhibitor polypeptide is administered once every 2 to 3 weeks.

E231. The method of embodiment 229, wherein the composition comprising the checkpoint inhibitor polypeptide is administered once every 2 weeks or once every 3 weeks.

E232. The method of any one of embodiments 222-231, wherein the composition comprising the checkpoint inhibitor polypeptide is administered prior to, concurrent with, or subsequent to administration of the lipid nanoparticle or pharmaceutical composition thereof.

E233. The method of any one of embodiments 217-232, wherein the subject has a histologically confirmed KRAS mutation selected from G12D, G12V, G13D or G12C.

E234. The method of any one of embodiments 217-233, wherein the tumor is metastatic colorectal cancer.

E235. The method of any of embodiments 217-233, wherein the tumor is non-small cell lung cancer (NSCLC).

E236. The method of any of embodiments 217-233, wherein the tumor is pancreatic cancer.

E237. An immunomodulatory therapeutic composition, comprising:

one or more mRNA each having an open reading frame encoding an activating oncogene mutation peptide, and a pharmaceutically acceptable carrier or excipient.

E238. The immunomodulatory therapeutic composition of embodiment 237, wherein the activating oncogene mutation is a KRAS mutation E239. The immunomodulatory therapeutic composition of embodiment 238, wherein the KRAS mutation is a G12 mutation.

E240. The immunomodulatory therapeutic composition of embodiment 239, wherein the G12 KRAS mutation is selected from a G12D, G12V, G12S, G12C, G12A, and a G12R KRAS mutation E241. The immunomodulatory therapeutic composition of embodiment 239, wherein the G12 KRAS mutation is selected from a G12D, G12V, and a G12S KRAS mutation.

E242. The immunomodulatory therapeutic composition of embodiment 238, wherein the KRAS mutation is a G13 mutation.

E243. The immunomodulatory therapeutic composition of embodiment 242, wherein the G13 KRAS mutation is a G13D KRAS mutation.

E244. The immunomodulatory therapeutic composition of embodiment 237, wherein the activating oncogene mutation is a H-RAS or N-RAS mutation.

E245. The immunomodulatory therapeutic composition of any one of embodiments 237-244, wherein the mRNA has an open reading frame encoding a concatemer of two or more activating oncogene mutation peptides.

E246. The immunomodulatory therapeutic composition of embodiment 245, wherein at least two of the peptide epitopes are separated from one another by a single Glycine.

E247. The immunomodulatory therapeutic composition of any one of embodiments 245-246, wherein the concatemer comprises 3-10 activating oncogene mutation peptides.

E248. The activating oncogene mutation peptides of any one of embodiments 245-247, wherein all of the peptide epitopes are separated from one another by a single Glycine.

E249. The activating oncogene mutation peptides of any one of embodiments 245-247, wherein at least two of the peptide epitopes are linked directly to one another without a linker.

E250. The immunomodulatory therapeutic composition of any one of embodiments 237-249, wherein the composition further comprises a cancer therapeutic agent.

E251. The immunomodulatory therapeutic composition of any one of embodiments 237-250, wherein the composition further comprises an inhibitory checkpoint polypeptide.

E252. The immunomodulatory therapeutic composition of embodiment 251, wherein the inhibitory checkpoint polypeptide is an antibody or fragment thereof that specifically binds to a molecule selected from the group consisting of PD-1, TIM-3, VISTA, A2AR, B7-H3, B7-H4, BTLA, CTLA-4, IDO, KIR and LAGS.

E253. The immunomodulatory therapeutic composition of any one of embodiments 237-252, wherein the composition further comprises a recall antigen.

E254. The immunomodulatory therapeutic composition of embodiment 253, wherein the recall antigen is an infectious disease antigen.

E255. The immunomodulatory therapeutic composition of any one of embodiments 237-254, wherein the composition does not comprise a stabilization agent.

E256. The immunomodulatory therapeutic composition of any one of embodiments 237-255, wherein the mRNA is formulated in a lipid nanoparticle carrier.

E257. The immunomodulatory therapeutic composition of embodiment 256, wherein the lipid nanoparticle carrier comprises a molar ratio of about 20-60% cationic lipid:5-25% non-cationic lipid:25-55% sterol; and 0.5-15% PEG-modified lipid.

E258. The immunomodulatory therapeutic composition of embodiment 257, wherein the cationic lipid is selected from the group consisting of for example, 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy)heptadecanedioate (L319).

E259. The immunomodulatory therapeutic composition of any one of embodiments 237-258, wherein the mRNA includes at least one chemical modification.

E260. The immunomodulatory therapeutic composition of embodiment 259, wherein the chemical modification is selected from the group consisting of pseudouridine, N1-methylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methyluridine, 5-methoxyuridine, and 2'-O-methyl uridine.

E261. A method for treating a subject, comprising: administering to a subject having cancer an immunomodulatory therapeutic composition of any one of embodiments 237-260.

E262. The method of embodiment 261, wherein immunomodulatory therapeutic composition is administered in combination with a cancer therapeutic agent.

E263. The method of embodiment 261 or 260, wherein immunomodulatory therapeutic composition is administered in combination with an inhibitory checkpoint polypeptide.

E264. The method of embodiment 263, wherein the inhibitory checkpoint polypeptide is an antibody or fragment thereof that specifically binds to a molecule selected from the group consisting of PD-1, TIM-3, VISTA, $A_2AR$, B7-H3, B7-H4, BTLA, CTLA-4, IDO, KIR and LAGS.

E265. The method of any one of embodiments 261-264, wherein the cancer is selected from cancer of the pancreas, peritoneum, large intestine, small intestine, biliary tract, lung, endometrium, ovary, genital tract, gastrointestinal tract, cervix, stomach, urinary tract, colon, rectum, and hematopoietic and lymphoid tissues.

E266. The method of embodiment 265, wherein the cancer is colorectal cancer.

Definitions

Administering: As used herein, "administering" refers to a method of delivering a composition to a subject or patient. A method of administration may be selected to target delivery (e.g., to specifically deliver) to a specific region or system of a body. For example, an administration may be parenteral (e.g., subcutaneous, intracutaneous, intravenous, intraperitoneal, intramuscular, intraarticular, intraarterial, intrasynovial, intrasternal, intrathecal, intralesional, or intracranial injection, as well as any suitable infusion technique), oral, trans- or intra-dermal, interdermal, rectal, intravaginal, topical (e.g. by powders, ointments, creams, gels, lotions, and/or drops), mucosal, nasal, buccal, enteral, vitreal, intratumoral, sublingual, intranasal; by intratracheal instillation, bronchial instillation, and/or inhalation; as an oral spray and/or powder, nasal spray, and/or aerosol, and/or through a portal vein catheter.

Approximately, about: As used herein, the terms "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Cancer: As used herein, "cancer" is a condition involving abnormal and/or unregulated cell growth. The term cancer encompasses benign and malignant cancers. Exemplary non-limiting cancers include adrenal cortical cancer, advanced cancer, anal cancer, aplastic anemia, bileduct cancer, bladder cancer, bone cancer, bone metastasis, brain tumors, brain cancer, breast cancer, childhood cancer, cancer of unknown primary origin, Castleman disease, cervical cancer, colorectal cancer, endometrial cancer, esophagus cancer, Ewing family of tumors, eye cancer, gallbladder cancer, gastrointestinal carcinoid tumors, gastrointestinal stromal tumors, gestational trophoblastic disease, Hodgkin disease, Kaposi sarcoma, renal cell carcinoma, laryngeal and hypopharyngeal cancer, acute lymphocytic leukemia, acute myeloid leukemia, chronic lymphocytic leukemia, chronic myeloid leukemia, chronic myelomonocytic leukemia, myelodysplastic syndrome (including refractory anemias and refractory cytopenias), myeloproliferative neoplasms or diseases (including polycythemia vera, essential thrombocytosis and primary myelofibrosis), liver cancer (e.g., hepatocellular carcinoma), non-small cell lung cancer, small cell lung cancer, lung carcinoid tumor, lymphoma of the skin, malignant mesothelioma, multiple myeloma, myelodysplasia syndrome, nasal cavity and paranasal sinus cancer, nasopharyngeal cancer, neuroblastoma, non-Hodgkin lymphoma, oral cavity and oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma in adult soft tissue, basal and squamous cell skin cancer, melanoma, small intestine cancer, stomach cancer, testicular cancer, throat cancer, thymus cancer, thyroid cancer, uterine sarcoma, vaginal cancer, vulvar cancer, Waldenstrom macroglobulinemia, Wilms tumor and secondary cancers caused by cancer treatment. In particular embodiments, the cancer is liver cancer (e.g., hepatocellular carcinoma) or colorectal cancer. In other embodiments, the cancer is a blood-based cancer or a hematopoetic cancer.

Cleavable Linker: As used herein, the term "cleavable linker" refers to a linker, typically a peptide linker (e.g., about 5-30 amino acids in length, typically about 10-20 amino acids in length) that can be incorporated into multicistronic mRNA constructs such that equimolar levels of multiple genes can be produced from the same mRNA. Non-limiting examples of cleavable linkers include the 2A family of peptides, including F2A, P2A, T2A and E2A, first discovered in picornaviruses, that when incorporated into an mRNA construct (e.g., between two polypeptide domains) function by making the ribosome skip the synthesis of a peptide bond at C-terminus of the 2A element, thereby leading to separation between the end of the 2A sequence and the next peptide downstream.

Conjugated: As used herein, the term "conjugated," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. In some embodiments, two or more moieties may be conjugated by direct covalent chemical bonding. In other embodiments, two or more moieties may be conjugated by ionic bonding or hydrogen bonding.

Contacting: As used herein, the term "contacting" means establishing a physical connection between two or more entities. For example, contacting a cell with an mRNA or a lipid nanoparticle composition means that the cell and mRNA or lipid nanoparticle are made to share a physical connection. Methods of contacting cells with external entities both in vivo, in vitro, and ex vivo are well known in the biological arts. In exemplary embodiments of the disclosure, the step of contacting a mammalian cell with a composition (e.g., an isolated mRNA, nanoparticle, or pharmaceutical composition of the disclosure) is performed in vivo. For example, contacting a lipid nanoparticle composition and a cell (for example, a mammalian cell) which may be disposed within an organism (e.g., a mammal) may be performed by any suitable administration route (e.g., parenteral administration to the organism, including intravenous, intramuscular, intradermal, and subcutaneous administration). For a cell present in vitro, a composition (e.g., a lipid nanoparticle or an isolated mRNA) and a cell may be contacted, for example, by adding the composition to the culture medium of the cell and may involve or result in transfection. Moreover, more than one cell may be contacted by a nanoparticle composition.

Encapsulate: As used herein, the term "encapsulate" means to enclose, surround, or encase. In some embodiments, a compound, polynucleotide (e.g., an mRNA), or other composition may be fully encapsulated, partially encapsulated, or substantially encapsulated. For example, in some embodiments, an mRNA of the disclosure may be encapsulated in a lipid nanoparticle, e.g., a liposome.

Effective amount: As used herein, the term "effective amount" of an agent is that amount sufficient to effect beneficial or desired results, for example, clinical results, and, as such, an "effective amount" depends upon the context in which it is being applied. For example, in the context of administering an agent that treats cancer, an effective amount of an agent is, for example, an amount sufficient to achieve treatment, as defined herein, of cancer, as compared to the response obtained without administration of the agent. In some embodiments, a therapeutically effective amount is an amount of an agent to be delivered (e.g., nucleic acid, drug, therapeutic agent, diagnostic agentor prophylactic agent) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

Identity: As used herein, the term "identity" refers to the overall relatedness between polymeric molecules, e.g., between polynucleotide molecules (e.g., DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in *Computational Molecular Biology*, Lesk, A. M., ed., Oxford University Press, New York, 1988*; Biocomputing: Informatics and Genome Projects*, Smith, D. W., ed., Academic Press, New York, 1993*; Sequence Analysis in Molecular*

*Biology*, von Heinje, *G., Academic Press,* 1987*; Computer Analysis of Sequence Data*, Part I, Griffin, A. M., and Griffin, H. G., eds., Humana Press, New Jersey, 1994; and *Sequence Analysis Primer*, Gribskov, M. and Devereux, J., eds., M Stockton Press, New York, 1991; each of which is incorporated herein by reference. For example, the percent identity between two nucleotide sequences can be determined using the algorithm of Meyers and Miller (*CABIOS,* 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., *SIAM J Applied Math.,* 48:1073 (1988); incorporated herein by reference. Techniques for determining identity are codified in publicly available computer programs. Exemplary computer software to determine homology between two sequences include, but are not limited to, GCG program package, Devereux et al., *Nucleic Acids Research,* 12(1): 387, 1984, BLASTP, BLASTN, and FASTA, Altschul, S. F. et al., *J. Molec. Biol.,* 215, 403, 1990.

Fragment: A "fragment," as used herein, refers to a portion. For example, fragments of proteins may include polypeptides obtained by digesting full-length protein isolated from cultured cells or obtained through recombinant DNA techniques.

GC-rich: As used herein, the term "GC-rich" refers to the nucleobase composition of a polynucleotide (e.g., mRNA), or any portion thereof (e.g., an RNA element), comprising guanine (G) and/or cytosine (C) nucleobases, or derivatives or analogs thereof, wherein the GC-content is greater than about 50%. The term "GC-rich" refers to all, or to a portion, of a polynucleotide, including, but not limited to, a gene, a non-coding region, a 5' UTR, a 3' UTR, an open reading frame, an RNA element, a sequence motif, or any discrete sequence, fragment, or segment thereof which comprises about 50% GC-content. In some embodiments of the disclosure, GC-rich polynucleotides, or any portions thereof, are exclusively comprised of guanine (G) and/or cytosine (C) nucleobases.

GC-content: As used herein, the term "GC-content" refers to the percentage of nucleobases in a polynucleotide (e.g., mRNA), or a portion thereof (e.g., an RNA element), that are either guanine (G) and cytosine (C) nucleobases, or derivatives or analogs thereof, (from a total number of possible nucleobases, including adenine (A) and thymine (T) or uracil (U), and derivatives or analogs thereof, in DNA and in RNA). The term "GC-content" refers to all, or to a portion, of a polynucleotide, including, but not limited to, a gene, a non-coding region, a 5' or 3' UTR, an open reading frame, an RNA element, a sequence motif, or any discrete sequence, fragment, or segment thereof.

Genetic Adjuvant: A "genetic adjuvant", as used herein, refers to an mRNA construct (e.g., an mmRNA construct) that enhances the immune response to a vaccine, for example by stimulating cytokine production and/or by stimulating the production of antigen-specific effector cells (e.g., CD8 T cells). A genetic adjuvant mRNA construct can, for example, encode a polypeptide that stimulates Type I interferon (e.g., activates Type I interferon pathway signaling) or that promotes dendritic cell development or activity.

Heterologous: As used herein, "heterologous" indicates that a sequence (e.g., an amino acid sequence or the polynucleotide that encodes an amino acid sequence) is not normally present in a given polypeptide or polynucleotide. For example, an amino acid sequence that corresponds to a domain or motif of one protein may be heterologous to a second protein.

Hydrophobic amino acid: As used herein, a "hydrophobic amino acid" is an amino acid having an uncharged, nonpolar side chain. Examples of naturally occurring hydrophobic amino acids are alanine (Ala), valine (Val), leucine (Leu), isoleucine (Be), proline (Pro), phenylalanine (Phe), methionine (Met), and tryptophan (Trp).

Immune Potentiator: An "immune potentiator", as used herein, refers to an mRNA construct (e.g., an mmRNA construct) that enhances an immune response, e.g., to an antigen of interest (either an endogenous antigen in a subject to which the immune potentiator is administered or to an exogenous antigen that is coadministered with the immune potentiator), for example by stimulating T cell, B cell or dendritic cell responses, including but not limited to cytokine production, stimulating antibody production or stimulating the production of antigen-specific immune cells (e.g., $CD8^+$ T cells or $CD4^+$ T cells).

Initiation Codon: As used herein, the term "initiation codon", used interchangeably with the term "start codon", refers to the first codon of an open reading frame that is translated by the ribosome and is comprised of a triplet of linked adenine-uracil-guanine nucleobases. The initiation codon is depicted by the first letter codes of adenine (A), uracil (U), and guanine (G) and is often written simply as "AUG". Although natural mRNAs may use codons other than AUG as the initiation codon, which are referred to herein as "alternative initiation codons", the initiation codons of polynucleotides described herein use the AUG codon. During the process of translation initiation, the sequence comprising the initiation codon is recognized via complementary base-pairing to the anticodon of an initiator tRNA (Met-$tRNA_i^{Met}$) bound by the ribosome. Open reading frames may contain more than one AUG initiation codon, which are referred to herein as "alternate initiation codons".

The initiation codon plays a critical role in translation initiation. The initiation codon is the first codon of an open reading frame that is translated by the ribosome. Typically, the initiation codon comprises the nucleotide triplet AUG, however, in some instances translation initiation can occur at other codons comprised of distinct nucleotides. The initiation of translation in eukaryotes is a multistep biochemical process that involves numerous protein-protein, protein-RNA, and RNA-RNA interactions between messenger RNA molecules (mRNAs), the 40S ribosomal subunit, other components of the translation machinery (e.g., eukaryotic initiation factors; eIFs). The current model of mRNA translation initiation postulates that the pre-initiation complex (alternatively "43S pre-initiation complex"; abbreviated as "PIC") translocates from the site of recruitment on the mRNA (typically the 5' cap) to the initiation codon by scanning nucleotides in a 5' to 3' direction until the first AUG codon that resides within a specific translation-promotive nucleotide context (the Kozak sequence) is encountered (Kozak (1989) *J Cell Biol* 108:229-241). Scanning by the PIC ends upon complementary base-pairing between nucleotides comprising the anticodon of the initiator Met-$tRNA_i^{Met}$ transfer RNA and nucleotides comprising the initiation codon of the mRNA. Productive base-pairing between the AUG codon and the Met-$tRNA_i^{Met}$ anticodon elicits a series of structural and biochemical events that culminate in the joining of the large 60S ribosomal subunit to the PIC to form an active ribosome that is competent for translation elongation.

Insertion: As used herein, an "insertion" or an "addition" refers to a change in an amino acid or nucleotide sequence resulting in the addition of one or more amino acid residues or nucleotides, respectively, to a molecule as compared to a reference sequence, for example, the sequence found in a naturally-occurring molecule. In some embodiments, an insertion may be a replacement.

Insertion Site: As used herein, an "insertion site" is a position or region of a scaffold polypeptide that is amenable to insertion of an amino acid sequence of a heterologous polypeptide. It is to be understood that an insertion site also may refer to the position or region of the polynucleotide that encodes the polypeptide (e.g., a codon of a polynucleotide that codes for a given amino acid in the scaffold polypeptide). In some embodiments, insertion of an amino acid sequence of a heterologous polypeptide into a scaffold polypeptide has little to no effect on the stability (e.g., conformational stability), expression level, or overall secondary structure of the scaffold polypeptide.

Isolated: As used herein, the term "isolated" refers to a substance or entity that has been separated from at least some of the components with which it was associated (whether in nature or in an experimental setting). Isolated substances may have varying levels of purity in reference to the substances from which they have been associated. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

Kozak Sequence: The term "Kozak sequence" (also referred to as "Kozak consensus sequence") refers to a translation initiation enhancer element to enhance expression of a gene or open reading frame, and which in eukaryotes, is located in the 5' UTR. The Kozak consensus sequence was originally defined as the sequence GCCRCC, where R=a purine, following an analysis of the effects of single mutations surrounding the initiation codon (AUG) on translation of the preproinsulin gene (Kozak (1986) Cell 44:283-292). Polynucleotides disclosed herein comprise a Kozak consensus sequence, or a derivative or modification thereof. (Examples of translational enhancer compositions and methods of use thereof, see U.S. Pat. No. 5,807,707 to Andrews et al., incorporated herein by reference in its entirety; U.S. Pat. No. 5,723,332 to Chernajovsky, incorporated herein by reference in its entirety; U.S. Pat. No. 5,891,665 to Wilson, incorporated herein by reference in its entirety.)

Leaky scanning: A phenomenon known as "leaky scanning" can occur whereby the PIC bypasses the initiation codon and instead continues scanning downstream until an alternate or alternative initiation codon is recognized. Depending on the frequency of occurrence, the bypass of the initiation codon by the PIC can result in a decrease in translation efficiency. Furthermore, translation from this downstream AUG codon can occur, which will result in the production of an undesired, aberrant translation product that may not be capable of eliciting the desired therapeutic response. In some cases, the aberrant translation product may in fact cause a deleterious response (Kracht et al., (2017) Nat Med 23(4):501-507).

Liposome: As used herein, by "liposome" is meant a structure including a lipid-containing membrane enclosing an aqueous interior. Liposomes may have one or more lipid membranes. Liposomes include single-layered liposomes (also known in the art as unilamellar liposomes) and multi-layered liposomes (also known in the art as multilamellar liposomes).

Metastasis: As used herein, the term "metastasis" means the process by which cancer spreads from the place at which it first arose as a primary tumor to distant locations in the body. A secondary tumor that arose as a result of this process may be referred to as "a metastasis."

Modified: As used herein "modified" or "modification" refers to a changed state or a change in composition or structure of a polynucleotide (e.g., mRNA). Polynucleotides may be modified in various ways including chemically, structurally, and/or functionally. For example, polynucleotides may be structurally modified by the incorporation of one or more RNA elements, wherein the RNA element comprises a sequence and/or an RNA secondary structure(s) that provides one or more functions (e.g., translational regulatory activity).

Accordingly, polynucleotides of the disclosure may be comprised of one or more modifications (e.g., may include one or more chemical, structural, or functional modifications, including any combination thereof).

mRNA: As used herein, an "mRNA" refers to a messenger ribonucleic acid. An mRNA may be naturally or non-naturally occurring. For example, an mRNA may include modified and/or non-naturally occurring components such as one or more nucleobases, nucleosides, nucleotides, or linkers. An mRNA may include a cap structure, a chain terminating nucleoside, a stem loop, a polyA sequence, and/or a polyadenylation signal. An mRNA may have a nucleotide sequence encoding a polypeptide. Translation of an mRNA, for example, in vivo translation of an mRNA inside a mammalian cell, may produce a polypeptide. Traditionally, the basic components of an mRNA molecule include at least a coding region, a 5'-untranslated region (5'-UTR), a 3'UTR, a 5' cap and a polyA sequence.

microRNA (miRNA): As used herein, a "microRNA (miRNA)" is a small non-coding RNA molecule which may function in post-transcriptional regulation of gene expression (e.g., by RNA silencing, such as by cleavage of the mRNA, destabilization of the mRNA by shortening its polyA tail, and/or by interfering with the efficiency of translation of the mRNA into a polypeptide by a ribosome). A mature miRNA is typically about 22 nucleotides long.

microRNA-122 (miR-122): As used herein, "microRNA-122 (miR-122)" refers to any native miR-122 from any vertebrate source, including, for example, humans, unless otherwise indicated. miR-122 is typically highly expressed in the liver, where it may regulate fatty-acid metabolism. miR-122 levels are reduced in liver cancer, for example, hepatocellular carcinoma. miR-122 is one of the most highly-expressed miRNAs in the liver, where it regulates targets including but not limited to CAT-1, CD320, AldoA, Hjv, Hfe, ADAM10, IGFR1, CCNG1, and ADAM17. Mature human miR-122 may have a sequence of AACGCCAUUAUCACACUAAAUA (SEQ ID NO: 172, corresponding to hsa-miR-122-3p) or UGGAGUGUGACAAUGGUGUUUG (SEQ ID NO: 174, corresponding to hsa-miR-122-5p).

microRNA-21 (miR-21): As used herein, "microRNA-21 (miR-21)" refers to any native miR-21 from any vertebrate source, including, for example, humans, unless otherwise indicated. miR-21 levels are increased in liver cancer, for example, hepatocellular carcinoma, as compared to normal liver. Mature human miR-21 may have a sequence of UAGCUUAUCAGACUGAUGUUGA (SEQ ID NO: 34, corresponding to has-miR-21-5p) or 5'-CAACACCAGUCGAUGGGCUGU-3' (SEQ ID NO: 35, corresponding to has-miR-21-3p).

microRNA-142 (miR-142): As used herein, "microRNA-142 (miR-142)" refers to any native miR-142 from any vertebrate source, including, for example, humans, unless otherwise indicated. miR-142 is typically highly expressed in myeloid cells. Mature human miR-142 may have a sequence of UGUAGUGUUUCCUACUUUAUGGA (SEQ ID NO: 28, corresponding to hsa-miR-142-3p) or CAUAAAGUAGAAAGCACUACU (SEQ ID NO: 30, corresponding to hsa-miR-142-5p).

microRNA (miRNA) binding site: As used herein, a "microRNA (miRNA) binding site" refers to a miRNA target site or a miRNA recognition site, or any nucleotide sequence to which a miRNA binds or associates. In some embodiments, a miRNA binding site represents a nucleotide location or region of a polynucleotide (e.g., an mRNA) to which at least the "seed" region of a miRNA binds. It should be understood that "binding" may follow traditional Watson-Crick hybridization rules or may reflect any stable association of the miRNA with the target sequence at or adjacent to the microRNA site.

miRNA seed: As used herein, a "seed" region of a miRNA refers to a sequence in the region of positions 2-8 of a mature miRNA, which typically has perfect Watson-Crick complementarity to the miRNA binding site. A miRNA seed may include positions 2-8 or 2-7 of a mature miRNA. In some embodiments, a miRNA seed may comprise 7 nucleotides (e.g., nucleotides 2-8 of a mature miRNA), wherein the seed-complementary site in the corresponding miRNA binding site is flanked by an adenine (A) opposed to miRNA position 1. In some embodiments, a miRNA seed may comprise 6 nucleotides (e.g., nucleotides 2-7 of a mature miRNA), wherein the seed-complementary site in the corresponding miRNA binding site is flanked by an adenine (A) opposed to miRNA position 1. When referring to a miRNA binding site, an miRNA seed sequence is to be understood as having complementarity (e.g., partial, substantial, or complete complementarity) with the seed sequence of the miRNA that binds to the miRNA binding site.

Modified: As used herein "modified" refers to a changed state or structure of a molecule of the disclosure. Molecules may be modified in many ways including chemically, structurally, and functionally. In one embodiment, the mRNA molecules of the present disclosure are modified by the introduction of non-natural nucleosides and/or nucleotides, e.g., as it relates to the natural ribonucleotides A, U, G, and C. Noncanonical nucleotides such as the cap structures are not considered "modified" although they differ from the chemical structure of the A, C, G, U ribonucleotides.

Nanoparticle: As used herein, "nanoparticle" refers to a particle having any one structural feature on a scale of less than about 1000 nm. that exhibits novel properties as compared to a bulk sample of the same material. Routinely, nanoparticles have any one structural feature on a scale of less than about 500 nm, less than about 200 nm, or about 100 nm. Also routinely, nanoparticles have any one structural feature on a scale of from about 50 nm to about 500 nm, from about 50 nm to about 200 μm or from about 70 to about 120 mn. In exemplary embodiments, a nanoparticle is a particle having one or more dimensions of the order of about 1-1000 nm. In other exemplary embodiments, a nanoparticle is a particle having one or more dimensions of the order of about 1.0-500 nm. In other exemplary embodiments, a nanoparticle is a particle having one or more dimensions of the order of about 50-200 nm. A spherical nanoparticle would have a diameter, for example, of between about 50-100 or 70-120 nanometers. A nanoparticle most often behaves as a unit in terms of its transport and properties. It is noted that novel properties that differentiate nanoparticles from the corresponding bulk material typically develop at a size scale of under 1000 nm, or at a size of about 100 nm, but nanoparticles can be of a larger size, for example, for particles that are oblong, tubular, and the like. Although the size of most molecules would fit into the above outline, individual molecules are usually not referred to as nanoparticles.

Nucleic acid: As used herein, the term "nucleic acid" is used in its broadest sense and encompasses any compound and/or substance that includes a polymer of nucleotides. These polymers are often referred to as polynucleotides. Exemplary nucleic acids or polynucleotides of the disclosure include, but are not limited to, ribonucleic acids (RNAs), deoxyribonucleic acids (DNAs), DNA-RNA hybrids, RNAi-inducing agents, RNAi agents, siRNAs, shRNAs, miRNAs, antisense RNAs, ribozymes, catalytic DNA, RNAs that induce triple helix formation, threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization) or hybrids thereof.

Nucleic Acid Structure: As used herein, the term "nucleic acid structure" (used interchangeably with "polynucleotide structure") refers to the arrangement or organization of atoms, chemical constituents, elements, motifs, and/or sequence of linked nucleotides, or derivatives or analogs thereof, that comprise a nucleic acid (e.g., an mRNA). The term also refers to the two-dimensional or three-dimensional state of a nucleic acid. Accordingly, the term "RNA structure" refers to the arrangement or organization of atoms, chemical constituents, elements, motifs, and/or sequence of linked nucleotides, or derivatives or analogs thereof, comprising an RNA molecule (e.g., an mRNA) and/or refers to a two-dimensional and/or three dimensional state of an RNA molecule. Nucleic acid structure can be further demarcated into four organizational categories referred to herein as "molecular structure", "primary structure", "secondary structure", and "tertiary structure" based on increasing organizational complexity.

Nucleobase: As used herein, the term "nucleobase" (alternatively "nucleotide base" or "nitrogenous base") refers to a purine or pyrimidine heterocyclic compound found in nucleic acids, including any derivatives or analogs of the naturally occurring purines and pyrimidines that confer improved properties (e.g., binding affinity, nuclease resistance, chemical stability) to a nucleic acid or a portion or segment thereof. Adenine, cytosine, guanine, thymine, and uracil are the nucleobases predominately found in natural nucleic acids. Other natural, non-natural, and/or synthetic nucleobases, as known in the art and/or described herein, can be incorporated into nucleic acids.

Nucleoside/Nucleotide: As used herein, the term "nucleoside" refers to a compound containing a sugar molecule (e.g., a ribose in RNA or a deoxyribose in DNA), or derivative or analog thereof, covalently linked to a nucleobase (e.g., a purine or pyrimidine), or a derivative or analog thereof (also referred to herein as "nucleobase"), but lacking an internucleoside linking group (e.g., a phosphate group). As used herein, the term "nucleotide" refers to a nucleoside covalently bonded to an internucleoside linking group (e.g., a phosphate group), or any derivative, analog, or modification thereof that confers improved chemical and/or functional properties (e.g., binding affinity, nuclease resistance, chemical stability) to a nucleic acid or a portion or segment thereof.

Open Reading Frame: As used herein, the term "open reading frame", abbreviated as "ORF", refers to a segment or region of an mRNA molecule that encodes a polypeptide. The ORF comprises a continuous stretch of non-overlapping, in-frame codons, beginning with the initiation codon and ending with a stop codon, and is translated by the ribosome.

Patient: As used herein, "patient" refers to a subject who may seek or be in need of treatment, requires treatment, is receiving treatment, will receive treatment, or a subject who is under care by a trained professional for a particular disease or condition. In particular embodiments, a patient is a human patient. In some embodiments, a patient is a patient suffering from cancer (e.g., liver cancer or colorectal cancer).

Pharmaceutically acceptable: The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio Pharmaceutically acceptable excipient: The phrase "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts: As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, *Pharmaceutical Salts: Properties, Selection, and Use*, P. H. Stahl and C. G. Wermuth (eds.), Wiley-VCH, 2008, and Berge et al., *Journal of Pharmaceutical Science,* 66, 1-19 (1977), each of which is incorporated herein by reference in its entirety.

Polypeptide: As used herein, the term "polypeptide" or "polypeptide of interest" refers to a polymer of amino acid residues typically joined by peptide bonds that can be produced naturally (e.g., isolated or purified) or synthetically.

Pre-Initiation Complex (PIC): As used herein, the term "pre-initiation complex" (alternatively "43S pre-initiation complex"; abbreviated as "PIC") refers to a ribonucleoprotein complex comprising a 40S ribosomal subunit, eukaryotic initiation factors (eIF1, eIF1A, eIF3, eIF5), and the eIF2-GTP-Met-tRNA$_i^{Met}$ ternary complex, that is intrinsically capable of attachment to the 5' cap of an mRNA molecule and, after attachment, of performing ribosome scanning of the 5' UTR.

RNA element: As used herein, the term "RNA element" refers to a portion, fragment, or segment of an RNA molecule that provides a biological function and/or has biological activity (e.g., translational regulatory activity). Modification of a polynucleotide by the incorporation of one or more RNA elements, such as those described herein, provides one or more desirable functional properties to the modified polynucleotide. RNA elements, as described herein, can be naturally-occurring, non-naturally occurring, synthetic, engineered, or any combination thereof. For example, naturally-occurring RNA elements that provide a regulatory activity include elements found throughout the transcriptomes of viruses, prokaryotic and eukaryotic organisms (e.g., humans). RNA elements in particular eukaryotic mRNAs and translated viral RNAs have been shown to be involved in mediating many functions in cells. Exemplary natural RNA elements include, but are not limited to, translation initiation elements (e.g., internal ribosome entry site (IRES), see Kieft et al., (2001) RNA 7(2):194-206), translation enhancer elements (e.g., the APP mRNA translation enhancer element, see Rogers et al., (1999) J Biol Chem 274(10):6421-6431), mRNA stability elements (e.g., AU-rich elements (AREs), see Garneau et al., (2007) Nat Rev Mol Cell Biol 8(2):113-126), translational repression element (see e.g., Blumer et al., (2002) Mech Dev 110(1-2):97-112), protein-binding RNA elements (e.g., iron-responsive element, see Selezneva et al., (2013) J Mol Biol 425(18):3301-3310), cytoplasmic polyadenylation elements (Villalba et al., (2011) Curr Opin Genet Dev 21(4):452-457), and catalytic RNA elements (e.g., ribozymes, see Scott et al., (2009) Biochim Biophys Acta 1789(9-10):634-641).

Residence time: As used herein, the term “residence time” refers to the time of occupancy of a pre-initiation complex (PIC) or a ribosome at a discrete position or location along an mRNA molecule.

Substantially: As used herein, the term “substantially” refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term “substantially” is therefore used herein to capture the potential lack of completeness inherent in many biological and chemical phenomena.

Suffering from: An individual who is “suffering from” a disease, disorder, and/or condition has been diagnosed with or displays one or more symptoms of a disease, disorder, and/or condition.

Targeting moiety: As used herein, a “targeting moiety” is a compound or agent that may target a nanoparticle to a particular cell, tissue, and/or organ type.

Therapeutic Agent: The term “therapeutic agent” refers to any agent that, when administered to a subject, has a therapeutic, diagnostic, and/or prophylactic effect and/or elicits a desired biological and/or pharmacological effect.

Transfection: As used herein, the term “transfection” refers to methods to introduce a species (e.g., a polynucleotide, such as a mRNA) into a cell.

Translational Regulatory Activity: As used herein, the term “translational regulatory activity” (used interchangeably with “translational regulatory function”) refers to a biological function, mechanism, or process that modulates (e.g., regulates, influences, controls, varies) the activity of the translational apparatus, including the activity of the PIC and/or ribosome. In some aspects, the desired translation regulatory activity promotes and/or enhances the translational fidelity of mRNA translation. In some aspects, the desired translational regulatory activity reduces and/or inhibits leaky scanning. Subject: As used herein, the term “subject” refers to any organism to which a composition in accordance with the disclosure may be administered, e.g., for experimental, diagnostic, prophylactic, and/or therapeutic purposes. Typical subjects include animals (e.g., mammals such as mice, rats, rabbits, non-human primates, and humans) and/or plants. In some embodiments, a subject may be a patient.

Treating: As used herein, the term “treating” refers to partially or completely alleviating, ameliorating, improving, relieving, delaying onset of, inhibiting progression of, reducing severity of, and/or reducing incidence of one or more symptoms or features of a particular infection, disease, disorder, and/or condition. For example, “treating” cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Preventing: As used herein, the term “preventing” refers to partially or completely inhibiting the onset of one or more symptoms or features of a particular infection, disease, disorder, and/or condition.

Tumor: As used herein, a “tumor” is an abnormal growth of tissue, whether benign or malignant.

Unmodified: As used herein, “unmodified” refers to any substance, compound or molecule prior to being changed in any way. Unmodified may, but does not always, refer to the wild type or native form of a biomolecule. Molecules may undergo a series of modifications whereby each modified molecule may serve as the “unmodified” starting molecule for a subsequent modification.

Uridine Content: The terms “uridine content” or “uracil content” are interchangeable and refer to the amount of uracil or uridine present in a certain nucleic acid sequence. Uridine content or uracil content can be expressed as an absolute value (total number of uridine or uracil in the sequence) or relative (uridine or uracil percentage respect to the total number of nucleobases in the nucleic acid sequence).

Uridine-Modified Sequence: The terms “uridine-modified sequence” refers to a sequence optimized nucleic acid (e.g., a synthetic mRNA sequence) with a different overall or local uridine content (higher or lower uridine content) or with different uridine patterns (e.g., gradient distribution or clustering) with respect to the uridine content and/or uridine patterns of a candidate nucleic acid sequence. In the content of the present disclosure, the terms “uridine-modified sequence” and “uracil-modified sequence” are considered equivalent and interchangeable.

A “high uridine codon” is defined as a codon comprising two or three uridines, a “low uridine codon” is defined as a codon comprising one uridine, and a “no uridine codon” is a codon without any uridines. In some embodiments, a uridine-modified sequence comprises substitutions of high uridine codons with low uridine codons, substitutions of high uridine codons with no uridine codons, substitutions of low uridine codons with high uridine codons, substitutions of low uridine codons with no uridine codons, substitution of no uridine codons with low uridine codons, substitutions of no uridine codons with high uridine codons, and combinations thereof. In some embodiments, a high uridine codon can be replaced with another high uridine codon. In some embodiments, a low uridine codon can be replaced with another low uridine codon. In some embodiments, a no uridine codon can be replaced with another no uridine codon. A uridine-modified sequence can be uridine enriched or uridine rarefied.

Uridine Enriched: As used herein, the terms “uridine enriched” and grammatical variants refer to the increase in uridine content (expressed in absolute value or as a percentage value) in a sequence optimized nucleic acid (e.g., a synthetic mRNA sequence) with respect to the uridine content of the corresponding candidate nucleic acid sequence. Uridine enrichment can be implemented by substituting codons in the candidate nucleic acid sequence with synonymous codons containing less uridine nucleobases.

Uridine enrichment can be global (i.e., relative to the entire length of a candidate nucleic acid sequence) or local (i.e., relative to a subsequence or region of a candidate nucleic acid sequence).

Uridine Rarefied: As used herein, the terms "uridine rarefied" and grammatical variants refer to a decrease in uridine content (expressed in absolute value or as a percentage value) in an sequence optimized nucleic acid (e.g., a synthetic mRNA sequence) with respect to the uridine content of the corresponding candidate nucleic acid sequence. Uridine rarefication can be implemented by substituting codons in the candidate nucleic acid sequence with synonymous codons containing less uridine nucleobases. Uridine rarefication can be global (i.e., relative to the entire length of a candidate nucleic acid sequence) or local (i.e., relative to a subsequence or region of a candidate nucleic acid sequence).

Equivalents and Scope

Those skilled in the art will recognize, or be able to ascertain using no more than routine experimentation, many equivalents to the specific embodiments in accordance with the disclosure described herein. The scope of the present disclosure is not intended to be limited to the Description below, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

It is also noted that the terms "comprising", "comprise", "comprises", "having", "have" and "has" are intended to be open and permit but does not require the inclusion of additional elements or steps. When these terms are used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise.

All cited sources, for example, references, publications, databases, database entries, and art cited herein, are incorporated into this application by reference, even if not expressly stated in the citation. In case of conflicting statements of a cited source and the instant application, the statement in the instant application shall control.

EXAMPLES

The disclosure will be more fully understood by reference to the following examples. They should not, however, be construed as limiting the scope of the disclosure. It is understood that the examples and embodiments described herein are for illustrative purposes only and that various modifications or changes in light thereof will be suggested to persons skilled in the art and are to be included within the spirit and purview of this application and scope of the appended claims.

Example 1: STING Immune Potentiator mRNA Constructs

In this example, a series of mmRNA constructs that encoded constitutively activated forms of human STING were made and tested for their ability to stimulate interferon-β (IFN-β) production. The human STING protein encoded by the constructs was constitutively activated through introduction of one or more point mutations. The following single or combination point mutations were tested: (i) V155M; (ii) R284T; (iii) V147L/N154S/V155M; and (iv) R284M/V147L/N154S/V155M. These constructs typically also encoded an epitope tag at either the N-terminus or C-terminus to facilitate detection. Different epitope tags were tested (FLAG, Myc, CT, HA, V5). Additionally, all constructs contained a Cap 1 5' Cap (7mG(5')ppp(5')NlmpNp), 5' UTR, 3' UTR, a poly A tail of 100 nucleotides and were fully modified with 1-methyl-pseudouridine (m1ψ). The ORF amino acid sequences of representative constitutively active human STING constructs without any epitope tag are shown in SEQ ID NOs: 1-10. An exemplary 5' UTR for use in the constructs is shown in SEQ ID NO: 21. An exemplary 3' UTR for use in the constructs is shown in SEQ ID NO: 22. An exemplary 3' UTR comprising miR-122 and miR-142.3p binding sites for use in the constructs is shown in SEQ ID NO: 23.

To determine whether constitutively active STING constructs could stimulate IFN-β production, the constructs were transfected into human TF1a cells. Wild-type (non-constitutively active) human and mouse STING constructs were used as negative controls. Twenty-five thousand cells/well were plated in 96 well plates and the mmRNA constructs (250 ng) were transfected into them using Lipofectamine 2000. After 24 and 48 hours, supernatants were harvested and IFN-β levels were determined by standard ELISA. The results are shown in FIG. 1, which demonstrate that the constitutively active STING constructs stimulated IFN-β production, as compared to the wild-type (non-constitutively active) human and mouse STING controls. While all four mutant STING constructs stimulated IFN-β production, the V155M mutant and the R284T mutant showed the highest activity. These results demonstrate the ability of constitutively active STING mRNA constructs to enhance immune responses through stimulation of IFN-β production.

Figure 2:
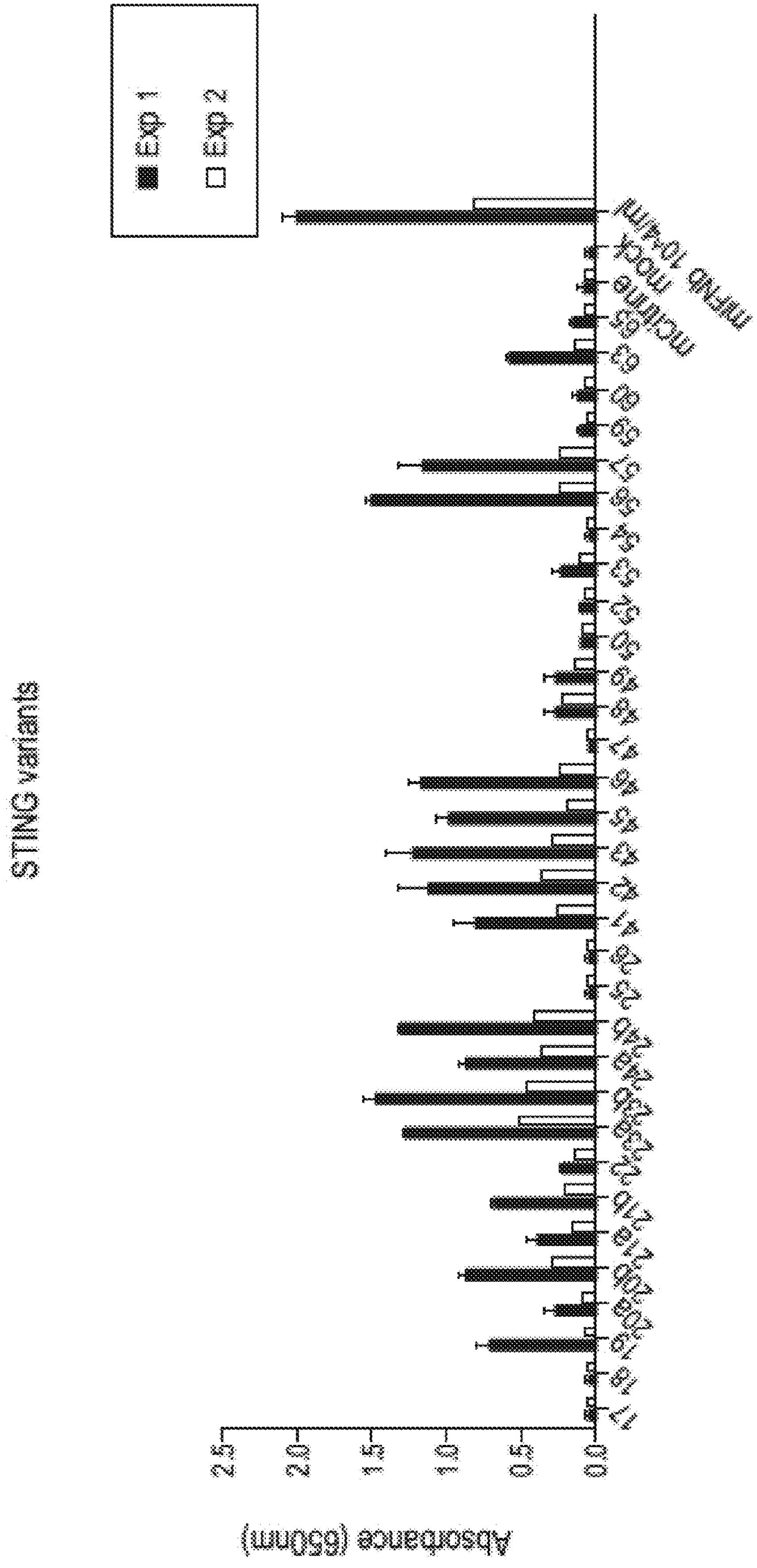
FIG. 2 is a bar graph showing activation of an interferon-sensitive response element (ISRE) by constitutively active STING constructs. STING variants 23a and 23b correspond to SEQ ID NO: 1, STING variant 42 corresponds to SEQ ID NO: 2, STING variants 19, 21a and 21b correspond to SEQ ID NO: 3, STING variant 41 corresponds to SEQ ID NO: 4, STING variant 43 corresponds to SEQ ID NO: 5, STING variant 45 corresponds to SEQ ID NO: 6, STING variant 46 corresponds to SEQ ID NO: 7, STING variant 47 corresponds to SEQ ID NO: 8, STING variant 56 corresponds to SEQ ID NO: 9 and STING variant 57 corresponds to SEQ ID NO: 10.

In a second set of experiments, a reporter gene whose transcription was driven by an interferon-sensitive response element (ISRE) was used to test the ability of a panel of constitutively active STING mRNA constructs to activate the ISRE in a STING KO reporter mouse line. The results are shown in FIG. 2, which demonstrates that the constitutively active STING constructs stimulated reporter gene expression, thereby indicating that the constructs were capable of activating the interferon-sensitive response element (ISRE).

Example 2: IRF3 and IRF7 Immune Potentiator mRNA Constructs

In this example, a series of mmRNA constructs that encoded constitutively activated forms of IRF3 or IRF7 were made and tested for their ability to activate an interferon-sensitive response element (ISRE). The ORF amino acid sequences of representative constitutively active mouse and human IRF3 constructs, comprising a 5396D point mutation, without any epitope tag are shown in SEQ ID NOs: 11-12. The ORF amino acid sequence of a wild-type human IRF7 construct without any epitope tag is shown in SEQ ID NO: 13. The ORF amino acid sequences of representative constitutively active human IRF7 constructs without any epitope tag are shown in SEQ ID NOs: 14-18. The ORF amino acid sequences of representative truncated human IRF7 constructs (inactive "null" mutations) without any epitope tag are shown in SEQ ID NOs: 19-20. These constructs typically also encoded an epitope tag at either the N-terminus or C-terminus to facilitate detection. Different epitope tags were tested (FLAG, Myc, CT, HA, V5). Additionally, all constructs contained a Cap 1 5' Cap (7mG(5') ppp(5')NlmpNp), 5' UTR, 3' UTR, a poly A tail of 100 nucleotides and were fully modified with 1-methyl-pseudouridine (m1ψ). An exemplary 5' UTR for use in the constructs is shown in SEQ ID NO: 21. An exemplary 3' UTR for use in the constructs is shown in SEQ ID NO: 22. An exemplary 3' UTR comprising miR-122 and miR-142.3p binding sites for use in the constructs is shown in SEQ ID NO: 23.

Figure 3B:
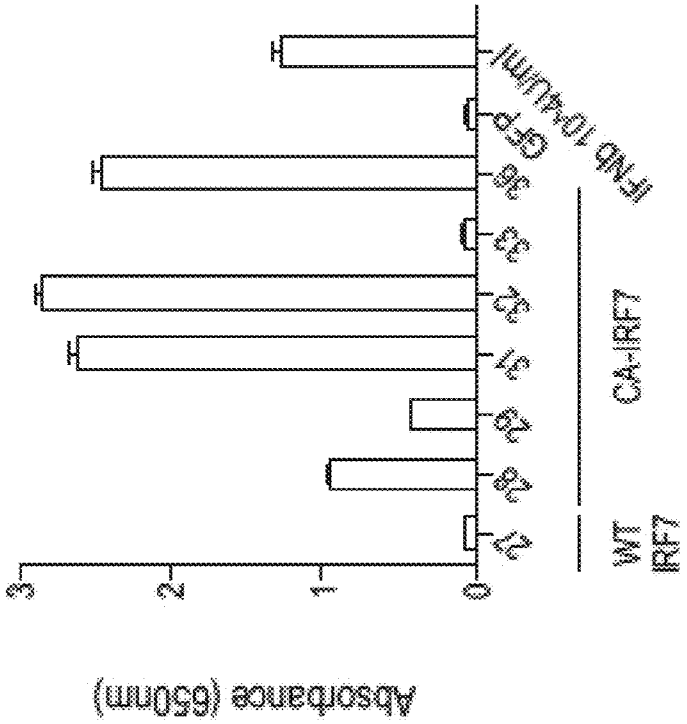
FIGS. 3A-3B are bar graphs showing activation of an interferon-sensitive response element (ISRE) by constitutively active IRF3 constructs (FIG. 3A) or constitutively active IRF7 constructs (FIG. 3B). IRF3 variants 1, 3 and 4 correspond to SEQ ID NO: 12 and IRF3 variants 2 and 5 correspond to SEQ ID NO: 11 (variants have different tags). IRF7 variant 36 corresponds to SEQ ID NO: 18 and variant 31 is the murine version of SEQ ID NO: 18. IRF7 variant 32 corresponds to SEQ ID NO: 17 and IRF7 variant 33 corresponds to SEQ ID NO: 14.
Figure 3A:
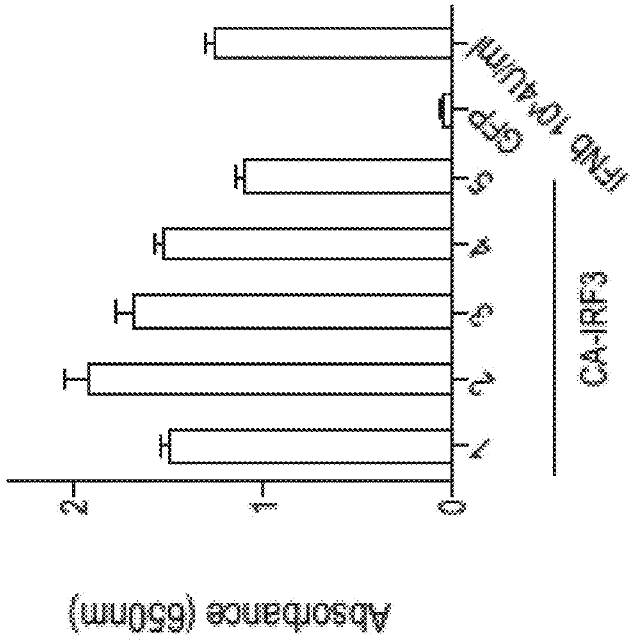

A reporter gene whose transcription was driven by an interferon-sensitive response element (ISRE) was used to test the ability of constitutively active IRF3 and IRF7 mRNA constructs to activate the ISRE. The results are shown in FIGS. 3A-3B, which demonstrate that the constitutively active IRF3 constructs (FIG. 3A) and the constitutively active IRF7 constructs (FIG. 3B) stimulated reporter gene expression, thereby indicating that the constructs were capable of activating the interferon-sensitive response element (ISRE).

Example 3: IKKβ, cFLIP and RIPK1 Immune Potentiator mRNA Constructs

In this example, a luciferase reporter gene whose transcription was driven by the NFκB signaling pathway was used to test the ability of constitutively active IKK, cFLIP and RIPK1 mRNA constructs to activate NFκB signaling.

Constitutively active IKKβ construct comprised the following two point mutations: S177E/S181E. Constitutively active IKKα or IKKβ constructs comprised PEST mutations. The ORF amino acid sequences of constitutively active IKKβ constructs without any epitope tag are shown in SEQ ID NOs: 87-90. The ORF amino acid sequences of constitutively active IKKα or IKKβ constructs comprising a PEST mutation, without any epitope tag, are shown in SEQ ID NOs: 91-98. Constitutively active cFLIP constructs comprised cFLIP-L, cFLIP-S(aa 1-227), cFLIP p22 (aa 1-198), cFLIP p43 (aa 1-376) or cFLIP p12 (aa 377-480). The ORF amino acid sequences of the cFLIP constructs without any epitope tag are shown in SEQ ID NOs: 82-86. Structures of various constitutively active RIPK1 constructs are described further in, for example, Yatim, N. et al. (2015) *Science* 350:328-334 or Orozco, S. et al. (2014) *Cell Death Differ.* 21:1511-1521. The ORF amino acid sequences of the constitutively active RIPK1 constructs without any epitope tag are shown in SEQ ID NOs: 99-104. In addition to the open reading frame, all constructs contained a Cap 1 5' Cap (7mG(5')ppp(5')NlmpNp), 5' UTR, 3' UTR, a poly A tail of 100 nucleotides and were fully modified with 1-methyl-pseudouridine (m1ψ). An exemplary 5' UTR for use in the constructs is shown in SEQ ID NO: 21. An exemplary 3' UTR for use in the constructs is shown in SEQ ID NO: 22. An exemplary 3' UTR comprising miR-122 and miR-142.3p binding sites for use in the constructs is shown in SEQ ID NO: 23.

Figure 4:
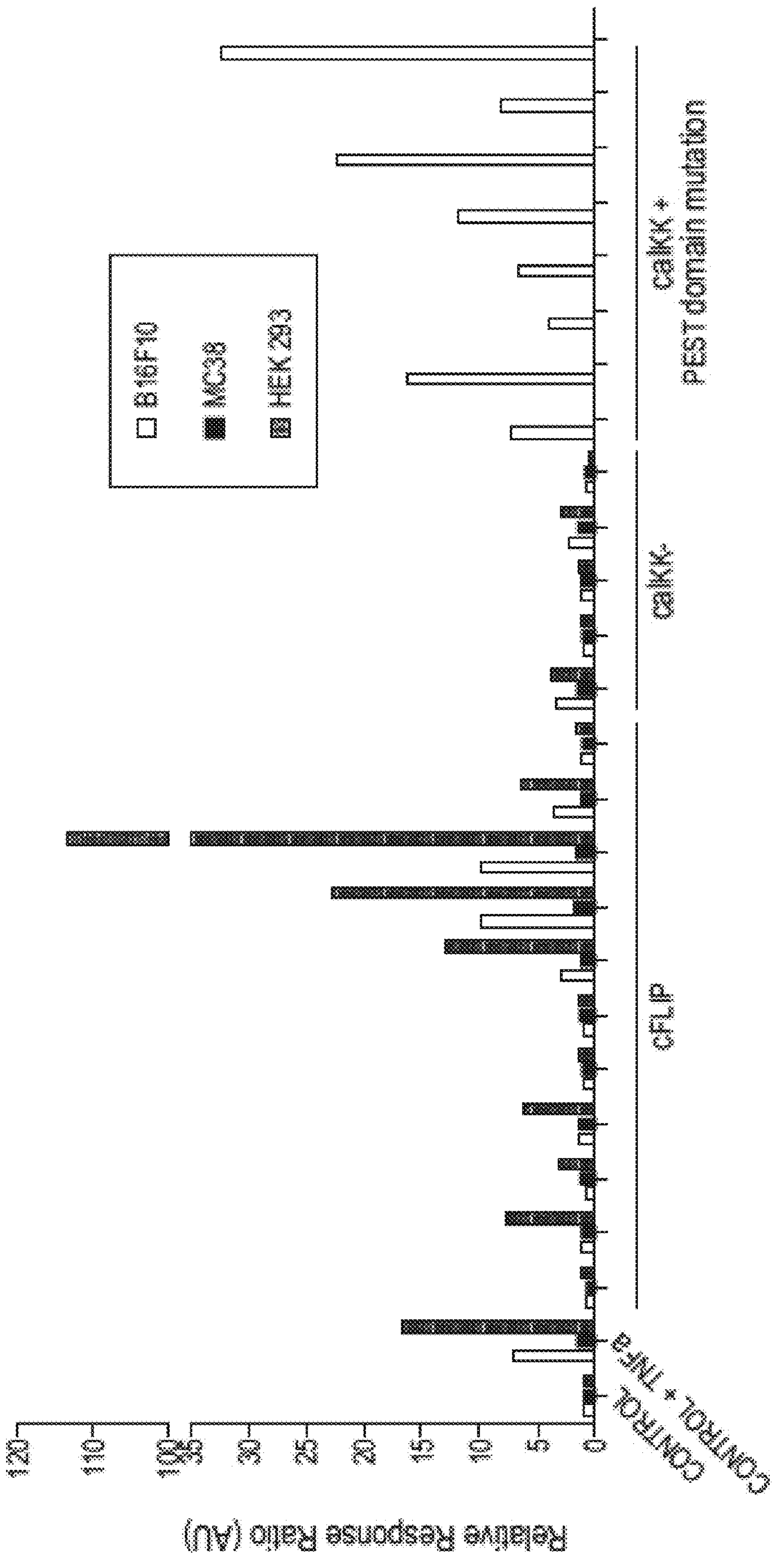
FIG. 4 is a bar graph showing activation of an NFκB-luciferase reporter gene by constitutively active cFLIP and IKKβ mRNA constructs.
Figure 5:
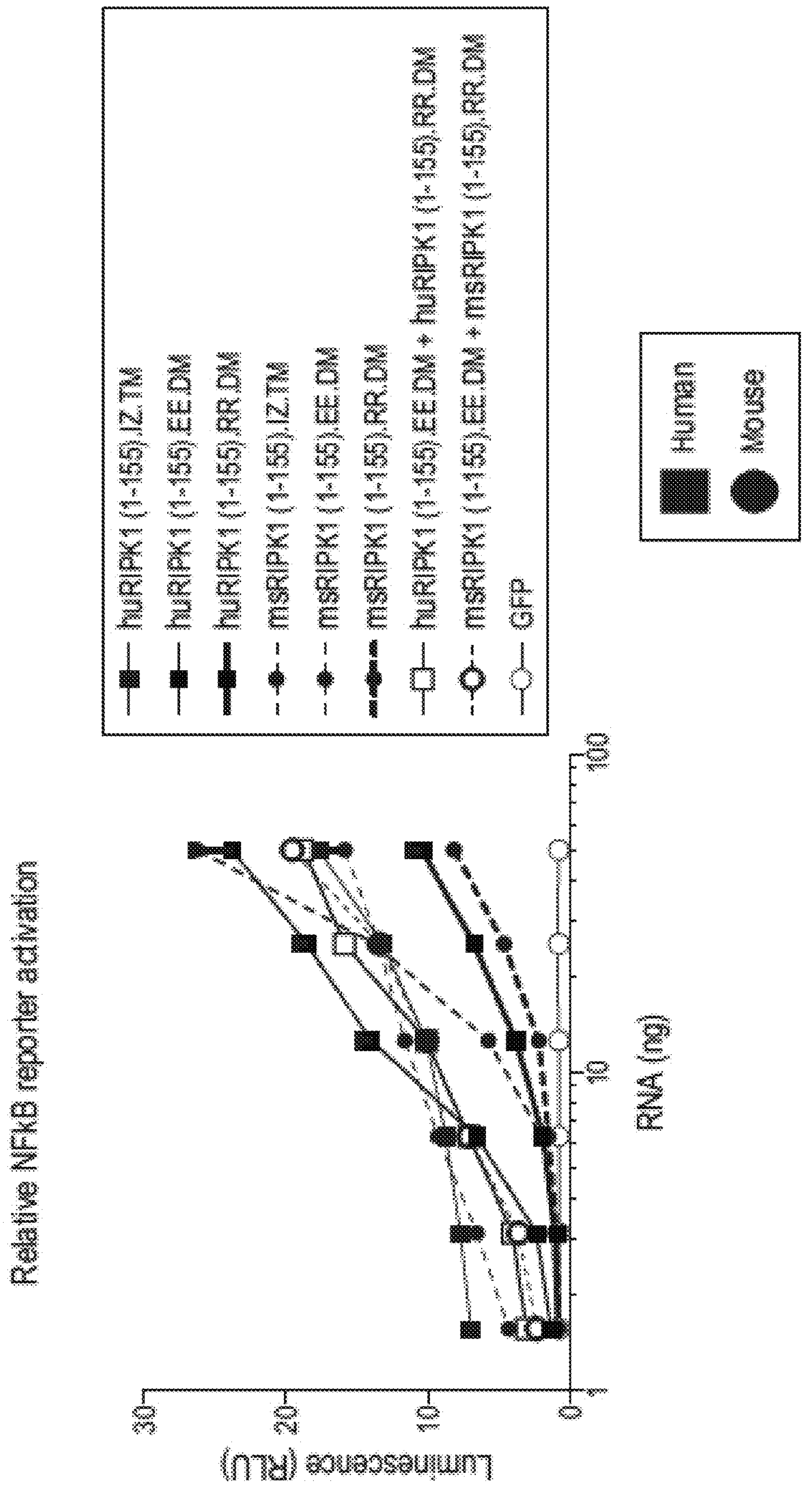
FIG. 5 is a graph showing activation of an NFκB-luciferase reporter gene by constitutively active RIPK1 mRNA constructs.

In a first series of experiments, either the cFLIP or IKKβ constructs (12.5 ng RNA) were transfected into B16F10, MC38 or HEK293 cells, together with the NFκB-luc reporter gene and the Dual Luc Assay was performed 24 hours post-transfection as an indicator of activation of NFκB signaling. The results are shown in FIG. 4, which demonstrates that the constitutively active cFLIP and IKKβ constructs stimulated reporter gene expression, thereby indicating that the constructs were capable of activating the NFκB signaling pathway. In a second series of experiments, the RIPK1 constructs were transfected into B16F10 cells, together with the NFκB-luc reporter gene and the Dual Luc Assay was performed 24 hours post-transfection as an indicator of activation of NFκB signaling. The results are shown in FIG. 5, which demonstrates that the constitutively active RIPK1 constructs stimulated reporter gene expression, thereby indicating that the constructs were capable of activating the NFκB signaling pathway.

Example 4: DIABLO Immune Potentiator mRNA Constructs

In this example, a series of mmRNA constructs that encoded DIABLO were made and tested for their ability to induce cytokine production. These constructs typically also encoded an epitope tag at either the N-terminus or C-terminus to facilitate detection. Different epitope tags were tested (FLAG, Myc, CT, HA, V5). Additionally, all constructs contained a Cap 1 5' Cap (7mG(5')ppp(5')NlmpNp), 5' UTR, 3' UTR, a poly A tail of 100 nucleotides and were fully modified with 1-methyl-pseudouridine (m1ψ). The ORF amino acid sequences of the DIABLO constructs without any epitope tag are shown in SEQ ID NOs: 106-113. An exemplary 5' UTR for use in the constructs is shown in SEQ ID NO: 21. An exemplary 3' UTR for use in the constructs is shown in SEQ ID NO: 22. An exemplary 3' UTR comprising miR-122 and miR-142.3p binding sites for use in the constructs is shown in SEQ ID NO: 23.

Figure 6:
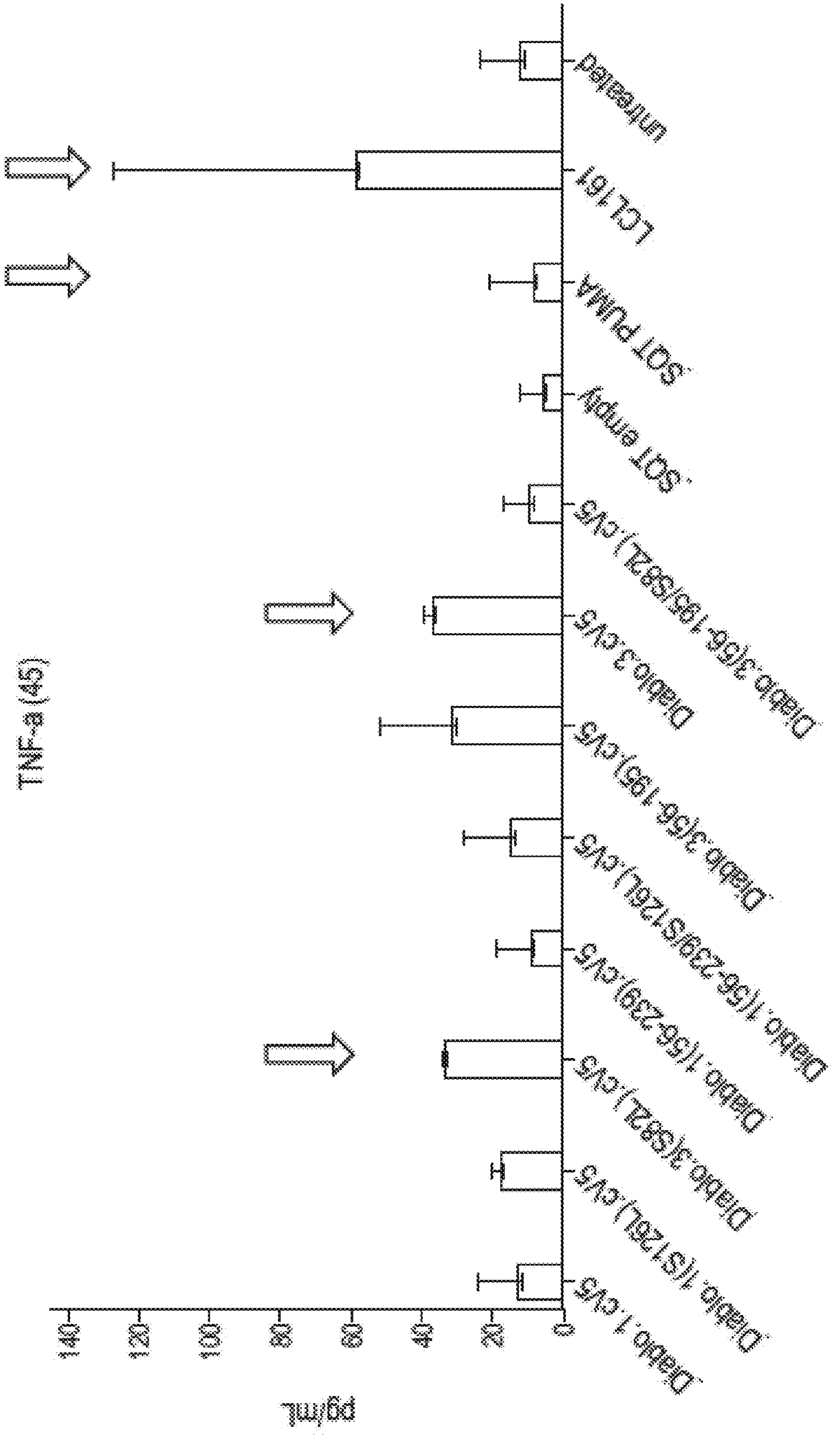
FIG. 6 is a bar graph showing TNF-α induction in SKOV3 cells transfected with DIABLO mmRNA constructs.
Figure 7:
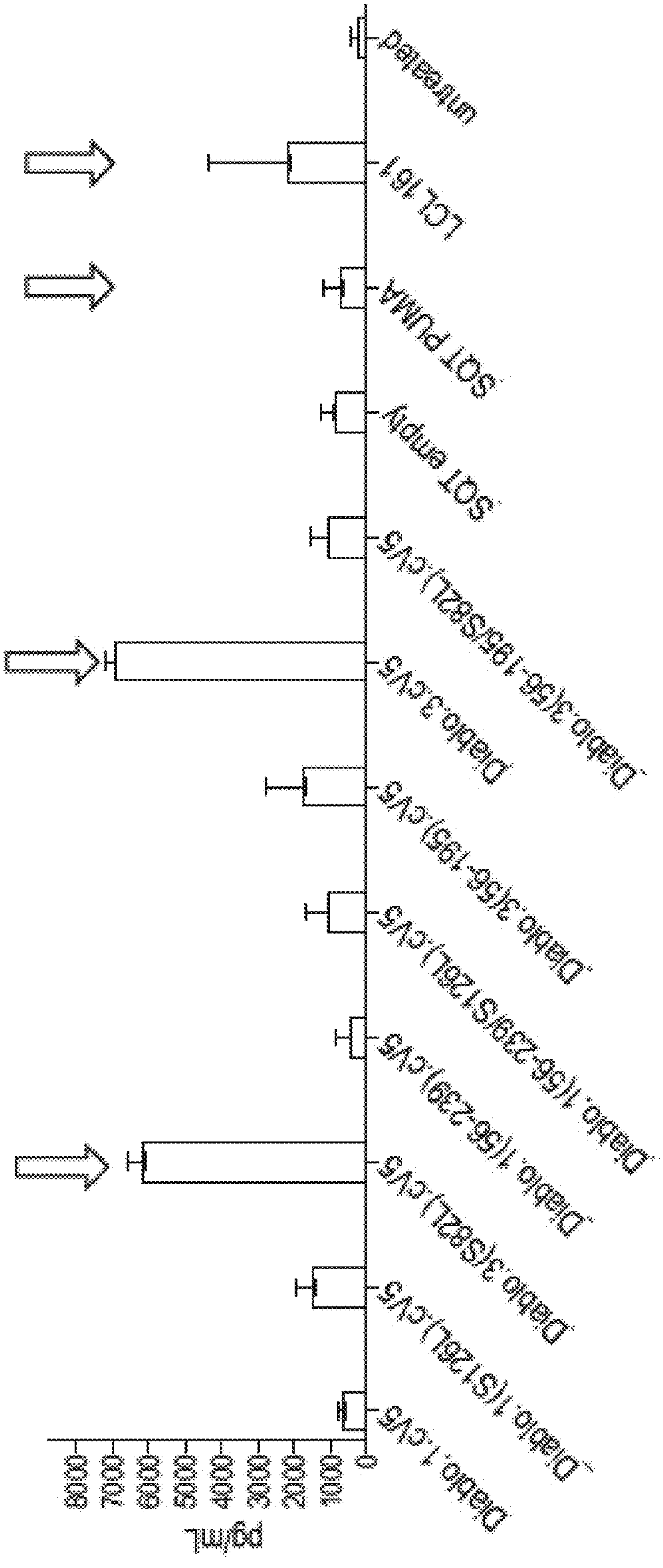
FIG. 7 is a bar graph showing interleukin 6 (IL-6) induction in SKOV3 cells transfected with DIABLO mmRNA constructs.

To determine wither the DIABLO constructs could induce cytokine production, the constructs were transfected into SKOV3 cells. Ten thousand cells/well were plated in 96 well plates and the mmRNA constructs were transfected into them using Lipofectamine 2000. Stimulation of cytokine production by the DIABLO mmRNA constructs in the SKOV3 cells was measured. The results, shown in FIG. 6 for TNF-α and in FIG. 7 for interleukin 6 (IL-6), demonstrate that a number of the DIABLO mmRNA constructs stimulate production of cytokines by the SKOV3 cells.

Example 5: Immune Potentiator mRNAs Enhance MC38 Cancer Vaccine Responses

In this example, the potency and durability of responses to an MC38 mRNA-based cancer vaccine used in combination with STING, IRF3 or IRF7 immune potentiator mRNA constructs were examined. The MC38 murine tumor model has been used to identify immunogenic mutant peptides containing neoepitopes capable of stimulating anti-tumor T cell responses (see e.g., Yadav, M. et al. (2014) *Nature* 515:572-576). Thus, a cancer vaccination approach that leads to a robust and durable immune response against tumor neoepitopes is highly desirable.

The MC38 vaccine used in this example was an mRNA construct encoding an ADR concatemer of three 25mer mutant peptides containing tumor neoepitopes derived from Adpgk, Dpagt1, and Reps1 (this vaccine is also referred to herein as ADRvax). The mRNA construct encodes the open reading frame shown in SEQ ID NO: 120, which also includes an N-terminal His-tag for easy detection. Mice were immunized intramuscularly with the ADRvax mRNA vaccine (at a dose of 0.25 mg/kg) on days 0 and 14, combination with either a control mRNA construct (NT-FIX), or a STING, IRF3 or IRF7 immune potentiator mRNA construct (at a dose of 0.25 mg/kg). The constitutively active STING immune potentiator contained a V155M mutation (mouse version corresponding to SEQ ID NO: 1). The constitutively active IRF3 immune potentiator contained a S396D mutation (corresponding to SEQ ID NO: 12). The constitutively active IRF7 immune potentiator contained an internal deletion and six point mutations (mouse version corresponding to SEQ ID NO: 18). The MC38 vaccine construct and the genetic adjuvant construct were coformulated in MC3 lipid nanoparticles.

Figure 8A:
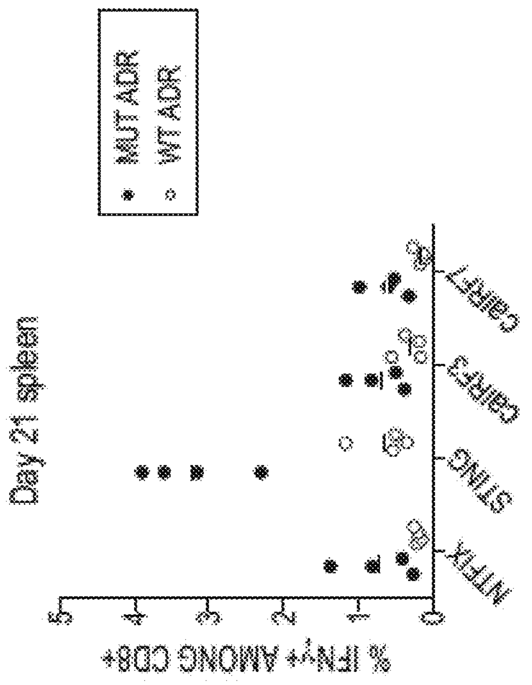
FIGS. 8A-8B are graphs showing MC38 antigen-specific responses by IFN-γ intracellular staining (ICS) of day 21 (FIG. 8A) or day 35 (FIG. 8B) $CD8^+$ spenocytes from mice immunized with MC38 neo-antigen vaccine construct (ADRvax) coformulated with either a STING, IRF3 or IRF7 immune potentiator mRNA construct.
Figure 8B:
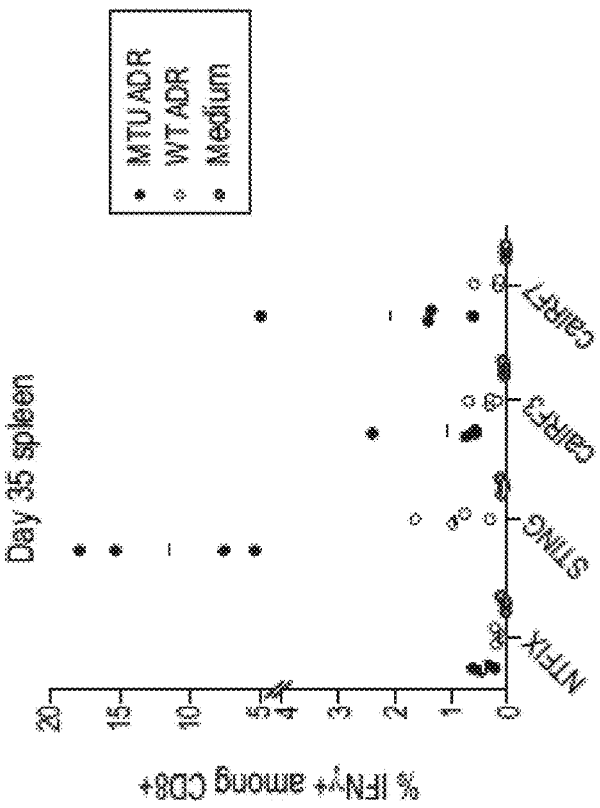

At day 21 and 35, $CD8^+$ spleen cells from mice in each test group were restimulated ex vivo for 4 hours at 37 degrees C. in the presence of GolgiPlug™ (containing Brefeldin A; BD Biosciences) with either wild-type or mutant MC38 ADR peptides (1 μg/ml per peptide) and CD8 vaccine responses were assessed by intracellular staining (ICS) for IFN-γ. Representative ICS results for MC38 ADR-specific responses by day 21 and day 35 $CD8^+$ spleen cells for IFN-γ are shown in FIG. 8A (day 21) and FIG. 8B (day 31). Similar results were observed for ICS for TNF-α and for $CD8^+$PBMCs. The results demonstrate that CD8 vaccine responses were greatly enhanced by the STING immune potentiator construct, and moderately enhanced by the IRF3 and IRF7 immune potentiator constructs. An initial improvement in the antigen-specific CD8 response for mice treated with immune potentiators was observed at day 21 (approximately 5% versus 1% for STING treatment vs. control), which continued to improve by day 35 (up to 15% for STING treatment compared to control), thereby demonstrating the durability of the response.

Figure 9A:
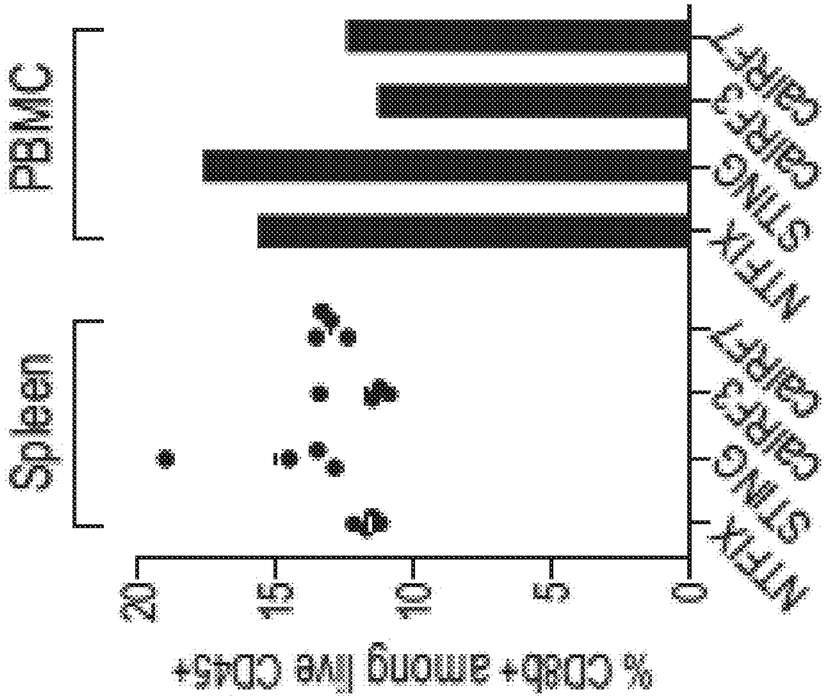
FIGS. 9A-9B are graphs showing the percentage of $CD8b^+$ cells among live $CD45^+$ cells in spleen or PBMCs (FIG. 9A) or the percentage of $CD62L^{lo}$ cells among $CD8b^+$ cell in spleen or PBMCs (FIG. 9B) from mice immunized with MC38 neo-antigen vaccine construct (ADRvax) coformulated with either a STING, IRF3 or IRF7 immune potentiator mRNA construct.
Figure 9B:
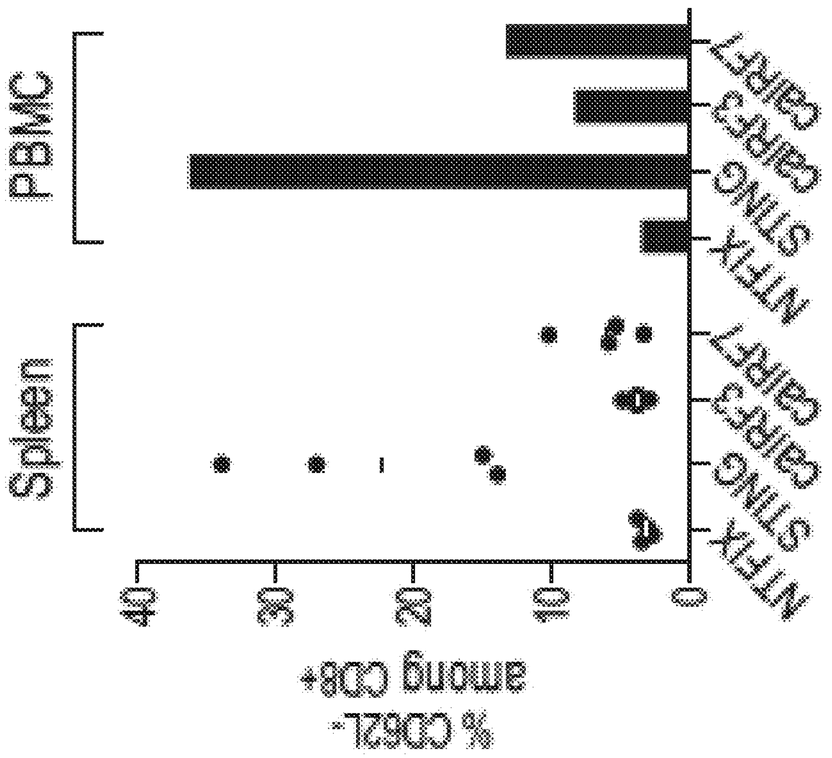

The percentage of $CD8b^+$ cells among the live $CD45^+$ cells was also examined. The results for day 35 spleen cells and PBMCs are shown in FIG. 9A, which demonstrates that the genetic adjuvants expand the total $CD8b^+$ population. As demonstrated in FIG. 9B, the majority of the $CD8^+$ spleen cells and PBMCs were found to have an "effector memory" $CD62L^{lo}$ phenotype. Additional staining experiments demonstrated that the STING and IRF7 immune potentiator construct slightly reduced the % of total $Foxp3^+$ Treg CD4 Tcells (data not shown). Additional staining experiments demonstrated that the immune potentiators did not change the % of $CD138^+$ plasmablasts (data not shown).

Example 6: KRAS-STING mRNA Constructs

A comprehensive survey of Ras mutations in various cancer types has been reported (Prior, I. A. et al. (2012) *Cancer Res.* 72:2457-2467). This survey demonstrated that the top four most frequent mutations of KRAS in colorectal cancer, pancreatic cancer and non-small cell lung cancer are G12D, G12V, G13D and G12C. A series of mutant KRAS mRNA constructs were prepared that encoded one or more KRAS peptides containing one of these four mutations, for use as KRAS anti-tumor mRNA-based vaccines. Furthermore, to examine the effect of mRNA-based immune potentiators on KRAS vaccine responses, a series of mRNA constructs were prepared that encoded one or more mutant KRAS peptides linked at the N-terminus or the C-terminus to sequence encoding STING as an immune potentiator. Thus, in these KRAS-STING mRNA constructs, the vaccine antigen(s) and the immune potentiator are encoded by the same mRNA construct.

Mutant KRAS peptide mRNA constructs were prepared that encoded: a 15mer peptide having the G12D, G12V or the G13D mutation (the amino acid sequence of which is shown in SEQ ID NOs: 36-38, respectively); a 25mer peptide having the G12D, G12V or the G13D mutation (SEQ ID NOs: 39-41, respectively); three copies of the 15mer peptide having the G12D, G12V or the G13D mutation (SEQ ID NOs: 42-44, respectively); or three copies of the 25mer peptide having the G12D, G12V or the G13D mutation (SEQ ID NOs: 45-47, respectively). Additional constructs encoded one copy or three copies of a 25mer peptide having a G12C mutation (SEQ ID NOs: 72-73, respectively) or a wild-type 25mer peptide (SEQ ID NO: 74). In certain embodiments, a G12C KRAS mutation may be used in combination with a G12D, G12V or G13D mutation, or combinations thereof. Nucleotide sequences encoding these mutant KRAS peptides are provided in Example 7.

Mutant KRAS peptide-STING mRNA constructs, having the STING coding sequence at the N-terminus, were prepared that encoded: a 15mer peptide having the G12D, G12V or the G13D mutation (the amino acid sequence of which is shown in SEQ ID NOs: 48-50, respectively); a 25mer peptide having the G12D, G12V or the G13D mutation (SEQ ID NOs: 51-53, respectively); three copies of the 15mer peptide having the G12D, G12V or the G13D mutation (SEQ ID NOs: 54-56, respectively); or three copies of the 25mer peptide having the G12D, G12V or the G13D mutation (SEQ ID NOs: 57-59, respectively). In certain embodiments, a G12C KRAS mutation may be used in combination with a G12D, G12V or G13D mutation, or combinations thereof. Representative nucleotide sequences encoding these KRAS peptide-STING constructs having the STING coding sequence at the N-terminus are shown in SEQ ID NOs: 160 and 162.

Mutant KRAS peptide-STING mRNA constructs, having the STING coding sequence at the C-terminus, were prepared that encoded: a 15mer peptide having the G12D, G12V or the G13D mutation (the amino acid sequence of which is shown in SEQ ID NOs: 60-62, respectively); a 25mer peptide having the G12D, G12V or the G13D mutation (SEQ ID NOs: 63-65, respectively); three copies of the 15mer peptide having the G12D, G12V or the G13D mutation (SEQ ID NOs: 66-68, respectively); or three copies of the 25mer peptide having the G12D, G12V or the G13D mutation (SEQ ID NOs: 69-70, respectively). In certain embodiments, a G12C KRAS mutation may be used in combination with a G12D, G12V or G13D mutation, or combinations thereof. Representative nucleotide sequences encoding these KRAS peptide-STING constructs having the STING coding sequence at the C-terminus are shown in SEQ ID NOs: 161 and 163.

These constructs can also encoded an epitope tag at either the N-terminus or C-terminus to facilitate detection. Different epitope tags can be used (e.g., FLAG, Myc, CT, HA, V5). Additionally, all constructs contained a Cap 1 5' Cap (7mG(5')ppp(5')NlmpNp), 5' UTR, 3' UTR, a poly A tail and were fully modified with 1-methyl-pseudouridine (m1ψ). An exemplary 5' UTR for use in the constructs is shown in SEQ ID NO: 21. An exemplary 3' UTR for use in the constructs is shown in SEQ ID NO: 22. An exemplary 3' UTR comprising miR-122 and miR-142.3p binding sites for use in the constructs is shown in SEQ ID NO: 23.

To test vaccine responses in mice treated either with a KRAS mutant peptide(s) mRNA vaccine construct or with a KRAS mutant peptide(s) vaccine-STING immune potentiator mRNA construct, mice (HLA-A*11:01 or HLA-A*2:01; Taconic) are immunized with a KRAS mutant peptide vaccine mRNA construct (e.g., encoding one of SEQ ID NOs: 36-47) or with a KRAS mutant peptide vaccine-STING immune potentiator mRNA construct (e.g., encoding one of SEQ ID NOs: 48-71). Mice are immunized intramuscularly on day 1 and day 15 (0.5 mg/kg) and sacrificed at day 22. To test CD8 vaccine responses, $CD8^+$ spleen cells and PBMCs are restimulated ex vivo for 5 hours at 37 degrees C. in the presence of GolgiPlug™ (containing Brefeldin A; BD Biosciences) with either mutant KRAS peptides (G12D, G12V or G13D) or with wild type KRAS peptide (2 μg/ml per peptide). CD8 vaccine responses can then be assessed by intracellular staining (ICS) for IFN-γ and/or TNF-α. Enhanced ICS responses for IFN-γ and/or TNF-α in mice treated with the KRAS mutant peptide vaccine-STING immune potentiator mRNA construct, as compared to treatment with the KRAS mutant peptide vaccine mRNA construct, indicates that the STING immune potentiator enhances KRAS-specific CD8 vaccine responses.

Example 7: Use of Immune Potentiator mRNA Construct in Combination with Activating Oncogene KRAS Mutant Peptide mRNA Constructs In this example, mutant KRAS peptide mRNA constructs are used in combination with a separate constitutively active STING immune potentiator mRNA construct to enhance immune responses to the mutant KRAS peptides.

The most frequently mutated oncogene in cancer is KRAS, which is mutated in roughly 30% of epithelial cancers, primarily lung, colorectal and pancreatic cancers (Pylayeva-Gupta Y, et al., *Nat Rev Cancer*, Vol. 11(11): 761-774, 2011). The 4 most prevalent KRAS mutant antigens in these three malignancies are G12D, G12V, G13D and G12C, which constitute 80-90% of the KRAS mutations (Prior et al. Cancer Res. 2012 May 15; 72(10): 2457-2467; Cox A D et al, *Nat Rev Drug Discov*, Vol. 13(11): 828-851, 2011). KRAS mutations occur mostly in a couple of "hotspots" and activate the oncogene. Prior research has shown limited ability to raise T cells specific to the oncogenic mutation. However, much of this was done in the context of the most common HLA allele (A2, which occurs in ~50% of Caucasians). More recently, it has been demonstrated that (a) specific T cells can be generated against point mutations in the context of less common HLA alleles (A11, C8), and (b) growing these cells ex-vivo and transferring them back to the patient has mediated a dramatic tumor response in a patient with lung cancer. (N Engl J Med 2016; 375:2255-2262 Dec. 8, 2016 DOI: 10.1056/NEJMoa1609279).

KRAS mutations occur in approximately 40% of colorectal cancers. As shown in Table 5 below, in CRC (colorectal cancer), only 3 mutations (G12V, G12D, and G13D) account for 96% of KRAS mutations in this malignancy. Furthermore, all CRC patients get typed for KRAS mutations as standard of care.

TABLE 5

| COSMIC* case counts | | | | |
|---|---|---|---|---|
| | All cancers | % | CRC | % |
| G12S | 1849 | 1% | | |
| G12V | 9213 | 4% | 5215 | 29% |
| G12C | 435 | 2% | | |
| G12D | 13634 | 7% | 8083 | 44% |
| G12A | 2179 | 1% | | |
| G12R | 1244 | 1% | | |
| G13D | 5084 | 2% | 4267 | 23% |
| | | 18% | | 96% |
| Tested | 208629 | | 18271 | |

*cancer.sanger.ac.uk/cosmic/gene/analysis?In=KRAS

In another COSMIC data set, 73.68% of KRAS mutations in colorectal cancer are accounted for by these 3 mutations (G12V, G12D, and G13D) (Table 6).

TABLE 6

| | colon | % | rectal | % | total | % |
|---|---|---|---|---|---|---|
| 12D | 635 | 35.04 | 178 | 33.46 | 813 | 34.68 |
| 12V | 364 | 20.09 | 124 | 23.31 | 488 | 20.82 |
| 13D | 338 | 18.65 | 88 | 16.54 | 426 | 18.17 |
| | | | | | | 73.68 |

Figure 10:
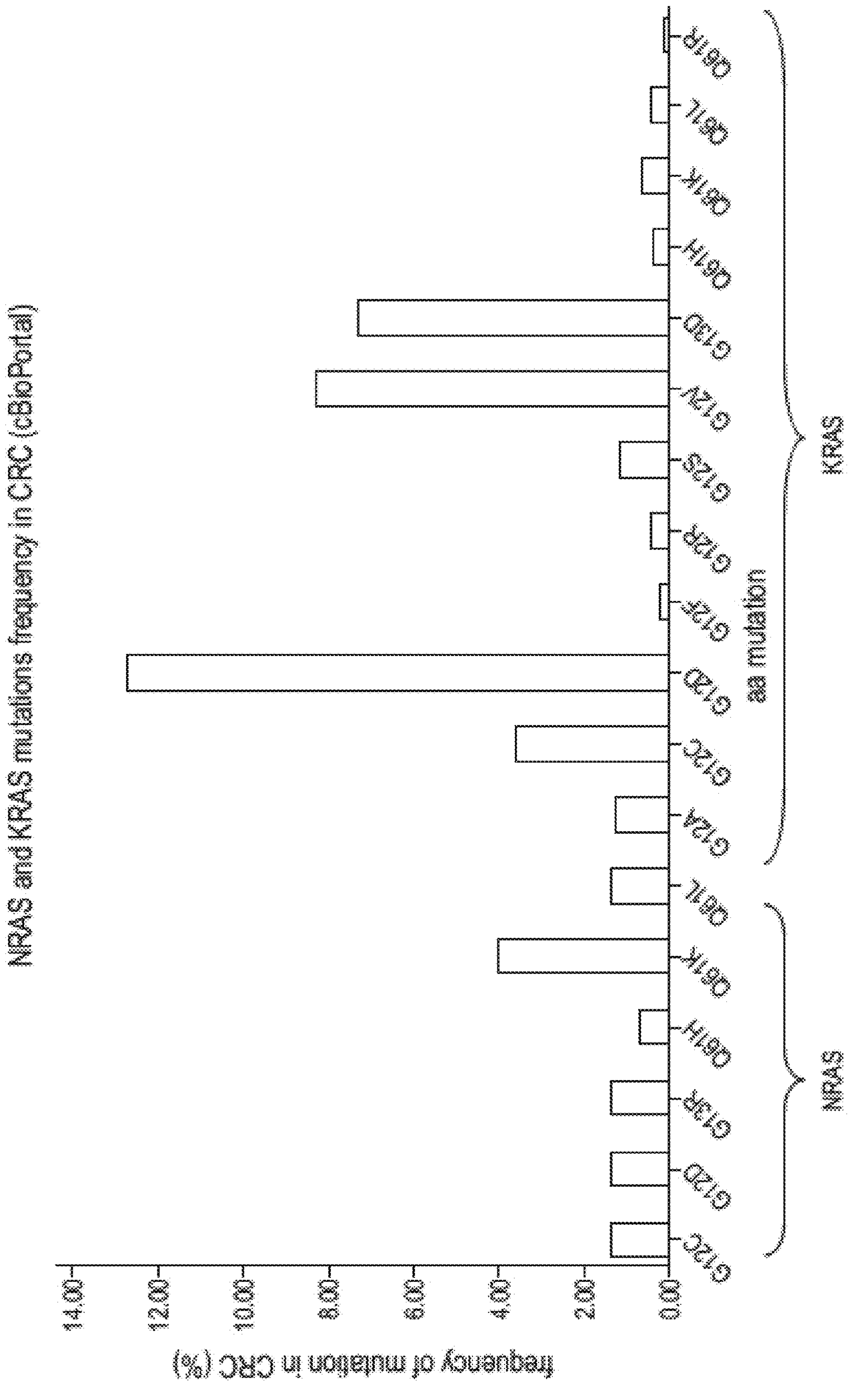
FIG. 10 depicts NRAS and KRAS mutation frequency in colorectal cancer as identified using cBioPortal.

Prior et al. investigated and summarized isoform-specific point mutation specificity for HRAS, KRAS and NRAS, respectively. Data representing total number of tumors with each point mutation were collated from COSMIC v52 release. The most frequent mutations for each isoform for each cancer type are reported (see Table 2 of Prior et al.). In addition, secondary KRAS mutations have been identified in EGFR blockade resistant patients. RAS is downstream of EGFR and it has been found to constitute a mechanism of resistance to EGFR blockade therapies. EGFR blockade resistant KRAS mutant tumors can be targeted using compositions and methods disclosed herein. In a few cases, more than one KRAS mutation was identified in the same patient (up to four different mutations co-occur). Diaz et al. report these secondary KRAS mutations after acquisition of EGFR blockade (see Supplementary Table 2), and Misale et al. reports secondary KRAS mutations after EGFR blockade (see FIG. 3*b*) (Diaz et al. The molecular evolution of acquired resistance to targeted EGFR blockade in colorectal cancers, *Nature* 486: 537 (2012); Misale et al. Emergence of KRAS mutations and acquired resistance to anti-EGFR therapy in colorectal cancer, *Nature* 486: 532 (2012)). This mutational spectrum appears to be at least somewhat different than primary tumor missense mutants in colorectal cancer. As shown in FIG. 10, NRAS is also mutated in colorectal cancer, but at a lower frequency than KRAS, based on analysis available in cBioPortal and Prior et al.

In addition to identification of KRAS mutations in colorectal cancer, such mutations have been found in non-small cell lung carcinoma and pancreatic cancer. Table 7 provides the frequencies of four KRAS mutations in these three cancers.

TABLE 7

| KRAS Allele | NSCLC[1] (30% mutant KRAS[4]) % Breakdown | Colorectal[2] (45% mutant KRAS[4]) % Breakdown | Pancreatic[3] (95% mutant KRAS[4]) % Breakdown |
|---|---|---|---|
| G12C | 46% | 8% | 2% |
| G12V | 20% | 22% | 30% |
| G12D | 11% | 36% | 51% |
| G13D | 3% | 19% | <1% |
| total | 80% | 85% | 83% |

[1]Mellema et al. Comparison of clinical outcome after first-line platinum-based chemotherapy in different types of KRAS mutated advanced NSCLC, Lung Cancer 90: 2 (2015) (Table 1)
[2]Neumann et al, Frequency and type of KRAS mutations in routine diagnostic analysis of metastatic colorectal cancer, Pathology Research and Practice 205 (2009) (FIG. 1)
[3]Kirsten L. Bryant, Joseph D. Mancias, Alec C. Kimmelman, Channing J. Der, KRAS: feeding pancreatic cancer proliferation, In Trends in Biochemical Sciences, 39: 2, 2014 (FIG. 2)
[4]Adrienne D. Cox et al., Drugging the undruggable RAS: Mission Possible?, Nature Reviews Drug Discovery 13, 828-851 (2014) (Table 1)

In this example, animals are administered an immunomodulatory therapeutic composition that includes an mRNA encoding at least one activating oncogene mutation peptide, e.g., at least one activating KRAS mutation, alone or in combination with an immune potentiator mRNA construct, e.g. a constitutively active STING mRNA construct, e.g., encoding a sequence as shown in any of SEQ ID NOs: 1-10, such as for example a mRNA construct encoding a constitutively active human STING protein comprising a V155M mutation, having the amino acid sequence shown in SEQ ID NO: 1 and encoded the nucleotide sequence shown in SEQ ID NO: 139.

Exemplary KRAS mutant peptide sequences and mRNA constructs are shown in Tables 8-10.

TABLE 8

KRAS mutant peptide sequences

| | 9 AA sequence | 15mer | 25mer |
|---|---|---|---|
| G12D | VVGADGVGK (SEQ ID NO: 121) | MKLVVVGADGVGKSAL (SEQ ID NO: 36) | MTEYKLVVVGADGVGKSALTIQLIQ (SEQ ID NO: 39) |
| G12V | VVGAVGVGK (SEQ ID NO: 122) | MKLVVVGAVGVGKSAL (SEQ ID NO: 37) | MTEYKLVVVGAVGVGKSALTIQLIQ (SEQ ID NO: 40) |
| G13D | VGAGDVGKS (SEQ ID NO: 123) | MLVVVGAGDVGKSALT (SEQ ID NO: 38) | MTEYKLVVVGAGDVGKSALTIQLIQ (SEQ ID NO: 41) |
| G12C | VVGACGVGK (SEQ ID NO: 124) | MKLVVVGACGVGKSA (SEQ ID NO: 125) | MTEYKLVVVGACGVGKSALTIQLIQ (SEQ ID NO: 72) |
| WT | | | MTEYKLVVVGAGGVGKSALTIQLIQ (SEQ ID NO: 74) |

TABLE 9

KRAS mutant amino acid sequences

| KRAS MUTANT | AMINO ACID SEQUENCE |
|---|---|
| KRAS(G12D)15mer | MKLVVVGADGVGKSAL (SEQ ID NO: 36) |
| KRAS(G12V)15mer | MKLVVVGAVGVGKSAL (SEQ ID NO: 37) |
| KRAS(G13D)15mer | MLVVVGAGDVGKSALT (SEQ ID NO: 38) |
| KRAS(G12D)25mer | MTEYKLVVVGADGVGKSALTIQLIQ (SEQ ID NO: 39) |
| KRAS(G12V)25mer | MTEYKLVVVGAVGVGKSALTIQLIQ (SEQ ID NO: 40) |
| KRAS(G13D)25mer | MTEYKLVVVGAGDVGKSALTIQLIQ (SEQ ID NO: 41) |
| KRAS(G12D)15mer^3 | MKLVVVGADGVGKSALKLVVVGADGVGKSALKLVVVGADGVGKSAL (SEQ ID NO: 42) |
| KRAS(G12V)15mer^3 | MKLVVVGAVGVGKSALKLVVVGAVGVGKSALKLVVVGAVGVGKSAL (SEQ ID NO: 43) |
| KRAS(G13D)15mer^3 | MLVVVGAGDVGKSALTLVVVGAGDVGKSALTLVVVGAGDVGKSALT (SEQ ID NO: 44) |
| KRAS(G12D)25mer^3 | MTEYKLVVVGADGVGKSALTIQLIQMTEYKLVVVGADGVGKSALTIQLIQMTEYKLVVVGADGVGKSALTIQLIQ (SEQ ID NO: 45) |
| KRAS(G12V)25mer^3 | MTEYKLVVVGAVGVGKSALTIQLIQMTEYKLVVVGAVGVGKSALTIQLIQMTEYKLVVVGAVGVGKSALTIQLIQ (SEQ ID NO: 46) |

TABLE 9-continued

| KRAS mutant amino acid sequences | |
|---|---|
| KRAS MUTANT | AMINO ACID SEQUENCE |
| KRAS(G13D)25mer^3 | MTEYKLVVVGAGDVGKSALTIQLIQMTEYKLVVVGAGDVGKSA LTIQLIQMTEYKLVVVGAGDVGKSALTIQLIQ (SEQ ID NO: 47) |
| KRAS(G12C)25mer | MTEYKLVVVGACGVGKSALTIQLIQ (SEQ ID NO: 72) |
| KRAS(G12C)25mer^3 | MTEYKLVVVGACGVGKSALTIQLIQMTEYKLVVVGACGVGKSA LTIQLIQMTEYKLVVVGACGVGKSALTIQLIQ (SEQ ID NO: 73) |
| KRAS(WT)25mer | MTEYKLVVVGAGGVGKSALTIQLIQ (SEQ ID NO: 74) |

TABLE 10

| KRAS mutant antigen mRNA sequences | | |
|---|---|---|
| mRNA Name | Orf Sequence (Amino Acid) | Orf Sequence (Nucleotide) |
| KRAS (G12D) 25mer | MTEYKLVVVGADGVG KSALTIQLIQ (SEQ ID NO: 39) | ATGACCGAGTACAAGCTGGTGGTGGTGGGCGCCGACGGCG TGGGCAAGAGCGCCCTGACCATCCAGCTGATCCAG (SEQ ID NO: 126) |
| KRAS (G12V) 25mer | MTEYKLVVVGAVGVG KSALTIQLIQ (SEQ ID NO: 40) | ATGACCGAGTACAAGCTGGTGGTGGTGGGCGCCGTGGGCG TGGGCAAGAGCGCCCTGACCATCCAGCTGATCCAG (SEQ ID NO: 127) |
| KRAS (G13D) 25mer | MTEYKLVVVGAGDVG KSALTIQLIQ (SEQ ID NO: 41) | ATGACCGAGTACAAGCTGGTGGTGGTGGGCGCCGGCGACG TGGGCAAGAGCGCCCTGACCATCCAGCTGATCCAG (SEQ ID NO: 128) |
| KRAS (G12D) 25mer^3 | MTEYKLVVVGADGVG KSALTIQLIQMTEYK LVVVGADGVGKSALT IQLIQMTEYKLVVVG ADGVGKSALTIQLIQ (SEQ ID NO: 45) | ATGACCGAGTACAAGTTAGTGGTTGTGGGCGCCGACGGCG TGGGCAAGAGCGCCCTCACCATCCAGCTTATCCAGATGAC GGAATATAAGTTAGTAGTAGTGGGAGCCGACGGTGTCGGC AAGTCCGCTTTGACCATTCAACTTATTCAGATGACAGAGT ATAAGCTGGTCGTTGTAGGCGCAGACGGCGTTGGAAAGTC GGCACTGACGATCCAGTTGATCCAG (SEQ ID NO: 129) |
| KRAS (G12V) 25mer^3 | MTEYKLVVVGAVGVG KSALTIQLIQMTEYK LVVVGAVGVGKSALT IQLIQMTEYKLVVVG AVGVGKSALTIQLIQ (SEQ ID NO: 46) | ATGACCGAGTACAAGCTCGTCGTGGTGGGCGCCGTGGGCG TGGGCAAGAGCGCCCTAACCATCCAGTTGATCCAGATGAC CGAATATAAGCTCGTGGTAGTCGGAGCGGTGGGCGTTGGC AAGTCAGCGCTAACAATACAACTAATCCAAATGACCGAAT ACAAGCTAGTTGTAGTCGGTGCCGTCGGCGTTGGAAAGTC AGCCCTTACAATTCAGCTCATTCAG (SEQ ID NO: 130) |
| KRAS (G13D) 25mer^3 | MTEYKLVVVGAGDVG KSALTIQLIQMTEYK LVVVGAGDVGKSALT IQLIQMTEYKLVVVG AGDVGKSALTIQLIQ (SEQ ID NO: 47) | ATGACCGAGTACAAGCTCGTAGTGGTTGGCGCCGGCGACG TGGGCAAGAGCGCCCTAACCATCCAGCTCATCCAGATGAC AGAATATAAGCTTGTGGTTGTGGGAGCAGGAGACGTGGGA AAGAGTGCGTTGACGATTCAACTCATACAGATGACCGAAT ACAAGTTGGTGGTGGTCGGCGCAGGTGACGTTGGTAAGTC TGCACTAACTATACAACTGATCCAG (SEQ ID NO: 190) |
| KRAS (G12C) 25mer | MTEYKLVVVGACGVG KSALTQILIQ (SEQ ID NO: 72) | ATGACCGAGTACAAGCTGGTGGTGGTGGGCGCCTGCGGCG TGGGCAAGAGCGCCCTGACCATCCAGCTGATCCAG (SEQ ID NO: 132) |
| KRAS (G12C) 25mer^3 | MTEYKLVVVGACGVG KSALTIQLIQMTEYK LVVVGACGVGKSALT IQLIQMTEYKLVVVG ACGVGKSALTIQLIQ (SEQ ID NO: 73) | ATGACCGAGTACAAGCTCGTGGTTGTTGGCGCCTGCGGCG TGGGCAAGAGCGCCCTCACCATCCAGCTCATCCAGATGAC AGAGTATAAGTTAGTCGTTGTCGGAGCTTGCGGAGTTGGA AAGTCGGCGCTCACCATTCAACTCATACAAATGACAGAAT ATAAGTTAGTGGTGGTGGGTGCGTGTGGCGTTGGCAAGAG TGCGCTTACTATCCAGCTCATTCAG (SEQ ID NO: 184) |
| KRAS (WT) 25mer | MTEYKLVVVGAGGVG KSALTIQLIQ (SEQ ID NO: 74) | ATGACCGAGTACAAGCTGGTGGTGGTGGGCGCCGGCGGCG TGGGCAAGAGCGCCCTGACCATCCAGCTGATCCAG (SEQ ID NO: 133) |

TABLE 10-continued

KRAS mutant antigen mRNA sequences

| mRNA Name | Orf Sequence (Amino Acid) | Orf Sequence (Nucleotide) |
|---|---|---|

Chemistry: uridines modified N1-methyl pseudouridine (m1Ψ)
Cap: C1
Tail: T100

5' UTR Sequence (standard 5' Flank (includes Production FP + T7 site + 5'UTR)):
TCAAGCTTTTGGACCCTCGTACAGAAGCTAATACGACTCACTATAGGGAAATAAGAGAGAAAAG
AAGAGTAAGAAGAAATATAAGAGCCACC (SEQ ID NO: 21)

5' UTR Sequence (No Promoter):
GGGAAATAAGAGAGAAAAGAAGAGTAAGAAGAAATATAAGAGCCAC
(SEQ ID NO: 134)

3' UTR Sequence (Human 3' UTR no XbaI):
TGATAATAGGCTGGAGCCTCGGTGGCCATGCTTCTTGCCCCTTGGGCCTCCCCCCAGCCCCTCC
TCCCCTTCCTGCACCCGTACCCCCGTGGTCTTTGAATAAAGTCTGAGTGGGCGGC
(SEQ ID NO: 22)

In a first study to examine the effect of a STING immune potentiator mRNA construct on KRAS antigen responses in vivo, HLA-A*2:01 Tg mice (Taconic, strain 9659F, n=4) are administered mRNA encoding various forms of mutated KRAS peptide antigens as follows: mRNA encoding mutated KRAS (alone or in combination with STING) administered on day 1, bleed taken on day 8, mRNA encoding mutated KRAS (alone or in combination with STING) administered on day 15, animal sacrificed on day 22. The test groups are shown in Table 11 as follows:

TABLE 11

| TEST group | Group | Test/Control Material | Immune Potentiator | Vehicle | Route | Dosing Regimen |
|---|---|---|---|---|---|---|
| KRAS-MUT | 1 | KRAS G12D | None (NTFIX) | Compound 25 | IM | Day 1, 15 |
| | 2 | KRAS G12V | None (NTFIX) | Compound 25 | IM | Day 1, 15 |
| | 3 | KRAS G13D | None (NTFIX) | Compound 25 | IM | Day 1, 15 |
| | 4 | KRAS G12C | None (NTFIX) | Compound 25 | IM | Day 1, 15 |
| KRAS-MUT + STING | 5 | KRAS G12D | STING (V155M) | Compound 25 | IM | Day 1, 15 |
| | 6 | KRAS G12V | STING (V155M) | Compound 25 | IM | Day 1, 15 |
| | 7 | KRAS G13D | STING (V155M) | Compound 25 | IM | Day 1, 15 |
| | 8 | KRAS G12C | STING (V155M) | Compound 25 | IM | Day 1, 15 |
| No Ag | 9 | NTFIX | NTFIX | Compound 25 | IM | Day 1, 15 |
| STING Only | 10 | NTFIX | STING V155M) | Compound 25 | IM | Day 1, 15 |

mRNA is administered to animals at a dose of 0.5 mg/kg (10 ug per 20-g animal). The KRAS and STING constructs are administered at a 1:1 ratio. Ex vivo restimulation (2 ug/ml per peptide) is tested for 4 hours at 37 degrees Celsius in the presence of GolgiPlug (Brefeldin A). Intracellular cytokine staining (ICS) is tested for KRAS G12D, KRAS G12V, KRAS G13D, KRAS WT, and no peptide.

mRNA encoding KRAS mutations, alone or in combination with mRNA encoding constitutively active STING, is tested for the ability to generate T cells. Efficacy of mRNA encoding KRAS mutations is compared, for example, to peptide vaccination. The effect of the STING immune potentiator is determined by comparing treatment with the KRAS mutant peptides alone versus in combination with the STING immune potentiator. For example, CD8 vaccine responses can be assessed by intracellular staining (ICS) for IFN-γ and/or TNF-α as described herein. Enhanced ICS responses for IFN-γ and/or TNF-α in mice treated with the KRAS mutant peptide vaccine in combination with the STING immune potentiator mRNA construct, as compared to treatment with the KRAS mutant peptide vaccine mRNA construct alone, indicates that the STING immune potentiator enhances KRAS-specific CD8 vaccine responses.

In a second study to examine the effect of the STING immune potentiator mRNA construct on immune responses to various different forms of the mutant KRAS peptide antigen mRNA constructs, HLA*A*11:01 Tg mice (Taconic, strain 9660F, n=4) are administered mRNA encoding various different forms of mutated KRAS peptide antigen mRNA constructs in combination with a STING immune potentiator mRNA construct as follows: mRNA encoding mutated KRAS in combination with STING administered on day 1, bleed taken on day 8, mRNA encoding mutated KRAS in combination with STING administered on day 15, animal sacrificed on day 22.

The types of mutated KRAS constructs tested were as follows: (i) mRNA encoding a single mutant KRAS 25mer peptide antigen containing either the G12D, G12V, G13D or G12C mutation ("singlet"); (ii) mRNA encoding a concatemer of three 25mer peptide antigens (thus creating a 75mer), one of each containing the G12D, G12V and G13D mutations ("KRAS-3MUT"); (iii) mRNA encoding a concatemer of four 25mer peptide antigens (thus creating a 100mer), one of each containing the G12D, G12V, G13D and G12C mutations ("KRAS-4MUT"); or (iv) four separate mRNAs coadministered together, each encoding a single mutant KRAS 25mer peptide antigen containing either the G12D, G12V, G13D or G12C mutation ("Single×4").

The amino acid and nucleotide sequences of the G12D 25mer are shown in SEQ ID NOs: 39 and 126, respectively. The amino acid and nucleotide sequences of the G12V 25mer are shown in SEQ ID NOs: 40 and 127, respectively. The amino acid and nucleotide sequences of the G13D 25mer are shown in SEQ ID NOs: 41 and 128, respectively. The amino acid and nucleotide sequences of the G12C 25mer are shown in SEQ ID NOs: 72 and 132 respectively. The amino acid and nucleotide sequences of the KRAS-3MUT 75mer are shown in SEQ ID NOs: 135 and 136, respectively. The amino acid and nucleotide sequences of the KRAS-4MUT 100mer are shown in SEQ ID NOs: 137 and 138, respectively.

The test groups are shown in Table 12 as follows:

TABLE 12

| TEST group | Group | Test/Control Material | Immune Potentiator | Vehicle | Route | Dosing Regimen |
|---|---|---|---|---|---|---|
| KRAS-MUT | 1 | KRAS G12D | STING (V155M) | Compound 25 | IM | Day 1, 15 |
| Singlet | 2 | KRAS G12V | STING (V155M) | Compound 25 | IM | Day 1, 15 |
| | 3 | KRAS G13D | STING (V155M) | Compound 25 | IM | Day 1, 15 |
| | 4 | KRAS G12C | STING (V155M) | Compound 25 | IM | Day 1, 15 |
| KRAS-MUT | 5 | KRAS-3MUT | STING (V155M) | Compound 25 | IM | Day 1, 15 |
| Concatemer | 6 | KRAS-4MUT | STING (V155M) | Compound 25 | IM | Day 1, 15 |
| Single X 4 | 7 | G12D + G12V + G12C + G13D | STING (V155M) | Compound 25 | IM | Day 1, 15 |
| STING Only | 8 | NTFIX | STING (V155M) | Compound 25 | IM | Day 1, 15 |

mRNA is administered to animals at a dose of 0.5 mg/kg (10 ug per 20-g animal). The KRAS and STING constructs are administered at a 5:1 ratio. Ex vivo restimulation (2 ug/ml per peptide) is carried out for 5 hours at 37 degrees Celsius in the presence of GolgiPlug (Brefeldin A). Intracellular cytokine staining (ICS) is tested for KRAS G12D, KRAS G12V, KRAS G13D, G12C, KRAS WT, and no peptide.

The ability of the various mRNAs encoding KRAS mutations in combination with mRNA encoding constitutively active STING to generate T cell responses is tested to allow for comparison of the effect of the STING immune potentiator on the various different KRAS constructs. For example, CD8 vaccine responses can be assessed by intracellular staining (ICS) for IFN-γ and/or TNF-α as described herein.

Example 8: Immune Potentiator mRNAs Enhance HPV Vaccine Responses

In this example, the potency and durability of responses to a human papillomavirus (HPV) E6/E7 mRNA-based vaccine used in combination with STING, IRF3 or IRF7 immune potentiators were examined. A specific immune response to human papillomavirus (HPV) in the cervical microenvironment is known to play a key role in eradicating infection and eliminating mutated cells. However, high-risk HPVs are known to modulate immune cells to create an immunosuppressive microenvironment (see e.g., Prata, T. T. et al. (2015) *Immunology* 146:113-121). Thus, an HPV vaccination approach that leads to a robust and durable immune response is highly desireable.

The HPV vaccines used in this example were mRNA constructs encoding either intracellular or soluble forms of HPV 16 antigens E6 and E7, referred to herein as iE6/E7 and sE6/E7, respectively. To create the soluble format, a signal peptide required for secretion was fused to the N-terminal of the antigen. The sequence of the signal peptide was derived from the Ig kappa chain V-III region HAH. Mice were immunized intramuscularly with either the iE6/E7 or sE6/E7 mRNA vaccine (at a dose of 0.25 mg/kg) on days 0 and 14, combination with either a control mRNA construct (NTFIX), or a STING, IRF3 or IRF7 immune potentiator mRNA construct (at a dose of 0.25 mg/kg). The constitutively active STING immune potentiator contained a V155M mutation (mouse version corresponding to SEQ ID NO: 1). The constitutively active IRF3 immune potentiator contained a S396D mutation (corresponding to SEQ ID NO: 12). The constitutively active IRF7 immune potentiator contained an internal deletion and six point mutations (mouse version corresponding to SEQ ID NO: 18). The HPV vaccine construct and the immune potentiator construct were coformulated in MC3 lipid nanoparticles.

At day 21 and 53, spleen cells and peripheral blood mononuclear cells (PBMC) from mice in each test group were restimulated ex vivo for 4 hours at 37 degrees C. in the presence of GolgiPlug™ (containing Brefeldin A; BD Biosciences) with either: an E6 peptide pool (containing 37 E6 peptides, the sequences of which are shown in SEQ ID NOs: 36-72), an E7 peptide pool (containing 22 E7 peptides, the sequences of which are shown in SEQ ID NOs: 73-94), E6 single peptides (8 individual peptides), E7 single peptides (7 individual peptides) or no peptides (control). CD8 vaccine responses were assessed by intracellular staining (ICS) for IFN-γ or TNF-α.

Figure 11A:
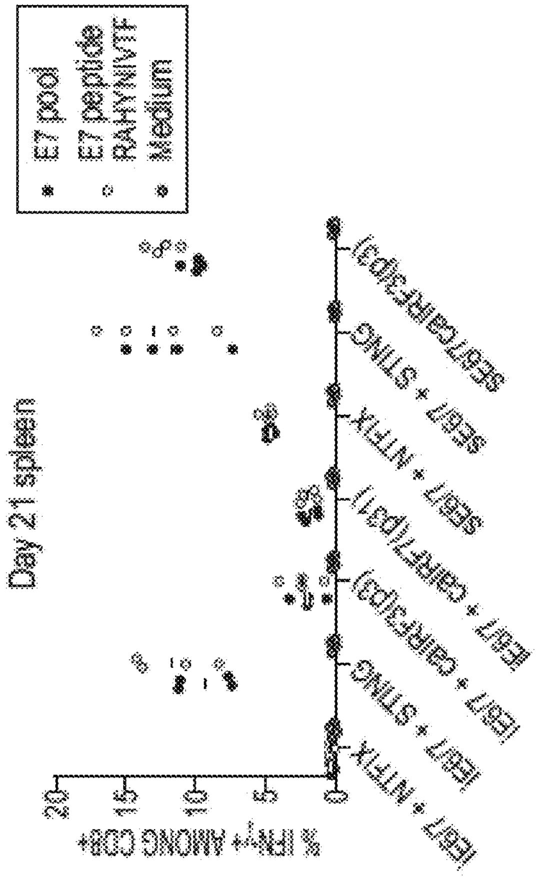
FIGS. 11A-11B are graphs showing intracellular staining (ICS) of $CD8^+$ splenocytes from mice immunized with HPV E6/E7 vaccine constructs coformulated with either a STING, IRF3 or IRF7 immune potentiator mRNA construct on day 21 post first immunization.
Figure 11B:
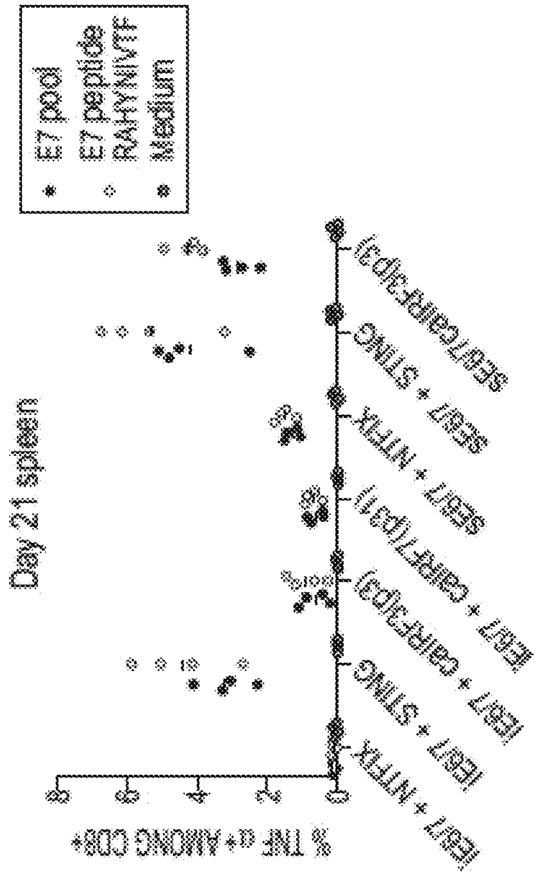
Figure 12A:
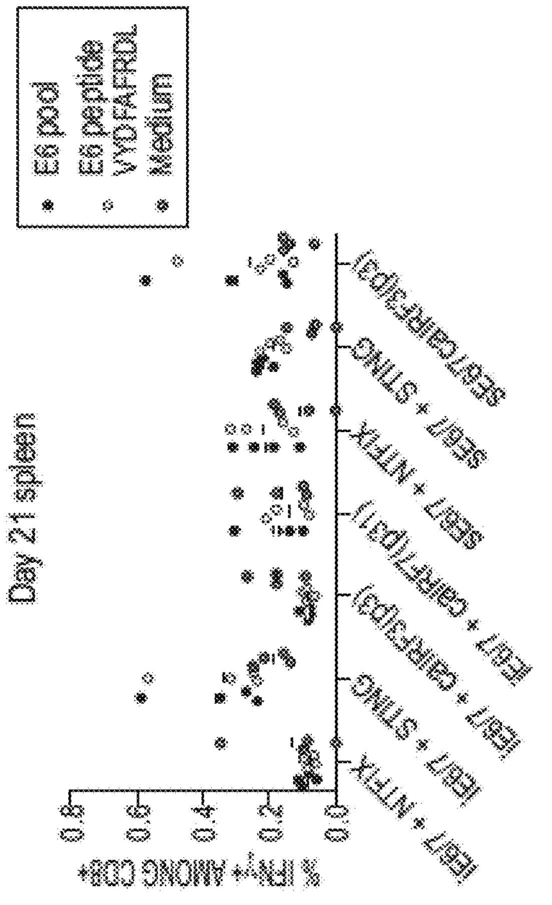
FIGS. 12A-12B are graphs showing intracellular staining (ICS) of $CD8^+$ splenocytes from mice immunized with HPV E6/E7 vaccine constructs coformulated with either a STING, IRF3 or IRF7 immune potentiator mRNA construct.
Figure 12B:
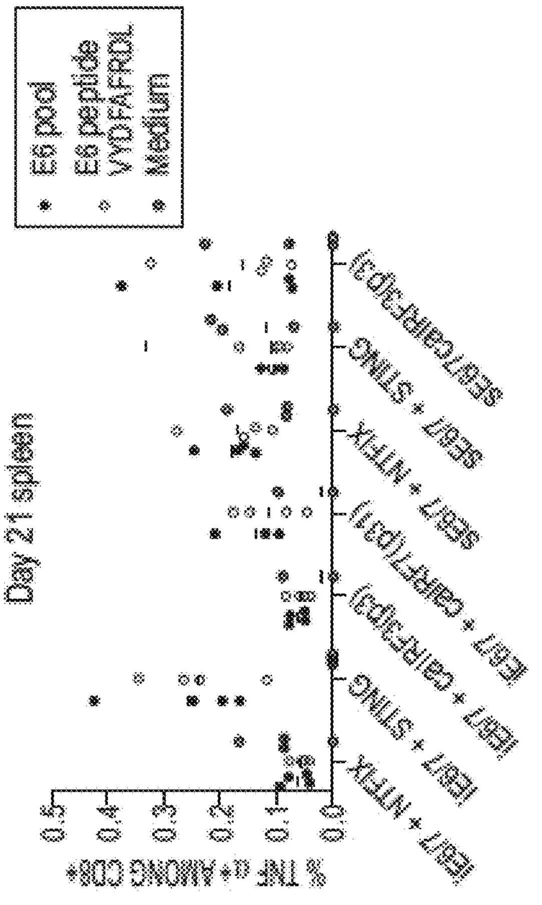
Figure 13A:
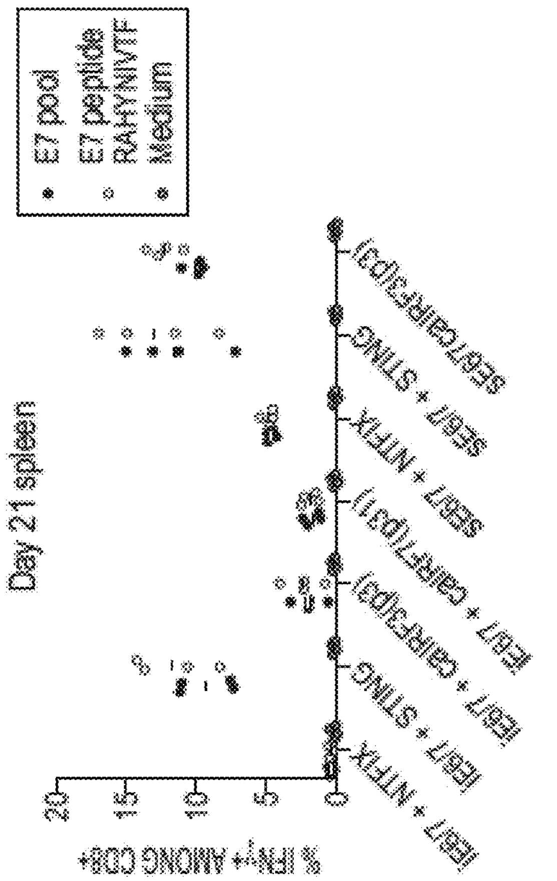
FIGS. 13A-13B are graphs showing E7-specific responses for IFN-γ intracellular staining (ICS) of day 21 (FIG. 13A) or day 53 (FIG. 13B) $CD8^+$ splenocytes from mice immunized with HPV E6/E7 vaccine constructs coformulated with either a STING, IRF3 or IRF7 immune potentiator mRNA construct.
Figure 13B:
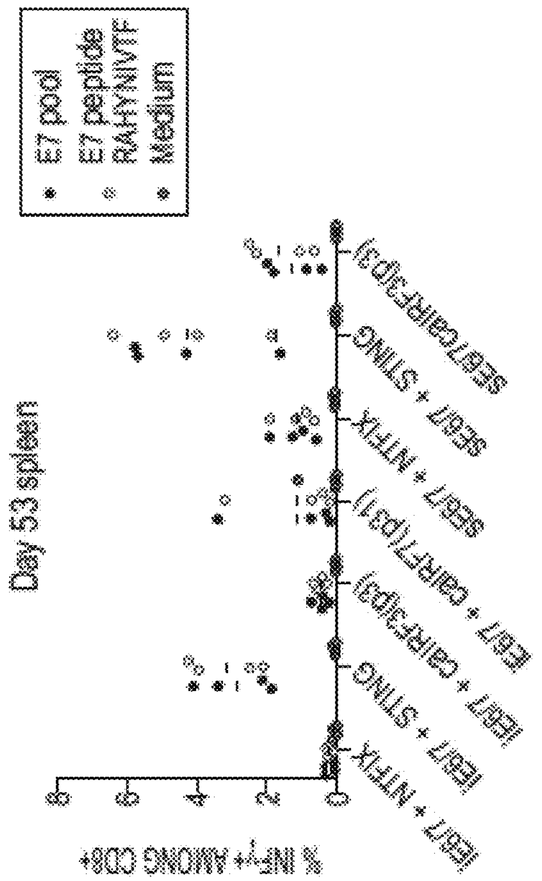

Representative ICS results for E7-specific responses by day 21 spleen cells for IFN-γ and TNF-α are shown in FIG. 11A (IFN-γ) and FIG. 11B (TNF-α). Representative ICS results for E6-specific responses by day 21 spleen cells for IFN-γ and TNF-α are shown in FIG. 12A (IFN-γ) and FIG. 12B (TNF-α). The results in FIGS. 11A-11B and 12A-12B demonstrate that CD8 vaccine responses (to both the intracellular and soluble antigen format) were greatly enhanced when the STING, IRF3 or IRF7 immune potentiators were coformulated with the vaccine, with the E7 epitope being stronger and less variable than the E6 epitope and with the soluble form of antigen being stronger than the intracellular form of antigen. This enhanced CD8 vaccine responses by the immune potentiators was shown to be durable, as evidenced by the representative day 21 versus day 53 E7-specific spleen cell IFN-γ ICS data shown in FIGS. 13A and 13B, respectively. Similar results to the spleen cell data were observed for the PBMC experiments (data not shown).

Figure 14B:
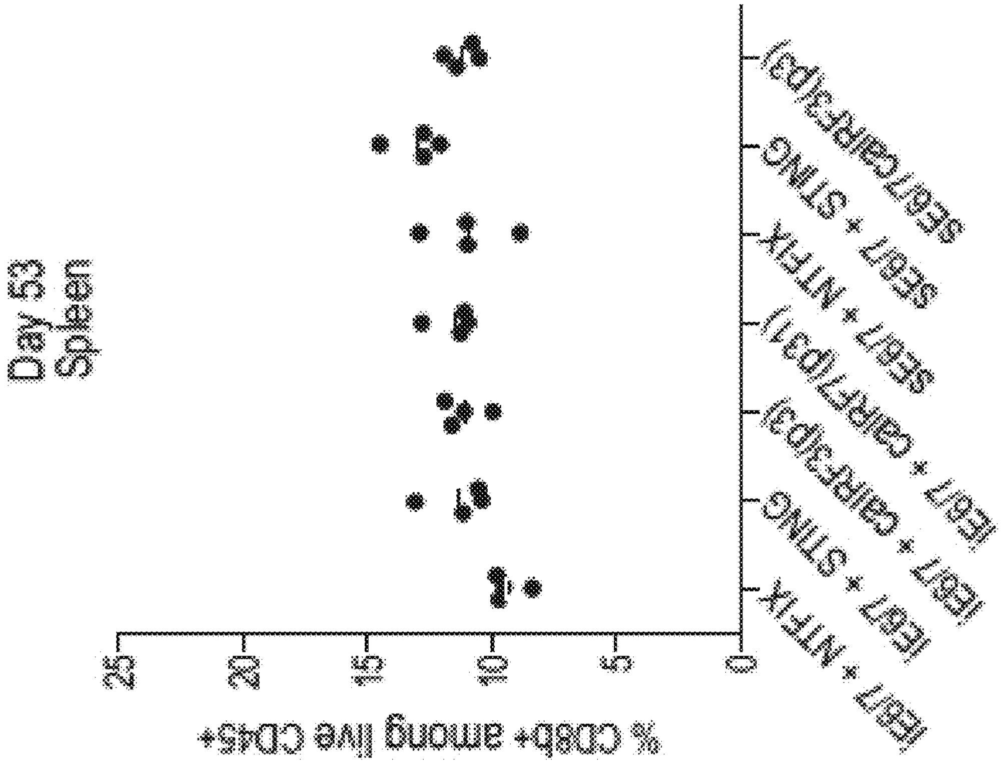
FIGS. 14A-14B are graphs showing the percentage of $CD8b^+$ cells among the live $CD45^+$ cells for day 21 (FIG. 14A) or day 53 (FIG. 14B) spleen cells from mice immunized with HPV E6/E7 vaccine constructs coformulated with either a STING, IRF3 or IRF7 immune potentiator mRNA construct.
Figure 14A:
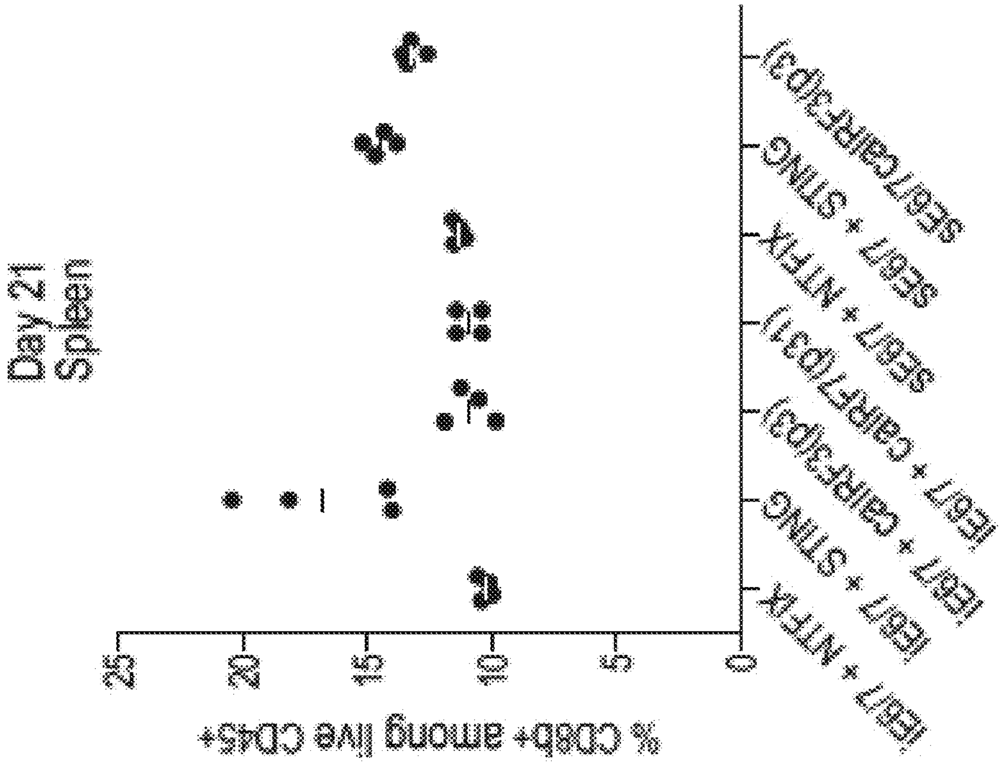

The percentage of $CD8b^+$ cells among the live $CD45^+$ cells was also examined. The results for day 21 versus day 53 spleen cells are shown in FIGS. 14A and 14B, respectively. The results demonstrate that the immune potentiators (in particular the STING construct) expand the total $CD8b^+$ population on day 21 but not day 53.

Figure 15A:
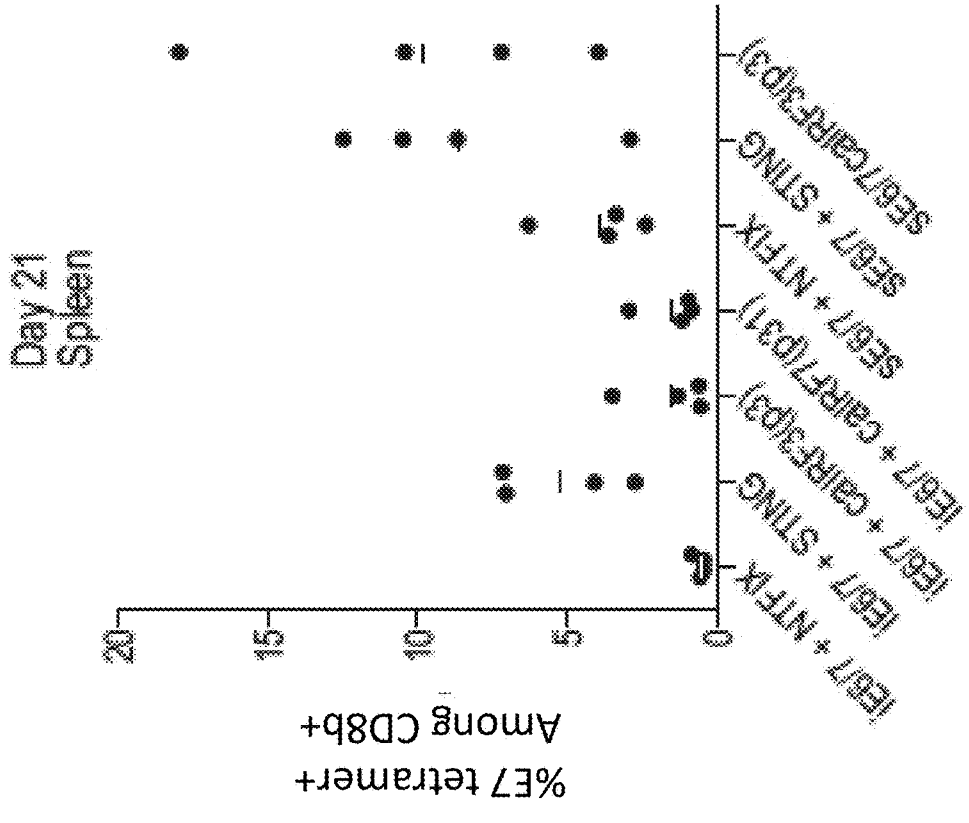
FIGS. 15A-15B are graphs showing E7-MHC1-tetramer staining of day 21 (FIG. 15A) or day 53 (FIG. 15B) $CD8b^+$ splenocytes from mice immunized with HPV E6/E7 vaccine constructs coformulated with either a STING, IRF3 or IRF7 immune potentiator mRNA construct.
Figure 15B:
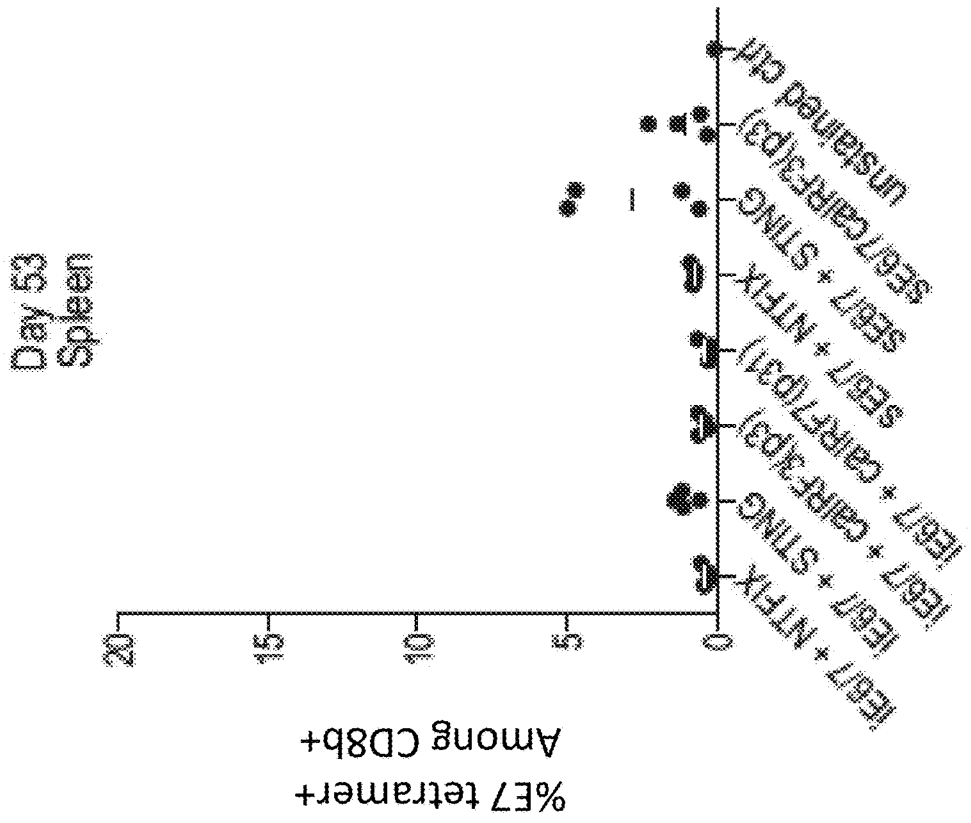
Figure 16B:
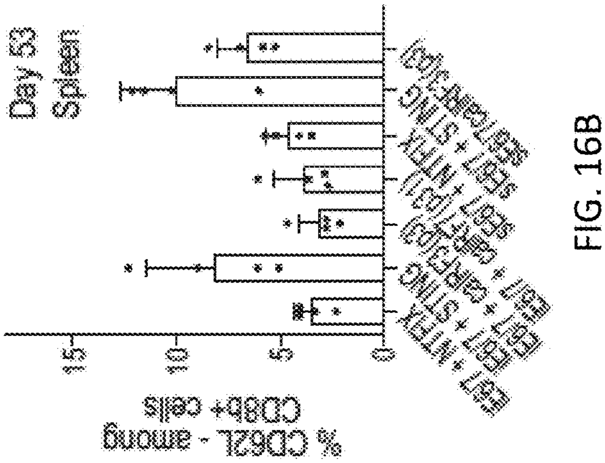
FIGS. 16A-16D are graphs showing that the majority of E7-tetramer$^+$ $CD8^+$ cells have an "effector memory" $CD62L^{lo}$ phenotype, with comparison of day 21 versus day 53 E7-tetramer$^+$ CD8 cells demonstrating that this "effector-memory" $CD62L^{lo}$ phenotype was maintained throughout the study.
Figure 16A:
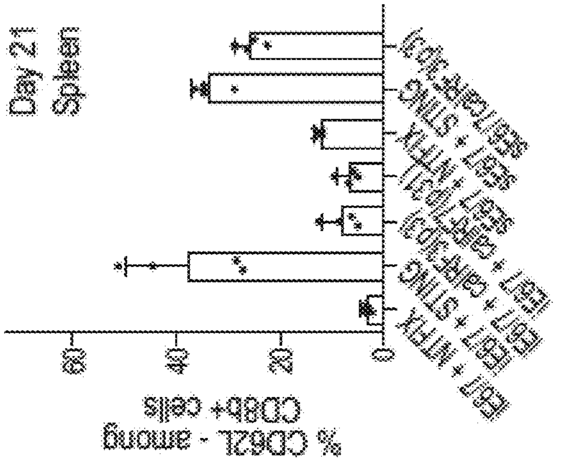
Figure 16D:
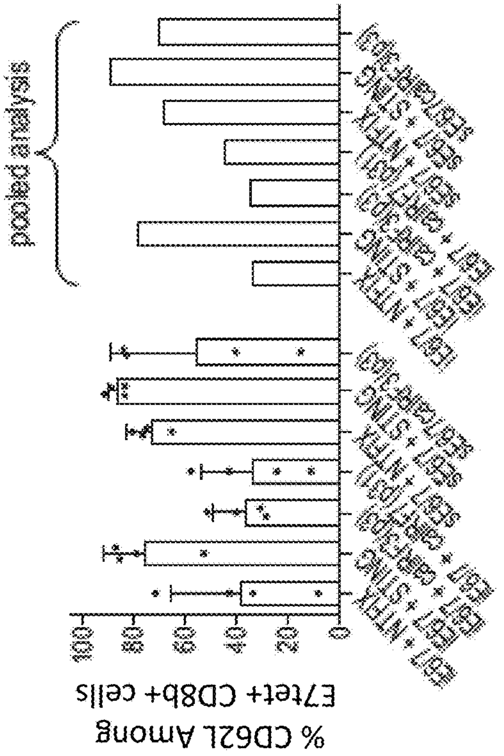
Figure 16C:
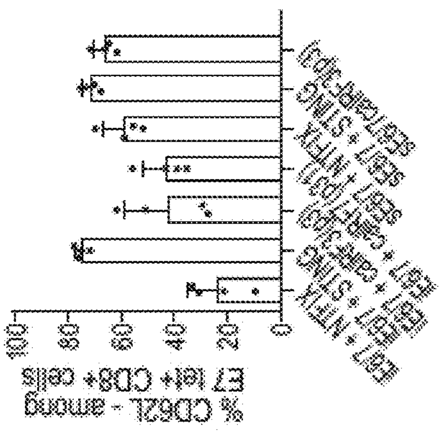

The ability of the immune potentiator constructs to enhance the CD8 vaccine response was further confirmed by E7-MHC1-tetramer staining. Representative results for day 21 versus day 53 spleen cells are shown in FIGS. 15A and 15B, respectively. The E7-MHC-1-tetramer staining results were consistent with the ICS results discussed above, although they were more variable. As demonstrated in FIGS. 16A-16D, the majority of the tetramer positive CD8 cells were found to have an "effector memory" $CD62L^{lo}$ phenotype. Comparison of day 21 versus day 53 $E7\text{-tetramer}^+$ CD8 cells demonstrated that this "effector-memory" $CD62L^{lo}$ phenotype was maintained throughout the study. Additional staining experiments demonstrated that the immune potentiators slightly reduced the % of total $Foxp3^+$ Treg CD4 Tcells (data not shown) and did not change the % of $CD138^+$ plasmablasts (data not shown).

Example 9: Prophylactic or Therapeutic Vaccination with HPV Vaccine in Combination with STING Immune Potentiator Inhibits Tumor Growth In this example, mice were treated with an HPV vaccine in combination with a STING immune potentiator either prior to, at the same time as, or after challenge with TC1 tumor cells. TC-1 is an HPV16 E7-expressing murine tumor model known in the art (see e.g., Bartkowiak et al. (2015) *Proc. Natl. Acad. Sci. USA* 112:E5290-5299). The HPV vaccines used in this example were mRNA constructs encoding either intracellular or soluble forms of HPV 16 antigens E6 and E7, referred to herein as iE6/E7 and sE6/E7, respectively, as described in Example 8. The constitutively active STING immune potentiator used in this example contained a V155M mutation, as described in Example 8. The HPV vaccine construct and the immune potentiator construct were coformulated in MC3 lipid nanoparticles. Certain mice were also treated with an immune checkpoint inhibitor (either anti-CTLA-4 or anti-PD-1).

Figure 17A:
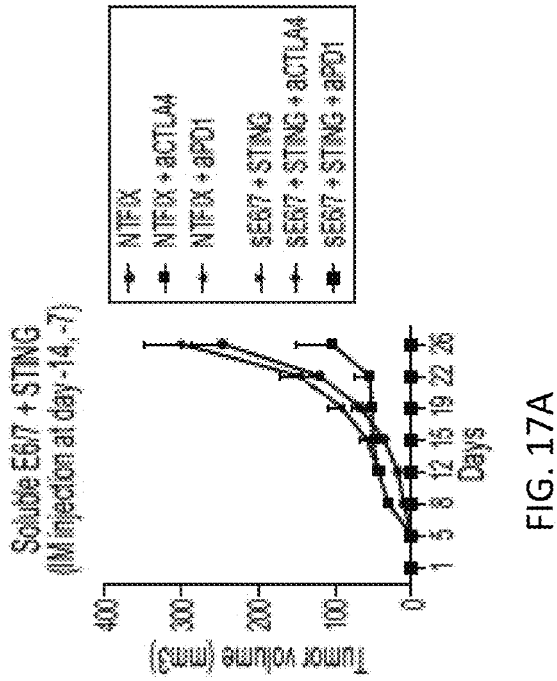
FIGS. 17A-17C are graphs showing tumor volume from mice vaccinated prophylactically as indicated with HPV E6/E7 construct together with a STING immune potentiator mRNA construct (alone or in combination with anti-CTLA-4 or anti-PD1 treatment), either prior to or at the time of challenge with a TC1 tumor that expresses HPV E7, showing inhibition of tumor growth by the HPV E6/E7+ STING treatment. Certain mice were treated on days −14 and −7 with soluble E6/E7+STING (FIG. 17A) or with intracellular E6/E7+STING (FIG. 17B), with tumor challenge on day 1. Other mice were treated on days 1 and 8 with soluble E6/E7+STING (FIG. 17C), with tumor challenge on day 1.
Figure 17B:
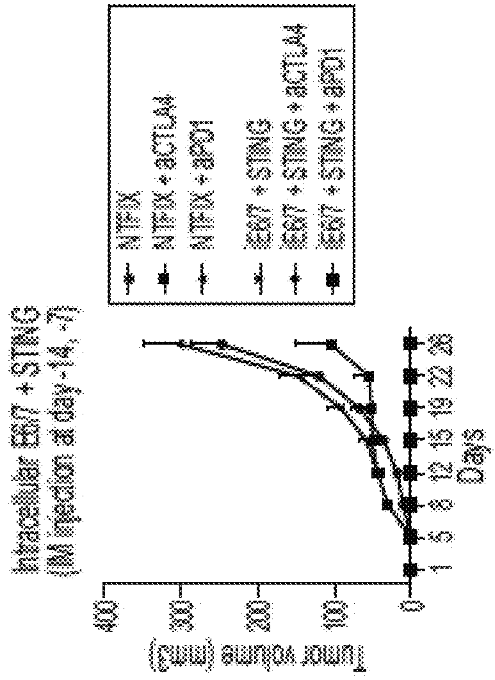
Figure 17C:
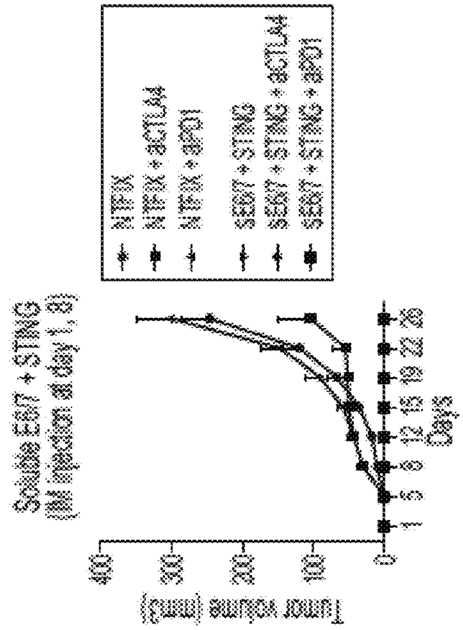

In a first set of experiments examining the prophylactic activity of the HPV+STING vaccination, C57/B6 mice were treated by intramuscular injection with 0.5 mg/kg of the HPV+STING vaccine (encoding either sE6/E7 or iE6/E7) on either (i) days −7 and −14, or (ii) days 1 and 8, followed by subcutaneous injection of $2\times10^5$ TC1 cells on day 1. Certain mice were also treated on days 6, 9 and 12 with either anti-CTLA-4 or anti-PD-1. Representative results, reported as tumor volume over time, are shown in the graphs of FIGS. 17A-17C, wherein FIGS. 17A and 17B show data for mice treated on days −14 and −7 with either sE6/E7 (FIG. 17A) or iE6/E7 (FIG. 17B) and FIG. 17C shows data for mice treated on days 1 and 8 with sE6/E7. The results demonstrate that all of the mice treated with the HPV+STING vaccine (alone or in combination with immune checkpoint inhibitors) showed complete inhibition of tumor growth over several weeks, as compared to the control mice (treated with the control mRNA construct NTFIX, alone or in combination with an immune checkpoint inhibitor). Thus, these experiments demonstrate that prophylactic vaccination (i.e., prior to or at the same time as tumor challenge) with the HPV vaccine together with the STING immune potentiator is effective in preventing growth of HPV-expressing tumor cells in vivo.

Figure 18B:
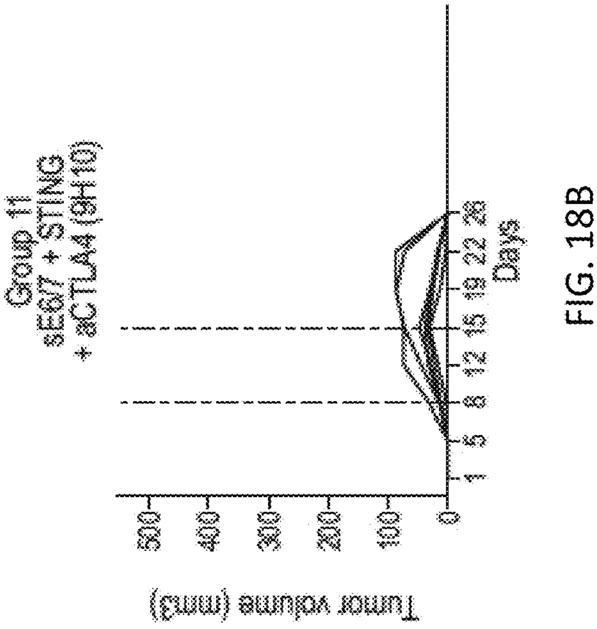
FIGS. 18A-18I are graphs showing tumor volume from mice vaccinated therapeutically as indicated with HPV E6/E7 construct together with a STING immune potentiator mRNA construct (FIG. 18A), alone or in combination with anti-CTLA-4 (FIG. 18B) or anti-PD1 treatment (FIG. 18C), after challenge with a TC1 tumor that expresses HPV E7, showing inhibition of tumor growth by the HPV E6/E7+ STING treatment.
Figure 18A:
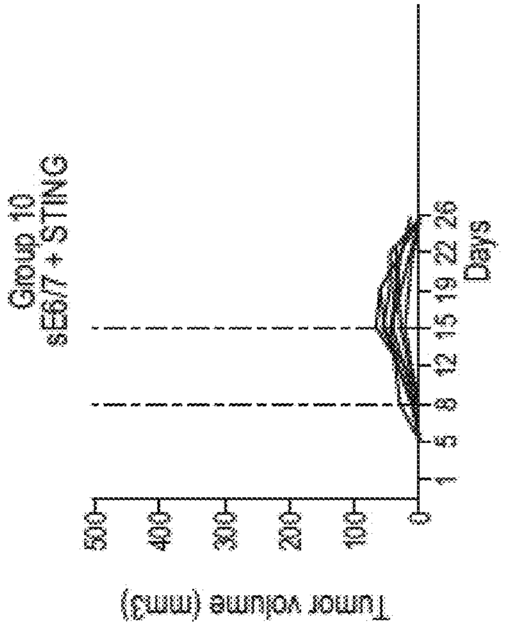
Figure 18C:
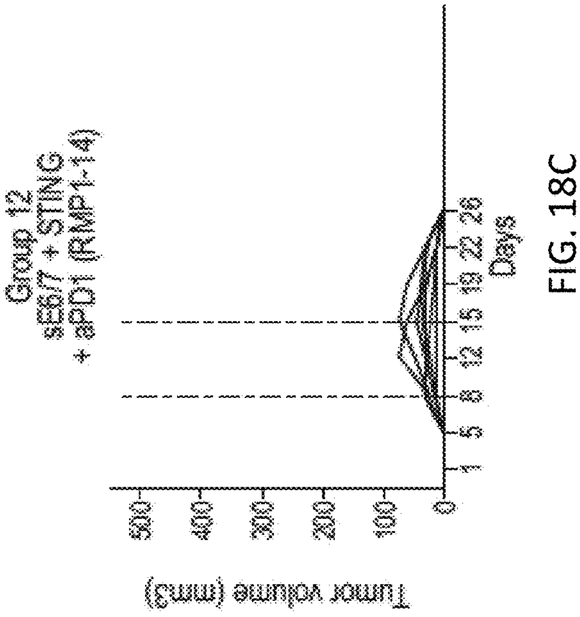
Figure 18E:
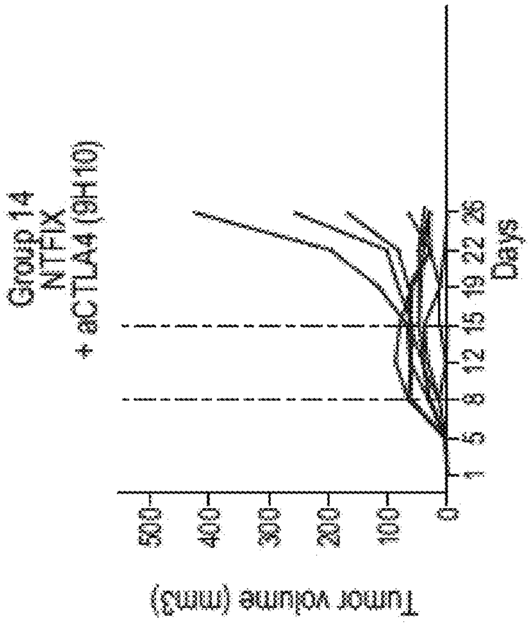
Figure 18D:
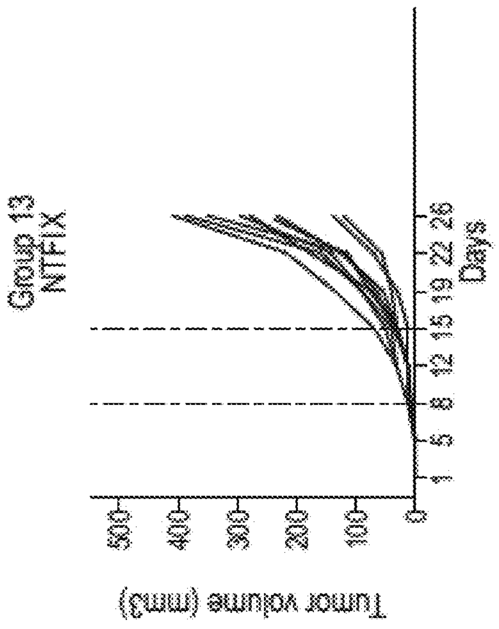
Figure 18F:
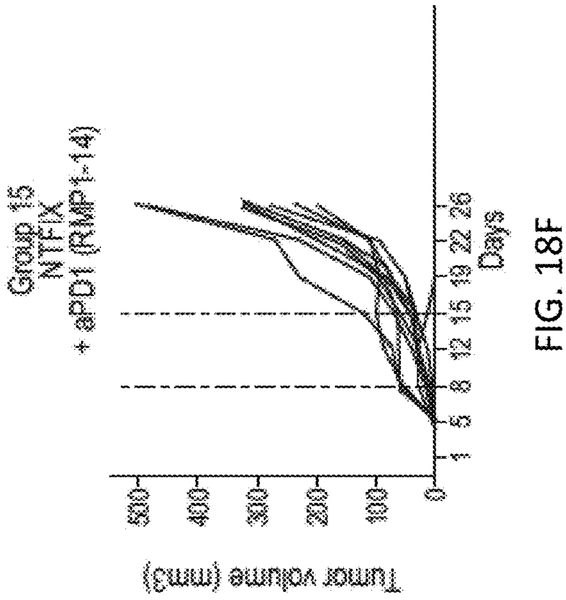
Figure 18G:
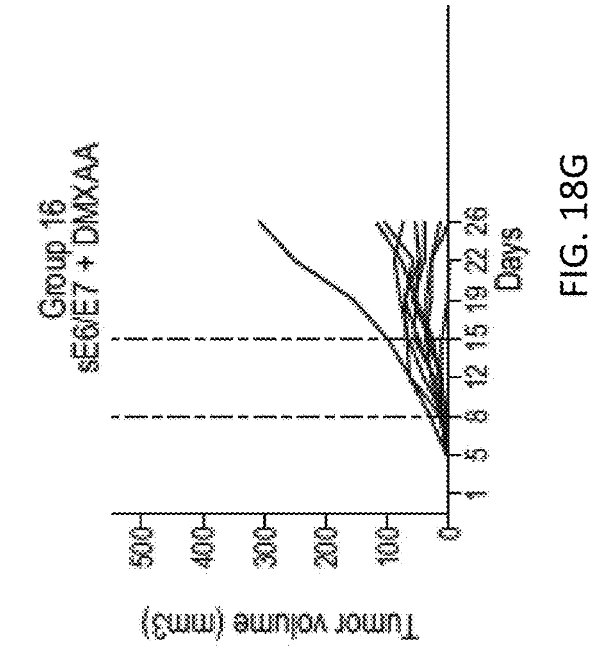
Figure 18H:
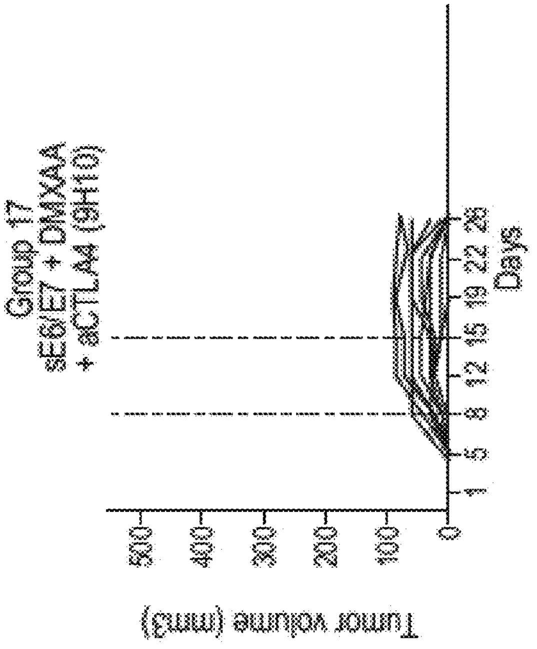
Figure 18I:
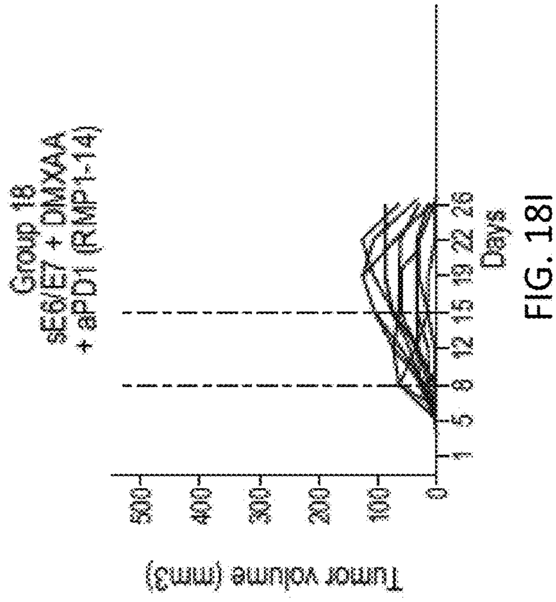

In a second set of experiments examining the therapeutic activity of the HPV+STING vaccination, C57/B6 mice were administered $2\times10^5$ TC1 cells subcutaneously on day 1, followed by treatment by intramuscular injection with 0.5 mg/kg of the HPV+STING vaccine (encoding sE6/E7) on days 8 and 15. Certain mice were also treated on days 13, 16 and 19 with either anti-CTLA-4 or anti-PD-1. Representative results, reported as tumor volume over time, are shown in the graphs of FIGS. 18A-18I. The results demonstrate that the mice treated with the HPV+STING vaccine (alone or in combination with immune checkpoint inhibitors) showed tumor regression (FIGS. 18A-18C), as compared to the control mice treated with the control mRNA construct NTFIX, alone or in combination with an immune checkpoint inhibitor (FIGS. 18D-18F) or the control mice treated with the sE6/E7 construct in combination with the control DMXAA construct, alone or in combination with an immune checkpoint inhibitor (FIGS. 18G-18I). Thus, these experiments demonstrate that therapeutic vaccination (i.e., subsequent to tumor challenge) with the HPV vaccine together with the STING immune potentiator is effective in inducing regression of HPV-expressing tumors in vivo.

Example 10. Determining Optimal Antigen:Immune Potentiator Mass Ratio in mRNA Vaccine Design In this example, studies were performed in animals treated with an antigen of interest in combination with an immune potentiator at different Ag:Immune Potentiator ratios, followed by examination of T cell responses to the antigen, to determine optimal Ag:Immune Potentiator ratios in enhancing the immune response to the antigen of interest.

In a first set of experiments, mice were treated with an MC38 vaccine encoding an ADR concatemer of three 25mer mutant peptides containing tumor neoepitopes derived from Adpgk, Dpagt1, and Reps1 (this vaccine is also referred to herein as ADRvax), as described in Example 5, in combination with a constitutively active STING immune potentiator construct. The constitutively active STING immune potentiator used in this example contained a V155M mutation, as described in Example 1. The ADRvax and STING constructs were coformulated in a lipid nanoparticle (comprising Compound 25 (Cmp25)) at varying Ag:STING ratios, according to the study design summarized below in Table 13.

TABLE 13

| Group | Ag:STING ratio | Ag dose (μg) | STING dose (μg) | NTFIX (μg) | Total mRNA (μg) | Vehicle | Route | Dosing Regimen |
|---|---|---|---|---|---|---|---|---|
| 1 | No Ag control | 0 | 3 | 3 | 6 | Cmp25 | IM | Day 1, 15 |
| 2 | 1:1 | 3 | 3 | 0 | | | | |
| 3 | 5:1 | | 0.6 | 2.4 | | | | |
| 4 | 10:1 | | 0.3 | 2.7 | | | | |
| 5 | 20:1 | | 0.15 | 2.85 | | | | |
| 6 | 1:0 (No STING) | | 0 | 3 | | | | |

TABLE 13-continued

| Group | Ag:STING ratio | Ag dose (μg) | STING dose (μg) | NTFIX (μg) | Total mRNA (μg) | Vehicle | Route | Dosing Regimen |
|---|---|---|---|---|---|---|---|---|
| 7 | 1:1 | 5 | 5 | 0 | 10 | | | |
| 8 | 1:0 (No STING) | | 0 | 5 | | | | |

Figure 19:
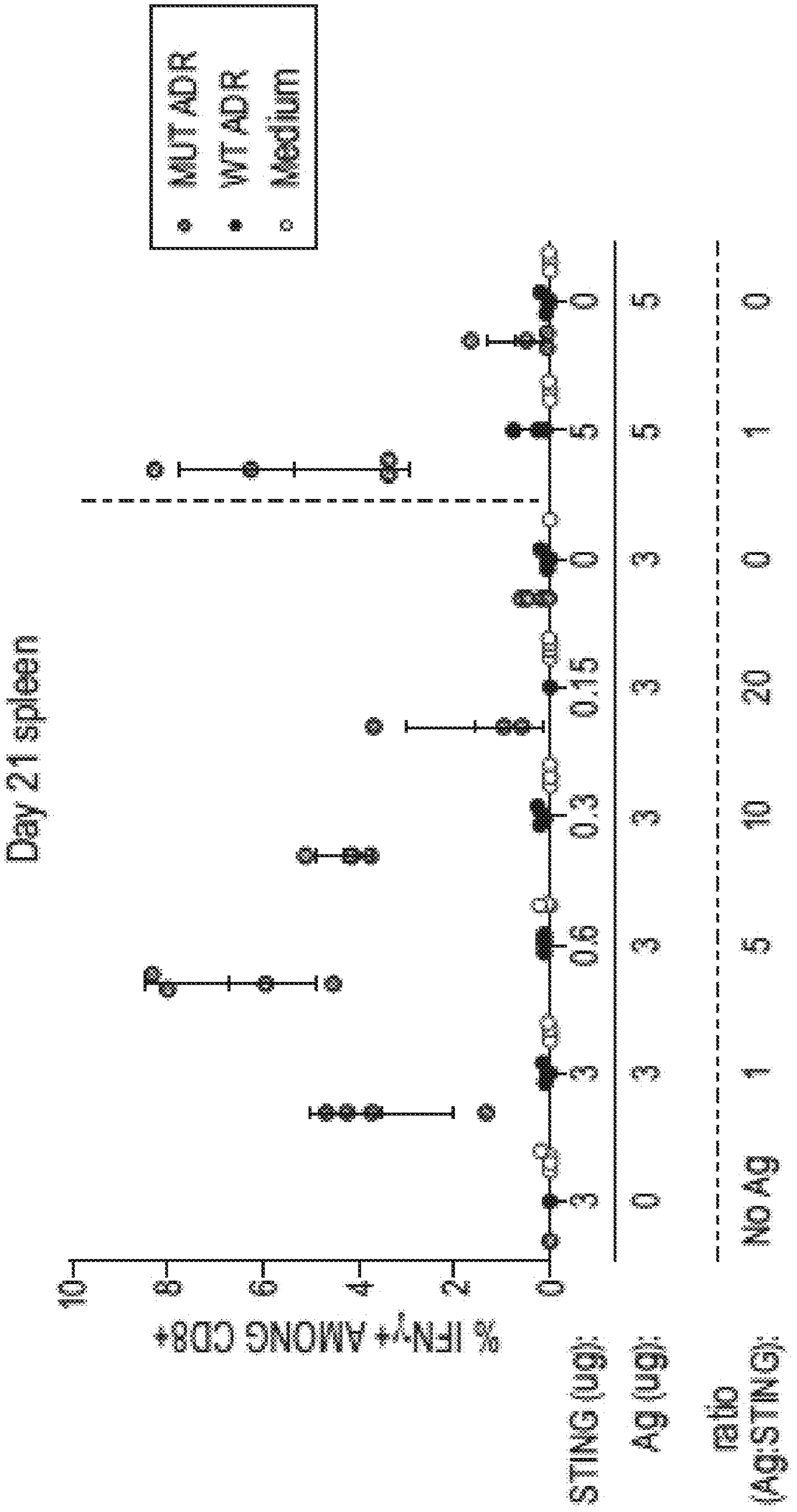
FIG. 19 is a graph showing intracellular staining (ICS) of $CD8^+$ splenocytes for IFN-γ from mice immunized with an ADR vaccine construct coformulated with a STING immune potentiator at the indicated Ag:STING ratios on day 21 post first immunization. CD8+ cells were restimulated with either the mutant ADR antigen composition (comprising three peptides) or the wild-type ADR composition (as a control).
Figure 20:
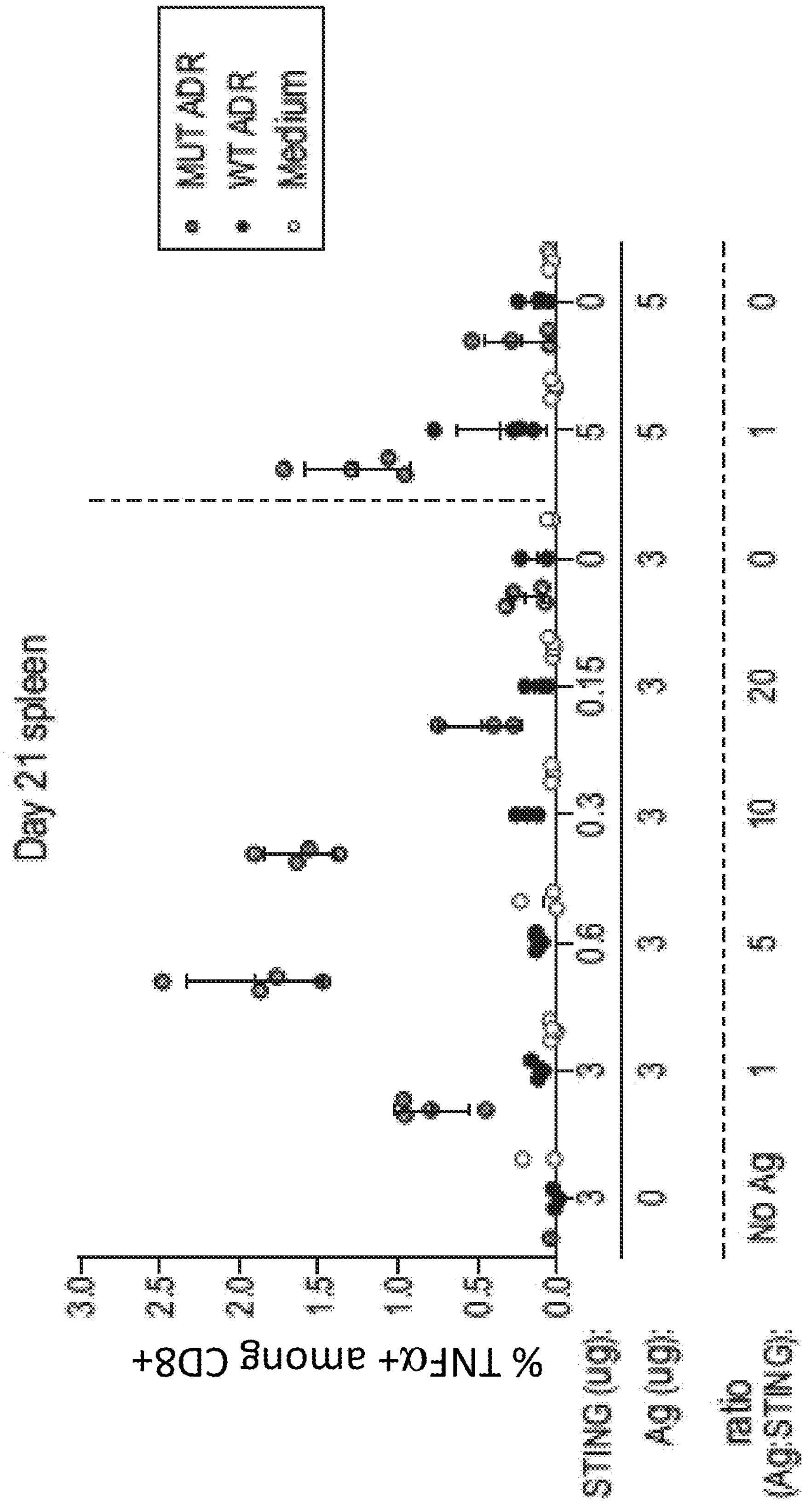
FIG. 20 is a graph showing intracellular staining (ICS) of $CD8^+$ splenocytes for TNF-α from mice immunized with an ADR vaccine construct coformulated with a STING immune potentiator at the indicated Ag:STING ratios on day 21 post first immunization. CD8+ cells were restimulated with either the mutant ADR antigen composition (comprising three peptides) or the wild-type ADR composition (as a control).
Figure 21A:
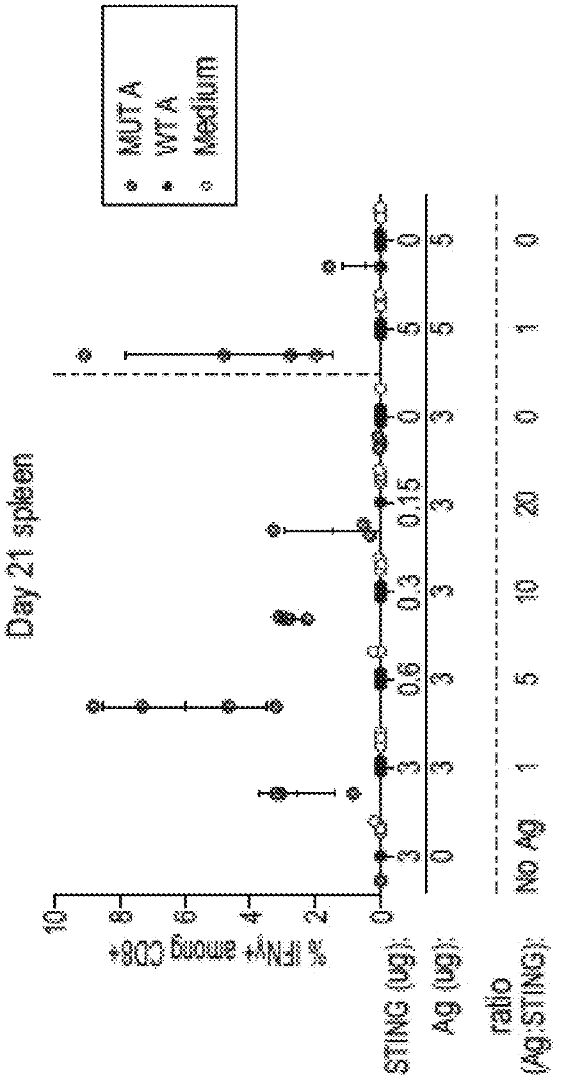
FIGS. 21A-21C are graphs showing intracellular staining (ICS) of $CD8^+$ splenocytes for IFN-γ from mice immunized with an ADR vaccine construct coformulated with a STING immune potentiator at the indicated Ag:STING ratios on day 21 post first immunization. CD8+ cells were restimulated with either a mutant or wild-type (as a control) peptide contained within the ADR antigen composition.
Figure 21B:
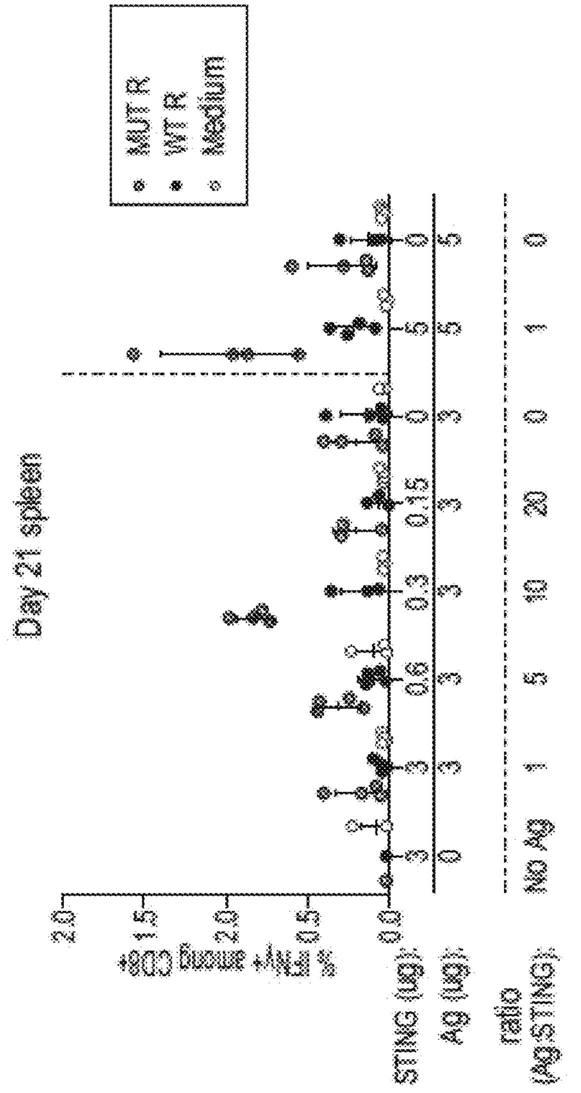
Figure 21C:
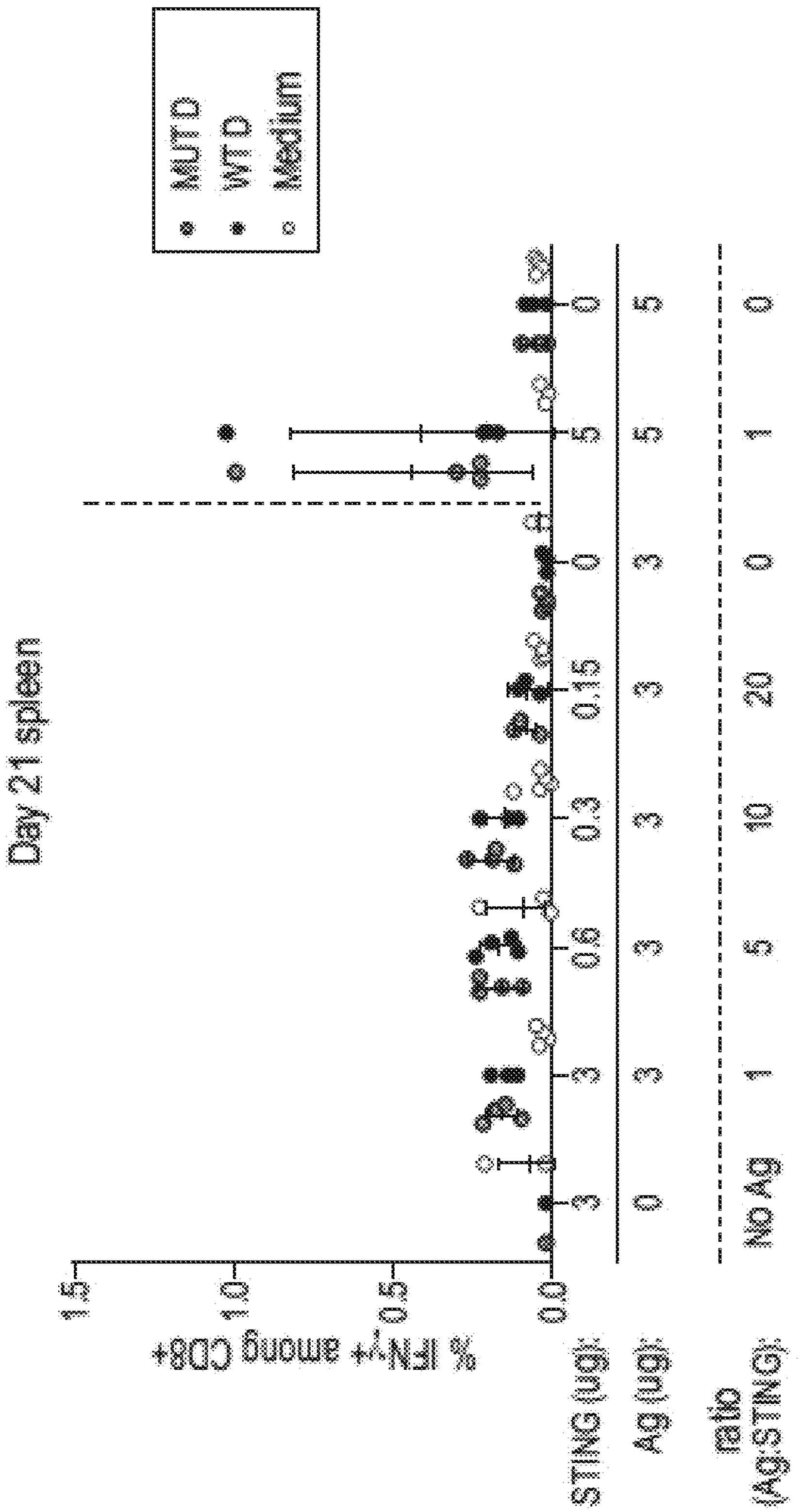

Mice were dosed intramuscularly on days 1 and 15. At day 21, $CD8^+$ spleen cells from mice in each test group were restimulated ex vivo for 4 hours at 37 degrees C. in the presence of GolgiPlug™ (containing Brefeldin A; BD Biosciences) with either wild-type or mutant MC38 ADR peptides (1 μg/ml per peptide, pooled) and CD8 vaccine responses were assessed by intracellular staining (ICS) for IFN-γ or TNF-α. Representative ICS results for MC38 ADR-specific responses by day 21 $CD8^+$ spleen cells for IFN-γ are shown in FIG. 19 and for TNF-α are shown in FIG. 20. Additionally, CD8 vaccine responses to each of the three individual epitopes within ADRvax (i.e., peptides Adpk1, Reps1 and Dpagt1) were also assessed by ICS for IFN-γ following stimulation with the individual epitopes. The results are shown in FIG. 21A (for peptide Adpk1), FIG. 21B (for peptide Reps1) and FIG. 21C (for peptide Dpagt1).

The results demonstrate that all Ag:STING ratios tested (ranging from 1:1 to 20:1) showed an adjuvant effect of STING as compared to control. For the ADRvax antigen as a whole, the optimal Ag:STING ratio was found to be 5:1. For the individual peptide epitopes within ADRvax, the optimal Ag:STING ratio for the Adpgkl peptide was 5:1, whereas the optimal Ag:STING ratio for the Reps1 peptide was 10:1 (the responses to the third peptide, Dpagt1, were very low with or without STING, consistent with it being a non-dominant epitope as was known in the art). STING was also found to increase the total percentage of CD8+ cells among CD45+ T cells, with dose responses observed (data not shown) and was found to increase the total percentage of CD62L cells among CD44hi CD8+ cells (effector/memory subset), with dose responses observed (data not shown). Furthermore, results obtained from PBMC cells were consistent with the spleen cell results (data not shown). Thus, these experiments confirmed the ability of STING to act as an immune potentiator in enhancing immune responses against the ADRvax antigen and, moreover, demonstrated the determination of an optimal Ag:Immune Potentiator ratio for treatment, with ratios other than 1:1 being found to be most optimal (e.g., ratios of 5:1 or 10:1 being more effective than 1:1). The results further indicate that the optimal Ag:Immune Potentiator ratio may differ depending on the particular antigen of interest used.

In a second set of experiments, non-human primates were treated with an HPV vaccine encoding intracellular E6/E7 (iE6/E7), as described in Example 8, in combination with the constitutively active STING immune potentiator construct at varying Ag:STING ratios (lipid nanoparticles comprising Compound 25), according to the study design summarized below in Table 14:

TABLE 14

| Group | Treatment | Ag:STING Ratio | μg Ag | μg STING | μg NTFIX | n | Total Ag Dose |
|---|---|---|---|---|---|---|---|
| 1 | STING only | — | — | 100 | — | 3 | 100 μg |
| 2 | Ag:STING | 1:1 | 50 | 50 | — | | |
| 3 | Ag:STING | 5:1 | 83.33 | 16.67 | — | | |
| 4 | Ag:STING | 10:1 | 90.9 | 9.09 | | | |
| 5 | Ag only | — | 90 | — | 10 | | |

No clinical findings were observed 24 hours after the first dose (administered intramuscularly), indicating no injection site reactions and that the initial treatment was received safely. After an initial dosing on Day 1, animals have a two week recover period and then are given a second dose at day 14, followed by another two week recovery period. Further safety analysis is determined by clinical pathology (clinical chemistry, hematology and coagulation) at days 2, 16 and 30. Anti-antibody and ELISpot analysis or ICS for IFN-γ for CD4 and CD8 cells are performed to assess enhancement of immune responses to the HPV vaccine by STING at the varying ratios tested.

In a third set of experiments, a model concatemeric antigen using known murine epitopes was tested in mice in combination with the constitutively active STING immune potentiator at varying ratios. The concatemeric antigen, referred to herein as CA-132, comprises 20 known murine epitopes thought to be presented on MHC Class I and Class II antigens of the CB6 mouse. These epitopes were sourced from the IEDB.org website, a public database of epitopes sourced from the literature. Class I epitopes are expected to be presented on MHC Class I molecules and trigger a CD8+ response, while Class II epitopes are expected to be presented on MHC Class II molecules and trigger CD4+ T cell responses. The CA-132 antigen construct encodes both Class I and Class II epitopes, allowing for assessment of both CD4 and CD8 T cell responses. Moreover, it is believed that inclusion of Class II epitopes in the concatemeric antigen (thus triggering a CD4 response) helps induce a stronger CD8 T cell response. Thus, the approach to the design of the CA-132 antigen can also be used in the design of other concatemeric antigen constructs.

Figure 22:
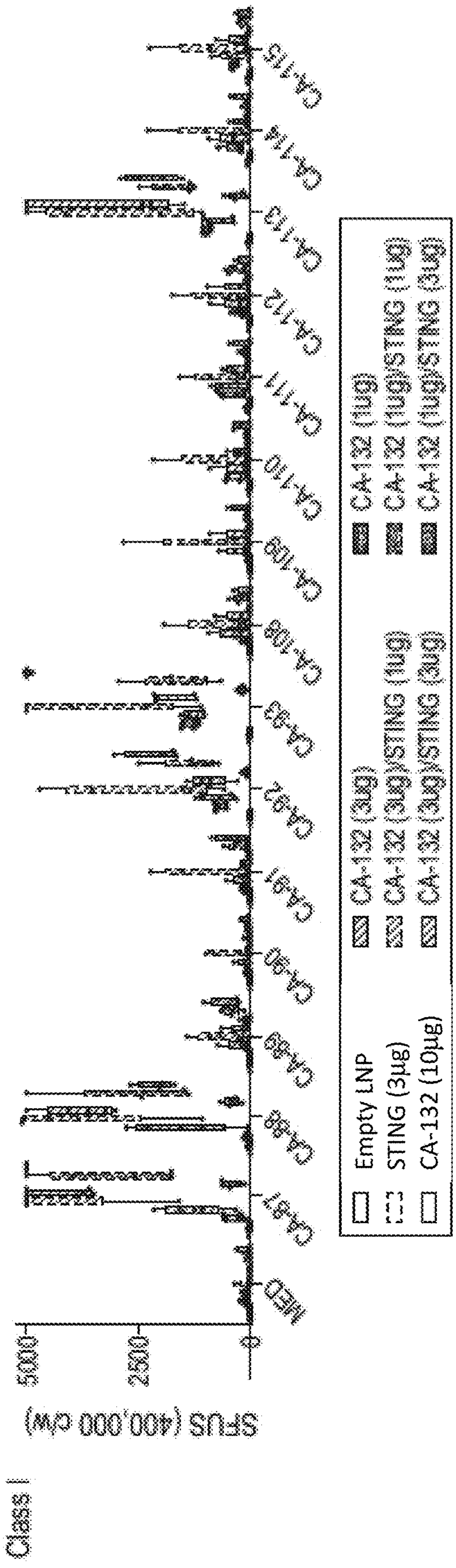
FIG. 22 is a graph showing antigen-specific T cell responses to MHC class I epitopes within the CA-132 vaccine, as measured by ELISpot analysis for IFN-γ, from mice treated with a coformulation of CA-132 and STING immune potentiator, at the indicated different Ag:STING ratios.

The CA-132 antigen construct and STING immune potentiator construct were coformulated in lipid nanoparticles comprising Compound 25 and administered intramuscularly to CB6 mice at the following dosages: CA-132 alone at 1 μg, 3 μg or 10 μg, STING alone at 3 μg, CA-132+STING at either 3 μg each or 1 μg each (1:1 ratio), CA-132 at 3 μg and STING at 1 μg (Ag:STING ratio of 3:1) or CA-132 at 1 μg and STING at 3 μg (Ag:STING ratio of 1:3). Antigen-specific T cell responses to the Class I epitopes within the CA-132 antigen construct were examined by ELISpot analysis for IFN-γ, the results of which are shown in FIG. 22. The results demonstrated an increase in IFN-γ responses to the Class I epitopes when formulated with STING.

In a fourth series of experiments, the HPV vaccine model described in Example 8 was used to study the effect of varying ratios of E6/E7 antigen to constitutively active STING immune potentiator. Mice were immunized intramuscularly with the iE6/E7 mRNA vaccine (3 μg or 5 μg) in combination with the V155M constitutively active STING immune potentiator mRNA construct at Ag:STING ratios of 1:1, 5:1, 10:1, 20:1 or 0.4:1. The HPV vaccine construct and the immune potentiator construct were coformulated in MC3 lipid nanoparticles. HPV vaccine or STING in combination with only a control mRNA (NTFIX) were used as controls.

Figure 23A:
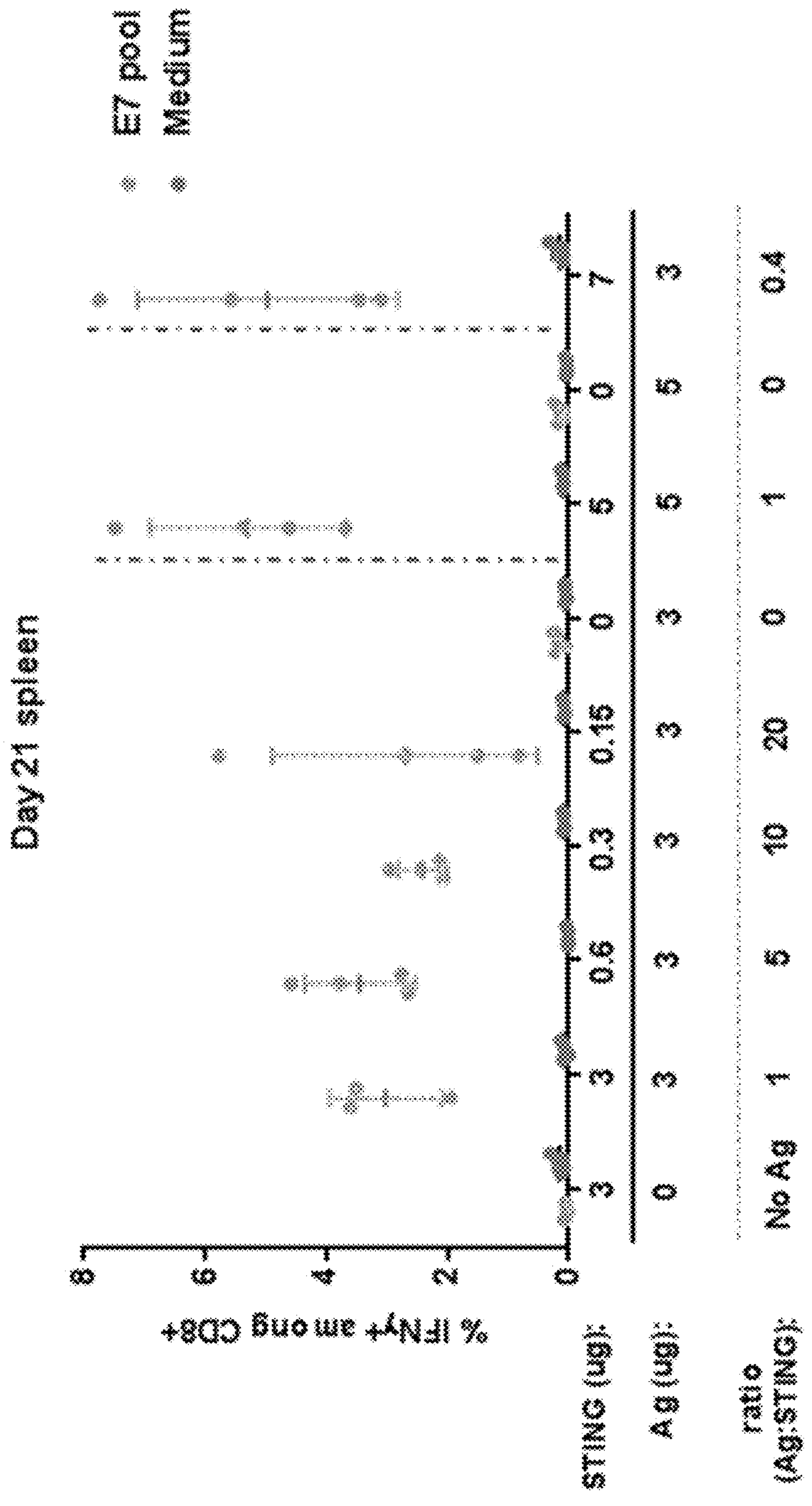
FIGS. 23A-23B show results for Ag:STING ratio studies from mice immunized with HPV E6/E7 vaccine construct coformulated with a STING immune protentiator mRNA construct.

At day 21, spleen cells from mice in each test group were restimulated ex vivo for 4 hours at 37 degrees C. in the presence of GolgiPlug™ (containing Brefeldin A; BD Biosciences) with an E7 peptide pool (described in Example 8). CD8 vaccine responses were assessed by intracellular staining (ICS) for IFN-γ. The results are shown in FIG. 23A. The results demonstrate that STING enhanced the antigen-specific T cell responses at all Ag:STING ratios tested. The largest enhancement was observed for the mice treated with the higher dose of antigen (5 μg) at a 1:1 ratio with STING and for the mice treated at an Ag:STING ratio of 0.4:1 (3 μg Ag to 7 μg STING).

Figure 23B:
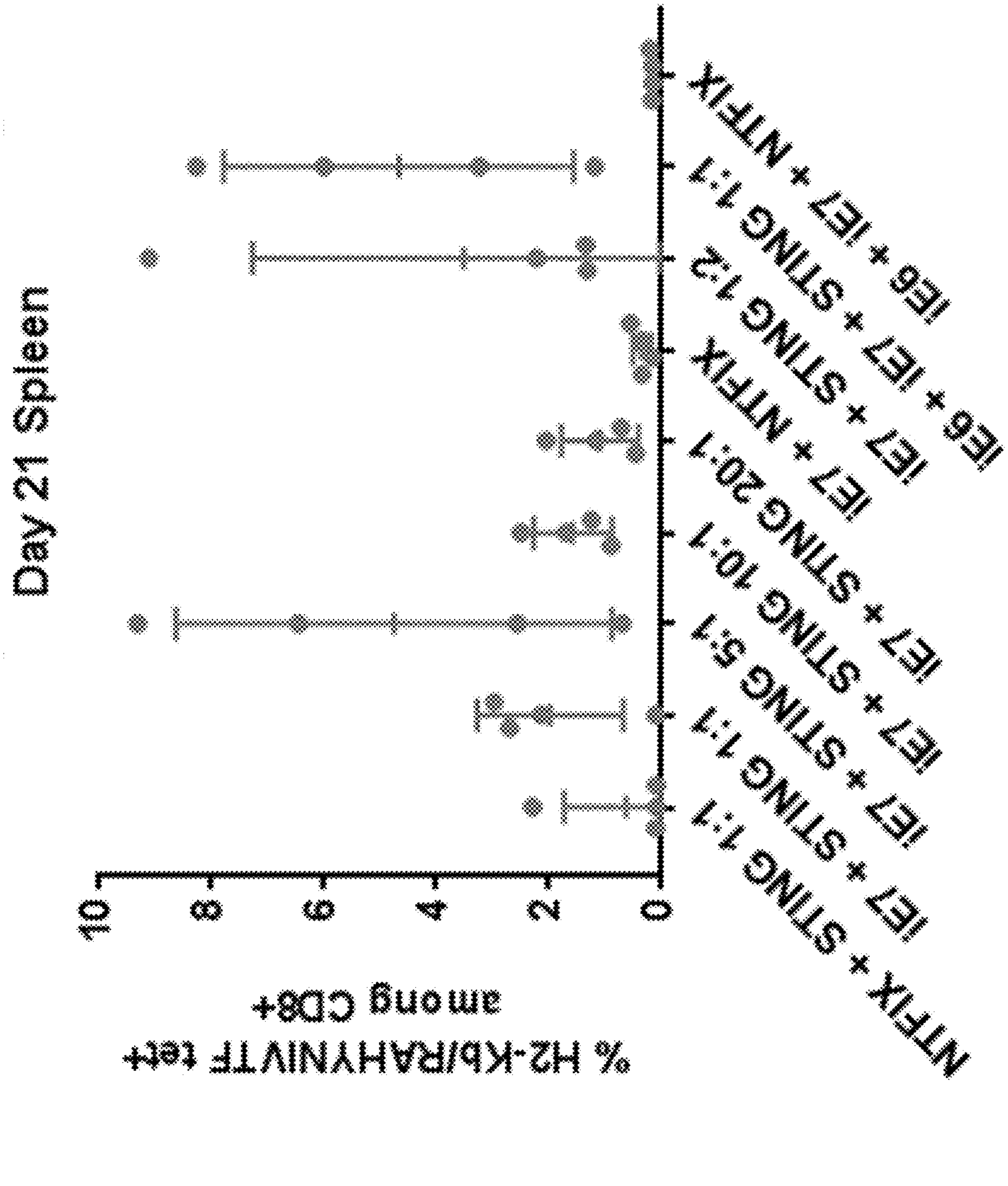

The ability of STING to enhance the CD8 vaccine response in the HPV model at various Ag:STING ratios tested was further confirmed by H2-Kb/E7 peptide-tetramer staining. Representative results for day 21 spleen cells are shown in FIG. 23B. The E7-MHC-1-tetramer staining results were consistent with the ICS results discussed above, although they were more variable.

In summary, these studies confirmed the ability of the STING immune potentiator construct to enhance immune responses to an antigen of interest and demonstrated the determination of optimal Ag:STING ratios for treatment.

Example 11: Immune Potentiation by STING in Non-Human Primates

In this example, non-human primates (cynomolgus monkeys) were treated with mRNAs encoding an HPV vaccine in combination with a STING immune potentiator, followed by assessment of antigen-specific T cell and antibody responses. The HPV vaccine construct used in this example is described in Example 8. The constitutively active STING immune potentiator construct used in this example contained a V155M mutation, as described in Example 8. The HPV vaccine construct and the immune potentiator mRNA constructs were coformulated in lipid nanoparticles comprising: Compound 25:Cholesterol:DSPC:PEG-DMG, at ratios of 50:38.5:10:1.5, respectively. Different ratios of STING:Ag were tested. Control animals were treated with mRNAs encoding either the HPV antigens alone or the STING immune potentiator alone.

Fifteen male cynomolgus monkeys, 2-5 years old and weighing 2-5 kg, were treated according to the study design shown below in Table 15:

TABLE 15

| Group | Desc. | Ratio | Total mRNA (μg) | NTFIX | STING (μg) | HPV Ag (μg) | n |
|---|---|---|---|---|---|---|---|
| 1 | Ag only | | 100 | 10 | | 90 | 3 |
| 2 | STING only | | 100 | | 100 | 0 | 3 |
| 3 | STING:Ag | 1:1 | 100 | | 50 | 50 | 3 |
| 4 | STING:Ag | 1:5 | 100 | | 17 | 83 | 3 |
| 5 | STING:Ag | 1:10 | 100 | | 9 | 91 | 3 |

A pre-dose sample of PBMCs were collected on day −4, followed by treatment of the animals intramuscularly with the mRNA LNPs on day 1 and day 15. A post-dose sample of PBMCs was collected on day 29. No toxicity or other major clinical observations were noted during the study, indicating the mRNA LNPs were well-tolerated.

To examine the ability of the STING immune potentiator to enhance antigen-specific CD8+ T cell responses, intracellular cytokine staining (ICS) for TNFα and IL-2 was conducted. PBMCs were stimulated ex vivo with the HPV16 E6 peptide pool or the HPV16 E7 peptide pool for 6 hours at 37° C. Stimulation with PMA/ionomycin was used as a positive control and stimulation with medium alone was used as a negative control.

Figure 24C:
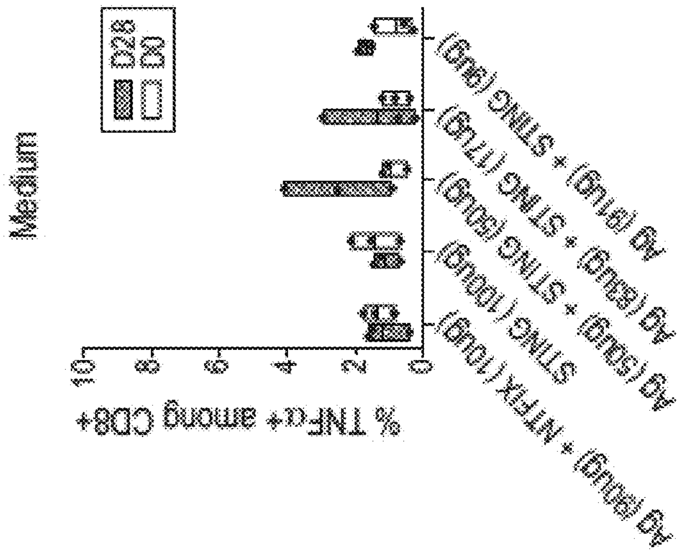
FIGS. 24A-24C are bar graphs showing TNFα intracellular staining (ICS) results for CD8+ T cells from cynomolgus monkeys vaccinated with HPV vaccine+STING constructs, followed by ex vivo stimulation with either HPV16 E6 peptide pool (FIG. 24A), HPV16 E7 peptide pool (FIG. 24B) or medium (negative control) (FIG. 24C).
Figure 24B:
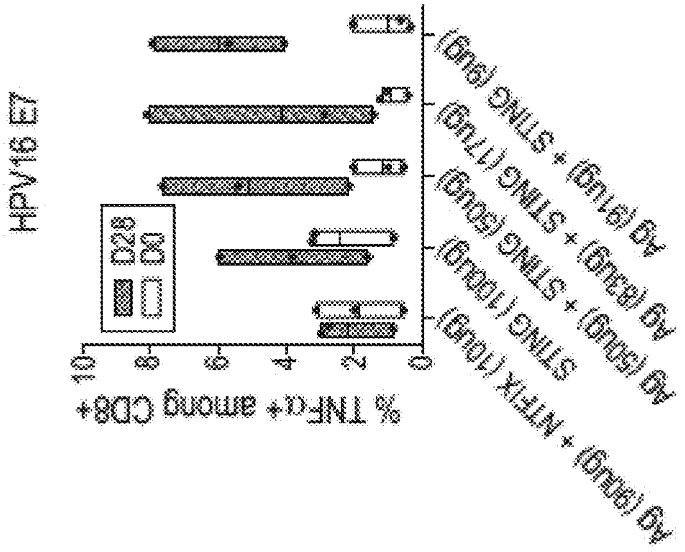
Figure 24A:
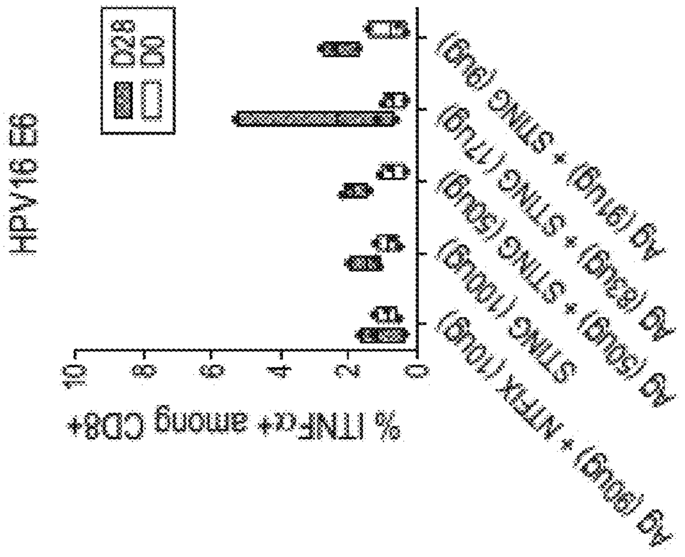

Representative results for ICS for TNFα are shown in FIGS. 24A-24C, wherein FIG. 24A shows results for ex vivo stimulation with the E6 peptide pool, FIG. 24B shows the results for ex vivo stimulation with the E7 peptide pool and FIG. 24C shows the results for ex vivo stimulation with the medium control. No increase in TNFα+CD8 T cell frequency was observed between the pre- and post-dose group immunized with antigen alone (Group 1).

Immunization with STING treatment alone (Group 2) had a marginal effect on TNFα+CD8 T cell frequency. In contrast, groups immunized with STING+Ag (Groups 3, 4, 5) showed a significant increase in antigen-specific TNFα+ CD8 T cells. Furthermore, Group 5, which was immunized with a "matching" antigen dose of STING:Ag (1:10 ratio), showed a significant increase in antigen-specific TNFα+ CD8 T cells when compared to the Group 1 and Group 2 controls.

Figure 25A:
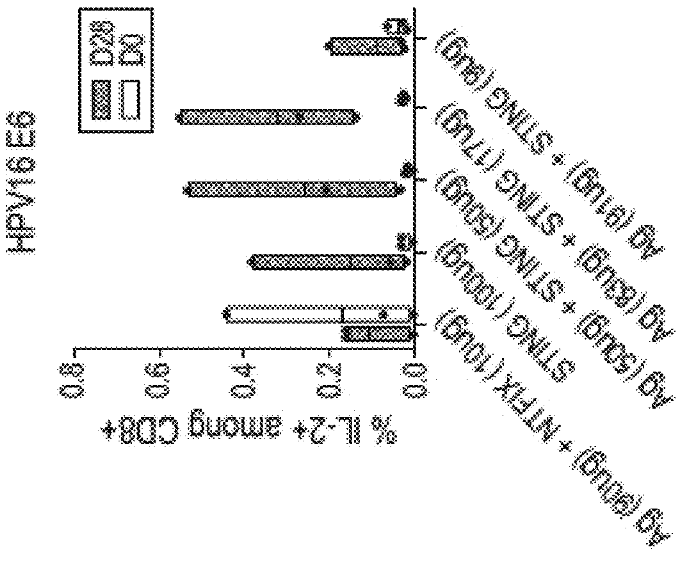
FIGS. 25A-25C are bar graphs showing IL-2 intracellular staining (ICS) results for CD8+ T cells from cynomolgus monkeys vaccinated with HPV vaccine+STING constructs, followed by ex vivo stimulation with either HPV16 E6 peptide pool (FIG. 25A), HPV16 E7 peptide pool (FIG. 25B) or medium (negative control) (FIG. 25C).
Figure 25B:
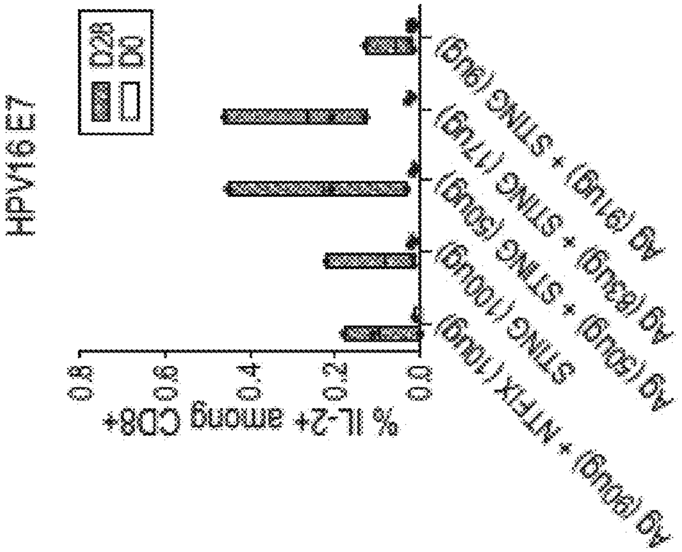
Figure 25C:
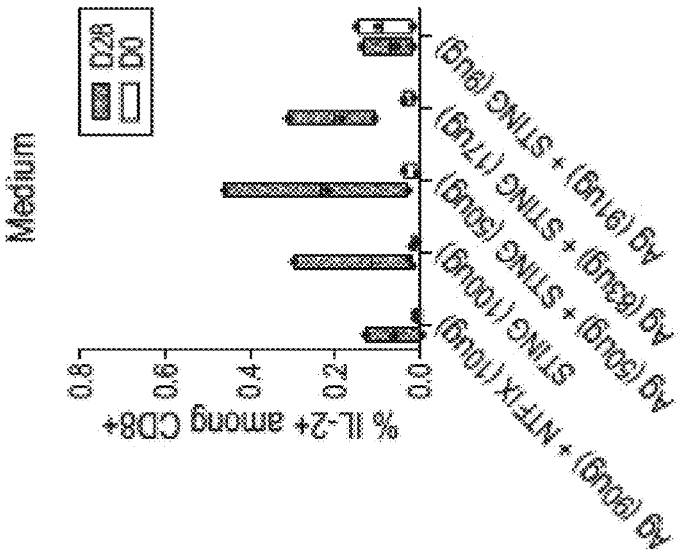

Representative results for ICS for IL-2 are shown in FIGS. 25A-25C, wherein FIG. 25A shows results for ex vivo stimulation with the E6 peptide pool, FIG. 25B shows the results for ex vivo stimulation with the E7 peptide pool and FIG. 25C shows the results for ex vivo stimulation with the medium control. A moderate increase in IL-2+CD8 T cell frequency between the pre- and post-dose was observed in all immunized animals (Groups 1-5). However, the increase in IL-2+CD8 T cells was most detectable in the groups treated with STING:Ag at ratios of 1:1 and 1:5 (Groups 3 and 4), whereas animals treated with STING:Ag at a 1:10 ratio did not exhibit increased IL-2+CD8 T cells as compared to controls. The increase in IL-2 is consistent with the known ability of subsets of T cells to secrete IL-2 during active T cell responses.

To examine the effect of STING:Ag treatment in the NHPs on antigen-specific antibody responses, E6-specific and E7-specific ELISAs were performed. Plates were coated with either recombinant E6 (Prospec; #HPV-005 His HPV16 E6) or recombinant E7 (ProteinX; #2003207 His HPV16 E7). A mouse anti-E6 monoclonal antibody from Alpha Diagnostics International (#HPV16E6 1-M) was used as a positive control. A mouse anti-E7 monoclonal antibody from Fisher/Life Technologies (#280006-EA) was used as a positive control. An anti-mouse IgG-HRP antibody from Jackson ImmunoResearch (#715-035-150) was used as the secondary antibody for the positive controls. Anti-monkey IgG-HRP from Abcam (#ab112767) was used as the secondary antibody for the NHP serum.

Plates were coated with recombinant E6 or E7 (500 ng/well; 100 μl/well) at 4° C. overnight and then blocked with TBS SuperBlock for 1 hour at room temperature. Primary antibody was added (100 μl/well) and incubated for 1 hour at room temperature. Positive control antibodies were serially diluted. NHP serum was diluted 1:5000. After washing, secondary antibody was added (100 μl/well) and incubated for 1 hour at room temperature. Positive control anti-mouse IgG-HRP was diluted 1:5000. For the NHP serums, anti-monkey IgG-HRP was diluted 1:30,000. Color was developed for 5 minutes (anti-E6) or for 10 minutes (anti-E7), then stopped and read at 450 nm.

Figure 26:
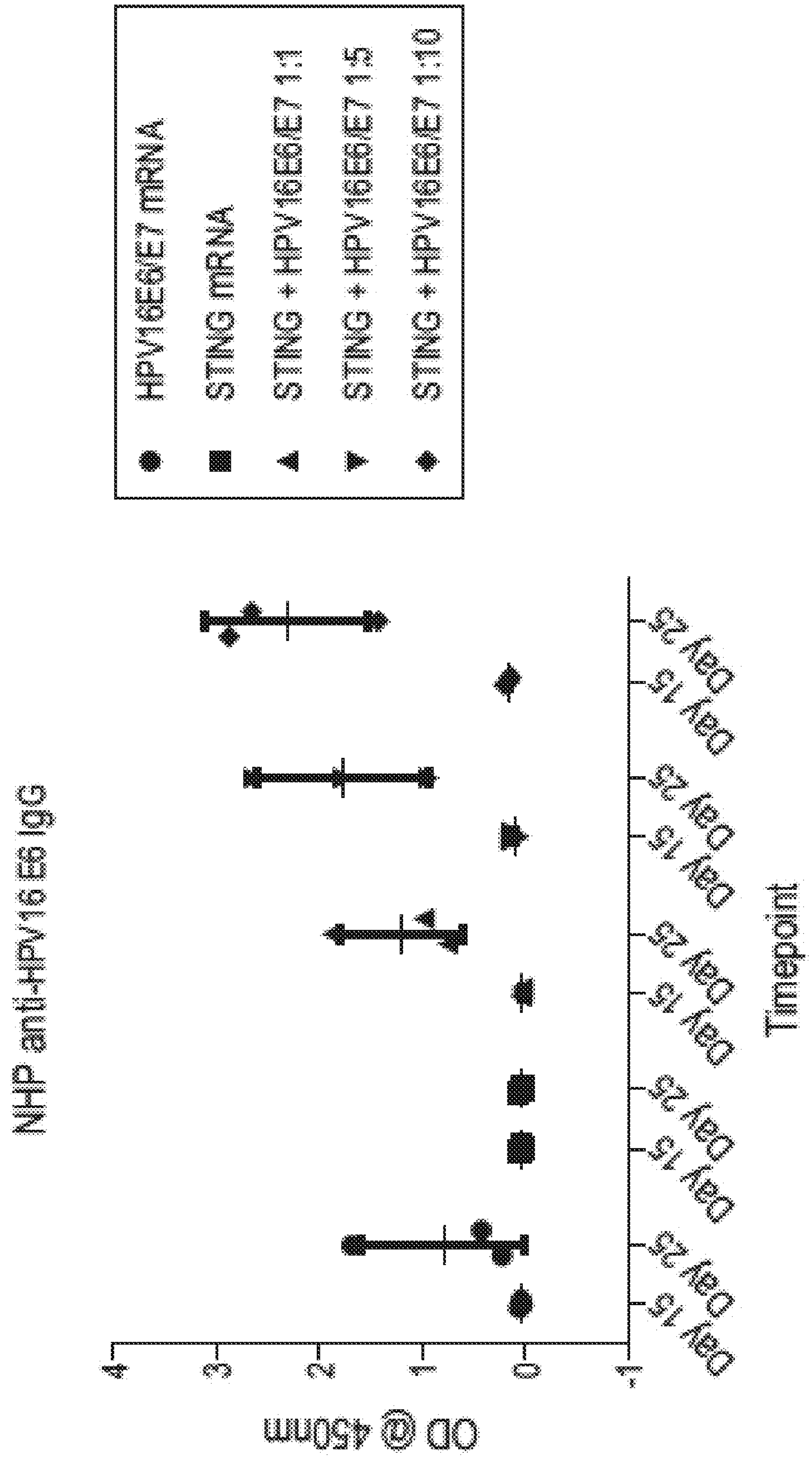
FIG. 26 is a graph showing ELISA results for anti-E6 IgG in serum from cynomolgus monkeys vaccinated/immunized with HPV vaccine+STING constructs.
Figure 27:
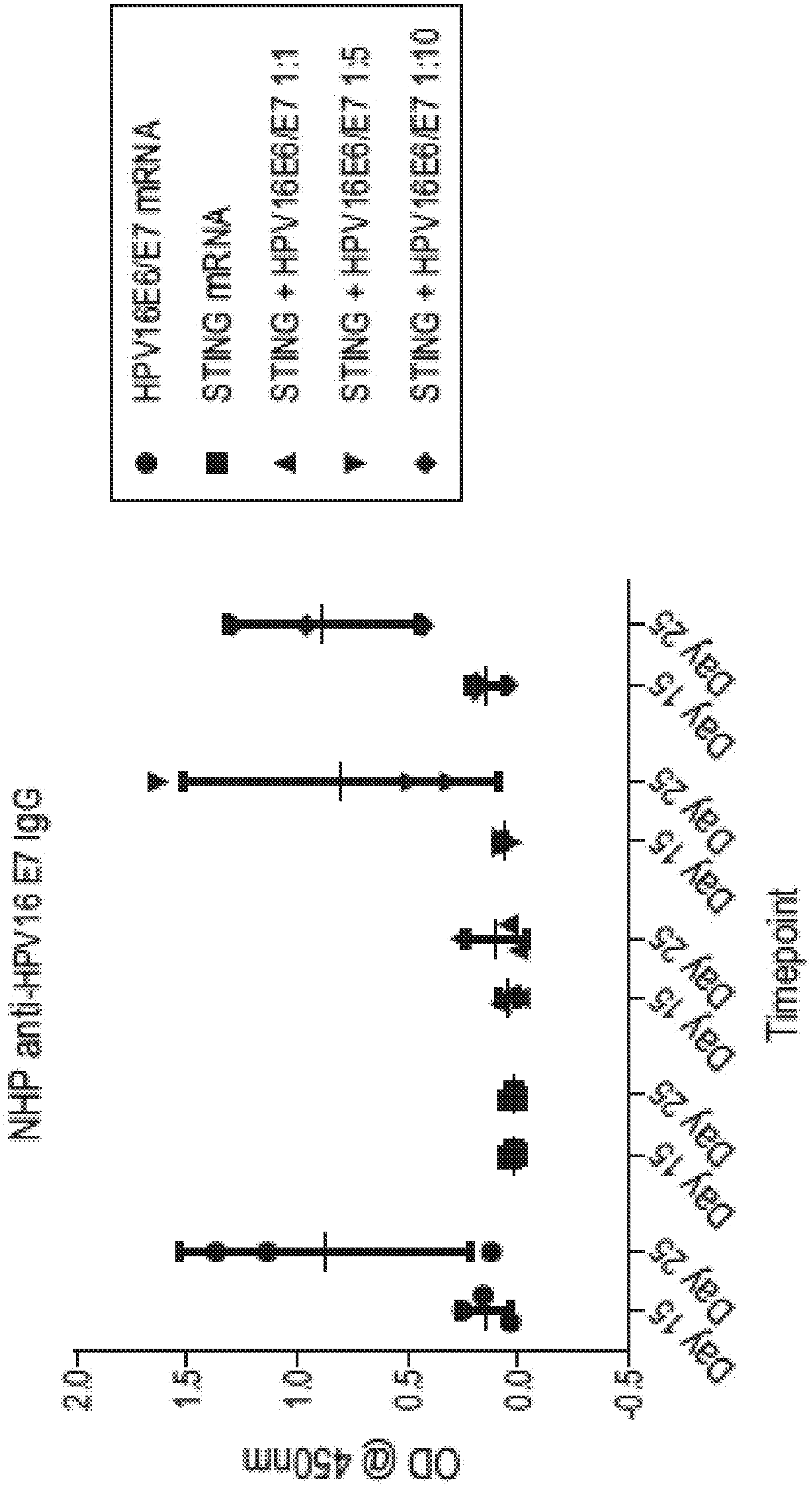
FIG. 27 is a graph showing ELISA results for anti-E7 IgG in serum from cynomolgus monkeys vaccinated/immunized with HPV vaccine+STING constructs.

Representative results for anti-HPV16 E6 IgG are shown in FIG. 26. Representative results for anti-HPV16 E7 IgG are shown in FIG. 27. The results for both anti-E6 and anti-E7 demonstrate that treatment of the animals with STING:Ag, particularly at ratios of 1:5 and 1:10 led to increased antigen-specific antibody responses.

Figure 28:
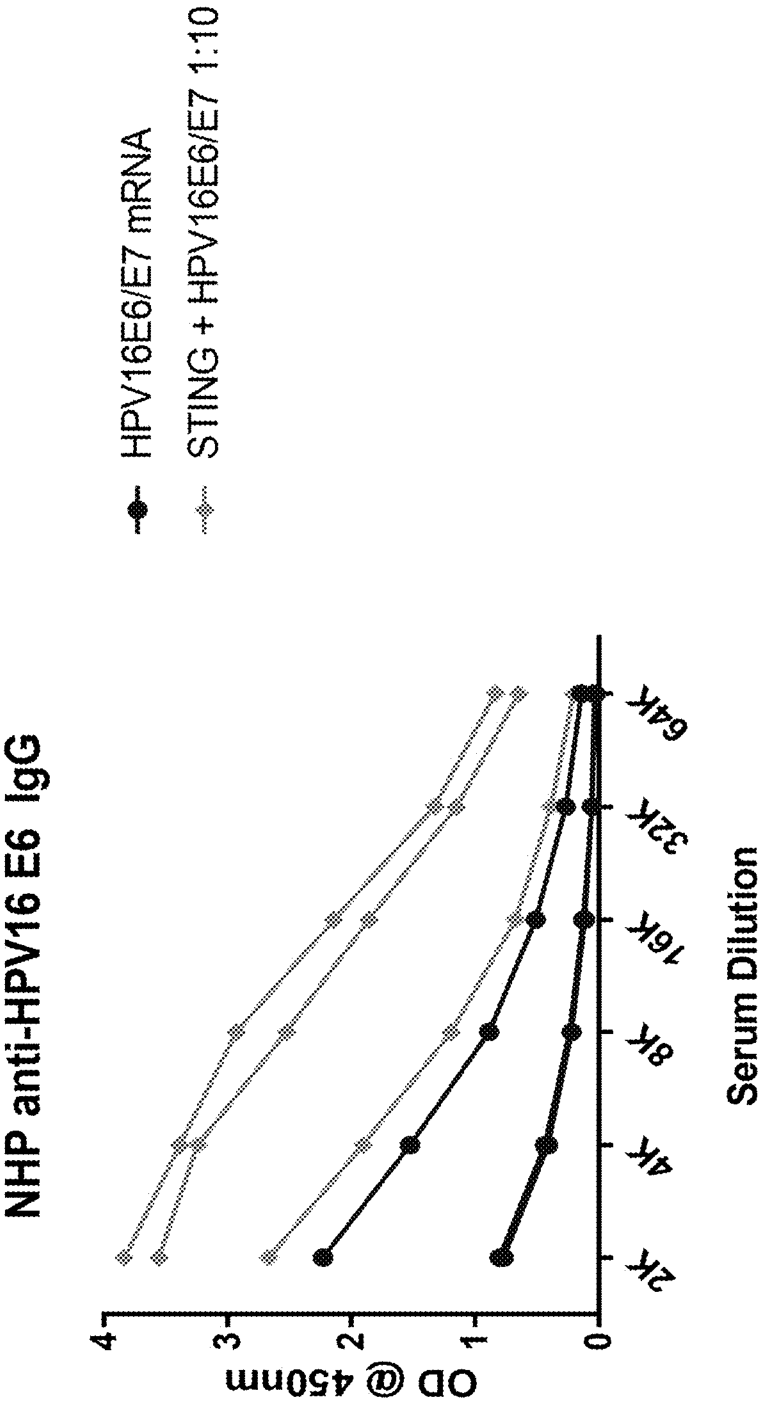
FIG. 28 is a graph showing ELISA results for anti-E6 IgG in a two-fold dilution series of day 25 serum from cynomolgus monkeys treated with HPV vaccine+STING construct at a 1:10 STING:Ag ratio.
Figure 29A:
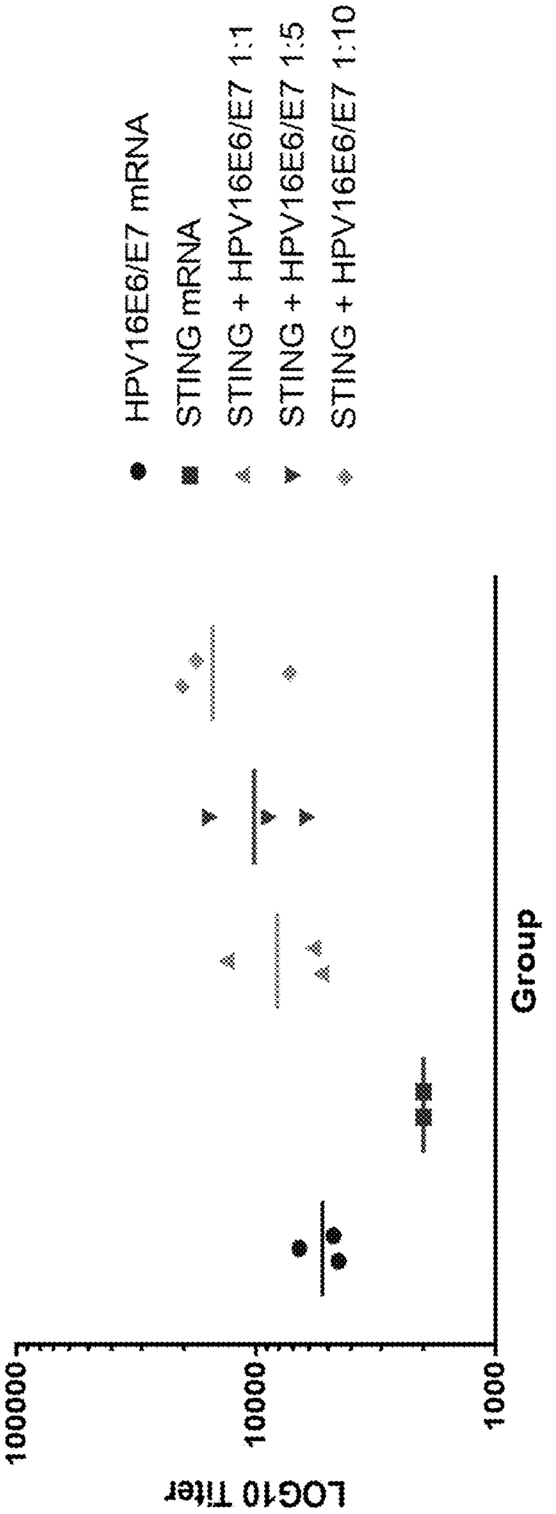
FIGS. 29A-29B are graphs showing calculated titer values of ELISA results for anti-E6 IgG (FIG. 29A) or anti-E7 IgG (FIG. 29B) in day 25 serum from cynomolgus monkeys treated with HPV vaccine+STING construct at the indicated STING:Ag ratios.
Figure 29B:
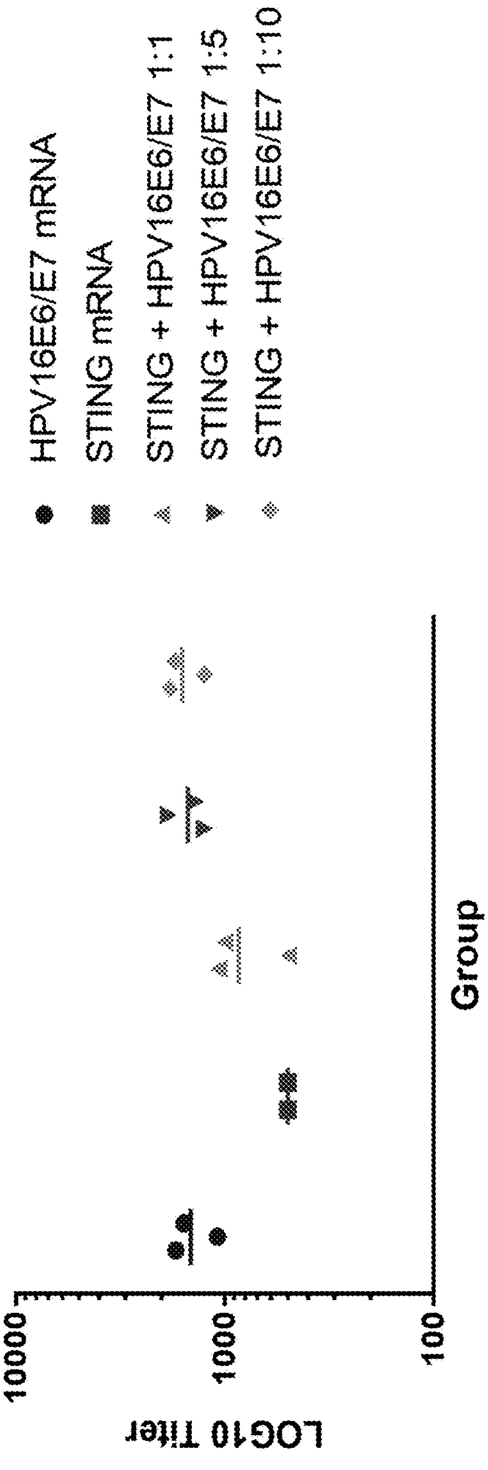

To further study the antigen-specific IgG response, further ELISA studies were performed using a two-fold dilution series for day 25 serums. As shown in FIG. 28, the two-fold dilution series for the animals treated at a 1:10 STING:Ag ratio exhibited a clear enhancement in the levels of anti-HPV16 E6-specific IgG antibodies, as compared to animals treated with the HPV vaccine alone. Calculated titer values from these ELISA studies with the day 25 serum two-fold dilution series for anti-E6 IgG and anti-E7 IgG are shown in FIGS. 29A and 29B, respectively. The calculated titer values, particularly for the anti-E6 specific response, confirm the enhancement by the STING immune potentiator, with the 1:10 STING:Ag ratio showing the greatest enhancement.

Accordingly, the results described herein for the non-human primate study confirm that STING immunopotentiates antigen-specific T cell and antibody responses against an mRNA vaccine antigen in vivo.

Example 12: Immunogenicity of Various KRAS-STING Vaccine Formats in HLA*A11 Transgenic Mice In this example, to examine the effect of the STING immune potentiator mRNA construct on immune responses to various different forms of the mutant KRAS peptide antigen mRNA constructs, HLA*A*11:01 Tg mice (Taconic, strain 9660F, n=3) were administered mRNA encoding various different forms of mutated KRAS peptide antigen mRNA constructs in combination with a STING immune potentiator mRNA construct as follows: mRNA encoding mutated KRAS in combination with STING administered on days 0 and 14, animals sacrificed on day 21. Mice were aged 6-9 weeks at day 0. mRNA was administered to the animals at a dose of 0.5 mg/kg (10 ug per 20-g animal). The KRAS and STING constructs are administered at a 5:1 ratio (Ag:STING).

The types of mutated KRAS constructs tested were as follows: (i) mRNA encoding a single mutant KRAS 25mer peptide antigen containing either the G12D, G12V, G13D or G12C mutation ("monomer"); (ii) mRNA encoding a concatemer of three 25mer peptide antigens (thus creating a 75mer), one of each containing the G12D, G12V and G13D mutations ("KRAS-3MUT concatemer"); (iii) mRNA encoding a concatemer of four 25mer peptide antigens (thus creating a 100mer), one of each containing the G12D, G12V, G13D and G12C mutations ("KRAS-4MUT concatemer"); or (iv) four separate mRNAs coadministered together, each encoding a single mutant KRAS 25mer peptide antigen containing either the G12D, G12V, G13D or G12C mutation ("pooled monomers"). The amino acid and nucleotide sequences of the constructs are as described in Example 7. An A11-viral epitope concatemer antigen was also tested in combination with STING or a control mRNA (NTFIX) ("validated A11 Ag").

The test groups are shown in Table 16 as follows:

TABLE 16

| TEST group | Group | Test/Control Material | Immune Potentiator | Vehicle | Route | Dosing Regimen |
|---|---|---|---|---|---|---|
| KRAS-MUT Monomer | 1 | KRAS G12D | STING (V155M) | Compound 25 | IM | Day 1, 14 |
| | 2 | KRAS G12V | STING (V155M) | Compound 25 | IM | Day 1, 14 |
| | 3 | KRAS G13D | STING (V155M) | Compound 25 | IM | Day 1, 14 |
| | 4 | KRAS G12C | STING (V155M) | Compound 25 | IM | Day 1, 14 |
| KRAS-MUT Concatemer | 5 | KRAS-3MUT | STING (V155M) | Compound 25 | IM | Day 1, 14 |
| | 6 | KRAS-4MUT | STING (V155M) | Compound 25 | IM | Day 1, 14 |
| | 7 | KRAS-4MUT.var1 | STING (V155M) | Compound 25 | IM | Day 1, 14 |
| Pooled Monomers | 8 | G12D + G12V + G12C + G13D | STING (V155M) | Compound 25 | IM | Day 1, 14 |
| Validated A11 Ags | 9 | A11-Viral epitope concatemer | STING (V155M) | Compound 25 | IM | Day 1, 14 |
| | 10 | A11-Viral epitope concatemer | NTFIX | Compound 25 | IM | Day 1, 14 |

In a first set of experiments to evaluate antigen-specific CD8+ T cell responses to the KRAS antigens, day 21 spleen cells from the mice were restimulated ex vivo with KRAS monomer peptides (2 ug/ml per peptide) for 5 hours at 37 degrees Celsius in the presence of GolgiPlug (Brefeldin A). Intracellular cytokine staining (ICS)(IFN-γ) was performed for KRAS G12D (aa*7/8-16), KRAS G12V (aa*7/8-16), KRAS G13D (aa*7/8-16), G12C (aa*7/8-16), KRAS WT (aa*7/8-16) and no peptide.

Figure 30:
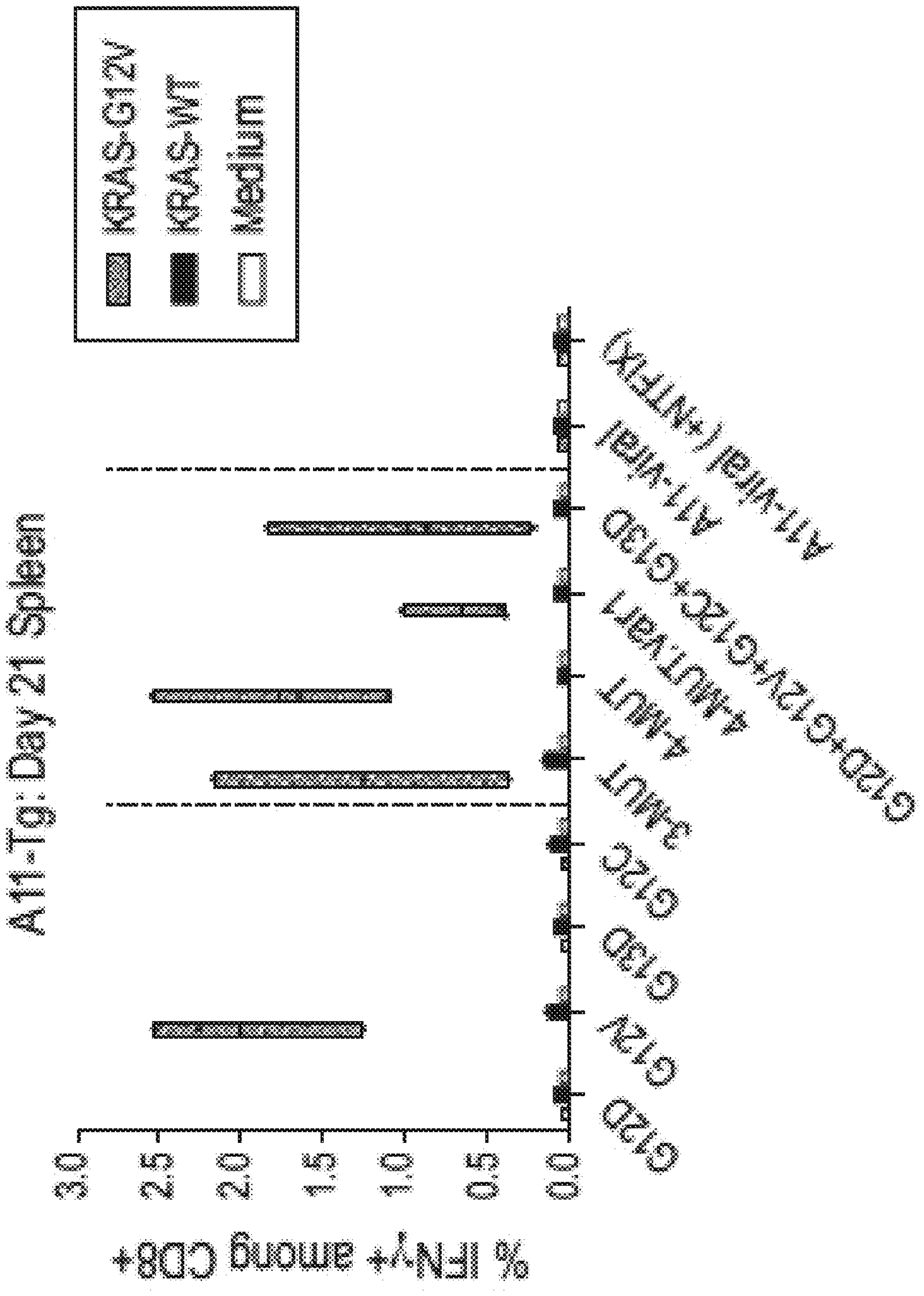
FIG. 30 is a graph showing the intracellular staining (ICS) results for CD8+ splenocytes for IFNγ from mice immunized with mutant KRAS vaccine+STING construct followed by ex vivo stimulation with KRAS-G12V peptide.
Figure 31:
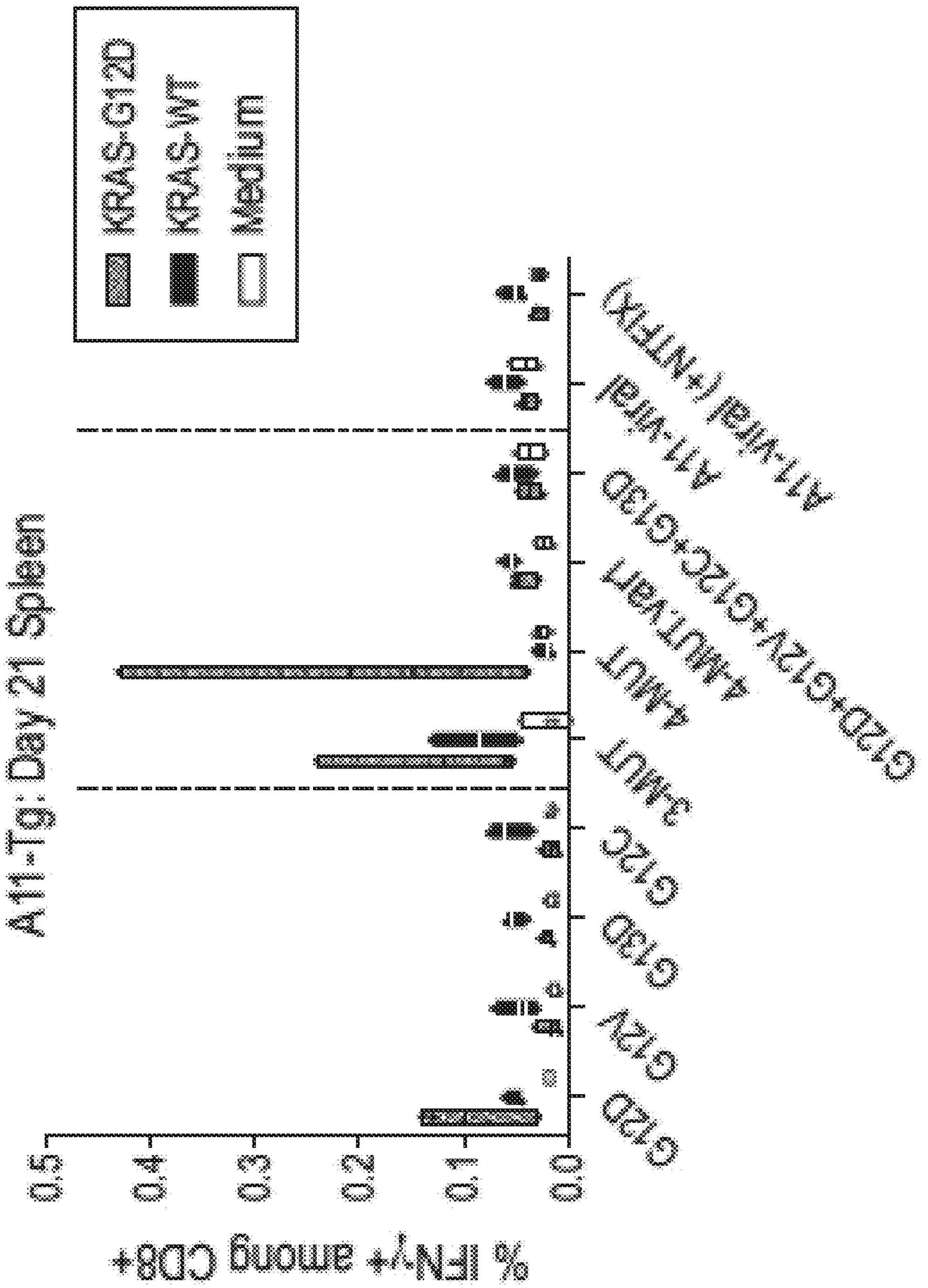
FIG. 31 is a graph showing the intracellular staining (ICS) results for CD8+ splenocytes for IFNγ from mice immunized with mutant KRAS vaccine+STING construct followed by ex vivo stimulation with KRAS-G12D peptide.

The ICS results for KRAS-G12V-specific responses are shown in FIG. 30. The ICS results for KRAS-G12D-specific responses are shown in FIG. 31. These results demonstrate that anti-KRAS-G12V and anti-KRAS-G12D specific CD8+ T cells were detected in mice immunized with the corresponding KRAS-STING vaccine (monomer or concatemer) and restimulated with the cognate peptide. Comparable % IFN-gamma positive CD8+ T cells were seen when the KRAS mutations were administered to the mice as a monomer or as concatemers. The responses observed with G12V were stronger than the responses observed with G12D. In this experiment, anti-KRAS G12C and anti-KRAS G13D responses were not observed (data not shown).

Figure 32:
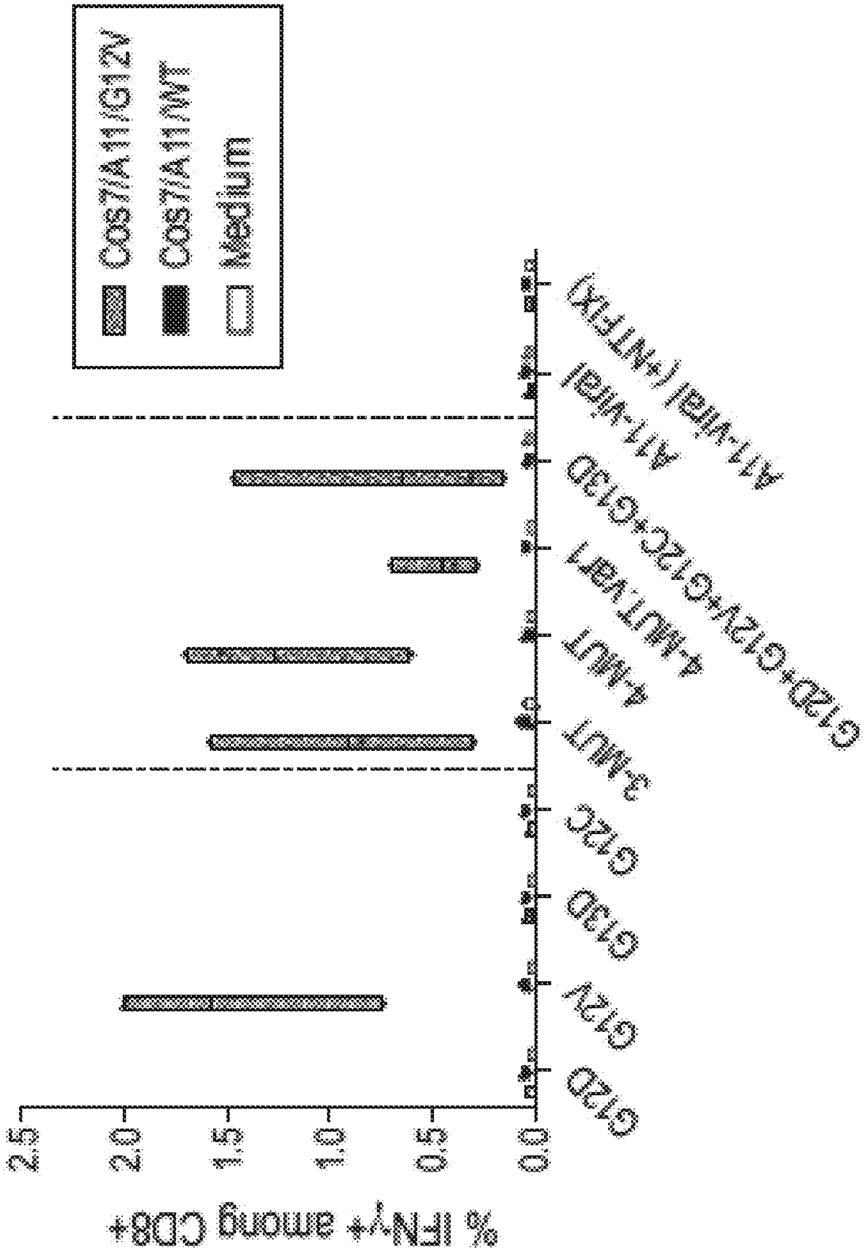
FIG. 32 is a graph showing the intracellular staining (ICS) results or CD8+ splenocytes for IFNγ from mice immunized with mutant KRAS vaccine+STING construct followed by ex vivo co-culture with Cos7 cells virally transduced with HLA*A11 allele and pulsed with KRAS-G12V.
Figure 33:
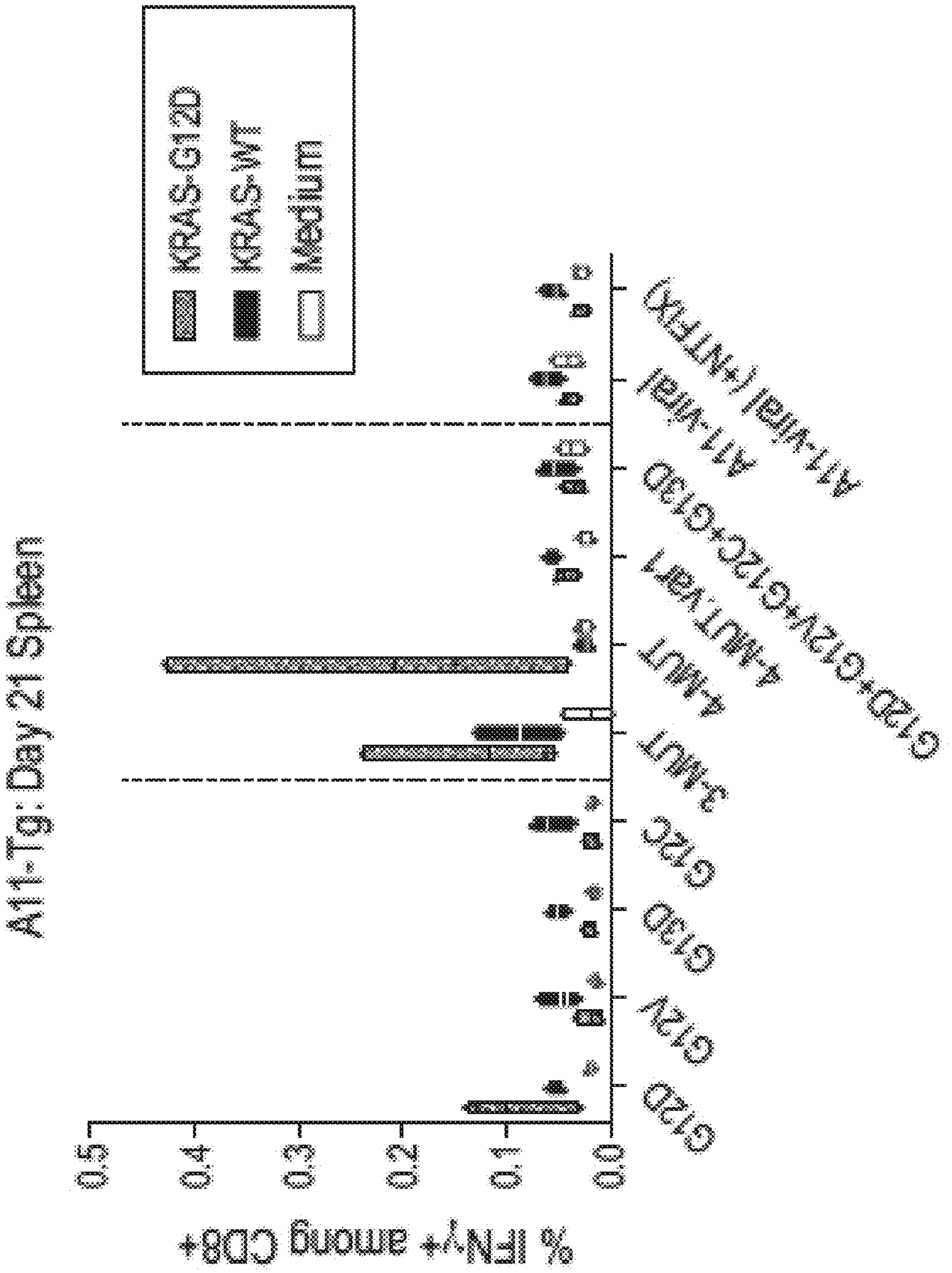
FIG. 33 is a graph showing the intracellular staining (ICS) results or CD8+ splenocytes for IFN-g from mice immunized with mutant KRAS vaccine+STING construct followed by ex vivo co-culture with Cos7 cells virally transduced with HLA*A11 allele and pulsed with KRAS-G12D.

In a second set of experiments to evaluate antigen-specific CD8+ T cell responses to KRAS antigens, day 21 spleen cells from the mice were co-cultured with HLA*A11-expressing target cells (Cos7-A11 cells) that had been pulsed with the corresponding KRAS peptides (G12V, G12D or WT control), followed by ICS (IFN-γ). The Cos7-A11 co-culture results for KRAS-G12V-specific responses are shown in FIG. 32. The Cos7-A11 co-culture results for KRAS-G12D-specific responses are shown in FIG. 33. These results demonstrate that anti-KRAS-G12V and anti-KRAS-G12D specific CD8+ T cell responses were detected in mice immunized with the corresponding KRAS-STING vaccine (monomer or concatemer) and restimulated with the A11+ expressing cell line pulsed with G12V or G12D. Thus, the results in this second set of experiments with respect to detection of antigen-specific CD8+ T cell responses to the KRAS antigens were very similar to the results from the first set of experiments using restimulation with cognate peptides.

Finally, the ability of STING to potentiate antigen-specific response to known A*11-restricted viral epitopes was evaluated using day 21 spleen cells from the mice immunized with an A11-viral epitope concatemer. Eight viral epitopes (EBV BRLF1, FLU, HIV NEF, EBV, HBV core antigen, HCV, CMV and BCL-2L1) (25 amino acids each) were concatemerized and encoded by mRNA for use as an antigen in combination with STING in the A11-transgenic mice (treatment group 9 in Table 16). The A11-viral epitope concatemer was also co-administered with an NTFIX control mRNA (treatment group 10 in Table 16). Five of the eight epitopes (EBV BRLF1, FLU, HIV NEF, EBV, HBV core antigen) were validated A11 binders with relatively low predicted IC50s; the other three epitopes (HCV, CMV and BCL-2L1) had more moderate predicted affinities for A11 but have not been experimentally validated. The amino acid sequences for the viral epitopes, as well as their IC50s, are shown below in Table 17:

TABLE 17

| Gene | Peptide | ann_IC50 | % rank | Literature validation |
|---|---|---|---|---|
| EBV BRLF1 | ATIGTAMYK (SEQ ID NO: 226) | 6.03 | 0.2 | Y |
| FLU | SIIPSGPLK (SEQ ID NO: 227) | 5 | 0.25 | Y |
| HIV NEF | AVDLSHFLK (SEQ ID NO: 228) | 20.31 | 0.25 | Y |
| EBV | AVFDRKSDAK (SEQ ID NO: 229) | 55.63 | 0.5 | Y |
| HBV core antigen | YVNVNMGLK (SEQ ID NO: 230) | 69.82 | 0.5 | Y |
| HCV | RVCEKMALY (SEQ ID NO: 231) | 304.91 | 1.3 | |
| CMV | KLGGALQAK (SEQ ID NO: 232) | 736.59 | 1.6 | |

Figure 34:
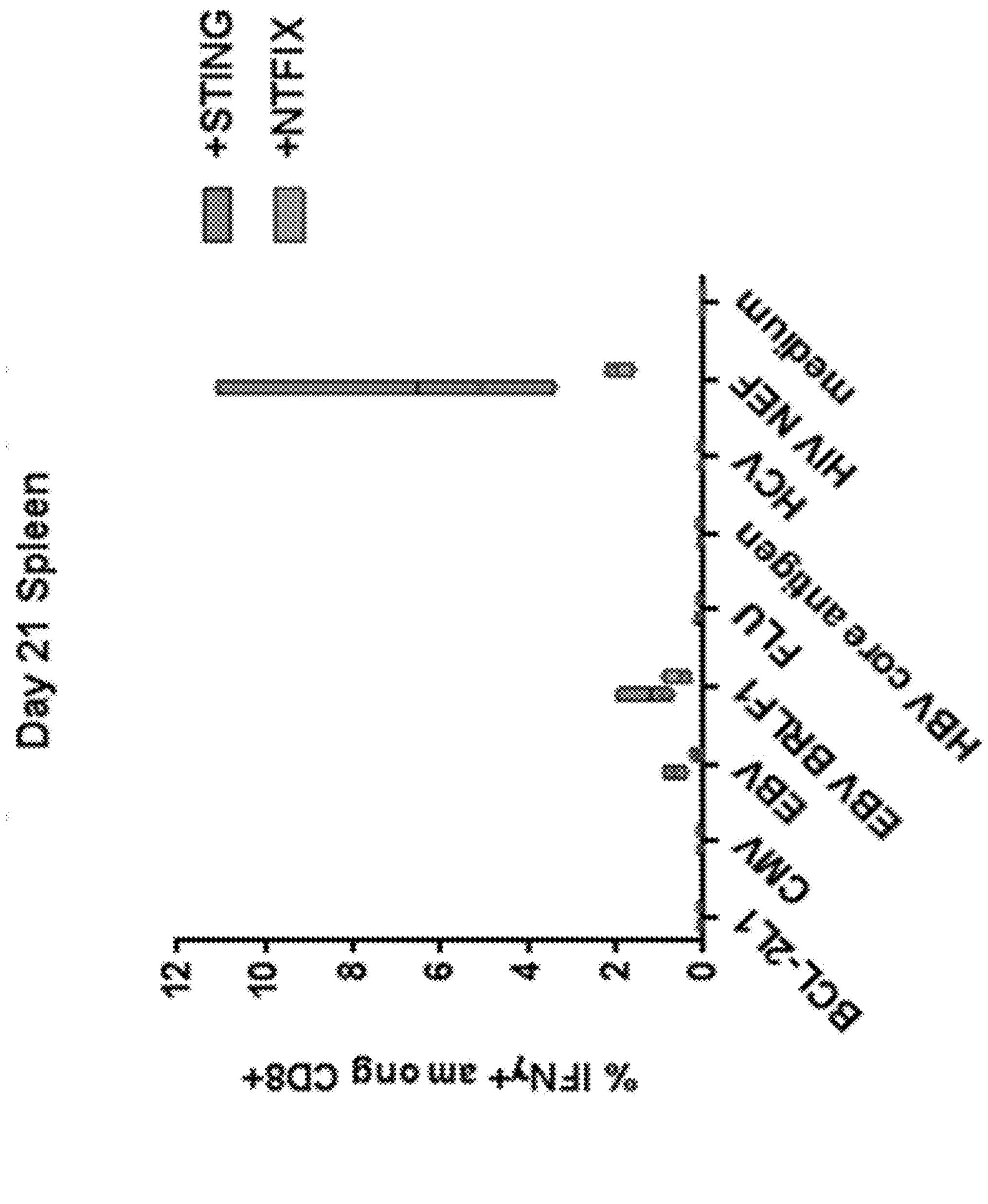
FIG. 34 is a graph showing the intracellular staining (ICS) results or CD8+ splenocytes for IFN-g from mice immunized with an A11 viral epitope concatemer+STING construct followed by ex vivo stimulation with individual viral epitopes.

Day 21 spleen cells were restimulated ex vivo with the individual A*11 viral epitopes, followed by ICS (IFN-γ and TNF-α), to detect antigen-specific CD8+ T cell responses. Antigen-specific CD8+ T cell responses were observed for four out of the eight viral epitopes (EBV, EBV BRLF1, FLU and HIV NEF) and, as shown in FIG. 34, STING potentiated T cell responses for these four viral epitopes.

A repeat study was performed in HLA*A11 transgenic mice using the KRAS-4MUT concatemer, at either a low dose (10 μg) or a high dose (30 μg), in combination with the STING immune potentiator mRNA at an Ag:STING ratio of 5:1. Significant enhancement of G12V-specific CD8 T cell responses by the STING immune potentiator construct was again observed, with the greatest enhancement being seen at the higher dose of antigen tested (30 μg).

Accordingly, the results described herein for HLA*A11 transgenic mice demonstrate that STING immunopotentiates antigen-specific T cell anti-KRAS responses, as well as antiviral responses to other A11-restricted viral antigens, and is able to immunopotentiate responses to vaccine antigens in various formats (monomers and concatemers).

Other Embodiments

It is to be understood that while the present disclosure has been described in conjunction with the detailed description thereof, the foregoing description is intended to illustrate and not limit the scope of the present disclosure, which is defined by the scope of the appended claims. Other aspects, advantages, and alterations are within the scope of the following claims.

All references described herein are incorporated by reference in their entireties.

SEQUENCE LISTING SUMMARY

| SEQ ID NO: | SEQUENCE |
|---|---|
| 1 | MPHSSLHPSIPCPRGHGAQKAALVLLSACLVTLWGLGEPPEHTLRYLVLHLASLQLGLLLNGVCSLAEELRHIHSRYRGS<br>YWRTVRACLGCPLRRGALLLLSIYFYYSLPNAVGPPFTWMLALLGLSQALNILLGLKGLAPAEISAVCEKGNFNMANGL<br>AWSYYIGYLRLILPELQARIRTYNQHYNNLLRGAVSQRLYILLPLDCGVPDNLSMADPNIRFLDKLPQQTGDHAGIKDR<br>VYSNSIYELLENGQRAGTCVLEYATPLQTLFAMSQYSQAGFSREDRLEQAKLFCRTLEDILADAPESQNNCRLIAYQEP<br>ADDSSFSLSQEVLRHLRQEEKEEVTVGSLKTSAVPSTSTMSQEPELLISGMEKPLPLRTDFS<br>(huSTING(V155M); no epitope tag) |
| 2 | MPHSSLHPSIPCPRGHGAQKAALVLLSACLVTLWGLGEPPEHTLRYLVLHLASLQLGLLLNGVCSLAEELRHIHSRYRGS<br>YWRTVRACLGCPLRRGALLLLSIYFYYSLPNAVGPPFTWMLALLGLSQALNILLGLKGLAPAEISAVCEKGNFNVAHGL<br>AWSYYIGYLRLILPELQARIRTYNQHYNNLLRGAVSQRLYILLPLDCGVPDNLSMADPNIRFLDKLPQQTGDHAGIKDR<br>VYSNSIYELLENGQRAGTCVLEYATPLQTLFAMSQYSQAGFSREDtLEQAKLFCRTLEDILADAPESQNNCRLIAYQEPA<br>DDSSFSLSQEVLRHLRQEEKEEVTVGSLKTSAVPSTSTMSQEPELLISGMEKPLPLRTDFS<br>(Hu STING(R284T); no epitope tag) |
| 3 | MPHSSLHPSIPCPRGHGAQKAALVLLSACLVTLWGLGEPPEHTLRYLVLHLASLQLGLLLNGVCSLAEELRHIHSRYRGS<br>YWRTVRACLGCPLRRGALLLLSIYFYYSLPNAVGPPFTWMLALLGLSQALNILLGLKGLAPAEISAVCEKGNFNVAHGL<br>AWSYYIGYLRLILPELQARIRTYNQHYNNLLRGAVSQRLYILLPLDCGVPDNLSMADPNIRFLDKLPQQTGDHAGIKDR<br>VYSNSIYELLENGQRAGTCVLEYATPLQTLFAMSQYSQAGFSREDmLEQAKLFCRTLEDILADAPESQNNCRLIAYQEP<br>ADDSSFSLSQEVLRHLRQEEKEEVTVGSLKTSAVPSTSTMSQEPELLISGMEKPLPLRTDFS<br>(hu STING (R284M); no epitope tag) |
| 4 | MPHSSLHPSIPCPRGHGAQKAALVLLSACLVTLWGLGEPPEHTLRYLVLHLASLQLGLLLNGVCSLAEELRHIHSRYRGS<br>YWRTVRACLGCPLRRGALLLLSIYFYYSLPNAVGPPFTWMLALLGLSQALNILLGLKGLAPAEISAVCEKGNFNVAHGL<br>AWSYYIGYLRLILPELQARIRTYNQHYNNLLRGAVSQRLYILLPLDCGVPDNLSMADPNIRFLDKLPQQTGDHAGIKDR<br>VYSNSIYELLENGQRAGTCVLEYATPLQTLFAMSQYSQAGFSREDkLEQAKLFCRTLEDILADAPESQNNCRLIAYQEP<br>ADDSSFSLSQEVLRHLRQEEKEEVTVGSLKTSAVPSTSTMSQEPELLISGMEKPLPLRTDFS<br>(Hu STING (R284K); no epitope tag) |
| 5 | MPHSSLHPSIPCPRGHGAQKAALVLLSACLVTLWGLGEPPEHTLRYLVLHLASLQLGLLLNGVCSLAEELRHIHSRYRGS<br>YWRTVRACLGCPLRRGALLLLSIYFYYSLPNAVGPPFTWMLALLGLSQALNILLGLKGLAPAEISAVCEKGNFsVAHGLA<br>WSYYIGYLRLILPELQARIRTYNQHYNNLLRGAVSQRLYILLPLDCGVPDNLSMADPNIRFLDKLPQQTGDHAGIKDRV<br>YSNSIYELLENGQRAGTCVLEYATPLQTLFAMSQYSQAGFSREDRLEQAKLFCRTLEDILADAPESQNNCRLIAYQEPA |

-continued

SEQUENCE LISTING SUMMARY

| SEQ ID NO: | SEQUENCE |
|---|---|
| | DDSSFSLSQEVLRHLRQEEKEEVTVGSLKTSAVPSTSTMSQEPELLISGMEKPLPLRTDFS<br>(Hu STING(N154S); no epitope tag) |
| 6 | MPHSSLHPSIPCPRGHGAQKAALVLLSACLVTLWGLGEPPEHTLRYLVLHLASLQLGLLLNGVCSLAEELRHIHSRYRGS<br>YWRTVRACLGCPLRRGALLLLSIYFYYSLPNAVGPPFTWMLALLGLSQALNILLGLKGLAPAEISAICEKGNFNVAHGLA<br>WSYYIGYLRLILPELQARIRTYNQHYNNLLRGAVSQRLYILLPLDCGVPDNLSMADPNIRFLDKLPQQTGDHAGIKDRV<br>YSNSIYELLENGQRAGTCVLEYATPLQTLFAMSQYSQAGFSREDRLEQAKLFCRTLEDILADAPESQNNCRLIAYQEPA<br>DDSSFSLSQEVLRHLRQEEKEEVTVGSLKTSAVPSTSTMSQEPELLISGMEKPLPLRTDFS<br>(Hu STING(V147L); no epitope tag) |
| 7 | MPHSSLHPSIPCPRGHGAQKAALVLLSACLVTLWGLGEPPEHTLRYLVLHLASLQLGLLLNGVCSLAEELRHIHSRYRGS<br>YWRTVRACLGCPLRRGALLLLSIYFYYSLPNAVGPPFTWMLALLGLSQALNILLGLKGLAPAEISAVCEKGNFNVAHGL<br>AWSYYIGYLRLILPELQARIRTYNQHYNNLLRGAVSQRLYILLPLDCGVPDNLSMADPNIRFLDKLPQQTGDHAGIKDR<br>VYSNSIYELLENGQRAGTCVLEYATPLQTLFAMSQYSQAGFSREDRLEQAKLFCRTLEDILADAPESQNNCRLIAYQqP<br>ADDSSFSLSQEVLRHLRQEEKEEVTVGSLKTSAVPSTSTMSQEPELLISGMEKPLPLRTDFS<br>(Hu STING (E315Q); no epitope tag) |
| 8 | MPHSSLHPSIPCPRGHGAQKAALVLLSACLVTLWGLGEPPEHTLRYLVLHLASLQLGLLLNGVCSLAEELRHIHSRYRGS<br>YWRTVRACLGCPLRRGALLLLSIYFYYSLPNAVGPPFTWMLALLGLSQALNILLGLKGLAPAEISAVCEKGNFNVAHGL<br>AWSYYIGYLRLILPELQARIRTYNQHYNNLLRGAVSQRLYILLPLDCGVPDNLSMADPNIRFLDKLPQQTGDHAGIKDR<br>VYSNSIYELLENGQRAGTCVLEYATPLQTLFAMSQYSQAGFSREDRLEQAKLFCRTLEDILADAPESQNNCRLIAYQEP<br>ADDSSFSLSQEVLRHLRQEEKEEVTVGSLKTSAVPSTSTMSQEPELLISGMEKPLPLaTDFS<br>(Hu STING (R375A); no epitope tag) |
| 9 | MPHSSLHPSIPCPRGHGAQKAALVLLSACLVTLWGLGEPPEHTLRYLVLHLASLQLGLLLNGVCSLAEELRH<br>IHSRYRGSYWRTVRACLGCPLRRGALLLLSIYFYYSLPNAVGPPFTWMLALLGLSQALNILLGLKGLAPAEIS<br>A**L**CEKGNF**SM**AHGLAWSYYIGYLRLILPELQARIRTYNQHYNNLLRGAVSQRLYILLPLDCGVPDNLSMAD<br>PNIRFLDKLPQQTGDHAGIKDRVYSNSIYELLENGQRAGTCVLEYATPLQTLFAMSQYSQAGFSREDRLEQ<br>AKLFCRTLEDILADAPESQNNCRLIAYQEPADDSSFSLSQEVLRHLRQEEKEEVTVGSLKTSAVPSTSTMSQE<br>PELLISGMEKPLPLRTDFS<br>(Hu STING(V147L/N154S/V155M); no epitope tag) |
| 10 | MPHSSLHPSIPCPRGHGAQKAALVLLSACLVTLWGLGEPPEHTLRYLVLHLASLQLGLLLNGVCSLAEELRH<br>IHSRYRGSYWRTVRACLGCPLRRGALLLLSIYFYYSLPNAVGPPFTWMLALLGLSQALNILLGLKGLAPAEIS<br>A**L**CEKGNF**SM**AHGLAWSYYIGYLRLILPELQARIRTYNQHYNNLLRGAVSQRLYILLPLDCGVPDNLSMAD<br>PNIRFLDKLPQQTGDHAGIKDRVYSNSIYELLENGQRAGTCVLEYATPLQTLFAMSQYSQAGFSRED**M**LEQ<br>AKLFCRTLEDILADAPESQNNCRLIAYQEPADDSSFSLSQEVLRHLRQEEKEEVTVGSLKTSAVPSTSTMSQE<br>PELLISGMEKPLPLRTDFS<br>(Hu STING(R284M/V147L/N154S/V155M); no epitope tag) |
| 11 | METPKPRILPWLVSQLDLGQLEGVAWLDESRTRFRIPWKHGLRQDAQMADFGIFQAWAEASGAYTPGKDKPDVST<br>WKRNFRSALNRKEVLRLAADNSKDPYDPHKVYEFVTPGARDFVHLGASPDTNGKSSLPHSQENLPKLFDGLILGPLKD<br>EGSSDLAIVSDPSQQLPSPNVNNFLNPAPQENPLKQLLAEEQWEFEVTAFYRGRQVFQQTLFCPGGLRLVGSTADMT<br>LPWQPVTLPDPEGFLTDKLVKEYVGQVLKGLGNGLALWQAGQCLWAQRLGHSHAFWALGEELLPDSGRGPDGEV<br>HKDKDGAVFDLRPFVADLIAFMEGSGHSPRYTLWFCMGEMWPQDQPWVKRLVMVKVVPTCLKELLEMAREGGA<br>SSLKTVDLHIDNSQPISLTSDQYKAYLQDLVEDMDFQATGNI<br>(super mouse IRF3 S396D; no epitope tag) |
| 12 | MGTPKPRILPWLVSQLDLGQLEGVAWVNKSRTRFRIPWKHGLRQDAQQEDFGIFQAWAEATGAYVPGRDKPDLPT<br>WKRNFRSALNRKEGLRLAEDRSKDPHDPHKIYEFVNSGVGDFSQPDTSPDTNGGGSTSDTQEDILDELLGNMVLAPL<br>PDPGPPSLAVAPEPCPQPLRSPSLDNPTPFPNLGPSENPLKRLLVPGEEWEFEVTAFYRGRQVFQQTISCPEGLRLVGS<br>EVGDRTLPGWPVTLPDPGMSLTDRGVMSYVRHVLSCLGGGLALWRAGQWLWAQRLGHCHTYWAVSEELLPNSG<br>HGPDGEVPKDKEGGVFDLGPFIVDLITFTEGSGRSPRYALWFCVGESWPQDQPWTKRLVMVKVVPTCLRALVEMA<br>RVGGASSLENTVDLHIDNSHPLSLTSDQYKAYLQDLVEGMDFQGPGET<br>(super human IRF3 S396D; no epitope tag) |
| 13 | MALAPERAAPRVLFGEWLLGEISSGCYEGLQWLDEARTCFRVPWKHFARKDLSEADARIFKAWAVARGRWPPSSRG<br>GGPPPEAETAERAGWKTNFRCALRSTRRFVMLRDNSGDPADPHKVYALSRELCWREGPGTDQTEAEAPAAVPPPQ<br>GGPPGPFLAHTHAGLQAPGPLPAPAGDKGDLLLQAVQQSCLADHLLTASWGADPVPTKAPGEGQEGLPLTGACAG<br>GPGLPAGELYGWAVETTPSPgpqpaalttgeaaapesphqaepylspspsactavqepspgaldvtimykgrtvlqkvvghpsctflyg<br>ppdpavratdpqqvafpspaelpdqkqlryteellrhvapglhlelrgpqlwarrmgkckvywevggppgsaspstpacllprncdtpifdfrvf<br>fqelvefrarqrrgsprytiylgfgqdlsagrpkekslvlvklepwlcrvhlegtqrEGVSSLDSSSLSLCLSSANSLYDDIECFLMELEQPA<br>(Wild-type Hu IRF7 isoform A; P037 without epitope tag) |
| 14 | MALAPERAAPRVLFGEWLLGEISSGCYEGLQWLDEARTCFRVPWKHFARKDLSEADARIFKAWAVARGRWPPSSRG<br>GGPPPEAETAERAGWKTNFRCALRSTRRFVMLRDNSGDPADPHKVYALSRELCWREGPGTDQTEAEAPAAVPPPQ<br>GGPPGPFLAHTHAGLQAPGPLPAPAGDKGDLLLQAVQQSCLADHLLTASWGADPVPTKAPGEGQEGLPLTGACAG<br>GPGLPAGELYGWAVETTPSPgpqpaalttgeaaapesphqaepylspspsactavqepspgaldvtimykgrtvlqkvvghpsctflyg<br>ppdpavratdpqqvafpspaelpdqkqlryteellrhvapglhlelrgpqlwarrmgkckvywevggppgsaspstpacllprncdtpifdfrvf<br>fqelvefrarqrrgsprytiylgfgqdlsagrpkekslvlvklepwlcrvhlegtqrEGVSSLDSSdLdLCLSSANSLYDDIECFLMELEQPA<br>(constitutively active Hu IRF7 S477D/S479D; P033 without epitope tag) |

-continued

SEQUENCE LISTING SUMMARY

| SEQ ID NO: | SEQUENCE |
|---|---|
| 15 | MALAPERAAPRVLFGEWLLGEISSGCYEGLQWLDEARTCFRVPWKHFARKDLSEADARIFKAWAVARGRWPPSSRG<br>GGPPPEAETAERAGWKTNFRCALRSTRRFVMLRDNSGDPADPHKVYALSRELCWREGPGTDQTEAEAPAAVPPPQ<br>GGPPGPFLAHTHAGLQAPGPLPAPAGDKGDLLLQAVQQSCLADHLLTASWGADPVPTKAPGEGQEGLPLTGACAG<br>GPGLPAGELYGWAVETTPSPgpqpaalttgeaaapesphqaepylspspsactavqepspgaldvtimykgrtvlqkvvghpsctflyg<br>ppdpavratdpqqvafpspaelpdqkqlryteellrhvapglhlelrgpqlwarrmgkckvywevggppgsaspstpacllprncdtpifdfrvf<br>fqelvefrarqrrgsprytiylgfgqdlsagrpkekslvlvklepwlcrvhlegtqrEGVSSLDdSdLSdCLSSANSLYDDIECFLMELEQPA<br>(constitutively active Hu IRF7 S475D/S477D/L480D; P034 without epitope tag) |
| 16 | MALAPERAAPRVLFGEWLLGEISSGCYEGLQWLDEARTCFRVPWKHFARKDLSEADARIFKAWAVARGRWPPSSRG<br>GGPPPEAETAERAGWKTNFRCALRSTRRFVMLRDNSGDPADPHKVYALSRELCWREGPGTDQTEAEAPAAVPPPQ<br>GGPPGPFLAHTHAGLQAPGPLPAPAGDKGDLLLQAVQQSCLADHLLTASWGADPVPTKAPGEGQEGLPLTGACAG<br>GPGLPAGELYGWAVETTPSPgpqpaalttgeaaapesphqaepylspspsactavqepspgaldvtimykgrtvlqkvvghpsctflyg<br>ppdpavratdpqqvafpspaelpdqkqlryteellrhvapglhlelrgpqlwarrmgkckvywevggppgsaspstpacllprncdtpifdfrvf<br>fqelvefrarqrrgsprytiylgfgqdlsagrpkekslvlvklepwlcrvhlegtqrEGVSSLDdddLdLCLdSANdLYDDIECFLMELEQP<br>A<br>(constitutively active Hu IRF7 S475D/S476D/S477D/S479D/S483D/S487D; P035 without epitope tag) |
| 17 | MALAPERAAPRVLFGEWLLGEISSGCYEGLQWLDEARTCFRVPWKHFARKDLSEADARIFKAWAVARGRWPPSSRG<br>GGPPPEAETAERAGWKTNFRCALRSTRRFVMLRDNSGDPADPHKVYALSRELCWREGPGTDQTEAEAPAAVPPPQ<br>GGPPGPFLAHTHAGLQAPGPLPAPAGDKGDLLLQAVQQSCLADHLLTASWGADPVPTKAPGEGQEGLPLTGACAG<br>GPGLPAGELYGWAVETTPSPEGVSSLDSSSLSLCLSSANSLYDDIECFLMELEQPA<br>(constitutively active truncated Hu IRF7 1-246 + 468-503; P032 without epitope tag) |
| 18 | MALAPERAAPRVLFGEWLLGEISSGCYEGLQWLDEARTCFRVPWKHFARKDLSEADARIFKAWAVARGRWPPSSRG<br>GGPPPEAETAERAGWKTNFRCALRSTRRFVMLRDNSGDPADPHKVYALSRELCWREGPGTDQTEAEAPAAVPPPQ<br>GGPPGPFLAHTHAGLQAPGPLPAPAGDKGDLLLQAVQQSCLADHLLTASWGADPVPTKAPGEGQEGLPLTGACAG<br>GPGLPAGELYGWAVETTPSPEGVSSLDdddLdLCLdSANdLYDDIECFLMELEQPA<br>(constitutively active truncated Hu IRF7 1-246 + 468-503 plus<br>S475D/S476D/S477D/S479D/S483D/S487D; P036 without epitope tag) |
| 19 | MALAPERAAPRVLFGEWLLGEISSGCYEGLQWLDEARTCFRVPWKHFARKDLSEADARIFKAWAVARGRWPPSSRG<br>GGPPPEAETAERAGWKTNFRCALRSTRRFVMLRDNSGDPADPHKVYALSRELCWREGPGTDQTEAEAPAAVPPPQ<br>gpqpaalttgeaaapesphqaepylspspsactavqepspgaldvtimykgrtvlqkvvghpsctflygppdpavratdpqqvafpspaelpd<br>qkqlryteellrhvapglhlelrgpqlwarrmgkckvywevggppgsaspstpacllprncdtpifdfrvffqelvefrarqrrgsprytiylg<br>fgqdlsagrpkekslvlvklepwlcrvhlegtqrEGVSSLDSSSLSLCLSSANSLYDDIECFLMELEQPA<br>(truncated Hu IRF7 1-151 + 247-503; P038 without epitope tag; null mutation) |
| 20 | MGGPPGPFLAHTHAGLQAPGPLPAPAGDKGDLLLQAVQQSCLADHLLTASWGADPVPTKAPGEGQEGLPLTGACA<br>GGPGLPAGELYGWAVETTPSPgpqpaalttgeaaapesphqaepylspspsactavqepspgaldvtimykgrtvlqkvvghpsctfly<br>gppdpavratdpqqvafpspaelpdqkqlryteellrhvapglhlelrgpqlwarrmgkckvywevggppgsaspstpacllprncdtpifdfr<br>vffqelvefrarqrrgsprytiylgfgqdlsagrpkekslvlvklepwlcrvhlegtqrEGVSSLDSSSLSLCLSSANSLYDDIECFLMELEQP<br>A<br>(truncated Hu IRF7 152-503; P039 without epitope tag; null mutation) |
| 21 | TCAAGCTTTTGGACCCTCGTACAGAAGCTAATACGACTCACTATAGGGAAATAAGAGAGAAAAGAAGAGTAAGA<br>AGAAATATAAGAGCCACC<br>(5' UTR) |
| 22 | TGATAATAGGCTGGAGCCTCGGTGGCCATGCTTCTTGCCCCTTGGGCCTCCCCCCAGCCCCTCCTCCCCTTCCTGC<br>ACCCGTACCCCCGTGGTCTTTGAATAAAGTCTGAGTGGGCGGC<br>(3' UTR) |
| 23 | TGATAATAGGCTGGAGCCTCGGTGGCCATGCTTCTTGCCCCTTGGGCCCAAACACCATTGTCACACTCCATCCCC<br>CCAGCCCCTCCTCCCCTTCCTCCATAAAGTAGGAAACACTACATGCACCCGTACCCCCGTGGTCTTTGAATAAAGT<br>CTGAGTGGGCGGC<br>(3' UTR with mi-122 and mi-142.3p sites) |
| 24 | GSGATNFSLLKQAGDVEENPGP<br>(2A peptide amino acid sequence) |
| 25 | GGAAGCGGAGCTACTAACTTCAGCCTGCTGAAGCAGGCTGGAGACGTGGAGGAGAACCCTGGACCT<br>(Nucleotide sequence encoding 2A peptide) |
| 26 | TCCGGACTCAGATCCGGGGATCTCAAAATTGTCGCTCCTGTCAAACAAACTCTTAACTTTGATTTACTCAAACTGG<br>CTGGGGATGTAGAAAGCAATCCAGGTCCACTC<br>(Nucleotide sequence encoding 2A peptide) |
| 27 | GACAGUGCAGUCACCCAUAAAGUAGAAAGCACUACUAACAGCACUGGAGGGUGUAGUGUUUCCUACUUUA<br>UGGAUGAGUGUACUGUG<br>(miR-142) |
| 28 | UGUAGUGUUUCCUACUUUAUGGA<br>(miR-142-3p) |

-continued

SEQUENCE LISTING SUMMARY

| SEQ ID NO: | SEQUENCE |
|---|---|
| 29 | UCCAUAAAGUAGGAAACACUACA<br>(miR-142-3p binding site) |
| 30 | CAUAAAGUAGAAAGCACUACU<br>(miR-142-5p) |
| 31 | AGUAGUGCUUUCUACUUUAUG<br>(miR-142-5p binding site) |
| 32 | AACGCCAUUAUCACACUAAAUA<br>(miR-122-3p) |
| 33 | UGGAGUGUGACAAUGGUGUUUG<br>(miR-122-5p) |
| 34 | UAGCUUAUCAGACUGAUGUUGA<br>(miR-21-5p) |
| 35 | CAACACCAGUCGAUGGGCUGU<br>(miR-21-3p) |
| 36 | MKLVVVGADGVGKSAL<br>(KRAS(G12D)15mer) |
| 37 | MKLVVVGAVGVGKSAL<br>(KRAS(G12V)15mer) |
| 38 | MLVVVGAGDVGKSALT<br>(KRAS(G13D)15mer) |
| 39 | MTEYKLVVVGADGVGKSALTIQLIQ<br>(KRAS(G12D)25mer) |
| 40 | MTEYKLVVVGAVGVGKSALTIQLIQ<br>(KRAS(G12V)25mer) |
| 41 | MTEYKLVVVGAGDVGKSALTIQLIQ<br>(KRAS(G13D)25mer) |
| 42 | MKLVVVGADGVGKSALKLVVVGADGVGKSALKLVVVGADGVGKSAL<br>(KRAS(G12D)15mer^3) |
| 43 | MKLVVVGAVGVGKSALKLVVVGAVGVGKSALKLVVVGAVGVGKSAL<br>(KRAS(G12V)15mer^3) |
| 44 | MLVVVGAGDVGKSALTLVVVGAGDVGKSALTLVVVGAGDVGKSALT<br>(KRAS(G13D)15mer^3) |
| 45 | MTEYKLVVVGADGVGKSALTIQUQMTEYKLVVVGADGVGKSALTIQULIMTEYKLVVVGADGVGKSALTILIUQ<br>(KRAS(G12D)25mer^3) |
| 46 | MTEYKLVVVGAVGVGKSALTIQLIQMTEYKLVVVGAVGVGKSALTIQLIQMTEYKLVVVGAVGVGKSALTIQLIQ<br>(KRAS(G12V)25mer^3) |
| 47 | MTEYKLVVVGAGDVGKSALTIQLIQMTEYKLVVVGAGDVGKSALTIQLIQMTEYKLVVVGAGDVGKSALTIQLIQ<br>(KRAS(G13D)25mer^3) |
| 48 | MPHSSLHPSIPCPRGHGAQKAALVLLSACLVTLWGLGEPPEHTLRYLVLHLASLQLGLLLNGVCSLAEELRHIHSRYR<br>GSYWRTVRACLGCPLRRGALLLLSIYFYYSLPNAVGPPFTWMLALLGLSQALNILLGLKGLAPAEISAVCEKGNFNM<br>AHGLAWSYYIGYLRLILPELQARIRTYNQHYNNLLRGAVSQRLYILLPLDCGVPDNLSMADPNIRFLDKLPQQTGDH<br>AGIKDRVYSNSIYELLENGQRAGTCVLEYATPLQTLFAMSQYSQAGFSREDRLEQAKLFCRTLEDILADAPESQNNC<br>RLIAYQEPADDSSFSLSQEVLRHLRQEEKEEVTVGSLKTSAVPSTSTMSQEPELLISGMEKPLPLRTDFSATNFSLLKQ<br>AGDVEENPGPMKLVVVGADGVGKSAL<br>(KRAS(G12D)15mer_nt.STING(V155M)) |
| 49 | MPHSSLHPSIPCPRGHGAQKAALVLLSACLVTLWGLGEPPEHTLRYLVLHLASLQLGLLLNGVCSLAEELRHIHSRYR<br>GSYWRTVRACLGCPLRRGALLLLSIYFYYSLPNAVGPPFTWMLALLGLSQALNILLGLKGLAPAEISAVCEKGNFNM<br>AHGLAWSYYIGYLRLILPELQARIRTYNQHYNNLLRGAVSQRLYILLPLDCGVPDNLSMADPNIRFLDKLPQQTGDH<br>AGIKDRVYSNSIYELLENGQRAGTCVLEYATPLQTLFAMSQYSQAGFSREDRLEQAKLFCRTLEDILADAPESQNNC<br>RLIAYQEPADDSSFSLSQEVLRHLRQEEKEEVTVGSLKTSAVPSTSTMSQEPELLISGMEKPLPLRTDFSATNFSLLKQ<br>AGDVEENPGPMKLVVVGAVGVGKSAL<br>(KRAS(G12V)15mer_nt.STING(V155M) |

-continued

SEQUENCE LISTING SUMMARY

| SEQ ID NO: | SEQUENCE |
|---|---|
| 50 | MPHSSLHPSIPCPRGHGAQKAALVLLSACLVTLWGLGEPPEHTLRYLVLHLASLQLGLLLNGVCSLAEELRHIHSRYR GSYWRTVRACLGCPLRRGALLLLSIYFYYSLPNAVGPPFTWMLALLGLSQALNILLGLKGLAPAEISAVCEKGNFNM AHGLAWSYYIGYLRLILPELQARIRTYNQHYNNLLRGAVSQRLYILLPLDCGVPDNLSMADPNIRFLDKLPQQTGDH AGIKDRVYSNSIYELLENGQRAGTCVLEYATPLQTLFAMSQYSQAGFSREDRLEQAKLFCRTLEDILADAPESQNNC RLIAYQEPADDSSFSLSQEVLRHLRQEEKEEVTVGSLKTSAVPSTSTMSQEPELLISGMEKPLPLRTDFSATNFSLLKQ AGDVEENPGPMLVVVGAGDVGKSALT (KRAS(G13D)15mer_nt.STING(V155M) |
| 51 | MPHSSLHPSIPCPRGHGAQKAALVLLSACLVTLWGLGEPPEHTLRYLVLHLASLQLGLLLNGVCSLAEELRHIHSRYR GSYWRTVRACLGCPLRRGALLLLSIYFYYSLPNAVGPPFTWMLALLGLSQALNILLGLKGLAPAEISAVCEKGNFNM AHGLAWSYYIGYLRLILPELQARIRTYNQHYNNLLRGAVSQRLYILLPLDCGVPDNLSMADPNIRFLDKLPQQTGDH AGIKDRVYSNSIYELLENGQRAGTCVLEYATPLQTLFAMSQYSQAGFSREDRLEQAKLFCRTLEDILADAPESQNNC RLIAYQEPADDSSFSLSQEVLRHLRQEEKEEVTVGSLKTSAVPSTSTMSQEPELLISGMEKPLPLRTDFSATNFSLLKQ AGDVEENPGPMTEYKLVVVGADGVGKSALTIQLIQ (KRAS(G12D)25mer_nt.STING(V155M)) |
| 52 | MPHSSLHPSIPCPRGHGAQKAALVLLSACLVTLWGLGEPPEHTLRYLVLHLASLQLGLLLNGVCSLAEELRHIHSRYR GSYWRTVRACLGCPLRRGALLLLSIYFYYSLPNAVGPPFTWMLALLGLSQALNILLGLKGLAPAEISAVCEKGNFNM AHGLAWSYYIGYLRLILPELQARIRTYNQHYNNLLRGAVSQRLYILLPLDCGVPDNLSMADPNIRFLDKLPQQTGDH AGIKDRVYSNSIYELLENGQRAGTCVLEYATPLQTLFAMSQYSQAGFSREDRLEQAKLFCRTLEDILADAPESQNNC RLIAYQEPADDSSFSLSQEVLRHLRQEEKEEVTVGSLKTSAVPSTSTMSQEPELLISGMEKPLPLRTDFSATNFSLLKQ AGDVEENPGPMTEYKLVVVGAVGVGKSALTIQLIQ (KRAS(G12V)25mer_nt.STING(V155M) |
| 53 | MPHSSLHPSIPCPRGHGAQKAALVLLSACLVTLWGLGEPPEHTLRYLVLHLASLQLGLLLNGVCSLAEELRHIHSRYR GSYWRTVRACLGCPLRRGALLLLSIYFYYSLPNAVGPPFTWMLALLGLSQALNILLGLKGLAPAEISAVCEKGNFNM AHGLAWSYYIGYLRLILPELQARIRTYNQHYNNLLRGAVSQRLYILLPLDCGVPDNLSMADPNIRFLDKLPQQTGDH AGIKDRVYSNSIYELLENGQRAGTCVLEYATPLQTLFAMSQYSQAGFSREDRLEQAKLFCRTLEDILADAPESQNNC RLIAYQEPADDSSFSLSQEVLRHLRQEEKEEVTVGSLKTSAVPSTSTMSQEPELLISGMEKPLPLRTDFSATNFSLLKQ AGDVEENPGPMTEYKLVVVGAGDVGKSALTIQLIQ (KRAS(G13D)25mer_nt.STING(V155M) |
| 54 | MPHSSLHPSIPCPRGHGAQKAALVLLSACLVTLWGLGEPPEHTLRYLVLHLASLQLGLLLNGVCSLAEELRHIHSRYRGS YWRTVRACLGCPLRRGALLLLSIYFYYSLPNAVGPPFTWMLALLGLSQALNILLGLKGLAPAEISAVCEKGNFNMAHGL AWSYYIGYLRLILPELQARIRTYNQHYNNLLRGAVSQRLYILLPLDCGVPDNLSMADPNIRFLDKLPQQTGDHAGIKDR VYSNSIYELLENGQRAGTCVLEYATPLQTLFAMSQYSQAGFSREDRLEQAKLFCRTLEDILADAPESQNNCRLIAYQEP ADDSSFSLSQEVLRHLRQEEKEEVTVGSLKTSAVPSTSTMSQEPELLISGMEKPLPLRTDFSATNFSLLKQAGDVEENP GPMKLVVVGADGVGKSALKLVVVGADGVGKSALKLVVVGADGVGKSAL (KRAS(G12D)15mer^3_nt.STING(V155M)) |
| 55 | MPHSSLHPSIPCPRGHGAQKAALVLLSACLVTLWGLGEPPEHTLRYLVLHLASLQLGLLLNGVCSLAEELRHIHSRYRGS YWRTVRACLGCPLRRGALLLLSIYFYYSLPNAVGPPFTWMLALLGLSQALNILLGLKGLAPAEISAVCEKGNFNMAHGL AWSYYIGYLRLILPELQARIRTYNQHYNNLLRGAVSQRLYILLPLDCGVPDNLSMADPNIRFLDKLPQQTGDHAGIKDR VYSNSIYELLENGQRAGTCVLEYATPLQTLFAMSQYSQAGFSREDRLEQAKLFCRTLEDILADAPESQNNCRLIAYQEP ADDSSFSLSQEVLRHLRQEEKEEVTVGSLKTSAVPSTSTMSQEPELLISGMEKPLPLRTDFSATNFSLLKQAGDVEENP GPMKLVVVGAVGVGKSALKLVVVGAVGVGKSALKLVVVGAVGVGKSAL (KRAS(G12V)15mer^3_nt.STING(V155M) |
| 56 | MPHSSLHPSIPCPRGHGAQKAALVLLSACLVTLWGLGEPPEHTLRYLVLHLASLQLGLLLNGVCSLAEELRHIHSRYRGS YWRTVRACLGCPLRRGALLLLSIYFYYSLPNAVGPPFTWMLALLGLSQALNILLGLKGLAPAEISAVCEKGNFNMAHGL AWSYYIGYLRLILPELQARIRTYNQHYNNLLRGAVSQRLYILLPLDCGVPDNLSMADPNIRFLDKLPQQTGDHAGIKDR VYSNSIYELLENGQRAGTCVLEYATPLQTLFAMSQYSQAGFSREDRLEQAKLFCRTLEDILADAPESQNNCRLIAYQEP ADDSSFSLSQEVLRHLRQEEKEEVTVGSLKTSAVPSTSTMSQEPELLISGMEKPLPLRTDFSATNFSLLKQAGDVEENP GPMLVVVGAGDVGKSALTLVVVGAGDVGKSALTLVVVGAGDVGKSALT (KRAS(G13D)15mer^3_nt.STING(V155M) |
| 57 | MPHSSLHPSIPCPRGHGAQKAALVLLSACLVTLWGLGEPPEHTLRYLVLHLASLQLGLLLNGVCSLAEELRHIHSRYRGS YWRTVRACLGCPLRRGALLLLSIYFYYSLPNAVGPPFTWMLALLGLSQALNILLGLKGLAPAEISAVCEKGNFNMAHGL AWSYYIGYLRLILPELQARIRTYNQHYNNLLRGAVSQRLYILLPLDCGVPDNLSMADPNIRFLDKLPQQTGDHAGIKDR VYSNSIYELLENGQRAGTCVLEYATPLQTLFAMSQYSQAGFSREDRLEQAKLFCRTLEDILADAPESQNNCRLIAYQEP ADDSSFSLSQEVLRHLRQEEKEEVTVGSLKTSAVPSTSTMSQEPELLISGMEKPLPLRTDFSATNFSLLKQAGDVEENP GPMTEYKLVVVGADGVGKSALTIQLIQMTEYKLVVVGADGVGKSALTIQLIQMTEYKLVVVGADGVGKSALTIQLIQ (KRAS(G12D)25mer^3_nt.STING(V155M)) |
| 58 | MPHSSLHPSIPCPRGHGAQKAALVLLSACLVTLWGLGEPPEHTLRYLVLHLASLQLGLLLNGVCSLAEELRHIHSRYRGS YWRTVRACLGCPLRRGALLLLSIYFYYSLPNAVGPPFTWMLALLGLSQALNILLGLKGLAPAEISAVCEKGNFNMAHGL AWSYYIGYLRLILPELQARIRTYNQHYNNLLRGAVSQRLYILLPLDCGVPDNLSMADPNIRFLDKLPQQTGDHAGIKDR VYSNSIYELLENGQRAGTCVLEYATPLQTLFAMSQYSQAGFSREDRLEQAKLFCRTLEDILADAPESQNNCRLIAYQEP ADDSSFSLSQEVLRHLRQEEKEEVTVGSLKTSAVPSTSTMSQEPELLISGMEKPLPLRTDFSATNFSLLKQAGDVEENP GPMTEYKLVVVGAVGVGKSALTIQLIQMTEYKLVVVGAVGVGKSALTIQLIQMTEYKLVVVGAVGVGKSALTIQLIQ (KRAS(G12V)25mer^3_nt.STING(V155M) |

-continued

SEQUENCE LISTING SUMMARY

| SEQ ID NO: | SEQUENCE |
|---|---|
| 59 | MPHSSLHPSIPCPRGHGAQKAALVLLSACLVTLWGLGEPPEHTLRYLVLHLASLQLGLLLNGVCSLAEELRHIHSRYRGS YWRTVRACLGCPLRRGALLLLSIYFYYSLPNAVGPPFTWMLALLGLSQALNILLGLKGLAPAEISAVCEKGNFNMAHGL AWSYYIGYLRLILPELQARIRTYNQHYNNLLRGAVSQRLYILLPLDCGVPDNLSMADPNIRFLDKLPQQTGDHAGIKDR VYSNSIYELLENGQRAGTCVLEYATPLQTLFAMSQYSQAGFSREDRLEQAKLFCRTLEDILADAPESQNNCRLIAYQEP ADDSSFSLSQEVLRHLRQEEKEEVTVGSLKTSAVPSTSTMSQEPELLISGMEKPLPLRTDFSATNFSLLKQAGDVEENP GPMTEYKLVVVGAGDVGKSALTIQLIQMTEYKLVVVGAGDVGKSALTIQLIQMTEYKLVVVGAGDVGKSALTIQLIQ (KRAS(G13D)25mer^3_nt.STING(V155M) |
| 60 | MKLVVVGADGVGKSALATNFSLLKQAGDVEENPGPMPHSSLHPSIPCPRGHGAQKAALVLLSACLVTLWGLGEP PEHTLRYLVLHLASLQLGLLLNGVCSLAEELRHIHSRYRGSYWRTVRACLGCPLRRGALLLLSIYFYYSLPNAVGPPFT WMLALLGLSQALNILLGLKGLAPAEISAVCEKGNFNMAHGLAWSYYIGYLRLILPELQARIRTYNQHYNNLLRGAV SQRLYILLPLDCGVPDNLSMADPNIRFLDKLPQQTGDHAGIKDRVYSNSIYELLENGQRAGTCVLEYATPLQTLFAM SQYSQAGFSREDRLEQAKLFCRTLEDILADAPESQNNCRLIAYQEPADDSSFSLSQEVLRHLRQEEKEEVTVGSLKTS AVPSTSTMSQEPELLISGMEKPLPLRTDFS (KRAS(G12D)15mer_ct.STING(V155M)) |
| 61 | MKLVVVGAVGVGKSALATNFSLLKQAGDVEENPGPMPHSSLHPSIPCPRGHGAQKAALVLLSACLVTLWGLGEP PEHTLRYLVLHLASLQLGLLLNGVCSLAEELRHIHSRYRGSYWRTVRACLGCPLRRGALLLLSIYFYYSLPNAVGPPFT WMLALLGLSQALNILLGLKGLAPAEISAVCEKGNFNMAHGLAWSYYIGYLRLILPELQARIRTYNQHYNNLLRGAV SQRLYILLPLDCGVPDNLSMADPNIRFLDKLPQQTGDHAGIKDRVYSNSIYELLENGQRAGTCVLEYATPLQTLFAM SQYSQAGFSREDRLEQAKLFCRTLEDILADAPESQNNCRLIAYQEPADDSSFSLSQEVLRHLRQEEKEEVTVGSLKTS AVPSTSTMSQEPELLISGMEKPLPLRTDFS (KRAS(G12V)15mer_ct.STING(V155m) |
| 62 | MLVVVGAGDVGKSALTATNFSLLKQAGDVEENPGPMPHSSLHPSIPCPRGHGAQKAALVLLSACLVTLWGLGEP PEHTLRYLVLHLASLQLGLLLNGVCSLAEELRHIHSRYRGSYWRTVRACLGCPLRRGALLLLSIYFYYSLPNAVGPPFT WMLALLGLSQALNILLGLKGLAPAEISAVCEKGNFNMAHGLAWSYYIGYLRLILPELQARIRTYNQHYNNLLRGAV SQRLYILLPLDCGVPDNLSMADPNIRFLDKLPQQTGDHAGIKDRVYSNSIYELLENGQRAGTCVLEYATPLQTLFAM SQYSQAGFSREDRLEQAKLFCRTLEDILADAPESQNNCRLIAYQEPADDSSFSLSQEVLRHLRQEEKEEVTVGSLKTS AVPSTSTMSQEPELLISGMEKPLPLRTDFS (KRAS(G13D)15mer_ct.STING(V155M) |
| 63 | MTEYKLVVVGADGVGKSALTIQLIQATNFSLLKQAGDVEENPGPMPHSSLHPSIPCPRGHGAQKAALVLLSACLVT LWGLGEPPEHTLRYLVLHLASLQLGLLLNGVCSLAEELRHIHSRYRGSYWRTVRACLGCPLRRGALLLLSIYFYYSLPN AVGPPFTVVMLALLGLSQALNILLGLKGLAPAEISAVCEKGNFNMAHGLAWSYYIGYLRLILPELQARIRTYNQHYN NLLRGAVSQRLYILLPLDCGVPDNLSMADPNIRFLDKLPQQTGDHAGIKDRVYSNSIYELLENGQRAGTCVLEYATP LQTLFAMSQYSQAGFSREDRLEQAKLFCRTLEDILADAPESQNNCRLIAYQEPADDSSFSLSQEVLRHLRQEEKEEV TVGSLKTSAVPSTSTMSQEPELLISGMEKPLPLRTDFS (KRAS(G12D)25mer_ct.STING(V155M)) |
| 64 | MTEYKLVVVGAVGVGKSALTIQLIQATNFSLLKQAGDVEENPGPMPHSSLHPSIPCPRGHGAQKAALVLLSACLVT LWGLGEPPEHTLRYLVLHLASLQLGLLLNGVCSLAEELRHIHSRYRGSYWRTVRACLGCPLRRGALLLLSIYFYYSLPN AVGPPFTVVMLALLGLSQALNILLGLKGLAPAEISAVCEKGNFNMAHGLAWSYYIGYLRLILPELQARIRTYNQHYN NLLRGAVSQRLYILLPLDCGVPDNLSMADPNIRFLDKLPQQTGDHAGIKDRVYSNSIYELLENGQRAGTCVLEYATP LQTLFAMSQYSQAGFSREDRLEQAKLFCRTLEDILADAPESQNNCRLIAYQEPADDSSFSLSQEVLRHLRQEEKEEV TVGSLKTSAVPSTSTMSQEPELLISGMEKPLPLRTDFS (KRAS(G12V)25mer_ct.STING(V155M) |
| 65 | MTEYKLVVVGAGDVGKSALTIQLIQATNFSLLKQAGDVEENPGPMPHSSLHPSIPCPRGHGAQKAALVLLSACLVT LWGLGEPPEHTLRYLVLHLASLQLGLLLNGVCSLAEELRHIHSRYRGSYWRTVRACLGCPLRRGALLLLSIYFYYSLPN AVGPPFTVVMLALLGLSQALNILLGLKGLAPAEISAVCEKGNFNMAHGLAWSYYIGYLRLILPELQARIRTYNQHYN NLLRGAVSQRLYILLPLDCGVPDNLSMADPNIRFLDKLPQQTGDHAGIKDRVYSNSIYELLENGQRAGTCVLEYATP LQTLFAMSQYSQAGFSREDRLEQAKLFCRTLEDILADAPESQNNCRLIAYQEPADDSSFSLSQEVLRHLRQEEKEEV TVGSLKTSAVPSTSTMSQEPELLISGMEKPLPLRTDFS (KRAS(G13D)25mer_ct.STING(V155M) |
| 66 | MKLVVVGADGVGKSALKLVVVGADGVGKSALKLVVVGADGVGKSALATNFSLLKQAGDVEENPGPMPHSSLHPSIP CPRGHGAQKAALVLLSACLVTLWGLGEPPEHTLRYLVLHLASLQLGLLLNGVCSLAEELRHIHSRYRGSYWRTVRACLG CPLRRGALLLLSIYFYYSLPNAVGPPFTWMLALLGLSQALNILLGLKGLAPAEISAVCEKGNFNMAHGLAWSYYIGYLRL ILPELQARIRTYNQHYNNLLRGAVSQRLYILLPLDCGVPDNLSMADPNIRFLDKLPQQTGDHAGIKDRVYSNSIYELLEN GQRAGTCVLEYATPLQTLFAMSQYSQAGFSREDRLEQAKLFCRTLEDILADAPESQNNCRLIAYQEPADDSSFSLSQEV LRHLRQEEKEEVTVGSLKTSAVPSTSTMSQEPELLISGMEKPLPLRTDFS (KRAS(G12D)15mer^3_ct.STING(V155M)) |
| 67 | MKLVVVGAVGVGKSALKLVVVGAVGVGKSALKLVVVGAVGVGKSALATNFSLLKQAGDVEENPGPMPHSSLHPSIP CPRGHGAQKAALVLLSACLVTLWGLGEPPEHTLRYLVLHLASLQLGLLLNGVCSLAEELRHIHSRYRGSYWRTVRACLG CPLRRGALLLLSIYFYYSLPNAVGPPFTWMLALLGLSQALNILLGLKGLAPAEISAVCEKGNFNMAHGLAWSYYIGYLRL ILPELQARIRTYNQHYNNLLRGAVSQRLYILLPLDCGVPDNLSMADPNIRFLDKLPQQTGDHAGIKDRVYSNSIYELLEN GQRAGTCVLEYATPLQTLFAMSQYSQAGFSREDRLEQAKLFCRTLEDILADAPESQNNCRLIAYQEPADDSSFSLSQEV LRHLRQEEKEEVTVGSLKTSAVPSTSTMSQEPELLISGMEKPLPLRTDFS (KRAS(G12V)15mer^3_ct.STING(V155M) |

-continued

SEQUENCE LISTING SUMMARY

| SEQ ID NO: | SEQUENCE |
|---|---|
| 68 | MLVVVGAGDVGKSALTLVVVGAGDVGKSALTLVVVGAGDVGKSALTATNFSLLKQAGDVEENPGPMPHSSLHPSIP CPRGHGAQKAALVLLSACLVTLWGLGEPPEHTLRYLVLHLASLQLGLLLNGVCSLAEELRHIHSRYRGSYWRTVRACLG CPLRRGALLLLSIYFYYSLPNAVGPPFTWMLALLGLSQALNILLGLKGLAPAEISAVCEKGNFNMAHGLAWSYYIGYLRL ILPELQARIRTYNQHYNNLLRGAVSQRLYILLPLDCGVPDNLSMADPNIRFLDKLPQQTGDHAGIKDRVYSNSIYELLEN GQRAGTCVLEYATPLQTLFAMSQYSQAGFSREDRLEQAKLFCRTLEDILADAPESQNNCRLIAYQEPADDSSFSLSQEV LRHLRQEEKEEVTVGSLKTSAVPSTSTMSQEPELLISGMEKPLPLRTDFS (KRAS(G13D)15mer^3_ct.STING(V155M) |
| 69 | MTEYKLVVVGADGVGKSALTIQLIQMTEYKLVVVGADGVGKSALTIQLIQMTEYKLVVVGADGVGKSALTIQLIQATN FSLLKQAGDVEENPGPMPHSSLHPSIPCPRGHGAQKAALVLLSACLVTLWGLGEPPEHTLRYLVLHLASLQLGLLLNG VCSLAEELRHIHSRYRGSYWRTVRACLGCPLRRGALLLLSIYFYYSLPNAVGPPFTVVMLALLGLSQALNILLGLKGLAPA EISAVCEKGNFNMAHGLAWSYYIGYLRLILPELQARIRTYNQHYNNLLRGAVSQRLYILLPLDCGVPDNLSMADPNIRF LDKLPQQTGDHAGIKDRVYSNSIYELLENGQRAGTCVLEYATPLQTLFAMSQYSQAGFSREDRLEQAKLFCRTLEDILA DAPESQNNCRLIAYQEPADDSSFSLSQEVLRHLRQEEKEEVTVGSLKTSAVPSTSTMSQEPELLISGMEKPLPLRTDFS (KRAS(G12D)25mer^3_ct.STING(V155M)) |
| 70 | MTEYKLVVVGAVGVGKSALTIQLIQMTEYKLVVVGAVGVGKSALTIQLIQMTEYKLVVVGAVGVGKSALTIQLIQATN FSLLKQAGDVEENPGPMPHSSLHPSIPCPRGHGAQKAALVLLSACLVTLWGLGEPPEHTLRYLVLHLASLQLGLLLNG VCSLAEELRHIHSRYRGSYWRTVRACLGCPLRRGALLLLSIYFYYSLPNAVGPPFTVVMLALLGLSQALNILLGLKGLAPA EISAVCEKGNFNMAHGLAWSYYIGYLRLILPELQARIRTYNQHYNNLLRGAVSQRLYILLPLDCGVPDNLSMADPNIRF LDKLPQQTGDHAGIKDRVYSNSIYELLENGQRAGTCVLEYATPLQTLFAMSQYSQAGFSREDRLEQAKLFCRTLEDILA DAPESQNNCRLIAYQEPADDSSFSLSQEVLRHLRQEEKEEVTVGSLKTSAVPSTSTMSQEPELLISGMEKPLPLRTDFS (KRAS(G12V)25mer^3_ct.STING(V155M) |
| 71 | MTEYKLVVVGAGDVGKSALTIQLIQMTEYKLVVVGAGDVGKSALTIQLIQMTEYKLVVVGAGDVGKSALTIQLIQATN FSLLKQAGDVEENPGPMPHSSLHPSIPCPRGHGAQKAALVLLSACLVTLWGLGEPPEHTLRYLVLHLASLQLGLLLNG VCSLAEELRHIHSRYRGSYWRTVRACLGCPLRRGALLLLSIYFYYSLPNAVGPPFTVVMLALLGLSQALNILLGLKGLAPA EISAVCEKGNFNMAHGLAWSYYIGYLRLILPELQARIRTYNQHYNNLLRGAVSQRLYILLPLDCGVPDNLSMADPNIRF LDKLPQQTGDHAGIKDRVYSNSIYELLENGQRAGTCVLEYATPLQTLFAMSQYSQAGFSREDRLEQAKLFCRTLEDILA DAPESQNNCRLIAYQEPADDSSFSLSQEVLRHLRQEEKEEVTVGSLKTSAVPSTSTMSQEPELLISGMEKPLPLRTDFS (KRAS(G13D)25mer^3_ct.STING(V155M) |
| 72 | MTEYKLVVVGACGVGKSALTIQLIQ (KRAS(G12C)25mer) |
| 73 | MTEYKLVVVGACGVGKSALTIQLIQMTEYKLVVVGACGVGKSALTIQLIQMTEYKLVVVGACGVGKSALTIQLIQ (KRAS(G12C)25mer^3) |
| 74 | MTEYKLVVVGAGGVGKSALTIQLIQ (KRAS(WT)25mer) |
| 75 | MSAGDPRVGSGSLDSFMFSIPLVALNVGVRRRLSLFLNPRTPVAADWTLLAEEMGFEYLEIRELETRPDPTRSLLDAW QGRSGASVGRLLELLALLDREDILKELKSRIEEDCQKYLGKQQNQESEKPLQVARVESSVPQTKELGGITTLDDPLGQTP ELFDAFICYCPNDIEFVQEMIRQLEQTDYRLKLCVSDRDVLPGTCVWSIASELIEKRCRRMVVVVSDDYLQSKECDFQT KFALSISPGVQQKRPIPIKYKAMKKDFPSILRFITICDYTNPCTKSWFWTRLAKALSLP (human myd88(L265P); P4027 without epitope tag) |
| 76 | MAAGGPGAGSAAPVSSTSSLPLAALNMRVRRRLSLFLNVRTQVAADWTALAEEMDFEYLEIRQLETQADPTGRLLD AWQGRPGASVGRLLELLTKLGRDDVLLELGPSIEEDCQKYILKQQQEEAEKPLQVAAVDSSVPRTAELAGITTLDDPLG HMPERFDAFICYCPSDIQFVQEMIRQLEQTNYRLKLCVSDRDVLPGTCVWSIASELIEKRCRRMVVVVSDDYLQSKEC DFQTKFALSLSPGAHOKRPIPIKYKAMKKEFPSILRFITVCDYTNPCTKSWFWTRLAKALSLP (mouse myd88(L265P); P4028 without epitope tag) |
| 77 | MGVGKSKLDKCPLSWHKKDSVDADQDGHESDSKNSEEACLRGFVEQSSGSEPPTGEQDQPEAKGAGPEEQDEEEF LKFVILHAEDDTDEALRVQDLLQNDFGIRPGIVFAEMPCGRLHLQNLDDAVNGSAWTILLLTENFLRDTWCNFQFYTS LMNSVSRQHKYNSVIPMRPLNSPLPRERTPLALQTINALEEESQGFSTQVERIFRESVFERQQSIWKETRSVSQKQFIA (Mouse TRAM (TICAM2); P4033 without epitope tag) |
| 78 | MSLWGLVSKMPPEKVQRLYVDFPQHLRHLLGDWLESQPWEFLVGSDAFCCNLASALLSDTVQHLQASVGEQGEGS TILQHISTLESIYQRDPLKLVATFRQILQGEKKAVMEQFRHLPMPFHWKQEELKFKTGLRRLQHRVGEIHLLREALQKG AEAGQVSLHSLIETPANGTGPSEALAMLLQETTGELEAAKALVLKRIQIWKRQQQLAGNGAPFEESLAPLQERCESLV DIYSQLQQEVGAAGGELEPKTRASLTGRLDEVLRTLVTSCFLVEKQPPQVLKTQTKFQAGVRFLLGLRFLGAPAKPPLV RADMVTEKQARELSVPQGPGAGAESTGEIINNTVPLENSIPGNCCSALFKNLLLKKIKRCERKGTESVTEEKCAVLFSAS FTLGPGKLPIQLQALSLPLVVIVHGNQDNNAKATILWDNAFSEMDRVPFVVAERVPWEKMCETLNLKFMAEVGTNR GLLPEHFLFLAQKIFNDNSLSMEAFQHRSVSWSQFNKEILLGRGFTFWQWFDGVLDLTKRCLRSYWSDRLIIGFISKQY AASLLLNEPDGTFLLRFSDSEIGGITIAHVIRGQDGSPQIENIQPFSAKDLSIRSLGDRIRDLAQLKNLYPKKPKDEAFRSH YKPEQMGKDGRGYVPATIKMTVERDQPLPTPELQMPTMVPSYDLGMAPDSSMSMQLGPDMVPQVYPPHSHSIPP YQGLSPEESVNVLSAFQEPHLQMPPSLGQMSLPFDQPHPQGLLPCQPQEHAVSSPDPLLCSDVTMVEDSCLSQPVT AFPQGTWIGEDIFPPLLPPTEQDLTKLLLEGQGESGGGSLGAQPLLQPSHYGQSGISMSHMDLRANPSW (STAT6 V547A/T548A); P008 with no epitope tag) |
| 79 | MSLWGLVSKMPPEKVQRLYVDFPQHLRHLLGDWLESQPWEFLVGSDAFCCNLASALLSDTVQHLQASVGEQGEGS TILQHISTLESIYQRDPLKLVATFRQILQGEKKAVMEQFRHLPMPFHWKQEELKFKTGLRRLQHRVGEIHLLREALQKG |

-continued

SEQUENCE LISTING SUMMARY

SEQ ID NO: SEQUENCE

AEAGQVSLHSLIETPANGTGPSEALAMLLQETTGELEAAKALVLKRIQIWKRQQQLAGNGAPFEESLAPLQERCESLV
DIYSQLQQEVGAAGGELEPKTRASLTGRLDEVLRTLVTSCFLVEKQPPQVLKTQTKFQAGVRFLLGLRFLGAPAKPPLV
RADMVTEKQARELSVPQGPGAGAESTGEIINNTVPLENSIPGNCCSALFKNLLLKKIKRCERKGTESVTEEKCAVLFSAS
FTLGPGKLPIQLQALDLPLVVIVHGNQDNNAKATILWDNAFSEMDRVPFVVAERVPWEKMCETLNLKFMAEVGTN
RGLLPEHFLFLAQKIFNDNSLSMEAFQHRSVSWSQFNKEILLGRGFTFWQWFDGVLDLTKRCLRSYWSDRLIIGFISKQ
YVTSLLLNEPDGTFLLRFSDSEIGGITIAHVIRGQDGSPQIENIQPFSAKDLSIRSLGDRIRDLAQLKNLYPKKPKDEAFRS
HYKPEQMGKDGRGYVPATIKMTVERDQPLPTPELQMPTMVPSYDLGMAPDSSMSMQLGPDMVPQVYPPHSHSI
PPYQGLSPEESVNVLSAFQEPHLQMPPSLGQMSLPFDQPHPQGLLPCQPQEHAVSSPDPLLCSDVTMVEDSCLSQP
VTAFPQGTWIGEDIFPPLLPPTEQDLTKLLLEGQGESGGGSLGAQPLLQPSHYGQSGISMSHMDLRANPSW
(STAT6 (S407D); P009 with no epitope tag)

80 MSLWGLVSKMPPEKVQRLYVDFPQHLRHLLGDWLESQPWEFLVGSDAFCCNLASALLSDTVQHLQASVGEQGEGS
TILQHISTLESIYQRDPLKLVATFRQILQGEKKAVMEQFRHLPMPFHWKQEELKFKTGLRRLQHRVGEIHLLREALQKG
AEAGQVSLHSLIETPANGTGPSEALAMLLQETTGELEAAKALVLKRIQIWKRQQQLAGNGAPFEESLAPLQERCESLV
DIYSQLQQEVGAAGGELEPKTRASLTGRLDEVLRTLVTSCFLVEKQPPQVLKTQTKFQAGVRFLLGLRFLGAPAKPPLV
RADMVTEKQARELSVPQGPGAGAESTGEIINNTVPLENSIPGNCCSALFKNLLLKKIKRCERKGTESVTEEKCAVLFSAS
FTLGPGKLPIQLQALDLPLVVIVHGNQDNNAKATILWDNAFSEMDRVPFVVAERVPWEKMCETLNLKFMAEVGTN
RGLLPEHFLFLAQKIFNDNSLSMEAFQHRSVSWSQFNKEILLGRGFTFWQWFDGVLDLTKRCLRSYWSDRLIIGFISKQ
YAASLLLNEPDGTFLLRFSDSEIGGITIAHVIRGQDGSPQIENIQPFSAKDLSIRSLGDRIRDLAQLKNLYPKKPKDEAFRS
HYKPEQMGKDGRGYVPATIKMTVERDQPLPTPELQMPTMVPSYDLGMAPDSSMSMQLGPDMVPQVYPPHSHSI
PPYQGLSPEESVNVLSAFQEPHLQMPPSLGQMSLPFDQPHPQGLLPCQPQEHAVSSPDPLLCSDVTMVEDSCLSQP
VTAFPQGTWIGEDIFPPLLPPTEQDLTKLLLEGQGESGGGSLGAQPLLQPSHYGQSGISMSHMDLRANPSW
(STAT6 (S407D/V547A/T5484 P010 with no epitope tag)

81 MSLWGLVSKMPPEKVQRLYVDFPQHLRHLLGDWLESQPWEFLVGSDAFCCNLASALLSDTVQHLQASVGEQGEGS
TILQHISTLESIYQRDPLKLVATFRQILQGEKKAVMEQFRHLPMPFHWKQEELKFKTGLRRLQHRVGEIHLLREALQKG
AEAGQVSLHSLIETPANGTGPSEALAMLLQETTGELEAAKALVLKRIQIWKRQQQLAGNGAPFEESLAPLQERCESLV
DIYSQLQQEVGAAGGELEPKTRASLTGRLDEVLRTLVTSCFLVEKQPPQVLKTQTKFQAGVRFLLGLRFLGAPAKPPLV
RADMVTEKQARELSVPQGPGAGAESTGEIINNTVPLENSIPGNCCSALFKNLLLKKIKRCERKGTESVTEEKCAVLFSAS
FTLGPGKLPIQLQALSLPLVVIVHGNQDNNAKATILWDNAFSEMDRVPFVVAERVPWEKMCETLNLKFMAEVGTNR
GLLPEHFLFLAQKIFNDNSLSMEAFQHRSVSWSQFNKEILLGRGFTFWQWFDGVLDLTKRCLRSYWSDRLIIGFISKQY
AASLLLNEPDGTFLLRFSDSEIGGITIAHVIRGQDGSPQIENIQPFSAKDLSIRSLGDRIRDLAQLKNLYPKKPKDEAFRSH
YKPEQMGKDGRGFVPATIKMTVERDQPLPTPELQMPTMVPSYDLGMAPDSSMSMQLGPDMVPQVYPPHSHSIPP
YQGLSPEESVNVLSAFQEPHLQMPPSLGQMSLPFDQPHPQGLLPCQPQEHAVSSPDPLLCSDVTMVEDSCLSQPVT
AFPQGTWIGEDIFPPLLPPTEQDLTKLLLEGQGESGGGSLGAQPLLQPSHYGQSGISMSHMDLRANPSW
(STAT6 (V547A/T548A/Y641F); P011 with no epitope tag)

82 SAEVIHQVEEALDTDEKEMLLFLCRDVAIDVVPPNVRDLLDILRERGKLSVGDLAELLYRVRRFDLLKRILKMDRKAVET
HLLRNPHLVSDYRVLMAEIGEDLDKSDVSSLIFLMKDYMGRGKISKEKSFLDLVVELEKLNLVAPDQLDLLEKCLKNIHRI
DLKTKIQKYKQSVQGAGTSYRNVLQAAIQKSLKDPSNNFRLHNGRSKEQRLKEQLGAQQEPVKKSIQESEAFLPQSIPE
ERYKMKSKPLGICLIIDCIGNETELLRDTFTSLGYEVQKFLHLSMHGISQILGQFACMPEHRDYDSFVCVLVSRGGSQSV
YGVDQTHSGLPLHHIRRMFMGDSCPYLAGKPKMFFIQNYVVSEGQLEDSSLLEVDGPAMKNVEFKAQKRGLCTVHR
EADFFWSLCTADMSLLEQSHSSPSLYLQCLSQKLRQERKRPLLDLHIELNGYMYDWNSRVSAKEKYYVWLQHTLRKKL
ILSYT
(hu-cFLIP-L; P1006 without epitope tag)

83 SAEVIHQVEEALDTDEKEMLLFLCRDVAIDVVPPNVRDLLDILRERGKLSVGDLAELLYRVRRFDLLKRILKMDRKAVET
HLLRNPHLVSDYRVLMAEIGEDLDKSDVSSLIFLMKDYMGRGKISKEKSFLDLVVELEKLNLVAPDQLDLLEKCLKNIHRI
DLKTKIQKYKQSVQGAGTSYRNVLQAAIQKSLKDPSNNFRLHNGRSKEQRLKEQLGAQQEPVKKS
(hu-cFLIP-S(1-227); P1007 without epitope tag)

84 SAEVIHQVEEALDTDEKEMLLFLCRDVAIDVVPPNVRDLLDILRERGKLSVGDLAELLYRVRRFDLLKRILKMDRKAVET
HLLRNPHLVSDYRVLMAEIGEDLDKSDVSSLIFLMKDYMGRGKISKEKSFLDLVVELEKLNLVAPDQLDLLEKCLKNIHRI
DLKTKIQKYKQSVQGAGTSYRNVLQAAIQKSLKD
(hu-cFLIP-p22(1-198); P1008 without epitope tag)

85 SAEVIHQVEEALDTDEKEMLLFLCRDVAIDVVPPNVRDLLDILRERGKLSVGDLAELLYRVRRFDLLKRILKMDRKAVET
HLLRNPHLVSDYRVLMAEIGEDLDKSDVSSLIFLMKDYMGRGKISKEKSFLDLVVELEKLNLVAPDQLDLLEKCLKNIHRI
DLKTKIQKYKQSVQGAGTSYRNVLQAAIQKSLKDPSNNFRLHNGRSKEQRLKEQLGAQQEPVKKSIQESEAFLPQSIPE
ERYKMKSKPLGICLIIDCIGNETELLRDTFTSLGYEVQKFLHLSMHGISQILGQFACMPEHRDYDSFVCVLVSRGGSQSV
YGVDQTHSGLPLHHIRRMFMGDSCPYLAGKPKMFFIQNYVVSEGQLEDSSLLEVD
(hu-cFLIP-p43(1-376); P1009 without epitope tag)

86 GPAMKNVEFKAQKRGLCTVHREADFFWSLCTADMSLLEQSHSSPSLYLQCLSQKLRQERKRPLLDLHIELNGYMYD
WNSRVSAKEKYYVWLQHTLRKKLILSYT
(hu-cFLIP-p12(377-480); P1010 without epitope tag)

87 MSWSPSLTTQTCGAWEMKERLGTGGFGNVIRWHNQETGEQIAIKQCRQELSPRNRERWCLEIQIMRRLTH
PNVVAARDVPEGMQNLAPNDLPLLAMEYCQGGDLRKYLNQFENCCGLREGAILTLLSDIASALRYLHEN
RIIHRDLKPENIVLQQGEQRLIHKIIDLGYAKELDQGELCTEFVGTLQYLAPELLEQQKYTVTVDYWSFGTLAF
ECITGFRPFLPNWQPVQWHSKVRQKSEVDIVVSEDLNGTVKFSSSLPYPNNLNSVLAERLEKWLQLMLM
WHPRQRGTDPTYGPNGCFKALDDILNLKLVHILNMVTGTIHTYPVTEDESLQSLKARIQQDTGIPEEDQELL
QEAGLALIPDKPATQCISDGKLNEGHTLDMDLVFLFDNSKITYETQISPRPQPESVSCILQEPKRNLAFFQLRK

-continued

SEQUENCE LISTING SUMMARY

| SEQ ID NO: | SEQUENCE |
|---|---|
| | VWGQVWHSIQTLKEDCNRLQQGQRAAMMNLLRNNSCLSKMKNSMASMSQQLKAKLDFFKTSIQIDLEK<br>YSEQTEFGITSDKLLLAWREMEQAVELCGRENEVKLLVERMMALQTDIVDLQRSPMGRKQGGTLDDLEEQ<br>ARELYRRLREKPRDQRTEGDSQEMVRLLLQAIQSFEKKVRVIYTQLSKTVVCKQKALELLPKVEEVVSLMN<br>EDEKTVVRLQEKRQKELWNLLKIACSKVRGPVSGSPDSMNASRLSQPGQLMSQPSTASNSLPEPAKKSEEL<br>VAEAHNLCTLLENAIQDTVREQDQSFTALDWSWLQTEEEEHSCLEQAS<br>(huIKK2ca(S177E/S181E); P4005 without epitope tag) |
| 88 | MSWSPSLTTQTCGAWEMKERLGTGGFGNVIRWHNQETGEQIAIKQCRQELSPRNRERWCLEIQIMRRLTH<br>PNVVAARDVPEGMQNLAPNDLPLLAMEYCQGGDLRKYLNQFENCCGLREGAILTLLSDIASALRYLHEN<br>RIIHRDLKPENIVLQQGEQRLIHKIIDLGYAKELDQGALCTAFVGTLQYLAPELLEQQKYTVTVDYWSFGTLAF<br>ECITGFRPFLPNWQPVQWHSKVRQKSEVDIVVSEDLNGTVKFSSSLPYPNNLNSVLAERLEKWLQLMLM<br>WHPRQRGTDPTYGPNGCFKALDDILNLKLVHILNMVTGTIHTYPVTEDESLQSLKARIQQDTGIPEEDQELL<br>QEAGLALIPDKPATQCISDGKLNEGHTLDMDLVFLFDNSKITYETQISPRPQPESVSCILQEPKRNLAFFQLRK<br>VWGQVWHSIQTLKEDCNRLQQGQRAAMMNLLRNNSCLSKMKNSMASMSQQLKAKLDFFKTSIQIDLEK<br>YSEQTEFGITSDKLLLAWREMEQAVELCGRENEVKLLVERMMALQTDIVDLQRSPMGRKQGGTLDDLEEQ<br>ARELYRRLREKPRDQRTEGDSQEMVRLLLQAIQSFEKKVRVIYTQLSKTVVCKQKALELLPKVEEVVSLMN<br>EDEKTVVRLQEKRQKELWNLLKIACSKVRGPVSGSPDSMNASRLSQPGQLMSQPSTASNSLPEPAKKSEEL<br>VAEAHNLCTLLENAIQDTVREQDQSFTALDWSWLQTEEEEHSCLEQAS<br>(huIKK2null(S177A/S181A); P4006 without epitope tag) |
| 89 | MSWSPSLPTQTCGAWEMKERLGTGGFGNVIRWHNQATGEQIAIKQCRQELSPKNRNRWCLEIQIMRRLNHPN<br>VVAARDVPEGMQNLAPNDLPLLAMEYCQGGDLRRYLNQFENCCGLREGAVLTLLSDIASALRYLHENRIIHRDLK<br>PENIVLQQGEKRLIHKIIDLGYAKELDQGELCTEFVGTLQYLAPELLEQQKYTVTVDYWSFGTLAFECITGFRPFLPN<br>WQPVQWHSKVRQKSEVDIVVSEDLNGAVKFSSSLPFPNNLNSVLAERLEKWLQLMLMWHPRQRGTDPQYGP<br>NGCFRALDDILNLKLVHVLNMVTGTVHTYPVTEDESLQSLKTRIQENTGILETDQELLQKAGLVLLPDKPATQCISD<br>SKTNEGLTLDMDLVFLLDNSKINYETQITPRPPPESVSCILQEPKRNLSFFQLRKVWGQVWHSIQTLKEDCNRLQQ<br>GQRAAMMSLLRNNSCLSKMKNAMASTAQQLKAKLDFFKTSIQIDLEKYKEQTEFGITSDKLLLAWREMEQAVEQ<br>CGRENDVKHLVERMMALQTDIVDLQRSPMGRKQGGTLDDLEEQARELYRKLREKPRDQRTEGDSQEMVRLLLQ<br>AIQSFEKKVRVIYTQLSKTVVCKQKALELLPKVEEVVSLMNEDERTVVRLQEKRQKELWNLLKIACSKVRGPVSGSP<br>DSMNVSRLSHPGQLMSQPSSACDSLPESDKKSEELVAEAHALCSRLESALQDTVKEQDRSFTTLDWSWLQMEDEE<br>RCSLEQACD<br>(muIKK2ca(S177E/S181E); P4002 without epitope tag) |
| 90 | MSWSPSLPTQTCGAWEMKERLGTGGFGNVIRWHNQATGEQIAIKQCRQELSPKNRNRWCLEIQIMRRLNHPN<br>VVAARDVPEGMQNLAPNDLPLLAMEYCQGGDLRRYLNQFENCCGLREGAVLTLLSDIASALRYLHENRIIHRDLK<br>PENIVLQQGEKRLIHKIIDLGYAKELDQGALCTAFVGTLQYLAPELLEQQKYTVTVDYWSFGTLAFECITGFRPFLPN<br>WQPVQWHSKVRQKSEVDIVVSEDLNGAVKFSSSLPFPNNLNSVLAERLEKWLQLMLMWHPRQRGTDPQYGP<br>NGCFRALDDILNLKLVHVLNMVTGTVHTYPVTEDESLQSLKTRIQENTGILETDQELLQKAGLVLLPDKPATQCISD<br>SKTNEGLTLDMDLVFLLDNSKINYETQITPRPPPESVSCILQEPKRNLSFFQLRKVWGQVWHSIQTLKEDCNRLQQ<br>GQRAAMMSLLRNNSCLSKMKNAMASTAQQLKAKLDFFKTSIQIDLEKYKEQTEFGITSDKLLLAWREMEQAVEQ<br>CGRENDVKHLVERMMALQTDIVDLQRSPMGRKQGGTLDDLEEQARELYRKLREKPRDQRTEGDSQEMVRLLLQ<br>AIQSFEKKVRVIYTQLSKTVVCKQKALELLPKVEEVVSLMNEDERTVVRLQEKRQKELWNLLKIACSKVRGPVSGSP<br>DSMNVSRLSHPGQLMSQPSSACDSLPESDKKSEELVAEAHALCSRLESALQDTVKEQDRSFTTLDWSWLQMEDEE<br>RCSLEQACD<br>muIKK2null(S177A/S181A); P4003 without epitope tag) |
| 91 | MERPPGLRPGAGGPWEMRERLGTGGFGNVCLYQHRELDLKIAIKSCRLELSTKNRERWCHEIQIMKKLNHANVVKA<br>CDVPEELNILIHDVPLLAMEYCSGGDLRKLLNKPENCCGLKESQILSLLSDIGSGIRYLHENKIIHRDLKPENIVLQDVGGK<br>IIHKIIDLGYAKDVDQGELCTEFVGTLQYLAPELFENKPYTATVDYWSFGTMVFECIAGYRPFLHHLQPFTWHEKIKKKD<br>PKCIFACEEMSGEVRFSSHLPQPNSLCSLVVEPMENWLQLMLNWDPQQRGGPVDLTLKQPRCFVLMDHILNLKIVH<br>ILNMTSAKIISFLLPPDESLHSLQSRIERETGINTGSQELLSETGISLDPRKPASQCVLDGVRGCDSYMVYLFDKSKTVYEG<br>PFASRSLSDCVNYIVQDSKIQLPIIQLRKVWAEAVHYVSGLKEDYSRLFQGQRAAMLSLLRYNANLTKMKNTLISASQQ<br>LKAKLEFFHKSIQLDLERYSEQMTYGISSEKMLKAWKEMEEKAIHYAEVGVIGYLEDQIMSLHAEIMELQKSPYRRQG<br>DLMESLEQRAIDLYKQLKHRPSDHSYSDSTEMVKIIVHTVQSQDRVLKELPGHLSKLLGCKQKIIDLLPKVEVALSNIKEA<br>DNTVMFMQGKRQKEIWHLLKIACTQAAARALVGAALEGAVAPQAAAWLPPAAAEHDHALACVVAPQDGEAAAQ<br>MIEENLNCLGHLAAIIHEANEEQGNSMMNLDWSWLTE<br>Human consitutively activ IKK alpha (PEST mutation) P.4013 without epitope tag |
| 92 | MERPPGLRPGAGGPWEMRERLGTGGFGNVCLYQHRELDLKIAIKSCRLELSTKNRERWCHEIQIMKKLNHANVVKA<br>CDVPEELNILIHDVPLLAMEYCSGGDLRKLLNKPENCCGLKESQILSLLSDIGSGIRYLHENKIIHRDLKPENIVLQDVGGK<br>IIHKIIDLGYAKDVDQGELCTEFVGTLQYLAPELFENKPYTATVDYWSFGTMVFECIAGYRPFLHHLQPFTWHEKIKKKD<br>PKCIFACEEMSGEVRFSSHLPQPNSLCSLVVEPMENWLQLMLNWDPQQRGGPVDLTLKQPRCFVLMDHILNLKIVH<br>ILNMTSAKIISFLLPPDESLHSLQSRIERETGINTGSQELLSETGISLDPRKPASQCVLDGVRGCDSYMVYLFDKSKTVYEG<br>PFASRSLSDCVNYIVQDSKIQLPIIQLRKVWAEAVHYVSGLKEDYSRLFQGQRAAMLSLLRYNANLTKMKNTLISASQQ<br>LKAKLEFFHKSIQLDLERYSEQMTYGISSEKMLKAWKEMEEKAIHYAEVGVIGYLEDQIMSLHAEIMELQKSPYRRQG<br>DLMESLEQRAIDLYKQLKHRPSDHSYSDTEMVKIIVHTVQSQDRVLKELFGHLSKLLGCKQKIIDLLPKVEVALSNIKEA<br>DNTVMFMQGKRQKEIWHLLKIACTQAAARALVGAALEGAVAPQAAAWLPPAAAEHDHALACVVAPQDGEAAAQ<br>MIEENLNCLGHLAAIIHEANEEQGNSMMNLDWSWLTE<br>Human consitutively activ IKK alpha (PEST mutation) P.4014 without epitope tag |
| 93 | MSWSPSLTTQTCGWEMKERLGTGFGNVIRWHNQETGEQIAIKQCRQELSPRNRERWCLEIQIMRRLTHPNVVA<br>ARDVPEGMQNLAPNDLPLLAMEYCQGGDLRKYLNQFENCCGLREGAILTLLSDIASALRYLHENRIIHRDLKPENIVLQ<br>QGEQRLIHKIIDLGYAKELDQGELCTEFVGTLQYLAPELLEQQKYTVTVDYWSFGTLAFECITGFRPFLPNWQPVQWH |

-continued

SEQUENCE LISTING SUMMARY

| SEQ ID NO: | SEQUENCE |
|---|---|
| | SKVRQKSEVDIVVSEDLNGTVKFSSSLPYPNNLNSVLAERLEKWLQLMLMWHPRQRGTDPTYGPNGCFKALDDILNL<br>KLVHILNMVTGTIHTVPVTEDESLQSLKARIQQDTGIPEEDQELLQEAGLALIPDKPATQCISDGLKNEGHTLDMDLVFL<br>FDNSKITYETQISPRPQPESVSCILQEPKRNLAFFQLRKVWGQVWHSIQTLKEDCNRLQQGQRAAMMNLLRNNSCLS<br>KMKNSMASMSQQLKAKLDFFKTSIQIDLEKYSEQTEFGITSDKLLLAWREMEQAVELCGRENEVKLLVERMMALQT<br>KIVDLQRSPMGRKQGGTLDDLEEQARELYRRLREKPRDQRTEGDSQEMVRLLLQAIQSFEKKVRVIYTQLSKTVVCKQ<br>KALELLPKVEEVVSLMNEDEKTVVRLQEKRQKELWNLLKIACSKVRGPVAGAPDAMNAARLAQPGQLMAQPATAA<br>NALPEPAKKAEELVAEAHNLCTLLENAIQDTVREQDQSFTALDWSWLQTEEEEHSCLEQAA<br>Human consitutively activ IKK alpha (PEST mutation) P.4015 without epitope tag |
| 94 | MSWSPSLTTQTCGAWEMKERLGTGGFGNVIRWHNQETGEQIAIKQCRQELSPRNRERWCLEIQIMRRLTHPNVVA<br>ARDVPEGMQNLAPNDLPLLAMEYCQGGDLRKYLNQFENCCGLREGAILTLLSDIASALRYLHENRIIHRDLKPENIVLQ<br>QGEQRLIHKIIDLGYAKELDQGELCTEFVGTLQYLAPELLEQQKYTVTVDYWSFGTLAFECITGFRPFLPNWQPVQWH<br>SKVRQKSEVDIVVSEDLNGTVKFSSSLPYPNNLNSVLAERLEKWLQLMLMWHPRQRGTDPTYGPNGCFKALDDILNL<br>KLVHILNMVTGTIHTYPVTEDESLQSLKARIQQDTGIPEEDQELLQEAGLALIPDKPATQCISDGLKNEGHTLDMDLVFL<br>FDNSKITYETQISPRPQPESVSCILQEPKRNLAFFQLRKVWGQVWHSIQTLKEDCNRLQQGQRAAMMNLLRNNSCLS<br>KMKNSMASMSQQLKAKLDFFKTSIQIDLEKYSEQTEFGITSDKLLLAWREMEQAVELCGRENEVKLLVERMMALQT<br>DIVDLQRSPMGRKQGGTLDDLEEQARELYRRLREKPRDQRTEGDSQEMVRLLLQAIQSFEKKVRVIYTQLSKTVVCKQ<br>KALELLPKVEEWSLMNEDEKTVVRLQEKRQKELWNLLKIACSKVRGPVAGAPDAMNAARLAQPGQLMAQPATAA<br>NALPEPAKKAEELVAEAHNLCTLLENAIQDTVREQDQSFTALDWSWLQTEEEEHSCLEQAS<br>Human consitutively activ IKK alpha (PEST mutation) P.4016 without epitope tag |
| 95 | MERPPGLRPGAGGPWEMRERLGTGGFGNVCLYQHRELDLKIAIKSCRLELSTKNRERWCHEIQIMKKLNHANVVKA<br>CDVPEELNILIHDVPLLAMEYCSGGDLRKLLNKPENCCGLKESQILSLLSDIGSGIRYLHENKIIHRDLKPENIVLQDVGGK<br>IIHKIIDLGYAKDVDQGELCTEFVGTLQYLAPELFENKPYTATVDYWSFGTMVFECIAGYRPFLHHLQPFTWHEKIKKD<br>PKCIFACEEMSGEVRFSSHLPQPNSLCSLVVEPMENWLQLMLNWDPQQRGGPVDLTLKQPRCFVLMDHILNLKIVH<br>ILNMTSAKIISFLLPPDESLHSLQSRIERETGINTGSQELLSETGISLDPRKPASQCVLDGVRGCDSYMVYLFDKSKTVYEG<br>PFASRSLSDCVNYIVQDSKIQLPIIQLRKVWAEAVHYVSGLKEDYSRLFQGQRAAMLSLLRYNANLTKMKNTLISASQQ<br>LKAKLEFFHKSIQLDLERYSEQMTYGISSEKMLKAWKEMEEKAIHYAEVGVIGYLEDQIMSLHAEIMELQKSPYRRQG<br>DLMESLEQRAIDLYKQLKHRPSDHSYSDTEMVKIIVHTVQSQDRVLKELFGHLSKLLGCKQKIIDLLPKVEVALSNIKEA<br>DNTVMFMQGKRQKEIWHLLKIACTQAAARALVGAALEGAVAPQAAAWLPPAAAEHDHALACVVAPQDGEAAAQ<br>MIEENLNCLGHLAAIIHEANEEQGNSMMNLDWSWLAE<br>Human consitutively activ IKK alpha (PEST mutation) P.4017 without epitope tag |
| 96 | MERPPGLRPGAGGPWEMRERLGTGGFGNVSLYQHRELDLKIAIKSCRLELSSKNRERWCHEIQIMKKLDHANVVKA<br>CDVPEELNFLINDVPLLAMEYCSGGDLRKLLNKPENCCGLKESQILSLLSDIGSGIRYLHENKIIHRDLKPENIVLQDVGG<br>KTIHKIIDLGYAKDVDQGELCTEFVGTLQYLAPELFENKPYTATVDYWSFGTMVFECIAGYRPFLHHLQPFTWHEKIKK<br>KDPKCIFACEEMTGEVRFSSHLPQPNSLCSLIVEPMESWLQLMLNWDPQQRGGPIDLILKQPRCFALMDHILNLKIV<br>HILNMTTSAKIISFLLPCDESLHSLQSRIERETGINTGSQELLSETGISLDPRKPASQCVLDGVRGCDSYMVYLFDKSKTVYE<br>GPFASRSLSDCVNYIVQDSKIQLPIIQLRKVWAEAVHYVSGLKEDYSRLFQGQRAAMLSLLRYNANLTKMKNTLISASQ<br>QLKAKLEFFRKSIQLDLERYSEQMTYGISSEKMLIKAWKEMEEKAIHYSEVGVIGYLEDQIMSLHTEIMELQKSPYGRRQ<br>GDLMESLEQRAIDLYKQLKHRPPDHLYSDSTEMVKIIVHTVQSQDRVLKELFGHLSKLLGCKQKIIDLLPKVEVALSNIKE<br>ADNWMFIVIQGKRQKEIWFILLKIACTQAAARALVGAALEGAVAPPVAAWLPPALADREHPLTCVVAPQDGEALAQ<br>MIEENLNCLGHLAAIIREANEDQSSSLMSLDWSWLAE<br>Mouse constitutively active IKK alpha (PEST mutation) P.4018 without epitope tag |
| 97 | MSWSPSIPTQTCGAWEIVIKERLGTGGFGNVIRWHNQATGEQIAIKQCRQELSPKNRNRWCLEIQIMRRLNHPNW<br>AARDVPEGMQNLAPNDLPLLAMEYCQGGDLRRYLNQFENCCGLREGAVLTLLSDIASALRYLHENRIIHRDLKPENIV<br>LQQGEKRLIHKIIDLGYAKELDQGELCTEFVGTLQYLAPELLEQQKYTVTVDYWSFGTLAFECITGFRPFLPNWQPVQ<br>WHSKVRQKSEVDIVVSEDLNGAVKFSSSLPFPNNLNSVLAERLEKWLQLMLMWHPRQRGTDPQYGPNGCFRALDD<br>ILNLKLVHVLNMVTGTVHTYPVTEDESLQSLKTRIQENTGILETDQELLQKAGLVLLPDKPATQOSDSKTNEGLTLDM<br>DLVFLLDNSKINYETQITPRPPPESVSCILQEPKRNLSFFQLRKVWGQVWHSIQTLKEDCNRLQQGQRAAMMSLLRN<br>NSCLSKMKNAMASTAQQLKAKLDFFKTSIQIDLEKYKEQTEFGITSDKLLLAWREMEQAVEQCGRENDVKHLVERM<br>MALQTDIVDLQRSPMGRKQGGILDDLEEQARELYRKLREKPRDQRTEGDSQEMVRIILQAIQSFEKKVRVIYTQLSK<br>TWOKQKALELLPKVEEVVSLMNEDERTVVRLQEKRQKELWNLLKIACSKVRGPVAGAPDAMNVARIAHPGQLMA<br>QPASACDALPESDKKAEELVAEAHALCSRLESALQDTVKEQDRSFTTLDWSWLQMEDEERCSLEQACD<br>Mouse constitutively active IKK beta (PEST mutation) P.4019 without epitope tag |
| 98 | MSWSPSLPTQTCGAWEMKERLGTGGFGNVIRWHNQATGEQIAIKQCRQELSPKNRNRWCLEIQIMRRLNHPNVV<br>AARDVPEGMQNLAPNDLPLLAMEYCQGGDLRRYLNQFENCCGLREGAVLILLSDIASALRYLHENRIIHRDLKPENIV<br>LQQGEKRLIHKIIDLGYAKELDQGELCTEFVGTLQYLAPELLEQQKYTVTVDYWSFGILAFECITGFRPFLPNWQPVQ<br>WHSKVRQKSEVDIVVSEDLNGAVKFSSSLPFPNNLNSVLAERLEKWLQLMLMWHPRQRGTDPQYGPNGCFRALDD<br>ILNLKLVHVLNMVTGTVHTYPVIEDESLQSLKTRIQENTGILETDQELLQKAGLVLLPDKPATQCSDSKTNEGLTLDM<br>DLVFLLDNSKINYETQITPRPPPESVSCILQEPKRNLSFFQLRKVWGQVWHSIQTLKEDCNRLQQGQRAAMMSLLRN<br>NSCLSKMKNAMASTAQQLKAKIDFFKTSIQIDLEKYKEQTEFGITSDKLLLAWREMEQAVEQCGRENDVICHLVERM<br>MALQTDIVDLQRSPMGRKQGGTLDDLEEQARELYRKLREKPRDQRTEGDSQEMVRLLLQAIQSFEKKVRVIYTQLSK<br>TVVCKQKALELLPKVEEVVSLMNEDERTVVRLQEKRQKELWNLLKIACSKVRGPVAGAPDAMNVARLAHPGQLMA<br>QPASACDALPESDIKKAEELVAEAHALCSRLESALQDTVIKEQDRSFTTLDWSWLQMEDEERCSLEQACD<br>Mouse constitutively active IKK beta (PEST mutation) P.4020 without epitope tag |
| 99 | MQPDMSLNVIKMKSSDFLESAELDSGGFGKVSLCFHRTQGLMIMKTVYKGPNCIEHNEALLEEAKMMNRLRHSRVV<br>KLLGVIIEEGKYSLVMEYMEKGNLMHVLKAEMSTPLSVKGRIILEIIEGMCYLHGKGVIHKDLKPENILVDNDFHIKIADL<br>GLASFKMWSKLNNEEHNELREVDGTAKKNGGTLYYMAPEHLNDVNAKPTEKSDVYSFAVVLWAIFANKEPYENAIC<br>EQQLIMCIKSGNRPDVDDITEYCPREIISLMKLCWEANPEARPTFPGIEEKFRPFYLSQLEESVEEDVKSLKKEYSNENAV |

-continued

SEQUENCE LISTING SUMMARY

| SEQ ID NO: | SEQUENCE |
|---|---|
| | VKRMQSLQLDCVAVPSSRSNSATEQPGSLHSSQGLGMGPVEESWFAPSLEHPQEENEPSLQSKLQDEANYHLYGSR<br>MDRQTKQQPRQNVAYNREEERRRRVSHDPFAQQRPYENFQNTEGKGTAYSSAASHGNAVHQPSGLTSQPQVLYQ<br>NNGLYSSHGFGTRPLDPGTAGPRVWYRPIPSHMPSLHNIPVPETNYLGNTPTMPFSSLPPTDESIKYTIYNSTGIQIGA<br>YNYMEIGGTSSSGGIKKEIEAIKKEQEAIKKKIEAIEKEIEA<br>(huRIPK1(1-555),IZ.TM; TH1021 without epitope tag) |
| 100 | MQPDMSLNVIKMKSSDFLESAELDSGGFGKVSLCFHRTQGLMIMKTVYKGPNCIEHNEALLEEAKMMNRLRHSRVV<br>KLLGVIIEEGKYSLVMEYMEKGNLMHVLKAEMSTPLSVKGRIILEIIEGMCYLHGKGVIHKDLKPENILVDNDFHIKIADL<br>GLASFKMWSKLNNEEHNELREVDGTAKKNGGTLYYMAPEHLNDVNAKPTEKSDVYSFAVVLWAIFANKEPYENAIC<br>EQQLIMCIKSGNRPDVDDITEYCPREIISLMKLCWEANPEARPTFPGIEEKFRPFYLSQLEESVEEDVKSLKKEYSNENAV<br>VKRMQSLQLDCVAVPSSRSNSATEQPGSLHSSQGLGMGPVEESWFAPSLEHPQEENEPSLQSKLQDEANYHLYGSR<br>MDRQTKQQPRQNVAYNREEERRRRVSHDPFAQQRPYENFQNTEGKGTAYSSAASHGNAVHQPSGLTSQPQVLYQ<br>NNGLYSSHGFGTRPLDPGTAGPRVWYRPIPSHMPSLHNIPVPETNYLGNTPTMPFSSLPPTDESIKYTIYNSTGIQIGA<br>YNYMEIGGTSSSGSDGSGSGSGSITIRAAFLEKENTALRTEIAELEKEVGRCENIVSKYETRYGPL<br>(huRIPK1(1-555).EE.DM; TH1022 without epitope tag) |
| 101 | MQPDMSLNVIKMKSSDFLESAELDSGGFGKVSLCFHRTQGLMIMKTVYKGPNCIEHNEALLEEAKMMNRLRHSRVV<br>KLLGVIIEEGKYSLVMEYMEKGNLMHVLKAEMSTPLSVKGRIILEIIEGMCYLHGKGVIHKDLKPENILVDNDFHIKIADL<br>GLASFKMWSKLNNEEHNELREVDGTAKKNGGTLYYMAPEHLNDVNAKPTEKSDVYSFAVVLWAIFANKEPYENAIC<br>EQQLIMCIKSGNRPDVDDITEYCPREIISLMKLCWEANPEARPTFPGIEEKFRPFYLSQLEESVEEDVKSLKKEYSNENAV<br>VKRMQSLQLDCVAVPSSRSNSATEQPGSLHSSQGLGMGPVEESWFAPSLEHPQEENEPSLQSKLQDEANYHLYGSR<br>MDRQTKQQPRQNVAYNREEERRRRVSHDPFAQQRPYENFQNTEGKGTAYSSAASHGNAVHQPSGLTSQPQVLYQ<br>NNGLYSSHGFGTRPLDPGTAGPRVWYRPIPSHMPSLHNIPVPETNYLGNTPTMPFSSLPPTDESIKYTIYNSTGIQIGA<br>YNYMEIGGTSSSGSDGSGSGSGSLEIRAAFLEKENTALRTRAAELRKRVGRCRNIVSKYETRYGPL<br>(huRIPK1(1-555).RR.DM; TH1023 without epitope tag) |
| 102 | MQPDMSLDNIKMASSDLLEKTDLDSGGFGKVSLCYHRSHGFVILKKVYTGPNRAEYNEVLLEEGKMMHRLRHSRVV<br>KLLGIIIEEGNYSLVMEYMEKGNLMHVLKTQIDVPLSLKGRIIVEAIEGMCYLHDKGVIHKDLKPENILVDRDFHIKIADL<br>GVASFKTWSKLTKEKDNKQKEVSSTTKKNNGGTLYYMAPEHLNDINAKPTEKSDVYSFGIVLWAIFAKKEPYENVICTE<br>QFVICIKSGNRPNVEEILEYCPREIISLMERCWQAIPEDRPTFLGIEEEFRPFYLSHFEEYVEEDVASLKKEYPDQSPVLQR<br>MFSLQHDCVPLPPSRSNSEQPGSLHSSQGLQMGPVEESWFSSSPEYPQDENDRSVQAKLQEEASYHAFGIFAEKQTK<br>PQPRQNEAYNREEERKRRVSHDPFAQQRARENIKSAGARGHSDPSTTSRGIAVQQLSWPATQTVWNNGLYNQHG<br>FGTTGTGVWYPPNLSQMYSTYKTPVPETNIPGSTPTMPYFSGPVADDLIKYTIFNSSGIQIGNHNYMDVGLNSQPPN<br>NTCKEESTSGGIKKEIEAIKKEQEAIKKKIEAIEKEIEA<br>(msRIPK1(1-555),IZ.TM; TH1024 without epitope tag) |
| 103 | MQPDMSLDNIKMASSDLLEKTDLDSGGFGKVSLCYHRSHGFVILKKVYTGPNRAEYNEVLLEEGKMMHRLRHSRVV<br>KLLGIIIEEGNYSLVMEYMEKGNLMHVLKTQIDVPLSLKGRIIVEAIEGMCYLHDKGVIHKDLKPENILVDRDFHIKIADL<br>GVASFKTWSKLTKEKDNKQKEVSSTTKKNNGGTLYYMAPEHLNDINAKPTEKSDVYSFGIVLWAIFAKKEPYENVICTE<br>QFVICIKSGNRPNVEEILEYCPREIISLMERCWQAIPEDRPTFLGIEEEFRPFYLSHFEEYVEEDVASLKKEYPDQSPVLQR<br>MFSLQHDCVPLPPSRSNSEQPGSLHSSQGLQMGPVEESWFSSSPEYPQDENDRSVQAKLQEEASYHAFGIFAEKQTK<br>PQPRQNEAYNREEERKRRVSHDPFAQQRARENIKSAGARGHSDPSTTSRGIAVQQLSWPATQTVWNNGLYNQHG<br>FGTTGTGVWYPPNLSQMYSTYKTPVPETNIPGSTPTMPYFSGPVADDLIKYTIFNSSGIQIGNHNYMDVGLNSQPPN<br>NTCKEESTSGSDGSGSGSGSITIRAAFLEKENTALRTEIAELEKEVGRCENIVSKYETRYGPL<br>(msRIPK1(1-555).EE.DM; TH1025 without epitope tag) |
| 104 | MQPDMSLDNIKMASSDLLEKTDLDSGGFGKVSLCYHRSHGFVILKKVYTGPNRAEYNEVLLEEGKMMHRLRHSRVV<br>KLLGIIIEEGNYSLVMEYMEKGNLMHVLKTQIDVPLSLKGRIIVEAIEGMCYLHDKGVIHKDLKPENILVDRDFHIKIADL<br>GVASFKTWSKLTKEKDNKQKEVSSTTKKNNGGTLYYMAPEHLNDINAKPTEKSDVYSFGIVLWAIFAKKEPYENVICTE<br>QFVICIKSGNRPNVEEILEYCPREIISLMERCWQAIPEDRPTFLGIEEEFRPFYLSHFEEYVEEDVASLKKEYPDQSPVLQR<br>MFSLQHDCVPLPPSRSNSEQPGSLHSSQGLQMGPVEESWFSSSPEYPQDENDRSVQAKLQEEASYHAFGIFAEKQTK<br>PQPRQNEAYNREEERKRRVSHDPFAQQRARENIKSAGARGHSDPSTTSRGIAVQQLSWPATQTVWNNGLYNQHG<br>FGTTGTGVWYPPNLSQMYSTYKTPVPETNIPGSTPTMPYFSGPVADDLIKYTIFNSSGIQIGNHNYMDVGLNSQPPN<br>NTCKEESTSGSDGSGSGSGSLEIRAAFLEKENTALRTRAAELRKRVGRCRNIVSKYETRYGPL<br>(msRIPK1(1-555).RR.DM; TH1026 without epitope tag) |
| 105 | MSTASAASSSSSSSAGEMIEAPSQVLNFEEIDYKEIEVEEWGRGAFGVVCKAKWRAKDVAIKQIESESERKAFIVELRQ<br>LSRVNHPNIVKLYGACLNPVCLVMEYAEGGSLYNVLHGAEPLPYYTAAHAMSWCLQCSQGVAYLFISMQPKALIHRD<br>LKPPNLLLVAGGTVLKICDFGTACDIQTHMTNNKGSAAWMAPEVFEGSNYSEKCDVFSWGIILWEVITRRKPFDEIG<br>GPAFRIMWAVHNGTRPPLIKNILPKPIESLMTRCWSKDPSQRPSMEIVKIMTHLMRYFPGADEPLQYPCQEFGGGG<br>GQSPTLTLQSTNTHTQSSSSSSDGGLFRSRPAHSLPPGEDGRVEPYVDFAEFYRLWSVDHGEQSVVTAP<br>(human TAK1-TAB1; P4031 without epitope tag) |
| 106 | MAALKSWLSRSVTSFFRYRQCLCVPVVANFKKRCFSELIRPWHKTVTIGFGVTLCAVPIAQKSEPHSLSSEALMRRAVS<br>LVTDSTSTFLSQTTYALIEAITEYTKAVYTLTSLYRQYTSLLGKMNSEEEDEVWQVIIGARAEMTSKHQEYLKLETTWMT<br>AVGLSEMAAEAAYQTGADQASITARNHIQLVKLQVEEVHQLSRKAETKLAEAQIEELRQKTQEEGEERAESEQEAYLR<br>ED<br>(Diablo.1; without epitope tag) |
| 107 | MAALKSWLSRSVTSFFRYRQCLCVPVVANFKKRCFSELIRPWHKTVTIGFGVTLCAVPIAQKSEPHSLSSEALMRRAVS<br>LVTDSTSTFLSQTTYALIEAITEYTKAVYTLTSLYRQYTSLLGKMNLEEEDEVWQVIIGARAEMTSKHQEYLKLETTWMT |

-continued

SEQUENCE LISTING SUMMARY

| SEQ ID NO: | SEQUENCE |
|---|---|
| | AVGLSEMAAEAAYQTGADQASITARNHIQLVKLQVEEVHQLSRKAETKLAEAQIEELRQKTQEEGEERAESEQEAYLR ED (Diablo.1(S126L); without epitope tag) |
| 108 | MAVPIAQKSEPHSLSSEALMRRAVSLVTDSTSTFLSQTTYALIEAITEYTKAVYTLTSLYRQYTSLLGKMNSEEEDEVWQ VIIGARAEMTSKHQEYLKLETTWMTAVGLSEMAAEAAYQTGADQASITARNHIQLVKLQVEEVHQLSRKAETKLAEA QIEELRQKTQEEGEERAESEQEAYLRED (Diablo.1(56-239); without epitope tag) |
| 109 | MAVPIAQKSEPHSLSSEALMRRAVSLVTDSTSTFLSQTTYALIEAITEYTKAVYTLTSLYRQYTSLLGKMNLEEEDEVWQ VIIGARAEMTSKHQEYLKLETTWMTAVGLSEMAAEAAYQTGADQASITARNHIQLVKLQVEEVHQLSRKAETKLAEA QIEELRQKTQEEGEERAESEQEAYLRED (Diablo.1(56-239/S126L); without epitope tag) |
| 110 | MAALKSWLSRSVTSFFRYRQCLCVPVVANFKKRCFSELIRPWHKTVTIGFGVTLCAVPIAQAVYTLTSLYRQYTSLLGK MNSEEEDEVWQVIIGARAEMTSKHQEYLKLETTWMTAVGLSEMAAEAAYQTGADQASITARNHIQLVKLQVEEVH QLSRKAETKLAEAQIEELRQKTQEEGEERAESEQEAYLRED (Diablo.3; TH2003 without epitope tag) |
| 111 | MAALKSWLSRSVTSFFRYRQCLCVPVVANFKKRCFSELIRPWHKTVTIGFGVTLCAVPIAQAVYTLTSLYRQYTSLLGK MNLEEEDEVWQVIIGARAEMTSKHQEYLKLETTWMTAVGLSEMAAEAAYQTGADQASITARNHIQLVKLQVEEVH QLSRKAETKLAEAQIEELRQKTQEEGEERAESEQEAYLRED (Diablo.3(S8214; TH2001 without epitope tag) |
| 112 | MAVPIAQAVYTLTSLYRQYTSLLGKMNSEEEDEVWQVIIGARAEMTSKHQEYLKLETTWMTAVGLSEMAAEAAYQT GADQASITARNHIQLVKLQVEEVHQLSRKAETKLAEAQIEELRQKTQEEGEERAESEQEAYLRED (Diablo.3(56-195); TH2002 without epitope tag) |
| 113 | MAVPIAQAVYTLTSLYRQYTSLLGKMNLEEEDEVWQVIIGARAEMTSKHQEYLKLETTWMTAVGLSEMAAEAAYQT GADQASITARNHIQLVKLQVEEVHQLSRKAETKLAEAQIEELRQKTQEEGEERAESEQEAYLRED (Diablo.3(56-195/S82L); without epitope tag) |
| 114 | MAAVILESIFLKRSQQKKKTSPLNFKKRLFLLTVHIKLSYYKYDFERGRRGSKKGSIDVEKITCVETWPEKNPPPERQIPRR GEESSEMEQISIIERFPYPFQVVYDEGPLYVFSPTEELRKRWIHQLKNVIRYNSDLVQKYHPCFWIDGQYLCCSQTAKN AMGCQILENRNGSLKPGSSFIRKTKKPLPPTPEEDQILKKPLPPEPAAAPVSTSELKKVVALYDYMPMNANDLQLRKG DEYFILEESNLPWWRARDKNGQEGYIPSNYVTEAEDSIEMYEWYSKHMTRSQAEQLLKQEGKEGGFIVRDSSKAGKY TVSVFAKSTGDPQGVIRHYVVCSTPQSQYYLAEKHLFSTIPELINYFIQHNSAGLISRLKYPVSQQNKNAPSTAGLGYGS WEIDPKDLTFLKELGTGQFGVVICYGKWRGQYDVAIKMIKEGSMSEDEFIEEAKVMMNLSHEKLVQLYGVCTKQRPIF IITEYMANGCLLNYLREMRHRFQTQQLLEMCKDVCEAMEYLESKQFLFIRDLAARNCLVNDQGVVKVSDFGLSRYVL DDEVTSSVGSKFPVRWSPPEVLMYSKFSSKSDIWAFGVLMWEIYSLGIKMPYERFTNSETAEHIAQGLRLYRPHLASEK VYTIMYSCWHEKADERPTFKILLSNILDVMDEES (Btk(E41K); P4029 without epitope tag) |
| 115 | MVTHSKFPAAGMSRPLDTSLRLKTFSSKSEYQLVVNAVRKLQESGFYWSAVTGGEANLLLSAEPAGTFLIRDSSDQRH FFTLSVKTQSGTKNLRIQCEGGSFSLCISDPRSTQPVPRFDCVLKLVHHYMPPPGAPSFPSPPTEPSSEVPEQPSAQPLP GSPPRRAYYIYSGGEKIPLVLSRPLSSNVATLQHLCRKTVNGHLDSVEKVTQLPGPIREFLDQYDAPL (SOCS3; P4030 without epitope tag) |
| 116 | MRVKQIEDKIEEILSKIYHIENEIARIKKLIGEADQTSGNYLNMQDSQGVLSSFPAPQAVQDNPAMPTSSGSEGNVKL CSLEEAQRIWKQKSAEIYPIMDKSSRTRLALIICNEEFDSIPRRTGAEVDITGMTMLLQNLGYSVDVIKKNLTASDMITEL EAFAHRPEFKTSDSTFLVFMSFIGIREGICGKKHSEQVPDILQLNAIFNMLNTKNCPSLKDKPKVIIIQACRGDSPGVVW FKDSVGVSGNLSLPTTEEFEDDAIKKAHIEKDFIAFCSSTPDNVSWRIIPTMGSVFIGRLIEHMQEYACSCDVEEIFRKVR FSFEQPDGRAQMPTTERVTLTRCEILFPGH (IZ_hsCASP1 (self-activating human Caspase 1); P2024 without epitope tag) |
| 117 | MRMKQLEDKIEELLSKIYHLENEIARLIKKLIGEADQTSGNYLNMQDSQGVLSSFPAPQAVQDNPAMPTSSGSEGNVK LCSLEEAQRIWKQKSAEWMDKSSRTRLALIICNEEFDSIPRRTGAEVDITGMTMLLQNLGYSVDVKIKNLTASDMTTE LEAFAHRPEHKTSDSTFLVFMSHGIREGICGKKHSEQVPDILQLNAIFNMLNTKNCPSLKDKPKVIIIQACRGDSPGVV WFKDSVGVSGNLSLPTTEEFEDDAIKKAHIEKDFIAFCSSTPDNVSVVRHPTIVIGSVFIGRLIEHMQEYACSCDVEEIFRK VRFSFEQPDGRAQMPTTERVTLTRCFYLFPGH (DM_hsCASP1 (self-activating human Caspase 1); P2025 without epitope tag) |
| 118 | MRMKQIEDKIEEILSKIYHIENEIARIKKLIGERSAPSAETFVATEDSKGGHPSSSETKEEQNKEDGTFPGLIGTLKFCPLE KAQKLWKENPSEIWIMNTTTRTRLALIICNTEFQHLSPRVGAQVDLREMKLLLEDLGYTVIMENLTALEMVKEVKEF AACPEFIKTSDSTFLVFMSFIGIQEGICGTTYSNEVSDILIKVDTIFQMMNTLKCPSLKDKPKVIIIQACRGEKQGVVLLKDS VRDSEEDFLTDAIFEDDGIKKAHIEKDFIAFCSSTPDNVSWRHPVRGSLFIESLIKHMKEYAWSCDLEDIFRKVRFSFEQP EFRLQMPTADRVTLIKRFYLFPGH (IZ_mmCASP1 (self-activating mouse Caspase 1); P2026 without epitope tag) |
| 119 | MRMKQLEDKIEELLSKIYHLENEIARLKKLIGERSAPSAETFVATEDSKGGHPSSSETKEEQNKEDGTFPGLIGTLKFCPL EKAQKLWKENPSEIYPIMNIIIRTRLALIICNTEFQHLSPRVGAQVDLREMKLLLEDLGYTVKVIKENLTALEMVIKEVKE FAACPEHICTSDSTFLVFMSHGIQEGICETTYSNEVSDILKVDTIFQMMNTLIKCPSLIKDKPKVIIIQACRGEKQGVVLLKD SVRDSEEDFLTDAIFEDDGIKKAHIEKDFIAFCSSTPDNVSWRHPVRGSLFIESLIKHMKEYAWSCDLEDIFRKVRFSFEQ |

-continued

SEQUENCE LISTING SUMMARY

| SEQ ID NO: | SEQUENCE |
|---|---|
| | PEFRLOMPTADRVTLTKRFYLFPGH<br>(DM_mmCASP1 (self-activating mouse Caspase 1); P2027 without epitope tag) |
| 120 | MHHHHHHHHHHGKPIPNPLLGLDSTGIPVHLELASMTNMELMSSIVHQQVFPTEAGQSLVISASIIVFNLLELEGDYR<br>GRVLELFRAAQLANDVVLQIMELCGATR<br>(ADR concatemer with HIS tag) |
| 121 | VVGADGVGK<br>(KRAS G12D 9mer) |
| 122 | VVGAVGVGK<br>(KRAS G12V 9mer) |
| 123 | VGAGDVGKS<br>(KRAS G13D 9mer) |
| 124 | VVGACGVGK<br>(KRAS G12C 9mer) |
| 125 | MKLVVVGACGVGKSA<br>(KRAS G12C 15mer) |
| 126 | ATGACCGAGTACAAGCTGGTGGTGGTGGGCGCCGACGGCGTGGGCAAGAGCGCCCTGACCATCCAGCTGATCC<br>AG<br>(KRAS G12D 25mer nucleotide sequence) |
| 127 | ATGACCGAGTACAAGCTGGTGGTGGTGGGCGCCGTGGGCGTGGGCAAGAGCGCCCTGACCATCCAGCTGATCC<br>AG<br>(KRAS G12V 25mer nucleotide sequence) |
| 128 | ATGACCGAGTACAAGCTGGTGGTGGTGGGCGCCGGCGACGTGGGCAAGAGCGCCCTGACCATCCAGCTGATCC<br>AG<br>(KRAS G13D 25mer nucleotide sequence) |
| 129 | ATGACCGAGTACAAGTTAGTGGTTGTGGGCGCCGACGGCGTGGGCAAGAGCGCCCTCACCATCCAGCTTATCCA<br>GATGACGGAATATAAGTTAGTAGTAGTGGGAGCCGACGGTGTCGGCAAGTCCGCTTTGACCATTCAACTTATTC<br>AGATGACAGAGTATAAGCTGGTCGTTGTAGGCGCAGACGGCGTTGGAAAGTCGGCACTGACGATCCAGTTGAT<br>CCAG<br>(KRAS G12D 25mer^3 nucleotide sequence) |
| 130 | ATGACCGAGTACAAGCTCGTCGTGGTGGGCGCCGTGGGCGTGGGCAAGAGCGCCCTAACCATCCAGTTGATCC<br>AGATGACCGAATATAAGCTCGTGGTAGTCGGAGCGGTGGGCGTTGGCAAGTCAGCGCTAACAATACAACTAAT<br>CCAAATGACCGAATACAAGCTAGTTGTAGTCGGTGCCGTCGGCGTTGGAAAGTCAGCCCTTACAATTCAGCTCAT<br>TCAG<br>(KRAS G12V 25mer^3 nucleotide sequence) |
| 131 | ATGACCGAGTACAAGCTCGTAGTGGTTGGCGCCGGCGACGTGGGCAAGAGCGCCCTAACCATCCAGCTCATCCA<br>GATGACAGAATATAAGCTTGTGGTTGTGGGAGCAGGAGACGTGGGAAAGAGTGCGTTGACGATTCAACTCATA<br>CAGATGACCGAATACAAGTTGGTGGTGGTCGGCGCAGGTGACGTTGGTAAGTCTGCACTAACTATACAACTGAT<br>CCAG<br>(KRAS G13D 25mer^3 nucleotide sequence) |
| 132 | ATGACCGAGTACAAGCTGGTGGTGGTGGGCGCCTGCGGCGTGGGCAAGAGCGCCCTGACCATCCAGCTGATCC<br>AG<br>(KRAS G12C 25mer nucleotide sequence) |
| 133 | ATGACCGAGTACAAGCTGGTGGTGGTGGGCGCCGGCGGCGTGGGCAAGAGCGCCCTGACCATCCAGCTGATCC<br>AG<br>(KRAS WT 25mer nucleotide sequence) |
| 134 | GGGAAATAAGAGAGAAAAGAAGAGTAAGAAGAAATATAAGAGCCACC<br>(5' UTR sequence; no promoter) |
| 135 | MTEYKLVVVGADGVGKSALTIQLIQMTEYKLVVVGAVGVGKSALTIQLIQMTEYKLVVVGAGDVGKSALTIQLIQ<br>(KRAS(G12D G12V G13D) 75mer "3MUT" aa. seq) |
| 136 | ATGACCGAGTACAAGCTCGTTGTAGTCGGCGCCGACGGCGTGGGCAAGAGCGCCTTGACCATCCAGTTGATCCA<br>GATGACCGAATATAAGTTGGTGGTGGTAGGCGCAGTGGGAGTTGGCAAGTCAGCACTCACAATTCAGCTCATTC<br>AAATGACAGAATACAAGTTAGTCGTTGTAGGAGCAGGCGACGTCGGCAAGAGTGCCTTAACCATTCAACTAATC<br>CAG<br>(KRAS(G12D G12V G13D) 75mer "3MUT" nt. seq) |

-continued

SEQUENCE LISTING SUMMARY

| SEQ ID NO: | SEQUENCE |
|---|---|
| 137 | MTEYKLVVVGADGVKSALTIQLIQMTEYKLVVVGAVGVGKSALTIQLIQMTEYKLVVVGAGDVGKSALTIQLIQMTE<br>YKLVVVGACGVGKSALTIQLIQ<br>(KRAS(G12D G12V G13D G12C) 100mer "4MUT" aa. seq) |
| 138 | ATGACCGAGTACAAGCTCGTGGTCGTCGGCGCCGACGGGGTAGGCAAGTCCGCTCTGACCATTCAGCTCATCCA<br>GATGACGGAGTACAAACTCGTGGTAGTGGGAGCCGTGGGTGTGGGCAAGAGCGCGCTCACCATCCAACTCATC<br>CAAATGACCGAATATAAACTCGTCGTGGTGGGAGCCGGCGACGTGGGAAAGAGCGCCCTTACCATCCAGTTAAT<br>CCAGATGACAGAATACAAGCTGGTGGTGGTCGGTGCCTGCGGCGTGGGTAAGTCCGCCCTGACAATCCAGCTG<br>ATCCAG<br>(KRAS(G12D G12V G13D G12C) 100mer "4MUT" nt. seq) |
| 139 | ATGCCCCACAGTAGCCTCCACCCCAGCATCCCCTGCCCCAGAGGCCACGGCGCACAGAAGGCCGCCCTGGTGCT<br>GCTGAGCGCCTGTCTGGTGACCCTGTGGGGTCTGGGCGAGCCCCCCGAGCACACCCTGCGGTACCTCGTGCTGC<br>ATCTGGCCAGCCTGCAGCTGGGCCTGCTGCTGAACGGCGTGTGCAGCCTGGCCGAAGAGCTGAGACACATCCAC<br>AGCAGATACAGAGGCTCCTACTGGAGAACCGTCAGAGCCTGCCTCGGCTGTCCCCTGAGAAGAGGCGCCCTGCT<br>GCTCCTGAGCATCTACTTCTACTACAGCCTGCCCAACGCCGTGGGCCCCCCCTTCACCTGGATGCTGGCCCTGCTG<br>GGCCTGAGCCAGGCCCTGAACATCCTGCTGGGCCTGAAGGGCTTGGCCCCCGCCGAGATCTCCGCCGTGTGCGA<br>GAAGGGCAACTTCAACATGGCCCATGGCCTTGCCTGGTCCTACTACATCGGCTACCTGAGACTGATCCTGCCCGA<br>GCTGCAGGCCAGAATCAGAACCTACAACCAGCACTACAACAACCTGCTGAGAGGCGCCGTGAGCCAAAGACTGT<br>ACATCCTGCTGCCCCTGGACTGCGGCGTGCCCGACAACCTTAGCATGGCCGACCCCAACATCAGATTCCTGGACA<br>AGCTGCCCCAGCAGACCGGCGACCACGCCGGCATCAAGGACAGAGTGTACAGCAACAGCATCTACGAGCTGCT<br>GGAGAACGGCCAGAGAGCCGGCACCTGCGTGCTGGAGTACGCCACCCCCCTGCAGACCCTGTTCGCCATGAGC<br>CAGTACAGCCAGGCCGGCTTCAGCAGAGAGGACAGACTGGAGCAAGCCAAGCTGTTCTGCAGAACCCTGGAGG<br>ACATCCTGGCGGACGCCCCCGAGAGCCAAAACAACTGCAGACTGATCGCCTACCAGGAGCCCGCCGACGACAG<br>CAGCTTCAGCCTGAGCCAGGAAGTGCTGAGACACCTGAGACAGGAAGAGAAGGAGGAGGTGACCGTGGGAAG<br>CCTGAAGACCAGCGCCGTGCCCAGCACCAGCACCATGAGCCAGGAGCCCGAGCTGCTGATCAGCGGCATGGAG<br>AAGCCCCTGCCCCTGAGAACCGACTTCAGC<br>(huSTING(V155M); no epitope tag; nucleotide sequence) |
| 140 | ATGCCTCACAGCAGCCTGCACCCTAGCATCCCTTGCCCTAGAGGCCACGGCGCCCAGAAGGCCGCCCTGGTGCT<br>GCTGAGCGCCTGCCTGGTGACCCTGTGGGGCCTGGGCGAGCCTCCTGAGCACACCCTGAGATACCTGGTGCTGC<br>ACCTGGCCAGCCTGCAGCTGGGCCTGCTGCTGAACGGCGTGTGCAGCCTGGCCGAGGAGCTGAGACACATCCA<br>CAGCAGATACAGAGGCAGCTACTGGAGAACCGTGAGAGCCTGCCTGGGCTGCCCTCTGAGAAGAGGCGCCCTG<br>CTGCTGCTGAGCATCTACTTCTACTACAGCCTGCCTAACGCCGTGGGCCCTCCTTTCACCTGGATGCTGGCCCTGC<br>TGGGCCTGAGCCAGGCCCTGAACATCCTGCTGGGCCTGAAGGGCCTGGCCCCTGCCGAGATCAGCGCCGTGTG<br>CGAGAAGGGCAACTTCAACGTGGCCCACGGCCTGGCCTGGAGCTACTACATCGGCTACCTGAGACTGATCCTGC<br>CTGAGCTGCAGGCCAGAATCAGAACCTACAACCAGCACTACAACAACCTGCTGAGAGGCGCCGTGAGCCAGAG<br>ACTGTACATCCTGCTGCCTCTGGACTGCGGCGTGCCTGACAACCTGAGCATGGCCGACCCTAACATCAGATTCCT<br>GGACAAGCTGCCTCAGCAGACCGGCGACCACGCCGGCATCAAGGACAGAGTGTACAGCAACAGCATCTACGAG<br>CTGCTGGAGAACGGCCAGAGAGCCGGCACCTGCGTGCTGGAGTACGCCACCCCTCTGCAGACCCTGTTCGCCAT<br>GAGCCAGTACAGCCAGGCCGGCTTCAGCAGAGAGGACACCCTGGAGCAGGCCAAGCTGTTCTGCAGAACCCTG<br>GAGGACATCCTGGCCGACGCCCCTGAGAGCCAGAACAACTGCAGACTGATCGCCTACCAGGAGCCTGCCGACG<br>ACAGCAGCTTCAGCCTGAGCCAGGAGGTGCTGAGACACCTGAGACAGGAGGAGAAGGAGGAGGTGACCGTGG<br>GCAGCCTGAAGACCAGCGCCGTGCCTAGCACCAGCACCATGAGCCAGGAGCCTGAGCTGCTGATCAGCGGCAT<br>GGAGAAGCCTCTGCCTCTGAGAACCGACTTCAGC<br>(Hu STING(R284T); no epitope tag; nucleotide sequence) |
| 141 | ATGCCCCACAGCAGCCTGCACCCCTCCATCCCCTGTCCCAGAGGCCACGGCGCCCAGAAGGCCGCCCTGGTGCT<br>GCTGAGCGCCTGCCTGGTGACCTTATGGGGCCTGGGCGAGCCCCCCGAGCACACCCTGAGATACCTGGTCCTGC<br>ACCTGGCCAGCCTCCAGCTGGGCCTGCTGCTCAACGGCGTGTGTAGCCTGGCCGAGGAGCTGAGACACATCCAC<br>AGCAGATACAGAGGCAGCTACTGGAGAACCGTGAGAGCCTGCCTGGGTTGCCCACTGAGAAGAGGAGCTCTGC<br>TGCTGCTGAGCATCTACTTCTACTACTCGCTGCCCAACGCTGTGGGCCCCCCCTTCACCTGGATGCTGGCCCTGCT<br>GGGTCTGAGCCAGGCCCTGAACATCCTCCTGGGCCTGAAGGGCCTGGCCCCCGCCGAGATAAGCGCCGTTTGCG<br>AGAAGGGCAACTTCAACGTGGCCCATGGCCTGGCCTGGAGCTACTACATCGGCTACTTACGCCTGATCCTGCCC<br>GAGCTGCAGGCCAGAATCAGAACCTACAACCAGCATTACAACAACCTGCTGAGAGGCGCCGTGAGCCAGAGAC<br>TGTATATCCTGCTGCCCCTGGACTGCGGCGTGCCCGACAACCTGAGCATGGCCGACCCCAACATCAGATTCCTGG<br>ACAAGCTCCCCCAGCAGACCGGCGACCACGCCGGAATCAAAGACAGAGTGTATAGCAACAGCATCTACGAGCT<br>GCTGGAGAACGGCCAGAGAGCCGGCACCTGCGTACTGGAGTACGCCACCCCCTTGCAGACCCTGTTTGCCATGA<br>GCCAGTACAGCCAGGCCGGCTTCAGCAGAGAGGACATGCTGGAGCAGGCCAAGCTGTTCTGCAGAACCCTGGA<br>GGACATCCTGGCCGACGCCCCCGAGAGCCAGAACAACTGCAGACTGATCGCCTACCAAGAGCCCGCCGACGAC<br>AGCAGCTTCAGCTTAAGCCAGGAGGTGCTGAGACATCTGAGACAGGAGGAGAAGGAGGAGGTGACCGTGGGC<br>AGCCTCAAGACCAGCGCTGTGCCCTCTACCAGCACCATGAGCCAGGAGCCCGAGCTGCTGATCAGCGGCATGGA<br>GAAGCCCCTGCCCCTGAGAACAGACTTCAGC<br>(hu STING (R284M); no epitope tag; nucleotide sequence) |
| 142 | ATGCCCCATAGCAGCCTGCACCCCAGCATCCCCTGCCCCAGAGGCCACGGCGCCCAGAAGGCCGCCCTGGTCCT<br>GCTGAGCGCATGCCTGGTCACCCTGTGGGGCCTGGGCGAGCCCCCCGAGCACACCCTGAGATACCTGGTGCTGC<br>ACCTCGCCAGCCTGCAGCTGGGCCTGCTGCTGAACGGCGTGTGCAGCCTGGCCGAGGAGCTGAGACACATCCAC<br>AGCAGATATAGAGGCAGCTACTGGAGAACCGTGAGAGCTTGCCTCGGCTGCCCCCTGAGAAGAGGCGCCCTGC<br>TGCTGCTGAGCATCTACTTTTACTACAGCCTGCCCAACGCTGTGGGCCCCCCTTTCACGTGGATGCTCGCCCTGCT<br>GGGACTGAGCCAGGCCCTGAACATCCTGCTGGGCCTTAAGGGCCTAGCCCCCGCCGAGATCAGCGCCGTGTGC<br>GAGAAGGGCAACTTCAATGTGGCCCACGGCCTGGCCTGGAGCTACTACATCGGCTACCTGAGACTGATCCTGCC<br>CGAGCTGCAGGCCAGAATCAGAACCTACAATCAGCACTACAACAACCTGCTGAGAGGCGCCGTGAGCCAGAGA |

-continued

SEQUENCE LISTING SUMMARY

| SEQ ID NO: | SEQUENCE |
|---|---|
| | CTGTACATCCTGCTGCCCCTGGACTGCGGCGTGCCCGACAACCTCAGCATGGCCGACCCCAACATCAGATTCCTG<br>GACAAGCTGCCCCAGCAGACCGGCGACCACGCCGGCATCAAGGATCGCGTGTACAGCAACAGCATCTACGAGC<br>TGCTGGAAAACGGCCAGAGAGCCGGAACCTGCGTGCTGGAGTACGCCACACCCCTGCAGACCCTGTTCGCCATG<br>AGCCAGTACAGCCAGGCCGGCTTCAGCAGAGAGGACAAGCTGGAGCAGGCCAAGCTGTTCTGCAGAACCCTGG<br>AGGATATCCTCGCCGACGCCCCCGAGAGCCAGAACAACTGCAGGCTGATCGCGTACCAGGAGCCCGCTGACGA<br>CAGCAGCTTTAGCCTGAGCCAGGAGGTGCTGAGACATCTGCGTCAAGAGGAAAAGGAGGAGGTGACCGTGGG<br>CTCCCTGAAGACCAGCGCCGTGCCCAGCACCAGCACCATGAGCCAGGAGCCCGAGCTGCTGATCAGCGGCATG<br>GAGAAGCCACTGCCCCTCAGAACCGACTTCAGC<br>(Hu STING (R284K); no epitope tag; nucleotide sequence) |
| 143 | ATGCCTCACAGCAGCCTGCACCCTAGCATCCCTTGCCCTAGAGGCCACGGCGCCCAGAAGGCCGCCCTGGTGCT<br>GCTGAGCGCCTGCCTGGTGACCCTGTGGGGCCTGGGCGAGCCTCCTGAGCACACCCTGAGATACCTGGTGCTGC<br>ACCTGGCCAGCCTGCAGCTGGGCCTGCTGCTGAACGGCGTGTGCAGCCTGGCCGAGGAGCTGAGACACATCCA<br>CAGCAGATACAGAGGCAGCTACTGGAGAACCGTGAGAGCCTGCCTGGGCTGCCCTCTGAGAAGAGGCGCCCTG<br>CTGCTGCTGAGCATCTACTTCTACTACAGCCTGCCTAACGCCGTGGGCCCTCCTTTCACCTGGATGCTGGCCCTGC<br>TGGGCCTGAGCCAGGCCCTGAACATCCTGCTGGGCCTGAAGGGCCTGGCCCCTGCCGAGATCAGCGCCGTGTG<br>CGAGAAGGGCAACTTCAGCGTGGCCCACGGCCTGGCCTGGAGCTACTACATCGGCTACCTGAGACTGATCCTGC<br>CTGAGCTGCAGGCCAGAATCAGAACCTACAACCAGCACTACAACAACCTGCTGAGAGGCGCCGTGAGCCAGAG<br>ACTGTACATCCTGCTGCCTCTGGACTGCGGCGTGCCTGACAACCTGAGCATGGCCGACCCTAACATCAGATTCCT<br>GGACAAGCTGCCTCAGCAGACCGGCGACCACGCCGGCATCAAGGACAGAGTGTACAGCAACAGCATCTACGAG<br>CTGCTGGAGAACGGCCAGAGAGCCGGCACCTGCGTGCTGGAGTACGCCACCCCTCTGCAGACCCTGTTCGCCAT<br>GAGCCAGTACAGCCAGGCCGGCTTCAGCAGAGAGGACAGACTGGAGCAGGCCAAGCTGTTCTGCAGAACCCTG<br>GAGGACATCCTGGCCGACGCCCCTGAGAGCCAGAACAACTGCAGACTGATCGCCTACCAGGAGCCTGCCGACG<br>ACAGCAGCTTCAGCCTGAGCCAGGAGGTGCTGAGACACCTGAGACAGGAGGAGAAGGAGGAGGTGACCGTGG<br>GCAGCCTGAAGACCAGCGCCGTGCCTAGCACCAGCACCATGAGCCAGGAGCCTGAGCTGCTGATCAGCGGCAT<br>GGAGAAGCCTCTGCCTCTGAGAACCGACTTCAGC<br>(Hu STING(N154S); no epitope tag; nucleotide sequence) |
| 144 | ATGCCTCACAGCAGCCTGCACCCTAGCATCCCTTGCCCTAGAGGCCACGGCGCCCAGAAGGCCGCCCTGGTGCT<br>GCTGAGCGCCTGCCTGGTGACCCTGTGGGGCCTGGGCGAGCCTCCTGAGCACACCCTGAGATACCTGGTGCTGC<br>ACCTGGCCAGCCTGCAGCTGGGCCTGCTGCTGAACGGCGTGTGCAGCCTGGCCGAGGAGCTGAGACACATCCA<br>CAGCAGATACAGAGGCAGCTACTGGAGAACCGTGAGAGCCTGCCTGGGCTGCCCTCTGAGAAGAGGCGCCCTG<br>CTGCTGCTGAGCATCTACTTCTACTACAGCCTGCCTAACGCCGTGGGCCCTCCTTTCACCTGGATGCTGGCCCTGC<br>TGGGCCTGAGCCAGGCCCTGAACATCCTGCTGGGCCTGAAGGGCCTGGCCCCTGCCGAGATCAGCGCCCTGTGC<br>GAGAAGGGCAACTTCAACGTGGCCCACGGCCTGGCCTGGAGCTACTACATCGGCTACCTGAGACTGATCCTGCC<br>TGAGCTGCAGGCCAGAATCAGAACCTACAACCAGCACTACAACAACCTGCTGAGAGGCGCCGTGAGCCAGAGA<br>CTGTACATCCTGCTGCCTCTGGACTGCGGCGTGCCTGACAACCTGAGCATGGCCGACCCTAACATCAGATTCCTG<br>GACAAGCTGCCTCAGCAGACCGGCGACCACGCCGGCATCAAGGACAGAGTGTACAGCAACAGCATCTACGAGC<br>TGCTGGAGAACGGCCAGAGAGCCGGCACCTGCGTGCTGGAGTACGCCACCCCTCTGCAGACCCTGTTCGCCATG<br>AGCCAGTACAGCCAGGCCGGCTTCAGCAGAGAGGACAGACTGGAGCAGGCCAAGCTGTTCTGCAGAACCCTGG<br>AGGACATCCTGGCCGACGCCCCTGAGAGCCAGAACAACTGCAGACTGATCGCCTACCAGGAGCCTGCCGACGA<br>CAGCAGCTTCAGCCTGAGCCAGGAGGTGCTGAGACACCTGAGACAGGAGGAGAAGGAGGAGGTGACCGTGGG<br>CAGCCTGAAGACCAGCGCCGTGCCTAGCACCAGCACCATGAGCCAGGAGCCTGAGCTGCTGATCAGCGGCATG<br>GAGAAGCCTCTGCCTCTGAGAACCGACTTCAGC<br>(Hu STING(V147L); no epitope tag; nucleotide sequence) |
| 145 | ATGCCTCACAGCAGCCTGCACCCTAGCATCCCTTGCCCTAGAGGCCACGGCGCCCAGAAGGCCGCCCTGGTGCT<br>GCTGAGCGCCTGCCTGGTGACCCTGTGGGGCCTGGGCGAGCCTCCTGAGCACACCCTGAGATACCTGGTGCTGC<br>ACCTGGCCAGCCTGCAGCTGGGCCTGCTGCTGAACGGCGTGTGCAGCCTGGCCGAGGAGCTGAGACACATCCA<br>CAGCAGATACAGAGGCAGCTACTGGAGAACCGTGAGAGCCTGCCTGGGCTGCCCTCTGAGAAGAGGCGCCCTG<br>CTGCTGCTGAGCATCTACTTCTACTACAGCCTGCCTAACGCCGTGGGCCCTCCTTTCACCTGGATGCTGGCCCTGC<br>TGGGCCTGAGCCAGGCCCTGAACATCCTGCTGGGCCTGAAGGGCCTGGCCCCTGCCGAGATCAGCGCCGTGTG<br>CGAGAAGGGCAACTTCAACGTGGCCCACGGCCTGGCCTGGAGCTACTACATCGGCTACCTGAGACTGATCCTGC<br>CTGAGCTGCAGGCCAGAATCAGAACCTACAACCAGCACTACAACAACCTGCTGAGAGGCGCCGTGAGCCAGAG<br>ACTGTACATCCTGCTGCCTCTGGACTGCGGCGTGCCTGACAACCTGAGCATGGCCGACCCTAACATCAGATTCCT<br>GGACAAGCTGCCTCAGCAGACCGGCGACCACGCCGGCATCAAGGACAGAGTGTACAGCAACAGCATCTACGAG<br>CTGCTGGAGAACGGCCAGAGAGCCGGCACCTGCGTGCTGGAGTACGCCACCCCTCTGCAGACCCTGTTCGCCAT<br>GAGCCAGTACAGCCAGGCCGGCTTCAGCAGAGAGGACAGACTGGAGCAGGCCAAGCTGTTCTGCAGAACCCTG<br>GAGGACATCCTGGCCGACGCCCCTGAGAGCCAGAACAACTGCAGACTGATCGCCTACCAGCAGCCTGCCGACG<br>ACAGCAGCTTCAGCCTGAGCCAGGAGGTGCTGAGACACCTGAGACAGGAGGAGAAGGAGGAGGTGACCGTGG<br>GCAGCCTGAAGACCAGCGCCGTGCCTAGCACCAGCACCATGAGCCAGGAGCCTGAGCTGCTGATCAGCGGCAT<br>GGAGAAGCCTCTGCCTCTGAGAACCGACTTCAGC<br>(Hu STING (E315Q); no epitope tag; nucleotide sequence) |
| 146 | ATGCCTCACAGCAGCCTGCACCCTAGCATCCCTTGCCCTAGAGGCCACGGCGCCCAGAAGGCCGCCCTGGTGCT<br>GCTGAGCGCCTGCCTGGTGACCCTGTGGGGCCTGGGCGAGCCTCCTGAGCACACCCTGAGATACCTGGTGCTGC<br>ACCTGGCCAGCCTGCAGCTGGGCCTGCTGCTGAACGGCGTGTGCAGCCTGGCCGAGGAGCTGAGACACATCCA<br>CAGCAGATACAGAGGCAGCTACTGGAGAACCGTGAGAGCCTGCCTGGGCTGCCCTCTGAGAAGAGGCGCCCTG<br>CTGCTGCTGAGCATCTACTTCTACTACAGCCTGCCTAACGCCGTGGGCCCTCCTTTCACCTGGATGCTGGCCCTGC<br>TGGGCCTGAGCCAGGCCCTGAACATCCTGCTGGGCCTGAAGGGCCTGGCCCCTGCCGAGATCAGCGCCGTGTG<br>CGAGAAGGGCAACTTCAACGTGGCCCACGGCCTGGCCTGGAGCTACTACATCGGCTACCTGAGACTGATCCTGC<br>CTGAGCTGCAGGCCAGAATCAGAACCTACAACCAGCACTACAACAACCTGCTGAGAGGCGCCGTGAGCCAGAG<br>ACTGTACATCCTGCTGCCTCTGGACTGCGGCGTGCCTGACAACCTGAGCATGGCCGACCCTAACATCAGATTCCT |

-continued

SEQUENCE LISTING SUMMARY

| SEQ ID NO: | SEQUENCE |
|---|---|
| | GGACAAGCTGCCTCAGCAGACCGGCGACCACGCCGGCATCAAGGACAGAGTGTACAGCAACAGCATCTACGAG<br>CTGCTGGAGAACGGCCAGAGAGCCGGCACCTGCGTGCTGGAGTACGCCACCCCTCTGCAGACCCTGTTCGCCAT<br>GAGCCAGTACAGCCAGGCCGGCTTCAGCAGAGAGGACAGACTGGAGCAGGCCAAGCTGTTCTGCAGAACCCTG<br>GAGGACATCCTGGCCGACGCCCCTGAGAGCCAGAACAACTGCAGACTGATCGCCTACCAGGAGCCTGCCGACG<br>ACAGCAGCTTCAGCCTGAGCCAGGAGGTGCTGAGACACCTGAGACAGGAGGAGAAGGAGGAGGTGACCGTGG<br>GCAGCCTGAAGACCAGCGCCGTGCCTAGCACCAGCACCATGAGCCAGGAGCCTGAGCTGCTGATCAGCGGCAT<br>GGAGAAGCCTCTGCCTCTGGCCACCGACTTCAGC<br>(Hu STING (R375A); no epitope tag; nudeotide sequence) |
| 147 | ATGCCTCACAGCAGCCTGCACCCTAGCATCCCTTGCCCTAGAGGCCACGGCGCCCAGAAGGCCGCCCTGGTGCT<br>GCTGAGCGCCTGCCTGGTGACCCTGTGGGGCCTGGGCGAGCCTCCTGAGCACACCCTGAGATACCTGGTGCTGC<br>ACCTGGCCAGCCTGCAGCTGGGCCTGCTGCTGAACGGCGTGTGCAGCCTGGCCGAGGAGCTGAGACACATCCA<br>CAGCAGATACAGAGGCAGCTACTGGAGAACCGTGAGAGCCTGCCTGGGCTGCCCTCTGAGAAGAGGCGCCCTG<br>CTGCTGCTGAGCATCTACTTCTACTACAGCCTGCCTAACGCCGTGGGCCCTCCTTTCACCTGGATGCTGGCCCTGC<br>TGGGCCTGAGCCAGGCCCTGAACATCCTGCTGGGCCTGAAGGGCCTGGCCCCTGCCGAGATCAGCGCCCTGTGC<br>GAGAAGGGCAACTTCAGCATGGCCCACGGCCTGGCCTGGAGCTACTACATCGGCTACCTGAGACTGATCCTGCC<br>TGAGCTGCAGGCCAGAATCAGAACCTACAACCAGCACTACAACAACCTGCTGAGAGGCGCCGTGAGCCAGAGA<br>CTGTACATCCTGCTGCCTCTGGACTGCGGCGTGCCTGACAACCTGAGCATGGCCGACCCTAACATCAGATTCCTG<br>GACAAGCTGCCTCAGCAGACCGGCGACCACGCCGGCATCAAGGACAGAGTGTACAGCAACAGCATCTACGAGC<br>TGCTGGAGAACGGCCAGAGAGCCGGCACCTGCGTGCTGGAGTACGCCACCCCTCTGCAGACCCTGTTCGCCATG<br>AGCCAGTACAGCCAGGCCGGCTTCAGCAGAGAGGACAGACTGGAGCAGGCCAAGCTGTTCTGCAGAACCCTGG<br>AGGACATCCTGGCCGACGCCCCTGAGAGCCAGAACAACTGCAGACTGATCGCCTACCAGGAGCCTGCCGACGA<br>CAGCAGCTTCAGCCTGAGCCAGGAGGTGCTGAGACACCTGAGACAGGAGGAGAAGGAGGAGGTGACCGTGGG<br>CAGCCTGAAGACCAGCGCCGTGCCTAGCACCAGCACCATGAGCCAGGAGCCTGAGCTGCTGATCAGCGGCATG<br>GAGAAGCCTCTGCCTCTGAGAACCGACTTCAGC<br>(Hu STING(V147L/N154S/V155M); no epitope tag; nucleotide sequence) |
| 148 | ATGCCTCACAGCAGCCTGCACCCTAGCATCCCTTGCCCTAGAGGCCACGGCGCCCAGAAGGCCGCCCTGGTGCT<br>GCTGAGCGCCTGCCTGGTGACCCTGTGGGGCCTGGGCGAGCCTCCTGAGCACACCCTGAGATACCTGGTGCTGC<br>ACCTGGCCAGCCTGCAGCTGGGCCTGCTGCTGAACGGCGTGTGCAGCCTGGCCGAGGAGCTGAGACACATCCA<br>CAGCAGATACAGAGGCAGCTACTGGAGAACCGTGAGAGCCTGCCTGGGCTGCCCTCTGAGAAGAGGCGCCCTG<br>CTGCTGCTGAGCATCTACTTCTACTACAGCCTGCCTAACGCCGTGGGCCCTCCTTTCACCTGGATGCTGGCCCTGC<br>TGGGCCTGAGCCAGGCCCTGAACATCCTGCTGGGCCTGAAGGGCCTGGCCCCTGCCGAGATCAGCGCCCTGTGC<br>GAGAAGGGCAACTTCAGCATGGCCCACGGCCTGGCCTGGAGCTACTACATCGGCTACCTGAGACTGATCCTGCC<br>TGAGCTGCAGGCCAGAATCAGAACCTACAACCAGCACTACAACAACCTGCTGAGAGGCGCCGTGAGCCAGAGA<br>CTGTACATCCTGCTGCCTCTGGACTGCGGCGTGCCTGACAACCTGAGCATGGCCGACCCTAACATCAGATTCCTG<br>GACAAGCTGCCTCAGCAGACCGGCGACCACGCCGGCATCAAGGACAGAGTGTACAGCAACAGCATCTACGAGC<br>TGCTGGAGAACGGCCAGAGAGCCGGCACCTGCGTGCTGGAGTACGCCACCCCTCTGCAGACCCTGTTCGCCATG<br>AGCCAGTACAGCCAGGCCGGCTTCAGCAGAGAGGACATGCTGGAGCAGGCCAAGCTGTTCTGCAGAACCCTGG<br>AGGACATCCTGGCCGACGCCCCTGAGAGCCAGAACAACTGCAGACTGATCGCCTACCAGGAGCCTGCCGACGA<br>CAGCAGCTTCAGCCTGAGCCAGGAGGTGCTGAGACACCTGAGACAGGAGGAGAAGGAGGAGGTGACCGTGGG<br>CAGCCTGAAGACCAGCGCCGTGCCTAGCACCAGCACCATGAGCCAGGAGCCTGAGCTGCTGATCAGCGGCATG<br>GAGAAGCCTCTGCCTCTGAGAACCGACTTCAGC<br>(Hu STING(R284M/V147L/N154S/V155M); no epitope tag; nucleotide sequence) |
| 149 | TGATAATAGGCTGGAGCCTCGGTGGCCTAGCTTCTTGCCCCTTGGGCCTCCCCCCAGCCCCTCCTCCCCTTCCTGC<br>ACCCGTACCCCCCAAACACCATTGTCACACTCCAGTGGTCTTTGAATAAAGTCTGAGTGGGCGGC<br>(3' UTR used in STING V155M construct, containing miR122 binding site) |
| 150 | ATGGAGACCCCCAAGCCTAGAATCCTGCCCTGGCTGGTGAGCCAGCTGGACCTGGGCCAGCTGGAGGGCGTAG<br>CCTGGCTGGACGAGAGCAGAACCAGATTCAGAATCCCCTGGAAGCACGGCCTGAGACAAGACGCCCAGATGGC<br>CGACTTCGGCATCTTCCAGGCCTGGGCCGAGGCCAGCGGCGCCTACACCCCTGGCAAGGATAAGCCCGATGTGA<br>GCACCTGGAAGAGAAACTTCAGAAGCGCCCTGAACAGAAAGGAGGTGCTGAGACTGGCCGCCGACAATAGCAA<br>GGACCCCTACGACCCCCACAAGGTGTACGAGTTCGTTACCCCCGGCGCCAGGGACTTCGTGCACCTGGGCGCCA<br>GCCCCGACACCAACGGCAAGAGCAGCCTGCCCCACAGCCAGGAGAACCTGCCCAAGCTGTTCGATGGCCTGATC<br>CTGGGCCCCCTGAAGGACGAGGGCAGCAGCGACCTGGCCATCGTGAGCGACCCTAGCCAGCAGCTGCCCTCCC<br>CCAACGTGAACAACTTCCTGAACCCCGCCCCCCAGGAGAACCCCCTGAAGCAACTGCTGGCCGAGGAGCAGTGG<br>GAGTTCGAGGTGACCGCCTTCTACAGAGGCAGACAGGTGTTCCAGCAGACCCTGTTCTGCCCCGGCGGCCTGAG<br>ACTGGTAGGCAGCACCGCTGACATGACCCTGCCCTGGCAGCCCGTGACCCTGCCCGACCCCGAAGGCTTTCTGA<br>CCGACAAGCTGGTGAAGGAGTACGTCGGCCAAGTGCTGAAGGGCCTGGGCAACGGCCTGGCCCTGTGGCAGG<br>CCGGCCAGTGCCTGTGGGCCCAGAGACTCGGCCACAGCCACGCCTTCTGGGCCCTGGGCGAGGAACTCCTGCCC<br>GATAGCGGCAGAGGCCCCGACGGCGAGGTGCACAAGGACAAGGACGGCGCCGTGTTCGACCTGCGCCCCTTCG<br>TGGCCGACCTGATCGCCTTCATGGAGGGCAGCGGCCACAGCCCCAGATATACCCTGTGGTTCTGCATGGGCGAG<br>ATGTGGCCCCAGGACCAGCCCTGGGTGAAGAGACTGGTGATGGTGAAGGTGGTGCCCACCTGCCTGAAAGAGC<br>TGCTGGAGATGGCCAGAGAGGGCGGCGCCAGCTCCCTGAAAACCGTGGACCTGCACATTGACAACAGCCAGCC<br>CATCAGCCTGACCAGCGACCAGTACAAGGCCTACCTGCAGGACCTGGTGGAGGACATGGACTTCCAGGCCACCG<br>GCAACATC<br>(super mouse IRF3 S396D; no epitope tag) |
| 151 | ATGGGCACCCCCAAGCCCAGAATCCTGCCCTGGCTGGTGAGCCAGCTGGACCTGGGCCAGCTGGAGGGAGTGG<br>CCTGGGTGAACAAGAGCAGAACCAGATTCAGAATCCCCTGGAAGCACGGCCTCAGACAGGACGCCCAGCAGGA<br>GGACTTCGGCATTTTTCAGGCTTGGGCCGAGGCCACCGGCGCCTACGTGCCCGGCAGAGACAAGCCCGACCTGC<br>CCACCTGGAAAAGAAACTTCAGAAGCGCCTTGAATAGAAAGGAGGGCCTGAGACTGGCCGAGGACAGAAGCA |

-continued

SEQUENCE LISTING SUMMARY

| SEQ ID NO: | SEQUENCE |
|---|---|
| | AGGACCCCCACGACCCTCACAAGATCTACGAGTTCGTGAATAGCGGCGTGGGCGACTTTAGCCAGCCCGACACC AGCCCCGACACCAACGGCGGCGGCAGCACCAGCGACACGCAGGAGGACATCCTGGATGAACTGCTGGGCAACA TGGTGCTGGCCCCCCTGCCCGATCCCGGCCCCCCTTCGCTTGCCGTGGCCCCCGAGCCCTGCCCCCAGCCCCTGA GAAGCCCCTCTCTGGATAACCCCACCCCCTTCCCCAACCTGGGCCCCAGCGAGAATCCACTGAAGAGACTTCTGG TCCCCGGCGAGGAGTGGGAGTTCGAGGTGACCGCCTTCTACAGAGGCAGACAGGTGTTCCAGCAGACCATCAG CTGCCCCGAAGGCCTGAGATTAGTGGGCAGCGAAGTGGGCGACAGGACCCTGCCCGGGTGGCCCGTGACCCTG CCCGATCCCGGCATGAGCCTGACCGACAGAGGTGTGATGAGCTACGTGAGACACGTGCTGAGCTGCCTGGGCG GCGGCCTGGCACTGTGGAGAGCCGGCCAGTGGCTGTGGGCCCAGAGACTGGGCCACTGCCACACCTACTGGGC CGTGAGCGAGGAGCTGCTGCCCAACAGCGGCCACGGCCCCGACGGCGAGGTGCCCAAGGACAAGGAAGGGGG CGTGTTCGACCTGGGCCCCTTCATCGTAGACCTGATCACCTTTACCGAGGGCAGCGGCAGGAGCCCCAGATACG CCCTGTGGTTCTGCGTGGGCGAAAGCTGGCCCCAGGACCAGCCCTGGACCAAGAGACTGGTGATGGTGAAGGT AGTGCCCACCTGCCTGAGAGCCTTAGTGGAGATGGCCAGAGTGGGCGGGGCCAGCAGCCTGGAGAACACCGTG GATCTTCACATCGACAACAGCCACCCCCTGAGCCTGACCAGCGACCAGTACAAGGCCTACCTGCAGGACCTGGT GGAGGGCATGGACTTCCAGGGCCCCGGCGAGACC<br>(super human IRF3 S396D; no epitope tag) |
| 152 | ATGGCGCTGGCCCCCGAAAGAGCCGCCCCCAGAGTCCTCTTCGGCGAATGGCTCCTTGGCGAAATTTCGTCGGG CTGCTACGAGGGCTTACAATGGCTGGATGAGGCGAGAACCTGTTTCAGGGTGCCCTGGAAACACTTCGCCAGAA AGGATCTAAGCGAAGCAGATGCTAGAATTTTTAAGGCTTGGGCCGTGGCCAGGGGAAGATGGCCCCCCTCGAG CAGAGGCGGCGGCCCTCCCCCCGAGGCAGAAACGGCCGAGAGAGCCGGATGGAAAACCAATTTCAGATGCGCC CTGAGATCTACAAGAAGATTCGTGATGCTTAGAGACAACAGCGGAGATCCCGCCGATCCCCATAAGGTGTATGC CCTGTCCCGGGAGCTGTGCTGGAGGGAAGGGCCTGGCACTGACCAGACCGAAGCCGAAGCCCCCGCGGCCGTG CCGCCGCCCCAAGGAGGCCCACCAGGCCCTTTCCTCGCTCACACCCACGCCGGTCTGCAAGCCCCGGGACCTCTA CCTGCCCCTGCCGGCGATAAAGGCGACCTGTTGCTGCAGGCCGTCCAACAGAGCTGCCTGGCCGATCATCTGCT CACAGCCAGCTGGGGCGCTGACCCCGTCCCAACAAAGGCCCCCGGTGAGGGCCAAGAAGGCCTGCCTCTGACC GGCGCCTGTGCCGGCGGCCCTGGCCTGCCTGCTGGCGAGCTGTACGGATGGGCTGTCGAAACCACTCCCTCCCC CGGCCCCCAACCTGCGGCCCTGACAACCGGCGAGGCAGCCGCACCCGAAAGCCCCCACCAGGCCGAACCCTACC TCAGTCCCAGCCCCTCCGCCTGCACCGCTGTGCAGGAGCCCAGCCCCGGTGCTCTGGACGTAACAATCATGTACA AAGGCAGAACCGTGCTTCAGAAGGTGGTTGGACACCCCTCCTGTACTTTTCTCTACGGCCCCCCCGACCCTGCCG TGAGAGCTACCGACCCGCAACAGGTGGCCTTTCCCTCGCCCGCCGAACTGCCCGATCAAAAACAGCTGAGATAC ACCGAGGAGCTGCTGAGACACGTGGCGCCGGGCTTACACCTAGAGTTGAGAGGCCCCCAACTCTGGGCCAGAC GCATGGGCAAGTGTAAGGTGTACTGGGAGGTCGGGGGCCCTCCCGGCTCTGCCAGCCCCAGCACCCCTGCTTGT CTCTTGCCCAGAAACTGTGATACCCCCATCTTCGACTTCCGTGTATTTTTCCAGGAACTGGTCGAGTTTAGAGCCA GACAGAGACGAGGCAGCCCCAGATATACAATCTACCTCGGCTTCGGCCAGGACCTGAGTGCCGGCAGACCTAA GGAGAAGTCGCTGGTCCTAGTGAAGTTAGAGCCCTGGCTATGTAGAGTGCACCTGGAGGGCACCCAGAGAGAA GGAGTGAGCAGCCTGGACAGCAGCAGCCTGAGTCTGTGCCTGAGCTCCGCCAACTCGCTGTATGATGACATCGA GTGTTTCCTCATGGAGCTGGAGCAGCCCGCC<br>(Wild-type Hu IRF7 isoform A; P037 without epitope tag) |
| 153 | ATGGCCCTTGCCCCTGAGCGGGCCGCCCCCAGAGTGTTATTCGGCGAGTGGCTGCTGGGCGAGATCAGCAGCG GCTGCTACGAGGGACTGCAGTGGCTGGACGAGGCTAGAACCTGCTTCAGAGTGCCCTGGAAGCATTTCGCCAG AAAAGACCTGAGCGAGGCTGATGCTAGAATCTTCAAAGCCTGGGCTGTGGCCCGAGGAAGATGGCCCCCCAGC AGCAGAGGAGGCGGCCCTCCTCCCGAGGCCGAAACCGCAGAGCGTGCTGGCTGGAAAACCAACTTTAGGTGTG CCCTGAGGAGCACCAGAAGATTCGTTATGCTCAGAGACAACAGCGGGGACCCCGCCGACCCGCACAAGGTGTA CGCCTTAAGTAGGGAGCTGTGCTGGAGAGAGGGACCGGGGACCGACCAAACCGAGGCTGAGGCGCCCGCCGC CGTTCCACCTCCCCAGGGTGGTCCCCCAGGGCCCTTTCTGGCACACACCCACGCCGGATTACAGGCGCCAGGGC CCTTACCCGCCCCCGCCGGAGACAAAGGCGACCTCCTGCTGCAAGCCGTGCAACAAAGCTGCCTGGCCGATCAC TTACTAACCGCTAGCTGGGGCGCCGATCCTGTTCCCACCAAGGCCCCCGGTGAAGGGCAAGAAGGACTGCCCTT AACCGGCGCCTGTGCCGGAGGCCCTGGTCTGCCAGCCGGCGAGCTGTACGGTTGGGCTGTCGAAACAACACCC AGTCCGGGCCCACAGCCTGCCGCTCTGACCACCGGCGAAGCCGCCGCCCCCGAGAGCCCACACCAGGCTGAACC CTACCTGAGCCCCAGCCCCAGCGCCTGCACCGCTGTGCAGGAGCCTAGCCCCGGCGCTCTTGATGTGACAATAAT GTACAAGGGCAGGACCGTGCTGCAAAAGGTCGTGGGCCATCCGTCGTGTACCTTTCTGTACGGCCCTCCAGACC CCGCGGTTAGAGCCACCGACCCCCAGCAAGTCGCCTTCCCCTCCCCCGCCGAACTGCCCGACCAAAAGCAGCTGC GGTACACAGAAGAACTACTTAGACACGTGGCCCCCGGTCTGCACTTGGAGCTGAGAGGCCCCCAGCTCTGGGCC AGAAGAATGGGCAAGTGCAAAGTGTACTGGGAGGTGGGCGGCCCACCCGGCTCAGCTTCGCCCTCCACACCCG CATGCCTGCTGCCCAGAAATTGCGACACGCCCATCTTCGATTTTAGAGTGTTCTTTCAGGAGTTGGTGGAGTTCA GAGCCAGACAAAGACGCGGCAGCCCCAGATACACCATTTACCTCGGCTTCGGCCAGGACCTCAGCGCTGGCAGA CCCAAGGAGAAGAGTCTGGTCCTCGTGAAGCTGGAGCCCTGGCTGTGCAGAGTGCACCTGGAGGGCACCCAGC GTGAAGGCGTGAGCAGCCTGGATTCAAGCGACCTGGACCTATGCCTAAGCAGCGCTAACTCACTGTACGACGAT ATCGAATGCTTCCTGATGGAACTGGAGCAGCCTGCC<br>(constitutively active Hu IRF7 S477D/S479D; P033 without epitope tag) |
| 154 | ATGGCCCTGGCACCCGAGAGGGCCGCCCCCAGGGTGCTCTTCGGCGAGTGGTTACTAGGCGAAATTAGCAGCG GCTGCTATGAAGGCCTTCAGTGGCTGGACGAGGCCAGAACCTGCTTTAGAGTTCCCTGGAAGCACTTCGCCCGG AAAGATCTCTCTGAAGCCGACGCCAGAATATTCAAGGCCTGGGCTGTCGCCAGGGGCAGGTGGCCACCCTCCAG CCGAGGTGGCGGCCCTCCCCCTGAGGCTGAGACTGCGGAAAGGGCGGGCTGGAAGACCAATTTCAGATGCGCT CTGAGAAGCACCAGACGTTTTGTGATGCTAAGAGACAATAGCGGCGATCCCGCCGACCCCCATAAGGTATACGC ACTGAGCCGAGAGCTCTGTTGGAGAGAAGGCCCCGGCACCGACCAGACCGAGGCTGAAGCCCCTGCAGCCGTG CCCCCCCCTCAAGGCGGGCCCCCCGGCCCCTTCCTGGCCCATACCCATGCAGGGTTACAAGCACCCGGGCCCTTG CCCGCCCCAGCGGGAGACAAGGGCGACCTCTTACTGCAGGCCGTGCAACAAAGTTGTCTGGCGGACCACCTGCT GACCGCATCATGGGGCGCGGATCCTGTGCCCACCAAGGCACCCGGCGAAGGCCAGGAGGGCCTGCCCTTGACC GGCGCCTGCGCTGGCGGACCCGGCCTACCTGCTGGCGAACTGTATGGCTGGGCCGTAGAGACGACTCCCAGCC CTGGCCCACAACCCGCGGCTTTGACCACCGGCGAAGCCGCCGCCCCCGAGTCTCCGCACCAGGCCGAGCCTTAC |

-continued

SEQUENCE LISTING SUMMARY

SEQ ID NO: SEQUENCE

CTCAGCCCAAGCCCTAGCGCCTGCACCGCCGTGCAAGAACCTAGCCCCGGAGCCCTGGATGTGACAATCATGTA
CAAGGGTAGAACCGTACTGCAAAAGGTGGTGGGTCATCCCAGCTGCACCTTTCTTTACGGCCCACCCGACCCTGC
CGTGCGAGCCACAGACCCACAACAGGTCGCCTTCCCAAGCCCCGCCGAACTGCCCGATCAGAAACAGCTGAGAT
ATACAGAGGAGCTTCTGCGGCACGTAGCTCCCGGCCTACATCTCGAGCTGAGGGGCCCACAACTGTGGGCCAGA
CGCATGGGCAAATGCAAGGTCTACTGGGAAGTGGGAGGCCCCCCCGGCAGCGCATCTCCCAGCACGCCCCGCGT
GCCTGCTGCCTAGAAATTGCGACACCCCCATCTTTGACTTCCGGGTATTCTTTCAGGAGCTGGTAGAGTTCAGAG
CCAGGCAGCGGAGGGGCTCCCCCAGATACACAATCTACCTGGGCTTCGGACAGGACCTGTCCGCCGGCCGCCCC
AAGGAAAAGAGCCTGGTGCTGGTGAAGCTGGAGCCCTGGCTGTGTAGGGTACACCTCGAAGGCACCCAGAGA
GAAGGAGTGAGCTCGCTTGATGACAGCGATCTGTCGGATTGCCTTAGCAGCGCCAACAGCCTGTATGATGATAT
CGAGTGCTTCCTTATGGAACTGGAGCAGCCCGCC
(constitutively active Hu IRF7 S475D/S477D/L480D; P034 without epitope tag)

155 ATGGCCCTAGCCCCCGAAAGAGCAGCTCCCAGAGTGCTGTTCGGCGAATGGCTGCTTGGCGAGATCAGCAGCG
GCTGCTACGAAGGCCTGCAGTGGCTGGACGAAGCCCGCACCTGTTTCAGAGTGCCCTGGAAGCACTTCGCTAGA
AAGGATTTGAGCGAGGCTGATGCTAGAATCTTTAAGGCTTGGGCTGTGGCAAGAGGCAGATGGCCGCCTAGTA
GCAGAGGGGGCGGACCTCCCCCCGAGGCTGAGACCGCTGAGAGAGCAGGGTGGAAAACCAACTTCAGATGCG
CGCTGAGAAGCACCCGAAGATTCGTGATGCTACGTGACAATAGCGGCGACCCCGCCGACCCCCACAAAGTGTAC
GCCCTGTCCCGAGAACTTTGCTGGAGAGAGGGACCCGGCACCGATCAAACAGAGGCTGAGGCCCCGGCCGCTG
TACCCCCGCCCCAAGGAGGCCCCCCAGGCCCCTTTCTGGCTCATACACATGCCGGCCTGCAGGCACCCGGGCCCC
TCCCGGCTCCTGCCGGCGACAAGGGCGATCTCCTTCTCCAGGCCGTGCAGCAGAGCTGCCTGGCCGATCACCTG
CTGACCGCCTCGTGGGGCGCCGACCCCGTGCCCACCAAAGCCCCGGGTGAAGGCCAAGAGGGGCTCCCTTTAAC
CGGAGCATGCGCCGGAGGCCCCGGCCTGCCAGCCGGCGAGTTATATGGCTGGGCTGTGGAGACCACACCCTCC
CCCGGCCCTCAACCCGCTGCCCTGACCACCGGTGAGGCCGCCGCCCCCGAGAGCCCACACCAGGCCGAACCCTA
CCTGAGCCCTAGCCCTAGCGCCTGCACCGCCGTGCAAGAACCCAGCCCCGGAGCCCTGGATGTGACCATTATGT
ACAAGGGCCGGACAGTGCTGCAAAAGGTTGTGGGACACCCGAGCTGCACCTTTCTGTACGGTCCGCCTGACCCC
GCCGTGAGAGCCACGGACCCGCAGCAGGTGGCCTTCCCCTCACCCGCGGAGCTGCCCGACCAAAAGCAACTCA
GATACACAGAAGAACTATTGCGTCACGTCGCGCCCGGCCTGCATCTGGAGCTGAGAGGCCCCCAGCTCTGGGCC
AGAAGGATGGGCAAATGCAAGGTGTACTGGGAGGTGGGAGGCCCCCCCGGCAGCGCCAGCCCCAGCACTCCC
GCGTGCCTGCTGCCCAGAAATTGCGACACTCCCATCTTCGATTTCAGGGTGTTCTTCCAGGAGCTGGTGGAGTTC
AGAGCCAGGCAGAGAAGGGGTAGCCCCAGATACACAATCTATCTAGGCTTTGGACAAGATCTGAGCGCCGGCC
GGCCTAAGGAAAAAAAGCCTGGTGCTGGTAAAGCTGGAGCCGTGGCTTTGTAGAGTGCACCTGGAGGGGACGCA
GCGAGAGGGCGTGAGCAGCTTAGACGACGATGACTTGGATCTGTGTCTCGACAGCGCCAACGACTTGTACGAC
GACATCGAGTGCTTCCTGATGGAACTGGAGCAGCCCGCC
(constitutively active Hu IRF7 S475D/S476D/S477D/S479D/S483D/S487D; P035 without epitope tag)

156 ATGGCCCTGGCCCCCGAGAGAGCCGCCCCCAGAGTGCTCTTCGGCGAGTGGCTGCTGGGCGAGATAAGCAGCG
GCTGCTACGAAGGTCTGCAGTGGCTAGACGAGGCCAGAACCTGCTTTAGAGTGCCCTGGAAGCACTTCGCTCGA
AAGGACCTGTCCGAGGCCGATGCTAGAATTTTTAAGGCTTGGGCCGTCGCTAGGGGAAGATGGCCCCCCTAGCA
GTAGAGGCGGCGGCCCCCCTCCCGAAGCCGAGACGGCCGAGAGGGCCGGCTGGAAAACCAATTTCAGATGCGC
CCTGAGGAGCACCCGCAGGTTCGTAATGCTGCGAGACAATAGCGGCGATCCTGCGGATCCTCACAAGGTTTACG
CCTTGAGTAGAGAACTGTGCTGGCGGGAGGGCCCCGGAACCGACCAGACGGAGGCAGAGGCACCCGCTGCCG
TGCCCCCCCCTCAAGGAGGACCCCCTGGACCCTTTCTGGCCCACACCCACGCTGGTCTGCAGGCCCCCAGGCCCAC
TGCCCGCCCCAGCGGGCGATAAGGGTGACCTGCTCCTACAGGCGGTGCAACAGAGCTGTCTGGCCGACCACCTG
TTGACCGCCAGCTGGGGGGCCGACCCGGTGCCCACCAAAGCTCCCGGAGAGGGCCAAGAAGGCCTCCCACTAA
CTGGCGCCTGCGCCGGGGGCCCGGGATTACCCGCCGGCGAGCTGTATGGCTGGGCCGTGGAGACCACGCCCAG
CCCCGAGGGCGTGTCGTCCCTGGACAGCAGCAGCCTGAGCCTGTGCCTGAGCTCCGCCAACAGCCTGTATGACG
ACATCGAGTGCTTCCTGATGGAGCTGGAACAACCCGCC
(constitutively active truncated Hu IRF7 1-246 + 468-503; P032 without epitope tag)

157 ATGGCACTGGCGCCTGAAAGAGCCGCTCCGCGTGTGCTCTTCGGCGAGTGGCTGCTGGGCGAGATCAGCTCCG
GCTGCTACGAGGGTCTACAGTGGCTGGACGAGGCCAGAACCTGTTTTAGAGTGCCCTGGAAGCACTTCGCGAG
AAAGGACCTGAGCGAGGCCGACGCCAGAATCTTCAAAGCCTGGGCAGTGGCTAGGGGCAGATGGCCTCCCAGC
AGCCGGGGCGGCGGCCCACCCCCCGAGGCCGAAACCGCCGAAAGAGCTGGCTGGAAGACCAACTTCAGATGC
GCCCTGAGAAGCACCAGAAGATTTGTCATGCTGAGAGATAATTCAGGAGACCCCGCCGACCCTCACAAGGTGTA
CGCCCTGTCCAGAGAGCTGTGTTGGAGAGAGGGCCCCGGAACCGACCAGACCGAGGCCGAGGCTCCAGCTGCC
GTGCCACCCCCCCAAGGCGGACCACCCGGCCCCCTTCTTGGCACATACGCACGCCGGCCTCCAGGCTCCCGGCCCT
CTGCCCGCCCCTGCTGGTGACAAAGGCGATCTGCTGCTGCAAGCCGTCCAGCAATCCTGCTTGGCTGACCACCTG
CTGACCGCTAGCTGGGGAGCCGACCCCGTTCCCACCAAGGCTCCCGGAGAAGGACAGGAGGGCCTGCCCCTTA
CCGGCGCTTGCGCGGGGGGCCCTGGCTTGCCTGCCGGCGAACTGTACGGCTGGGCCGTGGAGACCACGCCTTC
CCCCGAGGGCGTGTCCAGCCTGGACGATGATGACCTGGATCTGTGCCTGGACAGCGCCAACGACCTGTACGATG
ACATCGAGTGCTTTTTGATGGAGCTGGAGCAGCCCGCC
(constitutively active truncated Hu IRF7 1-246 + 468-503 plus S475D/S476D/S477D/S479D/S483D/S487D; P036 without epitope tag)

158 ATGGCCCTGGCCCCCGAGAGAGCCGCGCCCAGAGTGCTGTTCGGCGAATGGCTGCTGGGCGAGATCAGCAGCG
GCTGCTATGAGGGCCTGCAGTGGCTCGACGAAGCCAGGACGTGCTTCAGAGTCCCCTGGAAGCACTTCGCCAGA
AAGGATCTGAGCGAGGCTGACGCCAGAATCTTCAAGGCCTGGGCAGTTGCGCGTGGGAGATGGCCCCCCAGCT
CGCGGGGCGGCGGTCCCCCCCCTGAGGCCGAGACCGCCGAAAGAGCCGGATGGAAAACCAACTTTCGATGCGC
CCTCAGAAGCACCAGACGGTTTGTGATGCTGAGAGATAACAGCGGCGACCCTGCAGACCCCCATAAAGTGTATG
CCCTGAGCAGAGAGCTGTGTTGGCGAGAGGGCCCCGGAACCGACCAAACCGAGGCCGAGGCCCCCGCCGCCGT
ACCCCCCCCTCAAGGCCCCCAGCCTGCTGCTCTGACCACGGGAGAAGCCGCCGCTCCTGAGAGCCCCCACCAAG
CCGAGCCCTATCTGAGCCCTAGCCCCAGCGCCTGCACCGCCGTGCAGGAGCCCTCACCGGGCGCCCCTAGACGTG
ACCATCATGTACAAGGGGCGCACGGTGCTGCAAAAGGTGGTGGGCCACCCCAGCTGCACCTTCCTGTACGGCCC

-continued

SEQUENCE LISTING SUMMARY

| SEQ ID NO: | SEQUENCE |
|---|---|
| | CCCCGACCCTGCCGTGAGAGCCACCGACCCCCAGCAAGTCGCCTTCCCCAGCCCCGCCGAGCTGCCCGACCAGA<br>AGCAGCTGAGGTACACCGAGGAGTTGCTGAGACATGTGGCCCCCGGCTTGCACCTCGAGCTGAGAGGCCCGCA<br>GCTCTGGGCCAGAAGAATGGGCAAGTGCAAGGTGTACTGGGAGGTGGGCGGCCCCCCGGCAGCGCGAGCCC<br>AAGCACCCCGGCCTGCCTGCTGCCTAGAAACTGCGACACCCCTATCTTCGACTTCAGAGTATTTTTCCAGGAGCT<br>GGTCGAGTTCAGGGCCAGACAGCGTAGAGGCAGCCCCAGATACACCATCTACCTTGGATTCGGCCAGGACCTGA<br>GCGCCGGCAGACCCAAAGAGAAGTCCCTGGTACTGGTGAAGCTAGAGCCCTGGCTGTGTAGGGTGCATCTGGA<br>AGGCACCCAAAGAGAGGGCGTAAGCTCGCTTGACAGCAGCAGCCTCAGCCTGTGCCTGAGCAGCGCTAACAGC<br>TTATACGACGACATCGAGTGCTTCCTGATGGAGCTGGAACAACCCGCC<br>(truncated Hu IRF7 1-151 + 247-503; P038 without epitope tag; null mutation) |
| 159 | ATGGGCGGCCCTCCCGGGCCTTTCCTGGCCCATACACACGCCGGCCTACAGGCTCCTGGCCCTCTGCCCGCCCCG<br>GCCGGCGACAAGGGCGACCTCCTGCTGCAGGCCGTGCAGCAGTCCTGTCTGGCCGACCACCTGCTGACTGCTAG<br>CTGGGGCGCCGATCCCGTGCCCACCAAGGCCCCAGGAGAGGGGCAAGAGGGCCTGCCTCTAACCGGCGCATGC<br>GCAGGTGGACCAGGCCTCCCCGCCGGCGAGCTGTATGGTTGGGCCGTGGAGACAACCCCCAGCCCCGGCCCGC<br>AGCCTGCTGCGCTGACCACAGGCGAGGCCGCTGCCCCTGAGAGCCCCCACCAAGCTGAACCCTACCTGAGCCCC<br>AGCCCCTCTGCCTGCACAGCGGTGCAGGAGCCCAGTCCCGGCGCCTTGGACGTGACCATCATGTATAAGGGCAG<br>GACTGTGTTACAAAAGGTAGTGGGCCACCCAAGTTGTACCTTTCTGTACGGGCCCCCCGACCCAGCCGTGCGCG<br>CCACCGACCCCCAGCAGGTGGCCTTCCCCAGCCCCGCTGAGTTGCCCGATCAGAAACAACTCCGGTACACCGAG<br>GAATTACTTAGACATGTGGCTCCCGGCCTGCATCTGGAGCTTAGAGGTCCACAGTTGTGGGCCAGAAGAATGGG<br>CAAGTGCAAGGTTTATTGGGAGGTCGGAGGCCCCCGGGCAGCGCCAGCCCCAGCACCCCCGCCTGTCTTCTGC<br>CCAGAAACTGCGACACCCCAATCTTCGATTTCAGAGTGTTTTTCCAGGAACTGGTGGAGTTCAGAGCAAGGCAA<br>AGAAGAGGCAGCCCTAGATACACCATCTACCTGGGCTTTGGCCAAGACCTGAGCGCCGGCAGACCCAAGGAAA<br>AATCCCTGGTCCTGGTGAAACTGGAGCCCTGGCTGTGCAGAGTCCACCTGGAGGGCACCCAGAGAGAGGGCGT<br>GAGCAGCCTGGACTCGAGCAGCCTGTCCCTGTGTCTGAGCAGCGCGAATTCGCTATATGACGACATCGAATGCT<br>TTCTGATGGAGCTGGAACAGCCCGCC<br>(truncated Hu IRF7 152-503; P039 without epitope tag; null mutation) |
| 160 | ATGCCTCACAGCAGCCTCCACCCTAGCATCCCTTGCCCTAGAGGCCACGGCGCCCAGAAGGCCGCCCTCGTGCT<br>TTAAGCGCCTGCTTGGTGACCCTTTGGGGCTTGGGCGAGCCTCCAGAGCACACCTTGAGATATTTGGTGCTCCAC<br>CTGGCCAGCCTTCAGCTGGGCTTGTTACTCAACGGCGTGTGCAGCCTGGCCGAGGAGCTGAGACACATCCACAG<br>CAGATACAGAGGCAGCTACTGGAGAACCGTGAGAGCGTGTCTGGGCTGCCCTCTGAGAAGAGGCGCCTTGCTT<br>CTTCTCAGTATCTACTTCTACTACTCCCTGCCTAACGCCGTGGGCCCTCCTTTCACCTGGATGCTGGCACTGCTCG<br>GCCTCAGCCAGGCCCTGAACATCTTGTTGGGCTTGAAGGGCCTGGCCCCTGCCGAGATCAGCGCCGTGTGCGAG<br>AAGGGCAACTTCAACATGGCCCACGGATTGGCTTGGAGCTACTACATCGGCTACCTGAGACTGATCCTGCCTGA<br>GCTGCAGGCCAGAATCAGAACCTACAACCAGCACTACAACAACCTGCTGCGCGGCGCAGTGAGCCAGAGACTG<br>TATATTCTGCTGCCTCTGGACTGCGGCGTGCCTGACAACCTGAGCATGGCCGACCCTAACATCAGATTCCTGGAC<br>AAGCTGCCTCAGCAGACCGGCGACCACGCCGGCATCAAGGACAGAGTGTACAGCAACAGCATCTATGAGCTGC<br>TCGAGAATGGCCAGAGAGCCGGCACCTGCGTGCTGGAGTACGCCACCCCTCTGCAGACCCTGTTCGCCATGAGC<br>CAGTATAGTCAAGCTGGCTTCAGCAGAGAGGACAGACTGGAGCAGGCCAAGCTGTTCTGCAGAACCCTGGAGG<br>ACATTCTGGCTGACGCCCCTGAGAGCCAGAACAACTGCCGACTGATCGCCTACCAGGAACCAGCCGACGACAGC<br>AGCTTCAGTCTTTCTCAGGAGGTTCTTCGCCACTTGCGCCAGGAGGAGAAGGAGGAGGTGACCGTGGGCAGCC<br>TGAAGACCTCCGCAGTCCCTAGCACCAGCACCATGAGTCAGGAGCCGGAGCTATTAATCAGCGGCATGGAGAA<br>GCCTCTTCCACTCCGAACCGACTTCAGCGCCACCAACTTCAGCCTGCTGAAGCAGGCAGGTGACGTTGAGGAGA<br>ATCCGGGACCTATGACCGAGTACAAGCTGGTGGTTGTGGGCGCCGACGGCGTGGGCAAGAGCGCCCTGACCAT<br>CCAGCTGATCCAG<br>(KRAS(G12D)25mer_nt.STING(V155M)) |
| 161 | ATGACCGAGTACAAGCTAGTAGTCGTGGGCGCCGACGGCGTGGGCAAGAGCGCCCTCACCATCCAGCTAATCC<br>AGGCCACCAACTTCAGCTTGCTCAAGCAGGCCGGCGACGTGGAGGAGAACCCAGGCCCTATGCCTCACAGCAG<br>CCTTCACCCTAGCATCCCTTGCCCTAGAGGCCACGGCGCCCAGAAGGCCGCCCTGGTGCTGCTGAGCGCCTGCCT<br>GGTGACCCTGTGGGGCCTGGGCGAGCCTCCTGAGCACACCCTGAGATATCTGGTGCTTCACCTGGCCAGTTTAC<br>AGCTGGGCCTGCTTCTTAACGGCGTGTGCAGCCTGGCCGAGGAGCTGAGACACATCCACAGCAGATACAGAGG<br>CAGCTACTGGAGAACCGTGAGAGCCTGCCTAGGCTGCCCTCTGAGAAGAGGCGCTCTGTTGCTACTTTCCATCTA<br>CTTCTACTACTCCCTGCCTAACGCCGTGGGCCCTCCTTTCACTTGGATGCTGGCGTTGCTGGGTCTGAGCCAGGCC<br>CTGAACATCCTTCTCGGTCTGAAGGGCCTGGCCCCTGCCGAGATCAGCGCCGTGTGCGAGAAGGGCAACTTCAA<br>CATGGCCCACGGACTCGCCTGGAGCTACTACATCGGCTACCTGAGACTGATCCTGCCTGAGCTGCAGGCCAGAA<br>TCAGAACCTACAACCAGCACTACAACAACCTGCTGCGGGGCGCCGTGAGCCAGAGACTGTATATACTTCTTCCTC<br>TGGACTGCGGCGTGCCTGACAACCTGAGCATGGCCGACCCTAACATCAGATTCCTGGACAAGCTGCCTCAGCAG<br>ACCGGCGACCACGCCGGCATCAAGGACAGAGTGTACAGCAACTCCATTTATGAGCTGCTCGAGAATGGCCAGA<br>GAGCCGGCACCTGCGTGCTGGAGTACGCCACCCCTCTGCAGACCCTGTTCGCCATGAGCCAGTACAGTCAGGCT<br>GGATTCAGCAGAGAGGACAGACTGGAGCAGGCCAAGCTGTTCTGCAGGACACTGGAGGACATACTAGCAGAC<br>GCCCCTGAGAGCCAGAACAACTGCAGACTGATTGCCTACCAGGAGCCTGCGGACGACAGCTCCTTCAGTCTGAG<br>TCAGGAGGTGTTGCGGCACTTACGCCAAGAAGAGAAGGAGGAGGTGACCGTGGGCAGCCTGAAGACTAGCGC<br>TGTGCCTAGCACCAGCACAATGTCACAGGAGCCGGAATTGCTAATCAGCGGCATGGAGAAGCCTCTCCCATTAC<br>GTACCGACTTCAGC<br>(KRAS(G12D)25mer_ct.STING(V155M)) |
| 162 | ATGCCTCACAGCAGCCTTCACCCTAGCATCCCTTGCCCTAGAGGCCACGGCGCCCAGAAGGCCGCCCTAGTGCTC<br>CTTAGCGCCTGCCTCGTGACCCTATGGGGCTTAGGCGAGCCTCCAGAGCACACCTTGAGATACCTCGTCCTCCAC<br>CTGGCTAGTCTACAGCTGGGCCTTCTCCTCAACGGCGTGTGCAGCCTGGCCGAGGAGCTGAGACACATCCACAG<br>CAGATACAGAGGCAGCTACTGGAGAACCGTGAGAGCGTGCCTGGGCTGCCCTCTGAGAAGAGGCGCACTGCTG<br>TTACTCAGCATCTACTTCTACTACTCACTGCCAAACGCCGTGGGCCCTCCTTTCACCTGGATGCTGGCCTTGCTCG<br>GATTGAGCCAGGCCCTGAACATTTTACTGGGATTGAAGGGCCTGGCCCCTGCCGAGATCAGCGCCGTGTGCGAG |

-continued

SEQUENCE LISTING SUMMARY

| SEQ ID NO: | SEQUENCE |
|---|---|
| | AAGGGCAACTTCAACATGGCCCACGGCCTAGCTTGGAGCTACTACATCGGCTACCTGAGACTGATCCTGCCTGA<br>GCTGCAGGCCAGAATCAGAACCTACAACCAGCACTACAACAACCTGCTGCGTGGAGCGGTGAGCCAGAGACTG<br>TATATCCTCCTGCCTCTGGACTGCGGAGTGCCTGACAACCTGAGCATGGCCGACCCTAACATCAGATTCCTGGAC<br>AAGCTGCCTCAGCAGACCGGCGACCACGCCGGCATCAAGGACAGAGTGTACAGCAACTCAATCTACGAGCTGTT<br>GGAGAATGGCCAGAGAGCCGGCACCTGCGTGCTGGAGTACGCCACCCCTCTGCAGACCCTGTTCGCCATGAGCC<br>AGTACTCTCAGGCAGGCTTCAGCAGAGAGGACAGACTGGAGCAGGCCAAGCTGTTCTGCAGAACCCTGGAGGA<br>CATCCTGGCGGACGCCCCTGAGAGCCAGAACAACTGCCGGCTTATCGCCTACCAGGAGCCAGCAGACGACAGC<br>AGCTTCTCTCTCTCACAAGAGGTACTGCGCCATCTTCGCCAGGAGGAGAAGGAGGAGGTGACCGTGGGCAGCCT<br>GAAGACATCCGCCGTACCTAGCACCAGCACCATGTCTCAGGAACCGGAACTGTTGATCAGCGGCATGGAGAAGC<br>CTCTGCCACTGCGCACCGACTTCAGCGCCACCAACTTCTCCCTACTGAAGCAAGCCGGTGACGTTGAAGAGAACC<br>CTGGCCCTATGACCGAGTACAAGCTGGTAGTAGTAGGCGCCGACGGCGTGGGCAAGAGCGCCCTGACCATCCA<br>GCTGATCCAGATGACTGAATATAAGCTTGTCGTCGTGGGCGCAGATGGCGTTGGTAAGAGCGCACTTACAATTC<br>AACTCATTCAGATGACGGAGTATAAGCTGGTGGTGGTCGGAGCTGACGGCGTAGGCAAGAGTGCCCTTACTATT<br>CAGCTAATTCAG<br>(KRAS(G12D)25mer^3_nt.STING(V155M)) |
| 163 | ATGACCGAGTACAAGCTTGTGGTGGTTGGCGCCGACGGCGTGGGCAAGAGCGCCTTAACCATCCAGCTTATCCA<br>GATGACAGAGTATAAGCTAGTGGTGGTCGGCGCAGACGGAGTGGGAAAGAGTGCATTAACTATTCAACTCATC<br>CAAATGACCGAATACAAGCTAGTAGTTGTGGGTGCAGATGGCGTCGGCAAGTCTGCACTGACAATTCAGCTCAT<br>CCAGGCCACCAACTTCAGCCTGCTGAAGCAGGCCGGCGACGTGGAGGAGAACCCTGGCCCTATGCCTCACAGCA<br>GCCTGCACCCTAGCATCCCTTGCCCTAGAGGCCACGGCGCCCAGAAGGCCGCCCTGGTGCTGCTGAGCGCCTGC<br>CTGGTGACCCTGTGGGGCCTGGGCGAGCCTCCTGAGCACACCCTGAGATACCTAGTTTTGCACCTGGCTTCTCTG<br>CAGCTGGGCCTACTGCTCAACGGCGTGTGCAGCCTGGCCGAGGAGCTGAGACACATCCACAGCAGATACAGAG<br>GCAGCTACTGGAGAACCGTGAGAGCATGCTTAGGCTGCCCTCTGAGAAGAGGCGCTCTGCTCCTCTTGTCCATCT<br>ACTTCTACTACTCGCTACCTAACGCCGTGGGCCCTCCTTTCACCTGGATGCTGGCCCTCTTGGGATTAAGCCAGGC<br>CCTGAACATCTTGCTGGGACTGAAGGGCCTGGCCCCTGCCGAGATCAGCGCCGTGTGCGAGAAGGGCAACTTCA<br>ACATGGCCCACGGACTCGCTTGGAGCTACTACATCGGCTACCTGAGACTGATCCTGCCTGAGCTGCAGGCCAGA<br>ATCAGAACCTACAACCAGCACTACAACAACCTGCTGCGGGGAGCAGTGAGCCAGAGACTGTATATTCTGCTCCC<br>TCTGGACTGCGGCGTGCCTGACAACCTGAGCATGGCCGACCCTAACATCAGATTCCTGGACAAGCTGCCTCAGC<br>AGACCGGCGACCACGCCGGCATCAAGGACAGAGTGTACAGCAACAGCATTTACGAGCTGCTGGAGAACGGCCA<br>GAGAGCCGGCACCTGCGTGCTGGAGTACGCCACCCCTCTGCAGACCCTGTTCGCCATGAGCCAGTACTCCCAGG<br>CAGGATTCAGCAGAGAGGACAGACTGGAGCAGGCCAAGCTGTTCTGCCGTACTCTTGAGGACATCCTTGCAGAC<br>GCCCCTGAGAGCCAGAACAACTGCCGGTTGATTGCCTACCAGGAACCGGCAGACGACAGCTCATTCTCCTTGTCT<br>CAGGAGGTCCTTAGACACCTGCGGCAGGAGGAGAAGGAGGAGGTGACCGTGGGCAGCCTGAAGACATCCGCC<br>GTGCCTAGCACGTCTACCATGTCCCAGGAGCCGGAACTGCTAATCAGCGGCATGGAGAAGCCTCTGCCTCTCAG<br>GACCGACTTCAGC<br>(KRAS(G12D)25mer^3_ct.STING(V155M)) |
| 164 | mPHSSLHPSIPCPRGHGAQKAALVLLSACLVTLWGLGEPPEHTLRYLVLHLASLQLGLLLNGVCSLAEELRHIHSRYRGS<br>YWRTVRACLGCPLRRGALLLLSIYFYYSLPNAVGPPFTWMLALLGLSQALNILLGLKGLAPAEISAVCEKGNFNVAHGL<br>AWSYYIGYLRLILPELQARIRTYNQHYNNLLRGAVSQRLYILLPLDCGVPDNLSMADPNIRFLDKLPQQTGDHAGIKDR<br>VYSNSIYELLENGQRAGTCVLEYATPLQTLFAMSQYSQAGFSREDkLEQAKLFCRTLEDILADAPESQNNCRLIAYQEP<br>ADDSSFSLSQEVLRHLRQEEKEEVTVGSLKTSAVPSTSTMSQEPELLISGMEKPLPLRTDFST<br>(Hu STING (R284K) var; no epitope tag) |
| 165 | ATGCCCCATAGCAGCCTGCACCCCAGCATCCCCTGCCCCAGAGGCCACGGCGCCCAGAAGGCCGCCCTGGTCCT<br>GCTGAGCGCATGCCTGGTCACCCTGTGGGGCCTGGGCGAGCCCCCCGAGCACACCCTGAGATACCTGGTGCTGC<br>ACCTCGCCAGCCTGCAGCTGGGCCTGCTGCTGAACGGCGTGTGCAGCCTGGCCGAGGAGCTGAGACACATCCAC<br>AGCAGATATAGAGGCAGCTACTGGAGAACCGTGAGAGCTTGCCTCGGCTGCCCCCTGAGAAGAGGCGCCCTGC<br>TGCTGCTGAGCATCTACTTTTACTACAGCCTGCCCAACGCTGTGGGCCCCCCTTTCACGTGGATGCTCGCCCTGCT<br>GGGACTGAGCCAGGCCCTGAACATCCTGCTGGGCCTTAAGGGCCTAGCCCCCGCCGAGATCAGCGCCGTGTGC<br>GAGAAGGGCAACTTCAATGTGGCCCACGGCCTGGCCTGGAGCTACTACATCGGCTACCTGAGACTGATCCTGCC<br>CGAGCTGCAGGCCAGAATCAGAACCTACAATCAGCACTACAACAACCTGCTGAGAGGCGCCGTGAGCCAGAGA<br>CTGTACATCCTGCTGCCCCTGGACTGCGGCGTGCCCGACAACCTCAGCATGGCCGACCCCAACATCAGATTCCTG<br>GACAAGCTGCCCCAGCAGACCGGCGACCACGCCGGCATCAAGGATCGCGTGTACAGCAACAGCATCTACGAGC<br>TGCTGGAAAACGGCCAGAGAGCCGGAACCTGCGTGCTGGAGTACGCCACACCCCTGCAGACCCTGTTCGCCATG<br>AGCCAGTACAGCCAGGCCGGCTTCAGCAGAGAGGACAAGCTGGAGCAGGCCAAGCTGTTCTGCAGAACCCTGG<br>AGGATATCCTCGCCGACGCCCCCGAGAGCCAGAACAACTGCAGGCTGATCGCGTACCAGGAGCCCGCTGACGA<br>CAGCAGCTTTAGCCTGAGCCAGGAGGTGCTGAGACATCTGCGTCAAGAGGAAAAGGAGGAGGTGACCGTGGG<br>CTCCCTGAAGACCAGCGCCGTGCCCAGCACCAGCACCATGAGCCAGGAGCCCGAGCTGCTGATCAGCGGCATG<br>GAGAAGCCACTGCCCCTCAGAACCGACTTCAGCACC<br>(Hu STING (R284K) var; no epitope tag) |
| 166 | MTEYKLVVVGAGGVGKSALTIQLIQNHFVDEYDPTIEDSYRKQVVIDGETCLLDILDTAGQEEYSAMRDQYMRTGEG<br>FLCVFAINNTKSFEDIHHYREQIKRVKDSEDVPMVLVGNKCDLPSRTVDTKQAQDLARSYGIPFIETSAKTRQRVEDAF<br>YTLVRE1RQYRLKKISKEEKTPGCVKIKKC<br>Human KRAS sp/P01116[1-186] |
| 167 | 5'$^{7Me}G_{ppp}G_{2'OMe}$GGAAAUAAGAGAGAAAAGAAGAGUAAGAAGAAAUAUAAGAGCCACCAUG<br>ACCGAGUACAAGCUCGUGGUCGUCGGCGCCGACGGGGUAGGCAAGUCCGCUCUGACCAU<br>UCAGCUCAUCCAGAUGACGGAGUACAAACUCGUGGUAGUGGGAGCCGUGGGUGUGGGC<br>AAGAGCGCGCUCACCAUCCAACUCAUCCAAAUGACCGAAUAUAAACUCGUCGUGGUGGG<br>AGCCGGCGACGUGGGAAAGAGCGCCCUUACCAUCCAGUUAAUCCAGAUGACAGAAUACA |

-continued

SEQUENCE LISTING SUMMARY

| SEQ ID NO: | SEQUENCE |
|---|---|
| | AGCUGGUGGUGGUCGGUGCCUGCGGCGUGGGUAAGUCCGCCCUGACAAUCCAGCUGAUC<br>CAGUGAUAAUAGGCUGGAGCCUCGGUGGCCAUGCUUCUUGCCCCUUGGGCCUCCCCCCA<br>GCCCCUCCUCCCCUUCCUGCACCCGUACCCCCGUGGUCUUUGAAUAAAGUCUGAGUGGG<br>CGGCAAAAAAAAAAAAAAAAAAAAAAAAAAAAAAAAAAAAAAAAAAAAAAAAAAAAAA<br>AAAAAAAAAAAAAAAAAAAAAAAAAAAAAAAAAAAAAAAAAAAAAAUCUAG$_{OH}$3'<br>Where: A, C G & U = AMP, CMP, GMP & N1-ΨUMP, respectively; Me = methyl; p = inorganic phosphate<br>(KRAS concatemer mRNA sequence; CX-012908) |
| 168 | 5'$^{7Me}G_{ppp}G_{2'OMe}$GGAAAUAAGAGAGAAAAGAAGAGUAAGAAGAAAUAUAAGAGCCACCAUG<br>CCCCACAGUAGCCUCCACCCCAGCAUCCCCUGCCCCAGAGGCCACGGCGCACAGAAGGCC<br>GCCCUGGUGCUGCUGAGCGCCUGUCUGGUGACCCUGUGGGGUCUGGGCGAGCCCCCCGA<br>GCACACCCUGCGGUACCUCGUGCUGCAUCUGGCCAGCCUGCAGCUGGGCCUGCUGCUGA<br>ACGGCGUGUGCAGCCUGGCCGAAGAGCUGAGACACAUCCACAGCAGAUACAGAGGCUCC<br>UACUGGAGAACCGUCAGAGCCUGCCUCGGCUGUCCCCUGAGAAGAGGCGCCCUGCUGCU<br>CCUGAGCAUCUACUUCUACUACAGCCUGCCCAACGCCGUGGGCCCCCCCUUCACCUGGA<br>UGCUGGCCCUGCUGGGCCUGAGCCAGGCCCUGAACAUCCUGCUGGGCCUGAAGGGCUUG<br>GCCCCCGCCGAGAUCUCCGCCGUGUGCGAGAAGGGCAACUUCAACAUGGCCCAUGGCCU<br>UGCCUGGUCCUACUACAUCGGCUACCUGAGACUGAUCCUGCCCGAGCUGCAGGCCAGAA<br>UCAGAACCUACAACCAGCACUACAACAACCUGCUGAGAGGCGCCGUGAGCCAAAGACUG<br>UACAUCCUGCUGCCCCUGGACUGCGGCGUGCCCGACAACCUUAGCAUGGCCGACCCCAA<br>CAUCAGAUUCCUGGACAAGCUGCCCCAGCAGACCGGCGACCACGCCGGCAUCAAGGACA<br>GAGUGUACAGCAACAGCAUCUACGAGCUGCUGGAGAACGGCCAGAGAGCCGGCACCUGC<br>GUGCUGGAGUACGCCACCCCCCUGCAGACCCUGUUCGCCAUGAGCCAGUACAGCCAGGC<br>CGGCUUCAGCAGAGAGGACAGACUGGAGCAAGCCAAGCUGUUCUGCAGAACCCUGGAGG<br>ACAUCCUGGCGGACGCCCCCGAGAGCCAAAACAACUGCAGACUGAUCGCCUACCAGGAG<br>CCCGCCGACGACAGCAGCUUCAGCCUGAGCCAGGAAGUGCUGAGACACCUGAGACAGGA<br>AGAGAAGGAGGAGGUGACCGUGGGAAGCCUGAAGACCAGCGCCGUGCCCAGCACCAGCA<br>CCAUGAGCCAGGAGCCCGAGCUGCUGAUCAGCGGCAUGGAGAAGCCCCUGCCCCUGAGA<br>ACCGACUUCAGCUGAUAAUAGGCUGGAGCCUCGGUGGCCUAGCUUCUUGCCCCUUGGGC<br>CUCCCCCCAGCCCCUCCUCCCCUUCCUGCACCCGUACCCCCCAAACACCAUUGUCACACU<br>CCAGUGGUCUUUGAAUAAAGUCUGAGUGGGCGGCAAAAAAAAAAAAAAAAAAAAAAAA<br>AAAAAAAAAAAAAAAAAAAAAAAAAAAAAAAAAAAAAAAAAAAAAAAAAAAAAAAAAA<br>AAAAAAAAAAAAAAAAAAUCUAG$_{OH}$3'<br>Where: A, C G & U = AMP, CMP, GMP & N1-ΨUMP, respectively; Me = methyl; p = inorganic phosphate; underline = miR-122 binding site<br>(STING mRNA sequence; CX-012871) |
| 169 | AUGACCGAGUACAAGCUCGUGGUCGUCGGCGCCGACGGGGUAGGCAAGUCCGCUCUGACCAUUCAGCUCA<br>UCCAGAUGACGGAGUACAAACUCGUGGUAGUGGGAGCCGUGGGUGUGGGCAAGAGCGCGCUCACCAUCCA<br>ACUCAUCCAAAUGACCGAAUAUAAACUCGUCGUGGUGGGAGCCGGCGACGUGGGAAAGAGCGCCCUUACC<br>AUCCAGUUAAUCCAGAUGACAGAAUACAAGCUGGUGGUGGUCGGUGCCUGCGGCGUGGGUAAGUCCGCCC<br>UGACAAUCCAGCUGAUCCAG<br>(KRAS(G12D G12V G13D G12C) 100mer "4MUT" nt. seq) |
| 170 | AUGCCCCACAGUAGCCUCCACCCCAGCAUCCCCUGCCCCAGAGGCCACGGCGCACAGAAGGCCGCCCUGGUG<br>CUGCUGAGCGCCUGUCUGGUGACCCUGUGGGGUCUGGGCGAGCCCCCCGAGCACACCCUGCGGUACCUCG<br>UGCUGCAUCUGGCCAGCCUGCAGCUGGGCCUGCUGCUGAACGGCGUGUGCAGCCUGGCCGAAGAGCUGAG<br>ACACAUCCACAGCAGAUACAGAGGCUCCUACUGGAGAACCGUCAGAGCCUGCCUCGGCUGUCCCCUGAGAA<br>GAGGCGCCCUGCUGCUCCUGAGCAUCUACUUCUACUACAGCCUGCCCAACGCCGUGGGCCCCCCCUUCACC<br>UGGAUGCUGGCCCUGCUGGGCCUGAGCCAGGCCCUGAACAUCCUGCUGGGCCUGAAGGGCUUGGCCCCCG<br>CCGAGAUCUCCGCCGUGUGCGAGAAGGGCAACUUCAACAUGGCCCAUGGCCUUGCCUGGUCCUACUACAUC<br>GGCUACCUGAGACUGAUCCUGCCCGAGCUGCAGGCCAGAAUCAGAACCUACAACCAGCACUACAACAACCU<br>GCUGAGAGGCGCCGUGAGCCAAAGACUGUACAUCCUGCUGCCCCUGGACUGCGGCGUGCCCGACAACCUUA<br>GCAUGGCCGACCCCAACAUCAGAUUCCUGGACAAGCUGCCCCAGCAGACCGGCGACCACGCCGGCAUCAAGG<br>ACAGAGUGUACAGCAACAGCAUCUACGAGCUGCUGGAGAACGGCCAGAGAGCCGGCACCUGCGUGCUGGA<br>GUACGCCACCCCCCUGCAGACCCUGUUCGCCAUGAGCCAGUACAGCCAGGCCGGCUUCAGCAGAGAGGACA<br>GACUGGAGCAAGCCAAGCUGUUCUGCAGAACCCUGGAGGACAUCCUGGCGGACGCCCCCGAGAGCCAAAAC<br>AACUGCAGACUGAUCGCCUACCAGGAGCCCGCCGACGACAGCAGCUUCAGCCUGAGCCAGGAAGUGCUGAG<br>ACACCUGAGACAGGAAGAGAAGGAGGAGGUGACCGUGGGAAGCCUGAAGACCAGCGCCGUGCCCAGCACCA<br>GCACCAUGAGCCAGGAGCCCGAGCUGCUGAUCAGCGGCAUGGAGAAGCCCCUGCCCCUGAGAACCGACUUC<br>AGC<br>(huSTING(V155M); no epitope tag; nucleotide sequence) |
| 171 | CCUUAGCAGAGCUGUGGAGUGUGACAAUGGUGUUUGUGUCUAAACUAUCAAACGCCAUUAUCACACUAA<br>AUAGCUACUGCUAGGC<br>(mir-122) |
| 172 | AACGCCAUUAUCACACUAAAUA (mir-122-3p_ |
| 173 | UAUUUAGUGUGAUAAUGGCGUU (mir-122-3p binding site) |
| 174 | UGGAGUGUGACAAUGGUGUUUG (mir-122-5p) |

-continued

SEQUENCE LISTING SUMMARY

| SEQ ID NO: | SEQUENCE |
|---|---|
| 175 | CAAACACCAUUGUCACACUCCA (mir-122-5p binding site) |
| 176 | GGAAAUAAGAGAGAAAAGAAGAGUAAGAAGAAAUAUAAGAGCCACC<br>(5' UTR) |
| 177 | CCGCCGCCGCCG |
| 178 | CCGCCGCCGCCGCCG |
| 179 | CCCCGGCGCC (V1) |
| 180 | GGGAAATAAGAGAGAAAAGAAGAGTAAGAAGAAATATAAGA (5'UTR) |
| 181 | GGGAAATAAGAGAGAAAAGAAGAGTAAGAAGAAATATAAGACCCCGGCGCCGCCACC (V1-UTR) |
| 182 | GGGAAATAAGAGAGAAAAGAAGAGTAAGAAGAAATATAAGACCCCGGCGCCACC (V2-UTR) |
| 183 | MKLVVVGACGVGKSAMKLVVVGACGVGKSAMKLVVVGACGVGKSA<br>(KRAS G12C 15mer^3) |
| 184 | ATGACCGAGTACAAGCTCGTGGTTGTTGGCGCCTGCGGCGTGGGCAAGAGCGCCCTCACCATCCAGCTCATCCA<br>GATGACAGAGTATAAGTTAGTCGTTGTCGGAGCTTGCGGAGTTGGAAAGTCGGCGCTCACCATTCAACTCATAC<br>AAATGACAGAATATAAGTTAGTGGTGGTGGGTGCGTGTGGCGTTGGCAAGAGTGCGCTTACTATCCAGCTCATT<br>CAG<br>(KRAS G12C 25mer^3 nucleotide sequence) |
| 185 | UCAAGCUUUUGGACCCUCGUACAGAAGCUAAUACGACUCACUAUAGGGAAAUAAGAGAGAAAAGAAGAGU<br>AAGAAGAAAUAUAAGAGCCACC<br>(5' UTR) |
| 186 | UGAUAAUAGGCUGGAGCCUCGGUGGCCAUGCUUCUUGCCCCUUGGGCCUCCCCCCAGCCCCUCCUCCCCUU<br>CCUGCACCCGUACCCCCGUGGUCUUUGAAUAAAGUCUGAGUGGGCGGC<br>(3' UTR) |
| 187 | UGAUAAUAGGCUGGAGCCUCGGUGGCCAUGCUUCIJUGCCCCUUGGGCCCAAACACCAUUGUCACACUCCA<br>UCCCCCCAGCCCCUCCUCCCCUUCCUCCAUAAAGUAGGAAACACUACAUGCACCCGUACCCCCGUGGUCUUU<br>GAALJAAAGUCUGAGUGGGCCGC<br>(3' UTR with mi-122 and mi-142.3p sites) |
| 188 | GGAAGCGGAGCUACUAACUUCAGCCUGCUGAAGCAGGCUGGAGACGUGGAGGAGAACCCUGGACCU<br>(Nucleotide sequence encoding 2A peptide) |
| 189 | UCCGGACUCAGAUCCGGGGAUCUCAAAAUUGUCGCUCCUGUCAAACAAACUCUUAACUUUGAUUUACUCA<br>AACUGGCUGGGGAUGUAGAAAGCAAUCCAGGUCCACUC<br>(Nucleotide sequence encoding 2A peptide) |
| 190 | AUGACCGAGUACAAGCUGGUGGUGGUGGGCGCCGACGGCGUGGGCAAGAGCGCCCUGACCAUCCAGCUGA<br>UCCAG<br>(KRAS G12D 25mer nucleotide sequence) |
| 191 | AUGACCGAGUACAAGCUGGUGGUGGUGGGCGCCGUGGGCGUGGGCAAGAGCGCCCUGACCAUCCAGCUGA<br>UCCAG<br>(KRAS G12V 25mer nucleotide sequence) |
| 192 | AUGACCGAGUACAAGCUGGUGGUGGUGGGCGCCGGCGACGUGGGCAAGAGCGCCCUGACCAUCCAGCUGA<br>UCCAG<br>(KRAS G13D 25mer nucleotide sequence) |
| 193 | AUGACCGAGUACAAGUUAGUGGUUGUGGGCGCCGACGGCGUGGGCAAGAGCGCCCUCACCAUCCAGCUUA<br>UCCAGAUGACGGAAUAUAAGUUAGUAGUAGUGGGAGCCGACGGUGUCGGCAAGUCCGCUUUGACCAUUC<br>AACUUAUUCAGAUGACAGAGUAUAAGCUGGUCGUUGUAGGCGCAGACGGCGUUGGAAAGUCGGCACUGA<br>CGAUCCAGUUGAUCCAG<br>(KRAS G12D 25mer^3 nucleotide sequence) |
| 194 | AUGACCGAGUACAAGCUCGUCGUGGUGGGCGCCGUGGGCGUGGGCAAGAGCGCCCUAACCAUCCAGUUGA<br>UCCAGAUGACCGAAUAUAAGCUCGUGGUAGUCGGAGCGGUGGGCGUUGGCAAGUCAGCGCUAACAAUACA<br>ACUAAUCCAAAUGACCGAAUACAAGCUAGUUGUAGUCGGUGCCGUCGGCGUUGGAAAGUCAGCCCUUACA<br>AUUCAGCUCAUUCAG<br>(KRAS G12V 25mer^3 nucleotide sequence) |
| 195 | AUGACCGAGUACAAGCUCGUAGUGGUUGGCGCCGGCGACGUGGGCAAGAGCGCCCUAACCAUCCAGCUCA<br>UCCAGAUGACAGAAUAUAAGCUUGUGGUUGUGGGAGCAGGAGACGUGGGAAAGAGUGCGUUGACGAUUC |

-continued

SEQUENCE LISTING SUMMARY

| SEQ ID NO: | SEQUENCE |
|---|---|
| | AACUCAUACAGAUGACCGAAUACAAGUUGGUGGUGGUCGGCGCAGGUGACGUUGGUAAGUCUGCACUAA CUAUACAACUGAUCCAG (KRAS G13D 25mer^3 nucleotide sequence) |
| 196 | AUGACCGAGUACAAGCUGGUGGUGGUGGGCGCCUGCGGCGUGGGCAAGAGCGCCCUGACCAUCCAGCUGA UCCAG (KRAS G12C 25mer nucleotide sequence) |
| 197 | AUGACCGAGUACAAGCUCGUGGUUGUUGGCGCCUGCGGCGUGGGCAAGAGCGCCCUCACCAUCCAGCUCA UCCAGAUGACAGAGUAUAAGUUAGUCGUUGUCGGAGCUUGCGGAGUUGGAAAGUCGGCGCUCACCAUUC AACUCAUACAAAUGACAGAAUAUAAGUUAGUGGUGGUGGGUGCGUGUGGCGUUGGCAAGAGUGCGCUUA CUAUCCAGCUCAUUCAG (KRAS G12C 25mer^3 nucleotide sequence) |
| 198 | AUGACCGAGUACAAGCUGGUGGUGGUGGGCGCCGGCGGCGUGGGCAAGAGCGCCCUGACCAUCCAGCUGA UCCAG (KRAS WT 25mer nucleotide sequence) |
| 199 | GGGAAAUAAGAGAGAAAAGAAGAGUAAGAAGAAAUAUAAGAGCCACC (5' UTR sequence; no promoter) |
| 200 | AUGACCGAGUACAAGCUCGUUGUAGUCGGCGCCGACGGCGUGGGCAAGAGCGCCUUGACCAUCCAGUUGA UCCAGAUGACCGAAUAUAAGUUGGUGGUGGUAGGCGCAGUGGGAGUUGGCAAGUCAGCACUCACAAUUC AGCUCAUUCAAAUGACAGAAUACAAGUUAGUCGUUGUAGGAGCAGGCGACGUCGGCAAGAGUGCCUUAAC CAUUCAACUAAUCCAG (KRAS(G12D G12V G13D) 75mer "3MUT" nt. seq) |
| 201 | AUGCCUCACAGCAGCCUGCACCCUAGCAUCCCUUGCCCUAGAGGCCACGGCGCCCAGAAGGCCGCCCUGGU GCUGCUGAGCGCCUGCCUGGUGACCCUGUGGGGCCUGGGCGAGCCUCCUGAGCACACCCUGAGAUACCUG GUGCUGCACCUGGCCAGCCUGCAGCUGGGCCUGCUGCUGAACGGCGUGUGCAGCCUGGCCGAGGAGCUGA GACACAUCCACAGCAGAUACAGAGGCAGCUACUGGAGAACCGUGAGAGCCUGCCUGGGCUGCCCUCUGAGA AGAGGCGCCCUGCUGCUGCUGAGCAUCUACUUCUACUACAGCCUGCCUAACGCCGUGGGCCCUCCUUUCAC CUGGAUGCUGGCCCUGCUGGGCCUGAGCCAGGCCCUGAACAUCCUGCUGGGCCUGAAGGGCCUGGCCCCU GCCGAGAUCAGCGCCGUGUGCGAGAAGGGCAACUUCAACGUGGCCCACGGCCUGGCCUGGAGCUACUACA UCGGCUACCUGAGACUGAUCCUGCCUGAGCUGCAGGCCAGAAUCAGAACCUACAACCAGCACUACAACAAC CUGCUGAGAGGCGCCGUGAGCCAGAGACUGUACAUCCUGCUGCCUCUGGACUGCGGCGUGCCUGACAACC UGAGCAUGGCCGACCCUAACAUCAGAUUCCUGGACAAGCUGCCUCAGCAGACCGGCGACCACGCCGGCAUC AAGGACAGAGUGUACAGCAACAGCAUCUACGAGCUGCUGGAGAACGGCCAGAGAGCCGGCACCUGCGUGC UGGAGUACGCCACCCCUCUGCAGACCCUGUUCGCCAUGAGCCAGUACAGCCAGGCCGGCUUCAGCAGAGAG GACACCCUGGAGCAGGCCAAGCUGUUCUGCAGAACCCUGGAGGACAUCCUGGCCGACGCCCCUGAGAGCCA GAACAACUGCAGACUGAUCGCCUACCAGGAGCCUGCCGACGACAGCAGCUUCAGCCUGAGCCAGGAGGUGC UGAGACACCUGAGACAGGAGGAGAAGGAGGAGGUGACCGUGGGCAGCCUGAAGACCAGCGCCGUGCCUAG CACCAGCACCAUGAGCCAGGAGCCUGAGCUGCUGAUCAGCGGCAUGGAGAAGCCUCUGCCUCUGAGAACCG ACUUCAGC (Hu STING(R284T); no epitope tag; nucleotide sequence) |
| 202 | AUGCCCCACAGCAGCCUGCACCCCUCCAUCCCCUGUCCCAGAGGCCACGGCGCCCAGAAGGCCGCCCUGGUG CUGCUGAGCGCCUGCCUGGUGACCUUAUGGGGCCUGGGCGAGCCCCCCGAGCACACCCUGAGAUACCUGG UCCUGCACCUGGCCAGCCUCCAGCUGGGCCUGCUGCUCAACGGCGUGUGUAGCCUGGCCGAGGAGCUGAG ACACAUCCACAGCAGAUACAGAGGCAGCUACUGGAGAACCGUGAGAGCCUGCCUGGGUUGCCCACUGAGAA GAGGAGCUCUGCUGCUGCUGAGCAUCUACUUCUACUACUCGCUGCCCAACGCUGUGGGCCCCCCCUUCACC UGGAUGCUGGCCCUGCUGGGUCUGAGCCAGGCCCUGAACAUCCUCCUGGGCCUGAAGGGCCUGGCCCCG CCGAGAUAAGCGCCGUUUGCGAGAAGGGCAACUUCAACGUGGCCCAUGGCCUGGCCUGGAGCUACUACAU CGGCUACUUACGCCUGAUCCUGCCCGAGCUGCAGGCCAGAAUCAGAACCUACAACCAGCAUUACAACAACC UGCUGAGAGGCGCCGUGAGCCAGAGACUGUAUAUCCUGCUGCCCCUGGACUGCGGCGUGCCCGACAACCU GAGCAUGGCCGACCCCAACAUCAGAUUCCUGGACAAGCUCCCCCAGCAGACCGGCGACCACGCCGGAAUCAA AGACAGAGUGUAUAGCAACAGCAUCUACGAGCUGCUGGAGAACGGCCAGAGAGCCGGCACCUGCGUACUG GAGUACGCCACCCCCUUGCAGACCCUGUUUGCCAUGAGCCAGUACAGCCAGGCCGGCUUCAGCAGAGAGGA CAUGCUGGAGCAGGCCAAGCUGUUCUGCAGAACCCUGGAGGACAUCCUGGCCGACGCCCCCGAGAGCCAGA ACAACUGCAGACUGAUCGCCUACCAAGAGCCCGCCGACGACAGCAGCUUCAGCUUAAGCCAGGAGGUGCUG AGACAUCUGAGACAGGAGGAGAAGGAGGAGGUGACCGUGGGCAGCCUCAAGACCAGCGCUGUGCCCUCUA CCAGCACCAUGAGCCAGGAGCCCGAGCUGCUGAUCAGCGGCAUGGAGAAGCCCCUGCCCCUGAGAACAGAC UUCAGC (hu STING (R284M); no epitope tag; nudeotide sequence) |
| 203 | AUGCCCCAUAGCAGCCUGCACCCCAGCAUCCCCUGCCCCAGAGGCCACGGCGCCCAGAAGGCCGCCCUGGUC CUGCUGAGCGCAUGCCUGGUCACCCUGUGGGGCCUGGGCGAGCCCCCCGAGCACACCCUGAGAUACCUGGU GCUGCACCUCGCCAGCCUGCAGCUGGGCCUGCUGCUGAACGGCGUGUGCAGCCUGGCCGAGGAGCUGAGA CACAUCCACAGCAGAUAUAGAGGCAGCUACUGGAGAACCGUGAGAGCUUGCCUCGGCUGCCCCCUGAGAAG AGGCGCCCUGCUGCUGCUGAGCAUCUACUUUUACUACAGCCUGCCCAACGCUGUGGGCCCCCCUUUCACGU GGAUGCUCGCCCUGCUGGGACUGAGCCAGGCCCUGAACAUCCUGCUGGGCCUUAAGGGCCUAGCCCCCGCC GAGAUCAGCGCCGUGUGCGAGAAGGGCAACUUCAAUGUGGCCCACGGCCUGGCCUGGAGCUACUACAUCG GCUACCUGAGACUGAUCCUGCCCGAGCUGCAGGCCAGAAUCAGAACCUACAAUCAGCACUACAACAACCUG |

-continued

SEQUENCE LISTING SUMMARY

| SEQ ID NO: | SEQUENCE |
|---|---|
| | CUGAGAGGCGCCGUGAGCCAGAGACUGUACAUCCUGCUGCCCCUGGACUGCGGCGUGCCCGACAACCUCAG<br>CAUGGCCGACCCCAACAUCAGAUUCCUGGACAAGCUGCCCCAGCAGACCGGCGACCACGCCGGCAUCAAGGA<br>UCGCGUGUACAGCAACAGCAUCUACGAGCUGCUGGAAAACGGCCAGAGAGCCGGAACCUGCGUGCUGGAG<br>UACGCCACACCCCUGCAGACCCUGUUCGCCAUGAGCCAGUACAGCCAGGCCGGCUUCAGCAGAGAGGACAA<br>GCUGGAGCAGGCCAAGCUGUUCUGCAGAACCCUGGAGGAUAUCCUCGCCGACGCCCCCGAGAGCCAGAACA<br>ACUGCAGGCUGAUCGCGUACCAGGAGCCCGCUGACGACAGCAGCUUUAGCCUGAGCCAGGAGGUGCUGAG<br>ACAUCUGCGUCAAGAGGAAAAGGAGGAGGUGACCGUGGGCUCCCUGAAGACCAGCGCCGUGCCCAGCACCA<br>GCACCAUGAGCCAGGAGCCCGAGCUGCUGAUCAGCGGCAUGGAGAAGCCACUGCCCCUCAGAACCGACUUC<br>AGC<br>(Hu STING (R284K); no epitope tag; nudeotide sequence) |
| 204 | AUGCCUCACAGCAGCCUGCACCCUAGCAUCCCUUGCCCUAGAGGCCACGGCGCCCAGAAGGCCGCCCUGGU<br>GCUGCUGAGCGCCUGCCUGGUGACCCUGUGGGGCCUGGGCGAGCCUCCUGAGCACACCCUGAGAUACCUG<br>GUGCUGCACCUGGCCAGCCUGCAGCUGGGCCUGCUGCUGAACGGCGUGUGCAGCCUGGCCGAGGAGCUGA<br>GACACAUCCACAGCAGAUACAGAGGCAGCUACUGGAGAACCGUGAGAGCCUGCCUGGGCUGCCCUCUGAGA<br>AGAGGCGCCCUGCUGCUGCUGAGCAUCUACUUCUACUACAGCCUGCCUAACGCCGUGGGCCCUCCUUUCAC<br>CUGGAUGCUGGCCCUGCUGGGCCUGAGCCAGGCCCUGAACAUCCUGCUGGGCCUGAAGGGCCUGGCCCCU<br>GCCGAGAUCAGCGCCGUGUGCGAGAAGGGCAACUUCAGCGUGGCCCACGGCCUGGCCUGGAGCUACUACA<br>UCGGCUACCUGAGACUGAUCCUGCCUGAGCUGCAGGCCAGAAUCAGAACCUACAACCAGCACUACAACAAC<br>CUGCUGAGAGGCGCCGUGAGCCAGAGACUGUACAUCCUGCUGCCUCUGGACUGCGGCGUGCCUGACAACC<br>UGAGCAUGGCCGACCCUAACAUCAGAUUCCUGGACAAGCUGCCUCAGCAGACCGGCGACCACGCCGGCAUC<br>AAGGACAGAGUGUACAGCAACAGCAUCUACGAGCUGCUGGAGAACGGCCAGAGAGCCGGCACCUGCGUGC<br>UGGAGUACGCCACCCCUCUGCAGACCCUGUUCGCCAUGAGCCAGUACAGCCAGGCCGGCUUCAGCAGAGAG<br>GACAGACUGGAGCAGGCCAAGCUGUUCUGCAGAACCCUGGAGGACAUCCUGGCCGACGCCCCUGAGAGCCA<br>GAACAACUGCAGACUGAUCGCCUACCAGGAGCCUGCCGACGACAGCAGCUUCAGCCUGAGCCAGGAGGUGC<br>UGAGACACCUGAGACAGGAGGAGAAGGAGGAGGUGACCGUGGGCAGCCUGAAGACCAGCGCCGUGCCUAG<br>CACCAGCACCAUGAGCCAGGAGCCUGAGCUGCUGAUCAGCGGCAUGGAGAAGCCUCUGCCUCUGAGAACCG<br>ACUUCAGC<br>(Hu STING(N154S); no epitope tag; nucleotide sequence) |
| 205 | AUGCCUCACAGCAGCCUGCACCCUAGCAUCCCUUGCCCUAGAGGCCACGGCGCCCAGAAGGCCGCCCUGGU<br>GCUGCUGAGCGCCUGCCUGGUGACCCUGUGGGGCCUGGGCGAGCCUCCUGAGCACACCCUGAGAUACCUG<br>GUGCUGCACCUGGCCAGCCUGCAGCUGGGCCUGCUGCUGAACGGCGUGUGCAGCCUGGCCGAGGAGCUGA<br>GACACAUCCACAGCAGAUACAGAGGCAGCUACUGGAGAACCGUGAGAGCCUGCCUGGGCUGCCCUCUGAGA<br>AGAGGCGCCCUGCUGCUGCUGAGCAUCUACUUCUACUACAGCCUGCCUAACGCCGUGGGCCCUCCUUUCAC<br>CUGGAUGCUGGCCCUGCUGGGCCUGAGCCAGGCCCUGAACAUCCUGCUGGGCCUGAAGGGCCUGGCCCCU<br>GCCGAGAUCAGCGCCCUGUGCGAGAAGGGCAACUUCAACGUGGCCCACGGCCUGGCCUGGAGCUACUACAU<br>CGGCUACCUGAGACUGAUCCUGCCUGAGCUGCAGGCCAGAAUCAGAACCUACAACCAGCACUACAACAACC<br>UGCUGAGAGGCGCCGUGAGCCAGAGACUGUACAUCCUGCUGCCUCUGGACUGCGGCGUGCCUGACAACCU<br>GAGCAUGGCCGACCCUAACAUCAGAUUCCUGGACAAGCUGCCUCAGCAGACCGGCGACCACGCCGGCAUCA<br>AGGACAGAGUGUACAGCAACAGCAUCUACGAGCUGCUGGAGAACGGCCAGAGAGCCGGCACCUGCGUGCU<br>GGAGUACGCCACCCCUCUGCAGACCCUGUUCGCCAUGAGCCAGUACAGCCAGGCCGGCUUCAGCAGAGAGG<br>ACAGACUGGAGCAGGCCAAGCUGUUCUGCAGAACCCUGGAGGACAUCCUGGCCGACGCCCCUGAGAGCCAG<br>AACAACUGCAGACUGAUCGCCUACCAGGAGCCUGCCGACGACAGCAGCUUCAGCCUGAGCCAGGAGGUGCU<br>GAGACACCUGAGACAGGAGGAGAAGGAGGAGGUGACCGUGGGCAGCCUGAAGACCAGCGCCGUGCCUAGC<br>ACCAGCACCAUGAGCCAGGAGCCUGAGCUGCUGAUCAGCGGCAUGGAGAAGCCUCUGCCUCUGAGAACCGA<br>CUUCAGC<br>(Hu STING(V147L); no epitope tag; nucleotide sequence) |
| 206 | AUGCCUCACAGCAGCCUGCACCCUAGCAUCCCUUGCCCUAGAGGCCACGGCGCCCAGAAGGCCGCCCUGGU<br>GCUGCUGAGCGCCUGCCUGGUGACCCUGUGGGGCCUGGGCGAGCCUCCUGAGCACACCCUGAGAUACCUG<br>GUGCUGCACCUGGCCAGCCUGCAGCUGGGCCUGCUGCUGAACGGCGUGUGCAGCCUGGCCGAGGAGCUGA<br>GACACAUCCACAGCAGAUACAGAGGCAGCUACUGGAGAACCGUGAGAGCCUGCCUGGGCUGCCCUCUGAGA<br>AGAGGCGCCCUGCUGCUGCUGAGCAUCUACUUCUACUACAGCCUGCCUAACGCCGUGGGCCCUCCUUUCAC<br>CUGGAUGCUGGCCCUGCUGGGCCUGAGCCAGGCCCUGAACAUCCUGCUGGGCCUGAAGGGCCUGGCCCCU<br>GCCGAGAUCAGCGCCGUGUGCGAGAAGGGCAACUUCAACGUGGCCCACGGCCUGGCCUGGAGCUACUACA<br>UCGGCUACCUGAGACUGAUCCUGCCUGAGCUGCAGGCCAGAAUCAGAACCUACAACCAGCACUACAACAAC<br>CUGCUGAGAGGCGCCGUGAGCCAGAGACUGUACAUCCUGCUGCCUCUGGACUGCGGCGUGCCUGACAACC<br>UGAGCAUGGCCGACCCUAACAUCAGAUUCCUGGACAAGCUGCCUCAGCAGACCGGCGACCACGCCGGCAUC<br>AAGGACAGAGUGUACAGCAACAGCAUCUACGAGCUGCUGGAGAACGGCCAGAGAGCCGGCACCUGCGUGC<br>UGGAGUACGCCACCCCUCUGCAGACCCUGUUCGCCAUGAGCCAGUACAGCCAGGCCGGCUUCAGCAGAGAG<br>GACAGACUGGAGCAGGCCAAGCUGUUCUGCAGAACCCUGGAGGACAUCCUGGCCGACGCCCCUGAGAGCCA<br>GAACAACUGCAGACUGAUCGCCUACCAGCAGCCUGCCGACGACAGCAGCUUCAGCCUGAGCCAGGAGGUGC<br>UGAGACACCUGAGACAGGAGGAGAAGGAGGAGGUGACCGUGGGCAGCCUGAAGACCAGCGCCGUGCCUAG<br>CACCAGCACCAUGAGCCAGGAGCCUGAGCUGCUGAUCAGCGGCAUGGAGAAGCCUCUGCCUCUGAGAACCG<br>ACUUCAGC<br>(Hu STING (E315Q); no epitope tag; nucleotide sequence) |
| 207 | AUGCCUCACAGCAGCCUGCACCCUAGCAUCCCUUGCCCUAGAGGCCACGGCGCCCAGAAGGCCGCCCUGGU<br>GCUGCUGAGCGCCUGCCUGGUGACCCUGUGGGGCCUGGGCGAGCCUCCUGAGCACACCCUGAGAUACCUG<br>GUGCUGCACCUGGCCAGCCUGCAGCUGGGCCUGCUGCUGAACGGCGUGUGCAGCCUGGCCGAGGAGCUGA<br>GACACAUCCACAGCAGAUACAGAGGCAGCUACUGGAGAACCGUGAGAGCCUGCCUGGGCUGCCCUCUGAGA<br>AGAGGCGCCCUGCUGCUGCUGAGCAUCUACUUCUACUACAGCCUGCCUAACGCCGUGGGCCCUCCUUUCAC |

-continued

SEQUENCE LISTING SUMMARY

| SEQ ID NO: | SEQUENCE |
|---|---|
| | CUGGAUGCUGGCCCUGCUGGGCCUGAGCCAGGCCCUGAACAUCCUGCUGGGCCUGAAGGGCCUGGCCCCU<br>GCCGAGAUCAGCGCCGUGUGCGAGAAGGGCAACUUCAACGUGGCCCACGGCCUGGCCUGGAGCUACUACA<br>UCGGCUACCUGAGACUGAUCCUGCCUGAGCUGCAGGCCAGAAUCAGAACCUACAACCAGCACUACAACAAC<br>CUGCUGAGAGGCGCCGUGAGCCAGAGACUGUACAUCCUGCUGCCUCUGGACUGCGGCGUGCCUGACAACC<br>UGAGCAUGGCCGACCCUAACAUCAGAUUCCUGGACAAGCUGCCUCAGCAGACCGGCGACCACGCCGGCAUC<br>AAGGACAGAGUGUACAGCAACAGCAUCUACGAGCUGCUGGAGAACGGCCAGAGAGCCGGCACCUGCGUGC<br>UGGAGUACGCCACCCCUCUGCAGACCCUGUUCGCCAUGAGCCAGUACAGCCAGGCCGGCUUCAGCAGAGAG<br>GACAGACUGGAGCAGGCCAAGCUGUUCUGCAGAACCCUGGAGGACAUCCUGGCCGACGCCCCUGAGAGCCA<br>GAACAACUGCAGACUGAUCGCCUACCAGGAGCCUGCCGACGACAGCAGCUUCAGCCUGAGCCAGGAGGUGC<br>UGAGACACCUGAGACAGGAGGAGAAGGAGGAGGUGACCGUGGGCAGCCUGAAGACCAGCGCCGUGCCUAG<br>CACCAGCACCAUGAGCCAGGAGCCUGAGCUGCUGAUCAGCGGCAUGGAGAAGCCUCUGCCUCUGGCCACCG<br>ACUUCAGC<br>(Hu STING (R375A); no epitope tag; nucleotide sequence) |
| 208 | AUGCCUCACAGCAGCCUGCACCCUAGCAUCCCUUGCCCUAGAGGCCACGGCGCCCAGAAGGCCGCCCUGGU<br>GCUGCUGAGCGCCUGCCUGGUGACCCUGUGGGGCCUGGGCGAGCCUCCUGAGCACACCCUGAGAUACCUG<br>GUGCUGCACCUGGCCAGCCUGCAGCUGGGCCUGCUGCUGAACGGCGUGUGCAGCCUGGCCGAGGAGCUGA<br>GACACAUCCACAGCAGAUACAGAGGCAGCUACUGGAGAACCGUGAGAGCCUGCCUGGGCUGCCCUCUGAGA<br>AGAGGCGCCCUGCUGCUGCUGAGCAUCUACUUCUACUACAGCCUGCCUAACGCCGUGGGCCCUCCUUUCAC<br>CUGGAUGCUGGCCCUGCUGGGCCUGAGCCAGGCCCUGAACAUCCUGCUGGGCCUGAAGGGCCUGGCCCCU<br>GCCGAGAUCAGCGCCCUGUGCGAGAAGGGCAACUUCAGCAUGGCCCACGGCCUGGCCUGGAGCUACUACAU<br>CGGCUACCUGAGACUGAUCCUGCCUGAGCUGCAGGCCAGAAUCAGAACCUACAACCAGCACUACAACAACC<br>UGCUGAGAGGCGCCGUGAGCCAGAGACUGUACAUCCUGCUGCCUCUGGACUGCGGCGUGCCUGACAACCU<br>GAGCAUGGCCGACCCUAACAUCAGAUUCCUGGACAAGCUGCCUCAGCAGACCGGCGACCACGCCGGCAUCA<br>AGGACAGAGUGUACAGCAACAGCAUCUACGAGCUGCUGGAGAACGGCCAGAGAGCCGGCACCUGCGUGCU<br>GGAGUACGCCACCCCUCUGCAGACCCUGUUCGCCAUGAGCCAGUACAGCCAGGCCGGCUUCAGCAGAGAGG<br>ACAGACUGGAGCAGGCCAAGCUGUUCUGCAGAACCCUGGAGGACAUCCUGGCCGACGCCCCUGAGAGCCAG<br>AACAACUGCAGACUGAUCGCCUACCAGGAGCCUGCCGACGACAGCAGCUUCAGCCUGAGCCAGGAGGUGCU<br>GAGACACCUGAGACAGGAGGAGAAGGAGGAGGUGACCGUGGGCAGCCUGAAGACCAGCGCCGUGCCUAGC<br>ACCAGCACCAUGAGCCAGGAGCCUGAGCUGCUGAUCAGCGGCAUGGAGAAGCCUCUGCCUCUGAGAACCGA<br>CUUCAGC<br>(Hu STING(V147L/N154S/V155M); no epitope tag; nucleotide sequence) |
| 209 | AUGCCUCACAGCAGCCUGCACCCUAGCAUCCCUUGCCCUAGAGGCCACGGCGCCCAGAAGGCCGCCCUGGU<br>GCUGCUGAGCGCCUGCCUGGUGACCCUGUGGGGCCUGGGCGAGCCUCCUGAGCACACCCUGAGAUACCUG<br>GUGCUGCACCUGGCCAGCCUGCAGCUGGGCCUGCUGCUGAACGGCGUGUGCAGCCUGGCCGAGGAGCUGA<br>GACACAUCCACAGCAGAUACAGAGGCAGCUACUGGAGAACCGUGAGAGCCUGCCUGGGCUGCCCUCUGAGA<br>AGAGGCGCCCUGCUGCUGCUGAGCAUCUACUUCUACUACAGCCUGCCUAACGCCGUGGGCCCUCCUUUCAC<br>CUGGAUGCUGGCCCUGCUGGGCCUGAGCCAGGCCCUGAACAUCCUGCUGGGCCUGAAGGGCCUGGCCCCU<br>GCCGAGAUCAGCGCCCUGUGCGAGAAGGGCAACUUCAGCAUGGCCCACGGCCUGGCCUGGAGCUACUACAU<br>CGGCUACCUGAGACUGAUCCUGCCUGAGCUGCAGGCCAGAAUCAGAACCUACAACCAGCACUACAACAACC<br>UGCUGAGAGGCGCCGUGAGCCAGAGACUGUACAUCCUGCUGCCUCUGGACUGCGGCGUGCCUGACAACCU<br>GAGCAUGGCCGACCCUAACAUCAGAUUCCUGGACAAGCUGCCUCAGCAGACCGGCGACCACGCCGGCAUCA<br>AGGACAGAGUGUACAGCAACAGCAUCUACGAGCUGCUGGAGAACGGCCAGAGAGCCGGCACCUGCGUGCU<br>GGAGUACGCCACCCCUCUGCAGACCCUGUUCGCCAUGAGCCAGUACAGCCAGGCCGGCUUCAGCAGAGAGG<br>ACAUGCUGGAGCAGGCCAAGCUGUUCUGCAGAACCCUGGAGGACAUCCUGGCCGACGCCCCUGAGAGCCAG<br>AACAACUGCAGACUGAUCGCCUACCAGGAGCCUGCCGACGACAGCAGCUUCAGCCUGAGCCAGGAGGUGCU<br>GAGACACCUGAGACAGGAGGAGAAGGAGGAGGUGACCGUGGGCAGCCUGAAGACCAGCGCCGUGCCUAGC<br>ACCAGCACCAUGAGCCAGGAGCCUGAGCUGCUGAUCAGCGGCAUGGAGAAGCCUCUGCCUCUGAGAACCGA<br>CUUCAGC<br>(Hu STING(R284M/V147L/N154S/V155M); no epitope tag; nucleotide sequence) |
| 210 | UGAUAAUAGGCUGGAGCCUCGGUGGCCUAGCUUCUUGCCCCUUGGGCCUCCCCCCAGCCCCUCCUCCCCUU<br>CCUGCACCCGUACCCCCCAAACACCAUUGUCACACUCCAGUGGUCUUUGAAUAAAGUCUGAGUGGGCGGC<br>(3' UTR used in STING V155M construct, containing miR122 binding site) |
| 211 | AUGGAGACCCCCAAGCCUAGAAUCCUGCCCUGGCUGGUGAGCCAGCUGGACCUGGGCCAGCUGGAGGGCG<br>UAGCCUGGCUGGACGAGAGCAGAACCAGAUUCAGAAUCCCCUGGAAGCACGGCCUGAGACAAGACGCCCAG<br>AUGGCCGACUUCGGCAUCUUCCAGGCCUGGGCCGAGGCCAGCGGCGCCUACACCCCUGGCAAGGAUAAGCC<br>CGAUGUGAGCACCUGGAAGAGAAACUUCAGAAGCGCCCUGAACAGAAAGGAGGUGCUGAGACUGGCCGCC<br>GACAAUAGCAAGGACCCCUACGACCCCCACAAGGUGUACGAGUUCGUUACCCCCGGCGCCAGGGACUUCGU<br>GCACCUGGGCGCCAGCCCCGACACCAACGGCAAGAGCAGCCUGCCCCACAGCCAGGAGAACCUGCCCAAGCU<br>GUUCGAUGGCCUGAUCCUGGGCCCCCUGAAGGACGAGGGCAGCAGCGACCUGGCCAUCGUGAGCGACCCU<br>AGCCAGCAGCUGCCCUCCCCCAACGUGAACAACUUCCUGAACCCCGCCCCCCAGGAGAACCCCCUGAAGCAAC<br>UGCUGGCCGAGGAGCAGUGGGAGUUCGAGGUGACCGCCUUCUACAGAGGCAGACAGGUGUUCCAGCAGAC<br>CCUGUUCUGCCCCGGCGGCCUGAGACUGGUAGGCAGCACCGCUGACAUGACCCUGCCCUGGCAGCCCGUGA<br>CCCUGCCCGACCCCGAAGGCUUUCUGACCGACAAGCUGGUGAAGGAGUACGUCGGCCAAGUGCUGAAGGG<br>CCUGGGCAACGGCCUGGCCCUGUGGCAGGCCGGCCAGUGCCUGUGGGCCCAGAGACUCGGCCACAGCCACG<br>CCUUCUGGGCCCUGGGCGAGGAACUCCUGCCCGAUAGCGGCAGAGGCCCCGACGGCGAGGUGCACAAGGAC<br>AAGGACGGCGCCGUGUUCGACCUGCGCCCCUUCGUGGCCGACCUGAUCGCCUUCAUGGAGGGCAGCGGCC<br>ACAGCCCCAGAUAUACCCUGUGGUUCUGCAUGGGCGAGAUGUGGCCCCAGGACCAGCCCUGGGUGAAGAG<br>ACUGGUGAUGGUGAAGGUGGUGCCCACCUGCCUGAAAGAGCUGCUGGAGAUGGCCAGAGAGGGCGGCGC<br>CAGCUCCCUGAAAACCGUGGACCUGCACAUUGACAACAGCCAGCCCAUCAGCCUGACCAGCGACCAGUACAA |

-continued

SEQUENCE LISTING SUMMARY

| SEQ ID NO: | SEQUENCE |
|---|---|
| | GGCCUACCUGCAGGACCUGGUGGAGGACAUGGACUUCCAGGCCACCGGCAACAUC<br>(super mouse IRF3 S396D; no epitope tag) |
| 212 | AUGGGCACCCCCAAGCCCAGAAUCCUGCCCUGGCUGGUGAGCCAGCUGGACCUGGGCCAGCUGGAGGGAG<br>UGGCCUGGGUGAACAAGAGCAGAACCAGAUUCAGAAUCCCCUGGAAGCACGGCCUCAGACAGGACGCCCAG<br>CAGGAGGACUUCGGCAUUUUUCAGGCUUGGGCCGAGGCCACCGGCGCCUACGUGCCCGGCAGAGACAAGC<br>CCGACCUGCCCACCUGGAAAAGAAACUUCAGAAGCGCCUUGAAUAGAAAGGAGGGCCUGAGACUGGCCGAG<br>GACAGAAGCAAGGACCCCCACGACCCUCACAAGAUCUACGAGUUCGUGAAUAGCGGCGUGGGCGACUUUA<br>GCCAGCCCGACACCAGCCCCGACACCAACGGCGGCGGCAGCACCAGCGACACGCAGGAGGACAUCCUGGAUG<br>AACUGCUGGGCAACAUGGUGCUGGCCCCCCUGCCCGAUCCCGGCCCCCCUUCGCUUGCCGUGGCCCCCGAG<br>CCCUGCCCCCAGCCCCUGAGAAGCCCCUCUCUGGAUAACCCCACCCCCUUCCCCAACCUGGGCCCCAGCGAGA<br>AUCCACUGAAGAGACUUCUGGUCCCCGGCGAGGAGUGGGAGUUCGAGGUGACCGCCUUCUACAGAGGCAG<br>ACAGGUGUUCCAGCAGACCAUCAGCUGCCCCGAAGGCCUGAGAUUAGUGGGCAGCGAAGUGGGCGACAGG<br>ACCCUGCCCGGGUGGCCCGUGACCCUGCCCGAUCCCGGCAUGAGCCUGACCGACAGAGGUGUGAUGAGCUA<br>CGUGAGACACGUGCUGAGCUGCCUGGGCGGCGGCCUGGCACUGUGGAGAGCCGGCCAGUGGCUGUGGGC<br>CCAGAGACUGGGCCACUGCCACACCUACUGGGCCGUGAGCGAGGAGCUGCUGCCCAACAGCGGCCACGGCC<br>CCGACGGCGAGGUGCCCAAGGACAAGGAAGGGGGCGUGUUCGACCUGGGCCCCUUCAUCGUAGACCUGAU<br>CACCUUUACCGAGGGCAGCGGCAGGAGCCCCAGAUACGCCCUGUGGUUCUGCGUGGGCGAAAGCUGGCCC<br>CAGGACCAGCCCUGGACCAAGAGACUGGUGAUGGUGAAGGUAGUGCCCACCUGCCUGAGAGCCUUAGUGG<br>AGAUGGCCAGAGUGGGCGGGGCCAGCAGCCUGGAGAACACCGUGGAUCUUCACAUCGACAACAGCCACCCC<br>CUGAGCCUGACCAGCGACCAGUACAAGGCCUACCUGCAGGACCUGGUGGAGGGCAUGGACUUCCAGGCCCC<br>CGGCGAGACC<br>(super human IRF3 S396D; no epitope tag) |
| 213 | AUGGCGCUGGCCCCCGAAAGAGCCGCCCCCAGAGUCCUCUUCGGCGAAUGGCUCCUUGGCGAAAUUUCGUC<br>GGGCUGCUACGAGGGCUUACAAUGGCUGGAUGAGGCGAGAACCUGUUUCAGGGUGCCCUGGAAACACUU<br>CGCCAGAAAGGAUCUAAGCGAAGCAGAUGCUAGAAUUUUUAAGGCUUGGGCCGUGGCCAGGGGAAGAUG<br>GCCCCCCUCGAGCAGAGGCGGCGGCCCUCCCCCCGAGGCAGAAACGGCCGAGAGAGCCGGAUGGAAAACCAA<br>UUUCAGAUGCGCCCUGAGAUCUACAAGAAGAUUCGUGAUGCUUAGAGACAACAGCGGAGAUCCCGCCGAU<br>CCCCAUAAGGUGUAUGCCCUGUCCCGGGAGCUGUGCUGGAGGGAAGGGCCUGGCACUGACCAGACCGAAG<br>CCGAAGCCCCCGCGGCCGUGCCGCCGCCCCAAGGAGGCCCACCAGGCCCUUUCCUCGCUCACACCCACGCCGG<br>UCUGCAAGCCCCGGGACCUCUACCUGCCCCUGCCGGCGAUAAAGGCGACCUGUUGCUGCAGGCCGUCCAAC<br>AGAGCUGCCUGGCCGAUCAUCUGCUCACAGCCAGCUGGGGCGCUGACCCCGUCCCAACAAAGGCCCCCGGU<br>GAGGGCCAAGAAGGCCUGCCUCUGACCGGCGCCUGUGCCGGCGGCCCUGGCCUGCCUGCUGGCGAGCUGU<br>ACGGAUGGGCUGUCGAAACCACUCCCUCCCCCGGCCCCCAACCUGCGGCCCUGACAACCGGCGAGGCAGCCG<br>CACCCGAAAGCCCCCACCAGGCCGAACCCUACCUCAGUCCCAGCCCCUCCGCCUGCACCGCUGUGCAGGAGCC<br>CAGCCCCGGUGCUCUGGACGUAACAAUCAUGUACAAAGGCAGAACCGUGCUUCAGAAGGUGGUUGGACAC<br>CCCUCCUGUACUUUUCUCUACGGCCCCCCCGACCCUGCCGUGAGAGCUACCGACCCGCAACAGGUGGCCUU<br>UCCCUCGCCCGCCGAACUGCCCGAUCAAAAACAGCUGAGAUACACCGAGGAGCUGCUGAGACACGUGGCGC<br>CGGGCUUACACCUAGAGUUGAGAGGCCCCCAACUCUGGGCCAGACGCAUGGGCAAGUGUAAGGUGUACUG<br>GGAGGUCGGGGGCCCUCCCGGCUCUGCCAGCCCCAGCACCCCUGCUUGUCUCUUGCCCAGAAACUGUGAUA<br>CCCCCAUCUUCGACUUCCGUGUAUUUUUCCAGGAACUGGUCGAGUUUAGAGCCAGACAGAGACGAGGCAG<br>CCCCAGAUAUACAAUCUACCUCGGCUUCGGCCAGGACCUGAGUGCCGGCAGACCUAAGGAGAAGUCGCUGG<br>UCCUAGUGAAGUUAGAGCCCUGGCUAUGUAGAGUGCACCUGGAGGGCACCCAGAGAGAAGGAGUGAGCA<br>GCCUGGACAGCAGCAGCCUGAGUCUGUGCCUGAGCUCCGCCAACUCGCUGUAUGAUGACAUCGAGUGUUU<br>CCUCAUGGAGCUGGAGCAGCCCGCC<br>(Wild-type Hu IRF7 isoform A; P037 without epitope tag) |
| 214 | AUGGCCCUUGCCCCUGAGCGGGCCGCCCCCAGAGUGUUAUUCGGCGAGUGGCUGCUGGGCGAGAUCAGCA<br>GCGGCUGCUACGAGGGACUGCAGUGGCUGGACGAGGCUAGAACCUGCUUCAGAGUGCCCUGGAAGCAUU<br>UCGCCAGAAAAGACCUGAGCGAGGCUGAUGCUAGAAUCUUCAAAGCCUGGGCUGUGGCCCGAGGAAGAUG<br>GCCCCCCAGCAGCAGAGGAGGCGGCCCUCCUCCCGAGGCCGAAACCGCAGAGCGUGCUGGCUGGAAAACCA<br>ACUUUAGGUGUGCCCUGAGGAGCACCAGAAGAUUCGUUAUGCUCAGAGACAACAGCGGGGACCCCGCCGA<br>CCCGCACAAGGUGUACGCCUUAAGUAGGGAGCUGUGCUGGAGAGAGGGACCGGGGACCGACCAAACCGAG<br>GCUGAGGCGCCCGCCGCCGUUCCACCUCCCCAGGGUGGUCCCCCAGGGCCCUUUCUGGCACACACCCACGCC<br>GGAUUACAGGCGCCAGGGCCCUUACCCGCCCCCGCCGGAGACAAAGGCGACCUCCUGCUGCAAGCCGUGCA<br>ACAAAGCUGCCUGGCCGAUCACUUACUAACCGCUAGCUGGGGCGCCGAUCCUGUUCCCACCAAGGCCCCCG<br>GUGAAGGGCAAGAAGGACUGCCCUUAACCGGCGCCUGUGCCGGAGGCCCUGGUCUGCCAGCCGGCGAGCU<br>GUACGGUUGGGCUGUCGAAACAACACCCAGUCCGGGCCCACAGCCUGCCGCUCUGACCACCGGCGAAGCCG<br>CCGCCCCCGAGAGCCCACACCAGGCUGAACCCUACCUGAGCCCCAGCCCCAGCGCCUGCACCGCUGUGCAGG<br>AGCCUAGCCCCGGCGCUCUUGAUGUGACAAUAAUGUACAAGGGCAGGACCGUGCUGCAAAAGGUCGUGGG<br>CCAUCCGUCGUGUACCUUUCUGUACGGCCCUCCAGACCCCGCGGUUAGAGCCACCGACCCCCAGCAAGUCG<br>CCUUCCCCUCCCCCGCCGAACUGCCCGACCAAAAGCAGCUGCGGUACACAGAAGAACUACUUAGACACGUGG<br>CCCCCGGUCUGCACUUGGAGCUGAGAGGCCCCCAGCUCUGGGCCAGAAGAAUGGGCAAGUGCAAAGUGUA<br>CUGGGAGGUGGGCGGCCCACCCGGCUCAGCUUCGCCCUCCACACCCGCAUGCCUGCUGCCCAGAAAUUGCG<br>ACACGCCCAUCUUCGAUUUUAGAGUGUUCUUUCAGGAGUUGGUGGAGUUCAGAGCCAGACAAAGACGCG<br>GCAGCCCCAGAUACACCAUUUACCUCGGCUUCGGCCAGGACCUCAGCGCUGGCAGACCCAAGGAGAAGAGU<br>CUGGUCCUCGUGAAGCUGGAGCCCUGGCUGUGCAGAGUGCACCUGGAGGGCACCCAGCGUGAAGGCGUGA<br>GCAGCCUGGAUUCAAGCGACCUGGACCUAUGCCUAAGCAGCGCUAACUCACUGUACGACGAUAUCGAAUG<br>CUUCCUGAUGGAACUGGAGCAGCCUGCC<br>(constitutively active Hu IRF7 S477D/S479D; P033 without epitope tag) |

-continued

SEQUENCE LISTING SUMMARY

| SEQ ID NO: | SEQUENCE |
|---|---|
| 215 | AUGGCCCUGGCACCCGAGAGGGCCGCCCCCAGGGUGCUCUUCGGCGAGUGGUUACUAGGCGAAAUUAGCA<br>GCGGCUGCUAUGAAGGCCUUCAGUGGCUGGACGAGGCCAGAACCUGCUUUAGAGUUCCCUGGAAGCACUU<br>CGCCCGGAAAGAUCUCUCUGAAGCCGACGCCAGAAUAUUCAAGGCCUGGGCUGUCGCCAGGGGCAGGUGG<br>CCACCCUCCAGCCGAGGUGGCGGCCCUCCCCCUGAGGCUGAGACUGCGGAAAGGGCGGGCUGGAAGACCAA<br>UUUCAGAUGCGCUCUGAGAAGCACCAGACGUUUUGUGAUGCUAAGAGACAAUAGCGGCGAUCCCGCCGAC<br>CCCCAUAAGGUAUACGCACUGAGCCGAGAGCUCUGUUGGAGAGAAGGCCCCGGCACCGACCAGACCGAGGC<br>UGAAGCCCCUGCAGCCGUGCCCCCCCUCAAGGCGGGCCCCCCGGCCCCUUCCUGGCCCAUACCCAUGCAGG<br>GUUACAAGCACCCGGGCCCUUGCCCGCCCCAGCGGGAGACAAGGGCGACCUCUUACUGCAGGCCGUGCAAC<br>AAAGUUGUCUGGCGGACCACCUGCUGACCGCAUCAUGGGGCGCGGAUCCUGUGCCCACCAAGGCACCCGGC<br>GAAGGCCAGGAGGGCCUGCCCUUGACCGGCGCCUGCGCUGGCGGACCCGGCCUACCUGCUGGCGAACUGU<br>AUGGCUGGGCCGUAGAGACGACUCCCAGCCCUGGCCCACAACCCGCGGCUUUGACCACCGGCGAAGCCGCC<br>GCCCCCGAGUCUCCGCACCAGGCCGAGCCUUACCUCAGCCCAAGCCCUAGCGCCUGCACCGCCGUGCAAGAA<br>CCUAGCCCCGGAGCCCUGGAUGUGACAAUCAUGUACAAGGGUAGAACCGUACUGCAAAAGGUGGUGGGUC<br>AUCCCAGCUGCACCUUUCUUUACGGCCCACCCGACCCUGCCGUGCGAGCCACAGACCCACAACAGGUCGCCU<br>UCCCAAGCCCCGCCGAACUGCCCGAUCAGAAACAGCUGAGAUAUACAGAGGAGCUUCUGCGGCACGUAGCU<br>CCCGGCCUACAUCUCGAGCUGAGGGGCCCACAACUGUGGGCCAGACGCAUGGGCAAAUGCAAGGUCUACU<br>GGGAAGUGGGAGGCCCCCCGGCAGCGCAUCUCCCAGCACGCCCGCGUGCCUGCUGCCUAGAAAUUGCGAC<br>ACCCCCAUCUUUGACUUCCGGGUAUUCUUUCAGGAGCUGGUAGAGUUCAGAGCCAGGCAGCGGAGGGGC<br>UCCCCCAGAUACACAAUCUACCUGGGCUUCGGACAGGACCUGUCCGCCGGCCGCCCCAAGGAAAAGAGCCU<br>GGUGCUGGUGAAGCUGGAGCCCUGGCUGUGUAGGGUACACCUCGAAGGCACCCAGAGAGAAGGAGUGAG<br>CUCGCUUGAUGACAGCGAUCUGUCGGAUUGCCUUAGCAGCGCCAACAGCCUGUAUGAUGAUAUCGAGUGC<br>UUCCUUAUGGAACUGGAGCAGCCCGCC<br>(constitutively active Hu IRF7 S475D/S477D/L480D; P034 without epitope tag) |
| 216 | AUGGCCCUAGCCCCCGAAAGAGCAGCUCCCAGAGUGCUGUUCGGCGAAUGGCUGCUUGGCGAGAUCAGCA<br>GCGGCUGCUACGAAGGCCUGCAGUGGCUGGACGAAGCCCGCACCUGUUUCAGAGUGCCCUGGAAGCACUU<br>CGCUAGAAAGGAUUUGAGCGAGGCUGAUGCUAGAAUCUUUAAGGCUUGGGCUGUGGCAAGAGGCAGAUG<br>GCCGCCUAGUAGCAGAGGGGGCGGACCUCCCCCCGAGGCUGAGACCGCUGAGAGAGCAGGGUGGAAAACC<br>AACUUCAGAUGCGCGCUGAGAAGCACCCGAAGAUUCGUGAUGCUACGUGACAAUAGCGGCGACCCCGCCGA<br>CCCCCACAAAGUGUACGCCCUGUCCCGAGAACUUUGCUGGAGAGAGGGACCCGGCACCGAUCAAACAGAGG<br>CUGAGGCCCCGGCCGCUGUACCCCCGCCCCAAGGAGGCCCCCCAGGCCCCUUUCUGGCUCAUACACAUGCCG<br>GCCUGCAGGCACCCGGGCCCCUCCCGGCUCCUGCCGGCGACAAGGGCGAUCUCCUUCUCCAGGCCGUGCAG<br>CAGAGCUGCCUGGCCGAUCACCUGCUGACCGCCUCGUGGGGCGCCGACCCCGUGCCCACCAAAGCCCCGGG<br>UGAAGGCCAAGAGGGGCUCCCUUUAACCGGAGCAUGCGCCGGAGGCCCCGGCCUGCCAGCCGGCGAGUUA<br>UAUGGCUGGGCUGUGGAGACCACACCCUCCCCCGGCCCUCAACCCGCUGCCCUGACCACCGGUGAGGCCGCC<br>GCCCCCGAGAGCCCACACCAGGCCGAACCCUACCUGAGCCCUAGCCCUAGCGCCUGCACCGCCGUGCAAGAA<br>CCCAGCCCCGGAGCCCUGGAUGUGACCAUUAUGUACAAGGGCCGGACAGUGCUGCAAAAGGUUGUGGGAC<br>ACCCGAGCUGCACCUUUCUGUACGGUCCGCCUGACCCCGCCGUGAGAGCCACGGACCCGCAGCAGGUGGCC<br>UUCCCCUCACCCGCGGAGCUGCCCGACCAAAAGCAACUCAGAUACACAGAAGAACUAUUGCGUCACGUCGC<br>GCCCGGCCUGCAUCUGGAGCUGAGAGGCCCCCAGCUCUGGGCCAGAAGGAUGGGCAAAUGCAAGGUGUAC<br>UGGGAGGUGGGAGGCCCCCCGGCAGCGCCAGCCCCAGCACUCCCGCGUGCCUGCUGCCCAGAAAUUGCGA<br>CACUCCCAUCUUCGAUUUCAGGGUGUUCUUCCAGGAGCUGGUGGAGUUCAGAGCCAGGCAGAGAAGGGG<br>UAGCCCCAGAUACACAAUCUAUCUAGGCUUUGGACAAGAUCUGAGCGCCGGCCGGCCUAAGGAAAAAAGCC<br>UGGUGCUGGUAAAGCUGGAGCCGUGGCUUUGUAGAGUGCACCUGGAGGGGACGCAGCGAGAGGGCGUGA<br>GCAGCUUAGACGACGAUGACUUGGAUCUGUGUCUCGACAGCGCCAACGACUUGUACGACGACAUCGAGUG<br>CUUCCUGAUGGAACUGGAGCAGCCCGCC<br>(constitutively active Hu IRF7 S475D/S476D/S477D/S479D/S483D/S487D; P035 without epitope tag) |
| 217 | AUGGCCCUGGCCCCCGAGAGAGCCGCCCCCAGAGUGCUCUUCGGCGAGUGGCUGCUGGGCGAGAUAAGCA<br>GCGGCUGCUACGAAGGUCUGCAGUGGCUAGACGAGGCCAGAACCUGCUUUAGAGUGCCCUGGAAGCACUU<br>CGCUCGAAAGGACCUGUCCGAGGCCGAUGCUAGAAUUUUUAAGGCUUGGGCCGUCGCUAGGGGAAGAUG<br>GCCCCCUAGCAGUAGAGGCGGCGGCCCCCCUCCCGAAGCCGAGACGGCCGAGAGGGCCGGCUGGAAAACCA<br>AUUUCAGAUGCGCCCUGAGGAGCACCCGCAGGUUCGUAAUGCUGCGAGACAAUAGCGGCGAUCCUGCGGA<br>UCCUCACAAGGUUUACGCCUUGAGUAGAGAACUGUGCUGGCGGGAGGGCCCCGGAACCGACCAGACGGAG<br>GCAGAGGCACCCGCUGCCGUGCCCCCCCUCAAGGAGGACCCCCUGGACCCUUUCUGGCCCACACCCACGCU<br>GGUCUGCAGGCCCCAGGCCCACUGCCCGCCCCAGCGGGCGAUAAGGGUGACCUGCUCCUACAGGCGGUGCA<br>ACAGAGCUGUCUGGCCGACCACCUGUUGACCGCCAGCUGGGGGGCCGACCCGGUGCCCACCAAAGCUCCCG<br>GAGAGGGCCAAGAAGGCCUCCCACUAACUGGCGCCUGCGCCGGGGGCCCGGGAUUACCCGCCGGCGAGCUG<br>UAUGGCUGGGCCGUGGAGACCACGCCCAGCCCCGAGGGCGUGUCGUCCCUGGACAGCAGCAGCCUGAGCCU<br>GUGCCUGAGCUCCGCCAACAGCCUGUAUGACGACAUCGAGUGCUUCCUGAUGGAGCUGGAACAACCCGCC<br>(constitutively active truncated Hu IRF7 1-246 + 468-503; P032 without epitope tag) |
| 218 | AUGGCACUGGCGCCUGAAAGAGCCGCUCCGCGUGUGCUCUUCGGCGAGUGGCUGCUGGGCGAGAUCAGCU<br>CCGGCUGCUACGAGGGUCUACAGUGGCUGGACGAGGCCAGAACCUGUUUUAGAGUGCCCUGGAAGCACUU<br>CGCGAGAAAGGACCUGAGCGAGGCCGACGCCAGAAUCUUCAAAGCCUGGGCAGUGGCUAGGGGCAGAUGG<br>CCUCCCAGCAGCCGGGGCGGCGGCCCACCCCCCGAGGCCGAAACCGCCGAAAGAGCUGGCUGGAAGACCAAC<br>UUCAGAUGCGCCCUGAGAAGCACCAGAAGAUUUGUCAUGCUGAGAGAUAAUUCAGGAGACCCCGCCGACC<br>CUCACAAGGUGUACGCCCUGUCCAGAGAGCUGUGUUGGAGAGAGGGCCCCGGAACCGACCAGACCGAGGC<br>CGAGGCUCCAGCUGCCGUGCCACCCCCCCAAGGCGGACCACCCGGCCCCUUCUUGGCACAUACGCACGCCGG<br>CCUCCAGGCUCCCGGCCCUCUGCCCGCCCCUGCUGGUGACAAAGGCGAUCUGCUGCUGCAAGCCGUCCAGC<br>AAUCCUGCUUGGCUGACCACCUGCUGACCGCUAGCUGGGGAGCCGACCCCGUUCCCACCAAGGCUCCCGGA<br>GAAGGACAGGAGGGCCUGCCCCUUACCGGCGCUUGCGCGGGGGGCCCUGGCUUGCCUGCCGGCGAACUGU<br>ACGGCUGGGCCGUGGAGACCACGCCUUCCCCCGAGGGCGUGUCCAGCCUGGACGAUGAUGACCUGGAUCU |

-continued

SEQUENCE LISTING SUMMARY

| SEQ ID NO: | SEQUENCE |
|---|---|
| | GUGCCUGGACAGCGCCAACGACCUGUACGAUGACAUCGAGUGCUUUUUGAUGGAGCUGGAGCAGCCCGCC<br>(constitutively active truncated Hu IRF7 1-246 + 468-503 plus<br>S475D/S476D/S477D/S479D/S483D/S487D; P036 without epitope tag) |
| 219 | AUGGCCCUGGCCCCCGAGAGAGCCGCGCCCAGAGUGCUGUUCGGCGAAUGGCUGCUGGGCGAGAUCAGCA<br>GCGGCUGCUAUGAGGGCCUGCAGUGGCUCGACGAAGCCAGGACGUGCUUCAGAGUCCCCUGGAAGCACUU<br>CGCCAGAAAGGAUCUGAGCGAGGCUGACGCCAGAAUCUUCAAGGCCUGGGCAGUUGCGCGUGGGAGAUGG<br>CCCCCCAGCUCGCGGGGCGGCGGUCCCCCCCCUGAGGCCGAGACCGCCGAAAGAGCCGGAUGGAAAACCAAC<br>UUUCGAUGCGCCCUCAGAAGCACCAGACGGUUUGUGAUGCUGAGAGAUAACAGCGGCGACCCUGCAGACC<br>CCCAUAAAGUGUAUGCCCUGAGCAGAGAGCUGUGUUGGCGAGAGGGCCCCGGAACCGACCAAACCGAGGC<br>CGAGGCCCCCGCCGCCGUACCCCCCCUCAAGGCCCCCAGCCUGCUGCUCUGACCACGGGAGAAGCCGCCGC<br>UCCUGAGAGCCCCCACCAAGCCGAGCCCUAUCUGAGCCCUAGCCCCAGCGCCUGCACCGCCGUGCAGGAGCC<br>CUCACCGGGCGCCCUAGACGUGACCAUCAUGUACAAGGGGCGCACGGUGCUGCAAAAGGUGGUGGGCCAC<br>CCCAGCUGCACCUUCCUGUACGGCCCCCCGACCCUGCCGUGAGAGCCACCGACCCCCAGCAAGUCGCCUUC<br>CCCAGCCCCGCCGAGCUGCCCGACCAGAAGCAGCUGAGGUACACCGAGGAGUUGCUGAGACAUGUGGCCCC<br>CGGCUUGCACCUCGAGCUGAGAGGCCCGCAGCUCUGGGCCAGAAGAAUGGGCAAGUGCAAGGUGUACUGG<br>GAGGUGGGCGGCCCCCCCGGCAGCGCGAGCCCAAGCACCCCGGCCUGCCUGCUGCCUAGAAACUGCGACACC<br>CCUAUCUUCGACUUCAGAGUAUUUUUCCAGGAGCUGGUCGAGUUCAGGGCCAGACAGCGUAGAGGCAGCC<br>CCAGAUACACCAUCUACCUUGGAUUCGGCCAGGACCUGAGCGCCGGCAGACCCAAAGAGAAGUCCCUGGUA<br>CUGGUGAAGCUAGAGCCCUGGCUGUGUAGGGUGCAUCUGGAAGGCACCCAAAGAGAGGGCGUAAGCUCGC<br>UUGACAGCAGCAGCCUCAGCCUGUGCCUGAGCAGCGCUAACAGCUUAUACGACGACAUCGAGUGCUUCCU<br>GAUGGAGCUGGAACAACCCGCC<br>(truncated Hu IRF7 1-151 + 247-503; P038 without epitope tag; null mutation) |
| 220 | AUGGGCGGCCCUCCCGGGCCUUUCCUGGCCCAUACACACGCCGGCCUACAGGCUCCUGGCCCUCUGCCCGCC<br>CCGGCCGGCGACAAGGGCGACCUCCUGCUGCAGGCCGUGCAGCAGUCCUGUCUGGCCGACCACCUGCUGAC<br>UGCUAGCUGGGGCGCCGAUCCCGUGCCCACCAAGGCCCCAGGAGAGGGGCAAGAGGGCCUGCCUCUAACCG<br>GCGCAUGCGCAGGUGGACCAGGCCUCCCCGCCGGCGAGCUGUAUGGUUGGGCCGUGGAGACAACCCCCAGC<br>CCCGGCCCGCAGCCUGCUGCGCUGACCACAGGCGAGGCCGCUGCCCCUGAGAGCCCCCACCAAGCUGAACCC<br>UACCUGAGCCCCAGCCCCUCUGCCUGCACAGCGGUGCAGGAGCCCAGUCCCGGCGCCUUGGACGUGACCAU<br>CAUGUAUAAGGGCAGGACUGUGUUACAAAAGGUAGUGGGCCACCCAAGUUGUACCUUUCUGUACGGGCCC<br>CCCGACCCAGCCGUGCGCGCCACCGACCCCCAGCAGGUGGCCUUCCCCAGCCCCGCUGAGUUGCCCGAUCAG<br>AAACAACUCCGGUACACCGAGGAAUUACUUAGACAUGUGGCUCCCGGCCUGCAUCUGGAGCUUAGAGGUC<br>CACAGUUGUGGGCCAGAAGAAUGGGCAAGUGCAAGGUUUAUUGGGAGGUCGGAGGCCCCCCGGGCAGCG<br>CCAGCCCCAGCACCCCCGCCUGUCUUCUGCCCAGAAACUGCGACACCCCAAUCUUCGAUUUCAGAGUGUUU<br>UUCCAGGAACUGGUGGAGUUCAGAGCAAGGCAAAGAAGAGGCAGCCCUAGAUACACCAUCUACCUGGGCU<br>UUGGCCAAGACCUGAGCGCCGGCAGACCCAAGGAAAAAUCCCUGGUCCUGGUGAAACUGGAGCCCUGGCU<br>GUGCAGAGUCCACCUGGAGGGCACCCAGAGAGAGGGCGUGAGCAGCCUGGACUCGAGCAGCCUGUCCCUG<br>UGUCUGAGCAGCGCGAAUUCGCUAUAUGACGACAUCGAAUGCUUUCUGAUGGAGCUGGAACAGCCCGCC<br>(truncated Hu IRF7 152-503; P039 without epitope tag; null mutation) |
| 221 | AUGCCUCACAGCAGCCUCCACCCUAGCAUCCCUUGCCCUAGAGGCCACGGCGCCCAGAAGGCCGCCCUCGUG<br>CUUUUAAGCGCCUGCUUGGUGACCCUUUGGGGCUUGGGCGAGCCUCCAGAGCACACCUUGAGAUAUUUG<br>GUGCUCCACCUGGCCAGCCUUCAGCUGGGCUUGUUACUCAACGGCGUGUGCAGCCUGGCCGAGGAGCUGA<br>GACACAUCCACAGCAGAUACAGAGGCAGCUACUGGAGAACCGUGAGAGCGUGUCUGGGCUGCCCUCUGAG<br>AAGAGGCGCCUUGCUUCUUCUCAGUAUCUACUUCUACUACUCCCUGCCUAACGCCGUGGGCCCUCCUUUC<br>ACCUGGAUGCUGGCACUGCUCGGCCUCAGCCAGGCCCUGAACAUCUUGUUGGGCUUGAAGGGCCUGGCCC<br>CUGCCGAGAUCAGCGCCGUGUGCGAGAAGGGCAACUUCAACAUGGCCCACGGAUUGGCUUGGAGCUACUA<br>CAUCGGCUACCUGAGACUGAUCCUGCCUGAGCUGCAGGCCAGAAUCAGAACCUACAACCAGCACUACAACA<br>ACCUGCUGCGCGGCGCAGUGAGCCAGAGACUGUAUAUUCUGCUGCCUCUGGACUGCGGCGUGCCUGACAA<br>CCUGAGCAUGGCCGACCCUAACAUCAGAUUCCUGGACAAGCUGCCUCAGCAGACCGGCGACCACGCCGGCA<br>UCAAGGACAGAGUGUACAGCAACAGCAUCUAUGAGCUGCUCGAGAAUGGCCAGAGAGCCGGCACCUGCGU<br>GCUGGAGUACGCCACCCCUCUGCAGACCCUGUUCGCCAUGAGCCAGUAUAGUCAAGCUGGCUUCAGCAGA<br>GAGGACAGACUGGAGCAGGCCAAGCUGUUCUGCAGAACCCUGGAGGACAUUCUGGCUGACGCCCCUGAGA<br>GCCAGAACAACUGCCGACUGAUCGCCUACCAGGAACCAGCCGACGACAGCAGCUUCAGUCUUUCUCAGGAG<br>GUUCUUCGCCACUUGCGCCAGGAGGAGAAGGAGGAGGUGACCGUGGGCAGCCUGAAGACCUCCGCAGUCC<br>CUAGCACCAGCACCAUGAGUCAGGAGCCGGAGCUAUUAAUCAGCGGCAUGGAGAAGCCUCUUCCACUCCGA<br>ACCGACUUCAGCGCCACCAACUUCAGCCUGCUGAAGCAGGCAGGUGACGUUGAGGAGAAUCCGGGACCUA<br>UGACCGAGUACAAGCUGGUGGUUGUGGGCGCCGACGGCGUGGGCAAGAGCGCCCUGACCAUCCAGCUGAU<br>CCAG<br>(KRAS(G12D)25mer_nt.STING(V155M)) |
| 222 | AUGACCGAGUACAAGCUAGUAGUCGUGGGCGCCGACGGCGUGGGCAAGAGCGCCCUCACCAUCCAGCUAA<br>UCCAGGCCACCAACUUCAGCUUGCUCAAGCAGGCCGGCGACGUGGAGGAGAACCCAGGCCCUAUGCCUCAC<br>AGCAGCCUUCACCCUAGCAUCCCUUGCCCUAGAGGCCACGGCGCCCAGAAGGCCGCCCUGGUGCUGCUGAG<br>CGCCUGCCUGGUGACCCUGUGGGGCCUGGGCGAGCCUCCUGAGCACACCCUGAGAUAUCUGGUGCUUCAC<br>CUGGCCAGUUUACAGCUGGGCCUGCUUCUUAACGGCGUGUGCAGCCUGGCCGAGGAGCUGAGACACAUCC<br>ACAGCAGAUACAGAGGCAGCUACUGGAGAACCGUGAGAGCCUGCCUAGGCUGCCCUCUGAGAAGAGGCGC<br>UCUGUUGCUACUUUCCAUCUACUUCUACUACUCCCUGCCUAACGCCGUGGGCCCUCCUUUCACUUGGAUG<br>CUGGCGUUGCUGGGUCUGAGCCAGGCCCUGAACAUCCUUCUCGGUCUGAAGGGCCUGGCCCCUGCCGAGA<br>UCAGCGCCGUGUGCGAGAAGGGCAACUUCAACAUGGCCCACGGACUCGCCUGGAGCUACUACAUCGGCUAC<br>CUGAGACUGAUCCUGCCUGAGCUGCAGGCCAGAAUCAGAACCUACAACCAGCACUACAACAACCUGCUGCG<br>GGGCGCCGUGAGCCAGAGACUGUAUAUACUUCUUCCUCUGGACUGCGGCGUGCCUGACAACCUGAGCAUG |

-continued

SEQUENCE LISTING SUMMARY

| SEQ ID NO: | SEQUENCE |
|---|---|
| | GCCGACCCUAACAUCAGAUUCCUGGACAAGCUGCCUCAGCAGACCGGCGACCACGCCGGCAUCAAGGACAG<br>AGUGUACAGCAACUCCAUUUAUGAGCUGCUCGAGAAUGGCCAGAGAGCCGGCACCUGCGUGCUGGAGUAC<br>GCCACCCCUCUGCAGACCCUGUUCGCCAUGAGCCAGUACAGUCAGGCUGGAUUCAGCAGAGAGGACAGACU<br>GGAGCAGGCCAAGCUGUUCUGCAGGACACUGGAGGACAUACUAGCAGACGCCCCUGAGAGCCAGAACAACU<br>GCAGACUGAUUGCCUACCAGGAGCCUGCGGACGACAGCUCCUUCAGUCUGAGUCAGGAGGUGUUGCGGCA<br>CUUACGCCAAGAAGAGAAGGAGGAGGUGACCGUGGGCAGCCUGAAGACUAGCGCUGUGCCUAGCACCAGC<br>ACAAUGUCACAGGAGCCGGAAUUGCUAAUCAGCGGCAUGGAGAAGCCUCUCCCAUUACGUACCGACUUCA<br>GC<br>(KRAS(G12D)25mer_ct.STING(V155M)) |
| 223 | AUGCCUCACAGCAGCCUUCACCCUAGCAUCCCUUGCCCUAGAGGCCACGGCGCCCAGAAGGCCGCCCUAGUG<br>CUCCUUAGCGCCUGCCUCGUGACCCUAUGGGGCUUAGGCGAGCCUCCAGAGCACACCUUGAGAUACCUCGU<br>CCUCCACCUGGCUAGUCUACAGCUGGGCCUUCUCCUCAACGGCGUGUGCAGCCUGGCCGAGGAGCUGAGA<br>CACAUCCACAGCAGAUACAGAGGCAGCUACUGGAGAACCGUGAGAGCGUGCCUGGGCUGCCCUCUGAGAA<br>GAGGCGCACUGCUGUUACUCAGCAUCUACUUCUACUACUCACUGCCAAACGCCGUGGGCCCUCCUUUCACC<br>UGGAUGCUGGCCUUGCUCGGAUUGAGCCAGGCCCUGAACAUUUUACUGGGAUUGAAGGGCCUGGCCCCU<br>GCCGAGAUCAGCGCCGUGUGCGAGAAGGGCAACUUCAACAUGGCCCACGGCCUAGCUUGGAGCUACUACA<br>UCGGCUACCUGAGACUGAUCCUGCCUGAGCUGCAGGCCAGAAUCAGAACCUACAACCAGCACUACAACAAC<br>CUGCUGCGUGGAGCGGUGAGCCAGAGACUGUAUAUCCUCCUGCCUCUGGACUGCGGAGUGCCUGACAACC<br>UGAGCAUGGCCGACCCUAACAUCAGAUUCCUGGACAAGCUGCCUCAGCAGACCGGCGACCACGCCGGCAUC<br>AAGGACAGAGUGUACAGCAACUCAAUCUACGAGCUGUUGGAGAAUGGCCAGAGAGCCGGCACCUGCGUGC<br>UGGAGUACGCCACCCCUCUGCAGACCCUGUUCGCCAUGAGCCAGUACUCUCAGGCAGGCUUCAGCAGAGAG<br>GACAGACUGGAGCAGGCCAAGCUGUUCUGCAGAACCCUGGAGGACAUCCUGGCGGACGCCCCUGAGAGCCA<br>GAACAACUGCCGGCUUAUCGCCUACCAGGAGCCAGCAGACGACAGCAGCUUCUCUCUCUCACAAGAGGUAC<br>UGCGCCAUCUUCGCCAGGAGGAGAAGGAGGAGGUGACCGUGGGCAGCCUGAAGACAUCCGCCGUACCUAG<br>CACCAGCACCAUGUCUCAGGAACCGGAACUGUUGAUCAGCGGCAUGGAGAAGCCUCUGCCACUGCGCACCG<br>ACUUCAGCGCCACCAACUUCUCCCUACUGAAGCAAGCCGGUGACGUUGAAGAGAACCCUGGCCCUAUGACC<br>GAG UACAAGCUGGUAGUAGUAGGCGCCGACGGCGUGGGCAAGAGCGCCCUGACCAUCCAGCUGAUCCAGA<br>UGACUGAAUAUAAGCUUGUCGUCGUGGGCGCAGAUGGCGUUGGUAAGAGCGCACUUACAAUUCAACUCA<br>UUCAGAUGACGGAGUAUAAGCUGGUGGUGGUCGGAGCUGACGGCGUAGGCAAGAGUGCCCUUACUAUUC<br>AGCUAAUUCAG<br>(KRAS(G12D)25mer^3_nt.STING(V155M)) |
| 224 | AUGACCGAGUACAAGCUUGUGGUGGUUGGCGCCGACGGCGUGGGCAAGAGCGCCUUAACCAUCCAGCUUA<br>UCCAGAUGACAGAGUAUAAGCUAGUGGUGGUCGGCGCAGACGGAGUGGGAAAGAGUGCAUUAACUAUUC<br>AACUCAUCCAAAUGACCGAAUACAAGCUAGUAGUUGUGGGUGCAGAUGGCGUCGGCAAGUCUGCACUGAC<br>AAUUCAGCUCAUCCAGGCCACCAACUUCAGCCUGCUGAAGCAGGCCGGCGACGUGGAGGAGAACCCUGGCC<br>CUAUGCCUCACAGCAGCCUGCACCCUAGCAUCCCUUGCCCUAGAGGCCACGGCGCCCAGAAGGCCGCCCUGG<br>UGCUGCUGAGCGCCUGCCUGGUGACCCUGUGGGGCCUGGGCGAGCCUCCUGAGCACACCCUGAGAUACCU<br>AGUUUUGCACCUGGCUUCUCUGCAGCUGGGCCUACUGCUCAACGGCGUGUGCAGCCUGGCCGAGGAGCUG<br>AGACACAUCCACAGCAGAUACAGAGGCAGCUACUGGAGAACCGUGAGAGCAUGCUUAGGCUGCCCUCUGA<br>GAAGAGGCGCUCUGCUCCUCUUGUCCAUCUACUUCUACUACUCGCUACCUAACGCCGUGGGCCCUCCUUUC<br>ACCUGGAUGCUGGCCCUCUUGGGAUUAAGCCAGGCCCUGAACAUCUUGCUGGGACUGAAGGGCCUGGCCC<br>CUGCCGAGAUCAGCGCCGUGUGCGAGAAGGGCAACUUCAACAUGGCCCACGGACUCGCUUGGAGCUACUA<br>CAUCGGCUACCUGAGACUGAUCCUGCCUGAGCUGCAGGCCAGAAUCAGAACCUACAACCAGCACUACAACA<br>ACCUGCUGCGGGGAGCAGUGAGCCAGAGACUGUAUAUUCUGCUCCCUCUGGACUGCGGCGUGCCUGACAA<br>CCUGAGCAUGGCCGACCCUAACAUCAGAUUCCUGGACAAGCUGCCUCAGCAGACCGGCGACCACGCCGGCA<br>UCAAGGACAGAGUGUACAGCAACAGCAUUUACGAGCUGCUGGAGAACGGCCAGAGAGCCGGCACCUGCGU<br>GCUGGAGUACGCCACCCCUCUGCAGACCCUGUUCGCCAUGAGCCAGUACUCCCAGGCAGGAUUCAGCAGAG<br>AGGACAGACUGGAGCAGGCCAAGCUGUUCUGCCGUACUCUUGAGGACAUCCUUGCAGACGCCCCUGAGAG<br>CCAGAACAACUGCCGGUUGAUUGCCUACCAGGAACCGGCAGACGACAGCUCAUUCUCCUUGUCUCAGGAG<br>GUCCUUAGACACCUGCGGCAGGAGGAGAAGGAGGAGGUGACCGUGGGCAGCCUGAAGACAUCCGCCGUGC<br>CUAGCACGUCUACCAUGUCCCAGGAGCCGGAACUGCUAAUCAGCGGCAUGGAGAAGCCUCUGCCUCUCAGG<br>ACCGACUUCAGC<br>(KRAS(G12D)25mer^3_ct.STING(V155M)) |
| 225 | AUGCCCCAUAGCAGCCUGCACCCCAGCAUCCCCUGCCCCAGAGGCCACGGCGCCCAGAAGGCCGCCCUGGUC<br>CUGCUGAGCGCAUGCCUGGUCACCCUGUGGGGCCUGGGCGAGCCCCCCGAGCACACCCUGAGAUACCUGGU<br>GCUGCACCUCGCCAGCCUGCAGCUGGGCCUGCUGCUGAACGGCGUGUGCAGCCUGGCCGAGGAGCUGAGA<br>CACAUCCACAGCAGAUAUAGAGGCAGCUACUGGAGAACCGUGAGAGCUUGCCUCGGCUGCCCCCUGAGAAG<br>AGGCGCCCUGCUGCUGCUGAGCAUCUACUUUUACUACAGCCUGCCCAACGCUGUGGGCCCCCCUUUCACGU<br>GGAUGCUCGCCCUGCUGGGACUGAGCCAGGCCCUGAACAUCCUGCUGGGCCUUAAGGGCCUAGCCCCCGCC<br>GAGAUCAGCGCCGUGUGCGAGAAGGGCAACUUCAAUGUGGCCCACGGCCUGGCCUGGAGCUACUACAUCG<br>GCUACCUGAGACUGAUCCUGCCCGAGCUGCAGGCCAGAAUCAGAACCUACAAUCAGCACUACAACAACCUG<br>CUGAGAGGCGCCGUGAGCCAGAGACUGUACAUCCUGCUGCCCCUGGACUGCGGCGUGCCCGACAACCUCAG<br>CAUGGCCGACCCCAACAUCAGAUUCCUGGACAAGCUGCCCCAGCAGACCGGCGACCACGCCGGCAUCAAGGA<br>UCGCGUGUACAGCAACAGCAUCUACGAGCUGCUGGAAAACGGCCAGAGAGCCGGAACCUGCGUGCUGGAG<br>UACGCCACACCCCUGCAGACCCUGUUCGCCAUGAGCCAGUACAGCCAGGCCGGCUUCAGCAGAGAGGACAA<br>GCUGGAGCAGGCCAAGCUGUUCUGCAGAACCCUGGAGGAUAUCCUCGCCGACGCCCCCGAGAGCCAGAACA<br>ACUGCAGGCUGAUCGCGUACCAGGAGCCCGCUGACGACAGCAGCUUUAGCCUGAGCCAGGAGGUGCUGAG |

-continued

SEQUENCE LISTING SUMMARY

| SEQ ID NO: | SEQUENCE |
|---|---|
| | ACAUCUGCGUCAAGAGGAAAAGGAGGAGGUGACCGUGGGCUCCCUGAAGACCAGCGCCGUGCCCAGCACCA GCACCAUGAGCCAGGAGCCCGAGCUGCUGAUCAGCGGCAUGGAGAAGCCACUGCCCCUCAGAACCGACUUC AGCACC (Hu STING (R284K) var; no epitope tag) |
| 226 | ATIGTAMYK (EBV BRLF1 peptide) |
| 227 | SIIPSGPLK (FLU peptide) |
| 228 | AVDLSHFLK (HIV NEF peptide) |
| 229 | AVFDRKSDAK (EBV peptide) |
| 230 | YVNVNMGLK (HBV core antigen peptide) |
| 231 | RVCEKMALY (HC peptide) |
| 232 | KLGGALQAK (CMV peptide) |

What is claimed is:

1. An immunomodulatory therapeutic composition comprising an mRNA formulated in a lipid nanoparticle (LNP), wherein:

the mRNA comprises an open reading frame encoding a concatemer of four KRAS activating oncogene mutation peptides, each of the KRAS activating oncogene mutation peptides having an amino acid sequence independently selected from the group consisting of SEQ ID NOs: 121, 36, 39, 122, 37, 40, 123, 38, 41, 124, 125, and 72.

2. The immunomodulatory therapeutic composition of claim 1, wherein the concatemer comprises the KRAS activating oncogene mutation peptides having SEQ ID NOs: 39, 40, 41, and 72.

3. The immunomodulatory therapeutic composition of claim 1, wherein the concatemer comprises, from N- to C-terminus, the KRAS activating oncogene mutation peptides having respectively the amino acid sequences of SEQ ID NOs: 39, 40, 41, and 72.

4. The immunomodulatory therapeutic composition of claim 1, wherein the concatemer comprises amino acid sequence SEQ ID NO: 137.

5. The immunomodulatory therapeutic composition of claim 1, wherein the open reading frame comprises nucleotide sequence SEQ ID NO: 169.

6. The immunomodulatory therapeutic composition of claim 5, wherein all uridine nucleosides in the mRNA are N1-methylpseudouridine.

7. The immunomodulatory therapeutic composition of claim 1, wherein the mRNA comprises nucleotide sequence SEQ ID NO: 167.

8. The immunomodulatory therapeutic composition of claim 7, wherein all uridine nucleosides in the mRNA are N1-methylpseudouridine.

9. The immunomodulatory therapeutic composition of claim 1, wherein the LNP comprises a molar ratio of about 20-60% ionizable amino lipid: about 5-25% phospholipid: about 25-55% sterol: about 0.5-15% PEG-modified lipid.

10. The immunomodulatory therapeutic composition of claim 1, wherein the LNP comprises a molar ratio of about 20-60% Compound 25: about 5-25% DSPC: about 25-55% cholesterol: about 0.5-15% PEG-DMG.

11. The immunomodulatory therapeutic composition of claim 1, wherein the LNP comprises a molar ratio of about 50% Compound 25: about 10% DSPC: about 38.5% cholesterol: about 1.5% PEG-DMG.

12. An immunomodulatory therapeutic composition, comprising: an mRNA comprising an open reading frame encoding a concatemer of 3-10 KRAS activating oncogene mutation peptides, wherein each peptide is about 10-30 amino acids in length, and wherein each peptide comprises a mutation independently selected from the group consisting of G12D, G12V, G12C, G12S, G12A, G12R and G13D mutations in human KRAS of SEQ ID NO: 166.

13. The immunomodulatory therapeutic composition of claim 12, wherein the mutations are independently selected from the group consisting of the G12D, G12V, G12C and G13D mutations.

14. The immunomodulatory therapeutic composition of claim 12, wherein the concatemer comprises peptides.

15. The immunomodulatory therapeutic composition of claim 12, wherein each peptide is about 15-25 amino acids in length.

16. The immunomodulatory therapeutic composition of claim 12, wherein at least two of the peptides are linked directly to one another without a linker.

17. The immunomodulatory therapeutic composition of claim 12, wherein the mRNA comprises 200, 300, 400, 500, 600, 700, 800, or 900 nucleotides.

18. The immunomodulatory therapeutic composition of claim 12, wherein the concatemer is a 100-mer concatemer.

19. The immunomodulatory therapeutic composition of claim 12, wherein all uridine nucleosides in the mRNA are N1-methylpseudouridine.

20. The immunomodulatory therapeutic composition of claim 12, wherein the mRNA is formulated in a lipid nanoparticle.

21. The immunomodulatory therapeutic composition of claim 20, wherein the lipid nanoparticle comprises a molar ratio of about 20-60% ionizable amino lipid: about 5-25% phospholipid: about 25-55% sterol: about 0.5-15% PEG-modified lipid.

22. The immunomodulatory therapeutic composition of claim 20, wherein the LNP comprises a molar ratio of about 20-60% Compound 25: about 5-25% DSPC: about 25-55% cholesterol: about 0.5-15% PEG-DMG.

23. The immunomodulatory therapeutic composition of claim 20, wherein the LNP comprises a molar ratio of about 50% Compound 25: about 10% DSPC: about 38.5% cholesterol: about 1.5% PEG-DMG.

24. An immunomodulatory therapeutic composition, comprising: an mRNA comprising an open reading frame encoding a concatemer of four KRAS activating oncogene mutation peptides, wherein each peptide is about 10-30 amino acids in length, wherein each peptide comprises a mutation independently selected from the group consisting of G12D, G12V, G12C, and G13D mutations in human KRAS of SEQ ID NO: 166, and wherein the peptides are linked directly to one another without a linker.

25. The immunomodulatory therapeutic composition of claim 24, wherein the peptides are about 15-25 amino acids in length.

26. The immunomodulatory therapeutic composition of claim 24, wherein the mRNA comprises 200, 300, 400, 500, 600, 700, 800, or 900 nucleotides.

27. The immunomodulatory therapeutic composition of claim 24, wherein the concatemer is a 100-mer concatemer.

28. The immunomodulatory therapeutic composition of claim 24, wherein all uridine nucleosides in the mRNA are N1-methylpseudouridine.

29. The immunomodulatory therapeutic composition of claim 24, wherein the mRNA is formulated in a lipid nanoparticle.

30. The immunomodulatory therapeutic composition of claim 29, wherein the lipid nanoparticle comprises a molar ratio of about 20-60% ionizable amino lipid: about 5-25% phospholipid: about 25-55% sterol: about 0.5-15% PEG-modified lipid.

31. The immunomodulatory therapeutic composition of claim 29, wherein the LNP comprises a molar ratio of about 20-60% Compound 25: about 5-25% DSPC: about 25-55% cholesterol: about 0.5-15% PEG-DMG.

32. The immunomodulatory therapeutic composition of claim 29, wherein the LNP comprises a molar ratio of about 50% Compound 25: about 10% DSPC: about 38.5% cholesterol: about 1.5% PEG DMG.

33. An immunomodulatory therapeutic composition comprising an mRNA formulated in a lipid nanoparticle (LNP), wherein:

the mRNA comprises an open reading frame encoding a concatemer of four KRAS activating oncogene mutation peptides, the concatemer comprising amino acid sequence SEQ ID NO: 137;

the LNP comprises a molar ratio of about 20-60% Compound 25: about 5-25% DSPC: about 25-55% cholesterol: about 0.1-15% PEG-DMG; and wherein one or more uridine nucleosides in the mRNA are N1-methylpseudouridine.

34. The immunomodulatory therapeutic composition of claim 33, wherein the open reading frame comprises nucleotide sequences SEQ ID NO: 169.

35. The immunomodulatory therapeutic composition of claim 33, wherein the mRNA comprises nucleotide sequences SEQ ID NO: 167.

36. The immunomodulatory therapeutic composition of claim 33, wherein the LNP comprises the molar ratio of about 50% Compound 25: about 10% DSPC: about 38.5% cholesterol: about 1.5% PEG-DMG.

37. The immunomodulatory therapeutic composition of claim 36, wherein the open reading frame comprises nucleotide sequence SEQ ID NO: 169.

38. The immunomodulatory therapeutic composition of claim 36, wherein the mRNA comprises nucleotide sequences SEQ ID NO: 167.

39. The immunomodulatory therapeutic composition of claim 36, wherein all uridine nucleosides in the mRNA are N1-methylpseudouridine.

40. An immunomodulatory therapeutic composition comprising an mRNA formulated in a lipid nanoparticle (LNP), wherein:

the mRNA comprises an open reading frame encoding a concatemer of four KRAS activating oncogene mutation peptides, each of the KRAS activating oncogene mutation peptides having an amino acid sequence independently selected from the group consisting of SEQ ID NOs: 39, 40, 41, and 72.

41. The immunomodulatory therapeutic composition of claim 40, wherein all uridine nucleosides in the mRNA are N1-methylpseudouridine.

42. The immunomodulatory therapeutic composition of claim 40, wherein the LNP comprises a molar ratio of about 20-60% ionizable amino lipid: about 5-25% phospholipid: about 25-55% sterol: about 0.5-15% PEG-modified lipid.

43. The immunomodulatory therapeutic composition of claim 40, wherein the LNP comprises a molar ratio of about 20-60% Compound 25: about 5-25% DSPC: about 25-55% cholesterol: about 0.5-15% PEG-DMG.

44. The immunomodulatory therapeutic composition of claim 40, wherein the LNP comprises a molar ratio of about 50% Compound 25: about 10% DSPC: about 38.5% cholesterol: about 1.5% PEG-DMG.

* * * * *

UNITED STATES PATENT AND TRADEMARK OFFICE

CERTIFICATE OF CORRECTION

PATENT NO. : 10,881,730 B2
APPLICATION NO. : 16/279372
DATED : January 5, 2021
INVENTOR(S) : Eric Yi-Chun Huang et al.

It is certified that error appears in the above-identified patent and that said Letters Patent is hereby corrected as shown below:

In the Claims

At Column 727, Claim number 14, Line number 41, please delete “comprises peptides.” and insert -- comprises 4 peptides. --

At Column 728, Claim number 34, Line number 57, please delete “sequences” and insert -- sequence --

At Column 728, Claim number 35, Line number 60, please delete “sequences” and insert -- sequence --

At Column 729, Claim number 38, Line number 3, please delete “sequences” and insert -- sequence --

Signed and Sealed this
Twenty-third Day of February, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 232

<210> SEQ ID NO 1
<211> LENGTH: 379
<212> TYPE: PRT
<213> ORGANISM: Artificial Sequence
<220> FEATURE:
<223> OTHER INFORMATION: Synthetic: huSTING(V155M); no epitope tag

<400> SEQUENCE: 1

```
Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
            20                  25                  30

Leu Trp Gly Leu Gly Glu Pro Pro Glu His Thr Leu Arg Tyr Leu Val
        35                  40                  45

Leu His Leu Ala Ser Leu Gln Leu Gly Leu Leu Leu Asn Gly Val Cys
    50                  55                  60

Ser Leu Ala Glu Glu Leu Arg His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Tyr Ser Leu Pro Asn Ala
            100                 105                 110

Val Gly Pro Pro Phe Thr Trp Met Leu Ala Leu Leu Gly Leu Ser Gln
        115                 120                 125

Ala Leu Asn Ile Leu Leu Gly Leu Lys Gly Leu Ala Pro Ala Glu Ile
    130                 135                 140

Ser Ala Val Cys Glu Lys Gly Asn Phe Asn Met Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
```

```
        195                 200                 205

Pro Asp Asn Leu Ser Met Ala Asp Pro Asn Ile Arg Phe Leu Asp Lys
    210                 215                 220

Leu Pro Gln Gln Thr Gly Asp His Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
            260                 265                 270

Gln Tyr Ser Gln Ala Gly Phe Ser Arg Glu Asp Arg Leu Glu Gln Ala
        275                 280                 285

Lys Leu Phe Cys Arg Thr Leu Glu Asp Ile Leu Ala Asp Ala Pro Glu
    290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335

Glu Lys Glu Glu Val Thr Val Gly Ser Leu Lys Thr Ser Ala Val Pro
            340                 345                 350

Ser Thr Ser Thr Met Ser Gln Glu Pro Glu Leu Leu Ile Ser Gly Met
        355                 360                 365

Glu Lys Pro Leu Pro Leu Arg Thr Asp Phe Ser
    370                 375


<210> SEQ ID NO 2
<211> LENGTH: 379
<212> TYPE: PRT
<213> ORGANISM: Artificial Sequence
<220> FEATURE:
<223> OTHER INFORMATION: Synthetic: Hu STING(R284T); no epitope tag

<400> SEQUENCE: 2

Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
            20                  25                  30

Leu Trp Gly Leu Gly Glu Pro Pro Glu His Thr Leu Arg Tyr Leu Val
        35                  40                  45

Leu His Leu Ala Ser Leu Gln Leu Gly Leu Leu Leu Asn Gly Val Cys
    50                  55                  60

Ser Leu Ala Glu Glu Leu Arg His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Tyr Ser Leu Pro Asn Ala
            100                 105                 110

Val Gly Pro Pro Phe Thr Trp Met Leu Ala Leu Leu Gly Leu Ser Gln
        115                 120                 125

Ala Leu Asn Ile Leu Leu Gly Leu Lys Gly Leu Ala Pro Ala Glu Ile
    130                 135                 140

Ser Ala Val Cys Glu Lys Gly Asn Phe Asn Val Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
```

```
            180                 185                 190

Ala Val Ser Gln Arg Leu Tyr Ile Leu Leu Pro Leu Asp Cys Gly Val
        195                 200                 205

Pro Asp Asn Leu Ser Met Ala Asp Pro Asn Ile Arg Phe Leu Asp Lys
    210                 215                 220

Leu Pro Gln Gln Thr Gly Asp His Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
            260                 265                 270

Gln Tyr Ser Gln Ala Gly Phe Ser Arg Glu Asp Thr Leu Glu Gln Ala
        275                 280                 285

Lys Leu Phe Cys Arg Thr Leu Glu Asp Ile Leu Ala Asp Ala Pro Glu
    290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335

Glu Lys Glu Glu Val Thr Val Gly Ser Leu Lys Thr Ser Ala Val Pro
            340                 345                 350

Ser Thr Ser Thr Met Ser Gln Glu Pro Glu Leu Leu Ile Ser Gly Met
        355                 360                 365

Glu Lys Pro Leu Pro Leu Arg Thr Asp Phe Ser
    370                 375


<210> SEQ ID NO 3
<211> LENGTH: 379
<212> TYPE: PRT
<213> ORGANISM: Artificial Sequence
<220> FEATURE:
<223> OTHER INFORMATION: Synthetic: hu STING (R284M); no epitope tag

<400> SEQUENCE: 3

Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
            20                  25                  30

Leu Trp Gly Leu Gly Glu Pro Pro Glu His Thr Leu Arg Tyr Leu Val
        35                  40                  45

Leu His Leu Ala Ser Leu Gln Leu Gly Leu Leu Leu Asn Gly Val Cys
    50                  55                  60

Ser Leu Ala Glu Glu Leu Arg His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Tyr Ser Leu Pro Asn Ala
            100                 105                 110

Val Gly Pro Pro Phe Thr Trp Met Leu Ala Leu Leu Gly Leu Ser Gln
        115                 120                 125

Ala Leu Asn Ile Leu Leu Gly Leu Lys Gly Leu Ala Pro Ala Glu Ile
    130                 135                 140

Ser Ala Val Cys Glu Lys Gly Asn Phe Asn Val Ala His Gly Leu Ala
145                 150                 155                 160

Trp Ser Tyr Tyr Ile Gly Tyr Leu Arg Leu Ile Leu Pro Glu Leu Gln
```

```
                165                 170                 175

Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
        195                 200                 205

Pro Asp Asn Leu Ser Met Ala Asp Pro Asn Ile Arg Phe Leu Asp Lys
    210                 215                 220

Leu Pro Gln Gln Thr Gly Asp His Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
            260                 265                 270

Gln Tyr Ser Gln Ala Gly Phe Ser Arg Glu Asp Met Leu Glu Gln Ala
        275                 280                 285

Lys Leu Phe Cys Arg Thr Leu Glu Asp Ile Leu Ala Asp Ala Pro Glu
    290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335

Glu Lys Glu Glu Val Thr Val Gly Ser Leu Lys Thr Ser Ala Val Pro
            340                 345                 350

Ser Thr Ser Thr Met Ser Gln Glu Pro Glu Leu Leu Ile Ser Gly Met
        355                 360                 365

Glu Lys Pro Leu Pro Leu Arg Thr Asp Phe Ser
    370                 375


<210> SEQ ID NO 4
<211> LENGTH: 379
<212> TYPE: PRT
<213> ORGANISM: Artificial Sequence
<220> FEATURE:
<223> OTHER INFORMATION: Synthetic: Hu STING (R284K); no epitope tag

<400> SEQUENCE: 4

Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
            20                  25                  30

Leu Trp Gly Leu Gly Glu Pro Pro Glu His Thr Leu Arg Tyr Leu Val
        35                  40                  45

Leu His Leu Ala Ser Leu Gln Leu Gly Leu Leu Leu Asn Gly Val Cys
    50                  55                  60

Ser Leu Ala Glu Glu Leu Arg His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Tyr Ser Leu Pro Asn Ala
            100                 105                 110

Val Gly Pro Pro Phe Thr Trp Met Leu Ala Leu Leu Gly Leu Ser Gln
        115                 120                 125

Ala Leu Asn Ile Leu Leu Gly Leu Lys Gly Leu Ala Pro Ala Glu Ile
    130                 135                 140

Ser Ala Val Cys Glu Lys Gly Asn Phe Asn Val Ala His Gly Leu Ala
```

```
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
        195                 200                 205

Pro Asp Asn Leu Ser Met Ala Asp Pro Asn Ile Arg Phe Leu Asp Lys
    210                 215                 220

Leu Pro Gln Gln Thr Gly Asp His Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
            260                 265                 270

Gln Tyr Ser Gln Ala Gly Phe Ser Arg Glu Asp Lys Leu Glu Gln Ala
        275                 280                 285

Lys Leu Phe Cys Arg Thr Leu Glu Asp Ile Leu Ala Asp Ala Pro Glu
    290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335

Glu Lys Glu Glu Val Thr Val Gly Ser Leu Lys Thr Ser Ala Val Pro
            340                 345                 350

Ser Thr Ser Thr Met Ser Gln Glu Pro Glu Leu Leu Ile Ser Gly Met
        355                 360                 365

Glu Lys Pro Leu Pro Leu Arg Thr Asp Phe Ser
    370                 375
```

<210> SEQ ID NO 5
<211> LENGTH: 379
<212> TYPE: PRT
<213> ORGANISM: Artificial Sequence
<220> FEATURE:
<223> OTHER INFORMATION: Synthetic: Hu STING(N154S); no epitope tag

<400> SEQUENCE: 5

```
Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
            20                  25                  30

Leu Trp Gly Leu Gly Glu Pro Pro Glu His Thr Leu Arg Tyr Leu Val
        35                  40                  45

Leu His Leu Ala Ser Leu Gln Leu Gly Leu Leu Leu Asn Gly Val Cys
    50                  55                  60

Ser Leu Ala Glu Glu Leu Arg His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Tyr Ser Leu Pro Asn Ala
            100                 105                 110

Val Gly Pro Pro Phe Thr Trp Met Leu Ala Leu Leu Gly Leu Ser Gln
        115                 120                 125

Ala Leu Asn Ile Leu Leu Gly Leu Lys Gly Leu Ala Pro Ala Glu Ile
```

```
    130                 135                 140

Ser Ala Val Cys Glu Lys Gly Asn Phe Ser Val Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
        195                 200                 205

Pro Asp Asn Leu Ser Met Ala Asp Pro Asn Ile Arg Phe Leu Asp Lys
    210                 215                 220

Leu Pro Gln Gln Thr Gly Asp His Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
            260                 265                 270

Gln Tyr Ser Gln Ala Gly Phe Ser Arg Glu Asp Arg Leu Glu Gln Ala
        275                 280                 285

Lys Leu Phe Cys Arg Thr Leu Glu Asp Ile Leu Ala Asp Ala Pro Glu
    290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335

Glu Lys Glu Glu Val Thr Val Gly Ser Leu Lys Thr Ser Ala Val Pro
            340                 345                 350

Ser Thr Ser Thr Met Ser Gln Glu Pro Glu Leu Leu Ile Ser Gly Met
        355                 360                 365

Glu Lys Pro Leu Pro Leu Arg Thr Asp Phe Ser
    370                 375


<210> SEQ ID NO 6
<211> LENGTH: 379
<212> TYPE: PRT
<213> ORGANISM: Artificial Sequence
<220> FEATURE:
<223> OTHER INFORMATION: Synthetic: Hu STING(V147L); no epitope tag

<400> SEQUENCE: 6

Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
            20                  25                  30

Leu Trp Gly Leu Gly Glu Pro Pro Glu His Thr Leu Arg Tyr Leu Val
        35                  40                  45

Leu His Leu Ala Ser Leu Gln Leu Gly Leu Leu Leu Asn Gly Val Cys
    50                  55                  60

Ser Leu Ala Glu Glu Leu Arg His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Tyr Ser Leu Pro Asn Ala
            100                 105                 110

Val Gly Pro Pro Phe Thr Trp Met Leu Ala Leu Leu Gly Leu Ser Gln
```

```
        115                 120                 125

Ala Leu Asn Ile Leu Leu Gly Leu Lys Gly Leu Ala Pro Ala Glu Ile
    130                 135                 140

Ser Ala Leu Cys Glu Lys Gly Asn Phe Asn Val Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
        195                 200                 205

Pro Asp Asn Leu Ser Met Ala Asp Pro Asn Ile Arg Phe Leu Asp Lys
    210                 215                 220

Leu Pro Gln Gln Thr Gly Asp His Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
            260                 265                 270

Gln Tyr Ser Gln Ala Gly Phe Ser Arg Glu Asp Arg Leu Glu Gln Ala
        275                 280                 285

Lys Leu Phe Cys Arg Thr Leu Glu Asp Ile Leu Ala Asp Ala Pro Glu
    290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335

Glu Lys Glu Glu Val Thr Val Gly Ser Leu Lys Thr Ser Ala Val Pro
            340                 345                 350

Ser Thr Ser Thr Met Ser Gln Glu Pro Glu Leu Leu Ile Ser Gly Met
        355                 360                 365

Glu Lys Pro Leu Pro Leu Arg Thr Asp Phe Ser
    370                 375


<210> SEQ ID NO 7
<211> LENGTH: 379
<212> TYPE: PRT
<213> ORGANISM: Artificial Sequence
<220> FEATURE:
<223> OTHER INFORMATION: Synthetic: Hu STING (E315Q); no epitope tag

<400> SEQUENCE: 7

Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
            20                  25                  30

Leu Trp Gly Leu Gly Glu Pro Pro Glu His Thr Leu Arg Tyr Leu Val
        35                  40                  45

Leu His Leu Ala Ser Leu Gln Leu Gly Leu Leu Leu Asn Gly Val Cys
    50                  55                  60

Ser Leu Ala Glu Glu Leu Arg His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Tyr Ser Leu Pro Asn Ala
```

```
            100                 105                 110

Val Gly Pro Pro Phe Thr Trp Met Leu Ala Leu Leu Gly Leu Ser Gln
        115                 120                 125

Ala Leu Asn Ile Leu Leu Gly Leu Lys Gly Leu Ala Pro Ala Glu Ile
    130                 135                 140

Ser Ala Val Cys Glu Lys Gly Asn Phe Asn Val Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
        195                 200                 205

Pro Asp Asn Leu Ser Met Ala Asp Pro Asn Ile Arg Phe Leu Asp Lys
    210                 215                 220

Leu Pro Gln Gln Thr Gly Asp His Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
            260                 265                 270

Gln Tyr Ser Gln Ala Gly Phe Ser Arg Glu Asp Arg Leu Glu Gln Ala
        275                 280                 285

Lys Leu Phe Cys Arg Thr Leu Glu Asp Ile Leu Ala Asp Ala Pro Glu
    290                 295                 300

Ser Gln Asn Asn Cys Arg Leu Ile Ala Tyr Gln Gln Pro Ala Asp Asp
305                 310                 315                 320

Ser Ser Phe Ser Leu Ser Gln Glu Val Leu Arg His Leu Arg Gln Glu
                325                 330                 335

Glu Lys Glu Glu Val Thr Val Gly Ser Leu Lys Thr Ser Ala Val Pro
            340                 345                 350

Ser Thr Ser Thr Met Ser Gln Glu Pro Glu Leu Leu Ile Ser Gly Met
        355                 360                 365

Glu Lys Pro Leu Pro Leu Arg Thr Asp Phe Ser
    370                 375
```

<210> SEQ ID NO 8
<211> LENGTH: 379
<212> TYPE: PRT
<213> ORGANISM: Artificial Sequence
<220> FEATURE:
<223> OTHER INFORMATION: Synthetic: Hu STING (R375A); no epitope tag

<400> SEQUENCE: 8

```
Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
            20                  25                  30

Leu Trp Gly Leu Gly Glu Pro Pro Glu His Thr Leu Arg Tyr Leu Val
        35                  40                  45

Leu His Leu Ala Ser Leu Gln Leu Gly Leu Leu Leu Asn Gly Val Cys
    50                  55                  60

Ser Leu Ala Glu Glu Leu Arg His Ile His Ser Arg Tyr Arg Gly Ser
65                  70                  75                  80

Tyr Trp Arg Thr Val Arg Ala Cys Leu Gly Cys Pro Leu Arg Arg Gly
```

```
                85                  90                  95

Ala Leu Leu Leu Leu Ser Ile Tyr Phe Tyr Tyr Ser Leu Pro Asn Ala
            100                 105                 110

Val Gly Pro Pro Phe Thr Trp Met Leu Ala Leu Leu Gly Leu Ser Gln
        115                 120                 125

Ala Leu Asn Ile Leu Leu Gly Leu Lys Gly Leu Ala Pro Ala Glu Ile
    130                 135                 140

Ser Ala Val Cys Glu Lys Gly Asn Phe Asn Val Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
        195                 200                 205

Pro Asp Asn Leu Ser Met Ala Asp Pro Asn Ile Arg Phe Leu Asp Lys
    210                 215                 220

Leu Pro Gln Gln Thr Gly Asp His Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
            260                 265                 270

Gln Tyr Ser Gln Ala Gly Phe Ser Arg Glu Asp Arg Leu Glu Gln Ala
        275                 280                 285

Lys Leu Phe Cys Arg Thr Leu Glu Asp Ile Leu Ala Asp Ala Pro Glu
    290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335

Glu Lys Glu Glu Val Thr Val Gly Ser Leu Lys Thr Ser Ala Val Pro
            340                 345                 350

Ser Thr Ser Thr Met Ser Gln Glu Pro Glu Leu Leu Ile Ser Gly Met
        355                 360                 365

Glu Lys Pro Leu Pro Leu Ala Thr Asp Phe Ser
    370                 375


<210> SEQ ID NO 9
<211> LENGTH: 379
<212> TYPE: PRT
<213> ORGANISM: Artificial Sequence
<220> FEATURE:
<223> OTHER INFORMATION: Synthetic: Hu STING(V147L/N154S/V155M); no
      epitope tag

<400> SEQUENCE: 9

Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
            20                  25                  30

Leu Trp Gly Leu Gly Glu Pro Pro Glu His Thr Leu Arg Tyr Leu Val
        35                  40                  45

Leu His Leu Ala Ser Leu Gln Leu Gly Leu Leu Leu Asn Gly Val Cys
    50                  55                  60
```

```
Ser Leu Ala Glu Glu Leu Arg His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Tyr Ser Leu Pro Asn Ala
            100                 105                 110

Val Gly Pro Pro Phe Thr Trp Met Leu Ala Leu Leu Gly Leu Ser Gln
        115                 120                 125

Ala Leu Asn Ile Leu Leu Gly Leu Lys Gly Leu Ala Pro Ala Glu Ile
    130                 135                 140

Ser Ala Leu Cys Glu Lys Gly Asn Phe Ser Met Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
        195                 200                 205

Pro Asp Asn Leu Ser Met Ala Asp Pro Asn Ile Arg Phe Leu Asp Lys
    210                 215                 220

Leu Pro Gln Gln Thr Gly Asp His Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
            260                 265                 270

Gln Tyr Ser Gln Ala Gly Phe Ser Arg Glu Asp Arg Leu Glu Gln Ala
        275                 280                 285

Lys Leu Phe Cys Arg Thr Leu Glu Asp Ile Leu Ala Asp Ala Pro Glu
    290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335

Glu Lys Glu Glu Val Thr Val Gly Ser Leu Lys Thr Ser Ala Val Pro
            340                 345                 350

Ser Thr Ser Thr Met Ser Gln Glu Pro Glu Leu Leu Ile Ser Gly Met
        355                 360                 365

Glu Lys Pro Leu Pro Leu Arg Thr Asp Phe Ser
    370                 375
```

<210> SEQ ID NO 10
<211> LENGTH: 379
<212> TYPE: PRT
<213> ORGANISM: Artificial Sequence
<220> FEATURE:
<223> OTHER INFORMATION: Synthetic: Hu STING(R284M/V147L/N154S/V155M); no epitope tag

<400> SEQUENCE: 10

```
Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
            20                  25                  30

Leu Trp Gly Leu Gly Glu Pro Pro Glu His Thr Leu Arg Tyr Leu Val
        35                  40                  45
```

```
Leu His Leu Ala Ser Leu Gln Leu Gly Leu Leu Leu Asn Gly Val Cys
    50                  55                  60

Ser Leu Ala Glu Glu Leu Arg His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Tyr Ser Leu Pro Asn Ala
            100                 105                 110

Val Gly Pro Pro Phe Thr Trp Met Leu Ala Leu Leu Gly Leu Ser Gln
        115                 120                 125

Ala Leu Asn Ile Leu Leu Gly Leu Lys Gly Leu Ala Pro Ala Glu Ile
    130                 135                 140

Ser Ala Leu Cys Glu Lys Gly Asn Phe Ser Met Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
        195                 200                 205

Pro Asp Asn Leu Ser Met Ala Asp Pro Asn Ile Arg Phe Leu Asp Lys
    210                 215                 220

Leu Pro Gln Gln Thr Gly Asp His Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
            260                 265                 270

Gln Tyr Ser Gln Ala Gly Phe Ser Arg Glu Asp Met Leu Glu Gln Ala
        275                 280                 285

Lys Leu Phe Cys Arg Thr Leu Glu Asp Ile Leu Ala Asp Ala Pro Glu
    290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335

Glu Lys Glu Glu Val Thr Val Gly Ser Leu Lys Thr Ser Ala Val Pro
            340                 345                 350

Ser Thr Ser Thr Met Ser Gln Glu Pro Glu Leu Leu Ile Ser Gly Met
        355                 360                 365

Glu Lys Pro Leu Pro Leu Arg Thr Asp Phe Ser
    370                 375
```

```
<210> SEQ ID NO 11
<211> LENGTH: 419
<212> TYPE: PRT
<213> ORGANISM: Mus musculus
<220> FEATURE:
<221> NAME/KEY: misc_feature
<222> LOCATION: (1)..(419)
<223> OTHER INFORMATION: super mouse IRF3 S396D; no epitope tag

<400> SEQUENCE: 11

Met Glu Thr Pro Lys Pro Arg Ile Leu Pro Trp Leu Val Ser Gln Leu
1               5                   10                  15
```

```
Asp Leu Gly Gln Leu Glu Gly Val Ala Trp Leu Asp Glu Ser Arg Thr
            20                  25                  30

Arg Phe Arg Ile Pro Trp Lys His Gly Leu Arg Gln Asp Ala Gln Met
        35                  40                  45

Ala Asp Phe Gly Ile Phe Gln Ala Trp Ala Glu Ala Ser Gly Ala Tyr
    50                  55                  60

Thr Pro Gly Lys Asp Lys Pro Asp Val Ser Thr Trp Lys Arg Asn Phe
65                  70                  75                  80

Arg Ser Ala Leu Asn Arg Lys Glu Val Leu Arg Leu Ala Ala Asp Asn
                85                  90                  95

Ser Lys Asp Pro Tyr Asp Pro His Lys Val Tyr Glu Phe Val Thr Pro
            100                 105                 110

Gly Ala Arg Asp Phe Val His Leu Gly Ala Ser Pro Asp Thr Asn Gly
        115                 120                 125

Lys Ser Ser Leu Pro His Ser Gln Glu Asn Leu Pro Lys Leu Phe Asp
    130                 135                 140

Gly Leu Ile Leu Gly Pro Leu Lys Asp Glu Gly Ser Ser Asp Leu Ala
145                 150                 155                 160

Ile Val Ser Asp Pro Ser Gln Gln Leu Pro Ser Pro Asn Val Asn Asn
                165                 170                 175

Phe Leu Asn Pro Ala Pro Gln Glu Asn Pro Leu Lys Gln Leu Leu Ala
            180                 185                 190

Glu Glu Gln Trp Glu Phe Glu Val Thr Ala Phe Tyr Arg Gly Arg Gln
        195                 200                 205

Val Phe Gln Gln Thr Leu Phe Cys Pro Gly Gly Leu Arg Leu Val Gly
    210                 215                 220

Ser Thr Ala Asp Met Thr Leu Pro Trp Gln Pro Val Thr Leu Pro Asp
225                 230                 235                 240

Pro Glu Gly Phe Leu Thr Asp Lys Leu Val Lys Glu Tyr Val Gly Gln
                245                 250                 255

Val Leu Lys Gly Leu Gly Asn Gly Leu Ala Leu Trp Gln Ala Gly Gln
            260                 265                 270

Cys Leu Trp Ala Gln Arg Leu Gly His Ser His Ala Phe Trp Ala Leu
        275                 280                 285

Gly Glu Glu Leu Leu Pro Asp Ser Gly Arg Gly Pro Asp Gly Glu Val
    290                 295                 300

His Lys Asp Lys Asp Gly Ala Val Phe Asp Leu Arg Pro Phe Val Ala
305                 310                 315                 320

Asp Leu Ile Ala Phe Met Glu Gly Ser Gly His Ser Pro Arg Tyr Thr
                325                 330                 335

Leu Trp Phe Cys Met Gly Glu Met Trp Pro Gln Asp Gln Pro Trp Val
            340                 345                 350

Lys Arg Leu Val Met Val Lys Val Val Pro Thr Cys Leu Lys Glu Leu
        355                 360                 365

Leu Glu Met Ala Arg Glu Gly Gly Ala Ser Ser Leu Lys Thr Val Asp
    370                 375                 380

Leu His Ile Asp Asn Ser Gln Pro Ile Ser Leu Thr Ser Asp Gln Tyr
385                 390                 395                 400

Lys Ala Tyr Leu Gln Asp Leu Val Glu Asp Met Asp Phe Gln Ala Thr
                405                 410                 415

Gly Asn Ile
```

<210> SEQ ID NO 12

<211> LENGTH: 427
<212> TYPE: PRT
<213> ORGANISM: Homo sapiens
<220> FEATURE:
<221> NAME/KEY: misc_feature
<222> LOCATION: (1)..(427)
<223> OTHER INFORMATION: super human IRF3 S396D; no epitope tag

<400> SEQUENCE: 12

```
Met Gly Thr Pro Lys Pro Arg Ile Leu Pro Trp Leu Val Ser Gln Leu
1               5                   10                  15

Asp Leu Gly Gln Leu Glu Gly Val Ala Trp Val Asn Lys Ser Arg Thr
            20                  25                  30

Arg Phe Arg Ile Pro Trp Lys His Gly Leu Arg Gln Asp Ala Gln Gln
        35                  40                  45

Glu Asp Phe Gly Ile Phe Gln Ala Trp Ala Glu Ala Thr Gly Ala Tyr
    50                  55                  60

Val Pro Gly Arg Asp Lys Pro Asp Leu Pro Thr Trp Lys Arg Asn Phe
65                  70                  75                  80

Arg Ser Ala Leu Asn Arg Lys Glu Gly Leu Arg Leu Ala Glu Asp Arg
                85                  90                  95

Ser Lys Asp Pro His Asp Pro His Lys Ile Tyr Glu Phe Val Asn Ser
            100                 105                 110

Gly Val Gly Asp Phe Ser Gln Pro Asp Thr Ser Pro Asp Thr Asn Gly
        115                 120                 125

Gly Gly Ser Thr Ser Asp Thr Gln Glu Asp Ile Leu Asp Glu Leu Leu
    130                 135                 140

Gly Asn Met Val Leu Ala Pro Leu Pro Asp Pro Gly Pro Pro Ser Leu
145                 150                 155                 160

Ala Val Ala Pro Glu Pro Cys Pro Gln Pro Leu Arg Ser Pro Ser Leu
                165                 170                 175

Asp Asn Pro Thr Pro Phe Pro Asn Leu Gly Pro Ser Glu Asn Pro Leu
            180                 185                 190

Lys Arg Leu Leu Val Pro Gly Glu Glu Trp Glu Phe Glu Val Thr Ala
        195                 200                 205

Phe Tyr Arg Gly Arg Gln Val Phe Gln Gln Thr Ile Ser Cys Pro Glu
    210                 215                 220

Gly Leu Arg Leu Val Gly Ser Glu Val Gly Asp Arg Thr Leu Pro Gly
225                 230                 235                 240

Trp Pro Val Thr Leu Pro Asp Pro Gly Met Ser Leu Thr Asp Arg Gly
                245                 250                 255

Val Met Ser Tyr Val Arg His Val Leu Ser Cys Leu Gly Gly Gly Leu
            260                 265                 270

Ala Leu Trp Arg Ala Gly Gln Trp Leu Trp Ala Gln Arg Leu Gly His
        275                 280                 285

Cys His Thr Tyr Trp Ala Val Ser Glu Glu Leu Leu Pro Asn Ser Gly
    290                 295                 300

His Gly Pro Asp Gly Glu Val Pro Lys Asp Lys Glu Gly Gly Val Phe
305                 310                 315                 320

Asp Leu Gly Pro Phe Ile Val Asp Leu Ile Thr Phe Thr Glu Gly Ser
                325                 330                 335

Gly Arg Ser Pro Arg Tyr Ala Leu Trp Phe Cys Val Gly Glu Ser Trp
            340                 345                 350

Pro Gln Asp Gln Pro Trp Thr Lys Arg Leu Val Met Val Lys Val Val
        355                 360                 365
```

```
Pro Thr Cys Leu Arg Ala Leu Val Glu Met Ala Arg Val Gly Gly Ala
    370                 375                 380

Ser Ser Leu Glu Asn Thr Val Asp Leu His Ile Asp Asn Ser His Pro
385                 390                 395                 400

Leu Ser Leu Thr Ser Asp Gln Tyr Lys Ala Tyr Leu Gln Asp Leu Val
                405                 410                 415

Glu Gly Met Asp Phe Gln Gly Pro Gly Glu Thr
            420                 425


<210> SEQ ID NO 13
<211> LENGTH: 503
<212> TYPE: PRT
<213> ORGANISM: Artificial Sequence
<220> FEATURE:
<223> OTHER INFORMATION: Synthetic: Wild-type Hu IRF7 isoform A; P037
      without epitope tag

<400> SEQUENCE: 13

Met Ala Leu Ala Pro Glu Arg Ala Ala Pro Arg Val Leu Phe Gly Glu
1               5                   10                  15

Trp Leu Leu Gly Glu Ile Ser Ser Gly Cys Tyr Glu Gly Leu Gln Trp
            20                  25                  30

Leu Asp Glu Ala Arg Thr Cys Phe Arg Val Pro Trp Lys His Phe Ala
        35                  40                  45

Arg Lys Asp Leu Ser Glu Ala Asp Ala Arg Ile Phe Lys Ala Trp Ala
    50                  55                  60

Val Ala Arg Gly Arg Trp Pro Pro Ser Ser Arg Gly Gly Gly Pro Pro
65                  70                  75                  80

Pro Glu Ala Glu Thr Ala Glu Arg Ala Gly Trp Lys Thr Asn Phe Arg
                85                  90                  95

Cys Ala Leu Arg Ser Thr Arg Arg Phe Val Met Leu Arg Asp Asn Ser
            100                 105                 110

Gly Asp Pro Ala Asp Pro His Lys Val Tyr Ala Leu Ser Arg Glu Leu
        115                 120                 125

Cys Trp Arg Glu Gly Pro Gly Thr Asp Gln Thr Glu Ala Glu Ala Pro
    130                 135                 140

Ala Ala Val Pro Pro Pro Gln Gly Gly Pro Pro Gly Pro Phe Leu Ala
145                 150                 155                 160

His Thr His Ala Gly Leu Gln Ala Pro Gly Pro Leu Pro Ala Pro Ala
                165                 170                 175

Gly Asp Lys Gly Asp Leu Leu Leu Gln Ala Val Gln Gln Ser Cys Leu
            180                 185                 190

Ala Asp His Leu Leu Thr Ala Ser Trp Gly Ala Asp Pro Val Pro Thr
        195                 200                 205

Lys Ala Pro Gly Glu Gly Gln Glu Gly Leu Pro Leu Thr Gly Ala Cys
    210                 215                 220

Ala Gly Gly Pro Gly Leu Pro Ala Gly Glu Leu Tyr Gly Trp Ala Val
225                 230                 235                 240

Glu Thr Thr Pro Ser Pro Gly Pro Gln Pro Ala Ala Leu Thr Thr Gly
                245                 250                 255

Glu Ala Ala Ala Pro Glu Ser Pro His Gln Ala Glu Pro Tyr Leu Ser
            260                 265                 270

Pro Ser Pro Ser Ala Cys Thr Ala Val Gln Glu Pro Ser Pro Gly Ala
        275                 280                 285

Leu Asp Val Thr Ile Met Tyr Lys Gly Arg Thr Val Leu Gln Lys Val
    290                 295                 300
```

```
Val Gly His Pro Ser Cys Thr Phe Leu Tyr Gly Pro Pro Asp Pro Ala
305                 310                 315                 320

Val Arg Ala Thr Asp Pro Gln Gln Val Ala Phe Pro Ser Pro Ala Glu
                325                 330                 335

Leu Pro Asp Gln Lys Gln Leu Arg Tyr Thr Glu Glu Leu Leu Arg His
            340                 345                 350

Val Ala Pro Gly Leu His Leu Glu Leu Arg Gly Pro Gln Leu Trp Ala
        355                 360                 365

Arg Arg Met Gly Lys Cys Lys Val Tyr Trp Glu Val Gly Gly Pro Pro
    370                 375                 380

Gly Ser Ala Ser Pro Ser Thr Pro Ala Cys Leu Leu Pro Arg Asn Cys
385                 390                 395                 400

Asp Thr Pro Ile Phe Asp Phe Arg Val Phe Phe Gln Glu Leu Val Glu
                405                 410                 415

Phe Arg Ala Arg Gln Arg Arg Gly Ser Pro Arg Tyr Thr Ile Tyr Leu
            420                 425                 430

Gly Phe Gly Gln Asp Leu Ser Ala Gly Arg Pro Lys Glu Lys Ser Leu
        435                 440                 445

Val Leu Val Lys Leu Glu Pro Trp Leu Cys Arg Val His Leu Glu Gly
    450                 455                 460

Thr Gln Arg Glu Gly Val Ser Ser Leu Asp Ser Ser Ser Leu Ser Leu
465                 470                 475                 480

Cys Leu Ser Ser Ala Asn Ser Leu Tyr Asp Asp Ile Glu Cys Phe Leu
                485                 490                 495

Met Glu Leu Glu Gln Pro Ala
            500


<210> SEQ ID NO 14
<211> LENGTH: 503
<212> TYPE: PRT
<213> ORGANISM: Artificial Sequence
<220> FEATURE:
<223> OTHER INFORMATION: Synthetic: constitutively active Hu IRF7
      S477D/S479D; P033 without epitope tag

<400> SEQUENCE: 14

Met Ala Leu Ala Pro Glu Arg Ala Ala Pro Arg Val Leu Phe Gly Glu
1               5                   10                  15

Trp Leu Leu Gly Glu Ile Ser Ser Gly Cys Tyr Glu Gly Leu Gln Trp
            20                  25                  30

Leu Asp Glu Ala Arg Thr Cys Phe Arg Val Pro Trp Lys His Phe Ala
        35                  40                  45

Arg Lys Asp Leu Ser Glu Ala Asp Ala Arg Ile Phe Lys Ala Trp Ala
    50                  55                  60

Val Ala Arg Gly Arg Trp Pro Pro Ser Ser Arg Gly Gly Gly Pro Pro
65                  70                  75                  80

Pro Glu Ala Glu Thr Ala Glu Arg Ala Gly Trp Lys Thr Asn Phe Arg
                85                  90                  95

Cys Ala Leu Arg Ser Thr Arg Arg Phe Val Met Leu Arg Asp Asn Ser
            100                 105                 110

Gly Asp Pro Ala Asp Pro His Lys Val Tyr Ala Leu Ser Arg Glu Leu
        115                 120                 125

Cys Trp Arg Glu Gly Pro Gly Thr Asp Gln Thr Glu Ala Glu Ala Pro
    130                 135                 140

Ala Ala Val Pro Pro Pro Gln Gly Gly Pro Pro Gly Pro Phe Leu Ala
```

```
145                 150                 155                 160

His Thr His Ala Gly Leu Gln Ala Pro Gly Pro Leu Pro Ala Pro Ala
                165                 170                 175

Gly Asp Lys Gly Asp Leu Leu Leu Gln Ala Val Gln Gln Ser Cys Leu
            180                 185                 190

Ala Asp His Leu Leu Thr Ala Ser Trp Gly Ala Asp Pro Val Pro Thr
        195                 200                 205

Lys Ala Pro Gly Glu Gly Gln Glu Gly Leu Pro Leu Thr Gly Ala Cys
    210                 215                 220

Ala Gly Gly Pro Gly Leu Pro Ala Gly Glu Leu Tyr Gly Trp Ala Val
225                 230                 235                 240

Glu Thr Thr Pro Ser Pro Gly Pro Gln Pro Ala Ala Leu Thr Thr Gly
                245                 250                 255

Glu Ala Ala Ala Pro Glu Ser Pro His Gln Ala Glu Pro Tyr Leu Ser
            260                 265                 270

Pro Ser Pro Ser Ala Cys Thr Ala Val Gln Glu Pro Ser Pro Gly Ala
        275                 280                 285

Leu Asp Val Thr Ile Met Tyr Lys Gly Arg Thr Val Leu Gln Lys Val
    290                 295                 300

Val Gly His Pro Ser Cys Thr Phe Leu Tyr Gly Pro Pro Asp Pro Ala
305                 310                 315                 320

Val Arg Ala Thr Asp Pro Gln Gln Val Ala Phe Pro Ser Pro Ala Glu
                325                 330                 335

Leu Pro Asp Gln Lys Gln Leu Arg Tyr Thr Glu Glu Leu Leu Arg His
            340                 345                 350

Val Ala Pro Gly Leu His Leu Glu Leu Arg Gly Pro Gln Leu Trp Ala
        355                 360                 365

Arg Arg Met Gly Lys Cys Lys Val Tyr Trp Glu Val Gly Gly Pro Pro
    370                 375                 380

Gly Ser Ala Ser Pro Ser Thr Pro Ala Cys Leu Leu Pro Arg Asn Cys
385                 390                 395                 400

Asp Thr Pro Ile Phe Asp Phe Arg Val Phe Phe Gln Glu Leu Val Glu
                405                 410                 415

Phe Arg Ala Arg Gln Arg Arg Gly Ser Pro Arg Tyr Thr Ile Tyr Leu
            420                 425                 430

Gly Phe Gly Gln Asp Leu Ser Ala Gly Arg Pro Lys Glu Lys Ser Leu
        435                 440                 445

Val Leu Val Lys Leu Glu Pro Trp Leu Cys Arg Val His Leu Glu Gly
    450                 455                 460

Thr Gln Arg Glu Gly Val Ser Ser Leu Asp Ser Ser Asp Leu Asp Leu
465                 470                 475                 480

Cys Leu Ser Ser Ala Asn Ser Leu Tyr Asp Asp Ile Glu Cys Phe Leu
                485                 490                 495

Met Glu Leu Glu Gln Pro Ala
            500
```

<210> SEQ ID NO 15
<211> LENGTH: 503
<212> TYPE: PRT
<213> ORGANISM: Artificial Sequence
<220> FEATURE:
<223> OTHER INFORMATION: Synthetic: constitutively active Hu IRF7 S475D/S477D/L480D; P034 without epitope tag

<400> SEQUENCE: 15

-continued

```
Met Ala Leu Ala Pro Glu Arg Ala Ala Pro Arg Val Leu Phe Gly Glu
1               5                   10                  15

Trp Leu Leu Gly Glu Ile Ser Ser Gly Cys Tyr Glu Gly Leu Gln Trp
            20                  25                  30

Leu Asp Glu Ala Arg Thr Cys Phe Arg Val Pro Trp Lys His Phe Ala
        35                  40                  45

Arg Lys Asp Leu Ser Glu Ala Asp Ala Arg Ile Phe Lys Ala Trp Ala
    50                  55                  60

Val Ala Arg Gly Arg Trp Pro Pro Ser Ser Arg Gly Gly Gly Pro Pro
65                  70                  75                  80

Pro Glu Ala Glu Thr Ala Glu Arg Ala Gly Trp Lys Thr Asn Phe Arg
                85                  90                  95

Cys Ala Leu Arg Ser Thr Arg Arg Phe Val Met Leu Arg Asp Asn Ser
            100                 105                 110

Gly Asp Pro Ala Asp Pro His Lys Val Tyr Ala Leu Ser Arg Glu Leu
        115                 120                 125

Cys Trp Arg Glu Gly Pro Gly Thr Asp Gln Thr Glu Ala Glu Ala Pro
    130                 135                 140

Ala Ala Val Pro Pro Pro Gln Gly Gly Pro Pro Gly Pro Phe Leu Ala
145                 150                 155                 160

His Thr His Ala Gly Leu Gln Ala Pro Gly Pro Leu Pro Ala Pro Ala
                165                 170                 175

Gly Asp Lys Gly Asp Leu Leu Leu Gln Ala Val Gln Gln Ser Cys Leu
            180                 185                 190

Ala Asp His Leu Leu Thr Ala Ser Trp Gly Ala Asp Pro Val Pro Thr
        195                 200                 205

Lys Ala Pro Gly Glu Gly Gln Glu Gly Leu Pro Leu Thr Gly Ala Cys
    210                 215                 220

Ala Gly Gly Pro Gly Leu Pro Ala Gly Glu Leu Tyr Gly Trp Ala Val
225                 230                 235                 240

Glu Thr Thr Pro Ser Pro Gly Pro Gln Pro Ala Ala Leu Thr Thr Gly
                245                 250                 255

Glu Ala Ala Ala Pro Glu Ser Pro His Gln Ala Glu Pro Tyr Leu Ser
            260                 265                 270

Pro Ser Pro Ser Ala Cys Thr Ala Val Gln Glu Pro Ser Pro Gly Ala
        275                 280                 285

Leu Asp Val Thr Ile Met Tyr Lys Gly Arg Thr Val Leu Gln Lys Val
    290                 295                 300

Val Gly His Pro Ser Cys Thr Phe Leu Tyr Gly Pro Pro Asp Pro Ala
305                 310                 315                 320

Val Arg Ala Thr Asp Pro Gln Gln Val Ala Phe Pro Ser Pro Ala Glu
                325                 330                 335

Leu Pro Asp Gln Lys Gln Leu Arg Tyr Thr Glu Glu Leu Leu Arg His
            340                 345                 350

Val Ala Pro Gly Leu His Leu Glu Leu Arg Gly Pro Gln Leu Trp Ala
        355                 360                 365

Arg Arg Met Gly Lys Cys Lys Val Tyr Trp Glu Val Gly Gly Pro Pro
    370                 375                 380

Gly Ser Ala Ser Pro Ser Thr Pro Ala Cys Leu Leu Pro Arg Asn Cys
385                 390                 395                 400

Asp Thr Pro Ile Phe Asp Phe Arg Val Phe Phe Gln Glu Leu Val Glu
                405                 410                 415

Phe Arg Ala Arg Gln Arg Arg Gly Ser Pro Arg Tyr Thr Ile Tyr Leu
```

```
            420                 425                 430

Gly Phe Gly Gln Asp Leu Ser Ala Gly Arg Pro Lys Glu Lys Ser Leu
        435                 440                 445

Val Leu Val Lys Leu Glu Pro Trp Leu Cys Arg Val His Leu Glu Gly
    450                 455                 460

Thr Gln Arg Glu Gly Val Ser Ser Leu Asp Asp Ser Asp Leu Ser Asp
465                 470                 475                 480

Cys Leu Ser Ser Ala Asn Ser Leu Tyr Asp Asp Ile Glu Cys Phe Leu
                485                 490                 495

Met Glu Leu Glu Gln Pro Ala
            500


<210> SEQ ID NO 16
<211> LENGTH: 503
<212> TYPE: PRT
<213> ORGANISM: Artificial Sequence
<220> FEATURE:
<223> OTHER INFORMATION: Synthetic: constitutively active Hu IRF7
      S475D/S476D/S477D/S479D/S483D/S487D; P035 without epitope tag

<400> SEQUENCE: 16

Met Ala Leu Ala Pro Glu Arg Ala Ala Pro Arg Val Leu Phe Gly Glu
1               5                   10                  15

Trp Leu Leu Gly Glu Ile Ser Ser Gly Cys Tyr Glu Gly Leu Gln Trp
            20                  25                  30

Leu Asp Glu Ala Arg Thr Cys Phe Arg Val Pro Trp Lys His Phe Ala
        35                  40                  45

Arg Lys Asp Leu Ser Glu Ala Asp Ala Arg Ile Phe Lys Ala Trp Ala
    50                  55                  60

Val Ala Arg Gly Arg Trp Pro Pro Ser Ser Arg Gly Gly Gly Pro Pro
65                  70                  75                  80

Pro Glu Ala Glu Thr Ala Glu Arg Ala Gly Trp Lys Thr Asn Phe Arg
                85                  90                  95

Cys Ala Leu Arg Ser Thr Arg Arg Phe Val Met Leu Arg Asp Asn Ser
            100                 105                 110

Gly Asp Pro Ala Asp Pro His Lys Val Tyr Ala Leu Ser Arg Glu Leu
        115                 120                 125

Cys Trp Arg Glu Gly Pro Gly Thr Asp Gln Thr Glu Ala Glu Ala Pro
    130                 135                 140

Ala Ala Val Pro Pro Pro Gln Gly Gly Pro Pro Gly Pro Phe Leu Ala
145                 150                 155                 160

His Thr His Ala Gly Leu Gln Ala Pro Gly Pro Leu Pro Ala Pro Ala
                165                 170                 175

Gly Asp Lys Gly Asp Leu Leu Leu Gln Ala Val Gln Gln Ser Cys Leu
            180                 185                 190

Ala Asp His Leu Leu Thr Ala Ser Trp Gly Ala Asp Pro Val Pro Thr
        195                 200                 205

Lys Ala Pro Gly Glu Gly Gln Glu Gly Leu Pro Leu Thr Gly Ala Cys
    210                 215                 220

Ala Gly Gly Pro Gly Leu Pro Ala Gly Glu Leu Tyr Gly Trp Ala Val
225                 230                 235                 240

Glu Thr Thr Pro Ser Pro Gly Pro Gln Pro Ala Ala Leu Thr Thr Gly
                245                 250                 255

Glu Ala Ala Ala Pro Glu Ser Pro His Gln Ala Glu Pro Tyr Leu Ser
            260                 265                 270
```

```
Pro Ser Pro Ser Ala Cys Thr Ala Val Gln Glu Pro Ser Pro Gly Ala
        275                 280                 285

Leu Asp Val Thr Ile Met Tyr Lys Gly Arg Thr Val Leu Gln Lys Val
    290                 295                 300

Val Gly His Pro Ser Cys Thr Phe Leu Tyr Gly Pro Pro Asp Pro Ala
305                 310                 315                 320

Val Arg Ala Thr Asp Pro Gln Gln Val Ala Phe Pro Ser Pro Ala Glu
                325                 330                 335

Leu Pro Asp Gln Lys Gln Leu Arg Tyr Thr Glu Glu Leu Leu Arg His
            340                 345                 350

Val Ala Pro Gly Leu His Leu Glu Leu Arg Gly Pro Gln Leu Trp Ala
        355                 360                 365

Arg Arg Met Gly Lys Cys Lys Val Tyr Trp Glu Val Gly Gly Pro Pro
    370                 375                 380

Gly Ser Ala Ser Pro Ser Thr Pro Ala Cys Leu Leu Pro Arg Asn Cys
385                 390                 395                 400

Asp Thr Pro Ile Phe Asp Phe Arg Val Phe Phe Gln Glu Leu Val Glu
                405                 410                 415

Phe Arg Ala Arg Gln Arg Arg Gly Ser Pro Arg Tyr Thr Ile Tyr Leu
            420                 425                 430

Gly Phe Gly Gln Asp Leu Ser Ala Gly Arg Pro Lys Glu Lys Ser Leu
        435                 440                 445

Val Leu Val Lys Leu Glu Pro Trp Leu Cys Arg Val His Leu Glu Gly
    450                 455                 460

Thr Gln Arg Glu Gly Val Ser Ser Leu Asp Asp Asp Asp Leu Asp Leu
465                 470                 475                 480

Cys Leu Asp Ser Ala Asn Asp Leu Tyr Asp Asp Ile Glu Cys Phe Leu
                485                 490                 495

Met Glu Leu Glu Gln Pro Ala
            500


<210> SEQ ID NO 17
<211> LENGTH: 282
<212> TYPE: PRT
<213> ORGANISM: Artificial Sequence
<220> FEATURE:
<223> OTHER INFORMATION: Synthetic: constitutively active truncated Hu
      IRF7 1-246 + 468-503; P032 without epitope tag

<400> SEQUENCE: 17

Met Ala Leu Ala Pro Glu Arg Ala Ala Pro Arg Val Leu Phe Gly Glu
1               5                   10                  15

Trp Leu Leu Gly Glu Ile Ser Ser Gly Cys Tyr Glu Gly Leu Gln Trp
            20                  25                  30

Leu Asp Glu Ala Arg Thr Cys Phe Arg Val Pro Trp Lys His Phe Ala
        35                  40                  45

Arg Lys Asp Leu Ser Glu Ala Asp Ala Arg Ile Phe Lys Ala Trp Ala
    50                  55                  60

Val Ala Arg Gly Arg Trp Pro Pro Ser Ser Arg Gly Gly Gly Pro Pro
65                  70                  75                  80

Pro Glu Ala Glu Thr Ala Glu Arg Ala Gly Trp Lys Thr Asn Phe Arg
                85                  90                  95

Cys Ala Leu Arg Ser Thr Arg Arg Phe Val Met Leu Arg Asp Asn Ser
            100                 105                 110

Gly Asp Pro Ala Asp Pro His Lys Val Tyr Ala Leu Ser Arg Glu Leu
        115                 120                 125
```

```
Cys Trp Arg Glu Gly Pro Gly Thr Asp Gln Thr Glu Ala Glu Ala Pro
    130                 135                 140

Ala Ala Val Pro Pro Pro Gln Gly Gly Pro Pro Gly Pro Phe Leu Ala
145                 150                 155                 160

His Thr His Ala Gly Leu Gln Ala Pro Gly Pro Leu Pro Ala Pro Ala
                165                 170                 175

Gly Asp Lys Gly Asp Leu Leu Leu Gln Ala Val Gln Gln Ser Cys Leu
            180                 185                 190

Ala Asp His Leu Leu Thr Ala Ser Trp Gly Ala Asp Pro Val Pro Thr
        195                 200                 205

Lys Ala Pro Gly Glu Gly Gln Glu Gly Leu Pro Leu Thr Gly Ala Cys
    210                 215                 220

Ala Gly Gly Pro Gly Leu Pro Ala Gly Glu Leu Tyr Gly Trp Ala Val
225                 230                 235                 240

Glu Thr Thr Pro Ser Pro Glu Gly Val Ser Ser Leu Asp Ser Ser Ser
                245                 250                 255

Leu Ser Leu Cys Leu Ser Ser Ala Asn Ser Leu Tyr Asp Asp Ile Glu
            260                 265                 270

Cys Phe Leu Met Glu Leu Glu Gln Pro Ala
        275                 280


<210> SEQ ID NO 18
<211> LENGTH: 282
<212> TYPE: PRT
<213> ORGANISM: Artificial Sequence
<220> FEATURE:
<223> OTHER INFORMATION: Synthetic: constitutively active truncated Hu
      IRF7 1-246 + 468-503 plus S475D/S476D/S477D/S479D/S483D/S487D;
      P036 without epitope tag

<400> SEQUENCE: 18

Met Ala Leu Ala Pro Glu Arg Ala Ala Pro Arg Val Leu Phe Gly Glu
1               5                   10                  15

Trp Leu Leu Gly Glu Ile Ser Ser Gly Cys Tyr Glu Gly Leu Gln Trp
            20                  25                  30

Leu Asp Glu Ala Arg Thr Cys Phe Arg Val Pro Trp Lys His Phe Ala
        35                  40                  45

Arg Lys Asp Leu Ser Glu Ala Asp Ala Arg Ile Phe Lys Ala Trp Ala
    50                  55                  60

Val Ala Arg Gly Arg Trp Pro Pro Ser Ser Arg Gly Gly Gly Pro Pro
65                  70                  75                  80

Pro Glu Ala Glu Thr Ala Glu Arg Ala Gly Trp Lys Thr Asn Phe Arg
                85                  90                  95

Cys Ala Leu Arg Ser Thr Arg Arg Phe Val Met Leu Arg Asp Asn Ser
            100                 105                 110

Gly Asp Pro Ala Asp Pro His Lys Val Tyr Ala Leu Ser Arg Glu Leu
        115                 120                 125

Cys Trp Arg Glu Gly Pro Gly Thr Asp Gln Thr Glu Ala Glu Ala Pro
    130                 135                 140

Ala Ala Val Pro Pro Pro Gln Gly Gly Pro Pro Gly Pro Phe Leu Ala
145                 150                 155                 160

His Thr His Ala Gly Leu Gln Ala Pro Gly Pro Leu Pro Ala Pro Ala
                165                 170                 175

Gly Asp Lys Gly Asp Leu Leu Leu Gln Ala Val Gln Gln Ser Cys Leu
            180                 185                 190
```

```
Ala Asp His Leu Leu Thr Ala Ser Trp Gly Ala Asp Pro Val Pro Thr
        195                 200                 205

Lys Ala Pro Gly Glu Gly Gln Glu Gly Leu Pro Leu Thr Gly Ala Cys
    210                 215                 220

Ala Gly Gly Pro Gly Leu Pro Ala Gly Glu Leu Tyr Gly Trp Ala Val
225                 230                 235                 240

Glu Thr Thr Pro Ser Pro Glu Gly Val Ser Ser Leu Asp Asp Asp Asp
                245                 250                 255

Leu Asp Leu Cys Leu Asp Ser Ala Asn Asp Leu Tyr Asp Asp Ile Glu
            260                 265                 270

Cys Phe Leu Met Glu Leu Glu Gln Pro Ala
        275                 280


<210> SEQ ID NO 19
<211> LENGTH: 408
<212> TYPE: PRT
<213> ORGANISM: Artificial Sequence
<220> FEATURE:
<223> OTHER INFORMATION: Synthetic: truncated Hu IRF7 1-151 + 247-503;
      P038 without epitope tag; null mutation

<400> SEQUENCE: 19

Met Ala Leu Ala Pro Glu Arg Ala Ala Pro Arg Val Leu Phe Gly Glu
1               5                   10                  15

Trp Leu Leu Gly Glu Ile Ser Ser Gly Cys Tyr Glu Gly Leu Gln Trp
            20                  25                  30

Leu Asp Glu Ala Arg Thr Cys Phe Arg Val Pro Trp Lys His Phe Ala
        35                  40                  45

Arg Lys Asp Leu Ser Glu Ala Asp Ala Arg Ile Phe Lys Ala Trp Ala
    50                  55                  60

Val Ala Arg Gly Arg Trp Pro Pro Ser Ser Arg Gly Gly Gly Pro Pro
65                  70                  75                  80

Pro Glu Ala Glu Thr Ala Glu Arg Ala Gly Trp Lys Thr Asn Phe Arg
                85                  90                  95

Cys Ala Leu Arg Ser Thr Arg Arg Phe Val Met Leu Arg Asp Asn Ser
            100                 105                 110

Gly Asp Pro Ala Asp Pro His Lys Val Tyr Ala Leu Ser Arg Glu Leu
        115                 120                 125

Cys Trp Arg Glu Gly Pro Gly Thr Asp Gln Thr Glu Ala Glu Ala Pro
    130                 135                 140

Ala Ala Val Pro Pro Pro Gln Gly Pro Gln Pro Ala Ala Leu Thr Thr
145                 150                 155                 160

Gly Glu Ala Ala Ala Pro Glu Ser Pro His Gln Ala Glu Pro Tyr Leu
                165                 170                 175

Ser Pro Ser Pro Ser Ala Cys Thr Ala Val Gln Glu Pro Ser Pro Gly
            180                 185                 190

Ala Leu Asp Val Thr Ile Met Tyr Lys Gly Arg Thr Val Leu Gln Lys
        195                 200                 205

Val Val Gly His Pro Ser Cys Thr Phe Leu Tyr Gly Pro Pro Asp Pro
    210                 215                 220

Ala Val Arg Ala Thr Asp Pro Gln Gln Val Ala Phe Pro Ser Pro Ala
225                 230                 235                 240

Glu Leu Pro Asp Gln Lys Gln Leu Arg Tyr Thr Glu Glu Leu Leu Arg
                245                 250                 255

His Val Ala Pro Gly Leu His Leu Glu Leu Arg Gly Pro Gln Leu Trp
            260                 265                 270
```

```
Ala Arg Arg Met Gly Lys Cys Lys Val Tyr Trp Glu Val Gly Gly Pro
        275                 280                 285

Pro Gly Ser Ala Ser Pro Ser Thr Pro Ala Cys Leu Leu Pro Arg Asn
    290                 295                 300

Cys Asp Thr Pro Ile Phe Asp Phe Arg Val Phe Phe Gln Glu Leu Val
305                 310                 315                 320

Glu Phe Arg Ala Arg Gln Arg Arg Gly Ser Pro Arg Tyr Thr Ile Tyr
                325                 330                 335

Leu Gly Phe Gly Gln Asp Leu Ser Ala Gly Arg Pro Lys Glu Lys Ser
            340                 345                 350

Leu Val Leu Val Lys Leu Glu Pro Trp Leu Cys Arg Val His Leu Glu
        355                 360                 365

Gly Thr Gln Arg Glu Gly Val Ser Ser Leu Asp Ser Ser Ser Leu Ser
    370                 375                 380

Leu Cys Leu Ser Ser Ala Asn Ser Leu Tyr Asp Asp Ile Glu Cys Phe
385                 390                 395                 400

Leu Met Glu Leu Glu Gln Pro Ala
                405


<210> SEQ ID NO 20
<211> LENGTH: 353
<212> TYPE: PRT
<213> ORGANISM: Artificial Sequence
<220> FEATURE:
<223> OTHER INFORMATION: Synthetic: truncated Hu IRF7 152-503; P039
      without epitope tag; null mutation

<400> SEQUENCE: 20

Met Gly Gly Pro Pro Gly Pro Phe Leu Ala His Thr His Ala Gly Leu
1               5                   10                  15

Gln Ala Pro Gly Pro Leu Pro Ala Pro Ala Gly Asp Lys Gly Asp Leu
            20                  25                  30

Leu Leu Gln Ala Val Gln Gln Ser Cys Leu Ala Asp His Leu Leu Thr
        35                  40                  45

Ala Ser Trp Gly Ala Asp Pro Val Pro Thr Lys Ala Pro Gly Glu Gly
    50                  55                  60

Gln Glu Gly Leu Pro Leu Thr Gly Ala Cys Ala Gly Gly Pro Gly Leu
65                  70                  75                  80

Pro Ala Gly Glu Leu Tyr Gly Trp Ala Val Glu Thr Thr Pro Ser Pro
                85                  90                  95

Gly Pro Gln Pro Ala Ala Leu Thr Thr Gly Glu Ala Ala Ala Pro Glu
            100                 105                 110

Ser Pro His Gln Ala Glu Pro Tyr Leu Ser Pro Ser Pro Ser Ala Cys
        115                 120                 125

Thr Ala Val Gln Glu Pro Ser Pro Gly Ala Leu Asp Val Thr Ile Met
    130                 135                 140

Tyr Lys Gly Arg Thr Val Leu Gln Lys Val Val Gly His Pro Ser Cys
145                 150                 155                 160

Thr Phe Leu Tyr Gly Pro Pro Asp Pro Ala Val Arg Ala Thr Asp Pro
                165                 170                 175

Gln Gln Val Ala Phe Pro Ser Pro Ala Glu Leu Pro Asp Gln Lys Gln
            180                 185                 190

Leu Arg Tyr Thr Glu Glu Leu Leu Arg His Val Ala Pro Gly Leu His
        195                 200                 205

Leu Glu Leu Arg Gly Pro Gln Leu Trp Ala Arg Arg Met Gly Lys Cys
```

```
    210                 215                 220

Lys Val Tyr Trp Glu Val Gly Gly Pro Pro Gly Ser Ala Ser Pro Ser
225                 230                 235                 240

Thr Pro Ala Cys Leu Leu Pro Arg Asn Cys Asp Thr Pro Ile Phe Asp
                245                 250                 255

Phe Arg Val Phe Phe Gln Glu Leu Val Glu Phe Arg Ala Arg Gln Arg
            260                 265                 270

Arg Gly Ser Pro Arg Tyr Thr Ile Tyr Leu Gly Phe Gly Gln Asp Leu
        275                 280                 285

Ser Ala Gly Arg Pro Lys Glu Lys Ser Leu Val Leu Val Lys Leu Glu
    290                 295                 300

Pro Trp Leu Cys Arg Val His Leu Glu Gly Thr Gln Arg Glu Gly Val
305                 310                 315                 320

Ser Ser Leu Asp Ser Ser Ser Leu Ser Leu Cys Leu Ser Ser Ala Asn
                325                 330                 335

Ser Leu Tyr Asp Asp Ile Glu Cys Phe Leu Met Glu Leu Glu Gln Pro
            340                 345                 350

Ala


<210> SEQ ID NO 21
<211> LENGTH: 92
<212> TYPE: DNA
<213> ORGANISM: Artificial Sequence
<220> FEATURE:
<223> OTHER INFORMATION: Synthetic: 5 UTR

<400> SEQUENCE: 21

tcaagctttt ggaccctcgt acagaagcta atacgactca ctatagggaa ataagagaga     60

aaagaagagt aagaagaaat ataagagcca cc                                   92


<210> SEQ ID NO 22
<211> LENGTH: 119
<212> TYPE: DNA
<213> ORGANISM: Artificial Sequence
<220> FEATURE:
<223> OTHER INFORMATION: Synthetic: 3 UTR

<400> SEQUENCE: 22

tgataatagg ctggagcctc ggtggccatg cttcttgccc cttgggcctc cccccagccc     60

ctcctcccct tcctgcaccc gtacccccgt ggtctttgaa taaagtctga gtgggcggc     119


<210> SEQ ID NO 23
<211> LENGTH: 164
<212> TYPE: DNA
<213> ORGANISM: Artificial Sequence
<220> FEATURE:
<223> OTHER INFORMATION: Synthetic: 3 UTR with mi-122 and mi-142.3p
      sites

<400> SEQUENCE: 23

tgataatagg ctggagcctc ggtggccatg cttcttgccc cttgggccca aacaccattg     60

tcacactcca tccccccagc ccctcctccc cttcctccat aaagtaggaa acactacatg    120

cacccgtacc cccgtggtct ttgaataaag tctgagtggg cggc                     164


<210> SEQ ID NO 24
<211> LENGTH: 22
<212> TYPE: PRT
<213> ORGANISM: Artificial Sequence
<220> FEATURE:
```

<223> OTHER INFORMATION: Synthetic: 2A peptide amino acid sequence

<400> SEQUENCE: 24

Gly Ser Gly Ala Thr Asn Phe Ser Leu Leu Lys Gln Ala Gly Asp Val
1 5 10 15

Glu Glu Asn Pro Gly Pro
20

<210> SEQ ID NO 25
<211> LENGTH: 66
<212> TYPE: DNA
<213> ORGANISM: Artificial Sequence
<220> FEATURE:
<223> OTHER INFORMATION: Synthetic: Nucleotide sequence encoding 2A peptide

<400> SEQUENCE: 25
ggaagcggag ctactaactt cagcctgctg aagcaggctg gagacgtgga ggagaaccct 60
ggacct 66

<210> SEQ ID NO 26
<211> LENGTH: 108
<212> TYPE: DNA
<213> ORGANISM: Artificial Sequence
<220> FEATURE:
<223> OTHER INFORMATION: Synthetic: Nucleotide sequence encoding 2A peptide

<400> SEQUENCE: 26
tccggactca gatccgggga tctcaaaatt gtcgctcctg tcaaacaaac tcttaacttt 60
gatttactca aactggctgg ggatgtagaa agcaatccag gtccactc 108

<210> SEQ ID NO 27
<211> LENGTH: 87
<212> TYPE: RNA
<213> ORGANISM: Artificial Sequence
<220> FEATURE:
<223> OTHER INFORMATION: Synthetic: miR-142

<400> SEQUENCE: 27
gacagugcag ucacccauaa aguagaaagc acuacuaaca gcacuggagg guguaguguu 60
uccuacuuua uggaugagug uacugug 87

<210> SEQ ID NO 28
<211> LENGTH: 23
<212> TYPE: RNA
<213> ORGANISM: Artificial Sequence
<220> FEATURE:
<223> OTHER INFORMATION: Synthetic: miR-142-3p

<400> SEQUENCE: 28
uguaguguuu ccuacuuuau gga 23

<210> SEQ ID NO 29
<211> LENGTH: 23
<212> TYPE: RNA
<213> ORGANISM: Artificial Sequence
<220> FEATURE:
<223> OTHER INFORMATION: Synthetic: miR-142-3p binding site

<400> SEQUENCE: 29
uccauaaagu aggaaacacu aca 23

<210> SEQ ID NO 30
<211> LENGTH: 21
<212> TYPE: RNA
<213> ORGANISM: Artificial Sequence
<220> FEATURE:
<223> OTHER INFORMATION: Synthetic: miR-142-5p

<400> SEQUENCE: 30
cauaaaguag aaagcacuac u 21

<210> SEQ ID NO 31
<211> LENGTH: 21
<212> TYPE: RNA
<213> ORGANISM: Artificial Sequence
<220> FEATURE:
<223> OTHER INFORMATION: Synthetic: miR-142-5p binding site

<400> SEQUENCE: 31
aguagugcuu ucuacuuuau g 21

<210> SEQ ID NO 32
<211> LENGTH: 22
<212> TYPE: RNA
<213> ORGANISM: Artificial Sequence
<220> FEATURE:
<223> OTHER INFORMATION: Synthetic: miR-122-3p

<400> SEQUENCE: 32
aacgccauua ucacacuaaa ua 22

<210> SEQ ID NO 33
<211> LENGTH: 22
<212> TYPE: RNA
<213> ORGANISM: Artificial Sequence
<220> FEATURE:
<223> OTHER INFORMATION: Synthetic: miR-122-5p

<400> SEQUENCE: 33
uggaguguga caaugguguu ug 22

<210> SEQ ID NO 34
<211> LENGTH: 22
<212> TYPE: RNA
<213> ORGANISM: Artificial Sequence
<220> FEATURE:
<223> OTHER INFORMATION: Synthetic: miR-21-5p

<400> SEQUENCE: 34
uagcuuauca gacugauguu ga 22

<210> SEQ ID NO 35
<211> LENGTH: 21
<212> TYPE: RNA
<213> ORGANISM: Artificial Sequence
<220> FEATURE:
<223> OTHER INFORMATION: Synthetic: miR-21-3p

<400> SEQUENCE: 35
caacaccagu cgaugggcug u 21

<210> SEQ ID NO 36
<211> LENGTH: 16
<212> TYPE: PRT
<213> ORGANISM: Artificial Sequence
<220> FEATURE:
<223> OTHER INFORMATION: Synthetic: KRAS(G12D)15mer

<400> SEQUENCE: 36

Met Lys Leu Val Val Val Gly Ala Asp Gly Val Gly Lys Ser Ala Leu
1 5 10 15

<210> SEQ ID NO 37
<211> LENGTH: 16
<212> TYPE: PRT
<213> ORGANISM: Artificial Sequence
<220> FEATURE:
<223> OTHER INFORMATION: Synthetic: KRAS(G12V)15mer

<400> SEQUENCE: 37

Met Lys Leu Val Val Val Gly Ala Val Gly Val Gly Lys Ser Ala Leu
1 5 10 15

<210> SEQ ID NO 38
<211> LENGTH: 16
<212> TYPE: PRT
<213> ORGANISM: Artificial Sequence
<220> FEATURE:
<223> OTHER INFORMATION: Synthetic: KRAS(G13D)15mer

<400> SEQUENCE: 38

Met Leu Val Val Val Gly Ala Gly Asp Val Gly Lys Ser Ala Leu Thr
1 5 10 15

<210> SEQ ID NO 39
<211> LENGTH: 25
<212> TYPE: PRT
<213> ORGANISM: Artificial Sequence
<220> FEATURE:
<223> OTHER INFORMATION: Synthetic: KRAS(G12D)25mer

<400> SEQUENCE: 39

Met Thr Glu Tyr Lys Leu Val Val Val Gly Ala Asp Gly Val Gly Lys
1 5 10 15

Ser Ala Leu Thr Ile Gln Leu Ile Gln
20 25

<210> SEQ ID NO 40
<211> LENGTH: 25
<212> TYPE: PRT
<213> ORGANISM: Artificial Sequence
<220> FEATURE:
<223> OTHER INFORMATION: Synthetic: KRAS(G12V)25mer

<400> SEQUENCE: 40

Met Thr Glu Tyr Lys Leu Val Val Val Gly Ala Val Gly Val Gly Lys
1 5 10 15

Ser Ala Leu Thr Ile Gln Leu Ile Gln
20 25

<210> SEQ ID NO 41
<211> LENGTH: 25
<212> TYPE: PRT
<213> ORGANISM: Artificial Sequence
<220> FEATURE:
<223> OTHER INFORMATION: Synthetic: KRAS(G13D)25mer

<400> SEQUENCE: 41

Met Thr Glu Tyr Lys Leu Val Val Val Gly Ala Gly Asp Val Gly Lys
1 5 10 15

Ser Ala Leu Thr Ile Gln Leu Ile Gln
20 25

<210> SEQ ID NO 42
<211> LENGTH: 46
<212> TYPE: PRT
<213> ORGANISM: Artificial Sequence
<220> FEATURE:
<223> OTHER INFORMATION: Synthetic: KRAS(G12D)15mer^3

<400> SEQUENCE: 42

```
Met Lys Leu Val Val Val Gly Ala Asp Gly Val Gly Lys Ser Ala Leu
1               5                   10                  15

Lys Leu Val Val Val Gly Ala Asp Gly Val Gly Lys Ser Ala Leu Lys
            20                  25                  30

Leu Val Val Val Gly Ala Asp Gly Val Gly Lys Ser Ala Leu
        35                  40                  45
```

<210> SEQ ID NO 43
<211> LENGTH: 46
<212> TYPE: PRT
<213> ORGANISM: Artificial Sequence
<220> FEATURE:
<223> OTHER INFORMATION: Synthetic: KRAS(G12V)15mer^3

<400> SEQUENCE: 43

```
Met Lys Leu Val Val Val Gly Ala Val Gly Val Gly Lys Ser Ala Leu
1               5                   10                  15

Lys Leu Val Val Val Gly Ala Val Gly Val Gly Lys Ser Ala Leu Lys
            20                  25                  30

Leu Val Val Val Gly Ala Val Gly Val Gly Lys Ser Ala Leu
        35                  40                  45
```

<210> SEQ ID NO 44
<211> LENGTH: 46
<212> TYPE: PRT
<213> ORGANISM: Artificial Sequence
<220> FEATURE:
<223> OTHER INFORMATION: Synthetic: KRAS(G13D)15mer^3

<400> SEQUENCE: 44

```
Met Leu Val Val Val Gly Ala Gly Asp Val Gly Lys Ser Ala Leu Thr
1               5                   10                  15

Leu Val Val Val Gly Ala Gly Asp Val Gly Lys Ser Ala Leu Thr Leu
            20                  25                  30

Val Val Val Gly Ala Gly Asp Val Gly Lys Ser Ala Leu Thr
        35                  40                  45
```

<210> SEQ ID NO 45
<211> LENGTH: 75
<212> TYPE: PRT
<213> ORGANISM: Artificial Sequence
<220> FEATURE:
<223> OTHER INFORMATION: Synthetic: KRAS(G12D)25mer^3

<400> SEQUENCE: 45

```
Met Thr Glu Tyr Lys Leu Val Val Val Gly Ala Asp Gly Val Gly Lys
1               5                   10                  15

Ser Ala Leu Thr Ile Gln Leu Ile Gln Met Thr Glu Tyr Lys Leu Val
            20                  25                  30

Val Val Gly Ala Asp Gly Val Gly Lys Ser Ala Leu Thr Ile Gln Leu
        35                  40                  45

Ile Gln Met Thr Glu Tyr Lys Leu Val Val Val Gly Ala Asp Gly Val
    50                  55                  60
```

Gly Lys Ser Ala Leu Thr Ile Gln Leu Ile Gln
65 70 75

<210> SEQ ID NO 46
<211> LENGTH: 75
<212> TYPE: PRT
<213> ORGANISM: Artificial Sequence
<220> FEATURE:
<223> OTHER INFORMATION: Synthetic: KRAS(G12V)25mer^3

<400> SEQUENCE: 46

Met Thr Glu Tyr Lys Leu Val Val Val Gly Ala Val Gly Val Gly Lys
1 5 10 15

Ser Ala Leu Thr Ile Gln Leu Ile Gln Met Thr Glu Tyr Lys Leu Val
20 25 30

Val Val Gly Ala Val Gly Val Gly Lys Ser Ala Leu Thr Ile Gln Leu
35 40 45

Ile Gln Met Thr Glu Tyr Lys Leu Val Val Val Gly Ala Val Gly Val
50 55 60

Gly Lys Ser Ala Leu Thr Ile Gln Leu Ile Gln
65 70 75

<210> SEQ ID NO 47
<211> LENGTH: 75
<212> TYPE: PRT
<213> ORGANISM: Artificial Sequence
<220> FEATURE:
<223> OTHER INFORMATION: Synthetic: KRAS(G13D)25mer^3

<400> SEQUENCE: 47

Met Thr Glu Tyr Lys Leu Val Val Val Gly Ala Gly Asp Val Gly Lys
1 5 10 15

Ser Ala Leu Thr Ile Gln Leu Ile Gln Met Thr Glu Tyr Lys Leu Val
20 25 30

Val Val Gly Ala Gly Asp Val Gly Lys Ser Ala Leu Thr Ile Gln Leu
35 40 45

Ile Gln Met Thr Glu Tyr Lys Leu Val Val Val Gly Ala Gly Asp Val
50 55 60

Gly Lys Ser Ala Leu Thr Ile Gln Leu Ile Gln
65 70 75

<210> SEQ ID NO 48
<211> LENGTH: 414
<212> TYPE: PRT
<213> ORGANISM: Artificial Sequence
<220> FEATURE:
<223> OTHER INFORMATION: Synthetic: KRAS(G12D)15mer_nt.STING(V155M)

<400> SEQUENCE: 48

Met Pro His Ser Ser Leu His Pro Ser Ile Pro Cys Pro Arg Gly His
1 5 10 15

Gly Ala Gln Lys Ala Ala Leu Val Leu Leu Ser Ala Cys Leu Val Thr
20 25 30

Leu Trp Gly Leu Gly Glu Pro Pro Glu His Thr Leu Arg Tyr Leu Val
35 40 45

Leu His Leu Ala Ser Leu Gln Leu Gly Leu Leu Leu Asn Gly Val Cys
50 55 60

Ser Leu Ala Glu Glu Leu Arg His Ile His Ser Arg Tyr Arg Gly Ser
65 70 75 80

Tyr Trp Arg Thr Val Arg Ala Cys Leu Gly Cys Pro Leu Arg Arg Gly

```
                85                  90                  95

Ala Leu Leu Leu Leu Ser Ile Tyr Phe Tyr Tyr Ser Leu Pro Asn Ala
            100                 105                 110

Val Gly Pro Pro Phe Thr Trp Met Leu Ala Leu Leu Gly Leu Ser Gln
        115                 120                 125

Ala Leu Asn Ile Leu Leu Gly Leu Lys Gly Leu Ala Pro Ala Glu Ile
    130                 135                 140

Ser Ala Val Cys Glu Lys Gly Asn Phe Asn Met Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
        195                 200                 205

Pro Asp Asn Leu Ser Met Ala Asp Pro Asn Ile Arg Phe Leu Asp Lys
    210                 215                 220

Leu Pro Gln Gln Thr Gly Asp His Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
            260                 265                 270

Gln Tyr Ser Gln Ala Gly Phe Ser Arg Glu Asp Arg Leu Glu Gln Ala
        275                 280                 285

Lys Leu Phe Cys Arg Thr Leu Glu Asp Ile Leu Ala Asp Ala Pro Glu
    290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335

Glu Lys Glu Glu Val Thr Val Gly Ser Leu Lys Thr Ser Ala Val Pro
            340                 345                 350

Ser Thr Ser Thr Met Ser Gln Glu Pro Glu Leu Leu Ile Ser Gly Met
        355                 360                 365

Glu Lys Pro Leu Pro Leu Arg Thr Asp Phe Ser Ala Thr Asn Phe Ser
    370                 375                 380

Leu Leu Lys Gln Ala Gly Asp Val Glu Glu Asn Pro Gly Pro Met Lys
385                 390                 395                 400

Leu Val Val Val Gly Ala Asp Gly Val Gly Lys Ser Ala Leu
                405                 410
```

<210> SEQ ID NO 49
<211> LENGTH: 414
<212> TYPE: PRT
<213> ORGANISM: Artificial Sequence
<220> FEATURE:
<223> OTHER INFORMATION: Synthetic: KRAS(G12V)15mer_nt.STING(V155M

<400> SEQUENCE: 49

```
Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
            20                  25                  30

Leu Trp Gly Leu Gly Glu Pro Pro Glu His Thr Leu Arg Tyr Leu Val
```

-continued

```
        35                  40                  45

Leu His Leu Ala Ser Leu Gln Leu Gly Leu Leu Leu Asn Gly Val Cys
    50                  55                  60

Ser Leu Ala Glu Glu Leu Arg His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Tyr Ser Leu Pro Asn Ala
            100                 105                 110

Val Gly Pro Pro Phe Thr Trp Met Leu Ala Leu Leu Gly Leu Ser Gln
        115                 120                 125

Ala Leu Asn Ile Leu Leu Gly Leu Lys Gly Leu Ala Pro Ala Glu Ile
    130                 135                 140

Ser Ala Val Cys Glu Lys Gly Asn Phe Asn Met Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
        195                 200                 205

Pro Asp Asn Leu Ser Met Ala Asp Pro Asn Ile Arg Phe Leu Asp Lys
    210                 215                 220

Leu Pro Gln Gln Thr Gly Asp His Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
            260                 265                 270

Gln Tyr Ser Gln Ala Gly Phe Ser Arg Glu Asp Arg Leu Glu Gln Ala
        275                 280                 285

Lys Leu Phe Cys Arg Thr Leu Glu Asp Ile Leu Ala Asp Ala Pro Glu
    290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335

Glu Lys Glu Glu Val Thr Val Gly Ser Leu Lys Thr Ser Ala Val Pro
            340                 345                 350

Ser Thr Ser Thr Met Ser Gln Glu Pro Glu Leu Leu Ile Ser Gly Met
        355                 360                 365

Glu Lys Pro Leu Pro Leu Arg Thr Asp Phe Ser Ala Thr Asn Phe Ser
    370                 375                 380

Leu Leu Lys Gln Ala Gly Asp Val Glu Glu Asn Pro Gly Pro Met Lys
385                 390                 395                 400

Leu Val Val Val Gly Ala Val Gly Val Gly Lys Ser Ala Leu
                405                 410
```

<210> SEQ ID NO 50
<211> LENGTH: 414
<212> TYPE: PRT
<213> ORGANISM: Artificial Sequence
<220> FEATURE:
<223> OTHER INFORMATION: Synthetic: KRAS(G13D)15mer_nt.STING(V155M

<400> SEQUENCE: 50

Met Pro His Ser Ser Leu His Pro Ser Ile Pro Cys Pro Arg Gly His
1 5 10 15

Gly Ala Gln Lys Ala Ala Leu Val Leu Leu Ser Ala Cys Leu Val Thr
20 25 30

Leu Trp Gly Leu Gly Glu Pro Pro Glu His Thr Leu Arg Tyr Leu Val
35 40 45

Leu His Leu Ala Ser Leu Gln Leu Gly Leu Leu Leu Asn Gly Val Cys
50 55 60

Ser Leu Ala Glu Glu Leu Arg His Ile His Ser Arg Tyr Arg Gly Ser
65 70 75 80

Tyr Trp Arg Thr Val Arg Ala Cys Leu Gly Cys Pro Leu Arg Arg Gly
85 90 95

Ala Leu Leu Leu Leu Ser Ile Tyr Phe Tyr Tyr Ser Leu Pro Asn Ala
100 105 110

Val Gly Pro Pro Phe Thr Trp Met Leu Ala Leu Leu Gly Leu Ser Gln
115 120 125

Ala Leu Asn Ile Leu Leu Gly Leu Lys Gly Leu Ala Pro Ala Glu Ile
130 135 140

Ser Ala Val Cys Glu Lys Gly Asn Phe Asn Met Ala His Gly Leu Ala
145 150 155 160

Trp Ser Tyr Tyr Ile Gly Tyr Leu Arg Leu Ile Leu Pro Glu Leu Gln
165 170 175

Ala Arg Ile Arg Thr Tyr Asn Gln His Tyr Asn Asn Leu Leu Arg Gly
180 185 190

Ala Val Ser Gln Arg Leu Tyr Ile Leu Leu Pro Leu Asp Cys Gly Val
195 200 205

Pro Asp Asn Leu Ser Met Ala Asp Pro Asn Ile Arg Phe Leu Asp Lys
210 215 220

Leu Pro Gln Gln Thr Gly Asp His Ala Gly Ile Lys Asp Arg Val Tyr
225 230 235 240

Ser Asn Ser Ile Tyr Glu Leu Leu Glu Asn Gly Gln Arg Ala Gly Thr
245 250 255

Cys Val Leu Glu Tyr Ala Thr Pro Leu Gln Thr Leu Phe Ala Met Ser
260 265 270

Gln Tyr Ser Gln Ala Gly Phe Ser Arg Glu Asp Arg Leu Glu Gln Ala
275 280 285

Lys Leu Phe Cys Arg Thr Leu Glu Asp Ile Leu Ala Asp Ala Pro Glu
290 295 300

Ser Gln Asn Asn Cys Arg Leu Ile Ala Tyr Gln Glu Pro Ala Asp Asp
305 310 315 320

Ser Ser Phe Ser Leu Ser Gln Glu Val Leu Arg His Leu Arg Gln Glu
325 330 335

Glu Lys Glu Glu Val Thr Val Gly Ser Leu Lys Thr Ser Ala Val Pro
340 345 350

Ser Thr Ser Thr Met Ser Gln Glu Pro Glu Leu Leu Ile Ser Gly Met
355 360 365

Glu Lys Pro Leu Pro Leu Arg Thr Asp Phe Ser Ala Thr Asn Phe Ser
370 375 380

Leu Leu Lys Gln Ala Gly Asp Val Glu Glu Asn Pro Gly Pro Met Leu
385 390 395 400

Val Val Val Gly Ala Gly Asp Val Gly Lys Ser Ala Leu Thr
405 410

<210> SEQ ID NO 51
<211> LENGTH: 423
<212> TYPE: PRT
<213> ORGANISM: Artificial Sequence
<220> FEATURE:
<223> OTHER INFORMATION: Synthetic: KRAS(G12D)25mer_nt.STING(V155M)

<400> SEQUENCE: 51

```
Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
            20                  25                  30

Leu Trp Gly Leu Gly Glu Pro Pro Glu His Thr Leu Arg Tyr Leu Val
        35                  40                  45

Leu His Leu Ala Ser Leu Gln Leu Gly Leu Leu Leu Asn Gly Val Cys
    50                  55                  60

Ser Leu Ala Glu Glu Leu Arg His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Tyr Ser Leu Pro Asn Ala
            100                 105                 110

Val Gly Pro Pro Phe Thr Trp Met Leu Ala Leu Leu Gly Leu Ser Gln
        115                 120                 125

Ala Leu Asn Ile Leu Leu Gly Leu Lys Gly Leu Ala Pro Ala Glu Ile
    130                 135                 140

Ser Ala Val Cys Glu Lys Gly Asn Phe Asn Met Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
        195                 200                 205

Pro Asp Asn Leu Ser Met Ala Asp Pro Asn Ile Arg Phe Leu Asp Lys
    210                 215                 220

Leu Pro Gln Gln Thr Gly Asp His Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
            260                 265                 270

Gln Tyr Ser Gln Ala Gly Phe Ser Arg Glu Asp Arg Leu Glu Gln Ala
        275                 280                 285

Lys Leu Phe Cys Arg Thr Leu Glu Asp Ile Leu Ala Asp Ala Pro Glu
    290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335

Glu Lys Glu Glu Val Thr Val Gly Ser Leu Lys Thr Ser Ala Val Pro
            340                 345                 350

Ser Thr Ser Thr Met Ser Gln Glu Pro Glu Leu Leu Ile Ser Gly Met
        355                 360                 365
```

```
Glu Lys Pro Leu Pro Leu Arg Thr Asp Phe Ser Ala Thr Asn Phe Ser
    370                 375                 380

Leu Leu Lys Gln Ala Gly Asp Val Glu Glu Asn Pro Gly Pro Met Thr
385                 390                 395                 400

Glu Tyr Lys Leu Val Val Val Gly Ala Asp Gly Val Gly Lys Ser Ala
                405                 410                 415

Leu Thr Ile Gln Leu Ile Gln
            420
```

```
<210> SEQ ID NO 52
<211> LENGTH: 423
<212> TYPE: PRT
<213> ORGANISM: Artificial Sequence
<220> FEATURE:
<223> OTHER INFORMATION: Synthetic: KRAS(G12V)25mer_nt.STING(V155M

<400> SEQUENCE: 52

Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
            20                  25                  30

Leu Trp Gly Leu Gly Glu Pro Pro Glu His Thr Leu Arg Tyr Leu Val
        35                  40                  45

Leu His Leu Ala Ser Leu Gln Leu Gly Leu Leu Leu Asn Gly Val Cys
    50                  55                  60

Ser Leu Ala Glu Glu Leu Arg His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Tyr Ser Leu Pro Asn Ala
            100                 105                 110

Val Gly Pro Pro Phe Thr Trp Met Leu Ala Leu Leu Gly Leu Ser Gln
        115                 120                 125

Ala Leu Asn Ile Leu Leu Gly Leu Lys Gly Leu Ala Pro Ala Glu Ile
    130                 135                 140

Ser Ala Val Cys Glu Lys Gly Asn Phe Asn Met Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
        195                 200                 205

Pro Asp Asn Leu Ser Met Ala Asp Pro Asn Ile Arg Phe Leu Asp Lys
    210                 215                 220

Leu Pro Gln Gln Thr Gly Asp His Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
            260                 265                 270

Gln Tyr Ser Gln Ala Gly Phe Ser Arg Glu Asp Arg Leu Glu Gln Ala
        275                 280                 285

Lys Leu Phe Cys Arg Thr Leu Glu Asp Ile Leu Ala Asp Ala Pro Glu
    290                 295                 300
```

```
Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335

Glu Lys Glu Glu Val Thr Val Gly Ser Leu Lys Thr Ser Ala Val Pro
            340                 345                 350

Ser Thr Ser Thr Met Ser Gln Glu Pro Glu Leu Leu Ile Ser Gly Met
        355                 360                 365

Glu Lys Pro Leu Pro Leu Arg Thr Asp Phe Ser Ala Thr Asn Phe Ser
    370                 375                 380

Leu Leu Lys Gln Ala Gly Asp Val Glu Glu Asn Pro Gly Pro Met Thr
385                 390                 395                 400

Glu Tyr Lys Leu Val Val Val Gly Ala Val Gly Val Gly Lys Ser Ala
                405                 410                 415

Leu Thr Ile Gln Leu Ile Gln
            420
```

<210> SEQ ID NO 53
<211> LENGTH: 423
<212> TYPE: PRT
<213> ORGANISM: Artificial Sequence
<220> FEATURE:
<223> OTHER INFORMATION: Synthetic: KRAS(G13D)25mer_nt.STING(V155M

<400> SEQUENCE: 53

```
Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
            20                  25                  30

Leu Trp Gly Leu Gly Glu Pro Pro Glu His Thr Leu Arg Tyr Leu Val
        35                  40                  45

Leu His Leu Ala Ser Leu Gln Leu Gly Leu Leu Leu Asn Gly Val Cys
    50                  55                  60

Ser Leu Ala Glu Glu Leu Arg His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Tyr Ser Leu Pro Asn Ala
            100                 105                 110

Val Gly Pro Pro Phe Thr Trp Met Leu Ala Leu Leu Gly Leu Ser Gln
        115                 120                 125

Ala Leu Asn Ile Leu Leu Gly Leu Lys Gly Leu Ala Pro Ala Glu Ile
    130                 135                 140

Ser Ala Val Cys Glu Lys Gly Asn Phe Asn Met Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
        195                 200                 205

Pro Asp Asn Leu Ser Met Ala Asp Pro Asn Ile Arg Phe Leu Asp Lys
    210                 215                 220

Leu Pro Gln Gln Thr Gly Asp His Ala Gly Ile Lys Asp Arg Val Tyr
225                 230                 235                 240
```

Ser Asn Ser Ile Tyr Glu Leu Leu Glu Asn Gly Gln Arg Ala Gly Thr
245 250 255

Cys Val Leu Glu Tyr Ala Thr Pro Leu Gln Thr Leu Phe Ala Met Ser
260 265 270

Gln Tyr Ser Gln Ala Gly Phe Ser Arg Glu Asp Arg Leu Glu Gln Ala
275 280 285

Lys Leu Phe Cys Arg Thr Leu Glu Asp Ile Leu Ala Asp Ala Pro Glu
290 295 300

Ser Gln Asn Asn Cys Arg Leu Ile Ala Tyr Gln Glu Pro Ala Asp Asp
305 310 315 320

Ser Ser Phe Ser Leu Ser Gln Glu Val Leu Arg His Leu Arg Gln Glu
325 330 335

Glu Lys Glu Glu Val Thr Val Gly Ser Leu Lys Thr Ser Ala Val Pro
340 345 350

Ser Thr Ser Thr Met Ser Gln Glu Pro Glu Leu Leu Ile Ser Gly Met
355 360 365

Glu Lys Pro Leu Pro Leu Arg Thr Asp Phe Ser Ala Thr Asn Phe Ser
370 375 380

Leu Leu Lys Gln Ala Gly Asp Val Glu Glu Asn Pro Gly Pro Met Thr
385 390 395 400

Glu Tyr Lys Leu Val Val Val Gly Ala Gly Asp Val Gly Lys Ser Ala
405 410 415

Leu Thr Ile Gln Leu Ile Gln
420

<210> SEQ ID NO 54
<211> LENGTH: 444
<212> TYPE: PRT
<213> ORGANISM: Artificial Sequence
<220> FEATURE:
<223> OTHER INFORMATION: Synthetic: KRAS(G12D)15mer^3_nt.STING(V155M)

<400> SEQUENCE: 54

Met Pro His Ser Ser Leu His Pro Ser Ile Pro Cys Pro Arg Gly His
1 5 10 15

Gly Ala Gln Lys Ala Ala Leu Val Leu Leu Ser Ala Cys Leu Val Thr
20 25 30

Leu Trp Gly Leu Gly Glu Pro Pro Glu His Thr Leu Arg Tyr Leu Val
35 40 45

Leu His Leu Ala Ser Leu Gln Leu Gly Leu Leu Leu Asn Gly Val Cys
50 55 60

Ser Leu Ala Glu Glu Leu Arg His Ile His Ser Arg Tyr Arg Gly Ser
65 70 75 80

Tyr Trp Arg Thr Val Arg Ala Cys Leu Gly Cys Pro Leu Arg Arg Gly
85 90 95

Ala Leu Leu Leu Leu Ser Ile Tyr Phe Tyr Tyr Ser Leu Pro Asn Ala
100 105 110

Val Gly Pro Pro Phe Thr Trp Met Leu Ala Leu Leu Gly Leu Ser Gln
115 120 125

Ala Leu Asn Ile Leu Leu Gly Leu Lys Gly Leu Ala Pro Ala Glu Ile
130 135 140

Ser Ala Val Cys Glu Lys Gly Asn Phe Asn Met Ala His Gly Leu Ala
145 150 155 160

Trp Ser Tyr Tyr Ile Gly Tyr Leu Arg Leu Ile Leu Pro Glu Leu Gln
165 170 175

```
Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
        195                 200                 205

Pro Asp Asn Leu Ser Met Ala Asp Pro Asn Ile Arg Phe Leu Asp Lys
    210                 215                 220

Leu Pro Gln Gln Thr Gly Asp His Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
            260                 265                 270

Gln Tyr Ser Gln Ala Gly Phe Ser Arg Glu Asp Arg Leu Glu Gln Ala
        275                 280                 285

Lys Leu Phe Cys Arg Thr Leu Glu Asp Ile Leu Ala Asp Ala Pro Glu
    290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335

Glu Lys Glu Glu Val Thr Val Gly Ser Leu Lys Thr Ser Ala Val Pro
            340                 345                 350

Ser Thr Ser Thr Met Ser Gln Glu Pro Glu Leu Leu Ile Ser Gly Met
        355                 360                 365

Glu Lys Pro Leu Pro Leu Arg Thr Asp Phe Ser Ala Thr Asn Phe Ser
    370                 375                 380

Leu Leu Lys Gln Ala Gly Asp Val Glu Glu Asn Pro Gly Pro Met Lys
385                 390                 395                 400

Leu Val Val Val Gly Ala Asp Gly Val Gly Lys Ser Ala Leu Lys Leu
                405                 410                 415

Val Val Val Gly Ala Asp Gly Val Gly Lys Ser Ala Leu Lys Leu Val
            420                 425                 430

Val Val Gly Ala Asp Gly Val Gly Lys Ser Ala Leu
        435                 440


<210> SEQ ID NO 55
<211> LENGTH: 444
<212> TYPE: PRT
<213> ORGANISM: Artificial Sequence
<220> FEATURE:
<223> OTHER INFORMATION: Synthetic: KRAS(G12V)15mer^3_nt.STING(V155M

<400> SEQUENCE: 55

Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
            20                  25                  30

Leu Trp Gly Leu Gly Glu Pro Pro Glu His Thr Leu Arg Tyr Leu Val
        35                  40                  45

Leu His Leu Ala Ser Leu Gln Leu Gly Leu Leu Leu Asn Gly Val Cys
    50                  55                  60

Ser Leu Ala Glu Glu Leu Arg His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95
```

```
Ala Leu Leu Leu Leu Ser Ile Tyr Phe Tyr Tyr Ser Leu Pro Asn Ala
            100                 105                 110

Val Gly Pro Pro Phe Thr Trp Met Leu Ala Leu Leu Gly Leu Ser Gln
        115                 120                 125

Ala Leu Asn Ile Leu Leu Gly Leu Lys Gly Leu Ala Pro Ala Glu Ile
    130                 135                 140

Ser Ala Val Cys Glu Lys Gly Asn Phe Asn Met Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
        195                 200                 205

Pro Asp Asn Leu Ser Met Ala Asp Pro Asn Ile Arg Phe Leu Asp Lys
    210                 215                 220

Leu Pro Gln Gln Thr Gly Asp His Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
            260                 265                 270

Gln Tyr Ser Gln Ala Gly Phe Ser Arg Glu Asp Arg Leu Glu Gln Ala
        275                 280                 285

Lys Leu Phe Cys Arg Thr Leu Glu Asp Ile Leu Ala Asp Ala Pro Glu
    290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335

Glu Lys Glu Glu Val Thr Val Gly Ser Leu Lys Thr Ser Ala Val Pro
            340                 345                 350

Ser Thr Ser Thr Met Ser Gln Glu Pro Glu Leu Leu Ile Ser Gly Met
        355                 360                 365

Glu Lys Pro Leu Pro Leu Arg Thr Asp Phe Ser Ala Thr Asn Phe Ser
    370                 375                 380

Leu Leu Lys Gln Ala Gly Asp Val Glu Glu Asn Pro Gly Pro Met Lys
385                 390                 395                 400

Leu Val Val Val Gly Ala Val Gly Val Gly Lys Ser Ala Leu Lys Leu
                405                 410                 415

Val Val Val Gly Ala Val Gly Val Gly Lys Ser Ala Leu Lys Leu Val
            420                 425                 430

Val Val Gly Ala Val Gly Val Gly Lys Ser Ala Leu
        435                 440
```

<210> SEQ ID NO 56
<211> LENGTH: 444
<212> TYPE: PRT
<213> ORGANISM: Artificial Sequence
<220> FEATURE:
<223> OTHER INFORMATION: Synthetic: KRAS(G13D)15mer^3_nt.STING(V155M

<400> SEQUENCE: 56

```
Met Pro His Ser Ser Leu His Pro Ser Ile Pro Cys Pro Arg Gly His
1               5                   10                  15
```

```
Gly Ala Gln Lys Ala Ala Leu Val Leu Leu Ser Ala Cys Leu Val Thr
            20                  25                  30

Leu Trp Gly Leu Gly Glu Pro Pro Glu His Thr Leu Arg Tyr Leu Val
        35                  40                  45

Leu His Leu Ala Ser Leu Gln Leu Gly Leu Leu Leu Asn Gly Val Cys
    50                  55                  60

Ser Leu Ala Glu Glu Leu Arg His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Tyr Ser Leu Pro Asn Ala
            100                 105                 110

Val Gly Pro Pro Phe Thr Trp Met Leu Ala Leu Leu Gly Leu Ser Gln
        115                 120                 125

Ala Leu Asn Ile Leu Leu Gly Leu Lys Gly Leu Ala Pro Ala Glu Ile
    130                 135                 140

Ser Ala Val Cys Glu Lys Gly Asn Phe Asn Met Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
        195                 200                 205

Pro Asp Asn Leu Ser Met Ala Asp Pro Asn Ile Arg Phe Leu Asp Lys
    210                 215                 220

Leu Pro Gln Gln Thr Gly Asp His Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
            260                 265                 270

Gln Tyr Ser Gln Ala Gly Phe Ser Arg Glu Asp Arg Leu Glu Gln Ala
        275                 280                 285

Lys Leu Phe Cys Arg Thr Leu Glu Asp Ile Leu Ala Asp Ala Pro Glu
    290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335

Glu Lys Glu Glu Val Thr Val Gly Ser Leu Lys Thr Ser Ala Val Pro
            340                 345                 350

Ser Thr Ser Thr Met Ser Gln Glu Pro Glu Leu Leu Ile Ser Gly Met
        355                 360                 365

Glu Lys Pro Leu Pro Leu Arg Thr Asp Phe Ser Ala Thr Asn Phe Ser
    370                 375                 380

Leu Leu Lys Gln Ala Gly Asp Val Glu Glu Asn Pro Gly Pro Met Leu
385                 390                 395                 400

Val Val Val Gly Ala Gly Asp Val Gly Lys Ser Ala Leu Thr Leu Val
                405                 410                 415

Val Val Gly Ala Gly Asp Val Gly Lys Ser Ala Leu Thr Leu Val Val
            420                 425                 430
```

Val Gly Ala Gly Asp Val Gly Lys Ser Ala Leu Thr
435 440

<210> SEQ ID NO 57
<211> LENGTH: 473
<212> TYPE: PRT
<213> ORGANISM: Artificial Sequence
<220> FEATURE:
<223> OTHER INFORMATION: Synthetic: KRAS(G12D)25mer^3_nt.STING(V155M)

<400> SEQUENCE: 57

Met Pro His Ser Ser Leu His Pro Ser Ile Pro Cys Pro Arg Gly His
1 5 10 15

Gly Ala Gln Lys Ala Ala Leu Val Leu Leu Ser Ala Cys Leu Val Thr
20 25 30

Leu Trp Gly Leu Gly Glu Pro Pro Glu His Thr Leu Arg Tyr Leu Val
35 40 45

Leu His Leu Ala Ser Leu Gln Leu Gly Leu Leu Leu Asn Gly Val Cys
50 55 60

Ser Leu Ala Glu Glu Leu Arg His Ile His Ser Arg Tyr Arg Gly Ser
65 70 75 80

Tyr Trp Arg Thr Val Arg Ala Cys Leu Gly Cys Pro Leu Arg Arg Gly
85 90 95

Ala Leu Leu Leu Leu Ser Ile Tyr Phe Tyr Tyr Ser Leu Pro Asn Ala
100 105 110

Val Gly Pro Pro Phe Thr Trp Met Leu Ala Leu Leu Gly Leu Ser Gln
115 120 125

Ala Leu Asn Ile Leu Leu Gly Leu Lys Gly Leu Ala Pro Ala Glu Ile
130 135 140

Ser Ala Val Cys Glu Lys Gly Asn Phe Asn Met Ala His Gly Leu Ala
145 150 155 160

Trp Ser Tyr Tyr Ile Gly Tyr Leu Arg Leu Ile Leu Pro Glu Leu Gln
165 170 175

Ala Arg Ile Arg Thr Tyr Asn Gln His Tyr Asn Asn Leu Leu Arg Gly
180 185 190

Ala Val Ser Gln Arg Leu Tyr Ile Leu Leu Pro Leu Asp Cys Gly Val
195 200 205

Pro Asp Asn Leu Ser Met Ala Asp Pro Asn Ile Arg Phe Leu Asp Lys
210 215 220

Leu Pro Gln Gln Thr Gly Asp His Ala Gly Ile Lys Asp Arg Val Tyr
225 230 235 240

Ser Asn Ser Ile Tyr Glu Leu Leu Glu Asn Gly Gln Arg Ala Gly Thr
245 250 255

Cys Val Leu Glu Tyr Ala Thr Pro Leu Gln Thr Leu Phe Ala Met Ser
260 265 270

Gln Tyr Ser Gln Ala Gly Phe Ser Arg Glu Asp Arg Leu Glu Gln Ala
275 280 285

Lys Leu Phe Cys Arg Thr Leu Glu Asp Ile Leu Ala Asp Ala Pro Glu
290 295 300

Ser Gln Asn Asn Cys Arg Leu Ile Ala Tyr Gln Glu Pro Ala Asp Asp
305 310 315 320

Ser Ser Phe Ser Leu Ser Gln Glu Val Leu Arg His Leu Arg Gln Glu
325 330 335

Glu Lys Glu Glu Val Thr Val Gly Ser Leu Lys Thr Ser Ala Val Pro
340 345 350

```
Ser Thr Ser Thr Met Ser Gln Glu Pro Glu Leu Leu Ile Ser Gly Met
        355                 360                 365

Glu Lys Pro Leu Pro Leu Arg Thr Asp Phe Ser Ala Thr Asn Phe Ser
    370                 375                 380

Leu Leu Lys Gln Ala Gly Asp Val Glu Glu Asn Pro Gly Pro Met Thr
385                 390                 395                 400

Glu Tyr Lys Leu Val Val Val Gly Ala Asp Gly Val Gly Lys Ser Ala
                405                 410                 415

Leu Thr Ile Gln Leu Ile Gln Met Thr Glu Tyr Lys Leu Val Val Val
            420                 425                 430

Gly Ala Asp Gly Val Gly Lys Ser Ala Leu Thr Ile Gln Leu Ile Gln
        435                 440                 445

Met Thr Glu Tyr Lys Leu Val Val Val Gly Ala Asp Gly Val Gly Lys
    450                 455                 460

Ser Ala Leu Thr Ile Gln Leu Ile Gln
465                 470


<210> SEQ ID NO 58
<211> LENGTH: 473
<212> TYPE: PRT
<213> ORGANISM: Artificial Sequence
<220> FEATURE:
<223> OTHER INFORMATION: Synthetic: KRAS(G12V)25mer^3_nt.STING(V155M

<400> SEQUENCE: 58

Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
            20                  25                  30

Leu Trp Gly Leu Gly Glu Pro Pro Glu His Thr Leu Arg Tyr Leu Val
        35                  40                  45

Leu His Leu Ala Ser Leu Gln Leu Gly Leu Leu Leu Asn Gly Val Cys
    50                  55                  60

Ser Leu Ala Glu Glu Leu Arg His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Tyr Ser Leu Pro Asn Ala
            100                 105                 110

Val Gly Pro Pro Phe Thr Trp Met Leu Ala Leu Leu Gly Leu Ser Gln
        115                 120                 125

Ala Leu Asn Ile Leu Leu Gly Leu Lys Gly Leu Ala Pro Ala Glu Ile
    130                 135                 140

Ser Ala Val Cys Glu Lys Gly Asn Phe Asn Met Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
        195                 200                 205

Pro Asp Asn Leu Ser Met Ala Asp Pro Asn Ile Arg Phe Leu Asp Lys
    210                 215                 220

Leu Pro Gln Gln Thr Gly Asp His Ala Gly Ile Lys Asp Arg Val Tyr
225                 230                 235                 240
```

Ser Asn Ser Ile Tyr Glu Leu Leu Glu Asn Gly Gln Arg Ala Gly Thr
245 250 255

Cys Val Leu Glu Tyr Ala Thr Pro Leu Gln Thr Leu Phe Ala Met Ser
260 265 270

Gln Tyr Ser Gln Ala Gly Phe Ser Arg Glu Asp Arg Leu Glu Gln Ala
275 280 285

Lys Leu Phe Cys Arg Thr Leu Glu Asp Ile Leu Ala Asp Ala Pro Glu
290 295 300

Ser Gln Asn Asn Cys Arg Leu Ile Ala Tyr Gln Glu Pro Ala Asp Asp
305 310 315 320

Ser Ser Phe Ser Leu Ser Gln Glu Val Leu Arg His Leu Arg Gln Glu
325 330 335

Glu Lys Glu Glu Val Thr Val Gly Ser Leu Lys Thr Ser Ala Val Pro
340 345 350

Ser Thr Ser Thr Met Ser Gln Glu Pro Glu Leu Leu Ile Ser Gly Met
355 360 365

Glu Lys Pro Leu Pro Leu Arg Thr Asp Phe Ser Ala Thr Asn Phe Ser
370 375 380

Leu Leu Lys Gln Ala Gly Asp Val Glu Glu Asn Pro Gly Pro Met Thr
385 390 395 400

Glu Tyr Lys Leu Val Val Val Gly Ala Val Gly Val Gly Lys Ser Ala
405 410 415

Leu Thr Ile Gln Leu Ile Gln Met Thr Glu Tyr Lys Leu Val Val Val
420 425 430

Gly Ala Val Gly Val Gly Lys Ser Ala Leu Thr Ile Gln Leu Ile Gln
435 440 445

Met Thr Glu Tyr Lys Leu Val Val Val Gly Ala Val Gly Val Gly Lys
450 455 460

Ser Ala Leu Thr Ile Gln Leu Ile Gln
465 470

<210> SEQ ID NO 59
<211> LENGTH: 473
<212> TYPE: PRT
<213> ORGANISM: Artificial Sequence
<220> FEATURE:
<223> OTHER INFORMATION: Synthetic: KRAS(G13D)25mer^3_nt.STING(V155M

<400> SEQUENCE: 59

Met Pro His Ser Ser Leu His Pro Ser Ile Pro Cys Pro Arg Gly His
1 5 10 15

Gly Ala Gln Lys Ala Ala Leu Val Leu Leu Ser Ala Cys Leu Val Thr
20 25 30

Leu Trp Gly Leu Gly Glu Pro Pro Glu His Thr Leu Arg Tyr Leu Val
35 40 45

Leu His Leu Ala Ser Leu Gln Leu Gly Leu Leu Leu Asn Gly Val Cys
50 55 60

Ser Leu Ala Glu Glu Leu Arg His Ile His Ser Arg Tyr Arg Gly Ser
65 70 75 80

Tyr Trp Arg Thr Val Arg Ala Cys Leu Gly Cys Pro Leu Arg Arg Gly
85 90 95

Ala Leu Leu Leu Leu Ser Ile Tyr Phe Tyr Tyr Ser Leu Pro Asn Ala
100 105 110

Val Gly Pro Pro Phe Thr Trp Met Leu Ala Leu Leu Gly Leu Ser Gln
115 120 125

```
Ala Leu Asn Ile Leu Leu Gly Leu Lys Gly Leu Ala Pro Ala Glu Ile
    130                 135                 140

Ser Ala Val Cys Glu Lys Gly Asn Phe Asn Met Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
        195                 200                 205

Pro Asp Asn Leu Ser Met Ala Asp Pro Asn Ile Arg Phe Leu Asp Lys
    210                 215                 220

Leu Pro Gln Gln Thr Gly Asp His Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
            260                 265                 270

Gln Tyr Ser Gln Ala Gly Phe Ser Arg Glu Asp Arg Leu Glu Gln Ala
        275                 280                 285

Lys Leu Phe Cys Arg Thr Leu Glu Asp Ile Leu Ala Asp Ala Pro Glu
    290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335

Glu Lys Glu Glu Val Thr Val Gly Ser Leu Lys Thr Ser Ala Val Pro
            340                 345                 350

Ser Thr Ser Thr Met Ser Gln Glu Pro Glu Leu Leu Ile Ser Gly Met
        355                 360                 365

Glu Lys Pro Leu Pro Leu Arg Thr Asp Phe Ser Ala Thr Asn Phe Ser
    370                 375                 380

Leu Leu Lys Gln Ala Gly Asp Val Glu Glu Asn Pro Gly Pro Met Thr
385                 390                 395                 400

Glu Tyr Lys Leu Val Val Val Gly Ala Gly Asp Val Gly Lys Ser Ala
                405                 410                 415

Leu Thr Ile Gln Leu Ile Gln Met Thr Glu Tyr Lys Leu Val Val Val
            420                 425                 430

Gly Ala Gly Asp Val Gly Lys Ser Ala Leu Thr Ile Gln Leu Ile Gln
        435                 440                 445

Met Thr Glu Tyr Lys Leu Val Val Val Gly Ala Gly Asp Val Gly Lys
    450                 455                 460

Ser Ala Leu Thr Ile Gln Leu Ile Gln
465                 470
```

<210> SEQ ID NO 60
<211> LENGTH: 414
<212> TYPE: PRT
<213> ORGANISM: Artificial Sequence
<220> FEATURE:
<223> OTHER INFORMATION: Synthetic: KRAS(G12D)15mer_ct.STING(V155M)

<400> SEQUENCE: 60

```
Met Lys Leu Val Val Val Gly Ala Asp Gly Val Gly Lys Ser Ala Leu
1               5                   10                  15
```

```
Ala Thr Asn Phe Ser Leu Leu Lys Gln Ala Gly Asp Val Glu Glu Asn
            20                  25                  30

Pro Gly Pro Met Pro His Ser Ser Leu His Pro Ser Ile Pro Cys Pro
        35                  40                  45

Arg Gly His Gly Ala Gln Lys Ala Ala Leu Val Leu Leu Ser Ala Cys
    50                  55                  60

Leu Val Thr Leu Trp Gly Leu Gly Glu Pro Pro Glu His Thr Leu Arg
65                  70                  75                  80

Tyr Leu Val Leu His Leu Ala Ser Leu Gln Leu Gly Leu Leu Leu Asn
                85                  90                  95

Gly Val Cys Ser Leu Ala Glu Glu Leu Arg His Ile His Ser Arg Tyr
            100                 105                 110

Arg Gly Ser Tyr Trp Arg Thr Val Arg Ala Cys Leu Gly Cys Pro Leu
        115                 120                 125

Arg Arg Gly Ala Leu Leu Leu Leu Ser Ile Tyr Phe Tyr Tyr Ser Leu
    130                 135                 140

Pro Asn Ala Val Gly Pro Pro Phe Thr Trp Met Leu Ala Leu Leu Gly
145                 150                 155                 160

Leu Ser Gln Ala Leu Asn Ile Leu Leu Gly Leu Lys Gly Leu Ala Pro
                165                 170                 175

Ala Glu Ile Ser Ala Val Cys Glu Lys Gly Asn Phe Asn Met Ala His
            180                 185                 190

Gly Leu Ala Trp Ser Tyr Tyr Ile Gly Tyr Leu Arg Leu Ile Leu Pro
        195                 200                 205

Glu Leu Gln Ala Arg Ile Arg Thr Tyr Asn Gln His Tyr Asn Asn Leu
    210                 215                 220

Leu Arg Gly Ala Val Ser Gln Arg Leu Tyr Ile Leu Leu Pro Leu Asp
225                 230                 235                 240

Cys Gly Val Pro Asp Asn Leu Ser Met Ala Asp Pro Asn Ile Arg Phe
                245                 250                 255

Leu Asp Lys Leu Pro Gln Gln Thr Gly Asp His Ala Gly Ile Lys Asp
            260                 265                 270

Arg Val Tyr Ser Asn Ser Ile Tyr Glu Leu Leu Glu Asn Gly Gln Arg
        275                 280                 285

Ala Gly Thr Cys Val Leu Glu Tyr Ala Thr Pro Leu Gln Thr Leu Phe
    290                 295                 300

Ala Met Ser Gln Tyr Ser Gln Ala Gly Phe Ser Arg Glu Asp Arg Leu
305                 310                 315                 320

Glu Gln Ala Lys Leu Phe Cys Arg Thr Leu Glu Asp Ile Leu Ala Asp
                325                 330                 335

Ala Pro Glu Ser Gln Asn Asn Cys Arg Leu Ile Ala Tyr Gln Glu Pro
            340                 345                 350

Ala Asp Asp Ser Ser Phe Ser Leu Ser Gln Glu Val Leu Arg His Leu
        355                 360                 365

Arg Gln Glu Glu Lys Glu Glu Val Thr Val Gly Ser Leu Lys Thr Ser
    370                 375                 380

Ala Val Pro Ser Thr Ser Thr Met Ser Gln Glu Pro Glu Leu Leu Ile
385                 390                 395                 400

Ser Gly Met Glu Lys Pro Leu Pro Leu Arg Thr Asp Phe Ser
                405                 410
```

<210> SEQ ID NO 61
<211> LENGTH: 414
<212> TYPE: PRT

<213> ORGANISM: Artificial Sequence
<220> FEATURE:
<223> OTHER INFORMATION: Synthetic: KRAS(G12V)15mer_ct.STING(V155M

<400> SEQUENCE: 61

```
Met Lys Leu Val Val Val Gly Ala Val Gly Val Gly Lys Ser Ala Leu
1               5                   10                  15

Ala Thr Asn Phe Ser Leu Leu Lys Gln Ala Gly Asp Val Glu Glu Asn
            20                  25                  30

Pro Gly Pro Met Pro His Ser Ser Leu His Pro Ser Ile Pro Cys Pro
        35                  40                  45

Arg Gly His Gly Ala Gln Lys Ala Ala Leu Val Leu Leu Ser Ala Cys
    50                  55                  60

Leu Val Thr Leu Trp Gly Leu Gly Glu Pro Pro Glu His Thr Leu Arg
65                  70                  75                  80

Tyr Leu Val Leu His Leu Ala Ser Leu Gln Leu Gly Leu Leu Leu Asn
                85                  90                  95

Gly Val Cys Ser Leu Ala Glu Glu Leu Arg His Ile His Ser Arg Tyr
            100                 105                 110

Arg Gly Ser Tyr Trp Arg Thr Val Arg Ala Cys Leu Gly Cys Pro Leu
        115                 120                 125

Arg Arg Gly Ala Leu Leu Leu Leu Ser Ile Tyr Phe Tyr Tyr Ser Leu
    130                 135                 140

Pro Asn Ala Val Gly Pro Pro Phe Thr Trp Met Leu Ala Leu Leu Gly
145                 150                 155                 160

Leu Ser Gln Ala Leu Asn Ile Leu Leu Gly Leu Lys Gly Leu Ala Pro
                165                 170                 175

Ala Glu Ile Ser Ala Val Cys Glu Lys Gly Asn Phe Asn Met Ala His
            180                 185                 190

Gly Leu Ala Trp Ser Tyr Tyr Ile Gly Tyr Leu Arg Leu Ile Leu Pro
        195                 200                 205

Glu Leu Gln Ala Arg Ile Arg Thr Tyr Asn Gln His Tyr Asn Asn Leu
    210                 215                 220

Leu Arg Gly Ala Val Ser Gln Arg Leu Tyr Ile Leu Leu Pro Leu Asp
225                 230                 235                 240

Cys Gly Val Pro Asp Asn Leu Ser Met Ala Asp Pro Asn Ile Arg Phe
                245                 250                 255

Leu Asp Lys Leu Pro Gln Gln Thr Gly Asp His Ala Gly Ile Lys Asp
            260                 265                 270

Arg Val Tyr Ser Asn Ser Ile Tyr Glu Leu Leu Glu Asn Gly Gln Arg
        275                 280                 285

Ala Gly Thr Cys Val Leu Glu Tyr Ala Thr Pro Leu Gln Thr Leu Phe
    290                 295                 300

Ala Met Ser Gln Tyr Ser Gln Ala Gly Phe Ser Arg Glu Asp Arg Leu
305                 310                 315                 320

Glu Gln Ala Lys Leu Phe Cys Arg Thr Leu Glu Asp Ile Leu Ala Asp
                325                 330                 335

Ala Pro Glu Ser Gln Asn Asn Cys Arg Leu Ile Ala Tyr Gln Glu Pro
            340                 345                 350

Ala Asp Asp Ser Ser Phe Ser Leu Ser Gln Glu Val Leu Arg His Leu
        355                 360                 365

Arg Gln Glu Glu Lys Glu Glu Val Thr Val Gly Ser Leu Lys Thr Ser
    370                 375                 380

Ala Val Pro Ser Thr Ser Thr Met Ser Gln Glu Pro Glu Leu Leu Ile
```

385 390 395 400

Ser Gly Met Glu Lys Pro Leu Pro Leu Arg Thr Asp Phe Ser
405 410

<210> SEQ ID NO 62
<211> LENGTH: 414
<212> TYPE: PRT
<213> ORGANISM: Artificial Sequence
<220> FEATURE:
<223> OTHER INFORMATION: Synthetic: KRAS(G13D)15mer_ct.STING(V155M

<400> SEQUENCE: 62

Met Leu Val Val Val Gly Ala Gly Asp Val Gly Lys Ser Ala Leu Thr
1 5 10 15

Ala Thr Asn Phe Ser Leu Leu Lys Gln Ala Gly Asp Val Glu Glu Asn
20 25 30

Pro Gly Pro Met Pro His Ser Ser Leu His Pro Ser Ile Pro Cys Pro
35 40 45

Arg Gly His Gly Ala Gln Lys Ala Ala Leu Val Leu Leu Ser Ala Cys
50 55 60

Leu Val Thr Leu Trp Gly Leu Gly Glu Pro Pro Glu His Thr Leu Arg
65 70 75 80

Tyr Leu Val Leu His Leu Ala Ser Leu Gln Leu Gly Leu Leu Leu Asn
85 90 95

Gly Val Cys Ser Leu Ala Glu Glu Leu Arg His Ile His Ser Arg Tyr
100 105 110

Arg Gly Ser Tyr Trp Arg Thr Val Arg Ala Cys Leu Gly Cys Pro Leu
115 120 125

Arg Arg Gly Ala Leu Leu Leu Leu Ser Ile Tyr Phe Tyr Tyr Ser Leu
130 135 140

Pro Asn Ala Val Gly Pro Pro Phe Thr Trp Met Leu Ala Leu Leu Gly
145 150 155 160

Leu Ser Gln Ala Leu Asn Ile Leu Leu Gly Leu Lys Gly Leu Ala Pro
165 170 175

Ala Glu Ile Ser Ala Val Cys Glu Lys Gly Asn Phe Asn Met Ala His
180 185 190

Gly Leu Ala Trp Ser Tyr Tyr Ile Gly Tyr Leu Arg Leu Ile Leu Pro
195 200 205

Glu Leu Gln Ala Arg Ile Arg Thr Tyr Asn Gln His Tyr Asn Asn Leu
210 215 220

Leu Arg Gly Ala Val Ser Gln Arg Leu Tyr Ile Leu Leu Pro Leu Asp
225 230 235 240

Cys Gly Val Pro Asp Asn Leu Ser Met Ala Asp Pro Asn Ile Arg Phe
245 250 255

Leu Asp Lys Leu Pro Gln Gln Thr Gly Asp His Ala Gly Ile Lys Asp
260 265 270

Arg Val Tyr Ser Asn Ser Ile Tyr Glu Leu Leu Glu Asn Gly Gln Arg
275 280 285

Ala Gly Thr Cys Val Leu Glu Tyr Ala Thr Pro Leu Gln Thr Leu Phe
290 295 300

Ala Met Ser Gln Tyr Ser Gln Ala Gly Phe Ser Arg Glu Asp Arg Leu
305 310 315 320

Glu Gln Ala Lys Leu Phe Cys Arg Thr Leu Glu Asp Ile Leu Ala Asp
325 330 335

Ala Pro Glu Ser Gln Asn Asn Cys Arg Leu Ile Ala Tyr Gln Glu Pro

```
            340                 345                 350

Ala Asp Asp Ser Ser Phe Ser Leu Ser Gln Glu Val Leu Arg His Leu
        355                 360                 365

Arg Gln Glu Glu Lys Glu Glu Val Thr Val Gly Ser Leu Lys Thr Ser
    370                 375                 380

Ala Val Pro Ser Thr Ser Thr Met Ser Gln Glu Pro Glu Leu Leu Ile
385                 390                 395                 400

Ser Gly Met Glu Lys Pro Leu Pro Leu Arg Thr Asp Phe Ser
                405                 410


<210> SEQ ID NO 63
<211> LENGTH: 423
<212> TYPE: PRT
<213> ORGANISM: Artificial Sequence
<220> FEATURE:
<223> OTHER INFORMATION: Synthetic: KRAS(G12D)25mer_ct.STING(V155M)

<400> SEQUENCE: 63

Met Thr Glu Tyr Lys Leu Val Val Val Gly Ala Asp Gly Val Gly Lys
1               5                   10                  15

Ser Ala Leu Thr Ile Gln Leu Ile Gln Ala Thr Asn Phe Ser Leu Leu
            20                  25                  30

Lys Gln Ala Gly Asp Val Glu Glu Asn Pro Gly Pro Met Pro His Ser
        35                  40                  45

Ser Leu His Pro Ser Ile Pro Cys Pro Arg Gly His Gly Ala Gln Lys
    50                  55                  60

Ala Ala Leu Val Leu Leu Ser Ala Cys Leu Val Thr Leu Trp Gly Leu
65                  70                  75                  80

Gly Glu Pro Pro Glu His Thr Leu Arg Tyr Leu Val Leu His Leu Ala
                85                  90                  95

Ser Leu Gln Leu Gly Leu Leu Leu Asn Gly Val Cys Ser Leu Ala Glu
            100                 105                 110

Glu Leu Arg His Ile His Ser Arg Tyr Arg Gly Ser Tyr Trp Arg Thr
        115                 120                 125

Val Arg Ala Cys Leu Gly Cys Pro Leu Arg Arg Gly Ala Leu Leu Leu
    130                 135                 140

Leu Ser Ile Tyr Phe Tyr Tyr Ser Leu Pro Asn Ala Val Gly Pro Pro
145                 150                 155                 160

Phe Thr Trp Met Leu Ala Leu Leu Gly Leu Ser Gln Ala Leu Asn Ile
                165                 170                 175

Leu Leu Gly Leu Lys Gly Leu Ala Pro Ala Glu Ile Ser Ala Val Cys
            180                 185                 190

Glu Lys Gly Asn Phe Asn Met Ala His Gly Leu Ala Trp Ser Tyr Tyr
        195                 200                 205

Ile Gly Tyr Leu Arg Leu Ile Leu Pro Glu Leu Gln Ala Arg Ile Arg
    210                 215                 220

Thr Tyr Asn Gln His Tyr Asn Asn Leu Leu Arg Gly Ala Val Ser Gln
225                 230                 235                 240

Arg Leu Tyr Ile Leu Leu Pro Leu Asp Cys Gly Val Pro Asp Asn Leu
                245                 250                 255

Ser Met Ala Asp Pro Asn Ile Arg Phe Leu Asp Lys Leu Pro Gln Gln
            260                 265                 270

Thr Gly Asp His Ala Gly Ile Lys Asp Arg Val Tyr Ser Asn Ser Ile
        275                 280                 285

Tyr Glu Leu Leu Glu Asn Gly Gln Arg Ala Gly Thr Cys Val Leu Glu
```

```
    290                 295                 300

Tyr Ala Thr Pro Leu Gln Thr Leu Phe Ala Met Ser Gln Tyr Ser Gln
305                 310                 315                 320

Ala Gly Phe Ser Arg Glu Asp Arg Leu Glu Gln Ala Lys Leu Phe Cys
                325                 330                 335

Arg Thr Leu Glu Asp Ile Leu Ala Asp Ala Pro Glu Ser Gln Asn Asn
            340                 345                 350

Cys Arg Leu Ile Ala Tyr Gln Glu Pro Ala Asp Asp Ser Ser Phe Ser
        355                 360                 365

Leu Ser Gln Glu Val Leu Arg His Leu Arg Gln Glu Glu Lys Glu Glu
    370                 375                 380

Val Thr Val Gly Ser Leu Lys Thr Ser Ala Val Pro Ser Thr Ser Thr
385                 390                 395                 400

Met Ser Gln Glu Pro Glu Leu Leu Ile Ser Gly Met Glu Lys Pro Leu
                405                 410                 415

Pro Leu Arg Thr Asp Phe Ser
            420


<210> SEQ ID NO 64
<211> LENGTH: 423
<212> TYPE: PRT
<213> ORGANISM: Artificial Sequence
<220> FEATURE:
<223> OTHER INFORMATION: Synthetic: KRAS(G12V)25mer_ct.STING(V155M

<400> SEQUENCE: 64

Met Thr Glu Tyr Lys Leu Val Val Val Gly Ala Val Gly Val Gly Lys
1               5                   10                  15

Ser Ala Leu Thr Ile Gln Leu Ile Gln Ala Thr Asn Phe Ser Leu Leu
            20                  25                  30

Lys Gln Ala Gly Asp Val Glu Glu Asn Pro Gly Pro Met Pro His Ser
        35                  40                  45

Ser Leu His Pro Ser Ile Pro Cys Pro Arg Gly His Gly Ala Gln Lys
    50                  55                  60

Ala Ala Leu Val Leu Leu Ser Ala Cys Leu Val Thr Leu Trp Gly Leu
65                  70                  75                  80

Gly Glu Pro Pro Glu His Thr Leu Arg Tyr Leu Val Leu His Leu Ala
                85                  90                  95

Ser Leu Gln Leu Gly Leu Leu Leu Asn Gly Val Cys Ser Leu Ala Glu
            100                 105                 110

Glu Leu Arg His Ile His Ser Arg Tyr Arg Gly Ser Tyr Trp Arg Thr
        115                 120                 125

Val Arg Ala Cys Leu Gly Cys Pro Leu Arg Arg Gly Ala Leu Leu Leu
    130                 135                 140

Leu Ser Ile Tyr Phe Tyr Tyr Ser Leu Pro Asn Ala Val Gly Pro Pro
145                 150                 155                 160

Phe Thr Trp Met Leu Ala Leu Leu Gly Leu Ser Gln Ala Leu Asn Ile
                165                 170                 175

Leu Leu Gly Leu Lys Gly Leu Ala Pro Ala Glu Ile Ser Ala Val Cys
            180                 185                 190

Glu Lys Gly Asn Phe Asn Met Ala His Gly Leu Ala Trp Ser Tyr Tyr
        195                 200                 205

Ile Gly Tyr Leu Arg Leu Ile Leu Pro Glu Leu Gln Ala Arg Ile Arg
    210                 215                 220

Thr Tyr Asn Gln His Tyr Asn Asn Leu Leu Arg Gly Ala Val Ser Gln
```

```
225                 230                 235                 240

Arg Leu Tyr Ile Leu Leu Pro Leu Asp Cys Gly Val Pro Asp Asn Leu
                245                 250                 255

Ser Met Ala Asp Pro Asn Ile Arg Phe Leu Asp Lys Leu Pro Gln Gln
            260                 265                 270

Thr Gly Asp His Ala Gly Ile Lys Asp Arg Val Tyr Ser Asn Ser Ile
        275                 280                 285

Tyr Glu Leu Leu Glu Asn Gly Gln Arg Ala Gly Thr Cys Val Leu Glu
    290                 295                 300

Tyr Ala Thr Pro Leu Gln Thr Leu Phe Ala Met Ser Gln Tyr Ser Gln
305                 310                 315                 320

Ala Gly Phe Ser Arg Glu Asp Arg Leu Glu Gln Ala Lys Leu Phe Cys
                325                 330                 335

Arg Thr Leu Glu Asp Ile Leu Ala Asp Ala Pro Glu Ser Gln Asn Asn
            340                 345                 350

Cys Arg Leu Ile Ala Tyr Gln Glu Pro Ala Asp Asp Ser Ser Phe Ser
        355                 360                 365

Leu Ser Gln Glu Val Leu Arg His Leu Arg Gln Glu Glu Lys Glu Glu
    370                 375                 380

Val Thr Val Gly Ser Leu Lys Thr Ser Ala Val Pro Ser Thr Ser Thr
385                 390                 395                 400

Met Ser Gln Glu Pro Glu Leu Leu Ile Ser Gly Met Glu Lys Pro Leu
                405                 410                 415

Pro Leu Arg Thr Asp Phe Ser
            420


<210> SEQ ID NO 65
<211> LENGTH: 423
<212> TYPE: PRT
<213> ORGANISM: Artificial Sequence
<220> FEATURE:
<223> OTHER INFORMATION: Synthetic: KRAS(G13D)25mer_ct.STING(V155M

<400> SEQUENCE: 65

Met Thr Glu Tyr Lys Leu Val Val Val Gly Ala Gly Asp Val Gly Lys
1               5                   10                  15

Ser Ala Leu Thr Ile Gln Leu Ile Gln Ala Thr Asn Phe Ser Leu Leu
            20                  25                  30

Lys Gln Ala Gly Asp Val Glu Glu Asn Pro Gly Pro Met Pro His Ser
        35                  40                  45

Ser Leu His Pro Ser Ile Pro Cys Pro Arg Gly His Gly Ala Gln Lys
    50                  55                  60

Ala Ala Leu Val Leu Leu Ser Ala Cys Leu Val Thr Leu Trp Gly Leu
65                  70                  75                  80

Gly Glu Pro Pro Glu His Thr Leu Arg Tyr Leu Val Leu His Leu Ala
                85                  90                  95

Ser Leu Gln Leu Gly Leu Leu Leu Asn Gly Val Cys Ser Leu Ala Glu
            100                 105                 110

Glu Leu Arg His Ile His Ser Arg Tyr Arg Gly Ser Tyr Trp Arg Thr
        115                 120                 125

Val Arg Ala Cys Leu Gly Cys Pro Leu Arg Arg Gly Ala Leu Leu Leu
    130                 135                 140

Leu Ser Ile Tyr Phe Tyr Tyr Ser Leu Pro Asn Ala Val Gly Pro Pro
145                 150                 155                 160

Phe Thr Trp Met Leu Ala Leu Leu Gly Leu Ser Gln Ala Leu Asn Ile
```

```
                165                 170                 175

Leu Leu Gly Leu Lys Gly Leu Ala Pro Ala Glu Ile Ser Ala Val Cys
            180                 185                 190

Glu Lys Gly Asn Phe Asn Met Ala His Gly Leu Ala Trp Ser Tyr Tyr
        195                 200                 205

Ile Gly Tyr Leu Arg Leu Ile Leu Pro Glu Leu Gln Ala Arg Ile Arg
    210                 215                 220

Thr Tyr Asn Gln His Tyr Asn Asn Leu Leu Arg Gly Ala Val Ser Gln
225                 230                 235                 240

Arg Leu Tyr Ile Leu Leu Pro Leu Asp Cys Gly Val Pro Asp Asn Leu
                245                 250                 255

Ser Met Ala Asp Pro Asn Ile Arg Phe Leu Asp Lys Leu Pro Gln Gln
            260                 265                 270

Thr Gly Asp His Ala Gly Ile Lys Asp Arg Val Tyr Ser Asn Ser Ile
        275                 280                 285

Tyr Glu Leu Leu Glu Asn Gly Gln Arg Ala Gly Thr Cys Val Leu Glu
    290                 295                 300

Tyr Ala Thr Pro Leu Gln Thr Leu Phe Ala Met Ser Gln Tyr Ser Gln
305                 310                 315                 320

Ala Gly Phe Ser Arg Glu Asp Arg Leu Glu Gln Ala Lys Leu Phe Cys
                325                 330                 335

Arg Thr Leu Glu Asp Ile Leu Ala Asp Ala Pro Glu Ser Gln Asn Asn
            340                 345                 350

Cys Arg Leu Ile Ala Tyr Gln Glu Pro Ala Asp Asp Ser Ser Phe Ser
        355                 360                 365

Leu Ser Gln Glu Val Leu Arg His Leu Arg Gln Glu Glu Lys Glu Glu
    370                 375                 380

Val Thr Val Gly Ser Leu Lys Thr Ser Ala Val Pro Ser Thr Ser Thr
385                 390                 395                 400

Met Ser Gln Glu Pro Glu Leu Leu Ile Ser Gly Met Glu Lys Pro Leu
                405                 410                 415

Pro Leu Arg Thr Asp Phe Ser
            420


<210> SEQ ID NO 66
<211> LENGTH: 444
<212> TYPE: PRT
<213> ORGANISM: Artificial Sequence
<220> FEATURE:
<223> OTHER INFORMATION: Synthetic: KRAS(G12D)15mer^3_ct.STING(V155M)

<400> SEQUENCE: 66

Met Lys Leu Val Val Val Gly Ala Asp Gly Val Gly Lys Ser Ala Leu
1               5                   10                  15

Lys Leu Val Val Val Gly Ala Asp Gly Val Gly Lys Ser Ala Leu Lys
            20                  25                  30

Leu Val Val Val Gly Ala Asp Gly Val Gly Lys Ser Ala Leu Ala Thr
        35                  40                  45

Asn Phe Ser Leu Leu Lys Gln Ala Gly Asp Val Glu Glu Asn Pro Gly
    50                  55                  60

Pro Met Pro His Ser Ser Leu His Pro Ser Ile Pro Cys Pro Arg Gly
65                  70                  75                  80

His Gly Ala Gln Lys Ala Ala Leu Val Leu Leu Ser Ala Cys Leu Val
                85                  90                  95

Thr Leu Trp Gly Leu Gly Glu Pro Pro Glu His Thr Leu Arg Tyr Leu
```

```
            100                 105                 110

Val Leu His Leu Ala Ser Leu Gln Leu Gly Leu Leu Leu Asn Gly Val
        115                 120                 125

Cys Ser Leu Ala Glu Glu Leu Arg His Ile His Ser Arg Tyr Arg Gly
    130                 135                 140

Ser Tyr Trp Arg Thr Val Arg Ala Cys Leu Gly Cys Pro Leu Arg Arg
145                 150                 155                 160

Gly Ala Leu Leu Leu Leu Ser Ile Tyr Phe Tyr Tyr Ser Leu Pro Asn
                165                 170                 175

Ala Val Gly Pro Pro Phe Thr Trp Met Leu Ala Leu Leu Gly Leu Ser
            180                 185                 190

Gln Ala Leu Asn Ile Leu Leu Gly Leu Lys Gly Leu Ala Pro Ala Glu
        195                 200                 205

Ile Ser Ala Val Cys Glu Lys Gly Asn Phe Asn Met Ala His Gly Leu
    210                 215                 220

Ala Trp Ser Tyr Tyr Ile Gly Tyr Leu Arg Leu Ile Leu Pro Glu Leu
225                 230                 235                 240

Gln Ala Arg Ile Arg Thr Tyr Asn Gln His Tyr Asn Asn Leu Leu Arg
                245                 250                 255

Gly Ala Val Ser Gln Arg Leu Tyr Ile Leu Leu Pro Leu Asp Cys Gly
            260                 265                 270

Val Pro Asp Asn Leu Ser Met Ala Asp Pro Asn Ile Arg Phe Leu Asp
        275                 280                 285

Lys Leu Pro Gln Gln Thr Gly Asp His Ala Gly Ile Lys Asp Arg Val
    290                 295                 300

Tyr Ser Asn Ser Ile Tyr Glu Leu Leu Glu Asn Gly Gln Arg Ala Gly
305                 310                 315                 320

Thr Cys Val Leu Glu Tyr Ala Thr Pro Leu Gln Thr Leu Phe Ala Met
                325                 330                 335

Ser Gln Tyr Ser Gln Ala Gly Phe Ser Arg Glu Asp Arg Leu Glu Gln
            340                 345                 350

Ala Lys Leu Phe Cys Arg Thr Leu Glu Asp Ile Leu Ala Asp Ala Pro
        355                 360                 365

Glu Ser Gln Asn Asn Cys Arg Leu Ile Ala Tyr Gln Glu Pro Ala Asp
    370                 375                 380

Asp Ser Ser Phe Ser Leu Ser Gln Glu Val Leu Arg His Leu Arg Gln
385                 390                 395                 400

Glu Glu Lys Glu Glu Val Thr Val Gly Ser Leu Lys Thr Ser Ala Val
                405                 410                 415

Pro Ser Thr Ser Thr Met Ser Gln Glu Pro Glu Leu Leu Ile Ser Gly
            420                 425                 430

Met Glu Lys Pro Leu Pro Leu Arg Thr Asp Phe Ser
        435                 440
```

<210> SEQ ID NO 67
<211> LENGTH: 444
<212> TYPE: PRT
<213> ORGANISM: Artificial Sequence
<220> FEATURE:
<223> OTHER INFORMATION: Synthetic: KRAS(G12V)15mer^3_ct.STING(V155M

<400> SEQUENCE: 67

```
Met Lys Leu Val Val Val Gly Ala Val Gly Val Gly Lys Ser Ala Leu
1               5                   10                  15

Lys Leu Val Val Val Gly Ala Val Gly Val Gly Lys Ser Ala Leu Lys
```

```
            20                  25                  30

Leu Val Val Val Gly Ala Val Gly Val Gly Lys Ser Ala Leu Ala Thr
        35                  40                  45

Asn Phe Ser Leu Leu Lys Gln Ala Gly Asp Val Glu Glu Asn Pro Gly
    50                  55                  60

Pro Met Pro His Ser Ser Leu His Pro Ser Ile Pro Cys Pro Arg Gly
65                  70                  75                  80

His Gly Ala Gln Lys Ala Ala Leu Val Leu Leu Ser Ala Cys Leu Val
                85                  90                  95

Thr Leu Trp Gly Leu Gly Glu Pro Pro Glu His Thr Leu Arg Tyr Leu
            100                 105                 110

Val Leu His Leu Ala Ser Leu Gln Leu Gly Leu Leu Leu Asn Gly Val
        115                 120                 125

Cys Ser Leu Ala Glu Glu Leu Arg His Ile His Ser Arg Tyr Arg Gly
    130                 135                 140

Ser Tyr Trp Arg Thr Val Arg Ala Cys Leu Gly Cys Pro Leu Arg Arg
145                 150                 155                 160

Gly Ala Leu Leu Leu Leu Ser Ile Tyr Phe Tyr Tyr Ser Leu Pro Asn
                165                 170                 175

Ala Val Gly Pro Pro Phe Thr Trp Met Leu Ala Leu Leu Gly Leu Ser
            180                 185                 190

Gln Ala Leu Asn Ile Leu Leu Gly Leu Lys Gly Leu Ala Pro Ala Glu
        195                 200                 205

Ile Ser Ala Val Cys Glu Lys Gly Asn Phe Asn Met Ala His Gly Leu
    210                 215                 220

Ala Trp Ser Tyr Tyr Ile Gly Tyr Leu Arg Leu Ile Leu Pro Glu Leu
225                 230                 235                 240

Gln Ala Arg Ile Arg Thr Tyr Asn Gln His Tyr Asn Asn Leu Leu Arg
                245                 250                 255

Gly Ala Val Ser Gln Arg Leu Tyr Ile Leu Leu Pro Leu Asp Cys Gly
            260                 265                 270

Val Pro Asp Asn Leu Ser Met Ala Asp Pro Asn Ile Arg Phe Leu Asp
        275                 280                 285

Lys Leu Pro Gln Gln Thr Gly Asp His Ala Gly Ile Lys Asp Arg Val
    290                 295                 300

Tyr Ser Asn Ser Ile Tyr Glu Leu Leu Glu Asn Gly Gln Arg Ala Gly
305                 310                 315                 320

Thr Cys Val Leu Glu Tyr Ala Thr Pro Leu Gln Thr Leu Phe Ala Met
                325                 330                 335

Ser Gln Tyr Ser Gln Ala Gly Phe Ser Arg Glu Asp Arg Leu Glu Gln
            340                 345                 350

Ala Lys Leu Phe Cys Arg Thr Leu Glu Asp Ile Leu Ala Asp Ala Pro
        355                 360                 365

Glu Ser Gln Asn Asn Cys Arg Leu Ile Ala Tyr Gln Glu Pro Ala Asp
    370                 375                 380

Asp Ser Ser Phe Ser Leu Ser Gln Glu Val Leu Arg His Leu Arg Gln
385                 390                 395                 400

Glu Glu Lys Glu Glu Val Thr Val Gly Ser Leu Lys Thr Ser Ala Val
                405                 410                 415

Pro Ser Thr Ser Thr Met Ser Gln Glu Pro Glu Leu Leu Ile Ser Gly
            420                 425                 430

Met Glu Lys Pro Leu Pro Leu Arg Thr Asp Phe Ser
        435                 440
```

<210> SEQ ID NO 68
<211> LENGTH: 444
<212> TYPE: PRT
<213> ORGANISM: Artificial Sequence
<220> FEATURE:
<223> OTHER INFORMATION: Synthetic: KRAS(G13D)15mer^3_ct.STING(V155M

<400> SEQUENCE: 68

```
Met Leu Val Val Val Gly Ala Gly Asp Val Gly Lys Ser Ala Leu Thr
1               5                   10                  15

Leu Val Val Val Gly Ala Gly Asp Val Gly Lys Ser Ala Leu Thr Leu
            20                  25                  30

Val Val Val Gly Ala Gly Asp Val Gly Lys Ser Ala Leu Thr Ala Thr
        35                  40                  45

Asn Phe Ser Leu Leu Lys Gln Ala Gly Asp Val Glu Glu Asn Pro Gly
    50                  55                  60

Pro Met Pro His Ser Ser Leu His Pro Ser Ile Pro Cys Pro Arg Gly
65                  70                  75                  80

His Gly Ala Gln Lys Ala Ala Leu Val Leu Leu Ser Ala Cys Leu Val
                85                  90                  95

Thr Leu Trp Gly Leu Gly Glu Pro Pro Glu His Thr Leu Arg Tyr Leu
            100                 105                 110

Val Leu His Leu Ala Ser Leu Gln Leu Gly Leu Leu Leu Asn Gly Val
        115                 120                 125

Cys Ser Leu Ala Glu Glu Leu Arg His Ile His Ser Arg Tyr Arg Gly
    130                 135                 140

Ser Tyr Trp Arg Thr Val Arg Ala Cys Leu Gly Cys Pro Leu Arg Arg
145                 150                 155                 160

Gly Ala Leu Leu Leu Leu Ser Ile Tyr Phe Tyr Tyr Ser Leu Pro Asn
                165                 170                 175

Ala Val Gly Pro Pro Phe Thr Trp Met Leu Ala Leu Leu Gly Leu Ser
            180                 185                 190

Gln Ala Leu Asn Ile Leu Leu Gly Leu Lys Gly Leu Ala Pro Ala Glu
        195                 200                 205

Ile Ser Ala Val Cys Glu Lys Gly Asn Phe Asn Met Ala His Gly Leu
    210                 215                 220

Ala Trp Ser Tyr Tyr Ile Gly Tyr Leu Arg Leu Ile Leu Pro Glu Leu
225                 230                 235                 240

Gln Ala Arg Ile Arg Thr Tyr Asn Gln His Tyr Asn Asn Leu Leu Arg
                245                 250                 255

Gly Ala Val Ser Gln Arg Leu Tyr Ile Leu Leu Pro Leu Asp Cys Gly
            260                 265                 270

Val Pro Asp Asn Leu Ser Met Ala Asp Pro Asn Ile Arg Phe Leu Asp
        275                 280                 285

Lys Leu Pro Gln Gln Thr Gly Asp His Ala Gly Ile Lys Asp Arg Val
    290                 295                 300

Tyr Ser Asn Ser Ile Tyr Glu Leu Leu Glu Asn Gly Gln Arg Ala Gly
305                 310                 315                 320

Thr Cys Val Leu Glu Tyr Ala Thr Pro Leu Gln Thr Leu Phe Ala Met
                325                 330                 335

Ser Gln Tyr Ser Gln Ala Gly Phe Ser Arg Glu Asp Arg Leu Glu Gln
            340                 345                 350

Ala Lys Leu Phe Cys Arg Thr Leu Glu Asp Ile Leu Ala Asp Ala Pro
        355                 360                 365
```

```
Glu Ser Gln Asn Asn Cys Arg Leu Ile Ala Tyr Gln Glu Pro Ala Asp
    370                 375                 380

Asp Ser Ser Phe Ser Leu Ser Gln Glu Val Leu Arg His Leu Arg Gln
385                 390                 395                 400

Glu Glu Lys Glu Glu Val Thr Val Gly Ser Leu Lys Thr Ser Ala Val
                405                 410                 415

Pro Ser Thr Ser Thr Met Ser Gln Glu Pro Glu Leu Leu Ile Ser Gly
            420                 425                 430

Met Glu Lys Pro Leu Pro Leu Arg Thr Asp Phe Ser
        435                 440
```

```
<210> SEQ ID NO 69
<211> LENGTH: 473
<212> TYPE: PRT
<213> ORGANISM: Artificial Sequence
<220> FEATURE:
<223> OTHER INFORMATION: Synthetic: KRAS(G12D)25mer^3_ct.STING(V155M)

<400> SEQUENCE: 69

Met Thr Glu Tyr Lys Leu Val Val Val Gly Ala Asp Gly Val Gly Lys
1               5                   10                  15

Ser Ala Leu Thr Ile Gln Leu Ile Gln Met Thr Glu Tyr Lys Leu Val
            20                  25                  30

Val Val Gly Ala Asp Gly Val Gly Lys Ser Ala Leu Thr Ile Gln Leu
        35                  40                  45

Ile Gln Met Thr Glu Tyr Lys Leu Val Val Val Gly Ala Asp Gly Val
    50                  55                  60

Gly Lys Ser Ala Leu Thr Ile Gln Leu Ile Gln Ala Thr Asn Phe Ser
65                  70                  75                  80

Leu Leu Lys Gln Ala Gly Asp Val Glu Glu Asn Pro Gly Pro Met Pro
                85                  90                  95

His Ser Ser Leu His Pro Ser Ile Pro Cys Pro Arg Gly His Gly Ala
            100                 105                 110

Gln Lys Ala Ala Leu Val Leu Leu Ser Ala Cys Leu Val Thr Leu Trp
        115                 120                 125

Gly Leu Gly Glu Pro Pro Glu His Thr Leu Arg Tyr Leu Val Leu His
    130                 135                 140

Leu Ala Ser Leu Gln Leu Gly Leu Leu Leu Asn Gly Val Cys Ser Leu
145                 150                 155                 160

Ala Glu Glu Leu Arg His Ile His Ser Arg Tyr Arg Gly Ser Tyr Trp
                165                 170                 175

Arg Thr Val Arg Ala Cys Leu Gly Cys Pro Leu Arg Arg Gly Ala Leu
            180                 185                 190

Leu Leu Leu Ser Ile Tyr Phe Tyr Tyr Ser Leu Pro Asn Ala Val Gly
        195                 200                 205

Pro Pro Phe Thr Trp Met Leu Ala Leu Leu Gly Leu Ser Gln Ala Leu
    210                 215                 220

Asn Ile Leu Leu Gly Leu Lys Gly Leu Ala Pro Ala Glu Ile Ser Ala
225                 230                 235                 240

Val Cys Glu Lys Gly Asn Phe Asn Met Ala His Gly Leu Ala Trp Ser
                245                 250                 255

Tyr Tyr Ile Gly Tyr Leu Arg Leu Ile Leu Pro Glu Leu Gln Ala Arg
            260                 265                 270

Ile Arg Thr Tyr Asn Gln His Tyr Asn Asn Leu Leu Arg Gly Ala Val
        275                 280                 285
```

```
Ser Gln Arg Leu Tyr Ile Leu Leu Pro Leu Asp Cys Gly Val Pro Asp
    290                 295                 300

Asn Leu Ser Met Ala Asp Pro Asn Ile Arg Phe Leu Asp Lys Leu Pro
305                 310                 315                 320

Gln Gln Thr Gly Asp His Ala Gly Ile Lys Asp Arg Val Tyr Ser Asn
                325                 330                 335

Ser Ile Tyr Glu Leu Leu Glu Asn Gly Gln Arg Ala Gly Thr Cys Val
            340                 345                 350

Leu Glu Tyr Ala Thr Pro Leu Gln Thr Leu Phe Ala Met Ser Gln Tyr
        355                 360                 365

Ser Gln Ala Gly Phe Ser Arg Glu Asp Arg Leu Glu Gln Ala Lys Leu
    370                 375                 380

Phe Cys Arg Thr Leu Glu Asp Ile Leu Ala Asp Ala Pro Glu Ser Gln
385                 390                 395                 400

Asn Asn Cys Arg Leu Ile Ala Tyr Gln Glu Pro Ala Asp Asp Ser Ser
                405                 410                 415

Phe Ser Leu Ser Gln Glu Val Leu Arg His Leu Arg Gln Glu Glu Lys
            420                 425                 430

Glu Glu Val Thr Val Gly Ser Leu Lys Thr Ser Ala Val Pro Ser Thr
        435                 440                 445

Ser Thr Met Ser Gln Glu Pro Glu Leu Leu Ile Ser Gly Met Glu Lys
    450                 455                 460

Pro Leu Pro Leu Arg Thr Asp Phe Ser
465                 470


<210> SEQ ID NO 70
<211> LENGTH: 473
<212> TYPE: PRT
<213> ORGANISM: Artificial Sequence
<220> FEATURE:
<223> OTHER INFORMATION: Synthetic: KRAS(G12V)25mer^3_ct.STING(V155M

<400> SEQUENCE: 70

Met Thr Glu Tyr Lys Leu Val Val Val Gly Ala Val Gly Val Gly Lys
1               5                   10                  15

Ser Ala Leu Thr Ile Gln Leu Ile Gln Met Thr Glu Tyr Lys Leu Val
            20                  25                  30

Val Val Gly Ala Val Gly Val Gly Lys Ser Ala Leu Thr Ile Gln Leu
        35                  40                  45

Ile Gln Met Thr Glu Tyr Lys Leu Val Val Val Gly Ala Val Gly Val
    50                  55                  60

Gly Lys Ser Ala Leu Thr Ile Gln Leu Ile Gln Ala Thr Asn Phe Ser
65                  70                  75                  80

Leu Leu Lys Gln Ala Gly Asp Val Glu Glu Asn Pro Gly Pro Met Pro
                85                  90                  95

His Ser Ser Leu His Pro Ser Ile Pro Cys Pro Arg Gly His Gly Ala
            100                 105                 110

Gln Lys Ala Ala Leu Val Leu Leu Ser Ala Cys Leu Val Thr Leu Trp
        115                 120                 125

Gly Leu Gly Glu Pro Pro Glu His Thr Leu Arg Tyr Leu Val Leu His
    130                 135                 140

Leu Ala Ser Leu Gln Leu Gly Leu Leu Leu Asn Gly Val Cys Ser Leu
145                 150                 155                 160

Ala Glu Glu Leu Arg His Ile His Ser Arg Tyr Arg Gly Ser Tyr Trp
                165                 170                 175
```

```
Arg Thr Val Arg Ala Cys Leu Gly Cys Pro Leu Arg Arg Gly Ala Leu
            180                 185                 190

Leu Leu Leu Ser Ile Tyr Phe Tyr Tyr Ser Leu Pro Asn Ala Val Gly
        195                 200                 205

Pro Pro Phe Thr Trp Met Leu Ala Leu Leu Gly Leu Ser Gln Ala Leu
    210                 215                 220

Asn Ile Leu Leu Gly Leu Lys Gly Leu Ala Pro Ala Glu Ile Ser Ala
225                 230                 235                 240

Val Cys Glu Lys Gly Asn Phe Asn Met Ala His Gly Leu Ala Trp Ser
                245                 250                 255

Tyr Tyr Ile Gly Tyr Leu Arg Leu Ile Leu Pro Glu Leu Gln Ala Arg
            260                 265                 270

Ile Arg Thr Tyr Asn Gln His Tyr Asn Asn Leu Leu Arg Gly Ala Val
        275                 280                 285

Ser Gln Arg Leu Tyr Ile Leu Leu Pro Leu Asp Cys Gly Val Pro Asp
    290                 295                 300

Asn Leu Ser Met Ala Asp Pro Asn Ile Arg Phe Leu Asp Lys Leu Pro
305                 310                 315                 320

Gln Gln Thr Gly Asp His Ala Gly Ile Lys Asp Arg Val Tyr Ser Asn
                325                 330                 335

Ser Ile Tyr Glu Leu Leu Glu Asn Gly Gln Arg Ala Gly Thr Cys Val
            340                 345                 350

Leu Glu Tyr Ala Thr Pro Leu Gln Thr Leu Phe Ala Met Ser Gln Tyr
        355                 360                 365

Ser Gln Ala Gly Phe Ser Arg Glu Asp Arg Leu Glu Gln Ala Lys Leu
    370                 375                 380

Phe Cys Arg Thr Leu Glu Asp Ile Leu Ala Asp Ala Pro Glu Ser Gln
385                 390                 395                 400

Asn Asn Cys Arg Leu Ile Ala Tyr Gln Glu Pro Ala Asp Asp Ser Ser
                405                 410                 415

Phe Ser Leu Ser Gln Glu Val Leu Arg His Leu Arg Gln Glu Glu Lys
            420                 425                 430

Glu Glu Val Thr Val Gly Ser Leu Lys Thr Ser Ala Val Pro Ser Thr
        435                 440                 445

Ser Thr Met Ser Gln Glu Pro Glu Leu Leu Ile Ser Gly Met Glu Lys
    450                 455                 460

Pro Leu Pro Leu Arg Thr Asp Phe Ser
465                 470


<210> SEQ ID NO 71
<211> LENGTH: 473
<212> TYPE: PRT
<213> ORGANISM: Artificial Sequence
<220> FEATURE:
<223> OTHER INFORMATION: Synthetic: KRAS(G13D)25mer^3_ct.STING(V155M

<400> SEQUENCE: 71

Met Thr Glu Tyr Lys Leu Val Val Val Gly Ala Gly Asp Val Gly Lys
1               5                   10                  15

Ser Ala Leu Thr Ile Gln Leu Ile Gln Met Thr Glu Tyr Lys Leu Val
            20                  25                  30

Val Val Gly Ala Gly Asp Val Gly Lys Ser Ala Leu Thr Ile Gln Leu
        35                  40                  45

Ile Gln Met Thr Glu Tyr Lys Leu Val Val Val Gly Ala Gly Asp Val
    50                  55                  60
```

```
Gly Lys Ser Ala Leu Thr Ile Gln Leu Ile Gln Ala Thr Asn Phe Ser
65                  70                  75                  80

Leu Leu Lys Gln Ala Gly Asp Val Glu Glu Asn Pro Gly Pro Met Pro
                85                  90                  95

His Ser Ser Leu His Pro Ser Ile Pro Cys Pro Arg Gly His Gly Ala
            100                 105                 110

Gln Lys Ala Ala Leu Val Leu Leu Ser Ala Cys Leu Val Thr Leu Trp
        115                 120                 125

Gly Leu Gly Glu Pro Pro Glu His Thr Leu Arg Tyr Leu Val Leu His
    130                 135                 140

Leu Ala Ser Leu Gln Leu Gly Leu Leu Leu Asn Gly Val Cys Ser Leu
145                 150                 155                 160

Ala Glu Glu Leu Arg His Ile His Ser Arg Tyr Arg Gly Ser Tyr Trp
                165                 170                 175

Arg Thr Val Arg Ala Cys Leu Gly Cys Pro Leu Arg Arg Gly Ala Leu
            180                 185                 190

Leu Leu Leu Ser Ile Tyr Phe Tyr Tyr Ser Leu Pro Asn Ala Val Gly
        195                 200                 205

Pro Pro Phe Thr Trp Met Leu Ala Leu Leu Gly Leu Ser Gln Ala Leu
    210                 215                 220

Asn Ile Leu Leu Gly Leu Lys Gly Leu Ala Pro Ala Glu Ile Ser Ala
225                 230                 235                 240

Val Cys Glu Lys Gly Asn Phe Asn Met Ala His Gly Leu Ala Trp Ser
                245                 250                 255

Tyr Tyr Ile Gly Tyr Leu Arg Leu Ile Leu Pro Glu Leu Gln Ala Arg
            260                 265                 270

Ile Arg Thr Tyr Asn Gln His Tyr Asn Asn Leu Leu Arg Gly Ala Val
        275                 280                 285

Ser Gln Arg Leu Tyr Ile Leu Leu Pro Leu Asp Cys Gly Val Pro Asp
    290                 295                 300

Asn Leu Ser Met Ala Asp Pro Asn Ile Arg Phe Leu Asp Lys Leu Pro
305                 310                 315                 320

Gln Gln Thr Gly Asp His Ala Gly Ile Lys Asp Arg Val Tyr Ser Asn
                325                 330                 335

Ser Ile Tyr Glu Leu Leu Glu Asn Gly Gln Arg Ala Gly Thr Cys Val
            340                 345                 350

Leu Glu Tyr Ala Thr Pro Leu Gln Thr Leu Phe Ala Met Ser Gln Tyr
        355                 360                 365

Ser Gln Ala Gly Phe Ser Arg Glu Asp Arg Leu Glu Gln Ala Lys Leu
    370                 375                 380

Phe Cys Arg Thr Leu Glu Asp Ile Leu Ala Asp Ala Pro Glu Ser Gln
385                 390                 395                 400

Asn Asn Cys Arg Leu Ile Ala Tyr Gln Glu Pro Ala Asp Asp Ser Ser
                405                 410                 415

Phe Ser Leu Ser Gln Glu Val Leu Arg His Leu Arg Gln Glu Glu Lys
            420                 425                 430

Glu Glu Val Thr Val Gly Ser Leu Lys Thr Ser Ala Val Pro Ser Thr
        435                 440                 445

Ser Thr Met Ser Gln Glu Pro Glu Leu Leu Ile Ser Gly Met Glu Lys
    450                 455                 460

Pro Leu Pro Leu Arg Thr Asp Phe Ser
465                 470
```

<210> SEQ ID NO 72
<211> LENGTH: 25
<212> TYPE: PRT
<213> ORGANISM: Artificial Sequence
<220> FEATURE:
<223> OTHER INFORMATION: Synthetic: KRAS(G12C)25mer

<400> SEQUENCE: 72

```
Met Thr Glu Tyr Lys Leu Val Val Val Gly Ala Cys Gly Val Gly Lys
1               5                   10                  15

Ser Ala Leu Thr Ile Gln Leu Ile Gln
            20                  25
```

<210> SEQ ID NO 73
<211> LENGTH: 75
<212> TYPE: PRT
<213> ORGANISM: Artificial Sequence
<220> FEATURE:
<223> OTHER INFORMATION: Synthetic: KRAS(G12C)25mer^3

<400> SEQUENCE: 73

```
Met Thr Glu Tyr Lys Leu Val Val Val Gly Ala Cys Gly Val Gly Lys
1               5                   10                  15

Ser Ala Leu Thr Ile Gln Leu Ile Gln Met Thr Glu Tyr Lys Leu Val
            20                  25                  30

Val Val Gly Ala Cys Gly Val Gly Lys Ser Ala Leu Thr Ile Gln Leu
        35                  40                  45

Ile Gln Met Thr Glu Tyr Lys Leu Val Val Val Gly Ala Cys Gly Val
    50                  55                  60

Gly Lys Ser Ala Leu Thr Ile Gln Leu Ile Gln
65                  70                  75
```

<210> SEQ ID NO 74
<211> LENGTH: 25
<212> TYPE: PRT
<213> ORGANISM: Artificial Sequence
<220> FEATURE:
<223> OTHER INFORMATION: Synthetic: KRAS(WT)25mer

<400> SEQUENCE: 74

```
Met Thr Glu Tyr Lys Leu Val Val Val Gly Ala Gly Gly Val Gly Lys
1               5                   10                  15

Ser Ala Leu Thr Ile Gln Leu Ile Gln
            20                  25
```

<210> SEQ ID NO 75
<211> LENGTH: 296
<212> TYPE: PRT
<213> ORGANISM: Homo sapiens
<220> FEATURE:
<221> NAME/KEY: misc_feature
<222> LOCATION: (1)..(296)
<223> OTHER INFORMATION: human myd88(L265P); P4027 without epitope tag

<400> SEQUENCE: 75

```
Met Ser Ala Gly Asp Pro Arg Val Gly Ser Gly Ser Leu Asp Ser Phe
1               5                   10                  15

Met Phe Ser Ile Pro Leu Val Ala Leu Asn Val Gly Val Arg Arg Arg
            20                  25                  30

Leu Ser Leu Phe Leu Asn Pro Arg Thr Pro Val Ala Ala Asp Trp Thr
        35                  40                  45

Leu Leu Ala Glu Glu Met Gly Phe Glu Tyr Leu Glu Ile Arg Glu Leu
```

```
    50                  55                  60

Glu Thr Arg Pro Asp Pro Thr Arg Ser Leu Leu Asp Ala Trp Gln Gly
65                  70                  75                  80

Arg Ser Gly Ala Ser Val Gly Arg Leu Leu Glu Leu Leu Ala Leu Leu
                85                  90                  95

Asp Arg Glu Asp Ile Leu Lys Glu Leu Lys Ser Arg Ile Glu Glu Asp
            100                 105                 110

Cys Gln Lys Tyr Leu Gly Lys Gln Gln Asn Gln Glu Ser Glu Lys Pro
        115                 120                 125

Leu Gln Val Ala Arg Val Glu Ser Ser Val Pro Gln Thr Lys Glu Leu
    130                 135                 140

Gly Gly Ile Thr Thr Leu Asp Asp Pro Leu Gly Gln Thr Pro Glu Leu
145                 150                 155                 160

Phe Asp Ala Phe Ile Cys Tyr Cys Pro Asn Asp Ile Glu Phe Val Gln
                165                 170                 175

Glu Met Ile Arg Gln Leu Glu Gln Thr Asp Tyr Arg Leu Lys Leu Cys
            180                 185                 190

Val Ser Asp Arg Asp Val Leu Pro Gly Thr Cys Val Trp Ser Ile Ala
        195                 200                 205

Ser Glu Leu Ile Glu Lys Arg Cys Arg Arg Met Val Val Val Val Ser
    210                 215                 220

Asp Asp Tyr Leu Gln Ser Lys Glu Cys Asp Phe Gln Thr Lys Phe Ala
225                 230                 235                 240

Leu Ser Leu Ser Pro Gly Val Gln Gln Lys Arg Pro Ile Pro Ile Lys
                245                 250                 255

Tyr Lys Ala Met Lys Lys Asp Phe Pro Ser Ile Leu Arg Phe Ile Thr
            260                 265                 270

Ile Cys Asp Tyr Thr Asn Pro Cys Thr Lys Ser Trp Phe Trp Thr Arg
        275                 280                 285

Leu Ala Lys Ala Leu Ser Leu Pro
    290                 295
```

<210> SEQ ID NO 76
<211> LENGTH: 296
<212> TYPE: PRT
<213> ORGANISM: Mus musculus
<220> FEATURE:
<221> NAME/KEY: misc_feature
<222> LOCATION: (1)..(296)
<223> OTHER INFORMATION: mouse myd88(L265P); P4028 without epitope tag

<400> SEQUENCE: 76

```
Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
            20                  25                  30

Leu Ser Leu Phe Leu Asn Val Arg Thr Gln Val Ala Ala Asp Trp Thr
        35                  40                  45

Ala Leu Ala Glu Glu Met Asp Phe Glu Tyr Leu Glu Ile Arg Gln Leu
    50                  55                  60

Glu Thr Gln Ala Asp Pro Thr Gly Arg Leu Leu Asp Ala Trp Gln Gly
65                  70                  75                  80

Arg Pro Gly Ala Ser Val Gly Arg Leu Leu Glu Leu Leu Thr Lys Leu
                85                  90                  95

Gly Arg Asp Asp Val Leu Leu Glu Leu Gly Pro Ser Ile Glu Glu Asp
            100                 105                 110
```

Cys Gln Lys Tyr Ile Leu Lys Gln Gln Gln Glu Glu Ala Glu Lys Pro
115 120 125

Leu Gln Val Ala Ala Val Asp Ser Ser Val Pro Arg Thr Ala Glu Leu
130 135 140

Ala Gly Ile Thr Thr Leu Asp Asp Pro Leu Gly His Met Pro Glu Arg
145 150 155 160

Phe Asp Ala Phe Ile Cys Tyr Cys Pro Ser Asp Ile Gln Phe Val Gln
165 170 175

Glu Met Ile Arg Gln Leu Glu Gln Thr Asn Tyr Arg Leu Lys Leu Cys
180 185 190

Val Ser Asp Arg Asp Val Leu Pro Gly Thr Cys Val Trp Ser Ile Ala
195 200 205

Ser Glu Leu Ile Glu Lys Arg Cys Arg Arg Met Val Val Val Val Ser
210 215 220

Asp Asp Tyr Leu Gln Ser Lys Glu Cys Asp Phe Gln Thr Lys Phe Ala
225 230 235 240

Leu Ser Leu Ser Pro Gly Ala His Gln Lys Arg Pro Ile Pro Ile Lys
245 250 255

Tyr Lys Ala Met Lys Lys Glu Phe Pro Ser Ile Leu Arg Phe Ile Thr
260 265 270

Val Cys Asp Tyr Thr Asn Pro Cys Thr Lys Ser Trp Phe Trp Thr Arg
275 280 285

Leu Ala Lys Ala Leu Ser Leu Pro
290 295

<210> SEQ ID NO 77
<211> LENGTH: 232
<212> TYPE: PRT
<213> ORGANISM: Mus musculus
<220> FEATURE:
<221> NAME/KEY: misc_feature
<222> LOCATION: (1)..(232)
<223> OTHER INFORMATION: Mouse TRAM (TICAM2); P4033 without epitope tag

<400> SEQUENCE: 77

Met Gly Val Gly Lys Ser Lys Leu Asp Lys Cys Pro Leu Ser Trp His
1 5 10 15

Lys Lys Asp Ser Val Asp Ala Asp Gln Asp Gly His Glu Ser Asp Ser
20 25 30

Lys Asn Ser Glu Glu Ala Cys Leu Arg Gly Phe Val Glu Gln Ser Ser
35 40 45

Gly Ser Glu Pro Pro Thr Gly Glu Gln Asp Gln Pro Glu Ala Lys Gly
50 55 60

Ala Gly Pro Glu Glu Gln Asp Glu Glu Glu Phe Leu Lys Phe Val Ile
65 70 75 80

Leu His Ala Glu Asp Asp Thr Asp Glu Ala Leu Arg Val Gln Asp Leu
85 90 95

Leu Gln Asn Asp Phe Gly Ile Arg Pro Gly Ile Val Phe Ala Glu Met
100 105 110

Pro Cys Gly Arg Leu His Leu Gln Asn Leu Asp Asp Ala Val Asn Gly
115 120 125

Ser Ala Trp Thr Ile Leu Leu Leu Thr Glu Asn Phe Leu Arg Asp Thr
130 135 140

Trp Cys Asn Phe Gln Phe Tyr Thr Ser Leu Met Asn Ser Val Ser Arg
145 150 155 160

```
Gln His Lys Tyr Asn Ser Val Ile Pro Met Arg Pro Leu Asn Ser Pro
                165                 170                 175

Leu Pro Arg Glu Arg Thr Pro Leu Ala Leu Gln Thr Ile Asn Ala Leu
            180                 185                 190

Glu Glu Glu Ser Gln Gly Phe Ser Thr Gln Val Glu Arg Ile Phe Arg
        195                 200                 205

Glu Ser Val Phe Glu Arg Gln Gln Ser Ile Trp Lys Glu Thr Arg Ser
    210                 215                 220

Val Ser Gln Lys Gln Phe Ile Ala
225                 230


<210> SEQ ID NO 78
<211> LENGTH: 847
<212> TYPE: PRT
<213> ORGANISM: Artificial Sequence
<220> FEATURE:
<223> OTHER INFORMATION: Synthetic: STAT6 V547A/T548A); P008 with no
      epitope tag

<400> SEQUENCE: 78

Met Ser Leu Trp Gly Leu Val Ser Lys Met Pro Pro Glu Lys Val Gln
1               5                   10                  15

Arg Leu Tyr Val Asp Phe Pro Gln His Leu Arg His Leu Leu Gly Asp
            20                  25                  30

Trp Leu Glu Ser Gln Pro Trp Glu Phe Leu Val Gly Ser Asp Ala Phe
        35                  40                  45

Cys Cys Asn Leu Ala Ser Ala Leu Leu Ser Asp Thr Val Gln His Leu
    50                  55                  60

Gln Ala Ser Val Gly Glu Gln Gly Glu Gly Ser Thr Ile Leu Gln His
65                  70                  75                  80

Ile Ser Thr Leu Glu Ser Ile Tyr Gln Arg Asp Pro Leu Lys Leu Val
                85                  90                  95

Ala Thr Phe Arg Gln Ile Leu Gln Gly Glu Lys Lys Ala Val Met Glu
            100                 105                 110

Gln Phe Arg His Leu Pro Met Pro Phe His Trp Lys Gln Glu Glu Leu
        115                 120                 125

Lys Phe Lys Thr Gly Leu Arg Arg Leu Gln His Arg Val Gly Glu Ile
    130                 135                 140

His Leu Leu Arg Glu Ala Leu Gln Lys Gly Ala Glu Ala Gly Gln Val
145                 150                 155                 160

Ser Leu His Ser Leu Ile Glu Thr Pro Ala Asn Gly Thr Gly Pro Ser
                165                 170                 175

Glu Ala Leu Ala Met Leu Leu Gln Glu Thr Thr Gly Glu Leu Glu Ala
            180                 185                 190

Ala Lys Ala Leu Val Leu Lys Arg Ile Gln Ile Trp Lys Arg Gln Gln
        195                 200                 205

Gln Leu Ala Gly Asn Gly Ala Pro Phe Glu Glu Ser Leu Ala Pro Leu
    210                 215                 220

Gln Glu Arg Cys Glu Ser Leu Val Asp Ile Tyr Ser Gln Leu Gln Gln
225                 230                 235                 240

Glu Val Gly Ala Ala Gly Gly Glu Leu Glu Pro Lys Thr Arg Ala Ser
                245                 250                 255

Leu Thr Gly Arg Leu Asp Glu Val Leu Arg Thr Leu Val Thr Ser Cys
            260                 265                 270

Phe Leu Val Glu Lys Gln Pro Pro Gln Val Leu Lys Thr Gln Thr Lys
        275                 280                 285
```

```
Phe Gln Ala Gly Val Arg Phe Leu Leu Gly Leu Arg Phe Leu Gly Ala
    290                 295                 300

Pro Ala Lys Pro Pro Leu Val Arg Ala Asp Met Val Thr Glu Lys Gln
305                 310                 315                 320

Ala Arg Glu Leu Ser Val Pro Gln Gly Pro Gly Ala Gly Ala Glu Ser
                325                 330                 335

Thr Gly Glu Ile Ile Asn Asn Thr Val Pro Leu Glu Asn Ser Ile Pro
            340                 345                 350

Gly Asn Cys Cys Ser Ala Leu Phe Lys Asn Leu Leu Leu Lys Lys Ile
        355                 360                 365

Lys Arg Cys Glu Arg Lys Gly Thr Glu Ser Val Thr Glu Glu Lys Cys
    370                 375                 380

Ala Val Leu Phe Ser Ala Ser Phe Thr Leu Gly Pro Gly Lys Leu Pro
385                 390                 395                 400

Ile Gln Leu Gln Ala Leu Ser Leu Pro Leu Val Val Ile Val His Gly
                405                 410                 415

Asn Gln Asp Asn Asn Ala Lys Ala Thr Ile Leu Trp Asp Asn Ala Phe
            420                 425                 430

Ser Glu Met Asp Arg Val Pro Phe Val Val Ala Glu Arg Val Pro Trp
        435                 440                 445

Glu Lys Met Cys Glu Thr Leu Asn Leu Lys Phe Met Ala Glu Val Gly
    450                 455                 460

Thr Asn Arg Gly Leu Leu Pro Glu His Phe Leu Phe Leu Ala Gln Lys
465                 470                 475                 480

Ile Phe Asn Asp Asn Ser Leu Ser Met Glu Ala Phe Gln His Arg Ser
                485                 490                 495

Val Ser Trp Ser Gln Phe Asn Lys Glu Ile Leu Leu Gly Arg Gly Phe
            500                 505                 510

Thr Phe Trp Gln Trp Phe Asp Gly Val Leu Asp Leu Thr Lys Arg Cys
        515                 520                 525

Leu Arg Ser Tyr Trp Ser Asp Arg Leu Ile Ile Gly Phe Ile Ser Lys
    530                 535                 540

Gln Tyr Ala Ala Ser Leu Leu Leu Asn Glu Pro Asp Gly Thr Phe Leu
545                 550                 555                 560

Leu Arg Phe Ser Asp Ser Glu Ile Gly Gly Ile Thr Ile Ala His Val
                565                 570                 575

Ile Arg Gly Gln Asp Gly Ser Pro Gln Ile Glu Asn Ile Gln Pro Phe
            580                 585                 590

Ser Ala Lys Asp Leu Ser Ile Arg Ser Leu Gly Asp Arg Ile Arg Asp
        595                 600                 605

Leu Ala Gln Leu Lys Asn Leu Tyr Pro Lys Lys Pro Lys Asp Glu Ala
    610                 615                 620

Phe Arg Ser His Tyr Lys Pro Glu Gln Met Gly Lys Asp Gly Arg Gly
625                 630                 635                 640

Tyr Val Pro Ala Thr Ile Lys Met Thr Val Glu Arg Asp Gln Pro Leu
                645                 650                 655

Pro Thr Pro Glu Leu Gln Met Pro Thr Met Val Pro Ser Tyr Asp Leu
            660                 665                 670

Gly Met Ala Pro Asp Ser Ser Met Ser Met Gln Leu Gly Pro Asp Met
        675                 680                 685

Val Pro Gln Val Tyr Pro Pro His Ser His Ser Ile Pro Pro Tyr Gln
    690                 695                 700
```

Gly Leu Ser Pro Glu Glu Ser Val Asn Val Leu Ser Ala Phe Gln Glu
705 710 715 720

Pro His Leu Gln Met Pro Pro Ser Leu Gly Gln Met Ser Leu Pro Phe
725 730 735

Asp Gln Pro His Pro Gln Gly Leu Leu Pro Cys Gln Pro Gln Glu His
740 745 750

Ala Val Ser Ser Pro Asp Pro Leu Leu Cys Ser Asp Val Thr Met Val
755 760 765

Glu Asp Ser Cys Leu Ser Gln Pro Val Thr Ala Phe Pro Gln Gly Thr
770 775 780

Trp Ile Gly Glu Asp Ile Phe Pro Pro Leu Leu Pro Pro Thr Glu Gln
785 790 795 800

Asp Leu Thr Lys Leu Leu Leu Glu Gly Gln Gly Glu Ser Gly Gly Gly
805 810 815

Ser Leu Gly Ala Gln Pro Leu Leu Gln Pro Ser His Tyr Gly Gln Ser
820 825 830

Gly Ile Ser Met Ser His Met Asp Leu Arg Ala Asn Pro Ser Trp
835 840 845

<210> SEQ ID NO 79
<211> LENGTH: 847
<212> TYPE: PRT
<213> ORGANISM: Artificial Sequence
<220> FEATURE:
<223> OTHER INFORMATION: Synthetic: STAT6 (S407D); P009 with no epitope tag

<400> SEQUENCE: 79

Met Ser Leu Trp Gly Leu Val Ser Lys Met Pro Pro Glu Lys Val Gln
1 5 10 15

Arg Leu Tyr Val Asp Phe Pro Gln His Leu Arg His Leu Leu Gly Asp
20 25 30

Trp Leu Glu Ser Gln Pro Trp Glu Phe Leu Val Gly Ser Asp Ala Phe
35 40 45

Cys Cys Asn Leu Ala Ser Ala Leu Leu Ser Asp Thr Val Gln His Leu
50 55 60

Gln Ala Ser Val Gly Glu Gln Gly Glu Gly Ser Thr Ile Leu Gln His
65 70 75 80

Ile Ser Thr Leu Glu Ser Ile Tyr Gln Arg Asp Pro Leu Lys Leu Val
85 90 95

Ala Thr Phe Arg Gln Ile Leu Gln Gly Glu Lys Lys Ala Val Met Glu
100 105 110

Gln Phe Arg His Leu Pro Met Pro Phe His Trp Lys Gln Glu Glu Leu
115 120 125

Lys Phe Lys Thr Gly Leu Arg Arg Leu Gln His Arg Val Gly Glu Ile
130 135 140

His Leu Leu Arg Glu Ala Leu Gln Lys Gly Ala Glu Ala Gly Gln Val
145 150 155 160

Ser Leu His Ser Leu Ile Glu Thr Pro Ala Asn Gly Thr Gly Pro Ser
165 170 175

Glu Ala Leu Ala Met Leu Leu Gln Glu Thr Thr Gly Glu Leu Glu Ala
180 185 190

Ala Lys Ala Leu Val Leu Lys Arg Ile Gln Ile Trp Lys Arg Gln Gln
195 200 205

Gln Leu Ala Gly Asn Gly Ala Pro Phe Glu Glu Ser Leu Ala Pro Leu
210 215 220

```
Gln Glu Arg Cys Glu Ser Leu Val Asp Ile Tyr Ser Gln Leu Gln Gln
225                 230                 235                 240

Glu Val Gly Ala Ala Gly Gly Glu Leu Glu Pro Lys Thr Arg Ala Ser
                245                 250                 255

Leu Thr Gly Arg Leu Asp Glu Val Leu Arg Thr Leu Val Thr Ser Cys
            260                 265                 270

Phe Leu Val Glu Lys Gln Pro Pro Gln Val Leu Lys Thr Gln Thr Lys
        275                 280                 285

Phe Gln Ala Gly Val Arg Phe Leu Leu Gly Leu Arg Phe Leu Gly Ala
    290                 295                 300

Pro Ala Lys Pro Pro Leu Val Arg Ala Asp Met Val Thr Glu Lys Gln
305                 310                 315                 320

Ala Arg Glu Leu Ser Val Pro Gln Gly Pro Gly Ala Gly Ala Glu Ser
                325                 330                 335

Thr Gly Glu Ile Ile Asn Asn Thr Val Pro Leu Glu Asn Ser Ile Pro
            340                 345                 350

Gly Asn Cys Cys Ser Ala Leu Phe Lys Asn Leu Leu Leu Lys Lys Ile
        355                 360                 365

Lys Arg Cys Glu Arg Lys Gly Thr Glu Ser Val Thr Glu Glu Lys Cys
    370                 375                 380

Ala Val Leu Phe Ser Ala Ser Phe Thr Leu Gly Pro Gly Lys Leu Pro
385                 390                 395                 400

Ile Gln Leu Gln Ala Leu Asp Leu Pro Leu Val Val Ile Val His Gly
                405                 410                 415

Asn Gln Asp Asn Asn Ala Lys Ala Thr Ile Leu Trp Asp Asn Ala Phe
            420                 425                 430

Ser Glu Met Asp Arg Val Pro Phe Val Val Ala Glu Arg Val Pro Trp
        435                 440                 445

Glu Lys Met Cys Glu Thr Leu Asn Leu Lys Phe Met Ala Glu Val Gly
    450                 455                 460

Thr Asn Arg Gly Leu Leu Pro Glu His Phe Leu Phe Leu Ala Gln Lys
465                 470                 475                 480

Ile Phe Asn Asp Asn Ser Leu Ser Met Glu Ala Phe Gln His Arg Ser
                485                 490                 495

Val Ser Trp Ser Gln Phe Asn Lys Glu Ile Leu Leu Gly Arg Gly Phe
            500                 505                 510

Thr Phe Trp Gln Trp Phe Asp Gly Val Leu Asp Leu Thr Lys Arg Cys
        515                 520                 525

Leu Arg Ser Tyr Trp Ser Asp Arg Leu Ile Ile Gly Phe Ile Ser Lys
    530                 535                 540

Gln Tyr Val Thr Ser Leu Leu Leu Asn Glu Pro Asp Gly Thr Phe Leu
545                 550                 555                 560

Leu Arg Phe Ser Asp Ser Glu Ile Gly Gly Ile Thr Ile Ala His Val
                565                 570                 575

Ile Arg Gly Gln Asp Gly Ser Pro Gln Ile Glu Asn Ile Gln Pro Phe
            580                 585                 590

Ser Ala Lys Asp Leu Ser Ile Arg Ser Leu Gly Asp Arg Ile Arg Asp
        595                 600                 605

Leu Ala Gln Leu Lys Asn Leu Tyr Pro Lys Lys Pro Lys Asp Glu Ala
    610                 615                 620

Phe Arg Ser His Tyr Lys Pro Glu Gln Met Gly Lys Asp Gly Arg Gly
625                 630                 635                 640
```

```
Tyr Val Pro Ala Thr Ile Lys Met Thr Val Glu Arg Asp Gln Pro Leu
                645                 650                 655

Pro Thr Pro Glu Leu Gln Met Pro Thr Met Val Pro Ser Tyr Asp Leu
            660                 665                 670

Gly Met Ala Pro Asp Ser Ser Met Ser Met Gln Leu Gly Pro Asp Met
        675                 680                 685

Val Pro Gln Val Tyr Pro Pro His Ser His Ser Ile Pro Pro Tyr Gln
    690                 695                 700

Gly Leu Ser Pro Glu Glu Ser Val Asn Val Leu Ser Ala Phe Gln Glu
705                 710                 715                 720

Pro His Leu Gln Met Pro Pro Ser Leu Gly Gln Met Ser Leu Pro Phe
                725                 730                 735

Asp Gln Pro His Pro Gln Gly Leu Leu Pro Cys Gln Pro Gln Glu His
            740                 745                 750

Ala Val Ser Ser Pro Asp Pro Leu Leu Cys Ser Asp Val Thr Met Val
        755                 760                 765

Glu Asp Ser Cys Leu Ser Gln Pro Val Thr Ala Phe Pro Gln Gly Thr
    770                 775                 780

Trp Ile Gly Glu Asp Ile Phe Pro Pro Leu Leu Pro Pro Thr Glu Gln
785                 790                 795                 800

Asp Leu Thr Lys Leu Leu Leu Glu Gly Gln Gly Glu Ser Gly Gly Gly
                805                 810                 815

Ser Leu Gly Ala Gln Pro Leu Leu Gln Pro Ser His Tyr Gly Gln Ser
            820                 825                 830

Gly Ile Ser Met Ser His Met Asp Leu Arg Ala Asn Pro Ser Trp
        835                 840                 845


<210> SEQ ID NO 80
<211> LENGTH: 847
<212> TYPE: PRT
<213> ORGANISM: Artificial Sequence
<220> FEATURE:
<223> OTHER INFORMATION: Synthetic: STAT6 (S407D/V547A/T548A); P010 with
      no epitope tag

<400> SEQUENCE: 80

Met Ser Leu Trp Gly Leu Val Ser Lys Met Pro Pro Glu Lys Val Gln
1               5                   10                  15

Arg Leu Tyr Val Asp Phe Pro Gln His Leu Arg His Leu Leu Gly Asp
            20                  25                  30

Trp Leu Glu Ser Gln Pro Trp Glu Phe Leu Val Gly Ser Asp Ala Phe
        35                  40                  45

Cys Cys Asn Leu Ala Ser Ala Leu Leu Ser Asp Thr Val Gln His Leu
    50                  55                  60

Gln Ala Ser Val Gly Glu Gln Gly Glu Gly Ser Thr Ile Leu Gln His
65                  70                  75                  80

Ile Ser Thr Leu Glu Ser Ile Tyr Gln Arg Asp Pro Leu Lys Leu Val
                85                  90                  95

Ala Thr Phe Arg Gln Ile Leu Gln Gly Glu Lys Lys Ala Val Met Glu
            100                 105                 110

Gln Phe Arg His Leu Pro Met Pro Phe His Trp Lys Gln Glu Glu Leu
        115                 120                 125

Lys Phe Lys Thr Gly Leu Arg Arg Leu Gln His Arg Val Gly Glu Ile
    130                 135                 140

His Leu Leu Arg Glu Ala Leu Gln Lys Gly Ala Glu Ala Gly Gln Val
145                 150                 155                 160
```

```
Ser Leu His Ser Leu Ile Glu Thr Pro Ala Asn Gly Thr Gly Pro Ser
                165                 170                 175

Glu Ala Leu Ala Met Leu Leu Gln Glu Thr Thr Gly Glu Leu Glu Ala
            180                 185                 190

Ala Lys Ala Leu Val Leu Lys Arg Ile Gln Ile Trp Lys Arg Gln Gln
        195                 200                 205

Gln Leu Ala Gly Asn Gly Ala Pro Phe Glu Glu Ser Leu Ala Pro Leu
    210                 215                 220

Gln Glu Arg Cys Glu Ser Leu Val Asp Ile Tyr Ser Gln Leu Gln Gln
225                 230                 235                 240

Glu Val Gly Ala Ala Gly Gly Glu Leu Glu Pro Lys Thr Arg Ala Ser
                245                 250                 255

Leu Thr Gly Arg Leu Asp Glu Val Leu Arg Thr Leu Val Thr Ser Cys
            260                 265                 270

Phe Leu Val Glu Lys Gln Pro Pro Gln Val Leu Lys Thr Gln Thr Lys
        275                 280                 285

Phe Gln Ala Gly Val Arg Phe Leu Leu Gly Leu Arg Phe Leu Gly Ala
    290                 295                 300

Pro Ala Lys Pro Pro Leu Val Arg Ala Asp Met Val Thr Glu Lys Gln
305                 310                 315                 320

Ala Arg Glu Leu Ser Val Pro Gln Gly Pro Gly Ala Gly Ala Glu Ser
                325                 330                 335

Thr Gly Glu Ile Ile Asn Asn Thr Val Pro Leu Glu Asn Ser Ile Pro
            340                 345                 350

Gly Asn Cys Cys Ser Ala Leu Phe Lys Asn Leu Leu Leu Lys Lys Ile
        355                 360                 365

Lys Arg Cys Glu Arg Lys Gly Thr Glu Ser Val Thr Glu Glu Lys Cys
    370                 375                 380

Ala Val Leu Phe Ser Ala Ser Phe Thr Leu Gly Pro Gly Lys Leu Pro
385                 390                 395                 400

Ile Gln Leu Gln Ala Leu Asp Leu Pro Leu Val Val Ile Val His Gly
                405                 410                 415

Asn Gln Asp Asn Asn Ala Lys Ala Thr Ile Leu Trp Asp Asn Ala Phe
            420                 425                 430

Ser Glu Met Asp Arg Val Pro Phe Val Val Ala Glu Arg Val Pro Trp
        435                 440                 445

Glu Lys Met Cys Glu Thr Leu Asn Leu Lys Phe Met Ala Glu Val Gly
    450                 455                 460

Thr Asn Arg Gly Leu Leu Pro Glu His Phe Leu Phe Leu Ala Gln Lys
465                 470                 475                 480

Ile Phe Asn Asp Asn Ser Leu Ser Met Glu Ala Phe Gln His Arg Ser
                485                 490                 495

Val Ser Trp Ser Gln Phe Asn Lys Glu Ile Leu Leu Gly Arg Gly Phe
            500                 505                 510

Thr Phe Trp Gln Trp Phe Asp Gly Val Leu Asp Leu Thr Lys Arg Cys
        515                 520                 525

Leu Arg Ser Tyr Trp Ser Asp Arg Leu Ile Ile Gly Phe Ile Ser Lys
    530                 535                 540

Gln Tyr Ala Ala Ser Leu Leu Leu Asn Glu Pro Asp Gly Thr Phe Leu
545                 550                 555                 560

Leu Arg Phe Ser Asp Ser Glu Ile Gly Gly Ile Thr Ile Ala His Val
                565                 570                 575
```

-continued

```
Ile Arg Gly Gln Asp Gly Ser Pro Gln Ile Glu Asn Ile Gln Pro Phe
            580                 585                 590

Ser Ala Lys Asp Leu Ser Ile Arg Ser Leu Gly Asp Arg Ile Arg Asp
        595                 600                 605

Leu Ala Gln Leu Lys Asn Leu Tyr Pro Lys Lys Pro Lys Asp Glu Ala
    610                 615                 620

Phe Arg Ser His Tyr Lys Pro Glu Gln Met Gly Lys Asp Gly Arg Gly
625                 630                 635                 640

Tyr Val Pro Ala Thr Ile Lys Met Thr Val Glu Arg Asp Gln Pro Leu
                645                 650                 655

Pro Thr Pro Glu Leu Gln Met Pro Thr Met Val Pro Ser Tyr Asp Leu
            660                 665                 670

Gly Met Ala Pro Asp Ser Ser Met Ser Met Gln Leu Gly Pro Asp Met
        675                 680                 685

Val Pro Gln Val Tyr Pro Pro His Ser His Ser Ile Pro Pro Tyr Gln
    690                 695                 700

Gly Leu Ser Pro Glu Glu Ser Val Asn Val Leu Ser Ala Phe Gln Glu
705                 710                 715                 720

Pro His Leu Gln Met Pro Pro Ser Leu Gly Gln Met Ser Leu Pro Phe
                725                 730                 735

Asp Gln Pro His Pro Gln Gly Leu Leu Pro Cys Gln Pro Gln Glu His
            740                 745                 750

Ala Val Ser Ser Pro Asp Pro Leu Leu Cys Ser Asp Val Thr Met Val
        755                 760                 765

Glu Asp Ser Cys Leu Ser Gln Pro Val Thr Ala Phe Pro Gln Gly Thr
    770                 775                 780

Trp Ile Gly Glu Asp Ile Phe Pro Pro Leu Leu Pro Pro Thr Glu Gln
785                 790                 795                 800

Asp Leu Thr Lys Leu Leu Leu Glu Gly Gln Gly Glu Ser Gly Gly Gly
                805                 810                 815

Ser Leu Gly Ala Gln Pro Leu Leu Gln Pro Ser His Tyr Gly Gln Ser
            820                 825                 830

Gly Ile Ser Met Ser His Met Asp Leu Arg Ala Asn Pro Ser Trp
        835                 840                 845


<210> SEQ ID NO 81
<211> LENGTH: 847
<212> TYPE: PRT
<213> ORGANISM: Artificial Sequence
<220> FEATURE:
<223> OTHER INFORMATION: Synthetic: STAT6 (V547A/T548A/Y641F); P011 with
      no epitope tag

<400> SEQUENCE: 81

Met Ser Leu Trp Gly Leu Val Ser Lys Met Pro Pro Glu Lys Val Gln
1               5                   10                  15

Arg Leu Tyr Val Asp Phe Pro Gln His Leu Arg His Leu Leu Gly Asp
            20                  25                  30

Trp Leu Glu Ser Gln Pro Trp Glu Phe Leu Val Gly Ser Asp Ala Phe
        35                  40                  45

Cys Cys Asn Leu Ala Ser Ala Leu Leu Ser Asp Thr Val Gln His Leu
    50                  55                  60

Gln Ala Ser Val Gly Glu Gln Gly Glu Gly Ser Thr Ile Leu Gln His
65                  70                  75                  80

Ile Ser Thr Leu Glu Ser Ile Tyr Gln Arg Asp Pro Leu Lys Leu Val
                85                  90                  95
```

```
Ala Thr Phe Arg Gln Ile Leu Gln Gly Glu Lys Lys Ala Val Met Glu
            100                 105                 110

Gln Phe Arg His Leu Pro Met Pro Phe His Trp Lys Gln Glu Glu Leu
        115                 120                 125

Lys Phe Lys Thr Gly Leu Arg Arg Leu Gln His Arg Val Gly Glu Ile
    130                 135                 140

His Leu Leu Arg Glu Ala Leu Gln Lys Gly Ala Glu Ala Gly Gln Val
145                 150                 155                 160

Ser Leu His Ser Leu Ile Glu Thr Pro Ala Asn Gly Thr Gly Pro Ser
                165                 170                 175

Glu Ala Leu Ala Met Leu Leu Gln Glu Thr Thr Gly Glu Leu Glu Ala
            180                 185                 190

Ala Lys Ala Leu Val Leu Lys Arg Ile Gln Ile Trp Lys Arg Gln Gln
        195                 200                 205

Gln Leu Ala Gly Asn Gly Ala Pro Phe Glu Glu Ser Leu Ala Pro Leu
    210                 215                 220

Gln Glu Arg Cys Glu Ser Leu Val Asp Ile Tyr Ser Gln Leu Gln Gln
225                 230                 235                 240

Glu Val Gly Ala Ala Gly Gly Glu Leu Glu Pro Lys Thr Arg Ala Ser
                245                 250                 255

Leu Thr Gly Arg Leu Asp Glu Val Leu Arg Thr Leu Val Thr Ser Cys
            260                 265                 270

Phe Leu Val Glu Lys Gln Pro Pro Gln Val Leu Lys Thr Gln Thr Lys
        275                 280                 285

Phe Gln Ala Gly Val Arg Phe Leu Leu Gly Leu Arg Phe Leu Gly Ala
    290                 295                 300

Pro Ala Lys Pro Pro Leu Val Arg Ala Asp Met Val Thr Glu Lys Gln
305                 310                 315                 320

Ala Arg Glu Leu Ser Val Pro Gln Gly Pro Gly Ala Gly Ala Glu Ser
                325                 330                 335

Thr Gly Glu Ile Ile Asn Asn Thr Val Pro Leu Glu Asn Ser Ile Pro
            340                 345                 350

Gly Asn Cys Cys Ser Ala Leu Phe Lys Asn Leu Leu Leu Lys Lys Ile
        355                 360                 365

Lys Arg Cys Glu Arg Lys Gly Thr Glu Ser Val Thr Glu Glu Lys Cys
    370                 375                 380

Ala Val Leu Phe Ser Ala Ser Phe Thr Leu Gly Pro Gly Lys Leu Pro
385                 390                 395                 400

Ile Gln Leu Gln Ala Leu Ser Leu Pro Leu Val Val Ile Val His Gly
                405                 410                 415

Asn Gln Asp Asn Asn Ala Lys Ala Thr Ile Leu Trp Asp Asn Ala Phe
            420                 425                 430

Ser Glu Met Asp Arg Val Pro Phe Val Val Ala Glu Arg Val Pro Trp
        435                 440                 445

Glu Lys Met Cys Glu Thr Leu Asn Leu Lys Phe Met Ala Glu Val Gly
    450                 455                 460

Thr Asn Arg Gly Leu Leu Pro Glu His Phe Leu Phe Leu Ala Gln Lys
465                 470                 475                 480

Ile Phe Asn Asp Asn Ser Leu Ser Met Glu Ala Phe Gln His Arg Ser
                485                 490                 495

Val Ser Trp Ser Gln Phe Asn Lys Glu Ile Leu Leu Gly Arg Gly Phe
            500                 505                 510
```

Thr Phe Trp Gln Trp Phe Asp Gly Val Leu Asp Leu Thr Lys Arg Cys
        515                 520                 525

Leu Arg Ser Tyr Trp Ser Asp Arg Leu Ile Ile Gly Phe Ile Ser Lys
    530                 535                 540

Gln Tyr Ala Ala Ser Leu Leu Leu Asn Glu Pro Asp Gly Thr Phe Leu
545                 550                 555                 560

Leu Arg Phe Ser Asp Ser Glu Ile Gly Gly Ile Thr Ile Ala His Val
                565                 570                 575

Ile Arg Gly Gln Asp Gly Ser Pro Gln Ile Glu Asn Ile Gln Pro Phe
            580                 585                 590

Ser Ala Lys Asp Leu Ser Ile Arg Ser Leu Gly Asp Arg Ile Arg Asp
        595                 600                 605

Leu Ala Gln Leu Lys Asn Leu Tyr Pro Lys Lys Pro Lys Asp Glu Ala
    610                 615                 620

Phe Arg Ser His Tyr Lys Pro Glu Gln Met Gly Lys Asp Gly Arg Gly
625                 630                 635                 640

Phe Val Pro Ala Thr Ile Lys Met Thr Val Glu Arg Asp Gln Pro Leu
                645                 650                 655

Pro Thr Pro Glu Leu Gln Met Pro Thr Met Val Pro Ser Tyr Asp Leu
            660                 665                 670

Gly Met Ala Pro Asp Ser Ser Met Ser Met Gln Leu Gly Pro Asp Met
        675                 680                 685

Val Pro Gln Val Tyr Pro Pro His Ser His Ser Ile Pro Pro Tyr Gln
    690                 695                 700

Gly Leu Ser Pro Glu Glu Ser Val Asn Val Leu Ser Ala Phe Gln Glu
705                 710                 715                 720

Pro His Leu Gln Met Pro Pro Ser Leu Gly Gln Met Ser Leu Pro Phe
                725                 730                 735

Asp Gln Pro His Pro Gln Gly Leu Leu Pro Cys Gln Pro Gln Glu His
            740                 745                 750

Ala Val Ser Ser Pro Asp Pro Leu Leu Cys Ser Asp Val Thr Met Val
        755                 760                 765

Glu Asp Ser Cys Leu Ser Gln Pro Val Thr Ala Phe Pro Gln Gly Thr
    770                 775                 780

Trp Ile Gly Glu Asp Ile Phe Pro Pro Leu Leu Pro Pro Thr Glu Gln
785                 790                 795                 800

Asp Leu Thr Lys Leu Leu Leu Glu Gly Gln Gly Glu Ser Gly Gly Gly
                805                 810                 815

Ser Leu Gly Ala Gln Pro Leu Leu Gln Pro Ser His Tyr Gly Gln Ser
            820                 825                 830

Gly Ile Ser Met Ser His Met Asp Leu Arg Ala Asn Pro Ser Trp
        835                 840                 845

<210> SEQ ID NO 82
<211> LENGTH: 479
<212> TYPE: PRT
<213> ORGANISM: Artificial Sequence
<220> FEATURE:
<223> OTHER INFORMATION: Synthetic: hu-cFLIP-L; P1006 without epitope tag

<400> SEQUENCE: 82

Ser Ala Glu Val Ile His Gln Val Glu Glu Ala Leu Asp Thr Asp Glu
1               5                   10                  15

Lys Glu Met Leu Leu Phe Leu Cys Arg Asp Val Ala Ile Asp Val Val
            20                  25                  30

-continued

```
Pro Pro Asn Val Arg Asp Leu Leu Asp Ile Leu Arg Glu Arg Gly Lys
        35                  40                  45

Leu Ser Val Gly Asp Leu Ala Glu Leu Leu Tyr Arg Val Arg Arg Phe
    50                  55                  60

Asp Leu Leu Lys Arg Ile Leu Lys Met Asp Arg Lys Ala Val Glu Thr
65                  70                  75                  80

His Leu Leu Arg Asn Pro His Leu Val Ser Asp Tyr Arg Val Leu Met
                85                  90                  95

Ala Glu Ile Gly Glu Asp Leu Asp Lys Ser Asp Val Ser Ser Leu Ile
            100                 105                 110

Phe Leu Met Lys Asp Tyr Met Gly Arg Gly Lys Ile Ser Lys Glu Lys
        115                 120                 125

Ser Phe Leu Asp Leu Val Val Glu Leu Glu Lys Leu Asn Leu Val Ala
    130                 135                 140

Pro Asp Gln Leu Asp Leu Leu Glu Lys Cys Leu Lys Asn Ile His Arg
145                 150                 155                 160

Ile Asp Leu Lys Thr Lys Ile Gln Lys Tyr Lys Gln Ser Val Gln Gly
                165                 170                 175

Ala Gly Thr Ser Tyr Arg Asn Val Leu Gln Ala Ala Ile Gln Lys Ser
            180                 185                 190

Leu Lys Asp Pro Ser Asn Asn Phe Arg Leu His Asn Gly Arg Ser Lys
        195                 200                 205

Glu Gln Arg Leu Lys Glu Gln Leu Gly Ala Gln Gln Glu Pro Val Lys
    210                 215                 220

Lys Ser Ile Gln Glu Ser Glu Ala Phe Leu Pro Gln Ser Ile Pro Glu
225                 230                 235                 240

Glu Arg Tyr Lys Met Lys Ser Lys Pro Leu Gly Ile Cys Leu Ile Ile
                245                 250                 255

Asp Cys Ile Gly Asn Glu Thr Glu Leu Leu Arg Asp Thr Phe Thr Ser
            260                 265                 270

Leu Gly Tyr Glu Val Gln Lys Phe Leu His Leu Ser Met His Gly Ile
        275                 280                 285

Ser Gln Ile Leu Gly Gln Phe Ala Cys Met Pro Glu His Arg Asp Tyr
    290                 295                 300

Asp Ser Phe Val Cys Val Leu Val Ser Arg Gly Gly Ser Gln Ser Val
305                 310                 315                 320

Tyr Gly Val Asp Gln Thr His Ser Gly Leu Pro Leu His His Ile Arg
                325                 330                 335

Arg Met Phe Met Gly Asp Ser Cys Pro Tyr Leu Ala Gly Lys Pro Lys
            340                 345                 350

Met Phe Phe Ile Gln Asn Tyr Val Val Ser Glu Gly Gln Leu Glu Asp
        355                 360                 365

Ser Ser Leu Leu Glu Val Asp Gly Pro Ala Met Lys Asn Val Glu Phe
    370                 375                 380

Lys Ala Gln Lys Arg Gly Leu Cys Thr Val His Arg Glu Ala Asp Phe
385                 390                 395                 400

Phe Trp Ser Leu Cys Thr Ala Asp Met Ser Leu Leu Glu Gln Ser His
                405                 410                 415

Ser Ser Pro Ser Leu Tyr Leu Gln Cys Leu Ser Gln Lys Leu Arg Gln
            420                 425                 430

Glu Arg Lys Arg Pro Leu Leu Asp Leu His Ile Glu Leu Asn Gly Tyr
        435                 440                 445
```

-continued

Met Tyr Asp Trp Asn Ser Arg Val Ser Ala Lys Glu Lys Tyr Tyr Val
    450                 455                 460

Trp Leu Gln His Thr Leu Arg Lys Lys Leu Ile Leu Ser Tyr Thr
465                 470                 475

<210> SEQ ID NO 83
<211> LENGTH: 226
<212> TYPE: PRT
<213> ORGANISM: Artificial Sequence
<220> FEATURE:
<223> OTHER INFORMATION: Synthetic: hu-cFLIP-S(1-227); P1007 without epitope tag

<400> SEQUENCE: 83

Ser Ala Glu Val Ile His Gln Val Glu Glu Ala Leu Asp Thr Asp Glu
1               5                   10                  15

Lys Glu Met Leu Leu Phe Leu Cys Arg Asp Val Ala Ile Asp Val Val
            20                  25                  30

Pro Pro Asn Val Arg Asp Leu Leu Asp Ile Leu Arg Glu Arg Gly Lys
        35                  40                  45

Leu Ser Val Gly Asp Leu Ala Glu Leu Leu Tyr Arg Val Arg Arg Phe
    50                  55                  60

Asp Leu Leu Lys Arg Ile Leu Lys Met Asp Arg Lys Ala Val Glu Thr
65                  70                  75                  80

His Leu Leu Arg Asn Pro His Leu Val Ser Asp Tyr Arg Val Leu Met
                85                  90                  95

Ala Glu Ile Gly Glu Asp Leu Asp Lys Ser Asp Val Ser Ser Leu Ile
            100                 105                 110

Phe Leu Met Lys Asp Tyr Met Gly Arg Gly Lys Ile Ser Lys Glu Lys
        115                 120                 125

Ser Phe Leu Asp Leu Val Val Glu Leu Glu Lys Leu Asn Leu Val Ala
    130                 135                 140

Pro Asp Gln Leu Asp Leu Leu Glu Lys Cys Leu Lys Asn Ile His Arg
145                 150                 155                 160

Ile Asp Leu Lys Thr Lys Ile Gln Lys Tyr Lys Gln Ser Val Gln Gly
                165                 170                 175

Ala Gly Thr Ser Tyr Arg Asn Val Leu Gln Ala Ala Ile Gln Lys Ser
            180                 185                 190

Leu Lys Asp Pro Ser Asn Asn Phe Arg Leu His Asn Gly Arg Ser Lys
        195                 200                 205

Glu Gln Arg Leu Lys Glu Gln Leu Gly Ala Gln Gln Glu Pro Val Lys
    210                 215                 220

Lys Ser
225

<210> SEQ ID NO 84
<211> LENGTH: 195
<212> TYPE: PRT
<213> ORGANISM: Artificial Sequence
<220> FEATURE:
<223> OTHER INFORMATION: Synthetic: hu-cFLIP-p22(1-198); P1008 without epitope tag

<400> SEQUENCE: 84

Ser Ala Glu Val Ile His Gln Val Glu Glu Ala Leu Asp Thr Asp Glu
1               5                   10                  15

Lys Glu Met Leu Leu Phe Leu Cys Arg Asp Val Ala Ile Asp Val Val
            20                  25                  30

Pro Pro Asn Val Arg Asp Leu Leu Asp Ile Leu Arg Glu Arg Gly Lys
35 40 45

Leu Ser Val Gly Asp Leu Ala Glu Leu Leu Tyr Arg Val Arg Arg Phe
50 55 60

Asp Leu Leu Lys Arg Ile Leu Lys Met Asp Arg Lys Ala Val Glu Thr
65 70 75 80

His Leu Leu Arg Asn Pro His Leu Val Ser Asp Tyr Arg Val Leu Met
85 90 95

Ala Glu Ile Gly Glu Asp Leu Asp Lys Ser Asp Val Ser Ser Leu Ile
100 105 110

Phe Leu Met Lys Asp Tyr Met Gly Arg Gly Lys Ile Ser Lys Glu Lys
115 120 125

Ser Phe Leu Asp Leu Val Val Glu Leu Glu Lys Leu Asn Leu Val Ala
130 135 140

Pro Asp Gln Leu Asp Leu Leu Glu Lys Cys Leu Lys Asn Ile His Arg
145 150 155 160

Ile Asp Leu Lys Thr Lys Ile Gln Lys Tyr Lys Gln Ser Val Gln Gly
165 170 175

Ala Gly Thr Ser Tyr Arg Asn Val Leu Gln Ala Ala Ile Gln Lys Ser
180 185 190

Leu Lys Asp
195

<210> SEQ ID NO 85
<211> LENGTH: 375
<212> TYPE: PRT
<213> ORGANISM: Artificial Sequence
<220> FEATURE:
<223> OTHER INFORMATION: Synthetic: hu-cFLIP-p43(1-376); P1009 without epitope tag

<400> SEQUENCE: 85

Ser Ala Glu Val Ile His Gln Val Glu Glu Ala Leu Asp Thr Asp Glu
1 5 10 15

Lys Glu Met Leu Leu Phe Leu Cys Arg Asp Val Ala Ile Asp Val Val
20 25 30

Pro Pro Asn Val Arg Asp Leu Leu Asp Ile Leu Arg Glu Arg Gly Lys
35 40 45

Leu Ser Val Gly Asp Leu Ala Glu Leu Leu Tyr Arg Val Arg Arg Phe
50 55 60

Asp Leu Leu Lys Arg Ile Leu Lys Met Asp Arg Lys Ala Val Glu Thr
65 70 75 80

His Leu Leu Arg Asn Pro His Leu Val Ser Asp Tyr Arg Val Leu Met
85 90 95

Ala Glu Ile Gly Glu Asp Leu Asp Lys Ser Asp Val Ser Ser Leu Ile
100 105 110

Phe Leu Met Lys Asp Tyr Met Gly Arg Gly Lys Ile Ser Lys Glu Lys
115 120 125

Ser Phe Leu Asp Leu Val Val Glu Leu Glu Lys Leu Asn Leu Val Ala
130 135 140

Pro Asp Gln Leu Asp Leu Leu Glu Lys Cys Leu Lys Asn Ile His Arg
145 150 155 160

Ile Asp Leu Lys Thr Lys Ile Gln Lys Tyr Lys Gln Ser Val Gln Gly
165 170 175

Ala Gly Thr Ser Tyr Arg Asn Val Leu Gln Ala Ala Ile Gln Lys Ser
180 185 190

```
Leu Lys Asp Pro Ser Asn Asn Phe Arg Leu His Asn Gly Arg Ser Lys
        195                 200                 205

Glu Gln Arg Leu Lys Glu Gln Leu Gly Ala Gln Gln Glu Pro Val Lys
    210                 215                 220

Lys Ser Ile Gln Glu Ser Glu Ala Phe Leu Pro Gln Ser Ile Pro Glu
225                 230                 235                 240

Glu Arg Tyr Lys Met Lys Ser Lys Pro Leu Gly Ile Cys Leu Ile Ile
                245                 250                 255

Asp Cys Ile Gly Asn Glu Thr Glu Leu Leu Arg Asp Thr Phe Thr Ser
            260                 265                 270

Leu Gly Tyr Glu Val Gln Lys Phe Leu His Leu Ser Met His Gly Ile
        275                 280                 285

Ser Gln Ile Leu Gly Gln Phe Ala Cys Met Pro Glu His Arg Asp Tyr
    290                 295                 300

Asp Ser Phe Val Cys Val Leu Val Ser Arg Gly Gly Ser Gln Ser Val
305                 310                 315                 320

Tyr Gly Val Asp Gln Thr His Ser Gly Leu Pro Leu His His Ile Arg
                325                 330                 335

Arg Met Phe Met Gly Asp Ser Cys Pro Tyr Leu Ala Gly Lys Pro Lys
            340                 345                 350

Met Phe Phe Ile Gln Asn Tyr Val Val Ser Glu Gly Gln Leu Glu Asp
        355                 360                 365

Ser Ser Leu Leu Glu Val Asp
    370                 375


<210> SEQ ID NO 86
<211> LENGTH: 104
<212> TYPE: PRT
<213> ORGANISM: Artificial Sequence
<220> FEATURE:
<223> OTHER INFORMATION: Synthetic: hu-cFLIP-p12(377-480); P1010 without
      epitope tag

<400> SEQUENCE: 86

Gly Pro Ala Met Lys Asn Val Glu Phe Lys Ala Gln Lys Arg Gly Leu
1               5                   10                  15

Cys Thr Val His Arg Glu Ala Asp Phe Phe Trp Ser Leu Cys Thr Ala
            20                  25                  30

Asp Met Ser Leu Leu Glu Gln Ser His Ser Ser Pro Ser Leu Tyr Leu
        35                  40                  45

Gln Cys Leu Ser Gln Lys Leu Arg Gln Glu Arg Lys Arg Pro Leu Leu
    50                  55                  60

Asp Leu His Ile Glu Leu Asn Gly Tyr Met Tyr Asp Trp Asn Ser Arg
65                  70                  75                  80

Val Ser Ala Lys Glu Lys Tyr Tyr Val Trp Leu Gln His Thr Leu Arg
                85                  90                  95

Lys Lys Leu Ile Leu Ser Tyr Thr
            100


<210> SEQ ID NO 87
<211> LENGTH: 756
<212> TYPE: PRT
<213> ORGANISM: Artificial Sequence
<220> FEATURE:
<223> OTHER INFORMATION: Synthetic: huIKK2ca(S177E/S181E); P4005 without
      epitope tag

<400> SEQUENCE: 87
```

```
Met Ser Trp Ser Pro Ser Leu Thr Thr Gln Thr Cys Gly Ala Trp Glu
1               5                   10                  15

Met Lys Glu Arg Leu Gly Thr Gly Gly Phe Gly Asn Val Ile Arg Trp
            20                  25                  30

His Asn Gln Glu Thr Gly Glu Gln Ile Ala Ile Lys Gln Cys Arg Gln
        35                  40                  45

Glu Leu Ser Pro Arg Asn Arg Glu Arg Trp Cys Leu Glu Ile Gln Ile
    50                  55                  60

Met Arg Arg Leu Thr His Pro Asn Val Val Ala Ala Arg Asp Val Pro
65                  70                  75                  80

Glu Gly Met Gln Asn Leu Ala Pro Asn Asp Leu Pro Leu Leu Ala Met
                85                  90                  95

Glu Tyr Cys Gln Gly Gly Asp Leu Arg Lys Tyr Leu Asn Gln Phe Glu
            100                 105                 110

Asn Cys Cys Gly Leu Arg Glu Gly Ala Ile Leu Thr Leu Leu Ser Asp
        115                 120                 125

Ile Ala Ser Ala Leu Arg Tyr Leu His Glu Asn Arg Ile Ile His Arg
    130                 135                 140

Asp Leu Lys Pro Glu Asn Ile Val Leu Gln Gln Gly Glu Gln Arg Leu
145                 150                 155                 160

Ile His Lys Ile Ile Asp Leu Gly Tyr Ala Lys Glu Leu Asp Gln Gly
                165                 170                 175

Glu Leu Cys Thr Glu Phe Val Gly Thr Leu Gln Tyr Leu Ala Pro Glu
            180                 185                 190

Leu Leu Glu Gln Gln Lys Tyr Thr Val Thr Val Asp Tyr Trp Ser Phe
        195                 200                 205

Gly Thr Leu Ala Phe Glu Cys Ile Thr Gly Phe Arg Pro Phe Leu Pro
    210                 215                 220

Asn Trp Gln Pro Val Gln Trp His Ser Lys Val Arg Gln Lys Ser Glu
225                 230                 235                 240

Val Asp Ile Val Val Ser Glu Asp Leu Asn Gly Thr Val Lys Phe Ser
                245                 250                 255

Ser Ser Leu Pro Tyr Pro Asn Asn Leu Asn Ser Val Leu Ala Glu Arg
            260                 265                 270

Leu Glu Lys Trp Leu Gln Leu Met Leu Met Trp His Pro Arg Gln Arg
        275                 280                 285

Gly Thr Asp Pro Thr Tyr Gly Pro Asn Gly Cys Phe Lys Ala Leu Asp
    290                 295                 300

Asp Ile Leu Asn Leu Lys Leu Val His Ile Leu Asn Met Val Thr Gly
305                 310                 315                 320

Thr Ile His Thr Tyr Pro Val Thr Glu Asp Glu Ser Leu Gln Ser Leu
                325                 330                 335

Lys Ala Arg Ile Gln Gln Asp Thr Gly Ile Pro Glu Glu Asp Gln Glu
            340                 345                 350

Leu Leu Gln Glu Ala Gly Leu Ala Leu Ile Pro Asp Lys Pro Ala Thr
        355                 360                 365

Gln Cys Ile Ser Asp Gly Lys Leu Asn Glu Gly His Thr Leu Asp Met
    370                 375                 380

Asp Leu Val Phe Leu Phe Asp Asn Ser Lys Ile Thr Tyr Glu Thr Gln
385                 390                 395                 400

Ile Ser Pro Arg Pro Gln Pro Glu Ser Val Ser Cys Ile Leu Gln Glu
                405                 410                 415
```

```
Pro Lys Arg Asn Leu Ala Phe Phe Gln Leu Arg Lys Val Trp Gly Gln
            420                 425                 430

Val Trp His Ser Ile Gln Thr Leu Lys Glu Asp Cys Asn Arg Leu Gln
        435                 440                 445

Gln Gly Gln Arg Ala Ala Met Met Asn Leu Leu Arg Asn Asn Ser Cys
    450                 455                 460

Leu Ser Lys Met Lys Asn Ser Met Ala Ser Met Ser Gln Gln Leu Lys
465                 470                 475                 480

Ala Lys Leu Asp Phe Phe Lys Thr Ser Ile Gln Ile Asp Leu Glu Lys
                485                 490                 495

Tyr Ser Glu Gln Thr Glu Phe Gly Ile Thr Ser Asp Lys Leu Leu Leu
            500                 505                 510

Ala Trp Arg Glu Met Glu Gln Ala Val Glu Leu Cys Gly Arg Glu Asn
        515                 520                 525

Glu Val Lys Leu Leu Val Glu Arg Met Met Ala Leu Gln Thr Asp Ile
    530                 535                 540

Val Asp Leu Gln Arg Ser Pro Met Gly Arg Lys Gln Gly Gly Thr Leu
545                 550                 555                 560

Asp Asp Leu Glu Glu Gln Ala Arg Glu Leu Tyr Arg Arg Leu Arg Glu
                565                 570                 575

Lys Pro Arg Asp Gln Arg Thr Glu Gly Asp Ser Gln Glu Met Val Arg
            580                 585                 590

Leu Leu Leu Gln Ala Ile Gln Ser Phe Glu Lys Lys Val Arg Val Ile
        595                 600                 605

Tyr Thr Gln Leu Ser Lys Thr Val Val Cys Lys Gln Lys Ala Leu Glu
    610                 615                 620

Leu Leu Pro Lys Val Glu Glu Val Val Ser Leu Met Asn Glu Asp Glu
625                 630                 635                 640

Lys Thr Val Val Arg Leu Gln Glu Lys Arg Gln Lys Glu Leu Trp Asn
                645                 650                 655

Leu Leu Lys Ile Ala Cys Ser Lys Val Arg Gly Pro Val Ser Gly Ser
            660                 665                 670

Pro Asp Ser Met Asn Ala Ser Arg Leu Ser Gln Pro Gly Gln Leu Met
        675                 680                 685

Ser Gln Pro Ser Thr Ala Ser Asn Ser Leu Pro Glu Pro Ala Lys Lys
    690                 695                 700

Ser Glu Glu Leu Val Ala Glu Ala His Asn Leu Cys Thr Leu Leu Glu
705                 710                 715                 720

Asn Ala Ile Gln Asp Thr Val Arg Glu Gln Asp Gln Ser Phe Thr Ala
                725                 730                 735

Leu Asp Trp Ser Trp Leu Gln Thr Glu Glu Glu Glu His Ser Cys Leu
            740                 745                 750

Glu Gln Ala Ser
        755
```

<210> SEQ ID NO 88
<211> LENGTH: 756
<212> TYPE: PRT
<213> ORGANISM: Artificial Sequence
<220> FEATURE:
<223> OTHER INFORMATION: Synthetic: huIKK2null(S177A/S181A); P4006 without epitope tag

<400> SEQUENCE: 88

```
Met Ser Trp Ser Pro Ser Leu Thr Thr Gln Thr Cys Gly Ala Trp Glu
1               5                   10                  15
```

```
Met Lys Glu Arg Leu Gly Thr Gly Gly Phe Gly Asn Val Ile Arg Trp
            20                  25                  30

His Asn Gln Glu Thr Gly Glu Gln Ile Ala Ile Lys Gln Cys Arg Gln
        35                  40                  45

Glu Leu Ser Pro Arg Asn Arg Glu Arg Trp Cys Leu Glu Ile Gln Ile
    50                  55                  60

Met Arg Arg Leu Thr His Pro Asn Val Val Ala Ala Arg Asp Val Pro
65                  70                  75                  80

Glu Gly Met Gln Asn Leu Ala Pro Asn Asp Leu Pro Leu Leu Ala Met
                85                  90                  95

Glu Tyr Cys Gln Gly Gly Asp Leu Arg Lys Tyr Leu Asn Gln Phe Glu
            100                 105                 110

Asn Cys Cys Gly Leu Arg Glu Gly Ala Ile Leu Thr Leu Leu Ser Asp
        115                 120                 125

Ile Ala Ser Ala Leu Arg Tyr Leu His Glu Asn Arg Ile Ile His Arg
    130                 135                 140

Asp Leu Lys Pro Glu Asn Ile Val Leu Gln Gln Gly Glu Gln Arg Leu
145                 150                 155                 160

Ile His Lys Ile Ile Asp Leu Gly Tyr Ala Lys Glu Leu Asp Gln Gly
                165                 170                 175

Ala Leu Cys Thr Ala Phe Val Gly Thr Leu Gln Tyr Leu Ala Pro Glu
            180                 185                 190

Leu Leu Glu Gln Gln Lys Tyr Thr Val Thr Val Asp Tyr Trp Ser Phe
        195                 200                 205

Gly Thr Leu Ala Phe Glu Cys Ile Thr Gly Phe Arg Pro Phe Leu Pro
    210                 215                 220

Asn Trp Gln Pro Val Gln Trp His Ser Lys Val Arg Gln Lys Ser Glu
225                 230                 235                 240

Val Asp Ile Val Val Ser Glu Asp Leu Asn Gly Thr Val Lys Phe Ser
                245                 250                 255

Ser Ser Leu Pro Tyr Pro Asn Asn Leu Asn Ser Val Leu Ala Glu Arg
            260                 265                 270

Leu Glu Lys Trp Leu Gln Leu Met Leu Met Trp His Pro Arg Gln Arg
        275                 280                 285

Gly Thr Asp Pro Thr Tyr Gly Pro Asn Gly Cys Phe Lys Ala Leu Asp
    290                 295                 300

Asp Ile Leu Asn Leu Lys Leu Val His Ile Leu Asn Met Val Thr Gly
305                 310                 315                 320

Thr Ile His Thr Tyr Pro Val Thr Glu Asp Glu Ser Leu Gln Ser Leu
                325                 330                 335

Lys Ala Arg Ile Gln Gln Asp Thr Gly Ile Pro Glu Glu Asp Gln Glu
            340                 345                 350

Leu Leu Gln Glu Ala Gly Leu Ala Leu Ile Pro Asp Lys Pro Ala Thr
        355                 360                 365

Gln Cys Ile Ser Asp Gly Lys Leu Asn Glu Gly His Thr Leu Asp Met
    370                 375                 380

Asp Leu Val Phe Leu Phe Asp Asn Ser Lys Ile Thr Tyr Glu Thr Gln
385                 390                 395                 400

Ile Ser Pro Arg Pro Gln Pro Glu Ser Val Ser Cys Ile Leu Gln Glu
                405                 410                 415

Pro Lys Arg Asn Leu Ala Phe Phe Gln Leu Arg Lys Val Trp Gly Gln
            420                 425                 430
```

```
Val Trp His Ser Ile Gln Thr Leu Lys Glu Asp Cys Asn Arg Leu Gln
        435                 440                 445

Gln Gly Gln Arg Ala Ala Met Met Asn Leu Leu Arg Asn Asn Ser Cys
    450                 455                 460

Leu Ser Lys Met Lys Asn Ser Met Ala Ser Met Ser Gln Gln Leu Lys
465                 470                 475                 480

Ala Lys Leu Asp Phe Phe Lys Thr Ser Ile Gln Ile Asp Leu Glu Lys
                485                 490                 495

Tyr Ser Glu Gln Thr Glu Phe Gly Ile Thr Ser Asp Lys Leu Leu Leu
            500                 505                 510

Ala Trp Arg Glu Met Glu Gln Ala Val Glu Leu Cys Gly Arg Glu Asn
        515                 520                 525

Glu Val Lys Leu Leu Val Glu Arg Met Met Ala Leu Gln Thr Asp Ile
    530                 535                 540

Val Asp Leu Gln Arg Ser Pro Met Gly Arg Lys Gln Gly Gly Thr Leu
545                 550                 555                 560

Asp Asp Leu Glu Glu Gln Ala Arg Glu Leu Tyr Arg Arg Leu Arg Glu
                565                 570                 575

Lys Pro Arg Asp Gln Arg Thr Glu Gly Asp Ser Gln Glu Met Val Arg
            580                 585                 590

Leu Leu Leu Gln Ala Ile Gln Ser Phe Glu Lys Lys Val Arg Val Ile
        595                 600                 605

Tyr Thr Gln Leu Ser Lys Thr Val Val Cys Lys Gln Lys Ala Leu Glu
    610                 615                 620

Leu Leu Pro Lys Val Glu Glu Val Val Ser Leu Met Asn Glu Asp Glu
625                 630                 635                 640

Lys Thr Val Val Arg Leu Gln Glu Lys Arg Gln Lys Glu Leu Trp Asn
                645                 650                 655

Leu Leu Lys Ile Ala Cys Ser Lys Val Arg Gly Pro Val Ser Gly Ser
            660                 665                 670

Pro Asp Ser Met Asn Ala Ser Arg Leu Ser Gln Pro Gly Gln Leu Met
        675                 680                 685

Ser Gln Pro Ser Thr Ala Ser Asn Ser Leu Pro Glu Pro Ala Lys Lys
    690                 695                 700

Ser Glu Glu Leu Val Ala Glu Ala His Asn Leu Cys Thr Leu Leu Glu
705                 710                 715                 720

Asn Ala Ile Gln Asp Thr Val Arg Glu Gln Asp Gln Ser Phe Thr Ala
                725                 730                 735

Leu Asp Trp Ser Trp Leu Gln Thr Glu Glu Glu Glu His Ser Cys Leu
            740                 745                 750

Glu Gln Ala Ser
        755
```

```
<210> SEQ ID NO 89
<211> LENGTH: 757
<212> TYPE: PRT
<213> ORGANISM: Artificial Sequence
<220> FEATURE:
<223> OTHER INFORMATION: Synthetic: muIKK2ca(S177E/S181E); P4002 without
      epitope tag

<400> SEQUENCE: 89

Met Ser Trp Ser Pro Ser Leu Pro Thr Gln Thr Cys Gly Ala Trp Glu
1               5                   10                  15

Met Lys Glu Arg Leu Gly Thr Gly Gly Phe Gly Asn Val Ile Arg Trp
            20                  25                  30
```

```
His Asn Gln Ala Thr Gly Glu Gln Ile Ala Ile Lys Gln Cys Arg Gln
        35                  40                  45

Glu Leu Ser Pro Lys Asn Arg Asn Arg Trp Cys Leu Glu Ile Gln Ile
    50                  55                  60

Met Arg Arg Leu Asn His Pro Asn Val Val Ala Ala Arg Asp Val Pro
65                  70                  75                  80

Glu Gly Met Gln Asn Leu Ala Pro Asn Asp Leu Pro Leu Leu Ala Met
                85                  90                  95

Glu Tyr Cys Gln Gly Gly Asp Leu Arg Arg Tyr Leu Asn Gln Phe Glu
            100                 105                 110

Asn Cys Cys Gly Leu Arg Glu Gly Ala Val Leu Thr Leu Leu Ser Asp
        115                 120                 125

Ile Ala Ser Ala Leu Arg Tyr Leu His Glu Asn Arg Ile Ile His Arg
    130                 135                 140

Asp Leu Lys Pro Glu Asn Ile Val Leu Gln Gln Gly Glu Lys Arg Leu
145                 150                 155                 160

Ile His Lys Ile Ile Asp Leu Gly Tyr Ala Lys Glu Leu Asp Gln Gly
                165                 170                 175

Glu Leu Cys Thr Glu Phe Val Gly Thr Leu Gln Tyr Leu Ala Pro Glu
            180                 185                 190

Leu Leu Glu Gln Gln Lys Tyr Thr Val Thr Val Asp Tyr Trp Ser Phe
        195                 200                 205

Gly Thr Leu Ala Phe Glu Cys Ile Thr Gly Phe Arg Pro Phe Leu Pro
    210                 215                 220

Asn Trp Gln Pro Val Gln Trp His Ser Lys Val Arg Gln Lys Ser Glu
225                 230                 235                 240

Val Asp Ile Val Val Ser Glu Asp Leu Asn Gly Ala Val Lys Phe Ser
                245                 250                 255

Ser Ser Leu Pro Phe Pro Asn Asn Leu Asn Ser Val Leu Ala Glu Arg
            260                 265                 270

Leu Glu Lys Trp Leu Gln Leu Met Leu Met Trp His Pro Arg Gln Arg
        275                 280                 285

Gly Thr Asp Pro Gln Tyr Gly Pro Asn Gly Cys Phe Arg Ala Leu Asp
    290                 295                 300

Asp Ile Leu Asn Leu Lys Leu Val His Val Leu Asn Met Val Thr Gly
305                 310                 315                 320

Thr Val His Thr Tyr Pro Val Thr Glu Asp Glu Ser Leu Gln Ser Leu
                325                 330                 335

Lys Thr Arg Ile Gln Glu Asn Thr Gly Ile Leu Glu Thr Asp Gln Glu
            340                 345                 350

Leu Leu Gln Lys Ala Gly Leu Val Leu Leu Pro Asp Lys Pro Ala Thr
        355                 360                 365

Gln Cys Ile Ser Asp Ser Lys Thr Asn Glu Gly Leu Thr Leu Asp Met
    370                 375                 380

Asp Leu Val Phe Leu Leu Asp Asn Ser Lys Ile Asn Tyr Glu Thr Gln
385                 390                 395                 400

Ile Thr Pro Arg Pro Pro Pro Glu Ser Val Ser Cys Ile Leu Gln Glu
                405                 410                 415

Pro Lys Arg Asn Leu Ser Phe Phe Gln Leu Arg Lys Val Trp Gly Gln
            420                 425                 430

Val Trp His Ser Ile Gln Thr Leu Lys Glu Asp Cys Asn Arg Leu Gln
        435                 440                 445
```

```
Gln Gly Gln Arg Ala Ala Met Met Ser Leu Leu Arg Asn Asn Ser Cys
    450                 455                 460

Leu Ser Lys Met Lys Asn Ala Met Ala Ser Thr Ala Gln Gln Leu Lys
465                 470                 475                 480

Ala Lys Leu Asp Phe Phe Lys Thr Ser Ile Gln Ile Asp Leu Glu Lys
                485                 490                 495

Tyr Lys Glu Gln Thr Glu Phe Gly Ile Thr Ser Asp Lys Leu Leu Leu
            500                 505                 510

Ala Trp Arg Glu Met Glu Gln Ala Val Glu Gln Cys Gly Arg Glu Asn
        515                 520                 525

Asp Val Lys His Leu Val Glu Arg Met Met Ala Leu Gln Thr Asp Ile
    530                 535                 540

Val Asp Leu Gln Arg Ser Pro Met Gly Arg Lys Gln Gly Gly Thr Leu
545                 550                 555                 560

Asp Asp Leu Glu Glu Gln Ala Arg Glu Leu Tyr Arg Lys Leu Arg Glu
                565                 570                 575

Lys Pro Arg Asp Gln Arg Thr Glu Gly Asp Ser Gln Glu Met Val Arg
            580                 585                 590

Leu Leu Leu Gln Ala Ile Gln Ser Phe Glu Lys Lys Val Arg Val Ile
        595                 600                 605

Tyr Thr Gln Leu Ser Lys Thr Val Val Cys Lys Gln Lys Ala Leu Glu
    610                 615                 620

Leu Leu Pro Lys Val Glu Glu Val Val Ser Leu Met Asn Glu Asp Glu
625                 630                 635                 640

Arg Thr Val Val Arg Leu Gln Glu Lys Arg Gln Lys Glu Leu Trp Asn
                645                 650                 655

Leu Leu Lys Ile Ala Cys Ser Lys Val Arg Gly Pro Val Ser Gly Ser
            660                 665                 670

Pro Asp Ser Met Asn Val Ser Arg Leu Ser His Pro Gly Gln Leu Met
        675                 680                 685

Ser Gln Pro Ser Ser Ala Cys Asp Ser Leu Pro Glu Ser Asp Lys Lys
    690                 695                 700

Ser Glu Glu Leu Val Ala Glu Ala His Ala Leu Cys Ser Arg Leu Glu
705                 710                 715                 720

Ser Ala Leu Gln Asp Thr Val Lys Glu Gln Asp Arg Ser Phe Thr Thr
                725                 730                 735

Leu Asp Trp Ser Trp Leu Gln Met Glu Asp Glu Glu Arg Cys Ser Leu
            740                 745                 750

Glu Gln Ala Cys Asp
        755
```

<210> SEQ ID NO 90
<211> LENGTH: 757
<212> TYPE: PRT
<213> ORGANISM: Artificial Sequence
<220> FEATURE:
<223> OTHER INFORMATION: Synthetic: muIKK2null(S177A/S181A); P4003 without epitope tag

<400> SEQUENCE: 90

```
Met Ser Trp Ser Pro Ser Leu Pro Thr Gln Thr Cys Gly Ala Trp Glu
1               5                   10                  15

Met Lys Glu Arg Leu Gly Thr Gly Gly Phe Gly Asn Val Ile Arg Trp
            20                  25                  30

His Asn Gln Ala Thr Gly Glu Gln Ile Ala Ile Lys Gln Cys Arg Gln
        35                  40                  45
```

```
Glu Leu Ser Pro Lys Asn Arg Asn Arg Trp Cys Leu Glu Ile Gln Ile
    50                  55                  60

Met Arg Arg Leu Asn His Pro Asn Val Val Ala Ala Arg Asp Val Pro
65                  70                  75                  80

Glu Gly Met Gln Asn Leu Ala Pro Asn Asp Leu Pro Leu Leu Ala Met
                85                  90                  95

Glu Tyr Cys Gln Gly Gly Asp Leu Arg Arg Tyr Leu Asn Gln Phe Glu
            100                 105                 110

Asn Cys Cys Gly Leu Arg Glu Gly Ala Val Leu Thr Leu Leu Ser Asp
        115                 120                 125

Ile Ala Ser Ala Leu Arg Tyr Leu His Glu Asn Arg Ile Ile His Arg
    130                 135                 140

Asp Leu Lys Pro Glu Asn Ile Val Leu Gln Gln Gly Glu Lys Arg Leu
145                 150                 155                 160

Ile His Lys Ile Ile Asp Leu Gly Tyr Ala Lys Glu Leu Asp Gln Gly
                165                 170                 175

Ala Leu Cys Thr Ala Phe Val Gly Thr Leu Gln Tyr Leu Ala Pro Glu
            180                 185                 190

Leu Leu Glu Gln Gln Lys Tyr Thr Val Thr Val Asp Tyr Trp Ser Phe
        195                 200                 205

Gly Thr Leu Ala Phe Glu Cys Ile Thr Gly Phe Arg Pro Phe Leu Pro
    210                 215                 220

Asn Trp Gln Pro Val Gln Trp His Ser Lys Val Arg Gln Lys Ser Glu
225                 230                 235                 240

Val Asp Ile Val Val Ser Glu Asp Leu Asn Gly Ala Val Lys Phe Ser
                245                 250                 255

Ser Ser Leu Pro Phe Pro Asn Asn Leu Asn Ser Val Leu Ala Glu Arg
            260                 265                 270

Leu Glu Lys Trp Leu Gln Leu Met Leu Met Trp His Pro Arg Gln Arg
        275                 280                 285

Gly Thr Asp Pro Gln Tyr Gly Pro Asn Gly Cys Phe Arg Ala Leu Asp
    290                 295                 300

Asp Ile Leu Asn Leu Lys Leu Val His Val Leu Asn Met Val Thr Gly
305                 310                 315                 320

Thr Val His Thr Tyr Pro Val Thr Glu Asp Glu Ser Leu Gln Ser Leu
                325                 330                 335

Lys Thr Arg Ile Gln Glu Asn Thr Gly Ile Leu Glu Thr Asp Gln Glu
            340                 345                 350

Leu Leu Gln Lys Ala Gly Leu Val Leu Leu Pro Asp Lys Pro Ala Thr
        355                 360                 365

Gln Cys Ile Ser Asp Ser Lys Thr Asn Glu Gly Leu Thr Leu Asp Met
    370                 375                 380

Asp Leu Val Phe Leu Leu Asp Asn Ser Lys Ile Asn Tyr Glu Thr Gln
385                 390                 395                 400

Ile Thr Pro Arg Pro Pro Pro Glu Ser Val Ser Cys Ile Leu Gln Glu
                405                 410                 415

Pro Lys Arg Asn Leu Ser Phe Phe Gln Leu Arg Lys Val Trp Gly Gln
            420                 425                 430

Val Trp His Ser Ile Gln Thr Leu Lys Glu Asp Cys Asn Arg Leu Gln
        435                 440                 445

Gln Gly Gln Arg Ala Ala Met Met Ser Leu Leu Arg Asn Asn Ser Cys
    450                 455                 460
```

-continued

```
Leu Ser Lys Met Lys Asn Ala Met Ala Ser Thr Ala Gln Gln Leu Lys
465                 470                 475                 480

Ala Lys Leu Asp Phe Phe Lys Thr Ser Ile Gln Ile Asp Leu Glu Lys
                485                 490                 495

Tyr Lys Glu Gln Thr Glu Phe Gly Ile Thr Ser Asp Lys Leu Leu Leu
            500                 505                 510

Ala Trp Arg Glu Met Glu Gln Ala Val Glu Gln Cys Gly Arg Glu Asn
        515                 520                 525

Asp Val Lys His Leu Val Glu Arg Met Met Ala Leu Gln Thr Asp Ile
    530                 535                 540

Val Asp Leu Gln Arg Ser Pro Met Gly Arg Lys Gln Gly Gly Thr Leu
545                 550                 555                 560

Asp Asp Leu Glu Glu Gln Ala Arg Glu Leu Tyr Arg Lys Leu Arg Glu
                565                 570                 575

Lys Pro Arg Asp Gln Arg Thr Glu Gly Asp Ser Gln Glu Met Val Arg
            580                 585                 590

Leu Leu Leu Gln Ala Ile Gln Ser Phe Glu Lys Lys Val Arg Val Ile
        595                 600                 605

Tyr Thr Gln Leu Ser Lys Thr Val Val Cys Lys Gln Lys Ala Leu Glu
    610                 615                 620

Leu Leu Pro Lys Val Glu Glu Val Val Ser Leu Met Asn Glu Asp Glu
625                 630                 635                 640

Arg Thr Val Val Arg Leu Gln Glu Lys Arg Gln Lys Glu Leu Trp Asn
                645                 650                 655

Leu Leu Lys Ile Ala Cys Ser Lys Val Arg Gly Pro Val Ser Gly Ser
            660                 665                 670

Pro Asp Ser Met Asn Val Ser Arg Leu Ser His Pro Gly Gln Leu Met
        675                 680                 685

Ser Gln Pro Ser Ser Ala Cys Asp Ser Leu Pro Glu Ser Asp Lys Lys
    690                 695                 700

Ser Glu Glu Leu Val Ala Glu Ala His Ala Leu Cys Ser Arg Leu Glu
705                 710                 715                 720

Ser Ala Leu Gln Asp Thr Val Lys Glu Gln Asp Arg Ser Phe Thr Thr
                725                 730                 735

Leu Asp Trp Ser Trp Leu Gln Met Glu Asp Glu Glu Arg Cys Ser Leu
            740                 745                 750

Glu Gln Ala Cys Asp
        755


<210> SEQ ID NO 91
<211> LENGTH: 744
<212> TYPE: PRT
<213> ORGANISM: Homo sapiens
<220> FEATURE:
<221> NAME/KEY: misc_feature
<222> LOCATION: (1)..(744)
<223> OTHER INFORMATION: Human constitutively active IKK alpha (PEST
      mutation) P.4013 without epitope tag

<400> SEQUENCE: 91

Met Glu Arg Pro Pro Gly Leu Arg Pro Gly Ala Gly Gly Pro Trp Glu
1               5                   10                  15

Met Arg Glu Arg Leu Gly Thr Gly Gly Phe Gly Asn Val Cys Leu Tyr
            20                  25                  30

Gln His Arg Glu Leu Asp Leu Lys Ile Ala Ile Lys Ser Cys Arg Leu
        35                  40                  45
```

```
Glu Leu Ser Thr Lys Asn Arg Glu Arg Trp Cys His Glu Ile Gln Ile
    50                  55                  60

Met Lys Lys Leu Asn His Ala Asn Val Val Lys Ala Cys Asp Val Pro
65                  70                  75                  80

Glu Glu Leu Asn Ile Leu Ile His Asp Val Pro Leu Leu Ala Met Glu
                85                  90                  95

Tyr Cys Ser Gly Gly Asp Leu Arg Lys Leu Leu Asn Lys Pro Glu Asn
            100                 105                 110

Cys Cys Gly Leu Lys Glu Ser Gln Ile Leu Ser Leu Leu Ser Asp Ile
        115                 120                 125

Gly Ser Gly Ile Arg Tyr Leu His Glu Asn Lys Ile Ile His Arg Asp
    130                 135                 140

Leu Lys Pro Glu Asn Ile Val Leu Gln Asp Val Gly Gly Lys Ile Ile
145                 150                 155                 160

His Lys Ile Ile Asp Leu Gly Tyr Ala Lys Asp Val Asp Gln Gly Glu
                165                 170                 175

Leu Cys Thr Glu Phe Val Gly Thr Leu Gln Tyr Leu Ala Pro Glu Leu
            180                 185                 190

Phe Glu Asn Lys Pro Tyr Thr Ala Thr Val Asp Tyr Trp Ser Phe Gly
        195                 200                 205

Thr Met Val Phe Glu Cys Ile Ala Gly Tyr Arg Pro Phe Leu His His
    210                 215                 220

Leu Gln Pro Phe Thr Trp His Glu Lys Ile Lys Lys Lys Asp Pro Lys
225                 230                 235                 240

Cys Ile Phe Ala Cys Glu Glu Met Ser Gly Glu Val Arg Phe Ser Ser
                245                 250                 255

His Leu Pro Gln Pro Asn Ser Leu Cys Ser Leu Val Val Glu Pro Met
            260                 265                 270

Glu Asn Trp Leu Gln Leu Met Leu Asn Trp Asp Pro Gln Gln Arg Gly
        275                 280                 285

Gly Pro Val Asp Leu Thr Leu Lys Gln Pro Arg Cys Phe Val Leu Met
    290                 295                 300

Asp His Ile Leu Asn Leu Lys Ile Val His Ile Leu Asn Met Thr Ser
305                 310                 315                 320

Ala Lys Ile Ile Ser Phe Leu Leu Pro Pro Asp Glu Ser Leu His Ser
                325                 330                 335

Leu Gln Ser Arg Ile Glu Arg Glu Thr Gly Ile Asn Thr Gly Ser Gln
            340                 345                 350

Glu Leu Leu Ser Glu Thr Gly Ile Ser Leu Asp Pro Arg Lys Pro Ala
        355                 360                 365

Ser Gln Cys Val Leu Asp Gly Val Arg Gly Cys Asp Ser Tyr Met Val
    370                 375                 380

Tyr Leu Phe Asp Lys Ser Lys Thr Val Tyr Glu Gly Pro Phe Ala Ser
385                 390                 395                 400

Arg Ser Leu Ser Asp Cys Val Asn Tyr Ile Val Gln Asp Ser Lys Ile
                405                 410                 415

Gln Leu Pro Ile Ile Gln Leu Arg Lys Val Trp Ala Glu Ala Val His
            420                 425                 430

Tyr Val Ser Gly Leu Lys Glu Asp Tyr Ser Arg Leu Phe Gln Gly Gln
        435                 440                 445

Arg Ala Ala Met Leu Ser Leu Leu Arg Tyr Asn Ala Asn Leu Thr Lys
    450                 455                 460

Met Lys Asn Thr Leu Ile Ser Ala Ser Gln Gln Leu Lys Ala Lys Leu
```

```
465                 470                 475                 480

Glu Phe Phe His Lys Ser Ile Gln Leu Asp Leu Glu Arg Tyr Ser Glu
                485                 490                 495

Gln Met Thr Tyr Gly Ile Ser Ser Glu Lys Met Leu Lys Ala Trp Lys
            500                 505                 510

Glu Met Glu Glu Lys Ala Ile His Tyr Ala Glu Val Gly Val Ile Gly
        515                 520                 525

Tyr Leu Glu Asp Gln Ile Met Ser Leu His Ala Glu Ile Met Glu Leu
    530                 535                 540

Gln Lys Ser Pro Tyr Arg Arg Gln Gly Asp Leu Met Glu Ser Leu Glu
545                 550                 555                 560

Gln Arg Ala Ile Asp Leu Tyr Lys Gln Leu Lys His Arg Pro Ser Asp
                565                 570                 575

His Ser Tyr Ser Asp Ser Thr Glu Met Val Lys Ile Ile Val His Thr
            580                 585                 590

Val Gln Ser Gln Asp Arg Val Leu Lys Glu Leu Phe Gly His Leu Ser
        595                 600                 605

Lys Leu Leu Gly Cys Lys Gln Lys Ile Ile Asp Leu Leu Pro Lys Val
    610                 615                 620

Glu Val Ala Leu Ser Asn Ile Lys Glu Ala Asp Asn Thr Val Met Phe
625                 630                 635                 640

Met Gln Gly Lys Arg Gln Lys Glu Ile Trp His Leu Leu Lys Ile Ala
                645                 650                 655

Cys Thr Gln Ala Ala Ala Arg Ala Leu Val Gly Ala Ala Leu Glu Gly
            660                 665                 670

Ala Val Ala Pro Gln Ala Ala Ala Trp Leu Pro Pro Ala Ala Ala Glu
        675                 680                 685

His Asp His Ala Leu Ala Cys Val Val Ala Pro Gln Asp Gly Glu Ala
    690                 695                 700

Ala Ala Gln Met Ile Glu Glu Asn Leu Asn Cys Leu Gly His Leu Ala
705                 710                 715                 720

Ala Ile Ile His Glu Ala Asn Glu Glu Gln Gly Asn Ser Met Met Asn
                725                 730                 735

Leu Asp Trp Ser Trp Leu Thr Glu
            740


<210> SEQ ID NO 92
<211> LENGTH: 744
<212> TYPE: PRT
<213> ORGANISM: Homo sapiens
<220> FEATURE:
<221> NAME/KEY: misc_feature
<222> LOCATION: (1)..(744)
<223> OTHER INFORMATION: Human constitutively active IKK alpha (PEST
      mutation) P.4014 without epitope tag

<400> SEQUENCE: 92

Met Glu Arg Pro Pro Gly Leu Arg Pro Gly Ala Gly Gly Pro Trp Glu
1               5                   10                  15

Met Arg Glu Arg Leu Gly Thr Gly Gly Phe Gly Asn Val Cys Leu Tyr
            20                  25                  30

Gln His Arg Glu Leu Asp Leu Lys Ile Ala Ile Lys Ser Cys Arg Leu
        35                  40                  45

Glu Leu Ser Thr Lys Asn Arg Glu Arg Trp Cys His Glu Ile Gln Ile
    50                  55                  60

Met Lys Lys Leu Asn His Ala Asn Val Val Lys Ala Cys Asp Val Pro
```

```
65                  70                  75                  80

Glu Glu Leu Asn Ile Leu Ile His Asp Val Pro Leu Leu Ala Met Glu
                85                  90                  95

Tyr Cys Ser Gly Gly Asp Leu Arg Lys Leu Leu Asn Lys Pro Glu Asn
            100                 105                 110

Cys Cys Gly Leu Lys Glu Ser Gln Ile Leu Ser Leu Leu Ser Asp Ile
        115                 120                 125

Gly Ser Gly Ile Arg Tyr Leu His Glu Asn Lys Ile Ile His Arg Asp
    130                 135                 140

Leu Lys Pro Glu Asn Ile Val Leu Gln Asp Val Gly Gly Lys Ile Ile
145                 150                 155                 160

His Lys Ile Ile Asp Leu Gly Tyr Ala Lys Asp Val Asp Gln Gly Glu
                165                 170                 175

Leu Cys Thr Glu Phe Val Gly Thr Leu Gln Tyr Leu Ala Pro Glu Leu
            180                 185                 190

Phe Glu Asn Lys Pro Tyr Thr Ala Thr Val Asp Tyr Trp Ser Phe Gly
        195                 200                 205

Thr Met Val Phe Glu Cys Ile Ala Gly Tyr Arg Pro Phe Leu His His
    210                 215                 220

Leu Gln Pro Phe Thr Trp His Glu Lys Ile Lys Lys Lys Asp Pro Lys
225                 230                 235                 240

Cys Ile Phe Ala Cys Glu Glu Met Ser Gly Glu Val Arg Phe Ser Ser
                245                 250                 255

His Leu Pro Gln Pro Asn Ser Leu Cys Ser Leu Val Val Glu Pro Met
            260                 265                 270

Glu Asn Trp Leu Gln Leu Met Leu Asn Trp Asp Pro Gln Gln Arg Gly
        275                 280                 285

Gly Pro Val Asp Leu Thr Leu Lys Gln Pro Arg Cys Phe Val Leu Met
    290                 295                 300

Asp His Ile Leu Asn Leu Lys Ile Val His Ile Leu Asn Met Thr Ser
305                 310                 315                 320

Ala Lys Ile Ile Ser Phe Leu Leu Pro Pro Asp Glu Ser Leu His Ser
                325                 330                 335

Leu Gln Ser Arg Ile Glu Arg Glu Thr Gly Ile Asn Thr Gly Ser Gln
            340                 345                 350

Glu Leu Leu Ser Glu Thr Gly Ile Ser Leu Asp Pro Arg Lys Pro Ala
        355                 360                 365

Ser Gln Cys Val Leu Asp Gly Val Arg Gly Cys Asp Ser Tyr Met Val
    370                 375                 380

Tyr Leu Phe Asp Lys Ser Lys Thr Val Tyr Glu Gly Pro Phe Ala Ser
385                 390                 395                 400

Arg Ser Leu Ser Asp Cys Val Asn Tyr Ile Val Gln Asp Ser Lys Ile
                405                 410                 415

Gln Leu Pro Ile Ile Gln Leu Arg Lys Val Trp Ala Glu Ala Val His
            420                 425                 430

Tyr Val Ser Gly Leu Lys Glu Asp Tyr Ser Arg Leu Phe Gln Gly Gln
        435                 440                 445

Arg Ala Ala Met Leu Ser Leu Leu Arg Tyr Asn Ala Asn Leu Thr Lys
    450                 455                 460

Met Lys Asn Thr Leu Ile Ser Ala Ser Gln Gln Leu Lys Ala Lys Leu
465                 470                 475                 480

Glu Phe Phe His Lys Ser Ile Gln Leu Asp Leu Glu Arg Tyr Ser Glu
                485                 490                 495
```

```
Gln Met Thr Tyr Gly Ile Ser Ser Glu Lys Met Leu Lys Ala Trp Lys
            500                 505                 510

Glu Met Glu Glu Lys Ala Ile His Tyr Ala Glu Val Gly Val Ile Gly
        515                 520                 525

Tyr Leu Glu Asp Gln Ile Met Ser Leu His Ala Glu Ile Met Glu Leu
    530                 535                 540

Gln Lys Ser Pro Tyr Arg Arg Gln Gly Asp Leu Met Glu Ser Leu Glu
545                 550                 555                 560

Gln Arg Ala Ile Asp Leu Tyr Lys Gln Leu Lys His Arg Pro Ser Asp
                565                 570                 575

His Ser Tyr Ser Asp Ser Thr Glu Met Val Lys Ile Ile Val His Thr
            580                 585                 590

Val Gln Ser Gln Asp Arg Val Leu Lys Glu Leu Phe Gly His Leu Ser
        595                 600                 605

Lys Leu Leu Gly Cys Lys Gln Lys Ile Ile Asp Leu Leu Pro Lys Val
    610                 615                 620

Glu Val Ala Leu Ser Asn Ile Lys Glu Ala Asp Asn Thr Val Met Phe
625                 630                 635                 640

Met Gln Gly Lys Arg Gln Lys Glu Ile Trp His Leu Leu Lys Ile Ala
                645                 650                 655

Cys Thr Gln Ala Ala Ala Arg Ala Leu Val Gly Ala Ala Leu Glu Gly
            660                 665                 670

Ala Val Ala Pro Gln Ala Ala Ala Trp Leu Pro Pro Ala Ala Ala Glu
        675                 680                 685

His Asp His Ala Leu Ala Cys Val Val Ala Pro Gln Asp Gly Glu Ala
    690                 695                 700

Ala Ala Gln Met Ile Glu Glu Asn Leu Asn Cys Leu Gly His Leu Ala
705                 710                 715                 720

Ala Ile Ile His Glu Ala Asn Glu Glu Gln Gly Asn Ser Met Met Asn
                725                 730                 735

Leu Asp Trp Ser Trp Leu Thr Glu
            740


<210> SEQ ID NO 93
<211> LENGTH: 756
<212> TYPE: PRT
<213> ORGANISM: Homo sapiens
<220> FEATURE:
<221> NAME/KEY: misc_feature
<222> LOCATION: (1)..(756)
<223> OTHER INFORMATION: Human constitutively active IKK beta (PEST
      mutation) P.4015 without epitope tag

<400> SEQUENCE: 93

Met Ser Trp Ser Pro Ser Leu Thr Thr Gln Thr Cys Gly Ala Trp Glu
1               5                   10                  15

Met Lys Glu Arg Leu Gly Thr Gly Gly Phe Gly Asn Val Ile Arg Trp
            20                  25                  30

His Asn Gln Glu Thr Gly Glu Gln Ile Ala Ile Lys Gln Cys Arg Gln
        35                  40                  45

Glu Leu Ser Pro Arg Asn Arg Glu Arg Trp Cys Leu Glu Ile Gln Ile
    50                  55                  60

Met Arg Arg Leu Thr His Pro Asn Val Val Ala Ala Arg Asp Val Pro
65                  70                  75                  80

Glu Gly Met Gln Asn Leu Ala Pro Asn Asp Leu Pro Leu Leu Ala Met
                85                  90                  95
```

-continued

```
Glu Tyr Cys Gln Gly Gly Asp Leu Arg Lys Tyr Leu Asn Gln Phe Glu
            100                 105                 110

Asn Cys Cys Gly Leu Arg Glu Gly Ala Ile Leu Thr Leu Leu Ser Asp
        115                 120                 125

Ile Ala Ser Ala Leu Arg Tyr Leu His Glu Asn Arg Ile Ile His Arg
    130                 135                 140

Asp Leu Lys Pro Glu Asn Ile Val Leu Gln Gln Gly Glu Gln Arg Leu
145                 150                 155                 160

Ile His Lys Ile Ile Asp Leu Gly Tyr Ala Lys Glu Leu Asp Gln Gly
                165                 170                 175

Glu Leu Cys Thr Glu Phe Val Gly Thr Leu Gln Tyr Leu Ala Pro Glu
            180                 185                 190

Leu Leu Glu Gln Gln Lys Tyr Thr Val Thr Val Asp Tyr Trp Ser Phe
        195                 200                 205

Gly Thr Leu Ala Phe Glu Cys Ile Thr Gly Phe Arg Pro Phe Leu Pro
    210                 215                 220

Asn Trp Gln Pro Val Gln Trp His Ser Lys Val Arg Gln Lys Ser Glu
225                 230                 235                 240

Val Asp Ile Val Val Ser Glu Asp Leu Asn Gly Thr Val Lys Phe Ser
                245                 250                 255

Ser Ser Leu Pro Tyr Pro Asn Asn Leu Asn Ser Val Leu Ala Glu Arg
            260                 265                 270

Leu Glu Lys Trp Leu Gln Leu Met Leu Met Trp His Pro Arg Gln Arg
        275                 280                 285

Gly Thr Asp Pro Thr Tyr Gly Pro Asn Gly Cys Phe Lys Ala Leu Asp
    290                 295                 300

Asp Ile Leu Asn Leu Lys Leu Val His Ile Leu Asn Met Val Thr Gly
305                 310                 315                 320

Thr Ile His Thr Tyr Pro Val Thr Glu Asp Glu Ser Leu Gln Ser Leu
                325                 330                 335

Lys Ala Arg Ile Gln Gln Asp Thr Gly Ile Pro Glu Glu Asp Gln Glu
            340                 345                 350

Leu Leu Gln Glu Ala Gly Leu Ala Leu Ile Pro Asp Lys Pro Ala Thr
        355                 360                 365

Gln Cys Ile Ser Asp Gly Lys Leu Asn Glu Gly His Thr Leu Asp Met
    370                 375                 380

Asp Leu Val Phe Leu Phe Asp Asn Ser Lys Ile Thr Tyr Glu Thr Gln
385                 390                 395                 400

Ile Ser Pro Arg Pro Gln Pro Glu Ser Val Ser Cys Ile Leu Gln Glu
                405                 410                 415

Pro Lys Arg Asn Leu Ala Phe Phe Gln Leu Arg Lys Val Trp Gly Gln
            420                 425                 430

Val Trp His Ser Ile Gln Thr Leu Lys Glu Asp Cys Asn Arg Leu Gln
        435                 440                 445

Gln Gly Gln Arg Ala Ala Met Met Asn Leu Leu Arg Asn Asn Ser Cys
    450                 455                 460

Leu Ser Lys Met Lys Asn Ser Met Ala Ser Met Ser Gln Gln Leu Lys
465                 470                 475                 480

Ala Lys Leu Asp Phe Phe Lys Thr Ser Ile Gln Ile Asp Leu Glu Lys
                485                 490                 495

Tyr Ser Glu Gln Thr Glu Phe Gly Ile Thr Ser Asp Lys Leu Leu Leu
            500                 505                 510
```

```
Ala Trp Arg Glu Met Glu Gln Ala Val Glu Leu Cys Gly Arg Glu Asn
        515                 520                 525

Glu Val Lys Leu Leu Val Glu Arg Met Met Ala Leu Gln Thr Asp Ile
    530                 535                 540

Val Asp Leu Gln Arg Ser Pro Met Gly Arg Lys Gln Gly Gly Thr Leu
545                 550                 555                 560

Asp Asp Leu Glu Glu Gln Ala Arg Glu Leu Tyr Arg Arg Leu Arg Glu
                565                 570                 575

Lys Pro Arg Asp Gln Arg Thr Glu Gly Asp Ser Gln Glu Met Val Arg
            580                 585                 590

Leu Leu Leu Gln Ala Ile Gln Ser Phe Glu Lys Lys Val Arg Val Ile
        595                 600                 605

Tyr Thr Gln Leu Ser Lys Thr Val Val Cys Lys Gln Lys Ala Leu Glu
    610                 615                 620

Leu Leu Pro Lys Val Glu Glu Val Val Ser Leu Met Asn Glu Asp Glu
625                 630                 635                 640

Lys Thr Val Val Arg Leu Gln Glu Lys Arg Gln Lys Glu Leu Trp Asn
                645                 650                 655

Leu Leu Lys Ile Ala Cys Ser Lys Val Arg Gly Pro Val Ala Gly Ala
            660                 665                 670

Pro Asp Ala Met Asn Ala Ala Arg Leu Ala Gln Pro Gly Gln Leu Met
        675                 680                 685

Ala Gln Pro Ala Thr Ala Ala Asn Ala Leu Pro Glu Pro Ala Lys Lys
    690                 695                 700

Ala Glu Glu Leu Val Ala Glu Ala His Asn Leu Cys Thr Leu Leu Glu
705                 710                 715                 720

Asn Ala Ile Gln Asp Thr Val Arg Glu Gln Asp Gln Ser Phe Thr Ala
                725                 730                 735

Leu Asp Trp Ser Trp Leu Gln Thr Glu Glu Glu Glu His Ser Cys Leu
            740                 745                 750

Glu Gln Ala Ser
        755


<210> SEQ ID NO 94
<211> LENGTH: 756
<212> TYPE: PRT
<213> ORGANISM: Homo sapiens
<220> FEATURE:
<221> NAME/KEY: misc_feature
<222> LOCATION: (1)..(756)
<223> OTHER INFORMATION: Human constitutively active IKK beta (PEST
      mutation) P.4016 without epitope tag

<400> SEQUENCE: 94

Met Ser Trp Ser Pro Ser Leu Thr Thr Gln Thr Cys Gly Ala Trp Glu
1               5                   10                  15

Met Lys Glu Arg Leu Gly Thr Gly Gly Phe Gly Asn Val Ile Arg Trp
            20                  25                  30

His Asn Gln Glu Thr Gly Glu Gln Ile Ala Ile Lys Gln Cys Arg Gln
        35                  40                  45

Glu Leu Ser Pro Arg Asn Arg Glu Arg Trp Cys Leu Glu Ile Gln Ile
    50                  55                  60

Met Arg Arg Leu Thr His Pro Asn Val Val Ala Ala Arg Asp Val Pro
65                  70                  75                  80

Glu Gly Met Gln Asn Leu Ala Pro Asn Asp Leu Pro Leu Leu Ala Met
                85                  90                  95
```

-continued

```
Glu Tyr Cys Gln Gly Gly Asp Leu Arg Lys Tyr Leu Asn Gln Phe Glu
            100                 105                 110

Asn Cys Cys Gly Leu Arg Glu Gly Ala Ile Leu Thr Leu Leu Ser Asp
        115                 120                 125

Ile Ala Ser Ala Leu Arg Tyr Leu His Glu Asn Arg Ile Ile His Arg
    130                 135                 140

Asp Leu Lys Pro Glu Asn Ile Val Leu Gln Gln Gly Glu Gln Arg Leu
145                 150                 155                 160

Ile His Lys Ile Ile Asp Leu Gly Tyr Ala Lys Glu Leu Asp Gln Gly
                165                 170                 175

Glu Leu Cys Thr Glu Phe Val Gly Thr Leu Gln Tyr Leu Ala Pro Glu
            180                 185                 190

Leu Leu Glu Gln Gln Lys Tyr Thr Val Thr Val Asp Tyr Trp Ser Phe
        195                 200                 205

Gly Thr Leu Ala Phe Glu Cys Ile Thr Gly Phe Arg Pro Phe Leu Pro
    210                 215                 220

Asn Trp Gln Pro Val Gln Trp His Ser Lys Val Arg Gln Lys Ser Glu
225                 230                 235                 240

Val Asp Ile Val Val Ser Glu Asp Leu Asn Gly Thr Val Lys Phe Ser
                245                 250                 255

Ser Ser Leu Pro Tyr Pro Asn Asn Leu Asn Ser Val Leu Ala Glu Arg
            260                 265                 270

Leu Glu Lys Trp Leu Gln Leu Met Leu Met Trp His Pro Arg Gln Arg
        275                 280                 285

Gly Thr Asp Pro Thr Tyr Gly Pro Asn Gly Cys Phe Lys Ala Leu Asp
    290                 295                 300

Asp Ile Leu Asn Leu Lys Leu Val His Ile Leu Asn Met Val Thr Gly
305                 310                 315                 320

Thr Ile His Thr Tyr Pro Val Thr Glu Asp Glu Ser Leu Gln Ser Leu
                325                 330                 335

Lys Ala Arg Ile Gln Gln Asp Thr Gly Ile Pro Glu Glu Asp Gln Glu
            340                 345                 350

Leu Leu Gln Glu Ala Gly Leu Ala Leu Ile Pro Asp Lys Pro Ala Thr
        355                 360                 365

Gln Cys Ile Ser Asp Gly Lys Leu Asn Glu Gly His Thr Leu Asp Met
    370                 375                 380

Asp Leu Val Phe Leu Phe Asp Asn Ser Lys Ile Thr Tyr Glu Thr Gln
385                 390                 395                 400

Ile Ser Pro Arg Pro Gln Pro Glu Ser Val Ser Cys Ile Leu Gln Glu
                405                 410                 415

Pro Lys Arg Asn Leu Ala Phe Phe Gln Leu Arg Lys Val Trp Gly Gln
            420                 425                 430

Val Trp His Ser Ile Gln Thr Leu Lys Glu Asp Cys Asn Arg Leu Gln
        435                 440                 445

Gln Gly Gln Arg Ala Ala Met Met Asn Leu Leu Arg Asn Asn Ser Cys
    450                 455                 460

Leu Ser Lys Met Lys Asn Ser Met Ala Ser Met Ser Gln Gln Leu Lys
465                 470                 475                 480

Ala Lys Leu Asp Phe Phe Lys Thr Ser Ile Gln Ile Asp Leu Glu Lys
                485                 490                 495

Tyr Ser Glu Gln Thr Glu Phe Gly Ile Thr Ser Asp Lys Leu Leu Leu
            500                 505                 510

Ala Trp Arg Glu Met Glu Gln Ala Val Glu Leu Cys Gly Arg Glu Asn
```

```
        515                 520                 525

Glu Val Lys Leu Leu Val Glu Arg Met Met Ala Leu Gln Thr Asp Ile
    530                 535                 540

Val Asp Leu Gln Arg Ser Pro Met Gly Arg Lys Gln Gly Gly Thr Leu
545                 550                 555                 560

Asp Asp Leu Glu Glu Gln Ala Arg Glu Leu Tyr Arg Arg Leu Arg Glu
                565                 570                 575

Lys Pro Arg Asp Gln Arg Thr Glu Gly Asp Ser Gln Glu Met Val Arg
            580                 585                 590

Leu Leu Leu Gln Ala Ile Gln Ser Phe Glu Lys Lys Val Arg Val Ile
        595                 600                 605

Tyr Thr Gln Leu Ser Lys Thr Val Val Cys Lys Gln Lys Ala Leu Glu
    610                 615                 620

Leu Leu Pro Lys Val Glu Glu Val Val Ser Leu Met Asn Glu Asp Glu
625                 630                 635                 640

Lys Thr Val Val Arg Leu Gln Glu Lys Arg Gln Lys Glu Leu Trp Asn
                645                 650                 655

Leu Leu Lys Ile Ala Cys Ser Lys Val Arg Gly Pro Val Ala Gly Ala
            660                 665                 670

Pro Asp Ala Met Asn Ala Ala Arg Leu Ala Gln Pro Gly Gln Leu Met
        675                 680                 685

Ala Gln Pro Ala Thr Ala Ala Asn Ala Leu Pro Glu Pro Ala Lys Lys
    690                 695                 700

Ala Glu Glu Leu Val Ala Glu Ala His Asn Leu Cys Thr Leu Leu Glu
705                 710                 715                 720

Asn Ala Ile Gln Asp Thr Val Arg Glu Gln Asp Gln Ser Phe Thr Ala
                725                 730                 735

Leu Asp Trp Ser Trp Leu Gln Thr Glu Glu Glu Glu His Ser Cys Leu
            740                 745                 750

Glu Gln Ala Ser
        755


<210> SEQ ID NO 95
<211> LENGTH: 745
<212> TYPE: PRT
<213> ORGANISM: Mus musculus
<220> FEATURE:
<221> NAME/KEY: misc_feature
<222> LOCATION: (1)..(745)
<223> OTHER INFORMATION: Mouse constitutively active IKK alpha (PEST
      mutation) P.4017 without epitope tag

<400> SEQUENCE: 95

Met Glu Arg Pro Pro Gly Leu Arg Pro Gly Ala Gly Gly Pro Trp Glu
1               5                   10                  15

Met Arg Glu Arg Leu Gly Thr Gly Gly Phe Gly Asn Val Ser Leu Tyr
            20                  25                  30

Gln His Arg Glu Leu Asp Leu Lys Ile Ala Ile Lys Ser Cys Arg Leu
        35                  40                  45

Glu Leu Ser Ser Lys Asn Arg Glu Arg Trp Cys His Glu Ile Gln Ile
    50                  55                  60

Met Lys Lys Leu Asp His Ala Asn Val Val Lys Ala Cys Asp Val Pro
65                  70                  75                  80

Glu Glu Leu Asn Phe Leu Ile Asn Asp Val Pro Leu Leu Ala Met Glu
                85                  90                  95

Tyr Cys Ser Gly Gly Asp Leu Arg Lys Leu Leu Asn Lys Pro Glu Asn
```

-continued

```
            100                 105                 110

Cys Cys Gly Leu Lys Glu Ser Gln Ile Leu Ser Leu Leu Ser Asp Ile
        115                 120                 125

Gly Ser Gly Ile Arg Tyr Leu His Glu Asn Lys Ile Ile His Arg Asp
    130                 135                 140

Leu Lys Pro Glu Asn Ile Val Leu Gln Asp Val Gly Gly Lys Thr Ile
145                 150                 155                 160

His Lys Ile Ile Asp Leu Gly Tyr Ala Lys Asp Val Asp Gln Gly Glu
                165                 170                 175

Leu Cys Thr Glu Phe Val Gly Thr Leu Gln Tyr Leu Ala Pro Glu Leu
            180                 185                 190

Phe Glu Asn Lys Pro Tyr Thr Ala Thr Val Asp Tyr Trp Ser Phe Gly
        195                 200                 205

Thr Met Val Phe Glu Cys Ile Ala Gly Tyr Arg Pro Phe Leu His His
    210                 215                 220

Leu Gln Pro Phe Thr Trp His Glu Lys Ile Lys Lys Lys Asp Pro Lys
225                 230                 235                 240

Cys Ile Phe Ala Cys Glu Glu Met Thr Gly Glu Val Arg Phe Ser Ser
                245                 250                 255

His Leu Pro Gln Pro Asn Ser Leu Cys Ser Leu Ile Val Glu Pro Met
            260                 265                 270

Glu Ser Trp Leu Gln Leu Met Leu Asn Trp Asp Pro Gln Gln Arg Gly
        275                 280                 285

Gly Pro Ile Asp Leu Thr Leu Lys Gln Pro Arg Cys Phe Ala Leu Met
    290                 295                 300

Asp His Ile Leu Asn Leu Lys Ile Val His Ile Leu Asn Met Thr Ser
305                 310                 315                 320

Ala Lys Ile Ile Ser Phe Leu Leu Pro Cys Asp Glu Ser Leu His Ser
                325                 330                 335

Leu Gln Ser Arg Ile Glu Arg Glu Thr Gly Ile Asn Thr Gly Ser Gln
            340                 345                 350

Glu Leu Leu Ser Glu Thr Gly Ile Ser Leu Asp Pro Arg Lys Pro Ala
        355                 360                 365

Ser Gln Cys Val Leu Asp Gly Val Arg Gly Cys Asp Ser Tyr Met Val
    370                 375                 380

Tyr Leu Phe Asp Lys Ser Lys Thr Val Tyr Glu Gly Pro Phe Ala Ser
385                 390                 395                 400

Arg Ser Leu Ser Asp Cys Val Asn Tyr Ile Val Gln Asp Ser Lys Ile
                405                 410                 415

Gln Leu Pro Ile Ile Gln Leu Arg Lys Val Trp Ala Glu Ala Val His
            420                 425                 430

Tyr Val Ser Gly Leu Lys Glu Asp Tyr Ser Arg Leu Phe Gln Gly Gln
        435                 440                 445

Arg Ala Ala Met Leu Ser Leu Leu Arg Tyr Asn Ala Asn Leu Thr Lys
    450                 455                 460

Met Lys Asn Thr Leu Ile Ser Ala Ser Gln Gln Leu Lys Ala Lys Leu
465                 470                 475                 480

Glu Phe Phe Arg Lys Ser Ile Gln Leu Asp Leu Glu Arg Tyr Ser Glu
                485                 490                 495

Gln Met Thr Tyr Gly Ile Ser Ser Glu Lys Met Leu Lys Ala Trp Lys
            500                 505                 510

Glu Met Glu Glu Lys Ala Ile His Tyr Ser Glu Val Gly Val Ile Gly
        515                 520                 525
```

Tyr Leu Glu Asp Gln Ile Met Ser Leu His Thr Glu Ile Met Glu Leu
    530                 535                 540

Gln Lys Ser Pro Tyr Gly Arg Arg Gln Gly Asp Leu Met Glu Ser Leu
545                 550                 555                 560

Glu Gln Arg Ala Ile Asp Leu Tyr Lys Gln Leu Lys His Arg Pro Pro
                565                 570                 575

Asp His Leu Tyr Ser Asp Ser Thr Glu Met Val Lys Ile Ile Val His
            580                 585                 590

Thr Val Gln Ser Gln Asp Arg Val Leu Lys Glu Leu Phe Gly His Leu
        595                 600                 605

Ser Lys Leu Leu Gly Cys Lys Gln Lys Ile Ile Asp Leu Leu Pro Lys
    610                 615                 620

Val Glu Val Ala Leu Ser Asn Ile Lys Glu Ala Asp Asn Thr Val Met
625                 630                 635                 640

Phe Met Gln Gly Lys Arg Gln Lys Glu Ile Trp His Leu Leu Lys Ile
                645                 650                 655

Ala Cys Thr Gln Ala Ala Ala Arg Ala Leu Val Gly Ala Ala Leu Glu
            660                 665                 670

Gly Ala Val Ala Pro Pro Val Ala Ala Trp Leu Pro Pro Ala Leu Ala
        675                 680                 685

Asp Arg Glu His Pro Leu Thr Cys Val Val Ala Pro Gln Asp Gly Glu
    690                 695                 700

Ala Leu Ala Gln Met Ile Glu Glu Asn Leu Asn Cys Leu Gly His Leu
705                 710                 715                 720

Ala Ala Ile Ile Arg Glu Ala Asn Glu Asp Gln Ser Ser Ser Leu Met
                725                 730                 735

Ser Leu Asp Trp Ser Trp Leu Ala Glu
            740                 745

<210> SEQ ID NO 96
<211> LENGTH: 745
<212> TYPE: PRT
<213> ORGANISM: Mus musculus
<220> FEATURE:
<221> NAME/KEY: misc_feature
<222> LOCATION: (1)..(745)
<223> OTHER INFORMATION: Mouse constitutively active IKK alpha (PEST
      mutation) P.4018 without epitope tag

<400> SEQUENCE: 96

Met Glu Arg Pro Pro Gly Leu Arg Pro Gly Ala Gly Gly Pro Trp Glu
1               5                   10                  15

Met Arg Glu Arg Leu Gly Thr Gly Gly Phe Gly Asn Val Ser Leu Tyr
            20                  25                  30

Gln His Arg Glu Leu Asp Leu Lys Ile Ala Ile Lys Ser Cys Arg Leu
        35                  40                  45

Glu Leu Ser Ser Lys Asn Arg Glu Arg Trp Cys His Glu Ile Gln Ile
    50                  55                  60

Met Lys Lys Leu Asp His Ala Asn Val Val Lys Ala Cys Asp Val Pro
65                  70                  75                  80

Glu Glu Leu Asn Phe Leu Ile Asn Asp Val Pro Leu Leu Ala Met Glu
                85                  90                  95

Tyr Cys Ser Gly Gly Asp Leu Arg Lys Leu Leu Asn Lys Pro Glu Asn
            100                 105                 110

Cys Cys Gly Leu Lys Glu Ser Gln Ile Leu Ser Leu Leu Ser Asp Ile
        115                 120                 125

-continued

```
Gly Ser Gly Ile Arg Tyr Leu His Glu Asn Lys Ile Ile His Arg Asp
    130                 135                 140

Leu Lys Pro Glu Asn Ile Val Leu Gln Asp Val Gly Gly Lys Thr Ile
145                 150                 155                 160

His Lys Ile Ile Asp Leu Gly Tyr Ala Lys Asp Val Asp Gln Gly Glu
                165                 170                 175

Leu Cys Thr Glu Phe Val Gly Thr Leu Gln Tyr Leu Ala Pro Glu Leu
            180                 185                 190

Phe Glu Asn Lys Pro Tyr Thr Ala Thr Val Asp Tyr Trp Ser Phe Gly
        195                 200                 205

Thr Met Val Phe Glu Cys Ile Ala Gly Tyr Arg Pro Phe Leu His His
    210                 215                 220

Leu Gln Pro Phe Thr Trp His Glu Lys Ile Lys Lys Lys Asp Pro Lys
225                 230                 235                 240

Cys Ile Phe Ala Cys Glu Glu Met Thr Gly Glu Val Arg Phe Ser Ser
                245                 250                 255

His Leu Pro Gln Pro Asn Ser Leu Cys Ser Leu Ile Val Glu Pro Met
            260                 265                 270

Glu Ser Trp Leu Gln Leu Met Leu Asn Trp Asp Pro Gln Gln Arg Gly
        275                 280                 285

Gly Pro Ile Asp Leu Thr Leu Lys Gln Pro Arg Cys Phe Ala Leu Met
    290                 295                 300

Asp His Ile Leu Asn Leu Lys Ile Val His Ile Leu Asn Met Thr Ser
305                 310                 315                 320

Ala Lys Ile Ile Ser Phe Leu Leu Pro Cys Asp Glu Ser Leu His Ser
                325                 330                 335

Leu Gln Ser Arg Ile Glu Arg Glu Thr Gly Ile Asn Thr Gly Ser Gln
            340                 345                 350

Glu Leu Leu Ser Glu Thr Gly Ile Ser Leu Asp Pro Arg Lys Pro Ala
        355                 360                 365

Ser Gln Cys Val Leu Asp Gly Val Arg Gly Cys Asp Ser Tyr Met Val
    370                 375                 380

Tyr Leu Phe Asp Lys Ser Lys Thr Val Tyr Glu Gly Pro Phe Ala Ser
385                 390                 395                 400

Arg Ser Leu Ser Asp Cys Val Asn Tyr Ile Val Gln Asp Ser Lys Ile
                405                 410                 415

Gln Leu Pro Ile Ile Gln Leu Arg Lys Val Trp Ala Glu Ala Val His
            420                 425                 430

Tyr Val Ser Gly Leu Lys Glu Asp Tyr Ser Arg Leu Phe Gln Gly Gln
        435                 440                 445

Arg Ala Ala Met Leu Ser Leu Leu Arg Tyr Asn Ala Asn Leu Thr Lys
    450                 455                 460

Met Lys Asn Thr Leu Ile Ser Ala Ser Gln Gln Leu Lys Ala Lys Leu
465                 470                 475                 480

Glu Phe Phe Arg Lys Ser Ile Gln Leu Asp Leu Glu Arg Tyr Ser Glu
                485                 490                 495

Gln Met Thr Tyr Gly Ile Ser Ser Glu Lys Met Leu Lys Ala Trp Lys
            500                 505                 510

Glu Met Glu Glu Lys Ala Ile His Tyr Ser Glu Val Gly Val Ile Gly
        515                 520                 525

Tyr Leu Glu Asp Gln Ile Met Ser Leu His Thr Glu Ile Met Glu Leu
    530                 535                 540
```

```
Gln Lys Ser Pro Tyr Gly Arg Arg Gln Gly Asp Leu Met Glu Ser Leu
545                 550                 555                 560

Glu Gln Arg Ala Ile Asp Leu Tyr Lys Gln Leu Lys His Arg Pro Pro
                565                 570                 575

Asp His Leu Tyr Ser Asp Ser Thr Glu Met Val Lys Ile Ile Val His
            580                 585                 590

Thr Val Gln Ser Gln Asp Arg Val Leu Lys Glu Leu Phe Gly His Leu
        595                 600                 605

Ser Lys Leu Leu Gly Cys Lys Gln Lys Ile Ile Asp Leu Leu Pro Lys
    610                 615                 620

Val Glu Val Ala Leu Ser Asn Ile Lys Glu Ala Asp Asn Thr Val Met
625                 630                 635                 640

Phe Met Gln Gly Lys Arg Gln Lys Glu Ile Trp His Leu Leu Lys Ile
                645                 650                 655

Ala Cys Thr Gln Ala Ala Ala Arg Ala Leu Val Gly Ala Ala Leu Glu
            660                 665                 670

Gly Ala Val Ala Pro Pro Val Ala Ala Trp Leu Pro Pro Ala Leu Ala
        675                 680                 685

Asp Arg Glu His Pro Leu Thr Cys Val Val Ala Pro Gln Asp Gly Glu
    690                 695                 700

Ala Leu Ala Gln Met Ile Glu Glu Asn Leu Asn Cys Leu Gly His Leu
705                 710                 715                 720

Ala Ala Ile Ile Arg Glu Ala Asn Glu Asp Gln Ser Ser Ser Leu Met
                725                 730                 735

Ser Leu Asp Trp Ser Trp Leu Ala Glu
            740                 745


<210> SEQ ID NO 97
<211> LENGTH: 757
<212> TYPE: PRT
<213> ORGANISM: Mus musculus
<220> FEATURE:
<221> NAME/KEY: misc_feature
<222> LOCATION: (1)..(757)
<223> OTHER INFORMATION: Mouse constitutively active IKK beta (PEST
      mutation) P.4019 without epitope tag

<400> SEQUENCE: 97

Met Ser Trp Ser Pro Ser Leu Pro Thr Gln Thr Cys Gly Ala Trp Glu
1               5                   10                  15

Met Lys Glu Arg Leu Gly Thr Gly Gly Phe Gly Asn Val Ile Arg Trp
            20                  25                  30

His Asn Gln Ala Thr Gly Glu Gln Ile Ala Ile Lys Gln Cys Arg Gln
        35                  40                  45

Glu Leu Ser Pro Lys Asn Arg Asn Arg Trp Cys Leu Glu Ile Gln Ile
    50                  55                  60

Met Arg Arg Leu Asn His Pro Asn Val Val Ala Ala Arg Asp Val Pro
65                  70                  75                  80

Glu Gly Met Gln Asn Leu Ala Pro Asn Asp Leu Pro Leu Leu Ala Met
                85                  90                  95

Glu Tyr Cys Gln Gly Gly Asp Leu Arg Arg Tyr Leu Asn Gln Phe Glu
            100                 105                 110

Asn Cys Cys Gly Leu Arg Glu Gly Ala Val Leu Thr Leu Leu Ser Asp
        115                 120                 125

Ile Ala Ser Ala Leu Arg Tyr Leu His Glu Asn Arg Ile Ile His Arg
    130                 135                 140
```

-continued

```
Asp Leu Lys Pro Glu Asn Ile Val Leu Gln Gln Gly Glu Lys Arg Leu
145                 150                 155                 160

Ile His Lys Ile Ile Asp Leu Gly Tyr Ala Lys Glu Leu Asp Gln Gly
                165                 170                 175

Glu Leu Cys Thr Glu Phe Val Gly Thr Leu Gln Tyr Leu Ala Pro Glu
            180                 185                 190

Leu Leu Glu Gln Gln Lys Tyr Thr Val Thr Val Asp Tyr Trp Ser Phe
        195                 200                 205

Gly Thr Leu Ala Phe Glu Cys Ile Thr Gly Phe Arg Pro Phe Leu Pro
    210                 215                 220

Asn Trp Gln Pro Val Gln Trp His Ser Lys Val Arg Gln Lys Ser Glu
225                 230                 235                 240

Val Asp Ile Val Val Ser Glu Asp Leu Asn Gly Ala Val Lys Phe Ser
                245                 250                 255

Ser Ser Leu Pro Phe Pro Asn Asn Leu Asn Ser Val Leu Ala Glu Arg
            260                 265                 270

Leu Glu Lys Trp Leu Gln Leu Met Leu Met Trp His Pro Arg Gln Arg
        275                 280                 285

Gly Thr Asp Pro Gln Tyr Gly Pro Asn Gly Cys Phe Arg Ala Leu Asp
    290                 295                 300

Asp Ile Leu Asn Leu Lys Leu Val His Val Leu Asn Met Val Thr Gly
305                 310                 315                 320

Thr Val His Thr Tyr Pro Val Thr Glu Asp Glu Ser Leu Gln Ser Leu
                325                 330                 335

Lys Thr Arg Ile Gln Glu Asn Thr Gly Ile Leu Glu Thr Asp Gln Glu
            340                 345                 350

Leu Leu Gln Lys Ala Gly Leu Val Leu Leu Pro Asp Lys Pro Ala Thr
        355                 360                 365

Gln Cys Ile Ser Asp Ser Lys Thr Asn Glu Gly Leu Thr Leu Asp Met
    370                 375                 380

Asp Leu Val Phe Leu Leu Asp Asn Ser Lys Ile Asn Tyr Glu Thr Gln
385                 390                 395                 400

Ile Thr Pro Arg Pro Pro Pro Glu Ser Val Ser Cys Ile Leu Gln Glu
                405                 410                 415

Pro Lys Arg Asn Leu Ser Phe Phe Gln Leu Arg Lys Val Trp Gly Gln
            420                 425                 430

Val Trp His Ser Ile Gln Thr Leu Lys Glu Asp Cys Asn Arg Leu Gln
        435                 440                 445

Gln Gly Gln Arg Ala Ala Met Met Ser Leu Leu Arg Asn Asn Ser Cys
    450                 455                 460

Leu Ser Lys Met Lys Asn Ala Met Ala Ser Thr Ala Gln Gln Leu Lys
465                 470                 475                 480

Ala Lys Leu Asp Phe Phe Lys Thr Ser Ile Gln Ile Asp Leu Glu Lys
                485                 490                 495

Tyr Lys Glu Gln Thr Glu Phe Gly Ile Thr Ser Asp Lys Leu Leu Leu
            500                 505                 510

Ala Trp Arg Glu Met Glu Gln Ala Val Glu Gln Cys Gly Arg Glu Asn
        515                 520                 525

Asp Val Lys His Leu Val Glu Arg Met Met Ala Leu Gln Thr Asp Ile
    530                 535                 540

Val Asp Leu Gln Arg Ser Pro Met Gly Arg Lys Gln Gly Gly Thr Leu
545                 550                 555                 560

Asp Asp Leu Glu Glu Gln Ala Arg Glu Leu Tyr Arg Lys Leu Arg Glu
```

```
                565                 570                 575

Lys Pro Arg Asp Gln Arg Thr Glu Gly Asp Ser Gln Glu Met Val Arg
            580                 585                 590

Leu Leu Leu Gln Ala Ile Gln Ser Phe Glu Lys Lys Val Arg Val Ile
        595                 600                 605

Tyr Thr Gln Leu Ser Lys Thr Val Val Cys Lys Gln Lys Ala Leu Glu
    610                 615                 620

Leu Leu Pro Lys Val Glu Glu Val Val Ser Leu Met Asn Glu Asp Glu
625                 630                 635                 640

Arg Thr Val Val Arg Leu Gln Glu Lys Arg Gln Lys Glu Leu Trp Asn
                645                 650                 655

Leu Leu Lys Ile Ala Cys Ser Lys Val Arg Gly Pro Val Ala Gly Ala
            660                 665                 670

Pro Asp Ala Met Asn Val Ala Arg Leu Ala His Pro Gly Gln Leu Met
        675                 680                 685

Ala Gln Pro Ala Ser Ala Cys Asp Ala Leu Pro Glu Ser Asp Lys Lys
    690                 695                 700

Ala Glu Glu Leu Val Ala Glu Ala His Ala Leu Cys Ser Arg Leu Glu
705                 710                 715                 720

Ser Ala Leu Gln Asp Thr Val Lys Glu Gln Asp Arg Ser Phe Thr Thr
                725                 730                 735

Leu Asp Trp Ser Trp Leu Gln Met Glu Asp Glu Glu Arg Cys Ser Leu
            740                 745                 750

Glu Gln Ala Cys Asp
        755


<210> SEQ ID NO 98
<211> LENGTH: 757
<212> TYPE: PRT
<213> ORGANISM: Mus musculus
<220> FEATURE:
<221> NAME/KEY: misc_feature
<222> LOCATION: (1)..(757)
<223> OTHER INFORMATION: Mouse constitutively active IKK beta (PEST
      mutation) P.4020 without epitope tag

<400> SEQUENCE: 98

Met Ser Trp Ser Pro Ser Leu Pro Thr Gln Thr Cys Gly Ala Trp Glu
1               5                   10                  15

Met Lys Glu Arg Leu Gly Thr Gly Gly Phe Gly Asn Val Ile Arg Trp
            20                  25                  30

His Asn Gln Ala Thr Gly Glu Gln Ile Ala Ile Lys Gln Cys Arg Gln
        35                  40                  45

Glu Leu Ser Pro Lys Asn Arg Asn Arg Trp Cys Leu Glu Ile Gln Ile
    50                  55                  60

Met Arg Arg Leu Asn His Pro Asn Val Val Ala Ala Arg Asp Val Pro
65                  70                  75                  80

Glu Gly Met Gln Asn Leu Ala Pro Asn Asp Leu Pro Leu Leu Ala Met
                85                  90                  95

Glu Tyr Cys Gln Gly Gly Asp Leu Arg Arg Tyr Leu Asn Gln Phe Glu
            100                 105                 110

Asn Cys Cys Gly Leu Arg Glu Gly Ala Val Leu Thr Leu Leu Ser Asp
        115                 120                 125

Ile Ala Ser Ala Leu Arg Tyr Leu His Glu Asn Arg Ile Ile His Arg
    130                 135                 140

Asp Leu Lys Pro Glu Asn Ile Val Leu Gln Gln Gly Glu Lys Arg Leu
```

-continued

```
145                 150                 155                 160

Ile His Lys Ile Ile Asp Leu Gly Tyr Ala Lys Glu Leu Asp Gln Gly
                165                 170                 175

Glu Leu Cys Thr Glu Phe Val Gly Thr Leu Gln Tyr Leu Ala Pro Glu
            180                 185                 190

Leu Leu Glu Gln Gln Lys Tyr Thr Val Thr Val Asp Tyr Trp Ser Phe
        195                 200                 205

Gly Thr Leu Ala Phe Glu Cys Ile Thr Gly Phe Arg Pro Phe Leu Pro
    210                 215                 220

Asn Trp Gln Pro Val Gln Trp His Ser Lys Val Arg Gln Lys Ser Glu
225                 230                 235                 240

Val Asp Ile Val Val Ser Glu Asp Leu Asn Gly Ala Val Lys Phe Ser
                245                 250                 255

Ser Ser Leu Pro Phe Pro Asn Asn Leu Asn Ser Val Leu Ala Glu Arg
            260                 265                 270

Leu Glu Lys Trp Leu Gln Leu Met Leu Met Trp His Pro Arg Gln Arg
        275                 280                 285

Gly Thr Asp Pro Gln Tyr Gly Pro Asn Gly Cys Phe Arg Ala Leu Asp
    290                 295                 300

Asp Ile Leu Asn Leu Lys Leu Val His Val Leu Asn Met Val Thr Gly
305                 310                 315                 320

Thr Val His Thr Tyr Pro Val Thr Glu Asp Glu Ser Leu Gln Ser Leu
                325                 330                 335

Lys Thr Arg Ile Gln Glu Asn Thr Gly Ile Leu Glu Thr Asp Gln Glu
            340                 345                 350

Leu Leu Gln Lys Ala Gly Leu Val Leu Leu Pro Asp Lys Pro Ala Thr
        355                 360                 365

Gln Cys Ile Ser Asp Ser Lys Thr Asn Glu Gly Leu Thr Leu Asp Met
    370                 375                 380

Asp Leu Val Phe Leu Leu Asp Asn Ser Lys Ile Asn Tyr Glu Thr Gln
385                 390                 395                 400

Ile Thr Pro Arg Pro Pro Pro Glu Ser Val Ser Cys Ile Leu Gln Glu
                405                 410                 415

Pro Lys Arg Asn Leu Ser Phe Phe Gln Leu Arg Lys Val Trp Gly Gln
            420                 425                 430

Val Trp His Ser Ile Gln Thr Leu Lys Glu Asp Cys Asn Arg Leu Gln
        435                 440                 445

Gln Gly Gln Arg Ala Ala Met Met Ser Leu Leu Arg Asn Asn Ser Cys
    450                 455                 460

Leu Ser Lys Met Lys Asn Ala Met Ala Ser Thr Ala Gln Gln Leu Lys
465                 470                 475                 480

Ala Lys Leu Asp Phe Phe Lys Thr Ser Ile Gln Ile Asp Leu Glu Lys
                485                 490                 495

Tyr Lys Glu Gln Thr Glu Phe Gly Ile Thr Ser Asp Lys Leu Leu Leu
            500                 505                 510

Ala Trp Arg Glu Met Glu Gln Ala Val Glu Gln Cys Gly Arg Glu Asn
        515                 520                 525

Asp Val Lys His Leu Val Glu Arg Met Met Ala Leu Gln Thr Asp Ile
    530                 535                 540

Val Asp Leu Gln Arg Ser Pro Met Gly Arg Lys Gln Gly Gly Thr Leu
545                 550                 555                 560

Asp Asp Leu Glu Glu Gln Ala Arg Glu Leu Tyr Arg Lys Leu Arg Glu
                565                 570                 575
```

Lys Pro Arg Asp Gln Arg Thr Glu Gly Asp Ser Gln Glu Met Val Arg
580 585 590

Leu Leu Leu Gln Ala Ile Gln Ser Phe Glu Lys Lys Val Arg Val Ile
595 600 605

Tyr Thr Gln Leu Ser Lys Thr Val Val Cys Lys Gln Lys Ala Leu Glu
610 615 620

Leu Leu Pro Lys Val Glu Glu Val Val Ser Leu Met Asn Glu Asp Glu
625 630 635 640

Arg Thr Val Val Arg Leu Gln Glu Lys Arg Gln Lys Glu Leu Trp Asn
645 650 655

Leu Leu Lys Ile Ala Cys Ser Lys Val Arg Gly Pro Val Ala Gly Ala
660 665 670

Pro Asp Ala Met Asn Val Ala Arg Leu Ala His Pro Gly Gln Leu Met
675 680 685

Ala Gln Pro Ala Ser Ala Cys Asp Ala Leu Pro Glu Ser Asp Lys Lys
690 695 700

Ala Glu Glu Leu Val Ala Glu Ala His Ala Leu Cys Ser Arg Leu Glu
705 710 715 720

Ser Ala Leu Gln Asp Thr Val Lys Glu Gln Asp Arg Ser Phe Thr Thr
725 730 735

Leu Asp Trp Ser Trp Leu Gln Met Glu Asp Glu Glu Arg Cys Ser Leu
740 745 750

Glu Gln Ala Cys Asp
755

<210> SEQ ID NO 99
<211> LENGTH: 585
<212> TYPE: PRT
<213> ORGANISM: Artificial Sequence
<220> FEATURE:
<223> OTHER INFORMATION: Synthetic: huRIPK1(1-555).IZ.TM; TH1021 without epitope tag

<400> SEQUENCE: 99

Met Gln Pro Asp Met Ser Leu Asn Val Ile Lys Met Lys Ser Ser Asp
1 5 10 15

Phe Leu Glu Ser Ala Glu Leu Asp Ser Gly Gly Phe Gly Lys Val Ser
20 25 30

Leu Cys Phe His Arg Thr Gln Gly Leu Met Ile Met Lys Thr Val Tyr
35 40 45

Lys Gly Pro Asn Cys Ile Glu His Asn Glu Ala Leu Leu Glu Glu Ala
50 55 60

Lys Met Met Asn Arg Leu Arg His Ser Arg Val Val Lys Leu Leu Gly
65 70 75 80

Val Ile Ile Glu Glu Gly Lys Tyr Ser Leu Val Met Glu Tyr Met Glu
85 90 95

Lys Gly Asn Leu Met His Val Leu Lys Ala Glu Met Ser Thr Pro Leu
100 105 110

Ser Val Lys Gly Arg Ile Ile Leu Glu Ile Ile Glu Gly Met Cys Tyr
115 120 125

Leu His Gly Lys Gly Val Ile His Lys Asp Leu Lys Pro Glu Asn Ile
130 135 140

Leu Val Asp Asn Asp Phe His Ile Lys Ile Ala Asp Leu Gly Leu Ala
145 150 155 160

Ser Phe Lys Met Trp Ser Lys Leu Asn Asn Glu Glu His Asn Glu Leu

-continued

```
                165                 170                 175

Arg Glu Val Asp Gly Thr Ala Lys Lys Asn Gly Gly Thr Leu Tyr Tyr
            180                 185                 190

Met Ala Pro Glu His Leu Asn Asp Val Asn Ala Lys Pro Thr Glu Lys
        195                 200                 205

Ser Asp Val Tyr Ser Phe Ala Val Val Leu Trp Ala Ile Phe Ala Asn
    210                 215                 220

Lys Glu Pro Tyr Glu Asn Ala Ile Cys Glu Gln Gln Leu Ile Met Cys
225                 230                 235                 240

Ile Lys Ser Gly Asn Arg Pro Asp Val Asp Asp Ile Thr Glu Tyr Cys
                245                 250                 255

Pro Arg Glu Ile Ile Ser Leu Met Lys Leu Cys Trp Glu Ala Asn Pro
            260                 265                 270

Glu Ala Arg Pro Thr Phe Pro Gly Ile Glu Glu Lys Phe Arg Pro Phe
        275                 280                 285

Tyr Leu Ser Gln Leu Glu Glu Ser Val Glu Glu Asp Val Lys Ser Leu
    290                 295                 300

Lys Lys Glu Tyr Ser Asn Glu Asn Ala Val Val Lys Arg Met Gln Ser
305                 310                 315                 320

Leu Gln Leu Asp Cys Val Ala Val Pro Ser Ser Arg Ser Asn Ser Ala
                325                 330                 335

Thr Glu Gln Pro Gly Ser Leu His Ser Ser Gln Gly Leu Gly Met Gly
            340                 345                 350

Pro Val Glu Glu Ser Trp Phe Ala Pro Ser Leu Glu His Pro Gln Glu
        355                 360                 365

Glu Asn Glu Pro Ser Leu Gln Ser Lys Leu Gln Asp Glu Ala Asn Tyr
    370                 375                 380

His Leu Tyr Gly Ser Arg Met Asp Arg Gln Thr Lys Gln Gln Pro Arg
385                 390                 395                 400

Gln Asn Val Ala Tyr Asn Arg Glu Glu Glu Arg Arg Arg Arg Val Ser
                405                 410                 415

His Asp Pro Phe Ala Gln Gln Arg Pro Tyr Glu Asn Phe Gln Asn Thr
            420                 425                 430

Glu Gly Lys Gly Thr Ala Tyr Ser Ser Ala Ala Ser His Gly Asn Ala
        435                 440                 445

Val His Gln Pro Ser Gly Leu Thr Ser Gln Pro Gln Val Leu Tyr Gln
    450                 455                 460

Asn Asn Gly Leu Tyr Ser Ser His Gly Phe Gly Thr Arg Pro Leu Asp
465                 470                 475                 480

Pro Gly Thr Ala Gly Pro Arg Val Trp Tyr Arg Pro Ile Pro Ser His
                485                 490                 495

Met Pro Ser Leu His Asn Ile Pro Val Pro Glu Thr Asn Tyr Leu Gly
            500                 505                 510

Asn Thr Pro Thr Met Pro Phe Ser Ser Leu Pro Pro Thr Asp Glu Ser
        515                 520                 525

Ile Lys Tyr Thr Ile Tyr Asn Ser Thr Gly Ile Gln Ile Gly Ala Tyr
    530                 535                 540

Asn Tyr Met Glu Ile Gly Gly Thr Ser Ser Ser Gly Gly Ile Lys Lys
545                 550                 555                 560

Glu Ile Glu Ala Ile Lys Lys Glu Gln Glu Ala Ile Lys Lys Lys Ile
                565                 570                 575

Glu Ala Ile Glu Lys Glu Ile Glu Ala
            580                 585
```

<210> SEQ ID NO 100
<211> LENGTH: 609
<212> TYPE: PRT
<213> ORGANISM: Artificial Sequence
<220> FEATURE:
<223> OTHER INFORMATION: Synthetic: huRIPK1(1-555).EE.DM; TH1022 without
      epitope tag

<400> SEQUENCE: 100

```
Met Gln Pro Asp Met Ser Leu Asn Val Ile Lys Met Lys Ser Ser Asp
1               5                   10                  15

Phe Leu Glu Ser Ala Glu Leu Asp Ser Gly Gly Phe Gly Lys Val Ser
            20                  25                  30

Leu Cys Phe His Arg Thr Gln Gly Leu Met Ile Met Lys Thr Val Tyr
        35                  40                  45

Lys Gly Pro Asn Cys Ile Glu His Asn Glu Ala Leu Leu Glu Glu Ala
    50                  55                  60

Lys Met Met Asn Arg Leu Arg His Ser Arg Val Val Lys Leu Leu Gly
65                  70                  75                  80

Val Ile Ile Glu Glu Gly Lys Tyr Ser Leu Val Met Glu Tyr Met Glu
                85                  90                  95

Lys Gly Asn Leu Met His Val Leu Lys Ala Glu Met Ser Thr Pro Leu
            100                 105                 110

Ser Val Lys Gly Arg Ile Ile Leu Glu Ile Ile Glu Gly Met Cys Tyr
        115                 120                 125

Leu His Gly Lys Gly Val Ile His Lys Asp Leu Lys Pro Glu Asn Ile
    130                 135                 140

Leu Val Asp Asn Asp Phe His Ile Lys Ile Ala Asp Leu Gly Leu Ala
145                 150                 155                 160

Ser Phe Lys Met Trp Ser Lys Leu Asn Asn Glu Glu His Asn Glu Leu
                165                 170                 175

Arg Glu Val Asp Gly Thr Ala Lys Lys Asn Gly Gly Thr Leu Tyr Tyr
            180                 185                 190

Met Ala Pro Glu His Leu Asn Asp Val Asn Ala Lys Pro Thr Glu Lys
        195                 200                 205

Ser Asp Val Tyr Ser Phe Ala Val Val Leu Trp Ala Ile Phe Ala Asn
    210                 215                 220

Lys Glu Pro Tyr Glu Asn Ala Ile Cys Glu Gln Gln Leu Ile Met Cys
225                 230                 235                 240

Ile Lys Ser Gly Asn Arg Pro Asp Val Asp Asp Ile Thr Glu Tyr Cys
                245                 250                 255

Pro Arg Glu Ile Ile Ser Leu Met Lys Leu Cys Trp Glu Ala Asn Pro
            260                 265                 270

Glu Ala Arg Pro Thr Phe Pro Gly Ile Glu Glu Lys Phe Arg Pro Phe
        275                 280                 285

Tyr Leu Ser Gln Leu Glu Glu Ser Val Glu Glu Asp Val Lys Ser Leu
    290                 295                 300

Lys Lys Glu Tyr Ser Asn Glu Asn Ala Val Val Lys Arg Met Gln Ser
305                 310                 315                 320

Leu Gln Leu Asp Cys Val Ala Val Pro Ser Ser Arg Ser Asn Ser Ala
                325                 330                 335

Thr Glu Gln Pro Gly Ser Leu His Ser Ser Gln Gly Leu Gly Met Gly
            340                 345                 350

Pro Val Glu Glu Ser Trp Phe Ala Pro Ser Leu Glu His Pro Gln Glu
```

```
        355                 360                 365

Glu Asn Glu Pro Ser Leu Gln Ser Lys Leu Gln Asp Glu Ala Asn Tyr
    370                 375                 380

His Leu Tyr Gly Ser Arg Met Asp Arg Gln Thr Lys Gln Gln Pro Arg
385                 390                 395                 400

Gln Asn Val Ala Tyr Asn Arg Glu Glu Glu Arg Arg Arg Arg Val Ser
                405                 410                 415

His Asp Pro Phe Ala Gln Gln Arg Pro Tyr Glu Asn Phe Gln Asn Thr
            420                 425                 430

Glu Gly Lys Gly Thr Ala Tyr Ser Ser Ala Ala Ser His Gly Asn Ala
        435                 440                 445

Val His Gln Pro Ser Gly Leu Thr Ser Gln Pro Gln Val Leu Tyr Gln
    450                 455                 460

Asn Asn Gly Leu Tyr Ser Ser His Gly Phe Gly Thr Arg Pro Leu Asp
465                 470                 475                 480

Pro Gly Thr Ala Gly Pro Arg Val Trp Tyr Arg Pro Ile Pro Ser His
                485                 490                 495

Met Pro Ser Leu His Asn Ile Pro Val Pro Glu Thr Asn Tyr Leu Gly
            500                 505                 510

Asn Thr Pro Thr Met Pro Phe Ser Ser Leu Pro Pro Thr Asp Glu Ser
        515                 520                 525

Ile Lys Tyr Thr Ile Tyr Asn Ser Thr Gly Ile Gln Ile Gly Ala Tyr
    530                 535                 540

Asn Tyr Met Glu Ile Gly Gly Thr Ser Ser Ser Gly Ser Asp Gly Ser
545                 550                 555                 560

Gly Ser Gly Ser Gly Ser Ile Thr Ile Arg Ala Ala Phe Leu Glu Lys
                565                 570                 575

Glu Asn Thr Ala Leu Arg Thr Glu Ile Ala Glu Leu Glu Lys Glu Val
            580                 585                 590

Gly Arg Cys Glu Asn Ile Val Ser Lys Tyr Glu Thr Arg Tyr Gly Pro
        595                 600                 605

Leu


<210> SEQ ID NO 101
<211> LENGTH: 609
<212> TYPE: PRT
<213> ORGANISM: Artificial Sequence
<220> FEATURE:
<223> OTHER INFORMATION: Synthetic: huRIPK1(1-555).RR.DM; TH1023 without
      epitope tag

<400> SEQUENCE: 101

Met Gln Pro Asp Met Ser Leu Asn Val Ile Lys Met Lys Ser Ser Asp
1               5                   10                  15

Phe Leu Glu Ser Ala Glu Leu Asp Ser Gly Gly Phe Gly Lys Val Ser
            20                  25                  30

Leu Cys Phe His Arg Thr Gln Gly Leu Met Ile Met Lys Thr Val Tyr
        35                  40                  45

Lys Gly Pro Asn Cys Ile Glu His Asn Glu Ala Leu Leu Glu Glu Ala
    50                  55                  60

Lys Met Met Asn Arg Leu Arg His Ser Arg Val Val Lys Leu Leu Gly
65                  70                  75                  80

Val Ile Ile Glu Glu Gly Lys Tyr Ser Leu Val Met Glu Tyr Met Glu
                85                  90                  95

Lys Gly Asn Leu Met His Val Leu Lys Ala Glu Met Ser Thr Pro Leu
```

-continued

```
            100                 105                 110

Ser Val Lys Gly Arg Ile Ile Leu Glu Ile Ile Glu Gly Met Cys Tyr
        115                 120                 125

Leu His Gly Lys Gly Val Ile His Lys Asp Leu Lys Pro Glu Asn Ile
    130                 135                 140

Leu Val Asp Asn Asp Phe His Ile Lys Ile Ala Asp Leu Gly Leu Ala
145                 150                 155                 160

Ser Phe Lys Met Trp Ser Lys Leu Asn Asn Glu Glu His Asn Glu Leu
                165                 170                 175

Arg Glu Val Asp Gly Thr Ala Lys Lys Asn Gly Gly Thr Leu Tyr Tyr
            180                 185                 190

Met Ala Pro Glu His Leu Asn Asp Val Asn Ala Lys Pro Thr Glu Lys
        195                 200                 205

Ser Asp Val Tyr Ser Phe Ala Val Val Leu Trp Ala Ile Phe Ala Asn
    210                 215                 220

Lys Glu Pro Tyr Glu Asn Ala Ile Cys Glu Gln Gln Leu Ile Met Cys
225                 230                 235                 240

Ile Lys Ser Gly Asn Arg Pro Asp Val Asp Asp Ile Thr Glu Tyr Cys
                245                 250                 255

Pro Arg Glu Ile Ile Ser Leu Met Lys Leu Cys Trp Glu Ala Asn Pro
            260                 265                 270

Glu Ala Arg Pro Thr Phe Pro Gly Ile Glu Glu Lys Phe Arg Pro Phe
        275                 280                 285

Tyr Leu Ser Gln Leu Glu Glu Ser Val Glu Glu Asp Val Lys Ser Leu
    290                 295                 300

Lys Lys Glu Tyr Ser Asn Glu Asn Ala Val Val Lys Arg Met Gln Ser
305                 310                 315                 320

Leu Gln Leu Asp Cys Val Ala Val Pro Ser Ser Arg Ser Asn Ser Ala
                325                 330                 335

Thr Glu Gln Pro Gly Ser Leu His Ser Ser Gln Gly Leu Gly Met Gly
            340                 345                 350

Pro Val Glu Glu Ser Trp Phe Ala Pro Ser Leu Glu His Pro Gln Glu
        355                 360                 365

Glu Asn Glu Pro Ser Leu Gln Ser Lys Leu Gln Asp Glu Ala Asn Tyr
    370                 375                 380

His Leu Tyr Gly Ser Arg Met Asp Arg Gln Thr Lys Gln Gln Pro Arg
385                 390                 395                 400

Gln Asn Val Ala Tyr Asn Arg Glu Glu Glu Arg Arg Arg Arg Val Ser
                405                 410                 415

His Asp Pro Phe Ala Gln Gln Arg Pro Tyr Glu Asn Phe Gln Asn Thr
            420                 425                 430

Glu Gly Lys Gly Thr Ala Tyr Ser Ser Ala Ala Ser His Gly Asn Ala
        435                 440                 445

Val His Gln Pro Ser Gly Leu Thr Ser Gln Pro Gln Val Leu Tyr Gln
    450                 455                 460

Asn Asn Gly Leu Tyr Ser Ser His Gly Phe Gly Thr Arg Pro Leu Asp
465                 470                 475                 480

Pro Gly Thr Ala Gly Pro Arg Val Trp Tyr Arg Pro Ile Pro Ser His
                485                 490                 495

Met Pro Ser Leu His Asn Ile Pro Val Pro Glu Thr Asn Tyr Leu Gly
            500                 505                 510

Asn Thr Pro Thr Met Pro Phe Ser Ser Leu Pro Pro Thr Asp Glu Ser
        515                 520                 525
```

```
Ile Lys Tyr Thr Ile Tyr Asn Ser Thr Gly Ile Gln Ile Gly Ala Tyr
    530                 535                 540

Asn Tyr Met Glu Ile Gly Gly Thr Ser Ser Ser Gly Ser Asp Gly Ser
545                 550                 555                 560

Gly Ser Gly Ser Gly Ser Leu Glu Ile Arg Ala Ala Phe Leu Glu Lys
                565                 570                 575

Glu Asn Thr Ala Leu Arg Thr Arg Ala Ala Glu Leu Arg Lys Arg Val
            580                 585                 590

Gly Arg Cys Arg Asn Ile Val Ser Lys Tyr Glu Thr Arg Tyr Gly Pro
        595                 600                 605

Leu


<210> SEQ ID NO 102
<211> LENGTH: 585
<212> TYPE: PRT
<213> ORGANISM: Artificial Sequence
<220> FEATURE:
<223> OTHER INFORMATION: Synthetic: msRIPK1(1-555).IZ.TM; TH1024 without
      epitope tag

<400> SEQUENCE: 102

Met Gln Pro Asp Met Ser Leu Asp Asn Ile Lys Met Ala Ser Ser Asp
1               5                   10                  15

Leu Leu Glu Lys Thr Asp Leu Asp Ser Gly Gly Phe Gly Lys Val Ser
            20                  25                  30

Leu Cys Tyr His Arg Ser His Gly Phe Val Ile Leu Lys Lys Val Tyr
        35                  40                  45

Thr Gly Pro Asn Arg Ala Glu Tyr Asn Glu Val Leu Leu Glu Glu Gly
    50                  55                  60

Lys Met Met His Arg Leu Arg His Ser Arg Val Val Lys Leu Leu Gly
65                  70                  75                  80

Ile Ile Ile Glu Glu Gly Asn Tyr Ser Leu Val Met Glu Tyr Met Glu
                85                  90                  95

Lys Gly Asn Leu Met His Val Leu Lys Thr Gln Ile Asp Val Pro Leu
            100                 105                 110

Ser Leu Lys Gly Arg Ile Ile Val Glu Ala Ile Glu Gly Met Cys Tyr
        115                 120                 125

Leu His Asp Lys Gly Val Ile His Lys Asp Leu Lys Pro Glu Asn Ile
    130                 135                 140

Leu Val Asp Arg Asp Phe His Ile Lys Ile Ala Asp Leu Gly Val Ala
145                 150                 155                 160

Ser Phe Lys Thr Trp Ser Lys Leu Thr Lys Glu Lys Asp Asn Lys Gln
                165                 170                 175

Lys Glu Val Ser Ser Thr Thr Lys Lys Asn Asn Gly Gly Thr Leu Tyr
            180                 185                 190

Tyr Met Ala Pro Glu His Leu Asn Asp Ile Asn Ala Lys Pro Thr Glu
        195                 200                 205

Lys Ser Asp Val Tyr Ser Phe Gly Ile Val Leu Trp Ala Ile Phe Ala
    210                 215                 220

Lys Lys Glu Pro Tyr Glu Asn Val Ile Cys Thr Glu Gln Phe Val Ile
225                 230                 235                 240

Cys Ile Lys Ser Gly Asn Arg Pro Asn Val Glu Glu Ile Leu Glu Tyr
                245                 250                 255

Cys Pro Arg Glu Ile Ile Ser Leu Met Glu Arg Cys Trp Gln Ala Ile
            260                 265                 270
```

```
Pro Glu Asp Arg Pro Thr Phe Leu Gly Ile Glu Glu Glu Phe Arg Pro
        275                 280                 285

Phe Tyr Leu Ser His Phe Glu Glu Tyr Val Glu Glu Asp Val Ala Ser
    290                 295                 300

Leu Lys Lys Glu Tyr Pro Asp Gln Ser Pro Val Leu Gln Arg Met Phe
305                 310                 315                 320

Ser Leu Gln His Asp Cys Val Pro Leu Pro Pro Ser Arg Ser Asn Ser
                325                 330                 335

Glu Gln Pro Gly Ser Leu His Ser Ser Gln Gly Leu Gln Met Gly Pro
            340                 345                 350

Val Glu Glu Ser Trp Phe Ser Ser Ser Pro Glu Tyr Pro Gln Asp Glu
        355                 360                 365

Asn Asp Arg Ser Val Gln Ala Lys Leu Gln Glu Glu Ala Ser Tyr His
    370                 375                 380

Ala Phe Gly Ile Phe Ala Glu Lys Gln Thr Lys Pro Gln Pro Arg Gln
385                 390                 395                 400

Asn Glu Ala Tyr Asn Arg Glu Glu Glu Arg Lys Arg Arg Val Ser His
                405                 410                 415

Asp Pro Phe Ala Gln Gln Arg Ala Arg Glu Asn Ile Lys Ser Ala Gly
            420                 425                 430

Ala Arg Gly His Ser Asp Pro Ser Thr Thr Ser Arg Gly Ile Ala Val
        435                 440                 445

Gln Gln Leu Ser Trp Pro Ala Thr Gln Thr Val Trp Asn Asn Gly Leu
    450                 455                 460

Tyr Asn Gln His Gly Phe Gly Thr Thr Gly Thr Gly Val Trp Tyr Pro
465                 470                 475                 480

Pro Asn Leu Ser Gln Met Tyr Ser Thr Tyr Lys Thr Pro Val Pro Glu
                485                 490                 495

Thr Asn Ile Pro Gly Ser Thr Pro Thr Met Pro Tyr Phe Ser Gly Pro
            500                 505                 510

Val Ala Asp Asp Leu Ile Lys Tyr Thr Ile Phe Asn Ser Ser Gly Ile
        515                 520                 525

Gln Ile Gly Asn His Asn Tyr Met Asp Val Gly Leu Asn Ser Gln Pro
    530                 535                 540

Pro Asn Asn Thr Cys Lys Glu Glu Ser Thr Ser Gly Gly Ile Lys Lys
545                 550                 555                 560

Glu Ile Glu Ala Ile Lys Lys Glu Gln Glu Ala Ile Lys Lys Lys Ile
                565                 570                 575

Glu Ala Ile Glu Lys Glu Ile Glu Ala
            580                 585
```

<210> SEQ ID NO 103
<211> LENGTH: 609
<212> TYPE: PRT
<213> ORGANISM: Artificial Sequence
<220> FEATURE:
<223> OTHER INFORMATION: Synthetic: msRIPK1(1-555).EE.DM; TH1025 without epitope tag

<400> SEQUENCE: 103

```
Met Gln Pro Asp Met Ser Leu Asp Asn Ile Lys Met Ala Ser Ser Asp
1               5                   10                  15

Leu Leu Glu Lys Thr Asp Leu Asp Ser Gly Gly Phe Gly Lys Val Ser
            20                  25                  30

Leu Cys Tyr His Arg Ser His Gly Phe Val Ile Leu Lys Lys Val Tyr
```

-continued

```
        35                  40                  45

Thr Gly Pro Asn Arg Ala Glu Tyr Asn Glu Val Leu Leu Glu Glu Gly
    50                  55                  60

Lys Met Met His Arg Leu Arg His Ser Arg Val Val Lys Leu Leu Gly
65                  70                  75                  80

Ile Ile Ile Glu Glu Gly Asn Tyr Ser Leu Val Met Glu Tyr Met Glu
                85                  90                  95

Lys Gly Asn Leu Met His Val Leu Lys Thr Gln Ile Asp Val Pro Leu
            100                 105                 110

Ser Leu Lys Gly Arg Ile Ile Val Glu Ala Ile Glu Gly Met Cys Tyr
        115                 120                 125

Leu His Asp Lys Gly Val Ile His Lys Asp Leu Lys Pro Glu Asn Ile
    130                 135                 140

Leu Val Asp Arg Asp Phe His Ile Lys Ile Ala Asp Leu Gly Val Ala
145                 150                 155                 160

Ser Phe Lys Thr Trp Ser Lys Leu Thr Lys Glu Lys Asp Asn Lys Gln
                165                 170                 175

Lys Glu Val Ser Ser Thr Thr Lys Lys Asn Asn Gly Gly Thr Leu Tyr
            180                 185                 190

Tyr Met Ala Pro Glu His Leu Asn Asp Ile Asn Ala Lys Pro Thr Glu
        195                 200                 205

Lys Ser Asp Val Tyr Ser Phe Gly Ile Val Leu Trp Ala Ile Phe Ala
    210                 215                 220

Lys Lys Glu Pro Tyr Glu Asn Val Ile Cys Thr Glu Gln Phe Val Ile
225                 230                 235                 240

Cys Ile Lys Ser Gly Asn Arg Pro Asn Val Glu Glu Ile Leu Glu Tyr
                245                 250                 255

Cys Pro Arg Glu Ile Ile Ser Leu Met Glu Arg Cys Trp Gln Ala Ile
            260                 265                 270

Pro Glu Asp Arg Pro Thr Phe Leu Gly Ile Glu Glu Glu Phe Arg Pro
        275                 280                 285

Phe Tyr Leu Ser His Phe Glu Glu Tyr Val Glu Glu Asp Val Ala Ser
    290                 295                 300

Leu Lys Lys Glu Tyr Pro Asp Gln Ser Pro Val Leu Gln Arg Met Phe
305                 310                 315                 320

Ser Leu Gln His Asp Cys Val Pro Leu Pro Pro Ser Arg Ser Asn Ser
                325                 330                 335

Glu Gln Pro Gly Ser Leu His Ser Ser Gln Gly Leu Gln Met Gly Pro
            340                 345                 350

Val Glu Glu Ser Trp Phe Ser Ser Ser Pro Glu Tyr Pro Gln Asp Glu
        355                 360                 365

Asn Asp Arg Ser Val Gln Ala Lys Leu Gln Glu Glu Ala Ser Tyr His
    370                 375                 380

Ala Phe Gly Ile Phe Ala Glu Lys Gln Thr Lys Pro Gln Pro Arg Gln
385                 390                 395                 400

Asn Glu Ala Tyr Asn Arg Glu Glu Glu Arg Lys Arg Arg Val Ser His
                405                 410                 415

Asp Pro Phe Ala Gln Gln Arg Ala Arg Glu Asn Ile Lys Ser Ala Gly
            420                 425                 430

Ala Arg Gly His Ser Asp Pro Ser Thr Thr Ser Arg Gly Ile Ala Val
        435                 440                 445

Gln Gln Leu Ser Trp Pro Ala Thr Gln Thr Val Trp Asn Asn Gly Leu
    450                 455                 460
```

```
Tyr Asn Gln His Gly Phe Gly Thr Thr Gly Thr Gly Val Trp Tyr Pro
465                 470                 475                 480

Pro Asn Leu Ser Gln Met Tyr Ser Thr Tyr Lys Thr Pro Val Pro Glu
                485                 490                 495

Thr Asn Ile Pro Gly Ser Thr Pro Thr Met Pro Tyr Phe Ser Gly Pro
            500                 505                 510

Val Ala Asp Asp Leu Ile Lys Tyr Thr Ile Phe Asn Ser Ser Gly Ile
        515                 520                 525

Gln Ile Gly Asn His Asn Tyr Met Asp Val Gly Leu Asn Ser Gln Pro
    530                 535                 540

Pro Asn Asn Thr Cys Lys Glu Glu Ser Thr Ser Gly Ser Asp Gly Ser
545                 550                 555                 560

Gly Ser Gly Ser Gly Ser Ile Thr Ile Arg Ala Ala Phe Leu Glu Lys
                565                 570                 575

Glu Asn Thr Ala Leu Arg Thr Glu Ile Ala Glu Leu Glu Lys Glu Val
            580                 585                 590

Gly Arg Cys Glu Asn Ile Val Ser Lys Tyr Glu Thr Arg Tyr Gly Pro
        595                 600                 605

Leu


<210> SEQ ID NO 104
<211> LENGTH: 609
<212> TYPE: PRT
<213> ORGANISM: Artificial Sequence
<220> FEATURE:
<223> OTHER INFORMATION: Synthetic: msRIPK1(1-555).RR.DM; TH1026 without
      epitope tag

<400> SEQUENCE: 104

Met Gln Pro Asp Met Ser Leu Asp Asn Ile Lys Met Ala Ser Ser Asp
1               5                   10                  15

Leu Leu Glu Lys Thr Asp Leu Asp Ser Gly Gly Phe Gly Lys Val Ser
            20                  25                  30

Leu Cys Tyr His Arg Ser His Gly Phe Val Ile Leu Lys Lys Val Tyr
        35                  40                  45

Thr Gly Pro Asn Arg Ala Glu Tyr Asn Glu Val Leu Leu Glu Glu Gly
    50                  55                  60

Lys Met Met His Arg Leu Arg His Ser Arg Val Val Lys Leu Leu Gly
65                  70                  75                  80

Ile Ile Ile Glu Glu Gly Asn Tyr Ser Leu Val Met Glu Tyr Met Glu
                85                  90                  95

Lys Gly Asn Leu Met His Val Leu Lys Thr Gln Ile Asp Val Pro Leu
            100                 105                 110

Ser Leu Lys Gly Arg Ile Ile Val Glu Ala Ile Glu Gly Met Cys Tyr
        115                 120                 125

Leu His Asp Lys Gly Val Ile His Lys Asp Leu Lys Pro Glu Asn Ile
    130                 135                 140

Leu Val Asp Arg Asp Phe His Ile Lys Ile Ala Asp Leu Gly Val Ala
145                 150                 155                 160

Ser Phe Lys Thr Trp Ser Lys Leu Thr Lys Glu Lys Asp Asn Lys Gln
                165                 170                 175

Lys Glu Val Ser Ser Thr Thr Lys Lys Asn Asn Gly Gly Thr Leu Tyr
            180                 185                 190

Tyr Met Ala Pro Glu His Leu Asn Asp Ile Asn Ala Lys Pro Thr Glu
        195                 200                 205
```

-continued

```
Lys Ser Asp Val Tyr Ser Phe Gly Ile Val Leu Trp Ala Ile Phe Ala
    210                 215                 220

Lys Lys Glu Pro Tyr Glu Asn Val Ile Cys Thr Glu Gln Phe Val Ile
225                 230                 235                 240

Cys Ile Lys Ser Gly Asn Arg Pro Asn Val Glu Glu Ile Leu Glu Tyr
                245                 250                 255

Cys Pro Arg Glu Ile Ile Ser Leu Met Glu Arg Cys Trp Gln Ala Ile
            260                 265                 270

Pro Glu Asp Arg Pro Thr Phe Leu Gly Ile Glu Glu Glu Phe Arg Pro
        275                 280                 285

Phe Tyr Leu Ser His Phe Glu Glu Tyr Val Glu Glu Asp Val Ala Ser
    290                 295                 300

Leu Lys Lys Glu Tyr Pro Asp Gln Ser Pro Val Leu Gln Arg Met Phe
305                 310                 315                 320

Ser Leu Gln His Asp Cys Val Pro Leu Pro Pro Ser Arg Ser Asn Ser
                325                 330                 335

Glu Gln Pro Gly Ser Leu His Ser Ser Gln Gly Leu Gln Met Gly Pro
            340                 345                 350

Val Glu Glu Ser Trp Phe Ser Ser Ser Pro Glu Tyr Pro Gln Asp Glu
        355                 360                 365

Asn Asp Arg Ser Val Gln Ala Lys Leu Gln Glu Glu Ala Ser Tyr His
    370                 375                 380

Ala Phe Gly Ile Phe Ala Glu Lys Gln Thr Lys Pro Gln Pro Arg Gln
385                 390                 395                 400

Asn Glu Ala Tyr Asn Arg Glu Glu Glu Arg Lys Arg Arg Val Ser His
                405                 410                 415

Asp Pro Phe Ala Gln Gln Arg Ala Arg Glu Asn Ile Lys Ser Ala Gly
            420                 425                 430

Ala Arg Gly His Ser Asp Pro Ser Thr Thr Ser Arg Gly Ile Ala Val
        435                 440                 445

Gln Gln Leu Ser Trp Pro Ala Thr Gln Thr Val Trp Asn Asn Gly Leu
    450                 455                 460

Tyr Asn Gln His Gly Phe Gly Thr Thr Gly Thr Gly Val Trp Tyr Pro
465                 470                 475                 480

Pro Asn Leu Ser Gln Met Tyr Ser Thr Tyr Lys Thr Pro Val Pro Glu
                485                 490                 495

Thr Asn Ile Pro Gly Ser Thr Pro Thr Met Pro Tyr Phe Ser Gly Pro
            500                 505                 510

Val Ala Asp Asp Leu Ile Lys Tyr Thr Ile Phe Asn Ser Ser Gly Ile
        515                 520                 525

Gln Ile Gly Asn His Asn Tyr Met Asp Val Gly Leu Asn Ser Gln Pro
    530                 535                 540

Pro Asn Asn Thr Cys Lys Glu Glu Ser Thr Ser Gly Ser Asp Gly Ser
545                 550                 555                 560

Gly Ser Gly Ser Gly Ser Leu Glu Ile Arg Ala Ala Phe Leu Glu Lys
                565                 570                 575

Glu Asn Thr Ala Leu Arg Thr Arg Ala Ala Glu Leu Arg Lys Arg Val
            580                 585                 590

Gly Arg Cys Arg Asn Ile Val Ser Lys Tyr Glu Thr Arg Tyr Gly Pro
        595                 600                 605

Leu
```

<210> SEQ ID NO 105
<211> LENGTH: 378
<212> TYPE: PRT
<213> ORGANISM: Homo sapiens
<220> FEATURE:
<221> NAME/KEY: misc_feature
<222> LOCATION: (1)..(378)
<223> OTHER INFORMATION: human TAK1-TAB1; P4031 without epitope tag

<400> SEQUENCE: 105

Met Ser Thr Ala Ser Ala Ala Ser Ser Ser Ser Ser Ser Ser Ala Gly
1 5 10 15

Glu Met Ile Glu Ala Pro Ser Gln Val Leu Asn Phe Glu Glu Ile Asp
20 25 30

Tyr Lys Glu Ile Glu Val Glu Glu Val Val Gly Arg Gly Ala Phe Gly
35 40 45

Val Val Cys Lys Ala Lys Trp Arg Ala Lys Asp Val Ala Ile Lys Gln
50 55 60

Ile Glu Ser Glu Ser Glu Arg Lys Ala Phe Ile Val Glu Leu Arg Gln
65 70 75 80

Leu Ser Arg Val Asn His Pro Asn Ile Val Lys Leu Tyr Gly Ala Cys
85 90 95

Leu Asn Pro Val Cys Leu Val Met Glu Tyr Ala Glu Gly Gly Ser Leu
100 105 110

Tyr Asn Val Leu His Gly Ala Glu Pro Leu Pro Tyr Tyr Thr Ala Ala
115 120 125

His Ala Met Ser Trp Cys Leu Gln Cys Ser Gln Gly Val Ala Tyr Leu
130 135 140

His Ser Met Gln Pro Lys Ala Leu Ile His Arg Asp Leu Lys Pro Pro
145 150 155 160

Asn Leu Leu Leu Val Ala Gly Gly Thr Val Leu Lys Ile Cys Asp Phe
165 170 175

Gly Thr Ala Cys Asp Ile Gln Thr His Met Thr Asn Asn Lys Gly Ser
180 185 190

Ala Ala Trp Met Ala Pro Glu Val Phe Glu Gly Ser Asn Tyr Ser Glu
195 200 205

Lys Cys Asp Val Phe Ser Trp Gly Ile Ile Leu Trp Glu Val Ile Thr
210 215 220

Arg Arg Lys Pro Phe Asp Glu Ile Gly Gly Pro Ala Phe Arg Ile Met
225 230 235 240

Trp Ala Val His Asn Gly Thr Arg Pro Pro Leu Ile Lys Asn Leu Pro
245 250 255

Lys Pro Ile Glu Ser Leu Met Thr Arg Cys Trp Ser Lys Asp Pro Ser
260 265 270

Gln Arg Pro Ser Met Glu Glu Ile Val Lys Ile Met Thr His Leu Met
275 280 285

Arg Tyr Phe Pro Gly Ala Asp Glu Pro Leu Gln Tyr Pro Cys Gln Glu
290 295 300

Phe Gly Gly Gly Gly Gly Gln Ser Pro Thr Leu Thr Leu Gln Ser Thr
305 310 315 320

Asn Thr His Thr Gln Ser Ser Ser Ser Ser Ser Asp Gly Gly Leu Phe
325 330 335

Arg Ser Arg Pro Ala His Ser Leu Pro Pro Gly Glu Asp Gly Arg Val
340 345 350

Glu Pro Tyr Val Asp Phe Ala Glu Phe Tyr Arg Leu Trp Ser Val Asp
355 360 365

His Gly Glu Gln Ser Val Val Thr Ala Pro
370 375

<210> SEQ ID NO 106
<211> LENGTH: 239
<212> TYPE: PRT
<213> ORGANISM: Artificial Sequence
<220> FEATURE:
<223> OTHER INFORMATION: Synthetic: Diablo.1; without epitope tag

<400> SEQUENCE: 106

Met Ala Ala Leu Lys Ser Trp Leu Ser Arg Ser Val Thr Ser Phe Phe
1 5 10 15

Arg Tyr Arg Gln Cys Leu Cys Val Pro Val Val Ala Asn Phe Lys Lys
20 25 30

Arg Cys Phe Ser Glu Leu Ile Arg Pro Trp His Lys Thr Val Thr Ile
35 40 45

Gly Phe Gly Val Thr Leu Cys Ala Val Pro Ile Ala Gln Lys Ser Glu
50 55 60

Pro His Ser Leu Ser Ser Glu Ala Leu Met Arg Arg Ala Val Ser Leu
65 70 75 80

Val Thr Asp Ser Thr Ser Thr Phe Leu Ser Gln Thr Thr Tyr Ala Leu
85 90 95

Ile Glu Ala Ile Thr Glu Tyr Thr Lys Ala Val Tyr Thr Leu Thr Ser
100 105 110

Leu Tyr Arg Gln Tyr Thr Ser Leu Leu Gly Lys Met Asn Ser Glu Glu
115 120 125

Glu Asp Glu Val Trp Gln Val Ile Ile Gly Ala Arg Ala Glu Met Thr
130 135 140

Ser Lys His Gln Glu Tyr Leu Lys Leu Glu Thr Thr Trp Met Thr Ala
145 150 155 160

Val Gly Leu Ser Glu Met Ala Ala Glu Ala Ala Tyr Gln Thr Gly Ala
165 170 175

Asp Gln Ala Ser Ile Thr Ala Arg Asn His Ile Gln Leu Val Lys Leu
180 185 190

Gln Val Glu Glu Val His Gln Leu Ser Arg Lys Ala Glu Thr Lys Leu
195 200 205

Ala Glu Ala Gln Ile Glu Glu Leu Arg Gln Lys Thr Gln Glu Glu Gly
210 215 220

Glu Glu Arg Ala Glu Ser Glu Gln Glu Ala Tyr Leu Arg Glu Asp
225 230 235

<210> SEQ ID NO 107
<211> LENGTH: 239
<212> TYPE: PRT
<213> ORGANISM: Artificial Sequence
<220> FEATURE:
<223> OTHER INFORMATION: Synthetic: Diablo.1(S126L); without epitope tag

<400> SEQUENCE: 107

Met Ala Ala Leu Lys Ser Trp Leu Ser Arg Ser Val Thr Ser Phe Phe
1 5 10 15

Arg Tyr Arg Gln Cys Leu Cys Val Pro Val Val Ala Asn Phe Lys Lys
20 25 30

Arg Cys Phe Ser Glu Leu Ile Arg Pro Trp His Lys Thr Val Thr Ile
35 40 45

Gly Phe Gly Val Thr Leu Cys Ala Val Pro Ile Ala Gln Lys Ser Glu

```
    50                  55                  60

Pro His Ser Leu Ser Ser Glu Ala Leu Met Arg Arg Ala Val Ser Leu
65                  70                  75                  80

Val Thr Asp Ser Thr Ser Thr Phe Leu Ser Gln Thr Thr Tyr Ala Leu
                85                  90                  95

Ile Glu Ala Ile Thr Glu Tyr Thr Lys Ala Val Tyr Thr Leu Thr Ser
            100                 105                 110

Leu Tyr Arg Gln Tyr Thr Ser Leu Leu Gly Lys Met Asn Leu Glu Glu
        115                 120                 125

Glu Asp Glu Val Trp Gln Val Ile Ile Gly Ala Arg Ala Glu Met Thr
    130                 135                 140

Ser Lys His Gln Glu Tyr Leu Lys Leu Glu Thr Thr Trp Met Thr Ala
145                 150                 155                 160

Val Gly Leu Ser Glu Met Ala Ala Glu Ala Ala Tyr Gln Thr Gly Ala
                165                 170                 175

Asp Gln Ala Ser Ile Thr Ala Arg Asn His Ile Gln Leu Val Lys Leu
            180                 185                 190

Gln Val Glu Glu Val His Gln Leu Ser Arg Lys Ala Glu Thr Lys Leu
        195                 200                 205

Ala Glu Ala Gln Ile Glu Glu Leu Arg Gln Lys Thr Gln Glu Glu Gly
    210                 215                 220

Glu Glu Arg Ala Glu Ser Glu Gln Glu Ala Tyr Leu Arg Glu Asp
225                 230                 235


<210> SEQ ID NO 108
<211> LENGTH: 185
<212> TYPE: PRT
<213> ORGANISM: Artificial Sequence
<220> FEATURE:
<223> OTHER INFORMATION: Synthetic: Diablo.1(56-239); without epitope
      tag

<400> SEQUENCE: 108

Met Ala Val Pro Ile Ala Gln Lys Ser Glu Pro His Ser Leu Ser Ser
1               5                   10                  15

Glu Ala Leu Met Arg Arg Ala Val Ser Leu Val Thr Asp Ser Thr Ser
            20                  25                  30

Thr Phe Leu Ser Gln Thr Thr Tyr Ala Leu Ile Glu Ala Ile Thr Glu
        35                  40                  45

Tyr Thr Lys Ala Val Tyr Thr Leu Thr Ser Leu Tyr Arg Gln Tyr Thr
    50                  55                  60

Ser Leu Leu Gly Lys Met Asn Ser Glu Glu Glu Asp Glu Val Trp Gln
65                  70                  75                  80

Val Ile Ile Gly Ala Arg Ala Glu Met Thr Ser Lys His Gln Glu Tyr
                85                  90                  95

Leu Lys Leu Glu Thr Thr Trp Met Thr Ala Val Gly Leu Ser Glu Met
            100                 105                 110

Ala Ala Glu Ala Ala Tyr Gln Thr Gly Ala Asp Gln Ala Ser Ile Thr
        115                 120                 125

Ala Arg Asn His Ile Gln Leu Val Lys Leu Gln Val Glu Glu Val His
    130                 135                 140

Gln Leu Ser Arg Lys Ala Glu Thr Lys Leu Ala Glu Ala Gln Ile Glu
145                 150                 155                 160

Glu Leu Arg Gln Lys Thr Gln Glu Glu Gly Glu Glu Arg Ala Glu Ser
                165                 170                 175
```

```
Glu Gln Glu Ala Tyr Leu Arg Glu Asp
            180                 185


<210> SEQ ID NO 109
<211> LENGTH: 185
<212> TYPE: PRT
<213> ORGANISM: Artificial Sequence
<220> FEATURE:
<223> OTHER INFORMATION: Synthetic: Diablo.1(56-239/S126L); without
      epitope tag

<400> SEQUENCE: 109

Met Ala Val Pro Ile Ala Gln Lys Ser Glu Pro His Ser Leu Ser Ser
1               5                   10                  15

Glu Ala Leu Met Arg Arg Ala Val Ser Leu Val Thr Asp Ser Thr Ser
            20                  25                  30

Thr Phe Leu Ser Gln Thr Thr Tyr Ala Leu Ile Glu Ala Ile Thr Glu
        35                  40                  45

Tyr Thr Lys Ala Val Tyr Thr Leu Thr Ser Leu Tyr Arg Gln Tyr Thr
    50                  55                  60

Ser Leu Leu Gly Lys Met Asn Leu Glu Glu Glu Asp Glu Val Trp Gln
65                  70                  75                  80

Val Ile Ile Gly Ala Arg Ala Glu Met Thr Ser Lys His Gln Glu Tyr
                85                  90                  95

Leu Lys Leu Glu Thr Thr Trp Met Thr Ala Val Gly Leu Ser Glu Met
            100                 105                 110

Ala Ala Glu Ala Ala Tyr Gln Thr Gly Ala Asp Gln Ala Ser Ile Thr
        115                 120                 125

Ala Arg Asn His Ile Gln Leu Val Lys Leu Gln Val Glu Glu Val His
    130                 135                 140

Gln Leu Ser Arg Lys Ala Glu Thr Lys Leu Ala Glu Ala Gln Ile Glu
145                 150                 155                 160

Glu Leu Arg Gln Lys Thr Gln Glu Glu Gly Glu Glu Arg Ala Glu Ser
                165                 170                 175

Glu Gln Glu Ala Tyr Leu Arg Glu Asp
            180                 185


<210> SEQ ID NO 110
<211> LENGTH: 195
<212> TYPE: PRT
<213> ORGANISM: Artificial Sequence
<220> FEATURE:
<223> OTHER INFORMATION: Synthetic: Diablo.3; TH2003 without epitope tag

<400> SEQUENCE: 110

Met Ala Ala Leu Lys Ser Trp Leu Ser Arg Ser Val Thr Ser Phe Phe
1               5                   10                  15

Arg Tyr Arg Gln Cys Leu Cys Val Pro Val Val Ala Asn Phe Lys Lys
            20                  25                  30

Arg Cys Phe Ser Glu Leu Ile Arg Pro Trp His Lys Thr Val Thr Ile
        35                  40                  45

Gly Phe Gly Val Thr Leu Cys Ala Val Pro Ile Ala Gln Ala Val Tyr
    50                  55                  60

Thr Leu Thr Ser Leu Tyr Arg Gln Tyr Thr Ser Leu Leu Gly Lys Met
65                  70                  75                  80

Asn Ser Glu Glu Glu Asp Glu Val Trp Gln Val Ile Ile Gly Ala Arg
                85                  90                  95

Ala Glu Met Thr Ser Lys His Gln Glu Tyr Leu Lys Leu Glu Thr Thr
```

```
            100                 105                 110

Trp Met Thr Ala Val Gly Leu Ser Glu Met Ala Ala Glu Ala Ala Tyr
        115                 120                 125

Gln Thr Gly Ala Asp Gln Ala Ser Ile Thr Ala Arg Asn His Ile Gln
    130                 135                 140

Leu Val Lys Leu Gln Val Glu Glu Val His Gln Leu Ser Arg Lys Ala
145                 150                 155                 160

Glu Thr Lys Leu Ala Glu Ala Gln Ile Glu Glu Leu Arg Gln Lys Thr
                165                 170                 175

Gln Glu Glu Gly Glu Glu Arg Ala Glu Ser Glu Gln Glu Ala Tyr Leu
            180                 185                 190

Arg Glu Asp
        195


<210> SEQ ID NO 111
<211> LENGTH: 195
<212> TYPE: PRT
<213> ORGANISM: Artificial Sequence
<220> FEATURE:
<223> OTHER INFORMATION: Synthetic: Diablo.3(S82L); TH2001 without
      epitope tag

<400> SEQUENCE: 111

Met Ala Ala Leu Lys Ser Trp Leu Ser Arg Ser Val Thr Ser Phe Phe
1               5                   10                  15

Arg Tyr Arg Gln Cys Leu Cys Val Pro Val Val Ala Asn Phe Lys Lys
            20                  25                  30

Arg Cys Phe Ser Glu Leu Ile Arg Pro Trp His Lys Thr Val Thr Ile
        35                  40                  45

Gly Phe Gly Val Thr Leu Cys Ala Val Pro Ile Ala Gln Ala Val Tyr
    50                  55                  60

Thr Leu Thr Ser Leu Tyr Arg Gln Tyr Thr Ser Leu Leu Gly Lys Met
65                  70                  75                  80

Asn Leu Glu Glu Glu Asp Glu Val Trp Gln Val Ile Ile Gly Ala Arg
                85                  90                  95

Ala Glu Met Thr Ser Lys His Gln Glu Tyr Leu Lys Leu Glu Thr Thr
            100                 105                 110

Trp Met Thr Ala Val Gly Leu Ser Glu Met Ala Ala Glu Ala Ala Tyr
        115                 120                 125

Gln Thr Gly Ala Asp Gln Ala Ser Ile Thr Ala Arg Asn His Ile Gln
    130                 135                 140

Leu Val Lys Leu Gln Val Glu Glu Val His Gln Leu Ser Arg Lys Ala
145                 150                 155                 160

Glu Thr Lys Leu Ala Glu Ala Gln Ile Glu Glu Leu Arg Gln Lys Thr
                165                 170                 175

Gln Glu Glu Gly Glu Glu Arg Ala Glu Ser Glu Gln Glu Ala Tyr Leu
            180                 185                 190

Arg Glu Asp
        195


<210> SEQ ID NO 112
<211> LENGTH: 141
<212> TYPE: PRT
<213> ORGANISM: Artificial Sequence
<220> FEATURE:
<223> OTHER INFORMATION: Synthetic: Diablo.3(56-195); TH2002 without
      epitope tag
```

<400> SEQUENCE: 112

Met Ala Val Pro Ile Ala Gln Ala Val Tyr Thr Leu Thr Ser Leu Tyr
1 5 10 15

Arg Gln Tyr Thr Ser Leu Leu Gly Lys Met Asn Ser Glu Glu Glu Asp
20 25 30

Glu Val Trp Gln Val Ile Ile Gly Ala Arg Ala Glu Met Thr Ser Lys
35 40 45

His Gln Glu Tyr Leu Lys Leu Glu Thr Thr Trp Met Thr Ala Val Gly
50 55 60

Leu Ser Glu Met Ala Ala Glu Ala Ala Tyr Gln Thr Gly Ala Asp Gln
65 70 75 80

Ala Ser Ile Thr Ala Arg Asn His Ile Gln Leu Val Lys Leu Gln Val
85 90 95

Glu Glu Val His Gln Leu Ser Arg Lys Ala Glu Thr Lys Leu Ala Glu
100 105 110

Ala Gln Ile Glu Glu Leu Arg Gln Lys Thr Gln Glu Glu Gly Glu Glu
115 120 125

Arg Ala Glu Ser Glu Gln Glu Ala Tyr Leu Arg Glu Asp
130 135 140

<210> SEQ ID NO 113
<211> LENGTH: 141
<212> TYPE: PRT
<213> ORGANISM: Artificial Sequence
<220> FEATURE:
<223> OTHER INFORMATION: Synthetic: Diablo.3(56-195/S82L); without epitope tag

<400> SEQUENCE: 113

Met Ala Val Pro Ile Ala Gln Ala Val Tyr Thr Leu Thr Ser Leu Tyr
1 5 10 15

Arg Gln Tyr Thr Ser Leu Leu Gly Lys Met Asn Leu Glu Glu Glu Asp
20 25 30

Glu Val Trp Gln Val Ile Ile Gly Ala Arg Ala Glu Met Thr Ser Lys
35 40 45

His Gln Glu Tyr Leu Lys Leu Glu Thr Thr Trp Met Thr Ala Val Gly
50 55 60

Leu Ser Glu Met Ala Ala Glu Ala Ala Tyr Gln Thr Gly Ala Asp Gln
65 70 75 80

Ala Ser Ile Thr Ala Arg Asn His Ile Gln Leu Val Lys Leu Gln Val
85 90 95

Glu Glu Val His Gln Leu Ser Arg Lys Ala Glu Thr Lys Leu Ala Glu
100 105 110

Ala Gln Ile Glu Glu Leu Arg Gln Lys Thr Gln Glu Glu Gly Glu Glu
115 120 125

Arg Ala Glu Ser Glu Gln Glu Ala Tyr Leu Arg Glu Asp
130 135 140

<210> SEQ ID NO 114
<211> LENGTH: 659
<212> TYPE: PRT
<213> ORGANISM: Artificial Sequence
<220> FEATURE:
<223> OTHER INFORMATION: Synthetic: Btk(E41K); P4029 without epitope tag

<400> SEQUENCE: 114

Met Ala Ala Val Ile Leu Glu Ser Ile Phe Leu Lys Arg Ser Gln Gln
1 5 10 15

```
Lys Lys Lys Thr Ser Pro Leu Asn Phe Lys Lys Arg Leu Phe Leu Leu
            20                  25                  30

Thr Val His Lys Leu Ser Tyr Tyr Lys Tyr Asp Phe Glu Arg Gly Arg
        35                  40                  45

Arg Gly Ser Lys Lys Gly Ser Ile Asp Val Glu Lys Ile Thr Cys Val
    50                  55                  60

Glu Thr Val Val Pro Glu Lys Asn Pro Pro Pro Glu Arg Gln Ile Pro
65                  70                  75                  80

Arg Arg Gly Glu Glu Ser Ser Glu Met Glu Gln Ile Ser Ile Ile Glu
                85                  90                  95

Arg Phe Pro Tyr Pro Phe Gln Val Val Tyr Asp Glu Gly Pro Leu Tyr
            100                 105                 110

Val Phe Ser Pro Thr Glu Glu Leu Arg Lys Arg Trp Ile His Gln Leu
        115                 120                 125

Lys Asn Val Ile Arg Tyr Asn Ser Asp Leu Val Gln Lys Tyr His Pro
    130                 135                 140

Cys Phe Trp Ile Asp Gly Gln Tyr Leu Cys Cys Ser Gln Thr Ala Lys
145                 150                 155                 160

Asn Ala Met Gly Cys Gln Ile Leu Glu Asn Arg Asn Gly Ser Leu Lys
                165                 170                 175

Pro Gly Ser Ser His Arg Lys Thr Lys Lys Pro Leu Pro Pro Thr Pro
            180                 185                 190

Glu Glu Asp Gln Ile Leu Lys Lys Pro Leu Pro Pro Glu Pro Ala Ala
        195                 200                 205

Ala Pro Val Ser Thr Ser Glu Leu Lys Lys Val Val Ala Leu Tyr Asp
    210                 215                 220

Tyr Met Pro Met Asn Ala Asn Asp Leu Gln Leu Arg Lys Gly Asp Glu
225                 230                 235                 240

Tyr Phe Ile Leu Glu Glu Ser Asn Leu Pro Trp Trp Arg Ala Arg Asp
                245                 250                 255

Lys Asn Gly Gln Glu Gly Tyr Ile Pro Ser Asn Tyr Val Thr Glu Ala
            260                 265                 270

Glu Asp Ser Ile Glu Met Tyr Glu Trp Tyr Ser Lys His Met Thr Arg
        275                 280                 285

Ser Gln Ala Glu Gln Leu Leu Lys Gln Glu Gly Lys Glu Gly Gly Phe
    290                 295                 300

Ile Val Arg Asp Ser Ser Lys Ala Gly Lys Tyr Thr Val Ser Val Phe
305                 310                 315                 320

Ala Lys Ser Thr Gly Asp Pro Gln Gly Val Ile Arg His Tyr Val Val
                325                 330                 335

Cys Ser Thr Pro Gln Ser Gln Tyr Tyr Leu Ala Glu Lys His Leu Phe
            340                 345                 350

Ser Thr Ile Pro Glu Leu Ile Asn Tyr His Gln His Asn Ser Ala Gly
        355                 360                 365

Leu Ile Ser Arg Leu Lys Tyr Pro Val Ser Gln Gln Asn Lys Asn Ala
    370                 375                 380

Pro Ser Thr Ala Gly Leu Gly Tyr Gly Ser Trp Glu Ile Asp Pro Lys
385                 390                 395                 400

Asp Leu Thr Phe Leu Lys Glu Leu Gly Thr Gly Gln Phe Gly Val Val
                405                 410                 415

Lys Tyr Gly Lys Trp Arg Gly Gln Tyr Asp Val Ala Ile Lys Met Ile
            420                 425                 430
```

Lys Glu Gly Ser Met Ser Glu Asp Glu Phe Ile Glu Glu Ala Lys Val
435 440 445

Met Met Asn Leu Ser His Glu Lys Leu Val Gln Leu Tyr Gly Val Cys
450 455 460

Thr Lys Gln Arg Pro Ile Phe Ile Ile Thr Glu Tyr Met Ala Asn Gly
465 470 475 480

Cys Leu Leu Asn Tyr Leu Arg Glu Met Arg His Arg Phe Gln Thr Gln
485 490 495

Gln Leu Leu Glu Met Cys Lys Asp Val Cys Glu Ala Met Glu Tyr Leu
500 505 510

Glu Ser Lys Gln Phe Leu His Arg Asp Leu Ala Ala Arg Asn Cys Leu
515 520 525

Val Asn Asp Gln Gly Val Val Lys Val Ser Asp Phe Gly Leu Ser Arg
530 535 540

Tyr Val Leu Asp Asp Glu Tyr Thr Ser Ser Val Gly Ser Lys Phe Pro
545 550 555 560

Val Arg Trp Ser Pro Pro Glu Val Leu Met Tyr Ser Lys Phe Ser Ser
565 570 575

Lys Ser Asp Ile Trp Ala Phe Gly Val Leu Met Trp Glu Ile Tyr Ser
580 585 590

Leu Gly Lys Met Pro Tyr Glu Arg Phe Thr Asn Ser Glu Thr Ala Glu
595 600 605

His Ile Ala Gln Gly Leu Arg Leu Tyr Arg Pro His Leu Ala Ser Glu
610 615 620

Lys Val Tyr Thr Ile Met Tyr Ser Cys Trp His Glu Lys Ala Asp Glu
625 630 635 640

Arg Pro Thr Phe Lys Ile Leu Leu Ser Asn Ile Leu Asp Val Met Asp
645 650 655

Glu Glu Ser

<210> SEQ ID NO 115
<211> LENGTH: 225
<212> TYPE: PRT
<213> ORGANISM: Artificial Sequence
<220> FEATURE:
<223> OTHER INFORMATION: Synthetic: SOCS3; P4030 without epitope tag

<400> SEQUENCE: 115

Met Val Thr His Ser Lys Phe Pro Ala Ala Gly Met Ser Arg Pro Leu
1 5 10 15

Asp Thr Ser Leu Arg Leu Lys Thr Phe Ser Ser Lys Ser Glu Tyr Gln
20 25 30

Leu Val Val Asn Ala Val Arg Lys Leu Gln Glu Ser Gly Phe Tyr Trp
35 40 45

Ser Ala Val Thr Gly Gly Glu Ala Asn Leu Leu Leu Ser Ala Glu Pro
50 55 60

Ala Gly Thr Phe Leu Ile Arg Asp Ser Ser Asp Gln Arg His Phe Phe
65 70 75 80

Thr Leu Ser Val Lys Thr Gln Ser Gly Thr Lys Asn Leu Arg Ile Gln
85 90 95

Cys Glu Gly Gly Ser Phe Ser Leu Gln Ser Asp Pro Arg Ser Thr Gln
100 105 110

Pro Val Pro Arg Phe Asp Cys Val Leu Lys Leu Val His His Tyr Met
115 120 125

Pro Pro Pro Gly Ala Pro Ser Phe Pro Ser Pro Pro Thr Glu Pro Ser

```
    130                 135                 140

Ser Glu Val Pro Glu Gln Pro Ser Ala Gln Pro Leu Pro Gly Ser Pro
145                 150                 155                 160

Pro Arg Arg Ala Tyr Tyr Ile Tyr Ser Gly Gly Glu Lys Ile Pro Leu
                165                 170                 175

Val Leu Ser Arg Pro Leu Ser Ser Asn Val Ala Thr Leu Gln His Leu
            180                 185                 190

Cys Arg Lys Thr Val Asn Gly His Leu Asp Ser Tyr Glu Lys Val Thr
        195                 200                 205

Gln Leu Pro Gly Pro Ile Arg Glu Phe Leu Asp Gln Tyr Asp Ala Pro
    210                 215                 220

Leu
225


<210> SEQ ID NO 116
<211> LENGTH: 347
<212> TYPE: PRT
<213> ORGANISM: Homo sapiens
<220> FEATURE:
<221> NAME/KEY: misc_feature
<222> LOCATION: (1)..(347)
<223> OTHER INFORMATION: IZ_hsCASP1 (self-activating human Caspase 1);
      P2024 without epitope tag

<400> SEQUENCE: 116

Met Arg Met Lys Gln Ile Glu Asp Lys Ile Glu Glu Ile Leu Ser Lys
1               5                   10                  15

Ile Tyr His Ile Glu Asn Glu Ile Ala Arg Ile Lys Lys Leu Ile Gly
            20                  25                  30

Glu Ala Asp Gln Thr Ser Gly Asn Tyr Leu Asn Met Gln Asp Ser Gln
        35                  40                  45

Gly Val Leu Ser Ser Phe Pro Ala Pro Gln Ala Val Gln Asp Asn Pro
    50                  55                  60

Ala Met Pro Thr Ser Ser Gly Ser Glu Gly Asn Val Lys Leu Cys Ser
65                  70                  75                  80

Leu Glu Glu Ala Gln Arg Ile Trp Lys Gln Lys Ser Ala Glu Ile Tyr
                85                  90                  95

Pro Ile Met Asp Lys Ser Ser Arg Thr Arg Leu Ala Leu Ile Ile Cys
            100                 105                 110

Asn Glu Glu Phe Asp Ser Ile Pro Arg Arg Thr Gly Ala Glu Val Asp
        115                 120                 125

Ile Thr Gly Met Thr Met Leu Leu Gln Asn Leu Gly Tyr Ser Val Asp
    130                 135                 140

Val Lys Lys Asn Leu Thr Ala Ser Asp Met Thr Thr Glu Leu Glu Ala
145                 150                 155                 160

Phe Ala His Arg Pro Glu His Lys Thr Ser Asp Ser Thr Phe Leu Val
                165                 170                 175

Phe Met Ser His Gly Ile Arg Glu Gly Ile Cys Gly Lys Lys His Ser
            180                 185                 190

Glu Gln Val Pro Asp Ile Leu Gln Leu Asn Ala Ile Phe Asn Met Leu
        195                 200                 205

Asn Thr Lys Asn Cys Pro Ser Leu Lys Asp Lys Pro Lys Val Ile Ile
    210                 215                 220

Ile Gln Ala Cys Arg Gly Asp Ser Pro Gly Val Val Trp Phe Lys Asp
225                 230                 235                 240

Ser Val Gly Val Ser Gly Asn Leu Ser Leu Pro Thr Thr Glu Glu Phe
```

```
                245                 250                 255

Glu Asp Asp Ala Ile Lys Lys Ala His Ile Glu Lys Asp Phe Ile Ala
            260                 265                 270

Phe Cys Ser Ser Thr Pro Asp Asn Val Ser Trp Arg His Pro Thr Met
        275                 280                 285

Gly Ser Val Phe Ile Gly Arg Leu Ile Glu His Met Gln Glu Tyr Ala
    290                 295                 300

Cys Ser Cys Asp Val Glu Glu Ile Phe Arg Lys Val Arg Phe Ser Phe
305                 310                 315                 320

Glu Gln Pro Asp Gly Arg Ala Gln Met Pro Thr Thr Glu Arg Val Thr
                325                 330                 335

Leu Thr Arg Cys Phe Tyr Leu Phe Pro Gly His
            340                 345


<210> SEQ ID NO 117
<211> LENGTH: 347
<212> TYPE: PRT
<213> ORGANISM: Homo sapiens
<220> FEATURE:
<221> NAME/KEY: misc_feature
<222> LOCATION: (1)..(347)
<223> OTHER INFORMATION: DM_hsCASP1 (self-activating human Caspase 1);
      P2025 without epitope tag

<400> SEQUENCE: 117

Met Arg Met Lys Gln Leu Glu Asp Lys Ile Glu Glu Leu Leu Ser Lys
1               5                   10                  15

Ile Tyr His Leu Glu Asn Glu Ile Ala Arg Leu Lys Lys Leu Ile Gly
            20                  25                  30

Glu Ala Asp Gln Thr Ser Gly Asn Tyr Leu Asn Met Gln Asp Ser Gln
        35                  40                  45

Gly Val Leu Ser Ser Phe Pro Ala Pro Gln Ala Val Gln Asp Asn Pro
    50                  55                  60

Ala Met Pro Thr Ser Ser Gly Ser Glu Gly Asn Val Lys Leu Cys Ser
65                  70                  75                  80

Leu Glu Glu Ala Gln Arg Ile Trp Lys Gln Lys Ser Ala Glu Ile Tyr
                85                  90                  95

Pro Ile Met Asp Lys Ser Ser Arg Thr Arg Leu Ala Leu Ile Ile Cys
            100                 105                 110

Asn Glu Glu Phe Asp Ser Ile Pro Arg Arg Thr Gly Ala Glu Val Asp
        115                 120                 125

Ile Thr Gly Met Thr Met Leu Leu Gln Asn Leu Gly Tyr Ser Val Asp
    130                 135                 140

Val Lys Lys Asn Leu Thr Ala Ser Asp Met Thr Thr Glu Leu Glu Ala
145                 150                 155                 160

Phe Ala His Arg Pro Glu His Lys Thr Ser Asp Ser Thr Phe Leu Val
                165                 170                 175

Phe Met Ser His Gly Ile Arg Glu Gly Ile Cys Gly Lys Lys His Ser
            180                 185                 190

Glu Gln Val Pro Asp Ile Leu Gln Leu Asn Ala Ile Phe Asn Met Leu
        195                 200                 205

Asn Thr Lys Asn Cys Pro Ser Leu Lys Asp Lys Pro Lys Val Ile Ile
    210                 215                 220

Ile Gln Ala Cys Arg Gly Asp Ser Pro Gly Val Val Trp Phe Lys Asp
225                 230                 235                 240

Ser Val Gly Val Ser Gly Asn Leu Ser Leu Pro Thr Thr Glu Glu Phe
```

-continued

```
                245                 250                 255

Glu Asp Asp Ala Ile Lys Lys Ala His Ile Glu Lys Asp Phe Ile Ala
            260                 265                 270

Phe Cys Ser Ser Thr Pro Asp Asn Val Ser Trp Arg His Pro Thr Met
        275                 280                 285

Gly Ser Val Phe Ile Gly Arg Leu Ile Glu His Met Gln Glu Tyr Ala
    290                 295                 300

Cys Ser Cys Asp Val Glu Glu Ile Phe Arg Lys Val Arg Phe Ser Phe
305                 310                 315                 320

Glu Gln Pro Asp Gly Arg Ala Gln Met Pro Thr Thr Glu Arg Val Thr
                325                 330                 335

Leu Thr Arg Cys Phe Tyr Leu Phe Pro Gly His
            340                 345


<210> SEQ ID NO 118
<211> LENGTH: 346
<212> TYPE: PRT
<213> ORGANISM: Mus musculus
<220> FEATURE:
<221> NAME/KEY: misc_feature
<222> LOCATION: (1)..(346)
<223> OTHER INFORMATION: IZ_mmCASP1 (self-activating mouse Caspase 1);
      P2026 without epitope tag

<400> SEQUENCE: 118

Met Arg Met Lys Gln Ile Glu Asp Lys Ile Glu Glu Ile Leu Ser Lys
1               5                   10                  15

Ile Tyr His Ile Glu Asn Glu Ile Ala Arg Ile Lys Lys Leu Ile Gly
            20                  25                  30

Glu Arg Ser Ala Pro Ser Ala Glu Thr Phe Val Ala Thr Glu Asp Ser
        35                  40                  45

Lys Gly Gly His Pro Ser Ser Ser Glu Thr Lys Glu Glu Gln Asn Lys
    50                  55                  60

Glu Asp Gly Thr Phe Pro Gly Leu Thr Gly Thr Leu Lys Phe Cys Pro
65                  70                  75                  80

Leu Glu Lys Ala Gln Lys Leu Trp Lys Glu Asn Pro Ser Glu Ile Tyr
                85                  90                  95

Pro Ile Met Asn Thr Thr Thr Arg Thr Arg Leu Ala Leu Ile Ile Cys
            100                 105                 110

Asn Thr Glu Phe Gln His Leu Ser Pro Arg Val Gly Ala Gln Val Asp
        115                 120                 125

Leu Arg Glu Met Lys Leu Leu Leu Glu Asp Leu Gly Tyr Thr Val Lys
    130                 135                 140

Val Lys Glu Asn Leu Thr Ala Leu Glu Met Val Lys Glu Val Lys Glu
145                 150                 155                 160

Phe Ala Ala Cys Pro Glu His Lys Thr Ser Asp Ser Thr Phe Leu Val
                165                 170                 175

Phe Met Ser His Gly Ile Gln Glu Gly Ile Cys Gly Thr Thr Tyr Ser
            180                 185                 190

Asn Glu Val Ser Asp Ile Leu Lys Val Asp Thr Ile Phe Gln Met Met
        195                 200                 205

Asn Thr Leu Lys Cys Pro Ser Leu Lys Asp Lys Pro Lys Val Ile Ile
    210                 215                 220

Ile Gln Ala Cys Arg Gly Glu Lys Gln Gly Val Val Leu Leu Lys Asp
225                 230                 235                 240

Ser Val Arg Asp Ser Glu Glu Asp Phe Leu Thr Asp Ala Ile Phe Glu
```

```
                245                 250                 255

Asp Asp Gly Ile Lys Lys Ala His Ile Glu Lys Asp Phe Ile Ala Phe
            260                 265                 270

Cys Ser Ser Thr Pro Asp Asn Val Ser Trp Arg His Pro Val Arg Gly
        275                 280                 285

Ser Leu Phe Ile Glu Ser Leu Ile Lys His Met Lys Glu Tyr Ala Trp
    290                 295                 300

Ser Cys Asp Leu Glu Asp Ile Phe Arg Lys Val Arg Phe Ser Phe Glu
305                 310                 315                 320

Gln Pro Glu Phe Arg Leu Gln Met Pro Thr Ala Asp Arg Val Thr Leu
                325                 330                 335

Thr Lys Arg Phe Tyr Leu Phe Pro Gly His
            340                 345


<210> SEQ ID NO 119
<211> LENGTH: 346
<212> TYPE: PRT
<213> ORGANISM: Mus musculus
<220> FEATURE:
<221> NAME/KEY: misc_feature
<222> LOCATION: (1)..(346)
<223> OTHER INFORMATION: DM_mmCASP1 (self-activating mouse Caspase 1);
      P2027 without epitope tag

<400> SEQUENCE: 119

Met Arg Met Lys Gln Leu Glu Asp Lys Ile Glu Glu Leu Leu Ser Lys
1               5                   10                  15

Ile Tyr His Leu Glu Asn Glu Ile Ala Arg Leu Lys Lys Leu Ile Gly
            20                  25                  30

Glu Arg Ser Ala Pro Ser Ala Glu Thr Phe Val Ala Thr Glu Asp Ser
        35                  40                  45

Lys Gly Gly His Pro Ser Ser Ser Glu Thr Lys Glu Glu Gln Asn Lys
    50                  55                  60

Glu Asp Gly Thr Phe Pro Gly Leu Thr Gly Thr Leu Lys Phe Cys Pro
65                  70                  75                  80

Leu Glu Lys Ala Gln Lys Leu Trp Lys Glu Asn Pro Ser Glu Ile Tyr
                85                  90                  95

Pro Ile Met Asn Thr Thr Thr Arg Thr Arg Leu Ala Leu Ile Ile Cys
            100                 105                 110

Asn Thr Glu Phe Gln His Leu Ser Pro Arg Val Gly Ala Gln Val Asp
        115                 120                 125

Leu Arg Glu Met Lys Leu Leu Leu Glu Asp Leu Gly Tyr Thr Val Lys
    130                 135                 140

Val Lys Glu Asn Leu Thr Ala Leu Glu Met Val Lys Glu Val Lys Glu
145                 150                 155                 160

Phe Ala Ala Cys Pro Glu His Lys Thr Ser Asp Ser Thr Phe Leu Val
                165                 170                 175

Phe Met Ser His Gly Ile Gln Glu Gly Ile Cys Gly Thr Thr Tyr Ser
            180                 185                 190

Asn Glu Val Ser Asp Ile Leu Lys Val Asp Thr Ile Phe Gln Met Met
        195                 200                 205

Asn Thr Leu Lys Cys Pro Ser Leu Lys Asp Lys Pro Lys Val Ile Ile
    210                 215                 220

Ile Gln Ala Cys Arg Gly Glu Lys Gln Gly Val Val Leu Leu Lys Asp
225                 230                 235                 240

Ser Val Arg Asp Ser Glu Glu Asp Phe Leu Thr Asp Ala Ile Phe Glu
```

```
                245                 250                 255

Asp Asp Gly Ile Lys Lys Ala His Ile Glu Lys Asp Phe Ile Ala Phe
            260                 265                 270

Cys Ser Ser Thr Pro Asp Asn Val Ser Trp Arg His Pro Val Arg Gly
        275                 280                 285

Ser Leu Phe Ile Glu Ser Leu Ile Lys His Met Lys Glu Tyr Ala Trp
    290                 295                 300

Ser Cys Asp Leu Glu Asp Ile Phe Arg Lys Val Arg Phe Ser Phe Glu
305                 310                 315                 320

Gln Pro Glu Phe Arg Leu Gln Met Pro Thr Ala Asp Arg Val Thr Leu
                325                 330                 335

Thr Lys Arg Phe Tyr Leu Phe Pro Gly His
            340                 345


<210> SEQ ID NO 120
<211> LENGTH: 106
<212> TYPE: PRT
<213> ORGANISM: Artificial Sequence
<220> FEATURE:
<223> OTHER INFORMATION: Synthetic: ADR concatemer with HIS tag

<400> SEQUENCE: 120

Met His His His His His His His His His His Gly Lys Pro Ile Pro
1               5                   10                  15

Asn Pro Leu Leu Gly Leu Asp Ser Thr Gly Ile Pro Val His Leu Glu
            20                  25                  30

Leu Ala Ser Met Thr Asn Met Glu Leu Met Ser Ser Ile Val His Gln
        35                  40                  45

Gln Val Phe Pro Thr Glu Ala Gly Gln Ser Leu Val Ile Ser Ala Ser
    50                  55                  60

Ile Ile Val Phe Asn Leu Leu Glu Leu Glu Gly Asp Tyr Arg Gly Arg
65                  70                  75                  80

Val Leu Glu Leu Phe Arg Ala Ala Gln Leu Ala Asn Asp Val Val Leu
                85                  90                  95

Gln Ile Met Glu Leu Cys Gly Ala Thr Arg
            100                 105


<210> SEQ ID NO 121
<211> LENGTH: 9
<212> TYPE: PRT
<213> ORGANISM: Artificial Sequence
<220> FEATURE:
<223> OTHER INFORMATION: Synthetic: KRAS G12D 9mer

<400> SEQUENCE: 121

Val Val Gly Ala Asp Gly Val Gly Lys
1               5


<210> SEQ ID NO 122
<211> LENGTH: 9
<212> TYPE: PRT
<213> ORGANISM: Artificial Sequence
<220> FEATURE:
<223> OTHER INFORMATION: Synthetic: KRAS G12V 9mer

<400> SEQUENCE: 122

Val Val Gly Ala Val Gly Val Gly Lys
1               5


<210> SEQ ID NO 123
```

<211> LENGTH: 9
<212> TYPE: PRT
<213> ORGANISM: Artificial Sequence
<220> FEATURE:
<223> OTHER INFORMATION: Synthetic: KRAS G13D 9mer

<400> SEQUENCE: 123

Val Gly Ala Gly Asp Val Gly Lys Ser
1 5

<210> SEQ ID NO 124
<211> LENGTH: 9
<212> TYPE: PRT
<213> ORGANISM: Artificial Sequence
<220> FEATURE:
<223> OTHER INFORMATION: Synthetic: KRAS G12C 9mer

<400> SEQUENCE: 124

Val Val Gly Ala Cys Gly Val Gly Lys
1 5

<210> SEQ ID NO 125
<211> LENGTH: 15
<212> TYPE: PRT
<213> ORGANISM: Artificial Sequence
<220> FEATURE:
<223> OTHER INFORMATION: Synthetic: KRAS G12C 15mer

<400> SEQUENCE: 125

Met Lys Leu Val Val Val Gly Ala Cys Gly Val Gly Lys Ser Ala
1 5 10 15

<210> SEQ ID NO 126
<211> LENGTH: 75
<212> TYPE: DNA
<213> ORGANISM: Artificial Sequence
<220> FEATURE:
<223> OTHER INFORMATION: Synthetic: KRAS G12D 25mer nucleotide sequence

<400> SEQUENCE: 126
atgaccgagt acaagctggt ggtggtgggc gccgacggcg tgggcaagag cgccctgacc 60
atccagctga tccag 75

<210> SEQ ID NO 127
<211> LENGTH: 75
<212> TYPE: DNA
<213> ORGANISM: Artificial Sequence
<220> FEATURE:
<223> OTHER INFORMATION: Synthetic: KRAS G12V 25mer nucleotide sequence

<400> SEQUENCE: 127
atgaccgagt acaagctggt ggtggtgggc gccgtgggcg tgggcaagag cgccctgacc 60
atccagctga tccag 75

<210> SEQ ID NO 128
<211> LENGTH: 75
<212> TYPE: DNA
<213> ORGANISM: Artificial Sequence
<220> FEATURE:
<223> OTHER INFORMATION: Synthetic: KRAS G13D 25mer nucleotide sequence

<400> SEQUENCE: 128
atgaccgagt acaagctggt ggtggtgggc gccggcgacg tgggcaagag cgccctgacc 60
atccagctga tccag 75

<210> SEQ ID NO 129
<211> LENGTH: 225
<212> TYPE: DNA
<213> ORGANISM: Artificial Sequence
<220> FEATURE:
<223> OTHER INFORMATION: Synthetic: KRAS G12D 25mer^3 nucleotide sequence

<400> SEQUENCE: 129
atgaccgagt acaagttagt ggttgtgggc gccgacggcg tgggcaagag cgccctcacc 60
atccagctta tccagatgac ggaatataag ttagtagtag tgggagccga cggtgtcggc 120
aagtccgctt tgaccattca acttattcag atgacagagt ataagctggt cgttgtaggc 180
gcagacggcg ttggaaagtc ggcactgacg atccagttga tccag 225

<210> SEQ ID NO 130
<211> LENGTH: 225
<212> TYPE: DNA
<213> ORGANISM: Artificial Sequence
<220> FEATURE:
<223> OTHER INFORMATION: Synthetic: KRAS G12V 25mer^3 nucleotide sequence

<400> SEQUENCE: 130
atgaccgagt acaagctcgt cgtggtgggc gccgtgggcg tgggcaagag cgccctaacc 60
atccagttga tccagatgac cgaatataag ctcgtggtag tcggagcggt gggcgttggc 120
aagtcagcgc taacaataca actaatccaa atgaccgaat acaagctagt tgtagtcggt 180
gccgtcggcg ttggaaagtc agcccttaca attcagctca ttcag 225

<210> SEQ ID NO 131
<211> LENGTH: 225
<212> TYPE: DNA
<213> ORGANISM: Artificial Sequence
<220> FEATURE:
<223> OTHER INFORMATION: Synthetic: KRAS G13D 25mer^3 nucleotide sequence

<400> SEQUENCE: 131
atgaccgagt acaagctcgt agtggttggc gccggcgacg tgggcaagag cgccctaacc 60
atccagctca tccagatgac agaatataag cttgtggttg tgggagcagg agacgtggga 120
aagagtgcgt tgacgattca actcatacag atgaccgaat acaagttggt ggtggtcggc 180
gcaggtgacg ttggtaagtc tgcactaact atacaactga tccag 225

<210> SEQ ID NO 132
<211> LENGTH: 75
<212> TYPE: DNA
<213> ORGANISM: Artificial Sequence
<220> FEATURE:
<223> OTHER INFORMATION: Synthetic: KRAS G12C 25mer nucleotide sequence

<400> SEQUENCE: 132
atgaccgagt acaagctggt ggtggtgggc gcctgcggcg tgggcaagag cgccctgacc 60
atccagctga tccag 75

<210> SEQ ID NO 133
<211> LENGTH: 75
<212> TYPE: DNA
<213> ORGANISM: Artificial Sequence
<220> FEATURE:
<223> OTHER INFORMATION: Synthetic: KRAS WT 25mer nucleotide sequence

<400> SEQUENCE: 133
atgaccgagt acaagctggt ggtggtgggc gccggcggcg tgggcaagag cgccctgacc 60
atccagctga tccag 75

<210> SEQ ID NO 134
<211> LENGTH: 47
<212> TYPE: DNA
<213> ORGANISM: Artificial Sequence
<220> FEATURE:
<223> OTHER INFORMATION: Synthetic: 5 UTR sequence; no promoter

<400> SEQUENCE: 134
gggaaataag agagaaaaga agagtaagaa gaaatataag agccacc 47

<210> SEQ ID NO 135
<211> LENGTH: 75
<212> TYPE: PRT
<213> ORGANISM: Artificial Sequence
<220> FEATURE:
<223> OTHER INFORMATION: Synthetic: KRAS(G12D G12V G13D) 75mer 3MUT aa. seq

<400> SEQUENCE: 135

Met Thr Glu Tyr Lys Leu Val Val Val Gly Ala Asp Gly Val Gly Lys
1 5 10 15

Ser Ala Leu Thr Ile Gln Leu Ile Gln Met Thr Glu Tyr Lys Leu Val
20 25 30

Val Val Gly Ala Val Gly Val Gly Lys Ser Ala Leu Thr Ile Gln Leu
35 40 45

Ile Gln Met Thr Glu Tyr Lys Leu Val Val Val Gly Ala Gly Asp Val
50 55 60

Gly Lys Ser Ala Leu Thr Ile Gln Leu Ile Gln
65 70 75

<210> SEQ ID NO 136
<211> LENGTH: 225
<212> TYPE: DNA
<213> ORGANISM: Artificial Sequence
<220> FEATURE:
<223> OTHER INFORMATION: Synthetic: KRAS(G12D G12V G13D) 75mer 3MUT nt. seq

<400> SEQUENCE: 136
atgaccgagt acaagctcgt tgtagtcggc gccgacggcg tgggcaagag cgccttgacc 60
atccagttga tccagatgac cgaatataag ttggtggtgg taggcgcagt gggagttggc 120
aagtcagcac tcacaattca gctcattcaa atgacagaat acaagttagt cgttgtagga 180
gcaggcgacg tcggcaagag tgccttaacc attcaactaa tccag 225

<210> SEQ ID NO 137
<211> LENGTH: 100
<212> TYPE: PRT
<213> ORGANISM: Artificial Sequence
<220> FEATURE:
<223> OTHER INFORMATION: Synthetic: KRAS(G12D G12V G13D G12C) 100mer 4MUT aa. seq

<400> SEQUENCE: 137

Met Thr Glu Tyr Lys Leu Val Val Val Gly Ala Asp Gly Val Gly Lys
1 5 10 15

Ser Ala Leu Thr Ile Gln Leu Ile Gln Met Thr Glu Tyr Lys Leu Val
20 25 30

```
Val Val Gly Ala Val Gly Val Gly Lys Ser Ala Leu Thr Ile Gln Leu
        35                  40                  45

Ile Gln Met Thr Glu Tyr Lys Leu Val Val Val Gly Ala Gly Asp Val
    50                  55                  60

Gly Lys Ser Ala Leu Thr Ile Gln Leu Ile Gln Met Thr Glu Tyr Lys
65                  70                  75                  80

Leu Val Val Val Gly Ala Cys Gly Val Gly Lys Ser Ala Leu Thr Ile
                85                  90                  95

Gln Leu Ile Gln
            100


<210> SEQ ID NO 138
<211> LENGTH: 300
<212> TYPE: DNA
<213> ORGANISM: Artificial Sequence
<220> FEATURE:
<223> OTHER INFORMATION: Synthetic: KRAS(G12D G12V G13D G12C) 100mer
      4MUT nt. seq

<400> SEQUENCE: 138

atgaccgagt acaagctcgt ggtcgtcggc gccgacgggg taggcaagtc cgctctgacc     60

attcagctca tccagatgac ggagtacaaa ctcgtggtag tgggagccgt gggtgtgggc    120

aagagcgcgc tcaccatcca actcatccaa atgaccgaat ataaactcgt cgtggtggga    180

gccggcgacg tgggaaagag cgcccttacc atccagttaa tccagatgac agaatacaag    240

ctggtggtgg tcggtgcctg cggcgtgggt aagtccgccc tgacaatcca gctgatccag    300


<210> SEQ ID NO 139
<211> LENGTH: 1137
<212> TYPE: DNA
<213> ORGANISM: Artificial Sequence
<220> FEATURE:
<223> OTHER INFORMATION: Synthetic: huSTING(V155M); no epitope tag;
      nucleotide sequence

<400> SEQUENCE: 139

atgccccaca gtagcctcca ccccagcatc ccctgcccca gaggccacgg cgcacagaag     60

gccgccctgg tgctgctgag cgcctgtctg gtgaccctgt ggggtctggg cgagcccccc    120

gagcacaccc tgcggtacct cgtgctgcat ctggccagcc tgcagctggg cctgctgctg    180

aacggcgtgt gcagcctggc cgaagagctg agacacatcc acagcagata cagaggctcc    240

tactggagaa ccgtcagagc ctgcctcggc tgtcccctga gaagaggcgc cctgctgctc    300

ctgagcatct acttctacta cagcctgccc aacgccgtgg gcccccccctt cacctggatg    360

ctggccctgc tgggcctgag ccaggccctg aacatcctgc tgggcctgaa gggcttggcc    420

cccgccgaga tctccgccgt gtgcgagaag ggcaacttca acatggccca tggccttgcc    480

tggtcctact acatcggcta cctgagactg atcctgcccg agctgcaggc cagaatcaga    540

acctacaacc agcactacaa caacctgctg agaggcgccg tgagccaaag actgtacatc    600

ctgctgcccc tggactgcgg cgtgcccgac aaccttagca tggccgaccc caacatcaga    660

ttcctggaca agctgcccca gcagaccggc gaccacgccg gcatcaagga cagagtgtac    720

agcaacagca tctacgagct gctggagaac ggccagagag ccggcacctg cgtgctggag    780

tacgccaccc ccctgcagac cctgttcgcc atgagccagt acagccaggc cggcttcagc    840

agagaggaca gactggagca agccaagctg ttctgcagaa ccctggagga catcctggcg    900

gacgcccccg agagccaaaa caactgcaga ctgatcgcct accaggagcc cgccgacgac    960
```

agcagcttca gcctgagcca ggaagtgctg agacacctga gacaggaaga gaaggaggag 1020
gtgaccgtgg gaagcctgaa gaccagcgcc gtgcccagca ccagcaccat gagccaggag 1080
cccgagctgc tgatcagcgg catggagaag cccctgcccc tgagaaccga cttcagc 1137

<210> SEQ ID NO 140
<211> LENGTH: 1137
<212> TYPE: DNA
<213> ORGANISM: Artificial Sequence
<220> FEATURE:
<223> OTHER INFORMATION: Synthetic: Hu STING(R284T); no epitope tag;
nucleotide sequence

<400> SEQUENCE: 140
atgcctcaca gcagcctgca ccctagcatc ccttgcccta gaggccacgg cgcccagaag 60
gccgccctgg tgctgctgag cgcctgcctg gtgaccctgt ggggcctggg cgagcctcct 120
gagcacaccc tgagatacct ggtgctgcac ctggccagcc tgcagctggg cctgctgctg 180
aacggcgtgt gcagcctggc cgaggagctg agacacatcc acagcagata cagaggcagc 240
tactggagaa ccgtgagagc ctgcctgggc tgccctctga gaagaggcgc cctgctgctg 300
ctgagcatct acttctacta cagcctgcct aacgccgtgg gccctccttt cacctggatg 360
ctggccctgc tgggcctgag ccaggccctg aacatcctgc tgggcctgaa gggcctggcc 420
cctgccgaga tcagcgccgt gtgcgagaag ggcaacttca acgtggccca cggcctggcc 480
tggagctact acatcggcta cctgagactg atcctgcctg agctgcaggc cagaatcaga 540
acctacaacc agcactacaa caacctgctg agaggcgccg tgagccagag actgtacatc 600
ctgctgcctc tggactgcgg cgtgcctgac aacctgagca tggccgaccc taacatcaga 660
ttcctggaca agctgcctca gcagaccggc gaccacgccg gcatcaagga cagagtgtac 720
agcaacagca tctacgagct gctggagaac ggccagagag ccggcacctg cgtgctggag 780
tacgccaccc ctctgcagac cctgttcgcc atgagccagt acagccaggc cggcttcagc 840
agagaggaca ccctggagca ggccaagctg ttctgcagaa ccctggagga catcctggcc 900
gacgcccctg agagccagaa caactgcaga ctgatcgcct accaggagcc tgccgacgac 960
agcagcttca gcctgagcca ggaggtgctg agacacctga gacaggagga gaaggaggag 1020
gtgaccgtgg gcagcctgaa gaccagcgcc gtgcctagca ccagcaccat gagccaggag 1080
cctgagctgc tgatcagcgg catggagaag cctctgcctc tgagaaccga cttcagc 1137

<210> SEQ ID NO 141
<211> LENGTH: 1137
<212> TYPE: DNA
<213> ORGANISM: Artificial Sequence
<220> FEATURE:
<223> OTHER INFORMATION: Synthetic: hu STING (R284M); no epitope tag;
nucleotide sequence

<400> SEQUENCE: 141
atgccccaca gcagcctgca cccctccatc ccctgtccca gaggccacgg cgcccagaag 60
gccgccctgg tgctgctgag cgcctgcctg gtgaccttat ggggcctggg cgagcccccc 120
gagcacaccc tgagatacct ggtcctgcac ctggccagcc tccagctggg cctgctgctc 180
aacggcgtgt gtagcctggc cgaggagctg agacacatcc acagcagata cagaggcagc 240
tactggagaa ccgtgagagc ctgcctgggt tgcccactga gaagaggagc tctgctgctg 300
ctgagcatct acttctacta ctcgctgccc aacgctgtgg gccccccctt cacctggatg 360
ctggccctgc tgggtctgag ccaggccctg aacatcctcc tgggcctgaa gggcctggcc 420
cccgccgaga taagcgccgt ttgcgagaag ggcaacttca acgtggccca tggcctggcc 480
tggagctact acatcggcta cttacgcctg atcctgcccg agctgcaggc cagaatcaga 540
acctacaacc agcattacaa caacctgctg agaggcgccg tgagccagag actgtatatc 600
ctgctgcccc tggactgcgg cgtgcccgac aacctgagca tggccgaccc caacatcaga 660
ttcctggaca agctccccca gcagaccggc gaccacgccg gaatcaaaga cagagtgtat 720
agcaacagca tctacgagct gctggagaac ggccagagag ccggcacctg cgtactggag 780
tacgccaccc ccttgcagac cctgtttgcc atgagccagt acagccaggc cggcttcagc 840
agagaggaca tgctggagca ggccaagctg ttctgcagaa ccctggagga catcctggcc 900 gacgccccccg agagccagaa caactgcaga ctgatcgcct accaagagcc cgccgacgac 960
agcagcttca gcttaagcca ggaggtgctg agacatctga gacaggagga gaaggaggag 1020
gtgaccgtgg gcagcctcaa gaccagcgct gtgccctcta ccagcaccat gagccaggag 1080
cccgagctgc tgatcagcgg catggagaag cccctgcccc tgagaacaga cttcagc 1137

<210> SEQ ID NO 142
<211> LENGTH: 1137
<212> TYPE: DNA
<213> ORGANISM: Artificial Sequence
<220> FEATURE:
<223> OTHER INFORMATION: Synthetic: Hu STING (R284K); no epitope tag; nucleotide sequence

<400> SEQUENCE: 142
atgccccata gcagcctgca ccccagcatc ccctgcccca gaggccacgg cgcccagaag 60
gccgccctgg tcctgctgag cgcatgcctg gtcaccctgt ggggcctggg cgagcccccc 120
gagcacaccc tgagatacct ggtgctgcac ctcgccagcc tgcagctggg cctgctgctg 180
aacggcgtgt gcagcctggc cgaggagctg agacacatcc acagcagata tagaggcagc 240
tactggagaa ccgtgagagc ttgcctcggc tgccccctga gaagaggcgc cctgctgctg 300
ctgagcatct acttttacta cagcctgccc aacgctgtgg gcccccccttt cacgtggatg 360 ctcgccctgc tgggactgag ccaggccctg aacatcctgc tgggccttaa gggcctagcc 420
cccgccgaga tcagcgccgt gtgcgagaag ggcaacttca atgtggccca cggcctggcc 480
tggagctact acatcggcta cctgagactg atcctgcccg agctgcaggc cagaatcaga 540
acctacaatc agcactacaa caacctgctg agaggcgccg tgagccagag actgtacatc 600
ctgctgcccc tggactgcgg cgtgcccgac aacctcagca tggccgaccc caacatcaga 660
ttcctggaca agctgcccca gcagaccggc gaccacgccg gcatcaagga tcgcgtgtac 720
agcaacagca tctacgagct gctggaaaac ggccagagag ccggaacctg cgtgctggag 780
tacgccacac ccctgcagac cctgttcgcc atgagccagt acagccaggc cggcttcagc 840
agagaggaca agctggagca ggccaagctg ttctgcagaa ccctggagga tatcctcgcc 900
gacgcccccg agagccagaa caactgcagg ctgatcgcgt accaggagcc cgctgacgac 960
agcagcttta gcctgagcca ggaggtgctg agacatctgc gtcaagagga aaaggaggag 1020
gtgaccgtgg gctccctgaa gaccagcgcc gtgcccagca ccagcaccat gagccaggag 1080
cccgagctgc tgatcagcgg catggagaag ccactgcccc tcagaaccga cttcagc 1137

<210> SEQ ID NO 143
<211> LENGTH: 1137
<212> TYPE: DNA

<213> ORGANISM: Artificial Sequence
<220> FEATURE:
<223> OTHER INFORMATION: Synthetic: Hu STING(N154S); no epitope tag; nucleotide sequence

<400> SEQUENCE: 143
atgcctcaca gcagcctgca ccctagcatc ccttgcccta gaggccacgg cgcccagaag 60
gccgccctgg tgctgctgag cgcctgcctg gtgaccctgt ggggcctggg cgagcctcct 120
gagcacaccc tgagatacct ggtgctgcac ctggccagcc tgcagctggg cctgctgctg 180
aacggcgtgt gcagcctggc cgaggagctg agacacatcc acagcagata cagaggcagc 240
tactggagaa ccgtgagagc ctgcctgggc tgccctctga gaagaggcgc cctgctgctg 300
ctgagcatct acttctacta cagcctgcct aacgccgtgg gccctccttt cacctggatg 360
ctggccctgc tgggcctgag ccaggccctg aacatcctgc tgggcctgaa gggcctggcc 420
cctgccgaga tcagcgccgt gtgcgagaag ggcaacttca gcgtggccca cggcctggcc 480
tggagctact acatcggcta cctgagactg atcctgcctg agctgcaggc cagaatcaga 540
acctacaacc agcactacaa caacctgctg agaggcgccg tgagccagag actgtacatc 600
ctgctgcctc tggactgcgg cgtgcctgac aacctgagca tggccgaccc taacatcaga 660
ttcctggaca agctgcctca gcagaccggc gaccacgccg gcatcaagga cagagtgtac 720
agcaacagca tctacgagct gctggagaac ggccagagag ccggcacctg cgtgctggag 780
tacgccaccc ctctgcagac cctgttcgcc atgagccagt acagccaggc cggcttcagc 840
agagaggaca gactggagca ggccaagctg ttctgcagaa ccctggagga catcctggcc 900
gacgcccctg agagccagaa caactgcaga ctgatcgcct accaggagcc tgccgacgac 960
agcagcttca gcctgagcca ggaggtgctg agacacctga gacaggagga gaaggaggag 1020
gtgaccgtgg gcagcctgaa gaccagcgcc gtgcctagca ccagcaccat gagccaggag 1080
cctgagctgc tgatcagcgg catggagaag cctctgcctc tgagaaccga cttcagc 1137

<210> SEQ ID NO 144
<211> LENGTH: 1137
<212> TYPE: DNA
<213> ORGANISM: Artificial Sequence
<220> FEATURE:
<223> OTHER INFORMATION: Synthetic: Hu STING(V147L); no epitope tag; nucleotide sequence

<400> SEQUENCE: 144
atgcctcaca gcagcctgca ccctagcatc ccttgcccta gaggccacgg cgcccagaag 60
gccgccctgg tgctgctgag cgcctgcctg gtgaccctgt ggggcctggg cgagcctcct 120
gagcacaccc tgagatacct ggtgctgcac ctggccagcc tgcagctggg cctgctgctg 180
aacggcgtgt gcagcctggc cgaggagctg agacacatcc acagcagata cagaggcagc 240
tactggagaa ccgtgagagc ctgcctgggc tgccctctga gaagaggcgc cctgctgctg 300
ctgagcatct acttctacta cagcctgcct aacgccgtgg gccctccttt cacctggatg 360
ctggccctgc tgggcctgag ccaggccctg aacatcctgc tgggcctgaa gggcctggcc 420
cctgccgaga tcagcgccct gtgcgagaag ggcaacttca acgtggccca cggcctggcc 480
tggagctact acatcggcta cctgagactg atcctgcctg agctgcaggc cagaatcaga 540
acctacaacc agcactacaa caacctgctg agaggcgccg tgagccagag actgtacatc 600
ctgctgcctc tggactgcgg cgtgcctgac aacctgagca tggccgaccc taacatcaga 660
ttcctggaca agctgcctca gcagaccggc gaccacgccg gcatcaagga cagagtgtac 720

```
agcaacagca tctacgagct gctggagaac ggccagagag ccggcacctg cgtgctggag    780

tacgccaccc ctctgcagac cctgttcgcc atgagccagt acagccaggc cggcttcagc    840

agagaggaca gactggagca ggccaagctg ttctgcagaa ccctggagga catcctggcc    900

gacgcccctg agagccagaa caactgcaga ctgatcgcct accaggagcc tgccgacgac    960

agcagcttca gcctgagcca ggaggtgctg agacacctga gacaggagga gaaggaggag   1020

gtgaccgtgg gcagcctgaa gaccagcgcc gtgcctagca ccagcaccat gagccaggag   1080

cctgagctgc tgatcagcgg catggagaag cctctgcctc tgagaaccga cttcagc      1137
```

```
<210> SEQ ID NO 145
<211> LENGTH: 1137
<212> TYPE: DNA
<213> ORGANISM: Artificial Sequence
<220> FEATURE:
<223> OTHER INFORMATION: Synthetic: Hu STING (E315Q); no epitope tag;
      nucleotide sequence

<400> SEQUENCE: 145

atgcctcaca gcagcctgca ccctagcatc ccttgcccta gaggccacgg cgcccagaag     60

gccgccctgg tgctgctgag cgcctgcctg gtgaccctgt ggggcctggg cgagcctcct    120

gagcacaccc tgagatacct ggtgctgcac ctggccagcc tgcagctggg cctgctgctg    180

aacggcgtgt gcagcctggc cgaggagctg agacacatcc acagcagata cagaggcagc    240

tactggagaa ccgtgagagc ctgcctgggc tgccctctga gaagaggcgc cctgctgctg    300

ctgagcatct acttctacta cagcctgcct aacgccgtgg gccctccttt cacctggatg    360

ctggccctgc tgggcctgag ccaggccctg aacatcctgc tgggcctgaa gggcctggcc    420

cctgccgaga tcagcgccgt gtgcgagaag ggcaacttca acgtggccca cggcctggcc    480

tggagctact acatcggcta cctgagactg atcctgcctg agctgcaggc cagaatcaga    540

acctacaacc agcactacaa caacctgctg agaggcgccg tgagccagag actgtacatc    600

ctgctgcctc tggactgcgg cgtgcctgac aacctgagca tggccgaccc taacatcaga    660

ttcctggaca agctgcctca gcagaccggc gaccacgccg gcatcaagga cagagtgtac    720

agcaacagca tctacgagct gctggagaac ggccagagag ccggcacctg cgtgctggag    780

tacgccaccc ctctgcagac cctgttcgcc atgagccagt acagccaggc cggcttcagc    840

agagaggaca gactggagca ggccaagctg ttctgcagaa ccctggagga catcctggcc    900

gacgcccctg agagccagaa caactgcaga ctgatcgcct accagcagcc tgccgacgac    960

agcagcttca gcctgagcca ggaggtgctg agacacctga gacaggagga gaaggaggag   1020

gtgaccgtgg gcagcctgaa gaccagcgcc gtgcctagca ccagcaccat gagccaggag   1080

cctgagctgc tgatcagcgg catggagaag cctctgcctc tgagaaccga cttcagc      1137
```

```
<210> SEQ ID NO 146
<211> LENGTH: 1137
<212> TYPE: DNA
<213> ORGANISM: Artificial Sequence
<220> FEATURE:
<223> OTHER INFORMATION: Synthetic: Hu STING (R375A); no epitope tag;
      nucleotide sequence

<400> SEQUENCE: 146

atgcctcaca gcagcctgca ccctagcatc ccttgcccta gaggccacgg cgcccagaag     60

gccgccctgg tgctgctgag cgcctgcctg gtgaccctgt ggggcctggg cgagcctcct    120
```

```
gagcacaccc tgagatacct ggtgctgcac ctggccagcc tgcagctggg cctgctgctg    180

aacggcgtgt gcagcctggc cgaggagctg agacacatcc acagcagata cagaggcagc    240

tactggagaa ccgtgagagc ctgcctgggc tgccctctga gaagaggcgc cctgctgctg    300

ctgagcatct acttctacta cagcctgcct aacgccgtgg gccctccttt cacctggatg    360

ctggccctgc tgggcctgag ccaggccctg aacatcctgc tgggcctgaa gggcctggcc    420

cctgccgaga tcagcgccgt gtgcgagaag ggcaacttca acgtggccca cggcctggcc    480

tggagctact acatcggcta cctgagactg atcctgcctg agctgcaggc cagaatcaga    540

acctacaacc agcactacaa caacctgctg agaggcgccg tgagccagag actgtacatc    600

ctgctgcctc tggactgcgg cgtgcctgac aacctgagca tggccgaccc taacatcaga    660

ttcctggaca agctgcctca gcagaccggc gaccacgccg gcatcaagga cagagtgtac    720

agcaacagca tctacgagct gctggagaac ggccagagag ccggcacctg cgtgctggag    780

tacgccaccc ctctgcagac cctgttcgcc atgagccagt acagccaggc cggcttcagc    840

agagaggaca gactggagca ggccaagctg ttctgcagaa ccctggagga catcctggcc    900

gacgcccctg agagccagaa caactgcaga ctgatcgcct accaggagcc tgccgacgac    960

agcagcttca gcctgagcca ggaggtgctg agacacctga gacaggagga gaaggaggag   1020

gtgaccgtgg gcagcctgaa gaccagcgcc gtgcctagca ccagcaccat gagccaggag   1080

cctgagctgc tgatcagcgg catggagaag cctctgcctc tggccaccga cttcagc      1137
```

```
<210> SEQ ID NO 147
<211> LENGTH: 1137
<212> TYPE: DNA
<213> ORGANISM: Artificial Sequence
<220> FEATURE:
<223> OTHER INFORMATION: Synthetic: Hu STING(V147L/N154S/V155M); no
      epitope tag; nucleotide sequence

<400> SEQUENCE: 147
```

```
atgcctcaca gcagcctgca ccctagcatc ccttgcccta gaggccacgg cgcccagaag     60

gccgccctgg tgctgctgag cgcctgcctg gtgaccctgt ggggcctggg cgagcctcct    120

gagcacaccc tgagatacct ggtgctgcac ctggccagcc tgcagctggg cctgctgctg    180

aacggcgtgt gcagcctggc cgaggagctg agacacatcc acagcagata cagaggcagc    240

tactggagaa ccgtgagagc ctgcctgggc tgccctctga gaagaggcgc cctgctgctg    300

ctgagcatct acttctacta cagcctgcct aacgccgtgg gccctccttt cacctggatg    360

ctggccctgc tgggcctgag ccaggccctg aacatcctgc tgggcctgaa gggcctggcc    420

cctgccgaga tcagcgccct gtgcgagaag ggcaacttca gcatggccca cggcctggcc    480

tggagctact acatcggcta cctgagactg atcctgcctg agctgcaggc cagaatcaga    540

acctacaacc agcactacaa caacctgctg agaggcgccg tgagccagag actgtacatc    600

ctgctgcctc tggactgcgg cgtgcctgac aacctgagca tggccgaccc taacatcaga    660

ttcctggaca agctgcctca gcagaccggc gaccacgccg gcatcaagga cagagtgtac    720

agcaacagca tctacgagct gctggagaac ggccagagag ccggcacctg cgtgctggag    780

tacgccaccc ctctgcagac cctgttcgcc atgagccagt acagccaggc cggcttcagc    840

agagaggaca gactggagca ggccaagctg ttctgcagaa ccctggagga catcctggcc    900

gacgcccctg agagccagaa caactgcaga ctgatcgcct accaggagcc tgccgacgac    960

agcagcttca gcctgagcca ggaggtgctg agacacctga gacaggagga gaaggaggag   1020
```

-continued gtgaccgtgg gcagcctgaa gaccagcgcc gtgcctagca ccagcaccat gagccaggag 1080
cctgagctgc tgatcagcgg catggagaag cctctgcctc tgagaaccga cttcagc 1137

<210> SEQ ID NO 148
<211> LENGTH: 1137
<212> TYPE: DNA
<213> ORGANISM: Artificial Sequence
<220> FEATURE:
<223> OTHER INFORMATION: Synthetic: Hu STING(R284M/V147L/N154S/V155M); no epitope tag; nucleotide sequence

<400> SEQUENCE: 148
atgcctcaca gcagcctgca ccctagcatc ccttgcccta gaggccacgg cgcccagaag 60
gccgccctgg tgctgctgag cgcctgcctg gtgaccctgt ggggcctggg cgagcctcct 120
gagcacaccc tgagatacct ggtgctgcac ctggccagcc tgcagctggg cctgctgctg 180
aacggcgtgt gcagcctggc cgaggagctg agacacatcc acagcagata cagaggcagc 240
tactggagaa ccgtgagagc ctgcctgggc tgccctctga gaagaggcgc cctgctgctg 300
ctgagcatct acttctacta cagcctgcct aacgccgtgg gccctccttt cacctggatg 360
ctggccctgc tgggcctgag ccaggccctg aacatcctgc tgggcctgaa gggcctggcc 420
cctgccgaga tcagcgccct gtgcgagaag ggcaacttca gcatggccca cggcctggcc 480
tggagctact acatcggcta cctgagactg atcctgcctg agctgcaggc cagaatcaga 540
acctacaacc agcactacaa caacctgctg agaggcgccg tgagccagag actgtacatc 600
ctgctgcctc tggactgcgg cgtgcctgac aacctgagca tggccgaccc taacatcaga 660
ttcctggaca agctgcctca gcagaccggc gaccacgccg gcatcaagga cagagtgtac 720
agcaacagca tctacgagct gctggagaac ggccagagag ccggcacctg cgtgctggag 780
tacgccaccc ctctgcagac cctgttcgcc atgagccagt acagccaggc cggcttcagc 840
agagaggaca tgctggagca ggccaagctg ttctgcagaa ccctggagga catcctggcc 900
gacgcccctg agagccagaa caactgcaga ctgatcgcct accaggagcc tgccgacgac 960
agcagcttca gcctgagcca ggaggtgctg agacacctga gacaggagga gaaggaggag 1020
gtgaccgtgg gcagcctgaa gaccagcgcc gtgcctagca ccagcaccat gagccaggag 1080
cctgagctgc tgatcagcgg catggagaag cctctgcctc tgagaaccga cttcagc 1137

<210> SEQ ID NO 149
<211> LENGTH: 141
<212> TYPE: DNA
<213> ORGANISM: Artificial Sequence
<220> FEATURE:
<223> OTHER INFORMATION: Synthetic: 3 UTR used in STING V155M construct, containing miR122 binding site

<400> SEQUENCE: 149
tgataatagg ctggagcctc ggtggcctag cttcttgccc cttgggcctc cccccagccc 60
ctcctcccct tcctgcaccc gtacccccca aacaccattg tcacactcca gtggtctttg 120
aataaagtct gagtgggcgg c 141

<210> SEQ ID NO 150
<211> LENGTH: 1257
<212> TYPE: DNA
<213> ORGANISM: Mus musculus
<220> FEATURE:
<221> NAME/KEY: misc_feature
<222> LOCATION: (1)..(1257)
<223> OTHER INFORMATION: super mouse IRF3 S396D; no epitope tag

<400> SEQUENCE: 150
atggagaccc ccaagcctag aatcctgccc tggctggtga gccagctgga cctgggccag 60
ctggagggcg tagcctggct ggacgagagc agaaccagat tcagaatccc ctggaagcac 120
ggcctgagac aagacgccca gatggccgac ttcggcatct tccaggcctg ggccgaggcc 180
agcggcgcct acacccctgg caaggataag cccgatgtga gcacctggaa gagaaacttc 240
agaagcgccc tgaacagaaa ggaggtgctg agactggccg ccgacaatag caaggacccc 300
tacgaccccc acaaggtgta cgagttcgtt acccccggcg ccagggactt cgtgcacctg 360
ggcgccagcc ccgacaccaa cggcaagagc agcctgcccc acagccagga gaacctgccc 420
aagctgttcg atggcctgat cctgggcccc ctgaaggacg agggcagcag cgacctggcc 480
atcgtgagcg accctagcca gcagctgccc tcccccaacg tgaacaactt cctgaacccc 540
gccccccagg agaacccccct gaagcaactg ctggccgagg agcagtggga gttcgaggtg 600
accgccttct acagaggcag acaggtgttc cagcagaccc tgttctgccc cggcggcctg 660
agactggtag gcagcaccgc tgacatgacc ctgccctggc agcccgtgac cctgcccgac 720
cccgaaggct ttctgaccga caagctggtg aaggagtacg tcggccaagt gctgaagggc 780
ctgggcaacg gcctggccct gtggcaggcc ggccagtgcc tgtgggccca gagactcggc 840
cacagccacg ccttctgggc cctgggcgag gaactcctgc ccgatagcgg cagaggcccc 900
gacggcgagg tgcacaagga caaggacggc gccgtgttcg acctgcgccc cttcgtggcc 960
gacctgatcg ccttcatgga gggcagcggc cacagcccca gatataccct gtggttctgc 1020
atgggcgaga tgtggcccca ggaccagccc tgggtgaaga gactggtgat ggtgaaggtg 1080
gtgcccacct gcctgaaaga gctgctggag atggccagag agggcggcgc cagctccctg 1140
aaaaccgtgg acctgcacat tgacaacagc cagcccatca gcctgaccag cgaccagtac 1200
aaggcctacc tgcaggacct ggtggaggac atggacttcc aggccaccgg caacatc 1257

<210> SEQ ID NO 151
<211> LENGTH: 1281
<212> TYPE: DNA
<213> ORGANISM: Homo sapiens
<220> FEATURE:
<221> NAME/KEY: misc_feature
<222> LOCATION: (1)..(1281)
<223> OTHER INFORMATION: super human IRF3 S396D; no epitope tag

<400> SEQUENCE: 151
atgggcaccc ccaagcccag aatcctgccc tggctggtga gccagctgga cctgggccag 60
ctggagggag tggcctgggt gaacaagagc agaaccagat tcagaatccc ctggaagcac 120
ggcctcagac aggacgccca gcaggaggac ttcggcattt ttcaggcttg ggccgaggcc 180
accggcgcct acgtgcccgg cagagacaag cccgacctgc ccacctggaa aagaaacttc 240
agaagcgcct tgaatagaaa ggagggcctg agactggccg aggacagaag caaggacccc 300
cacgaccctc acaagatcta cgagttcgtg aatagcggcg tgggcgactt tagccagccc 360
gacaccagcc ccgacaccaa cggcggcggc agcaccagcg acacgcagga ggacatcctg 420
gatgaactgc tgggcaacat ggtgctggcc cccctgcccg atcccggccc cccttcgctt 480
gccgtggccc ccgagccctg cccccagccc ctgagaagcc cctctctgga taaccccacc 540
cccttcccca acctgggccc cagcgagaat ccactgaaga gacttctggt ccccggcgag 600
gagtgggagt tcgaggtgac cgccttctac agaggcagac aggtgttcca gcagaccatc 660

```
agctgccccg aaggcctgag attagtgggc agcgaagtgg gcgacaggac cctgcccggg    720
tggcccgtga ccctgcccga tcccggcatg agcctgaccg acagaggtgt gatgagctac    780
gtgagacacg tgctgagctg cctgggcggc ggcctggcac tgtggagagc cggccagtgg    840
ctgtgggccc agagactggg ccactgccac acctactggg ccgtgagcga ggagctgctg    900
cccaacagcg gccacggccc cgacggcgag gtgcccaagg acaaggaagg gggcgtgttc    960
gacctgggcc ccttcatcgt agacctgatc acctttaccg agggcagcgg caggagcccc   1020
agatacgccc tgtggttctg cgtgggcgaa agctggcccc aggaccagcc ctggaccaag   1080
agactggtga tggtgaaggt agtgcccacc tgcctgagag ccttagtgga gatggccaga   1140
gtgggcgggg ccagcagcct ggagaacacc gtggatcttc acatcgacaa cagccacccc   1200
ctgagcctga ccagcgacca gtacaaggcc tacctgcagg acctggtgga gggcatggac   1260
ttccagggcc ccggcgagac c                                             1281
```

<210> SEQ ID NO 152
<211> LENGTH: 1509
<212> TYPE: DNA
<213> ORGANISM: Artificial Sequence
<220> FEATURE:
<223> OTHER INFORMATION: Synthetic: Wild-type Hu IRF7 isoform A; P037 without epitope tag

<400> SEQUENCE: 152

```
atggcgctgg cccccgaaag agccgccccc agagtcctct tcggcgaatg gctccttggc     60
gaaatttcgt cgggctgcta cgagggctta caatggctgg atgaggcgag aacctgtttc    120
agggtgccct ggaaacactt cgccagaaag gatctaagcg aagcagatgc tagaattttt    180
aaggcttggg ccgtggccag gggaagatgg ccccccctcga gcagaggcgg cggccctccc   240
cccgaggcag aaacggccga gagagccgga tggaaaacca atttcagatg cgccctgaga    300
tctacaagaa gattcgtgat gcttagagac aacagcggag atcccgccga tccccataag    360
gtgtatgccc tgtcccggga gctgtgctgg agggaaggcc ctggcactga ccagaccgaa    420
gccgaagccc ccgcggccgt gccgccgccc caaggaggcc caccaggccc tttcctcgct    480
cacacccacg ccggtctgca agccccggga cctctacctg cccctgccgg cgataaaggc    540
gacctgttgc tgcaggccgt ccaacagagc tgcctggccg atcatctgct cacagccagc    600
tggggcgctg accccgtccc aacaaaggcc cccggtgagg gccaagaagg cctgcctctg    660
accggcgcct gtgccggcgg ccctggcctg cctgctggcg agctgtacgg atgggctgtc    720
gaaaccactc cctcccccgg cccccaacct gcggccctga caaccggcga ggcagccgca    780
cccgaaagcc cccaccaggc cgaaccctac ctcagtccca gcccctccgc ctgcaccgct    840
gtgcaggagc ccagccccgg tgctctggac gtaacaatca tgtacaaagg cagaaccgtg    900
cttcagaagg tggttggaca cccctcctgt acttttctct acggccccccc cgaccctgcc   960
gtgagagcta ccgacccgca acaggtggcc tttccctcgc ccgccgaact gcccgatcaa   1020
aaacagctga gatacaccga ggagctgctg agacacgtgg cgccgggctt acacctagag   1080
ttgagaggcc cccaactctg ggccagacgc atgggcaagt gtaaggtgta ctgggaggtc   1140
gggggccctc ccggctctgc cagccccagc accccctgctt gtctcttgcc cagaaactgt  1200
gataccccca tcttcgactt ccgtgtattt ttccaggaac tggtcgagtt tagagccaga   1260
cagagacgag gcagccccag atatacaatc tacctcggct tcggccagga cctgagtgcc   1320
ggcagaccta aggagaagtc gctggtccta gtgaagttag agccctggct atgtagagtg   1380
```

cacctggagg gcacccagag agaaggagtg agcagcctgg acagcagcag cctgagtctg 1440
tgcctgagct ccgccaactc gctgtatgat gacatcgagt gtttcctcat ggagctggag 1500
cagcccgcc 1509

<210> SEQ ID NO 153
<211> LENGTH: 1509
<212> TYPE: DNA
<213> ORGANISM: Artificial Sequence
<220> FEATURE:
<223> OTHER INFORMATION: Synthetic: constitutively active Hu IRF7 S477D/S479D; P033 without epitope tag

<400> SEQUENCE: 153
atggcccttg cccctgagcg ggccgccccc agagtgttat tcggcgagtg gctgctgggc 60
gagatcagca gcggctgcta cgagggactg cagtggctgg acgaggctag aacctgcttc 120
agagtgccct ggaagcattt cgccagaaaa gacctgagcg aggctgatgc tagaatcttc 180
aaagcctggg ctgtggcccg aggaagatgg ccccccagca gcagaggagg cggccctcct 240
cccgaggccg aaaccgcaga gcgtgctggc tggaaaacca actttaggtg tgccctgagg 300
agcaccagaa gattcgttat gctcagagac aacagcgggg accccgccga cccgcacaag 360
gtgtacgcct taagtaggga gctgtgctgg agagagggac cggggaccga ccaaaccgag 420
gctgaggcgc ccgccgccgt tccacctccc cagggtggtc cccagggcc ctttctggca 480 cacacccacg ccggattaca ggcgccaggg cccttacccg cccccgccgg agacaaaggc 540
gacctcctgc tgcaagccgt gcaacaaagc tgcctggccg atcacttact aaccgctagc 600
tggggcgccg atcctgttcc caccaaggcc cccggtgaag ggcaagaagg actgccctta 660
accggcgcct gtgccggagg ccctggtctg ccagccggcg agctgtacgg ttgggctgtc 720
gaaacaacac ccagtccggg cccacagcct gccgctctga ccaccggcga agccgccgcc 780
cccgagagcc cacaccaggc tgaaccctac ctgagcccca gccccagcgc ctgcaccgct 840
gtgcaggagc ctagccccgg cgctcttgat gtgacaataa tgtacaaggg caggaccgtg 900
ctgcaaaagg tcgtgggcca tccgtcgtgt acctttctgt acggccctcc agaccccgcg 960
gttagagcca ccgaccccca gcaagtcgcc ttcccctccc ccgccgaact gcccgaccaa 1020
aagcagctgc ggtacacaga agaactactt agacacgtgg cccccggtct gcacttggag 1080
ctgagaggcc cccagctctg ggccagaaga atgggcaagt gcaaagtgta ctgggaggtg 1140
ggcggcccac ccggctcagc ttcgccctcc acacccgcat gcctgctgcc cagaaattgc 1200
gacacgccca tcttcgattt tagagtgttc tttcaggagt tggtggagtt cagagccaga 1260
caaagacgcg gcagccccag atacaccatt tacctcggct tcggccagga cctcagcgct 1320
ggcagaccca aggagaagag tctggtcctc gtgaagctgg agccctggct gtgcagagtg 1380
cacctggagg gcacccagcg tgaaggcgtg agcagcctgg attcaagcga cctggaccta 1440
tgcctaagca gcgctaactc actgtacgac gatatcgaat gcttcctgat ggaactggag 1500
cagcctgcc 1509

<210> SEQ ID NO 154
<211> LENGTH: 1509
<212> TYPE: DNA
<213> ORGANISM: Artificial Sequence
<220> FEATURE:
<223> OTHER INFORMATION: Synthetic: constitutively active Hu IRF7 S475D/S477D/L480D; P034 without epitope tag

<400> SEQUENCE: 154

```
atggccctgg cacccgagag ggccgccccc agggtgctct tcggcgagtg gttactaggc     60
gaaattagca gcggctgcta tgaaggcctt cagtggctgg acgaggccag aacctgcttt    120
agagttccct ggaagcactt cgcccggaaa gatctctctg aagccgacgc cagaatattc    180
aaggcctggg ctgtcgccag gggcaggtgg ccaccctcca gccgaggtgg cggccctccc    240
cctgaggctg agactgcgga aagggcgggc tggaagacca atttcagatg cgctctgaga    300
agcaccagac gttttgtgat gctaagagac aatagcggcg atcccgccga cccccataag    360
gtatacgcac tgagccgaga gctctgttgg agagaaggcc ccggcaccga ccagaccgag    420
gctgaagccc ctgcagccgt gccccccct caaggcgggc cccccggccc cttcctggcc    480
catacccatg cagggttaca agcacccggg cccttgcccg ccccagcggg agacaagggc    540
gacctcttac tgcaggccgt gcaacaaagt tgtctggcgg accacctgct gaccgcatca    600
tggggcgcgg atcctgtgcc caccaaggca cccggcgaag gccaggaggg cctgcccttg    660
accggcgcct gcgctggcgg acccggccta cctgctggcg aactgtatgg ctgggccgta    720
gagacgactc ccagccctgg cccacaaccc gcggctttga ccaccggcga agccgccgcc    780
cccgagtctc cgcaccaggc cgagccttac ctcagcccaa gccctagcgc ctgcaccgcc    840
gtgcaagaac ctagccccgg agccctggat gtgacaatca tgtacaaggg tagaaccgta    900
ctgcaaaagg tggtgggtca tcccagctgc acctttcttt acggcccacc cgaccctgcc    960
gtgcgagcca cagacccaca acaggtcgcc ttcccaagcc ccgccgaact gcccgatcag   1020
aaacagctga gatatacaga ggagcttctg cggcacgtag ctcccggcct acatctcgag   1080
ctgaggggcc cacaactgtg ggccagacgc atgggcaaat gcaaggtcta ctgggaagtg   1140
ggaggccccc ccggcagcgc atctcccagc acgcccgcgt gcctgctgcc tagaaattgc   1200
gacaccccca tctttgactt ccgggtattc tttcaggagc tggtagagtt cagagccagg   1260
cagcggaggg gctcccccag atacacaatc tacctgggct tcggacagga cctgtccgcc   1320
ggccgcccca aggaaaagag cctggtgctg gtgaagctgg agccctggct gtgtagggta   1380
cacctcgaag gcacccagag agaaggagtg agctcgcttg atgacagcga tctgtcggat   1440
tgccttagca gcgccaacag cctgtatgat gatatcgagt gcttccttat ggaactggag   1500
cagcccgcc                                                            1509
```

<210> SEQ ID NO 155
<211> LENGTH: 1509
<212> TYPE: DNA
<213> ORGANISM: Artificial Sequence
<220> FEATURE:
<223> OTHER INFORMATION: Synthetic: constitutively active Hu IRF7
S475D/S476D/S477D/S479D/S483D/S487D; P035 without epitope tag

<400> SEQUENCE: 155

```
atggccctag cccccgaaag agcagctccc agagtgctgt tcggcgaatg gctgcttggc     60
gagatcagca gcggctgcta cgaaggcctg cagtggctgg acgaagcccg cacctgtttc    120
agagtgccct ggaagcactt cgctagaaag gatttgagcg aggctgatgc tagaatcttt    180
aaggcttggg ctgtggcaag aggcagatgg ccgcctagta gcagaggggg cggacctccc    240
cccgaggctg agaccgctga gagagcaggg tggaaaacca acttcagatg cgcgctgaga    300
agcacccgaa gattcgtgat gctacgtgac aatagcggcg accccgccga cccccacaaa    360
gtgtacgccc tgtcccgaga actttgctgg agagagggac ccggcaccga tcaaacagag    420
gctgaggccc cggccgctgt acccccgccc caaggaggcc ccccaggccc ctttctggct    480
```

catacacatg ccggcctgca ggcacccggg cccctcccgg ctcctgccgg cgacaagggc 540
gatctccttc tccaggccgt gcagcagagc tgcctggccg atcacctgct gaccgcctcg 600
tggggcgccg accccgtgcc caccaaagcc ccgggtgaag gccaagaggg gctccccttta 660 accggagcat gcgccggagg ccccggcctg ccagccggcg agttatatgg ctgggctgtg 720
gagaccacac cctcccccgg ccctcaaccc gctgccctga ccaccggtga ggccgccgcc 780
cccgagagcc cacaccaggc cgaaccctac ctgagcccta gccctagcgc ctgcaccgcc 840
gtgcaagaac ccagccccgg agccctggat gtgaccatta tgtacaaggg ccggacagtg 900
ctgcaaaagg ttgtgggaca cccgagctgc acctttctgt acggtccgcc tgaccccgcc 960
gtgagagcca cggacccgca gcaggtggcc ttcccctcac ccgcggagct gcccgaccaa 1020
aagcaactca gatacacaga agaactattg cgtcacgtcg cgcccggcct gcatctggag 1080
ctgagaggcc cccagctctg ggccagaagg atgggcaaat gcaaggtgta ctgggaggtg 1140
ggaggccccc ccggcagcgc cagccccagc actcccgcgt gcctgctgcc cagaaattgc 1200
gacactccca tcttcgattt cagggtgttc ttccaggagc tggtggagtt cagagccagg 1260
cagagaaggg gtagccccag atacacaatc tatctaggct ttggacaaga tctgagcgcc 1320
ggccggccta aggaaaaaag cctggtgctg gtaaagctgg agccgtggct ttgtagagtg 1380
cacctggagg ggacgcagcg agagggcgtg agcagcttag acgacgatga cttggatctg 1440
tgtctcgaca gcgccaacga cttgtacgac gacatcgagt gcttcctgat ggaactggag 1500
cagcccgcc 1509

<210> SEQ ID NO 156
<211> LENGTH: 846
<212> TYPE: DNA
<213> ORGANISM: Artificial Sequence
<220> FEATURE:
<223> OTHER INFORMATION: Synthetic: constitutively active truncated Hu IRF7 1-246 + 468-503; P032 without epitope tag

<400> SEQUENCE: 156
atggccctgg cccccgagag agccgccccc agagtgctct tcggcgagtg gctgctgggc 60
gagataagca gcggctgcta cgaaggtctg cagtggctag acgaggccag aacctgcttt 120
agagtgccct ggaagcactt cgctcgaaag gacctgtccg aggccgatgc tagaattttt 180
aaggcttggg ccgtcgctag gggaagatgg ccccctagca gtagaggcgg cggcccccct 240
cccgaagccg agacggccga gagggccggc tggaaaacca atttcagatg cgccctgagg 300
agcacccgca ggttcgtaat gctgcgagac aatagcggcg atcctgcgga tcctcacaag 360
gtttacgcct tgagtagaga actgtgctgg cgggagggcc ccggaaccga ccagacggag 420
gcagaggcac ccgctgccgt gcccccccct caaggaggac cccctggacc ctttctggcc 480
cacacccacg ctggtctgca ggccccaggc ccactgcccg ccccagcggg cgataagggt 540
gacctgctcc tacaggcggt gcaacagagc tgtctggccg accacctgtt gaccgccagc 600
tggggggccg acccggtgcc caccaaagct cccggagagg gccaagaagg cctcccacta 660
actggcgcct gcgccggggg cccgggatta cccgccggcg agctgtatgg ctgggccgtg 720
gagaccacgc ccagccccga gggcgtgtcg tccctggaca gcagcagcct gagcctgtgc 780
ctgagctccg ccaacagcct gtatgacgac atcgagtgct tcctgatgga gctggaacaa 840
cccgcc 846

<210> SEQ ID NO 157
<211> LENGTH: 846
<212> TYPE: DNA
<213> ORGANISM: Artificial Sequence
<220> FEATURE:
<223> OTHER INFORMATION: Synthetic: constitutively active truncated Hu IRF7 1-246 + 468-503 plus S475D/S476D/S477D/S479D/S483D/S487D; P036 without epitope tag

<400> SEQUENCE: 157

```
atggcactgg cgcctgaaag agccgctccg cgtgtgctct tcggcgagtg gctgctgggc     60

gagatcagct ccggctgcta cgagggtcta cagtggctgg acgaggccag aacctgtttt    120

agagtgccct ggaagcactt cgcgagaaag gacctgagcg aggccgacgc cagaatcttc    180

aaagcctggg cagtggctag gggcagatgg cctcccagca gccggggcgg cggcccaccc    240

cccgaggccg aaaccgccga aagagctggc tggaagacca acttcagatg cgccctgaga    300

agcaccagaa gatttgtcat gctgagagat aattcaggag accccgccga ccctcacaag    360

gtgtacgccc tgtccagaga gctgtgttgg agagagggcc ccggaaccga ccagaccgag    420

gccgaggctc cagctgccgt gccacccccc caaggcggac cacccggccc cttcttggca    480

catacgcacg ccggcctcca ggctcccggc cctctgcccg cccctgctgg tgacaaaggc    540

gatctgctgc tgcaagccgt ccagcaatcc tgcttggctg accacctgct gaccgctagc    600

tggggagccg accccgttcc caccaaggct cccggagaag gacaggaggg cctgcccctt    660

accggcgctt gcgcgggggg ccctggcttg cctgccggcg aactgtacgg ctgggccgtg    720

gagaccacgc cttcccccga gggcgtgtcc agcctggacg atgatgacct ggatctgtgc    780

ctggacagcg ccaacgacct gtacgatgac atcgagtgct tttgatgga gctggagcag     840

cccgcc                                                               846
```

<210> SEQ ID NO 158
<211> LENGTH: 1224
<212> TYPE: DNA
<213> ORGANISM: Artificial Sequence
<220> FEATURE:
<223> OTHER INFORMATION: Synthetic: truncated Hu IRF7 1-151 + 247-503; P038 without epitope tag; null mutation

<400> SEQUENCE: 158

```
atggccctgg cccccgagag agccgcgccc agagtgctgt tcggcgaatg gctgctgggc     60

gagatcagca gcggctgcta tgagggcctg cagtggctcg acgaagccag gacgtgcttc    120

agagtcccct ggaagcactt cgccagaaag gatctgagcg aggctgacgc cagaatcttc    180

aaggcctggg cagttgcgcg tgggagatgg ccccccagct cgcggggcgg cggtcccccc    240

cctgaggccg agaccgccga aagagccgga tggaaaacca actttcgatg cgccctcaga    300

agcaccagac ggtttgtgat gctgagagat aacagcggcg accctgcaga cccccataaa    360

gtgtatgccc tgagcagaga gctgtgttgg cgagagggcc ccggaaccga ccaaaccgag    420

gccgaggccc ccgccgccgt accccccct caaggccccc agcctgctgc tctgaccacg    480

ggagaagccg ccgctcctga gagcccccac caagccgagc cctatctgag ccctagcccc    540

agcgcctgca ccgccgtgca ggagccctca ccgggcgccc tagacgtgac catcatgtac    600

aaggggcgca cggtgctgca aaaggtggtg ggccacccca gctgcacctt cctgtacggc    660

ccccccgacc ctgccgtgag agccaccgac ccccagcaag tcgccttccc cagccccgcc    720

gagctgcccg accagaagca gctgaggtac accgaggagt tgctgagaca tgtggccccc    780

ggcttgcacc tcgagctgag aggcccgcag ctctgggcca gaagaatggg caagtgcaag    840
```

gtgtactggg aggtgggcgg cccccccggc agcgcgagcc caagcacccc ggcctgcctg 900
ctgcctagaa actgcgacac ccctatcttc gacttcagag tatttttcca ggagctggtc 960
gagttcaggg ccagacagcg tagaggcagc cccagataca ccatctacct tggattcggc 1020
caggacctga gcgccggcag acccaaagag aagtccctgg tactggtgaa gctagagccc 1080
tggctgtgta gggtgcatct ggaaggcacc caaagagagg gcgtaagctc gcttgacagc 1140
agcagcctca gcctgtgcct gagcagcgct aacagcttat acgacgacat cgagtgcttc 1200
ctgatggagc tggaacaacc cgcc 1224

<210> SEQ ID NO 159
<211> LENGTH: 1059
<212> TYPE: DNA
<213> ORGANISM: Artificial Sequence
<220> FEATURE:
<223> OTHER INFORMATION: Synthetic: truncated Hu IRF7 152-503; P039 without epitope tag; null mutation

<400> SEQUENCE: 159
atgggcggcc ctcccgggcc tttcctggcc catacacacg ccggcctaca ggctcctggc 60
cctctgcccg ccccggccgg cgacaagggc gacctcctgc tgcaggccgt gcagcagtcc 120
tgtctggccg accacctgct gactgctagc tggggcgccg atcccgtgcc caccaaggcc 180
ccaggagagg ggcaagaggg cctgcctcta accggcgcat gcgcaggtgg accaggcctc 240
cccgccggcg agctgtatgg ttgggccgtg gagacaaccc ccagccccgg cccgcagcct 300
gctgcgctga ccacaggcga ggccgctgcc cctgagagcc cccaccaagc tgaaccctac 360
ctgagcccca gcccctctgc ctgcacagcg gtgcaggagc ccagtcccgg cgccttggac 420
gtgaccatca tgtataaggg caggactgtg ttacaaaagg tagtgggcca cccaagttgt 480
acctttctgt acgggccccc cgacccagcc gtgcgcgcca ccgaccccca gcaggtggcc 540
ttccccagcc ccgctgagtt gcccgatcag aaacaactcc ggtacaccga ggaattactt 600
agacatgtgg ctcccggcct gcatctggag cttagaggtc cacagttgtg ggccagaaga 660
atgggcaagt gcaaggttta ttgggaggtc ggaggccccc cgggcagcgc cagccccagc 720
acccccgcct gtcttctgcc cagaaactgc gacaccccaa tcttcgattt cagagtgttt 780
ttccaggaac tggtggagtt cagagcaagg caaagaagag gcagccctag atacaccatc 840
tacctgggct ttggccaaga cctgagcgcc ggcagaccca aggaaaaatc cctggtcctg 900
gtgaaactgg agccctggct gtgcagagtc cacctggagg gcacccagag agagggcgtg 960
agcagcctgg actcgagcag cctgtccctg tgtctgagca gcgcgaattc gctatatgac 1020
gacatcgaat gctttctgat ggagctggaa cagcccgcc 1059

<210> SEQ ID NO 160
<211> LENGTH: 1269
<212> TYPE: DNA
<213> ORGANISM: Artificial Sequence
<220> FEATURE:
<223> OTHER INFORMATION: Synthetic: KRAS(G12D)25mer_nt.STING(V155M)

<400> SEQUENCE: 160
atgcctcaca gcagcctcca ccctagcatc ccttgcccta gaggccacgg cgcccagaag 60
gccgccctcg tgcttttaag cgcctgcttg gtgacccttt ggggcttggg cgagcctcca 120
gagcacacct tgagatattt ggtgctccac ctggccagcc ttcagctggg cttgttactc 180
aacggcgtgt gcagcctggc cgaggagctg agacacatcc acagcagata cagaggcagc 240

```
tactggagaa ccgtgagagc gtgtctgggc tgccctctga gaagaggcgc cttgcttctt    300
ctcagtatct acttctacta ctccctgcct aacgccgtgg gccctccttt cacctggatg    360
ctggcactgc tcggcctcag ccaggccctg aacatcttgt tgggcttgaa gggcctggcc    420
cctgccgaga tcagcgccgt gtgcgagaag ggcaacttca acatggccca cggattggct    480
tggagctact acatcggcta cctgagactg atcctgcctg agctgcaggc cagaatcaga    540
acctacaacc agcactacaa caacctgctg cgcggcgcag tgagccagag actgtatatt    600
ctgctgcctc tggactgcgg cgtgcctgac aacctgagca tggccgaccc taacatcaga    660
ttcctggaca agctgcctca gcagaccggc gaccacgccg gcatcaagga cagagtgtac    720
agcaacagca tctatgagct gctcgagaat ggccagagag ccggcacctg cgtgctggag    780
tacgccaccc ctctgcagac cctgttcgcc atgagccagt atagtcaagc tggcttcagc    840
agagaggaca gactggagca ggccaagctg ttctgcagaa ccctggagga cattctggct    900
gacgcccctg agagccagaa caactgccga ctgatcgcct accaggaacc agccgacgac    960
agcagcttca gtctttctca ggaggttctt cgccacttgc gccaggagga gaaggaggag   1020
gtgaccgtgg gcagcctgaa gacctccgca gtccctagca ccagcaccat gagtcaggag   1080
ccggagctat taatcagcgg catggagaag cctcttccac tccgaaccga cttcagcgcc   1140
accaacttca gcctgctgaa gcaggcaggt gacgttgagg agaatccggg acctatgacc   1200
gagtacaagc tggtggttgt gggcgccgac ggcgtgggca agagcgccct gaccatccag   1260
ctgatccag                                                           1269
```

<210> SEQ ID NO 161
<211> LENGTH: 1269
<212> TYPE: DNA
<213> ORGANISM: Artificial Sequence
<220> FEATURE:
<223> OTHER INFORMATION: Synthetic: KRAS(G12D)25mer_ct.STING(V155M)

<400> SEQUENCE: 161

```
atgaccgagt acaagctagt agtcgtgggc gccgacggcg tgggcaagag cgccctcacc     60
atccagctaa tccaggccac caacttcagc ttgctcaagc aggccggcga cgtggaggag    120
aacccaggcc ctatgcctca cagcagcctt caccctagca tcccttgccc tagaggccac    180
ggcgcccaga aggccgccct ggtgctgctg agcgcctgcc tggtgaccct gtggggcctg    240
ggcgagcctc ctgagcacac cctgagatat ctggtgcttc acctggccag tttacagctg    300
ggcctgcttc ttaacggcgt gtgcagcctg gccgaggagc tgagacacat ccacagcaga    360
tacagaggca gctactggag aaccgtgaga gcctgcctag gctgccctct gagaagaggc    420
gctctgttgc tactttccat ctacttctac tactccctgc ctaacgccgt gggccctcct    480
ttcacttgga tgctggcgtt gctgggtctg agccaggccc tgaacatcct tctcggtctg    540
aagggcctgg cccctgccga gatcagcgcc gtgtgcgaga agggcaactt caacatggcc    600
cacggactcg cctggagcta ctacatcggc tacctgagac tgatcctgcc tgagctgcag    660
gccagaatca gaacctacaa ccagcactac aacaacctgc tgcggggcgc cgtgagccag    720
agactgtata tacttcttcc tctggactgc ggcgtgcctg acaacctgag catggccgac    780
cctaacatca gattcctgga caagctgcct cagcagaccg gcgaccacgc cggcatcaag    840
gacagagtgt acagcaactc catttatgag ctgctcgaga atggccagag agccggcacc    900
tgcgtgctgg agtacgccac ccctctgcag accctgttcg ccatgagcca gtacagtcag    960
```

```
gctggattca gcagagagga cagactggag caggccaagc tgttctgcag gacactggag   1020

gacatactag cagacgcccc tgagagccag aacaactgca gactgattgc ctaccaggag   1080

cctgcggacg acagctcctt cagtctgagt caggaggtgt tgcggcactt acgccaagaa   1140

gagaaggagg aggtgaccgt gggcagcctg aagactagcg ctgtgcctag caccagcaca   1200

atgtcacagg agccggaatt gctaatcagc ggcatggaga agcctctccc attacgtacc   1260

gacttcagc                                                           1269


<210> SEQ ID NO 162
<211> LENGTH: 1419
<212> TYPE: DNA
<213> ORGANISM: Artificial Sequence
<220> FEATURE:
<223> OTHER INFORMATION: Synthetic: KRAS(G12D)25mer^3_nt.STING(V155M)

<400> SEQUENCE: 162

atgcctcaca gcagccttca ccctagcatc ccttgcccta gaggccacgg cgcccagaag     60

gccgccctag tgctccttag cgcctgcctc gtgaccctat ggggcttagg cgagcctcca    120

gagcacacct tgagatacct cgtcctccac ctggctagtc tacagctggg ccttctcctc    180

aacggcgtgt gcagcctggc cgaggagctg agacacatcc acagcagata cagaggcagc    240

tactggagaa ccgtgagagc gtgcctgggc tgccctctga gaagaggcgc actgctgtta    300

ctcagcatct acttctacta ctcactgcca aacgccgtgg gccctccttt cacctggatg    360

ctggccttgc tcggattgag ccaggccctg aacattttac tgggattgaa gggcctggcc    420

cctgccgaga tcagcgccgt gtgcgagaag ggcaacttca acatggccca cggcctagct    480

tggagctact acatcggcta cctgagactg atcctgcctg agctgcaggc cagaatcaga    540

acctacaacc agcactacaa caacctgctg cgtggagcgg tgagccagag actgtatatc    600

ctcctgcctc tggactgcgg agtgcctgac aacctgagca tggccgaccc taacatcaga    660

ttcctggaca agctgcctca gcagaccggc gaccacgccg gcatcaagga cagagtgtac    720

agcaactcaa tctacgagct gttggagaat ggccagagag ccggcacctg cgtgctggag    780

tacgccaccc ctctgcagac cctgttcgcc atgagccagt actctcaggc aggcttcagc    840

agagaggaca gactggagca ggccaagctg ttctgcagaa ccctggagga catcctggcg    900

gacgcccctg agagccagaa caactgccgg cttatcgcct accaggagcc agcagacgac    960

agcagcttct ctctctcaca agaggtactg cgccatcttc gccaggagga gaaggaggag   1020

gtgaccgtgg gcagcctgaa gacatccgcc gtacctagca ccagcaccat gtctcaggaa   1080

ccggaactgt tgatcagcgg catggagaag cctctgccac tgcgcaccga cttcagcgcc   1140

accaacttct ccctactgaa gcaagccggt gacgttgaag agaaccctgg ccctatgacc   1200

gagtacaagc tggtagtagt aggcgccgac ggcgtgggca agagcgccct gaccatccag   1260

ctgatccaga tgactgaata taagcttgtc gtcgtgggcg cagatggcgt tggtaagagc   1320

gcacttacaa ttcaactcat tcagatgacg gagtataagc tggtggtggt cggagctgac   1380

ggcgtaggca agagtgccct tactattcag ctaattcag                          1419


<210> SEQ ID NO 163
<211> LENGTH: 1419
<212> TYPE: DNA
<213> ORGANISM: Artificial Sequence
<220> FEATURE:
<223> OTHER INFORMATION: Synthetic: KRAS(G12D)25mer^3_ct.STING(V155M)

<400> SEQUENCE: 163
```

```
atgaccgagt acaagcttgt ggtggttggc gccgacggcg tgggcaagag cgccttaacc     60

atccagctta tccagatgac agagtataag ctagtggtgg tcggcgcaga cggagtggga    120

aagagtgcat taactattca actcatccaa atgaccgaat acaagctagt agttgtgggt    180

gcagatggcg tcggcaagtc tgcactgaca attcagctca tccaggccac caacttcagc    240

ctgctgaagc aggccggcga cgtggaggag aaccctggcc ctatgcctca cagcagcctg    300

caccctagca tcccttgccc tagaggccac ggcgcccaga aggccgccct ggtgctgctg    360

agcgcctgcc tggtgaccct gtggggcctg ggcgagcctc ctgagcacac cctgagatac    420

ctagttttgc acctggcttc tctgcagctg ggcctactgc tcaacggcgt gtgcagcctg    480

gccgaggagc tgagacacat ccacagcaga tacagaggca gctactggag aaccgtgaga    540

gcatgcttag gctgccctct gagaagaggc gctctgctcc tcttgtccat ctacttctac    600

tactcgctac ctaacgccgt gggccctcct ttcacctgga tgctggccct cttgggatta    660

agccaggccc tgaacatctt gctgggactg aagggcctgg cccctgccga gatcagcgcc    720

gtgtgcgaga agggcaactt caacatggcc cacggactcg cttggagcta ctacatcggc    780

tacctgagac tgatcctgcc tgagctgcag gccagaatca gaacctacaa ccagcactac    840

aacaacctgc tgcggggagc agtgagccag agactgtata ttctgctccc tctggactgc    900

ggcgtgcctg acaacctgag catggccgac cctaacatca gattcctgga caagctgcct    960

cagcagaccg gcgaccacgc cggcatcaag gacagagtgt acagcaacag catttacgag   1020

ctgctggaga acggccagag agccggcacc tgcgtgctgg agtacgccac ccctctgcag   1080

accctgttcg ccatgagcca gtactcccag gcaggattca gcagagagga cagactggag   1140

caggccaagc tgttctgccg tactcttgag gacatccttg cagacgcccc tgagagccag   1200

aacaactgcc ggttgattgc ctaccaggaa ccggcagacg acagctcatt ctccttgtct   1260

caggaggtcc ttagacacct gcggcaggag gagaaggagg aggtgaccgt gggcagcctg   1320

aagacatccg ccgtgcctag cacgtctacc atgtcccagg agccggaact gctaatcagc   1380

ggcatggaga agcctctgcc tctcaggacc gacttcagc                          1419
```

<210> SEQ ID NO 164
<211> LENGTH: 380
<212> TYPE: PRT
<213> ORGANISM: Artificial Sequence
<220> FEATURE:
<223> OTHER INFORMATION: Synthetic: Hu STING (R284K) var; no epitope tag

<400> SEQUENCE: 164

```
Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
            20                  25                  30

Leu Trp Gly Leu Gly Glu Pro Pro Glu His Thr Leu Arg Tyr Leu Val
        35                  40                  45

Leu His Leu Ala Ser Leu Gln Leu Gly Leu Leu Leu Asn Gly Val Cys
    50                  55                  60

Ser Leu Ala Glu Glu Leu Arg His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Tyr Ser Leu Pro Asn Ala
            100                 105                 110
```

Val Gly Pro Pro Phe Thr Trp Met Leu Ala Leu Leu Gly Leu Ser Gln
115 120 125

Ala Leu Asn Ile Leu Leu Gly Leu Lys Gly Leu Ala Pro Ala Glu Ile
130 135 140

Ser Ala Val Cys Glu Lys Gly Asn Phe Asn Val Ala His Gly Leu Ala
145 150 155 160

Trp Ser Tyr Tyr Ile Gly Tyr Leu Arg Leu Ile Leu Pro Glu Leu Gln
165 170 175

Ala Arg Ile Arg Thr Tyr Asn Gln His Tyr Asn Asn Leu Leu Arg Gly
180 185 190

Ala Val Ser Gln Arg Leu Tyr Ile Leu Leu Pro Leu Asp Cys Gly Val
195 200 205

Pro Asp Asn Leu Ser Met Ala Asp Pro Asn Ile Arg Phe Leu Asp Lys
210 215 220

Leu Pro Gln Gln Thr Gly Asp His Ala Gly Ile Lys Asp Arg Val Tyr
225 230 235 240

Ser Asn Ser Ile Tyr Glu Leu Leu Glu Asn Gly Gln Arg Ala Gly Thr
245 250 255

Cys Val Leu Glu Tyr Ala Thr Pro Leu Gln Thr Leu Phe Ala Met Ser
260 265 270

Gln Tyr Ser Gln Ala Gly Phe Ser Arg Glu Asp Lys Leu Glu Gln Ala
275 280 285

Lys Leu Phe Cys Arg Thr Leu Glu Asp Ile Leu Ala Asp Ala Pro Glu
290 295 300

Ser Gln Asn Asn Cys Arg Leu Ile Ala Tyr Gln Glu Pro Ala Asp Asp
305 310 315 320

Ser Ser Phe Ser Leu Ser Gln Glu Val Leu Arg His Leu Arg Gln Glu
325 330 335

Glu Lys Glu Glu Val Thr Val Gly Ser Leu Lys Thr Ser Ala Val Pro
340 345 350

Ser Thr Ser Thr Met Ser Gln Glu Pro Glu Leu Leu Ile Ser Gly Met
355 360 365

Glu Lys Pro Leu Pro Leu Arg Thr Asp Phe Ser Thr
370 375 380

<210> SEQ ID NO 165
<211> LENGTH: 1140
<212> TYPE: DNA
<213> ORGANISM: Artificial Sequence
<220> FEATURE:
<223> OTHER INFORMATION: Synthetic: Hu STING (R284K) var; no epitope tag

<400> SEQUENCE: 165
atgccccata gcagcctgca ccccagcatc cctgccccca gaggccacgg cgcccagaag 60
gccgccctgg tcctgctgag cgcatgcctg gtcaccctgt ggggcctggg cgagcccccc 120
gagcacaccc tgagatacct ggtgctgcac ctcgccagcc tgcagctggg cctgctgctg 180
aacggcgtgt gcagcctggc cgaggagctg agacacatcc acagcagata tagaggcagc 240
tactggagaa ccgtgagagc ttgcctcggc tgcccccctga gaagaggcgc cctgctgctg 300
ctgagcatct acttttacta cagcctgccc aacgctgtgg gcccccccttt cacgtggatg 360 ctcgccctgc tgggactgag ccaggccctg aacatcctgc tgggccttaa gggcctagcc 420
cccgccgaga tcagcgccgt gtgcgagaag ggcaacttca atgtggccca cggcctggcc 480
tggagctact acatcggcta cctgagactg atcctgcccg agctgcaggc cagaatcaga 540

```
acctacaatc agcactacaa caacctgctg agaggcgccg tgagccagag actgtacatc    600

ctgctgcccc tggactgcgg cgtgcccgac aacctcagca tggccgaccc caacatcaga    660

ttcctggaca agctgcccca gcagaccggc gaccacgccg gcatcaagga tcgcgtgtac    720

agcaacagca tctacgagct gctggaaaac ggccagagag ccggaacctg cgtgctggag    780

tacgccacac ccctgcagac cctgttcgcc atgagccagt acagccaggc cggcttcagc    840

agagaggaca agctggagca ggccaagctg ttctgcagaa ccctggagga tatcctcgcc    900

gacgccccog agagccagaa caactgcagg ctgatcgcgt accaggagcc cgctgacgac    960

agcagcttta gcctgagcca ggaggtgctg agacatctgc gtcaagagga aaaggaggag   1020

gtgaccgtgg gctccctgaa gaccagcgcc gtgcccagca ccagcaccat gagccaggag   1080

cccgagctgc tgatcagcgg catggagaag ccactgcccc tcagaaccga cttcagcacc   1140
```

```
<210> SEQ ID NO 166
<211> LENGTH: 186
<212> TYPE: PRT
<213> ORGANISM: Homo sapiens
<220> FEATURE:
<221> NAME/KEY: misc_feature
<222> LOCATION: (1)..(186)
<223> OTHER INFORMATION: Human KRAS sp/P01116[1-186]

<400> SEQUENCE: 166

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys
            180                 185


<210> SEQ ID NO 167
<211> LENGTH: 570
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 5' 7 MeGpppG 2'Ome - OH 3'; Where:  A,C G & U =
```

AMP, CMP, GMP & N1-psi-UMP, respectively; Me = methyl; p = inorganic phosphate(KRAS concatemer mRNA sequence; CX-012908)

<400> SEQUENCE: 167
ggaaauaaga gagaaaagaa gaguaagaag aaauauaaga gccaccauga ccgaguacaa 60
gcucgugguc gucggcgccg acggguagg caaguccgcu cugaccauuc agcucaucca 120
gaugacggag uacaaacucg ugguaguggg agccgugggu gugggcaaga gcgcgcucac 180
cauccaacuc auccaaauga ccgaauauaa acucgucgug gugggagccg gcgacguggg 240
aaagagcgcc cuuaccaucc aguuaaucca gaugacagaa uacaagcugg ugguggucgg 300
ugccugcggc gugguaagu ccgcccugac aauccagcug auccagugau aauaggcugg 360
agccucggug gccaugcuuc uugccccuug ggccuccccc cagccccucc uccccuuccu 420
gcacccguac cccgugguc uuugaauaaa gucugagugg gcggcaaaaa aaaaaaaaaa 480
aaaaaaaaaa aaaaaaaaaa aaaaaaaaaa aaaaaaaaaa aaaaaaaaaa aaaaaaaaaa 540
aaaaaaaaaa aaaaaaaaaa aaaaaaucuag 570

<210> SEQ ID NO 168
<211> LENGTH: 1429
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 5' 7 MeGpppG 2'Ome - OH 3'; Where: A,C G & U = AMP, CMP, GMP & N1-psi-UMP, respectively; Me = methyl; p = inorganic phosphate; underline = miR-122 binding site(STING mRNA sequence; CX-012871)

<400> SEQUENCE: 168
ggaaauaaga gagaaaagaa gaguaagaag aaauauaaga gccaccaugc cccacaguag 60
ccuccacccc agcaucccu gccccagagg ccacggcgca cagaaggccg cccuggugcu 120
gcugagcgcc ugucugguga cccugugggg ucugggcgag cccccgagc acacccugcg 180 guaccucgug cugcaucugg ccagccugca gcugggccug cugcugaacg gcgugugcag 240
ccuggccgaa gagcugagac acauccacag cagauacaga ggcuccuacu ggagaaccgu 300
cagagccugc cucggcuguc cccugagaag aggcgcccug cugcuccuga gcaucuacuu 360
cuacuacagc cugcccaacg ccgugggccc ccccuucacc uggaugcugg cccugcuggg 420
ccugagccag gcccugaaca uccugcuggg ccugaagggc uuggccccg ccgagaucuc 480 cgccgugugc gagaagggca acuucaacau ggcccauggc cuugccuggu ccuacuacau 540
cggcuaccug agacugaucc ugcccgagcu gcaggccaga aucagaaccu acaaccagca 600
cuacaacaac cugcugagag gcgccgugag ccaaagacug uacauccugc ugccccugga 660
cugcggcgug cccgacaacc uuagcauggc cgaccccaac aucagauucc uggacaagcu 720
gccccagcag accggcgacc acgccggcau caaggacaga guguacagca acagcaucua 780
cgagcugcug gagaacggcc agagagccgg caccugcgug cuggaguacg ccacccccu 840 gcagacccug uucgccauga gccaguacag ccaggccggc uucagcagag aggacagacu 900
ggagcaagcc aagcuguucu gcagaacccu ggaggacauc cuggcggacg cccccgagag 960
ccaaaacaac ugcagacuga ucgccuacca ggagcccgcc gacgacagca gcuucagccu 1020
gagccaggaa gugcugagac accugagaca ggaagagaag gaggagguga ccgugggaag 1080
ccugaagacc agcgccgugc ccagcaccag caccaugagc caggagcccg agcugcugau 1140
cagcggcaug gagaagcccc ugccccugag aaccgacuuc agcugauaau aggcuggagc 1200
cucgguggcc uagcuucuug ccccuugggc cuccccccag ccccuccucc ccuuccugca 1260
cccguacccc ccaaacacca uugucacacu ccaguggucu uugaauaaag ucugaguggg 1320
cggcaaaaaa aaaaaaaaaa aaaaaaaaaa aaaaaaaaaa aaaaaaaaaa aaaaaaaaaa 1380
aaaaaaaaaa aaaaaaaaaa aaaaaaaaaa aaaaaaaaaa aaaaucuag 1429

<210> SEQ ID NO 169
<211> LENGTH: 300
<212> TYPE: RNA
<213> ORGANISM: Artificial Sequence
<220> FEATURE:
<223> OTHER INFORMATION: Synthetic: KRAS(G12D G12V G13D G12C) 100mer 4MUT nt. seq

<400> SEQUENCE: 169
augaccgagu acaagcucgu ggucgucggc gccgacgggg uaggcaaguc cgcucugacc 60
auucagcuca uccagaugac ggaguacaaa cucgugguag ugggagccgu gggugugggc 120
aagagcgcgc ucaccaucca acucauccaa augaccgaau auaaacucgu cgugguggga 180
gccggcgacg ugggaaagag cgcccuuacc auccaguuaa uccagaugac agaauacaag 240
cugguggugg ucggugccug cggcgugggu aaguccgccc ugacaaucca gcugauccag 300

<210> SEQ ID NO 170
<211> LENGTH: 1137
<212> TYPE: RNA
<213> ORGANISM: Artificial Sequence
<220> FEATURE:
<223> OTHER INFORMATION: Synthetic: huSTING(V155M); no epitope tag; nucleotide sequence

<400> SEQUENCE: 170
augccccaca guagccucca ccccagcauc cccugcccca gaggccacgg cgcacagaag 60
gccgcccugg ugcugcugag cgccugucug gugacccugu ggggucuggg cgagcccccc 120
gagcacaccc ugcgguaccu cgugcugcau cuggccagcc ugcagcuggg ccugcugcug 180
aacggcgugu gcagccuggc cgaagagcug agacacaucc acagcagaua cagaggcucc 240
uacuggagaa ccgucagagc cugccucggc uguccccuga gaagaggcgc ccugcugcuc 300
cugagcaucu acuucuacua cagccugccc aacgccgugg gccccccuu caccuggaug 360 cuggcccugc ugggccugag ccaggcccug aacauccugc ugggccugaa gggcuuggcc 420
cccgccgaga ucuccgccgu gugcgagaag ggcaacuuca acauggccca uggccuugcc 480
ugguccuacu acaucggcua ccugagacug auccugcccg agcugcaggc cagaaucaga 540
accuacaacc agcacuacaa caaccugcug agaggcgccg ugagccaaag acuguacauc 600
cugcugcccc uggacugcgg cgugcccgac aaccuuagca uggccgaccc caacaucaga 660
uuccuggaca agcugcccca gcagaccggc gaccacgccg gcaucaagga cagaguguac 720
agcaacagca ucuacgagcu gcuggagaac ggccagagag ccggcaccug cgugcuggag 780
uacgccaccc cccugcagac ccuguucgcc augagccagu acagccaggc cggcuucagc 840
agagaggaca gacuggagca agccaagcug uucugcagaa cccuggagga cauccuggcg 900
gacgcccccg agagccaaaa caacugcaga cugaucgccu accaggagcc cgccgacgac 960
agcagcuuca gccugagcca ggaagugcug agacaccuga gacaggaaga gaaggaggag 1020
gugaccgugg gaagccugaa gaccagcgcc gugcccagca ccagcaccau gagccaggag 1080
cccgagcugc ugaucagcgg cauggagaag ccccugcccc ugagaaccga cuucagc 1137

<210> SEQ ID NO 171
<211> LENGTH: 85
<212> TYPE: RNA
<213> ORGANISM: Artificial Sequence
<220> FEATURE:
<223> OTHER INFORMATION: Synthetic: mir-122

<400> SEQUENCE: 171
ccuuagcaga gcuguggagu gugacaaugg uguuuguguc uaaacuauca aacgccauua 60
ucacacuaaa uagcuacugc uaggc 85

<210> SEQ ID NO 172
<211> LENGTH: 22
<212> TYPE: RNA
<213> ORGANISM: Artificial Sequence
<220> FEATURE:
<223> OTHER INFORMATION: Synthetic: mir-122-3p_

<400> SEQUENCE: 172
aacgccauua ucacacuaaa ua 22

<210> SEQ ID NO 173
<211> LENGTH: 22
<212> TYPE: RNA
<213> ORGANISM: Artificial Sequence
<220> FEATURE:
<223> OTHER INFORMATION: Synthetic: mir-122-3p binding site

<400> SEQUENCE: 173
uauuuagugu gauaauggcg uu 22

<210> SEQ ID NO 174
<211> LENGTH: 22
<212> TYPE: RNA
<213> ORGANISM: Artificial Sequence
<220> FEATURE:
<223> OTHER INFORMATION: Synthetic: mir-122-5p

<400> SEQUENCE: 174
uggaguguga caaugguguu ug 22

<210> SEQ ID NO 175
<211> LENGTH: 22
<212> TYPE: RNA
<213> ORGANISM: Artificial Sequence
<220> FEATURE:
<223> OTHER INFORMATION: Synthetic: mir-122-5p binding site

<400> SEQUENCE: 175
caaacaccau ugucacacuc ca 22

<210> SEQ ID NO 176
<211> LENGTH: 46
<212> TYPE: RNA
<213> ORGANISM: Artificial Sequence
<220> FEATURE:
<223> OTHER INFORMATION: Synthetic: 5 UTR

<400> SEQUENCE: 176
ggaaauaaga gagaaaagaa gaguaagaag aaauauaaga gccacc 46

<210> SEQ ID NO 177
<211> LENGTH: 12
<212> TYPE: DNA

<213> ORGANISM: Artificial Sequence
<220> FEATURE:
<223> OTHER INFORMATION: Synthetic: GC-Rich RNA Element

<400> SEQUENCE: 177
ccgccgccgc cg 12

<210> SEQ ID NO 178
<211> LENGTH: 15
<212> TYPE: DNA
<213> ORGANISM: Artificial Sequence
<220> FEATURE:
<223> OTHER INFORMATION: Synthetic: GC-Rich RNA Element

<400> SEQUENCE: 178
ccgccgccgc cgccg 15

<210> SEQ ID NO 179
<211> LENGTH: 10
<212> TYPE: DNA
<213> ORGANISM: Artificial Sequence
<220> FEATURE:
<223> OTHER INFORMATION: Synthetic: V1 - GC-Rich RNA Element

<400> SEQUENCE: 179
ccccggcgcc 10

<210> SEQ ID NO 180
<211> LENGTH: 41
<212> TYPE: DNA
<213> ORGANISM: Artificial Sequence
<220> FEATURE:
<223> OTHER INFORMATION: Synthetic: 5UTR

<400> SEQUENCE: 180
gggaaataag agagaaaaga agagtaagaa gaaatataag a 41

<210> SEQ ID NO 181
<211> LENGTH: 57
<212> TYPE: DNA
<213> ORGANISM: Artificial Sequence
<220> FEATURE:
<223> OTHER INFORMATION: Synthetic: V1-UTR

<400> SEQUENCE: 181
gggaaataag agagaaaaga agagtaagaa gaaatataag accccggcgc cgccacc 57

<210> SEQ ID NO 182
<211> LENGTH: 54
<212> TYPE: DNA
<213> ORGANISM: Artificial Sequence
<220> FEATURE:
<223> OTHER INFORMATION: Synthetic: V2-UTR

<400> SEQUENCE: 182
gggaaataag agagaaaaga agagtaagaa gaaatataag accccggcgc cacc 54

<210> SEQ ID NO 183
<211> LENGTH: 45
<212> TYPE: PRT
<213> ORGANISM: Artificial Sequence
<220> FEATURE:
<223> OTHER INFORMATION: Synthetic: KRAS G12C 15mer^3

<400> SEQUENCE: 183

Met Lys Leu Val Val Val Gly Ala Cys Gly Val Gly Lys Ser Ala Met

```
1               5                   10                  15

Lys Leu Val Val Val Gly Ala Cys Gly Val Gly Lys Ser Ala Met Lys
            20                  25                  30

Leu Val Val Val Gly Ala Cys Gly Val Gly Lys Ser Ala
        35                  40                  45
```

<210> SEQ ID NO 184
<211> LENGTH: 225
<212> TYPE: DNA
<213> ORGANISM: Artificial Sequence
<220> FEATURE:
<223> OTHER INFORMATION: Synthetic: KRAS G12C 25mer^3 nucleotide sequence

<400> SEQUENCE: 184

```
atgaccgagt acaagctcgt ggttgttggc gcctgcggcg tgggcaagag cgccctcacc     60

atccagctca tccagatgac agagtataag ttagtcgttg tcggagcttg cggagttgga    120

aagtcggcgc tcaccattca actcatacaa atgacagaat ataagttagt ggtggtgggt    180

gcgtgtggcg ttggcaagag tgcgcttact atccagctca ttcag                     225
```

<210> SEQ ID NO 185
<211> LENGTH: 92
<212> TYPE: RNA
<213> ORGANISM: Artificial Sequence
<220> FEATURE:
<223> OTHER INFORMATION: Synthetic: 5 UTR

<400> SEQUENCE: 185

```
ucaagcuuuu ggacccucgu acagaagcua auacgacuca cuauagggaa auaagagaga     60

aaagaagagu aagaagaaau auaagagcca cc                                   92
```

<210> SEQ ID NO 186
<211> LENGTH: 119
<212> TYPE: RNA
<213> ORGANISM: Artificial Sequence
<220> FEATURE:
<223> OTHER INFORMATION: Synthetic: 3 UTR

<400> SEQUENCE: 186

```
ugauaauagg cuggagccuc gguggccaug cuucuugccc cuugggccuc cccccagccc     60

cuccuccccu uccugcaccc guacccccgu ggucuuugaa uaaagucuga gugggcggc     119
```

<210> SEQ ID NO 187
<211> LENGTH: 164
<212> TYPE: RNA
<213> ORGANISM: Artificial Sequence
<220> FEATURE:
<223> OTHER INFORMATION: Synthetic: 3 UTR with mi-122 and mi-142.3p sites

<400> SEQUENCE: 187

```
ugauaauagg cuggagccuc gguggccaug cuucuugccc cuugggccca aacaccauug     60

ucacacucca uccccccagc cccuccuccc cuuccuccau aaaguaggaa acacuacaug    120

cacccguacc cccguggucu uugaauaaag ucugaguggg cggc                     164
```

<210> SEQ ID NO 188
<211> LENGTH: 66
<212> TYPE: RNA
<213> ORGANISM: Artificial Sequence
<220> FEATURE:
<223> OTHER INFORMATION: Synthetic: Nucleotide sequence encoding 2A peptide

<400> SEQUENCE: 188
ggaagcggag cuacuaacuu cagccugcug aagcaggcug gagacgugga ggagaacccu 60
ggaccu 66

<210> SEQ ID NO 189
<211> LENGTH: 108
<212> TYPE: RNA
<213> ORGANISM: Artificial Sequence
<220> FEATURE:
<223> OTHER INFORMATION: Synthetic: Nucleotide sequence encoding 2A
peptide

<400> SEQUENCE: 189
uccggacuca gauccgggga ucucaaaauu gucgcuccug ucaaacaaac ucuuaacuuu 60
gauuuacuca aacuggcugg ggauguagaa agcaauccag guccacuc 108

<210> SEQ ID NO 190
<211> LENGTH: 75
<212> TYPE: RNA
<213> ORGANISM: Artificial Sequence
<220> FEATURE:
<223> OTHER INFORMATION: Synthetic: KRAS G12D 25mer nucleotide sequence

<400> SEQUENCE: 190
augaccgagu acaagcuggu gguggugggc gccgacggcg ugggcaagag cgcccugacc 60
auccagcuga uccag 75

<210> SEQ ID NO 191
<211> LENGTH: 75
<212> TYPE: RNA
<213> ORGANISM: Artificial Sequence
<220> FEATURE:
<223> OTHER INFORMATION: Synthetic: KRAS G12V 25mer nucleotide sequence

<400> SEQUENCE: 191
augaccgagu acaagcuggu gguggugggc gccgugggcg ugggcaagag cgcccugacc 60
auccagcuga uccag 75

<210> SEQ ID NO 192
<211> LENGTH: 75
<212> TYPE: RNA
<213> ORGANISM: Artificial Sequence
<220> FEATURE:
<223> OTHER INFORMATION: Synthetic: KRAS G13D 25mer nucleotide sequence

<400> SEQUENCE: 192
augaccgagu acaagcuggu gguggugggc gccggcgacg ugggcaagag cgcccugacc 60
auccagcuga uccag 75

<210> SEQ ID NO 193
<211> LENGTH: 225
<212> TYPE: RNA
<213> ORGANISM: Artificial Sequence
<220> FEATURE:
<223> OTHER INFORMATION: Synthetic: KRAS G12D 25mer^3 nucleotide
sequence

<400> SEQUENCE: 193
augaccgagu acaaguuagu gguugugggc gccgacggcg ugggcaagag cgcccucacc 60
auccagcuua uccagaugac ggaauauaag uuaguaguag ugggagccga cggugucggc 120
aaguccgcuu ugaccauuca acuuauucag augacagagu auaagcuggu cguuguaggc 180
gcagacggcg uuggaaaguc ggcacugacg auccaguuga uccag 225

<210> SEQ ID NO 194
<211> LENGTH: 225
<212> TYPE: RNA
<213> ORGANISM: Artificial Sequence
<220> FEATURE:
<223> OTHER INFORMATION: Synthetic: KRAS G12V 25mer^3 nucleotide sequence

<400> SEQUENCE: 194
augaccgagu acaagcucgu cgugguggc gccgugggcg ugggcaagag cgcccuaacc 60
auccaguuga uccagaugac cgaauauaag cucgugguag ucggagcggu gggcguuggc 120
aagucagcgc uaacaauaca acuaauccaa augaccgaau acaagcuagu uguagucggu 180
gccgucggcg uuggaaaguc agcccuuaca auucagcuca uucag 225

<210> SEQ ID NO 195
<211> LENGTH: 225
<212> TYPE: RNA
<213> ORGANISM: Artificial Sequence
<220> FEATURE:
<223> OTHER INFORMATION: Synthetic: KRAS G13D 25mer^3 nucleotide sequence

<400> SEQUENCE: 195
augaccgagu acaagcucgu agugguuggc gccggcgacg ugggcaagag cgcccuaacc 60
auccagcuca uccagaugac agaauauaag cuugugguug ugggagcagg agacguggga 120
aagagugcgu ugacgauuca acucauacag augaccgaau acaaguuggu gguggucggc 180
gcaggugacg uugguaaguc ugcacuaacu auacaacuga uccag 225

<210> SEQ ID NO 196
<211> LENGTH: 75
<212> TYPE: RNA
<213> ORGANISM: Artificial Sequence
<220> FEATURE:
<223> OTHER INFORMATION: Synthetic: KRAS G12C 25mer nucleotide sequence

<400> SEQUENCE: 196
augaccgagu acaagcuggu ggugguggc gccugcggcg ugggcaagag cgcccugacc 60
auccagcuga uccag 75

<210> SEQ ID NO 197
<211> LENGTH: 225
<212> TYPE: RNA
<213> ORGANISM: Artificial Sequence
<220> FEATURE:
<223> OTHER INFORMATION: Synthetic: KRAS G12C 25mer^3 nucleotide sequence

<400> SEQUENCE: 197
augaccgagu acaagcucgu gguuguuggc gccugcggcg ugggcaagag cgcccucacc 60
auccagcuca uccagaugac agaguauaag uuagucguug ucggagcuug cggaguugga 120
aagucggcgc ucaccauuca acucauacaa augacagaau auaaguuagu gguggugggu 180
gcguguggcg uuggcaagag ugcgcuuacu auccagcuca uucag 225

<210> SEQ ID NO 198
<211> LENGTH: 75

<212> TYPE: RNA
<213> ORGANISM: Artificial Sequence
<220> FEATURE:
<223> OTHER INFORMATION: Synthetic: KRAS WT 25mer nucleotide sequence

<400> SEQUENCE: 198
augaccgagu acaagcuggu gguggugggc gccggcggcg ugggcaagag cgcccugacc 60
auccagcuga uccag 75

<210> SEQ ID NO 199
<211> LENGTH: 47
<212> TYPE: RNA
<213> ORGANISM: Artificial Sequence
<220> FEATURE:
<223> OTHER INFORMATION: Synthetic: 5 UTR sequence; no promoter

<400> SEQUENCE: 199
gggaaauaag agagaaaaga agaguaagaa gaaauauaag agccacc 47

<210> SEQ ID NO 200
<211> LENGTH: 225
<212> TYPE: RNA
<213> ORGANISM: Artificial Sequence
<220> FEATURE:
<223> OTHER INFORMATION: Synthetic: KRAS(G12D G12V G13D) 75mer 3MUT nt. seq

<400> SEQUENCE: 200
augaccgagu acaagcucgu uguagucggc gccgacggcg ugggcaagag cgccuugacc 60
auccaguuga uccagaugac cgaauauaag uugguggugg uaggcgcagu gggaguuggc 120
aagucagcac ucacaauuca gcucauucaa augacagaau acaaguuagu cguuguagga 180
gcaggcgacg ucggcaagag ugccuuaacc auucaacuaa uccag 225

<210> SEQ ID NO 201
<211> LENGTH: 1137
<212> TYPE: RNA
<213> ORGANISM: Artificial Sequence
<220> FEATURE:
<223> OTHER INFORMATION: Synthetic: Hu STING(R284T); no epitope tag; nucleotide sequence

<400> SEQUENCE: 201
augccucaca gcagccugca cccuagcauc ccuugcccua gaggccacgg cgcccagaag 60
gccgcccugg ugcugcugag cgccugccug gugacccugu ggggccuggg cgagccuccu 120
gagcacaccc ugagauaccu ggugcugcac cuggccagcc ugcagcuggg ccugcugcug 180
aacggcgugu gcagccuggc cgaggagcug agacacaucc acagcagaua cagaggcagc 240
uacuggagaa ccgugagagc cugccugggc ugcccucuga gaagaggcgc ccugcugcug 300
cugagcaucu acuucuacua cagccugccu aacgccgugg gcccuccuuu caccuggaug 360
cuggcccugc ugggccugag ccaggcccug aacauccugc ugggccugaa gggccuggcc 420
ccugccgaga ucagcgccgu gugcgagaag ggcaacuuca acguggccca cggccuggcc 480
uggagcuacu acaucggcua ccugagacug auccugccug agcugcaggc cagaaucaga 540
accuacaacc agcacuacaa caaccugcug agaggcgccg ugagccagag acuguacauc 600
cugcugccuc uggacugcgg cgugccugac aaccugagca uggccgaccc uaacaucaga 660
uuccuggaca agcugccuca gcagaccggc gaccacgccg gcaucaagga cagaguguac 720
agcaacagca ucuacgagcu gcuggagaac ggccagagag ccggcaccug cgugcuggag 780
uacgccaccc cucugcagac ccuguucgcc augagccagu acagccaggc cggcuucagc 840
agagaggaca cccuggagca ggccaagcug uucugcagaa cccuggagga cauccuggcc 900
gacgccccug agagccagaa caacugcaga cugaucgccu accaggagcc ugccgacgac 960
agcagcuuca gccugagcca ggaggugcug agacaccuga gacaggagga gaaggaggag 1020
gugaccgugg gcagccugaa gaccagcgcc gugccuagca ccagcaccau gagccaggag 1080
ccugagcugc ugaucagcgg cauggagaag cccucugccuc ugagaaccga cuucagc 1137

<210> SEQ ID NO 202
<211> LENGTH: 1137
<212> TYPE: RNA
<213> ORGANISM: Artificial Sequence
<220> FEATURE:
<223> OTHER INFORMATION: Synthetic: hu STING (R284M); no epitope tag; nucleotide sequence

<400> SEQUENCE: 202
augccccaca gcagccugca ccccuccauc cccuguccca gaggccacgg cgcccagaag 60
gccgcccugg ugcugcugag cgccugccug gugaccuuau ggggccuggg cgagcccccc 120
gagcacaccc ugagauaccu gguccugcac cuggccagcc uccagcuggg ccugcugcuc 180
aacggcgugu guagccuggc cgaggagcug agacacaucc acagcagaua cagaggcagc 240
uacuggagaa ccgugagagc cugccugggu ugcccacuga gaagaggagc ucugcugcug 300
cugagcaucu acuucuacua cucgcugccc aacgcugugg gcccccccuu caccuggaug 360
cuggcccugc ugggucugag ccaggcccug aacauccucc ugggccugaa gggccuggcc 420
cccgccgaga uaagcgccgu uugcgagaag ggcaacuuca acguggccca uggccuggcc 480
uggagcuacu acaucggcua cuuacgccug auccugcccg agcugcaggc cagaaucaga 540
accuacaacc agcauuacaa caaccugcug agaggcgccg ugagccagag acuguauauc 600
cugcugcccc uggacugcgg cgugcccgac aaccugagca uggccgaccc caacaucaga 660
uuccuggaca agcuccccca gcagaccggc gaccacgccg gaaucaaaga cagaguguau 720
agcaacagca ucuacgagcu gcuggagaac ggccagagag ccggcaccug cguacuggag 780
uacgccaccc ccuugcagac ccuguuugcc augagccagu acagccaggc cggcuucagc 840
agagaggaca ugcuggagca ggccaagcug uucugcagaa cccuggagga cauccuggcc 900
gacgcccccg agagccagaa caacugcaga cugaucgccu accaagagcc cgccgacgac 960
agcagcuuca gcuuaagcca ggaggugcug agacaucuga gacaggagga gaaggaggag 1020
gugaccgugg gcagccucaa gaccagcgcu gugcccucua ccagcaccau gagccaggag 1080
cccgagcugc ugaucagcgg cauggagaag ccccugcccc ugagaacaga cuucagc 1137

<210> SEQ ID NO 203
<211> LENGTH: 1137
<212> TYPE: RNA
<213> ORGANISM: Artificial Sequence
<220> FEATURE:
<223> OTHER INFORMATION: Synthetic: Hu STING (R284K); no epitope tag; nucleotide sequence

<400> SEQUENCE: 203
augccccaua gcagccugca ccccagcauc cccugcccca gaggccacgg cgcccagaag 60
gccgcccugg uccugcugag cgcaugccug gucacccugu ggggccuggg cgagcccccc 120
gagcacaccc ugagauaccu ggugcugcac cucgccagcc ugcagcuggg ccugcugcug 180
aacggcgugu gcagccuggc cgaggagcug agacacaucc acagcagaua uagaggcagc 240

```
uacuggagaa ccgugagagc uugccucggc ugcccccuga gaagaggcgc ccugcugcug    300

cugagcaucu acuuuuacua cagccugccc aacgcugugg gcccccccuuu cacguggaug   360

cucgccccugc ugggacugag ccaggcccug aacauccugc ugggccuuaa gggccuagcc   420

cccgccgaga ucagcgccgu gugcgagaag ggcaacuuca auguggccca cggccuggcc    480

uggagcuacu acaucggcua ccugagacug auccugcccg agcugcaggc cagaaucaga    540

accuacaauc agcacuacaa caaccugcug agaggcgccg ugagccagag acuguacauc    600

cugcugcccc uggacugcgg cgugcccgac aaccucagca uggccgaccc caacaucaga    660

uuccuggaca agcugcccca gcagaccggc gaccacgccg gcaucaagga ucgcguguac    720

agcaacagca ucuacgagcu gcuggaaaac ggccagagag ccggaaccug cgugcuggag    780

uacgccacac cccugcagac ccuguucgcc augagccagu acagccaggc cggcuucagc    840

agagaggaca agcuggagca ggccaagcug uucugcagaa cccuggagga uauccucgcc    900

gacgcccccg agagccagaa caacugcagg cugaucgcgu accaggagcc cgcugacgac    960

agcagcuuua gccugagcca ggaggugcug agacaucugc gucaagagga aaaggaggag   1020

gugaccgugg gcucccugaa gaccagcgcc gugcccagca ccagcaccau gagccaggag   1080

cccgagcugc ugaucagcgg cauggagaag ccacugcccc ucagaaccga cuucagc      1137
```

<210> SEQ ID NO 204
<211> LENGTH: 1137
<212> TYPE: RNA
<213> ORGANISM: Artificial Sequence
<220> FEATURE:
<223> OTHER INFORMATION: Synthetic: Hu STING(N154S); no epitope tag; nucleotide sequence

<400> SEQUENCE: 204

```
augccucaca gcagccugca cccuagcauc ccuugcccua gaggccacgg cgcccagaag     60

gccgcccugg ugcugcugag cgccugccug gugacccugu ggggccuggg cgagccuccu    120

gagcacaccc ugagauaccu ggugcugcac cuggccagcc ugcagcuggg ccugcugcug    180

aacggcgugu gcagccuggc cgaggagcug agacacaucc acagcagaua cagaggcagc    240

uacuggagaa ccgugagagc cugccugggc ugcccucuga gaagaggcgc ccugcugcug    300

cugagcaucu acuucuacua cagccugccu aacgccgugg gcccuccuuu caccuggaug    360

cuggcccugc ugggccugag ccaggcccug aacauccugc ugggccugaa gggccuggcc    420

ccugccgaga ucagcgccgu gugcgagaag ggcaacuuca gcguggccca cggccuggcc    480

uggagcuacu acaucggcua ccugagacug auccugccug agcugcaggc cagaaucaga    540

accuacaacc agcacuacaa caaccugcug agaggcgccg ugagccagag acuguacauc    600

cugcugccuc uggacugcgg cgugccugac aaccugagca uggccgaccc uaacaucaga    660

uuccuggaca agcugccuca gcagaccggc gaccacgccg gcaucaagga cagaguguac    720

agcaacagca ucuacgagcu gcuggagaac ggccagagag ccggcaccug cgugcuggag    780

uacgccaccc cucugcagac ccuguucgcc augagccagu acagccaggc cggcuucagc    840

agagaggaca gacuggagca ggccaagcug uucugcagaa cccuggagga cauccuggcc    900

gacgccccug agagccagaa caacugcaga cugaucgccu accaggagcc ugccgacgac    960

agcagcuuca gccugagcca ggaggugcug agacaccuga gacaggagga gaaggaggag   1020

gugaccgugg gcagccugaa gaccagcgcc gugccuagca ccagcaccau gagccaggag   1080

ccugagcugc ugaucagcgg cauggagaag ccucugccuc ugagaaccga cuucagc      1137
```

<210> SEQ ID NO 205
<211> LENGTH: 1137
<212> TYPE: RNA
<213> ORGANISM: Artificial Sequence
<220> FEATURE:
<223> OTHER INFORMATION: Synthetic: Hu STING(V147L); no epitope tag; nucleotide sequence

<400> SEQUENCE: 205
augccucaca gcagccugca cccuagcauc ccuugcccua gaggccacgg cgcccagaag 60
gccgcccugg ugcugcugag cgccugccug gugacccugu ggggccuggg cgagccuccu 120
gagcacaccc ugagauaccu ggugcugcac cuggccagcc ugcagcuggg ccugcugcug 180
aacggcgugu gcagccuggc cgaggagcug agacacaucc acagcagaua cagaggcagc 240
uacuggagaa ccgugagagc cugccugggc ugcccucuga gaagaggcgc ccugcugcug 300
cugagcaucu acuucuacua cagccugccu aacgccgugg gcccuccuuu caccuggaug 360
cuggcccugc ugggccugag ccaggcccug aacauccugc ugggccugaa gggccuggcc 420
ccugccgaga ucagcgcccu gugcgagaag ggcaacuuca acguggccca cggccuggcc 480
uggagcuacu acaucggcua ccugagacug auccugccug agcugcaggc cagaaucaga 540
accuacaacc agcacuacaa caaccugcug agaggcgccg ugagccagag acuguacauc 600
cugcugccuc uggacugcgg cgugccugac aaccugagca uggccgaccc uaacaucaga 660
uuccuggaca agcugccuca gcagaccggc gaccacgccg gcaucaagga cagaguguac 720
agcaacagca ucuacgagcu gcuggagaac ggccagagag ccggcaccug cgugcuggag 780
uacgccaccc cucugcagac ccuguucgcc augagccagu acagccaggc cggcuucagc 840
agagaggaca gacuggagca ggccaagcug uucugcagaa cccuggagga cauccuggcc 900
gacgccccug agagccagaa caacugcaga cugaucgccu accaggagcc ugccgacgac 960
agcagcuuca gccugagcca ggaggugcug agacaccuga gacaggagga gaaggaggag 1020
gugaccgugg gcagccugaa gaccagcgcc gugccuagca ccagcaccau gagccaggag 1080
ccugagcugc ugaucagcgg cauggagaag ccucugccuc ugagaaccga cuucagc 1137

<210> SEQ ID NO 206
<211> LENGTH: 1137
<212> TYPE: RNA
<213> ORGANISM: Artificial Sequence
<220> FEATURE:
<223> OTHER INFORMATION: Synthetic: Hu STING (E315Q); no epitope tag; nucleotide sequence

<400> SEQUENCE: 206
augccucaca gcagccugca cccuagcauc ccuugcccua gaggccacgg cgcccagaag 60
gccgcccugg ugcugcugag cgccugccug gugacccugu ggggccuggg cgagccuccu 120
gagcacaccc ugagauaccu ggugcugcac cuggccagcc ugcagcuggg ccugcugcug 180
aacggcgugu gcagccuggc cgaggagcug agacacaucc acagcagaua cagaggcagc 240
uacuggagaa ccgugagagc cugccugggc ugcccucuga gaagaggcgc ccugcugcug 300
cugagcaucu acuucuacua cagccugccu aacgccgugg gcccuccuuu caccuggaug 360
cuggcccugc ugggccugag ccaggcccug aacauccugc ugggccugaa gggccuggcc 420
ccugccgaga ucagcgccgu gugcgagaag ggcaacuuca acguggccca cggccuggcc 480
uggagcuacu acaucggcua ccugagacug auccugccug agcugcaggc cagaaucaga 540

```
accuacaacc agcacuacaa caaccugcug agaggcgccg ugagccagag acuguacauc    600

cugcugccuc uggacugcgg cgugccugac aaccugagca uggccgaccc uaacaucaga    660

uuccuggaca agcugccuca gcagaccggc gaccacgccg gcaucaagga cagaguguac    720

agcaacagca ucuacgagcu gcuggagaac ggccagagag ccggcaccug cgugcuggag    780

uacgccaccc cucugcagac ccuguucgcc augagccagu acagccaggc cggcuucagc    840

agagaggaca gacuggagca ggccaagcug uucugcagaa cccuggagga cauccuggcc    900

gacgccccug agagccagaa caacugcaga cugaucgccu accagcagcc ugccgacgac    960

agcagcuuca gccugagcca ggaggugcug agacaccuga gacaggagga gaaggaggag   1020

gugaccgugg gcagccugaa gaccagcgcc gugccuagca ccagcaccau gagccaggag   1080

ccugagcugc ugaucagcgg cauggagaag ccucugccuc ugagaaccga cuucagc      1137
```

```
<210> SEQ ID NO 207
<211> LENGTH: 1137
<212> TYPE: RNA
<213> ORGANISM: Artificial Sequence
<220> FEATURE:
<223> OTHER INFORMATION: Synthetic: Hu STING (R375A); no epitope tag;
      nucleotide sequence

<400> SEQUENCE: 207

augccucaca gcagccugca cccuagcauc ccuugcccua gaggccacgg cgcccagaag     60

gccgccccugg ugcugcugag cgccugccug gugacccugu ggggccuggg cgagccuccu    120

gagcacaccc ugagauaccu ggugcugcac cuggccagcc ugcagcuggg ccugcugcug    180

aacggcgugu gcagccuggc cgaggagcug agacacaucc acagcagaua cagaggcagc    240

uacuggagaa ccgugagagc cugccugggc ugcccucuga gaagaggcgc ccugcugcug    300

cugagcaucu acuucuacua cagccugccu aacgccgugg gcccuccuuu caccuggaug    360

cuggcccugc ugggccugag ccaggcccug aacauccugc ugggccugaa gggccuggcc    420

ccugccgaga ucagcgccgu gugcgagaag ggcaacuuca acguggccca cggccuggcc    480

uggagcuacu acaucggcua ccugagacug auccugccug agcugcaggc cagaaucaga    540

accuacaacc agcacuacaa caaccugcug agaggcgccg ugagccagag acuguacauc    600

cugcugccuc uggacugcgg cgugccugac aaccugagca uggccgaccc uaacaucaga    660

uuccuggaca agcugccuca gcagaccggc gaccacgccg gcaucaagga cagaguguac    720

agcaacagca ucuacgagcu gcuggagaac ggccagagag ccggcaccug cgugcuggag    780

uacgccaccc cucugcagac ccuguucgcc augagccagu acagccaggc cggcuucagc    840

agagaggaca gacuggagca ggccaagcug uucugcagaa cccuggagga cauccuggcc    900

gacgccccug agagccagaa caacugcaga cugaucgccu accaggagcc ugccgacgac    960

agcagcuuca gccugagcca ggaggugcug agacaccuga gacaggagga gaaggaggag   1020

gugaccgugg gcagccugaa gaccagcgcc gugccuagca ccagcaccau gagccaggag   1080

ccugagcugc ugaucagcgg cauggagaag ccucugccuc uggccaccga cuucagc      1137
```

```
<210> SEQ ID NO 208
<211> LENGTH: 1137
<212> TYPE: RNA
<213> ORGANISM: Artificial Sequence
<220> FEATURE:
<223> OTHER INFORMATION: Synthetic: Hu STING(V147L/N154S/V155M); no
      epitope tag; nucleotide sequence

<400> SEQUENCE: 208
```

augccucaca gcagccugca cccuagcauc ccuugcccua gaggccacgg cgcccagaag 60
gccgcccugg ugcugcugag cgccugccug gugacccugu ggggccuggg cgagccuccu 120
gagcacaccc ugagauaccu ggugcugcac cuggccagcc ugcagcuggg ccugcugcug 180
aacggcgugu gcagccuggc cgaggagcug agacacaucc acagcagaua cagaggcagc 240
uacuggagaa ccgugagagc cugccugggc ugcccucuga gaagaggcgc ccugcugcug 300
cugagcaucu acuucuacua cagccugccu aacgccgugg gcccuccuuu caccuggaug 360
cuggcccugc ugggccugag ccaggcccug aacauccugc ugggccugaa gggccuggcc 420
ccugccgaga ucagcgcccu gugcgagaag ggcaacuuca gcauggccca cggccuggcc 480
uggagcuacu acaucggcua ccugagacug auccugccug agcugcaggc cagaaucaga 540
accuacaacc agcacuacaa caaccugcug agaggcgccg ugagccagag acuguacauc 600
cugcugccuc uggacugcgg cgugccugac aaccugagca uggccgaccc uaacaucaga 660
uuccuggaca agcugccuca gcagaccggc gaccacgccg gcaucaagga cagaguguac 720
agcaacagca ucuacgagcu gcuggagaac ggccagagag ccggcaccug cgugcuggag 780
uacgccaccc cucugcagac ccuguucgcc augagccagu acagccaggc cggcuucagc 840
agagaggaca gacuggagca ggccaagcug uucugcagaa cccuggagga cauccuggcc 900
gacgccccug agagccagaa caacugcaga cugaucgccu accaggagcc ugccgacgac 960
agcagcuuca gccugagcca ggaggugcug agacaccuga gacaggagga gaaggaggag 1020
gugaccgugg gcagccugaa gaccagcgcc gugccuagca ccagcaccau gagccaggag 1080
ccugagcugc ugaucagcgg cauggagaag ccucugccuc ugagaaccga cuucagc 1137

<210> SEQ ID NO 209
<211> LENGTH: 1137
<212> TYPE: RNA
<213> ORGANISM: Artificial Sequence
<220> FEATURE:
<223> OTHER INFORMATION: Synthetic: Hu STING(R284M/V147L/N154S/V155M); no epitope tag; nucleotide sequence

<400> SEQUENCE: 209
augccucaca gcagccugca cccuagcauc ccuugcccua gaggccacgg cgcccagaag 60
gccgcccugg ugcugcugag cgccugccug gugacccugu ggggccuggg cgagccuccu 120
gagcacaccc ugagauaccu ggugcugcac cuggccagcc ugcagcuggg ccugcugcug 180
aacggcgugu gcagccuggc cgaggagcug agacacaucc acagcagaua cagaggcagc 240
uacuggagaa ccgugagagc cugccugggc ugcccucuga gaagaggcgc ccugcugcug 300
cugagcaucu acuucuacua cagccugccu aacgccgugg gcccuccuuu caccuggaug 360
cuggcccugc ugggccugag ccaggcccug aacauccugc ugggccugaa gggccuggcc 420
ccugccgaga ucagcgcccu gugcgagaag ggcaacuuca gcauggccca cggccuggcc 480
uggagcuacu acaucggcua ccugagacug auccugccug agcugcaggc cagaaucaga 540
accuacaacc agcacuacaa caaccugcug agaggcgccg ugagccagag acuguacauc 600
cugcugccuc uggacugcgg cgugccugac aaccugagca uggccgaccc uaacaucaga 660
uuccuggaca agcugccuca gcagaccggc gaccacgccg gcaucaagga cagaguguac 720
agcaacagca ucuacgagcu gcuggagaac ggccagagag ccggcaccug cgugcuggag 780
uacgccaccc cucugcagac ccuguucgcc augagccagu acagccaggc cggcuucagc 840
agagaggaca ugcuggagca ggccaagcug uucugcagaa cccuggagga cauccuggcc 900
gacgccccug agagccagaa caacugcaga cugaucgccu accaggagcc ugccgacgac 960
agcagcuuca gccugagcca ggaggugcug agacaccuga gacaggagga gaaggaggag 1020
gugaccgugg gcagccugaa gaccagcgcc gugccuagca ccagcaccau gagccaggag 1080
ccugagcugc ugaucagcgg cauggagaag ccucugccuc ugagaaccga cuucagc 1137

<210> SEQ ID NO 210
<211> LENGTH: 141
<212> TYPE: RNA
<213> ORGANISM: Artificial Sequence
<220> FEATURE:
<223> OTHER INFORMATION: Synthetic: 3 UTR used in STING V155M construct, containing miR122 binding site

<400> SEQUENCE: 210
ugauaauagg cuggagccuc gguggccuag cuucuugccc cuugggccuc cccccagccc 60
cuccuccccu uccugcaccc guaccccca aacaccauug ucacacucca guggucuuug 120
aauaaagucu gagugggcgg c 141

<210> SEQ ID NO 211
<211> LENGTH: 1257
<212> TYPE: RNA
<213> ORGANISM: Mus musculus
<220> FEATURE:
<221> NAME/KEY: misc_feature
<222> LOCATION: (1)..(1257)
<223> OTHER INFORMATION: super mouse IRF3 S396D; no epitope tag

<400> SEQUENCE: 211
auggagaccc ccaagccuag aauccugccc uggcugguga gccagcugga ccugggccag 60
cuggagggcg uagccuggcu ggacgagagc agaaccagau ucagaauccc cuggaagcac 120
ggccugagac aagacgccca gauggccgac uucggcaucu uccaggccug ggccgaggcc 180
agcggcgccu acaccccugg caaggauaag cccgauguga gcaccuggaa gagaaacuuc 240
agaagcgccc ugaacagaaa ggaggugcug agacuggccg ccgacaauag caaggacccc 300
uacgaccccc acaaggugua cgaguucguu acccccggcg ccagggacuu cgugcaccug 360
ggcgccagcc ccgacaccaa cggcaagagc agccugcccc acagccagga gaaccugccc 420
aagcuguucg auggccugau ccugggcccc cugaaggacg agggcagcag cgaccuggcc 480
aucgugagcg acccuagcca gcagcugccc ucccccaacg ugaacaacuu ccugaacccc 540 gcccccccagg agaacccccu gaagcaacug cuggccgagg agcaguggga guucgaggug 600
accgccuucu acagaggcag acagguguuc cagcagaccc uguucugccc cggcggccug 660
agacugguag gcagcaccgc ugacaugacc cugcccuggc agcccgugac ccugcccgac 720
cccgaaggcu uucugaccga caagcuggug aaggaguacg ucggccaagu gcugaagggc 780
cugggcaacg gccuggcccu guggcaggcc ggccagugcc ugugggccca gagacucggc 840
cacagccacg ccuucugggc ccugggcgag gaacuccugc ccgauagcgg cagaggcccc 900
gacggcgagg ugcacaagga caaggacggc gccguguucg accugcgccc cuucguggcc 960
gaccugaucg ccuucaugga gggcagcggc cacagcccca gauauacccu gugguucugc 1020
augggcgaga uguggcccca ggaccagccc ugggugaaga gacuggugau ggugaaggug 1080
gugcccaccu gccugaaaga gcugcuggag auggccagag agggcggcgc cagcucccug 1140
aaaaccgugg accugcacau ugacaacagc cagcccauca gccugaccag cgaccaguac 1200
aaggccuacc ugcaggaccu gguggaggac auggacuucc aggccaccgg caacauc 1257

<210> SEQ ID NO 212
<211> LENGTH: 1281
<212> TYPE: RNA
<213> ORGANISM: Homo sapiens
<220> FEATURE:
<221> NAME/KEY: misc_feature
<222> LOCATION: (1)..(1281)
<223> OTHER INFORMATION: super human IRF3 S396D; no epitope tag

<400> SEQUENCE: 212
augggcaccc ccaagcccag aauccugccc uggcugguga gccagcugga ccugggccag 60
cuggagggag uggccugggu gaacaagagc agaaccagau ucagaauccc cuggaagcac 120
ggccucagac aggacgccca gcaggaggac uucggcauuu uucaggcuug ggccgaggcc 180
accggcgccu acgugcccgg cagagacaag cccgaccugc ccaccuggaa aagaaacuuc 240
agaagcgccu ugaauagaaa ggagggccug agacuggccg aggacagaag caaggacccc 300
cacgacccuc acaagaucua cgaguucgug aauagcggcg ugggcgacuu uagccagccc 360
gacaccagcc ccgacaccaa cggcggcggc agcaccagcg acacgcagga ggacauccug 420
gaugaacugc ugggcaacau ggugcuggcc ccccugcccg aucccggccc cccuucgcuu 480
gccguggccc ccgagcccug cccccagccc cugagaagcc ccucucugga uaaccccacc 540 cccuuccccca accugggccc cagcgagaau ccacugaaga gacuucuggu ccccggcgag 600
gagugggagu ucgaggugac cgccuucuac agaggcagac agguguucca gcagaccauc 660
agcugccccg aaggccugag auuagugggc agcgaagugg gcgacaggac ccugcccggg 720
uggcccguga cccugcccga ucccggcaug agccugaccg acagaggugu gaugagcuac 780
gugagacacg ugcugagcug ccugggcggc ggccuggcac uguggagagc cggccagugg 840
cugugggccc agagacuggg ccacugccac accuacuggg ccgugagcga ggagcugcug 900
cccaacagcg gccacggccc cgacggcgag gugcccaagg acaaggaagg gggcguguuc 960
gaccugggcc ccuucaucgu agaccugauc accuuuaccg agggcagcgg caggagcccc 1020
agauacgccc ugugguucug cgugggcgaa agcuggcccc aggaccagcc cuggaccaag 1080
agacugguga uggugaaggu agugcccacc ugccugagag ccuuagugga gauggccaga 1140
gugggcgggg ccagcagccu ggagaacacc guggaucuuc acaucgacaa cagccacccc 1200
cugagccuga ccagcgacca guacaaggcc uaccugcagg accuggugga gggcauggac 1260
uuccagggcc ccggcgagac c 1281

<210> SEQ ID NO 213
<211> LENGTH: 1509
<212> TYPE: RNA
<213> ORGANISM: Artificial Sequence
<220> FEATURE:
<223> OTHER INFORMATION: Synthetic: Wild-type Hu IRF7 isoform A; P037
without epitope tag

<400> SEQUENCE: 213
auggcgcugg cccccgaaag agccgccccc agaguccucu ucggcgaaug gcuccuuggc 60
gaaauuucgu cgggcugcua cgagggcuua caauggcugg augaggcgag aaccuguuuc 120
agggugcccu ggaaacacuu cgccagaaag gaucuaagcg aagcagaugc uagaauuuuu 180
aaggcuuggg ccguggccag gggaagaugg ccccccucga gcagaggcgg cggcccuccc 240
cccgaggcag aaacggccga gagagccgga uggaaaacca auuucagaug cgcccugaga 300
ucuacaagaa gauucgugau gcuuagagac aacagcggag aucccgccga uccccauaag 360
guguaugccc ugucccggga gcugugcugg agggaagggc cuggcacuga ccagaccgaa 420
gccgaagccc ccgcggccgu gccgccgccc caaggaggcc caccaggccc uuuccucgcu 480
cacacccacg ccggucugca agccccggga ccucuaccug ccccugccgg cgauaaaggc 540
gaccuguugc ugcaggccgu ccaacagagc ugccuggccg aucaucugcu cacagccagc 600
uggggcgcug accccguccc aacaaaggcc cccggugagg gccaagaagg ccugccucug 660
accggcgccu gugccggcgg cccuggccug ccugcuggcg agcuguacgg augggcuguc 720
gaaaccacuc ccucccccgg cccccaaccu gcggcccuga caaccggcga ggcagccgca 780
cccgaaagcc cccaccaggc cgaacccuac cucaguccca gccccuccgc cugcaccgcu 840
gugcaggagc ccagccccgg ugcucuggac guaacaauca uguacaaagg cagaaccgug 900
cuucagaagg ugguuggaca ccccuccugu acuuuucucu acggcccccc cgacccugcc 960
gugagagcua ccgacccgca acagguggcc uuucccucgc ccgccgaacu gcccgaucaa 1020
aaacagcuga gauacaccga ggagcugcug agacacgugg cgccgggcuu acaccuagag 1080
uugagaggcc cccaacucug ggccagacgc augggcaagu guaaggugua cugggagguc 1140
gggggcccuc ccggcucugc cagccccagc accccugcuu gucucuugcc cagaaacugu 1200 gauacccccca ucuucgacuu ccguguauuu uuccaggaac uggucgaguu uagagccaga 1260
cagagacgag gcagccccag auauacaauc uaccucggcu ucggccagga ccugagugcc 1320
ggcagaccua aggagaaguc gcugguccua gugaaguuag agcccuggcu auguagagug 1380
caccuggagg gcacccagag agaaggagug agcagccugg acagcagcag ccugagucug 1440
ugccugagcu ccgccaacuc gcuguaugau gacaucgagu guuuccucau ggagcuggag 1500
cagcccgcc 1509

<210> SEQ ID NO 214
<211> LENGTH: 1509
<212> TYPE: RNA
<213> ORGANISM: Artificial Sequence
<220> FEATURE:
<223> OTHER INFORMATION: Synthetic: constitutively active Hu IRF7
S477D/S479D; P033 without epitope tag

<400> SEQUENCE: 214
auggcccuug ccccugagcg ggccgccccc agaguguuau ucggcgagug gcugcugggc 60
gagaucagca gcggcugcua cgagggacug caguggcugg acgaggcuag aaccugcuuc 120
agagugcccu ggaagcauuu cgccagaaaa gaccugagcg aggcugaugc uagaaucuuc 180
aaagccuggg cuguggcccg aggaagaugg ccccccagca gcagaggagg cggcccuccu 240
cccgaggccg aaaccgcaga gcgugcuggc uggaaaacca acuuuaggug ugcccugagg 300
agcaccagaa gauucguuau gcucagagac aacagcgggg accccgccga cccgcacaag 360
guguacgccu uaaguaggga gcugugcugg agagagggac cggggaccga ccaaaccgag 420
gcugaggcgc ccgccgccgu uccaccuccc cagggugguc ccccagggcc cuuucuggca 480
cacacccacg ccggauuaca ggcgccaggg cccuuacccg cccccgccgg agacaaaggc 540
gaccuccugc ugcaagccgu gcaacaaagc ugccuggccg aucacuuacu aaccgcuagc 600
uggggcgccg auccuguucc caccaaggcc cccggugaag ggcaagaagg acugcccuua 660
accggcgccu gugccggagg cccuggucug ccagccggcg agcuguacgg uugggcuguc 720
gaaacaacac ccaguccggg cccacagccu gccgcucuga ccaccggcga agccgccgcc 780
cccgagagcc cacaccaggc ugaacccuac cugagcccca gccccagcgc cugcaccgcu 840
gugcaggagc cuagccccgg cgcucuugau gugacaauaa uguacaaggg caggaccgug 900
cugcaaaagg ucgugggcca uccgucgugu accuuucugu acggcccucc agaccccgcg 960
guuagagcca ccgaccccca gcaagucgcc uuccccuccc ccgccgaacu gcccgaccaa 1020
aagcagcugc gguacacaga agaacuacuu agacacgugg cccccggucu gcacuuggag 1080
cugagaggcc cccagcucug ggccagaaga augggcaagu gcaaagugua cugggaggug 1140
ggcggcccac ccggcucagc uucgcccucc acacccgcau gccugcugcc cagaaauugc 1200
gacacgccca ucuucgauuu uagaguguuc uuucaggagu ugguggaguu cagagccaga 1260
caaagacgcg gcagccccag auacaccauu uaccucggcu ucggccagga ccucagcgcu 1320
ggcagaccca aggagaagag ucugguccuc gugaagcugg agcccuggcu gugcagagug 1380
caccuggagg gcacccagcg ugaaggcgug agcagccugg auucaagcga ccuggaccua 1440
ugccuaagca gcgcuaacuc acuguacgac gauaucgaau gcuuccugau ggaacuggag 1500
cagccugcc 1509

<210> SEQ ID NO 215
<211> LENGTH: 1509
<212> TYPE: RNA
<213> ORGANISM: Artificial Sequence
<220> FEATURE:
<223> OTHER INFORMATION: Synthetic: constitutively active Hu IRF7 S475D/S477D/L480D; P034 without epitope tag

<400> SEQUENCE: 215
auggcccugg cacccgagag ggccgccccc agggugcucu ucggcgagug guuacuaggc 60
gaaauuagca gcggcugcua ugaaggccuu caguggcugg acgaggccag aaccugcuuu 120
agaguucccu ggaagcacuu cgcccggaaa gaucucucug aagccgacgc cagaauauuc 180
aaggccuggg cugucgccag ggcaggugg ccacccucca gccgaggugg cggcccuccc 240
ccugaggcug agacugcgga aagggcgggc uggaagacca auuucagaug cgcucugaga 300
agcaccagac guuuugugau gcuaagagac aauagcggcg aucccgccga cccccauaag 360
guauacgcac ugagccgaga gcucuguugg agagaaggcc ccggcaccga ccagaccgag 420
gcugaagccc cugcagccgu gcccccccu caaggcgggc cccccggccc cuuccuggcc 480
cauacccaug cagggguaca agcacccggg cccuugcccg ccccagcggg agacaagggc 540
gaccucuuac ugcaggccgu gcaacaaagu ugucuggcgg accaccugcu gaccgcauca 600
uggggcgcgg auccugugcc caccaaggca cccggcgaag gccaggaggg ccugcccuug 660
accggcgccu gcgcuggcgg acccggccua ccugcuggcg aacuguaugg cugggccgua 720
gagacgacuc ccagcccugg cccacaaccc gcggcuuuga ccaccggcga agccgccgcc 780
cccgagucuc cgcaccaggc cgagccuuac cucagcccaa gcccuagcgc cugcaccgcc 840
gugcaagaac cuagccccgg agcccuggau gugacaauca uguacaaggg uagaaccgua 900
cugcaaaagg ugguggguca ucccagcugc accuuucuuu acggcccacc cgacccugcc 960
gugcgagcca cagacccaca acaggucgcc uucccaagcc ccgccgaacu gcccgaucag 1020
aaacagcuga gauauacaga ggagcuucug cggcacguag cucccggccu acaucucgag 1080
cugaggggcc cacaacugug ggccagacgc augggcaaau gcaaggucua cugggaagug 1140
ggaggccccc ccggcagcgc aucucccagc acgcccgcgu gccugcugcc uagaaauugc 1200 gacacccca ucuuugacuu ccggguauuc uuucaggagc ugguagaguu cagagccagg 1260
cagcggaggg gcucccccag auacacaauc uaccugggcu ucggacagga ccuguccgcc 1320
ggccgcccca aggaaaagag ccuggugcug gugaagcugg agcccuggcu guguagggua 1380
caccucgaag gcacccagag agaaggagug agcucgcuug augacagcga ucugucggau 1440
ugccuuagca gcgccaacag ccuguaugau gauaucgagu gcuuccuuau ggaacuggag 1500
cagcccgcc 1509

<210> SEQ ID NO 216
<211> LENGTH: 1509
<212> TYPE: RNA
<213> ORGANISM: Artificial Sequence
<220> FEATURE:
<223> OTHER INFORMATION: Synthetic: constitutively active Hu IRF7
S475D/S476D/S477D/S479D/S483D/S487D; P035 without epitope tag

<400> SEQUENCE: 216
auggcccuag cccccgaaag agcagcuccc agagugcugu ucggcgaaug gcugcuuggc 60
gagaucagca gcggcugcua cgaaggccug caguggcugg acgaagcccg caccuguuuc 120
agagugcccu ggaagcacuu cgcuagaaag gauuugagcg aggcugaugc uagaaucuuu 180
aaggcuuggg cuguggcaag aggcagaugg ccgccuagua gcagaggggg cggaccuccc 240
cccgaggcug agaccgcuga gagagcaggg uggaaaacca acuucagaug cgcgcugaga 300
agcacccgaa gauucgugau gcuacgugac aauagcggcg accccgccga cccccacaaa 360
guguacgccc ugucccgaga acuuugcugg agagagggac ccggcaccga ucaaacagag 420
gcugaggccc cggccgcugu acccccgccc caaggaggcc ccccaggccc cuuucuggcu 480
cauacacaug ccggccugca ggcacccggg ccccucccgg cuccugccgg cgacaagggc 540
gaucuccuuc uccaggccgu gcagcagagc ugccuggccg aucaccugcu gaccgccucg 600
uggggcgccg accccgugcc caccaaagcc ccgggugaag gccaagaggg gcucccuuua 660
accggagcau gcgccggagg ccccggccug ccagccggcg aguuauaugg cugggcugug 720
gagaccacac ccucccccgg cccucaaccc gcugcccuga ccaccgguga ggccgccgcc 780
cccgagagcc cacaccaggc cgaacccuac cugagcccua gcccuagcgc cugcaccgcc 840
gugcaagaac ccagccccgg agcccuggau gugaccauua uguacaaggg ccggacagug 900
cugcaaaagg uugugggaca cccgagcugc accuuucugu acgguccgcc ugaccccgcc 960
gugagagcca cggacccgca gcagguggcc uuccccucac ccgcggagcu gcccgaccaa 1020
aagcaacuca gauacacaga agaacuauug cgucacgucg cgcccggccu gcaucuggag 1080
cugagaggcc cccagcucug ggccagaagg augggcaaau gcaaggugua cugggaggug 1140
ggaggccccc ccggcagcgc cagccccagc acucccgcgu gccugcugcc cagaaauugc 1200
gacacuccca ucuucgauuu cagggugguc uuccaggagc ugguggaguu cagagccagg 1260
cagagaaggg guagccccag auacacaauc uaucuaggcu uuggacaaga ucugagcgcc 1320
ggccggccua aggaaaaaag ccuggugcug guaaagcugg agccguggcu uuguagagug 1380
caccuggagg ggacgcagcg agagggcgug agcagcuuag acgacgauga cuuggaucug 1440
ugucucgaca gcgccaacga cuuguacgac gacaucgagu gcuuccugau ggaacuggag 1500
cagcccgcc 1509

<210> SEQ ID NO 217
<211> LENGTH: 846
<212> TYPE: RNA
<213> ORGANISM: Artificial Sequence
<220> FEATURE:
<223> OTHER INFORMATION: Synthetic: constitutively active truncated Hu IRF7 1-246 + 468-503; P032 without epitope tag

<400> SEQUENCE: 217
auggcccugg cccccgagag agccgccccc agagugcucu ucggcgagug gcugcugggc 60
gagauaagca gcggcugcua cgaaggucug caguggcuag acgaggccag aaccugcuuu 120
agagugcccu ggaagcacuu cgcucgaaag gaccuguccg aggccgaugc uagaauuuuu 180
aaggcuuggg ccgucgcuag gggaagaugg cccccuagca guagaggcgg cggccccccu 240
cccgaagccg agacggccga gagggccggc uggaaaacca auuucagaug cgcccugagg 300
agcacccgca gguucguaau gcugcgagac aauagcggcg auccugcgga uccucacaag 360
guuuacgccu ugaguagaga acugugcugg cgggagggcc ccggaaccga ccagacggag 420
gcagaggcac ccgcugccgu gcccccccu caaggaggac ccccuggacc cuuucuggcc 480
cacacccacg cuggucugca ggccccaggc ccacugcccg ccccagcggg cgauaagggu 540
gaccugcucc uacaggcggu gcaacagagc ugucuggccg accaccuguu gaccgccagc 600
uggggggccg acccggugcc caccaaagcu cccggagagg gccaagaagg ccucccacua 660
acuggcgccu gcgccggggg cccgggauua cccgccggcg agcuguaugg cugggccgug 720
gagaccacgc ccagccccga gggcgugucg ucccuggaca gcagcagccu gagccugugc 780
cugagcuccg ccaacagccu guaugacgac aucgagugcu uccugaugga gcuggaacaa 840
cccgcc 846

<210> SEQ ID NO 218
<211> LENGTH: 846
<212> TYPE: RNA
<213> ORGANISM: Artificial Sequence
<220> FEATURE:
<223> OTHER INFORMATION: Synthetic: constitutively active truncated Hu
IRF7 1-246 + 468-503 plus S475D/S476D/S477D/S479D/S483D/S487D;
P036 without epitope tag

<400> SEQUENCE: 218
auggcacugg cgccugaaag agccgcuccg cgugugcucu ucggcgagug gcugcugggc 60
gagaucagcu ccggcugcua cgagggucua caguggcugg acgaggccag aaccuguuuu 120
agagugcccu ggaagcacuu cgcgagaaag gaccugagcg aggccgacgc cagaaucuuc 180
aaagccuggg caguggcuag gggcagaugg ccucccagca gccggggcgg cggcccaccc 240
cccgaggccg aaaccgccga aagagcuggc uggaagacca acuucagaug cgcccugaga 300
agcaccagaa gauuugucau gcugagagau aauucaggag accccgccga cccucacaag 360
guguacgccc uguccagaga gcuguguugg agagagggcc ccggaaccga ccagaccgag 420
gccgaggcuc cagcugccgu gccacccccc caaggcggac cacccggccc cuucuuggca 480
cauacgcacg ccggccucca ggcucccggc ccucugcccg ccccugcugg ugacaaaggc 540
gaucugcugc ugcaagccgu ccagcaaucc ugcuuggcug accaccugcu gaccgcuagc 600
uggggagccg accccguucc caccaaggcu cccggagaag gacaggaggg ccugccccuu 660
accggcgcuu gcgcgggggg cccuggcuug ccugccggcg aacuguacgg cugggccgug 720
gagaccacgc cuucccccga gggcgugucc agccuggacg augaugaccu ggaucugugc 780
cuggacagcg ccaacgaccu guacgaugac aucgagugcu uuuugaugga gcuggagcag 840
cccgcc 846

<210> SEQ ID NO 219
<211> LENGTH: 1224

<212> TYPE: RNA
<213> ORGANISM: Artificial Sequence
<220> FEATURE:
<223> OTHER INFORMATION: Synthetic: truncated Hu IRF7 1-151 + 247-503;
P038 without epitope tag; null mutation

<400> SEQUENCE: 219
auggcccugg cccccgagag agccgcgccc agagugcugu ucggcgaaug gcugcugggc 60
gagaucagca gcggcugcua ugagggccug caguggcucg acgaagccag gacgugcuuc 120
agaguccccu ggaagcacuu cgccagaaag gaucugagcg aggcugacgc cagaaucuuc 180
aaggccuggg caguugcgcg ugggagaugg cccccccagcu cgcggggcgg cggucccccc 240
ccugaggccg agaccgccga aagagccgga uggaaaacca acuuucgaug cgcccucaga 300
agcaccagac gguuugugau gcugagagau aacagcggcg acccugcaga cccccauaaa 360
guguaugccc ugagcagaga gcuguguugg cgagagggcc ccggaaccga ccaaaccgag 420
gccgaggccc ccgccgccgu accccccccu caaggccccc agccugcugc ucugaccacg 480
ggagaagccg ccgcuccuga gagcccccac caagccgagc ccuaucugag cccuagcccc 540
agcgccugca ccgccgugca ggagcccuca ccgggcgccc uagacgugac caucauguac 600
aaggggcgca cggugcugca aaagguggug ggccacccca gcugcaccuu ccuguacggc 660
ccccccgacc cugccgugag agccaccgac ccccagcaag ucgccuuccc cagccccgcc 720
gagcugcccg accagaagca gcugagguac accgaggagu ugcugagaca uguggccccc 780
ggcuugcacc ucgagcugag aggcccgcag cucugggcca gaagaauggg caagugcaag 840
guguacuggg aggugggcgg cccccccggc agcgcgagcc caagcacccc ggccugccug 900
cugccuagaa acugcgacac cccuaucuuc gacuucagag uauuuuucca ggagcugguc 960
gaguucaggg ccagacagcg uagaggcagc cccagauaca ccaucuaccu uggauucggc 1020
caggaccuga gcgccggcag acccaaagag aagucccugg uacuggugaa gcuagagccc 1080
uggcugugua gggugcaucu ggaaggcacc caaagagagg gcguaagcuc gcuugacagc 1140
agcagccuca gccugugccu gagcagcgcu aacagcuuau acgacgacau cgagugcuuc 1200
cugauggagc uggaacaacc cgcc 1224

<210> SEQ ID NO 220
<211> LENGTH: 1059
<212> TYPE: RNA
<213> ORGANISM: Artificial Sequence
<220> FEATURE:
<223> OTHER INFORMATION: Synthetic: truncated Hu IRF7 152-503; P039
without epitope tag; null mutation

<400> SEQUENCE: 220
augggcggcc cucccgggcc uuuccuggcc cauacacacg ccggccuaca ggcuccuggc 60
ccucugcccg ccccggccgg cgacaagggc gaccuccugc ugcaggccgu gcagcagucc 120
ugucuggccg accaccugcu gacugcuagc uggggcgccg aucccgugcc caccaaggcc 180
ccaggagagg ggcaagaggg ccugccucua accggcgcau gcgcaggugg accaggccuc 240
cccgccggcg agcuguaugg uugggccgug gagacaaccc ccagccccgg cccgcagccu 300
gcugcgcuga ccacaggcga ggccgcugcc ccugagagcc cccaccaagc ugaacccuac 360
cugagcccca gccccucugc cugcacagcg gugcaggagc ccagucccgg cgccuuggac 420
gugaccauca uguauaaggg caggacugug uuacaaaagg uagugggcca cccaaguugu 480
accuuucugu acgggccccc cgacccagcc gugcgcgcca ccgaccccca gcagguggcc 540

```
uuccccagcc ccgcugaguu gcccgaucag aaacaacucc gguacaccga ggaauuacuu    600

agacaugugg cucccggccu gcaucuggag cuuagagguc cacaguugug ggccagaaga    660

augggcaagu gcaagguuua uugggagguc ggaggccccc cgggcagcgc cagccccagc    720

accccgccu gucuucugcc cagaaacugc gacaccccaa ucuucgauuu cagaguguuu    780

uuccaggaac ugguggaguu cagagcaagg caaagaagag gcagcccuag auacaccauc    840

uaccugggcu uuggccaaga ccugagcgcc ggcagaccca aggaaaaauc ccugguccug    900

gugaaacugg agcccuggcu gugcagaguc caccuggagg gcacccagag agagggcgug    960

agcagccugg acucgagcag ccugucccug ugucugagca gcgcgaauuc gcuauaugac   1020

gacaucgaau gcuuucugau ggagcuggaa cagcccgcc                          1059
```

<210> SEQ ID NO 221
<211> LENGTH: 1269
<212> TYPE: RNA
<213> ORGANISM: Artificial Sequence
<220> FEATURE:
<223> OTHER INFORMATION: Synthetic: KRAS(G12D)25mer_nt.STING(V155M)

<400> SEQUENCE: 221

```
augccucaca gcagccucca cccuagcauc ccuugcccua gaggccacgg cgcccagaag     60

gccgcccucg ugcuuuuaag cgccugcuug gugacccuuu ggggcuuggg cgagccucca    120

gagcacaccu ugagauauuu ggugcuccac cuggccagcc uucagcuggg cuuguuacuc    180

aacggcgugu gcagccuggc cgaggagcug agacacaucc acagcagaua cagaggcagc    240

uacuggagaa ccgugagagc gugucugggc ugcccucuga gaagaggcgc cuugcuucuu    300

cucaguaucu acuucuacua cucccugccu aacgccgugg gcccuccuuu caccuggaug    360

cuggcacugc ucggccucag ccaggcccug aacaucuugu ugggcuugaa gggccuggcc    420

ccugccgaga ucagcgccgu gugcgagaag ggcaacuuca acauggccca cggauuggcu    480

uggagcuacu acaucggcua ccugagacug auccugccug agcugcaggc cagaaucaga    540

accuacaacc agcacuacaa caaccugcug cgcggcgcag ugagccagag acuguauauu    600

cugcugccuc uggacugcgg cgugccugac aaccugagca uggccgaccc uaacaucaga    660

uuccuggaca agcugccuca gcagaccggc gaccacgccg gcaucaagga cagaguguac    720

agcaacagca ucuaugagcu gcucgagaau ggccagagag ccggcaccug cgugcuggag    780

uacgccaccc cucugcagac ccuguucgcc augagccagu auagucaagc uggcuucagc    840

agagaggaca gacuggagca ggccaagcug uucugcagaa cccuggagga cauucuggcu    900

gacgccccug agagccagaa caacugccga cugaucgccu accaggaacc agccgacgac    960

agcagcuuca gucuuucuca ggagguucuu cgccacuugc gccaggagga gaaggaggag   1020

gugaccgugg gcagccugaa gaccuccgca gucccuagca ccagcaccau gagucaggag   1080

ccggagcuau uaaucagcgg cauggagaag ccucuuccac uccgaaccga cuucagcgcc   1140

accaacuuca gccugcugaa gcaggcaggu gacguugagg agaauccggg accuaugacc   1200

gaguacaagc ugguguugu gggcgccgac ggcgugggca agagcgcccu gaccauccag   1260

cugauccag                                                           1269
```

<210> SEQ ID NO 222
<211> LENGTH: 1269
<212> TYPE: RNA
<213> ORGANISM: Artificial Sequence
<220> FEATURE:
<223> OTHER INFORMATION: Synthetic: KRAS(G12D)25mer_ct.STING(V155M)

<400> SEQUENCE: 222
augaccgagu acaagcuagu agucgugggc gccgacggcg ugggcaagag cgcccucacc 60
auccagcuaa uccaggccac caacuucagc uugcucaagc aggccggcga cguggaggag 120
aacccaggcc cuaugccuca cagcagccuu cacccuagca ucccuugccc uagaggccac 180
ggcgcccaga aggccgcccu ggugcugcug agcgccugcc uggugacccu guggggccug 240
ggcgagccuc cugagcacac ccugagauau cuggugcuuc accuggccag uuuacagcug 300
ggccugcuuc uuaacggcgu gugcagccug gccgaggagc ugagacacau ccacagcaga 360
uacagaggca gcuacuggag aaccgugaga gccugccuag gcugcccucu gagaagaggc 420
gcucuguugc uacuuuccau cuacuucuac uacucccugc cuaacgccgu gggcccuccu 480
uucacuugga ugcuggcguu gcugggucug agccaggccc ugaacauccu ucucggucug 540
aagggccugg ccccugccga gaucagcgcc gugugcgaga agggcaacuu caacauggcc 600
cacggacucg ccuggagcua cuacaucggc uaccugagac ugauccugcc ugagcugcag 660
gccagaauca gaaccuacaa ccagcacuac aacaaccugc ugcggggcgc cgugagccag 720
agacuguaua uacuucuucc ucuggacugc ggcgugccug acaaccugag cauggccgac 780
ccuaacauca gauuccugga caagcugccu cagcagaccg gcgaccacgc cggcaucaag 840
gacagagugu acagcaacuc cauuuaugag cugcucgaga auggccagag agccggcacc 900
ugcgugcugg aguacgccac cccucugcag acccuguucg ccaugagcca guacagucag 960
gcuggauuca gcagagagga cagacuggag caggccaagc uguucugcag gacacuggag 1020
gacauacuag cagacgcccc ugagagccag aacaacugca gacugauugc cuaccaggag 1080
ccugcggacg acagcuccuu cagucugagu caggaggugu ugcggcacuu acgccaagaa 1140
gagaaggagg aggugaccgu gggcagccug aagacuagcg cugugccuag caccagcaca 1200
augucacagg agccggaauu gcuaaucagc ggcauggaga agccucuccc auuacguacc 1260
gacuucagc 1269

<210> SEQ ID NO 223
<211> LENGTH: 1419
<212> TYPE: RNA
<213> ORGANISM: Artificial Sequence
<220> FEATURE:
<223> OTHER INFORMATION: Synthetic: KRAS(G12D)25mer^3_nt.STING(V155M)

<400> SEQUENCE: 223
augccucaca gcagccuuca cccuagcauc ccuugcccua gaggccacgg cgcccagaag 60
gccgcccuag ugcuccuuag cgccugccuc gugacccuau ggggcuuagg cgagccucca 120
gagcacaccu ugagauaccu cguccuccac cuggcuaguc uacagcuggg ccuucuccuc 180
aacggcgugu gcagccuggc cgaggagcug agacacaucc acagcagaua cagaggcagc 240
uacuggagaa ccgugagagc gugccugggc ugcccucuga gaagaggcgc acugcuguua 300
cucagcaucu acuucuacua cucacugcca aacgccgugg gcccuccuuu caccuggaug 360
cuggccuugc ucggauugag ccaggcccug aacauuuuac ugggauugaa gggccuggcc 420
ccugccgaga ucagcgccgu gugcgagaag ggcaacuuca acauggccca cggccuagcu 480
uggagcuacu acaucggcua ccugagacug auccugccug agcugcaggc cagaaucaga 540
accuacaacc agcacuacaa caaccugcug cguggagcgg ugagccagag acuguauauc 600
cuccugccuc uggacugcgg agugccugac aaccugagca uggccgaccc uaacaucaga 660

```
uuccuggaca agcugccuca gcagaccggc gaccacgccg gcaucaagga cagaguguac    720

agcaacucaa ucuacgagcu guuggagaau ggccagagag ccggcaccug cgugcuggag    780

uacgccaccc cucugcagac ccuguucgcc augagccagu acucucaggc aggcuucagc    840

agagaggaca gacuggagca ggccaagcug uucugcagaa ccccuggagga cauccuggcg    900

gacgccccug agagccagaa caacugccgg cuuaucgccu accaggagcc agcagacgac    960

agcagcuucu cucucucaca agagguacug cgccaucuuc gccaggagga gaaggaggag   1020

gugaccgugg gcagccugaa gacauccgcc guaccuagca ccagcaccau gucucaggaa   1080

ccggaacugu ugaucagcgg cauggagaag ccucugccac ugcgcaccga cuucagcgcc   1140

accaacuucu cccuacugaa gcaagccggu gacguugaag agaacccugg cccuaugacc   1200

gaguacaagc ugguaguagu aggcgccgac ggcgugggca agagcgcccu gaccauccag   1260

cugauccaga ugacugaaua uaagcuuguc gucguggggcg cagauggcgu ugguaagagc   1320

gcacuuacaa uucaacucau ucagaugacg gaguauaagc ugguggugu cggagcugac   1380

ggcguaggca agagugcccu uacuauucag cuaauucag                         1419
```

<210> SEQ ID NO 224
<211> LENGTH: 1419
<212> TYPE: RNA
<213> ORGANISM: Artificial Sequence
<220> FEATURE:
<223> OTHER INFORMATION: Synthetic: KRAS(G12D)25mer^3_ct.STING(V155M)

<400> SEQUENCE: 224

```
augaccgagu acaagcuugu gguggguuggc gccgacggcg ugggcaagag cgccuuaacc     60

auccagcuua uccagaugac agaguauaag cuaguggugg ucggcgcaga cggagguggga    120

aagagugcau uaacuauuca acucauccaa augaccgaau acaagcuagu aguugugggu    180

gcagauggcg ucggcaaguc ugcacugaca auucagcuca uccaggccac caacuucagc    240

cugcugaagc aggccggcga cguggaggag aacccuggcc cuaugccuca cagcagccug    300

cacccuagca ucccuugccc uagaggccac ggcgcccaga aggccgcccu ggugcugcug    360

agcgccugcc uggugacccu guggggccug ggcgagccuc cugagcacac ccugagauac    420

cuaguuuugc accuggcuuc ucugcagcug ggccuacugc ucaacggcgu gugcagccug    480

gccgaggagc ugagacacau ccacagcaga uacagaggca gcuacuggag aaccgugaga    540

gcaugcuuag gcugcccucu gagaagaggc gcucugcucc ucuuguccau cuacuucuac    600

uacucgcuac cuaacgccgu gggcccuccu uucaccugga ugcuggcccu cuugggauua    660

agccaggccc ugaacaucuu gcugggacug aagggccugg ccccugccga gaucagcgcc    720

gugugcgaga agggcaacuu caacauggcc cacggacucg cuuggagcua cuacaucggc    780

uaccugagac ugauccugcc ugagcugcag gccagaauca gaaccuacaa ccagcacuac    840

aacaaccugc ugcggggagc agugagccag agacuguaua uucugcuccc ucuggacugc    900

ggcgugccug acaaccugag cauggccgac ccuaacauca gauuccugga caagcugccu    960

cagcagaccg gcgaccacgc cggcaucaag gacagagugu acagcaacag cauuuacgag   1020

cugcuggaga acggccagag agccggcacc ugcgugcugg aguacgccac cccucugcag   1080

acccuguucg ccaugagcca guacucccag gcaggauuca gcagagagga cagacuggag   1140

caggccaagc uguucugccg uacucuugag gacauccuug cagacgcccc ugagagccag   1200

aacaacugcc gguugauugc cuaccaggaa ccggcagacg acagcucauu cuccuugucu   1260

caggagguccc uuagacaccu gcggcaggag gagaaggagg aggugaccgu gggcagccug   1320
```

aagacauccg ccgugccuag cacgucuacc augucccagg agccggaacu gcuaaucagc 1380
ggcauggaga agccucugcc ucucaggacc gacuucagc 1419

<210> SEQ ID NO 225
<211> LENGTH: 1140
<212> TYPE: RNA
<213> ORGANISM: Artificial Sequence
<220> FEATURE:
<223> OTHER INFORMATION: Synthetic: Hu STING (R284K) var; no epitope tag

<400> SEQUENCE: 225
augccccaua gcagccugca ccccagcauc cccugcccca gaggccacgg cgcccagaag 60
gccgcccugg uccugcugag cgcaugccug gucacccugu ggggccuggg cgagcccccc 120
gagcacaccc ugagauaccu ggugcugcac cucgccagcc ugcagcuggg ccugcugcug 180
aacggcgugu gcagccuggc cgaggagcug agacacaucc acagcagaua uagaggcagc 240
uacuggagaa ccgugagagc uugccucggc ugcccccuga gaagaggcgc ccugcugcug 300
cugagcaucu acuuuuacua cagccugccc aacgcugugg gcccccccuuu cacguggaug 360 cucgcccugc ugggacugag ccaggcccug aacauccugc ugggccuuaa gggccuagcc 420
cccgccgaga ucagcgccgu gugcgagaag ggcaacuuca auguggccca cggccuggcc 480
uggagcuacu acaucggcua ccugagacug auccugcccg agcugcaggc cagaaucaga 540
accuacaauc agcacuacaa caaccugcug agaggcgccg ugagccagag acuguacauc 600
cugcugcccc uggacugcgg cgugcccgac aaccucagca uggccgaccc caacaucaga 660
uuccuggaca agcugcccca gcagaccggc gaccacgccg gcaucaagga ucgcguguac 720
agcaacagca ucuacgagcu gcuggaaaac ggccagagag ccggaaccug cgugcuggag 780
uacgccacac cccugcagac ccuguucgcc augagccagu acagccaggc cggcuucagc 840
agagaggaca agcuggagca ggccaagcug uucugcagaa cccuggagga uauccucgcc 900
gacgcccccg agagccagaa caacugcagg cugaucgcgu accaggagcc cgcugacgac 960
agcagcuuua gccugagcca ggaggugcug agacaucugc gucaagagga aaaggaggag 1020
gugaccgugg gcucccugaa gaccagcgcc gugcccagca ccagcaccau gagccaggag 1080
cccgagcugc ugaucagcgg cauggagaag ccacugcccc ucagaaccga cuucagcacc 1140

<210> SEQ ID NO 226
<211> LENGTH: 9
<212> TYPE: PRT
<213> ORGANISM: Artificial Sequence
<220> FEATURE:
<223> OTHER INFORMATION: Synthetic: EBV BRLF1 peptide

<400> SEQUENCE: 226

Ala Thr Ile Gly Thr Ala Met Tyr Lys
1               5

<210> SEQ ID NO 227
<211> LENGTH: 9
<212> TYPE: PRT
<213> ORGANISM: Artificial Sequence
<220> FEATURE:
<223> OTHER INFORMATION: Synthetic: FLU peptide

<400> SEQUENCE: 227

Ser Ile Ile Pro Ser Gly Pro Leu Lys
1               5

-continued

```
<210> SEQ ID NO 228
<211> LENGTH: 9
<212> TYPE: PRT
<213> ORGANISM: Artificial Sequence
<220> FEATURE:
<223> OTHER INFORMATION: Synthetic: HIV NEF peptide

<400> SEQUENCE: 228

Ala Val Asp Leu Ser His Phe Leu Lys
1               5


<210> SEQ ID NO 229
<211> LENGTH: 10
<212> TYPE: PRT
<213> ORGANISM: Artificial Sequence
<220> FEATURE:
<223> OTHER INFORMATION: Synthetic: EBV peptide

<400> SEQUENCE: 229

Ala Val Phe Asp Arg Lys Ser Asp Ala Lys
1               5                   10


<210> SEQ ID NO 230
<211> LENGTH: 9
<212> TYPE: PRT
<213> ORGANISM: Artificial Sequence
<220> FEATURE:
<223> OTHER INFORMATION: Synthetic: HBV core antigen peptide

<400> SEQUENCE: 230

Tyr Val Asn Val Asn Met Gly Leu Lys
1               5


<210> SEQ ID NO 231
<211> LENGTH: 9
<212> TYPE: PRT
<213> ORGANISM: Artificial Sequence
<220> FEATURE:
<223> OTHER INFORMATION: Synthetic: HC peptide

<400> SEQUENCE: 231

Arg Val Cys Glu Lys Met Ala Leu Tyr
1               5


<210> SEQ ID NO 232
<211> LENGTH: 9
<212> TYPE: PRT
<213> ORGANISM: Artificial Sequence
<220> FEATURE:
<223> OTHER INFORMATION: Synthetic: CMV peptide

<400> SEQUENCE: 232

Lys Leu Gly Gly Ala Leu Gln Ala Lys
1               5
```